(12) United States Patent
Aertgeerts et al.

(10) Patent No.: US 7,297,508 B1
(45) Date of Patent: Nov. 20, 2007

(54) CRYSTALLIZATION OF FIBROBLAST ACTIVATION PROTEIN ALPHA (FAPα)

(75) Inventors: Kathleen Aertgeerts, San Diego, CA (US); Sridhar Prasad, San Diego, CA (US); Vandana Sridhar, San Diego, CA (US); Robert A. Wijnands, Vista, CA (US); Sheng Ye, Allen, TX (US)

(73) Assignee: Takeda San Diego, Inc., San Diego, CA (US)

( * ) Notice: Subject to any disclaimer, the term of this patent is extended or adjusted under 35 U.S.C. 154(b) by 291 days.

(21) Appl. No.: 10/681,659

(22) Filed: Oct. 7, 2003

Related U.S. Application Data

(60) Provisional application No. 60/417,335, filed on Oct. 8, 2002.

(51) Int. Cl.
*C12Q 1/37* (2006.01)
*C12N 9/50* (2006.01)

(52) U.S. Cl. .......................................... 435/23; 435/219
(58) Field of Classification Search .................... None
See application file for complete search history.

(56) References Cited

OTHER PUBLICATIONS

Wiencek et al. New strategies for protein crystal growth. Ann. Rev. Biomed. Eng. 1999, 1, 505-534.*
Gilliland et al. Crystallization of biological molecules for X-ray diffraction studies. Current Opinion in Structure Biology 1996, 6, 595-603.*
Ke et al. Crystallization of RNA and RNA-protein complexes. Methods 34, 2004, 408-414.*

* cited by examiner

*Primary Examiner*—Nashaat T. Nashed
(74) *Attorney, Agent, or Firm*—David J. Weitz

(57) ABSTRACT

Provided are crystals relating to FAPα and its various uses.

12 Claims, 245 Drawing Sheets

FIGURE 1

Amino acid sequence for full-length human wild type FAPα [SEQ. ID No. 1]

(Residues 27-760 are underlined)

```
MKTWVKIVFG VATSAVLALL VMCIVLRPSR VHNSEENTMR ALTLKDILNG TFSYKTFFPN    60
WISGQEYLHQ SADNNIVLYN IETGQSYTIL SNRTMKSVNA SNYGLSPDRQ FVYLESDYSK   120
LWRYSYTATY YIYDLSNGEF VRGNELPRPI QYLCWSPVGS KLAYVYQNNI YLKQRPGDPP   180
FQITFNGREN KIFNGIPDWV YEEEMLATKY ALWWSPNGKF LAYAEFNDTD IPVIAYSYYG   240
DEQYPRTINI PYPKAGAKNP VVRIFIIDTT YPAYVGPQEV PVPAMIASSD YYFSWLTWVT   300
DERVCLQWLK RVQNVSVLSI CDFREDWQTW DCPKTQEHIE ESRTGWAGGF FVSTPVFSYD   360
AISYYKIFSD KDGYKHIHYI KDTVENAIQI TSGKWEAINI FRVTQDSLFY SSNEFEEYPG   420
RRNIYRISIG SYPPSKKCVT CHLRKERCQY YTASFSDYAK YYALVCYGPG IPISTLHDGR   480
TDQEIKILEE NKELENALKN IQLPKEEIKK LEVDEITLWY KMILPPQFDR SKKYPLLIQV   540
YGGPCSQSVR SVFAVNWISY LASKEGMVIA LVDGRGTAFQ GDKLLYAVYR KLGVYEVEDQ   600
ITAVRKFIEM GFIDEKRIAI WGWSYGGYVS SLALASGTGL FKCGIAVAPV SSWEYYASVY   660
TERFMGLPTK DDNLEHYKNS TVMARAEYFR NVDYLLIHGT ADDNVHFQNS AQIAKALVNA   720
QVDFQAMWYS DQNHGLSGLS TNHLYTHMTH FLKQCFSLSD                         760
```

Amino acid sequence for residues 27-760 of FAPα with a

C-terminal 6x-histidine tag and a N-terminal signal sequence [SEQ. ID No. 3]

(6x-histidine C-terminal tag and signal sequence are underlined)

```
ADPGRPSRVH NSEENTMRAL TLKDILNGTF SYKTFFPNWI SGQEYLHQSA DNNIVLYNIE    60
TGQSYTILSN RTMKSVNASN YGLSPDRQFV YLESDYSKLW RYSYTATYYI YDLSNGEFVR   120
GNELPRPIQY LCWSPVGSKL AYVYQNNIYL KQRPGDPPFQ ITFNGRENKI FNGIPDWVYE   180
EEMLATKYAL WWSPNGKFLA YAEFNDTDIP VIAYSYYGDE QYPRTINIPY PKAGAKNPVV   240
RIFIIDTTYP AYVGPQEVPV PAMIASSDYY FSWLTWVTDE RVCLQWLKRV QNVSVLSICD   300
FREDWQTWDC PKTQEHIEES RTGWAGGFFV STPVFSYDAI SYYKIFSDKD GYKHIHYIKD   360
TVENAIQITS GKWEAINIFR VTQDSLFYSS NEFEEYPGRR NIYRISIGSY PPSKKCVTCH   420
LRKERCQYYT ASFSDYAKYY ALVCYGPGIP ISTLHDGRTD QEIKILEENK ELENALKNIQ   480
LPKEEIKKLE VDEITLWYKM ILPPQFDRSK KYPLLIQVYG GPCSQSVRSV FAVNWISYLA   540
SKEGMVIALV DGRGTAFQGD KLLYAVYRKL GVYEVEDQIT AVRKFIEMGF IDEKRIAIWG   600
WSYGGYVSSL ALASGTGLFK CGIAVAPVSS WEYYASVYTE RFMGLPTKDD NLEHYKNSTV   660
MARAEYFRNV DYLLIHGTAD DNVHFQNSAQ IAKALVNAQV DFQAMWYSDQ NHGLSGLSTN   720
HLYTHMTHFL KQCFSLSDHH HHHH                                          744
```

FIGURE 1 (Cont.)

Human cDNA sequence encoding residues 27-760 of FAPα [SEQ: ID No. 2]

```
CGCCCTTCAA GAGTTCATAA CTCTGAAGAA AATACAATGA GAGCACTCAC ACTGAAGGAT    60
ATTTTAAATG GAACATTTTC TTATAAAACA TTTTTTCCAA ACTGGATTTC AGGACAAGAA   120
TATCTTCATC AATCTGCAGA TAACAATATA GTACTTTATA ATATTGAAAC AGGACAATCA   180
TATACCATTT TGAGTAATAG AACCATGAAA AGTGTGAATG CTTCAAATTA CGGCTTATCA   240
CCTGATCGGC AATTTGTATA TCTAGAAAGT GATTATTCAA AGCTTTGGAG ATACTCTTAC   300
ACAGCAACAT ATTACATCTA TGACCTTAGC AATGGAGAAT TTGTAAGAGG AAATGAGCTT   360
CCTCGTCCAA TTCAGTATTT ATGCTGGTCG CCTGTTGGGA GTAAATTAGC ATATGTCTAT   420
CAAAACAATA TCTATTTGAA ACAAAGACCA GGAGATCCAC CTTTTCAAAT AACATTTAAT   480
GGAAGAGAAA ATAAAATATT TAATGGAATC CCAGACTGGG TTTATGAAGA GGAAATGCTT   540
GCTACAAAAT ATGCTCTCTG GTGGTCTCCT AATGGAAAAT TTTTGGCATA TGCGGAATTT   600
AATGATACGG ATATACCAGT TATTGCCTAT TCCTATTATG GCGATGAACA ATATCCTAGA   660
ACAATAAATA TTCCATACCC AAAGGCTGGA GCTAAGAATC CCGTTGTTCG ATATTTATT    720
ATCGATACCA CTTACCCTGC GTATGTAGGT CCCCAGGAAG TGCCTGTTCC AGCAATGATA   780
GCCTCAAGTG ATTATTATTT CAGTTGGCTC ACGTGGGTTA CTGATGAACG AGTATGTTTG   840
CAGTGGCTAA AAAGAGTCCA GAATGTTTCG GTCCTGTCTA TATGTGACTT CAGGGAAGAC   900
TGGCAGACAT GGGATTGTCC AAAGACCCAG GAGCATATAG AAGAAAGCAG AACTGGATGG   960
GCTGGTGGAT TCTTTGTTTC AACACCAGTT TTCAGCTATG ATGCCATTTC GTACTACAAA  1020
ATATTTAGTG ACAAGGATGG CTACAAACAT ATTCACTATA TCAAAGACAC TGTGGAAAAT  1080
GCTATTCAAA TTACAAGTGG CAAGTGGGAG GCCATAAATA TATTCAGAGT AACACAGGAT  1140
TCACTGTTTT ATTCTAGCAA TGAATTTGAA GAATACCCTG GAAGAAGAAA CATCTACAGA  1200
ATTAGCATTG GAAGCTATCC TCCAAGCAAG AAGTGTGTTA CTTGCCATCT AAGGAAAGAA  1260
AGGTGCCAAT ATTACACAGC AAGTTTCAGC GACTACGCCA AGTACTATGC ACTTGTCTGC  1320
TACGGCCCAG GCATCCCCAT TTCCACCCTT CATGATGGAC GCACTGATCA AGAAATTAAA  1380
ATCCTGGAAG AAAACAAGGA ATTGGAAAAT GCTTTGAAAA ATATCCAGCT GCCTAAAGAG  1440
GAAATTAAGA AACTTGAAGT AGATGAAATT ACTTTATGGT ACAAGATGAT TCTTCCTCCT  1500
CAATTTGACA GATCAAAGAA GTATCCCTTG CTAATTCAAG TGTATGGTGG TCCCTGCAGT  1560
CAGAGTGTAA GGTCTGTATT TGCTGTTAAT TGGATATCTT ATCTTGCAAG TAAGGAAGGG  1620
ATGGTCATTG CCTTGGTGGA TGGTCGAGGA ACAGCTTTCC AAGGTGACAA ACTCCTCTAT  1680
GCAGTGTATC GAAAGCTGGG TGTTTATGAA GTTGAAGACC AGATTACAGC TGTCAGAAAA  1740
TTCATAGAAA TGGGTTTCAT TGATGAAAAA AGAATAGCCA TATGGGGCTG GTCCTATGGA  1800
GGATACGTTT CATCACTGGC CCTTGCATCT GGAACTGGTC TTTTCAAATG TGGTATAGCA  1860
GTGGCTCCAG TCTCCAGCTG GGAATATTAC GCGTCTGTCT ACACAGAGAG ATTCATGGGT  1920
CTCCCAACAA AGGATGATAA TCTTGAGCAC TATAAGAATT CAACTGTGAT GGCAAGAGCA  1980
GAATATTTCA GAAATGTAGA CTATCTTCTC ATCCACGGAA CAGCAGATGA TAATGTGCAC  2040
TTTCAAAACT CAGCACAGAT TGCTAAAGCT CTGGTTAATG CACAAGTGGA TTTCCAGGCA  2100
ATGTGGTACT CTGACCAGAA CCACGGCTTA TCCGGCCTGT CCACGAACCA CTTATACACC  2160
CACATGACCC ACTTCCTAAA GCAGTGTTTC TCTTTGTCAG AC                     2202
```

FIGURE 3

LEGEND

Column headings from left to right are (A)'Atom Number', (B)'Atom Type', (C)'Amino Acid', (D)'Chain Identifier', (E)'Amino Acid Number' (SEQ. ID No. 1), (F)'X Coordinate', (G)'Y Coordinate', (H)'Z Coordinate', (I)'Occupancy' (OCC) and (J)'B factor'.

| A | B | C | D | E | F | G | H | I | J |
|---|---|---|---|---|---|---|---|---|---|
| 1 | N | MET | A | 39 | 5.996 | -20.235 | 69.783 | 1.00 | 18.72 |
| 2 | CA | MET | A | 39 | 7.324 | -20.790 | 69.338 | 1.00 | 19.11 |
| 3 | CB | MET | A | 39 | 7.346 | -22.312 | 69.513 | 1.00 | 20.53 |
| 4 | CG | MET | A | 39 | 8.358 | -22.796 | 70.590 | 1.00 | 24.21 |
| 5 | SD | MET | A | 39 | 9.670 | -21.516 | 71.105 | 1.00 | 32.68 |
| 6 | CE | MET | A | 39 | 10.431 | -22.591 | 72.605 | 1.00 | 28.08 |
| 7 | C | MET | A | 39 | 7.711 | -20.442 | 67.883 | 1.00 | 18.40 |
| 8 | O | MET | A | 39 | 6.962 | -20.696 | 66.950 | 1.00 | 18.52 |
| 9 | N | ARG | A | 40 | 8.884 | -19.871 | 67.661 | 1.00 | 16.98 |
| 10 | CA | ARG | A | 40 | 9.131 | -19.326 | 66.323 | 1.00 | 15.95 |
| 11 | CB | ARG | A | 40 | 8.357 | -18.006 | 66.139 | 1.00 | 15.89 |
| 12 | CG | ARG | A | 40 | 9.195 | -16.728 | 65.961 | 1.00 | 12.97 |
| 13 | CD | ARG | A | 40 | 8.391 | -15.625 | 65.382 | 1.00 | 10.58 |
| 14 | NE | ARG | A | 40 | 8.571 | -14.408 | 66.124 | 1.00 | 8.31 |
| 15 | CZ | ARG | A | 40 | 9.339 | -13.389 | 65.717 | 1.00 | 9.61 |
| 16 | NH1 | ARG | A | 40 | 10.025 | -13.429 | 64.565 | 1.00 | 8.91 |
| 17 | NH2 | ARG | A | 40 | 9.413 | -12.317 | 66.478 | 1.00 | 7.17 |
| 18 | C | ARG | A | 40 | 10.576 | -19.104 | 65.952 | 1.00 | 15.09 |
| 19 | O | ARG | A | 40 | 11.399 | -18.790 | 66.791 | 1.00 | 14.36 |
| 20 | N | ALA | A | 41 | 10.836 | -19.219 | 64.656 | 1.00 | 14.38 |
| 21 | CA | ALA | A | 41 | 12.120 | -18.829 | 64.080 | 1.00 | 14.10 |
| 22 | CB | ALA | A | 41 | 12.368 | -19.592 | 62.710 | 1.00 | 14.32 |
| 23 | C | ALA | A | 41 | 12.330 | -17.265 | 63.949 | 1.00 | 13.47 |
| 24 | O | ALA | A | 41 | 11.382 | -16.437 | 63.808 | 1.00 | 12.80 |
| 25 | N | LEU | A | 42 | 13.606 | -16.902 | 64.046 | 1.00 | 12.98 |
| 26 | CA | LEU | A | 42 | 14.034 | -15.508 | 63.901 | 1.00 | 12.60 |
| 27 | CB | LEU | A | 42 | 15.515 | -15.320 | 64.228 | 1.00 | 12.38 |
| 28 | CG | LEU | A | 42 | 16.113 | -15.110 | 65.616 | 1.00 | 10.25 |
| 29 | CD1 | LEU | A | 42 | 17.663 | -15.173 | 65.390 | 1.00 | 3.66 |
| 30 | CD2 | LEU | A | 42 | 15.762 | -13.787 | 66.312 | 1.00 | 5.75 |
| 31 | C | LEU | A | 42 | 13.791 | -15.029 | 62.476 | 1.00 | 12.73 |
| 32 | O | LEU | A | 42 | 13.827 | -15.769 | 61.502 | 1.00 | 11.78 |
| 33 | N | THR | A | 43 | 13.609 | -13.735 | 62.390 | 1.00 | 13.33 |
| 34 | CA | THR | A | 43 | 13.086 | -13.041 | 61.211 | 1.00 | 13.59 |
| 35 | CB | THR | A | 43 | 11.783 | -12.404 | 61.712 | 1.00 | 14.28 |
| 36 | OG1 | THR | A | 43 | 10.694 | -13.134 | 61.178 | 1.00 | 15.37 |
| 37 | CG2 | THR | A | 43 | 11.531 | -10.976 | 61.322 | 1.00 | 11.61 |
| 38 | C | THR | A | 43 | 14.124 | -12.063 | 60.852 | 1.00 | 14.41 |
| 39 | O | THR | A | 43 | 14.790 | -11.603 | 61.742 | 1.00 | 15.57 |
| 40 | N | LEU | A | 44 | 14.371 | -11.760 | 59.576 | 1.00 | 15.51 |
| 41 | CA | LEU | A | 44 | 15.348 | -10.660 | 59.246 | 1.00 | 15.05 |
| 42 | CB | LEU | A | 44 | 15.599 | -10.568 | 57.755 | 1.00 | 14.85 |

FIGURE 3 (Cont.)

| A | B | C | D | E | F | G | H | I | J |
|---|---|---|---|---|---|---|---|---|---|
| 43 | CG | LEU | A | 44 | 16.765 | -9.733 | 57.155 | 1.00 | 16.98 |
| 44 | CD1 | LEU | A | 44 | 16.536 | -8.203 | 57.295 | 1.00 | 19.26 |
| 45 | CD2 | LEU | A | 44 | 18.188 | -10.106 | 57.657 | 1.00 | 14.48 |
| 46 | C | LEU | A | 44 | 14.865 | -9.316 | 59.801 | 1.00 | 15.15 |
| 47 | O | LEU | A | 44 | 15.647 | -8.525 | 60.240 | 1.00 | 15.85 |
| 48 | N | LYS | A | 45 | 13.569 | -9.080 | 59.830 | 1.00 | 16.01 |
| 49 | CA | LYS | A | 45 | 13.000 | -7.786 | 60.296 | 1.00 | 17.60 |
| 50 | CB | LYS | A | 45 | 11.511 | -7.634 | 59.839 | 1.00 | 17.78 |
| 51 | CG | LYS | A | 45 | 11.241 | -8.169 | 58.306 | 1.00 | 22.65 |
| 52 | CD | LYS | A | 45 | 10.926 | -9.808 | 58.154 | 1.00 | 27.02 |
| 53 | CE | LYS | A | 45 | 12.047 | -10.704 | 57.361 | 1.00 | 27.25 |
| 54 | NZ | LYS | A | 45 | 12.270 | -12.324 | 57.621 | 1.00 | 26.30 |
| 55 | C | LYS | A | 45 | 13.228 | -7.684 | 61.834 | 1.00 | 17.36 |
| 56 | O | LYS | A | 45 | 13.500 | -6.594 | 62.393 | 1.00 | 17.04 |
| 57 | N | ASP | A | 46 | 13.285 | -8.859 | 62.457 | 1.00 | 15.66 |
| 58 | CA | ASP | A | 46 | 13.723 | -8.969 | 63.826 | 1.00 | 15.42 |
| 59 | CB | ASP | A | 46 | 13.814 | -10.429 | 64.299 | 1.00 | 14.04 |
| 60 | CG | ASP | A | 46 | 12.462 | -11.073 | 64.572 | 1.00 | 17.02 |
| 61 | OD1 | ASP | A | 46 | 11.405 | -10.350 | 64.568 | 1.00 | 13.30 |
| 62 | OD2 | ASP | A | 46 | 12.392 | -12.344 | 64.792 | 1.00 | 16.49 |
| 63 | C | ASP | A | 46 | 15.075 | -8.333 | 64.062 | 1.00 | 14.62 |
| 64 | O | ASP | A | 46 | 15.207 | -7.574 | 65.013 | 1.00 | 15.32 |
| 65 | N | ILE | A | 47 | 16.066 | -8.722 | 63.260 | 1.00 | 14.42 |
| 66 | CA | ILE | A | 47 | 17.463 | -8.293 | 63.457 | 1.00 | 14.69 |
| 67 | CB | ILE | A | 47 | 18.497 | -8.955 | 62.519 | 1.00 | 14.52 |
| 68 | CG1 | ILE | A | 47 | 19.072 | -10.305 | 63.008 | 1.00 | 13.75 |
| 69 | CD1 | ILE | A | 47 | 18.159 | -11.185 | 63.829 | 1.00 | 11.25 |
| 70 | CG2 | ILE | A | 47 | 19.743 | -8.002 | 62.393 | 1.00 | 13.86 |
| 71 | C | ILE | A | 47 | 17.614 | -6.834 | 63.178 | 1.00 | 15.62 |
| 72 | O | ILE | A | 47 | 18.456 | -6.188 | 63.780 | 1.00 | 15.77 |
| 73 | N | LEU | A | 48 | 16.823 | -6.348 | 62.219 | 1.00 | 16.62 |
| 74 | CA | LEU | A | 48 | 16.849 | -4.953 | 61.793 | 1.00 | 17.97 |
| 75 | CB | LEU | A | 48 | 16.372 | -4.903 | 60.333 | 1.00 | 18.29 |
| 76 | CG | LEU | A | 48 | 17.355 | -5.333 | 59.270 | 1.00 | 18.92 |
| 77 | CD1 | LEU | A | 48 | 16.676 | -5.369 | 57.928 | 1.00 | 19.37 |
| 78 | CD2 | LEU | A | 48 | 18.541 | -4.366 | 59.295 | 1.00 | 15.65 |
| 79 | C | LEU | A | 48 | 15.930 | -4.013 | 62.561 | 1.00 | 18.54 |
| 80 | O | LEU | A | 48 | 15.990 | -2.805 | 62.333 | 1.00 | 19.45 |
| 81 | N | ASN | A | 49 | 15.000 | -4.534 | 63.373 | 1.00 | 20.15 |
| 82 | CA | ASN | A | 49 | 14.146 | -3.605 | 64.195 | 1.00 | 21.20 |
| 83 | CB | ASN | A | 49 | 12.785 | -4.135 | 64.705 | 1.00 | 20.43 |
| 84 | CG | ASN | A | 49 | 12.037 | -3.088 | 65.641 | 1.00 | 22.53 |
| 85 | OD1 | ASN | A | 49 | 11.804 | -1.960 | 65.197 | 1.00 | 19.77 |
| 86 | ND2 | ASN | A | 49 | 11.678 | -3.470 | 66.923 | 1.00 | 30.07 |
| 87 | C | ASN | A | 49 | 14.931 | -3.198 | 65.417 | 1.00 | 21.33 |
| 88 | O | ASN | A | 49 | 14.663 | -2.145 | 66.007 | 1.00 | 23.07 |
| 89 | N | GLY | A | 50 | 15.885 | -4.020 | 65.815 | 1.00 | 20.02 |
| 90 | CA | GLY | A | 50 | 16.498 | -3.815 | 67.101 | 1.00 | 19.31 |
| 91 | C | GLY | A | 50 | 15.747 | -4.590 | 68.144 | 1.00 | 17.27 |
| 92 | O | GLY | A | 50 | 16.054 | -4.438 | 69.281 | 1.00 | 18.84 |
| 93 | N | THR | A | 51 | 14.875 | -5.505 | 67.735 | 1.00 | 15.74 |

FIGURE 3 (Cont.)

| A | B | C | D | E | F | G | H | I | J |
|---|---|---|---|---|---|---|---|---|---|
| 94 | CA | THR | A | 51 | 13.996 | -6.248 | 68.644 | 1.00 | 14.31 |
| 95 | CB | THR | A | 51 | 13.109 | -7.210 | 67.780 | 1.00 | 14.30 |
| 96 | OG1 | THR | A | 51 | 12.302 | -6.469 | 66.844 | 1.00 | 15.09 |
| 97 | CG2 | THR | A | 51 | 12.069 | -7.897 | 68.652 | 1.00 | 14.72 |
| 98 | C | THR | A | 51 | 14.681 | -7.031 | 69.829 | 1.00 | 12.68 |
| 99 | O | THR | A | 51 | 14.119 | -7.116 | 70.920 | 1.00 | 11.50 |
| 100 | N | PHE | A | 52 | 15.876 | -7.581 | 69.588 | 1.00 | 12.04 |
| 101 | CA | PHE | A | 52 | 16.603 | -8.489 | 70.545 | 1.00 | 11.64 |
| 102 | CB | PHE | A | 52 | 16.654 | -9.955 | 70.080 | 1.00 | 11.15 |
| 103 | CG | PHE | A | 52 | 15.308 | -10.485 | 69.668 | 1.00 | 12.45 |
| 104 | CD1 | PHE | A | 52 | 14.995 | -10.697 | 68.317 | 1.00 | 15.96 |
| 105 | CE1 | PHE | A | 52 | 13.681 | -11.194 | 67.947 | 1.00 | 16.74 |
| 106 | CZ | PHE | A | 52 | 12.716 | -11.409 | 68.924 | 1.00 | 14.74 |
| 107 | CE2 | PHE | A | 52 | 13.024 | -11.173 | 70.242 | 1.00 | 11.99 |
| 108 | CD2 | PHE | A | 52 | 14.304 | -10.705 | 70.611 | 1.00 | 11.32 |
| 109 | C | PHE | A | 52 | 17.990 | -7.941 | 70.817 | 1.00 | 11.42 |
| 110 | O | PHE | A | 52 | 19.005 | -8.630 | 70.807 | 1.00 | 11.89 |
| 111 | N | SER | A | 53 | 17.993 | -6.649 | 71.057 | 1.00 | 11.22 |
| 112 | CA | SER | A | 53 | 19.156 | -6.013 | 71.563 | 1.00 | 10.82 |
| 113 | CB | SER | A | 53 | 19.324 | -4.626 | 70.948 | 1.00 | 9.12 |
| 114 | OG | SER | A | 53 | 18.402 | -3.717 | 71.518 | 1.00 | 12.04 |
| 115 | C | SER | A | 53 | 18.938 | -5.901 | 73.030 | 1.00 | 9.91 |
| 116 | O | SER | A | 53 | 17.819 | -6.139 | 73.568 | 1.00 | 11.56 |
| 117 | N | TYR | A | 54 | 20.018 | -5.422 | 73.629 | 1.00 | 9.85 |
| 118 | CA | TYR | A | 54 | 20.271 | -5.483 | 75.029 | 1.00 | 9.01 |
| 119 | CB | TYR | A | 54 | 21.205 | -6.624 | 75.318 | 1.00 | 8.61 |
| 120 | CG | TYR | A | 54 | 22.611 | -6.556 | 74.799 | 1.00 | 9.19 |
| 121 | CD1 | TYR | A | 54 | 23.026 | -7.360 | 73.746 | 1.00 | 12.75 |
| 122 | CE1 | TYR | A | 54 | 24.384 | -7.353 | 73.313 | 1.00 | 13.40 |
| 123 | CZ | TYR | A | 54 | 25.298 | -6.536 | 73.945 | 1.00 | 12.20 |
| 124 | OH | TYR | A | 54 | 26.581 | -6.488 | 73.554 | 1.00 | 10.82 |
| 125 | CE2 | TYR | A | 54 | 24.920 | -5.754 | 74.978 | 1.00 | 13.01 |
| 126 | CD2 | TYR | A | 54 | 23.551 | -5.766 | 75.397 | 1.00 | 14.53 |
| 127 | C | TYR | A | 54 | 20.911 | -4.258 | 75.525 | 1.00 | 9.27 |
| 128 | O | TYR | A | 54 | 21.561 | -3.551 | 74.779 | 1.00 | 8.44 |
| 129 | N | LYS | A | 55 | 20.720 | -4.041 | 76.821 | 1.00 | 10.40 |
| 130 | CA | LYS | A | 55 | 20.974 | -2.770 | 77.458 | 1.00 | 11.62 |
| 131 | CB | LYS | A | 55 | 19.750 | -2.284 | 78.281 | 1.00 | 11.72 |
| 132 | CG | LYS | A | 55 | 18.645 | -1.501 | 77.484 | 1.00 | 10.17 |
| 133 | CD | LYS | A | 55 | 17.297 | -1.188 | 78.224 | 1.00 | 11.24 |
| 134 | CE | LYS | A | 55 | 15.998 | -1.598 | 77.356 | 1.00 | 15.81 |
| 135 | NZ | LYS | A | 55 | 14.771 | -0.650 | 77.106 | 1.00 | 14.91 |
| 136 | C | LYS | A | 55 | 22.210 | -3.004 | 78.297 | 1.00 | 12.86 |
| 137 | O | LYS | A | 55 | 22.493 | -4.139 | 78.634 | 1.00 | 13.09 |
| 138 | N | THR | A | 56 | 22.948 | -1.943 | 78.599 | 1.00 | 13.45 |
| 139 | CA | THR | A | 56 | 24.189 | -2.050 | 79.314 | 1.00 | 14.77 |
| 140 | CB | THR | A | 56 | 25.334 | -1.785 | 78.343 | 1.00 | 15.88 |
| 141 | OG1 | THR | A | 56 | 26.333 | -2.807 | 78.470 | 1.00 | 16.48 |
| 142 | CG2 | THR | A | 56 | 26.059 | -0.380 | 78.595 | 1.00 | 15.73 |
| 143 | C | THR | A | 56 | 24.142 | -0.985 | 80.336 | 1.00 | 15.69 |
| 144 | O | THR | A | 56 | 23.364 | -0.062 | 80.179 | 1.00 | 16.61 |

FIGURE 3 (Cont.)

| A | B | C | D | E | F | G | H | I | J |
|---|---|---|---|---|---|---|---|---|---|
| 145 | N | PHE | A | 57 | 24.948 | -1.083 | 81.390 | 1.00 | 15.93 |
| 146 | CA | PHE | A | 57 | 24.946 | -0.039 | 82.404 | 1.00 | 16.55 |
| 147 | CB | PHE | A | 57 | 24.073 | -0.419 | 83.581 | 1.00 | 16.39 |
| 148 | CG | PHE | A | 57 | 23.646 | 0.762 | 84.368 | 1.00 | 17.84 |
| 149 | CD1 | PHE | A | 57 | 22.336 | 1.216 | 84.291 | 1.00 | 15.89 |
| 150 | CE1 | PHE | A | 57 | 21.950 | 2.338 | 85.033 | 1.00 | 17.15 |
| 151 | CZ | PHE | A | 57 | 22.903 | 3.019 | 85.824 | 1.00 | 17.56 |
| 152 | CE2 | PHE | A | 57 | 24.238 | 2.590 | 85.872 | 1.00 | 16.66 |
| 153 | CD2 | PHE | A | 57 | 24.599 | 1.487 | 85.143 | 1.00 | 17.63 |
| 154 | C | PHE | A | 57 | 26.323 | 0.394 | 82.909 | 1.00 | 17.33 |
| 155 | O | PHE | A | 57 | 26.897 | -0.265 | 83.809 | 1.00 | 17.28 |
| 156 | N | PHE | A | 58 | 26.837 | 1.511 | 82.352 | 1.00 | 17.62 |
| 157 | CA | PHE | A | 58 | 28.131 | 2.054 | 82.776 | 1.00 | 17.62 |
| 158 | CB | PHE | A | 58 | 28.966 | 2.435 | 81.565 | 1.00 | 18.16 |
| 159 | CG | PHE | A | 58 | 29.630 | 1.257 | 80.936 | 1.00 | 20.34 |
| 160 | CD1 | PHE | A | 58 | 30.973 | 0.991 | 81.150 | 1.00 | 21.80 |
| 161 | CE1 | PHE | A | 58 | 31.581 | -0.119 | 80.561 | 1.00 | 22.82 |
| 162 | CZ | PHE | A | 58 | 30.803 | -0.982 | 79.762 | 1.00 | 23.50 |
| 163 | CE2 | PHE | A | 58 | 29.454 | -0.714 | 79.563 | 1.00 | 21.00 |
| 164 | CD2 | PHE | A | 58 | 28.888 | 0.394 | 80.159 | 1.00 | 19.20 |
| 165 | C | PHE | A | 58 | 27.913 | 3.281 | 83.577 | 1.00 | 16.92 |
| 166 | O | PHE | A | 58 | 27.682 | 4.333 | 82.954 | 1.00 | 18.18 |
| 167 | N | PRO | A | 59 | 27.991 | 3.200 | 84.911 | 1.00 | 15.53 |
| 168 | CA | PRO | A | 59 | 27.721 | 4.383 | 85.768 | 1.00 | 14.83 |
| 169 | CB | PRO | A | 59 | 28.125 | 3.940 | 87.215 | 1.00 | 14.69 |
| 170 | CG | PRO | A | 59 | 28.472 | 2.514 | 87.153 | 1.00 | 15.46 |
| 171 | CD | PRO | A | 59 | 28.317 | 2.012 | 85.697 | 1.00 | 15.74 |
| 172 | C | PRO | A | 59 | 28.501 | 5.629 | 85.323 | 1.00 | 13.68 |
| 173 | O | PRO | A | 59 | 29.683 | 5.477 | 85.115 | 1.00 | 12.82 |
| 174 | N | ASN | A | 60 | 27.847 | 6.774 | 85.133 | 1.00 | 13.18 |
| 175 | CA | ASN | A | 60 | 28.571 | 8.011 | 84.786 | 1.00 | 13.19 |
| 176 | CB | ASN | A | 60 | 27.609 | 9.077 | 84.170 | 1.00 | 13.54 |
| 177 | CG | ASN | A | 60 | 28.337 | 10.369 | 83.666 | 1.00 | 15.33 |
| 178 | OD1 | ASN | A | 60 | 29.575 | 10.446 | 83.690 | 1.00 | 17.17 |
| 179 | ND2 | ASN | A | 60 | 27.553 | 11.392 | 83.243 | 1.00 | 10.26 |
| 180 | C | ASN | A | 60 | 29.242 | 8.541 | 86.055 | 1.00 | 12.64 |
| 181 | O | ASN | A | 60 | 28.732 | 9.461 | 86.685 | 1.00 | 12.85 |
| 182 | N | TRP | A | 61 | 30.399 | 7.977 | 86.422 | 1.00 | 11.55 |
| 183 | CA | TRP | A | 61 | 31.048 | 8.301 | 87.708 | 1.00 | 10.82 |
| 184 | CB | TRP | A | 61 | 32.389 | 7.580 | 87.845 | 1.00 | 10.12 |
| 185 | CG | TRP | A | 61 | 32.326 | 6.147 | 87.828 | 1.00 | 11.57 |
| 186 | CD1 | TRP | A | 61 | 32.857 | 5.313 | 86.890 | 1.00 | 13.87 |
| 187 | NE1 | TRP | A | 61 | 32.601 | 4.010 | 87.224 | 1.00 | 13.21 |
| 188 | CE2 | TRP | A | 61 | 31.905 | 3.983 | 88.388 | 1.00 | 10.56 |
| 189 | CD2 | TRP | A | 61 | 31.717 | 5.307 | 88.797 | 1.00 | 11.82 |
| 190 | CE3 | TRP | A | 61 | 31.041 | 5.542 | 89.995 | 1.00 | 12.82 |
| 191 | CZ3 | TRP | A | 61 | 30.572 | 4.480 | 90.681 | 1.00 | 9.33 |
| 192 | CH2 | TRP | A | 61 | 30.783 | 3.192 | 90.235 | 1.00 | 10.60 |
| 193 | CZ2 | TRP | A | 61 | 31.458 | 2.931 | 89.092 | 1.00 | 13.27 |
| 194 | C | TRP | A | 61 | 31.323 | 9.834 | 87.885 | 1.00 | 10.54 |
| 195 | O | TRP | A | 61 | 31.470 | 10.608 | 86.921 | 1.00 | 11.34 |

FIGURE 3 (Cont.)

| A | B | C | D | E | F | G | H | I | J |
|---|---|---|---|---|---|---|---|---|---|
| 196 | N | ILE | A | 62 | 31.393 | 10.252 | 89.131 | 1.00 | 9.39 |
| 197 | CA | ILE | A | 62 | 31.720 | 11.607 | 89.428 | 1.00 | 9.06 |
| 198 | CB | ILE | A | 62 | 30.395 | 12.487 | 89.455 | 1.00 | 9.36 |
| 199 | CG1 | ILE | A | 62 | 29.432 | 12.124 | 90.605 | 1.00 | 7.29 |
| 200 | CD1 | ILE | A | 62 | 28.562 | 13.338 | 90.961 | 1.00 | 5.84 |
| 201 | CG2 | ILE | A | 62 | 29.660 | 12.481 | 88.103 | 1.00 | 6.47 |
| 202 | C | ILE | A | 62 | 32.503 | 11.727 | 90.731 | 1.00 | 9.87 |
| 203 | O | ILE | A | 62 | 32.757 | 12.824 | 91.206 | 1.00 | 10.88 |
| 204 | N | SER | A | 63 | 32.883 | 10.604 | 91.316 | 1.00 | 9.24 |
| 205 | CA | SER | A | 63 | 33.346 | 10.590 | 92.693 | 1.00 | 9.36 |
| 206 | CB | SER | A | 63 | 32.292 | 11.212 | 93.634 | 1.00 | 9.16 |
| 207 | OG | SER | A | 63 | 31.861 | 10.376 | 94.711 | 1.00 | 9.23 |
| 208 | C | SER | A | 63 | 33.683 | 9.134 | 92.998 | 1.00 | 9.93 |
| 209 | O | SER | A | 63 | 33.630 | 8.276 | 92.099 | 1.00 | 9.48 |
| 210 | N | GLY | A | 64 | 34.082 | 8.848 | 94.237 | 1.00 | 10.65 |
| 211 | CA | GLY | A | 64 | 34.439 | 7.496 | 94.599 | 1.00 | 11.15 |
| 212 | C | GLY | A | 64 | 33.243 | 6.572 | 94.712 | 1.00 | 11.77 |
| 213 | O | GLY | A | 64 | 33.377 | 5.314 | 94.545 | 1.00 | 12.75 |
| 214 | N | GLN | A | 65 | 32.090 | 7.210 | 94.936 | 1.00 | 11.89 |
| 215 | CA | GLN | A | 65 | 30.863 | 6.591 | 95.432 | 1.00 | 12.79 |
| 216 | CB | GLN | A | 65 | 30.871 | 6.725 | 96.989 | 1.00 | 13.12 |
| 217 | CG | GLN | A | 65 | 30.850 | 8.225 | 97.521 | 1.00 | 14.83 |
| 218 | CD | GLN | A | 65 | 32.243 | 8.767 | 97.953 | 1.00 | 16.43 |
| 219 | OE1 | GLN | A | 65 | 32.697 | 9.852 | 97.477 | 1.00 | 15.70 |
| 220 | NE2 | GLN | A | 65 | 32.916 | 8.009 | 98.845 | 1.00 | 14.44 |
| 221 | C | GLN | A | 65 | 29.555 | 7.184 | 94.862 | 1.00 | 12.40 |
| 222 | O | GLN | A | 65 | 28.478 | 6.670 | 95.126 | 1.00 | 11.85 |
| 223 | N | GLU | A | 66 | 29.657 | 8.280 | 94.116 | 1.00 | 12.78 |
| 224 | CA | GLU | A | 66 | 28.532 | 8.875 | 93.387 | 1.00 | 12.93 |
| 225 | CB | GLU | A | 66 | 28.474 | 10.353 | 93.709 | 1.00 | 12.49 |
| 226 | CG | GLU | A | 66 | 27.824 | 10.658 | 95.042 | 1.00 | 12.51 |
| 227 | CD | GLU | A | 66 | 28.404 | 11.874 | 95.710 | 1.00 | 12.33 |
| 228 | OE1 | GLU | A | 66 | 29.628 | 12.025 | 95.602 | 1.00 | 12.64 |
| 229 | OE2 | GLU | A | 66 | 27.645 | 12.646 | 96.353 | 1.00 | 12.79 |
| 230 | C | GLU | A | 66 | 28.657 | 8.717 | 91.867 | 1.00 | 14.11 |
| 231 | O | GLU | A | 66 | 29.772 | 8.744 | 91.359 | 1.00 | 14.76 |
| 232 | N | TYR | A | 67 | 27.512 | 8.517 | 91.167 | 1.00 | 15.04 |
| 233 | CA | TYR | A | 67 | 27.346 | 8.571 | 89.683 | 1.00 | 15.44 |
| 234 | CB | TYR | A | 67 | 27.515 | 7.172 | 89.066 | 1.00 | 15.00 |
| 235 | CG | TYR | A | 67 | 26.475 | 6.140 | 89.470 | 1.00 | 15.73 |
| 236 | CD1 | TYR | A | 67 | 25.225 | 6.089 | 88.842 | 1.00 | 16.82 |
| 237 | CE1 | TYR | A | 67 | 24.242 | 5.114 | 89.200 | 1.00 | 14.43 |
| 238 | CZ | TYR | A | 67 | 24.509 | 4.191 | 90.181 | 1.00 | 14.47 |
| 239 | OH | TYR | A | 67 | 23.522 | 3.242 | 90.534 | 1.00 | 12.72 |
| 240 | CE2 | TYR | A | 67 | 25.764 | 4.228 | 90.816 | 1.00 | 13.29 |
| 241 | CD2 | TYR | A | 67 | 26.734 | 5.193 | 90.457 | 1.00 | 14.13 |
| 242 | C | TYR | A | 67 | 25.997 | 9.159 | 89.217 | 1.00 | 15.99 |
| 243 | O | TYR | A | 67 | 25.002 | 9.097 | 89.908 | 1.00 | 16.12 |
| 244 | N | LEU | A | 68 | 25.971 | 9.711 | 88.018 | 1.00 | 17.23 |
| 245 | CA | LEU | A | 68 | 24.740 | 10.223 | 87.408 | 1.00 | 18.97 |
| 246 | CB | LEU | A | 68 | 24.914 | 11.630 | 86.857 | 1.00 | 18.44 |

FIGURE 3 (Cont.)

| A | B | C | D | E | F | G | H | I | J |
|---|---|---|---|---|---|---|---|---|---|
| 247 | CG | LEU | A | 68 | 25.495 | 12.644 | 87.827 | 1.00 | 18.39 |
| 248 | CD1 | LEU | A | 68 | 25.843 | 13.968 | 87.139 | 1.00 | 17.07 |
| 249 | CD2 | LEU | A | 68 | 24.533 | 12.894 | 88.937 | 1.00 | 18.71 |
| 250 | C | LEU | A | 68 | 24.261 | 9.341 | 86.257 | 1.00 | 20.37 |
| 251 | O | LEU | A | 68 | 25.041 | 8.890 | 85.398 | 1.00 | 20.91 |
| 252 | N | HIS | A | 69 | 22.956 | 9.090 | 86.253 | 1.00 | 22.04 |
| 253 | CA | HIS | A | 69 | 22.335 | 8.339 | 85.174 | 1.00 | 23.79 |
| 254 | CB | HIS | A | 69 | 22.457 | 6.778 | 85.317 | 1.00 | 24.32 |
| 255 | CG | HIS | A | 69 | 21.478 | 6.045 | 84.448 | 1.00 | 28.84 |
| 256 | ND1 | HIS | A | 69 | 21.536 | 6.092 | 83.061 | 1.00 | 32.10 |
| 257 | CE1 | HIS | A | 69 | 20.502 | 5.446 | 82.556 | 1.00 | 33.99 |
| 258 | NE2 | HIS | A | 69 | 19.779 | 4.977 | 83.567 | 1.00 | 34.77 |
| 259 | CD2 | HIS | A | 69 | 20.350 | 5.359 | 84.758 | 1.00 | 30.61 |
| 260 | C | HIS | A | 69 | 20.895 | 8.812 | 85.013 | 1.00 | 23.62 |
| 261 | O | HIS | A | 69 | 20.347 | 9.378 | 85.931 | 1.00 | 23.90 |
| 262 | N | GLN | A | 70 | 20.340 | 8.577 | 83.814 | 1.00 | 24.31 |
| 263 | CA | GLN | A | 70 | 19.129 | 9.210 | 83.263 | 1.00 | 24.62 |
| 264 | CB | GLN | A | 70 | 19.385 | 9.621 | 81.793 | 1.00 | 24.67 |
| 265 | CG | GLN | A | 70 | 18.642 | 10.891 | 81.321 | 1.00 | 24.32 |
| 266 | CD | GLN | A | 70 | 18.525 | 11.010 | 79.803 | 1.00 | 25.83 |
| 267 | OE1 | GLN | A | 70 | 19.451 | 11.472 | 79.134 | 1.00 | 26.88 |
| 268 | NE2 | GLN | A | 70 | 17.381 | 10.610 | 79.264 | 1.00 | 26.14 |
| 269 | C | GLN | A | 70 | 17.935 | 8.283 | 83.283 | 1.00 | 25.21 |
| 270 | O | GLN | A | 70 | 18.041 | 7.128 | 82.859 | 1.00 | 25.68 |
| 271 | N | SER | A | 71 | 16.786 | 8.795 | 83.714 | 1.00 | 25.33 |
| 272 | CA | SER | A | 71 | 15.586 | 7.977 | 83.764 | 1.00 | 25.53 |
| 273 | CB | SER | A | 71 | 14.616 | 8.532 | 84.817 | 1.00 | 25.68 |
| 274 | OG | SER | A | 71 | 14.653 | 9.965 | 84.916 | 1.00 | 25.72 |
| 275 | C | SER | A | 71 | 14.959 | 7.927 | 82.371 | 1.00 | 25.84 |
| 276 | O | SER | A | 71 | 15.424 | 8.619 | 81.467 | 1.00 | 25.27 |
| 277 | N | ALA | A | 72 | 13.915 | 7.093 | 82.206 | 1.00 | 26.61 |
| 278 | CA | ALA | A | 72 | 13.007 | 7.127 | 81.010 | 1.00 | 27.01 |
| 279 | CB | ALA | A | 72 | 12.646 | 5.675 | 80.518 | 1.00 | 27.13 |
| 280 | C | ALA | A | 72 | 11.718 | 7.976 | 81.254 | 1.00 | 27.14 |
| 281 | O | ALA | A | 72 | 10.603 | 7.660 | 80.771 | 1.00 | 27.08 |
| 282 | N | ASP | A | 73 | 11.988 | 8.991 | 82.231 | 1.00 | 27.21 |
| 283 | CA | ASP | A | 73 | 11.209 | 10.256 | 82.215 | 1.00 | 26.90 |
| 284 | CB | ASP | A | 73 | 10.346 | 10.367 | 83.495 | 1.00 | 27.37 |
| 285 | CG | ASP | A | 73 | 11.104 | 9.909 | 84.775 | 1.00 | 29.80 |
| 286 | OD1 | ASP | A | 73 | 11.355 | 8.675 | 84.978 | 1.00 | 31.78 |
| 287 | OD2 | ASP | A | 73 | 11.510 | 10.741 | 85.623 | 1.00 | 31.90 |
| 288 | C | ASP | A | 73 | 12.244 | 11.442 | 82.035 | 1.00 | 25.82 |
| 289 | O | ASP | A | 73 | 11.920 | 12.663 | 82.142 | 1.00 | 25.70 |
| 290 | N | ASN | A | 74 | 13.338 | 11.081 | 81.640 | 1.00 | 24.10 |
| 291 | CA | ASN | A | 74 | 14.463 | 11.928 | 81.225 | 1.00 | 22.99 |
| 292 | CB | ASN | A | 74 | 14.195 | 12.605 | 79.862 | 1.00 | 23.27 |
| 293 | CG | ASN | A | 74 | 13.935 | 11.599 | 78.757 | 1.00 | 23.78 |
| 294 | OD1 | ASN | A | 74 | 12.981 | 11.761 | 77.991 | 1.00 | 22.98 |
| 295 | ND2 | ASN | A | 74 | 14.779 | 10.542 | 78.670 | 1.00 | 24.57 |
| 296 | C | ASN | A | 74 | 14.979 | 12.930 | 82.243 | 1.00 | 22.14 |
| 297 | O | ASN | A | 74 | 15.091 | 14.134 | 81.959 | 1.00 | 22.81 |

FIGURE 3 (Cont.)

| A | B | C | D | E | F | G | H | I | J |
|---|---|---|---|---|---|---|---|---|---|
| 298 | N | ASN | A | 75 | 15.355 | 12.406 | 83.402 | 1.00 | 20.65 |
| 299 | CA | ASN | A | 75 | 15.893 | 13.220 | 84.473 | 1.00 | 18.67 |
| 300 | CB | ASN | A | 75 | 14.959 | 13.130 | 85.695 | 1.00 | 18.68 |
| 301 | CG | ASN | A | 75 | 14.044 | 14.363 | 85.813 | 1.00 | 19.45 |
| 302 | OD1 | ASN | A | 75 | 14.535 | 15.494 | 85.685 | 1.00 | 21.53 |
| 303 | ND2 | ASN | A | 75 | 12.729 | 14.163 | 86.029 | 1.00 | 17.11 |
| 304 | C | ASN | A | 75 | 17.324 | 12.811 | 84.766 | 1.00 | 17.19 |
| 305 | O | ASN | A | 75 | 17.648 | 11.651 | 84.676 | 1.00 | 16.62 |
| 306 | N | ILE | A | 76 | 18.199 | 13.770 | 85.045 | 1.00 | 16.09 |
| 307 | CA | ILE | A | 76 | 19.592 | 13.437 | 85.390 | 1.00 | 15.84 |
| 308 | CB | ILE | A | 76 | 20.633 | 14.457 | 84.788 | 1.00 | 16.02 |
| 309 | CG1 | ILE | A | 76 | 20.816 | 14.301 | 83.261 | 1.00 | 16.34 |
| 310 | CD1 | ILE | A | 76 | 19.618 | 14.732 | 82.374 | 1.00 | 16.89 |
| 311 | CG2 | ILE | A | 76 | 22.027 | 14.207 | 85.405 | 1.00 | 15.17 |
| 312 | C | ILE | A | 76 | 19.788 | 13.335 | 86.918 | 1.00 | 15.48 |
| 313 | O | ILE | A | 76 | 19.919 | 14.370 | 87.612 | 1.00 | 15.41 |
| 314 | N | VAL | A | 77 | 19.858 | 12.103 | 87.426 | 1.00 | 14.62 |
| 315 | CA | VAL | A | 77 | 19.832 | 11.851 | 88.867 | 1.00 | 14.32 |
| 316 | CB | VAL | A | 77 | 18.554 | 11.000 | 89.323 | 1.00 | 14.25 |
| 317 | CG1 | VAL | A | 77 | 18.814 | 10.182 | 90.590 | 1.00 | 14.77 |
| 318 | CG2 | VAL | A | 77 | 18.022 | 10.077 | 88.240 | 1.00 | 13.50 |
| 319 | C | VAL | A | 77 | 21.176 | 11.275 | 89.388 | 1.00 | 14.33 |
| 320 | O | VAL | A | 77 | 21.778 | 10.346 | 88.777 | 1.00 | 13.65 |
| 321 | N | LEU | A | 78 | 21.610 | 11.893 | 90.508 | 1.00 | 13.90 |
| 322 | CA | LEU | A | 78 | 22.829 | 11.578 | 91.262 | 1.00 | 13.45 |
| 323 | CB | LEU | A | 78 | 23.308 | 12.842 | 91.990 | 1.00 | 13.32 |
| 324 | CG | LEU | A | 78 | 24.655 | 12.932 | 92.728 | 1.00 | 14.74 |
| 325 | CD1 | LEU | A | 78 | 25.251 | 14.378 | 92.805 | 1.00 | 14.33 |
| 326 | CD2 | LEU | A | 78 | 24.537 | 12.357 | 94.170 | 1.00 | 16.01 |
| 327 | C | LEU | A | 78 | 22.478 | 10.503 | 92.252 | 1.00 | 13.05 |
| 328 | O | LEU | A | 78 | 21.584 | 10.688 | 93.046 | 1.00 | 12.82 |
| 329 | N | TYR | A | 79 | 23.122 | 9.347 | 92.143 | 1.00 | 12.79 |
| 330 | CA | TYR | A | 79 | 22.912 | 8.262 | 93.088 | 1.00 | 12.79 |
| 331 | CB | TYR | A | 79 | 22.486 | 6.887 | 92.455 | 1.00 | 13.37 |
| 332 | CG | TYR | A | 79 | 21.356 | 6.862 | 91.384 | 1.00 | 15.77 |
| 333 | CD1 | TYR | A | 79 | 19.996 | 6.715 | 91.736 | 1.00 | 17.71 |
| 334 | CE1 | TYR | A | 79 | 18.968 | 6.687 | 90.740 | 1.00 | 17.02 |
| 335 | CZ | TYR | A | 79 | 19.312 | 6.801 | 89.394 | 1.00 | 18.44 |
| 336 | OH | TYR | A | 79 | 18.365 | 6.776 | 88.378 | 1.00 | 19.37 |
| 337 | CE2 | TYR | A | 79 | 20.655 | 6.935 | 89.021 | 1.00 | 17.96 |
| 338 | CD2 | TYR | A | 79 | 21.666 | 6.939 | 90.001 | 1.00 | 17.47 |
| 339 | C | TYR | A | 79 | 24.259 | 8.133 | 93.771 | 1.00 | 12.29 |
| 340 | O | TYR | A | 79 | 25.297 | 8.183 | 93.135 | 1.00 | 10.21 |
| 341 | N | ASN | A | 80 | 24.215 | 7.986 | 95.094 | 1.00 | 12.78 |
| 342 | CA | ASN | A | 80 | 25.379 | 7.750 | 95.930 | 1.00 | 13.50 |
| 343 | CB | ASN | A | 80 | 25.420 | 8.835 | 97.021 | 1.00 | 13.43 |
| 344 | CG | ASN | A | 80 | 26.538 | 8.645 | 98.036 | 1.00 | 14.23 |
| 345 | OD1 | ASN | A | 80 | 27.027 | 7.549 | 98.231 | 1.00 | 13.93 |
| 346 | ND2 | ASN | A | 80 | 26.924 | 9.734 | 98.708 | 1.00 | 16.40 |
| 347 | C | ASN | A | 80 | 25.125 | 6.345 | 96.457 | 1.00 | 14.57 |
| 348 | O | ASN | A | 80 | 23.972 | 5.986 | 96.817 | 1.00 | 15.19 |

FIGURE 3 (Cont.)

| A | B | C | D | E | F | G | H | I | J |
|---|---|---|---|---|---|---|---|---|---|
| 349 | N | THR | A | 81 | 26.173 | 5.524 | 96.453 | 1.00 | 14.93 |
| 350 | CA | THR | A | 81 | 26.003 | 4.101 | 96.799 | 1.00 | 15.23 |
| 351 | CB | THR | A | 81 | 26.840 | 3.101 | 95.873 | 1.00 | 15.43 |
| 352 | OG1 | THR | A | 81 | 28.009 | 2.584 | 96.547 | 1.00 | 16.74 |
| 353 | CG2 | THR | A | 81 | 27.365 | 3.775 | 94.560 | 1.00 | 15.35 |
| 354 | C | THR | A | 81 | 26.232 | 3.912 | 98.293 | 1.00 | 14.71 |
| 355 | O | THR | A | 81 | 25.419 | 3.241 | 98.944 | 1.00 | 15.33 |
| 356 | N | GLU | A | 82 | 27.293 | 4.537 | 98.819 | 1.00 | 13.94 |
| 357 | CA | GLU | A | 82 | 27.545 | 4.751 | 100.280 | 1.00 | 13.54 |
| 358 | CB | GLU | A | 82 | 28.582 | 5.886 | 100.463 | 1.00 | 13.43 |
| 359 | CG | GLU | A | 82 | 29.322 | 5.940 | 101.803 | 1.00 | 16.22 |
| 360 | CD | GLU | A | 82 | 30.823 | 5.615 | 101.711 | 1.00 | 18.50 |
| 361 | OE1 | GLU | A | 82 | 31.444 | 5.751 | 100.620 | 1.00 | 18.49 |
| 362 | OE2 | GLU | A | 82 | 31.387 | 5.209 | 102.756 | 1.00 | 19.04 |
| 363 | C | GLU | A | 82 | 26.317 | 5.105 | 101.149 | 1.00 | 13.15 |
| 364 | O | GLU | A | 82 | 26.162 | 4.645 | 102.277 | 1.00 | 12.25 |
| 365 | N | THR | A | 83 | 25.454 | 5.933 | 100.577 | 1.00 | 12.83 |
| 366 | CA | THR | A | 83 | 24.427 | 6.660 | 101.293 | 1.00 | 12.03 |
| 367 | CB | THR | A | 83 | 24.895 | 8.156 | 101.145 | 1.00 | 11.57 |
| 368 | OG1 | THR | A | 83 | 25.093 | 8.702 | 102.433 | 1.00 | 13.35 |
| 369 | CG2 | THR | A | 83 | 23.924 | 9.131 | 100.443 | 1.00 | 11.74 |
| 370 | C | THR | A | 83 | 23.010 | 6.218 | 100.785 | 1.00 | 11.88 |
| 371 | O | THR | A | 83 | 21.971 | 6.439 | 101.415 | 1.00 | 10.56 |
| 372 | N | GLY | A | 84 | 23.007 | 5.501 | 99.655 | 1.00 | 12.41 |
| 373 | CA | GLY | A | 84 | 21.832 | 4.802 | 99.146 | 1.00 | 12.95 |
| 374 | C | GLY | A | 84 | 20.725 | 5.756 | 98.786 | 1.00 | 13.34 |
| 375 | O | GLY | A | 84 | 19.583 | 5.335 | 98.668 | 1.00 | 13.62 |
| 376 | N | GLN | A | 85 | 21.108 | 7.032 | 98.617 | 1.00 | 13.64 |
| 377 | CA | GLN | A | 85 | 20.222 | 8.179 | 98.387 | 1.00 | 13.55 |
| 378 | CB | GLN | A | 85 | 20.612 | 9.419 | 99.230 | 1.00 | 13.67 |
| 379 | CG | GLN | A | 85 | 20.151 | 9.519 | 100.699 | 1.00 | 12.71 |
| 380 | CD | GLN | A | 85 | 18.840 | 8.890 | 100.999 | 1.00 | 10.49 |
| 381 | OE1 | GLN | A | 85 | 18.758 | 7.665 | 101.074 | 1.00 | 7.86 |
| 382 | NE2 | GLN | A | 85 | 17.817 | 9.716 | 101.254 | 1.00 | 10.34 |
| 383 | C | GLN | A | 85 | 20.399 | 8.596 | 96.960 | 1.00 | 13.91 |
| 384 | O | GLN | A | 85 | 21.196 | 8.017 | 96.208 | 1.00 | 14.43 |
| 385 | N | SER | A | 86 | 19.618 | 9.614 | 96.609 | 1.00 | 14.07 |
| 386 | CA | SER | A | 86 | 19.557 | 10.202 | 95.280 | 1.00 | 13.78 |
| 387 | CB | SER | A | 86 | 18.835 | 9.290 | 94.261 | 1.00 | 13.75 |
| 388 | OG | SER | A | 86 | 19.102 | 7.908 | 94.481 | 1.00 | 14.63 |
| 389 | C | SER | A | 86 | 18.792 | 11.505 | 95.347 | 1.00 | 13.87 |
| 390 | O | SER | A | 86 | 17.909 | 11.652 | 96.191 | 1.00 | 14.26 |
| 391 | N | TYR | A | 87 | 19.166 | 12.444 | 94.472 | 1.00 | 13.71 |
| 392 | CA | TYR | A | 87 | 18.257 | 13.473 | 93.977 | 1.00 | 13.48 |
| 393 | CB | TYR | A | 87 | 18.462 | 14.813 | 94.711 | 1.00 | 13.38 |
| 394 | CG | TYR | A | 87 | 19.836 | 15.431 | 94.516 | 1.00 | 13.97 |
| 395 | CD1 | TYR | A | 87 | 20.008 | 16.560 | 93.710 | 1.00 | 13.86 |
| 396 | CE1 | TYR | A | 87 | 21.284 | 17.150 | 93.525 | 1.00 | 14.46 |
| 397 | CZ | TYR | A | 87 | 22.403 | 16.593 | 94.137 | 1.00 | 14.95 |
| 398 | OH | TYR | A | 87 | 23.650 | 17.159 | 93.943 | 1.00 | 14.77 |
| 399 | CE2 | TYR | A | 87 | 22.256 | 15.460 | 94.942 | 1.00 | 15.24 |

FIGURE 3 (Cont.)

| A | B | C | D | E | F | G | H | I | J |
|---|---|---|---|---|---|---|---|---|---|
| 400 | CD2 | TYR | A | 87 | 20.969 | 14.886 | 95.131 | 1.00 | 14.84 |
| 401 | C | TYR | A | 87 | 18.402 | 13.634 | 92.440 | 1.00 | 13.50 |
| 402 | O | TYR | A | 87 | 19.367 | 13.183 | 91.846 | 1.00 | 12.60 |
| 403 | N | THR | A | 88 | 17.388 | 14.240 | 91.825 | 1.00 | 14.12 |
| 404 | CA | THR | A | 88 | 17.439 | 14.842 | 90.476 | 1.00 | 14.18 |
| 405 | CB | THR | A | 88 | 15.957 | 15.310 | 90.022 | 1.00 | 14.15 |
| 406 | OG1 | THR | A | 88 | 14.960 | 14.290 | 90.226 | 1.00 | 12.95 |
| 407 | CG2 | THR | A | 88 | 15.898 | 15.542 | 88.555 | 1.00 | 13.55 |
| 408 | C | THR | A | 88 | 18.350 | 16.104 | 90.488 | 1.00 | 14.38 |
| 409 | O | THR | A | 88 | 18.011 | 17.081 | 91.154 | 1.00 | 14.61 |
| 410 | N | ILE | A | 89 | 19.482 | 16.114 | 89.783 | 1.00 | 14.78 |
| 411 | CA | ILE | A | 89 | 20.183 | 17.404 | 89.604 | 1.00 | 15.33 |
| 412 | CB | ILE | A | 89 | 21.652 | 17.327 | 89.167 | 1.00 | 15.69 |
| 413 | CG1 | ILE | A | 89 | 22.439 | 16.249 | 89.835 | 1.00 | 13.64 |
| 414 | CD1 | ILE | A | 89 | 23.919 | 16.540 | 89.677 | 1.00 | 13.30 |
| 415 | CG2 | ILE | A | 89 | 22.327 | 18.734 | 89.469 | 1.00 | 16.02 |
| 416 | C | ILE | A | 89 | 19.619 | 18.314 | 88.556 | 1.00 | 15.23 |
| 417 | O | ILE | A | 89 | 19.716 | 19.511 | 88.711 | 1.00 | 15.60 |
| 418 | N | LEU | A | 90 | 19.195 | 17.746 | 87.431 | 1.00 | 15.41 |
| 419 | CA | LEU | A | 90 | 18.829 | 18.533 | 86.229 | 1.00 | 15.67 |
| 420 | CB | LEU | A | 90 | 19.888 | 18.362 | 85.097 | 1.00 | 15.06 |
| 421 | CG | LEU | A | 90 | 20.796 | 19.541 | 84.642 | 1.00 | 12.97 |
| 422 | CD1 | LEU | A | 90 | 21.690 | 19.111 | 83.496 | 1.00 | 10.18 |
| 423 | CD2 | LEU | A | 90 | 20.013 | 20.735 | 84.222 | 1.00 | 9.17 |
| 424 | C | LEU | A | 90 | 17.429 | 18.122 | 85.755 | 1.00 | 16.27 |
| 425 | O | LEU | A | 90 | 17.137 | 16.936 | 85.531 | 1.00 | 16.12 |
| 426 | N | SER | A | 91 | 16.570 | 19.101 | 85.577 | 1.00 | 17.29 |
| 427 | CA | SER | A | 91 | 15.146 | 18.805 | 85.465 | 1.00 | 17.94 |
| 428 | CB | SER | A | 91 | 14.312 | 20.017 | 85.887 | 1.00 | 18.08 |
| 429 | OG | SER | A | 91 | 15.142 | 21.113 | 86.229 | 1.00 | 18.37 |
| 430 | C | SER | A | 91 | 14.841 | 18.045 | 84.179 | 1.00 | 18.46 |
| 431 | O | SER | A | 91 | 15.725 | 17.752 | 83.274 | 1.00 | 17.80 |
| 432 | N | ASN | A | 92 | 13.633 | 17.391 | 84.081 | 1.00 | 18.80 |
| 433 | CA | ASN | A | 92 | 13.209 | 16.645 | 82.884 | 1.00 | 18.76 |
| 434 | CB | ASN | A | 92 | 11.959 | 15.677 | 83.058 | 1.00 | 19.07 |
| 435 | CG | ASN | A | 92 | 10.713 | 16.301 | 83.767 | 1.00 | 20.75 |
| 436 | OD1 | ASN | A | 92 | 10.818 | 17.373 | 84.396 | 1.00 | 21.44 |
| 437 | ND2 | ASN | A | 92 | 9.567 | 15.661 | 83.659 | 1.00 | 29.44 |
| 438 | C | ASN | A | 92 | 13.072 | 17.708 | 81.833 | 1.00 | 18.24 |
| 439 | O | ASN | A | 92 | 13.427 | 17.500 | 80.672 | 1.00 | 17.99 |
| 440 | N | ARG | A | 93 | 12.678 | 18.886 | 82.329 | 1.00 | 17.90 |
| 441 | CA | ARG | A | 93 | 12.330 | 20.065 | 81.537 | 1.00 | 17.98 |
| 442 | CB | ARG | A | 93 | 11.086 | 20.780 | 82.170 | 1.00 | 18.46 |
| 443 | CG | ARG | A | 93 | 9.662 | 20.410 | 81.569 | 1.00 | 18.83 |
| 444 | CD | ARG | A | 93 | 9.451 | 18.918 | 81.215 | 1.00 | 19.16 |
| 445 | NE | ARG | A | 93 | 10.042 | 18.493 | 79.912 | 1.00 | 19.11 |
| 446 | CZ | ARG | A | 93 | 10.369 | 17.207 | 79.570 | 1.00 | 17.90 |
| 447 | NH1 | ARG | A | 93 | 10.179 | 16.187 | 80.408 | 1.00 | 18.19 |
| 448 | NH2 | ARG | A | 93 | 10.888 | 16.932 | 78.371 | 1.00 | 17.47 |
| 449 | C | ARG | A | 93 | 13.456 | 21.087 | 81.311 | 1.00 | 17.30 |
| 450 | O | ARG | A | 93 | 13.238 | 22.010 | 80.553 | 1.00 | 17.07 |

FIGURE 3 (Cont.)

| A | B | C | D | E | F | G | H | I | J |
|---|---|---|---|---|---|---|---|---|---|
| 451 | N | THR | A | 94 | 14.621 | 20.977 | 81.948 | 1.00 | 16.64 |
| 452 | CA | THR | A | 94 | 15.673 | 21.973 | 81.672 | 1.00 | 16.21 |
| 453 | CB | THR | A | 94 | 16.431 | 22.460 | 82.982 | 1.00 | 16.20 |
| 454 | OG1 | THR | A | 94 | 15.682 | 23.522 | 83.563 | 1.00 | 15.55 |
| 455 | CG2 | THR | A | 94 | 17.764 | 23.194 | 82.709 | 1.00 | 14.48 |
| 456 | C | THR | A | 94 | 16.580 | 21.436 | 80.540 | 1.00 | 16.45 |
| 457 | O | THR | A | 94 | 17.100 | 22.210 | 79.687 | 1.00 | 16.45 |
| 458 | N | MET | A | 95 | 16.745 | 20.112 | 80.501 | 1.00 | 15.70 |
| 459 | CA | MET | A | 95 | 17.289 | 19.483 | 79.305 | 1.00 | 15.42 |
| 460 | CB | MET | A | 95 | 17.330 | 17.951 | 79.404 | 1.00 | 14.82 |
| 461 | CG | MET | A | 95 | 18.372 | 17.444 | 80.352 | 1.00 | 15.62 |
| 462 | SD | MET | A | 95 | 20.097 | 17.885 | 79.972 | 1.00 | 17.82 |
| 463 | CE | MET | A | 95 | 20.783 | 16.258 | 79.598 | 1.00 | 16.02 |
| 464 | C | MET | A | 95 | 16.394 | 19.892 | 78.139 | 1.00 | 15.45 |
| 465 | O | MET | A | 95 | 16.874 | 20.494 | 77.182 | 1.00 | 15.29 |
| 466 | N | LYS | A | 96 | 15.097 | 19.592 | 78.230 | 1.00 | 15.36 |
| 467 | CA | LYS | A | 96 | 14.246 | 19.839 | 77.096 | 1.00 | 15.26 |
| 468 | CB | LYS | A | 96 | 12.773 | 19.507 | 77.369 | 1.00 | 15.23 |
| 469 | CG | LYS | A | 96 | 11.843 | 19.456 | 76.117 | 1.00 | 15.45 |
| 470 | CD | LYS | A | 96 | 12.169 | 18.246 | 75.197 | 1.00 | 17.12 |
| 471 | CE | LYS | A | 96 | 11.514 | 18.401 | 73.790 | 1.00 | 15.82 |
| 472 | NZ | LYS | A | 96 | 12.411 | 19.054 | 72.795 | 1.00 | 14.49 |
| 473 | C | LYS | A | 96 | 14.451 | 21.315 | 76.753 | 1.00 | 15.40 |
| 474 | O | LYS | A | 96 | 14.842 | 21.624 | 75.623 | 1.00 | 15.41 |
| 475 | N | SER | A | 97 | 14.276 | 22.208 | 77.748 | 1.00 | 15.45 |
| 476 | CA | SER | A | 97 | 14.265 | 23.667 | 77.537 | 1.00 | 14.60 |
| 477 | CB | SER | A | 97 | 14.750 | 24.457 | 78.783 | 1.00 | 14.42 |
| 478 | OG | SER | A | 97 | 16.141 | 24.724 | 78.788 | 1.00 | 13.32 |
| 479 | C | SER | A | 97 | 15.035 | 24.002 | 76.252 | 1.00 | 14.60 |
| 480 | O | SER | A | 97 | 14.470 | 24.617 | 75.360 | 1.00 | 14.41 |
| 481 | N | VAL | A | 98 | 16.274 | 23.511 | 76.117 | 1.00 | 14.43 |
| 482 | CA | VAL | A | 98 | 17.045 | 23.700 | 74.882 | 1.00 | 14.56 |
| 483 | CB | VAL | A | 98 | 18.154 | 24.834 | 75.089 | 1.00 | 14.28 |
| 484 | CG1 | VAL | A | 98 | 18.454 | 25.572 | 73.746 | 1.00 | 15.69 |
| 485 | CG2 | VAL | A | 98 | 19.412 | 24.329 | 75.781 | 1.00 | 14.91 |
| 486 | C | VAL | A | 98 | 17.547 | 22.365 | 74.234 | 1.00 | 14.01 |
| 487 | O | VAL | A | 98 | 18.697 | 22.037 | 74.336 | 1.00 | 13.69 |
| 488 | N | ASN | A | 99 | 16.673 | 21.710 | 73.460 | 1.00 | 13.73 |
| 489 | CA | ASN | A | 99 | 16.708 | 20.244 | 73.193 | 1.00 | 13.79 |
| 490 | CB | ASN | A | 99 | 15.700 | 19.780 | 72.079 | 1.00 | 13.45 |
| 491 | CG | ASN | A | 99 | 15.779 | 20.579 | 70.763 | 1.00 | 13.60 |
| 492 | OD1 | ASN | A | 99 | 16.610 | 20.275 | 69.886 | 1.00 | 9.80 |
| 493 | ND2 | ASN | A | 99 | 14.836 | 21.552 | 70.582 | 1.00 | 15.11 |
| 494 | C | ASN | A | 99 | 18.079 | 19.490 | 73.132 | 1.00 | 13.68 |
| 495 | O | ASN | A | 99 | 18.738 | 19.348 | 72.094 | 1.00 | 13.58 |
| 496 | N | ALA | A | 100 | 18.458 | 18.971 | 74.292 | 1.00 | 14.19 |
| 497 | CA | ALA | A | 100 | 19.820 | 18.500 | 74.513 | 1.00 | 14.31 |
| 498 | CB | ALA | A | 100 | 20.459 | 19.173 | 75.760 | 1.00 | 13.05 |
| 499 | C | ALA | A | 100 | 19.790 | 16.976 | 74.606 | 1.00 | 14.94 |
| 500 | O | ALA | A | 100 | 18.783 | 16.370 | 74.953 | 1.00 | 14.98 |
| 501 | N | SER | A | 101 | 20.895 | 16.389 | 74.175 | 1.00 | 15.50 |

FIGURE 3 (Cont.)

| A | B | C | D | E | F | G | H | I | J |
|---|---|---|---|---|---|---|---|---|---|
| 502 | CA | SER | A | 101 | 21.016 | 14.957 | 73.975 | 1.00 | 15.66 |
| 503 | CB | SER | A | 101 | 21.579 | 14.693 | 72.567 | 1.00 | 16.21 |
| 504 | OG | SER | A | 101 | 22.718 | 15.517 | 72.313 | 1.00 | 16.66 |
| 505 | C | SER | A | 101 | 21.962 | 14.370 | 74.974 | 1.00 | 15.49 |
| 506 | O | SER | A | 101 | 22.069 | 13.147 | 75.053 | 1.00 | 16.60 |
| 507 | N | ASN | A | 102 | 22.645 | 15.230 | 75.730 | 1.00 | 14.55 |
| 508 | CA | ASN | A | 102 | 23.762 | 14.818 | 76.607 | 1.00 | 14.22 |
| 509 | CB | ASN | A | 102 | 24.941 | 14.341 | 75.746 | 1.00 | 13.75 |
| 510 | CG | ASN | A | 102 | 25.844 | 13.386 | 76.457 | 1.00 | 12.45 |
| 511 | OD1 | ASN | A | 102 | 25.987 | 13.396 | 77.681 | 1.00 | 10.24 |
| 512 | ND2 | ASN | A | 102 | 26.483 | 12.554 | 75.685 | 1.00 | 13.73 |
| 513 | C | ASN | A | 102 | 24.249 | 15.924 | 77.605 | 1.00 | 13.76 |
| 514 | O | ASN | A | 102 | 24.018 | 17.132 | 77.385 | 1.00 | 13.41 |
| 515 | N | TYR | A | 103 | 24.869 | 15.490 | 78.716 | 1.00 | 13.13 |
| 516 | CA | TYR | A | 103 | 25.297 | 16.399 | 79.773 | 1.00 | 12.85 |
| 517 | CB | TYR | A | 103 | 24.410 | 16.238 | 81.018 | 1.00 | 12.57 |
| 518 | CG | TYR | A | 103 | 24.407 | 14.816 | 81.583 | 1.00 | 13.86 |
| 519 | CD1 | TYR | A | 103 | 25.227 | 14.437 | 82.688 | 1.00 | 13.68 |
| 520 | CE1 | TYR | A | 103 | 25.209 | 13.081 | 83.171 | 1.00 | 13.35 |
| 521 | CZ | TYR | A | 103 | 24.370 | 12.119 | 82.547 | 1.00 | 13.41 |
| 522 | OH | TYR | A | 103 | 24.296 | 10.817 | 82.915 | 1.00 | 14.37 |
| 523 | CE2 | TYR | A | 103 | 23.575 | 12.466 | 81.497 | 1.00 | 15.78 |
| 524 | CD2 | TYR | A | 103 | 23.598 | 13.836 | 81.004 | 1.00 | 15.40 |
| 525 | C | TYR | A | 103 | 26.736 | 16.165 | 80.163 | 1.00 | 12.91 |
| 526 | O | TYR | A | 103 | 27.384 | 15.196 | 79.764 | 1.00 | 13.08 |
| 527 | N | GLY | A | 104 | 27.229 | 17.094 | 80.968 | 1.00 | 12.92 |
| 528 | CA | GLY | A | 104 | 28.501 | 16.956 | 81.651 | 1.00 | 13.22 |
| 529 | C | GLY | A | 104 | 28.472 | 17.803 | 82.917 | 1.00 | 13.37 |
| 530 | O | GLY | A | 104 | 27.844 | 18.844 | 82.927 | 1.00 | 13.85 |
| 531 | N | LEU | A | 105 | 29.133 | 17.340 | 83.981 | 1.00 | 13.56 |
| 532 | CA | LEU | A | 105 | 29.035 | 17.932 | 85.312 | 1.00 | 12.93 |
| 533 | CB | LEU | A | 105 | 28.426 | 16.952 | 86.302 | 1.00 | 13.61 |
| 534 | CG | LEU | A | 105 | 27.836 | 17.433 | 87.636 | 1.00 | 12.41 |
| 535 | CD1 | LEU | A | 105 | 28.788 | 18.286 | 88.308 | 1.00 | 12.64 |
| 536 | CD2 | LEU | A | 105 | 26.519 | 18.146 | 87.486 | 1.00 | 11.21 |
| 537 | C | LEU | A | 105 | 30.427 | 18.233 | 85.717 | 1.00 | 13.12 |
| 538 | O | LEU | A | 105 | 31.345 | 17.394 | 85.552 | 1.00 | 12.33 |
| 539 | N | SER | A | 106 | 30.585 | 19.455 | 86.219 | 1.00 | 13.17 |
| 540 | CA | SER | A | 106 | 31.879 | 19.975 | 86.520 | 1.00 | 13.66 |
| 541 | CB | SER | A | 106 | 31.828 | 21.509 | 86.685 | 1.00 | 13.46 |
| 542 | OG | SER | A | 106 | 31.832 | 21.947 | 88.032 | 1.00 | 15.39 |
| 543 | C | SER | A | 106 | 32.367 | 19.246 | 87.760 | 1.00 | 14.46 |
| 544 | O | SER | A | 106 | 31.572 | 18.980 | 88.661 | 1.00 | 13.56 |
| 545 | N | PRO | A | 107 | 33.655 | 18.867 | 87.787 | 1.00 | 15.93 |
| 546 | CA | PRO | A | 107 | 34.247 | 18.305 | 89.013 | 1.00 | 16.98 |
| 547 | CB | PRO | A | 107 | 35.728 | 18.637 | 88.875 | 1.00 | 16.91 |
| 548 | CG | PRO | A | 107 | 35.957 | 18.565 | 87.370 | 1.00 | 16.95 |
| 549 | CD | PRO | A | 107 | 34.629 | 18.874 | 86.669 | 1.00 | 15.40 |
| 550 | C | PRO | A | 107 | 33.656 | 18.923 | 90.261 | 1.00 | 17.96 |
| 551 | O | PRO | A | 107 | 33.230 | 18.178 | 91.116 | 1.00 | 18.74 |
| 552 | N | ASP | A | 108 | 33.098 | 20.252 | 90.376 | 1.00 | 19.13 |

FIGURE 3 (Cont.)

| A | B | C | D | E | F | G | H | I | J |
|---|---|---|---|---|---|---|---|---|---|
| 553 | CA | ASP | A | 108 | 32.765 | 21.468 | 91.089 | 1.00 | 20.26 |
| 554 | CB | ASP | A | 108 | 33.944 | 22.428 | 90.991 | 1.00 | 21.23 |
| 555 | CG | ASP | A | 108 | 33.466 | 23.932 | 91.000 | 1.00 | 25.39 |
| 556 | OD1 | ASP | A | 108 | 34.321 | 24.861 | 91.194 | 1.00 | 28.11 |
| 557 | OD2 | ASP | A | 108 | 32.264 | 24.265 | 90.751 | 1.00 | 31.18 |
| 558 | C | ASP | A | 108 | 31.387 | 22.057 | 90.738 | 1.00 | 19.65 |
| 559 | O | ASP | A | 108 | 31.200 | 23.264 | 90.683 | 1.00 | 20.13 |
| 560 | N | ARG | A | 109 | 30.808 | 20.609 | 90.722 | 1.00 | 18.09 |
| 561 | CA | ARG | A | 109 | 29.354 | 20.504 | 90.844 | 1.00 | 15.99 |
| 562 | CB | ARG | A | 109 | 29.006 | 19.645 | 92.034 | 1.00 | 16.01 |
| 563 | CG | ARG | A | 109 | 29.645 | 18.259 | 92.036 | 1.00 | 14.39 |
| 564 | CD | ARG | A | 109 | 29.166 | 17.394 | 93.174 | 1.00 | 12.88 |
| 565 | NE | ARG | A | 109 | 29.938 | 16.159 | 93.271 | 1.00 | 11.09 |
| 566 | CZ | ARG | A | 109 | 29.522 | 15.046 | 93.859 | 1.00 | 8.03 |
| 567 | NH1 | ARG | A | 109 | 30.324 | 13.987 | 93.906 | 1.00 | 5.18 |
| 568 | NH2 | ARG | A | 109 | 28.312 | 14.975 | 94.381 | 1.00 | 7.36 |
| 569 | C | ARG | A | 109 | 28.545 | 21.757 | 90.922 | 1.00 | 15.53 |
| 570 | O | ARG | A | 109 | 27.329 | 21.659 | 91.050 | 1.00 | 15.26 |
| 571 | N | GLN | A | 110 | 29.203 | 22.909 | 90.796 | 1.00 | 14.87 |
| 572 | CA | GLN | A | 110 | 28.538 | 24.189 | 90.634 | 1.00 | 14.35 |
| 573 | CB | GLN | A | 110 | 29.570 | 25.311 | 90.785 | 1.00 | 14.65 |
| 574 | CG | GLN | A | 110 | 30.301 | 25.503 | 92.143 | 1.00 | 15.66 |
| 575 | CD | GLN | A | 110 | 31.191 | 26.779 | 92.102 | 1.00 | 17.10 |
| 576 | OE1 | GLN | A | 110 | 30.709 | 27.853 | 91.729 | 1.00 | 16.95 |
| 577 | NE2 | GLN | A | 110 | 32.475 | 26.643 | 92.439 | 1.00 | 17.28 |
| 578 | C | GLN | A | 110 | 27.896 | 24.341 | 89.216 | 1.00 | 13.99 |
| 579 | O | GLN | A | 110 | 26.981 | 25.147 | 89.007 | 1.00 | 13.35 |
| 580 | N | PHE | A | 111 | 28.414 | 23.582 | 88.244 | 1.00 | 13.37 |
| 581 | CA | PHE | A | 111 | 27.998 | 23.676 | 86.844 | 1.00 | 13.26 |
| 582 | CB | PHE | A | 111 | 29.081 | 24.436 | 86.047 | 1.00 | 13.13 |
| 583 | CG | PHE | A | 111 | 29.356 | 25.820 | 86.591 | 1.00 | 14.25 |
| 584 | CD1 | PHE | A | 111 | 30.260 | 26.010 | 87.636 | 1.00 | 14.17 |
| 585 | CE1 | PHE | A | 111 | 30.498 | 27.280 | 88.161 | 1.00 | 13.78 |
| 586 | CZ | PHE | A | 111 | 29.825 | 28.366 | 87.641 | 1.00 | 14.17 |
| 587 | CE2 | PHE | A | 111 | 28.915 | 28.185 | 86.603 | 1.00 | 13.77 |
| 588 | CD2 | PHE | A | 111 | 28.679 | 26.927 | 86.092 | 1.00 | 13.81 |
| 589 | C | PHE | A | 111 | 27.683 | 22.304 | 86.170 | 1.00 | 12.97 |
| 590 | O | PHE | A | 111 | 28.167 | 21.191 | 86.587 | 1.00 | 12.11 |
| 591 | N | VAL | A | 112 | 26.858 | 22.424 | 85.117 | 1.00 | 12.61 |
| 592 | CA | VAL | A | 112 | 26.622 | 21.323 | 84.170 | 1.00 | 12.28 |
| 593 | CB | VAL | A | 112 | 25.289 | 20.531 | 84.531 | 1.00 | 12.34 |
| 594 | CG1 | VAL | A | 112 | 24.121 | 21.460 | 84.677 | 1.00 | 10.65 |
| 595 | CG2 | VAL | A | 112 | 25.025 | 19.354 | 83.519 | 1.00 | 11.02 |
| 596 | C | VAL | A | 112 | 26.641 | 21.818 | 82.703 | 1.00 | 12.23 |
| 597 | O | VAL | A | 112 | 26.043 | 22.856 | 82.413 | 1.00 | 11.92 |
| 598 | N | TYR | A | 113 | 27.346 | 21.113 | 81.801 | 1.00 | 12.03 |
| 599 | CA | TYR | A | 113 | 27.283 | 21.407 | 80.332 | 1.00 | 12.24 |
| 600 | CB | TYR | A | 113 | 28.606 | 21.149 | 79.496 | 1.00 | 12.14 |
| 601 | CG | TYR | A | 113 | 29.107 | 19.695 | 79.118 | 1.00 | 12.30 |
| 602 | CD1 | TYR | A | 113 | 30.470 | 19.303 | 79.352 | 1.00 | 14.32 |
| 603 | CE1 | TYR | A | 113 | 30.997 | 17.995 | 78.971 | 1.00 | 14.18 |

FIGURE 3 (Cont.)

| A | B | C | D | E | F | G | H | I | J |
|---|---|---|---|---|---|---|---|---|---|
| 604 | CZ | TYR | A | 113 | 30.152 | 17.100 | 78.375 | 1.00 | 14.48 |
| 605 | OH | TYR | A | 113 | 30.565 | 15.827 | 78.027 | 1.00 | 17.08 |
| 606 | CE2 | TYR | A | 113 | 28.809 | 17.485 | 78.124 | 1.00 | 15.47 |
| 607 | CD2 | TYR | A | 113 | 28.304 | 18.774 | 78.497 | 1.00 | 11.37 |
| 608 | C | TYR | A | 113 | 26.117 | 20.636 | 79.788 | 1.00 | 11.99 |
| 609 | O | TYR | A | 113 | 25.852 | 19.553 | 80.243 | 1.00 | 12.39 |
| 610 | N | LEU | A | 114 | 25.411 | 21.237 | 78.850 | 1.00 | 11.94 |
| 611 | CA | LEU | A | 114 | 24.291 | 20.621 | 78.176 | 1.00 | 11.95 |
| 612 | CB | LEU | A | 114 | 22.991 | 21.371 | 78.520 | 1.00 | 12.02 |
| 613 | CG | LEU | A | 114 | 22.389 | 21.212 | 79.927 | 1.00 | 11.16 |
| 614 | CD1 | LEU | A | 114 | 23.175 | 21.912 | 81.011 | 1.00 | 10.15 |
| 615 | CD2 | LEU | A | 114 | 20.997 | 21.778 | 79.924 | 1.00 | 11.01 |
| 616 | C | LEU | A | 114 | 24.601 | 20.735 | 76.678 | 1.00 | 12.36 |
| 617 | O | LEU | A | 114 | 24.698 | 21.852 | 76.123 | 1.00 | 12.64 |
| 618 | N | GLU | A | 115 | 24.798 | 19.588 | 76.026 | 1.00 | 12.26 |
| 619 | CA | GLU | A | 115 | 25.059 | 19.559 | 74.588 | 1.00 | 12.04 |
| 620 | CB | GLU | A | 115 | 26.288 | 18.680 | 74.262 | 1.00 | 12.26 |
| 621 | CG | GLU | A | 115 | 26.095 | 17.477 | 73.373 | 1.00 | 13.15 |
| 622 | CD | GLU | A | 115 | 27.280 | 16.518 | 73.410 | 1.00 | 13.38 |
| 623 | OE1 | GLU | A | 115 | 28.416 | 16.847 | 73.839 | 1.00 | 11.20 |
| 624 | OE2 | GLU | A | 115 | 27.056 | 15.393 | 72.969 | 1.00 | 15.02 |
| 625 | C | GLU | A | 115 | 23.762 | 19.253 | 73.783 | 1.00 | 12.16 |
| 626 | O | GLU | A | 115 | 23.063 | 18.300 | 74.087 | 1.00 | 11.12 |
| 627 | N | SER | A | 116 | 23.455 | 20.169 | 72.827 | 1.00 | 11.48 |
| 628 | CA | SER | A | 116 | 22.432 | 20.035 | 71.783 | 1.00 | 11.21 |
| 629 | CB | SER | A | 116 | 21.298 | 20.986 | 72.125 | 1.00 | 11.81 |
| 630 | OG | SER | A | 116 | 21.771 | 22.319 | 72.186 | 1.00 | 12.07 |
| 631 | C | SER | A | 116 | 22.991 | 20.424 | 70.374 | 1.00 | 10.73 |
| 632 | O | SER | A | 116 | 24.182 | 20.772 | 70.262 | 1.00 | 9.85 |
| 633 | N | ASP | A | 117 | 22.131 | 20.383 | 69.328 | 1.00 | 10.60 |
| 634 | CA | ASP | A | 117 | 22.559 | 20.422 | 67.904 | 1.00 | 10.26 |
| 635 | CB | ASP | A | 117 | 22.823 | 21.849 | 67.476 | 1.00 | 9.89 |
| 636 | CG | ASP | A | 117 | 21.877 | 22.869 | 68.113 | 1.00 | 10.31 |
| 637 | OD1 | ASP | A | 117 | 20.669 | 22.933 | 67.750 | 1.00 | 8.52 |
| 638 | OD2 | ASP | A | 117 | 22.298 | 23.687 | 68.961 | 1.00 | 10.56 |
| 639 | C | ASP | A | 117 | 23.835 | 19.528 | 67.587 | 1.00 | 11.05 |
| 640 | O | ASP | A | 117 | 24.812 | 19.971 | 67.024 | 1.00 | 10.82 |
| 641 | N | TYR | A | 118 | 23.828 | 18.265 | 67.992 | 1.00 | 11.51 |
| 642 | CA | TYR | A | 118 | 24.853 | 17.300 | 67.588 | 1.00 | 12.13 |
| 643 | CB | TYR | A | 118 | 24.609 | 15.993 | 68.366 | 1.00 | 11.94 |
| 644 | CG | TYR | A | 118 | 25.371 | 14.754 | 67.954 | 1.00 | 13.22 |
| 645 | CD1 | TYR | A | 118 | 24.839 | 13.869 | 67.020 | 1.00 | 15.77 |
| 646 | CE1 | TYR | A | 118 | 25.524 | 12.699 | 66.695 | 1.00 | 15.66 |
| 647 | CZ | TYR | A | 118 | 26.759 | 12.415 | 67.296 | 1.00 | 15.35 |
| 648 | OH | TYR | A | 118 | 27.414 | 11.254 | 66.964 | 1.00 | 20.05 |
| 649 | CE2 | TYR | A | 118 | 27.275 | 13.230 | 68.260 | 1.00 | 15.77 |
| 650 | CD2 | TYR | A | 118 | 26.592 | 14.404 | 68.583 | 1.00 | 15.09 |
| 651 | C | TYR | A | 118 | 24.811 | 17.013 | 66.074 | 1.00 | 13.14 |
| 652 | O | TYR | A | 118 | 23.800 | 16.518 | 65.579 | 1.00 | 13.13 |
| 653 | N | SER | A | 119 | 25.904 | 17.342 | 65.369 | 1.00 | 13.72 |
| 654 | CA | SER | A | 119 | 26.209 | 16.819 | 64.019 | 1.00 | 14.52 |

FIGURE 3 (Cont.)

| A | B | C | D | E | F | G | H | I | J |
|---|---|---|---|---|---|---|---|---|---|
| 655 | CB | SER | A | 119 | 26.536 | 17.957 | 62.977 | 1.00 | 14.86 |
| 656 | OG | SER | A | 119 | 27.907 | 17.913 | 62.448 | 1.00 | 17.94 |
| 657 | C | SER | A | 119 | 27.387 | 15.859 | 64.084 | 1.00 | 14.32 |
| 658 | O | SER | A | 119 | 28.435 | 16.194 | 64.603 | 1.00 | 14.35 |
| 659 | N | LYS | A | 120 | 27.226 | 14.684 | 63.494 | 1.00 | 14.29 |
| 660 | CA | LYS | A | 120 | 28.328 | 13.755 | 63.380 | 1.00 | 13.28 |
| 661 | CB | LYS | A | 120 | 27.766 | 12.401 | 63.005 | 1.00 | 13.10 |
| 662 | CG | LYS | A | 120 | 28.754 | 11.273 | 63.090 | 1.00 | 11.85 |
| 663 | CD | LYS | A | 120 | 28.020 | 9.890 | 63.203 | 1.00 | 8.90 |
| 664 | CE | LYS | A | 120 | 29.080 | 8.748 | 63.463 | 1.00 | 12.56 |
| 665 | NZ | LYS | A | 120 | 29.707 | 8.547 | 62.108 | 1.00 | 10.58 |
| 666 | C | LYS | A | 120 | 29.312 | 14.196 | 62.281 | 1.00 | 13.61 |
| 667 | O | LYS | A | 120 | 28.876 | 14.606 | 61.206 | 1.00 | 14.34 |
| 668 | N | LEU | A | 121 | 30.614 | 14.088 | 62.538 | 1.00 | 13.10 |
| 669 | CA | LEU | A | 121 | 31.570 | 13.996 | 61.476 | 1.00 | 13.22 |
| 670 | CB | LEU | A | 121 | 32.660 | 15.016 | 61.749 | 1.00 | 12.73 |
| 671 | CG | LEU | A | 121 | 33.693 | 15.410 | 60.690 | 1.00 | 14.73 |
| 672 | CD1 | LEU | A | 121 | 33.058 | 16.004 | 59.488 | 1.00 | 10.38 |
| 673 | CD2 | LEU | A | 121 | 34.730 | 16.428 | 61.253 | 1.00 | 15.45 |
| 674 | C | LEU | A | 121 | 32.071 | 12.521 | 61.329 | 1.00 | 13.24 |
| 675 | O | LEU | A | 121 | 31.396 | 11.695 | 60.698 | 1.00 | 14.30 |
| 676 | N | TRP | A | 122 | 33.230 | 12.152 | 61.860 | 1.00 | 12.46 |
| 677 | CA | TRP | A | 122 | 33.774 | 10.800 | 61.572 | 1.00 | 13.16 |
| 678 | CB | TRP | A | 122 | 35.285 | 10.867 | 61.341 | 1.00 | 12.39 |
| 679 | CG | TRP | A | 122 | 35.755 | 11.989 | 60.271 | 1.00 | 12.34 |
| 680 | CD1 | TRP | A | 122 | 36.766 | 12.902 | 60.448 | 1.00 | 12.94 |
| 681 | NE1 | TRP | A | 122 | 36.945 | 13.643 | 59.314 | 1.00 | 12.95 |
| 682 | CE2 | TRP | A | 122 | 36.014 | 13.260 | 58.384 | 1.00 | 13.63 |
| 683 | CD2 | TRP | A | 122 | 35.269 | 12.194 | 58.943 | 1.00 | 12.10 |
| 684 | CE3 | TRP | A | 122 | 34.225 | 11.632 | 58.176 | 1.00 | 14.71 |
| 685 | CZ3 | TRP | A | 122 | 33.973 | 12.127 | 56.872 | 1.00 | 16.79 |
| 686 | CH2 | TRP | A | 122 | 34.748 | 13.197 | 56.342 | 1.00 | 17.41 |
| 687 | CZ2 | TRP | A | 122 | 35.760 | 13.772 | 57.083 | 1.00 | 15.31 |
| 688 | C | TRP | A | 122 | 33.351 | 9.724 | 62.630 | 1.00 | 13.37 |
| 689 | O | TRP | A | 122 | 32.257 | 9.786 | 63.106 | 1.00 | 13.82 |
| 690 | N | ARG | A | 123 | 34.161 | 8.730 | 62.987 | 1.00 | 13.95 |
| 691 | CA | ARG | A | 123 | 33.683 | 7.757 | 63.943 | 1.00 | 14.68 |
| 692 | CB | ARG | A | 123 | 34.658 | 6.584 | 64.148 | 1.00 | 15.15 |
| 693 | CG | ARG | A | 123 | 34.006 | 5.376 | 64.884 | 1.00 | 14.90 |
| 694 | CD | ARG | A | 123 | 34.989 | 4.298 | 65.090 | 1.00 | 21.01 |
| 695 | NE | ARG | A | 123 | 35.344 | 3.792 | 63.800 | 1.00 | 25.96 |
| 696 | CZ | ARG | A | 123 | 34.589 | 2.922 | 63.155 | 1.00 | 27.95 |
| 697 | NH1 | ARG | A | 123 | 33.497 | 2.426 | 63.727 | 1.00 | 31.36 |
| 698 | NH2 | ARG | A | 123 | 34.947 | 2.498 | 61.952 | 1.00 | 24.55 |
| 699 | C | ARG | A | 123 | 33.363 | 8.361 | 65.308 | 1.00 | 15.78 |
| 700 | O | ARG | A | 123 | 32.293 | 8.124 | 65.869 | 1.00 | 15.75 |
| 701 | N | TYR | A | 124 | 34.303 | 9.111 | 65.851 | 1.00 | 15.22 |
| 702 | CA | TYR | A | 124 | 34.110 | 9.701 | 67.155 | 1.00 | 14.18 |
| 703 | CB | TYR | A | 124 | 35.283 | 9.313 | 68.028 | 1.00 | 14.00 |
| 704 | CG | TYR | A | 124 | 35.716 | 7.854 | 68.004 | 1.00 | 14.03 |
| 705 | CD1 | TYR | A | 124 | 35.127 | 6.898 | 68.793 | 1.00 | 13.67 |

FIGURE 3 (Cont.)

| A | B | C | D | E | F | G | H | I | J |
|---|---|---|---|---|---|---|---|---|---|
| 706 | CE1 | TYR | A | 124 | 35.619 | 5.527 | 68.770 | 1.00 | 17.10 |
| 707 | CZ | TYR | A | 124 | 36.709 | 5.211 | 67.932 | 1.00 | 15.79 |
| 708 | OH | TYR | A | 124 | 37.298 | 3.964 | 67.792 | 1.00 | 13.31 |
| 709 | CE2 | TYR | A | 124 | 37.261 | 6.210 | 67.176 | 1.00 | 14.47 |
| 710 | CD2 | TYR | A | 124 | 36.781 | 7.478 | 67.221 | 1.00 | 13.46 |
| 711 | C | TYR | A | 124 | 33.925 | 11.227 | 67.128 | 1.00 | 14.58 |
| 712 | O | TYR | A | 124 | 33.203 | 11.775 | 67.936 | 1.00 | 15.31 |
| 713 | N | SER | A | 125 | 34.537 | 11.922 | 66.180 | 1.00 | 13.19 |
| 714 | CA | SER | A | 125 | 34.353 | 13.386 | 66.089 | 1.00 | 12.18 |
| 715 | CB | SER | A | 125 | 35.313 | 14.116 | 65.099 | 1.00 | 12.42 |
| 716 | OG | SER | A | 125 | 35.430 | 13.442 | 63.875 | 1.00 | 12.72 |
| 717 | C | SER | A | 125 | 32.923 | 13.717 | 65.787 | 1.00 | 11.13 |
| 718 | O | SER | A | 125 | 32.128 | 12.877 | 65.388 | 1.00 | 11.13 |
| 719 | N | TYR | A | 126 | 32.600 | 14.936 | 66.102 | 1.00 | 9.76 |
| 720 | CA | TYR | A | 126 | 31.252 | 15.439 | 66.045 | 1.00 | 9.29 |
| 721 | CB | TYR | A | 126 | 30.183 | 14.511 | 66.743 | 1.00 | 8.45 |
| 722 | CG | TYR | A | 126 | 30.205 | 14.551 | 68.271 | 1.00 | 7.02 |
| 723 | CD1 | TYR | A | 126 | 29.699 | 15.662 | 68.972 | 1.00 | 6.45 |
| 724 | CE1 | TYR | A | 126 | 29.734 | 15.742 | 70.339 | 1.00 | 6.81 |
| 725 | CZ | TYR | A | 126 | 30.291 | 14.698 | 71.086 | 1.00 | 6.54 |
| 726 | OH | TYR | A | 126 | 30.274 | 14.824 | 72.469 | 1.00 | 2.00 |
| 727 | CE2 | TYR | A | 126 | 30.819 | 13.605 | 70.433 | 1.00 | 6.23 |
| 728 | CD2 | TYR | A | 126 | 30.767 | 13.526 | 69.000 | 1.00 | 2.77 |
| 729 | C | TYR | A | 126 | 31.338 | 16.784 | 66.699 | 1.00 | 9.88 |
| 730 | O | TYR | A | 126 | 32.382 | 17.222 | 67.214 | 1.00 | 10.67 |
| 731 | N | THR | A | 127 | 30.185 | 17.396 | 66.725 | 1.00 | 10.50 |
| 732 | CA | THR | A | 127 | 30.066 | 18.792 | 66.792 | 1.00 | 11.23 |
| 733 | CB | THR | A | 127 | 30.151 | 19.269 | 65.344 | 1.00 | 11.87 |
| 734 | OG1 | THR | A | 127 | 31.518 | 19.645 | 65.111 | 1.00 | 13.79 |
| 735 | CG2 | THR | A | 127 | 29.235 | 20.504 | 65.042 | 1.00 | 11.59 |
| 736 | C | THR | A | 127 | 28.728 | 19.128 | 67.429 | 1.00 | 11.84 |
| 737 | O | THR | A | 127 | 27.659 | 18.468 | 67.208 | 1.00 | 12.95 |
| 738 | N | ALA | A | 128 | 28.777 | 20.197 | 68.204 | 1.00 | 11.55 |
| 739 | CA | ALA | A | 128 | 27.690 | 20.480 | 69.088 | 1.00 | 11.51 |
| 740 | CB | ALA | A | 128 | 27.764 | 19.494 | 70.329 | 1.00 | 11.47 |
| 741 | C | ALA | A | 128 | 27.753 | 21.909 | 69.528 | 1.00 | 11.50 |
| 742 | O | ALA | A | 128 | 28.761 | 22.599 | 69.332 | 1.00 | 11.30 |
| 743 | N | THR | A | 129 | 26.629 | 22.306 | 70.117 | 1.00 | 11.72 |
| 744 | CA | THR | A | 129 | 26.457 | 23.518 | 70.918 | 1.00 | 11.98 |
| 745 | CB | THR | A | 129 | 25.131 | 24.085 | 70.547 | 1.00 | 11.58 |
| 746 | OG1 | THR | A | 129 | 25.133 | 24.382 | 69.141 | 1.00 | 13.93 |
| 747 | CG2 | THR | A | 129 | 24.871 | 25.383 | 71.291 | 1.00 | 11.83 |
| 748 | C | THR | A | 129 | 26.472 | 23.209 | 72.452 | 1.00 | 11.81 |
| 749 | O | THR | A | 129 | 25.831 | 22.245 | 72.935 | 1.00 | 12.46 |
| 750 | N | TYR | A | 130 | 27.193 | 24.027 | 73.210 | 1.00 | 11.22 |
| 751 | CA | TYR | A | 130 | 27.254 | 23.849 | 74.646 | 1.00 | 10.53 |
| 752 | CB | TYR | A | 130 | 28.674 | 23.570 | 75.088 | 1.00 | 10.01 |
| 753 | CG | TYR | A | 130 | 29.122 | 22.258 | 74.579 | 1.00 | 9.29 |
| 754 | CD1 | TYR | A | 130 | 29.486 | 22.117 | 73.264 | 1.00 | 10.18 |
| 755 | CE1 | TYR | A | 130 | 29.884 | 20.903 | 72.742 | 1.00 | 10.15 |
| 756 | CZ | TYR | A | 130 | 29.933 | 19.781 | 73.558 | 1.00 | 11.94 |

FIGURE 3 (Cont.)

| A | B | C | D | E | F | G | H | I | J |
|---|---|---|---|---|---|---|---|---|---|
| 757 | OH | TYR | A | 130 | 30.344 | 18.550 | 73.018 | 1.00 | 12.11 |
| 758 | CE2 | TYR | A | 130 | 29.564 | 19.920 | 74.902 | 1.00 | 10.26 |
| 759 | CD2 | TYR | A | 130 | 29.145 | 21.151 | 75.387 | 1.00 | 8.84 |
| 760 | C | TYR | A | 130 | 26.668 | 25.085 | 75.340 | 1.00 | 10.84 |
| 761 | O | TYR | A | 130 | 27.003 | 26.243 | 75.005 | 1.00 | 11.03 |
| 762 | N | TYR | A | 131 | 25.705 | 24.813 | 76.229 | 1.00 | 10.72 |
| 763 | CA | TYR | A | 131 | 25.214 | 25.778 | 77.184 | 1.00 | 10.52 |
| 764 | CB | TYR | A | 131 | 23.681 | 26.000 | 77.106 | 1.00 | 10.32 |
| 765 | CG | TYR | A | 131 | 23.023 | 26.165 | 75.750 | 1.00 | 10.05 |
| 766 | CD1 | TYR | A | 131 | 22.794 | 25.067 | 74.922 | 1.00 | 10.98 |
| 767 | CE1 | TYR | A | 131 | 22.113 | 25.234 | 73.660 | 1.00 | 11.53 |
| 768 | CZ | TYR | A | 131 | 21.667 | 26.492 | 73.275 | 1.00 | 10.61 |
| 769 | OH | TYR | A | 131 | 21.019 | 26.626 | 72.056 | 1.00 | 14.25 |
| 770 | CE2 | TYR | A | 131 | 21.866 | 27.568 | 74.107 | 1.00 | 9.11 |
| 771 | CD2 | TYR | A | 131 | 22.531 | 27.409 | 75.327 | 1.00 | 9.68 |
| 772 | C | TYR | A | 131 | 25.597 | 25.307 | 78.600 | 1.00 | 10.32 |
| 773 | O | TYR | A | 131 | 25.715 | 24.102 | 78.925 | 1.00 | 9.69 |
| 774 | N | ILE | A | 132 | 25.790 | 26.300 | 79.439 | 1.00 | 10.36 |
| 775 | CA | ILE | A | 132 | 26.180 | 26.080 | 80.792 | 1.00 | 10.70 |
| 776 | CB | ILE | A | 132 | 27.558 | 26.738 | 81.013 | 1.00 | 10.23 |
| 777 | CG1 | ILE | A | 132 | 28.614 | 25.977 | 80.199 | 1.00 | 9.33 |
| 778 | CD1 | ILE | A | 132 | 29.486 | 26.835 | 79.367 | 1.00 | 11.17 |
| 779 | CG2 | ILE | A | 132 | 27.975 | 26.748 | 82.482 | 1.00 | 9.20 |
| 780 | C | ILE | A | 132 | 25.036 | 26.567 | 81.681 | 1.00 | 12.08 |
| 781 | O | ILE | A | 132 | 24.498 | 27.640 | 81.491 | 1.00 | 12.65 |
| 782 | N | TYR | A | 133 | 24.625 | 25.709 | 82.609 | 1.00 | 13.97 |
| 783 | CA | TYR | A | 133 | 23.523 | 25.983 | 83.539 | 1.00 | 15.69 |
| 784 | CB | TYR | A | 133 | 22.434 | 24.911 | 83.374 | 1.00 | 16.18 |
| 785 | CG | TYR | A | 133 | 21.229 | 25.079 | 84.260 | 1.00 | 17.06 |
| 786 | CD1 | TYR | A | 133 | 20.945 | 24.129 | 85.230 | 1.00 | 18.33 |
| 787 | CE1 | TYR | A | 133 | 19.849 | 24.254 | 86.060 | 1.00 | 19.67 |
| 788 | CZ | TYR | A | 133 | 19.017 | 25.323 | 85.919 | 1.00 | 17.97 |
| 789 | OH | TYR | A | 133 | 17.990 | 25.359 | 86.783 | 1.00 | 19.01 |
| 790 | CE2 | TYR | A | 133 | 19.257 | 26.300 | 84.970 | 1.00 | 17.83 |
| 791 | CD2 | TYR | A | 133 | 20.371 | 26.171 | 84.135 | 1.00 | 18.15 |
| 792 | C | TYR | A | 133 | 24.096 | 26.046 | 84.974 | 1.00 | 16.11 |
| 793 | O | TYR | A | 133 | 24.603 | 25.037 | 85.555 | 1.00 | 15.92 |
| 794 | N | ASP | A | 134 | 24.054 | 27.272 | 85.502 | 1.00 | 16.54 |
| 795 | CA | ASP | A | 134 | 24.669 | 27.591 | 86.777 | 1.00 | 16.91 |
| 796 | CB | ASP | A | 134 | 24.874 | 29.090 | 86.935 | 1.00 | 17.12 |
| 797 | CG | ASP | A | 134 | 25.488 | 29.465 | 88.286 | 1.00 | 18.52 |
| 798 | OD1 | ASP | A | 134 | 25.397 | 30.662 | 88.643 | 1.00 | 21.14 |
| 799 | OD2 | ASP | A | 134 | 26.069 | 28.650 | 89.046 | 1.00 | 18.91 |
| 800 | C | ASP | A | 134 | 23.719 | 27.084 | 87.822 | 1.00 | 16.97 |
| 801 | O | ASP | A | 134 | 22.576 | 27.570 | 87.948 | 1.00 | 17.03 |
| 802 | N | LEU | A | 135 | 24.238 | 26.135 | 88.591 | 1.00 | 16.73 |
| 803 | CA | LEU | A | 135 | 23.439 | 25.183 | 89.325 | 1.00 | 16.63 |
| 804 | CB | LEU | A | 135 | 24.170 | 23.860 | 89.258 | 1.00 | 16.31 |
| 805 | CG | LEU | A | 135 | 23.308 | 22.621 | 89.388 | 1.00 | 16.75 |
| 806 | CD1 | LEU | A | 135 | 22.574 | 22.267 | 88.091 | 1.00 | 14.59 |
| 807 | CD2 | LEU | A | 135 | 24.242 | 21.496 | 89.855 | 1.00 | 18.84 |

FIGURE 3 (Cont.)

| A | B | C | D | E | F | G | H | I | J |
|---|---|---|---|---|---|---|---|---|---|
| 808 | C | LEU | A | 135 | 23.070 | 25.554 | 90.790 | 1.00 | 16.63 |
| 809 | O | LEU | A | 135 | 22.406 | 24.771 | 91.446 | 1.00 | 16.81 |
| 810 | N | SER | A | 136 | 23.462 | 26.733 | 91.302 | 1.00 | 16.38 |
| 811 | CA | SER | A | 136 | 22.886 | 27.212 | 92.564 | 1.00 | 15.86 |
| 812 | CB | SER | A | 136 | 23.909 | 27.883 | 93.511 | 1.00 | 15.83 |
| 813 | OG | SER | A | 136 | 25.218 | 27.879 | 92.994 | 1.00 | 13.86 |
| 814 | C | SER | A | 136 | 21.730 | 28.154 | 92.250 | 1.00 | 15.88 |
| 815 | O | SER | A | 136 | 20.867 | 28.379 | 93.092 | 1.00 | 15.66 |
| 816 | N | ASN | A | 137 | 21.706 | 28.700 | 91.037 | 1.00 | 15.85 |
| 817 | CA | ASN | A | 137 | 20.771 | 29.798 | 90.721 | 1.00 | 16.27 |
| 818 | CB | ASN | A | 137 | 21.568 | 30.953 | 90.116 | 1.00 | 16.19 |
| 819 | CG | ASN | A | 137 | 22.611 | 31.489 | 91.095 | 1.00 | 15.22 |
| 820 | OD1 | ASN | A | 137 | 23.803 | 31.170 | 91.018 | 1.00 | 12.53 |
| 821 | ND2 | ASN | A | 137 | 22.142 | 32.267 | 92.064 | 1.00 | 14.67 |
| 822 | C | ASN | A | 137 | 19.584 | 29.366 | 89.856 | 1.00 | 16.58 |
| 823 | O | ASN | A | 137 | 18.507 | 29.978 | 89.882 | 1.00 | 16.23 |
| 824 | N | GLY | A | 138 | 19.795 | 28.266 | 89.127 | 1.00 | 16.89 |
| 825 | CA | GLY | A | 138 | 18.730 | 27.581 | 88.418 | 1.00 | 17.29 |
| 826 | C | GLY | A | 138 | 18.302 | 28.355 | 87.189 | 1.00 | 17.49 |
| 827 | O | GLY | A | 138 | 17.143 | 28.240 | 86.715 | 1.00 | 17.79 |
| 828 | N | GLU | A | 139 | 19.255 | 29.155 | 86.692 | 1.00 | 17.28 |
| 829 | CA | GLU | A | 139 | 19.076 | 30.017 | 85.509 | 1.00 | 16.72 |
| 830 | CB | GLU | A | 139 | 18.659 | 31.490 | 85.894 | 1.00 | 16.19 |
| 831 | CG | GLU | A | 139 | 17.148 | 31.779 | 85.797 | 1.00 | 15.30 |
| 832 | CD | GLU | A | 139 | 16.655 | 33.001 | 86.606 | 1.00 | 14.25 |
| 833 | OE1 | GLU | A | 139 | 16.833 | 33.059 | 87.839 | 1.00 | 13.44 |
| 834 | OE2 | GLU | A | 139 | 16.043 | 33.905 | 86.015 | 1.00 | 13.32 |
| 835 | C | GLU | A | 139 | 20.413 | 29.908 | 84.727 | 1.00 | 16.50 |
| 836 | O | GLU | A | 139 | 21.492 | 29.857 | 85.349 | 1.00 | 16.18 |
| 837 | N | PHE | A | 140 | 20.312 | 29.832 | 83.387 | 1.00 | 16.05 |
| 838 | CA | PHE | A | 140 | 21.450 | 29.587 | 82.488 | 1.00 | 15.44 |
| 839 | CB | PHE | A | 140 | 20.948 | 29.474 | 81.055 | 1.00 | 15.20 |
| 840 | CG | PHE | A | 140 | 20.418 | 28.095 | 80.697 | 1.00 | 14.33 |
| 841 | CD1 | PHE | A | 140 | 21.308 | 27.007 | 80.533 | 1.00 | 12.29 |
| 842 | CE1 | PHE | A | 140 | 20.830 | 25.737 | 80.197 | 1.00 | 9.98 |
| 843 | CZ | PHE | A | 140 | 19.433 | 25.534 | 80.024 | 1.00 | 11.72 |
| 844 | CE2 | PHE | A | 140 | 18.525 | 26.611 | 80.191 | 1.00 | 10.86 |
| 845 | CD2 | PHE | A | 140 | 19.030 | 27.883 | 80.515 | 1.00 | 12.91 |
| 846 | C | PHE | A | 140 | 22.486 | 30.684 | 82.570 | 1.00 | 15.56 |
| 847 | O | PHE | A | 140 | 22.160 | 31.789 | 82.952 | 1.00 | 16.20 |
| 848 | N | VAL | A | 141 | 23.739 | 30.392 | 82.246 | 1.00 | 15.66 |
| 849 | CA | VAL | A | 141 | 24.791 | 31.419 | 82.321 | 1.00 | 16.09 |
| 850 | CB | VAL | A | 141 | 26.290 | 30.833 | 82.320 | 1.00 | 16.40 |
| 851 | CG1 | VAL | A | 141 | 27.340 | 31.975 | 82.424 | 1.00 | 16.39 |
| 852 | CG2 | VAL | A | 141 | 26.526 | 29.833 | 83.418 | 1.00 | 14.57 |
| 853 | C | VAL | A | 141 | 24.632 | 32.405 | 81.141 | 1.00 | 16.54 |
| 854 | O | VAL | A | 141 | 24.955 | 32.062 | 79.988 | 1.00 | 15.94 |
| 855 | N | ARG | A | 142 | 24.085 | 33.602 | 81.448 | 1.00 | 17.41 |
| 856 | CA | ARG | A | 142 | 24.133 | 34.803 | 80.567 | 1.00 | 17.56 |
| 857 | CB | ARG | A | 142 | 22.955 | 35.792 | 80.828 | 1.00 | 17.94 |
| 858 | CG | ARG | A | 142 | 21.671 | 35.460 | 80.039 | 1.00 | 18.50 |

FIGURE 3 (Cont.)

| A | B | C | D | E | F | G | H | I | J |
|---|---|---|---|---|---|---|---|---|---|
| 859 | CD | ARG | A | 142 | 21.327 | 33.942 | 80.029 | 1.00 | 17.49 |
| 860 | NE | ARG | A | 142 | 19.894 | 33.702 | 79.919 | 1.00 | 18.05 |
| 861 | CZ | ARG | A | 142 | 19.313 | 32.834 | 79.097 | 1.00 | 18.90 |
| 862 | NH1 | ARG | A | 142 | 20.018 | 32.057 | 78.276 | 1.00 | 20.45 |
| 863 | NH2 | ARG | A | 142 | 17.997 | 32.724 | 79.101 | 1.00 | 18.60 |
| 864 | C | ARG | A | 142 | 25.486 | 35.479 | 80.863 | 1.00 | 17.37 |
| 865 | O | ARG | A | 142 | 25.718 | 36.037 | 81.948 | 1.00 | 18.02 |
| 866 | N | GLY | A | 143 | 26.401 | 35.359 | 79.915 | 1.00 | 16.48 |
| 867 | CA | GLY | A | 143 | 27.710 | 35.926 | 80.084 | 1.00 | 16.19 |
| 868 | C | GLY | A | 143 | 28.320 | 35.895 | 78.708 | 1.00 | 15.81 |
| 869 | O | GLY | A | 143 | 27.643 | 36.160 | 77.709 | 1.00 | 16.28 |
| 870 | N | ASN | A | 144 | 29.583 | 35.504 | 78.647 | 1.00 | 15.01 |
| 871 | CA | ASN | A | 144 | 30.369 | 35.687 | 77.432 | 1.00 | 14.52 |
| 872 | CB | ASN | A | 144 | 31.788 | 36.080 | 77.796 | 1.00 | 14.23 |
| 873 | CG | ASN | A | 144 | 31.896 | 37.524 | 77.988 | 1.00 | 12.58 |
| 874 | OD1 | ASN | A | 144 | 31.223 | 38.291 | 77.300 | 1.00 | 7.95 |
| 875 | ND2 | ASN | A | 144 | 32.695 | 37.927 | 78.944 | 1.00 | 13.26 |
| 876 | C | ASN | A | 144 | 30.347 | 34.482 | 76.538 | 1.00 | 14.36 |
| 877 | O | ASN | A | 144 | 31.381 | 33.843 | 76.293 | 1.00 | 14.40 |
| 878 | N | GLU | A | 145 | 29.148 | 34.243 | 76.009 | 1.00 | 14.24 |
| 879 | CA | GLU | A | 145 | 28.732 | 32.916 | 75.563 | 1.00 | 13.77 |
| 880 | CB | GLU | A | 145 | 27.335 | 32.947 | 74.926 | 1.00 | 14.30 |
| 881 | CG | GLU | A | 145 | 26.183 | 33.338 | 75.858 | 1.00 | 16.73 |
| 882 | CD | GLU | A | 145 | 24.890 | 33.576 | 75.083 | 1.00 | 19.38 |
| 883 | OE1 | GLU | A | 145 | 23.946 | 34.195 | 75.646 | 1.00 | 18.10 |
| 884 | OE2 | GLU | A | 145 | 24.836 | 33.131 | 73.888 | 1.00 | 21.87 |
| 885 | C | GLU | A | 145 | 29.717 | 32.244 | 74.597 | 1.00 | 12.61 |
| 886 | O | GLU | A | 145 | 30.273 | 32.844 | 73.665 | 1.00 | 12.35 |
| 887 | N | LEU | A | 146 | 29.928 | 30.974 | 74.862 | 1.00 | 11.53 |
| 888 | CA | LEU | A | 146 | 30.552 | 30.089 | 73.923 | 1.00 | 10.62 |
| 889 | CB | LEU | A | 146 | 30.256 | 28.646 | 74.348 | 1.00 | 10.66 |
| 890 | CG | LEU | A | 146 | 30.957 | 28.136 | 75.618 | 1.00 | 9.79 |
| 891 | CD1 | LEU | A | 146 | 30.418 | 26.734 | 75.951 | 1.00 | 9.13 |
| 892 | CD2 | LEU | A | 146 | 32.485 | 28.145 | 75.434 | 1.00 | 8.23 |
| 893 | C | LEU | A | 146 | 30.056 | 30.299 | 72.498 | 1.00 | 10.26 |
| 894 | O | LEU | A | 146 | 28.894 | 30.544 | 72.247 | 1.00 | 10.07 |
| 895 | N | PRO | A | 147 | 30.968 | 30.171 | 71.563 | 1.00 | 10.22 |
| 896 | CA | PRO | A | 147 | 30.609 | 30.183 | 70.148 | 1.00 | 10.59 |
| 897 | CB | PRO | A | 147 | 31.953 | 30.351 | 69.460 | 1.00 | 10.58 |
| 898 | CG | PRO | A | 147 | 32.925 | 29.681 | 70.419 | 1.00 | 9.80 |
| 899 | CD | PRO | A | 147 | 32.416 | 29.993 | 71.773 | 1.00 | 9.47 |
| 900 | C | PRO | A | 147 | 30.041 | 28.865 | 69.718 | 1.00 | 11.44 |
| 901 | O | PRO | A | 147 | 30.514 | 27.768 | 70.150 | 1.00 | 11.02 |
| 902 | N | ARG | A | 148 | 29.067 | 28.933 | 68.816 | 1.00 | 12.00 |
| 903 | CA | ARG | A | 148 | 28.540 | 27.680 | 68.290 | 1.00 | 12.39 |
| 904 | CB | ARG | A | 148 | 27.012 | 27.566 | 68.452 | 1.00 | 12.26 |
| 905 | CG | ARG | A | 148 | 26.101 | 28.565 | 67.770 | 1.00 | 13.36 |
| 906 | CD | ARG | A | 148 | 24.662 | 28.315 | 68.193 | 1.00 | 15.04 |
| 907 | NE | ARG | A | 148 | 24.538 | 28.396 | 69.660 | 1.00 | 16.22 |
| 908 | CZ | ARG | A | 148 | 23.449 | 28.802 | 70.341 | 1.00 | 15.82 |
| 909 | NH1 | ARG | A | 148 | 23.542 | 28.829 | 71.664 | 1.00 | 16.66 |

FIGURE 3 (Cont.)

| A | B | C | D | E | F | G | H | I | J |
|---|---|---|---|---|---|---|---|---|---|
| 910 | NH2 | ARG | A | 148 | 22.288 | 29.199 | 69.747 | 1.00 | 14.56 |
| 911 | C | ARG | A | 148 | 29.123 | 27.187 | 66.952 | 1.00 | 12.63 |
| 912 | O | ARG | A | 148 | 29.600 | 27.950 | 66.098 | 1.00 | 10.85 |
| 913 | N | PRO | A | 149 | 28.883 | 25.896 | 66.723 | 1.00 | 13.52 |
| 914 | CA | PRO | A | 149 | 29.865 | 24.876 | 66.416 | 1.00 | 13.41 |
| 915 | CB | PRO | A | 149 | 29.984 | 25.107 | 64.930 | 1.00 | 13.92 |
| 916 | CG | PRO | A | 149 | 28.319 | 25.322 | 64.640 | 1.00 | 14.02 |
| 917 | CD | PRO | A | 149 | 27.615 | 25.459 | 66.116 | 1.00 | 14.34 |
| 918 | C | PRO | A | 149 | 31.203 | 24.749 | 67.156 | 1.00 | 13.54 |
| 919 | O | PRO | A | 149 | 32.197 | 25.281 | 66.667 | 1.00 | 14.92 |
| 920 | N | ILE | A | 150 | 31.189 | 23.966 | 68.253 | 1.00 | 12.30 |
| 921 | CA | ILE | A | 150 | 32.364 | 23.499 | 68.993 | 1.00 | 10.32 |
| 922 | CB | ILE | A | 150 | 32.273 | 23.866 | 70.534 | 1.00 | 10.37 |
| 923 | CG1 | ILE | A | 150 | 32.752 | 25.307 | 70.771 | 1.00 | 9.57 |
| 924 | CD1 | ILE | A | 150 | 32.470 | 25.840 | 72.210 | 1.00 | 8.03 |
| 925 | CG2 | ILE | A | 150 | 33.142 | 22.976 | 71.402 | 1.00 | 5.50 |
| 926 | C | ILE | A | 150 | 32.645 | 21.967 | 68.773 | 1.00 | 10.94 |
| 927 | O | ILE | A | 150 | 31.774 | 21.063 | 68.746 | 1.00 | 10.29 |
| 928 | N | GLN | A | 151 | 33.910 | 21.693 | 68.583 | 1.00 | 10.50 |
| 929 | CA | GLN | A | 151 | 34.289 | 20.351 | 68.338 | 1.00 | 10.93 |
| 930 | CB | GLN | A | 151 | 35.569 | 20.381 | 67.507 | 1.00 | 11.89 |
| 931 | CG | GLN | A | 151 | 35.260 | 20.824 | 66.037 | 1.00 | 13.54 |
| 932 | CD | GLN | A | 151 | 36.061 | 22.015 | 65.599 | 1.00 | 18.93 |
| 933 | OE1 | GLN | A | 151 | 37.240 | 21.857 | 65.315 | 1.00 | 22.74 |
| 934 | NE2 | GLN | A | 151 | 35.417 | 23.218 | 65.497 | 1.00 | 19.65 |
| 935 | C | GLN | A | 151 | 34.339 | 19.679 | 69.723 | 1.00 | 10.99 |
| 936 | O | GLN | A | 151 | 33.318 | 19.172 | 70.196 | 1.00 | 11.07 |
| 937 | N | TYR | A | 152 | 35.441 | 19.827 | 70.435 | 1.00 | 9.79 |
| 938 | CA | TYR | A | 152 | 35.589 | 19.192 | 71.726 | 1.00 | 9.29 |
| 939 | CB | TYR | A | 152 | 36.970 | 18.533 | 71.850 | 1.00 | 8.70 |
| 940 | CG | TYR | A | 152 | 37.154 | 17.774 | 73.125 | 1.00 | 11.43 |
| 941 | CD1 | TYR | A | 152 | 38.224 | 18.072 | 73.984 | 1.00 | 11.70 |
| 942 | CE1 | TYR | A | 152 | 38.387 | 17.413 | 75.173 | 1.00 | 10.79 |
| 943 | CZ | TYR | A | 152 | 37.480 | 16.448 | 75.517 | 1.00 | 12.41 |
| 944 | OH | TYR | A | 152 | 37.651 | 15.799 | 76.711 | 1.00 | 11.53 |
| 945 | CE2 | TYR | A | 152 | 36.386 | 16.167 | 74.702 | 1.00 | 12.36 |
| 946 | CD2 | TYR | A | 152 | 36.243 | 16.799 | 73.510 | 1.00 | 10.40 |
| 947 | C | TYR | A | 152 | 35.426 | 20.174 | 72.821 | 1.00 | 8.96 |
| 948 | O | TYR | A | 152 | 35.732 | 21.356 | 72.696 | 1.00 | 8.21 |
| 949 | N | LEU | A | 153 | 34.950 | 19.670 | 73.929 | 1.00 | 8.94 |
| 950 | CA | LEU | A | 153 | 34.914 | 20.468 | 75.133 | 1.00 | 9.72 |
| 951 | CB | LEU | A | 153 | 33.666 | 21.363 | 75.152 | 1.00 | 9.03 |
| 952 | CG | LEU | A | 153 | 33.379 | 22.157 | 76.419 | 1.00 | 7.16 |
| 953 | CD1 | LEU | A | 153 | 32.564 | 23.286 | 76.041 | 1.00 | 7.04 |
| 954 | CD2 | LEU | A | 153 | 32.605 | 21.355 | 77.424 | 1.00 | 7.39 |
| 955 | C | LEU | A | 153 | 34.957 | 19.524 | 76.324 | 1.00 | 10.60 |
| 956 | O | LEU | A | 153 | 34.406 | 18.416 | 76.293 | 1.00 | 11.35 |
| 957 | N | CYS | A | 154 | 35.675 | 19.937 | 77.359 | 1.00 | 11.17 |
| 958 | CA | CYS | A | 154 | 35.631 | 19.224 | 78.612 | 1.00 | 11.25 |
| 959 | CB | CYS | A | 154 | 36.720 | 18.172 | 78.682 | 1.00 | 11.76 |
| 960 | SG | CYS | A | 154 | 38.293 | 18.847 | 78.211 | 1.00 | 14.03 |

FIGURE 3 (Cont.)

| A | B | C | D | E | F | G | H | I | J |
|---|---|---|---|---|---|---|---|---|---|
| 961 | C | CYS | A | 154 | 35.850 | 20.202 | 79.713 | 1.00 | 10.71 |
| 962 | O | CYS | A | 154 | 36.097 | 21.378 | 79.483 | 1.00 | 10.97 |
| 963 | N | TRP | A | 155 | 35.778 | 19.688 | 80.925 | 1.00 | 10.79 |
| 964 | CA | TRP | A | 155 | 36.191 | 20.468 | 82.057 | 1.00 | 11.06 |
| 965 | CB | TRP | A | 155 | 35.180 | 20.264 | 83.155 | 1.00 | 10.28 |
| 966 | CG | TRP | A | 155 | 34.231 | 21.374 | 83.223 | 1.00 | 9.94 |
| 967 | CD1 | TRP | A | 155 | 34.468 | 22.783 | 83.457 | 1.00 | 10.88 |
| 968 | NE1 | TRP | A | 155 | 33.272 | 23.480 | 83.456 | 1.00 | 8.08 |
| 969 | CE2 | TRP | A | 155 | 32.270 | 22.556 | 83.251 | 1.00 | 8.12 |
| 970 | CD2 | TRP | A | 155 | 32.874 | 21.230 | 83.080 | 1.00 | 6.80 |
| 971 | CE3 | TRP | A | 155 | 32.065 | 20.126 | 82.878 | 1.00 | 3.23 |
| 972 | CZ3 | TRP | A | 155 | 30.754 | 20.309 | 82.811 | 1.00 | 3.74 |
| 973 | CH2 | TRP | A | 155 | 30.173 | 21.605 | 82.966 | 1.00 | 6.67 |
| 974 | CZ2 | TRP | A | 155 | 30.924 | 22.745 | 83.175 | 1.00 | 7.15 |
| 975 | C | TRP | A | 155 | 37.589 | 20.135 | 82.557 | 1.00 | 11.11 |
| 976 | O | TRP | A | 155 | 38.229 | 19.242 | 82.088 | 1.00 | 10.88 |
| 977 | N | SER | A | 156 | 38.042 | 20.894 | 83.534 | 1.00 | 12.18 |
| 978 | CA | SER | A | 156 | 39.161 | 20.455 | 84.348 | 1.00 | 13.18 |
| 979 | CB | SER | A | 156 | 39.660 | 21.598 | 85.215 | 1.00 | 12.34 |
| 980 | OG | SER | A | 156 | 38.668 | 22.588 | 85.294 | 1.00 | 12.21 |
| 981 | C | SER | A | 156 | 38.727 | 19.240 | 85.207 | 1.00 | 13.88 |
| 982 | O | SER | A | 156 | 37.546 | 18.986 | 85.434 | 1.00 | 12.74 |
| 983 | N | PRO | A | 157 | 39.690 | 18.421 | 85.588 | 1.00 | 15.44 |
| 984 | CA | PRO | A | 157 | 39.510 | 17.501 | 86.712 | 1.00 | 16.11 |
| 985 | CB | PRO | A | 157 | 40.817 | 16.714 | 86.715 | 1.00 | 16.22 |
| 986 | CG | PRO | A | 157 | 41.258 | 16.746 | 85.306 | 1.00 | 16.09 |
| 987 | CD | PRO | A | 157 | 40.973 | 18.167 | 84.904 | 1.00 | 16.08 |
| 988 | C | PRO | A | 157 | 39.307 | 18.192 | 88.053 | 1.00 | 16.44 |
| 989 | O | PRO | A | 157 | 38.963 | 17.459 | 88.983 | 1.00 | 17.52 |
| 990 | N | VAL | A | 158 | 39.530 | 19.509 | 88.170 | 1.00 | 16.49 |
| 991 | CA | VAL | A | 158 | 39.180 | 20.228 | 89.393 | 1.00 | 16.71 |
| 992 | CB | VAL | A | 158 | 40.403 | 20.353 | 90.371 | 1.00 | 16.57 |
| 993 | CG1 | VAL | A | 158 | 39.989 | 20.906 | 91.773 | 1.00 | 18.58 |
| 994 | CG2 | VAL | A | 158 | 41.113 | 18.996 | 90.571 | 1.00 | 16.16 |
| 995 | C | VAL | A | 158 | 38.463 | 21.581 | 89.101 | 1.00 | 17.14 |
| 996 | O | VAL | A | 158 | 38.781 | 22.331 | 88.159 | 1.00 | 17.37 |
| 997 | N | GLY | A | 159 | 37.460 | 21.854 | 89.934 | 1.00 | 17.41 |
| 998 | CA | GLY | A | 159 | 36.578 | 22.983 | 89.770 | 1.00 | 17.14 |
| 999 | C | GLY | A | 159 | 35.673 | 22.900 | 88.544 | 1.00 | 16.55 |
| 1000 | O | GLY | A | 159 | 34.905 | 21.957 | 88.321 | 1.00 | 15.31 |
| 1001 | N | SER | A | 160 | 35.806 | 23.951 | 87.750 | 1.00 | 16.11 |
| 1002 | CA | SER | A | 160 | 34.801 | 24.349 | 86.774 | 1.00 | 16.17 |
| 1003 | CB | SER | A | 160 | 33.703 | 25.096 | 87.506 | 1.00 | 15.86 |
| 1004 | OG | SER | A | 160 | 33.995 | 25.069 | 88.907 | 1.00 | 17.76 |
| 1005 | C | SER | A | 160 | 35.410 | 25.265 | 85.709 | 1.00 | 16.07 |
| 1006 | O | SER | A | 160 | 34.732 | 26.171 | 85.228 | 1.00 | 15.87 |
| 1007 | N | LYS | A | 161 | 36.686 | 24.989 | 85.380 | 1.00 | 15.92 |
| 1008 | CA | LYS | A | 161 | 37.486 | 25.647 | 84.346 | 1.00 | 15.46 |
| 1009 | CB | LYS | A | 161 | 38.965 | 25.799 | 84.766 | 1.00 | 15.46 |
| 1010 | CG | LYS | A | 161 | 39.124 | 26.413 | 86.164 | 1.00 | 17.24 |
| 1011 | CD | LYS | A | 161 | 40.453 | 27.165 | 86.411 | 1.00 | 21.95 |

FIGURE 3 (Cont.)

| A | B | C | D | E | F | G | H | I | J |
|---|---|---|---|---|---|---|---|---|---|
| 1012 | CE | LYS | A | 161 | 41.710 | 26.418 | 85.910 | 1.00 | 23.57 |
| 1013 | NZ | LYS | A | 161 | 42.753 | 26.169 | 86.980 | 1.00 | 24.44 |
| 1014 | C | LYS | A | 161 | 37.392 | 24.855 | 83.049 | 1.00 | 14.79 |
| 1015 | O | LYS | A | 161 | 37.559 | 23.595 | 83.015 | 1.00 | 14.49 |
| 1016 | N | LEU | A | 162 | 37.182 | 25.632 | 81.983 | 1.00 | 13.63 |
| 1017 | CA | LEU | A | 162 | 36.771 | 25.121 | 80.681 | 1.00 | 12.64 |
| 1018 | CB | LEU | A | 162 | 35.593 | 25.936 | 80.144 | 1.00 | 12.40 |
| 1019 | CG | LEU | A | 162 | 34.327 | 25.223 | 80.545 | 1.00 | 9.98 |
| 1020 | CD1 | LEU | A | 162 | 33.198 | 26.086 | 80.170 | 1.00 | 7.37 |
| 1021 | CD2 | LEU | A | 162 | 34.271 | 23.868 | 79.871 | 1.00 | 6.97 |
| 1022 | C | LEU | A | 162 | 37.853 | 25.086 | 79.611 | 1.00 | 12.38 |
| 1023 | O | LEU | A | 162 | 38.588 | 26.074 | 79.424 | 1.00 | 12.92 |
| 1024 | N | ALA | A | 163 | 37.910 | 23.956 | 78.901 | 1.00 | 10.32 |
| 1025 | CA | ALA | A | 163 | 38.772 | 23.847 | 77.747 | 1.00 | 9.69 |
| 1026 | CB | ALA | A | 163 | 39.904 | 22.779 | 77.990 | 1.00 | 9.12 |
| 1027 | C | ALA | A | 163 | 37.895 | 23.484 | 76.560 | 1.00 | 8.70 |
| 1028 | O | ALA | A | 163 | 37.121 | 22.590 | 76.628 | 1.00 | 9.42 |
| 1029 | N | TYR | A | 164 | 37.993 | 24.213 | 75.473 | 1.00 | 8.29 |
| 1030 | CA | TYR | A | 164 | 37.263 | 23.850 | 74.283 | 1.00 | 8.12 |
| 1031 | CB | TYR | A | 164 | 35.955 | 24.531 | 74.291 | 1.00 | 7.93 |
| 1032 | CG | TYR | A | 164 | 35.976 | 26.021 | 74.142 | 1.00 | 7.82 |
| 1033 | CD1 | TYR | A | 164 | 35.640 | 26.617 | 72.931 | 1.00 | 7.37 |
| 1034 | CE1 | TYR | A | 164 | 35.589 | 28.009 | 72.793 | 1.00 | 7.03 |
| 1035 | CZ | TYR | A | 164 | 35.862 | 28.802 | 73.871 | 1.00 | 6.70 |
| 1036 | OH | TYR | A | 164 | 35.789 | 30.160 | 73.737 | 1.00 | 8.47 |
| 1037 | CE2 | TYR | A | 164 | 36.203 | 28.236 | 75.096 | 1.00 | 5.57 |
| 1038 | CD2 | TYR | A | 164 | 36.254 | 26.854 | 75.234 | 1.00 | 7.58 |
| 1039 | C | TYR | A | 164 | 37.919 | 24.156 | 72.980 | 1.00 | 8.21 |
| 1040 | O | TYR | A | 164 | 38.603 | 25.177 | 72.833 | 1.00 | 7.60 |
| 1041 | N | VAL | A | 165 | 37.688 | 23.248 | 72.019 | 1.00 | 9.36 |
| 1042 | CA | VAL | A | 165 | 38.210 | 23.415 | 70.654 | 1.00 | 9.64 |
| 1043 | CB | VAL | A | 165 | 38.828 | 22.132 | 70.028 | 1.00 | 9.86 |
| 1044 | CG1 | VAL | A | 165 | 39.299 | 22.440 | 68.615 | 1.00 | 8.01 |
| 1045 | CG2 | VAL | A | 165 | 40.000 | 21.565 | 70.877 | 1.00 | 7.80 |
| 1046 | C | VAL | A | 165 | 37.120 | 23.979 | 69.753 | 1.00 | 9.75 |
| 1047 | O | VAL | A | 165 | 35.995 | 23.465 | 69.661 | 1.00 | 9.50 |
| 1048 | N | TYR | A | 166 | 37.500 | 25.078 | 69.117 | 1.00 | 10.36 |
| 1049 | CA | TYR | A | 166 | 36.676 | 25.767 | 68.170 | 1.00 | 10.50 |
| 1050 | CB | TYR | A | 166 | 36.146 | 26.975 | 68.832 | 1.00 | 9.79 |
| 1051 | CG | TYR | A | 166 | 35.338 | 27.826 | 67.917 | 1.00 | 9.30 |
| 1052 | CD1 | TYR | A | 166 | 34.122 | 27.381 | 67.442 | 1.00 | 6.42 |
| 1053 | CE1 | TYR | A | 166 | 33.342 | 28.204 | 66.615 | 1.00 | 8.78 |
| 1054 | CZ | TYR | A | 166 | 33.806 | 29.460 | 66.280 | 1.00 | 6.87 |
| 1055 | OH | TYR | A | 166 | 33.046 | 30.283 | 65.517 | 1.00 | 10.62 |
| 1056 | CE2 | TYR | A | 166 | 35.013 | 29.901 | 66.735 | 1.00 | 8.03 |
| 1057 | CD2 | TYR | A | 166 | 35.776 | 29.108 | 67.551 | 1.00 | 7.65 |
| 1058 | C | TYR | A | 166 | 37.398 | 26.180 | 66.887 | 1.00 | 11.53 |
| 1059 | O | TYR | A | 166 | 38.462 | 26.823 | 66.928 | 1.00 | 12.29 |
| 1060 | N | GLN | A | 167 | 36.767 | 25.850 | 65.758 | 1.00 | 12.10 |
| 1061 | CA | GLN | A | 167 | 37.344 | 26.065 | 64.450 | 1.00 | 12.86 |
| 1062 | CB | GLN | A | 167 | 37.035 | 27.500 | 63.971 | 1.00 | 13.63 |

FIGURE 3 (Cont.)

| A | B | C | D | E | F | G | H | I | J |
|---|---|---|---|---|---|---|---|---|---|
| 1063 | CG | GLN | A | 167 | 35.587 | 27.697 | 63.326 | 1.00 | 15.22 |
| 1064 | CD | GLN | A | 167 | 35.394 | 29.083 | 62.679 | 1.00 | 19.05 |
| 1065 | OE1 | GLN | A | 167 | 34.634 | 29.227 | 61.698 | 1.00 | 20.45 |
| 1066 | NE2 | GLN | A | 167 | 36.083 | 30.103 | 63.226 | 1.00 | 17.54 |
| 1067 | C | GLN | A | 167 | 38.841 | 25.726 | 64.511 | 1.00 | 12.78 |
| 1068 | O | GLN | A | 167 | 39.688 | 26.539 | 64.198 | 1.00 | 12.18 |
| 1069 | N | ASN | A | 168 | 39.132 | 24.512 | 64.989 | 1.00 | 12.64 |
| 1070 | CA | ASN | A | 168 | 40.505 | 23.948 | 65.036 | 1.00 | 12.77 |
| 1071 | CB | ASN | A | 168 | 41.114 | 23.877 | 63.634 | 1.00 | 12.77 |
| 1072 | CG | ASN | A | 168 | 40.521 | 22.771 | 62.785 | 1.00 | 14.48 |
| 1073 | OD1 | ASN | A | 168 | 41.216 | 22.185 | 61.948 | 1.00 | 16.08 |
| 1074 | ND2 | ASN | A | 168 | 39.234 | 22.489 | 62.981 | 1.00 | 15.27 |
| 1075 | C | ASN | A | 168 | 41.554 | 24.575 | 65.953 | 1.00 | 12.40 |
| 1076 | O | ASN | A | 168 | 42.715 | 24.255 | 65.846 | 1.00 | 12.34 |
| 1077 | N | ASN | A | 169 | 41.142 | 25.447 | 66.855 | 1.00 | 12.18 |
| 1078 | CA | ASN | A | 169 | 42.040 | 26.229 | 67.686 | 1.00 | 11.73 |
| 1079 | CB | ASN | A | 169 | 41.745 | 27.703 | 67.444 | 1.00 | 12.32 |
| 1080 | CG | ASN | A | 169 | 42.704 | 28.364 | 66.511 | 1.00 | 13.44 |
| 1081 | OD1 | ASN | A | 169 | 42.312 | 29.253 | 65.778 | 1.00 | 13.56 |
| 1082 | ND2 | ASN | A | 169 | 43.960 | 27.985 | 66.566 | 1.00 | 13.99 |
| 1083 | C | ASN | A | 169 | 41.681 | 25.941 | 69.155 | 1.00 | 11.39 |
| 1084 | O | ASN | A | 169 | 40.499 | 25.777 | 69.461 | 1.00 | 11.88 |
| 1085 | N | ILE | A | 170 | 42.642 | 25.935 | 70.086 | 1.00 | 10.98 |
| 1086 | CA | ILE | A | 170 | 42.299 | 25.770 | 71.501 | 1.00 | 10.05 |
| 1087 | CB | ILE | A | 170 | 43.395 | 25.048 | 72.305 | 1.00 | 9.84 |
| 1088 | CG1 | ILE | A | 170 | 43.548 | 23.634 | 71.802 | 1.00 | 9.96 |
| 1089 | CD1 | ILE | A | 170 | 44.530 | 22.772 | 72.608 | 1.00 | 9.30 |
| 1090 | CG2 | ILE | A | 170 | 43.034 | 25.013 | 73.792 | 1.00 | 7.03 |
| 1091 | C | ILE | A | 170 | 41.913 | 27.099 | 72.163 | 1.00 | 10.48 |
| 1092 | O | ILE | A | 170 | 42.468 | 28.192 | 71.897 | 1.00 | 9.91 |
| 1093 | N | TYR | A | 171 | 40.938 | 26.979 | 73.048 | 1.00 | 10.63 |
| 1094 | CA | TYR | A | 171 | 40.451 | 28.129 | 73.760 | 1.00 | 10.39 |
| 1095 | CB | TYR | A | 171 | 39.086 | 28.469 | 73.219 | 1.00 | 10.01 |
| 1096 | CG | TYR | A | 171 | 39.121 | 29.404 | 72.051 | 1.00 | 9.84 |
| 1097 | CD1 | TYR | A | 171 | 39.322 | 30.731 | 72.245 | 1.00 | 8.07 |
| 1098 | CE1 | TYR | A | 171 | 39.311 | 31.610 | 71.211 | 1.00 | 6.78 |
| 1099 | CZ | TYR | A | 171 | 39.119 | 31.187 | 69.985 | 1.00 | 6.33 |
| 1100 | OH | TYR | A | 171 | 39.139 | 32.126 | 69.070 | 1.00 | 6.47 |
| 1101 | CE2 | TYR | A | 171 | 38.875 | 29.901 | 69.706 | 1.00 | 7.97 |
| 1102 | CD2 | TYR | A | 171 | 38.877 | 28.982 | 70.755 | 1.00 | 9.51 |
| 1103 | C | TYR | A | 171 | 40.377 | 27.670 | 75.203 | 1.00 | 10.29 |
| 1104 | O | TYR | A | 171 | 40.278 | 26.437 | 75.440 | 1.00 | 9.87 |
| 1105 | N | LEU | A | 172 | 40.410 | 28.631 | 76.150 | 1.00 | 9.58 |
| 1106 | CA | LEU | A | 172 | 40.296 | 28.314 | 77.589 | 1.00 | 9.56 |
| 1107 | CB | LEU | A | 172 | 41.694 | 28.151 | 78.166 | 1.00 | 8.98 |
| 1108 | CG | LEU | A | 172 | 41.891 | 28.287 | 79.660 | 1.00 | 9.55 |
| 1109 | CD1 | LEU | A | 172 | 41.598 | 26.925 | 80.339 | 1.00 | 9.28 |
| 1110 | CD2 | LEU | A | 172 | 43.328 | 28.882 | 79.999 | 1.00 | 5.44 |
| 1111 | C | LEU | A | 172 | 39.467 | 29.345 | 78.366 | 1.00 | 9.63 |
| 1112 | O | LEU | A | 172 | 39.677 | 30.536 | 78.199 | 1.00 | 9.77 |
| 1113 | N | LYS | A | 173 | 38.526 | 28.891 | 79.198 | 1.00 | 9.75 |

FIGURE 3 (Cont.)

| A | B | C | D | E | F | G | H | I | J |
|---|---|---|---|---|---|---|---|---|---|
| 1114 | CA | LYS | A | 173 | 37.596 | 29.785 | 79.928 | 1.00 | 10.17 |
| 1115 | CB | LYS | A | 173 | 36.116 | 29.417 | 79.655 | 1.00 | 10.38 |
| 1116 | CG | LYS | A | 173 | 35.196 | 30.455 | 78.909 | 1.00 | 9.48 |
| 1117 | CD | LYS | A | 173 | 33.716 | 29.936 | 78.847 | 1.00 | 8.40 |
| 1118 | CE | LYS | A | 173 | 32.693 | 30.954 | 78.409 | 1.00 | 7.04 |
| 1119 | NZ | LYS | A | 173 | 33.136 | 31.746 | 77.183 | 1.00 | 10.88 |
| 1120 | C | LYS | A | 173 | 37.878 | 29.601 | 81.406 | 1.00 | 10.66 |
| 1121 | O | LYS | A | 173 | 37.599 | 28.534 | 81.938 | 1.00 | 10.17 |
| 1122 | N | GLN | A | 174 | 38.417 | 30.639 | 82.067 | 1.00 | 11.71 |
| 1123 | CA | GLN | A | 174 | 38.855 | 30.556 | 83.488 | 1.00 | 12.19 |
| 1124 | CB | GLN | A | 174 | 39.473 | 31.899 | 83.960 | 1.00 | 12.71 |
| 1125 | CG | GLN | A | 174 | 40.732 | 31.726 | 84.832 | 1.00 | 13.71 |
| 1126 | CD | GLN | A | 174 | 41.752 | 30.847 | 84.143 | 1.00 | 14.60 |
| 1127 | OE1 | GLN | A | 174 | 42.402 | 31.308 | 83.211 | 1.00 | 15.90 |
| 1128 | NE2 | GLN | A | 174 | 41.849 | 29.562 | 84.544 | 1.00 | 14.07 |
| 1129 | C | GLN | A | 174 | 37.745 | 30.095 | 84.449 | 1.00 | 11.72 |
| 1130 | O | GLN | A | 174 | 37.887 | 29.105 | 85.153 | 1.00 | 11.21 |
| 1131 | N | ARG | A | 175 | 36.649 | 30.827 | 84.460 | 1.00 | 11.85 |
| 1132 | CA | ARG | A | 175 | 35.419 | 30.308 | 84.983 | 1.00 | 12.04 |
| 1133 | CB | ARG | A | 175 | 35.110 | 30.930 | 86.355 | 1.00 | 12.48 |
| 1134 | CG | ARG | A | 175 | 34.723 | 32.451 | 86.514 | 1.00 | 13.28 |
| 1135 | CD | ARG | A | 175 | 33.941 | 32.805 | 87.862 | 1.00 | 14.84 |
| 1136 | NE | ARG | A | 175 | 34.105 | 31.786 | 88.934 | 1.00 | 16.76 |
| 1137 | CZ | ARG | A | 175 | 33.233 | 30.772 | 89.273 | 1.00 | 15.95 |
| 1138 | NH1 | ARG | A | 175 | 32.053 | 30.611 | 88.673 | 1.00 | 16.22 |
| 1139 | NH2 | ARG | A | 175 | 33.554 | 29.912 | 90.247 | 1.00 | 13.83 |
| 1140 | C | ARG | A | 175 | 34.343 | 30.469 | 83.895 | 1.00 | 12.26 |
| 1141 | O | ARG | A | 175 | 34.606 | 31.095 | 82.881 | 1.00 | 12.42 |
| 1142 | N | PRO | A | 176 | 33.198 | 29.805 | 84.047 | 1.00 | 12.22 |
| 1143 | CA | PRO | A | 176 | 32.178 | 29.653 | 82.990 | 1.00 | 12.18 |
| 1144 | CB | PRO | A | 176 | 31.055 | 28.911 | 83.714 | 1.00 | 11.80 |
| 1145 | CG | PRO | A | 176 | 31.812 | 28.009 | 84.615 | 1.00 | 11.87 |
| 1146 | CD | PRO | A | 176 | 32.841 | 28.983 | 85.213 | 1.00 | 12.40 |
| 1147 | C | PRO | A | 176 | 31.584 | 30.830 | 82.244 | 1.00 | 12.74 |
| 1148 | O | PRO | A | 176 | 31.497 | 30.747 | 81.002 | 1.00 | 12.93 |
| 1149 | N | GLY | A | 177 | 31.128 | 31.852 | 82.950 | 1.00 | 13.13 |
| 1150 | CA | GLY | A | 177 | 30.612 | 33.012 | 82.272 | 1.00 | 13.90 |
| 1151 | C | GLY | A | 177 | 31.692 | 34.064 | 82.097 | 1.00 | 14.77 |
| 1152 | O | GLY | A | 177 | 31.432 | 35.237 | 82.380 | 1.00 | 14.96 |
| 1153 | N | ASP | A | 178 | 32.894 | 33.650 | 81.670 | 1.00 | 15.18 |
| 1154 | CA | ASP | A | 178 | 34.021 | 34.558 | 81.383 | 1.00 | 15.87 |
| 1155 | CB | ASP | A | 178 | 35.316 | 34.065 | 82.025 | 1.00 | 16.20 |
| 1156 | CG | ASP | A | 178 | 35.382 | 34.288 | 83.515 | 1.00 | 17.13 |
| 1157 | OD1 | ASP | A | 178 | 34.838 | 35.292 | 84.038 | 1.00 | 16.64 |
| 1158 | OD2 | ASP | A | 178 | 36.028 | 33.491 | 84.225 | 1.00 | 16.43 |
| 1159 | C | ASP | A | 178 | 34.373 | 34.622 | 79.893 | 1.00 | 16.19 |
| 1160 | O | ASP | A | 178 | 34.130 | 33.657 | 79.140 | 1.00 | 16.28 |
| 1161 | N | PRO | A | 179 | 35.041 | 35.716 | 79.496 | 1.00 | 16.37 |
| 1162 | CA | PRO | A | 179 | 35.678 | 35.800 | 78.188 | 1.00 | 16.34 |
| 1163 | CB | PRO | A | 179 | 36.524 | 37.060 | 78.284 | 1.00 | 16.18 |
| 1164 | CG | PRO | A | 179 | 35.833 | 37.902 | 79.232 | 1.00 | 17.16 |

FIGURE 3 (Cont.)

| A | B | C | D | E | F | G | H | I | J |
|---|---|---|---|---|---|---|---|---|---|
| 1165 | CD  | PRO | A | 179 | 35.258 | 36.950 | 80.262 | 1.00 | 16.51 |
| 1166 | C   | PRO | A | 179 | 36.582 | 34.589 | 77.998 | 1.00 | 16.40 |
| 1167 | O   | PRO | A | 179 | 37.166 | 34.115 | 78.974 | 1.00 | 16.83 |
| 1168 | N   | PRO | A | 180 | 36.676 | 34.071 | 76.780 | 1.00 | 15.86 |
| 1169 | CA  | PRO | A | 180 | 37.535 | 32.940 | 76.540 | 1.00 | 15.28 |
| 1170 | CB  | PRO | A | 180 | 36.968 | 32.368 | 75.240 | 1.00 | 15.73 |
| 1171 | CG  | PRO | A | 180 | 35.698 | 33.113 | 74.983 | 1.00 | 16.02 |
| 1172 | CD  | PRO | A | 180 | 35.989 | 34.468 | 75.541 | 1.00 | 15.89 |
| 1173 | C   | PRO | A | 180 | 38.914 | 33.424 | 76.324 | 1.00 | 14.84 |
| 1174 | O   | PRO | A | 180 | 39.093 | 34.544 | 75.831 | 1.00 | 15.04 |
| 1175 | N   | PHE | A | 181 | 39.877 | 32.585 | 76.643 | 1.00 | 13.82 |
| 1176 | CA  | PHE | A | 181 | 41.261 | 32.913 | 76.381 | 1.00 | 13.86 |
| 1177 | CB  | PHE | A | 181 | 42.086 | 32.828 | 77.664 | 1.00 | 14.05 |
| 1178 | CG  | PHE | A | 181 | 43.529 | 33.114 | 77.463 | 1.00 | 14.49 |
| 1179 | CD1 | PHE | A | 181 | 44.014 | 34.408 | 77.590 | 1.00 | 14.78 |
| 1180 | CE1 | PHE | A | 181 | 45.354 | 34.682 | 77.383 | 1.00 | 14.57 |
| 1181 | CZ  | PHE | A | 181 | 46.224 | 33.666 | 77.052 | 1.00 | 14.67 |
| 1182 | CE2 | PHE | A | 181 | 45.758 | 32.382 | 76.896 | 1.00 | 13.23 |
| 1183 | CD2 | PHE | A | 181 | 44.409 | 32.096 | 77.109 | 1.00 | 13.84 |
| 1184 | C   | PHE | A | 181 | 41.810 | 31.981 | 75.310 | 1.00 | 13.27 |
| 1185 | O   | PHE | A | 181 | 41.871 | 30.754 | 75.509 | 1.00 | 13.81 |
| 1186 | N   | GLN | A | 182 | 42.208 | 32.557 | 74.177 | 1.00 | 12.71 |
| 1187 | CA  | GLN | A | 182 | 42.679 | 31.773 | 73.031 | 1.00 | 11.75 |
| 1188 | CB  | GLN | A | 182 | 42.767 | 32.680 | 71.791 | 1.00 | 11.62 |
| 1189 | CG  | GLN | A | 182 | 43.019 | 31.857 | 70.509 | 1.00 | 8.18 |
| 1190 | CD  | GLN | A | 182 | 42.633 | 32.524 | 69.219 | 1.00 | 5.24 |
| 1191 | OE1 | GLN | A | 182 | 42.953 | 31.963 | 68.194 | 1.00 | 5.41 |
| 1192 | NE2 | GLN | A | 182 | 41.942 | 33.693 | 69.250 | 1.00 | 2.00 |
| 1193 | C   | GLN | A | 182 | 44.042 | 31.117 | 73.241 | 1.00 | 11.86 |
| 1194 | O   | GLN | A | 182 | 44.977 | 31.813 | 73.570 | 1.00 | 12.61 |
| 1195 | N   | ILE | A | 183 | 44.206 | 29.816 | 73.010 | 1.00 | 11.88 |
| 1196 | CA  | ILE | A | 183 | 45.576 | 29.233 | 73.159 | 1.00 | 12.01 |
| 1197 | CB  | ILE | A | 183 | 45.559 | 27.811 | 73.744 | 1.00 | 11.95 |
| 1198 | CG1 | ILE | A | 183 | 44.819 | 27.747 | 75.107 | 1.00 | 11.36 |
| 1199 | CD1 | ILE | A | 183 | 45.362 | 28.636 | 76.232 | 1.00 | 12.57 |
| 1200 | CG2 | ILE | A | 183 | 46.977 | 27.280 | 73.815 | 1.00 | 12.05 |
| 1201 | C   | ILE | A | 183 | 46.395 | 29.214 | 71.867 | 1.00 | 12.11 |
| 1202 | O   | ILE | A | 183 | 47.399 | 29.916 | 71.743 | 1.00 | 11.31 |
| 1203 | N   | THR | A | 184 | 45.931 | 28.406 | 70.915 | 1.00 | 12.44 |
| 1204 | CA  | THR | A | 184 | 46.464 | 28.418 | 69.537 | 1.00 | 12.68 |
| 1205 | CB  | THR | A | 184 | 46.360 | 27.035 | 68.958 | 1.00 | 11.79 |
| 1206 | OG1 | THR | A | 184 | 45.010 | 26.812 | 68.635 | 1.00 | 12.45 |
| 1207 | CG2 | THR | A | 184 | 46.616 | 25.991 | 69.999 | 1.00 | 11.65 |
| 1208 | C   | THR | A | 184 | 45.747 | 29.413 | 68.585 | 1.00 | 13.14 |
| 1209 | O   | THR | A | 184 | 44.515 | 29.623 | 68.623 | 1.00 | 13.23 |
| 1210 | N   | PHE | A | 185 | 46.536 | 29.984 | 67.697 | 1.00 | 14.09 |
| 1211 | CA  | PHE | A | 185 | 45.999 | 30.909 | 66.683 | 1.00 | 15.41 |
| 1212 | CB  | PHE | A | 185 | 46.639 | 32.334 | 66.822 | 1.00 | 15.60 |
| 1213 | CG  | PHE | A | 185 | 46.460 | 32.968 | 68.195 | 1.00 | 15.69 |
| 1214 | CD1 | PHE | A | 185 | 47.221 | 32.533 | 69.285 | 1.00 | 14.03 |
| 1215 | CE1 | PHE | A | 185 | 47.070 | 33.114 | 70.566 | 1.00 | 14.34 |

FIGURE 3 (Cont.)

| A | B | C | D | E | F | G | H | I | J |
|---|---|---|---|---|---|---|---|---|---|
| 1216 | CZ | PHE | A | 185 | 46.139 | 34.157 | 70.766 | 1.00 | 15.92 |
| 1217 | CE2 | PHE | A | 185 | 45.364 | 34.620 | 69.668 | 1.00 | 17.50 |
| 1218 | CD2 | PHE | A | 185 | 45.530 | 34.015 | 68.385 | 1.00 | 17.05 |
| 1219 | C | PHE | A | 185 | 46.202 | 30.364 | 65.249 | 1.00 | 15.63 |
| 1220 | O | PHE | A | 185 | 45.875 | 31.062 | 64.270 | 1.00 | 15.35 |
| 1221 | N | ASN | A | 186 | 46.766 | 29.153 | 65.123 | 1.00 | 15.37 |
| 1222 | CA | ASN | A | 186 | 47.272 | 28.740 | 63.817 | 1.00 | 15.86 |
| 1223 | CB | ASN | A | 186 | 48.686 | 28.155 | 63.909 | 1.00 | 14.84 |
| 1224 | CG | ASN | A | 186 | 48.708 | 26.804 | 64.514 | 1.00 | 13.79 |
| 1225 | OD1 | ASN | A | 186 | 47.703 | 26.332 | 65.044 | 1.00 | 12.50 |
| 1226 | ND2 | ASN | A | 186 | 49.855 | 26.158 | 64.456 | 1.00 | 10.92 |
| 1227 | C | ASN | A | 186 | 46.275 | 27.838 | 63.076 | 1.00 | 16.95 |
| 1228 | O | ASN | A | 186 | 46.567 | 27.350 | 61.962 | 1.00 | 17.27 |
| 1229 | N | GLY | A | 187 | 45.075 | 27.725 | 63.670 | 1.00 | 17.63 |
| 1230 | CA | GLY | A | 187 | 44.086 | 26.701 | 63.349 | 1.00 | 17.57 |
| 1231 | C | GLY | A | 187 | 43.219 | 27.092 | 62.173 | 1.00 | 18.40 |
| 1232 | O | GLY | A | 187 | 42.717 | 28.258 | 62.102 | 1.00 | 18.22 |
| 1233 | N | ARG | A | 188 | 43.062 | 26.125 | 61.247 | 1.00 | 18.99 |
| 1234 | CA | ARG | A | 188 | 42.322 | 26.289 | 59.969 | 1.00 | 19.50 |
| 1235 | CB | ARG | A | 188 | 43.180 | 27.110 | 58.926 | 1.00 | 19.67 |
| 1236 | CG | ARG | A | 188 | 43.556 | 28.639 | 59.389 | 1.00 | 20.84 |
| 1237 | CD | ARG | A | 188 | 44.409 | 29.503 | 58.436 | 1.00 | 24.90 |
| 1238 | NE | ARG | A | 188 | 44.860 | 28.738 | 57.266 | 1.00 | 27.06 |
| 1239 | CZ | ARG | A | 188 | 45.081 | 29.227 | 56.036 | 1.00 | 27.45 |
| 1240 | NH1 | ARG | A | 188 | 44.931 | 30.532 | 55.760 | 1.00 | 26.54 |
| 1241 | NH2 | ARG | A | 188 | 45.477 | 28.377 | 55.073 | 1.00 | 25.86 |
| 1242 | C | ARG | A | 188 | 41.805 | 24.931 | 59.414 | 1.00 | 19.06 |
| 1243 | O | ARG | A | 188 | 42.545 | 23.955 | 59.376 | 1.00 | 19.35 |
| 1244 | N | GLU | A | 189 | 40.527 | 24.905 | 59.008 | 1.00 | 18.60 |
| 1245 | CA | GLU | A | 189 | 39.810 | 23.685 | 58.627 | 1.00 | 18.34 |
| 1246 | CB | GLU | A | 189 | 38.348 | 23.945 | 58.133 | 1.00 | 18.44 |
| 1247 | CG | GLU | A | 189 | 38.046 | 23.929 | 56.618 | 1.00 | 21.01 |
| 1248 | CD | GLU | A | 189 | 37.776 | 25.322 | 55.970 | 1.00 | 26.60 |
| 1249 | OE1 | GLU | A | 189 | 37.672 | 26.366 | 56.645 | 1.00 | 31.18 |
| 1250 | OE2 | GLU | A | 189 | 37.683 | 25.425 | 54.735 | 1.00 | 25.38 |
| 1251 | C | GLU | A | 189 | 40.608 | 22.814 | 57.680 | 1.00 | 17.54 |
| 1252 | O | GLU | A | 189 | 41.400 | 23.269 | 56.892 | 1.00 | 17.43 |
| 1253 | N | ASN | A | 190 | 40.443 | 21.523 | 57.865 | 1.00 | 17.29 |
| 1254 | CA | ASN | A | 190 | 41.115 | 20.503 | 57.075 | 1.00 | 16.64 |
| 1255 | CB | ASN | A | 190 | 40.420 | 20.349 | 55.708 | 1.00 | 16.61 |
| 1256 | CG | ASN | A | 190 | 39.195 | 19.485 | 55.797 | 1.00 | 19.21 |
| 1257 | OD1 | ASN | A | 190 | 39.265 | 18.395 | 56.349 | 1.00 | 19.97 |
| 1258 | ND2 | ASN | A | 190 | 38.066 | 19.955 | 55.262 | 1.00 | 18.70 |
| 1259 | C | ASN | A | 190 | 42.638 | 20.618 | 56.921 | 1.00 | 15.48 |
| 1260 | O | ASN | A | 190 | 43.188 | 20.016 | 55.998 | 1.00 | 15.04 |
| 1261 | N | LYS | A | 191 | 43.326 | 21.306 | 57.833 | 1.00 | 14.74 |
| 1262 | CA | LYS | A | 191 | 44.783 | 21.553 | 57.636 | 1.00 | 14.88 |
| 1263 | CB | LYS | A | 191 | 45.007 | 22.897 | 56.876 | 1.00 | 15.19 |
| 1264 | CG | LYS | A | 191 | 45.016 | 22.837 | 55.282 | 1.00 | 16.18 |
| 1265 | CD | LYS | A | 191 | 44.979 | 24.332 | 54.608 | 1.00 | 22.93 |
| 1266 | CE | LYS | A | 191 | 45.347 | 24.355 | 53.045 | 1.00 | 25.29 |

FIGURE 3 (Cont.)

| A | B | C | D | E | F | G | H | I | J |
|---|---|---|---|---|---|---|---|---|---|
| 1267 | NZ | LYS | A | 191 | 45.375 | 25.705 | 52.339 | 1.00 | 25.60 |
| 1268 | C | LYS | A | 191 | 45.595 | 21.512 | 58.962 | 1.00 | 14.64 |
| 1269 | O | LYS | A | 191 | 46.489 | 20.639 | 59.192 | 1.00 | 14.88 |
| 1270 | N | ILE | A | 192 | 45.239 | 22.444 | 59.842 | 1.00 | 13.52 |
| 1271 | CA | ILE | A | 192 | 45.906 | 22.618 | 61.120 | 1.00 | 12.38 |
| 1272 | CB | ILE | A | 192 | 46.429 | 24.104 | 61.271 | 1.00 | 12.82 |
| 1273 | CG1 | ILE | A | 192 | 47.502 | 24.400 | 60.204 | 1.00 | 12.63 |
| 1274 | CD1 | ILE | A | 192 | 48.631 | 23.325 | 60.135 | 1.00 | 12.75 |
| 1275 | CG2 | ILE | A | 192 | 46.945 | 24.351 | 62.668 | 1.00 | 13.02 |
| 1276 | C | ILE | A | 192 | 44.877 | 22.309 | 62.155 | 1.00 | 11.01 |
| 1277 | O | ILE | A | 192 | 43.788 | 22.862 | 62.109 | 1.00 | 10.29 |
| 1278 | N | PHE | A | 193 | 45.244 | 21.431 | 63.088 | 1.00 | 10.02 |
| 1279 | CA | PHE | A | 193 | 44.322 | 20.869 | 64.049 | 1.00 | 9.24 |
| 1280 | CB | PHE | A | 193 | 44.107 | 19.388 | 63.694 | 1.00 | 9.10 |
| 1281 | CG | PHE | A | 193 | 43.259 | 19.118 | 62.442 | 1.00 | 8.90 |
| 1282 | CD1 | PHE | A | 193 | 41.858 | 19.145 | 62.498 | 1.00 | 7.28 |
| 1283 | CE1 | PHE | A | 193 | 41.047 | 18.805 | 61.361 | 1.00 | 7.26 |
| 1284 | CZ | PHE | A | 193 | 41.660 | 18.429 | 60.202 | 1.00 | 6.78 |
| 1285 | CE2 | PHE | A | 193 | 43.100 | 18.430 | 60.128 | 1.00 | 6.82 |
| 1286 | CD2 | PHE | A | 193 | 43.866 | 18.763 | 61.237 | 1.00 | 7.56 |
| 1287 | C | PHE | A | 193 | 44.880 | 20.918 | 65.498 | 1.00 | 9.12 |
| 1288 | O | PHE | A | 193 | 45.672 | 20.021 | 65.899 | 1.00 | 8.63 |
| 1289 | N | ASN | A | 194 | 44.454 | 21.913 | 66.290 | 1.00 | 8.20 |
| 1290 | CA | ASN | A | 194 | 44.766 | 21.930 | 67.749 | 1.00 | 7.46 |
| 1291 | CB | ASN | A | 194 | 45.177 | 23.323 | 68.247 | 1.00 | 6.48 |
| 1292 | CG | ASN | A | 194 | 46.115 | 24.038 | 67.294 | 1.00 | 5.66 |
| 1293 | OD1 | ASN | A | 194 | 47.366 | 23.957 | 67.411 | 1.00 | 2.00 |
| 1294 | ND2 | ASN | A | 194 | 45.510 | 24.827 | 66.371 | 1.00 | 4.57 |
| 1295 | C | ASN | A | 194 | 43.683 | 21.369 | 68.724 | 1.00 | 7.23 |
| 1296 | O | ASN | A | 194 | 42.561 | 21.889 | 68.834 | 1.00 | 6.18 |
| 1297 | N | GLY | A | 195 | 44.069 | 20.329 | 69.469 | 1.00 | 6.92 |
| 1298 | CA | GLY | A | 195 | 43.247 | 19.790 | 70.539 | 1.00 | 8.49 |
| 1299 | C | GLY | A | 195 | 42.233 | 18.747 | 70.080 | 1.00 | 9.66 |
| 1300 | O | GLY | A | 195 | 41.592 | 18.083 | 70.890 | 1.00 | 10.67 |
| 1301 | N | ILE | A | 196 | 42.039 | 18.632 | 68.775 | 1.00 | 9.95 |
| 1302 | CA | ILE | A | 196 | 41.422 | 17.453 | 68.214 | 1.00 | 10.06 |
| 1303 | CB | ILE | A | 196 | 40.064 | 17.777 | 67.602 | 1.00 | 8.78 |
| 1304 | CG1 | ILE | A | 196 | 40.274 | 18.444 | 66.261 | 1.00 | 8.59 |
| 1305 | CD1 | ILE | A | 196 | 39.396 | 19.599 | 65.981 | 1.00 | 12.00 |
| 1306 | CG2 | ILE | A | 196 | 39.298 | 18.626 | 68.541 | 1.00 | 7.72 |
| 1307 | C | ILE | A | 196 | 42.384 | 16.807 | 67.222 | 1.00 | 10.51 |
| 1308 | O | ILE | A | 196 | 43.507 | 17.309 | 66.974 | 1.00 | 11.98 |
| 1309 | N | PRO | A | 197 | 41.998 | 15.651 | 66.718 | 1.00 | 10.15 |
| 1310 | CA | PRO | A | 197 | 42.814 | 15.020 | 65.700 | 1.00 | 9.75 |
| 1311 | CB | PRO | A | 197 | 42.593 | 13.515 | 65.945 | 1.00 | 9.63 |
| 1312 | CG | PRO | A | 197 | 41.598 | 13.523 | 67.116 | 1.00 | 9.67 |
| 1313 | CD | PRO | A | 197 | 40.901 | 14.791 | 67.144 | 1.00 | 8.91 |
| 1314 | C | PRO | A | 197 | 42.436 | 15.419 | 64.319 | 1.00 | 9.66 |
| 1315 | O | PRO | A | 197 | 41.308 | 15.882 | 64.031 | 1.00 | 9.52 |
| 1316 | N | ASP | A | 198 | 43.439 | 15.225 | 63.461 | 1.00 | 9.47 |
| 1317 | CA | ASP | A | 198 | 43.221 | 15.059 | 62.057 | 1.00 | 9.99 |

FIGURE 3 (Cont.)

| A | B | C | D | E | F | G | H | I | J |
|---|---|---|---|---|---|---|---|---|---|
| 1318 | CB | ASP | A | 198 | 44.563 | 15.181 | 61.314 | 1.00 | 10.00 |
| 1319 | CG | ASP | A | 198 | 45.432 | 13.888 | 61.381 | 1.00 | 15.73 |
| 1320 | OD1 | ASP | A | 198 | 45.022 | 12.821 | 61.980 | 1.00 | 18.50 |
| 1321 | OD2 | ASP | A | 198 | 46.549 | 13.829 | 60.812 | 1.00 | 20.20 |
| 1322 | C | ASP | A | 198 | 42.536 | 13.667 | 61.966 | 1.00 | 8.92 |
| 1323 | O | ASP | A | 198 | 42.370 | 12.996 | 63.001 | 1.00 | 8.89 |
| 1324 | N | TRP | A | 199 | 42.196 | 13.260 | 60.742 | 1.00 | 7.92 |
| 1325 | CA | TRP | A | 199 | 41.417 | 12.064 | 60.447 | 1.00 | 7.30 |
| 1326 | CB | TRP | A | 199 | 41.143 | 11.941 | 58.954 | 1.00 | 6.13 |
| 1327 | CG | TRP | A | 199 | 40.078 | 10.932 | 58.648 | 1.00 | 4.99 |
| 1328 | CD1 | TRP | A | 199 | 38.754 | 11.148 | 58.516 | 1.00 | 2.84 |
| 1329 | NE1 | TRP | A | 199 | 38.096 | 9.969 | 58.255 | 1.00 | 2.00 |
| 1330 | CE2 | TRP | A | 199 | 39.027 | 8.975 | 58.209 | 1.00 | 3.79 |
| 1331 | CD2 | TRP | A | 199 | 40.277 | 9.558 | 58.413 | 1.00 | 4.71 |
| 1332 | CE3 | TRP | A | 199 | 41.386 | 8.737 | 58.440 | 1.00 | 2.00 |
| 1333 | CZ3 | TRP | A | 199 | 41.214 | 7.419 | 58.240 | 1.00 | 2.00 |
| 1334 | CH2 | TRP | A | 199 | 39.996 | 6.899 | 58.050 | 1.00 | 2.00 |
| 1335 | CZ2 | TRP | A | 199 | 38.875 | 7.658 | 58.047 | 1.00 | 3.85 |
| 1336 | C | TRP | A | 199 | 42.127 | 10.818 | 60.787 | 1.00 | 8.48 |
| 1337 | O | TRP | A | 199 | 41.543 | 9.940 | 61.388 | 1.00 | 9.66 |
| 1338 | N | VAL | A | 200 | 43.368 | 10.677 | 60.334 | 1.00 | 8.98 |
| 1339 | CA | VAL | A | 200 | 44.075 | 9.423 | 60.558 | 1.00 | 8.44 |
| 1340 | CB | VAL | A | 200 | 45.350 | 9.261 | 59.686 | 1.00 | 8.16 |
| 1341 | CG1 | VAL | A | 200 | 45.715 | 7.778 | 59.667 | 1.00 | 7.03 |
| 1342 | CG2 | VAL | A | 200 | 46.490 | 10.097 | 60.195 | 1.00 | 4.31 |
| 1343 | C | VAL | A | 200 | 44.389 | 9.197 | 62.030 | 1.00 | 9.57 |
| 1344 | O | VAL | A | 200 | 44.444 | 8.048 | 62.490 | 1.00 | 11.04 |
| 1345 | N | TYR | A | 201 | 44.623 | 10.293 | 62.760 | 1.00 | 9.82 |
| 1346 | CA | TYR | A | 201 | 44.782 | 10.190 | 64.207 | 1.00 | 9.28 |
| 1347 | CB | TYR | A | 201 | 45.395 | 11.507 | 64.820 | 1.00 | 7.70 |
| 1348 | CG | TYR | A | 201 | 46.938 | 11.408 | 64.935 | 1.00 | 6.66 |
| 1349 | CD1 | TYR | A | 201 | 47.533 | 10.905 | 66.047 | 1.00 | 2.00 |
| 1350 | CE1 | TYR | A | 201 | 48.908 | 10.806 | 66.138 | 1.00 | 8.22 |
| 1351 | CZ | TYR | A | 201 | 49.701 | 11.193 | 65.095 | 1.00 | 9.66 |
| 1352 | OH | TYR | A | 201 | 51.048 | 11.109 | 65.135 | 1.00 | 9.82 |
| 1353 | CE2 | TYR | A | 201 | 49.116 | 11.699 | 63.955 | 1.00 | 11.05 |
| 1354 | CD2 | TYR | A | 201 | 47.758 | 11.820 | 63.890 | 1.00 | 5.39 |
| 1355 | C | TYR | A | 201 | 43.474 | 9.805 | 64.877 | 1.00 | 9.82 |
| 1356 | O | TYR | A | 201 | 43.510 | 9.263 | 65.904 | 1.00 | 10.15 |
| 1357 | N | GLU | A | 202 | 42.334 | 10.118 | 64.311 | 1.00 | 11.33 |
| 1358 | CA | GLU | A | 202 | 41.093 | 9.775 | 64.995 | 1.00 | 15.25 |
| 1359 | CB | GLU | A | 202 | 40.000 | 10.794 | 64.666 | 1.00 | 15.22 |
| 1360 | CG | GLU | A | 202 | 38.695 | 10.174 | 64.193 | 1.00 | 24.35 |
| 1361 | CD | GLU | A | 202 | 38.523 | 10.259 | 62.690 | 1.00 | 41.08 |
| 1362 | OE1 | GLU | A | 202 | 37.600 | 9.607 | 62.157 | 1.00 | 43.03 |
| 1363 | OE2 | GLU | A | 202 | 39.311 | 10.981 | 62.040 | 1.00 | 42.98 |
| 1364 | C | GLU | A | 202 | 40.822 | 8.276 | 64.927 | 1.00 | 15.80 |
| 1365 | O | GLU | A | 202 | 40.742 | 7.628 | 65.914 | 1.00 | 17.02 |
| 1366 | N | GLU | A | 203 | 40.727 | 7.832 | 63.690 | 1.00 | 15.94 |
| 1367 | CA | GLU | A | 203 | 40.387 | 6.468 | 63.453 | 1.00 | 15.80 |
| 1368 | CB | GLU | A | 203 | 40.188 | 6.316 | 61.949 | 1.00 | 15.80 |

FIGURE 3 (Cont.)

| A | B | C | D | E | F | G | H | I | J |
|---|---|---|---|---|---|---|---|---|---|
| 1369 | CG | GLU | A | 203 | 39.839 | 4.888 | 61.504 | 1.00 | 15.27 |
| 1370 | CD | GLU | A | 203 | 38.447 | 4.443 | 61.924 | 1.00 | 16.72 |
| 1371 | OE1 | GLU | A | 203 | 38.240 | 3.183 | 61.868 | 1.00 | 16.79 |
| 1372 | OE2 | GLU | A | 203 | 37.607 | 5.336 | 62.294 | 1.00 | 18.04 |
| 1373 | C | GLU | A | 203 | 41.467 | 5.534 | 63.884 | 1.00 | 15.81 |
| 1374 | O | GLU | A | 203 | 41.226 | 4.420 | 64.375 | 1.00 | 17.28 |
| 1375 | N | GLU | A | 204 | 42.677 | 5.977 | 63.687 | 1.00 | 16.87 |
| 1376 | CA | GLU | A | 204 | 43.744 | 5.015 | 63.491 | 1.00 | 18.22 |
| 1377 | CB | GLU | A | 204 | 44.293 | 5.243 | 62.081 | 1.00 | 19.35 |
| 1378 | CG | GLU | A | 204 | 44.438 | 3.960 | 61.294 | 1.00 | 24.63 |
| 1379 | CD | GLU | A | 204 | 43.151 | 3.208 | 61.003 | 1.00 | 27.80 |
| 1380 | OE1 | GLU | A | 204 | 42.855 | 2.191 | 61.676 | 1.00 | 31.06 |
| 1381 | OE2 | GLU | A | 204 | 42.498 | 3.578 | 60.036 | 1.00 | 31.17 |
| 1382 | C | GLU | A | 204 | 44.825 | 5.000 | 64.578 | 1.00 | 17.66 |
| 1383 | O | GLU | A | 204 | 45.573 | 4.004 | 64.706 | 1.00 | 17.52 |
| 1384 | N | MET | A | 205 | 44.887 | 6.060 | 65.386 | 1.00 | 16.35 |
| 1385 | CA | MET | A | 205 | 45.914 | 6.153 | 66.431 | 1.00 | 15.62 |
| 1386 | CB | MET | A | 205 | 46.774 | 7.374 | 66.227 | 1.00 | 14.60 |
| 1387 | CG | MET | A | 205 | 47.935 | 7.441 | 67.092 | 1.00 | 12.29 |
| 1388 | SD | MET | A | 205 | 48.735 | 5.887 | 67.337 | 1.00 | 12.50 |
| 1389 | CE | MET | A | 205 | 49.775 | 5.686 | 65.960 | 1.00 | 8.70 |
| 1390 | C | MET | A | 205 | 45.256 | 6.183 | 67.801 | 1.00 | 15.79 |
| 1391 | O | MET | A | 205 | 45.314 | 5.159 | 68.524 | 1.00 | 15.63 |
| 1392 | N | LEU | A | 206 | 44.532 | 7.287 | 68.046 | 1.00 | 15.09 |
| 1393 | CA | LEU | A | 206 | 43.925 | 7.645 | 69.321 | 1.00 | 14.60 |
| 1394 | CB | LEU | A | 206 | 43.618 | 9.119 | 69.405 | 1.00 | 14.24 |
| 1395 | CG | LEU | A | 206 | 44.844 | 9.983 | 69.191 | 1.00 | 13.66 |
| 1396 | CD1 | LEU | A | 206 | 44.472 | 11.356 | 69.626 | 1.00 | 12.77 |
| 1397 | CD2 | LEU | A | 206 | 46.073 | 9.434 | 69.949 | 1.00 | 11.61 |
| 1398 | C | LEU | A | 206 | 42.619 | 7.011 | 69.543 | 1.00 | 14.20 |
| 1399 | O | LEU | A | 206 | 42.319 | 6.653 | 70.655 | 1.00 | 15.54 |
| 1400 | N | ALA | A | 207 | 41.829 | 6.922 | 68.496 | 1.00 | 14.62 |
| 1401 | CA | ALA | A | 207 | 40.422 | 6.486 | 68.598 | 1.00 | 14.74 |
| 1402 | CB | ALA | A | 207 | 40.331 | 5.017 | 68.897 | 1.00 | 14.85 |
| 1403 | C | ALA | A | 207 | 39.628 | 7.274 | 69.604 | 1.00 | 15.01 |
| 1404 | O | ALA | A | 207 | 38.956 | 6.718 | 70.452 | 1.00 | 15.29 |
| 1405 | N | THR | A | 208 | 39.720 | 8.585 | 69.438 | 1.00 | 15.41 |
| 1406 | CA | THR | A | 208 | 39.149 | 9.562 | 70.297 | 1.00 | 16.34 |
| 1407 | CB | THR | A | 208 | 40.228 | 10.070 | 71.125 | 1.00 | 16.62 |
| 1408 | OG1 | THR | A | 208 | 40.965 | 8.998 | 71.778 | 1.00 | 20.37 |
| 1409 | CG2 | THR | A | 208 | 39.617 | 10.789 | 72.211 | 1.00 | 18.89 |
| 1410 | C | THR | A | 208 | 38.702 | 10.774 | 69.512 | 1.00 | 16.53 |
| 1411 | O | THR | A | 208 | 39.426 | 11.225 | 68.609 | 1.00 | 16.01 |
| 1412 | N | LYS | A | 209 | 37.570 | 11.367 | 69.891 | 1.00 | 15.37 |
| 1413 | CA | LYS | A | 209 | 37.186 | 12.612 | 69.283 | 1.00 | 13.41 |
| 1414 | CB | LYS | A | 209 | 35.689 | 12.905 | 69.599 | 1.00 | 13.69 |
| 1415 | CG | LYS | A | 209 | 35.316 | 14.081 | 70.583 | 1.00 | 13.74 |
| 1416 | CD | LYS | A | 209 | 34.528 | 15.279 | 69.863 | 1.00 | 13.48 |
| 1417 | CE | LYS | A | 209 | 33.443 | 15.885 | 70.715 | 1.00 | 15.26 |
| 1418 | NZ | LYS | A | 209 | 32.467 | 16.787 | 69.988 | 1.00 | 17.91 |
| 1419 | C | LYS | A | 209 | 38.145 | 13.768 | 69.663 | 1.00 | 12.86 |

FIGURE 3 (Cont.)

| A | B | C | D | E | F | G | H | I | J |
|---|---|---|---|---|---|---|---|---|---|
| 1420 | O | LYS | A | 209 | 38.145 | 14.803 | 68.998 | 1.00 | 13.32 |
| 1421 | N | TYR | A | 210 | 38.943 | 13.603 | 70.730 | 1.00 | 13.44 |
| 1422 | CA | TYR | A | 210 | 39.670 | 14.718 | 71.404 | 1.00 | 12.77 |
| 1423 | CB | TYR | A | 210 | 39.184 | 14.991 | 72.874 | 1.00 | 12.71 |
| 1424 | CG | TYR | A | 210 | 39.445 | 13.783 | 73.758 | 1.00 | 14.64 |
| 1425 | CD1 | TYR | A | 210 | 38.452 | 12.806 | 73.915 | 1.00 | 13.22 |
| 1426 | CE1 | TYR | A | 210 | 38.658 | 11.665 | 74.660 | 1.00 | 12.26 |
| 1427 | CZ | TYR | A | 210 | 39.883 | 11.447 | 75.189 | 1.00 | 14.02 |
| 1428 | OH | TYR | A | 210 | 40.049 | 10.295 | 75.843 | 1.00 | 8.69 |
| 1429 | CE2 | TYR | A | 210 | 40.929 | 12.381 | 75.043 | 1.00 | 14.83 |
| 1430 | CD2 | TYR | A | 210 | 40.697 | 13.555 | 74.334 | 1.00 | 12.05 |
| 1431 | C | TYR | A | 210 | 41.159 | 14.416 | 71.466 | 1.00 | 12.47 |
| 1432 | O | TYR | A | 210 | 41.604 | 13.204 | 71.414 | 1.00 | 11.88 |
| 1433 | N | ALA | A | 211 | 41.899 | 15.526 | 71.590 | 1.00 | 10.98 |
| 1434 | CA | ALA | A | 211 | 43.325 | 15.503 | 71.832 | 1.00 | 11.91 |
| 1435 | CB | ALA | A | 211 | 44.072 | 15.446 | 70.581 | 1.00 | 11.27 |
| 1436 | C | ALA | A | 211 | 43.733 | 16.711 | 72.690 | 1.00 | 13.18 |
| 1437 | O | ALA | A | 211 | 44.620 | 17.523 | 72.382 | 1.00 | 13.55 |
| 1438 | N | LEU | A | 212 | 43.022 | 16.828 | 73.784 | 1.00 | 13.41 |
| 1439 | CA | LEU | A | 212 | 43.618 | 17.443 | 74.922 | 1.00 | 14.68 |
| 1440 | CB | LEU | A | 212 | 43.225 | 18.899 | 75.051 | 1.00 | 13.96 |
| 1441 | CG | LEU | A | 212 | 41.710 | 19.040 | 74.987 | 1.00 | 12.20 |
| 1442 | CD1 | LEU | A | 212 | 41.179 | 19.286 | 76.320 | 1.00 | 12.61 |
| 1443 | CD2 | LEU | A | 212 | 41.328 | 20.127 | 74.075 | 1.00 | 9.98 |
| 1444 | C | LEU | A | 212 | 43.276 | 16.628 | 76.197 | 1.00 | 16.15 |
| 1445 | O | LEU | A | 212 | 42.234 | 15.933 | 76.350 | 1.00 | 16.74 |
| 1446 | N | TRP | A | 213 | 44.230 | 16.727 | 77.095 | 1.00 | 16.90 |
| 1447 | CA | TRP | A | 213 | 44.151 | 16.180 | 78.423 | 1.00 | 17.56 |
| 1448 | CB | TRP | A | 213 | 45.145 | 15.053 | 78.523 | 1.00 | 17.59 |
| 1449 | CG | TRP | A | 213 | 45.140 | 14.256 | 77.262 | 1.00 | 18.92 |
| 1450 | CD1 | TRP | A | 213 | 44.428 | 13.104 | 77.017 | 1.00 | 19.54 |
| 1451 | NE1 | TRP | A | 213 | 44.702 | 12.648 | 75.752 | 1.00 | 21.55 |
| 1452 | CE2 | TRP | A | 213 | 45.576 | 13.520 | 75.135 | 1.00 | 20.14 |
| 1453 | CD2 | TRP | A | 213 | 45.864 | 14.547 | 76.054 | 1.00 | 19.64 |
| 1454 | CE3 | TRP | A | 213 | 46.752 | 15.564 | 75.659 | 1.00 | 17.89 |
| 1455 | CZ3 | TRP | A | 213 | 47.306 | 15.518 | 74.366 | 1.00 | 16.32 |
| 1456 | CH2 | TRP | A | 213 | 46.990 | 14.486 | 73.486 | 1.00 | 17.18 |
| 1457 | CZ2 | TRP | A | 213 | 46.143 | 13.482 | 73.844 | 1.00 | 18.30 |
| 1458 | C | TRP | A | 213 | 44.511 | 17.305 | 79.365 | 1.00 | 17.50 |
| 1459 | O | TRP | A | 213 | 45.566 | 17.975 | 79.251 | 1.00 | 17.10 |
| 1460 | N | TRP | A | 214 | 43.606 | 17.555 | 80.274 | 1.00 | 17.44 |
| 1461 | CA | TRP | A | 214 | 44.022 | 18.271 | 81.445 | 1.00 | 17.19 |
| 1462 | CB | TRP | A | 214 | 42.846 | 18.638 | 82.273 | 1.00 | 17.35 |
| 1463 | CG | TRP | A | 214 | 42.042 | 19.668 | 81.735 | 1.00 | 16.87 |
| 1464 | CD1 | TRP | A | 214 | 41.030 | 19.507 | 80.885 | 1.00 | 16.34 |
| 1465 | NE1 | TRP | A | 214 | 40.430 | 20.717 | 80.659 | 1.00 | 16.27 |
| 1466 | CE2 | TRP | A | 214 | 41.070 | 21.679 | 81.388 | 1.00 | 14.10 |
| 1467 | CD2 | TRP | A | 214 | 42.086 | 21.047 | 82.081 | 1.00 | 14.65 |
| 1468 | CE3 | TRP | A | 214 | 42.894 | 21.809 | 82.914 | 1.00 | 15.54 |
| 1469 | CZ3 | TRP | A | 214 | 42.671 | 23.182 | 83.005 | 1.00 | 13.96 |
| 1470 | CH2 | TRP | A | 214 | 41.641 | 23.779 | 82.311 | 1.00 | 14.70 |

FIGURE 3 (Cont.)

| A | B | C | D | E | F | G | H | I | J |
|---|---|---|---|---|---|---|---|---|---|
| 1471 | CZ2 | TRP | A | 214 | 40.826 | 23.042 | 81.484 | 1.00 | 14.74 |
| 1472 | C | TRP | A | 214 | 44.863 | 17.372 | 82.327 | 1.00 | 17.51 |
| 1473 | O | TRP | A | 214 | 44.571 | 16.185 | 82.433 | 1.00 | 17.40 |
| 1474 | N | SER | A | 215 | 45.876 | 17.988 | 82.967 | 1.00 | 17.31 |
| 1475 | CA | SER | A | 215 | 46.630 | 17.393 | 84.056 | 1.00 | 17.49 |
| 1476 | CB | SER | A | 215 | 47.945 | 18.180 | 84.290 | 1.00 | 17.99 |
| 1477 | OG | SER | A | 215 | 47.822 | 19.303 | 85.150 | 1.00 | 17.25 |
| 1478 | C | SER | A | 215 | 45.720 | 17.282 | 85.305 | 1.00 | 17.59 |
| 1479 | O | SER | A | 215 | 44.715 | 17.998 | 85.430 | 1.00 | 17.95 |
| 1480 | N | PRO | A | 216 | 46.054 | 16.365 | 86.202 | 1.00 | 17.58 |
| 1481 | CA | PRO | A | 216 | 45.032 | 15.701 | 87.032 | 1.00 | 18.06 |
| 1482 | CB | PRO | A | 216 | 45.839 | 14.640 | 87.785 | 1.00 | 18.09 |
| 1483 | CG | PRO | A | 216 | 47.282 | 15.202 | 87.861 | 1.00 | 17.70 |
| 1484 | CD | PRO | A | 216 | 47.421 | 15.900 | 86.527 | 1.00 | 17.79 |
| 1485 | C | PRO | A | 216 | 44.304 | 16.621 | 88.014 | 1.00 | 18.30 |
| 1486 | O | PRO | A | 216 | 43.176 | 16.289 | 88.447 | 1.00 | 17.67 |
| 1487 | N | ASN | A | 217 | 44.975 | 17.729 | 88.355 | 1.00 | 18.21 |
| 1488 | CA | ASN | A | 217 | 44.401 | 18.805 | 89.132 | 1.00 | 18.80 |
| 1489 | CB | ASN | A | 217 | 45.420 | 19.400 | 90.098 | 1.00 | 19.15 |
| 1490 | CG | ASN | A | 217 | 45.316 | 18.788 | 91.503 | 1.00 | 20.23 |
| 1491 | OD1 | ASN | A | 217 | 44.677 | 19.379 | 92.375 | 1.00 | 22.84 |
| 1492 | ND2 | ASN | A | 217 | 45.911 | 17.595 | 91.714 | 1.00 | 17.62 |
| 1493 | C | ASN | A | 217 | 43.866 | 19.906 | 88.251 | 1.00 | 19.26 |
| 1494 | O | ASN | A | 217 | 42.879 | 20.534 | 88.618 | 1.00 | 20.09 |
| 1495 | N | GLY | A | 218 | 44.510 | 20.159 | 87.106 | 1.00 | 18.87 |
| 1496 | CA | GLY | A | 218 | 44.125 | 21.255 | 86.223 | 1.00 | 17.96 |
| 1497 | C | GLY | A | 218 | 44.993 | 22.490 | 86.361 | 1.00 | 18.15 |
| 1498 | O | GLY | A | 218 | 44.561 | 23.647 | 86.164 | 1.00 | 17.76 |
| 1499 | N | LYS | A | 219 | 46.247 | 22.219 | 86.702 | 1.00 | 18.02 |
| 1500 | CA | LYS | A | 219 | 47.235 | 23.261 | 86.909 | 1.00 | 18.20 |
| 1501 | CB | LYS | A | 219 | 48.299 | 22.827 | 87.971 | 1.00 | 18.61 |
| 1502 | CG | LYS | A | 219 | 48.165 | 23.492 | 89.384 | 1.00 | 17.63 |
| 1503 | CD | LYS | A | 219 | 49.552 | 23.615 | 90.099 | 1.00 | 19.60 |
| 1504 | CE | LYS | A | 219 | 49.530 | 23.131 | 91.599 | 1.00 | 19.51 |
| 1505 | NZ | LYS | A | 219 | 49.538 | 21.610 | 91.820 | 1.00 | 17.13 |
| 1506 | C | LYS | A | 219 | 47.863 | 23.592 | 85.557 | 1.00 | 17.84 |
| 1507 | O | LYS | A | 219 | 48.490 | 24.663 | 85.398 | 1.00 | 18.65 |
| 1508 | N | PHE | A | 220 | 47.651 | 22.683 | 84.602 | 1.00 | 16.74 |
| 1509 | CA | PHE | A | 220 | 48.290 | 22.676 | 83.293 | 1.00 | 15.78 |
| 1510 | CB | PHE | A | 220 | 49.446 | 21.688 | 83.334 | 1.00 | 16.30 |
| 1511 | CG | PHE | A | 220 | 50.713 | 22.227 | 83.845 | 1.00 | 17.42 |
| 1512 | CD1 | PHE | A | 220 | 51.743 | 22.524 | 82.966 | 1.00 | 18.41 |
| 1513 | CE1 | PHE | A | 220 | 52.950 | 23.019 | 83.449 | 1.00 | 21.23 |
| 1514 | CZ | PHE | A | 220 | 53.148 | 23.212 | 84.874 | 1.00 | 19.91 |
| 1515 | CE2 | PHE | A | 220 | 52.131 | 22.920 | 85.745 | 1.00 | 20.23 |
| 1516 | CD2 | PHE | A | 220 | 50.910 | 22.400 | 85.222 | 1.00 | 20.19 |
| 1517 | C | PHE | A | 220 | 47.363 | 22.074 | 82.231 | 1.00 | 15.14 |
| 1518 | O | PHE | A | 220 | 46.510 | 21.219 | 82.536 | 1.00 | 15.22 |
| 1519 | N | LEU | A | 221 | 47.599 | 22.393 | 80.963 | 1.00 | 14.21 |
| 1520 | CA | LEU | A | 221 | 46.869 | 21.712 | 79.878 | 1.00 | 12.91 |
| 1521 | CB | LEU | A | 221 | 45.753 | 22.632 | 79.392 | 1.00 | 12.39 |

FIGURE 3 (Cont.)

| A | B | C | D | E | F | G | H | I | J |
|---|---|---|---|---|---|---|---|---|---|
| 1522 | CG | LEU | A | 221 | 44.921 | 22.165 | 78.222 | 1.00 | 12.82 |
| 1523 | CD1 | LEU | A | 221 | 43.912 | 21.016 | 78.653 | 1.00 | 12.32 |
| 1524 | CD2 | LEU | A | 221 | 44.252 | 23.422 | 77.569 | 1.00 | 11.48 |
| 1525 | C | LEU | A | 221 | 47.789 | 21.233 | 78.732 | 1.00 | 11.76 |
| 1526 | O | LEU | A | 221 | 48.613 | 21.995 | 78.202 | 1.00 | 12.26 |
| 1527 | N | ALA | A | 222 | 47.682 | 19.964 | 78.389 | 1.00 | 9.42 |
| 1528 | CA | ALA | A | 222 | 48.375 | 19.449 | 77.216 | 1.00 | 8.68 |
| 1529 | CB | ALA | A | 222 | 49.053 | 18.098 | 77.513 | 1.00 | 8.21 |
| 1530 | C | ALA | A | 222 | 47.452 | 19.306 | 75.969 | 1.00 | 8.72 |
| 1531 | O | ALA | A | 222 | 46.206 | 19.127 | 76.041 | 1.00 | 8.83 |
| 1532 | N | TYR | A | 223 | 48.100 | 19.383 | 74.820 | 1.00 | 7.95 |
| 1533 | CA | TYR | A | 223 | 47.413 | 19.275 | 73.573 | 1.00 | 7.77 |
| 1534 | CB | TYR | A | 223 | 46.648 | 20.546 | 73.224 | 1.00 | 7.86 |
| 1535 | CG | TYR | A | 223 | 47.479 | 21.807 | 73.141 | 1.00 | 8.92 |
| 1536 | CD1 | TYR | A | 223 | 47.865 | 22.486 | 74.288 | 1.00 | 10.16 |
| 1537 | CE1 | TYR | A | 223 | 48.600 | 23.675 | 74.184 | 1.00 | 11.86 |
| 1538 | CZ | TYR | A | 223 | 48.942 | 24.155 | 72.937 | 1.00 | 9.55 |
| 1539 | OH | TYR | A | 223 | 49.672 | 25.294 | 72.847 | 1.00 | 12.01 |
| 1540 | CE2 | TYR | A | 223 | 48.597 | 23.484 | 71.809 | 1.00 | 6.61 |
| 1541 | CD2 | TYR | A | 223 | 47.859 | 22.343 | 71.903 | 1.00 | 7.70 |
| 1542 | C | TYR | A | 223 | 48.375 | 18.916 | 72.505 | 1.00 | 7.74 |
| 1543 | O | TYR | A | 223 | 49.595 | 18.936 | 72.692 | 1.00 | 8.37 |
| 1544 | N | ALA | A | 224 | 47.791 | 18.535 | 71.395 | 1.00 | 7.72 |
| 1545 | CA | ALA | A | 224 | 48.514 | 18.166 | 70.230 | 1.00 | 8.33 |
| 1546 | CB | ALA | A | 224 | 48.091 | 16.771 | 69.822 | 1.00 | 8.39 |
| 1547 | C | ALA | A | 224 | 48.233 | 19.151 | 69.114 | 1.00 | 9.32 |
| 1548 | O | ALA | A | 224 | 47.191 | 19.892 | 69.086 | 1.00 | 9.01 |
| 1549 | N | GLU | A | 225 | 49.198 | 19.194 | 68.201 | 1.00 | 9.93 |
| 1550 | CA | GLU | A | 225 | 49.072 | 19.989 | 66.963 | 1.00 | 10.96 |
| 1551 | CB | GLU | A | 225 | 50.050 | 21.148 | 66.895 | 1.00 | 9.98 |
| 1552 | CG | GLU | A | 225 | 49.985 | 21.922 | 65.607 | 1.00 | 10.97 |
| 1553 | CD | GLU | A | 225 | 51.062 | 23.023 | 65.527 | 1.00 | 14.97 |
| 1554 | OE1 | GLU | A | 225 | 50.848 | 24.149 | 66.090 | 1.00 | 16.22 |
| 1555 | OE2 | GLU | A | 225 | 52.132 | 22.764 | 64.916 | 1.00 | 15.71 |
| 1556 | C | GLU | A | 225 | 49.328 | 19.018 | 65.818 | 1.00 | 11.43 |
| 1557 | O | GLU | A | 225 | 50.353 | 18.298 | 65.792 | 1.00 | 11.92 |
| 1558 | N | PHE | A | 226 | 48.363 | 18.948 | 64.903 | 1.00 | 10.84 |
| 1559 | CA | PHE | A | 226 | 48.575 | 18.158 | 63.746 | 1.00 | 10.56 |
| 1560 | CB | PHE | A | 226 | 47.456 | 17.131 | 63.613 | 1.00 | 10.08 |
| 1561 | CG | PHE | A | 226 | 47.202 | 16.302 | 64.842 | 1.00 | 10.23 |
| 1562 | CD1 | PHE | A | 226 | 46.193 | 16.652 | 65.743 | 1.00 | 11.00 |
| 1563 | CE1 | PHE | A | 226 | 45.912 | 15.864 | 66.874 | 1.00 | 10.45 |
| 1564 | CZ | PHE | A | 226 | 46.608 | 14.689 | 67.052 | 1.00 | 11.00 |
| 1565 | CE2 | PHE | A | 226 | 47.596 | 14.319 | 66.121 | 1.00 | 11.50 |
| 1566 | CD2 | PHE | A | 226 | 47.858 | 15.099 | 65.022 | 1.00 | 9.36 |
| 1567 | C | PHE | A | 226 | 48.597 | 19.157 | 62.598 | 1.00 | 10.55 |
| 1568 | O | PHE | A | 226 | 47.727 | 20.063 | 62.536 | 1.00 | 10.60 |
| 1569 | N | ASN | A | 227 | 49.601 | 19.027 | 61.725 | 1.00 | 10.90 |
| 1570 | CA | ASN | A | 227 | 49.771 | 19.871 | 60.540 | 1.00 | 12.05 |
| 1571 | CB | ASN | A | 227 | 51.157 | 20.694 | 60.531 | 1.00 | 12.33 |
| 1572 | CG | ASN | A | 227 | 51.597 | 21.176 | 59.124 | 1.00 | 14.31 |

FIGURE 3 (Cont.)

| A | B | C | D | E | F | G | H | I | J |
|---|---|---|---|---|---|---|---|---|---|
| 1573 | OD1 | ASN | A | 227 | 50.914 | 21.021 | 58.066 | 1.00 | 17.92 |
| 1574 | ND2 | ASN | A | 227 | 52.764 | 21.726 | 59.102 | 1.00 | 24.00 |
| 1575 | C | ASN | A | 227 | 49.596 | 18.837 | 59.412 | 1.00 | 12.31 |
| 1576 | O | ASN | A | 227 | 50.449 | 17.953 | 59.238 | 1.00 | 11.08 |
| 1577 | N | ASP | A | 228 | 48.475 | 18.963 | 58.672 | 1.00 | 13.24 |
| 1578 | CA | ASP | A | 228 | 48.157 | 18.072 | 57.576 | 1.00 | 13.95 |
| 1579 | CB | ASP | A | 228 | 46.668 | 17.712 | 57.641 | 1.00 | 14.37 |
| 1580 | CG | ASP | A | 228 | 46.377 | 16.574 | 58.571 | 1.00 | 15.21 |
| 1581 | OD1 | ASP | A | 228 | 47.126 | 16.377 | 59.550 | 1.00 | 17.68 |
| 1582 | OD2 | ASP | A | 228 | 45.403 | 15.841 | 58.417 | 1.00 | 15.95 |
| 1583 | C | ASP | A | 228 | 48.536 | 18.573 | 56.149 | 1.00 | 14.20 |
| 1584 | O | ASP | A | 228 | 48.276 | 17.904 | 55.165 | 1.00 | 14.82 |
| 1585 | N | THR | A | 229 | 49.201 | 19.700 | 56.057 | 1.00 | 14.55 |
| 1586 | CA | THR | A | 229 | 49.311 | 20.467 | 54.827 | 1.00 | 15.14 |
| 1587 | CB | THR | A | 229 | 50.122 | 21.804 | 55.087 | 1.00 | 15.17 |
| 1588 | OG1 | THR | A | 229 | 49.916 | 22.262 | 56.416 | 1.00 | 14.48 |
| 1589 | CG2 | THR | A | 229 | 49.577 | 22.972 | 54.243 | 1.00 | 13.29 |
| 1590 | C | THR | A | 229 | 49.875 | 19.818 | 53.541 | 1.00 | 16.31 |
| 1591 | O | THR | A | 229 | 49.470 | 20.251 | 52.416 | 1.00 | 17.13 |
| 1592 | N | ASP | A | 230 | 50.835 | 18.900 | 53.591 | 1.00 | 16.35 |
| 1593 | CA | ASP | A | 230 | 51.110 | 18.234 | 52.299 | 1.00 | 17.72 |
| 1594 | CB | ASP | A | 230 | 52.526 | 18.268 | 51.735 | 1.00 | 18.15 |
| 1595 | CG | ASP | A | 230 | 53.225 | 19.570 | 51.968 | 1.00 | 24.39 |
| 1596 | OD1 | ASP | A | 230 | 53.037 | 20.070 | 53.107 | 1.00 | 30.74 |
| 1597 | OD2 | ASP | A | 230 | 53.995 | 20.134 | 51.112 | 1.00 | 28.33 |
| 1598 | C | ASP | A | 230 | 50.713 | 16.833 | 52.353 | 1.00 | 17.55 |
| 1599 | O | ASP | A | 230 | 51.243 | 16.061 | 51.592 | 1.00 | 19.14 |
| 1600 | N | ILE | A | 231 | 49.799 | 16.480 | 53.247 | 1.00 | 16.72 |
| 1601 | CA | ILE | A | 231 | 49.198 | 15.182 | 53.202 | 1.00 | 14.42 |
| 1602 | CB | ILE | A | 231 | 48.375 | 14.909 | 54.438 | 1.00 | 13.97 |
| 1603 | CG1 | ILE | A | 231 | 49.234 | 15.020 | 55.675 | 1.00 | 13.23 |
| 1604 | CD1 | ILE | A | 231 | 48.945 | 13.946 | 56.723 | 1.00 | 13.72 |
| 1605 | CG2 | ILE | A | 231 | 47.659 | 13.456 | 54.359 | 1.00 | 14.63 |
| 1606 | C | ILE | A | 231 | 48.284 | 15.327 | 52.014 | 1.00 | 14.49 |
| 1607 | O | ILE | A | 231 | 47.502 | 16.272 | 51.955 | 1.00 | 14.80 |
| 1608 | N | PRO | A | 232 | 48.367 | 14.397 | 51.085 | 1.00 | 14.06 |
| 1609 | CA | PRO | A | 232 | 47.494 | 14.425 | 49.946 | 1.00 | 13.55 |
| 1610 | CB | PRO | A | 232 | 47.888 | 13.160 | 49.189 | 1.00 | 14.34 |
| 1611 | CG | PRO | A | 232 | 49.259 | 12.783 | 49.683 | 1.00 | 12.99 |
| 1612 | CD | PRO | A | 232 | 49.272 | 13.241 | 51.066 | 1.00 | 13.51 |
| 1613 | C | PRO | A | 232 | 46.120 | 14.252 | 50.497 | 1.00 | 13.34 |
| 1614 | O | PRO | A | 232 | 45.996 | 13.910 | 51.641 | 1.00 | 13.89 |
| 1615 | N | VAL | A | 233 | 45.111 | 14.426 | 49.675 | 1.00 | 11.29 |
| 1616 | CA | VAL | A | 233 | 43.726 | 14.347 | 50.107 | 1.00 | 10.64 |
| 1617 | CB | VAL | A | 233 | 42.960 | 15.726 | 49.810 | 1.00 | 9.54 |
| 1618 | CG1 | VAL | A | 233 | 43.630 | 16.858 | 50.511 | 1.00 | 9.53 |
| 1619 | CG2 | VAL | A | 233 | 42.907 | 15.963 | 48.427 | 1.00 | 7.79 |
| 1620 | C | VAL | A | 233 | 43.057 | 13.185 | 49.368 | 1.00 | 10.11 |
| 1621 | O | VAL | A | 233 | 43.407 | 12.872 | 48.228 | 1.00 | 7.91 |
| 1622 | N | ILE | A | 234 | 42.110 | 12.514 | 49.995 | 1.00 | 11.28 |
| 1623 | CA | ILE | A | 234 | 41.290 | 11.638 | 49.189 | 1.00 | 13.63 |

FIGURE 3 (Cont.)

| A | B | C | D | E | F | G | H | I | J |
|---|---|---|---|---|---|---|---|---|---|
| 1624 | CB | ILE | A | 234 | 40.995 | 10.305 | 49.866 | 1.00 | 13.33 |
| 1625 | CG1 | ILE | A | 234 | 40.540 | 9.352 | 48.776 | 1.00 | 13.40 |
| 1626 | CD1 | ILE | A | 234 | 39.256 | 9.191 | 48.754 | 1.00 | 2.00 |
| 1627 | CG2 | ILE | A | 234 | 39.935 | 10.373 | 51.032 | 1.00 | 14.37 |
| 1628 | C | ILE | A | 234 | 40.045 | 12.400 | 48.828 | 1.00 | 14.35 |
| 1629 | O | ILE | A | 234 | 39.526 | 13.018 | 49.687 | 1.00 | 16.85 |
| 1630 | N | ALA | A | 235 | 39.606 | 12.375 | 47.579 | 1.00 | 13.84 |
| 1631 | CA | ALA | A | 235 | 38.406 | 13.121 | 47.140 | 1.00 | 15.67 |
| 1632 | CB | ALA | A | 235 | 38.752 | 14.091 | 46.015 | 1.00 | 13.12 |
| 1633 | C | ALA | A | 235 | 37.283 | 12.199 | 46.699 | 1.00 | 16.17 |
| 1634 | O | ALA | A | 235 | 37.515 | 11.180 | 46.019 | 1.00 | 18.68 |
| 1635 | N | TYR | A | 236 | 36.070 | 12.499 | 47.125 | 1.00 | 16.59 |
| 1636 | CA | TYR | A | 236 | 34.910 | 11.660 | 46.767 | 1.00 | 15.78 |
| 1637 | CB | TYR | A | 236 | 34.644 | 10.510 | 47.794 | 1.00 | 16.36 |
| 1638 | CG | TYR | A | 236 | 34.337 | 10.889 | 49.282 | 1.00 | 16.00 |
| 1639 | CD1 | TYR | A | 236 | 33.067 | 11.378 | 49.667 | 1.00 | 17.93 |
| 1640 | CE1 | TYR | A | 236 | 32.778 | 11.732 | 51.000 | 1.00 | 15.24 |
| 1641 | CZ | TYR | A | 236 | 33.760 | 11.589 | 51.982 | 1.00 | 17.78 |
| 1642 | OH | TYR | A | 236 | 33.428 | 11.885 | 53.309 | 1.00 | 19.43 |
| 1643 | CE2 | TYR | A | 236 | 35.031 | 11.139 | 51.617 | 1.00 | 13.29 |
| 1644 | CD2 | TYR | A | 236 | 35.290 | 10.749 | 50.276 | 1.00 | 14.26 |
| 1645 | C | TYR | A | 236 | 33.744 | 12.598 | 46.535 | 1.00 | 15.31 |
| 1646 | O | TYR | A | 236 | 33.863 | 13.785 | 46.828 | 1.00 | 16.56 |
| 1647 | N | SER | A | 237 | 32.695 | 12.084 | 45.879 | 1.00 | 14.25 |
| 1648 | CA | SER | A | 237 | 31.490 | 12.820 | 45.568 | 1.00 | 13.06 |
| 1649 | CB | SER | A | 237 | 30.842 | 12.276 | 44.335 | 1.00 | 12.64 |
| 1650 | OG | SER | A | 237 | 31.666 | 12.499 | 43.219 | 1.00 | 16.53 |
| 1651 | C | SER | A | 237 | 30.525 | 12.661 | 46.635 | 1.00 | 12.28 |
| 1652 | O | SER | A | 237 | 30.498 | 11.648 | 47.258 | 1.00 | 14.53 |
| 1653 | N | TYR | A | 238 | 29.745 | 13.682 | 46.877 | 1.00 | 11.53 |
| 1654 | CA | TYR | A | 238 | 28.622 | 13.594 | 47.764 | 1.00 | 12.47 |
| 1655 | CB | TYR | A | 238 | 28.818 | 14.234 | 49.142 | 1.00 | 11.70 |
| 1656 | CG | TYR | A | 238 | 27.642 | 14.101 | 50.102 | 1.00 | 14.33 |
| 1657 | CD1 | TYR | A | 238 | 26.702 | 15.137 | 50.247 | 1.00 | 15.51 |
| 1658 | CE1 | TYR | A | 238 | 25.684 | 15.060 | 51.145 | 1.00 | 15.57 |
| 1659 | CZ | TYR | A | 238 | 25.579 | 13.914 | 51.983 | 1.00 | 19.11 |
| 1660 | OH | TYR | A | 238 | 24.530 | 13.794 | 52.901 | 1.00 | 20.40 |
| 1661 | CE2 | TYR | A | 238 | 26.510 | 12.907 | 51.899 | 1.00 | 16.71 |
| 1662 | CD2 | TYR | A | 238 | 27.534 | 13.013 | 50.924 | 1.00 | 14.86 |
| 1663 | C | TYR | A | 238 | 27.542 | 14.277 | 47.029 | 1.00 | 12.15 |
| 1664 | O | TYR | A | 238 | 27.511 | 15.532 | 46.826 | 1.00 | 14.69 |
| 1665 | N | TYR | A | 239 | 26.637 | 13.422 | 46.644 | 1.00 | 11.10 |
| 1666 | CA | TYR | A | 239 | 25.595 | 13.817 | 45.750 | 1.00 | 10.79 |
| 1667 | CB | TYR | A | 239 | 24.888 | 12.567 | 45.281 | 1.00 | 10.20 |
| 1668 | CG | TYR | A | 239 | 25.870 | 11.748 | 44.583 | 1.00 | 7.32 |
| 1669 | CD1 | TYR | A | 239 | 26.345 | 12.175 | 43.374 | 1.00 | 4.79 |
| 1670 | CE1 | TYR | A | 239 | 27.321 | 11.470 | 42.690 | 1.00 | 10.51 |
| 1671 | CZ | TYR | A | 239 | 27.821 | 10.283 | 43.246 | 1.00 | 9.98 |
| 1672 | OH | TYR | A | 239 | 28.728 | 9.686 | 42.528 | 1.00 | 15.80 |
| 1673 | CE2 | TYR | A | 239 | 27.432 | 9.862 | 44.513 | 1.00 | 4.55 |
| 1674 | CD2 | TYR | A | 239 | 26.420 | 10.590 | 45.185 | 1.00 | 2.00 |

FIGURE 3 (Cont.)

| A | B | C | D | E | F | G | H | I | J |
|---|---|---|---|---|---|---|---|---|---|
| 1675 | C | TYR | A | 239 | 24.595 | 14.659 | 46.405 | 1.00 | 10.97 |
| 1676 | O | TYR | A | 239 | 24.055 | 15.572 | 45.774 | 1.00 | 12.85 |
| 1677 | N | GLY | A | 240 | 24.243 | 14.301 | 47.624 | 1.00 | 10.20 |
| 1678 | CA | GLY | A | 240 | 23.415 | 15.183 | 48.383 | 1.00 | 11.05 |
| 1679 | C | GLY | A | 240 | 22.065 | 15.345 | 47.762 | 1.00 | 11.71 |
| 1680 | O | GLY | A | 240 | 21.582 | 14.379 | 47.201 | 1.00 | 13.42 |
| 1681 | N | ASP | A | 241 | 21.452 | 16.501 | 47.957 | 1.00 | 11.09 |
| 1682 | CA | ASP | A | 241 | 20.160 | 16.795 | 47.388 | 1.00 | 12.91 |
| 1683 | CB | ASP | A | 241 | 19.063 | 16.784 | 48.534 | 1.00 | 14.56 |
| 1684 | CG | ASP | A | 241 | 19.188 | 15.522 | 49.551 | 1.00 | 20.34 |
| 1685 | OD1 | ASP | A | 241 | 19.564 | 15.780 | 50.769 | 1.00 | 24.58 |
| 1686 | OD2 | ASP | A | 241 | 18.982 | 14.278 | 49.210 | 1.00 | 23.77 |
| 1687 | C | ASP | A | 241 | 20.175 | 18.156 | 46.544 | 1.00 | 13.09 |
| 1688 | O | ASP | A | 241 | 19.138 | 18.652 | 46.069 | 1.00 | 12.60 |
| 1689 | N | GLU | A | 242 | 21.327 | 18.769 | 46.315 | 1.00 | 12.17 |
| 1690 | CA | GLU | A | 242 | 21.314 | 19.932 | 45.414 | 1.00 | 12.38 |
| 1691 | CB | GLU | A | 242 | 22.505 | 20.878 | 45.785 | 1.00 | 13.56 |
| 1692 | CG | GLU | A | 242 | 22.588 | 21.395 | 47.237 | 1.00 | 16.39 |
| 1693 | CD | GLU | A | 242 | 21.375 | 22.326 | 47.554 | 1.00 | 26.19 |
| 1694 | OE1 | GLU | A | 242 | 20.751 | 22.906 | 46.574 | 1.00 | 27.28 |
| 1695 | OE2 | GLU | A | 242 | 21.006 | 22.467 | 48.777 | 1.00 | 31.30 |
| 1696 | C | GLU | A | 242 | 21.412 | 19.468 | 43.943 | 1.00 | 10.99 |
| 1697 | O | GLU | A | 242 | 21.585 | 18.261 | 43.600 | 1.00 | 11.75 |
| 1698 | N | GLN | A | 243 | 21.333 | 20.419 | 43.050 | 1.00 | 9.18 |
| 1699 | CA | GLN | A | 243 | 21.374 | 20.097 | 41.669 | 1.00 | 7.90 |
| 1700 | CB | GLN | A | 243 | 21.055 | 21.332 | 40.864 | 1.00 | 8.08 |
| 1701 | CG | GLN | A | 243 | 21.136 | 20.996 | 39.427 | 1.00 | 4.62 |
| 1702 | CD | GLN | A | 243 | 20.781 | 22.049 | 38.590 | 1.00 | 2.78 |
| 1703 | OE1 | GLN | A | 243 | 20.062 | 21.803 | 37.637 | 1.00 | 6.87 |
| 1704 | NE2 | GLN | A | 243 | 21.216 | 23.251 | 38.899 | 1.00 | 2.00 |
| 1705 | C | GLN | A | 243 | 22.700 | 19.504 | 41.241 | 1.00 | 9.46 |
| 1706 | O | GLN | A | 243 | 22.723 | 18.641 | 40.381 | 1.00 | 8.80 |
| 1707 | N | TYR | A | 244 | 23.821 | 19.940 | 41.850 | 1.00 | 11.40 |
| 1708 | CA | TYR | A | 244 | 25.161 | 19.336 | 41.548 | 1.00 | 11.40 |
| 1709 | CB | TYR | A | 244 | 26.175 | 20.421 | 41.319 | 1.00 | 11.04 |
| 1710 | CG | TYR | A | 244 | 26.012 | 21.174 | 40.022 | 1.00 | 12.46 |
| 1711 | CD1 | TYR | A | 244 | 26.622 | 20.710 | 38.864 | 1.00 | 9.62 |
| 1712 | CE1 | TYR | A | 244 | 26.457 | 21.352 | 37.705 | 1.00 | 12.86 |
| 1713 | CZ | TYR | A | 244 | 25.705 | 22.492 | 37.648 | 1.00 | 14.41 |
| 1714 | OH | TYR | A | 244 | 25.602 | 23.121 | 36.405 | 1.00 | 15.83 |
| 1715 | CE2 | TYR | A | 244 | 25.031 | 22.940 | 38.766 | 1.00 | 11.85 |
| 1716 | CD2 | TYR | A | 244 | 25.212 | 22.307 | 39.944 | 1.00 | 10.00 |
| 1717 | C | TYR | A | 244 | 25.707 | 18.592 | 42.706 | 1.00 | 11.84 |
| 1718 | O | TYR | A | 244 | 25.566 | 19.053 | 43.773 | 1.00 | 12.65 |
| 1719 | N | PRO | A | 245 | 26.342 | 17.455 | 42.505 | 1.00 | 11.92 |
| 1720 | CA | PRO | A | 245 | 27.027 | 16.799 | 43.595 | 1.00 | 11.27 |
| 1721 | CB | PRO | A | 245 | 27.605 | 15.567 | 42.956 | 1.00 | 10.50 |
| 1722 | CG | PRO | A | 245 | 27.648 | 15.837 | 41.614 | 1.00 | 12.61 |
| 1723 | CD | PRO | A | 245 | 26.445 | 16.643 | 41.293 | 1.00 | 11.53 |
| 1724 | C | PRO | A | 245 | 28.091 | 17.696 | 44.032 | 1.00 | 10.77 |
| 1725 | O | PRO | A | 245 | 28.403 | 18.666 | 43.380 | 1.00 | 11.43 |

FIGURE 3 (Cont.)

| A | B | C | D | E | F | G | H | I | J |
|---|---|---|---|---|---|---|---|---|---|
| 1726 | N | ARG | A | 246 | 28.547 | 17.472 | 45.223 | 1.00 | 11.00 |
| 1727 | CA | ARG | A | 246 | 29.678 | 18.316 | 45.681 | 1.00 | 10.93 |
| 1728 | CB | ARG | A | 246 | 29.279 | 19.340 | 46.726 | 1.00 | 10.70 |
| 1729 | CG | ARG | A | 246 | 28.906 | 18.763 | 48.024 | 1.00 | 14.72 |
| 1730 | CD | ARG | A | 246 | 28.544 | 19.865 | 49.025 | 1.00 | 22.87 |
| 1731 | NE | ARG | A | 246 | 28.496 | 19.371 | 50.397 | 1.00 | 27.06 |
| 1732 | CZ | ARG | A | 246 | 27.441 | 18.714 | 50.953 | 1.00 | 27.60 |
| 1733 | NH1 | ARG | A | 246 | 27.555 | 18.277 | 52.201 | 1.00 | 19.53 |
| 1734 | NH2 | ARG | A | 246 | 26.288 | 18.482 | 50.271 | 1.00 | 29.12 |
| 1735 | C | ARG | A | 246 | 30.775 | 17.406 | 46.095 | 1.00 | 9.58 |
| 1736 | O | ARG | A | 246 | 30.621 | 16.159 | 46.090 | 1.00 | 8.81 |
| 1737 | N | THR | A | 247 | 31.914 | 18.029 | 46.316 | 1.00 | 10.00 |
| 1738 | CA | THR | A | 247 | 33.193 | 17.301 | 46.376 | 1.00 | 9.95 |
| 1739 | CB | THR | A | 247 | 34.172 | 17.929 | 45.373 | 1.00 | 10.67 |
| 1740 | OG1 | THR | A | 247 | 33.747 | 17.645 | 44.039 | 1.00 | 9.02 |
| 1741 | CG2 | THR | A | 247 | 35.559 | 17.327 | 45.410 | 1.00 | 9.65 |
| 1742 | C | THR | A | 247 | 33.662 | 17.345 | 47.802 | 1.00 | 10.53 |
| 1743 | O | THR | A | 247 | 33.772 | 18.359 | 48.402 | 1.00 | 10.79 |
| 1744 | N | ILE | A | 248 | 33.844 | 16.198 | 48.381 | 1.00 | 11.56 |
| 1745 | CA | ILE | A | 248 | 34.392 | 16.106 | 49.714 | 1.00 | 12.98 |
| 1746 | CB | ILE | A | 248 | 33.758 | 14.925 | 50.422 | 1.00 | 12.40 |
| 1747 | CG1 | ILE | A | 248 | 32.300 | 15.268 | 50.725 | 1.00 | 15.02 |
| 1748 | CD1 | ILE | A | 248 | 31.941 | 15.380 | 52.101 | 1.00 | 20.22 |
| 1749 | CG2 | ILE | A | 248 | 34.473 | 14.627 | 51.622 | 1.00 | 8.79 |
| 1750 | C | ILE | A | 248 | 35.908 | 15.843 | 49.625 | 1.00 | 13.55 |
| 1751 | O | ILE | A | 248 | 36.332 | 14.903 | 48.948 | 1.00 | 14.13 |
| 1752 | N | ASN | A | 249 | 36.698 | 16.609 | 50.367 | 1.00 | 13.90 |
| 1753 | CA | ASN | A | 249 | 38.133 | 16.324 | 50.482 | 1.00 | 13.69 |
| 1754 | CB | ASN | A | 249 | 38.862 | 17.624 | 50.120 | 1.00 | 15.72 |
| 1755 | CG | ASN | A | 249 | 38.725 | 18.044 | 48.618 | 1.00 | 15.42 |
| 1756 | OD1 | ASN | A | 249 | 37.962 | 18.912 | 48.332 | 1.00 | 19.30 |
| 1757 | ND2 | ASN | A | 249 | 39.543 | 17.471 | 47.711 | 1.00 | 15.03 |
| 1758 | C | ASN | A | 249 | 38.565 | 15.959 | 51.899 | 1.00 | 13.46 |
| 1759 | O | ASN | A | 249 | 38.095 | 16.474 | 52.844 | 1.00 | 13.52 |
| 1760 | N | ILE | A | 250 | 39.510 | 15.094 | 52.072 | 1.00 | 13.73 |
| 1761 | CA | ILE | A | 250 | 40.015 | 14.798 | 53.423 | 1.00 | 14.41 |
| 1762 | CB | ILE | A | 250 | 39.365 | 13.556 | 54.085 | 1.00 | 13.86 |
| 1763 | CG1 | ILE | A | 250 | 37.882 | 13.407 | 53.814 | 1.00 | 13.07 |
| 1764 | CD1 | ILE | A | 250 | 37.297 | 12.255 | 54.531 | 1.00 | 3.67 |
| 1765 | CG2 | ILE | A | 250 | 39.599 | 13.581 | 55.597 | 1.00 | 14.87 |
| 1766 | C | ILE | A | 250 | 41.529 | 14.446 | 53.365 | 1.00 | 14.72 |
| 1767 | O | ILE | A | 250 | 41.896 | 13.405 | 52.723 | 1.00 | 16.40 |
| 1768 | N | PRO | A | 251 | 42.370 | 15.175 | 54.097 | 1.00 | 12.63 |
| 1769 | CA | PRO | A | 251 | 43.787 | 14.804 | 54.207 | 1.00 | 11.69 |
| 1770 | CB | PRO | A | 251 | 44.357 | 15.830 | 55.163 | 1.00 | 10.04 |
| 1771 | CG | PRO | A | 251 | 43.377 | 16.929 | 55.181 | 1.00 | 11.46 |
| 1772 | CD | PRO | A | 251 | 42.017 | 16.350 | 54.888 | 1.00 | 12.36 |
| 1773 | C | PRO | A | 251 | 43.863 | 13.404 | 54.776 | 1.00 | 11.53 |
| 1774 | O | PRO | A | 251 | 43.447 | 13.273 | 55.889 | 1.00 | 13.40 |
| 1775 | N | TYR | A | 252 | 44.353 | 12.423 | 54.014 | 1.00 | 12.09 |
| 1776 | CA | TYR | A | 252 | 44.368 | 10.987 | 54.338 | 1.00 | 11.84 |

FIGURE 3 (Cont.)

| A | B | C | D | E | F | G | H | I | J |
|---|---|---|---|---|---|---|---|---|---|
| 1777 | CB | TYR | A | 252 | 43.259 | 10.338 | 53.633 | 1.00 | 9.92 |
| 1778 | CG | TYR | A | 252 | 42.905 | 8.950 | 54.021 | 1.00 | 9.52 |
| 1779 | CD1 | TYR | A | 252 | 41.723 | 8.687 | 54.710 | 1.00 | 9.33 |
| 1780 | CE1 | TYR | A | 252 | 41.332 | 7.435 | 55.020 | 1.00 | 12.90 |
| 1781 | CZ | TYR | A | 252 | 42.122 | 6.341 | 54.611 | 1.00 | 14.42 |
| 1782 | OH | TYR | A | 252 | 41.763 | 5.043 | 54.880 | 1.00 | 14.51 |
| 1783 | CE2 | TYR | A | 252 | 43.253 | 6.577 | 53.890 | 1.00 | 10.13 |
| 1784 | CD2 | TYR | A | 252 | 43.597 | 7.904 | 53.553 | 1.00 | 10.81 |
| 1785 | C | TYR | A | 252 | 45.622 | 10.417 | 53.718 | 1.00 | 13.21 |
| 1786 | O | TYR | A | 252 | 45.759 | 10.402 | 52.469 | 1.00 | 14.83 |
| 1787 | N | PRO | A | 253 | 46.539 | 10.034 | 54.555 | 1.00 | 12.63 |
| 1788 | CA | PRO | A | 253 | 47.789 | 9.380 | 54.143 | 1.00 | 13.49 |
| 1789 | CB | PRO | A | 253 | 48.761 | 9.661 | 55.299 | 1.00 | 13.59 |
| 1790 | CG | PRO | A | 253 | 47.977 | 10.440 | 56.317 | 1.00 | 13.58 |
| 1791 | CD | PRO | A | 253 | 46.480 | 10.309 | 55.981 | 1.00 | 13.29 |
| 1792 | C | PRO | A | 253 | 47.698 | 7.905 | 53.958 | 1.00 | 14.24 |
| 1793 | O | PRO | A | 253 | 47.458 | 7.184 | 54.930 | 1.00 | 16.06 |
| 1794 | N | LYS | A | 254 | 47.964 | 7.461 | 52.736 | 1.00 | 13.94 |
| 1795 | CA | LYS | A | 254 | 47.866 | 6.060 | 52.382 | 1.00 | 12.94 |
| 1796 | CB | LYS | A | 254 | 47.278 | 5.941 | 50.975 | 1.00 | 12.37 |
| 1797 | CG | LYS | A | 254 | 45.776 | 6.376 | 50.907 | 1.00 | 16.73 |
| 1798 | CD | LYS | A | 254 | 45.351 | 6.972 | 49.499 | 1.00 | 14.57 |
| 1799 | CE | LYS | A | 254 | 44.317 | 6.201 | 48.797 | 1.00 | 15.51 |
| 1800 | NZ | LYS | A | 254 | 43.004 | 6.610 | 49.180 | 1.00 | 15.21 |
| 1801 | C | LYS | A | 254 | 49.284 | 5.507 | 52.464 | 1.00 | 10.97 |
| 1802 | O | LYS | A | 254 | 50.204 | 6.220 | 52.738 | 1.00 | 12.29 |
| 1803 | N | ALA | A | 255 | 49.463 | 4.240 | 52.221 | 1.00 | 9.66 |
| 1804 | CA | ALA | A | 255 | 50.742 | 3.597 | 52.435 | 1.00 | 8.83 |
| 1805 | CB | ALA | A | 255 | 50.713 | 2.137 | 52.009 | 1.00 | 8.02 |
| 1806 | C | ALA | A | 255 | 51.903 | 4.317 | 51.769 | 1.00 | 8.42 |
| 1807 | O | ALA | A | 255 | 52.008 | 4.425 | 50.545 | 1.00 | 8.08 |
| 1808 | N | GLY | A | 256 | 52.712 | 4.879 | 52.634 | 1.00 | 8.46 |
| 1809 | CA | GLY | A | 256 | 54.029 | 5.342 | 52.291 | 1.00 | 8.08 |
| 1810 | C | GLY | A | 256 | 54.021 | 6.774 | 51.908 | 1.00 | 7.63 |
| 1811 | O | GLY | A | 256 | 55.052 | 7.261 | 51.460 | 1.00 | 6.56 |
| 1812 | N | ALA | A | 257 | 52.863 | 7.409 | 52.051 | 1.00 | 6.97 |
| 1813 | CA | ALA | A | 257 | 52.732 | 8.791 | 51.694 | 1.00 | 8.33 |
| 1814 | CB | ALA | A | 257 | 51.296 | 9.127 | 51.354 | 1.00 | 6.37 |
| 1815 | C | ALA | A | 257 | 53.170 | 9.612 | 52.847 | 1.00 | 9.33 |
| 1816 | O | ALA | A | 257 | 53.356 | 9.124 | 53.916 | 1.00 | 9.16 |
| 1817 | N | LYS | A | 258 | 53.285 | 10.896 | 52.581 | 1.00 | 10.60 |
| 1818 | CA | LYS | A | 258 | 53.585 | 11.918 | 53.560 | 1.00 | 11.29 |
| 1819 | CB | LYS | A | 258 | 53.839 | 13.253 | 52.789 | 1.00 | 11.75 |
| 1820 | CG | LYS | A | 258 | 53.924 | 14.580 | 53.571 | 1.00 | 13.64 |
| 1821 | CD | LYS | A | 258 | 54.789 | 14.531 | 54.835 | 1.00 | 19.86 |
| 1822 | CE | LYS | A | 258 | 55.946 | 15.555 | 54.858 | 1.00 | 19.33 |
| 1823 | NZ | LYS | A | 258 | 56.672 | 15.345 | 56.167 | 1.00 | 22.71 |
| 1824 | C | LYS | A | 258 | 52.463 | 11.975 | 54.626 | 1.00 | 10.87 |
| 1825 | O | LYS | A | 258 | 51.381 | 12.344 | 54.348 | 1.00 | 11.47 |
| 1826 | N | ASN | A | 259 | 52.785 | 11.485 | 55.820 | 1.00 | 11.06 |
| 1827 | CA | ASN | A | 259 | 52.051 | 11.606 | 57.106 | 1.00 | 10.06 |

FIGURE 3 (Cont.)

| A | B | C | D | E | F | G | H | I | J |
|---|---|---|---|---|---|---|---|---|---|
| 1828 | CB | ASN | A | 259 | 52.695 | 10.669 | 58.127 | 1.00 | 8.02 |
| 1829 | CG | ASN | A | 259 | 52.018 | 9.276 | 58.168 | 1.00 | 8.20 |
| 1830 | OD1 | ASN | A | 259 | 52.565 | 8.323 | 58.775 | 1.00 | 10.00 |
| 1831 | ND2 | ASN | A | 259 | 50.864 | 9.141 | 57.530 | 1.00 | 2.00 |
| 1832 | C | ASN | A | 259 | 52.013 | 13.009 | 57.754 | 1.00 | 9.74 |
| 1833 | O | ASN | A | 259 | 52.840 | 13.890 | 57.447 | 1.00 | 9.92 |
| 1834 | N | PRO | A | 260 | 51.131 | 13.186 | 58.736 | 1.00 | 9.50 |
| 1835 | CA | PRO | A | 260 | 51.085 | 14.489 | 59.413 | 1.00 | 8.94 |
| 1836 | CB | PRO | A | 260 | 49.844 | 14.415 | 60.274 | 1.00 | 9.07 |
| 1837 | CG | PRO | A | 260 | 49.237 | 12.928 | 60.055 | 1.00 | 8.15 |
| 1838 | CD | PRO | A | 260 | 50.259 | 12.146 | 59.356 | 1.00 | 8.42 |
| 1839 | C | PRO | A | 260 | 52.323 | 14.526 | 60.285 | 1.00 | 10.00 |
| 1840 | O | PRO | A | 260 | 52.739 | 13.404 | 60.720 | 1.00 | 8.96 |
| 1841 | N | VAL | A | 261 | 52.934 | 15.715 | 60.460 | 1.00 | 10.41 |
| 1842 | CA | VAL | A | 261 | 53.874 | 15.955 | 61.554 | 1.00 | 11.15 |
| 1843 | CB | VAL | A | 261 | 55.019 | 16.990 | 61.193 | 1.00 | 12.43 |
| 1844 | CG1 | VAL | A | 261 | 54.696 | 18.474 | 61.664 | 1.00 | 12.99 |
| 1845 | CG2 | VAL | A | 261 | 55.406 | 16.900 | 59.678 | 1.00 | 11.88 |
| 1846 | C | VAL | A | 261 | 53.079 | 16.355 | 62.817 | 1.00 | 11.01 |
| 1847 | O | VAL | A | 261 | 52.052 | 17.014 | 62.717 | 1.00 | 11.02 |
| 1848 | N | VAL | A | 262 | 53.518 | 15.891 | 63.992 | 1.00 | 10.08 |
| 1849 | CA | VAL | A | 262 | 52.806 | 16.197 | 65.231 | 1.00 | 10.02 |
| 1850 | CB | VAL | A | 262 | 52.198 | 14.926 | 65.942 | 1.00 | 10.04 |
| 1851 | CG1 | VAL | A | 262 | 51.377 | 15.315 | 67.193 | 1.00 | 7.24 |
| 1852 | CG2 | VAL | A | 262 | 53.275 | 13.886 | 66.276 | 1.00 | 9.45 |
| 1853 | C | VAL | A | 262 | 53.699 | 16.887 | 66.202 | 1.00 | 10.79 |
| 1854 | O | VAL | A | 262 | 54.887 | 16.641 | 66.228 | 1.00 | 12.09 |
| 1855 | N | ARG | A | 263 | 53.119 | 17.739 | 67.014 | 1.00 | 11.09 |
| 1856 | CA | ARG | A | 263 | 53.859 | 18.428 | 68.057 | 1.00 | 12.31 |
| 1857 | CB | ARG | A | 263 | 54.167 | 19.900 | 67.652 | 1.00 | 12.57 |
| 1858 | CG | ARG | A | 263 | 55.606 | 20.121 | 67.132 | 1.00 | 12.34 |
| 1859 | CD | ARG | A | 263 | 55.729 | 20.624 | 65.727 | 1.00 | 15.06 |
| 1860 | NE | ARG | A | 263 | 55.264 | 21.997 | 65.738 | 1.00 | 18.80 |
| 1861 | CZ | ARG | A | 263 | 55.998 | 23.066 | 66.048 | 1.00 | 19.91 |
| 1862 | NH1 | ARG | A | 263 | 55.402 | 24.248 | 66.069 | 1.00 | 19.24 |
| 1863 | NH2 | ARG | A | 263 | 57.307 | 22.988 | 66.330 | 1.00 | 21.73 |
| 1864 | C | ARG | A | 263 | 53.031 | 18.355 | 69.324 | 1.00 | 12.40 |
| 1865 | O | ARG | A | 263 | 51.795 | 18.398 | 69.262 | 1.00 | 12.69 |
| 1866 | N | ILE | A | 264 | 53.693 | 18.227 | 70.477 | 1.00 | 12.11 |
| 1867 | CA | ILE | A | 264 | 52.927 | 18.245 | 71.720 | 1.00 | 11.72 |
| 1868 | CB | ILE | A | 264 | 52.908 | 16.875 | 72.457 | 1.00 | 11.92 |
| 1869 | CG1 | ILE | A | 264 | 52.032 | 15.869 | 71.678 | 1.00 | 13.59 |
| 1870 | CD1 | ILE | A | 264 | 52.840 | 14.723 | 71.055 | 1.00 | 15.14 |
| 1871 | CG2 | ILE | A | 264 | 52.335 | 17.031 | 73.845 | 1.00 | 11.59 |
| 1872 | C | ILE | A | 264 | 53.398 | 19.356 | 72.591 | 1.00 | 10.76 |
| 1873 | O | ILE | A | 264 | 54.568 | 19.625 | 72.672 | 1.00 | 9.65 |
| 1874 | N | PHE | A | 265 | 52.397 | 19.950 | 73.228 | 1.00 | 10.54 |
| 1875 | CA | PHE | A | 265 | 52.424 | 21.251 | 73.809 | 1.00 | 10.38 |
| 1876 | CB | PHE | A | 265 | 51.594 | 22.236 | 72.957 | 1.00 | 11.00 |
| 1877 | CG | PHE | A | 265 | 52.370 | 23.041 | 71.935 | 1.00 | 9.69 |
| 1878 | CD1 | PHE | A | 265 | 51.884 | 23.152 | 70.623 | 1.00 | 12.62 |

FIGURE 3 (Cont.)

| A | B | C | D | E | F | G | H | I | J |
|---|---|---|---|---|---|---|---|---|---|
| 1879 | CE1 | PHE | A | 265 | 52.542 | 23.934 | 69.629 | 1.00 | 11.57 |
| 1880 | CZ | PHE | A | 265 | 53.682 | 24.608 | 69.976 | 1.00 | 13.82 |
| 1881 | CE2 | PHE | A | 265 | 54.179 | 24.511 | 71.303 | 1.00 | 11.36 |
| 1882 | CD2 | PHE | A | 265 | 53.507 | 23.722 | 72.265 | 1.00 | 10.14 |
| 1883 | C | PHE | A | 265 | 51.732 | 21.140 | 75.143 | 1.00 | 10.37 |
| 1884 | O | PHE | A | 265 | 50.594 | 20.678 | 75.243 | 1.00 | 9.80 |
| 1885 | N | ILE | A | 266 | 52.429 | 21.624 | 76.161 | 1.00 | 10.68 |
| 1886 | CA | ILE | A | 266 | 51.832 | 21.943 | 77.453 | 1.00 | 10.28 |
| 1887 | CB | ILE | A | 266 | 52.544 | 21.110 | 78.565 | 1.00 | 9.74 |
| 1888 | CG1 | ILE | A | 266 | 52.907 | 19.709 | 78.062 | 1.00 | 9.79 |
| 1889 | CD1 | ILE | A | 266 | 53.294 | 18.743 | 79.180 | 1.00 | 8.11 |
| 1890 | CG2 | ILE | A | 266 | 51.666 | 20.983 | 79.742 | 1.00 | 9.37 |
| 1891 | C | ILE | A | 266 | 51.839 | 23.481 | 77.775 | 1.00 | 10.24 |
| 1892 | O | ILE | A | 266 | 52.802 | 24.213 | 77.493 | 1.00 | 9.21 |
| 1893 | N | ILE | A | 267 | 50.743 | 23.904 | 78.419 | 1.00 | 10.91 |
| 1894 | CA | ILE | A | 267 | 50.486 | 25.289 | 78.825 | 1.00 | 11.93 |
| 1895 | CB | ILE | A | 267 | 49.285 | 25.861 | 77.995 | 1.00 | 12.43 |
| 1896 | CG1 | ILE | A | 267 | 49.243 | 27.399 | 77.976 | 1.00 | 12.21 |
| 1897 | CD1 | ILE | A | 267 | 50.141 | 28.016 | 76.983 | 1.00 | 11.80 |
| 1898 | CG2 | ILE | A | 267 | 47.965 | 25.347 | 78.548 | 1.00 | 13.96 |
| 1899 | C | ILE | A | 267 | 50.156 | 25.363 | 80.319 | 1.00 | 12.10 |
| 1900 | O | ILE | A | 267 | 49.563 | 24.456 | 80.848 | 1.00 | 12.32 |
| 1901 | N | ASP | A | 268 | 50.549 | 26.453 | 80.988 | 1.00 | 12.28 |
| 1902 | CA | ASP | A | 268 | 50.021 | 26.790 | 82.312 | 1.00 | 11.91 |
| 1903 | CB | ASP | A | 268 | 50.769 | 27.942 | 82.968 | 1.00 | 11.81 |
| 1904 | CG | ASP | A | 268 | 50.464 | 28.040 | 84.443 | 1.00 | 11.22 |
| 1905 | OD1 | ASP | A | 268 | 49.363 | 28.460 | 84.845 | 1.00 | 10.58 |
| 1906 | OD2 | ASP | A | 268 | 51.269 | 27.678 | 85.284 | 1.00 | 12.74 |
| 1907 | C | ASP | A | 268 | 48.594 | 27.229 | 82.152 | 1.00 | 11.97 |
| 1908 | O | ASP | A | 268 | 48.295 | 27.977 | 81.256 | 1.00 | 12.29 |
| 1909 | N | THR | A | 269 | 47.722 | 26.784 | 83.028 | 1.00 | 12.12 |
| 1910 | CA | THR | A | 269 | 46.339 | 27.109 | 82.904 | 1.00 | 12.40 |
| 1911 | CB | THR | A | 269 | 45.520 | 26.035 | 83.446 | 1.00 | 12.18 |
| 1912 | OG1 | THR | A | 269 | 45.405 | 25.036 | 82.423 | 1.00 | 12.78 |
| 1913 | CG2 | THR | A | 269 | 44.091 | 26.545 | 83.726 | 1.00 | 10.95 |
| 1914 | C | THR | A | 269 | 46.010 | 28.330 | 83.639 | 1.00 | 13.27 |
| 1915 | O | THR | A | 269 | 45.170 | 29.061 | 83.215 | 1.00 | 13.39 |
| 1916 | N | THR | A | 270 | 46.607 | 28.529 | 84.791 | 1.00 | 14.71 |
| 1917 | CA | THR | A | 270 | 46.271 | 29.708 | 85.561 | 1.00 | 16.17 |
| 1918 | CB | THR | A | 270 | 46.637 | 29.482 | 87.051 | 1.00 | 16.70 |
| 1919 | OG1 | THR | A | 270 | 45.960 | 28.300 | 87.524 | 1.00 | 17.35 |
| 1920 | CG2 | THR | A | 270 | 46.094 | 30.605 | 87.944 | 1.00 | 17.07 |
| 1921 | C | THR | A | 270 | 46.906 | 30.962 | 84.924 | 1.00 | 16.38 |
| 1922 | O | THR | A | 270 | 46.200 | 31.954 | 84.659 | 1.00 | 16.82 |
| 1923 | N | TYR | A | 271 | 48.203 | 30.874 | 84.601 | 1.00 | 16.44 |
| 1924 | CA | TYR | A | 271 | 48.971 | 31.964 | 83.985 | 1.00 | 16.27 |
| 1925 | CB | TYR | A | 271 | 50.194 | 32.266 | 84.865 | 1.00 | 16.51 |
| 1926 | CG | TYR | A | 271 | 50.063 | 33.028 | 86.210 | 1.00 | 16.63 |
| 1927 | CD1 | TYR | A | 271 | 50.868 | 34.162 | 86.425 | 1.00 | 19.71 |
| 1928 | CE1 | TYR | A | 271 | 50.875 | 34.890 | 87.654 | 1.00 | 20.59 |
| 1929 | CZ | TYR | A | 271 | 50.077 | 34.471 | 88.704 | 1.00 | 19.63 |

FIGURE 3 (Cont.)

| A | B | C | D | E | F | G | H | I | J |
|---|---|---|---|---|---|---|---|---|---|
| 1930 | OH | TYR | A | 271 | 50.165 | 35.290 | 89.831 | 1.00 | 18.08 |
| 1931 | CE2 | TYR | A | 271 | 49.255 | 33.297 | 88.546 | 1.00 | 17.66 |
| 1932 | CD2 | TYR | A | 271 | 49.271 | 32.575 | 87.290 | 1.00 | 16.65 |
| 1933 | C | TYR | A | 271 | 49.465 | 31.637 | 82.513 | 1.00 | 16.01 |
| 1934 | O | TYR | A | 271 | 50.688 | 31.497 | 82.261 | 1.00 | 15.67 |
| 1935 | N | PRO | A | 272 | 48.536 | 31.559 | 81.540 | 1.00 | 15.77 |
| 1936 | CA | PRO | A | 272 | 48.899 | 31.273 | 80.135 | 1.00 | 16.18 |
| 1937 | CB | PRO | A | 272 | 47.572 | 30.848 | 79.495 | 1.00 | 15.66 |
| 1938 | CG | PRO | A | 272 | 46.459 | 31.452 | 80.375 | 1.00 | 14.89 |
| 1939 | CD | PRO | A | 272 | 47.080 | 31.789 | 81.693 | 1.00 | 15.41 |
| 1940 | C | PRO | A | 272 | 49.391 | 32.544 | 79.490 | 1.00 | 17.20 |
| 1941 | O | PRO | A | 272 | 50.329 | 32.522 | 78.665 | 1.00 | 17.60 |
| 1942 | N | ALA | A | 273 | 48.636 | 33.608 | 79.810 | 1.00 | 18.00 |
| 1943 | CA | ALA | A | 273 | 49.103 | 34.943 | 80.038 | 1.00 | 17.91 |
| 1944 | CB | ALA | A | 273 | 48.548 | 35.428 | 81.433 | 1.00 | 17.56 |
| 1945 | C | ALA | A | 273 | 50.626 | 34.886 | 79.992 | 1.00 | 18.27 |
| 1946 | O | ALA | A | 273 | 51.222 | 35.169 | 78.923 | 1.00 | 18.00 |
| 1947 | N | TYR | A | 274 | 51.209 | 34.381 | 81.103 | 1.00 | 18.96 |
| 1948 | CA | TYR | A | 274 | 52.643 | 34.560 | 81.511 | 1.00 | 19.63 |
| 1949 | CB | TYR | A | 274 | 52.902 | 33.776 | 82.825 | 1.00 | 19.55 |
| 1950 | CG | TYR | A | 274 | 54.242 | 33.976 | 83.569 | 1.00 | 20.36 |
| 1951 | CD1 | TYR | A | 274 | 54.716 | 32.978 | 84.454 | 1.00 | 20.71 |
| 1952 | CE1 | TYR | A | 274 | 55.926 | 33.148 | 85.186 | 1.00 | 20.47 |
| 1953 | CZ | TYR | A | 274 | 56.666 | 34.311 | 85.039 | 1.00 | 19.95 |
| 1954 | OH | TYR | A | 274 | 57.818 | 34.418 | 85.739 | 1.00 | 19.26 |
| 1955 | CE2 | TYR | A | 274 | 56.243 | 35.342 | 84.189 | 1.00 | 20.80 |
| 1956 | CD2 | TYR | A | 274 | 55.014 | 35.176 | 83.454 | 1.00 | 20.75 |
| 1957 | C | TYR | A | 274 | 53.756 | 34.217 | 80.489 | 1.00 | 19.82 |
| 1958 | O | TYR | A | 274 | 54.612 | 35.102 | 80.159 | 1.00 | 19.29 |
| 1959 | N | VAL | A | 275 | 53.783 | 32.955 | 80.019 | 1.00 | 19.54 |
| 1960 | CA | VAL | A | 275 | 54.929 | 32.511 | 79.219 | 1.00 | 19.27 |
| 1961 | CB | VAL | A | 275 | 56.056 | 31.925 | 80.118 | 1.00 | 19.54 |
| 1962 | CG1 | VAL | A | 275 | 56.196 | 30.381 | 79.969 | 1.00 | 18.56 |
| 1963 | CG2 | VAL | A | 275 | 57.409 | 32.692 | 79.867 | 1.00 | 18.70 |
| 1964 | C | VAL | A | 275 | 54.633 | 31.604 | 78.064 | 1.00 | 19.31 |
| 1965 | O | VAL | A | 275 | 55.572 | 31.172 | 77.374 | 1.00 | 19.08 |
| 1966 | N | GLY | A | 276 | 53.345 | 31.295 | 77.867 | 1.00 | 19.56 |
| 1967 | CA | GLY | A | 276 | 52.865 | 30.669 | 76.645 | 1.00 | 19.17 |
| 1968 | C | GLY | A | 276 | 53.230 | 29.194 | 76.447 | 1.00 | 18.86 |
| 1969 | O | GLY | A | 276 | 54.072 | 28.644 | 77.161 | 1.00 | 19.43 |
| 1970 | N | PRO | A | 277 | 52.631 | 28.565 | 75.442 | 1.00 | 18.00 |
| 1971 | CA | PRO | A | 277 | 52.728 | 27.112 | 75.257 | 1.00 | 17.16 |
| 1972 | CB | PRO | A | 277 | 52.052 | 26.857 | 73.911 | 1.00 | 17.13 |
| 1973 | CG | PRO | A | 277 | 51.200 | 28.068 | 73.631 | 1.00 | 18.44 |
| 1974 | CD | PRO | A | 277 | 51.846 | 29.221 | 74.380 | 1.00 | 17.97 |
| 1975 | C | PRO | A | 277 | 54.134 | 26.618 | 75.159 | 1.00 | 16.43 |
| 1976 | O | PRO | A | 277 | 55.017 | 27.234 | 74.564 | 1.00 | 16.54 |
| 1977 | N | GLN | A | 278 | 54.310 | 25.431 | 75.711 | 1.00 | 15.81 |
| 1978 | CA | GLN | A | 278 | 55.630 | 24.891 | 75.946 | 1.00 | 14.79 |
| 1979 | CB | GLN | A | 278 | 55.924 | 24.901 | 77.470 | 1.00 | 15.09 |
| 1980 | CG | GLN | A | 278 | 56.231 | 26.341 | 78.058 | 1.00 | 14.91 |

FIGURE 3 (Cont.)

| A | B | C | D | E | F | G | H | I | J |
|---|---|---|---|---|---|---|---|---|---|
| 1981 | CD | GLN | A | 278 | 57.474 | 27.011 | 77.437 | 1.00 | 15.99 |
| 1982 | OE1 | GLN | A | 278 | 57.592 | 28.258 | 77.377 | 1.00 | 17.05 |
| 1983 | NE2 | GLN | A | 278 | 58.418 | 26.174 | 76.999 | 1.00 | 16.16 |
| 1984 | C | GLN | A | 278 | 55.680 | 23.516 | 75.273 | 1.00 | 13.77 |
| 1985 | O | GLN | A | 278 | 54.820 | 22.684 | 75.501 | 1.00 | 12.65 |
| 1986 | N | GLU | A | 279 | 56.668 | 23.337 | 74.393 | 1.00 | 13.07 |
| 1987 | CA | GLU | A | 279 | 56.740 | 22.155 | 73.529 | 1.00 | 12.59 |
| 1988 | CB | GLU | A | 279 | 57.233 | 22.513 | 72.120 | 1.00 | 12.19 |
| 1989 | CG | GLU | A | 279 | 56.955 | 21.431 | 71.077 | 1.00 | 11.81 |
| 1990 | CD | GLU | A | 279 | 57.868 | 21.512 | 69.843 | 1.00 | 12.89 |
| 1991 | OE1 | GLU | A | 279 | 58.535 | 22.583 | 69.632 | 1.00 | 11.28 |
| 1992 | OE2 | GLU | A | 279 | 57.916 | 20.500 | 69.086 | 1.00 | 8.96 |
| 1993 | C | GLU | A | 279 | 57.601 | 21.061 | 74.140 | 1.00 | 12.21 |
| 1994 | O | GLU | A | 279 | 58.728 | 21.279 | 74.570 | 1.00 | 13.01 |
| 1995 | N | VAL | A | 280 | 57.052 | 19.872 | 74.162 | 1.00 | 11.45 |
| 1996 | CA | VAL | A | 280 | 57.644 | 18.804 | 74.912 | 1.00 | 10.83 |
| 1997 | CB | VAL | A | 280 | 56.629 | 17.808 | 75.301 | 1.00 | 9.84 |
| 1998 | CG1 | VAL | A | 280 | 55.523 | 18.513 | 76.078 | 1.00 | 8.03 |
| 1999 | CG2 | VAL | A | 280 | 57.303 | 16.651 | 76.111 | 1.00 | 10.14 |
| 2000 | C | VAL | A | 280 | 58.697 | 18.117 | 74.071 | 1.00 | 11.20 |
| 2001 | O | VAL | A | 280 | 58.419 | 17.602 | 73.005 | 1.00 | 11.34 |
| 2002 | N | PRO | A | 281 | 59.915 | 18.077 | 74.594 | 1.00 | 11.58 |
| 2003 | CA | PRO | A | 281 | 60.997 | 17.309 | 73.954 | 1.00 | 11.55 |
| 2004 | CB | PRO | A | 281 | 62.023 | 17.106 | 75.100 | 1.00 | 11.12 |
| 2005 | CG | PRO | A | 281 | 61.814 | 18.328 | 76.052 | 1.00 | 11.43 |
| 2006 | CD | PRO | A | 281 | 60.348 | 18.723 | 75.862 | 1.00 | 11.27 |
| 2007 | C | PRO | A | 281 | 60.537 | 15.954 | 73.404 | 1.00 | 11.57 |
| 2008 | O | PRO | A | 281 | 59.845 | 15.171 | 74.088 | 1.00 | 11.21 |
| 2009 | N | VAL | A | 282 | 60.924 | 15.726 | 72.149 | 1.00 | 11.72 |
| 2010 | CA | VAL | A | 282 | 60.794 | 14.426 | 71.481 | 1.00 | 11.62 |
| 2011 | CB | VAL | A | 282 | 60.162 | 14.537 | 70.002 | 1.00 | 11.82 |
| 2012 | CG1 | VAL | A | 282 | 60.490 | 15.872 | 69.250 | 1.00 | 11.43 |
| 2013 | CG2 | VAL | A | 282 | 60.500 | 13.296 | 69.133 | 1.00 | 11.05 |
| 2014 | C | VAL | A | 282 | 62.152 | 13.645 | 71.545 | 1.00 | 11.62 |
| 2015 | O | VAL | A | 282 | 63.192 | 14.169 | 71.187 | 1.00 | 12.08 |
| 2016 | N | PRO | A | 283 | 62.152 | 12.414 | 72.052 | 1.00 | 11.36 |
| 2017 | CA | PRO | A | 283 | 63.419 | 11.661 | 72.180 | 1.00 | 10.08 |
| 2018 | CB | PRO | A | 283 | 62.982 | 10.226 | 72.478 | 1.00 | 10.70 |
| 2019 | CG | PRO | A | 283 | 61.466 | 10.304 | 72.932 | 1.00 | 11.36 |
| 2020 | CD | PRO | A | 283 | 60.964 | 11.686 | 72.548 | 1.00 | 11.04 |
| 2021 | C | PRO | A | 283 | 64.158 | 11.691 | 70.868 | 1.00 | 9.64 |
| 2022 | O | PRO | A | 283 | 63.558 | 11.563 | 69.819 | 1.00 | 8.68 |
| 2023 | N | ALA | A | 284 | 65.445 | 11.922 | 70.926 | 1.00 | 8.62 |
| 2024 | CA | ALA | A | 284 | 66.294 | 11.940 | 69.741 | 1.00 | 8.96 |
| 2025 | CB | ALA | A | 284 | 67.806 | 12.265 | 70.164 | 1.00 | 8.44 |
| 2026 | C | ALA | A | 284 | 66.233 | 10.635 | 68.903 | 1.00 | 8.76 |
| 2027 | O | ALA | A | 284 | 66.365 | 10.654 | 67.684 | 1.00 | 7.89 |
| 2028 | N | MET | A | 285 | 66.071 | 9.504 | 69.566 | 1.00 | 9.75 |
| 2029 | CA | MET | A | 285 | 65.823 | 8.217 | 68.887 | 1.00 | 10.78 |
| 2030 | CB | MET | A | 285 | 65.649 | 7.120 | 69.955 | 1.00 | 11.82 |
| 2031 | CG | MET | A | 285 | 65.335 | 5.731 | 69.438 | 1.00 | 13.95 |

FIGURE 3 (Cont.)

| A | B | C | D | E | F | G | H | I | J |
|---|---|---|---|---|---|---|---|---|---|
| 2032 | SD | MET | A | 285 | 64.810 | 4.586 | 70.781 | 1.00 | 17.48 |
| 2033 | CE | MET | A | 285 | 65.222 | 5.606 | 72.446 | 1.00 | 15.49 |
| 2034 | C | MET | A | 285 | 64.560 | 8.290 | 67.995 | 1.00 | 10.40 |
| 2035 | O | MET | A | 285 | 64.539 | 7.747 | 66.879 | 1.00 | 10.50 |
| 2036 | N | ILE | A | 286 | 63.533 | 8.986 | 68.496 | 1.00 | 9.33 |
| 2037 | CA | ILE | A | 286 | 62.300 | 9.268 | 67.749 | 1.00 | 8.87 |
| 2038 | CB | ILE | A | 286 | 61.229 | 9.755 | 68.758 | 1.00 | 8.50 |
| 2039 | CG1 | ILE | A | 286 | 60.856 | 8.630 | 69.748 | 1.00 | 7.80 |
| 2040 | CD1 | ILE | A | 286 | 60.064 | 7.388 | 69.097 | 1.00 | 5.73 |
| 2041 | CG2 | ILE | A | 286 | 59.991 | 10.203 | 68.045 | 1.00 | 8.07 |
| 2042 | C | ILE | A | 286 | 62.443 | 10.256 | 66.528 | 1.00 | 8.64 |
| 2043 | O | ILE | A | 286 | 62.087 | 9.915 | 65.401 | 1.00 | 8.37 |
| 2044 | N | ALA | A | 287 | 62.957 | 11.459 | 66.743 | 1.00 | 8.37 |
| 2045 | CA | ALA | A | 287 | 63.057 | 12.463 | 65.690 | 1.00 | 8.43 |
| 2046 | CB | ALA | A | 287 | 63.494 | 13.783 | 66.297 | 1.00 | 8.64 |
| 2047 | C | ALA | A | 287 | 63.943 | 12.099 | 64.471 | 1.00 | 8.78 |
| 2048 | O | ALA | A | 287 | 63.852 | 12.752 | 63.450 | 1.00 | 7.95 |
| 2049 | N | SER | A | 288 | 64.754 | 11.047 | 64.578 | 1.00 | 9.93 |
| 2050 | CA | SER | A | 288 | 65.660 | 10.588 | 63.499 | 1.00 | 11.32 |
| 2051 | CB | SER | A | 288 | 66.476 | 9.292 | 63.913 | 1.00 | 11.51 |
| 2052 | OG | SER | A | 288 | 65.798 | 8.021 | 63.736 | 1.00 | 12.01 |
| 2053 | C | SER | A | 288 | 64.930 | 10.422 | 62.154 | 1.00 | 11.81 |
| 2054 | O | SER | A | 288 | 65.382 | 10.924 | 61.136 | 1.00 | 12.02 |
| 2055 | N | SER | A | 289 | 63.809 | 9.704 | 62.152 | 1.00 | 12.43 |
| 2056 | CA | SER | A | 289 | 62.819 | 9.805 | 61.044 | 1.00 | 12.76 |
| 2057 | CB | SER | A | 289 | 62.836 | 8.553 | 60.136 | 1.00 | 13.25 |
| 2058 | OG | SER | A | 289 | 63.045 | 7.361 | 60.869 | 1.00 | 13.82 |
| 2059 | C | SER | A | 289 | 61.413 | 10.090 | 61.572 | 1.00 | 12.54 |
| 2060 | O | SER | A | 289 | 61.226 | 10.192 | 62.786 | 1.00 | 12.33 |
| 2061 | N | ASP | A | 290 | 60.439 | 10.226 | 60.645 | 1.00 | 13.01 |
| 2062 | CA | ASP | A | 290 | 58.993 | 10.473 | 60.969 | 1.00 | 12.13 |
| 2063 | CB | ASP | A | 290 | 57.979 | 10.006 | 59.883 | 1.00 | 12.34 |
| 2064 | CG | ASP | A | 290 | 58.183 | 10.582 | 58.547 | 1.00 | 10.09 |
| 2065 | OD1 | ASP | A | 290 | 58.565 | 11.758 | 58.428 | 1.00 | 10.13 |
| 2066 | OD2 | ASP | A | 290 | 57.906 | 9.885 | 57.550 | 1.00 | 7.49 |
| 2067 | C | ASP | A | 290 | 58.490 | 9.664 | 62.150 | 1.00 | 12.14 |
| 2068 | O | ASP | A | 290 | 58.909 | 8.498 | 62.406 | 1.00 | 12.12 |
| 2069 | N | TYR | A | 291 | 57.449 | 10.210 | 62.760 | 1.00 | 11.31 |
| 2070 | CA | TYR | A | 291 | 56.987 | 9.606 | 63.976 | 1.00 | 9.83 |
| 2071 | CB | TYR | A | 291 | 57.930 | 9.949 | 65.144 | 1.00 | 9.21 |
| 2072 | CG | TYR | A | 291 | 57.996 | 11.418 | 65.560 | 1.00 | 5.44 |
| 2073 | CD1 | TYR | A | 291 | 58.936 | 12.294 | 65.006 | 1.00 | 2.00 |
| 2074 | CE1 | TYR | A | 291 | 58.978 | 13.568 | 65.402 | 1.00 | 2.00 |
| 2075 | CZ | TYR | A | 291 | 58.082 | 14.015 | 66.374 | 1.00 | 2.00 |
| 2076 | OH | TYR | A | 291 | 58.082 | 15.316 | 66.816 | 1.00 | 2.70 |
| 2077 | CE2 | TYR | A | 291 | 57.165 | 13.212 | 66.915 | 1.00 | 2.00 |
| 2078 | CD2 | TYR | A | 291 | 57.114 | 11.919 | 66.523 | 1.00 | 2.07 |
| 2079 | C | TYR | A | 291 | 55.548 | 9.956 | 64.297 | 1.00 | 10.09 |
| 2080 | O | TYR | A | 291 | 55.020 | 11.003 | 63.898 | 1.00 | 9.53 |
| 2081 | N | TYR | A | 292 | 54.932 | 8.998 | 64.977 | 1.00 | 9.32 |
| 2082 | CA | TYR | A | 292 | 53.613 | 9.179 | 65.509 | 1.00 | 10.29 |

FIGURE 3 (Cont.)

| A | B | C | D | E | F | G | H | I | J |
|---|---|---|---|---|---|---|---|---|---|
| 2083 | CB | TYR | A | 292 | 52.704 | 7.998 | 65.273 | 1.00 | 9.65 |
| 2084 | CG | TYR | A | 292 | 52.690 | 7.508 | 63.884 | 1.00 | 10.17 |
| 2085 | CD1 | TYR | A | 292 | 52.047 | 8.204 | 62.888 | 1.00 | 10.19 |
| 2086 | CE1 | TYR | A | 292 | 51.981 | 7.722 | 61.600 | 1.00 | 10.47 |
| 2087 | CZ | TYR | A | 292 | 52.597 | 6.528 | 61.282 | 1.00 | 11.56 |
| 2088 | OH | TYR | A | 292 | 52.603 | 6.012 | 60.002 | 1.00 | 11.74 |
| 2089 | CE2 | TYR | A | 292 | 53.241 | 5.812 | 62.250 | 1.00 | 13.14 |
| 2090 | CD2 | TYR | A | 292 | 53.272 | 6.298 | 63.566 | 1.00 | 12.76 |
| 2091 | C | TYR | A | 292 | 53.788 | 9.331 | 66.970 | 1.00 | 9.66 |
| 2092 | O | TYR | A | 292 | 54.638 | 8.684 | 67.583 | 1.00 | 10.26 |
| 2093 | N | PHE | A | 293 | 52.994 | 10.235 | 67.498 | 1.00 | 9.98 |
| 2094 | CA | PHE | A | 293 | 52.697 | 10.278 | 68.904 | 1.00 | 10.69 |
| 2095 | CB | PHE | A | 293 | 52.378 | 11.725 | 69.341 | 1.00 | 10.61 |
| 2096 | CG | PHE | A | 293 | 51.223 | 11.850 | 70.205 | 1.00 | 7.03 |
| 2097 | CD1 | PHE | A | 293 | 49.984 | 11.920 | 69.667 | 1.00 | 5.16 |
| 2098 | CE1 | PHE | A | 293 | 48.932 | 11.988 | 70.467 | 1.00 | 6.47 |
| 2099 | CZ | PHE | A | 293 | 49.113 | 11.989 | 71.872 | 1.00 | 4.50 |
| 2100 | CE2 | PHE | A | 293 | 50.359 | 11.917 | 72.403 | 1.00 | 3.71 |
| 2101 | CD2 | PHE | A | 293 | 51.392 | 11.835 | 71.575 | 1.00 | 3.92 |
| 2102 | C | PHE | A | 293 | 51.524 | 9.322 | 68.975 | 1.00 | 11.09 |
| 2103 | O | PHE | A | 293 | 50.842 | 9.067 | 67.984 | 1.00 | 11.24 |
| 2104 | N | SER | A | 294 | 51.340 | 8.763 | 70.153 | 1.00 | 12.08 |
| 2105 | CA | SER | A | 294 | 50.626 | 7.529 | 70.310 | 1.00 | 12.80 |
| 2106 | CB | SER | A | 294 | 51.624 | 6.399 | 70.610 | 1.00 | 12.58 |
| 2107 | OG | SER | A | 294 | 50.929 | 5.271 | 71.176 | 1.00 | 16.81 |
| 2108 | C | SER | A | 294 | 49.558 | 7.571 | 71.382 | 1.00 | 12.70 |
| 2109 | O | SER | A | 294 | 48.479 | 6.953 | 71.229 | 1.00 | 13.71 |
| 2110 | N | TRP | A | 295 | 49.891 | 8.218 | 72.473 | 1.00 | 12.62 |
| 2111 | CA | TRP | A | 295 | 49.022 | 8.385 | 73.640 | 1.00 | 13.84 |
| 2112 | CB | TRP | A | 295 | 48.498 | 7.058 | 74.243 | 1.00 | 13.96 |
| 2113 | CG | TRP | A | 295 | 47.377 | 7.379 | 75.114 | 1.00 | 17.31 |
| 2114 | CD1 | TRP | A | 295 | 47.350 | 7.287 | 76.449 | 1.00 | 19.53 |
| 2115 | NE1 | TRP | A | 295 | 46.148 | 7.756 | 76.930 | 1.00 | 20.89 |
| 2116 | CE2 | TRP | A | 295 | 45.374 | 8.185 | 75.891 | 1.00 | 21.73 |
| 2117 | CD2 | TRP | A | 295 | 46.130 | 7.990 | 74.722 | 1.00 | 20.26 |
| 2118 | CE3 | TRP | A | 295 | 45.557 | 8.346 | 73.491 | 1.00 | 21.60 |
| 2119 | CZ3 | TRP | A | 295 | 44.257 | 8.918 | 73.488 | 1.00 | 21.02 |
| 2120 | CH2 | TRP | A | 295 | 43.547 | 9.108 | 74.684 | 1.00 | 22.74 |
| 2121 | CZ2 | TRP | A | 295 | 44.077 | 8.745 | 75.886 | 1.00 | 22.19 |
| 2122 | C | TRP | A | 295 | 49.780 | 9.170 | 74.728 | 1.00 | 14.24 |
| 2123 | O | TRP | A | 295 | 51.024 | 9.095 | 74.808 | 1.00 | 15.37 |
| 2124 | N | LEU | A | 296 | 49.050 | 9.951 | 75.531 | 1.00 | 14.19 |
| 2125 | CA | LEU | A | 296 | 49.690 | 10.630 | 76.653 | 1.00 | 14.15 |
| 2126 | CB | LEU | A | 296 | 50.004 | 12.119 | 76.396 | 1.00 | 14.05 |
| 2127 | CG | LEU | A | 296 | 49.911 | 13.264 | 77.448 | 1.00 | 12.71 |
| 2128 | CD1 | LEU | A | 296 | 50.564 | 14.593 | 76.926 | 1.00 | 7.43 |
| 2129 | CD2 | LEU | A | 296 | 48.448 | 13.499 | 77.977 | 1.00 | 12.04 |
| 2130 | C | LEU | A | 296 | 48.808 | 10.433 | 77.813 | 1.00 | 14.72 |
| 2131 | O | LEU | A | 296 | 47.579 | 10.271 | 77.738 | 1.00 | 14.48 |
| 2132 | N | THR | A | 297 | 49.510 | 10.395 | 78.912 | 1.00 | 15.64 |
| 2133 | CA | THR | A | 297 | 48.930 | 10.056 | 80.174 | 1.00 | 16.89 |

FIGURE 3 (Cont.)

| A | B | C | D | E | F | G | H | I | J |
|---|---|---|---|---|---|---|---|---|---|
| 2134 | CB  | THR | A | 297 | 49.036 | 8.475  | 80.494 | 1.00 | 16.21 |
| 2135 | OG1 | THR | A | 297 | 49.874 | 8.274  | 81.630 | 1.00 | 17.21 |
| 2136 | CG2 | THR | A | 297 | 49.717 | 7.633  | 79.379 | 1.00 | 12.58 |
| 2137 | C   | THR | A | 297 | 49.629 | 10.988 | 81.211 | 1.00 | 18.13 |
| 2138 | O   | THR | A | 297 | 50.853 | 11.228 | 81.189 | 1.00 | 17.85 |
| 2139 | N   | TRP | A | 298 | 48.808 | 11.540 | 82.086 | 1.00 | 18.93 |
| 2140 | CA  | TRP | A | 298 | 49.288 | 12.370 | 83.146 | 1.00 | 18.75 |
| 2141 | CB  | TRP | A | 298 | 48.224 | 13.379 | 83.442 | 1.00 | 18.70 |
| 2142 | CG  | TRP | A | 298 | 48.308 | 14.501 | 82.572 | 1.00 | 19.22 |
| 2143 | CD1 | TRP | A | 298 | 47.443 | 14.819 | 81.569 | 1.00 | 19.25 |
| 2144 | NE1 | TRP | A | 298 | 47.851 | 15.983 | 80.970 | 1.00 | 18.71 |
| 2145 | CE2 | TRP | A | 298 | 48.988 | 16.445 | 81.592 | 1.00 | 18.00 |
| 2146 | CD2 | TRP | A | 298 | 49.312 | 15.525 | 82.592 | 1.00 | 15.98 |
| 2147 | CE3 | TRP | A | 298 | 50.435 | 15.744 | 83.345 | 1.00 | 14.73 |
| 2148 | CZ3 | TRP | A | 298 | 51.198 | 16.869 | 83.101 | 1.00 | 18.52 |
| 2149 | CH2 | TRP | A | 298 | 50.866 | 17.778 | 82.091 | 1.00 | 18.42 |
| 2150 | CZ2 | TRP | A | 298 | 49.760 | 17.586 | 81.329 | 1.00 | 18.59 |
| 2151 | C   | TRP | A | 298 | 49.440 | 11.521 | 84.363 | 1.00 | 19.53 |
| 2152 | O   | TRP | A | 298 | 48.593 | 10.675 | 84.595 | 1.00 | 20.10 |
| 2153 | N   | VAL | A | 299 | 50.491 | 11.763 | 85.156 | 1.00 | 19.51 |
| 2154 | CA  | VAL | A | 299 | 50.567 | 11.168 | 86.505 | 1.00 | 20.08 |
| 2155 | CB  | VAL | A | 299 | 51.765 | 10.116 | 86.670 | 1.00 | 19.64 |
| 2156 | CG1 | VAL | A | 299 | 52.363 | 9.701  | 85.302 | 1.00 | 19.24 |
| 2157 | CG2 | VAL | A | 299 | 52.868 | 10.642 | 87.471 | 1.00 | 19.22 |
| 2158 | C   | VAL | A | 299 | 50.483 | 12.348 | 87.515 | 1.00 | 20.12 |
| 2159 | O   | VAL | A | 299 | 49.467 | 12.508 | 88.179 | 1.00 | 21.31 |
| 2160 | N   | THR | A | 300 | 51.465 | 13.229 | 87.594 | 1.00 | 19.16 |
| 2161 | CA  | THR | A | 300 | 51.281 | 14.361 | 88.493 | 1.00 | 18.99 |
| 2162 | CB  | THR | A | 300 | 52.401 | 14.483 | 89.521 | 1.00 | 18.84 |
| 2163 | OG1 | THR | A | 300 | 53.459 | 15.257 | 88.948 | 1.00 | 19.14 |
| 2164 | CG2 | THR | A | 300 | 53.013 | 13.117 | 89.905 | 1.00 | 17.75 |
| 2165 | C   | THR | A | 300 | 51.185 | 15.635 | 87.682 | 1.00 | 18.81 |
| 2166 | O   | THR | A | 300 | 51.190 | 15.588 | 86.450 | 1.00 | 19.01 |
| 2167 | N   | ASP | A | 301 | 51.075 | 16.765 | 88.361 | 1.00 | 18.52 |
| 2168 | CA  | ASP | A | 301 | 50.942 | 18.020 | 87.648 | 1.00 | 18.16 |
| 2169 | CB  | ASP | A | 301 | 50.115 | 19.039 | 88.419 | 1.00 | 18.20 |
| 2170 | CG  | ASP | A | 301 | 48.713 | 18.555 | 88.634 | 1.00 | 18.49 |
| 2171 | OD1 | ASP | A | 301 | 48.459 | 17.841 | 89.599 | 1.00 | 22.77 |
| 2172 | OD2 | ASP | A | 301 | 47.781 | 18.779 | 87.880 | 1.00 | 17.91 |
| 2173 | C   | ASP | A | 301 | 52.301 | 18.558 | 87.267 | 1.00 | 17.88 |
| 2174 | O   | ASP | A | 301 | 52.363 | 19.410 | 86.407 | 1.00 | 18.34 |
| 2175 | N   | GLU | A | 302 | 53.366 | 18.054 | 87.883 | 1.00 | 17.56 |
| 2176 | CA  | GLU | A | 302 | 54.741 | 18.341 | 87.491 | 1.00 | 16.92 |
| 2177 | CB  | GLU | A | 302 | 55.614 | 18.516 | 88.751 | 1.00 | 17.91 |
| 2178 | CG  | GLU | A | 302 | 55.205 | 19.611 | 89.749 | 1.00 | 19.43 |
| 2179 | CD  | GLU | A | 302 | 53.807 | 19.417 | 90.328 | 1.00 | 20.29 |
| 2180 | OE1 | GLU | A | 302 | 52.983 | 20.329 | 90.129 | 1.00 | 20.95 |
| 2181 | OE2 | GLU | A | 302 | 53.535 | 18.365 | 90.973 | 1.00 | 19.67 |
| 2182 | C   | GLU | A | 302 | 55.317 | 17.164 | 86.667 | 1.00 | 16.02 |
| 2183 | O   | GLU | A | 302 | 56.526 | 17.064 | 86.475 | 1.00 | 15.56 |
| 2184 | N   | ARG | A | 303 | 54.462 | 16.257 | 86.196 | 1.00 | 15.37 |

FIGURE 3 (Cont.)

| A | B | C | D | E | F | G | H | I | J |
|---|---|---|---|---|---|---|---|---|---|
| 2185 | CA | ARG | A | 303 | 54.936 | 14.998 | 85.592 | 1.00 | 14.80 |
| 2186 | CB | ARG | A | 303 | 55.282 | 13.970 | 86.682 | 1.00 | 15.84 |
| 2187 | CG | ARG | A | 303 | 56.576 | 13.149 | 86.446 | 1.00 | 17.04 |
| 2188 | CD | ARG | A | 303 | 56.694 | 11.839 | 87.240 | 1.00 | 17.40 |
| 2189 | NE | ARG | A | 303 | 57.928 | 11.782 | 88.037 | 1.00 | 17.65 |
| 2190 | CZ | ARG | A | 303 | 59.179 | 11.698 | 87.550 | 1.00 | 16.23 |
| 2191 | NH1 | ARG | A | 303 | 60.201 | 11.646 | 88.408 | 1.00 | 13.53 |
| 2192 | NH2 | ARG | A | 303 | 59.425 | 11.694 | 86.232 | 1.00 | 13.39 |
| 2193 | C | ARG | A | 303 | 53.941 | 14.348 | 84.647 | 1.00 | 14.10 |
| 2194 | O | ARG | A | 303 | 52.732 | 14.372 | 84.881 | 1.00 | 14.66 |
| 2195 | N | VAL | A | 304 | 54.477 | 13.681 | 83.627 | 1.00 | 12.90 |
| 2196 | CA | VAL | A | 304 | 53.698 | 13.295 | 82.439 | 1.00 | 10.73 |
| 2197 | CB | VAL | A | 304 | 53.450 | 14.554 | 81.572 | 1.00 | 10.55 |
| 2198 | CG1 | VAL | A | 304 | 52.455 | 14.309 | 80.500 | 1.00 | 9.31 |
| 2199 | CG2 | VAL | A | 304 | 54.774 | 15.093 | 81.009 | 1.00 | 10.13 |
| 2200 | C | VAL | A | 304 | 54.405 | 12.198 | 81.609 | 1.00 | 10.22 |
| 2201 | O | VAL | A | 304 | 55.638 | 12.049 | 81.605 | 1.00 | 9.76 |
| 2202 | N | CYS | A | 305 | 53.606 | 11.384 | 80.962 | 1.00 | 9.47 |
| 2203 | CA | CYS | A | 305 | 54.131 | 10.375 | 80.090 | 1.00 | 10.06 |
| 2204 | CB | CYS | A | 305 | 53.657 | 8.994 | 80.552 | 1.00 | 10.10 |
| 2205 | SG | CYS | A | 305 | 54.680 | 7.600 | 79.969 | 1.00 | 11.27 |
| 2206 | C | CYS | A | 305 | 53.639 | 10.668 | 78.667 | 1.00 | 10.74 |
| 2207 | O | CYS | A | 305 | 52.441 | 10.900 | 78.437 | 1.00 | 11.65 |
| 2208 | N | LEU | A | 306 | 54.586 | 10.717 | 77.734 | 1.00 | 10.26 |
| 2209 | CA | LEU | A | 306 | 54.278 | 10.646 | 76.327 | 1.00 | 9.75 |
| 2210 | CB | LEU | A | 306 | 54.977 | 11.744 | 75.532 | 1.00 | 9.33 |
| 2211 | CG | LEU | A | 306 | 54.207 | 13.038 | 75.692 | 1.00 | 9.35 |
| 2212 | CD1 | LEU | A | 306 | 54.203 | 13.488 | 77.190 | 1.00 | 4.35 |
| 2213 | CD2 | LEU | A | 306 | 54.765 | 14.084 | 74.753 | 1.00 | 9.66 |
| 2214 | C | LEU | A | 306 | 54.732 | 9.312 | 75.807 | 1.00 | 9.83 |
| 2215 | O | LEU | A | 306 | 55.688 | 8.728 | 76.278 | 1.00 | 9.30 |
| 2216 | N | GLN | A | 307 | 54.008 | 8.839 | 74.812 | 1.00 | 10.76 |
| 2217 | CA | GLN | A | 307 | 54.321 | 7.617 | 74.095 | 1.00 | 10.90 |
| 2218 | CB | GLN | A | 307 | 53.233 | 6.528 | 74.340 | 1.00 | 10.35 |
| 2219 | CG | GLN | A | 307 | 53.045 | 6.193 | 75.828 | 1.00 | 8.48 |
| 2220 | CD | GLN | A | 307 | 52.359 | 4.847 | 76.080 | 1.00 | 7.38 |
| 2221 | OE1 | GLN | A | 307 | 51.166 | 4.821 | 76.490 | 1.00 | 4.38 |
| 2222 | NE2 | GLN | A | 307 | 53.128 | 3.722 | 75.916 | 1.00 | 4.70 |
| 2223 | C | GLN | A | 307 | 54.444 | 8.034 | 72.635 | 1.00 | 11.50 |
| 2224 | O | GLN | A | 307 | 53.705 | 8.886 | 72.171 | 1.00 | 12.60 |
| 2225 | N | TRP | A | 308 | 55.394 | 7.414 | 71.957 | 1.00 | 12.17 |
| 2226 | CA | TRP | A | 308 | 55.797 | 7.719 | 70.615 | 1.00 | 12.17 |
| 2227 | CB | TRP | A | 308 | 57.118 | 8.454 | 70.675 | 1.00 | 10.89 |
| 2228 | CG | TRP | A | 308 | 57.146 | 9.809 | 71.446 | 1.00 | 11.95 |
| 2229 | CD1 | TRP | A | 308 | 57.778 | 10.026 | 72.643 | 1.00 | 11.68 |
| 2230 | NE1 | TRP | A | 308 | 57.668 | 11.349 | 73.027 | 1.00 | 12.74 |
| 2231 | CE2 | TRP | A | 308 | 56.986 | 12.050 | 72.072 | 1.00 | 13.42 |
| 2232 | CD2 | TRP | A | 308 | 56.636 | 11.133 | 71.047 | 1.00 | 12.05 |
| 2233 | CE3 | TRP | A | 308 | 55.924 | 11.621 | 69.960 | 1.00 | 12.51 |
| 2234 | CZ3 | TRP | A | 308 | 55.580 | 13.018 | 69.930 | 1.00 | 15.55 |
| 2235 | CH2 | TRP | A | 308 | 55.959 | 13.880 | 70.954 | 1.00 | 14.66 |

FIGURE 3 (Cont.)

| A | B | C | D | E | F | G | H | I | J |
|---|---|---|---|---|---|---|---|---|---|
| 2236 | CZ2 | TRP | A | 308 | 56.659 | 13.415 | 72.030 | 1.00 | 14.70 |
| 2237 | C | TRP | A | 308 | 55.945 | 6.414 | 69.790 | 1.00 | 12.63 |
| 2238 | O | TRP | A | 308 | 56.127 | 5.346 | 70.337 | 1.00 | 13.33 |
| 2239 | N | LEU | A | 309 | 55.920 | 6.492 | 68.468 | 1.00 | 12.64 |
| 2240 | CA | LEU | A | 309 | 55.973 | 5.275 | 67.652 | 1.00 | 13.01 |
| 2241 | CB | LEU | A | 309 | 54.566 | 4.788 | 67.278 | 1.00 | 13.64 |
| 2242 | CG | LEU | A | 309 | 54.219 | 3.352 | 67.636 | 1.00 | 15.48 |
| 2243 | CD1 | LEU | A | 309 | 52.754 | 3.073 | 67.233 | 1.00 | 17.67 |
| 2244 | CD2 | LEU | A | 309 | 55.180 | 2.321 | 67.000 | 1.00 | 17.53 |
| 2245 | C | LEU | A | 309 | 56.765 | 5.559 | 66.408 | 1.00 | 12.71 |
| 2246 | O | LEU | A | 309 | 56.332 | 6.235 | 65.493 | 1.00 | 12.40 |
| 2247 | N | LYS | A | 310 | 57.986 | 5.082 | 66.374 | 1.00 | 13.08 |
| 2248 | CA | LYS | A | 310 | 58.762 | 5.249 | 65.152 | 1.00 | 13.62 |
| 2249 | CB | LYS | A | 310 | 60.087 | 4.445 | 65.238 | 1.00 | 13.36 |
| 2250 | CG | LYS | A | 310 | 61.232 | 5.071 | 66.042 | 1.00 | 12.07 |
| 2251 | CD | LYS | A | 310 | 62.629 | 4.515 | 65.593 | 1.00 | 12.65 |
| 2252 | CE | LYS | A | 310 | 63.151 | 5.106 | 64.244 | 1.00 | 13.87 |
| 2253 | NZ | LYS | A | 310 | 62.971 | 6.609 | 64.124 | 1.00 | 13.90 |
| 2254 | C | LYS | A | 310 | 57.824 | 4.752 | 63.994 | 1.00 | 14.15 |
| 2255 | O | LYS | A | 310 | 57.238 | 3.615 | 64.072 | 1.00 | 14.36 |
| 2256 | N | ARG | A | 311 | 57.626 | 5.620 | 62.987 | 1.00 | 13.83 |
| 2257 | CA | ARG | A | 311 | 56.826 | 5.266 | 61.817 | 1.00 | 14.54 |
| 2258 | CB | ARG | A | 311 | 57.157 | 6.165 | 60.658 | 1.00 | 14.97 |
| 2259 | CG | ARG | A | 311 | 56.387 | 5.829 | 59.341 | 1.00 | 16.18 |
| 2260 | CD | ARG | A | 311 | 56.739 | 6.749 | 58.193 | 1.00 | 17.21 |
| 2261 | NE | ARG | A | 311 | 55.618 | 7.562 | 57.721 | 1.00 | 19.68 |
| 2262 | CZ | ARG | A | 311 | 55.008 | 7.415 | 56.537 | 1.00 | 21.13 |
| 2263 | NH1 | ARG | A | 311 | 55.324 | 6.468 | 55.680 | 1.00 | 19.20 |
| 2264 | NH2 | ARG | A | 311 | 54.022 | 8.216 | 56.205 | 1.00 | 24.44 |
| 2265 | C | ARG | A | 311 | 57.067 | 3.841 | 61.340 | 1.00 | 14.62 |
| 2266 | O | ARG | A | 311 | 56.144 | 3.163 | 60.859 | 1.00 | 15.67 |
| 2267 | N | VAL | A | 312 | 58.304 | 3.395 | 61.447 | 1.00 | 13.52 |
| 2268 | CA | VAL | A | 312 | 58.637 | 2.021 | 61.169 | 1.00 | 13.53 |
| 2269 | CB | VAL | A | 312 | 60.159 | 1.831 | 60.792 | 1.00 | 14.22 |
| 2270 | CG1 | VAL | A | 312 | 60.303 | 0.790 | 59.626 | 1.00 | 14.10 |
| 2271 | CG2 | VAL | A | 312 | 60.905 | 3.232 | 60.462 | 1.00 | 13.33 |
| 2272 | C | VAL | A | 312 | 58.281 | 1.320 | 62.470 | 1.00 | 13.27 |
| 2273 | O | VAL | A | 312 | 59.099 | 1.266 | 63.349 | 1.00 | 12.36 |
| 2274 | N | GLN | A | 313 | 57.061 | 0.778 | 62.557 | 1.00 | 13.19 |
| 2275 | CA | GLN | A | 313 | 56.304 | 0.666 | 63.808 | 1.00 | 12.60 |
| 2276 | CB | GLN | A | 313 | 54.788 | 0.553 | 63.497 | 1.00 | 13.33 |
| 2277 | CG | GLN | A | 313 | 54.009 | 1.881 | 63.954 | 1.00 | 15.55 |
| 2278 | CD | GLN | A | 313 | 52.566 | 2.118 | 63.399 | 1.00 | 18.36 |
| 2279 | OE1 | GLN | A | 313 | 51.561 | 1.778 | 64.066 | 1.00 | 19.76 |
| 2280 | NE2 | GLN | A | 313 | 52.474 | 2.796 | 62.241 | 1.00 | 19.28 |
| 2281 | C | GLN | A | 313 | 56.774 | -0.420 | 64.806 | 1.00 | 11.95 |
| 2282 | O | GLN | A | 313 | 56.032 | -0.780 | 65.726 | 1.00 | 11.90 |
| 2283 | N | ASN | A | 314 | 58.013 | -0.914 | 64.648 | 1.00 | 10.79 |
| 2284 | CA | ASN | A | 314 | 58.545 | -1.941 | 65.512 | 1.00 | 8.38 |
| 2285 | CB | ASN | A | 314 | 59.499 | -2.942 | 64.813 | 1.00 | 7.86 |
| 2286 | CG | ASN | A | 314 | 60.621 | -2.301 | 64.041 | 1.00 | 6.38 |

FIGURE 3 (Cont.)

| A | B | C | D | E | F | G | H | I | J |
|---|---|---|---|---|---|---|---|---|---|
| 2287 | OD1 | ASN | A | 314 | 61.217 | -1.342 | 64.442 | 1.00 | 7.65 |
| 2288 | ND2 | ASN | A | 314 | 60.922 | -2.869 | 62.919 | 1.00 | 8.89 |
| 2289 | C | ASN | A | 314 | 59.160 | -1.406 | 66.754 | 1.00 | 8.27 |
| 2290 | O | ASN | A | 314 | 59.595 | -2.208 | 67.574 | 1.00 | 7.97 |
| 2291 | N | VAL | A | 315 | 59.216 | -0.088 | 66.917 | 1.00 | 7.36 |
| 2292 | CA | VAL | A | 315 | 59.797 | 0.442 | 68.141 | 1.00 | 8.13 |
| 2293 | CB | VAL | A | 315 | 61.390 | 0.725 | 68.089 | 1.00 | 8.18 |
| 2294 | CG1 | VAL | A | 315 | 61.834 | 1.711 | 69.223 | 1.00 | 7.69 |
| 2295 | CG2 | VAL | A | 315 | 61.900 | 1.213 | 66.736 | 1.00 | 10.59 |
| 2296 | C | VAL | A | 315 | 59.102 | 1.660 | 68.656 | 1.00 | 7.95 |
| 2297 | O | VAL | A | 315 | 58.917 | 2.620 | 67.939 | 1.00 | 8.00 |
| 2298 | N | SER | A | 316 | 58.773 | 1.615 | 69.944 | 1.00 | 8.39 |
| 2299 | CA | SER | A | 316 | 58.025 | 2.679 | 70.622 | 1.00 | 8.32 |
| 2300 | CB | SER | A | 316 | 56.727 | 2.121 | 71.123 | 1.00 | 6.94 |
| 2301 | OG | SER | A | 316 | 56.473 | 2.607 | 72.388 | 1.00 | 7.98 |
| 2302 | C | SER | A | 316 | 58.804 | 3.196 | 71.822 | 1.00 | 7.98 |
| 2303 | O | SER | A | 316 | 59.417 | 2.424 | 72.515 | 1.00 | 9.30 |
| 2304 | N | VAL | A | 317 | 58.753 | 4.493 | 72.071 | 1.00 | 7.84 |
| 2305 | CA | VAL | A | 317 | 59.429 | 5.134 | 73.189 | 1.00 | 6.85 |
| 2306 | CB | VAL | A | 317 | 60.376 | 6.195 | 72.662 | 1.00 | 6.77 |
| 2307 | CG1 | VAL | A | 317 | 61.349 | 5.580 | 71.638 | 1.00 | 6.49 |
| 2308 | CG2 | VAL | A | 317 | 61.134 | 6.881 | 73.846 | 1.00 | 6.41 |
| 2309 | C | VAL | A | 317 | 58.450 | 5.775 | 74.208 | 1.00 | 6.70 |
| 2310 | O | VAL | A | 317 | 57.733 | 6.713 | 73.907 | 1.00 | 7.14 |
| 2311 | N | LEU | A | 318 | 58.413 | 5.228 | 75.401 | 1.00 | 5.33 |
| 2312 | CA | LEU | A | 318 | 57.649 | 5.784 | 76.478 | 1.00 | 5.26 |
| 2313 | CB | LEU | A | 318 | 57.168 | 4.667 | 77.417 | 1.00 | 3.75 |
| 2314 | CG | LEU | A | 318 | 56.446 | 5.232 | 78.645 | 1.00 | 2.77 |
| 2315 | CD1 | LEU | A | 318 | 57.410 | 5.550 | 79.785 | 1.00 | 2.00 |
| 2316 | CD2 | LEU | A | 318 | 55.441 | 4.294 | 79.176 | 1.00 | 2.00 |
| 2317 | C | LEU | A | 318 | 58.600 | 6.769 | 77.154 | 1.00 | 5.72 |
| 2318 | O | LEU | A | 318 | 59.723 | 6.412 | 77.516 | 1.00 | 5.84 |
| 2319 | N | SER | A | 319 | 58.139 | 8.008 | 77.322 | 1.00 | 6.58 |
| 2320 | CA | SER | A | 319 | 58.949 | 9.114 | 77.801 | 1.00 | 7.85 |
| 2321 | CB | SER | A | 319 | 59.171 | 10.181 | 76.720 | 1.00 | 7.09 |
| 2322 | OG | SER | A | 319 | 59.816 | 11.342 | 77.307 | 1.00 | 9.02 |
| 2323 | C | SER | A | 319 | 58.310 | 9.791 | 78.984 | 1.00 | 8.73 |
| 2324 | O | SER | A | 319 | 57.184 | 10.253 | 78.906 | 1.00 | 8.98 |
| 2325 | N | ILE | A | 320 | 59.069 | 9.923 | 80.077 | 1.00 | 11.02 |
| 2326 | CA | ILE | A | 320 | 58.558 | 10.695 | 81.209 | 1.00 | 11.83 |
| 2327 | CB | ILE | A | 320 | 58.566 | 9.890 | 82.485 | 1.00 | 11.67 |
| 2328 | CG1 | ILE | A | 320 | 58.284 | 8.402 | 82.159 | 1.00 | 11.82 |
| 2329 | CD1 | ILE | A | 320 | 57.910 | 7.476 | 83.370 | 1.00 | 10.55 |
| 2330 | CG2 | ILE | A | 320 | 57.449 | 10.416 | 83.385 | 1.00 | 13.21 |
| 2331 | C | ILE | A | 320 | 59.232 | 12.032 | 81.328 | 1.00 | 11.96 |
| 2332 | O | ILE | A | 320 | 60.418 | 12.127 | 81.106 | 1.00 | 11.50 |
| 2333 | N | CYS | A | 321 | 58.432 | 13.067 | 81.598 | 1.00 | 13.48 |
| 2334 | CA | CYS | A | 321 | 58.925 | 14.438 | 81.742 | 1.00 | 15.68 |
| 2335 | CB | CYS | A | 321 | 58.498 | 15.350 | 80.583 | 1.00 | 15.99 |
| 2336 | SG | CYS | A | 321 | 58.659 | 14.529 | 79.014 | 1.00 | 18.45 |
| 2337 | C | CYS | A | 321 | 58.447 | 15.126 | 82.994 | 1.00 | 16.30 |

FIGURE 3 (Cont.)

| A | B | C | D | E | F | G | H | I | J |
|---|---|---|---|---|---|---|---|---|---|
| 2338 | O | CYS | A | 321 | 57.324 | 14.917 | 83.456 | 1.00 | 17.49 |
| 2339 | N | ASP | A | 322 | 59.298 | 16.020 | 83.473 | 1.00 | 16.43 |
| 2340 | CA | ASP | A | 322 | 59.050 | 16.775 | 84.670 | 1.00 | 16.77 |
| 2341 | CB | ASP | A | 322 | 60.073 | 16.396 | 85.772 | 1.00 | 16.93 |
| 2342 | CG | ASP | A | 322 | 60.189 | 14.885 | 85.958 | 1.00 | 16.75 |
| 2343 | OD1 | ASP | A | 322 | 59.254 | 14.294 | 86.547 | 1.00 | 17.82 |
| 2344 | OD2 | ASP | A | 322 | 61.155 | 14.219 | 85.521 | 1.00 | 14.51 |
| 2345 | C | ASP | A | 322 | 59.154 | 18.265 | 84.321 | 1.00 | 16.89 |
| 2346 | O | ASP | A | 322 | 60.197 | 18.751 | 83.814 | 1.00 | 17.09 |
| 2347 | N | PHE | A | 323 | 58.050 | 18.964 | 84.599 | 1.00 | 16.57 |
| 2348 | CA | PHE | A | 323 | 58.052 | 20.406 | 84.770 | 1.00 | 16.11 |
| 2349 | CB | PHE | A | 323 | 56.671 | 20.819 | 85.242 | 1.00 | 15.52 |
| 2350 | CG | PHE | A | 323 | 56.509 | 22.276 | 85.244 | 1.00 | 13.92 |
| 2351 | CD1 | PHE | A | 323 | 56.571 | 23.012 | 86.423 | 1.00 | 9.47 |
| 2352 | CE1 | PHE | A | 323 | 56.419 | 24.396 | 86.386 | 1.00 | 8.61 |
| 2353 | CZ | PHE | A | 323 | 56.228 | 25.042 | 85.166 | 1.00 | 7.79 |
| 2354 | CE2 | PHE | A | 323 | 56.188 | 24.313 | 83.970 | 1.00 | 7.38 |
| 2355 | CD2 | PHE | A | 323 | 56.328 | 22.939 | 84.004 | 1.00 | 10.91 |
| 2356 | C | PHE | A | 323 | 59.137 | 20.958 | 85.758 | 1.00 | 16.47 |
| 2357 | O | PHE | A | 323 | 59.208 | 20.516 | 86.917 | 1.00 | 17.32 |
| 2358 | N | ARG | A | 324 | 59.970 | 21.907 | 85.305 | 1.00 | 16.46 |
| 2359 | CA | ARG | A | 324 | 60.967 | 22.585 | 86.166 | 1.00 | 16.58 |
| 2360 | CB | ARG | A | 324 | 62.406 | 22.490 | 85.613 | 1.00 | 16.77 |
| 2361 | CG | ARG | A | 324 | 62.560 | 22.685 | 84.094 | 1.00 | 16.71 |
| 2362 | CD | ARG | A | 324 | 63.933 | 22.282 | 83.519 | 1.00 | 16.93 |
| 2363 | NE | ARG | A | 324 | 65.049 | 23.079 | 84.063 | 1.00 | 16.58 |
| 2364 | CZ | ARG | A | 324 | 66.030 | 23.648 | 83.337 | 1.00 | 17.71 |
| 2365 | NH1 | ARG | A | 324 | 66.988 | 24.340 | 83.964 | 1.00 | 16.18 |
| 2366 | NH2 | ARG | A | 324 | 66.069 | 23.552 | 82.001 | 1.00 | 17.48 |
| 2367 | C | ARG | A | 324 | 60.597 | 24.048 | 86.415 | 1.00 | 16.81 |
| 2368 | O | ARG | A | 324 | 60.222 | 24.769 | 85.486 | 1.00 | 16.36 |
| 2369 | N | GLU | A | 325 | 60.755 | 24.483 | 87.669 | 1.00 | 17.21 |
| 2370 | CA | GLU | A | 325 | 60.170 | 25.733 | 88.170 | 1.00 | 17.85 |
| 2371 | CB | GLU | A | 325 | 60.136 | 25.693 | 89.715 | 1.00 | 17.77 |
| 2372 | CG | GLU | A | 325 | 58.897 | 24.978 | 90.260 | 1.00 | 18.07 |
| 2373 | CD | GLU | A | 325 | 57.640 | 25.763 | 89.944 | 1.00 | 19.21 |
| 2374 | OE1 | GLU | A | 325 | 57.754 | 27.015 | 89.899 | 1.00 | 20.61 |
| 2375 | OE2 | GLU | A | 325 | 56.574 | 25.165 | 89.702 | 1.00 | 16.54 |
| 2376 | C | GLU | A | 325 | 60.840 | 27.023 | 87.643 | 1.00 | 18.22 |
| 2377 | O | GLU | A | 325 | 60.153 | 27.941 | 87.185 | 1.00 | 18.04 |
| 2378 | N | ASP | A | 326 | 62.171 | 27.067 | 87.741 | 1.00 | 18.91 |
| 2379 | CA | ASP | A | 326 | 63.038 | 28.171 | 87.251 | 1.00 | 19.74 |
| 2380 | CB | ASP | A | 326 | 64.534 | 27.798 | 87.455 | 1.00 | 20.04 |
| 2381 | CG | ASP | A | 326 | 64.876 | 26.332 | 86.998 | 1.00 | 20.35 |
| 2382 | OD1 | ASP | A | 326 | 63.987 | 25.622 | 86.450 | 1.00 | 22.89 |
| 2383 | OD2 | ASP | A | 326 | 66.005 | 25.800 | 87.142 | 1.00 | 19.43 |
| 2384 | C | ASP | A | 326 | 62.853 | 28.584 | 85.771 | 1.00 | 20.16 |
| 2385 | O | ASP | A | 326 | 62.752 | 29.787 | 85.458 | 1.00 | 20.46 |
| 2386 | N | TRP | A | 327 | 62.841 | 27.582 | 84.881 | 1.00 | 20.39 |
| 2387 | CA | TRP | A | 327 | 62.897 | 27.786 | 83.427 | 1.00 | 20.70 |
| 2388 | CB | TRP | A | 327 | 64.083 | 26.965 | 82.800 | 1.00 | 21.26 |

FIGURE 3 (Cont.)

| A | B | C | D | E | F | G | H | I | J |
|---|---|---|---|---|---|---|---|---|---|
| 2389 | CG | TRP | A | 327 | 65.491 | 27.762 | 82.750 | 1.00 | 22.92 |
| 2390 | CD1 | TRP | A | 327 | 66.137 | 28.413 | 83.809 | 1.00 | 24.18 |
| 2391 | NE1 | TRP | A | 327 | 67.309 | 29.006 | 83.381 | 1.00 | 24.84 |
| 2392 | CE2 | TRP | A | 327 | 67.471 | 28.781 | 82.031 | 1.00 | 25.85 |
| 2393 | CD2 | TRP | A | 327 | 66.346 | 27.984 | 81.590 | 1.00 | 25.69 |
| 2394 | CE3 | TRP | A | 327 | 66.279 | 27.603 | 80.215 | 1.00 | 26.61 |
| 2395 | CZ3 | TRP | A | 327 | 67.331 | 28.030 | 79.323 | 1.00 | 27.00 |
| 2396 | CH2 | TRP | A | 327 | 68.434 | 28.813 | 79.810 | 1.00 | 27.25 |
| 2397 | CZ2 | TRP | A | 327 | 68.524 | 29.192 | 81.148 | 1.00 | 26.31 |
| 2398 | C | TRP | A | 327 | 61.522 | 27.478 | 82.786 | 1.00 | 20.02 |
| 2399 | O | TRP | A | 327 | 61.402 | 27.518 | 81.568 | 1.00 | 20.00 |
| 2400 | N | GLN | A | 328 | 60.517 | 27.203 | 83.642 | 1.00 | 19.55 |
| 2401 | CA | GLN | A | 328 | 59.087 | 26.902 | 83.329 | 1.00 | 19.48 |
| 2402 | CB | GLN | A | 328 | 58.270 | 28.214 | 83.289 | 1.00 | 19.70 |
| 2403 | CG | GLN | A | 328 | 58.229 | 28.998 | 84.621 | 1.00 | 19.55 |
| 2404 | CD | GLN | A | 328 | 57.246 | 28.424 | 85.650 | 1.00 | 19.47 |
| 2405 | OE1 | GLN | A | 328 | 56.032 | 28.431 | 85.451 | 1.00 | 17.74 |
| 2406 | NE2 | GLN | A | 328 | 57.782 | 27.940 | 86.755 | 1.00 | 20.44 |
| 2407 | C | GLN | A | 328 | 58.704 | 25.973 | 82.115 | 1.00 | 19.43 |
| 2408 | O | GLN | A | 328 | 57.535 | 25.963 | 81.658 | 1.00 | 19.06 |
| 2409 | N | THR | A | 329 | 59.674 | 25.178 | 81.641 | 1.00 | 19.53 |
| 2410 | CA | THR | A | 329 | 59.471 | 24.276 | 80.476 | 1.00 | 19.99 |
| 2411 | CB | THR | A | 329 | 60.680 | 24.317 | 79.466 | 1.00 | 19.97 |
| 2412 | OG1 | THR | A | 329 | 60.362 | 23.575 | 78.279 | 1.00 | 20.46 |
| 2413 | CG2 | THR | A | 329 | 61.916 | 23.592 | 80.024 | 1.00 | 20.68 |
| 2414 | C | THR | A | 329 | 59.291 | 22.868 | 80.981 | 1.00 | 19.89 |
| 2415 | O | THR | A | 329 | 59.111 | 22.672 | 82.173 | 1.00 | 19.69 |
| 2416 | N | TRP | A | 330 | 59.306 | 21.884 | 80.069 | 1.00 | 20.43 |
| 2417 | CA | TRP | A | 330 | 59.236 | 20.466 | 80.402 | 1.00 | 20.25 |
| 2418 | CB | TRP | A | 330 | 57.859 | 19.900 | 80.049 | 1.00 | 20.45 |
| 2419 | CG | TRP | A | 330 | 56.744 | 20.486 | 80.860 | 1.00 | 21.52 |
| 2420 | CD1 | TRP | A | 330 | 56.194 | 21.727 | 80.718 | 1.00 | 21.92 |
| 2421 | NE1 | TRP | A | 330 | 55.193 | 21.911 | 81.642 | 1.00 | 24.80 |
| 2422 | CE2 | TRP | A | 330 | 55.083 | 20.772 | 82.404 | 1.00 | 24.92 |
| 2423 | CD2 | TRP | A | 330 | 56.045 | 19.854 | 81.939 | 1.00 | 24.07 |
| 2424 | CE3 | TRP | A | 330 | 56.139 | 18.603 | 82.554 | 1.00 | 25.29 |
| 2425 | CZ3 | TRP | A | 330 | 55.284 | 18.313 | 83.600 | 1.00 | 26.93 |
| 2426 | CH2 | TRP | A | 330 | 54.331 | 19.247 | 84.045 | 1.00 | 27.22 |
| 2427 | CZ2 | TRP | A | 330 | 54.219 | 20.480 | 83.458 | 1.00 | 25.33 |
| 2428 | C | TRP | A | 330 | 60.516 | 19.742 | 79.996 | 1.00 | 19.83 |
| 2429 | O | TRP | A | 330 | 61.219 | 20.169 | 79.016 | 1.00 | 19.61 |
| 2430 | N | ASP | A | 331 | 60.986 | 18.719 | 80.755 | 1.00 | 20.02 |
| 2431 | CA | ASP | A | 331 | 62.286 | 18.034 | 80.607 | 1.00 | 19.95 |
| 2432 | CB | ASP | A | 331 | 63.153 | 18.359 | 81.821 | 1.00 | 20.18 |
| 2433 | CG | ASP | A | 331 | 64.580 | 17.846 | 81.685 | 1.00 | 21.37 |
| 2434 | OD1 | ASP | A | 331 | 65.464 | 18.720 | 81.633 | 1.00 | 20.97 |
| 2435 | OD2 | ASP | A | 331 | 64.912 | 16.626 | 81.635 | 1.00 | 20.97 |
| 2436 | C | ASP | A | 331 | 62.126 | 16.526 | 80.575 | 1.00 | 19.74 |
| 2437 | O | ASP | A | 331 | 61.544 | 15.964 | 81.481 | 1.00 | 19.27 |
| 2438 | N | CYS | A | 332 | 62.688 | 15.866 | 79.572 | 1.00 | 19.50 |
| 2439 | CA | CYS | A | 332 | 62.549 | 14.407 | 79.476 | 1.00 | 19.77 |

FIGURE 3 (Cont.)

| A | B | C | D | E | F | G | H | I | J |
|---|---|---|---|---|---|---|---|---|---|
| 2440 | CB | CYS | A | 332 | 61.644 | 14.016 | 78.271 | 1.00 | 19.54 |
| 2441 | SG | CYS | A | 332 | 60.237 | 15.158 | 77.926 | 1.00 | 20.44 |
| 2442 | C | CYS | A | 332 | 63.927 | 13.684 | 79.424 | 1.00 | 19.58 |
| 2443 | O | CYS | A | 332 | 64.552 | 13.618 | 78.377 | 1.00 | 20.24 |
| 2444 | N | PRO | A | 333 | 64.396 | 13.128 | 80.540 | 1.00 | 19.33 |
| 2445 | CA | PRO | A | 333 | 65.721 | 12.493 | 80.567 | 1.00 | 19.20 |
| 2446 | CB | PRO | A | 333 | 65.898 | 12.109 | 82.054 | 1.00 | 19.70 |
| 2447 | CG | PRO | A | 333 | 64.869 | 12.907 | 82.825 | 1.00 | 19.48 |
| 2448 | CD | PRO | A | 333 | 63.728 | 13.063 | 81.853 | 1.00 | 19.10 |
| 2449 | C | PRO | A | 333 | 65.887 | 11.237 | 79.691 | 1.00 | 19.01 |
| 2450 | O | PRO | A | 333 | 65.020 | 10.358 | 79.707 | 1.00 | 18.73 |
| 2451 | N | LYS | A | 334 | 67.013 | 11.145 | 78.971 | 1.00 | 18.83 |
| 2452 | CA | LYS | A | 334 | 67.436 | 9.877 | 78.320 | 1.00 | 18.43 |
| 2453 | CB | LYS | A | 334 | 68.809 | 9.984 | 77.574 | 1.00 | 18.56 |
| 2454 | CG | LYS | A | 334 | 69.905 | 11.036 | 78.099 | 1.00 | 18.86 |
| 2455 | CD | LYS | A | 334 | 69.821 | 12.395 | 77.297 | 1.00 | 18.09 |
| 2456 | CE | LYS | A | 334 | 71.167 | 12.904 | 76.747 | 1.00 | 17.81 |
| 2457 | NZ | LYS | A | 334 | 72.078 | 13.353 | 77.867 | 1.00 | 17.30 |
| 2458 | C | LYS | A | 334 | 67.455 | 8.681 | 79.290 | 1.00 | 18.25 |
| 2459 | O | LYS | A | 334 | 67.395 | 7.537 | 78.827 | 1.00 | 17.82 |
| 2460 | N | THR | A | 335 | 67.569 | 8.957 | 80.611 | 1.00 | 18.14 |
| 2461 | CA | THR | A | 335 | 67.347 | 7.952 | 81.685 | 1.00 | 18.15 |
| 2462 | CB | THR | A | 335 | 67.824 | 8.443 | 83.098 | 1.00 | 18.71 |
| 2463 | OG1 | THR | A | 335 | 66.720 | 9.100 | 83.753 | 1.00 | 20.04 |
| 2464 | CG2 | THR | A | 335 | 69.045 | 9.469 | 83.085 | 1.00 | 18.29 |
| 2465 | C | THR | A | 335 | 65.872 | 7.484 | 81.865 | 1.00 | 17.92 |
| 2466 | O | THR | A | 335 | 65.641 | 6.359 | 82.299 | 1.00 | 17.37 |
| 2467 | N | GLN | A | 336 | 64.898 | 8.359 | 81.569 | 1.00 | 17.85 |
| 2468 | CA | GLN | A | 336 | 63.470 | 8.051 | 81.712 | 1.00 | 17.63 |
| 2469 | CB | GLN | A | 336 | 62.778 | 9.215 | 82.420 | 1.00 | 17.56 |
| 2470 | CG | GLN | A | 336 | 63.405 | 9.574 | 83.747 | 1.00 | 18.60 |
| 2471 | CD | GLN | A | 336 | 62.555 | 10.529 | 84.583 | 1.00 | 19.93 |
| 2472 | OE1 | GLN | A | 336 | 62.072 | 11.546 | 84.088 | 1.00 | 21.77 |
| 2473 | NE2 | GLN | A | 336 | 62.390 | 10.210 | 85.853 | 1.00 | 20.06 |
| 2474 | C | GLN | A | 336 | 62.763 | 7.720 | 80.356 | 1.00 | 18.09 |
| 2475 | O | GLN | A | 336 | 61.510 | 7.684 | 80.264 | 1.00 | 16.86 |
| 2476 | N | GLU | A | 337 | 63.601 | 7.487 | 79.330 | 1.00 | 18.39 |
| 2477 | CA | GLU | A | 337 | 63.202 | 6.941 | 78.027 | 1.00 | 18.88 |
| 2478 | CB | GLU | A | 337 | 64.226 | 7.319 | 76.942 | 1.00 | 19.06 |
| 2479 | CG | GLU | A | 337 | 64.026 | 8.668 | 76.264 | 1.00 | 18.72 |
| 2480 | CD | GLU | A | 337 | 65.129 | 8.894 | 75.267 | 1.00 | 22.93 |
| 2481 | OE1 | GLU | A | 337 | 65.580 | 7.899 | 74.609 | 1.00 | 24.17 |
| 2482 | OE2 | GLU | A | 337 | 65.513 | 10.080 | 75.138 | 1.00 | 24.50 |
| 2483 | C | GLU | A | 337 | 63.174 | 5.419 | 78.090 | 1.00 | 18.98 |
| 2484 | O | GLU | A | 337 | 64.192 | 4.760 | 78.275 | 1.00 | 19.14 |
| 2485 | N | HIS | A | 338 | 62.000 | 4.872 | 77.874 | 1.00 | 19.30 |
| 2486 | CA | HIS | A | 338 | 61.738 | 3.469 | 78.116 | 1.00 | 19.68 |
| 2487 | CB | HIS | A | 338 | 60.627 | 3.318 | 79.189 | 1.00 | 19.55 |
| 2488 | CG | HIS | A | 338 | 61.080 | 3.640 | 80.605 | 1.00 | 21.91 |
| 2489 | ND1 | HIS | A | 338 | 60.220 | 3.639 | 81.687 | 1.00 | 23.61 |
| 2490 | CE1 | HIS | A | 338 | 60.901 | 3.931 | 82.787 | 1.00 | 22.08 |

FIGURE 3 (Cont.)

| A | B | C | D | E | F | G | H | I | J |
|---|---|---|---|---|---|---|---|---|---|
| 2491 | NE2 | HIS | A | 338 | 62.168 | 4.123 | 82.464 | 1.00 | 21.63 |
| 2492 | CD2 | HIS | A | 338 | 62.309 | 3.946 | 81.110 | 1.00 | 22.11 |
| 2493 | C | HIS | A | 338 | 61.384 | 2.908 | 76.732 | 1.00 | 19.58 |
| 2494 | O | HIS | A | 338 | 60.372 | 3.255 | 76.128 | 1.00 | 19.93 |
| 2495 | N | ILE | A | 339 | 62.289 | 2.112 | 76.193 | 1.00 | 19.33 |
| 2496 | CA | ILE | A | 339 | 62.130 | 1.551 | 74.866 | 1.00 | 19.18 |
| 2497 | CB | ILE | A | 339 | 63.540 | 1.216 | 74.250 | 1.00 | 19.60 |
| 2498 | CG1 | ILE | A | 339 | 64.214 | 2.463 | 73.665 | 1.00 | 19.03 |
| 2499 | CD1 | ILE | A | 339 | 65.716 | 2.263 | 73.296 | 1.00 | 18.95 |
| 2500 | CG2 | ILE | A | 339 | 63.416 | 0.172 | 73.142 | 1.00 | 19.51 |
| 2501 | C | ILE | A | 339 | 61.278 | 0.280 | 74.947 | 1.00 | 18.94 |
| 2502 | O | ILE | A | 339 | 61.530 | -0.612 | 75.801 | 1.00 | 19.97 |
| 2503 | N | GLU | A | 340 | 60.289 | 0.158 | 74.063 | 1.00 | 17.84 |
| 2504 | CA | GLU | A | 340 | 59.611 | -1.115 | 73.896 | 1.00 | 16.89 |
| 2505 | CB | GLU | A | 340 | 58.194 | -1.013 | 74.371 | 1.00 | 15.59 |
| 2506 | CG | GLU | A | 340 | 57.402 | -2.208 | 73.907 | 1.00 | 16.58 |
| 2507 | CD | GLU | A | 340 | 56.027 | -2.250 | 74.532 | 1.00 | 19.66 |
| 2508 | OE1 | GLU | A | 340 | 54.993 | -2.278 | 73.786 | 1.00 | 22.04 |
| 2509 | OE2 | GLU | A | 340 | 55.968 | -2.233 | 75.776 | 1.00 | 19.08 |
| 2510 | C | GLU | A | 340 | 59.634 | -1.468 | 72.438 | 1.00 | 16.57 |
| 2511 | O | GLU | A | 340 | 59.110 | -0.677 | 71.656 | 1.00 | 17.65 |
| 2512 | N | GLU | A | 341 | 60.179 | -2.637 | 72.071 | 1.00 | 16.42 |
| 2513 | CA | GLU | A | 341 | 60.375 | -3.028 | 70.652 | 1.00 | 16.28 |
| 2514 | CB | GLU | A | 341 | 61.852 | -2.767 | 70.207 | 1.00 | 15.95 |
| 2515 | CG | GLU | A | 341 | 62.977 | -3.386 | 71.056 | 1.00 | 14.08 |
| 2516 | CD | GLU | A | 341 | 64.424 | -3.191 | 70.506 | 1.00 | 13.39 |
| 2517 | OE1 | GLU | A | 341 | 65.385 | -3.805 | 71.081 | 1.00 | 12.71 |
| 2518 | OE2 | GLU | A | 341 | 64.644 | -2.467 | 69.515 | 1.00 | 8.20 |
| 2519 | C | GLU | A | 341 | 59.906 | -4.476 | 70.268 | 1.00 | 17.28 |
| 2520 | O | GLU | A | 341 | 59.633 | -5.315 | 71.161 | 1.00 | 16.95 |
| 2521 | N | SER | A | 342 | 59.796 | -4.769 | 68.956 | 1.00 | 17.63 |
| 2522 | CA | SER | A | 342 | 59.697 | -6.173 | 68.515 | 1.00 | 18.95 |
| 2523 | CB | SER | A | 342 | 58.248 | -6.636 | 68.381 | 1.00 | 19.31 |
| 2524 | OG | SER | A | 342 | 58.224 | -8.073 | 68.280 | 1.00 | 21.61 |
| 2525 | C | SER | A | 342 | 60.382 | -6.497 | 67.214 | 1.00 | 19.15 |
| 2526 | O | SER | A | 342 | 59.979 | -6.031 | 66.192 | 1.00 | 20.09 |
| 2527 | N | ARG | A | 343 | 61.501 | -7.364 | 67.211 | 1.00 | 20.15 |
| 2528 | CA | ARG | A | 343 | 62.084 | -7.813 | 65.942 | 1.00 | 21.25 |
| 2529 | CB | ARG | A | 343 | 63.582 | -7.409 | 65.727 | 1.00 | 22.04 |
| 2530 | CG | ARG | A | 343 | 63.942 | -6.741 | 64.317 | 1.00 | 22.05 |
| 2531 | CD | ARG | A | 343 | 62.998 | -5.613 | 63.834 | 1.00 | 22.39 |
| 2532 | NE | ARG | A | 343 | 63.452 | -4.238 | 64.088 | 1.00 | 22.49 |
| 2533 | CZ | ARG | A | 343 | 63.320 | -3.199 | 63.228 | 1.00 | 22.98 |
| 2534 | NH1 | ARG | A | 343 | 62.561 | -3.250 | 62.110 | 1.00 | 21.68 |
| 2535 | NH2 | ARG | A | 343 | 63.981 | -2.078 | 63.477 | 1.00 | 23.14 |
| 2536 | C | ARG | A | 343 | 61.861 | -9.299 | 65.871 | 1.00 | 20.88 |
| 2537 | O | ARG | A | 343 | 62.791 | -10.100 | 66.028 | 1.00 | 20.91 |
| 2538 | N | THR | A | 344 | 60.221 | -9.577 | 66.012 | 1.00 | 20.04 |
| 2539 | CA | THR | A | 344 | 59.527 | -10.487 | 65.124 | 1.00 | 19.11 |
| 2540 | CB | THR | A | 344 | 59.020 | -11.783 | 65.919 | 1.00 | 19.72 |
| 2541 | OG1 | THR | A | 344 | 59.968 | -12.858 | 65.689 | 1.00 | 17.97 |

FIGURE 3 (Cont.)

| A | B | C | D | E | F | G | H | I | J |
|---|---|---|---|---|---|---|---|---|---|
| 2542 | CG2 | THR | A | 344 | 57.578 | -12.379 | 65.476 | 1.00 | 18.16 |
| 2543 | C | THR | A | 344 | 58.473 | -9.559 | 64.437 | 1.00 | 18.77 |
| 2544 | O | THR | A | 344 | 58.595 | -9.293 | 63.222 | 1.00 | 19.80 |
| 2545 | N | GLY | A | 345 | 57.540 | -8.953 | 65.200 | 1.00 | 17.54 |
| 2546 | CA | GLY | A | 345 | 56.525 | -8.066 | 64.646 | 1.00 | 15.54 |
| 2547 | C | GLY | A | 345 | 56.500 | -6.525 | 64.900 | 1.00 | 14.85 |
| 2548 | O | GLY | A | 345 | 57.550 | -5.839 | 64.857 | 1.00 | 13.91 |
| 2549 | N | TRP | A | 346 | 55.256 | -6.009 | 65.080 | 1.00 | 13.95 |
| 2550 | CA | TRP | A | 346 | 54.915 | -4.589 | 65.386 | 1.00 | 12.98 |
| 2551 | CB | TRP | A | 346 | 53.555 | -4.060 | 64.673 | 1.00 | 12.27 |
| 2552 | CG | TRP | A | 346 | 52.232 | -4.859 | 64.938 | 1.00 | 9.91 |
| 2553 | CD1 | TRP | A | 346 | 51.337 | -4.665 | 65.927 | 1.00 | 6.40 |
| 2554 | NE1 | TRP | A | 346 | 50.328 | -5.611 | 65.859 | 1.00 | 4.61 |
| 2555 | CE2 | TRP | A | 346 | 50.539 | -6.402 | 64.761 | 1.00 | 8.14 |
| 2556 | CD2 | TRP | A | 346 | 51.712 | -5.940 | 64.144 | 1.00 | 7.63 |
| 2557 | CE3 | TRP | A | 346 | 52.198 | -6.640 | 63.022 | 1.00 | 7.42 |
| 2558 | CZ3 | TRP | A | 346 | 51.475 | -7.728 | 62.522 | 1.00 | 7.28 |
| 2559 | CH2 | TRP | A | 346 | 50.309 | -8.169 | 63.168 | 1.00 | 8.70 |
| 2560 | CZ2 | TRP | A | 346 | 49.860 | -7.554 | 64.317 | 1.00 | 10.04 |
| 2561 | C | TRP | A | 346 | 54.824 | -4.322 | 66.884 | 1.00 | 13.75 |
| 2562 | O | TRP | A | 346 | 54.260 | -5.087 | 67.645 | 1.00 | 13.60 |
| 2563 | N | ALA | A | 347 | 55.360 | -3.188 | 67.309 | 1.00 | 14.45 |
| 2564 | CA | ALA | A | 347 | 55.319 | -2.799 | 68.729 | 1.00 | 14.58 |
| 2565 | CB | ALA | A | 347 | 56.137 | -1.455 | 68.957 | 1.00 | 13.98 |
| 2566 | C | ALA | A | 347 | 53.876 | -2.629 | 69.136 | 1.00 | 14.60 |
| 2567 | O | ALA | A | 347 | 53.179 | -1.795 | 68.546 | 1.00 | 15.40 |
| 2568 | N | GLY | A | 348 | 53.424 | -3.434 | 70.085 | 1.00 | 13.89 |
| 2569 | CA | GLY | A | 348 | 52.174 | -3.204 | 70.771 | 1.00 | 14.29 |
| 2570 | C | GLY | A | 348 | 51.188 | -4.327 | 70.517 | 1.00 | 15.34 |
| 2571 | O | GLY | A | 348 | 51.597 | -5.520 | 70.301 | 1.00 | 14.96 |
| 2572 | N | GLY | A | 349 | 49.896 | -3.942 | 70.597 | 1.00 | 15.27 |
| 2573 | CA | GLY | A | 349 | 48.767 | -4.806 | 70.234 | 1.00 | 16.49 |
| 2574 | C | GLY | A | 349 | 48.113 | -4.299 | 68.956 | 1.00 | 17.04 |
| 2575 | O | GLY | A | 349 | 48.783 | -4.102 | 67.923 | 1.00 | 16.86 |
| 2576 | N | PHE | A | 350 | 46.811 | -4.059 | 68.989 | 1.00 | 17.74 |
| 2577 | CA | PHE | A | 350 | 46.238 | -3.185 | 67.950 | 1.00 | 18.51 |
| 2578 | CB | PHE | A | 350 | 44.717 | -3.119 | 68.173 | 1.00 | 20.24 |
| 2579 | CG | PHE | A | 350 | 43.898 | -2.560 | 67.008 | 1.00 | 22.65 |
| 2580 | CD1 | PHE | A | 350 | 42.644 | -3.175 | 66.710 | 1.00 | 26.92 |
| 2581 | CE1 | PHE | A | 350 | 41.830 | -2.675 | 65.673 | 1.00 | 28.30 |
| 2582 | CZ | PHE | A | 350 | 42.306 | -1.517 | 64.919 | 1.00 | 29.05 |
| 2583 | CE2 | PHE | A | 350 | 43.573 | -0.887 | 65.254 | 1.00 | 25.07 |
| 2584 | CD2 | PHE | A | 350 | 44.323 | -1.405 | 66.277 | 1.00 | 23.91 |
| 2585 | C | PHE | A | 350 | 46.926 | -1.767 | 68.072 | 1.00 | 17.96 |
| 2586 | O | PHE | A | 350 | 47.511 | -1.230 | 67.120 | 1.00 | 16.43 |
| 2587 | N | PHE | A | 351 | 46.834 | -1.230 | 69.288 | 1.00 | 18.44 |
| 2588 | CA | PHE | A | 351 | 47.404 | 0.032 | 69.698 | 1.00 | 18.92 |
| 2589 | CB | PHE | A | 351 | 46.353 | 0.782 | 70.532 | 1.00 | 19.45 |
| 2590 | CG | PHE | A | 351 | 45.097 | 1.098 | 69.802 | 1.00 | 21.02 |
| 2591 | CD1 | PHE | A | 351 | 43.869 | 0.583 | 70.243 | 1.00 | 23.08 |
| 2592 | CE1 | PHE | A | 351 | 42.628 | 0.890 | 69.541 | 1.00 | 21.81 |

FIGURE 3 (Cont.)

| A | B | C | D | E | F | G | H | I | J |
|---|---|---|---|---|---|---|---|---|---|
| 2593 | CZ | PHE | A | 351 | 42.656 | 1.720 | 68.429 | 1.00 | 21.68 |
| 2594 | CE2 | PHE | A | 351 | 43.895 | 2.272 | 68.009 | 1.00 | 19.68 |
| 2595 | CD2 | PHE | A | 351 | 45.111 | 1.938 | 68.681 | 1.00 | 21.51 |
| 2596 | C | PHE | A | 351 | 48.613 | -0.246 | 70.618 | 1.00 | 18.64 |
| 2597 | O | PHE | A | 351 | 48.690 | -1.340 | 71.221 | 1.00 | 19.40 |
| 2598 | N | VAL | A | 352 | 49.547 | 0.730 | 70.750 | 1.00 | 17.60 |
| 2599 | CA | VAL | A | 352 | 50.590 | 0.654 | 71.794 | 1.00 | 16.00 |
| 2600 | CB | VAL | A | 352 | 51.527 | 1.864 | 71.930 | 1.00 | 15.44 |
| 2601 | CG1 | VAL | A | 352 | 52.708 | 1.503 | 72.878 | 1.00 | 16.82 |
| 2602 | CG2 | VAL | A | 352 | 52.038 | 2.375 | 70.598 | 1.00 | 15.44 |
| 2603 | C | VAL | A | 352 | 49.858 | 0.683 | 73.088 | 1.00 | 15.45 |
| 2604 | O | VAL | A | 352 | 48.878 | 1.359 | 73.191 | 1.00 | 15.38 |
| 2605 | N | SER | A | 353 | 50.391 | -0.044 | 74.057 | 1.00 | 16.48 |
| 2606 | CA | SER | A | 353 | 49.848 | -0.249 | 75.398 | 1.00 | 16.05 |
| 2607 | CB | SER | A | 353 | 50.630 | -1.346 | 76.115 | 1.00 | 15.79 |
| 2608 | OG | SER | A | 353 | 50.038 | -2.568 | 75.849 | 1.00 | 19.00 |
| 2609 | C | SER | A | 353 | 50.031 | 0.950 | 76.262 | 1.00 | 15.60 |
| 2610 | O | SER | A | 353 | 51.100 | 1.514 | 76.367 | 1.00 | 13.88 |
| 2611 | N | THR | A | 354 | 48.976 | 1.228 | 76.988 | 1.00 | 15.71 |
| 2612 | CA | THR | A | 354 | 49.020 | 2.311 | 77.915 | 1.00 | 15.66 |
| 2613 | CB | THR | A | 354 | 47.629 | 3.003 | 77.913 | 1.00 | 15.78 |
| 2614 | OG1 | THR | A | 354 | 47.515 | 3.845 | 79.048 | 1.00 | 18.82 |
| 2615 | CG2 | THR | A | 354 | 46.405 | 1.935 | 78.018 | 1.00 | 18.86 |
| 2616 | C | THR | A | 354 | 49.617 | 1.814 | 79.338 | 1.00 | 14.83 |
| 2617 | O | THR | A | 354 | 49.419 | 0.655 | 79.798 | 1.00 | 13.82 |
| 2618 | N | PRO | A | 355 | 50.417 | 2.679 | 79.990 | 1.00 | 13.33 |
| 2619 | CA | PRO | A | 355 | 50.941 | 2.392 | 81.335 | 1.00 | 12.67 |
| 2620 | CB | PRO | A | 355 | 52.255 | 3.182 | 81.366 | 1.00 | 11.36 |
| 2621 | CG | PRO | A | 355 | 51.891 | 4.429 | 80.628 | 1.00 | 12.60 |
| 2622 | CD | PRO | A | 355 | 50.860 | 3.999 | 79.547 | 1.00 | 11.96 |
| 2623 | C | PRO | A | 355 | 50.001 | 2.937 | 82.391 | 1.00 | 12.02 |
| 2624 | O | PRO | A | 355 | 49.306 | 3.963 | 82.168 | 1.00 | 12.86 |
| 2625 | N | VAL | A | 356 | 49.965 | 2.220 | 83.501 | 1.00 | 11.37 |
| 2626 | CA | VAL | A | 356 | 49.266 | 2.637 | 84.695 | 1.00 | 11.87 |
| 2627 | CB | VAL | A | 356 | 48.066 | 1.706 | 85.001 | 1.00 | 11.64 |
| 2628 | CG1 | VAL | A | 356 | 47.179 | 2.308 | 86.103 | 1.00 | 11.42 |
| 2629 | CG2 | VAL | A | 356 | 47.290 | 1.490 | 83.716 | 1.00 | 10.84 |
| 2630 | C | VAL | A | 356 | 50.233 | 2.703 | 85.853 | 1.00 | 12.11 |
| 2631 | O | VAL | A | 356 | 50.922 | 1.738 | 86.177 | 1.00 | 12.78 |
| 2632 | N | PHE | A | 357 | 50.249 | 3.876 | 86.470 | 1.00 | 12.90 |
| 2633 | CA | PHE | A | 357 | 51.255 | 4.299 | 87.454 | 1.00 | 14.25 |
| 2634 | CB | PHE | A | 357 | 51.465 | 5.820 | 87.284 | 1.00 | 13.68 |
| 2635 | CG | PHE | A | 357 | 52.211 | 6.149 | 86.053 | 1.00 | 12.05 |
| 2636 | CD1 | PHE | A | 357 | 53.592 | 6.199 | 86.071 | 1.00 | 10.20 |
| 2637 | CE1 | PHE | A | 357 | 54.299 | 6.425 | 84.941 | 1.00 | 10.14 |
| 2638 | CZ | PHE | A | 357 | 53.668 | 6.605 | 83.782 | 1.00 | 6.71 |
| 2639 | CE2 | PHE | A | 357 | 52.283 | 6.553 | 83.732 | 1.00 | 10.64 |
| 2640 | CD2 | PHE | A | 357 | 51.560 | 6.306 | 84.861 | 1.00 | 11.85 |
| 2641 | C | PHE | A | 357 | 50.852 | 3.960 | 88.888 | 1.00 | 15.17 |
| 2642 | O | PHE | A | 357 | 49.657 | 3.794 | 89.135 | 1.00 | 15.46 |
| 2643 | N | SER | A | 358 | 51.817 | 3.925 | 89.827 | 1.00 | 16.75 |

FIGURE 3 (Cont.)

| A | B | C | D | E | F | G | H | I | J |
|---|---|---|---|---|---|---|---|---|---|
| 2644 | CA | SER | A | 358 | 51.562 | 3.323 | 91.140 | 1.00 | 18.63 |
| 2645 | CB | SER | A | 358 | 52.406 | 2.031 | 91.361 | 1.00 | 18.51 |
| 2646 | OG | SER | A | 358 | 53.808 | 2.242 | 91.515 | 1.00 | 17.97 |
| 2647 | C | SER | A | 358 | 51.706 | 4.253 | 92.319 | 1.00 | 20.37 |
| 2648 | O | SER | A | 358 | 52.815 | 4.486 | 92.800 | 1.00 | 21.37 |
| 2649 | N | TYR | A | 359 | 50.575 | 4.720 | 92.838 | 1.00 | 22.01 |
| 2650 | CA | TYR | A | 359 | 50.493 | 5.775 | 93.881 | 1.00 | 22.59 |
| 2651 | CB | TYR | A | 359 | 49.920 | 5.210 | 95.196 | 1.00 | 23.44 |
| 2652 | CG | TYR | A | 359 | 48.517 | 5.762 | 95.504 | 1.00 | 26.11 |
| 2653 | CD1 | TYR | A | 359 | 47.509 | 5.799 | 94.486 | 1.00 | 29.57 |
| 2654 | CE1 | TYR | A | 359 | 46.229 | 6.335 | 94.736 | 1.00 | 30.80 |
| 2655 | CZ | TYR | A | 359 | 45.937 | 6.835 | 96.022 | 1.00 | 30.46 |
| 2656 | OH | TYR | A | 359 | 44.678 | 7.341 | 96.250 | 1.00 | 30.73 |
| 2657 | CE2 | TYR | A | 359 | 46.909 | 6.820 | 97.057 | 1.00 | 29.53 |
| 2658 | CD2 | TYR | A | 359 | 48.198 | 6.278 | 96.793 | 1.00 | 28.26 |
| 2659 | C | TYR | A | 359 | 51.720 | 6.678 | 94.117 | 1.00 | 22.53 |
| 2660 | O | TYR | A | 359 | 51.591 | 7.921 | 94.167 | 1.00 | 22.75 |
| 2661 | N | ASP | A | 360 | 52.885 | 6.054 | 94.273 | 1.00 | 22.25 |
| 2662 | CA | ASP | A | 360 | 54.178 | 6.750 | 94.249 | 1.00 | 22.34 |
| 2663 | CB | ASP | A | 360 | 55.338 | 5.752 | 94.554 | 1.00 | 22.19 |
| 2664 | CG | ASP | A | 360 | 55.962 | 5.163 | 93.303 | 1.00 | 21.66 |
| 2665 | OD1 | ASP | A | 360 | 57.111 | 4.711 | 93.383 | 1.00 | 19.75 |
| 2666 | OD2 | ASP | A | 360 | 55.391 | 5.114 | 92.192 | 1.00 | 22.67 |
| 2667 | C | ASP | A | 360 | 54.515 | 7.591 | 92.989 | 1.00 | 22.26 |
| 2668 | O | ASP | A | 360 | 55.524 | 8.329 | 93.012 | 1.00 | 22.36 |
| 2669 | N | ALA | A | 361 | 53.701 | 7.445 | 91.919 | 1.00 | 21.79 |
| 2670 | CA | ALA | A | 361 | 53.750 | 8.246 | 90.670 | 1.00 | 21.38 |
| 2671 | CB | ALA | A | 361 | 53.184 | 9.684 | 90.900 | 1.00 | 21.22 |
| 2672 | C | ALA | A | 361 | 55.141 | 8.266 | 89.994 | 1.00 | 21.11 |
| 2673 | O | ALA | A | 361 | 55.653 | 9.317 | 89.562 | 1.00 | 21.07 |
| 2674 | N | ILE | A | 362 | 55.746 | 7.082 | 89.902 | 1.00 | 20.92 |
| 2675 | CA | ILE | A | 362 | 57.034 | 6.925 | 89.198 | 1.00 | 20.87 |
| 2676 | CB | ILE | A | 362 | 58.253 | 7.276 | 90.127 | 1.00 | 20.75 |
| 2677 | CG1 | ILE | A | 362 | 59.336 | 7.980 | 89.305 | 1.00 | 22.63 |
| 2678 | CD1 | ILE | A | 362 | 60.438 | 8.669 | 90.164 | 1.00 | 23.93 |
| 2679 | CG2 | ILE | A | 362 | 58.835 | 6.064 | 90.834 | 1.00 | 21.46 |
| 2680 | C | ILE | A | 362 | 57.157 | 5.553 | 88.493 | 1.00 | 20.01 |
| 2681 | O | ILE | A | 362 | 57.278 | 5.504 | 87.248 | 1.00 | 18.05 |
| 2682 | N | SER | A | 363 | 57.086 | 4.477 | 89.292 | 1.00 | 18.89 |
| 2683 | CA | SER | A | 363 | 57.039 | 3.098 | 88.803 | 1.00 | 18.37 |
| 2684 | CB | SER | A | 363 | 57.259 | 2.209 | 89.994 | 1.00 | 18.68 |
| 2685 | OG | SER | A | 363 | 56.028 | 2.186 | 90.702 | 1.00 | 21.23 |
| 2686 | C | SER | A | 363 | 55.655 | 2.720 | 88.223 | 1.00 | 17.34 |
| 2687 | O | SER | A | 363 | 54.650 | 3.196 | 88.722 | 1.00 | 17.51 |
| 2688 | N | TYR | A | 364 | 55.598 | 1.841 | 87.210 | 1.00 | 15.38 |
| 2689 | CA | TYR | A | 364 | 54.322 | 1.601 | 86.530 | 1.00 | 15.17 |
| 2690 | CB | TYR | A | 364 | 54.241 | 2.523 | 85.331 | 1.00 | 15.62 |
| 2691 | CG | TYR | A | 364 | 55.404 | 2.315 | 84.364 | 1.00 | 17.57 |
| 2692 | CD1 | TYR | A | 364 | 56.601 | 2.996 | 84.509 | 1.00 | 24.32 |
| 2693 | CE1 | TYR | A | 364 | 57.657 | 2.847 | 83.592 | 1.00 | 24.41 |
| 2694 | CZ | TYR | A | 364 | 57.501 | 2.021 | 82.481 | 1.00 | 20.60 |

FIGURE 3 (Cont.)

| A | B | C | D | E | F | G | H | I | J |
|---|---|---|---|---|---|---|---|---|---|
| 2695 | OH | TYR | A | 364 | 58.512 | 1.976 | 81.504 | 1.00 | 19.91 |
| 2696 | CE2 | TYR | A | 364 | 56.264 | 1.339 | 82.293 | 1.00 | 16.73 |
| 2697 | CD2 | TYR | A | 364 | 55.239 | 1.482 | 83.255 | 1.00 | 15.08 |
| 2698 | C | TYR | A | 364 | 54.167 | 0.195 | 86.023 | 1.00 | 14.05 |
| 2699 | O | TYR | A | 364 | 55.143 | -0.576 | 86.022 | 1.00 | 14.47 |
| 2700 | N | TYR | A | 365 | 52.929 | -0.125 | 85.637 | 1.00 | 12.07 |
| 2701 | CA | TYR | A | 365 | 52.566 | -1.404 | 85.052 | 1.00 | 11.57 |
| 2702 | CB | TYR | A | 365 | 51.480 | -2.124 | 85.880 | 1.00 | 11.41 |
| 2703 | CG | TYR | A | 365 | 51.880 | -2.281 | 87.328 | 1.00 | 9.06 |
| 2704 | CD1 | TYR | A | 365 | 51.783 | -1.221 | 88.186 | 1.00 | 8.68 |
| 2705 | CE1 | TYR | A | 365 | 52.147 | -1.320 | 89.565 | 1.00 | 7.14 |
| 2706 | CZ | TYR | A | 365 | 52.604 | -2.472 | 90.083 | 1.00 | 7.82 |
| 2707 | OH | TYR | A | 365 | 52.920 | -2.451 | 91.429 | 1.00 | 2.00 |
| 2708 | CE2 | TYR | A | 365 | 52.712 | -3.599 | 89.229 | 1.00 | 9.23 |
| 2709 | CD2 | TYR | A | 365 | 52.354 | -3.478 | 87.839 | 1.00 | 9.02 |
| 2710 | C | TYR | A | 365 | 52.115 | -1.267 | 83.598 | 1.00 | 11.83 |
| 2711 | O | TYR | A | 365 | 51.513 | -0.296 | 83.197 | 1.00 | 11.59 |
| 2712 | N | LYS | A | 366 | 52.361 | -2.309 | 82.828 | 1.00 | 12.20 |
| 2713 | CA | LYS | A | 366 | 52.329 | -2.202 | 81.409 | 1.00 | 12.21 |
| 2714 | CB | LYS | A | 366 | 53.489 | -1.314 | 80.920 | 1.00 | 12.23 |
| 2715 | CG | LYS | A | 366 | 53.451 | -1.129 | 79.391 | 1.00 | 12.14 |
| 2716 | CD | LYS | A | 366 | 54.052 | 0.184 | 78.839 | 1.00 | 10.82 |
| 2717 | CE | LYS | A | 366 | 54.029 | 0.164 | 77.293 | 1.00 | 10.79 |
| 2718 | NZ | LYS | A | 366 | 53.060 | -0.828 | 76.717 | 1.00 | 10.47 |
| 2719 | C | LYS | A | 366 | 52.387 | -3.574 | 80.739 | 1.00 | 12.99 |
| 2720 | O | LYS | A | 366 | 53.277 | -4.359 | 80.983 | 1.00 | 12.58 |
| 2721 | N | ILE | A | 367 | 51.452 | -3.825 | 79.828 | 1.00 | 15.00 |
| 2722 | CA | ILE | A | 367 | 51.335 | -5.148 | 79.200 | 1.00 | 15.67 |
| 2723 | CB | ILE | A | 367 | 49.877 | -5.448 | 78.810 | 1.00 | 15.37 |
| 2724 | CG1 | ILE | A | 367 | 49.057 | -5.617 | 80.091 | 1.00 | 14.66 |
| 2725 | CD1 | ILE | A | 367 | 47.621 | -5.433 | 79.937 | 1.00 | 9.27 |
| 2726 | CG2 | ILE | A | 367 | 49.858 | -6.727 | 77.993 | 1.00 | 16.04 |
| 2727 | C | ILE | A | 367 | 52.207 | -5.228 | 77.966 | 1.00 | 15.97 |
| 2728 | O | ILE | A | 367 | 52.150 | -4.315 | 77.123 | 1.00 | 17.06 |
| 2729 | N | PHE | A | 368 | 52.982 | -6.299 | 77.837 | 1.00 | 15.13 |
| 2730 | CA | PHE | A | 368 | 53.646 | -6.579 | 76.577 | 1.00 | 14.90 |
| 2731 | CB | PHE | A | 368 | 54.806 | -5.619 | 76.306 | 1.00 | 14.51 |
| 2732 | CG | PHE | A | 368 | 55.636 | -5.318 | 77.521 | 1.00 | 16.56 |
| 2733 | CD1 | PHE | A | 368 | 56.793 | -6.004 | 77.768 | 1.00 | 17.21 |
| 2734 | CE1 | PHE | A | 368 | 57.563 | -5.719 | 78.917 | 1.00 | 18.46 |
| 2735 | CZ | PHE | A | 368 | 57.165 | -4.736 | 79.785 | 1.00 | 17.94 |
| 2736 | CE2 | PHE | A | 368 | 56.014 | -4.047 | 79.545 | 1.00 | 16.88 |
| 2737 | CD2 | PHE | A | 368 | 55.249 | -4.343 | 78.434 | 1.00 | 19.11 |
| 2738 | C | PHE | A | 368 | 54.145 | -7.986 | 76.533 | 1.00 | 15.22 |
| 2739 | O | PHE | A | 368 | 54.308 | -8.638 | 77.588 | 1.00 | 14.25 |
| 2740 | N | SER | A | 369 | 54.455 | -8.463 | 75.322 | 1.00 | 15.31 |
| 2741 | CA | SER | A | 369 | 55.002 | -9.806 | 75.244 | 1.00 | 15.54 |
| 2742 | CB | SER | A | 369 | 55.373 | -10.371 | 73.833 | 1.00 | 15.77 |
| 2743 | OG | SER | A | 369 | 55.733 | -9.476 | 72.811 | 1.00 | 13.50 |
| 2744 | C | SER | A | 369 | 56.129 | -9.949 | 76.271 | 1.00 | 16.30 |
| 2745 | O | SER | A | 369 | 56.967 | -9.061 | 76.418 | 1.00 | 16.96 |

FIGURE 3 (Cont.)

| A | B | C | D | E | F | G | H | I | J |
|---|---|---|---|---|---|---|---|---|---|
| 2746 | N | ASP | A | 370 | 56.039 | -11.049 | 77.025 | 1.00 | 16.41 |
| 2747 | CA | ASP | A | 370 | 57.060 | -11.503 | 77.917 | 1.00 | 16.12 |
| 2748 | CB | ASP | A | 370 | 56.540 | -12.557 | 78.915 | 1.00 | 16.13 |
| 2749 | CG | ASP | A | 370 | 55.951 | -13.847 | 78.263 | 1.00 | 16.47 |
| 2750 | OD1 | ASP | A | 370 | 55.121 | -14.512 | 78.979 | 1.00 | 14.88 |
| 2751 | OD2 | ASP | A | 370 | 56.284 | -14.287 | 77.122 | 1.00 | 14.91 |
| 2752 | C | ASP | A | 370 | 58.129 | -11.974 | 76.983 | 1.00 | 16.16 |
| 2753 | O | ASP | A | 370 | 58.278 | -11.385 | 75.907 | 1.00 | 16.82 |
| 2754 | N | LYS | A | 371 | 58.864 | -13.011 | 77.353 | 1.00 | 15.43 |
| 2755 | CA | LYS | A | 371 | 60.066 | -13.375 | 76.640 | 1.00 | 15.27 |
| 2756 | CB | LYS | A | 371 | 61.209 | -13.610 | 77.650 | 1.00 | 16.07 |
| 2757 | CG | LYS | A | 371 | 61.178 | -12.680 | 78.934 | 1.00 | 18.26 |
| 2758 | CD | LYS | A | 371 | 62.572 | -12.666 | 79.719 | 1.00 | 23.20 |
| 2759 | CE | LYS | A | 371 | 63.312 | -11.272 | 79.588 | 1.00 | 24.23 |
| 2760 | NZ | LYS | A | 371 | 64.526 | -11.109 | 80.485 | 1.00 | 23.83 |
| 2761 | C | LYS | A | 371 | 59.822 | -14.607 | 75.811 | 1.00 | 14.20 |
| 2762 | O | LYS | A | 371 | 60.656 | -14.972 | 75.001 | 1.00 | 14.01 |
| 2763 | N | ASP | A | 372 | 58.690 | -15.264 | 76.039 | 1.00 | 13.54 |
| 2764 | CA | ASP | A | 372 | 58.286 | -16.459 | 75.272 | 1.00 | 13.39 |
| 2765 | CB | ASP | A | 372 | 57.672 | -17.535 | 76.214 | 1.00 | 13.78 |
| 2766 | CG | ASP | A | 372 | 58.665 | -18.078 | 77.241 | 1.00 | 14.39 |
| 2767 | OD1 | ASP | A | 372 | 59.743 | -18.593 | 76.861 | 1.00 | 14.18 |
| 2768 | OD2 | ASP | A | 372 | 58.429 | -18.034 | 78.462 | 1.00 | 14.01 |
| 2769 | C | ASP | A | 372 | 57.276 | -16.076 | 74.174 | 1.00 | 13.02 |
| 2770 | O | ASP | A | 372 | 56.704 | -16.953 | 73.491 | 1.00 | 12.78 |
| 2771 | N | GLY | A | 373 | 57.092 | -14.754 | 74.017 | 1.00 | 12.47 |
| 2772 | CA | GLY | A | 373 | 56.055 | -14.192 | 73.215 | 1.00 | 11.69 |
| 2773 | C | GLY | A | 373 | 54.633 | -14.026 | 73.743 | 1.00 | 11.32 |
| 2774 | O | GLY | A | 373 | 53.764 | -13.845 | 72.916 | 1.00 | 12.26 |
| 2775 | N | TYR | A | 374 | 54.334 | -14.007 | 75.030 | 1.00 | 11.49 |
| 2776 | CA | TYR | A | 374 | 52.934 | -13.785 | 75.432 | 1.00 | 11.77 |
| 2777 | CB | TYR | A | 374 | 52.439 | -14.875 | 76.347 | 1.00 | 11.82 |
| 2778 | CG | TYR | A | 374 | 52.148 | -16.166 | 75.641 | 1.00 | 14.72 |
| 2779 | CD1 | TYR | A | 374 | 50.827 | -16.578 | 75.393 | 1.00 | 15.77 |
| 2780 | CE1 | TYR | A | 374 | 50.555 | -17.799 | 74.748 | 1.00 | 18.52 |
| 2781 | CZ | TYR | A | 374 | 51.617 | -18.620 | 74.369 | 1.00 | 20.51 |
| 2782 | OH | TYR | A | 374 | 51.399 | -19.839 | 73.765 | 1.00 | 20.99 |
| 2783 | CE2 | TYR | A | 374 | 52.935 | -18.229 | 74.617 | 1.00 | 19.57 |
| 2784 | CD2 | TYR | A | 374 | 53.192 | -17.004 | 75.243 | 1.00 | 17.39 |
| 2785 | C | TYR | A | 374 | 52.740 | -12.458 | 76.116 | 1.00 | 11.26 |
| 2786 | O | TYR | A | 374 | 53.536 | -12.126 | 76.951 | 1.00 | 11.73 |
| 2787 | N | LYS | A | 375 | 51.676 | -11.706 | 75.793 | 1.00 | 10.33 |
| 2788 | CA | LYS | A | 375 | 51.497 | -10.344 | 76.330 | 1.00 | 9.44 |
| 2789 | CB | LYS | A | 375 | 50.569 | -9.492 | 75.465 | 1.00 | 9.72 |
| 2790 | CG | LYS | A | 375 | 51.259 | -8.702 | 74.352 | 1.00 | 6.97 |
| 2791 | CD | LYS | A | 375 | 50.278 | -8.237 | 73.219 | 1.00 | 6.44 |
| 2792 | CE | LYS | A | 375 | 50.909 | -8.424 | 71.791 | 1.00 | 2.42 |
| 2793 | NZ | LYS | A | 375 | 52.321 | -9.029 | 71.739 | 1.00 | 2.00 |
| 2794 | C | LYS | A | 375 | 50.965 | -10.409 | 77.692 | 1.00 | 9.24 |
| 2795 | O | LYS | A | 375 | 49.981 | -11.057 | 77.907 | 1.00 | 9.80 |
| 2796 | N | HIS | A | 376 | 51.651 | -9.736 | 78.608 | 1.00 | 9.24 |

FIGURE 3 (Cont.)

| A | B | C | D | E | F | G | H | I | J |
|---|---|---|---|---|---|---|---|---|---|
| 2797 | CA | HIS | A | 376 | 51.494 | -9.884 | 80.083 | 1.00 | 8.84 |
| 2798 | CB | HIS | A | 376 | 52.293 | -11.110 | 80.631 | 1.00 | 9.38 |
| 2799 | CG | HIS | A | 376 | 51.523 | -12.401 | 80.636 | 1.00 | 8.02 |
| 2800 | ND1 | HIS | A | 376 | 51.883 | -13.488 | 79.860 | 1.00 | 9.63 |
| 2801 | CE1 | HIS | A | 376 | 51.035 | -14.478 | 80.066 | 1.00 | 7.76 |
| 2802 | NE2 | HIS | A | 376 | 50.124 | -14.065 | 80.928 | 1.00 | 6.58 |
| 2803 | CD2 | HIS | A | 376 | 50.406 | -12.773 | 81.303 | 1.00 | 5.25 |
| 2804 | C | HIS | A | 376 | 51.957 | -8.599 | 80.880 | 1.00 | 9.02 |
| 2805 | O | HIS | A | 376 | 52.937 | -7.905 | 80.487 | 1.00 | 9.41 |
| 2806 | N | ILE | A | 377 | 51.298 | -8.340 | 82.027 | 1.00 | 8.37 |
| 2807 | CA | ILE | A | 377 | 51.663 | -7.204 | 82.877 | 1.00 | 7.98 |
| 2808 | CB | ILE | A | 377 | 50.786 | -7.100 | 84.085 | 1.00 | 6.89 |
| 2809 | CG1 | ILE | A | 377 | 49.334 | -6.949 | 83.658 | 1.00 | 5.84 |
| 2810 | CD1 | ILE | A | 377 | 48.416 | -6.810 | 84.759 | 1.00 | 3.98 |
| 2811 | CG2 | ILE | A | 377 | 51.208 | -5.934 | 84.894 | 1.00 | 4.29 |
| 2812 | C | ILE | A | 377 | 53.112 | -7.310 | 83.304 | 1.00 | 9.38 |
| 2813 | O | ILE | A | 377 | 53.660 | -8.386 | 83.444 | 1.00 | 10.15 |
| 2814 | N | HIS | A | 378 | 53.726 | -6.166 | 83.488 | 1.00 | 10.50 |
| 2815 | CA | HIS | A | 378 | 55.081 | -6.094 | 83.847 | 1.00 | 10.42 |
| 2816 | CB | HIS | A | 378 | 55.921 | -5.904 | 82.579 | 1.00 | 11.18 |
| 2817 | CG | HIS | A | 378 | 56.308 | -7.172 | 81.871 | 1.00 | 10.37 |
| 2818 | ND1 | HIS | A | 378 | 55.453 | -7.847 | 81.032 | 1.00 | 10.48 |
| 2819 | CE1 | HIS | A | 378 | 56.073 | -8.903 | 80.530 | 1.00 | 11.11 |
| 2820 | NE2 | HIS | A | 378 | 57.308 | -8.936 | 81.007 | 1.00 | 13.63 |
| 2821 | CD2 | HIS | A | 378 | 57.490 | -7.848 | 81.825 | 1.00 | 11.44 |
| 2822 | C | HIS | A | 378 | 55.187 | -4.859 | 84.737 | 1.00 | 11.71 |
| 2823 | O | HIS | A | 378 | 54.596 | -3.842 | 84.422 | 1.00 | 11.74 |
| 2824 | N | TYR | A | 379 | 55.941 | -4.954 | 85.845 | 1.00 | 13.98 |
| 2825 | CA | TYR | A | 379 | 56.263 | -3.809 | 86.692 | 1.00 | 14.70 |
| 2826 | CB | TYR | A | 379 | 56.171 | -4.209 | 88.130 | 1.00 | 14.91 |
| 2827 | CG | TYR | A | 379 | 56.338 | -3.085 | 89.121 | 1.00 | 16.19 |
| 2828 | CD1 | TYR | A | 379 | 55.379 | -2.061 | 89.234 | 1.00 | 17.36 |
| 2829 | CE1 | TYR | A | 379 | 55.529 | -1.043 | 90.191 | 1.00 | 18.61 |
| 2830 | CZ | TYR | A | 379 | 56.667 | -1.045 | 91.048 | 1.00 | 16.97 |
| 2831 | OH | TYR | A | 379 | 56.896 | -0.072 | 92.017 | 1.00 | 12.89 |
| 2832 | CE2 | TYR | A | 379 | 57.605 | -2.057 | 90.931 | 1.00 | 17.20 |
| 2833 | CD2 | TYR | A | 379 | 57.443 | -3.061 | 89.974 | 1.00 | 16.80 |
| 2834 | C | TYR | A | 379 | 57.647 | -3.228 | 86.429 | 1.00 | 15.06 |
| 2835 | O | TYR | A | 379 | 58.693 | -3.903 | 86.632 | 1.00 | 14.56 |
| 2836 | N | ILE | A | 380 | 57.626 | -1.949 | 86.010 | 1.00 | 16.16 |
| 2837 | CA | ILE | A | 380 | 58.849 | -1.190 | 85.726 | 1.00 | 16.59 |
| 2838 | CB | ILE | A | 380 | 58.723 | -0.620 | 84.297 | 1.00 | 16.81 |
| 2839 | CG1 | ILE | A | 380 | 58.459 | -1.777 | 83.305 | 1.00 | 14.37 |
| 2840 | CD1 | ILE | A | 380 | 58.577 | -1.373 | 81.828 | 1.00 | 14.04 |
| 2841 | CG2 | ILE | A | 380 | 59.972 | 0.216 | 83.895 | 1.00 | 15.63 |
| 2842 | C | ILE | A | 380 | 59.274 | -0.112 | 86.794 | 1.00 | 17.92 |
| 2843 | O | ILE | A | 380 | 58.834 | 1.041 | 86.716 | 1.00 | 17.23 |
| 2844 | N | LYS | A | 381 | 60.148 | -0.492 | 87.767 | 1.00 | 19.47 |
| 2845 | CA | LYS | A | 381 | 60.563 | 0.447 | 88.839 | 1.00 | 21.41 |
| 2846 | CB | LYS | A | 381 | 61.447 | -0.187 | 89.928 | 1.00 | 21.40 |
| 2847 | CG | LYS | A | 381 | 60.759 | -0.257 | 91.338 | 1.00 | 22.98 |

FIGURE 3 (Cont.)

| A | B | C | D | E | F | G | H | I | J |
|---|---|---|---|---|---|---|---|---|---|
| 2848 | CD | LYS | A | 381 | 61.585 | 0.313 | 92.529 | 1.00 | 23.98 |
| 2849 | CE | LYS | A | 381 | 60.710 | 0.594 | 93.800 | 1.00 | 24.43 |
| 2850 | NZ | LYS | A | 381 | 61.523 | 1.048 | 95.008 | 1.00 | 22.75 |
| 2851 | C | LYS | A | 381 | 61.310 | 1.589 | 88.211 | 1.00 | 22.47 |
| 2852 | O | LYS | A | 381 | 60.865 | 2.735 | 88.279 | 1.00 | 23.04 |
| 2853 | N | ASP | A | 382 | 62.400 | 1.245 | 87.532 | 1.00 | 23.31 |
| 2854 | CA | ASP | A | 382 | 63.278 | 2.252 | 86.934 | 1.00 | 23.86 |
| 2855 | CB | ASP | A | 382 | 64.444 | 2.602 | 87.903 | 1.00 | 23.80 |
| 2856 | CG | ASP | A | 382 | 65.403 | 1.405 | 88.187 | 1.00 | 25.83 |
| 2857 | OD1 | ASP | A | 382 | 64.961 | 0.227 | 88.203 | 1.00 | 27.37 |
| 2858 | OD2 | ASP | A | 382 | 66.633 | 1.561 | 88.430 | 1.00 | 29.76 |
| 2859 | C | ASP | A | 382 | 63.788 | 1.936 | 85.496 | 1.00 | 23.37 |
| 2860 | O | ASP | A | 382 | 64.049 | 2.872 | 84.723 | 1.00 | 23.42 |
| 2861 | N | THR | A | 383 | 63.944 | 0.662 | 85.124 | 1.00 | 22.73 |
| 2862 | CA | THR | A | 383 | 64.427 | 0.373 | 83.773 | 1.00 | 22.52 |
| 2863 | CB | THR | A | 383 | 65.947 | 0.108 | 83.735 | 1.00 | 22.84 |
| 2864 | OG1 | THR | A | 383 | 66.299 | -0.856 | 84.746 | 1.00 | 25.40 |
| 2865 | CG2 | THR | A | 383 | 66.835 | 1.403 | 84.052 | 1.00 | 23.22 |
| 2866 | C | THR | A | 383 | 63.689 | -0.778 | 83.117 | 1.00 | 21.69 |
| 2867 | O | THR | A | 383 | 63.114 | -1.625 | 83.781 | 1.00 | 21.98 |
| 2868 | N | VAL | A | 384 | 63.739 | -0.778 | 81.788 | 1.00 | 20.30 |
| 2869 | CA | VAL | A | 384 | 63.111 | -1.790 | 80.968 | 1.00 | 19.66 |
| 2870 | CB | VAL | A | 384 | 63.304 | -1.518 | 79.474 | 1.00 | 19.68 |
| 2871 | CG1 | VAL | A | 384 | 62.531 | -2.582 | 78.647 | 1.00 | 18.47 |
| 2872 | CG2 | VAL | A | 384 | 62.876 | -0.058 | 79.102 | 1.00 | 20.73 |
| 2873 | C | VAL | A | 384 | 63.674 | -3.185 | 81.172 | 1.00 | 19.43 |
| 2874 | O | VAL | A | 384 | 62.932 | -4.157 | 81.006 | 1.00 | 19.66 |
| 2875 | N | GLU | A | 385 | 64.968 | -3.282 | 81.474 | 1.00 | 18.67 |
| 2876 | CA | GLU | A | 385 | 65.708 | -4.561 | 81.490 | 1.00 | 18.63 |
| 2877 | CB | GLU | A | 385 | 67.201 | -4.404 | 80.996 | 1.00 | 19.00 |
| 2878 | CG | GLU | A | 385 | 67.892 | -3.015 | 81.068 | 1.00 | 21.03 |
| 2879 | CD | GLU | A | 385 | 67.319 | -1.959 | 80.077 | 1.00 | 23.99 |
| 2880 | OE1 | GLU | A | 385 | 67.038 | -0.781 | 80.501 | 1.00 | 24.04 |
| 2881 | OE2 | GLU | A | 385 | 67.139 | -2.304 | 78.874 | 1.00 | 24.91 |
| 2882 | C | GLU | A | 385 | 65.595 | -5.175 | 82.908 | 1.00 | 17.90 |
| 2883 | O | GLU | A | 385 | 65.662 | -6.395 | 83.107 | 1.00 | 17.71 |
| 2884 | N | ASN | A | 386 | 65.378 | -4.281 | 83.866 | 1.00 | 17.23 |
| 2885 | CA | ASN | A | 386 | 65.054 | -4.587 | 85.257 | 1.00 | 16.56 |
| 2886 | CB | ASN | A | 386 | 65.748 | -3.482 | 86.080 | 1.00 | 16.52 |
| 2887 | CG | ASN | A | 386 | 65.792 | -3.740 | 87.540 | 1.00 | 18.57 |
| 2888 | OD1 | ASN | A | 386 | 66.779 | -4.250 | 88.072 | 1.00 | 20.70 |
| 2889 | ND2 | ASN | A | 386 | 64.759 | -3.301 | 88.233 | 1.00 | 21.05 |
| 2890 | C | ASN | A | 386 | 63.473 | -4.596 | 85.398 | 1.00 | 15.91 |
| 2891 | O | ASN | A | 386 | 62.914 | -4.425 | 86.465 | 1.00 | 15.41 |
| 2892 | N | ALA | A | 387 | 62.756 | -4.773 | 84.298 | 1.00 | 14.79 |
| 2893 | CA | ALA | A | 387 | 61.320 | -5.034 | 84.358 | 1.00 | 14.58 |
| 2894 | CB | ALA | A | 387 | 60.736 | -5.077 | 82.950 | 1.00 | 14.56 |
| 2895 | C | ALA | A | 387 | 61.054 | -6.371 | 85.029 | 1.00 | 14.46 |
| 2896 | O | ALA | A | 387 | 61.653 | -7.364 | 84.651 | 1.00 | 14.38 |
| 2897 | N | ILE | A | 388 | 60.133 | -6.440 | 85.985 | 1.00 | 14.33 |
| 2898 | CA | ILE | A | 388 | 59.776 | -7.758 | 86.524 | 1.00 | 13.90 |

FIGURE 3 (Cont.)

| A | B | C | D | E | F | G | H | I | J |
|---|---|---|---|---|---|---|---|---|---|
| 2899 | CB | ILE | A | 388 | 59.908 | -7.828 | 88.090 | 1.00 | 14.99 |
| 2900 | CG1 | ILE | A | 388 | 58.855 | -8.768 | 88.709 | 1.00 | 16.03 |
| 2901 | CD1 | ILE | A | 388 | 57.601 | -8.107 | 89.172 | 1.00 | 16.01 |
| 2902 | CG2 | ILE | A | 388 | 60.007 | -6.418 | 88.775 | 1.00 | 16.68 |
| 2903 | C | ILE | A | 388 | 58.420 | -8.222 | 85.975 | 1.00 | 13.51 |
| 2904 | O | ILE | A | 388 | 57.454 | -7.434 | 85.960 | 1.00 | 10.45 |
| 2905 | N | GLN | A | 389 | 58.388 | -9.491 | 85.503 | 1.00 | 13.06 |
| 2906 | CA | GLN | A | 389 | 57.179 | -10.060 | 84.884 | 1.00 | 12.72 |
| 2907 | CB | GLN | A | 389 | 57.442 | -11.335 | 84.061 | 1.00 | 12.38 |
| 2908 | CG | GLN | A | 389 | 56.281 | -11.684 | 83.004 | 1.00 | 14.88 |
| 2909 | CD | GLN | A | 389 | 56.617 | -12.873 | 82.029 | 1.00 | 16.63 |
| 2910 | OE1 | GLN | A | 389 | 57.793 | -13.096 | 81.675 | 1.00 | 17.64 |
| 2911 | NE2 | GLN | A | 389 | 55.585 | -13.628 | 81.614 | 1.00 | 14.65 |
| 2912 | C | GLN | A | 389 | 56.264 | -10.360 | 86.027 | 1.00 | 12.14 |
| 2913 | O | GLN | A | 389 | 56.734 | -10.883 | 87.022 | 1.00 | 12.78 |
| 2914 | N | ILE | A | 390 | 54.980 | -10.025 | 85.867 | 1.00 | 11.15 |
| 2915 | CA | ILE | A | 390 | 53.989 | -9.985 | 86.943 | 1.00 | 10.01 |
| 2916 | CB | ILE | A | 390 | 53.476 | -8.542 | 87.068 | 1.00 | 10.49 |
| 2917 | CG1 | ILE | A | 390 | 54.593 | -7.616 | 87.601 | 1.00 | 10.04 |
| 2918 | CD1 | ILE | A | 390 | 54.710 | -7.559 | 89.095 | 1.00 | 6.61 |
| 2919 | CG2 | ILE | A | 390 | 52.108 | -8.481 | 87.861 | 1.00 | 11.13 |
| 2920 | C | ILE | A | 390 | 52.798 | -10.904 | 86.661 | 1.00 | 9.77 |
| 2921 | O | ILE | A | 390 | 52.217 | -11.419 | 87.591 | 1.00 | 8.97 |
| 2922 | N | THR | A | 391 | 52.369 | -11.027 | 85.390 | 1.00 | 8.89 |
| 2923 | CA | THR | A | 391 | 51.480 | -12.134 | 84.981 | 1.00 | 9.40 |
| 2924 | CB | THR | A | 391 | 50.046 | -11.742 | 84.507 | 1.00 | 8.22 |
| 2925 | OG1 | THR | A | 391 | 50.031 | -10.591 | 83.610 | 1.00 | 12.13 |
| 2926 | CG2 | THR | A | 391 | 49.257 | -11.308 | 85.660 | 1.00 | 6.43 |
| 2927 | C | THR | A | 391 | 52.224 | -12.958 | 83.975 | 1.00 | 9.72 |
| 2928 | O | THR | A | 391 | 53.070 | -12.442 | 83.297 | 1.00 | 10.08 |
| 2929 | N | SER | A | 392 | 51.963 | -14.426 | 84.141 | 1.00 | 10.77 |
| 2930 | CA | SER | A | 392 | 52.672 | -15.049 | 83.045 | 1.00 | 11.75 |
| 2931 | CB | SER | A | 392 | 54.196 | -15.409 | 83.436 | 1.00 | 11.91 |
| 2932 | OG | SER | A | 392 | 54.389 | -16.147 | 84.655 | 1.00 | 12.28 |
| 2933 | C | SER | A | 392 | 51.845 | -16.259 | 82.658 | 1.00 | 11.99 |
| 2934 | O | SER | A | 392 | 50.987 | -16.695 | 83.416 | 1.00 | 12.51 |
| 2935 | N | GLY | A | 393 | 52.378 | -17.021 | 81.720 | 1.00 | 12.37 |
| 2936 | CA | GLY | A | 393 | 51.843 | -18.345 | 81.385 | 1.00 | 12.97 |
| 2937 | C | GLY | A | 393 | 51.402 | -18.278 | 79.976 | 1.00 | 14.22 |
| 2938 | O | GLY | A | 393 | 51.772 | -17.341 | 79.319 | 1.00 | 14.01 |
| 2939 | N | LYS | A | 394 | 50.481 | -18.999 | 79.262 | 1.00 | 15.07 |
| 2940 | CA | LYS | A | 394 | 50.083 | -19.225 | 77.870 | 1.00 | 16.36 |
| 2941 | CB | LYS | A | 394 | 50.310 | -20.691 | 77.343 | 1.00 | 16.27 |
| 2942 | CG | LYS | A | 394 | 50.756 | -21.779 | 78.348 | 1.00 | 19.02 |
| 2943 | CD | LYS | A | 394 | 50.760 | -23.192 | 77.715 | 1.00 | 21.32 |
| 2944 | CE | LYS | A | 394 | 52.022 | -23.408 | 76.846 | 1.00 | 23.31 |
| 2945 | NZ | LYS | A | 394 | 52.016 | -22.611 | 75.589 | 1.00 | 20.46 |
| 2946 | C | LYS | A | 394 | 48.634 | -18.715 | 77.654 | 1.00 | 17.08 |
| 2947 | O | LYS | A | 394 | 47.656 | -19.441 | 77.415 | 1.00 | 17.68 |
| 2948 | N | TRP | A | 395 | 48.554 | -17.408 | 77.716 | 1.00 | 16.68 |
| 2949 | CA | TRP | A | 395 | 47.305 | -16.693 | 77.632 | 1.00 | 16.68 |

FIGURE 3 (Cont.)

| A | B | C | D | E | F | G | H | I | J |
|---|---|---|---|---|---|---|---|---|---|
| 2950 | CB | TRP | A | 395 | 46.336 | -17.178 | 78.719 | 1.00 | 16.19 |
| 2951 | CG | TRP | A | 395 | 46.993 | -17.293 | 80.028 | 1.00 | 15.59 |
| 2952 | CD1 | TRP | A | 395 | 47.629 | -18.409 | 80.560 | 1.00 | 16.01 |
| 2953 | NE1 | TRP | A | 395 | 48.127 | -18.107 | 81.805 | 1.00 | 15.69 |
| 2954 | CE2 | TRP | A | 395 | 47.850 | -16.799 | 82.104 | 1.00 | 12.60 |
| 2955 | CD2 | TRP | A | 395 | 47.138 | -16.253 | 80.998 | 1.00 | 13.15 |
| 2956 | CE3 | TRP | A | 395 | 46.698 | -14.928 | 81.068 | 1.00 | 11.29 |
| 2957 | CZ3 | TRP | A | 395 | 47.007 | -14.167 | 82.210 | 1.00 | 9.88 |
| 2958 | CH2 | TRP | A | 395 | 47.726 | -14.731 | 83.288 | 1.00 | 11.62 |
| 2959 | CZ2 | TRP | A | 395 | 48.158 | -16.053 | 83.256 | 1.00 | 12.90 |
| 2960 | C | TRP | A | 395 | 47.702 | -15.209 | 77.781 | 1.00 | 16.90 |
| 2961 | O | TRP | A | 395 | 48.912 | -14.868 | 77.744 | 1.00 | 17.25 |
| 2962 | N | GLU | A | 396 | 46.737 | -14.320 | 77.928 | 1.00 | 16.40 |
| 2963 | CA | GLU | A | 396 | 47.092 | -12.927 | 77.836 | 1.00 | 16.88 |
| 2964 | CB | GLU | A | 396 | 47.000 | -12.451 | 76.390 | 1.00 | 16.28 |
| 2965 | CG | GLU | A | 396 | 48.296 | -12.676 | 75.646 | 1.00 | 17.30 |
| 2966 | CD | GLU | A | 396 | 48.466 | -11.940 | 74.320 | 1.00 | 16.64 |
| 2967 | OE1 | GLU | A | 396 | 47.753 | -10.905 | 74.029 | 1.00 | 17.89 |
| 2968 | OE2 | GLU | A | 396 | 49.358 | -12.470 | 73.588 | 1.00 | 12.57 |
| 2969 | C | GLU | A | 396 | 46.337 | -12.012 | 78.745 | 1.00 | 16.70 |
| 2970 | O | GLU | A | 396 | 45.151 | -12.161 | 78.995 | 1.00 | 16.78 |
| 2971 | N | ALA | A | 397 | 47.088 | -11.072 | 79.267 | 1.00 | 17.01 |
| 2972 | CA | ALA | A | 397 | 46.540 | -9.933 | 79.959 | 1.00 | 17.34 |
| 2973 | CB | ALA | A | 397 | 47.612 | -9.336 | 80.830 | 1.00 | 16.89 |
| 2974 | C | ALA | A | 397 | 46.090 | -8.929 | 78.880 | 1.00 | 17.18 |
| 2975 | O | ALA | A | 397 | 46.915 | -8.491 | 78.080 | 1.00 | 17.27 |
| 2976 | N | ILE | A | 398 | 44.799 | -8.603 | 78.830 | 1.00 | 16.92 |
| 2977 | CA | ILE | A | 398 | 44.306 | -7.781 | 77.744 | 1.00 | 16.77 |
| 2978 | CB | ILE | A | 398 | 42.856 | -8.044 | 77.362 | 1.00 | 17.26 |
| 2979 | CG1 | ILE | A | 398 | 42.759 | -9.412 | 76.636 | 1.00 | 15.98 |
| 2980 | CD1 | ILE | A | 398 | 43.101 | -10.546 | 77.433 | 1.00 | 5.32 |
| 2981 | CG2 | ILE | A | 398 | 42.296 | -6.850 | 76.415 | 1.00 | 13.28 |
| 2982 | C | ILE | A | 398 | 44.511 | -6.355 | 78.063 | 1.00 | 17.84 |
| 2983 | O | ILE | A | 398 | 45.168 | -5.670 | 77.267 | 1.00 | 16.45 |
| 2984 | N | ASN | A | 399 | 44.003 | -5.887 | 79.260 | 1.00 | 19.67 |
| 2985 | CA | ASN | A | 399 | 44.459 | -4.592 | 79.751 | 1.00 | 21.11 |
| 2986 | CB | ASN | A | 399 | 43.726 | -3.458 | 79.033 | 1.00 | 23.66 |
| 2987 | CG | ASN | A | 399 | 44.518 | -2.166 | 79.023 | 1.00 | 30.34 |
| 2988 | OD1 | ASN | A | 399 | 45.731 | -2.169 | 79.227 | 1.00 | 36.25 |
| 2989 | ND2 | ASN | A | 399 | 43.832 | -1.055 | 78.784 | 1.00 | 31.00 |
| 2990 | C | ASN | A | 399 | 44.260 | -4.473 | 81.259 | 1.00 | 19.26 |
| 2991 | O | ASN | A | 399 | 43.534 | -5.164 | 81.957 | 1.00 | 19.19 |
| 2992 | N | ILE | A | 400 | 45.015 | -3.487 | 81.782 | 1.00 | 17.53 |
| 2993 | CA | ILE | A | 400 | 45.017 | -3.050 | 83.170 | 1.00 | 15.47 |
| 2994 | CB | ILE | A | 400 | 46.385 | -2.434 | 83.431 | 1.00 | 14.26 |
| 2995 | CG1 | ILE | A | 400 | 47.480 | -3.507 | 83.255 | 1.00 | 11.09 |
| 2996 | CD1 | ILE | A | 400 | 48.888 | -2.917 | 82.871 | 1.00 | 6.78 |
| 2997 | CG2 | ILE | A | 400 | 46.431 | -1.847 | 84.799 | 1.00 | 13.16 |
| 2998 | C | ILE | A | 400 | 43.934 | -1.996 | 83.364 | 1.00 | 15.34 |
| 2999 | O | ILE | A | 400 | 43.946 | -0.961 | 82.712 | 1.00 | 13.99 |
| 3000 | N | PHE | A | 401 | 42.965 | -2.287 | 84.225 | 1.00 | 15.85 |

FIGURE 3 (Cont.)

| A | B | C | D | E | F | G | H | I | J |
|---|---|---|---|---|---|---|---|---|---|
| 3001 | CA | PHE | A | 401 | 41.912 | -1.337 | 84.507 | 1.00 | 15.07 |
| 3002 | CB | PHE | A | 401 | 40.606 | -2.002 | 84.890 | 1.00 | 14.93 |
| 3003 | CG | PHE | A | 401 | 39.967 | -2.730 | 83.803 | 1.00 | 16.15 |
| 3004 | CD1 | PHE | A | 401 | 39.179 | -2.055 | 82.876 | 1.00 | 17.19 |
| 3005 | CE1 | PHE | A | 401 | 38.582 | -2.745 | 81.791 | 1.00 | 20.03 |
| 3006 | CZ | PHE | A | 401 | 38.768 | -4.143 | 81.678 | 1.00 | 22.03 |
| 3007 | CE2 | PHE | A | 401 | 39.544 | -4.838 | 82.683 | 1.00 | 22.42 |
| 3008 | CD2 | PHE | A | 401 | 40.132 | -4.110 | 83.703 | 1.00 | 19.58 |
| 3009 | C | PHE | A | 401 | 42.255 | -0.472 | 85.661 | 1.00 | 15.32 |
| 3010 | O | PHE | A | 401 | 41.667 | 0.608 | 85.742 | 1.00 | 15.11 |
| 3011 | N | ARG | A | 402 | 43.095 | -0.955 | 86.605 | 1.00 | 14.76 |
| 3012 | CA | ARG | A | 402 | 43.312 | -0.260 | 87.885 | 1.00 | 15.46 |
| 3013 | CB | ARG | A | 402 | 42.123 | -0.492 | 88.823 | 1.00 | 16.31 |
| 3014 | CG | ARG | A | 402 | 41.391 | 0.766 | 89.336 | 1.00 | 18.76 |
| 3015 | CD | ARG | A | 402 | 41.701 | 2.081 | 88.629 | 1.00 | 22.61 |
| 3016 | NE | ARG | A | 402 | 41.504 | 3.216 | 89.529 | 1.00 | 25.08 |
| 3017 | CZ | ARG | A | 402 | 40.884 | 4.367 | 89.233 | 1.00 | 24.02 |
| 3018 | NH1 | ARG | A | 402 | 40.821 | 5.319 | 90.173 | 1.00 | 25.80 |
| 3019 | NH2 | ARG | A | 402 | 40.356 | 4.585 | 88.030 | 1.00 | 21.43 |
| 3020 | C | ARG | A | 402 | 44.573 | -0.555 | 88.683 | 1.00 | 15.20 |
| 3021 | O | ARG | A | 402 | 44.869 | -1.716 | 89.008 | 1.00 | 15.78 |
| 3022 | N | VAL | A | 403 | 45.322 | 0.477 | 89.059 | 1.00 | 14.59 |
| 3023 | CA | VAL | A | 403 | 46.390 | 0.243 | 90.060 | 1.00 | 14.17 |
| 3024 | CB | VAL | A | 403 | 47.873 | 0.451 | 89.524 | 1.00 | 13.92 |
| 3025 | CG1 | VAL | A | 403 | 48.149 | -0.383 | 88.277 | 1.00 | 14.04 |
| 3026 | CG2 | VAL | A | 403 | 48.867 | 0.029 | 90.485 | 1.00 | 11.40 |
| 3027 | C | VAL | A | 403 | 46.069 | 1.121 | 91.221 | 1.00 | 14.05 |
| 3028 | O | VAL | A | 403 | 45.955 | 2.302 | 91.116 | 1.00 | 13.79 |
| 3029 | N | THR | A | 404 | 45.926 | 0.485 | 92.356 | 1.00 | 15.12 |
| 3030 | CA | THR | A | 404 | 45.703 | 1.123 | 93.643 | 1.00 | 16.10 |
| 3031 | CB | THR | A | 404 | 44.531 | 0.359 | 94.312 | 1.00 | 15.32 |
| 3032 | OG1 | THR | A | 404 | 43.372 | 0.479 | 93.438 | 1.00 | 17.75 |
| 3033 | CG2 | THR | A | 404 | 44.090 | 0.985 | 95.560 | 1.00 | 16.00 |
| 3034 | C | THR | A | 404 | 46.999 | 1.094 | 94.483 | 1.00 | 16.66 |
| 3035 | O | THR | A | 404 | 48.089 | 0.615 | 94.045 | 1.00 | 17.35 |
| 3036 | N | GLN | A | 405 | 46.904 | 1.672 | 95.673 | 1.00 | 16.89 |
| 3037 | CA | GLN | A | 405 | 47.924 | 1.473 | 96.667 | 1.00 | 16.49 |
| 3038 | CB | GLN | A | 405 | 47.599 | 2.343 | 97.859 | 1.00 | 16.68 |
| 3039 | CG | GLN | A | 405 | 48.731 | 2.634 | 98.779 | 1.00 | 18.46 |
| 3040 | CD | GLN | A | 405 | 48.197 | 3.292 | 100.040 | 1.00 | 20.92 |
| 3041 | OE1 | GLN | A | 405 | 48.585 | 2.929 | 101.158 | 1.00 | 19.76 |
| 3042 | NE2 | GLN | A | 405 | 47.244 | 4.245 | 99.849 | 1.00 | 23.75 |
| 3043 | C | GLN | A | 405 | 48.007 | -0.010 | 97.032 | 1.00 | 15.88 |
| 3044 | O | GLN | A | 405 | 49.067 | -0.578 | 97.040 | 1.00 | 16.52 |
| 3045 | N | ASP | A | 406 | 46.877 | -0.643 | 97.278 | 1.00 | 14.95 |
| 3046 | CA | ASP | A | 406 | 46.876 | -2.030 | 97.731 | 1.00 | 14.53 |
| 3047 | CB | ASP | A | 406 | 45.792 | -2.261 | 98.872 | 1.00 | 15.81 |
| 3048 | CG | ASP | A | 406 | 44.418 | -1.350 | 98.754 | 1.00 | 17.58 |
| 3049 | OD1 | ASP | A | 406 | 43.616 | -1.398 | 99.749 | 1.00 | 19.19 |
| 3050 | OD2 | ASP | A | 406 | 44.055 | -0.558 | 97.822 | 1.00 | 14.14 |
| 3051 | C | ASP | A | 406 | 46.846 | -3.129 | 96.621 | 1.00 | 12.79 |

FIGURE 3 (Cont.)

| A | B | C | D | E | F | G | H | I | J |
|---|---|---|---|---|---|---|---|---|---|
| 3052 | O | ASP | A | 406 | 47.179 | -4.263 | 96.883 | 1.00 | 11.71 |
| 3053 | N | SER | A | 407 | 46.505 | -2.813 | 95.367 | 1.00 | 13.15 |
| 3054 | CA | SER | A | 407 | 45.810 | -3.811 | 94.539 | 1.00 | 12.04 |
| 3055 | CB | SER | A | 407 | 44.374 | -3.939 | 95.123 | 1.00 | 12.40 |
| 3056 | OG | SER | A | 407 | 44.341 | -3.775 | 96.591 | 1.00 | 10.89 |
| 3057 | C | SER | A | 407 | 45.774 | -3.581 | 93.031 | 1.00 | 12.04 |
| 3058 | O | SER | A | 407 | 45.662 | -2.450 | 92.568 | 1.00 | 12.53 |
| 3059 | N | LEU | A | 408 | 45.842 | -4.658 | 92.237 | 1.00 | 11.88 |
| 3060 | CA | LEU | A | 408 | 45.770 | -4.544 | 90.723 | 1.00 | 9.78 |
| 3061 | CB | LEU | A | 408 | 47.091 | -4.960 | 90.037 | 1.00 | 9.13 |
| 3062 | CG | LEU | A | 408 | 47.237 | -4.576 | 88.548 | 1.00 | 8.39 |
| 3063 | CD1 | LEU | A | 408 | 48.702 | -4.591 | 88.235 | 1.00 | 9.72 |
| 3064 | CD2 | LEU | A | 408 | 46.501 | -5.492 | 87.584 | 1.00 | 2.00 |
| 3065 | C | LEU | A | 408 | 44.675 | -5.300 | 90.005 | 1.00 | 9.59 |
| 3066 | O | LEU | A | 408 | 44.661 | -6.529 | 90.033 | 1.00 | 10.71 |
| 3067 | N | PHE | A | 409 | 43.846 | -4.559 | 89.269 | 1.00 | 8.34 |
| 3068 | CA | PHE | A | 409 | 42.751 | -5.091 | 88.449 | 1.00 | 7.78 |
| 3069 | CB | PHE | A | 409 | 41.570 | -4.181 | 88.585 | 1.00 | 7.69 |
| 3070 | CG | PHE | A | 409 | 41.060 | -4.151 | 89.916 | 1.00 | 5.89 |
| 3071 | CD1 | PHE | A | 409 | 41.638 | -3.371 | 90.829 | 1.00 | 7.21 |
| 3072 | CE1 | PHE | A | 409 | 41.193 | -3.374 | 92.129 | 1.00 | 10.59 |
| 3073 | CZ | PHE | A | 409 | 40.112 | -4.159 | 92.453 | 1.00 | 8.64 |
| 3074 | CE2 | PHE | A | 409 | 39.548 | -4.980 | 91.504 | 1.00 | 6.29 |
| 3075 | CD2 | PHE | A | 409 | 40.033 | -4.970 | 90.265 | 1.00 | 7.07 |
| 3076 | C | PHE | A | 409 | 43.006 | -5.198 | 86.955 | 1.00 | 7.53 |
| 3077 | O | PHE | A | 409 | 43.422 | -4.246 | 86.330 | 1.00 | 8.73 |
| 3078 | N | TYR | A | 410 | 42.696 | -6.345 | 86.374 | 1.00 | 7.34 |
| 3079 | CA | TYR | A | 410 | 43.052 | -6.587 | 84.997 | 1.00 | 8.15 |
| 3080 | CB | TYR | A | 410 | 44.564 | -6.817 | 84.854 | 1.00 | 7.49 |
| 3081 | CG | TYR | A | 410 | 44.958 | -8.200 | 85.236 | 1.00 | 8.82 |
| 3082 | CD1 | TYR | A | 410 | 45.108 | -9.173 | 84.254 | 1.00 | 7.91 |
| 3083 | CE1 | TYR | A | 410 | 45.439 | -10.462 | 84.575 | 1.00 | 6.87 |
| 3084 | CZ | TYR | A | 410 | 45.601 | -10.831 | 85.846 | 1.00 | 6.77 |
| 3085 | OH | TYR | A | 410 | 45.918 | -12.157 | 86.018 | 1.00 | 8.25 |
| 3086 | CE2 | TYR | A | 410 | 45.473 | -9.887 | 86.869 | 1.00 | 6.06 |
| 3087 | CD2 | TYR | A | 410 | 45.132 | -8.578 | 86.567 | 1.00 | 7.40 |
| 3088 | C | TYR | A | 410 | 42.257 | -7.723 | 84.350 | 1.00 | 8.47 |
| 3089 | O | TYR | A | 410 | 41.760 | -8.584 | 85.045 | 1.00 | 8.75 |
| 3090 | N | SER | A | 411 | 42.180 | -7.686 | 83.022 | 1.00 | 9.81 |
| 3091 | CA | SER | A | 411 | 41.285 | -8.526 | 82.215 | 1.00 | 11.43 |
| 3092 | CB | SER | A | 411 | 40.683 | -7.761 | 81.052 | 1.00 | 10.74 |
| 3093 | OG | SER | A | 411 | 41.695 | -7.304 | 80.153 | 1.00 | 13.57 |
| 3094 | C | SER | A | 411 | 42.083 | -9.612 | 81.614 | 1.00 | 12.01 |
| 3095 | O | SER | A | 411 | 43.268 | -9.424 | 81.251 | 1.00 | 12.61 |
| 3096 | N | SER | A | 412 | 41.413 | -10.731 | 81.388 | 1.00 | 12.71 |
| 3097 | CA | SER | A | 412 | 42.135 | -11.947 | 81.023 | 1.00 | 13.61 |
| 3098 | CB | SER | A | 412 | 42.736 | -12.586 | 82.285 | 1.00 | 13.14 |
| 3099 | OG | SER | A | 412 | 44.090 | -12.841 | 82.015 | 1.00 | 16.91 |
| 3100 | C | SER | A | 412 | 41.451 | -13.053 | 80.219 | 1.00 | 13.27 |
| 3101 | O | SER | A | 412 | 40.307 | -13.479 | 80.421 | 1.00 | 12.36 |
| 3102 | N | ASN | A | 413 | 42.336 | -13.587 | 79.416 | 1.00 | 14.39 |

FIGURE 3 (Cont.)

| A | B | C | D | E | F | G | H | I | J |
|---|---|---|---|---|---|---|---|---|---|
| 3103 | CA | ASN | A | 413 | 42.152 | -14.690 | 78.483 | 1.00 | 16.01 |
| 3104 | CB | ASN | A | 413 | 43.434 | -14.724 | 77.639 | 1.00 | 16.45 |
| 3105 | CG | ASN | A | 413 | 43.261 | -15.393 | 76.362 | 1.00 | 19.16 |
| 3106 | OD1 | ASN | A | 413 | 42.475 | -14.950 | 75.549 | 1.00 | 19.97 |
| 3107 | ND2 | ASN | A | 413 | 44.015 | -16.510 | 76.140 | 1.00 | 24.58 |
| 3108 | C | ASN | A | 413 | 42.015 | -16.014 | 79.283 | 1.00 | 15.25 |
| 3109 | O | ASN | A | 413 | 41.156 | -16.843 | 78.961 | 1.00 | 16.19 |
| 3110 | N | GLU | A | 414 | 42.804 | -16.087 | 80.375 | 1.00 | 14.33 |
| 3111 | CA | GLU | A | 414 | 43.167 | -17.283 | 81.181 | 1.00 | 13.04 |
| 3112 | CB | GLU | A | 414 | 43.922 | -16.844 | 82.457 | 1.00 | 13.29 |
| 3113 | CG | GLU | A | 414 | 44.771 | -17.943 | 83.176 | 1.00 | 11.26 |
| 3114 | CD | GLU | A | 414 | 45.319 | -17.511 | 84.555 | 1.00 | 12.69 |
| 3115 | OE1 | GLU | A | 414 | 45.357 | -16.257 | 84.806 | 1.00 | 15.09 |
| 3116 | OE2 | GLU | A | 414 | 45.754 | -18.357 | 85.377 | 1.00 | 9.17 |
| 3117 | C | GLU | A | 414 | 42.119 | -18.358 | 81.600 | 1.00 | 12.34 |
| 3118 | O | GLU | A | 414 | 42.353 | -19.532 | 81.383 | 1.00 | 12.38 |
| 3119 | N | PHE | A | 415 | 41.029 | -18.012 | 82.258 | 1.00 | 10.77 |
| 3120 | CA | PHE | A | 415 | 40.069 | -19.045 | 82.666 | 1.00 | 9.63 |
| 3121 | CB | PHE | A | 415 | 38.704 | -18.430 | 82.833 | 1.00 | 9.68 |
| 3122 | CG | PHE | A | 415 | 37.781 | -19.247 | 83.621 | 1.00 | 7.76 |
| 3123 | CD1 | PHE | A | 415 | 38.117 | -19.649 | 84.887 | 1.00 | 7.08 |
| 3124 | CE1 | PHE | A | 415 | 37.250 | -20.354 | 85.590 | 1.00 | 9.10 |
| 3125 | CZ | PHE | A | 415 | 36.002 | -20.724 | 85.025 | 1.00 | 7.85 |
| 3126 | CE2 | PHE | A | 415 | 35.689 | -20.373 | 83.803 | 1.00 | 3.22 |
| 3127 | CD2 | PHE | A | 415 | 36.566 | -19.612 | 83.091 | 1.00 | 8.41 |
| 3128 | C | PHE | A | 415 | 39.920 | -20.180 | 81.696 | 1.00 | 9.73 |
| 3129 | O | PHE | A | 415 | 39.650 | -19.938 | 80.526 | 1.00 | 11.26 |
| 3130 | N | GLU | A | 416 | 40.144 | -21.408 | 82.182 | 1.00 | 10.34 |
| 3131 | CA | GLU | A | 416 | 39.945 | -22.635 | 81.432 | 1.00 | 9.90 |
| 3132 | CB | GLU | A | 416 | 38.455 | -23.018 | 81.402 | 1.00 | 9.93 |
| 3133 | CG | GLU | A | 416 | 37.722 | -22.852 | 82.713 | 1.00 | 7.34 |
| 3134 | CD | GLU | A | 416 | 36.324 | -23.495 | 82.716 | 1.00 | 6.03 |
| 3135 | OE1 | GLU | A | 416 | 35.967 | -24.140 | 83.732 | 1.00 | 9.30 |
| 3136 | OE2 | GLU | A | 416 | 35.559 | -23.355 | 81.757 | 1.00 | 2.57 |
| 3137 | C | GLU | A | 416 | 40.436 | -22.589 | 80.010 | 1.00 | 10.35 |
| 3138 | O | GLU | A | 416 | 39.840 | -23.190 | 79.168 | 1.00 | 11.27 |
| 3139 | N | GLU | A | 417 | 41.481 | -21.829 | 79.733 | 1.00 | 11.14 |
| 3140 | CA | GLU | A | 417 | 42.263 | -21.872 | 78.470 | 1.00 | 11.93 |
| 3141 | CB | GLU | A | 417 | 42.924 | -23.281 | 78.221 | 1.00 | 12.95 |
| 3142 | CG | GLU | A | 417 | 43.909 | -23.807 | 79.289 | 1.00 | 13.87 |
| 3143 | CD | GLU | A | 417 | 43.417 | -23.562 | 80.716 | 1.00 | 18.76 |
| 3144 | OE1 | GLU | A | 417 | 43.459 | -22.364 | 81.137 | 1.00 | 20.13 |
| 3145 | OE2 | GLU | A | 417 | 42.982 | -24.530 | 81.416 | 1.00 | 19.32 |
| 3146 | C | GLU | A | 417 | 41.528 | -21.426 | 77.239 | 1.00 | 12.26 |
| 3147 | O | GLU | A | 417 | 42.002 | -21.674 | 76.148 | 1.00 | 12.36 |
| 3148 | N | TYR | A | 418 | 40.396 | -20.736 | 77.417 | 1.00 | 12.95 |
| 3149 | CA | TYR | A | 418 | 39.583 | -20.191 | 76.320 | 1.00 | 12.63 |
| 3150 | CB | TYR | A | 418 | 38.124 | -20.142 | 76.728 | 1.00 | 12.47 |
| 3151 | CG | TYR | A | 418 | 37.458 | -21.487 | 76.713 | 1.00 | 13.26 |
| 3152 | CD1 | TYR | A | 418 | 36.733 | -21.929 | 75.611 | 1.00 | 15.19 |
| 3153 | CE1 | TYR | A | 418 | 36.069 | -23.190 | 75.611 | 1.00 | 17.13 |

FIGURE 3 (Cont.)

| A | B | C | D | E | F | G | H | I | J |
|---|---|---|---|---|---|---|---|---|---|
| 3154 | CZ | TYR | A | 418 | 36.133 | -23.999 | 76.725 | 1.00 | 17.69 |
| 3155 | OH | TYR | A | 418 | 35.531 | -25.205 | 76.757 | 1.00 | 19.39 |
| 3156 | CE2 | TYR | A | 418 | 36.849 | -23.584 | 77.833 | 1.00 | 18.53 |
| 3157 | CD2 | TYR | A | 418 | 37.524 | -22.310 | 77.810 | 1.00 | 15.67 |
| 3158 | C | TYR | A | 418 | 39.998 | -18.763 | 75.877 | 1.00 | 13.14 |
| 3159 | O | TYR | A | 418 | 39.722 | -17.785 | 76.581 | 1.00 | 13.74 |
| 3160 | N | PRO | A | 419 | 40.630 | -18.623 | 74.714 | 1.00 | 11.96 |
| 3161 | CA | PRO | A | 419 | 41.053 | -17.295 | 74.278 | 1.00 | 11.31 |
| 3162 | CB | PRO | A | 419 | 41.796 | -17.563 | 72.950 | 1.00 | 11.84 |
| 3163 | CG | PRO | A | 419 | 42.172 | -18.996 | 72.993 | 1.00 | 11.34 |
| 3164 | CD | PRO | A | 419 | 41.025 | -19.666 | 73.743 | 1.00 | 12.19 |
| 3165 | C | PRO | A | 419 | 39.839 | -16.416 | 74.093 | 1.00 | 11.38 |
| 3166 | O | PRO | A | 419 | 39.923 | -15.190 | 74.103 | 1.00 | 10.45 |
| 3167 | N | GLY | A | 420 | 38.695 | -17.079 | 73.962 | 1.00 | 11.76 |
| 3168 | CA | GLY | A | 420 | 37.450 | -16.399 | 73.722 | 1.00 | 11.23 |
| 3169 | C | GLY | A | 420 | 37.033 | -15.379 | 74.720 | 1.00 | 10.49 |
| 3170 | O | GLY | A | 420 | 36.427 | -14.431 | 74.387 | 1.00 | 9.42 |
| 3171 | N | ARG | A | 421 | 37.307 | -15.581 | 75.979 | 1.00 | 11.63 |
| 3172 | CA | ARG | A | 421 | 36.563 | -14.850 | 77.016 | 1.00 | 12.47 |
| 3173 | CB | ARG | A | 421 | 35.726 | -15.801 | 77.888 | 1.00 | 12.85 |
| 3174 | CG | ARG | A | 421 | 36.327 | -17.234 | 78.321 | 1.00 | 10.88 |
| 3175 | CD | ARG | A | 421 | 35.372 | -18.405 | 78.118 | 1.00 | 8.44 |
| 3176 | NE | ARG | A | 421 | 35.375 | -19.300 | 79.269 | 1.00 | 13.45 |
| 3177 | CZ | ARG | A | 421 | 34.774 | -20.505 | 79.354 | 1.00 | 9.83 |
| 3178 | NH1 | ARG | A | 421 | 34.100 | -21.003 | 78.379 | 1.00 | 6.23 |
| 3179 | NH2 | ARG | A | 421 | 34.791 | -21.162 | 80.487 | 1.00 | 13.19 |
| 3180 | C | ARG | A | 421 | 37.417 | -13.972 | 77.862 | 1.00 | 14.12 |
| 3181 | O | ARG | A | 421 | 38.648 | -14.186 | 77.977 | 1.00 | 16.24 |
| 3182 | N | ARG | A | 422 | 36.759 | -13.001 | 78.482 | 1.00 | 14.58 |
| 3183 | CA | ARG | A | 422 | 37.415 | -12.061 | 79.386 | 1.00 | 15.26 |
| 3184 | CB | ARG | A | 422 | 37.430 | -10.683 | 78.727 | 1.00 | 15.54 |
| 3185 | CG | ARG | A | 422 | 37.670 | -10.707 | 77.166 | 1.00 | 18.58 |
| 3186 | CD | ARG | A | 422 | 39.160 | -10.940 | 76.737 | 1.00 | 23.49 |
| 3187 | NE | ARG | A | 422 | 39.347 | -10.982 | 75.276 | 1.00 | 25.95 |
| 3188 | CZ | ARG | A | 422 | 39.227 | -9.919 | 74.494 | 1.00 | 29.72 |
| 3189 | NH1 | ARG | A | 422 | 38.898 | -8.739 | 75.007 | 1.00 | 32.29 |
| 3190 | NH2 | ARG | A | 422 | 39.424 | -10.013 | 73.184 | 1.00 | 30.66 |
| 3191 | C | ARG | A | 422 | 36.787 | -12.067 | 80.816 | 1.00 | 15.03 |
| 3192 | O | ARG | A | 422 | 35.575 | -11.827 | 80.950 | 1.00 | 16.53 |
| 3193 | N | ASN | A | 423 | 37.586 | -12.435 | 81.857 | 1.00 | 13.32 |
| 3194 | CA | ASN | A | 423 | 37.149 | -12.372 | 83.271 | 1.00 | 12.14 |
| 3195 | CB | ASN | A | 423 | 37.278 | -13.690 | 83.969 | 1.00 | 11.18 |
| 3196 | CG | ASN | A | 423 | 36.250 | -14.598 | 83.553 | 1.00 | 8.12 |
| 3197 | OD1 | ASN | A | 423 | 36.486 | -15.371 | 82.634 | 1.00 | 3.58 |
| 3198 | ND2 | ASN | A | 423 | 35.058 | -14.514 | 84.181 | 1.00 | 2.99 |
| 3199 | C | ASN | A | 423 | 38.028 | -11.428 | 83.952 | 1.00 | 12.13 |
| 3200 | O | ASN | A | 423 | 39.069 | -11.117 | 83.414 | 1.00 | 12.45 |
| 3201 | N | ILE | A | 424 | 37.644 | -10.941 | 85.127 | 1.00 | 11.97 |
| 3202 | CA | ILE | A | 424 | 38.527 | -9.998 | 85.814 | 1.00 | 12.40 |
| 3203 | CB | ILE | A | 424 | 37.815 | -8.711 | 86.105 | 1.00 | 12.49 |
| 3204 | CG1 | ILE | A | 424 | 37.081 | -8.241 | 84.842 | 1.00 | 14.67 |

FIGURE 3 (Cont.)

| A | B | C | D | E | F | G | H | I | J |
|---|---|---|---|---|---|---|---|---|---|
| 3205 | CD1 | ILE | A | 424 | 35.628 | -8.335 | 85.010 | 1.00 | 18.34 |
| 3206 | CG2 | ILE | A | 424 | 38.828 | -7.602 | 86.372 | 1.00 | 13.47 |
| 3207 | C | ILE | A | 424 | 39.252 | -10.595 | 87.031 | 1.00 | 12.07 |
| 3208 | O | ILE | A | 424 | 38.771 | -11.433 | 87.699 | 1.00 | 11.87 |
| 3209 | N | TYR | A | 425 | 40.453 | -10.105 | 87.248 | 1.00 | 12.30 |
| 3210 | CA | TYR | A | 425 | 41.388 | -10.666 | 88.164 | 1.00 | 13.17 |
| 3211 | CB | TYR | A | 425 | 42.538 | -11.296 | 87.372 | 1.00 | 13.85 |
| 3212 | CG | TYR | A | 425 | 42.185 | -12.583 | 86.709 | 1.00 | 14.39 |
| 3213 | CD1 | TYR | A | 425 | 42.615 | -13.784 | 87.225 | 1.00 | 16.72 |
| 3214 | CE1 | TYR | A | 425 | 42.318 | -14.963 | 86.614 | 1.00 | 16.50 |
| 3215 | CZ | TYR | A | 425 | 41.591 | -14.937 | 85.484 | 1.00 | 15.92 |
| 3216 | OH | TYR | A | 425 | 41.251 | -16.120 | 84.894 | 1.00 | 17.68 |
| 3217 | CE2 | TYR | A | 425 | 41.143 | -13.747 | 84.967 | 1.00 | 17.86 |
| 3218 | CD2 | TYR | A | 425 | 41.445 | -12.599 | 85.585 | 1.00 | 14.23 |
| 3219 | C | TYR | A | 425 | 41.887 | -9.526 | 89.056 | 1.00 | 12.52 |
| 3220 | O | TYR | A | 425 | 42.182 | -8.422 | 88.572 | 1.00 | 13.05 |
| 3221 | N | ARG | A | 426 | 41.906 | -9.780 | 90.355 | 1.00 | 10.67 |
| 3222 | CA | ARG | A | 426 | 42.381 | -8.801 | 91.299 | 1.00 | 10.34 |
| 3223 | CB | ARG | A | 426 | 41.313 | -8.559 | 92.371 | 1.00 | 10.34 |
| 3224 | CG | ARG | A | 426 | 41.682 | -7.451 | 93.327 | 1.00 | 8.81 |
| 3225 | CD | ARG | A | 426 | 40.864 | -7.413 | 94.607 | 1.00 | 12.89 |
| 3226 | NE | ARG | A | 426 | 41.270 | -6.267 | 95.423 | 1.00 | 14.61 |
| 3227 | CZ | ARG | A | 426 | 40.494 | -5.250 | 95.828 | 1.00 | 11.73 |
| 3228 | NH1 | ARG | A | 426 | 41.046 | -4.277 | 96.542 | 1.00 | 9.68 |
| 3229 | NH2 | ARG | A | 426 | 39.182 | -5.210 | 95.576 | 1.00 | 5.93 |
| 3230 | C | ARG | A | 426 | 43.612 | -9.446 | 91.895 | 1.00 | 10.50 |
| 3231 | O | ARG | A | 426 | 43.503 | -10.552 | 92.329 | 1.00 | 10.20 |
| 3232 | N | ILE | A | 427 | 44.778 | -8.804 | 91.811 | 1.00 | 10.39 |
| 3233 | CA | ILE | A | 427 | 46.000 | -9.264 | 92.461 | 1.00 | 10.85 |
| 3234 | CB | ILE | A | 427 | 47.176 | -9.596 | 91.476 | 1.00 | 10.70 |
| 3235 | CG1 | ILE | A | 427 | 47.624 | -8.411 | 90.602 | 1.00 | 10.79 |
| 3236 | CD1 | ILE | A | 427 | 48.574 | -8.794 | 89.415 | 1.00 | 11.03 |
| 3237 | CG2 | ILE | A | 427 | 46.827 | -10.753 | 90.646 | 1.00 | 11.02 |
| 3238 | C | ILE | A | 427 | 46.473 | -8.230 | 93.465 | 1.00 | 11.73 |
| 3239 | O | ILE | A | 427 | 46.012 | -7.063 | 93.392 | 1.00 | 12.68 |
| 3240 | N | SER | A | 428 | 47.366 | -8.651 | 94.403 | 1.00 | 10.55 |
| 3241 | CA | SER | A | 428 | 48.044 | -7.722 | 95.336 | 1.00 | 11.38 |
| 3242 | CB | SER | A | 428 | 48.412 | -8.412 | 96.600 | 1.00 | 10.03 |
| 3243 | OG | SER | A | 428 | 47.209 | -8.858 | 97.154 | 1.00 | 8.52 |
| 3244 | C | SER | A | 428 | 49.314 | -7.123 | 94.802 | 1.00 | 12.13 |
| 3245 | O | SER | A | 428 | 49.893 | -7.636 | 93.858 | 1.00 | 11.39 |
| 3246 | N | ILE | A | 429 | 49.644 | -5.951 | 95.351 | 1.00 | 13.26 |
| 3247 | CA | ILE | A | 429 | 50.925 | -5.249 | 95.091 | 1.00 | 13.72 |
| 3248 | CB | ILE | A | 429 | 50.846 | -4.073 | 93.985 | 1.00 | 13.63 |
| 3249 | CG1 | ILE | A | 429 | 49.619 | -3.169 | 94.158 | 1.00 | 13.68 |
| 3250 | CD1 | ILE | A | 429 | 49.450 | -1.981 | 93.069 | 1.00 | 12.45 |
| 3251 | CG2 | ILE | A | 429 | 50.817 | -4.659 | 92.561 | 1.00 | 13.30 |
| 3252 | C | ILE | A | 429 | 51.340 | -4.707 | 96.426 | 1.00 | 14.64 |
| 3253 | O | ILE | A | 429 | 50.527 | -4.182 | 97.188 | 1.00 | 15.37 |
| 3254 | N | GLY | A | 430 | 52.615 | -4.882 | 96.739 | 1.00 | 14.86 |
| 3255 | CA | GLY | A | 430 | 53.204 | -4.307 | 97.920 | 1.00 | 14.08 |

FIGURE 3 (Cont.)

| A | B | C | D | E | F | G | H | I | J |
|---|---|---|---|---|---|---|---|---|---|
| 3256 | C | GLY | A | 430 | 53.137 | -5.274 | 99.055 | 1.00 | 13.92 |
| 3257 | O | GLY | A | 430 | 53.650 | -4.956 | 100.131 | 1.00 | 14.46 |
| 3258 | N | SER | A | 431 | 52.534 | -6.449 | 98.853 | 1.00 | 13.30 |
| 3259 | CA | SER | A | 431 | 52.412 | -7.405 | 99.963 | 1.00 | 13.07 |
| 3260 | CB | SER | A | 431 | 50.992 | -7.399 | 100.552 | 1.00 | 13.10 |
| 3261 | OG | SER | A | 431 | 50.036 | -7.671 | 99.567 | 1.00 | 9.41 |
| 3262 | C | SER | A | 431 | 52.826 | -8.829 | 99.623 | 1.00 | 13.14 |
| 3263 | O | SER | A | 431 | 52.551 | -9.350 | 98.550 | 1.00 | 13.22 |
| 3264 | N | TYR | A | 432 | 53.497 | -9.461 | 100.578 | 1.00 | 13.14 |
| 3265 | CA | TYR | A | 432 | 53.845 | -10.846 | 100.445 | 1.00 | 12.96 |
| 3266 | CB | TYR | A | 432 | 55.327 | -11.047 | 100.815 | 1.00 | 11.68 |
| 3267 | CG | TYR | A | 432 | 55.862 | -12.424 | 100.484 | 1.00 | 11.21 |
| 3268 | CD1 | TYR | A | 432 | 56.112 | -12.814 | 99.169 | 1.00 | 10.85 |
| 3269 | CE1 | TYR | A | 432 | 56.606 | -14.166 | 98.909 | 1.00 | 10.91 |
| 3270 | CZ | TYR | A | 432 | 56.830 | -15.073 | 100.010 | 1.00 | 8.09 |
| 3271 | OH | TYR | A | 432 | 57.279 | -16.381 | 99.909 | 1.00 | 11.30 |
| 3272 | CE2 | TYR | A | 432 | 56.587 | -14.688 | 101.301 | 1.00 | 11.16 |
| 3273 | CD2 | TYR | A | 432 | 56.132 | -13.384 | 101.544 | 1.00 | 10.67 |
| 3274 | C | TYR | A | 432 | 52.700 | -11.509 | 101.256 | 1.00 | 13.26 |
| 3275 | O | TYR | A | 432 | 52.058 | -10.905 | 102.343 | 1.00 | 14.26 |
| 3276 | N | PRO | A | 433 | 52.661 | -12.831 | 100.989 | 1.00 | 12.25 |
| 3277 | CA | PRO | A | 433 | 51.856 | -13.538 | 100.026 | 1.00 | 11.56 |
| 3278 | CB | PRO | A | 433 | 50.925 | -14.349 | 100.914 | 1.00 | 12.24 |
| 3279 | CG | PRO | A | 433 | 51.823 | -14.967 | 101.788 | 1.00 | 11.17 |
| 3280 | CD | PRO | A | 433 | 53.043 | -13.877 | 101.986 | 1.00 | 12.39 |
| 3281 | C | PRO | A | 433 | 51.098 | -12.751 | 99.016 | 1.00 | 10.12 |
| 3282 | O | PRO | A | 433 | 50.073 | -12.139 | 99.318 | 1.00 | 9.81 |
| 3283 | N | PRO | A | 434 | 51.578 | -12.810 | 97.783 | 1.00 | 9.19 |
| 3284 | CA | PRO | A | 434 | 50.763 | -12.347 | 96.724 | 1.00 | 8.66 |
| 3285 | CB | PRO | A | 434 | 51.604 | -12.699 | 95.476 | 1.00 | 8.61 |
| 3286 | CG | PRO | A | 434 | 53.043 | -12.485 | 96.014 | 1.00 | 7.54 |
| 3287 | CD | PRO | A | 434 | 52.889 | -13.266 | 97.272 | 1.00 | 8.90 |
| 3288 | C | PRO | A | 434 | 49.388 | -13.001 | 96.814 | 1.00 | 8.42 |
| 3289 | O | PRO | A | 434 | 49.234 | -14.155 | 97.265 | 1.00 | 7.80 |
| 3290 | N | SER | A | 435 | 48.392 | -12.192 | 96.395 | 1.00 | 9.27 |
| 3291 | CA | SER | A | 435 | 47.043 | -12.656 | 96.230 | 1.00 | 9.85 |
| 3292 | CB | SER | A | 435 | 46.108 | -11.716 | 96.957 | 1.00 | 8.64 |
| 3293 | OG | SER | A | 435 | 46.754 | -11.358 | 98.144 | 1.00 | 10.22 |
| 3294 | C | SER | A | 435 | 46.786 | -12.636 | 94.749 | 1.00 | 10.57 |
| 3295 | O | SER | A | 435 | 47.174 | -11.667 | 94.046 | 1.00 | 11.15 |
| 3296 | N | LYS | A | 436 | 46.136 | -13.702 | 94.272 | 1.00 | 11.45 |
| 3297 | CA | LYS | A | 436 | 45.459 | -13.702 | 92.953 | 1.00 | 11.93 |
| 3298 | CB | LYS | A | 436 | 46.168 | -14.647 | 91.980 | 1.00 | 12.33 |
| 3299 | CG | LYS | A | 436 | 46.180 | -14.209 | 90.501 | 1.00 | 14.19 |
| 3300 | CD | LYS | A | 436 | 45.236 | -14.972 | 89.568 | 1.00 | 18.35 |
| 3301 | CE | LYS | A | 436 | 45.939 | -16.108 | 88.762 | 1.00 | 19.33 |
| 3302 | NZ | LYS | A | 436 | 46.703 | -15.592 | 87.606 | 1.00 | 14.52 |
| 3303 | C | LYS | A | 436 | 43.984 | -14.141 | 93.094 | 1.00 | 11.81 |
| 3304 | O | LYS | A | 436 | 43.700 | -15.193 | 93.660 | 1.00 | 10.78 |
| 3305 | N | LYS | A | 437 | 43.045 | -13.372 | 92.564 | 1.00 | 11.26 |
| 3306 | CA | LYS | A | 437 | 41.655 | -13.766 | 92.671 | 1.00 | 11.98 |

FIGURE 3 (Cont.)

| A | B | C | D | E | F | G | H | I | J |
|---|---|---|---|---|---|---|---|---|---|
| 3307 | CB | LYS | A | 437 | 40.924 | -13.013 | 93.793 | 1.00 | 12.12 |
| 3308 | CG | LYS | A | 437 | 39.368 | -12.852 | 93.563 | 1.00 | 12.44 |
| 3309 | CD | LYS | A | 437 | 38.528 | -12.843 | 94.862 | 1.00 | 17.97 |
| 3310 | CE | LYS | A | 437 | 38.234 | -11.416 | 95.421 | 1.00 | 19.63 |
| 3311 | NZ | LYS | A | 437 | 36.745 | -11.049 | 95.534 | 1.00 | 20.23 |
| 3312 | C | LYS | A | 437 | 40.981 | -13.486 | 91.364 | 1.00 | 12.87 |
| 3313 | O | LYS | A | 437 | 41.104 | -12.359 | 90.827 | 1.00 | 14.19 |
| 3314 | N | CYS | A | 438 | 40.250 | -14.478 | 90.840 | 1.00 | 12.63 |
| 3315 | CA | CYS | A | 438 | 39.226 | -14.209 | 89.809 | 1.00 | 11.26 |
| 3316 | CB | CYS | A | 438 | 39.055 | -15.378 | 88.913 | 1.00 | 11.30 |
| 3317 | SG | CYS | A | 438 | 38.621 | -14.783 | 87.318 | 1.00 | 15.83 |
| 3318 | C | CYS | A | 438 | 37.840 | -13.759 | 90.303 | 1.00 | 10.40 |
| 3319 | O | CYS | A | 438 | 36.986 | -14.568 | 90.682 | 1.00 | 9.57 |
| 3320 | N | VAL | A | 439 | 37.609 | -12.450 | 90.217 | 1.00 | 9.63 |
| 3321 | CA | VAL | A | 439 | 36.359 | -11.901 | 90.608 | 1.00 | 9.47 |
| 3322 | CB | VAL | A | 439 | 36.343 | -10.410 | 90.394 | 1.00 | 9.89 |
| 3323 | CG1 | VAL | A | 439 | 34.902 | -9.796 | 90.650 | 1.00 | 9.54 |
| 3324 | CG2 | VAL | A | 439 | 37.431 | -9.756 | 91.289 | 1.00 | 8.80 |
| 3325 | C | VAL | A | 439 | 35.255 | -12.562 | 89.854 | 1.00 | 9.73 |
| 3326 | O | VAL | A | 439 | 34.251 | -12.887 | 90.445 | 1.00 | 9.91 |
| 3327 | N | THR | A | 440 | 35.415 | -12.788 | 88.555 | 1.00 | 9.76 |
| 3328 | CA | THR | A | 440 | 34.247 | -13.142 | 87.758 | 1.00 | 9.38 |
| 3329 | CB | THR | A | 440 | 33.981 | -12.156 | 86.592 | 1.00 | 9.09 |
| 3330 | OG1 | THR | A | 440 | 35.141 | -11.928 | 85.772 | 1.00 | 9.20 |
| 3331 | CG2 | THR | A | 440 | 33.622 | -10.870 | 87.129 | 1.00 | 9.43 |
| 3332 | C | THR | A | 440 | 34.172 | -14.533 | 87.221 | 1.00 | 9.55 |
| 3333 | O | THR | A | 440 | 33.088 | -14.929 | 86.855 | 1.00 | 10.99 |
| 3334 | N | CYS | A | 441 | 35.264 | -15.279 | 87.174 | 1.00 | 9.10 |
| 3335 | CA | CYS | A | 441 | 35.227 | -16.673 | 86.658 | 1.00 | 10.56 |
| 3336 | CB | CYS | A | 441 | 36.536 | -17.407 | 87.004 | 1.00 | 10.46 |
| 3337 | SG | CYS | A | 441 | 38.020 | -16.496 | 86.350 | 1.00 | 19.33 |
| 3338 | C | CYS | A | 441 | 33.962 | -17.504 | 87.060 | 1.00 | 9.80 |
| 3339 | O | CYS | A | 441 | 33.437 | -18.320 | 86.297 | 1.00 | 8.39 |
| 3340 | N | HIS | A | 442 | 33.447 | -17.223 | 88.240 | 1.00 | 10.65 |
| 3341 | CA | HIS | A | 442 | 32.464 | -18.085 | 88.892 | 1.00 | 12.21 |
| 3342 | CB | HIS | A | 442 | 33.155 | -18.893 | 90.037 | 1.00 | 12.54 |
| 3343 | CG | HIS | A | 442 | 33.673 | -20.230 | 89.596 | 1.00 | 14.98 |
| 3344 | ND1 | HIS | A | 442 | 35.022 | -20.502 | 89.471 | 1.00 | 17.74 |
| 3345 | CE1 | HIS | A | 442 | 35.180 | -21.742 | 89.045 | 1.00 | 17.77 |
| 3346 | NE2 | HIS | A | 442 | 33.981 | -22.282 | 88.883 | 1.00 | 19.42 |
| 3347 | CD2 | HIS | A | 442 | 33.020 | -21.357 | 89.221 | 1.00 | 16.71 |
| 3348 | C | HIS | A | 442 | 31.261 | -17.312 | 89.392 | 1.00 | 11.64 |
| 3349 | O | HIS | A | 442 | 30.324 | -17.882 | 89.967 | 1.00 | 10.87 |
| 3350 | N | LEU | A | 443 | 31.274 | -16.028 | 89.087 | 1.00 | 11.53 |
| 3351 | CA | LEU | A | 443 | 30.222 | -15.127 | 89.456 | 1.00 | 11.44 |
| 3352 | CB | LEU | A | 443 | 30.554 | -13.767 | 88.921 | 1.00 | 10.32 |
| 3353 | CG | LEU | A | 443 | 29.635 | -12.726 | 89.506 | 1.00 | 11.14 |
| 3354 | CD1 | LEU | A | 443 | 29.772 | -12.720 | 91.024 | 1.00 | 11.35 |
| 3355 | CD2 | LEU | A | 443 | 29.970 | -11.362 | 88.875 | 1.00 | 10.44 |
| 3356 | C | LEU | A | 443 | 28.879 | -15.628 | 88.930 | 1.00 | 12.11 |
| 3357 | O | LEU | A | 443 | 27.943 | -15.800 | 89.725 | 1.00 | 11.92 |

FIGURE 3 (Cont.)

| A | B | C | D | E | F | G | H | I | J |
|---|---|---|---|---|---|---|---|---|---|
| 3358 | N | ARG | A | 444 | 28.811 | -15.805 | 87.588 | 1.00 | 13.07 |
| 3359 | CA | ARG | A | 444 | 27.763 | -16.553 | 86.865 | 1.00 | 13.65 |
| 3360 | CB | ARG | A | 444 | 26.656 | -15.654 | 86.309 | 1.00 | 13.41 |
| 3361 | CG | ARG | A | 444 | 25.568 | -15.128 | 87.257 | 1.00 | 13.69 |
| 3362 | CD | ARG | A | 444 | 25.072 | -13.722 | 86.821 | 1.00 | 13.53 |
| 3363 | NE | ARG | A | 444 | 25.226 | -12.660 | 87.824 | 1.00 | 14.33 |
| 3364 | CZ | ARG | A | 444 | 24.226 | -12.143 | 88.534 | 1.00 | 14.40 |
| 3365 | NH1 | ARG | A | 444 | 22.945 | -12.555 | 88.383 | 1.00 | 16.56 |
| 3366 | NH2 | ARG | A | 444 | 24.504 | -11.221 | 89.430 | 1.00 | 11.57 |
| 3367 | C | ARG | A | 444 | 28.431 | -17.376 | 85.706 | 1.00 | 14.32 |
| 3368 | O | ARG | A | 444 | 28.512 | -16.935 | 84.532 | 1.00 | 13.60 |
| 3369 | N | LYS | A | 445 | 28.875 | -18.593 | 86.061 | 1.00 | 14.58 |
| 3370 | CA | LYS | A | 445 | 29.894 | -19.325 | 85.302 | 1.00 | 15.87 |
| 3371 | CB | LYS | A | 445 | 30.344 | -20.647 | 86.016 | 1.00 | 16.52 |
| 3372 | CG | LYS | A | 445 | 30.507 | -22.010 | 85.151 | 1.00 | 18.35 |
| 3373 | CD | LYS | A | 445 | 31.863 | -22.782 | 85.419 | 1.00 | 19.22 |
| 3374 | CE | LYS | A | 445 | 32.743 | -22.926 | 84.144 | 1.00 | 21.19 |
| 3375 | NZ | LYS | A | 445 | 32.964 | -24.364 | 83.840 | 1.00 | 24.76 |
| 3376 | C | LYS | A | 445 | 29.401 | -19.572 | 83.926 | 1.00 | 15.80 |
| 3377 | O | LYS | A | 445 | 30.173 | -19.482 | 82.991 | 1.00 | 16.74 |
| 3378 | N | GLU | A | 446 | 28.105 | -19.814 | 83.796 | 1.00 | 15.95 |
| 3379 | CA | GLU | A | 446 | 27.526 | -20.323 | 82.565 | 1.00 | 15.98 |
| 3380 | CB | GLU | A | 446 | 26.444 | -21.323 | 82.932 | 1.00 | 16.25 |
| 3381 | CG | GLU | A | 446 | 25.300 | -21.385 | 81.951 | 1.00 | 19.85 |
| 3382 | CD | GLU | A | 446 | 24.785 | -22.802 | 81.719 | 1.00 | 22.86 |
| 3383 | OE1 | GLU | A | 446 | 24.420 | -23.156 | 80.560 | 1.00 | 20.81 |
| 3384 | OE2 | GLU | A | 446 | 24.766 | -23.569 | 82.694 | 1.00 | 24.63 |
| 3385 | C | GLU | A | 446 | 27.032 | -19.177 | 81.674 | 1.00 | 15.58 |
| 3386 | O | GLU | A | 446 | 27.148 | -19.230 | 80.429 | 1.00 | 15.49 |
| 3387 | N | ARG | A | 447 | 26.544 | -18.113 | 82.316 | 1.00 | 14.86 |
| 3388 | CA | ARG | A | 447 | 25.978 | -16.939 | 81.610 | 1.00 | 13.84 |
| 3389 | CB | ARG | A | 447 | 24.948 | -16.326 | 82.536 | 1.00 | 13.45 |
| 3390 | CG | ARG | A | 447 | 24.023 | -15.341 | 81.887 | 1.00 | 14.18 |
| 3391 | CD | ARG | A | 447 | 23.128 | -14.705 | 82.880 | 1.00 | 15.23 |
| 3392 | NE | ARG | A | 447 | 22.554 | -13.474 | 82.403 | 1.00 | 16.96 |
| 3393 | CZ | ARG | A | 447 | 21.648 | -12.743 | 83.060 | 1.00 | 15.50 |
| 3394 | NH1 | ARG | A | 447 | 21.195 | -11.610 | 82.527 | 1.00 | 13.66 |
| 3395 | NH2 | ARG | A | 447 | 21.203 | -13.125 | 84.223 | 1.00 | 14.18 |
| 3396 | C | ARG | A | 447 | 26.991 | -15.834 | 81.231 | 1.00 | 13.36 |
| 3397 | O | ARG | A | 447 | 26.986 | -15.251 | 80.142 | 1.00 | 13.22 |
| 3398 | N | CYS | A | 448 | 27.824 | -15.503 | 82.195 | 1.00 | 13.40 |
| 3399 | CA | CYS | A | 448 | 28.856 | -14.508 | 82.019 | 1.00 | 12.72 |
| 3400 | CB | CYS | A | 448 | 28.648 | -13.455 | 83.051 | 1.00 | 12.44 |
| 3401 | SG | CYS | A | 448 | 26.998 | -12.854 | 82.768 | 1.00 | 13.33 |
| 3402 | C | CYS | A | 448 | 30.278 | -15.051 | 82.027 | 1.00 | 12.50 |
| 3403 | O | CYS | A | 448 | 30.802 | -15.506 | 83.048 | 1.00 | 13.96 |
| 3404 | N | GLN | A | 449 | 30.871 | -15.054 | 80.834 | 1.00 | 12.49 |
| 3405 | CA | GLN | A | 449 | 32.271 | -15.252 | 80.671 | 1.00 | 11.22 |
| 3406 | CB | GLN | A | 449 | 32.522 | -16.577 | 79.949 | 1.00 | 10.73 |
| 3407 | CG | GLN | A | 449 | 32.470 | -17.799 | 80.788 | 1.00 | 8.21 |
| 3408 | CD | GLN | A | 449 | 33.354 | -17.782 | 82.006 | 1.00 | 8.58 |

FIGURE 3 (Cont.)

| A | B | C | D | E | F | G | H | I | J |
|---|---|---|---|---|---|---|---|---|---|
| 3409 | OE1 | GLN | A | 449 | 32.876 | -18.043 | 83.073 | 1.00 | 11.80 |
| 3410 | NE2 | GLN | A | 449 | 34.636 | -17.517 | 81.852 | 1.00 | 8.87 |
| 3411 | C | GLN | A | 449 | 32.851 | -14.115 | 79.845 | 1.00 | 11.83 |
| 3412 | O | GLN | A | 449 | 33.976 | -14.283 | 79.370 | 1.00 | 12.83 |
| 3413 | N | TYR | A | 450 | 32.162 | -12.982 | 79.635 | 1.00 | 11.02 |
| 3414 | CA | TYR | A | 450 | 32.821 | -11.891 | 78.881 | 1.00 | 11.47 |
| 3415 | CB | TYR | A | 450 | 32.435 | -11.901 | 77.389 | 1.00 | 11.93 |
| 3416 | CG | TYR | A | 450 | 33.387 | -11.116 | 76.477 | 1.00 | 13.91 |
| 3417 | CD1 | TYR | A | 450 | 34.233 | -11.745 | 75.592 | 1.00 | 14.49 |
| 3418 | CE1 | TYR | A | 450 | 35.076 | -11.019 | 74.810 | 1.00 | 14.78 |
| 3419 | CZ | TYR | A | 450 | 35.087 | -9.664 | 74.898 | 1.00 | 13.72 |
| 3420 | OH | TYR | A | 450 | 35.876 | -8.924 | 74.120 | 1.00 | 16.82 |
| 3421 | CE2 | TYR | A | 450 | 34.286 | -9.034 | 75.730 | 1.00 | 14.98 |
| 3422 | CD2 | TYR | A | 450 | 33.459 | -9.748 | 76.540 | 1.00 | 16.44 |
| 3423 | C | TYR | A | 450 | 32.516 | -10.510 | 79.508 | 1.00 | 11.82 |
| 3424 | O | TYR | A | 450 | 31.422 | -9.907 | 79.391 | 1.00 | 11.96 |
| 3425 | N | TYR | A | 451 | 33.512 | -10.008 | 80.193 | 1.00 | 11.06 |
| 3426 | CA | TYR | A | 451 | 33.270 | -8.927 | 81.093 | 1.00 | 10.71 |
| 3427 | CB | TYR | A | 451 | 33.633 | -9.359 | 82.496 | 1.00 | 9.84 |
| 3428 | CG | TYR | A | 451 | 32.630 | -10.122 | 83.196 | 1.00 | 8.93 |
| 3429 | CD1 | TYR | A | 451 | 31.640 | -9.502 | 83.929 | 1.00 | 9.60 |
| 3430 | CE1 | TYR | A | 451 | 30.682 | -10.270 | 84.651 | 1.00 | 14.38 |
| 3431 | CZ | TYR | A | 451 | 30.784 | -11.649 | 84.632 | 1.00 | 16.38 |
| 3432 | OH | TYR | A | 451 | 29.941 | -12.490 | 85.347 | 1.00 | 14.32 |
| 3433 | CE2 | TYR | A | 451 | 31.778 | -12.240 | 83.888 | 1.00 | 14.98 |
| 3434 | CD2 | TYR | A | 451 | 32.682 | -11.487 | 83.185 | 1.00 | 10.85 |
| 3435 | C | TYR | A | 451 | 34.217 | -7.857 | 80.813 | 1.00 | 11.04 |
| 3436 | O | TYR | A | 451 | 35.349 | -8.185 | 80.522 | 1.00 | 10.33 |
| 3437 | N | THR | A | 452 | 33.760 | -6.623 | 81.023 | 1.00 | 11.90 |
| 3438 | CA | THR | A | 452 | 34.628 | -5.459 | 81.223 | 1.00 | 13.92 |
| 3439 | CB | THR | A | 452 | 34.443 | -4.397 | 80.074 | 1.00 | 14.49 |
| 3440 | OG1 | THR | A | 452 | 35.401 | -3.346 | 80.259 | 1.00 | 16.37 |
| 3441 | CG2 | THR | A | 452 | 33.009 | -3.637 | 80.096 | 1.00 | 11.89 |
| 3442 | C | THR | A | 452 | 34.383 | -4.799 | 82.589 | 1.00 | 14.84 |
| 3443 | O | THR | A | 452 | 33.625 | -5.334 | 83.367 | 1.00 | 14.95 |
| 3444 | N | ALA | A | 453 | 35.037 | -3.662 | 82.904 | 1.00 | 15.55 |
| 3445 | CA | ALA | A | 453 | 34.757 | -2.977 | 84.181 | 1.00 | 16.62 |
| 3446 | CB | ALA | A | 453 | 35.670 | -3.459 | 85.241 | 1.00 | 16.15 |
| 3447 | C | ALA | A | 453 | 34.881 | -1.456 | 84.109 | 1.00 | 17.84 |
| 3448 | O | ALA | A | 453 | 35.664 | -0.912 | 83.278 | 1.00 | 18.26 |
| 3449 | N | SER | A | 454 | 34.149 | -0.791 | 85.029 | 1.00 | 17.70 |
| 3450 | CA | SER | A | 454 | 34.198 | 0.628 | 85.188 | 1.00 | 17.33 |
| 3451 | CB | SER | A | 454 | 32.872 | 1.254 | 84.791 | 1.00 | 17.78 |
| 3452 | OG | SER | A | 454 | 32.975 | 2.681 | 84.847 | 1.00 | 19.62 |
| 3453 | C | SER | A | 454 | 34.446 | 0.930 | 86.619 | 1.00 | 17.52 |
| 3454 | O | SER | A | 454 | 33.557 | 0.765 | 87.430 | 1.00 | 18.34 |
| 3455 | N | PHE | A | 455 | 35.637 | 1.432 | 86.919 | 1.00 | 17.09 |
| 3456 | CA | PHE | A | 455 | 36.009 | 1.817 | 88.275 | 1.00 | 17.10 |
| 3457 | CB | PHE | A | 455 | 37.516 | 1.580 | 88.542 | 1.00 | 17.22 |
| 3458 | CG | PHE | A | 455 | 37.860 | 0.171 | 88.582 | 1.00 | 16.23 |
| 3459 | CD1 | PHE | A | 455 | 37.824 | -0.587 | 87.407 | 1.00 | 14.30 |

FIGURE 3 (Cont.)

| A | B | C | D | E | F | G | H | I | J |
|---|---|---|---|---|---|---|---|---|---|
| 3460 | CE1 | PHE | A | 455 | 38.084 | -1.950 | 87.422 | 1.00 | 13.93 |
| 3461 | CZ | PHE | A | 455 | 38.375 | -2.569 | 88.620 | 1.00 | 16.10 |
| 3462 | CE2 | PHE | A | 455 | 38.388 | -1.831 | 89.803 | 1.00 | 17.00 |
| 3463 | CD2 | PHE | A | 455 | 38.118 | -0.440 | 89.771 | 1.00 | 14.22 |
| 3464 | C | PHE | A | 455 | 35.743 | 3.248 | 88.608 | 1.00 | 16.83 |
| 3465 | O | PHE | A | 455 | 36.235 | 4.162 | 87.966 | 1.00 | 15.02 |
| 3466 | N | SER | A | 456 | 34.993 | 3.424 | 89.678 | 1.00 | 17.08 |
| 3467 | CA | SER | A | 456 | 34.995 | 4.693 | 90.395 | 1.00 | 18.13 |
| 3468 | CB | SER | A | 456 | 34.209 | 4.549 | 91.677 | 1.00 | 18.75 |
| 3469 | OG | SER | A | 456 | 34.143 | 5.784 | 92.355 | 1.00 | 21.01 |
| 3470 | C | SER | A | 456 | 36.401 | 5.199 | 90.780 | 1.00 | 18.57 |
| 3471 | O | SER | A | 456 | 37.367 | 4.414 | 90.887 | 1.00 | 19.20 |
| 3472 | N | ASP | A | 457 | 36.459 | 6.521 | 91.018 | 1.00 | 18.71 |
| 3473 | CA | ASP | A | 457 | 37.584 | 7.203 | 91.615 | 1.00 | 18.17 |
| 3474 | CB | ASP | A | 457 | 37.247 | 8.657 | 92.013 | 1.00 | 18.08 |
| 3475 | CG | ASP | A | 457 | 37.033 | 9.548 | 90.837 | 1.00 | 17.42 |
| 3476 | OD1 | ASP | A | 457 | 37.163 | 10.760 | 90.966 | 1.00 | 18.94 |
| 3477 | OD2 | ASP | A | 457 | 36.734 | 9.124 | 89.733 | 1.00 | 18.51 |
| 3478 | C | ASP | A | 457 | 38.020 | 6.494 | 92.860 | 1.00 | 18.13 |
| 3479 | O | ASP | A | 457 | 37.208 | 6.157 | 93.743 | 1.00 | 17.23 |
| 3480 | N | TYR | A | 458 | 39.339 | 6.305 | 92.911 | 1.00 | 18.68 |
| 3481 | CA | TYR | A | 458 | 40.005 | 5.834 | 94.077 | 1.00 | 19.02 |
| 3482 | CB | TYR | A | 458 | 39.504 | 6.640 | 95.326 | 1.00 | 19.36 |
| 3483 | CG | TYR | A | 458 | 39.984 | 8.111 | 95.379 | 1.00 | 21.40 |
| 3484 | CD1 | TYR | A | 458 | 41.323 | 8.397 | 95.563 | 1.00 | 22.37 |
| 3485 | CE1 | TYR | A | 458 | 41.796 | 9.674 | 95.610 | 1.00 | 25.56 |
| 3486 | CZ | TYR | A | 458 | 40.955 | 10.732 | 95.464 | 1.00 | 26.81 |
| 3487 | OH | TYR | A | 458 | 41.547 | 11.971 | 95.564 | 1.00 | 29.63 |
| 3488 | CE2 | TYR | A | 458 | 39.593 | 10.514 | 95.266 | 1.00 | 25.24 |
| 3489 | CD2 | TYR | A | 458 | 39.112 | 9.195 | 95.242 | 1.00 | 23.83 |
| 3490 | C | TYR | A | 458 | 39.731 | 4.323 | 94.121 | 1.00 | 18.96 |
| 3491 | O | TYR | A | 458 | 40.080 | 3.641 | 95.107 | 1.00 | 18.40 |
| 3492 | N | ALA | A | 459 | 39.134 | 3.807 | 93.029 | 1.00 | 18.90 |
| 3493 | CA | ALA | A | 459 | 38.612 | 2.415 | 92.950 | 1.00 | 18.62 |
| 3494 | CB | ALA | A | 459 | 39.776 | 1.418 | 92.900 | 1.00 | 19.08 |
| 3495 | C | ALA | A | 459 | 37.693 | 2.023 | 94.087 | 1.00 | 18.16 |
| 3496 | O | ALA | A | 459 | 37.733 | 0.885 | 94.564 | 1.00 | 17.68 |
| 3497 | N | LYS | A | 460 | 36.896 | 2.965 | 94.562 | 1.00 | 17.55 |
| 3498 | CA | LYS | A | 460 | 36.160 | 2.691 | 95.778 | 1.00 | 17.51 |
| 3499 | CB | LYS | A | 460 | 35.710 | 3.981 | 96.480 | 1.00 | 17.28 |
| 3500 | CG | LYS | A | 460 | 36.260 | 4.125 | 97.943 | 1.00 | 20.33 |
| 3501 | CD | LYS | A | 460 | 36.534 | 5.618 | 98.372 | 1.00 | 23.22 |
| 3502 | CE | LYS | A | 460 | 35.250 | 6.451 | 98.556 | 1.00 | 22.99 |
| 3503 | NZ | LYS | A | 460 | 34.511 | 6.034 | 99.790 | 1.00 | 22.93 |
| 3504 | C | LYS | A | 460 | 35.012 | 1.724 | 95.448 | 1.00 | 16.83 |
| 3505 | O | LYS | A | 460 | 34.571 | 0.989 | 96.307 | 1.00 | 15.95 |
| 3506 | N | TYR | A | 461 | 34.591 | 1.689 | 94.185 | 1.00 | 16.12 |
| 3507 | CA | TYR | A | 461 | 33.478 | 0.847 | 93.744 | 1.00 | 14.92 |
| 3508 | CB | TYR | A | 461 | 32.105 | 1.551 | 93.916 | 1.00 | 14.60 |
| 3509 | CG | TYR | A | 461 | 31.661 | 1.689 | 95.340 | 1.00 | 11.53 |
| 3510 | CD1 | TYR | A | 461 | 31.011 | 0.655 | 95.980 | 1.00 | 10.27 |

FIGURE 3 (Cont.)

| A | B | C | D | E | F | G | H | I | J |
|---|---|---|---|---|---|---|---|---|---|
| 3511 | CE1 | TYR | A | 461 | 30.636 | 0.749 | 97.307 | 1.00 | 9.63 |
| 3512 | CZ | TYR | A | 461 | 30.885 | 1.895 | 97.993 | 1.00 | 9.31 |
| 3513 | OH | TYR | A | 461 | 30.532 | 1.978 | 99.305 | 1.00 | 10.92 |
| 3514 | CE2 | TYR | A | 461 | 31.551 | 2.938 | 97.380 | 1.00 | 9.17 |
| 3515 | CD2 | TYR | A | 461 | 31.938 | 2.825 | 96.054 | 1.00 | 9.42 |
| 3516 | C | TYR | A | 461 | 33.679 | 0.587 | 92.283 | 1.00 | 15.44 |
| 3517 | O | TYR | A | 461 | 34.052 | 1.484 | 91.545 | 1.00 | 16.61 |
| 3518 | N | TYR | A | 462 | 33.401 | -0.622 | 91.815 | 1.00 | 15.32 |
| 3519 | CA | TYR | A | 462 | 33.430 | -0.841 | 90.371 | 1.00 | 14.30 |
| 3520 | CB | TYR | A | 462 | 34.752 | -1.516 | 89.960 | 1.00 | 13.82 |
| 3521 | CG | TYR | A | 462 | 34.897 | -2.895 | 90.489 | 1.00 | 12.24 |
| 3522 | CD1 | TYR | A | 462 | 34.290 | -3.934 | 89.840 | 1.00 | 11.05 |
| 3523 | CE1 | TYR | A | 462 | 34.386 | -5.259 | 90.311 | 1.00 | 13.08 |
| 3524 | CZ | TYR | A | 462 | 35.116 | -5.538 | 91.449 | 1.00 | 9.79 |
| 3525 | OH | TYR | A | 462 | 35.167 | -6.885 | 91.878 | 1.00 | 9.89 |
| 3526 | CE2 | TYR | A | 462 | 35.747 | -4.462 | 92.141 | 1.00 | 11.11 |
| 3527 | CD2 | TYR | A | 462 | 35.611 | -3.160 | 91.661 | 1.00 | 11.74 |
| 3528 | C | TYR | A | 462 | 32.208 | -1.613 | 89.829 | 1.00 | 14.59 |
| 3529 | O | TYR | A | 462 | 31.678 | -2.522 | 90.473 | 1.00 | 13.21 |
| 3530 | N | ALA | A | 463 | 31.803 | -1.215 | 88.614 | 1.00 | 15.48 |
| 3531 | CA | ALA | A | 463 | 30.721 | -1.844 | 87.883 | 1.00 | 16.23 |
| 3532 | CB | ALA | A | 463 | 30.005 | -0.811 | 87.074 | 1.00 | 15.36 |
| 3533 | C | ALA | A | 463 | 31.270 | -2.968 | 86.981 | 1.00 | 17.36 |
| 3534 | O | ALA | A | 463 | 32.475 | -2.986 | 86.629 | 1.00 | 18.34 |
| 3535 | N | LEU | A | 464 | 30.396 | -3.884 | 86.583 | 1.00 | 17.11 |
| 3536 | CA | LEU | A | 464 | 30.852 | -5.099 | 85.914 | 1.00 | 16.79 |
| 3537 | CB | LEU | A | 464 | 30.936 | -6.240 | 86.938 | 1.00 | 16.32 |
| 3538 | CG | LEU | A | 464 | 32.085 | -7.226 | 86.924 | 1.00 | 14.93 |
| 3539 | CD1 | LEU | A | 464 | 31.898 | -8.123 | 88.070 | 1.00 | 14.75 |
| 3540 | CD2 | LEU | A | 464 | 33.453 | -6.600 | 87.002 | 1.00 | 14.81 |
| 3541 | C | LEU | A | 464 | 29.874 | -5.421 | 84.783 | 1.00 | 16.29 |
| 3542 | O | LEU | A | 464 | 28.730 | -5.776 | 85.036 | 1.00 | 17.65 |
| 3543 | N | VAL | A | 465 | 30.309 | -5.248 | 83.541 | 1.00 | 16.12 |
| 3544 | CA | VAL | A | 465 | 29.449 | -5.486 | 82.413 | 1.00 | 14.84 |
| 3545 | CB | VAL | A | 465 | 29.333 | -4.270 | 81.419 | 1.00 | 15.32 |
| 3546 | CG1 | VAL | A | 465 | 27.977 | -4.312 | 80.712 | 1.00 | 13.36 |
| 3547 | CG2 | VAL | A | 465 | 29.429 | -2.990 | 82.143 | 1.00 | 13.04 |
| 3548 | C | VAL | A | 465 | 29.917 | -6.762 | 81.768 | 1.00 | 14.79 |
| 3549 | O | VAL | A | 465 | 31.087 | -6.909 | 81.342 | 1.00 | 13.35 |
| 3550 | N | CYS | A | 466 | 28.971 | -7.704 | 81.811 | 1.00 | 15.42 |
| 3551 | CA | CYS | A | 466 | 29.088 | -9.054 | 81.227 | 1.00 | 15.80 |
| 3552 | CB | CYS | A | 466 | 28.481 | -10.133 | 82.150 | 1.00 | 15.76 |
| 3553 | SG | CYS | A | 466 | 27.607 | -11.501 | 81.332 | 1.00 | 17.27 |
| 3554 | C | CYS | A | 466 | 28.293 | -8.950 | 79.949 | 1.00 | 16.11 |
| 3555 | O | CYS | A | 466 | 27.129 | -8.426 | 79.969 | 1.00 | 16.58 |
| 3556 | N | TYR | A | 467 | 28.920 | -9.416 | 78.857 | 1.00 | 15.07 |
| 3557 | CA | TYR | A | 467 | 28.442 | -9.162 | 77.501 | 1.00 | 13.93 |
| 3558 | CB | TYR | A | 467 | 29.551 | -8.576 | 76.679 | 1.00 | 13.13 |
| 3559 | CG | TYR | A | 467 | 29.672 | -7.090 | 76.763 | 1.00 | 13.61 |
| 3560 | CD1 | TYR | A | 467 | 28.684 | -6.302 | 76.294 | 1.00 | 15.60 |
| 3561 | CE1 | TYR | A | 467 | 28.774 | -4.961 | 76.328 | 1.00 | 15.92 |

FIGURE 3 (Cont.)

| A | B | C | D | E | F | G | H | I | J |
|---|---|---|---|---|---|---|---|---|---|
| 3562 | CZ | TYR | A | 467 | 29.879 | -4.342 | 76.838 | 1.00 | 15.16 |
| 3563 | OH | TYR | A | 467 | 29.854 | -2.969 | 76.806 | 1.00 | 19.10 |
| 3564 | CE2 | TYR | A | 467 | 30.920 | -5.062 | 77.311 | 1.00 | 10.22 |
| 3565 | CD2 | TYR | A | 467 | 30.810 | -6.463 | 77.285 | 1.00 | 12.65 |
| 3566 | C | TYR | A | 467 | 27.943 | -10.416 | 76.835 | 1.00 | 13.08 |
| 3567 | O | TYR | A | 467 | 27.251 | -10.277 | 75.832 | 1.00 | 13.81 |
| 3568 | N | GLY | A | 468 | 28.302 | -11.596 | 77.370 | 1.00 | 11.59 |
| 3569 | CA | GLY | A | 468 | 27.803 | -12.914 | 76.938 | 1.00 | 10.36 |
| 3570 | C | GLY | A | 468 | 28.378 | -14.086 | 77.702 | 1.00 | 9.84 |
| 3571 | O | GLY | A | 468 | 29.142 | -13.870 | 78.594 | 1.00 | 10.34 |
| 3572 | N | PRO | A | 469 | 28.115 | -15.337 | 77.357 | 1.00 | 9.58 |
| 3573 | CA | PRO | A | 469 | 27.376 | -15.778 | 76.174 | 1.00 | 9.22 |
| 3574 | CB | PRO | A | 469 | 27.903 | -17.209 | 75.931 | 1.00 | 9.10 |
| 3575 | CG | PRO | A | 469 | 28.706 | -17.596 | 77.143 | 1.00 | 8.53 |
| 3576 | CD | PRO | A | 469 | 28.628 | -16.495 | 78.112 | 1.00 | 8.97 |
| 3577 | C | PRO | A | 469 | 25.887 | -15.804 | 76.331 | 1.00 | 8.82 |
| 3578 | O | PRO | A | 469 | 25.229 | -15.605 | 75.334 | 1.00 | 9.39 |
| 3579 | N | GLY | A | 470 | 25.364 | -16.059 | 77.516 | 1.00 | 9.04 |
| 3580 | CA | GLY | A | 470 | 23.953 | -15.721 | 77.800 | 1.00 | 8.61 |
| 3581 | C | GLY | A | 470 | 23.675 | -14.221 | 77.693 | 1.00 | 7.97 |
| 3582 | O | GLY | A | 470 | 24.582 | -13.466 | 77.450 | 1.00 | 7.08 |
| 3583 | N | ILE | A | 471 | 22.421 | -13.812 | 77.859 | 1.00 | 7.64 |
| 3584 | CA | ILE | A | 471 | 22.049 | -12.397 | 77.985 | 1.00 | 7.12 |
| 3585 | CB | ILE | A | 471 | 20.701 | -12.330 | 78.632 | 1.00 | 6.11 |
| 3586 | CG1 | ILE | A | 471 | 19.598 | -12.613 | 77.632 | 1.00 | 6.22 |
| 3587 | CD1 | ILE | A | 471 | 18.795 | -13.957 | 77.839 | 1.00 | 8.05 |
| 3588 | CG2 | ILE | A | 471 | 20.518 | -11.008 | 79.204 | 1.00 | 6.70 |
| 3589 | C | ILE | A | 471 | 23.013 | -11.601 | 78.888 | 1.00 | 7.61 |
| 3590 | O | ILE | A | 471 | 23.303 | -12.068 | 79.964 | 1.00 | 9.03 |
| 3591 | N | PRO | A | 472 | 23.521 | -10.440 | 78.471 | 1.00 | 8.44 |
| 3592 | CA | PRO | A | 472 | 24.197 | -9.498 | 79.363 | 1.00 | 8.51 |
| 3593 | CB | PRO | A | 472 | 24.482 | -8.296 | 78.469 | 1.00 | 7.94 |
| 3594 | CG | PRO | A | 472 | 24.609 | -8.830 | 77.181 | 1.00 | 8.29 |
| 3595 | CD | PRO | A | 472 | 23.610 | -9.969 | 77.075 | 1.00 | 9.21 |
| 3596 | C | PRO | A | 472 | 23.365 | -8.966 | 80.506 | 1.00 | 9.89 |
| 3597 | O | PRO | A | 472 | 22.136 | -8.932 | 80.498 | 1.00 | 10.20 |
| 3598 | N | ILE | A | 473 | 24.128 | -8.438 | 81.461 | 1.00 | 10.61 |
| 3599 | CA | ILE | A | 473 | 23.703 | -8.115 | 82.801 | 1.00 | 9.90 |
| 3600 | CB | ILE | A | 473 | 23.562 | -9.370 | 83.737 | 1.00 | 10.14 |
| 3601 | CG1 | ILE | A | 473 | 23.766 | -8.978 | 85.211 | 1.00 | 9.80 |
| 3602 | CD1 | ILE | A | 473 | 22.672 | -9.403 | 86.125 | 1.00 | 11.24 |
| 3603 | CG2 | ILE | A | 473 | 24.598 | -10.491 | 83.423 | 1.00 | 8.91 |
| 3604 | C | ILE | A | 473 | 24.867 | -7.337 | 83.237 | 1.00 | 9.78 |
| 3605 | O | ILE | A | 473 | 25.993 | -7.691 | 82.933 | 1.00 | 9.96 |
| 3606 | N | SER | A | 474 | 24.589 | -6.298 | 83.983 | 1.00 | 10.64 |
| 3607 | CA | SER | A | 474 | 25.588 | -5.410 | 84.506 | 1.00 | 12.01 |
| 3608 | CB | SER | A | 474 | 25.479 | -4.086 | 83.770 | 1.00 | 11.73 |
| 3609 | OG | SER | A | 474 | 24.497 | -4.132 | 82.702 | 1.00 | 15.57 |
| 3610 | C | SER | A | 474 | 25.316 | -5.275 | 86.021 | 1.00 | 13.05 |
| 3611 | O | SER | A | 474 | 24.126 | -5.342 | 86.497 | 1.00 | 13.14 |
| 3612 | N | THR | A | 475 | 26.409 | -5.111 | 86.778 | 1.00 | 13.21 |

FIGURE 3 (Cont.)

| A | B | C | D | E | F | G | H | I | J |
|---|---|---|---|---|---|---|---|---|---|
| 3613 | CA | THR | A | 475 | 26.403 | -5.281 | 88.231 | 1.00 | 13.45 |
| 3614 | CB | THR | A | 475 | 26.849 | -6.717 | 88.611 | 1.00 | 13.25 |
| 3615 | OG1 | THR | A | 475 | 28.035 | -7.056 | 87.888 | 1.00 | 16.72 |
| 3616 | CG2 | THR | A | 475 | 25.839 | -7.748 | 88.127 | 1.00 | 12.51 |
| 3617 | C | THR | A | 475 | 27.323 | -4.257 | 88.905 | 1.00 | 13.81 |
| 3618 | O | THR | A | 475 | 28.105 | -3.547 | 88.240 | 1.00 | 15.25 |
| 3619 | N | LEU | A | 476 | 27.185 | -4.172 | 90.229 | 1.00 | 12.93 |
| 3620 | CA | LEU | A | 476 | 27.904 | -3.183 | 91.043 | 1.00 | 10.97 |
| 3621 | CB | LEU | A | 476 | 26.972 | -2.097 | 91.551 | 1.00 | 9.94 |
| 3622 | CG | LEU | A | 476 | 27.795 | -0.959 | 92.114 | 1.00 | 7.39 |
| 3623 | CD1 | LEU | A | 476 | 28.804 | -0.415 | 91.050 | 1.00 | 4.37 |
| 3624 | CD2 | LEU | A | 476 | 26.868 | 0.087 | 92.647 | 1.00 | 2.00 |
| 3625 | C | LEU | A | 476 | 28.597 | -3.871 | 92.192 | 1.00 | 9.67 |
| 3626 | O | LEU | A | 476 | 28.029 | -4.769 | 92.768 | 1.00 | 9.52 |
| 3627 | N | HIS | A | 477 | 29.841 | -3.485 | 92.455 | 1.00 | 9.11 |
| 3628 | CA | HIS | A | 477 | 30.726 | -4.234 | 93.369 | 1.00 | 9.59 |
| 3629 | CB | HIS | A | 477 | 31.748 | -5.090 | 92.582 | 1.00 | 8.92 |
| 3630 | CG | HIS | A | 477 | 31.089 | -6.127 | 91.750 | 1.00 | 8.79 |
| 3631 | ND1 | HIS | A | 477 | 31.067 | -7.461 | 92.105 | 1.00 | 10.73 |
| 3632 | CE1 | HIS | A | 477 | 30.301 | -8.122 | 91.258 | 1.00 | 7.06 |
| 3633 | NE2 | HIS | A | 477 | 29.821 | -7.261 | 90.378 | 1.00 | 9.36 |
| 3634 | CD2 | HIS | A | 477 | 30.309 | -6.010 | 90.659 | 1.00 | 7.26 |
| 3635 | C | HIS | A | 477 | 31.454 | -3.295 | 94.327 | 1.00 | 10.29 |
| 3636 | O | HIS | A | 477 | 31.646 | -2.087 | 94.017 | 1.00 | 10.17 |
| 3637 | N | ASP | A | 478 | 31.905 | -3.878 | 95.436 | 1.00 | 10.08 |
| 3638 | CA | ASP | A | 478 | 32.618 | -3.172 | 96.470 | 1.00 | 11.22 |
| 3639 | CB | ASP | A | 478 | 32.484 | -3.965 | 97.749 | 1.00 | 11.06 |
| 3640 | CG | ASP | A | 478 | 32.962 | -3.221 | 98.912 | 1.00 | 14.96 |
| 3641 | OD1 | ASP | A | 478 | 34.148 | -3.349 | 99.208 | 1.00 | 19.00 |
| 3642 | OD2 | ASP | A | 478 | 32.243 | -2.449 | 99.595 | 1.00 | 20.34 |
| 3643 | C | ASP | A | 478 | 34.104 | -2.931 | 96.154 | 1.00 | 11.09 |
| 3644 | O | ASP | A | 478 | 34.648 | -1.809 | 96.179 | 1.00 | 11.34 |
| 3645 | N | GLY | A | 479 | 34.771 | -3.994 | 95.808 | 1.00 | 10.66 |
| 3646 | CA | GLY | A | 479 | 36.201 | -3.892 | 95.637 | 1.00 | 11.01 |
| 3647 | C | GLY | A | 479 | 36.952 | -2.922 | 96.542 | 1.00 | 11.18 |
| 3648 | O | GLY | A | 479 | 37.559 | -1.926 | 96.102 | 1.00 | 11.17 |
| 3649 | N | ARG | A | 480 | 36.743 | -3.162 | 97.815 | 1.00 | 10.70 |
| 3650 | CA | ARG | A | 480 | 37.808 | -3.529 | 98.738 | 1.00 | 11.52 |
| 3651 | CB | ARG | A | 480 | 37.655 | -2.653 | 99.994 | 1.00 | 12.29 |
| 3652 | CG | ARG | A | 480 | 38.539 | -2.950 | 101.186 | 1.00 | 12.41 |
| 3653 | CD | ARG | A | 480 | 37.859 | -2.625 | 102.519 | 1.00 | 15.43 |
| 3654 | NE | ARG | A | 480 | 36.904 | -3.700 | 102.871 | 1.00 | 14.24 |
| 3655 | CZ | ARG | A | 480 | 36.855 | -4.388 | 104.005 | 1.00 | 8.47 |
| 3656 | NH1 | ARG | A | 480 | 35.920 | -5.303 | 104.149 | 1.00 | 4.98 |
| 3657 | NH2 | ARG | A | 480 | 37.682 | -4.143 | 105.007 | 1.00 | 12.43 |
| 3658 | C | ARG | A | 480 | 37.673 | -5.125 | 99.004 | 1.00 | 11.62 |
| 3659 | O | ARG | A | 480 | 38.627 | -5.811 | 99.501 | 1.00 | 12.53 |
| 3660 | N | THR | A | 481 | 36.501 | -5.640 | 98.555 | 1.00 | 10.42 |
| 3661 | CA | THR | A | 481 | 35.818 | -6.898 | 98.864 | 1.00 | 9.72 |
| 3662 | CB | THR | A | 481 | 34.499 | -6.493 | 99.623 | 1.00 | 9.23 |
| 3663 | OG1 | THR | A | 481 | 34.373 | -7.220 | 100.822 | 1.00 | 8.52 |

FIGURE 3 (Cont.)

| A | B | C | D | E | F | G | H | I | J |
|---|---|---|---|---|---|---|---|---|---|
| 3664 | CG2 | THR | A | 481 | 33.220 | -6.862 | 98.982 | 1.00 | 7.49 |
| 3665 | C | THR | A | 481 | 35.454 | -7.672 | 97.580 | 1.00 | 10.22 |
| 3666 | O | THR | A | 481 | 35.443 | -8.887 | 97.535 | 1.00 | 10.39 |
| 3667 | N | ASP | A | 482 | 35.097 | -6.915 | 96.548 | 1.00 | 11.83 |
| 3668 | CA | ASP | A | 482 | 34.619 | -7.365 | 95.217 | 1.00 | 11.65 |
| 3669 | CB | ASP | A | 482 | 35.571 | -8.375 | 94.655 | 1.00 | 12.02 |
| 3670 | CG | ASP | A | 482 | 37.062 | -7.924 | 94.760 | 1.00 | 13.28 |
| 3671 | OD1 | ASP | A | 482 | 37.466 | -7.043 | 95.548 | 1.00 | 16.27 |
| 3672 | OD2 | ASP | A | 482 | 37.939 | -8.434 | 94.068 | 1.00 | 14.80 |
| 3673 | C | ASP | A | 482 | 33.191 | -7.890 | 95.254 | 1.00 | 11.61 |
| 3674 | O | ASP | A | 482 | 32.667 | -8.174 | 94.240 | 1.00 | 11.00 |
| 3675 | N | GLN | A | 483 | 32.563 | -7.968 | 96.441 | 1.00 | 12.56 |
| 3676 | CA | GLN | A | 483 | 31.155 | -8.409 | 96.623 | 1.00 | 13.37 |
| 3677 | CB | GLN | A | 483 | 30.692 | -8.388 | 98.116 | 1.00 | 14.11 |
| 3678 | CG | GLN | A | 483 | 29.194 | -8.903 | 98.389 | 1.00 | 19.68 |
| 3679 | CD | GLN | A | 483 | 28.932 | -10.458 | 98.099 | 1.00 | 27.86 |
| 3680 | OE1 | GLN | A | 483 | 27.766 | -10.880 | 97.917 | 1.00 | 30.80 |
| 3681 | NE2 | GLN | A | 483 | 30.008 | -11.278 | 98.080 | 1.00 | 28.76 |
| 3682 | C | GLN | A | 483 | 30.149 | -7.649 | 95.739 | 1.00 | 11.89 |
| 3683 | O | GLN | A | 483 | 30.245 | -6.460 | 95.546 | 1.00 | 11.84 |
| 3684 | N | GLU | A | 484 | 29.182 | -8.390 | 95.242 | 1.00 | 10.96 |
| 3685 | CA | GLU | A | 484 | 28.169 | -7.861 | 94.397 | 1.00 | 10.43 |
| 3686 | CB | GLU | A | 484 | 27.582 | -8.960 | 93.527 | 1.00 | 10.55 |
| 3687 | CG | GLU | A | 484 | 26.699 | -8.417 | 92.384 | 1.00 | 14.43 |
| 3688 | CD | GLU | A | 484 | 25.960 | -9.538 | 91.674 | 1.00 | 19.06 |
| 3689 | OE1 | GLU | A | 484 | 24.697 | -9.571 | 91.709 | 1.00 | 20.27 |
| 3690 | OE2 | GLU | A | 484 | 26.664 | -10.406 | 91.092 | 1.00 | 21.19 |
| 3691 | C | GLU | A | 484 | 27.053 | -7.195 | 95.195 | 1.00 | 10.19 |
| 3692 | O | GLU | A | 484 | 26.377 | -7.865 | 95.991 | 1.00 | 9.15 |
| 3693 | N | ILE | A | 485 | 26.798 | -5.923 | 94.862 | 1.00 | 10.27 |
| 3694 | CA | ILE | A | 485 | 25.932 | -5.008 | 95.630 | 1.00 | 10.02 |
| 3695 | CB | ILE | A | 485 | 26.684 | -3.663 | 95.794 | 1.00 | 9.87 |
| 3696 | CG1 | ILE | A | 485 | 27.862 | -3.897 | 96.770 | 1.00 | 10.48 |
| 3697 | CD1 | ILE | A | 485 | 28.746 | -2.705 | 97.021 | 1.00 | 10.91 |
| 3698 | CG2 | ILE | A | 485 | 25.737 | -2.564 | 96.188 | 1.00 | 8.04 |
| 3699 | C | ILE | A | 485 | 24.510 | -4.812 | 95.052 | 1.00 | 10.17 |
| 3700 | O | ILE | A | 485 | 23.546 | -5.148 | 95.720 | 1.00 | 8.08 |
| 3701 | N | LYS | A | 486 | 24.373 | -4.236 | 93.851 | 1.00 | 10.24 |
| 3702 | CA | LYS | A | 486 | 23.168 | -4.492 | 93.039 | 1.00 | 11.66 |
| 3703 | CB | LYS | A | 486 | 22.069 | -3.403 | 93.042 | 1.00 | 11.49 |
| 3704 | CG | LYS | A | 486 | 22.306 | -2.205 | 93.871 | 1.00 | 15.18 |
| 3705 | CD | LYS | A | 486 | 22.775 | -0.979 | 93.050 | 1.00 | 18.25 |
| 3706 | CE | LYS | A | 486 | 22.494 | 0.415 | 93.813 | 1.00 | 22.51 |
| 3707 | NZ | LYS | A | 486 | 22.133 | 0.333 | 95.326 | 1.00 | 19.50 |
| 3708 | C | LYS | A | 486 | 23.485 | -4.824 | 91.581 | 1.00 | 12.70 |
| 3709 | O | LYS | A | 486 | 24.432 | -4.273 | 90.944 | 1.00 | 13.17 |
| 3710 | N | ILE | A | 487 | 22.671 | -5.757 | 91.081 | 1.00 | 12.91 |
| 3711 | CA | ILE | A | 487 | 22.318 | -5.871 | 89.660 | 1.00 | 13.71 |
| 3712 | CB | ILE | A | 487 | 21.202 | -7.007 | 89.496 | 1.00 | 13.21 |
| 3713 | CG1 | ILE | A | 487 | 21.647 | -8.363 | 90.090 | 1.00 | 11.99 |
| 3714 | CD1 | ILE | A | 487 | 20.498 | -9.343 | 90.384 | 1.00 | 11.90 |

FIGURE 3 (Cont.)

| A | B | C | D | E | F | G | H | I | J |
|---|---|---|---|---|---|---|---|---|---|
| 3715 | CG2 | ILE | A | 487 | 20.849 | -7.139 | 88.054 | 1.00 | 14.66 |
| 3716 | C | ILE | A | 487 | 21.827 | -4.502 | 89.070 | 1.00 | 13.29 |
| 3717 | O | ILE | A | 487 | 20.705 | -4.077 | 89.340 | 1.00 | 14.46 |
| 3718 | N | LEU | A | 488 | 22.671 | -3.829 | 88.269 | 1.00 | 12.94 |
| 3719 | CA | LEU | A | 488 | 22.406 | -2.476 | 87.683 | 1.00 | 11.84 |
| 3720 | CB | LEU | A | 488 | 23.694 | -1.837 | 87.266 | 1.00 | 10.56 |
| 3721 | CG | LEU | A | 488 | 24.780 | -1.694 | 88.276 | 1.00 | 8.39 |
| 3722 | CD1 | LEU | A | 488 | 26.008 | -1.078 | 87.664 | 1.00 | 5.54 |
| 3723 | CD2 | LEU | A | 488 | 24.259 | -0.866 | 89.375 | 1.00 | 10.40 |
| 3724 | C | LEU | A | 488 | 21.553 | -2.477 | 86.429 | 1.00 | 13.03 |
| 3725 | O | LEU | A | 488 | 20.838 | -1.485 | 86.176 | 1.00 | 13.37 |
| 3726 | N | GLU | A | 489 | 21.709 | -3.545 | 85.619 | 1.00 | 13.74 |
| 3727 | CA | GLU | A | 489 | 20.836 | -3.883 | 84.464 | 1.00 | 14.49 |
| 3728 | CB | GLU | A | 489 | 21.155 | -3.020 | 83.216 | 1.00 | 15.20 |
| 3729 | CG | GLU | A | 489 | 20.317 | -3.358 | 81.957 | 1.00 | 16.38 |
| 3730 | CD | GLU | A | 489 | 18.798 | -3.264 | 82.140 | 1.00 | 19.14 |
| 3731 | OE1 | GLU | A | 489 | 18.225 | -2.130 | 82.170 | 1.00 | 20.61 |
| 3732 | OE2 | GLU | A | 489 | 18.153 | -4.324 | 82.222 | 1.00 | 22.26 |
| 3733 | C | GLU | A | 489 | 20.890 | -5.375 | 84.077 | 1.00 | 14.38 |
| 3734 | O | GLU | A | 489 | 21.937 | -5.913 | 83.766 | 1.00 | 14.41 |
| 3735 | N | GLU | A | 490 | 19.721 | -5.995 | 84.046 | 1.00 | 14.59 |
| 3736 | CA | GLU | A | 490 | 19.557 | -7.462 | 84.001 | 1.00 | 15.07 |
| 3737 | CB | GLU | A | 490 | 18.594 | -7.855 | 85.186 | 1.00 | 15.54 |
| 3738 | CG | GLU | A | 490 | 18.446 | -9.331 | 85.628 | 1.00 | 16.77 |
| 3739 | CD | GLU | A | 490 | 17.757 | -9.458 | 87.009 | 1.00 | 20.41 |
| 3740 | OE1 | GLU | A | 490 | 16.902 | -10.353 | 87.182 | 1.00 | 22.54 |
| 3741 | OE2 | GLU | A | 490 | 18.039 | -8.649 | 87.946 | 1.00 | 20.30 |
| 3742 | C | GLU | A | 490 | 18.947 | -7.898 | 82.671 | 1.00 | 13.71 |
| 3743 | O | GLU | A | 490 | 18.953 | -9.074 | 82.355 | 1.00 | 12.93 |
| 3744 | N | ASN | A | 491 | 18.469 | -6.917 | 81.901 | 1.00 | 14.21 |
| 3745 | CA | ASN | A | 491 | 17.386 | -7.030 | 80.864 | 1.00 | 13.72 |
| 3746 | CB | ASN | A | 491 | 17.889 | -6.740 | 79.421 | 1.00 | 13.76 |
| 3747 | CG | ASN | A | 491 | 19.361 | -7.050 | 79.257 | 1.00 | 10.49 |
| 3748 | OD1 | ASN | A | 491 | 20.132 | -6.212 | 78.835 | 1.00 | 9.68 |
| 3749 | ND2 | ASN | A | 491 | 19.749 | -8.257 | 79.623 | 1.00 | 5.82 |
| 3750 | C | ASN | A | 491 | 16.577 | -8.305 | 80.885 | 1.00 | 13.89 |
| 3751 | O | ASN | A | 491 | 16.812 | -9.228 | 80.116 | 1.00 | 12.98 |
| 3752 | N | LYS | A | 492 | 15.616 | -8.311 | 81.795 | 1.00 | 14.35 |
| 3753 | CA | LYS | A | 492 | 14.543 | -9.276 | 81.780 | 1.00 | 15.37 |
| 3754 | CB | LYS | A | 492 | 13.768 | -9.256 | 83.148 | 1.00 | 15.25 |
| 3755 | CG | LYS | A | 492 | 14.638 | -9.705 | 84.375 | 1.00 | 16.86 |
| 3756 | CD | LYS | A | 492 | 13.978 | -10.713 | 85.343 | 1.00 | 19.26 |
| 3757 | CE | LYS | A | 492 | 13.527 | -12.076 | 84.691 | 1.00 | 22.59 |
| 3758 | NZ | LYS | A | 492 | 12.198 | -12.628 | 85.251 | 1.00 | 25.29 |
| 3759 | C | LYS | A | 492 | 13.631 | -9.048 | 80.537 | 1.00 | 15.22 |
| 3760 | O | LYS | A | 492 | 13.199 | -10.002 | 79.925 | 1.00 | 15.47 |
| 3761 | N | GLU | A | 493 | 13.321 | -7.814 | 80.154 | 1.00 | 15.46 |
| 3762 | CA | GLU | A | 493 | 12.511 | -7.600 | 78.899 | 1.00 | 17.01 |
| 3763 | CB | GLU | A | 493 | 12.234 | -6.106 | 78.473 | 1.00 | 17.25 |
| 3764 | CG | GLU | A | 493 | 13.275 | -5.039 | 78.839 | 1.00 | 19.82 |
| 3765 | CD | GLU | A | 493 | 13.444 | -4.875 | 80.354 | 1.00 | 22.93 |

FIGURE 3 (Cont.)

| A | B | C | D | E | F | G | H | I | J |
|---|---|---|---|---|---|---|---|---|---|
| 3766 | OE1 | GLU | A | 493 | 14.626 | -4.607 | 80.754 | 1.00 | 25.06 |
| 3767 | OE2 | GLU | A | 493 | 12.426 | -5.075 | 81.113 | 1.00 | 19.74 |
| 3768 | C | GLU | A | 493 | 13.068 | -8.368 | 77.675 | 1.00 | 16.27 |
| 3769 | O | GLU | A | 493 | 12.341 | -9.126 | 77.045 | 1.00 | 17.24 |
| 3770 | N | LEU | A | 494 | 14.324 | -8.154 | 77.342 | 1.00 | 15.39 |
| 3771 | CA | LEU | A | 494 | 15.000 | -9.020 | 76.390 | 1.00 | 14.45 |
| 3772 | CB | LEU | A | 494 | 16.464 | -8.673 | 76.376 | 1.00 | 13.55 |
| 3773 | CG | LEU | A | 494 | 17.236 | -8.994 | 75.111 | 1.00 | 15.69 |
| 3774 | CD1 | LEU | A | 494 | 18.613 | -9.467 | 75.481 | 1.00 | 16.62 |
| 3775 | CD2 | LEU | A | 494 | 16.615 | -9.950 | 74.065 | 1.00 | 12.90 |
| 3776 | C | LEU | A | 494 | 14.880 | -10.558 | 76.687 | 1.00 | 14.70 |
| 3777 | O | LEU | A | 494 | 14.563 | -11.348 | 75.777 | 1.00 | 13.48 |
| 3778 | N | GLU | A | 495 | 15.142 | -10.984 | 77.934 | 1.00 | 14.49 |
| 3779 | CA | GLU | A | 495 | 14.950 | -12.424 | 78.354 | 1.00 | 15.14 |
| 3780 | CB | GLU | A | 495 | 15.186 | -12.617 | 79.886 | 1.00 | 15.34 |
| 3781 | CG | GLU | A | 495 | 15.916 | -13.903 | 80.260 | 1.00 | 17.23 |
| 3782 | CD | GLU | A | 495 | 15.498 | -14.516 | 81.604 | 1.00 | 21.30 |
| 3783 | OE1 | GLU | A | 495 | 15.172 | -15.731 | 81.597 | 1.00 | 22.67 |
| 3784 | OE2 | GLU | A | 495 | 15.502 | -13.799 | 82.659 | 1.00 | 23.69 |
| 3785 | C | GLU | A | 495 | 13.571 | -13.003 | 78.031 | 1.00 | 15.01 |
| 3786 | O | GLU | A | 495 | 13.415 | -14.182 | 77.804 | 1.00 | 15.70 |
| 3787 | N | ASN | A | 496 | 12.563 | -12.160 | 78.047 | 1.00 | 15.18 |
| 3788 | CA | ASN | A | 496 | 11.211 | -12.657 | 77.989 | 1.00 | 16.91 |
| 3789 | CB | ASN | A | 496 | 10.278 | -11.878 | 78.965 | 1.00 | 16.61 |
| 3790 | CG | ASN | A | 496 | 10.380 | -12.392 | 80.434 | 1.00 | 18.02 |
| 3791 | OD1 | ASN | A | 496 | 10.392 | -13.601 | 80.708 | 1.00 | 20.05 |
| 3792 | ND2 | ASN | A | 496 | 10.482 | -11.461 | 81.364 | 1.00 | 18.03 |
| 3793 | C | ASN | A | 496 | 10.729 | -12.606 | 76.544 | 1.00 | 17.29 |
| 3794 | O | ASN | A | 496 | 9.831 | -13.349 | 76.162 | 1.00 | 18.57 |
| 3795 | N | ALA | A | 497 | 11.326 | -11.762 | 75.719 | 1.00 | 17.36 |
| 3796 | CA | ALA | A | 497 | 10.916 | -11.736 | 74.329 | 1.00 | 17.70 |
| 3797 | CB | ALA | A | 497 | 11.419 | -10.515 | 73.644 | 1.00 | 16.88 |
| 3798 | C | ALA | A | 497 | 11.413 | -13.033 | 73.672 | 1.00 | 17.98 |
| 3799 | O | ALA | A | 497 | 10.627 | -13.765 | 73.046 | 1.00 | 19.18 |
| 3800 | N | LEU | A | 498 | 12.677 | -13.371 | 73.902 | 1.00 | 16.78 |
| 3801 | CA | LEU | A | 498 | 13.238 | -14.653 | 73.478 | 1.00 | 15.45 |
| 3802 | CB | LEU | A | 498 | 14.676 | -14.736 | 73.948 | 1.00 | 14.72 |
| 3803 | CG | LEU | A | 498 | 15.604 | -13.561 | 73.528 | 1.00 | 12.84 |
| 3804 | CD1 | LEU | A | 498 | 17.062 | -13.861 | 73.855 | 1.00 | 10.55 |
| 3805 | CD2 | LEU | A | 498 | 15.495 | -13.193 | 72.043 | 1.00 | 10.27 |
| 3806 | C | LEU | A | 498 | 12.517 | -15.935 | 73.950 | 1.00 | 16.58 |
| 3807 | O | LEU | A | 498 | 12.968 | -17.058 | 73.603 | 1.00 | 17.18 |
| 3808 | N | LYS | A | 499 | 11.442 | -15.805 | 74.748 | 1.00 | 16.44 |
| 3809 | CA | LYS | A | 499 | 10.644 | -16.965 | 75.164 | 1.00 | 16.44 |
| 3810 | CB | LYS | A | 499 | 9.548 | -16.532 | 76.189 | 1.00 | 16.76 |
| 3811 | CG | LYS | A | 499 | 9.735 | -17.025 | 77.687 | 1.00 | 18.25 |
| 3812 | CD | LYS | A | 499 | 8.421 | -17.582 | 78.332 | 1.00 | 17.41 |
| 3813 | CE | LYS | A | 499 | 7.436 | -16.442 | 78.792 | 1.00 | 18.35 |
| 3814 | NZ | LYS | A | 499 | 6.411 | -16.865 | 79.851 | 1.00 | 13.03 |
| 3815 | C | LYS | A | 499 | 10.022 | -17.627 | 73.904 | 1.00 | 16.05 |
| 3816 | O | LYS | A | 499 | 10.114 | -18.847 | 73.687 | 1.00 | 15.43 |

FIGURE 3 (Cont.)

| A | B | C | D | E | F | G | H | I | J |
|---|---|---|---|---|---|---|---|---|---|
| 3817 | N | ASN | A | 500 | 9.359 | -16.754 | 73.136 | 1.00 | 15.93 |
| 3818 | CA | ASN | A | 500 | 8.931 | -16.904 | 71.730 | 1.00 | 16.45 |
| 3819 | CB | ASN | A | 500 | 9.010 | -15.487 | 71.091 | 1.00 | 16.29 |
| 3820 | CG | ASN | A | 500 | 7.696 | -14.675 | 71.151 | 1.00 | 17.32 |
| 3821 | OD1 | ASN | A | 500 | 7.175 | -14.327 | 72.224 | 1.00 | 17.47 |
| 3822 | ND2 | ASN | A | 500 | 7.229 | -14.269 | 69.966 | 1.00 | 18.04 |
| 3823 | C | ASN | A | 500 | 9.808 | -17.745 | 70.785 | 1.00 | 16.51 |
| 3824 | O | ASN | A | 500 | 9.281 | -18.429 | 69.882 | 1.00 | 16.58 |
| 3825 | N | ILE | A | 501 | 11.141 | -17.626 | 70.969 | 1.00 | 16.28 |
| 3826 | CA | ILE | A | 501 | 12.138 | -17.666 | 69.880 | 1.00 | 14.86 |
| 3827 | CB | ILE | A | 501 | 12.887 | -16.351 | 69.868 | 1.00 | 14.29 |
| 3828 | CG1 | ILE | A | 501 | 12.273 | -15.466 | 68.807 | 1.00 | 14.54 |
| 3829 | CD1 | ILE | A | 501 | 11.781 | -14.189 | 69.349 | 1.00 | 16.15 |
| 3830 | CG2 | ILE | A | 501 | 14.350 | -16.501 | 69.484 | 1.00 | 12.16 |
| 3831 | C | ILE | A | 501 | 13.132 | -18.835 | 69.896 | 1.00 | 15.72 |
| 3832 | O | ILE | A | 501 | 13.813 | -19.071 | 70.882 | 1.00 | 16.21 |
| 3833 | N | GLN | A | 502 | 13.212 | -19.578 | 68.799 | 1.00 | 16.04 |
| 3834 | CA | GLN | A | 502 | 14.058 | -20.759 | 68.780 | 1.00 | 17.20 |
| 3835 | CB | GLN | A | 502 | 13.411 | -22.031 | 68.090 | 1.00 | 17.89 |
| 3836 | CG | GLN | A | 502 | 12.520 | -21.745 | 66.805 | 1.00 | 20.85 |
| 3837 | CD | GLN | A | 502 | 12.119 | -22.991 | 65.930 | 1.00 | 23.80 |
| 3838 | OE1 | GLN | A | 502 | 11.969 | -22.835 | 64.695 | 1.00 | 24.79 |
| 3839 | NE2 | GLN | A | 502 | 11.987 | -24.187 | 66.544 | 1.00 | 17.89 |
| 3840 | C | GLN | A | 502 | 15.304 | -20.268 | 68.128 | 1.00 | 17.07 |
| 3841 | O | GLN | A | 502 | 15.385 | -20.223 | 66.894 | 1.00 | 17.73 |
| 3842 | N | LEU | A | 503 | 16.248 | -19.852 | 68.979 | 1.00 | 16.78 |
| 3843 | CA | LEU | A | 503 | 17.573 | -19.455 | 68.537 | 1.00 | 16.50 |
| 3844 | CB | LEU | A | 503 | 18.314 | -18.603 | 69.567 | 1.00 | 16.65 |
| 3845 | CG | LEU | A | 503 | 17.621 | -17.553 | 70.425 | 1.00 | 15.47 |
| 3846 | CD1 | LEU | A | 503 | 18.214 | -17.710 | 71.827 | 1.00 | 16.08 |
| 3847 | CD2 | LEU | A | 503 | 17.731 | -16.091 | 69.894 | 1.00 | 15.89 |
| 3848 | C | LEU | A | 503 | 18.418 | -20.672 | 68.270 | 1.00 | 16.48 |
| 3849 | O | LEU | A | 503 | 18.042 | -21.785 | 68.593 | 1.00 | 16.59 |
| 3850 | N | PRO | A | 504 | 19.535 | -20.448 | 67.589 | 1.00 | 16.89 |
| 3851 | CA | PRO | A | 504 | 20.429 | -21.537 | 67.181 | 1.00 | 16.86 |
| 3852 | CB | PRO | A | 504 | 21.160 | -20.915 | 65.944 | 1.00 | 15.52 |
| 3853 | CG | PRO | A | 504 | 21.236 | -19.593 | 66.217 | 1.00 | 14.77 |
| 3854 | CD | PRO | A | 504 | 20.007 | -19.166 | 67.015 | 1.00 | 15.94 |
| 3855 | C | PRO | A | 504 | 21.414 | -21.907 | 68.284 | 1.00 | 17.29 |
| 3856 | O | PRO | A | 504 | 21.610 | -21.118 | 69.224 | 1.00 | 18.24 |
| 3857 | N | LYS | A | 505 | 22.015 | -23.085 | 68.168 | 1.00 | 17.78 |
| 3858 | CA | LYS | A | 505 | 23.013 | -23.515 | 69.122 | 1.00 | 18.36 |
| 3859 | CB | LYS | A | 505 | 23.070 | -25.039 | 69.193 | 1.00 | 18.91 |
| 3860 | CG | LYS | A | 505 | 23.387 | -25.632 | 70.626 | 1.00 | 22.57 |
| 3861 | CD | LYS | A | 505 | 24.902 | -25.810 | 70.853 | 1.00 | 27.28 |
| 3862 | CE | LYS | A | 505 | 25.283 | -26.353 | 72.317 | 1.00 | 31.84 |
| 3863 | NZ | LYS | A | 505 | 26.560 | -25.759 | 72.942 | 1.00 | 30.25 |
| 3864 | C | LYS | A | 505 | 24.358 | -22.923 | 68.669 | 1.00 | 18.40 |
| 3865 | O | LYS | A | 505 | 24.687 | -22.924 | 67.475 | 1.00 | 18.15 |
| 3866 | N | GLU | A | 506 | 25.117 | -22.413 | 69.632 | 1.00 | 18.31 |
| 3867 | CA | GLU | A | 506 | 26.448 | -21.884 | 69.383 | 1.00 | 16.85 |

FIGURE 3 (Cont.)

| A | B | C | D | E | F | G | H | I | J |
|---|---|---|---|---|---|---|---|---|---|
| 3868 | CB | GLU | A | 506 | 26.548 | -20.466 | 69.874 | 1.00 | 15.98 |
| 3869 | CG | GLU | A | 506 | 25.359 | -19.615 | 69.461 | 1.00 | 16.42 |
| 3870 | CD | GLU | A | 506 | 25.724 | -18.097 | 69.272 | 1.00 | 20.89 |
| 3871 | OE1 | GLU | A | 506 | 24.813 | -17.271 | 68.850 | 1.00 | 17.53 |
| 3872 | OE2 | GLU | A | 506 | 26.898 | -17.726 | 69.598 | 1.00 | 18.26 |
| 3873 | C | GLU | A | 506 | 27.409 | -22.750 | 70.149 | 1.00 | 17.69 |
| 3874 | O | GLU | A | 506 | 27.020 | -23.673 | 70.927 | 1.00 | 16.42 |
| 3875 | N | GLU | A | 507 | 28.685 | -22.486 | 69.940 | 1.00 | 16.98 |
| 3876 | CA | GLU | A | 507 | 29.685 | -23.499 | 70.268 | 1.00 | 16.31 |
| 3877 | CB | GLU | A | 507 | 29.345 | -24.805 | 69.490 | 1.00 | 16.13 |
| 3878 | CG | GLU | A | 507 | 29.127 | -26.079 | 70.337 | 1.00 | 17.79 |
| 3879 | CD | GLU | A | 507 | 28.563 | -27.279 | 69.534 | 1.00 | 18.04 |
| 3880 | OE1 | GLU | A | 507 | 28.891 | -27.424 | 68.309 | 1.00 | 16.13 |
| 3881 | OE2 | GLU | A | 507 | 27.794 | -28.101 | 70.148 | 1.00 | 18.88 |
| 3882 | C | GLU | A | 507 | 31.051 | -22.955 | 69.850 | 1.00 | 15.57 |
| 3883 | O | GLU | A | 507 | 31.325 | -22.764 | 68.643 | 1.00 | 15.24 |
| 3884 | N | ILE | A | 508 | 31.930 | -22.697 | 70.789 | 1.00 | 14.39 |
| 3885 | CA | ILE | A | 508 | 33.237 | -22.360 | 70.340 | 1.00 | 14.18 |
| 3886 | CB | ILE | A | 508 | 33.642 | -20.991 | 70.875 | 1.00 | 14.66 |
| 3887 | CG1 | ILE | A | 508 | 34.900 | -21.060 | 71.766 | 1.00 | 15.86 |
| 3888 | CD1 | ILE | A | 508 | 35.619 | -19.634 | 72.162 | 1.00 | 19.50 |
| 3889 | CG2 | ILE | A | 508 | 32.390 | -20.250 | 71.467 | 1.00 | 16.52 |
| 3890 | C | ILE | A | 508 | 34.240 | -23.490 | 70.615 | 1.00 | 13.39 |
| 3891 | O | ILE | A | 508 | 34.397 | -23.863 | 71.724 | 1.00 | 12.68 |
| 3892 | N | LYS | A | 509 | 34.894 | -24.021 | 69.586 | 1.00 | 13.06 |
| 3893 | CA | LYS | A | 509 | 35.863 | -25.081 | 69.745 | 1.00 | 13.17 |
| 3894 | CB | LYS | A | 509 | 35.312 | -26.381 | 69.177 | 1.00 | 13.46 |
| 3895 | CG | LYS | A | 509 | 33.869 | -26.747 | 69.596 | 1.00 | 16.07 |
| 3896 | CD | LYS | A | 509 | 33.592 | -28.302 | 69.291 | 1.00 | 19.22 |
| 3897 | CE | LYS | A | 509 | 32.341 | -28.870 | 69.940 | 1.00 | 18.09 |
| 3898 | NZ | LYS | A | 509 | 32.625 | -29.755 | 71.154 | 1.00 | 21.00 |
| 3899 | C | LYS | A | 509 | 37.185 | -24.740 | 69.077 | 1.00 | 12.40 |
| 3900 | O | LYS | A | 509 | 37.327 | -23.681 | 68.530 | 1.00 | 10.80 |
| 3901 | N | LYS | A | 510 | 38.149 | -25.660 | 69.165 | 1.00 | 13.25 |
| 3902 | CA | LYS | A | 510 | 39.456 | -25.546 | 68.510 | 1.00 | 13.94 |
| 3903 | CB | LYS | A | 510 | 40.616 | -25.405 | 69.583 | 1.00 | 13.37 |
| 3904 | CG | LYS | A | 510 | 40.962 | -26.655 | 70.505 | 1.00 | 16.16 |
| 3905 | CD | LYS | A | 510 | 42.462 | -26.788 | 71.062 | 1.00 | 14.97 |
| 3906 | CE | LYS | A | 510 | 43.271 | -27.943 | 70.357 | 1.00 | 17.44 |
| 3907 | NZ | LYS | A | 510 | 43.097 | -29.475 | 70.722 | 1.00 | 12.16 |
| 3908 | C | LYS | A | 510 | 39.710 | -26.635 | 67.392 | 1.00 | 14.47 |
| 3909 | O | LYS | A | 510 | 39.100 | -27.745 | 67.393 | 1.00 | 15.88 |
| 3910 | N | LEU | A | 511 | 40.625 | -26.312 | 66.457 | 1.00 | 14.20 |
| 3911 | CA | LEU | A | 511 | 41.148 | -27.239 | 65.429 | 1.00 | 14.43 |
| 3912 | CB | LEU | A | 511 | 40.837 | -26.763 | 64.021 | 1.00 | 13.47 |
| 3913 | CG | LEU | A | 511 | 39.353 | -26.787 | 63.796 | 1.00 | 11.98 |
| 3914 | CD1 | LEU | A | 511 | 39.036 | -25.800 | 62.758 | 1.00 | 12.61 |
| 3915 | CD2 | LEU | A | 511 | 38.928 | -28.165 | 63.447 | 1.00 | 10.30 |
| 3916 | C | LEU | A | 511 | 42.653 | -27.383 | 65.502 | 1.00 | 16.18 |
| 3917 | O | LEU | A | 511 | 43.381 | -26.426 | 65.749 | 1.00 | 16.64 |
| 3918 | N | GLU | A | 512 | 43.128 | -28.595 | 65.259 | 1.00 | 17.73 |

FIGURE 3 (Cont.)

| A | B | C | D | E | F | G | H | I | J |
|---|---|---|---|---|---|---|---|---|---|
| 3919 | CA | GLU | A | 512 | 44.544 | -28.832 | 65.355 | 1.00 | 19.35 |
| 3920 | CB | GLU | A | 512 | 44.819 | -29.849 | 66.496 | 1.00 | 20.34 |
| 3921 | CG | GLU | A | 512 | 45.857 | -29.458 | 67.596 | 1.00 | 23.22 |
| 3922 | CD | GLU | A | 512 | 46.260 | -27.963 | 67.587 | 1.00 | 26.37 |
| 3923 | OE1 | GLU | A | 512 | 46.809 | -27.489 | 66.538 | 1.00 | 25.98 |
| 3924 | OE2 | GLU | A | 512 | 46.037 | -27.283 | 68.632 | 1.00 | 26.81 |
| 3925 | C | GLU | A | 512 | 45.030 | -29.272 | 63.976 | 1.00 | 20.07 |
| 3926 | O | GLU | A | 512 | 44.812 | -30.430 | 63.552 | 1.00 | 20.43 |
| 3927 | N | VAL | A | 513 | 45.635 | -28.324 | 63.244 | 1.00 | 20.74 |
| 3928 | CA | VAL | A | 513 | 46.282 | -28.665 | 61.957 | 1.00 | 21.36 |
| 3929 | CB | VAL | A | 513 | 45.472 | -28.237 | 60.765 | 1.00 | 20.71 |
| 3930 | CG1 | VAL | A | 513 | 45.500 | -26.658 | 60.623 | 1.00 | 21.76 |
| 3931 | CG2 | VAL | A | 513 | 44.050 | -28.809 | 60.851 | 1.00 | 18.85 |
| 3932 | C | VAL | A | 513 | 47.709 | -28.123 | 61.741 | 1.00 | 22.09 |
| 3933 | O | VAL | A | 513 | 47.924 | -26.897 | 61.797 | 1.00 | 20.97 |
| 3934 | N | ASP | A | 514 | 48.652 | -29.065 | 61.476 | 1.00 | 23.01 |
| 3935 | CA | ASP | A | 514 | 50.035 | -28.739 | 61.046 | 1.00 | 23.37 |
| 3936 | CB | ASP | A | 514 | 50.078 | -28.004 | 59.660 | 1.00 | 23.65 |
| 3937 | CG | ASP | A | 514 | 49.706 | -28.905 | 58.444 | 1.00 | 23.18 |
| 3938 | OD1 | ASP | A | 514 | 49.297 | -28.325 | 57.397 | 1.00 | 23.65 |
| 3939 | OD2 | ASP | A | 514 | 49.802 | -30.164 | 58.423 | 1.00 | 23.82 |
| 3940 | C | ASP | A | 514 | 50.629 | -27.823 | 62.135 | 1.00 | 23.31 |
| 3941 | O | ASP | A | 514 | 50.894 | -26.630 | 61.885 | 1.00 | 23.03 |
| 3942 | N | GLU | A | 515 | 50.756 | -28.380 | 63.347 | 1.00 | 22.76 |
| 3943 | CA | GLU | A | 515 | 51.181 | -27.641 | 64.558 | 1.00 | 21.44 |
| 3944 | CB | GLU | A | 515 | 52.749 | -27.668 | 64.695 | 1.00 | 21.92 |
| 3945 | CG | GLU | A | 515 | 53.380 | -28.772 | 65.578 | 1.00 | 23.19 |
| 3946 | CD | GLU | A | 515 | 52.856 | -28.837 | 67.045 | 1.00 | 25.65 |
| 3947 | OE1 | GLU | A | 515 | 53.337 | -29.733 | 67.860 | 1.00 | 21.81 |
| 3948 | OE2 | GLU | A | 515 | 51.944 | -28.015 | 67.376 | 1.00 | 26.69 |
| 3949 | C | GLU | A | 515 | 50.644 | -26.164 | 64.718 | 1.00 | 19.62 |
| 3950 | O | GLU | A | 515 | 51.345 | -25.293 | 65.219 | 1.00 | 19.22 |
| 3951 | N | ILE | A | 516 | 49.423 | -25.855 | 64.336 | 1.00 | 17.25 |
| 3952 | CA | ILE | A | 516 | 48.915 | -24.496 | 64.688 | 1.00 | 16.23 |
| 3953 | CB | ILE | A | 516 | 49.476 | -23.357 | 63.726 | 1.00 | 15.48 |
| 3954 | CG1 | ILE | A | 516 | 48.653 | -22.054 | 63.854 | 1.00 | 15.50 |
| 3955 | CD1 | ILE | A | 516 | 47.505 | -21.904 | 62.916 | 1.00 | 4.33 |
| 3956 | CG2 | ILE | A | 516 | 49.564 | -23.804 | 62.296 | 1.00 | 15.93 |
| 3957 | C | ILE | A | 516 | 47.386 | -24.466 | 64.848 | 1.00 | 14.78 |
| 3958 | O | ILE | A | 516 | 46.685 | -25.037 | 64.024 | 1.00 | 14.47 |
| 3959 | N | THR | A | 517 | 46.899 | -23.835 | 65.921 | 1.00 | 12.97 |
| 3960 | CA | THR | A | 517 | 45.560 | -24.151 | 66.397 | 1.00 | 12.25 |
| 3961 | CB | THR | A | 517 | 45.554 | -24.465 | 67.935 | 1.00 | 13.15 |
| 3962 | OG1 | THR | A | 517 | 44.640 | -23.614 | 68.644 | 1.00 | 14.53 |
| 3963 | CG2 | THR | A | 517 | 46.975 | -24.264 | 68.629 | 1.00 | 12.04 |
| 3964 | C | THR | A | 517 | 44.516 | -23.076 | 65.985 | 1.00 | 11.66 |
| 3965 | O | THR | A | 517 | 44.875 | -21.884 | 65.798 | 1.00 | 10.98 |
| 3966 | N | LEU | A | 518 | 43.246 | -23.526 | 65.836 | 1.00 | 10.07 |
| 3967 | CA | LEU | A | 518 | 42.177 | -22.747 | 65.147 | 1.00 | 10.34 |
| 3968 | CB | LEU | A | 518 | 41.930 | -23.289 | 63.744 | 1.00 | 8.91 |
| 3969 | CG | LEU | A | 518 | 42.526 | -22.494 | 62.588 | 1.00 | 10.53 |

FIGURE 3 (Cont.)

| A | B | C | D | E | F | G | H | I | J |
|---|---|---|---|---|---|---|---|---|---|
| 3970 | CD1 | LEU | A | 518 | 43.932 | -22.015 | 62.766 | 1.00 | 10.26 |
| 3971 | CD2 | LEU | A | 518 | 42.480 | -23.328 | 61.330 | 1.00 | 7.80 |
| 3972 | C | LEU | A | 518 | 40.838 | -22.653 | 65.902 | 1.00 | 9.91 |
| 3973 | O | LEU | A | 518 | 40.041 | -23.592 | 65.981 | 1.00 | 8.87 |
| 3974 | N | TRP | A | 519 | 40.598 | -21.448 | 66.425 | 1.00 | 9.64 |
| 3975 | CA | TRP | A | 519 | 39.464 | -21.249 | 67.322 | 1.00 | 8.99 |
| 3976 | CB | TRP | A | 519 | 39.778 | -20.188 | 68.397 | 1.00 | 7.64 |
| 3977 | CG | TRP | A | 519 | 40.474 | -20.825 | 69.591 | 1.00 | 8.74 |
| 3978 | CD1 | TRP | A | 519 | 41.770 | -20.788 | 69.835 | 1.00 | 5.39 |
| 3979 | NE1 | TRP | A | 519 | 42.060 | -21.456 | 70.979 | 1.00 | 4.02 |
| 3980 | CE2 | TRP | A | 519 | 40.910 | -21.954 | 71.500 | 1.00 | 5.21 |
| 3981 | CD2 | TRP | A | 519 | 39.886 | -21.557 | 70.664 | 1.00 | 2.85 |
| 3982 | CE3 | TRP | A | 519 | 38.591 | -21.914 | 70.995 | 1.00 | 3.39 |
| 3983 | CZ3 | TRP | A | 519 | 38.374 | -22.658 | 72.102 | 1.00 | 2.00 |
| 3984 | CH2 | TRP | A | 519 | 39.427 | -23.033 | 72.939 | 1.00 | 2.00 |
| 3985 | CZ2 | TRP | A | 519 | 40.701 | -22.690 | 72.651 | 1.00 | 2.00 |
| 3986 | C | TRP | A | 519 | 38.309 | -20.869 | 66.450 | 1.00 | 8.88 |
| 3987 | O | TRP | A | 519 | 38.502 | -20.087 | 65.523 | 1.00 | 9.79 |
| 3988 | N | TYR | A | 520 | 37.139 | -21.454 | 66.690 | 1.00 | 8.94 |
| 3989 | CA | TYR | A | 520 | 35.945 | -21.036 | 65.945 | 1.00 | 9.77 |
| 3990 | CB | TYR | A | 520 | 35.758 | -21.926 | 64.686 | 1.00 | 9.97 |
| 3991 | CG | TYR | A | 520 | 35.428 | -23.354 | 64.976 | 1.00 | 9.56 |
| 3992 | CD1 | TYR | A | 520 | 34.132 | -23.842 | 64.841 | 1.00 | 4.58 |
| 3993 | CE1 | TYR | A | 520 | 33.856 | -25.191 | 65.147 | 1.00 | 4.25 |
| 3994 | CZ | TYR | A | 520 | 34.878 | -26.051 | 65.601 | 1.00 | 4.10 |
| 3995 | OH | TYR | A | 520 | 34.670 | -27.379 | 65.939 | 1.00 | 6.24 |
| 3996 | CE2 | TYR | A | 520 | 36.152 | -25.590 | 65.710 | 1.00 | 6.09 |
| 3997 | CD2 | TYR | A | 520 | 36.426 | -24.220 | 65.414 | 1.00 | 7.25 |
| 3998 | C | TYR | A | 520 | 34.671 | -20.968 | 66.764 | 1.00 | 10.00 |
| 3999 | O | TYR | A | 520 | 34.641 | -21.362 | 67.919 | 1.00 | 10.70 |
| 4000 | N | LYS | A | 521 | 33.621 | -20.411 | 66.189 | 1.00 | 10.73 |
| 4001 | CA | LYS | A | 521 | 32.297 | -20.461 | 66.788 | 1.00 | 10.75 |
| 4002 | CB | LYS | A | 521 | 31.859 | -19.103 | 67.325 | 1.00 | 10.99 |
| 4003 | CG | LYS | A | 521 | 30.534 | -18.502 | 66.899 | 1.00 | 9.66 |
| 4004 | CD | LYS | A | 521 | 29.796 | -17.960 | 68.083 | 1.00 | 13.15 |
| 4005 | CE | LYS | A | 521 | 30.406 | -16.653 | 68.623 | 1.00 | 13.91 |
| 4006 | NZ | LYS | A | 521 | 29.682 | -16.202 | 69.861 | 1.00 | 14.60 |
| 4007 | C | LYS | A | 521 | 31.473 | -20.884 | 65.688 | 1.00 | 12.26 |
| 4008 | O | LYS | A | 521 | 31.689 | -20.457 | 64.541 | 1.00 | 13.60 |
| 4009 | N | MET | A | 522 | 30.479 | -21.703 | 65.982 | 1.00 | 12.85 |
| 4010 | CA | MET | A | 522 | 29.775 | -22.365 | 64.883 | 1.00 | 12.31 |
| 4011 | CB | MET | A | 522 | 30.424 | -23.743 | 64.574 | 1.00 | 12.13 |
| 4012 | CG | MET | A | 522 | 29.423 | -24.935 | 64.420 | 1.00 | 14.92 |
| 4013 | SD | MET | A | 522 | 29.535 | -26.004 | 62.954 | 1.00 | 17.58 |
| 4014 | CE | MET | A | 522 | 31.287 | -25.737 | 62.268 | 1.00 | 13.56 |
| 4015 | C | MET | A | 522 | 28.305 | -22.450 | 65.211 | 1.00 | 10.97 |
| 4016 | O | MET | A | 522 | 27.904 | -22.978 | 66.253 | 1.00 | 11.56 |
| 4017 | N | ILE | A | 523 | 27.477 | -21.973 | 64.301 | 1.00 | 9.78 |
| 4018 | CA | ILE | A | 523 | 26.093 | -21.696 | 64.671 | 1.00 | 8.45 |
| 4019 | CB | ILE | A | 523 | 25.758 | -20.270 | 64.231 | 1.00 | 6.62 |
| 4020 | CG1 | ILE | A | 523 | 26.864 | -19.307 | 64.702 | 1.00 | 5.63 |

FIGURE 3 (Cont.)

| A | B | C | D | E | F | G | H | I | J |
|---|---|---|---|---|---|---|---|---|---|
| 4021 | CD1 | ILE | A | 523 | 26.481 | -17.642 | 64.803 | 1.00 | 3.96 |
| 4022 | CG2 | ILE | A | 523 | 24.507 | -19.820 | 64.858 | 1.00 | 5.91 |
| 4023 | C | ILE | A | 523 | 25.155 | -22.781 | 64.111 | 1.00 | 8.15 |
| 4024 | O | ILE | A | 523 | 25.053 | -22.911 | 62.902 | 1.00 | 9.20 |
| 4025 | N | LEU | A | 524 | 24.491 | -23.558 | 64.940 | 1.00 | 5.92 |
| 4026 | CA | LEU | A | 524 | 23.725 | -24.615 | 64.348 | 1.00 | 6.86 |
| 4027 | CB | LEU | A | 524 | 23.995 | -25.975 | 65.041 | 1.00 | 6.74 |
| 4028 | CG | LEU | A | 524 | 25.505 | -26.247 | 65.050 | 1.00 | 5.91 |
| 4029 | CD1 | LEU | A | 524 | 25.929 | -26.882 | 66.368 | 1.00 | 5.20 |
| 4030 | CD2 | LEU | A | 524 | 26.007 | -27.040 | 63.830 | 1.00 | 2.57 |
| 4031 | C | LEU | A | 524 | 22.251 | -24.250 | 64.337 | 1.00 | 7.99 |
| 4032 | O | LEU | A | 524 | 21.747 | -23.738 | 65.315 | 1.00 | 8.37 |
| 4033 | N | PRO | A | 525 | 21.556 | -24.463 | 63.232 | 1.00 | 9.29 |
| 4034 | CA | PRO | A | 525 | 20.098 | -24.411 | 63.234 | 1.00 | 10.98 |
| 4035 | CB | PRO | A | 525 | 19.698 | -24.889 | 61.815 | 1.00 | 10.67 |
| 4036 | CG | PRO | A | 525 | 20.885 | -24.710 | 60.998 | 1.00 | 9.58 |
| 4037 | CD | PRO | A | 525 | 22.086 | -24.678 | 61.879 | 1.00 | 9.64 |
| 4038 | C | PRO | A | 525 | 19.434 | -25.346 | 64.243 | 1.00 | 13.25 |
| 4039 | O | PRO | A | 525 | 19.903 | -26.460 | 64.585 | 1.00 | 12.72 |
| 4040 | N | PRO | A | 526 | 18.281 | -24.857 | 64.686 | 1.00 | 14.80 |
| 4041 | CA | PRO | A | 526 | 17.464 | -25.556 | 65.670 | 1.00 | 15.52 |
| 4042 | CB | PRO | A | 526 | 16.391 | -24.526 | 65.992 | 1.00 | 15.36 |
| 4043 | CG | PRO | A | 526 | 16.250 | -23.753 | 64.718 | 1.00 | 14.51 |
| 4044 | CD | PRO | A | 526 | 17.668 | -23.580 | 64.258 | 1.00 | 14.31 |
| 4045 | C | PRO | A | 526 | 16.920 | -26.842 | 65.037 | 1.00 | 16.69 |
| 4046 | O | PRO | A | 526 | 16.784 | -26.933 | 63.812 | 1.00 | 17.17 |
| 4047 | N | GLN | A | 527 | 16.618 | -27.811 | 65.885 | 1.00 | 18.22 |
| 4048 | CA | GLN | A | 527 | 16.790 | -29.260 | 65.544 | 1.00 | 20.10 |
| 4049 | CB | GLN | A | 527 | 15.493 | -30.193 | 65.688 | 1.00 | 20.08 |
| 4050 | CG | GLN | A | 527 | 14.279 | -29.974 | 64.689 | 1.00 | 23.59 |
| 4051 | CD | GLN | A | 527 | 13.379 | -28.735 | 65.015 | 1.00 | 26.75 |
| 4052 | OE1 | GLN | A | 527 | 12.730 | -28.164 | 64.117 | 1.00 | 27.12 |
| 4053 | NE2 | GLN | A | 527 | 13.348 | -28.334 | 66.290 | 1.00 | 27.37 |
| 4054 | C | GLN | A | 527 | 17.664 | -29.518 | 64.279 | 1.00 | 19.57 |
| 4055 | O | GLN | A | 527 | 17.207 | -30.029 | 63.268 | 1.00 | 19.22 |
| 4056 | N | PHE | A | 528 | 18.933 | -29.136 | 64.409 | 1.00 | 19.30 |
| 4057 | CA | PHE | A | 528 | 20.072 | -29.708 | 63.665 | 1.00 | 19.63 |
| 4058 | CB | PHE | A | 528 | 21.296 | -29.182 | 64.352 | 1.00 | 19.59 |
| 4059 | CG | PHE | A | 528 | 22.594 | -29.591 | 63.751 | 1.00 | 21.04 |
| 4060 | CD1 | PHE | A | 528 | 22.883 | -29.324 | 62.404 | 1.00 | 19.63 |
| 4061 | CE1 | PHE | A | 528 | 24.127 | -29.660 | 61.857 | 1.00 | 18.95 |
| 4062 | CZ | PHE | A | 528 | 25.110 | -30.213 | 62.671 | 1.00 | 20.79 |
| 4063 | CE2 | PHE | A | 528 | 24.855 | -30.454 | 64.051 | 1.00 | 21.34 |
| 4064 | CD2 | PHE | A | 528 | 23.604 | -30.135 | 64.582 | 1.00 | 21.45 |
| 4065 | C | PHE | A | 528 | 20.124 | -31.243 | 63.711 | 1.00 | 20.09 |
| 4066 | O | PHE | A | 528 | 20.079 | -31.848 | 64.790 | 1.00 | 19.88 |
| 4067 | N | ASP | A | 529 | 20.191 | -31.883 | 62.548 | 1.00 | 20.15 |
| 4068 | CA | ASP | A | 529 | 20.392 | -33.342 | 62.460 | 1.00 | 20.15 |
| 4069 | CB | ASP | A | 529 | 19.267 | -34.072 | 61.680 | 1.00 | 19.53 |
| 4070 | CG | ASP | A | 529 | 19.502 | -35.625 | 61.582 | 1.00 | 20.33 |
| 4071 | OD1 | ASP | A | 529 | 18.812 | -36.341 | 60.772 | 1.00 | 19.80 |

FIGURE 3 (Cont.)

| A | B | C | D | E | F | G | H | I | J |
|---|---|---|---|---|---|---|---|---|---|
| 4072 | OD2 | ASP | A | 529 | 20.384 | -36.202 | 62.279 | 1.00 | 19.04 |
| 4073 | C | ASP | A | 529 | 21.735 | -33.530 | 61.770 | 1.00 | 20.69 |
| 4074 | O | ASP | A | 529 | 21.791 | -33.703 | 60.550 | 1.00 | 21.24 |
| 4075 | N | ARG | A | 530 | 22.807 | -33.393 | 62.553 | 1.00 | 20.89 |
| 4076 | CA | ARG | A | 530 | 24.141 | -34.006 | 62.291 | 1.00 | 21.20 |
| 4077 | CB | ARG | A | 530 | 24.692 | -34.558 | 63.655 | 1.00 | 21.63 |
| 4078 | CG | ARG | A | 530 | 25.774 | -35.677 | 63.652 | 1.00 | 25.10 |
| 4079 | CD | ARG | A | 530 | 26.684 | -35.737 | 64.931 | 1.00 | 28.33 |
| 4080 | NE | ARG | A | 530 | 28.101 | -35.630 | 64.526 | 1.00 | 30.23 |
| 4081 | CZ | ARG | A | 530 | 28.882 | -34.530 | 64.542 | 1.00 | 30.48 |
| 4082 | NH1 | ARG | A | 530 | 28.470 | -33.339 | 64.997 | 1.00 | 30.55 |
| 4083 | NH2 | ARG | A | 530 | 30.119 | -34.641 | 64.095 | 1.00 | 28.18 |
| 4084 | C | ARG | A | 530 | 24.225 | -35.055 | 61.132 | 1.00 | 20.09 |
| 4085 | O | ARG | A | 530 | 25.192 | -35.014 | 60.357 | 1.00 | 20.72 |
| 4086 | N | SER | A | 531 | 23.224 | -35.938 | 61.000 | 1.00 | 18.26 |
| 4087 | CA | SER | A | 531 | 23.165 | -36.968 | 59.910 | 1.00 | 17.11 |
| 4088 | CB | SER | A | 531 | 22.062 | -37.985 | 60.232 | 1.00 | 16.91 |
| 4089 | OG | SER | A | 531 | 20.796 | -37.508 | 59.728 | 1.00 | 17.34 |
| 4090 | C | SER | A | 531 | 22.902 | -36.476 | 58.445 | 1.00 | 16.02 |
| 4091 | O | SER | A | 531 | 22.852 | -37.273 | 57.499 | 1.00 | 15.34 |
| 4092 | N | LYS | A | 532 | 22.687 | -35.178 | 58.294 | 1.00 | 14.66 |
| 4093 | CA | LYS | A | 532 | 22.169 | -34.597 | 57.072 | 1.00 | 13.98 |
| 4094 | CB | LYS | A | 532 | 20.704 | -34.172 | 57.275 | 1.00 | 14.32 |
| 4095 | CG | LYS | A | 532 | 19.594 | -35.280 | 57.207 | 1.00 | 15.19 |
| 4096 | CD | LYS | A | 532 | 18.216 | -34.774 | 57.808 | 1.00 | 16.43 |
| 4097 | CE | LYS | A | 532 | 17.867 | -33.203 | 57.449 | 1.00 | 18.07 |
| 4098 | NZ | LYS | A | 532 | 17.139 | -32.993 | 56.146 | 1.00 | 15.15 |
| 4099 | C | LYS | A | 532 | 23.070 | -33.375 | 56.775 | 1.00 | 13.10 |
| 4100 | O | LYS | A | 532 | 24.048 | -33.134 | 57.513 | 1.00 | 13.51 |
| 4101 | N | LYS | A | 533 | 22.756 | -32.596 | 55.730 | 1.00 | 11.19 |
| 4102 | CA | LYS | A | 533 | 23.758 | -31.756 | 55.133 | 1.00 | 9.95 |
| 4103 | CB | LYS | A | 533 | 24.352 | -32.433 | 53.872 | 1.00 | 9.26 |
| 4104 | CG | LYS | A | 533 | 25.724 | -33.171 | 54.162 | 1.00 | 10.39 |
| 4105 | CD | LYS | A | 533 | 26.594 | -33.553 | 52.916 | 1.00 | 10.98 |
| 4106 | CE | LYS | A | 533 | 27.166 | -35.062 | 52.975 | 1.00 | 14.00 |
| 4107 | NZ | LYS | A | 533 | 28.548 | -35.188 | 53.559 | 1.00 | 12.38 |
| 4108 | C | LYS | A | 533 | 23.280 | -30.294 | 54.941 | 1.00 | 10.05 |
| 4109 | O | LYS | A | 533 | 22.103 | -30.024 | 54.682 | 1.00 | 11.05 |
| 4110 | N | TYR | A | 534 | 24.209 | -29.364 | 55.122 | 1.00 | 8.50 |
| 4111 | CA | TYR | A | 534 | 23.844 | -27.990 | 55.410 | 1.00 | 8.03 |
| 4112 | CB | TYR | A | 534 | 23.747 | -27.671 | 56.948 | 1.00 | 7.29 |
| 4113 | CG | TYR | A | 534 | 22.775 | -28.445 | 57.796 | 1.00 | 7.67 |
| 4114 | CD1 | TYR | A | 534 | 21.624 | -27.861 | 58.353 | 1.00 | 5.27 |
| 4115 | CE1 | TYR | A | 534 | 20.739 | -28.595 | 59.129 | 1.00 | 4.76 |
| 4116 | CZ | TYR | A | 534 | 21.027 | -29.964 | 59.376 | 1.00 | 10.56 |
| 4117 | OH | TYR | A | 534 | 20.287 | -30.821 | 60.154 | 1.00 | 10.84 |
| 4118 | CE2 | TYR | A | 534 | 22.167 | -30.561 | 58.868 | 1.00 | 10.44 |
| 4119 | CD2 | TYR | A | 534 | 23.037 | -29.780 | 58.076 | 1.00 | 11.14 |
| 4120 | C | TYR | A | 534 | 24.854 | -26.988 | 54.740 | 1.00 | 7.96 |
| 4121 | O | TYR | A | 534 | 26.105 | -27.095 | 54.841 | 1.00 | 7.16 |
| 4122 | N | PRO | A | 535 | 24.276 | -26.021 | 54.050 | 1.00 | 8.15 |

FIGURE 3 (Cont.)

| A | B | C | D | E | F | G | H | I | J |
|---|---|---|---|---|---|---|---|---|---|
| 4123 | CA | PRO | A | 535 | 25.087 | -24.985 | 53.458 | 1.00 | 8.44 |
| 4124 | CB | PRO | A | 535 | 24.063 | -24.090 | 52.755 | 1.00 | 8.32 |
| 4125 | CG | PRO | A | 535 | 22.730 | -24.452 | 53.311 | 1.00 | 7.30 |
| 4126 | CD | PRO | A | 535 | 22.828 | -25.818 | 53.822 | 1.00 | 7.98 |
| 4127 | C | PRO | A | 535 | 25.820 | -24.315 | 54.607 | 1.00 | 8.76 |
| 4128 | O | PRO | A | 535 | 25.402 | -24.418 | 55.762 | 1.00 | 9.01 |
| 4129 | N | LEU | A | 536 | 26.961 | -23.755 | 54.329 | 1.00 | 8.85 |
| 4130 | CA | LEU | A | 536 | 27.751 | -23.284 | 55.396 | 1.00 | 10.23 |
| 4131 | CB | LEU | A | 536 | 28.915 | -24.212 | 55.595 | 1.00 | 9.65 |
| 4132 | CG | LEU | A | 536 | 29.987 | -23.427 | 56.368 | 1.00 | 13.03 |
| 4133 | CD1 | LEU | A | 536 | 29.574 | -23.374 | 57.857 | 1.00 | 14.75 |
| 4134 | CD2 | LEU | A | 536 | 31.462 | -23.927 | 56.180 | 1.00 | 12.80 |
| 4135 | C | LEU | A | 536 | 28.213 | -21.885 | 54.971 | 1.00 | 11.58 |
| 4136 | O | LEU | A | 536 | 28.901 | -21.745 | 53.948 | 1.00 | 12.89 |
| 4137 | N | LEU | A | 537 | 27.754 | -20.858 | 55.699 | 1.00 | 12.01 |
| 4138 | CA | LEU | A | 537 | 28.236 | -19.522 | 55.587 | 1.00 | 11.92 |
| 4139 | CB | LEU | A | 537 | 27.156 | -18.524 | 55.985 | 1.00 | 11.67 |
| 4140 | CG | LEU | A | 537 | 27.699 | -17.086 | 55.922 | 1.00 | 12.15 |
| 4141 | CD1 | LEU | A | 537 | 28.177 | -16.748 | 54.545 | 1.00 | 10.48 |
| 4142 | CD2 | LEU | A | 537 | 26.607 | -16.138 | 56.299 | 1.00 | 11.65 |
| 4143 | C | LEU | A | 537 | 29.392 | -19.428 | 56.543 | 1.00 | 12.68 |
| 4144 | O | LEU | A | 537 | 29.313 | -19.982 | 57.635 | 1.00 | 13.55 |
| 4145 | N | ILE | A | 538 | 30.474 | -18.811 | 56.095 | 1.00 | 12.03 |
| 4146 | CA | ILE | A | 538 | 31.584 | -18.463 | 56.912 | 1.00 | 11.40 |
| 4147 | CB | ILE | A | 538 | 32.880 | -18.808 | 56.196 | 1.00 | 11.19 |
| 4148 | CG1 | ILE | A | 538 | 33.103 | -20.328 | 56.029 | 1.00 | 10.47 |
| 4149 | CD1 | ILE | A | 538 | 33.284 | -21.191 | 57.365 | 1.00 | 6.46 |
| 4150 | CG2 | ILE | A | 538 | 34.138 | -18.257 | 56.991 | 1.00 | 10.45 |
| 4151 | C | ILE | A | 538 | 31.526 | -16.954 | 57.044 | 1.00 | 12.09 |
| 4152 | O | ILE | A | 538 | 31.613 | -16.289 | 56.072 | 1.00 | 12.11 |
| 4153 | N | GLN | A | 539 | 31.340 | -16.381 | 58.225 | 1.00 | 12.79 |
| 4154 | CA | GLN | A | 539 | 31.541 | -14.925 | 58.398 | 1.00 | 13.15 |
| 4155 | CB | GLN | A | 539 | 30.623 | -14.363 | 59.450 | 1.00 | 13.29 |
| 4156 | CG | GLN | A | 539 | 30.805 | -12.937 | 59.659 | 1.00 | 11.49 |
| 4157 | CD | GLN | A | 539 | 29.805 | -12.314 | 60.585 | 1.00 | 12.96 |
| 4158 | OE1 | GLN | A | 539 | 30.186 | -11.874 | 61.706 | 1.00 | 9.92 |
| 4159 | NE2 | GLN | A | 539 | 28.522 | -12.221 | 60.141 | 1.00 | 15.50 |
| 4160 | C | GLN | A | 539 | 33.007 | -14.709 | 58.813 | 1.00 | 13.96 |
| 4161 | O | GLN | A | 539 | 33.470 | -15.218 | 59.814 | 1.00 | 14.57 |
| 4162 | N | VAL | A | 540 | 33.748 | -13.981 | 58.001 | 1.00 | 13.99 |
| 4163 | CA | VAL | A | 540 | 35.158 | -13.702 | 58.264 | 1.00 | 12.97 |
| 4164 | CB | VAL | A | 540 | 36.069 | -14.224 | 57.162 | 1.00 | 12.76 |
| 4165 | CG1 | VAL | A | 540 | 35.652 | -13.656 | 55.795 | 1.00 | 9.30 |
| 4166 | CG2 | VAL | A | 540 | 37.587 | -13.910 | 57.511 | 1.00 | 8.79 |
| 4167 | C | VAL | A | 540 | 35.406 | -12.218 | 58.387 | 1.00 | 13.59 |
| 4168 | O | VAL | A | 540 | 34.628 | -11.370 | 57.868 | 1.00 | 11.02 |
| 4169 | N | TYR | A | 541 | 36.432 | -11.937 | 59.194 | 1.00 | 14.18 |
| 4170 | CA | TYR | A | 541 | 37.035 | -10.611 | 59.363 | 1.00 | 15.10 |
| 4171 | CB | TYR | A | 541 | 36.692 | -9.952 | 60.730 | 1.00 | 14.36 |
| 4172 | CG | TYR | A | 541 | 37.218 | -8.512 | 60.833 | 1.00 | 17.60 |
| 4173 | CD1 | TYR | A | 541 | 36.622 | -7.489 | 60.113 | 1.00 | 17.43 |

FIGURE 3 (Cont.)

| A | B | C | D | E | F | G | H | I | J |
|---|---|---|---|---|---|---|---|---|---|
| 4174 | CE1 | TYR | A | 541 | 37.104 | -6.219 | 60.170 | 1.00 | 16.06 |
| 4175 | CZ | TYR | A | 541 | 38.187 | -5.945 | 60.941 | 1.00 | 15.42 |
| 4176 | OH | TYR | A | 541 | 38.565 | -4.702 | 60.936 | 1.00 | 15.23 |
| 4177 | CE2 | TYR | A | 541 | 38.793 | -6.882 | 61.689 | 1.00 | 15.11 |
| 4178 | CD2 | TYR | A | 541 | 38.329 | -8.183 | 61.629 | 1.00 | 16.74 |
| 4179 | C | TYR | A | 541 | 38.545 | -10.874 | 59.155 | 1.00 | 15.43 |
| 4180 | O | TYR | A | 541 | 39.040 | -10.783 | 58.040 | 1.00 | 15.14 |
| 4181 | N | GLY | A | 542 | 39.291 | -11.270 | 60.175 | 1.00 | 14.32 |
| 4182 | CA | GLY | A | 542 | 40.667 | -11.645 | 59.925 | 1.00 | 15.44 |
| 4183 | C | GLY | A | 542 | 41.739 | -10.599 | 60.079 | 1.00 | 15.74 |
| 4184 | O | GLY | A | 542 | 42.945 | -10.959 | 60.034 | 1.00 | 17.53 |
| 4185 | N | GLY | A | 543 | 41.329 | -9.351 | 60.339 | 1.00 | 14.18 |
| 4186 | CA | GLY | A | 543 | 42.283 | -8.280 | 60.621 | 1.00 | 15.06 |
| 4187 | C | GLY | A | 543 | 43.260 | -8.441 | 61.787 | 1.00 | 15.07 |
| 4188 | O | GLY | A | 543 | 42.878 | -8.654 | 62.935 | 1.00 | 15.53 |
| 4189 | N | PRO | A | 544 | 44.533 | -8.207 | 61.514 | 1.00 | 15.13 |
| 4190 | CA | PRO | A | 544 | 45.558 | -8.347 | 62.519 | 1.00 | 14.17 |
| 4191 | CB | PRO | A | 544 | 46.742 | -7.571 | 61.905 | 1.00 | 12.90 |
| 4192 | CG | PRO | A | 544 | 46.244 | -6.798 | 60.846 | 1.00 | 14.71 |
| 4193 | CD | PRO | A | 544 | 45.106 | -7.605 | 60.295 | 1.00 | 15.50 |
| 4194 | C | PRO | A | 544 | 45.136 | -7.669 | 63.809 | 1.00 | 13.88 |
| 4195 | O | PRO | A | 544 | 44.800 | -6.466 | 63.734 | 1.00 | 13.96 |
| 4196 | N | CYS | A | 545 | 45.184 | -8.410 | 64.933 | 1.00 | 13.83 |
| 4197 | CA | CYS | A | 545 | 44.907 | -7.922 | 66.299 | 1.00 | 14.52 |
| 4198 | CB | CYS | A | 545 | 45.346 | -6.478 | 66.513 | 1.00 | 13.79 |
| 4199 | SG | CYS | A | 545 | 47.051 | -6.212 | 65.999 | 1.00 | 17.65 |
| 4200 | C | CYS | A | 545 | 43.445 | -8.010 | 66.626 | 1.00 | 15.26 |
| 4201 | O | CYS | A | 545 | 43.061 | -7.677 | 67.714 | 1.00 | 17.26 |
| 4202 | N | SER | A | 546 | 42.622 | -8.442 | 65.674 | 1.00 | 14.43 |
| 4203 | CA | SER | A | 546 | 41.197 | -8.627 | 65.882 | 1.00 | 14.02 |
| 4204 | CB | SER | A | 546 | 40.490 | -8.663 | 64.504 | 1.00 | 13.96 |
| 4205 | OG | SER | A | 546 | 40.632 | -9.924 | 63.851 | 1.00 | 14.48 |
| 4206 | C | SER | A | 546 | 40.965 | -9.946 | 66.575 | 1.00 | 13.43 |
| 4207 | O | SER | A | 546 | 41.902 | -10.694 | 66.740 | 1.00 | 11.89 |
| 4208 | N | GLN | A | 547 | 39.706 | -10.238 | 66.916 | 1.00 | 13.91 |
| 4209 | CA | GLN | A | 547 | 39.310 | -11.648 | 67.068 | 1.00 | 14.36 |
| 4210 | CB | GLN | A | 547 | 39.836 | -12.293 | 68.371 | 1.00 | 13.97 |
| 4211 | CG | GLN | A | 547 | 38.966 | -12.096 | 69.595 | 1.00 | 14.91 |
| 4212 | CD | GLN | A | 547 | 39.289 | -13.051 | 70.753 | 1.00 | 19.67 |
| 4213 | OE1 | GLN | A | 547 | 39.223 | -12.662 | 71.916 | 1.00 | 12.98 |
| 4214 | NE2 | GLN | A | 547 | 39.580 | -14.323 | 70.432 | 1.00 | 22.95 |
| 4215 | C | GLN | A | 547 | 37.800 | -11.801 | 66.988 | 1.00 | 14.36 |
| 4216 | O | GLN | A | 547 | 37.086 | -11.091 | 67.684 | 1.00 | 15.77 |
| 4217 | N | SER | A | 548 | 37.341 | -12.732 | 66.162 | 1.00 | 13.36 |
| 4218 | CA | SER | A | 548 | 35.938 | -12.914 | 65.872 | 1.00 | 14.31 |
| 4219 | CB | SER | A | 548 | 35.822 | -13.212 | 64.381 | 1.00 | 13.86 |
| 4220 | OG | SER | A | 548 | 36.282 | -12.104 | 63.619 | 1.00 | 16.42 |
| 4221 | C | SER | A | 548 | 35.263 | -14.038 | 66.678 | 1.00 | 14.79 |
| 4222 | O | SER | A | 548 | 34.003 | -14.071 | 66.829 | 1.00 | 16.14 |
| 4223 | N | VAL | A | 549 | 36.079 | -14.928 | 67.240 | 1.00 | 13.16 |
| 4224 | CA | VAL | A | 549 | 35.569 | -15.924 | 68.136 | 1.00 | 13.86 |

FIGURE 3 (Cont.)

| A | B | C | D | E | F | G | H | I | J |
|---|---|---|---|---|---|---|---|---|---|
| 4225 | CB | VAL | A | 549 | 36.366 | -17.203 | 68.076 | 1.00 | 13.16 |
| 4226 | CG1 | VAL | A | 549 | 35.617 | -18.262 | 68.761 | 1.00 | 10.93 |
| 4227 | CG2 | VAL | A | 549 | 36.603 | -17.593 | 66.591 | 1.00 | 14.95 |
| 4228 | C | VAL | A | 549 | 35.408 | -15.390 | 69.578 | 1.00 | 14.68 |
| 4229 | O | VAL | A | 549 | 36.367 | -15.193 | 70.317 | 1.00 | 15.11 |
| 4230 | N | ARG | A | 550 | 34.163 | -15.090 | 69.935 | 1.00 | 14.86 |
| 4231 | CA | ARG | A | 550 | 33.883 | -14.437 | 71.205 | 1.00 | 15.08 |
| 4232 | CB | ARG | A | 550 | 33.878 | -12.882 | 71.090 | 1.00 | 15.08 |
| 4233 | CG | ARG | A | 550 | 35.238 | -12.257 | 70.931 | 1.00 | 16.73 |
| 4234 | CD | ARG | A | 550 | 35.225 | -10.736 | 70.460 | 1.00 | 21.61 |
| 4235 | NE | ARG | A | 550 | 36.585 | -10.110 | 70.447 | 1.00 | 23.62 |
| 4236 | CZ | ARG | A | 550 | 36.815 | -8.771 | 70.519 | 1.00 | 26.38 |
| 4237 | NH1 | ARG | A | 550 | 35.784 | -7.939 | 70.656 | 1.00 | 26.59 |
| 4238 | NH2 | ARG | A | 550 | 38.066 | -8.249 | 70.463 | 1.00 | 22.17 |
| 4239 | C | ARG | A | 550 | 32.561 | -14.984 | 71.767 | 1.00 | 15.01 |
| 4240 | O | ARG | A | 550 | 31.704 | -15.464 | 71.050 | 1.00 | 14.95 |
| 4241 | N | SER | A | 551 | 32.426 | -14.804 | 73.073 | 1.00 | 15.49 |
| 4242 | CA | SER | A | 551 | 31.651 | -15.594 | 73.994 | 1.00 | 15.06 |
| 4243 | CB | SER | A | 551 | 32.635 | -15.945 | 75.111 | 1.00 | 17.05 |
| 4244 | OG | SER | A | 551 | 33.896 | -15.292 | 74.731 | 1.00 | 18.91 |
| 4245 | C | SER | A | 551 | 30.599 | -14.640 | 74.436 | 1.00 | 13.72 |
| 4246 | O | SER | A | 551 | 30.265 | -14.492 | 75.580 | 1.00 | 13.47 |
| 4247 | N | VAL | A | 552 | 30.064 | -14.001 | 73.412 | 1.00 | 13.06 |
| 4248 | CA | VAL | A | 552 | 29.438 | -12.687 | 73.486 | 1.00 | 10.40 |
| 4249 | CB | VAL | A | 552 | 30.123 | -11.669 | 72.630 | 1.00 | 9.26 |
| 4250 | CG1 | VAL | A | 552 | 29.215 | -10.498 | 72.412 | 1.00 | 7.24 |
| 4251 | CG2 | VAL | A | 552 | 31.271 | -11.237 | 73.305 | 1.00 | 7.29 |
| 4252 | C | VAL | A | 552 | 28.182 | -12.866 | 72.845 | 1.00 | 9.58 |
| 4253 | O | VAL | A | 552 | 28.149 | -13.287 | 71.733 | 1.00 | 9.33 |
| 4254 | N | PHE | A | 553 | 27.166 | -12.418 | 73.528 | 1.00 | 10.34 |
| 4255 | CA | PHE | A | 553 | 25.809 | -12.545 | 73.104 | 1.00 | 10.81 |
| 4256 | CB | PHE | A | 553 | 24.868 | -12.112 | 74.237 | 1.00 | 10.50 |
| 4257 | CG | PHE | A | 553 | 23.445 | -12.357 | 73.944 | 1.00 | 8.39 |
| 4258 | CD1 | PHE | A | 553 | 22.919 | -13.616 | 74.108 | 1.00 | 4.29 |
| 4259 | CE1 | PHE | A | 553 | 21.598 | -13.855 | 73.827 | 1.00 | 6.02 |
| 4260 | CZ | PHE | A | 553 | 20.763 | -12.796 | 73.384 | 1.00 | 5.88 |
| 4261 | CE2 | PHE | A | 553 | 21.271 | -11.533 | 73.256 | 1.00 | 5.23 |
| 4262 | CD2 | PHE | A | 553 | 22.621 | -11.315 | 73.490 | 1.00 | 6.95 |
| 4263 | C | PHE | A | 553 | 25.569 | -11.686 | 71.926 | 1.00 | 11.10 |
| 4264 | O | PHE | A | 553 | 25.845 | -10.505 | 71.956 | 1.00 | 11.09 |
| 4265 | N | ALA | A | 554 | 24.975 | -12.260 | 70.889 | 1.00 | 12.62 |
| 4266 | CA | ALA | A | 554 | 24.572 | -11.409 | 69.731 | 1.00 | 13.09 |
| 4267 | CB | ALA | A | 554 | 25.767 | -11.230 | 68.795 | 1.00 | 12.80 |
| 4268 | C | ALA | A | 554 | 23.343 | -12.001 | 69.010 | 1.00 | 14.30 |
| 4269 | O | ALA | A | 554 | 23.320 | -13.227 | 68.534 | 1.00 | 14.84 |
| 4270 | N | VAL | A | 555 | 22.257 | -11.231 | 69.032 | 1.00 | 13.09 |
| 4271 | CA | VAL | A | 555 | 21.237 | -11.589 | 68.071 | 1.00 | 13.15 |
| 4272 | CB | VAL | A | 555 | 19.825 | -11.415 | 68.521 | 1.00 | 12.99 |
| 4273 | CG1 | VAL | A | 555 | 18.962 | -12.215 | 67.601 | 1.00 | 11.44 |
| 4274 | CG2 | VAL | A | 555 | 19.654 | -11.895 | 69.885 | 1.00 | 11.57 |
| 4275 | C | VAL | A | 555 | 21.519 | -10.767 | 66.802 | 1.00 | 13.45 |

FIGURE 3 (Cont.)

| A | B | C | D | E | F | G | H | I | J |
|---|---|---|---|---|---|---|---|---|---|
| 4276 | O | VAL | A | 555 | 21.189 | -9.582 | 66.783 | 1.00 | 13.37 |
| 4277 | N | ASN | A | 556 | 22.139 | -11.416 | 65.806 | 1.00 | 13.15 |
| 4278 | CA | ASN | A | 556 | 22.492 | -10.783 | 64.609 | 1.00 | 14.79 |
| 4279 | CB | ASN | A | 556 | 23.930 | -10.296 | 64.681 | 1.00 | 15.48 |
| 4280 | CG | ASN | A | 556 | 24.996 | -11.423 | 64.873 | 1.00 | 18.36 |
| 4281 | OD1 | ASN | A | 556 | 26.159 | -11.060 | 65.196 | 1.00 | 22.85 |
| 4282 | ND2 | ASN | A | 556 | 24.648 | -12.745 | 64.678 | 1.00 | 12.68 |
| 4283 | C | ASN | A | 556 | 22.179 | -11.545 | 63.338 | 1.00 | 16.10 |
| 4284 | O | ASN | A | 556 | 21.601 | -12.636 | 63.375 | 1.00 | 15.64 |
| 4285 | N | TRP | A | 557 | 22.471 | -10.978 | 62.161 | 1.00 | 18.06 |
| 4286 | CA | TRP | A | 557 | 22.108 | -11.572 | 60.879 | 1.00 | 21.05 |
| 4287 | CB | TRP | A | 557 | 22.944 | -10.963 | 59.751 | 1.00 | 24.24 |
| 4288 | CG | TRP | A | 557 | 24.259 | -10.410 | 60.210 | 1.00 | 38.16 |
| 4289 | CD1 | TRP | A | 557 | 25.466 | -11.048 | 60.197 | 1.00 | 44.60 |
| 4290 | NE1 | TRP | A | 557 | 26.444 | -10.223 | 60.696 | 1.00 | 44.47 |
| 4291 | CE2 | TRP | A | 557 | 25.872 | -9.021 | 61.042 | 1.00 | 46.39 |
| 4292 | CD2 | TRP | A | 557 | 24.497 | -9.105 | 60.750 | 1.00 | 46.46 |
| 4293 | CE3 | TRP | A | 557 | 23.681 | -8.001 | 61.013 | 1.00 | 48.93 |
| 4294 | CZ3 | TRP | A | 557 | 24.256 | -6.866 | 61.553 | 1.00 | 52.17 |
| 4295 | CH2 | TRP | A | 557 | 25.632 | -6.808 | 61.835 | 1.00 | 51.75 |
| 4296 | CZ2 | TRP | A | 557 | 26.453 | -7.877 | 61.587 | 1.00 | 47.27 |
| 4297 | C | TRP | A | 557 | 22.284 | -13.086 | 60.904 | 1.00 | 19.83 |
| 4298 | O | TRP | A | 557 | 21.393 | -13.854 | 60.557 | 1.00 | 18.53 |
| 4299 | N | ILE | A | 558 | 23.516 | -13.532 | 61.102 | 1.00 | 19.06 |
| 4300 | CA | ILE | A | 558 | 23.837 | -14.935 | 60.971 | 1.00 | 18.60 |
| 4301 | CB | ILE | A | 558 | 25.358 | -15.217 | 61.111 | 1.00 | 19.25 |
| 4302 | CG1 | ILE | A | 558 | 25.910 | -14.584 | 62.402 | 1.00 | 17.80 |
| 4303 | CD1 | ILE | A | 558 | 27.310 | -15.032 | 62.697 | 1.00 | 20.13 |
| 4304 | CG2 | ILE | A | 558 | 26.137 | -14.685 | 59.852 | 1.00 | 18.70 |
| 4305 | C | ILE | A | 558 | 23.039 | -15.741 | 61.958 | 1.00 | 17.74 |
| 4306 | O | ILE | A | 558 | 22.720 | -16.938 | 61.672 | 1.00 | 18.05 |
| 4307 | N | SER | A | 559 | 22.693 | -15.108 | 63.088 | 1.00 | 15.85 |
| 4308 | CA | SER | A | 559 | 21.664 | -15.705 | 63.933 | 1.00 | 15.56 |
| 4309 | CB | SER | A | 559 | 21.373 | -14.894 | 65.193 | 1.00 | 15.45 |
| 4310 | OG | SER | A | 559 | 22.547 | -14.427 | 65.842 | 1.00 | 15.99 |
| 4311 | C | SER | A | 559 | 20.368 | -15.996 | 63.111 | 1.00 | 14.77 |
| 4312 | O | SER | A | 559 | 19.871 | -17.128 | 63.121 | 1.00 | 14.62 |
| 4313 | N | TYR | A | 560 | 19.867 | -14.986 | 62.400 | 1.00 | 13.67 |
| 4314 | CA | TYR | A | 560 | 18.673 | -15.114 | 61.562 | 1.00 | 13.20 |
| 4315 | CB | TYR | A | 560 | 18.288 | -13.800 | 60.792 | 1.00 | 12.55 |
| 4316 | CG | TYR | A | 560 | 17.586 | -14.042 | 59.440 | 1.00 | 12.59 |
| 4317 | CD1 | TYR | A | 560 | 16.461 | -14.853 | 59.376 | 1.00 | 13.62 |
| 4318 | CE1 | TYR | A | 560 | 15.824 | -15.112 | 58.202 | 1.00 | 15.44 |
| 4319 | CZ | TYR | A | 560 | 16.285 | -14.598 | 57.018 | 1.00 | 15.99 |
| 4320 | OH | TYR | A | 560 | 15.557 | -14.989 | 55.896 | 1.00 | 16.12 |
| 4321 | CE2 | TYR | A | 560 | 17.384 | -13.729 | 57.026 | 1.00 | 12.91 |
| 4322 | CD2 | TYR | A | 560 | 18.039 | -13.476 | 58.251 | 1.00 | 13.64 |
| 4323 | C | TYR | A | 560 | 18.837 | -16.217 | 60.577 | 1.00 | 13.07 |
| 4324 | O | TYR | A | 560 | 17.863 | -16.796 | 60.163 | 1.00 | 14.25 |
| 4325 | N | LEU | A | 561 | 20.046 | -16.500 | 60.143 | 1.00 | 12.29 |
| 4326 | CA | LEU | A | 561 | 20.176 | -17.361 | 58.992 | 1.00 | 11.38 |

FIGURE 3 (Cont.)

| A | B | C | D | E | F | G | H | I | J |
|---|---|---|---|---|---|---|---|---|---|
| 4327 | CB | LEU | A | 561 | 21.491 | -17.136 | 58.222 | 1.00 | 11.22 |
| 4328 | CG | LEU | A | 561 | 21.469 | -15.740 | 57.595 | 1.00 | 8.15 |
| 4329 | CD1 | LEU | A | 561 | 22.830 | -15.366 | 57.066 | 1.00 | 2.00 |
| 4330 | CD2 | LEU | A | 561 | 20.361 | -15.689 | 56.509 | 1.00 | 6.38 |
| 4331 | C | LEU | A | 561 | 20.119 | -18.736 | 59.458 | 1.00 | 11.61 |
| 4332 | O | LEU | A | 561 | 19.630 | -19.630 | 58.739 | 1.00 | 11.12 |
| 4333 | N | ALA | A | 562 | 20.641 | -18.950 | 60.646 | 1.00 | 11.54 |
| 4334 | CA | ALA | A | 562 | 20.762 | -20.332 | 61.034 | 1.00 | 13.14 |
| 4335 | CB | ALA | A | 562 | 21.814 | -20.509 | 62.065 | 1.00 | 13.69 |
| 4336 | C | ALA | A | 562 | 19.385 | -20.737 | 61.508 | 1.00 | 13.10 |
| 4337 | O | ALA | A | 562 | 18.886 | -21.835 | 61.177 | 1.00 | 11.98 |
| 4338 | N | SER | A | 563 | 18.752 | -19.740 | 62.147 | 1.00 | 12.99 |
| 4339 | CA | SER | A | 563 | 17.470 | -19.917 | 62.803 | 1.00 | 13.21 |
| 4340 | CB | SER | A | 563 | 17.067 | -18.637 | 63.551 | 1.00 | 12.53 |
| 4341 | OG | SER | A | 563 | 15.775 | -18.764 | 64.161 | 1.00 | 13.80 |
| 4342 | C | SER | A | 563 | 16.414 | -20.245 | 61.794 | 1.00 | 13.32 |
| 4343 | O | SER | A | 563 | 15.675 | -21.203 | 61.949 | 1.00 | 12.95 |
| 4344 | N | LYS | A | 564 | 16.310 | -19.420 | 60.766 | 1.00 | 13.24 |
| 4345 | CA | LYS | A | 564 | 15.189 | -19.575 | 59.821 | 1.00 | 14.40 |
| 4346 | CB | LYS | A | 564 | 14.504 | -18.239 | 59.492 | 1.00 | 12.96 |
| 4347 | CG | LYS | A | 564 | 13.546 | -18.269 | 58.290 | 1.00 | 13.94 |
| 4348 | CD | LYS | A | 564 | 11.991 | -17.922 | 58.607 | 1.00 | 17.28 |
| 4349 | CE | LYS | A | 564 | 11.468 | -16.438 | 58.217 | 1.00 | 18.24 |
| 4350 | NZ | LYS | A | 564 | 12.269 | -15.512 | 57.258 | 1.00 | 19.11 |
| 4351 | C | LYS | A | 564 | 15.627 | -20.284 | 58.530 | 1.00 | 14.87 |
| 4352 | O | LYS | A | 564 | 14.904 | -21.129 | 58.008 | 1.00 | 14.55 |
| 4353 | N | GLU | A | 565 | 16.801 | -19.910 | 58.026 | 1.00 | 14.30 |
| 4354 | CA | GLU | A | 565 | 17.165 | -20.244 | 56.677 | 1.00 | 14.07 |
| 4355 | CB | GLU | A | 565 | 17.912 | -19.045 | 56.002 | 1.00 | 13.68 |
| 4356 | CG | GLU | A | 565 | 17.062 | -18.012 | 55.208 | 1.00 | 14.19 |
| 4357 | CD | GLU | A | 565 | 15.566 | -18.377 | 54.974 | 1.00 | 20.62 |
| 4358 | OE1 | GLU | A | 565 | 14.663 | -17.468 | 55.138 | 1.00 | 22.89 |
| 4359 | OE2 | GLU | A | 565 | 15.268 | -19.555 | 54.606 | 1.00 | 20.29 |
| 4360 | C | GLU | A | 565 | 17.950 | -21.557 | 56.500 | 1.00 | 14.02 |
| 4361 | O | GLU | A | 565 | 18.256 | -21.866 | 55.356 | 1.00 | 15.56 |
| 4362 | N | GLY | A | 566 | 18.289 | -22.319 | 57.546 | 1.00 | 12.86 |
| 4363 | CA | GLY | A | 566 | 18.968 | -23.584 | 57.319 | 1.00 | 11.89 |
| 4364 | C | GLY | A | 566 | 20.500 | -23.532 | 57.274 | 1.00 | 12.25 |
| 4365 | O | GLY | A | 566 | 21.158 | -24.616 | 57.287 | 1.00 | 12.19 |
| 4366 | N | MET | A | 567 | 21.102 | -22.327 | 57.263 | 1.00 | 11.49 |
| 4367 | CA | MET | A | 567 | 22.583 | -22.263 | 57.184 | 1.00 | 11.28 |
| 4368 | CB | MET | A | 567 | 23.076 | -20.979 | 56.613 | 1.00 | 11.04 |
| 4369 | CG | MET | A | 567 | 22.461 | -20.617 | 55.308 | 1.00 | 11.92 |
| 4370 | SD | MET | A | 567 | 22.634 | -18.863 | 55.042 | 1.00 | 18.77 |
| 4371 | CE | MET | A | 567 | 21.283 | -18.760 | 53.861 | 1.00 | 17.29 |
| 4372 | C | MET | A | 567 | 23.380 | -22.457 | 58.463 | 1.00 | 11.00 |
| 4373 | O | MET | A | 567 | 23.122 | -21.821 | 59.442 | 1.00 | 10.72 |
| 4374 | N | VAL | A | 568 | 24.322 | -23.387 | 58.416 | 1.00 | 10.41 |
| 4375 | CA | VAL | A | 568 | 25.395 | -23.487 | 59.376 | 1.00 | 9.51 |
| 4376 | CB | VAL | A | 568 | 26.154 | -24.799 | 59.199 | 1.00 | 9.63 |
| 4377 | CG1 | VAL | A | 568 | 27.388 | -24.873 | 60.159 | 1.00 | 8.42 |

FIGURE 3 (Cont.)

| A | B | C | D | E | F | G | H | I | J |
|---|---|---|---|---|---|---|---|---|---|
| 4378 | CG2 | VAL | A | 568 | 25.226 | -25.947 | 59.482 | 1.00 | 11.47 |
| 4379 | C | VAL | A | 568 | 26.370 | -22.458 | 59.094 | 1.00 | 8.66 |
| 4380 | O | VAL | A | 568 | 26.722 | -22.328 | 57.984 | 1.00 | 8.86 |
| 4381 | N | ILE | A | 569 | 26.867 | -21.795 | 60.122 | 1.00 | 9.17 |
| 4382 | CA | ILE | A | 569 | 27.708 | -20.582 | 60.032 | 1.00 | 8.92 |
| 4383 | CB | ILE | A | 569 | 26.957 | -19.407 | 60.675 | 1.00 | 8.87 |
| 4384 | CG1 | ILE | A | 569 | 25.429 | -19.462 | 60.360 | 1.00 | 9.45 |
| 4385 | CD1 | ILE | A | 569 | 25.035 | -19.356 | 58.896 | 1.00 | 3.36 |
| 4386 | CG2 | ILE | A | 569 | 27.498 | -18.146 | 60.269 | 1.00 | 4.34 |
| 4387 | C | ILE | A | 569 | 28.958 | -20.773 | 60.851 | 1.00 | 10.44 |
| 4388 | O | ILE | A | 569 | 28.946 | -21.534 | 61.820 | 1.00 | 10.60 |
| 4389 | N | ALA | A | 570 | 30.050 | -20.098 | 60.499 | 1.00 | 10.46 |
| 4390 | CA | ALA | A | 570 | 31.292 | -20.272 | 61.269 | 1.00 | 10.96 |
| 4391 | CB | ALA | A | 570 | 32.008 | -21.464 | 60.850 | 1.00 | 9.62 |
| 4392 | C | ALA | A | 570 | 32.218 | -19.040 | 61.207 | 1.00 | 11.61 |
| 4393 | O | ALA | A | 570 | 32.232 | -18.243 | 60.221 | 1.00 | 12.43 |
| 4394 | N | LEU | A | 571 | 32.943 | -18.840 | 62.302 | 1.00 | 10.36 |
| 4395 | CA | LEU | A | 571 | 33.916 | -17.738 | 62.368 | 1.00 | 10.99 |
| 4396 | CB | LEU | A | 571 | 33.437 | -16.497 | 63.179 | 1.00 | 10.27 |
| 4397 | CG | LEU | A | 571 | 31.900 | -16.261 | 62.977 | 1.00 | 12.24 |
| 4398 | CD1 | LEU | A | 571 | 31.055 | -17.481 | 63.368 | 1.00 | 5.20 |
| 4399 | CD2 | LEU | A | 571 | 31.284 | -14.976 | 63.741 | 1.00 | 8.52 |
| 4400 | C | LEU | A | 571 | 35.133 | -18.461 | 62.920 | 1.00 | 9.68 |
| 4401 | O | LEU | A | 571 | 35.025 | -19.178 | 63.900 | 1.00 | 9.36 |
| 4402 | N | VAL | A | 572 | 36.218 | -18.373 | 62.156 | 1.00 | 9.26 |
| 4403 | CA | VAL | A | 572 | 37.493 | -18.907 | 62.464 | 1.00 | 10.75 |
| 4404 | CB | VAL | A | 572 | 38.029 | -19.739 | 61.322 | 1.00 | 11.55 |
| 4405 | CG1 | VAL | A | 572 | 39.259 | -20.616 | 61.832 | 1.00 | 11.95 |
| 4406 | CG2 | VAL | A | 572 | 36.969 | -20.653 | 60.741 | 1.00 | 11.36 |
| 4407 | C | VAL | A | 572 | 38.458 | -17.744 | 62.719 | 1.00 | 10.86 |
| 4408 | O | VAL | A | 572 | 38.457 | -16.747 | 62.023 | 1.00 | 9.81 |
| 4409 | N | ASP | A | 573 | 39.186 | -17.875 | 63.815 | 1.00 | 10.44 |
| 4410 | CA | ASP | A | 573 | 40.226 | -16.981 | 64.213 | 1.00 | 9.92 |
| 4411 | CB | ASP | A | 573 | 40.063 | -16.763 | 65.722 | 1.00 | 10.95 |
| 4412 | CG | ASP | A | 573 | 39.085 | -15.609 | 66.100 | 1.00 | 11.51 |
| 4413 | OD1 | ASP | A | 573 | 38.772 | -14.697 | 65.302 | 1.00 | 14.51 |
| 4414 | OD2 | ASP | A | 573 | 38.618 | -15.518 | 67.265 | 1.00 | 13.57 |
| 4415 | C | ASP | A | 573 | 41.548 | -17.785 | 63.948 | 1.00 | 10.68 |
| 4416 | O | ASP | A | 573 | 41.705 | -18.937 | 64.409 | 1.00 | 8.95 |
| 4417 | N | GLY | A | 574 | 42.468 | -17.242 | 63.176 | 1.00 | 10.29 |
| 4418 | CA | GLY | A | 574 | 43.713 | -17.917 | 62.964 | 1.00 | 11.65 |
| 4419 | C | GLY | A | 574 | 44.857 | -16.951 | 63.069 | 1.00 | 12.87 |
| 4420 | O | GLY | A | 574 | 45.051 | -16.207 | 64.035 | 1.00 | 13.45 |
| 4421 | N | ARG | A | 575 | 45.632 | -16.897 | 62.014 | 1.00 | 14.44 |
| 4422 | CA | ARG | A | 575 | 46.834 | -16.156 | 62.129 | 1.00 | 14.95 |
| 4423 | CB | ARG | A | 575 | 47.851 | -16.692 | 61.175 | 1.00 | 15.63 |
| 4424 | CG | ARG | A | 575 | 48.377 | -18.035 | 61.574 | 1.00 | 15.26 |
| 4425 | CD | ARG | A | 575 | 49.299 | -18.605 | 60.603 | 1.00 | 17.89 |
| 4426 | NE | ARG | A | 575 | 48.669 | -19.505 | 59.631 | 1.00 | 22.80 |
| 4427 | CZ | ARG | A | 575 | 49.374 | -20.157 | 58.700 | 1.00 | 25.89 |
| 4428 | NH1 | ARG | A | 575 | 50.694 | -20.015 | 58.620 | 1.00 | 27.49 |

FIGURE 3 (Cont.)

| A | B | C | D | E | F | G | H | I | J |
|---|---|---|---|---|---|---|---|---|---|
| 4429 | NH2 | ARG | A | 575 | 48.770 | -20.969 | 57.850 | 1.00 | 28.63 |
| 4430 | C | ARG | A | 575 | 46.466 | -14.735 | 61.860 | 1.00 | 15.92 |
| 4431 | O | ARG | A | 575 | 45.595 | -14.382 | 60.983 | 1.00 | 16.48 |
| 4432 | N | GLY | A | 576 | 47.064 | -13.913 | 62.707 | 1.00 | 16.10 |
| 4433 | CA | GLY | A | 576 | 46.855 | -12.477 | 62.682 | 1.00 | 15.88 |
| 4434 | C | GLY | A | 576 | 46.011 | -12.020 | 63.846 | 1.00 | 15.63 |
| 4435 | O | GLY | A | 576 | 46.046 | -10.861 | 64.181 | 1.00 | 16.27 |
| 4436 | N | THR | A | 577 | 45.288 | -12.958 | 64.441 | 1.00 | 15.40 |
| 4437 | CA | THR | A | 577 | 44.314 | -12.768 | 65.500 | 1.00 | 15.95 |
| 4438 | CB | THR | A | 577 | 43.457 | -14.050 | 65.515 | 1.00 | 16.46 |
| 4439 | OG1 | THR | A | 577 | 42.772 | -14.182 | 64.232 | 1.00 | 16.24 |
| 4440 | CG2 | THR | A | 577 | 42.390 | -13.943 | 66.541 | 1.00 | 17.77 |
| 4441 | C | THR | A | 577 | 45.025 | -12.640 | 66.828 | 1.00 | 15.45 |
| 4442 | O | THR | A | 577 | 45.962 | -13.378 | 67.061 | 1.00 | 15.76 |
| 4443 | N | ALA | A | 578 | 44.598 | -11.721 | 67.691 | 1.00 | 14.72 |
| 4444 | CA | ALA | A | 578 | 45.281 | -11.463 | 68.992 | 1.00 | 13.87 |
| 4445 | CB | ALA | A | 578 | 45.036 | -10.010 | 69.444 | 1.00 | 13.67 |
| 4446 | C | ALA | A | 578 | 44.900 | -12.408 | 70.137 | 1.00 | 13.14 |
| 4447 | O | ALA | A | 578 | 43.970 | -13.171 | 70.032 | 1.00 | 13.78 |
| 4448 | N | PHE | A | 579 | 45.685 | -12.356 | 71.201 | 1.00 | 12.39 |
| 4449 | CA | PHE | A | 579 | 45.345 | -12.867 | 72.535 | 1.00 | 11.81 |
| 4450 | CB | PHE | A | 579 | 43.871 | -12.592 | 72.846 | 1.00 | 11.61 |
| 4451 | CG | PHE | A | 579 | 43.447 | -11.171 | 72.527 | 1.00 | 9.34 |
| 4452 | CD1 | PHE | A | 579 | 44.193 | -10.081 | 73.007 | 1.00 | 8.78 |
| 4453 | CE1 | PHE | A | 579 | 43.869 | -8.747 | 72.700 | 1.00 | 9.02 |
| 4454 | CZ | PHE | A | 579 | 42.755 | -8.469 | 71.928 | 1.00 | 10.82 |
| 4455 | CE2 | PHE | A | 579 | 42.011 | -9.569 | 71.394 | 1.00 | 11.42 |
| 4456 | CD2 | PHE | A | 579 | 42.378 | -10.930 | 71.730 | 1.00 | 10.26 |
| 4457 | C | PHE | A | 579 | 45.738 | -14.328 | 72.737 | 1.00 | 12.03 |
| 4458 | O | PHE | A | 579 | 45.432 | -14.910 | 73.765 | 1.00 | 10.94 |
| 4459 | N | GLN | A | 580 | 46.388 | -14.945 | 71.739 | 1.00 | 13.07 |
| 4460 | CA | GLN | A | 580 | 47.001 | -16.252 | 71.943 | 1.00 | 13.72 |
| 4461 | CB | GLN | A | 580 | 46.131 | -17.354 | 71.335 | 1.00 | 14.99 |
| 4462 | CG | GLN | A | 580 | 45.711 | -18.430 | 72.323 | 1.00 | 27.33 |
| 4463 | CD | GLN | A | 580 | 46.195 | -19.809 | 71.922 | 1.00 | 36.83 |
| 4464 | OE1 | GLN | A | 580 | 45.512 | -20.808 | 72.146 | 1.00 | 34.60 |
| 4465 | NE2 | GLN | A | 580 | 47.380 | -19.867 | 71.324 | 1.00 | 39.88 |
| 4466 | C | GLN | A | 580 | 48.504 | -16.201 | 71.689 | 1.00 | 11.88 |
| 4467 | O | GLN | A | 580 | 49.197 | -17.159 | 71.437 | 1.00 | 10.04 |
| 4468 | N | GLY | A | 581 | 49.043 | -14.972 | 71.900 | 1.00 | 11.31 |
| 4469 | CA | GLY | A | 581 | 50.484 | -14.863 | 71.853 | 1.00 | 11.23 |
| 4470 | C | GLY | A | 581 | 50.927 | -14.421 | 70.457 | 1.00 | 11.88 |
| 4471 | O | GLY | A | 581 | 50.104 | -14.134 | 69.623 | 1.00 | 12.19 |
| 4472 | N | ASP | A | 582 | 52.232 | -14.401 | 70.244 | 1.00 | 11.67 |
| 4473 | CA | ASP | A | 582 | 52.874 | -13.641 | 69.226 | 1.00 | 11.49 |
| 4474 | CB | ASP | A | 582 | 54.135 | -12.948 | 69.817 | 1.00 | 12.09 |
| 4475 | CG | ASP | A | 582 | 53.827 | -11.563 | 70.567 | 1.00 | 13.20 |
| 4476 | OD1 | ASP | A | 582 | 54.819 | -10.912 | 71.158 | 1.00 | 10.28 |
| 4477 | OD2 | ASP | A | 582 | 52.627 | -11.116 | 70.635 | 1.00 | 13.29 |
| 4478 | C | ASP | A | 582 | 53.267 | -14.569 | 68.086 | 1.00 | 11.66 |
| 4479 | O | ASP | A | 582 | 53.441 | -14.081 | 66.970 | 1.00 | 10.95 |

FIGURE 3 (Cont.)

| A | B | C | D | E | F | G | H | I | J |
|---|---|---|---|---|---|---|---|---|---|
| 4480 | N | LYS | A | 583 | 53.465 | -15.887 | 68.320 | 1.00 | 11.86 |
| 4481 | CA | LYS | A | 583 | 53.697 | -16.761 | 67.164 | 1.00 | 12.29 |
| 4482 | CB | LYS | A | 583 | 54.098 | -18.163 | 67.529 | 1.00 | 12.77 |
| 4483 | CG | LYS | A | 583 | 54.984 | -18.830 | 66.413 | 1.00 | 14.18 |
| 4484 | CD | LYS | A | 583 | 55.647 | -20.131 | 66.856 | 1.00 | 13.18 |
| 4485 | CE | LYS | A | 583 | 54.950 | -21.359 | 66.230 | 1.00 | 13.10 |
| 4486 | NZ | LYS | A | 583 | 55.813 | -22.529 | 66.444 | 1.00 | 15.22 |
| 4487 | C | LYS | A | 583 | 52.446 | -16.775 | 66.293 | 1.00 | 12.66 |
| 4488 | O | LYS | A | 583 | 52.558 | -16.845 | 65.054 | 1.00 | 13.89 |
| 4489 | N | LEU | A | 584 | 51.263 | -16.648 | 66.915 | 1.00 | 11.39 |
| 4490 | CA | LEU | A | 584 | 49.987 | -16.450 | 66.181 | 1.00 | 8.84 |
| 4491 | CB | LEU | A | 584 | 48.734 | -16.711 | 67.061 | 1.00 | 8.55 |
| 4492 | CG | LEU | A | 584 | 47.672 | -17.727 | 66.540 | 1.00 | 8.39 |
| 4493 | CD1 | LEU | A | 584 | 46.227 | -17.556 | 67.025 | 1.00 | 2.00 |
| 4494 | CD2 | LEU | A | 584 | 47.655 | -17.778 | 65.041 | 1.00 | 2.00 |
| 4495 | C | LEU | A | 584 | 49.881 | -15.039 | 65.611 | 1.00 | 8.67 |
| 4496 | O | LEU | A | 584 | 49.669 | -14.845 | 64.385 | 1.00 | 9.11 |
| 4497 | N | LEU | A | 585 | 49.998 | -14.046 | 66.480 | 1.00 | 6.85 |
| 4498 | CA | LEU | A | 585 | 49.571 | -12.725 | 66.093 | 1.00 | 5.34 |
| 4499 | CB | LEU | A | 585 | 49.618 | -11.791 | 67.286 | 1.00 | 5.06 |
| 4500 | CG | LEU | A | 585 | 49.097 | -10.385 | 66.917 | 1.00 | 5.14 |
| 4501 | CD1 | LEU | A | 585 | 47.628 | -10.484 | 66.963 | 1.00 | 2.84 |
| 4502 | CD2 | LEU | A | 585 | 49.647 | -9.297 | 67.874 | 1.00 | 2.00 |
| 4503 | C | LEU | A | 585 | 50.445 | -12.162 | 64.971 | 1.00 | 5.12 |
| 4504 | O | LEU | A | 585 | 49.964 | -11.847 | 63.916 | 1.00 | 3.74 |
| 4505 | N | TYR | A | 586 | 51.737 | -12.077 | 65.220 | 1.00 | 4.89 |
| 4506 | CA | TYR | A | 586 | 52.659 | -11.493 | 64.272 | 1.00 | 6.30 |
| 4507 | CB | TYR | A | 586 | 54.010 | -11.232 | 64.971 | 1.00 | 6.74 |
| 4508 | CG | TYR | A | 586 | 53.966 | -10.189 | 66.073 | 1.00 | 7.60 |
| 4509 | CD1 | TYR | A | 586 | 53.264 | -8.946 | 65.891 | 1.00 | 8.39 |
| 4510 | CE1 | TYR | A | 586 | 53.223 | -8.013 | 66.881 | 1.00 | 7.15 |
| 4511 | CZ | TYR | A | 586 | 53.887 | -8.258 | 68.057 | 1.00 | 11.01 |
| 4512 | OH | TYR | A | 586 | 53.887 | -7.317 | 69.068 | 1.00 | 13.43 |
| 4513 | CE2 | TYR | A | 586 | 54.597 | -9.440 | 68.239 | 1.00 | 14.31 |
| 4514 | CD2 | TYR | A | 586 | 54.631 | -10.391 | 67.257 | 1.00 | 12.20 |
| 4515 | C | TYR | A | 586 | 52.928 | -12.328 | 63.027 | 1.00 | 7.23 |
| 4516 | O | TYR | A | 586 | 53.581 | -11.798 | 62.139 | 1.00 | 8.19 |
| 4517 | N | ALA | A | 587 | 52.494 | -13.613 | 62.964 | 1.00 | 6.76 |
| 4518 | CA | ALA | A | 587 | 52.699 | -14.448 | 61.767 | 1.00 | 6.08 |
| 4519 | CB | ALA | A | 587 | 51.948 | -15.675 | 61.886 | 1.00 | 4.46 |
| 4520 | C | ALA | A | 587 | 52.295 | -13.773 | 60.479 | 1.00 | 7.93 |
| 4521 | O | ALA | A | 587 | 52.783 | -14.123 | 59.428 | 1.00 | 8.91 |
| 4522 | N | VAL | A | 588 | 51.365 | -12.819 | 60.543 | 1.00 | 7.92 |
| 4523 | CA | VAL | A | 588 | 50.993 | -12.039 | 59.381 | 1.00 | 8.93 |
| 4524 | CB | VAL | A | 588 | 49.481 | -11.619 | 59.443 | 1.00 | 8.36 |
| 4525 | CG1 | VAL | A | 588 | 48.602 | -12.817 | 59.490 | 1.00 | 7.91 |
| 4526 | CG2 | VAL | A | 588 | 49.164 | -10.742 | 60.647 | 1.00 | 8.49 |
| 4527 | C | VAL | A | 588 | 51.903 | -10.805 | 59.085 | 1.00 | 9.94 |
| 4528 | O | VAL | A | 588 | 51.676 | -10.058 | 58.102 | 1.00 | 11.19 |
| 4529 | N | TYR | A | 589 | 52.947 | -10.586 | 59.872 | 1.00 | 11.04 |
| 4530 | CA | TYR | A | 589 | 53.739 | -9.374 | 59.695 | 1.00 | 11.11 |

FIGURE 3 (Cont.)

| A | B | C | D | E | F | G | H | I | J |
|---|---|---|---|---|---|---|---|---|---|
| 4531 | CB | TYR | A | 589 | 54.853 | -9.342 | 60.717 | 1.00 | 9.60 |
| 4532 | CG | TYR | A | 589 | 55.590 | -8.043 | 60.841 | 1.00 | 9.16 |
| 4533 | CD1 | TYR | A | 589 | 54.899 | -6.839 | 60.921 | 1.00 | 11.09 |
| 4534 | CE1 | TYR | A | 589 | 55.583 | -5.647 | 61.022 | 1.00 | 12.19 |
| 4535 | CZ | TYR | A | 589 | 56.969 | -5.683 | 61.094 | 1.00 | 10.53 |
| 4536 | OH | TYR | A | 589 | 57.618 | -4.502 | 61.189 | 1.00 | 12.33 |
| 4537 | CE2 | TYR | A | 589 | 57.654 | -6.850 | 61.019 | 1.00 | 6.10 |
| 4538 | CD2 | TYR | A | 589 | 56.979 | -8.015 | 60.907 | 1.00 | 5.62 |
| 4539 | C | TYR | A | 589 | 54.293 | -9.347 | 58.282 | 1.00 | 10.91 |
| 4540 | O | TYR | A | 589 | 55.146 | -10.099 | 57.928 | 1.00 | 9.89 |
| 4541 | N | ARG | A | 590 | 53.696 | -8.555 | 57.441 | 1.00 | 11.92 |
| 4542 | CA | ARG | A | 590 | 54.221 | -8.295 | 56.099 | 1.00 | 12.72 |
| 4543 | CB | ARG | A | 590 | 55.734 | -8.093 | 56.120 | 1.00 | 12.73 |
| 4544 | CG | ARG | A | 590 | 56.207 | -6.945 | 56.984 | 1.00 | 13.41 |
| 4545 | CD | ARG | A | 590 | 57.594 | -7.177 | 57.567 | 1.00 | 21.21 |
| 4546 | NE | ARG | A | 590 | 58.570 | -7.670 | 56.602 | 1.00 | 23.70 |
| 4547 | CZ | ARG | A | 590 | 59.204 | -6.907 | 55.713 | 1.00 | 26.77 |
| 4548 | NH1 | ARG | A | 590 | 58.966 | -5.570 | 55.630 | 1.00 | 22.55 |
| 4549 | NH2 | ARG | A | 590 | 60.102 | -7.497 | 54.902 | 1.00 | 27.70 |
| 4550 | C | ARG | A | 590 | 53.840 | -9.315 | 55.034 | 1.00 | 13.10 |
| 4551 | O | ARG | A | 590 | 54.136 | -9.095 | 53.872 | 1.00 | 14.10 |
| 4552 | N | LYS | A | 591 | 53.224 | -10.432 | 55.405 | 1.00 | 13.94 |
| 4553 | CA | LYS | A | 591 | 52.529 | -11.252 | 54.411 | 1.00 | 14.97 |
| 4554 | CB | LYS | A | 591 | 53.149 | -12.676 | 54.152 | 1.00 | 13.83 |
| 4555 | CG | LYS | A | 591 | 53.763 | -13.470 | 55.301 | 1.00 | 17.32 |
| 4556 | CD | LYS | A | 591 | 54.871 | -14.577 | 54.790 | 1.00 | 17.47 |
| 4557 | CE | LYS | A | 591 | 55.900 | -15.029 | 55.929 | 1.00 | 16.68 |
| 4558 | NZ | LYS | A | 591 | 57.370 | -14.646 | 55.821 | 1.00 | 16.34 |
| 4559 | C | LYS | A | 591 | 50.999 | -11.226 | 54.669 | 1.00 | 14.34 |
| 4560 | O | LYS | A | 591 | 50.363 | -12.273 | 54.905 | 1.00 | 15.99 |
| 4561 | N | LEU | A | 592 | 50.422 | -10.023 | 54.634 | 1.00 | 13.54 |
| 4562 | CA | LEU | A | 592 | 48.965 | -9.864 | 54.754 | 1.00 | 13.28 |
| 4563 | CB | LEU | A | 592 | 48.578 | -8.373 | 54.817 | 1.00 | 13.24 |
| 4564 | CG | LEU | A | 592 | 48.048 | -7.730 | 56.096 | 1.00 | 13.13 |
| 4565 | CD1 | LEU | A | 592 | 48.494 | -8.525 | 57.305 | 1.00 | 7.36 |
| 4566 | CD2 | LEU | A | 592 | 48.513 | -6.342 | 56.216 | 1.00 | 8.89 |
| 4567 | C | LEU | A | 592 | 48.155 | -10.494 | 53.582 | 1.00 | 14.34 |
| 4568 | O | LEU | A | 592 | 48.597 | -10.504 | 52.390 | 1.00 | 14.72 |
| 4569 | N | GLY | A | 593 | 46.930 | -10.935 | 53.914 | 1.00 | 14.33 |
| 4570 | CA | GLY | A | 593 | 46.114 | -11.693 | 52.992 | 1.00 | 14.24 |
| 4571 | C | GLY | A | 593 | 46.494 | -13.170 | 53.015 | 1.00 | 15.51 |
| 4572 | O | GLY | A | 593 | 45.645 | -14.053 | 52.854 | 1.00 | 16.92 |
| 4573 | N | VAL | A | 594 | 47.741 | -13.490 | 53.266 | 1.00 | 13.17 |
| 4574 | CA | VAL | A | 594 | 48.151 | -14.821 | 52.955 | 1.00 | 13.10 |
| 4575 | CB | VAL | A | 594 | 49.699 | -14.904 | 52.710 | 1.00 | 13.65 |
| 4576 | CG1 | VAL | A | 594 | 50.078 | -16.356 | 52.273 | 1.00 | 13.16 |
| 4577 | CG2 | VAL | A | 594 | 50.154 | -13.833 | 51.609 | 1.00 | 11.24 |
| 4578 | C | VAL | A | 594 | 47.637 | -15.860 | 53.937 | 1.00 | 12.82 |
| 4579 | O | VAL | A | 594 | 46.782 | -16.653 | 53.567 | 1.00 | 12.78 |
| 4580 | N | TYR | A | 595 | 48.115 | -15.851 | 55.179 | 1.00 | 12.06 |
| 4581 | CA | TYR | A | 595 | 47.757 | -16.931 | 56.123 | 1.00 | 12.45 |

FIGURE 3 (Cont.)

| A | B | C | D | E | F | G | H | I | J |
|---|---|---|---|---|---|---|---|---|---|
| 4582 | CB | TYR | A | 595 | 48.671 | -16.894 | 57.347 | 1.00 | 12.43 |
| 4583 | CG | TYR | A | 595 | 50.149 | -17.089 | 57.008 | 1.00 | 15.05 |
| 4584 | CD1 | TYR | A | 595 | 51.102 | -16.270 | 57.553 | 1.00 | 16.35 |
| 4585 | CE1 | TYR | A | 595 | 52.453 | -16.439 | 57.224 | 1.00 | 24.06 |
| 4586 | CZ | TYR | A | 595 | 52.851 | -17.447 | 56.316 | 1.00 | 24.25 |
| 4587 | OH | TYR | A | 595 | 54.196 | -17.594 | 56.013 | 1.00 | 27.94 |
| 4588 | CE2 | TYR | A | 595 | 51.895 | -18.274 | 55.746 | 1.00 | 21.46 |
| 4589 | CD2 | TYR | A | 595 | 50.568 | -18.105 | 56.101 | 1.00 | 18.14 |
| 4590 | C | TYR | A | 595 | 46.286 | -16.883 | 56.557 | 1.00 | 12.49 |
| 4591 | O | TYR | A | 595 | 45.619 | -17.938 | 56.830 | 1.00 | 11.41 |
| 4592 | N | GLU | A | 596 | 45.784 | -15.644 | 56.609 | 1.00 | 12.02 |
| 4593 | CA | GLU | A | 596 | 44.394 | -15.447 | 57.008 | 1.00 | 11.94 |
| 4594 | CB | GLU | A | 596 | 44.051 | -13.987 | 57.218 | 1.00 | 13.32 |
| 4595 | CG | GLU | A | 596 | 44.610 | -13.075 | 56.168 | 1.00 | 14.34 |
| 4596 | CD | GLU | A | 596 | 45.873 | -12.431 | 56.582 | 1.00 | 16.31 |
| 4597 | OE1 | GLU | A | 596 | 46.985 | -12.852 | 56.179 | 1.00 | 17.84 |
| 4598 | OE2 | GLU | A | 596 | 45.708 | -11.484 | 57.307 | 1.00 | 22.24 |
| 4599 | C | GLU | A | 596 | 43.506 | -16.138 | 56.016 | 1.00 | 11.91 |
| 4600 | O | GLU | A | 596 | 42.588 | -16.779 | 56.396 | 1.00 | 13.30 |
| 4601 | N | VAL | A | 597 | 43.852 | -16.134 | 54.756 | 1.00 | 10.88 |
| 4602 | CA | VAL | A | 597 | 43.090 | -16.877 | 53.799 | 1.00 | 10.06 |
| 4603 | CB | VAL | A | 597 | 43.360 | -16.455 | 52.325 | 1.00 | 10.82 |
| 4604 | CG1 | VAL | A | 597 | 42.923 | -17.587 | 51.281 | 1.00 | 7.82 |
| 4605 | CG2 | VAL | A | 597 | 42.622 | -15.182 | 52.042 | 1.00 | 7.58 |
| 4606 | C | VAL | A | 597 | 43.348 | -18.347 | 53.983 | 1.00 | 10.96 |
| 4607 | O | VAL | A | 597 | 42.413 | -19.134 | 53.990 | 1.00 | 9.95 |
| 4608 | N | GLU | A | 598 | 44.607 | -18.739 | 54.120 | 1.00 | 11.61 |
| 4609 | CA | GLU | A | 598 | 44.854 | -20.155 | 54.178 | 1.00 | 12.52 |
| 4610 | CB | GLU | A | 598 | 46.361 | -20.436 | 54.079 | 1.00 | 13.48 |
| 4611 | CG | GLU | A | 598 | 46.709 | -21.939 | 54.005 | 1.00 | 17.69 |
| 4612 | CD | GLU | A | 598 | 48.125 | -22.237 | 54.470 | 1.00 | 22.64 |
| 4613 | OE1 | GLU | A | 598 | 48.366 | -23.351 | 54.981 | 1.00 | 22.96 |
| 4614 | OE2 | GLU | A | 598 | 48.988 | -21.335 | 54.338 | 1.00 | 25.80 |
| 4615 | C | GLU | A | 598 | 44.139 | -20.829 | 55.415 | 1.00 | 12.62 |
| 4616 | O | GLU | A | 598 | 43.853 | -22.032 | 55.381 | 1.00 | 11.45 |
| 4617 | N | ASP | A | 599 | 43.782 | -20.045 | 56.459 | 1.00 | 12.38 |
| 4618 | CA | ASP | A | 599 | 43.226 | -20.631 | 57.719 | 1.00 | 12.29 |
| 4619 | CB | ASP | A | 599 | 43.682 | -19.843 | 58.969 | 1.00 | 11.04 |
| 4620 | CG | ASP | A | 599 | 45.155 | -20.001 | 59.248 | 1.00 | 12.73 |
| 4621 | OD1 | ASP | A | 599 | 45.798 | -20.909 | 58.686 | 1.00 | 12.24 |
| 4622 | OD2 | ASP | A | 599 | 45.798 | -19.265 | 60.009 | 1.00 | 18.02 |
| 4623 | C | ASP | A | 599 | 41.667 | -20.718 | 57.602 | 1.00 | 11.70 |
| 4624 | O | ASP | A | 599 | 41.033 | -21.626 | 58.108 | 1.00 | 11.89 |
| 4625 | N | GLN | A | 600 | 41.050 | -19.817 | 56.866 | 1.00 | 9.80 |
| 4626 | CA | GLN | A | 600 | 39.647 | -20.041 | 56.579 | 1.00 | 9.50 |
| 4627 | CB | GLN | A | 600 | 39.058 | -18.842 | 55.884 | 1.00 | 8.45 |
| 4628 | CG | GLN | A | 600 | 39.376 | -17.559 | 56.610 | 1.00 | 7.55 |
| 4629 | CD | GLN | A | 600 | 38.616 | -17.307 | 57.915 | 1.00 | 9.31 |
| 4630 | OE1 | GLN | A | 600 | 37.385 | -17.108 | 57.894 | 1.00 | 9.90 |
| 4631 | NE2 | GLN | A | 600 | 39.375 | -17.134 | 59.037 | 1.00 | 2.74 |
| 4632 | C | GLN | A | 600 | 39.502 | -21.243 | 55.674 | 1.00 | 10.25 |

FIGURE 3 (Cont.)

| A | B | C | D | E | F | G | H | I | J |
|---|---|---|---|---|---|---|---|---|---|
| 4633 | O | GLN | A | 600 | 38.459 | -21.868 | 55.598 | 1.00 | 10.93 |
| 4634 | N | ILE | A | 601 | 40.536 | -21.542 | 54.922 | 1.00 | 10.65 |
| 4635 | CA | ILE | A | 601 | 40.400 | -22.594 | 53.965 | 1.00 | 11.51 |
| 4636 | CB | ILE | A | 601 | 41.447 | -22.479 | 52.849 | 1.00 | 11.20 |
| 4637 | CG1 | ILE | A | 601 | 40.968 | -21.427 | 51.883 | 1.00 | 10.52 |
| 4638 | CD1 | ILE | A | 601 | 42.009 | -21.038 | 50.852 | 1.00 | 12.17 |
| 4639 | CG2 | ILE | A | 601 | 41.583 | -23.780 | 52.037 | 1.00 | 9.81 |
| 4640 | C | ILE | A | 601 | 40.477 | -23.876 | 54.794 | 1.00 | 12.33 |
| 4641 | O | ILE | A | 601 | 39.560 | -24.689 | 54.783 | 1.00 | 12.62 |
| 4642 | N | THR | A | 602 | 41.570 | -23.999 | 55.530 | 1.00 | 13.02 |
| 4643 | CA | THR | A | 602 | 41.791 | -25.070 | 56.478 | 1.00 | 13.47 |
| 4644 | CB | THR | A | 602 | 42.953 | -24.645 | 57.399 | 1.00 | 13.38 |
| 4645 | OG1 | THR | A | 602 | 44.195 | -24.707 | 56.685 | 1.00 | 14.93 |
| 4646 | CG2 | THR | A | 602 | 43.152 | -25.643 | 58.518 | 1.00 | 14.12 |
| 4647 | C | THR | A | 602 | 40.509 | -25.380 | 57.270 | 1.00 | 12.72 |
| 4648 | O | THR | A | 602 | 39.979 | -26.430 | 57.177 | 1.00 | 12.54 |
| 4649 | N | ALA | A | 603 | 40.010 | -24.453 | 58.040 | 1.00 | 13.09 |
| 4650 | CA | ALA | A | 603 | 38.724 | -24.656 | 58.679 | 1.00 | 13.77 |
| 4651 | CB | ALA | A | 603 | 38.170 | -23.343 | 59.125 | 1.00 | 13.36 |
| 4652 | C | ALA | A | 603 | 37.711 | -25.353 | 57.778 | 1.00 | 14.11 |
| 4653 | O | ALA | A | 603 | 37.254 | -26.445 | 58.076 | 1.00 | 13.61 |
| 4654 | N | VAL | A | 604 | 37.351 | -24.709 | 56.674 | 1.00 | 14.50 |
| 4655 | CA | VAL | A | 604 | 36.304 | -25.284 | 55.845 | 1.00 | 14.59 |
| 4656 | CB | VAL | A | 604 | 36.150 | -24.523 | 54.546 | 1.00 | 15.04 |
| 4657 | CG1 | VAL | A | 604 | 35.093 | -25.247 | 53.631 | 1.00 | 13.44 |
| 4658 | CG2 | VAL | A | 604 | 35.843 | -23.001 | 54.796 | 1.00 | 14.13 |
| 4659 | C | VAL | A | 604 | 36.626 | -26.774 | 55.566 | 1.00 | 14.97 |
| 4660 | O | VAL | A | 604 | 35.923 | -27.652 | 55.993 | 1.00 | 15.49 |
| 4661 | N | ARG | A | 605 | 37.715 | -27.037 | 54.869 | 1.00 | 15.00 |
| 4662 | CA | ARG | A | 605 | 38.221 | -28.390 | 54.661 | 1.00 | 15.18 |
| 4663 | CB | ARG | A | 605 | 39.728 | -28.334 | 54.289 | 1.00 | 15.84 |
| 4664 | CG | ARG | A | 605 | 40.044 | -28.464 | 52.770 | 1.00 | 16.02 |
| 4665 | CD | ARG | A | 605 | 41.561 | -28.340 | 52.376 | 1.00 | 16.78 |
| 4666 | NE | ARG | A | 605 | 41.832 | -27.483 | 51.231 | 1.00 | 15.94 |
| 4667 | CZ | ARG | A | 605 | 41.151 | -27.492 | 50.071 | 1.00 | 18.12 |
| 4668 | NH1 | ARG | A | 605 | 41.480 | -26.638 | 49.116 | 1.00 | 17.31 |
| 4669 | NH2 | ARG | A | 605 | 40.129 | -28.315 | 49.841 | 1.00 | 20.50 |
| 4670 | C | ARG | A | 605 | 38.001 | -29.337 | 55.862 | 1.00 | 15.04 |
| 4671 | O | ARG | A | 605 | 37.660 | -30.488 | 55.674 | 1.00 | 14.72 |
| 4672 | N | LYS | A | 606 | 38.233 | -28.822 | 57.071 | 1.00 | 15.13 |
| 4673 | CA | LYS | A | 606 | 38.010 | -29.528 | 58.354 | 1.00 | 14.83 |
| 4674 | CB | LYS | A | 606 | 38.927 | -28.986 | 59.471 | 1.00 | 14.64 |
| 4675 | CG | LYS | A | 606 | 39.922 | -29.995 | 60.036 | 1.00 | 13.98 |
| 4676 | CD | LYS | A | 606 | 41.190 | -30.206 | 59.148 | 1.00 | 14.55 |
| 4677 | CE | LYS | A | 606 | 41.871 | -31.714 | 59.160 | 1.00 | 13.37 |
| 4678 | NZ | LYS | A | 606 | 41.841 | -32.537 | 60.462 | 1.00 | 7.93 |
| 4679 | C | LYS | A | 606 | 36.513 | -29.561 | 58.778 | 1.00 | 14.49 |
| 4680 | O | LYS | A | 606 | 36.023 | -30.629 | 59.130 | 1.00 | 15.32 |
| 4681 | N | PHE | A | 607 | 35.752 | -28.468 | 58.677 | 1.00 | 13.72 |
| 4682 | CA | PHE | A | 607 | 34.295 | -28.588 | 58.823 | 1.00 | 13.15 |
| 4683 | CB | PHE | A | 607 | 33.629 | -27.256 | 58.612 | 1.00 | 12.87 |

FIGURE 3 (Cont.)

| A | B | C | D | E | F | G | H | I | J |
|---|---|---|---|---|---|---|---|---|---|
| 4684 | CG | PHE | A | 607 | 34.144 | -26.162 | 59.515 | 1.00 | 12.76 |
| 4685 | CD1 | PHE | A | 607 | 34.078 | -24.829 | 59.090 | 1.00 | 10.84 |
| 4686 | CE1 | PHE | A | 607 | 34.505 | -23.784 | 59.876 | 1.00 | 9.29 |
| 4687 | CZ | PHE | A | 607 | 35.068 | -24.064 | 61.104 | 1.00 | 14.26 |
| 4688 | CE2 | PHE | A | 607 | 35.161 | -25.425 | 61.572 | 1.00 | 11.70 |
| 4689 | CD2 | PHE | A | 607 | 34.680 | -26.455 | 60.772 | 1.00 | 12.28 |
| 4690 | C | PHE | A | 607 | 33.672 | -29.556 | 57.817 | 1.00 | 13.41 |
| 4691 | O | PHE | A | 607 | 32.672 | -30.203 | 58.126 | 1.00 | 13.97 |
| 4692 | N | ILE | A | 608 | 34.252 | -29.653 | 56.617 | 1.00 | 12.25 |
| 4693 | CA | ILE | A | 608 | 33.706 | -30.499 | 55.587 | 1.00 | 11.81 |
| 4694 | CB | ILE | A | 608 | 34.366 | -30.221 | 54.210 | 1.00 | 11.35 |
| 4695 | CG1 | ILE | A | 608 | 33.997 | -28.844 | 53.685 | 1.00 | 9.14 |
| 4696 | CD1 | ILE | A | 608 | 34.846 | -28.371 | 52.453 | 1.00 | 6.43 |
| 4697 | CG2 | ILE | A | 608 | 33.947 | -31.267 | 53.216 | 1.00 | 8.46 |
| 4698 | C | ILE | A | 608 | 33.854 | -31.980 | 55.980 | 1.00 | 12.69 |
| 4699 | O | ILE | A | 608 | 32.896 | -32.728 | 55.871 | 1.00 | 12.56 |
| 4700 | N | GLU | A | 609 | 35.032 | -32.409 | 56.430 | 1.00 | 13.38 |
| 4701 | CA | GLU | A | 609 | 35.167 | -33.793 | 56.895 | 1.00 | 14.81 |
| 4702 | CB | GLU | A | 609 | 36.662 | -34.229 | 56.934 | 1.00 | 15.48 |
| 4703 | CG | GLU | A | 609 | 37.731 | -33.277 | 57.496 | 1.00 | 17.08 |
| 4704 | CD | GLU | A | 609 | 38.968 | -34.024 | 58.076 | 1.00 | 20.41 |
| 4705 | OE1 | GLU | A | 609 | 39.473 | -35.026 | 57.478 | 1.00 | 16.53 |
| 4706 | OE2 | GLU | A | 609 | 39.444 | -33.614 | 59.163 | 1.00 | 21.73 |
| 4707 | C | GLU | A | 609 | 34.345 | -34.132 | 58.219 | 1.00 | 15.02 |
| 4708 | O | GLU | A | 609 | 34.172 | -35.292 | 58.614 | 1.00 | 15.29 |
| 4709 | N | MET | A | 610 | 33.790 | -33.111 | 58.870 | 1.00 | 15.00 |
| 4710 | CA | MET | A | 610 | 32.876 | -33.335 | 59.966 | 1.00 | 14.92 |
| 4711 | CB | MET | A | 610 | 32.600 | -32.017 | 60.710 | 1.00 | 16.28 |
| 4712 | CG | MET | A | 610 | 33.802 | -31.569 | 61.639 | 1.00 | 18.15 |
| 4713 | SD | MET | A | 610 | 33.645 | -29.990 | 62.645 | 1.00 | 20.37 |
| 4714 | CE | MET | A | 610 | 33.711 | -30.806 | 64.409 | 1.00 | 19.73 |
| 4715 | C | MET | A | 610 | 31.616 | -34.046 | 59.486 | 1.00 | 14.08 |
| 4716 | O | MET | A | 610 | 31.124 | -34.949 | 60.151 | 1.00 | 14.29 |
| 4717 | N | GLY | A | 611 | 31.130 | -33.678 | 58.313 | 1.00 | 13.31 |
| 4718 | CA | GLY | A | 611 | 30.237 | -34.515 | 57.526 | 1.00 | 12.32 |
| 4719 | C | GLY | A | 611 | 28.791 | -34.150 | 57.449 | 1.00 | 11.97 |
| 4720 | O | GLY | A | 611 | 28.015 | -34.902 | 56.961 | 1.00 | 12.15 |
| 4721 | N | PHE | A | 612 | 28.438 | -32.979 | 57.935 | 1.00 | 12.46 |
| 4722 | CA | PHE | A | 612 | 27.102 | -32.384 | 57.816 | 1.00 | 11.84 |
| 4723 | CB | PHE | A | 612 | 26.526 | -32.060 | 59.222 | 1.00 | 12.42 |
| 4724 | CG | PHE | A | 612 | 27.503 | -31.333 | 60.151 | 1.00 | 9.08 |
| 4725 | CD1 | PHE | A | 612 | 27.648 | -29.973 | 60.098 | 1.00 | 9.40 |
| 4726 | CE1 | PHE | A | 612 | 28.542 | -29.290 | 60.930 | 1.00 | 8.65 |
| 4727 | CZ | PHE | A | 612 | 29.314 | -29.997 | 61.839 | 1.00 | 10.43 |
| 4728 | CE2 | PHE | A | 612 | 29.183 | -31.382 | 61.908 | 1.00 | 8.19 |
| 4729 | CD2 | PHE | A | 612 | 28.273 | -32.033 | 61.066 | 1.00 | 9.35 |
| 4730 | C | PHE | A | 612 | 27.251 | -31.092 | 57.008 | 1.00 | 12.08 |
| 4731 | O | PHE | A | 612 | 26.418 | -30.188 | 57.086 | 1.00 | 13.20 |
| 4732 | N | ILE | A | 613 | 28.339 | -30.938 | 56.257 | 1.00 | 11.16 |
| 4733 | CA | ILE | A | 613 | 28.399 | -29.810 | 55.350 | 1.00 | 9.97 |
| 4734 | CB | ILE | A | 613 | 29.749 | -29.073 | 55.431 | 1.00 | 9.97 |

FIGURE 3 (Cont.)

| A | B | C | D | E | F | G | H | I | J |
|---|---|---|---|---|---|---|---|---|---|
| 4735 | CG1 | ILE | A | 613 | 30.020 | -28.452 | 56.820 | 1.00 | 8.67 |
| 4736 | CD1 | ILE | A | 613 | 28.850 | -27.889 | 57.547 | 1.00 | 6.92 |
| 4737 | CG2 | ILE | A | 613 | 29.804 | -28.048 | 54.326 | 1.00 | 6.40 |
| 4738 | C | ILE | A | 613 | 28.203 | -30.312 | 53.918 | 1.00 | 10.19 |
| 4739 | O | ILE | A | 613 | 28.819 | -31.300 | 53.484 | 1.00 | 8.85 |
| 4740 | N | ASP | A | 614 | 27.374 | -29.581 | 53.183 | 1.00 | 9.76 |
| 4741 | CA | ASP | A | 614 | 27.255 | -29.804 | 51.750 | 1.00 | 10.17 |
| 4742 | CB | ASP | A | 614 | 25.824 | -29.538 | 51.331 | 1.00 | 9.90 |
| 4743 | CG | ASP | A | 614 | 25.641 | -29.473 | 49.830 | 1.00 | 10.74 |
| 4744 | OD1 | ASP | A | 614 | 24.588 | -28.928 | 49.429 | 1.00 | 4.70 |
| 4745 | OD2 | ASP | A | 614 | 26.464 | -29.916 | 48.996 | 1.00 | 11.41 |
| 4746 | C | ASP | A | 614 | 28.277 | -28.915 | 51.029 | 1.00 | 10.81 |
| 4747 | O | ASP | A | 614 | 28.140 | -27.666 | 50.982 | 1.00 | 11.11 |
| 4748 | N | GLU | A | 615 | 29.288 | -29.592 | 50.481 | 1.00 | 10.81 |
| 4749 | CA | GLU | A | 615 | 30.496 | -29.015 | 49.857 | 1.00 | 11.62 |
| 4750 | CB | GLU | A | 615 | 31.493 | -30.132 | 49.417 | 1.00 | 11.81 |
| 4751 | CG | GLU | A | 615 | 30.954 | -31.583 | 49.515 | 1.00 | 16.20 |
| 4752 | CD | GLU | A | 615 | 32.043 | -32.628 | 49.463 | 1.00 | 20.20 |
| 4753 | OE1 | GLU | A | 615 | 31.755 | -33.714 | 48.908 | 1.00 | 25.77 |
| 4754 | OE2 | GLU | A | 615 | 33.178 | -32.394 | 49.966 | 1.00 | 18.11 |
| 4755 | C | GLU | A | 615 | 30.142 | -28.221 | 48.635 | 1.00 | 11.16 |
| 4756 | O | GLU | A | 615 | 30.822 | -27.280 | 48.277 | 1.00 | 9.88 |
| 4757 | N | LYS | A | 616 | 29.094 | -28.667 | 47.959 | 1.00 | 11.30 |
| 4758 | CA | LYS | A | 616 | 28.542 | -27.897 | 46.849 | 1.00 | 12.48 |
| 4759 | CB | LYS | A | 616 | 27.528 | -28.743 | 46.011 | 1.00 | 12.18 |
| 4760 | CG | LYS | A | 616 | 28.202 | -29.873 | 45.123 | 1.00 | 16.17 |
| 4761 | CD | LYS | A | 616 | 27.224 | -30.908 | 44.525 | 1.00 | 19.16 |
| 4762 | CE | LYS | A | 616 | 27.938 | -32.197 | 44.031 | 1.00 | 21.90 |
| 4763 | NZ | LYS | A | 616 | 27.877 | -33.375 | 44.992 | 1.00 | 24.39 |
| 4764 | C | LYS | A | 616 | 27.927 | -26.537 | 47.285 | 1.00 | 11.96 |
| 4765 | O | LYS | A | 616 | 27.682 | -25.713 | 46.436 | 1.00 | 12.93 |
| 4766 | N | ARG | A | 617 | 27.678 | -26.295 | 48.563 | 1.00 | 11.31 |
| 4767 | CA | ARG | A | 617 | 27.043 | -25.028 | 48.957 | 1.00 | 11.23 |
| 4768 | CB | ARG | A | 617 | 25.668 | -25.404 | 49.457 | 1.00 | 12.19 |
| 4769 | CG | ARG | A | 617 | 24.805 | -26.094 | 48.426 | 1.00 | 13.63 |
| 4770 | CD | ARG | A | 617 | 23.321 | -25.878 | 48.649 | 1.00 | 14.81 |
| 4771 | NE | ARG | A | 617 | 22.785 | -26.978 | 49.439 | 1.00 | 18.47 |
| 4772 | CZ | ARG | A | 617 | 21.870 | -26.856 | 50.401 | 1.00 | 19.10 |
| 4773 | NH1 | ARG | A | 617 | 21.444 | -27.945 | 51.086 | 1.00 | 16.15 |
| 4774 | NH2 | ARG | A | 617 | 21.345 | -25.654 | 50.648 | 1.00 | 18.00 |
| 4775 | C | ARG | A | 617 | 27.784 | -24.166 | 50.041 | 1.00 | 10.56 |
| 4776 | O | ARG | A | 617 | 27.451 | -24.175 | 51.239 | 1.00 | 10.43 |
| 4777 | N | ILE | A | 618 | 28.804 | -23.431 | 49.671 | 1.00 | 9.14 |
| 4778 | CA | ILE | A | 618 | 29.467 | -22.718 | 50.723 | 1.00 | 9.12 |
| 4779 | CB | ILE | A | 618 | 30.775 | -23.478 | 51.247 | 1.00 | 9.17 |
| 4780 | CG1 | ILE | A | 618 | 30.421 | -24.839 | 51.824 | 1.00 | 6.78 |
| 4781 | CD1 | ILE | A | 618 | 31.554 | -25.771 | 51.815 | 1.00 | 8.56 |
| 4782 | CG2 | ILE | A | 618 | 31.502 | -22.598 | 52.340 | 1.00 | 8.60 |
| 4783 | C | ILE | A | 618 | 29.823 | -21.348 | 50.337 | 1.00 | 9.07 |
| 4784 | O | ILE | A | 618 | 30.297 | -21.081 | 49.275 | 1.00 | 9.77 |
| 4785 | N | ALA | A | 619 | 29.676 | -20.461 | 51.256 | 1.00 | 9.51 |

FIGURE 3 (Cont.)

| A | B | C | D | E | F | G | H | I | J |
|---|---|---|---|---|---|---|---|---|---|
| 4786 | CA | ALA | A | 619 | 29.979 | -19.098 | 50.952 | 1.00 | 10.86 |
| 4787 | CB | ALA | A | 619 | 28.691 | -18.330 | 50.819 | 1.00 | 10.62 |
| 4788 | C | ALA | A | 619 | 30.794 | -18.539 | 52.080 | 1.00 | 12.51 |
| 4789 | O | ALA | A | 619 | 30.996 | -19.163 | 53.115 | 1.00 | 13.12 |
| 4790 | N | ILE | A | 620 | 31.217 | -17.318 | 51.906 | 1.00 | 13.35 |
| 4791 | CA | ILE | A | 620 | 31.996 | -16.646 | 52.917 | 1.00 | 13.40 |
| 4792 | CB | ILE | A | 620 | 33.479 | -16.996 | 52.743 | 1.00 | 13.78 |
| 4793 | CG1 | ILE | A | 620 | 34.414 | -16.025 | 53.475 | 1.00 | 14.69 |
| 4794 | CD1 | ILE | A | 620 | 35.824 | -16.651 | 53.697 | 1.00 | 8.65 |
| 4795 | CG2 | ILE | A | 620 | 33.884 | -17.130 | 51.233 | 1.00 | 11.93 |
| 4796 | C | ILE | A | 620 | 31.755 | -15.256 | 52.618 | 1.00 | 14.53 |
| 4797 | O | ILE | A | 620 | 31.867 | -14.844 | 51.462 | 1.00 | 16.67 |
| 4798 | N | TRP | A | 621 | 31.349 | -14.510 | 53.628 | 1.00 | 14.53 |
| 4799 | CA | TRP | A | 621 | 31.116 | -13.093 | 53.479 | 1.00 | 12.70 |
| 4800 | CB | TRP | A | 621 | 29.631 | -12.803 | 53.702 | 1.00 | 12.58 |
| 4801 | CG | TRP | A | 621 | 29.283 | -12.398 | 55.145 | 1.00 | 14.47 |
| 4802 | CD1 | TRP | A | 621 | 29.060 | -13.234 | 56.145 | 1.00 | 12.45 |
| 4803 | NE1 | TRP | A | 621 | 28.750 | -12.532 | 57.273 | 1.00 | 14.58 |
| 4804 | CE2 | TRP | A | 621 | 28.720 | -11.200 | 56.995 | 1.00 | 9.17 |
| 4805 | CD2 | TRP | A | 621 | 29.067 | -11.062 | 55.683 | 1.00 | 8.77 |
| 4806 | CE3 | TRP | A | 621 | 29.130 | -9.800 | 55.164 | 1.00 | 10.64 |
| 4807 | CZ3 | TRP | A | 621 | 28.897 | -8.718 | 55.977 | 1.00 | 10.03 |
| 4808 | CH2 | TRP | A | 621 | 28.604 | -8.882 | 57.288 | 1.00 | 13.30 |
| 4809 | CZ2 | TRP | A | 621 | 28.495 | -10.145 | 57.818 | 1.00 | 11.01 |
| 4810 | C | TRP | A | 621 | 31.960 | -12.362 | 54.498 | 1.00 | 12.73 |
| 4811 | O | TRP | A | 621 | 32.392 | -12.955 | 55.473 | 1.00 | 11.60 |
| 4812 | N | GLY | A | 622 | 32.143 | -11.054 | 54.270 | 1.00 | 12.02 |
| 4813 | CA | GLY | A | 622 | 32.806 | -10.199 | 55.213 | 1.00 | 12.09 |
| 4814 | C | GLY | A | 622 | 32.797 | -8.743 | 54.939 | 1.00 | 12.24 |
| 4815 | O | GLY | A | 622 | 32.431 | -8.391 | 53.862 | 1.00 | 13.74 |
| 4816 | N | TRP | A | 623 | 33.212 | -7.918 | 55.911 | 1.00 | 11.66 |
| 4817 | CA | TRP | A | 623 | 33.119 | -6.465 | 55.868 | 1.00 | 12.58 |
| 4818 | CB | TRP | A | 623 | 32.061 | -5.980 | 56.843 | 1.00 | 11.02 |
| 4819 | CG | TRP | A | 623 | 31.622 | -4.612 | 56.781 | 1.00 | 13.75 |
| 4820 | CD1 | TRP | A | 623 | 32.382 | -3.497 | 56.552 | 1.00 | 14.66 |
| 4821 | NE1 | TRP | A | 623 | 31.601 | -2.362 | 56.570 | 1.00 | 14.74 |
| 4822 | CE2 | TRP | A | 623 | 30.299 | -2.693 | 56.865 | 1.00 | 15.20 |
| 4823 | CD2 | TRP | A | 623 | 30.251 | -4.116 | 56.978 | 1.00 | 16.48 |
| 4824 | CE3 | TRP | A | 623 | 29.021 | -4.716 | 57.326 | 1.00 | 12.70 |
| 4825 | CZ3 | TRP | A | 623 | 27.875 | -3.904 | 57.416 | 1.00 | 15.67 |
| 4826 | CH2 | TRP | A | 623 | 27.956 | -2.486 | 57.297 | 1.00 | 14.84 |
| 4827 | CZ2 | TRP | A | 623 | 29.158 | -1.877 | 57.031 | 1.00 | 15.03 |
| 4828 | C | TRP | A | 623 | 34.451 | -5.895 | 56.221 | 1.00 | 13.24 |
| 4829 | O | TRP | A | 623 | 34.954 | -6.171 | 57.228 | 1.00 | 16.07 |
| 4830 | N | SER | A | 624 | 35.075 | -5.148 | 55.342 | 1.00 | 15.07 |
| 4831 | CA | SER | A | 624 | 36.226 | -4.302 | 55.665 | 1.00 | 16.21 |
| 4832 | CB | SER | A | 624 | 36.074 | -3.605 | 57.007 | 1.00 | 15.51 |
| 4833 | OG | SER | A | 624 | 36.949 | -2.544 | 57.045 | 1.00 | 16.34 |
| 4834 | C | SER | A | 624 | 37.515 | -5.064 | 55.484 | 1.00 | 16.43 |
| 4835 | O | SER | A | 624 | 37.753 | -5.517 | 54.336 | 1.00 | 18.83 |
| 4836 | N | TYR | A | 625 | 38.347 | -5.264 | 56.492 | 1.00 | 15.36 |

FIGURE 3 (Cont.)

| A | B | C | D | E | F | G | H | I | J |
|---|---|---|---|---|---|---|---|---|---|
| 4837 | CA | TYR | A | 625 | 39.242 | -6.395 | 56.351 | 1.00 | 14.66 |
| 4838 | CB | TYR | A | 625 | 40.123 | -6.583 | 57.599 | 1.00 | 14.31 |
| 4839 | CG | TYR | A | 625 | 41.492 | -7.224 | 57.309 | 1.00 | 10.39 |
| 4840 | CD1 | TYR | A | 625 | 41.587 | -8.605 | 57.055 | 1.00 | 7.83 |
| 4841 | CE1 | TYR | A | 625 | 42.856 | -9.234 | 56.806 | 1.00 | 5.06 |
| 4842 | CZ | TYR | A | 625 | 44.030 | -8.443 | 56.804 | 1.00 | 5.78 |
| 4843 | OH | TYR | A | 625 | 45.253 | -9.115 | 56.613 | 1.00 | 5.14 |
| 4844 | CE2 | TYR | A | 625 | 43.944 | -7.030 | 57.016 | 1.00 | 3.65 |
| 4845 | CD2 | TYR | A | 625 | 42.682 | -6.449 | 57.285 | 1.00 | 6.39 |
| 4846 | C | TYR | A | 625 | 38.455 | -7.669 | 56.032 | 1.00 | 15.04 |
| 4847 | O | TYR | A | 625 | 38.956 | -8.638 | 55.480 | 1.00 | 13.81 |
| 4848 | N | GLY | A | 626 | 37.175 | -7.641 | 56.337 | 1.00 | 15.70 |
| 4849 | CA | GLY | A | 626 | 36.374 | -8.829 | 56.151 | 1.00 | 16.69 |
| 4850 | C | GLY | A | 626 | 36.128 | -9.215 | 54.720 | 1.00 | 16.15 |
| 4851 | O | GLY | A | 626 | 35.874 | -10.395 | 54.370 | 1.00 | 18.83 |
| 4852 | N | GLY | A | 627 | 36.162 | -8.234 | 53.868 | 1.00 | 13.61 |
| 4853 | CA | GLY | A | 627 | 35.808 | -8.460 | 52.491 | 1.00 | 12.86 |
| 4854 | C | GLY | A | 627 | 37.054 | -8.553 | 51.702 | 1.00 | 12.04 |
| 4855 | O | GLY | A | 627 | 36.983 | -9.105 | 50.698 | 1.00 | 12.34 |
| 4856 | N | TYR | A | 628 | 38.140 | -7.913 | 52.090 | 1.00 | 11.43 |
| 4857 | CA | TYR | A | 628 | 39.431 | -8.321 | 51.680 | 1.00 | 11.89 |
| 4858 | CB | TYR | A | 628 | 40.432 | -7.731 | 52.618 | 1.00 | 11.71 |
| 4859 | CG | TYR | A | 628 | 41.847 | -7.932 | 52.227 | 1.00 | 16.10 |
| 4860 | CD1 | TYR | A | 628 | 42.743 | -8.668 | 53.023 | 1.00 | 18.56 |
| 4861 | CE1 | TYR | A | 628 | 44.115 | -8.855 | 52.613 | 1.00 | 16.59 |
| 4862 | CZ | TYR | A | 628 | 44.509 | -8.290 | 51.429 | 1.00 | 17.02 |
| 4863 | OH | TYR | A | 628 | 45.797 | -8.396 | 50.913 | 1.00 | 16.07 |
| 4864 | CE2 | TYR | A | 628 | 43.591 | -7.574 | 50.681 | 1.00 | 13.18 |
| 4865 | CD2 | TYR | A | 628 | 42.325 | -7.391 | 51.076 | 1.00 | 16.12 |
| 4866 | C | TYR | A | 628 | 39.518 | -9.869 | 51.745 | 1.00 | 12.73 |
| 4867 | O | TYR | A | 628 | 39.635 | -10.528 | 50.694 | 1.00 | 13.16 |
| 4868 | N | VAL | A | 629 | 39.434 | -10.485 | 52.924 | 1.00 | 11.39 |
| 4869 | CA | VAL | A | 629 | 39.787 | -11.910 | 52.943 | 1.00 | 12.54 |
| 4870 | CB | VAL | A | 629 | 40.379 | -12.437 | 54.267 | 1.00 | 11.92 |
| 4871 | CG1 | VAL | A | 629 | 40.744 | -11.357 | 55.192 | 1.00 | 10.65 |
| 4872 | CG2 | VAL | A | 629 | 39.438 | -13.440 | 54.929 | 1.00 | 14.30 |
| 4873 | C | VAL | A | 629 | 38.673 | -12.857 | 52.385 | 1.00 | 13.10 |
| 4874 | O | VAL | A | 629 | 38.988 | -13.918 | 51.774 | 1.00 | 12.36 |
| 4875 | N | SER | A | 630 | 37.406 | -12.494 | 52.548 | 1.00 | 12.75 |
| 4876 | CA | SER | A | 630 | 36.369 | -13.219 | 51.753 | 1.00 | 12.71 |
| 4877 | CB | SER | A | 630 | 34.975 | -12.662 | 52.041 | 1.00 | 12.76 |
| 4878 | OG | SER | A | 630 | 34.798 | -11.493 | 51.286 | 1.00 | 13.87 |
| 4879 | C | SER | A | 630 | 36.646 | -13.109 | 50.203 | 1.00 | 12.20 |
| 4880 | O | SER | A | 630 | 36.626 | -14.100 | 49.451 | 1.00 | 9.29 |
| 4881 | N | SER | A | 631 | 36.902 | -11.875 | 49.753 | 1.00 | 11.55 |
| 4882 | CA | SER | A | 631 | 37.203 | -11.660 | 48.327 | 1.00 | 12.48 |
| 4883 | CB | SER | A | 631 | 37.633 | -10.200 | 47.993 | 1.00 | 11.83 |
| 4884 | OG | SER | A | 631 | 36.499 | -9.302 | 48.057 | 1.00 | 14.43 |
| 4885 | C | SER | A | 631 | 38.330 | -12.600 | 47.986 | 1.00 | 12.88 |
| 4886 | O | SER | A | 631 | 38.235 | -13.385 | 47.067 | 1.00 | 13.04 |
| 4887 | N | LEU | A | 632 | 39.368 | -12.547 | 48.805 | 1.00 | 12.82 |

FIGURE 3 (Cont.)

| A | B | C | D | E | F | G | H | I | J |
|---|---|---|---|---|---|---|---|---|---|
| 4888 | CA | LEU | A | 632 | 40.614 | -13.228 | 48.563 | 1.00 | 13.35 |
| 4889 | CB | LEU | A | 632 | 41.661 | -12.667 | 49.547 | 1.00 | 13.19 |
| 4890 | CG | LEU | A | 632 | 43.004 | -12.230 | 49.007 | 1.00 | 13.85 |
| 4891 | CD1 | LEU | A | 632 | 42.852 | -11.338 | 47.823 | 1.00 | 11.96 |
| 4892 | CD2 | LEU | A | 632 | 43.803 | -11.520 | 50.125 | 1.00 | 15.63 |
| 4893 | C | LEU | A | 632 | 40.440 | -14.765 | 48.679 | 1.00 | 12.41 |
| 4894 | O | LEU | A | 632 | 41.147 | -15.538 | 48.047 | 1.00 | 12.10 |
| 4895 | N | ALA | A | 633 | 39.470 | -15.173 | 49.467 | 1.00 | 12.15 |
| 4896 | CA | ALA | A | 633 | 39.190 | -16.608 | 49.690 | 1.00 | 12.07 |
| 4897 | CB | ALA | A | 633 | 38.544 | -16.832 | 50.968 | 1.00 | 10.67 |
| 4898 | C | ALA | A | 633 | 38.321 | -17.188 | 48.599 | 1.00 | 11.93 |
| 4899 | O | ALA | A | 633 | 38.549 | -18.314 | 48.160 | 1.00 | 10.42 |
| 4900 | N | LEU | A | 634 | 37.311 | -16.422 | 48.176 | 1.00 | 12.68 |
| 4901 | CA | LEU | A | 634 | 36.534 | -16.809 | 47.019 | 1.00 | 12.46 |
| 4902 | CB | LEU | A | 634 | 35.533 | -15.760 | 46.731 | 1.00 | 13.56 |
| 4903 | CG | LEU | A | 634 | 34.363 | -16.197 | 45.866 | 1.00 | 15.51 |
| 4904 | CD1 | LEU | A | 634 | 33.740 | -17.467 | 46.339 | 1.00 | 14.37 |
| 4905 | CD2 | LEU | A | 634 | 33.395 | -15.048 | 45.920 | 1.00 | 16.95 |
| 4906 | C | LEU | A | 634 | 37.408 | -16.962 | 45.798 | 1.00 | 12.86 |
| 4907 | O | LEU | A | 634 | 37.179 | -17.798 | 44.945 | 1.00 | 12.92 |
| 4908 | N | ALA | A | 635 | 38.454 | -16.158 | 45.733 | 1.00 | 13.21 |
| 4909 | CA | ALA | A | 635 | 39.306 | -16.155 | 44.577 | 1.00 | 12.57 |
| 4910 | CB | ALA | A | 635 | 39.818 | -14.761 | 44.341 | 1.00 | 12.57 |
| 4911 | C | ALA | A | 635 | 40.468 | -17.092 | 44.700 | 1.00 | 13.49 |
| 4912 | O | ALA | A | 635 | 41.343 | -17.006 | 43.858 | 1.00 | 13.98 |
| 4913 | N | SER | A | 636 | 40.487 | -17.990 | 45.702 | 1.00 | 13.45 |
| 4914 | CA | SER | A | 636 | 41.709 | -18.759 | 46.018 | 1.00 | 13.98 |
| 4915 | CB | SER | A | 636 | 41.829 | -19.076 | 47.529 | 1.00 | 14.23 |
| 4916 | OG | SER | A | 636 | 40.760 | -18.507 | 48.239 | 1.00 | 13.87 |
| 4917 | C | SER | A | 636 | 41.895 | -20.060 | 45.223 | 1.00 | 13.63 |
| 4918 | O | SER | A | 636 | 42.788 | -20.821 | 45.496 | 1.00 | 12.81 |
| 4919 | N | GLY | A | 637 | 41.018 | -20.317 | 44.285 | 1.00 | 13.71 |
| 4920 | CA | GLY | A | 637 | 41.263 | -21.304 | 43.261 | 1.00 | 15.56 |
| 4921 | C | GLY | A | 637 | 41.026 | -22.741 | 43.659 | 1.00 | 16.59 |
| 4922 | O | GLY | A | 637 | 41.285 | -23.634 | 42.850 | 1.00 | 16.13 |
| 4923 | N | THR | A | 638 | 40.501 | -22.932 | 44.883 | 1.00 | 17.77 |
| 4924 | CA | THR | A | 638 | 40.291 | -24.242 | 45.548 | 1.00 | 18.30 |
| 4925 | CB | THR | A | 638 | 40.499 | -24.071 | 47.075 | 1.00 | 18.55 |
| 4926 | OG1 | THR | A | 638 | 39.379 | -23.392 | 47.641 | 1.00 | 19.89 |
| 4927 | CG2 | THR | A | 638 | 41.681 | -23.162 | 47.443 | 1.00 | 18.17 |
| 4928 | C | THR | A | 638 | 38.865 | -24.812 | 45.376 | 1.00 | 17.95 |
| 4929 | O | THR | A | 638 | 38.572 | -25.912 | 45.877 | 1.00 | 17.75 |
| 4930 | N | GLY | A | 639 | 37.959 | -24.015 | 44.777 | 1.00 | 17.48 |
| 4931 | CA | GLY | A | 639 | 36.593 | -24.446 | 44.504 | 1.00 | 16.92 |
| 4932 | C | GLY | A | 639 | 35.930 | -25.093 | 45.701 | 1.00 | 16.70 |
| 4933 | O | GLY | A | 639 | 35.228 | -26.047 | 45.595 | 1.00 | 15.17 |
| 4934 | N | LEU | A | 640 | 36.198 | -24.549 | 46.880 | 1.00 | 17.54 |
| 4935 | CA | LEU | A | 640 | 35.464 | -24.916 | 48.078 | 1.00 | 16.47 |
| 4936 | CB | LEU | A | 640 | 36.297 | -24.662 | 49.311 | 1.00 | 16.24 |
| 4937 | CG | LEU | A | 640 | 37.299 | -25.762 | 49.561 | 1.00 | 15.48 |
| 4938 | CD1 | LEU | A | 640 | 38.187 | -25.405 | 50.715 | 1.00 | 12.76 |

FIGURE 3 (Cont.)

| A | B | C | D | E | F | G | H | I | J |
|---|---|---|---|---|---|---|---|---|---|
| 4939 | CD2 | LEU | A | 640 | 36.572 | -27.090 | 49.804 | 1.00 | 14.98 |
| 4940 | C | LEU | A | 640 | 34.260 | -23.999 | 48.087 | 1.00 | 16.08 |
| 4941 | O | LEU | A | 640 | 33.121 | -24.473 | 48.248 | 1.00 | 15.75 |
| 4942 | N | PHE | A | 641 | 34.501 | -22.708 | 47.859 | 1.00 | 14.87 |
| 4943 | CA | PHE | A | 641 | 33.430 | -21.754 | 48.044 | 1.00 | 15.75 |
| 4944 | CB | PHE | A | 641 | 33.974 | -20.399 | 48.384 | 1.00 | 14.32 |
| 4945 | CG | PHE | A | 641 | 34.775 | -20.358 | 49.583 | 1.00 | 14.91 |
| 4946 | CD1 | PHE | A | 641 | 34.180 | -20.305 | 50.820 | 1.00 | 14.96 |
| 4947 | CE1 | PHE | A | 641 | 34.961 | -20.217 | 51.989 | 1.00 | 14.00 |
| 4948 | CZ | PHE | A | 641 | 36.336 | -20.187 | 51.926 | 1.00 | 14.48 |
| 4949 | CE2 | PHE | A | 641 | 36.944 | -20.230 | 50.667 | 1.00 | 18.71 |
| 4950 | CD2 | PHE | A | 641 | 36.149 | -20.307 | 49.496 | 1.00 | 15.25 |
| 4951 | C | PHE | A | 641 | 32.632 | -21.580 | 46.777 | 1.00 | 15.93 |
| 4952 | O | PHE | A | 641 | 33.194 | -21.180 | 45.794 | 1.00 | 17.47 |
| 4953 | N | LYS | A | 642 | 31.330 | -21.812 | 46.807 | 1.00 | 16.18 |
| 4954 | CA | LYS | A | 642 | 30.452 | -21.633 | 45.635 | 1.00 | 16.80 |
| 4955 | CB | LYS | A | 642 | 29.088 | -22.344 | 45.844 | 1.00 | 16.74 |
| 4956 | CG | LYS | A | 642 | 28.217 | -22.435 | 44.659 | 1.00 | 19.00 |
| 4957 | CD | LYS | A | 642 | 26.687 | -22.283 | 44.974 | 1.00 | 23.40 |
| 4958 | CE | LYS | A | 642 | 25.797 | -23.530 | 44.362 | 1.00 | 25.84 |
| 4959 | NZ | LYS | A | 642 | 25.728 | -23.695 | 42.857 | 1.00 | 21.29 |
| 4960 | C | LYS | A | 642 | 30.252 | -20.141 | 45.396 | 1.00 | 17.07 |
| 4961 | O | LYS | A | 642 | 30.258 | -19.685 | 44.217 | 1.00 | 18.16 |
| 4962 | N | CYS | A | 643 | 30.095 | -19.367 | 46.477 | 1.00 | 17.02 |
| 4963 | CA | CYS | A | 643 | 30.003 | -17.855 | 46.348 | 1.00 | 17.67 |
| 4964 | CB | CYS | A | 643 | 28.576 | -17.357 | 46.098 | 1.00 | 17.56 |
| 4965 | SG | CYS | A | 643 | 27.482 | -17.746 | 47.458 | 1.00 | 23.21 |
| 4966 | C | CYS | A | 643 | 30.588 | -17.103 | 47.530 | 1.00 | 15.89 |
| 4967 | O | CYS | A | 643 | 31.096 | -17.746 | 48.498 | 1.00 | 16.49 |
| 4968 | N | GLY | A | 644 | 30.574 | -15.774 | 47.425 | 1.00 | 12.87 |
| 4969 | CA | GLY | A | 644 | 31.068 | -14.930 | 48.485 | 1.00 | 12.14 |
| 4970 | C | GLY | A | 644 | 30.687 | -13.451 | 48.399 | 1.00 | 12.36 |
| 4971 | O | GLY | A | 644 | 30.349 | -12.957 | 47.362 | 1.00 | 12.48 |
| 4972 | N | ILE | A | 645 | 30.726 | -12.739 | 49.504 | 1.00 | 10.84 |
| 4973 | CA | ILE | A | 645 | 30.272 | -11.380 | 49.483 | 1.00 | 10.70 |
| 4974 | CB | ILE | A | 645 | 28.970 | -11.162 | 50.288 | 1.00 | 10.77 |
| 4975 | CG1 | ILE | A | 645 | 27.897 | -12.197 | 49.981 | 1.00 | 7.07 |
| 4976 | CD1 | ILE | A | 645 | 26.512 | -11.908 | 50.785 | 1.00 | 9.49 |
| 4977 | CG2 | ILE | A | 645 | 28.503 | -9.691 | 50.128 | 1.00 | 5.10 |
| 4978 | C | ILE | A | 645 | 31.357 | -10.573 | 50.126 | 1.00 | 11.96 |
| 4979 | O | ILE | A | 645 | 32.027 | -11.132 | 51.021 | 1.00 | 11.82 |
| 4980 | N | ALA | A | 646 | 31.504 | -9.304 | 49.705 | 1.00 | 10.31 |
| 4981 | CA | ALA | A | 646 | 32.462 | -8.395 | 50.317 | 1.00 | 10.58 |
| 4982 | CB | ALA | A | 646 | 33.583 | -8.304 | 49.494 | 1.00 | 9.85 |
| 4983 | C | ALA | A | 646 | 31.866 | -7.013 | 50.458 | 1.00 | 12.00 |
| 4984 | O | ALA | A | 646 | 31.690 | -6.286 | 49.504 | 1.00 | 12.56 |
| 4985 | N | VAL | A | 647 | 31.528 | -6.647 | 51.663 | 1.00 | 12.86 |
| 4986 | CA | VAL | A | 647 | 31.083 | -5.307 | 51.881 | 1.00 | 13.55 |
| 4987 | CB | VAL | A | 647 | 30.013 | -5.345 | 52.951 | 1.00 | 13.42 |
| 4988 | CG1 | VAL | A | 647 | 29.364 | -3.980 | 53.089 | 1.00 | 16.16 |
| 4989 | CG2 | VAL | A | 647 | 28.973 | -6.349 | 52.597 | 1.00 | 11.54 |

FIGURE 3 (Cont.)

| A | B | C | D | E | F | G | H | I | J |
|---|---|---|---|---|---|---|---|---|---|
| 4990 | C | VAL | A | 647 | 32.324 | -4.452 | 52.266 | 1.00 | 13.47 |
| 4991 | O | VAL | A | 647 | 33.158 | -4.881 | 53.061 | 1.00 | 11.89 |
| 4992 | N | ALA | A | 648 | 32.377 | -3.275 | 51.696 | 1.00 | 12.54 |
| 4993 | CA | ALA | A | 648 | 33.463 | -2.333 | 51.748 | 1.00 | 13.46 |
| 4994 | CB | ALA | A | 648 | 33.244 | -1.407 | 52.814 | 1.00 | 13.66 |
| 4995 | C | ALA | A | 648 | 34.866 | -2.887 | 51.897 | 1.00 | 13.33 |
| 4996 | O | ALA | A | 648 | 35.531 | -2.486 | 52.794 | 1.00 | 15.25 |
| 4997 | N | PRO | A | 649 | 35.297 | -3.819 | 51.065 | 1.00 | 13.42 |
| 4998 | CA | PRO | A | 649 | 36.636 | -4.397 | 51.192 | 1.00 | 13.75 |
| 4999 | CB | PRO | A | 649 | 36.633 | -5.476 | 50.140 | 1.00 | 11.52 |
| 5000 | CG | PRO | A | 649 | 35.557 | -5.119 | 49.252 | 1.00 | 11.02 |
| 5001 | CD | PRO | A | 649 | 34.505 | -4.536 | 50.048 | 1.00 | 13.47 |
| 5002 | C | PRO | A | 649 | 37.779 | -3.460 | 50.906 | 1.00 | 14.12 |
| 5003 | O | PRO | A | 649 | 37.791 | -2.849 | 49.896 | 1.00 | 15.24 |
| 5004 | N | VAL | A | 650 | 38.794 | -3.447 | 51.720 | 1.00 | 14.37 |
| 5005 | CA | VAL | A | 650 | 40.058 | -3.019 | 51.215 | 1.00 | 13.28 |
| 5006 | CB | VAL | A | 650 | 41.123 | -3.140 | 52.300 | 1.00 | 14.17 |
| 5007 | CG1 | VAL | A | 650 | 42.482 | -3.325 | 51.649 | 1.00 | 7.16 |
| 5008 | CG2 | VAL | A | 650 | 41.115 | -1.813 | 53.233 | 1.00 | 13.77 |
| 5009 | C | VAL | A | 650 | 40.446 | -3.918 | 50.037 | 1.00 | 14.13 |
| 5010 | O | VAL | A | 650 | 40.337 | -5.154 | 50.149 | 1.00 | 14.72 |
| 5011 | N | SER | A | 651 | 40.933 | -3.313 | 48.940 | 1.00 | 13.23 |
| 5012 | CA | SER | A | 651 | 41.398 | -4.050 | 47.724 | 1.00 | 13.03 |
| 5013 | CB | SER | A | 651 | 40.758 | -3.400 | 46.502 | 1.00 | 13.27 |
| 5014 | OG | SER | A | 651 | 41.311 | -2.092 | 46.254 | 1.00 | 16.60 |
| 5015 | C | SER | A | 651 | 42.909 | -4.134 | 47.528 | 1.00 | 12.89 |
| 5016 | O | SER | A | 651 | 43.408 | -5.003 | 46.902 | 1.00 | 12.66 |
| 5017 | N | SER | A | 652 | 43.641 | -3.189 | 48.087 | 1.00 | 14.21 |
| 5018 | CA | SER | A | 652 | 45.090 | -3.256 | 48.187 | 1.00 | 15.25 |
| 5019 | CB | SER | A | 652 | 45.667 | -2.943 | 46.806 | 1.00 | 14.95 |
| 5020 | OG | SER | A | 652 | 46.562 | -1.833 | 46.841 | 1.00 | 18.04 |
| 5021 | C | SER | A | 652 | 45.666 | -2.245 | 49.250 | 1.00 | 14.95 |
| 5022 | O | SER | A | 652 | 45.206 | -1.081 | 49.413 | 1.00 | 16.14 |
| 5023 | N | TRP | A | 653 | 46.723 | -2.653 | 49.910 | 1.00 | 13.58 |
| 5024 | CA | TRP | A | 653 | 47.191 | -1.866 | 51.023 | 1.00 | 13.09 |
| 5025 | CB | TRP | A | 653 | 48.152 | -2.737 | 51.815 | 1.00 | 12.08 |
| 5026 | CG | TRP | A | 653 | 47.386 | -3.886 | 52.332 | 1.00 | 11.78 |
| 5027 | CD1 | TRP | A | 653 | 47.461 | -5.209 | 51.947 | 1.00 | 12.61 |
| 5028 | NE1 | TRP | A | 653 | 46.485 | -5.941 | 52.607 | 1.00 | 4.60 |
| 5029 | CE2 | TRP | A | 653 | 45.786 | -5.113 | 53.442 | 1.00 | 7.02 |
| 5030 | CD2 | TRP | A | 653 | 46.263 | -3.806 | 53.236 | 1.00 | 9.81 |
| 5031 | CE3 | TRP | A | 653 | 45.661 | -2.757 | 53.944 | 1.00 | 6.95 |
| 5032 | CZ3 | TRP | A | 653 | 44.666 | -3.054 | 54.815 | 1.00 | 6.65 |
| 5033 | CH2 | TRP | A | 653 | 44.177 | -4.352 | 54.937 | 1.00 | 7.35 |
| 5034 | CZ2 | TRP | A | 653 | 44.742 | -5.389 | 54.283 | 1.00 | 5.97 |
| 5035 | C | TRP | A | 653 | 47.760 | -0.514 | 50.604 | 1.00 | 13.29 |
| 5036 | O | TRP | A | 653 | 47.925 | 0.354 | 51.411 | 1.00 | 14.07 |
| 5037 | N | GLU | A | 654 | 47.986 | -0.315 | 49.316 | 1.00 | 13.55 |
| 5038 | CA | GLU | A | 654 | 48.320 | 0.979 | 48.697 | 1.00 | 13.93 |
| 5039 | CB | GLU | A | 654 | 48.517 | 0.741 | 47.183 | 1.00 | 14.72 |
| 5040 | CG | GLU | A | 654 | 49.161 | 1.836 | 46.334 | 1.00 | 20.37 |

FIGURE 3 (Cont.)

| A | B | C | D | E | F | G | H | I | J |
|---|---|---|---|---|---|---|---|---|---|
| 5041 | CD | GLU | A | 654 | 48.933 | 1.601 | 44.836 | 1.00 | 24.97 |
| 5042 | OE1 | GLU | A | 654 | 49.500 | 2.372 | 44.042 | 1.00 | 26.69 |
| 5043 | OE2 | GLU | A | 654 | 48.171 | 0.641 | 44.432 | 1.00 | 23.80 |
| 5044 | C | GLU | A | 654 | 47.221 | 1.985 | 48.952 | 1.00 | 12.33 |
| 5045 | O | GLU | A | 654 | 47.481 | 3.173 | 49.049 | 1.00 | 11.75 |
| 5046 | N | TYR | A | 655 | 45.983 | 1.499 | 49.064 | 1.00 | 13.37 |
| 5047 | CA | TYR | A | 655 | 44.802 | 2.358 | 49.119 | 1.00 | 13.96 |
| 5048 | CB | TYR | A | 655 | 43.631 | 1.697 | 48.398 | 1.00 | 14.70 |
| 5049 | CG | TYR | A | 655 | 43.817 | 1.535 | 46.927 | 1.00 | 14.36 |
| 5050 | CD1 | TYR | A | 655 | 44.450 | 2.463 | 46.201 | 1.00 | 15.50 |
| 5051 | CE1 | TYR | A | 655 | 44.614 | 2.301 | 44.817 | 1.00 | 15.29 |
| 5052 | CZ | TYR | A | 655 | 44.179 | 1.167 | 44.167 | 1.00 | 15.82 |
| 5053 | OH | TYR | A | 655 | 44.393 | 1.009 | 42.775 | 1.00 | 12.80 |
| 5054 | CE2 | TYR | A | 655 | 43.533 | 0.227 | 44.915 | 1.00 | 15.17 |
| 5055 | CD2 | TYR | A | 655 | 43.365 | 0.412 | 46.278 | 1.00 | 15.34 |
| 5056 | C | TYR | A | 655 | 44.370 | 2.704 | 50.524 | 1.00 | 13.82 |
| 5057 | O | TYR | A | 655 | 43.524 | 3.544 | 50.698 | 1.00 | 16.65 |
| 5058 | N | TYR | A | 656 | 44.990 | 2.107 | 51.526 | 1.00 | 14.46 |
| 5059 | CA | TYR | A | 656 | 44.550 | 2.239 | 52.927 | 1.00 | 12.77 |
| 5060 | CB | TYR | A | 656 | 44.415 | 0.877 | 53.593 | 1.00 | 11.13 |
| 5061 | CG | TYR | A | 656 | 43.466 | 0.949 | 54.730 | 1.00 | 16.75 |
| 5062 | CD1 | TYR | A | 656 | 42.263 | 1.774 | 54.645 | 1.00 | 13.82 |
| 5063 | CE1 | TYR | A | 656 | 41.365 | 1.862 | 55.719 | 1.00 | 15.50 |
| 5064 | CZ | TYR | A | 656 | 41.641 | 1.199 | 56.922 | 1.00 | 17.53 |
| 5065 | OH | TYR | A | 656 | 40.741 | 1.291 | 57.953 | 1.00 | 18.27 |
| 5066 | CE2 | TYR | A | 656 | 42.781 | 0.385 | 57.022 | 1.00 | 16.53 |
| 5067 | CD2 | TYR | A | 656 | 43.709 | 0.266 | 55.918 | 1.00 | 12.60 |
| 5068 | C | TYR | A | 656 | 45.425 | 3.129 | 53.748 | 1.00 | 12.41 |
| 5069 | O | TYR | A | 656 | 46.593 | 3.444 | 53.338 | 1.00 | 12.62 |
| 5070 | N | ALA | A | 657 | 44.864 | 3.606 | 54.859 | 1.00 | 13.20 |
| 5071 | CA | ALA | A | 657 | 45.628 | 4.467 | 55.775 | 1.00 | 12.38 |
| 5072 | CB | ALA | A | 657 | 44.858 | 4.750 | 57.063 | 1.00 | 12.40 |
| 5073 | C | ALA | A | 657 | 46.963 | 3.867 | 56.134 | 1.00 | 13.70 |
| 5074 | O | ALA | A | 657 | 47.071 | 2.614 | 56.419 | 1.00 | 13.93 |
| 5075 | N | SER | A | 658 | 47.941 | 4.797 | 56.208 | 1.00 | 13.26 |
| 5076 | CA | SER | A | 658 | 49.338 | 4.559 | 56.575 | 1.00 | 13.48 |
| 5077 | CB | SER | A | 658 | 50.134 | 5.888 | 56.601 | 1.00 | 13.29 |
| 5078 | OG | SER | A | 658 | 49.445 | 6.923 | 57.300 | 1.00 | 15.07 |
| 5079 | C | SER | A | 658 | 49.456 | 3.915 | 57.950 | 1.00 | 14.15 |
| 5080 | O | SER | A | 658 | 50.037 | 2.853 | 58.122 | 1.00 | 12.14 |
| 5081 | N | VAL | A | 659 | 48.881 | 4.578 | 58.927 | 1.00 | 14.41 |
| 5082 | CA | VAL | A | 659 | 49.032 | 4.145 | 60.269 | 1.00 | 14.99 |
| 5083 | CB | VAL | A | 659 | 48.153 | 4.924 | 61.175 | 1.00 | 14.50 |
| 5084 | CG1 | VAL | A | 659 | 48.114 | 4.245 | 62.508 | 1.00 | 15.32 |
| 5085 | CG2 | VAL | A | 659 | 48.714 | 6.349 | 61.308 | 1.00 | 16.72 |
| 5086 | C | VAL | A | 659 | 48.649 | 2.714 | 60.329 | 1.00 | 14.14 |
| 5087 | O | VAL | A | 659 | 49.408 | 1.886 | 60.768 | 1.00 | 15.96 |
| 5088 | N | TYR | A | 660 | 47.499 | 2.370 | 59.836 | 1.00 | 12.83 |
| 5089 | CA | TYR | A | 660 | 47.157 | 0.989 | 59.951 | 1.00 | 12.37 |
| 5090 | CB | TYR | A | 660 | 45.779 | 0.825 | 59.472 | 1.00 | 11.68 |
| 5091 | CG | TYR | A | 660 | 45.222 | -0.520 | 59.550 | 1.00 | 11.72 |

FIGURE 3 (Cont.)

| A | B | C | D | E | F | G | H | I | J |
|---|---|---|---|---|---|---|---|---|---|
| 5092 | CD1 | TYR | A | 660 | 44.262 | -0.818 | 60.512 | 1.00 | 16.15 |
| 5093 | CE1 | TYR | A | 660 | 43.685 | -2.065 | 60.567 | 1.00 | 16.29 |
| 5094 | CZ | TYR | A | 660 | 44.102 | -3.073 | 59.646 | 1.00 | 17.90 |
| 5095 | OH | TYR | A | 660 | 43.567 | -4.334 | 59.731 | 1.00 | 21.06 |
| 5096 | CE2 | TYR | A | 660 | 45.020 | -2.772 | 58.652 | 1.00 | 16.13 |
| 5097 | CD2 | TYR | A | 660 | 45.548 | -1.474 | 58.595 | 1.00 | 13.55 |
| 5098 | C | TYR | A | 660 | 48.108 | 0.111 | 59.153 | 1.00 | 12.38 |
| 5099 | O | TYR | A | 660 | 48.531 | -0.865 | 59.585 | 1.00 | 12.74 |
| 5100 | N | THR | A | 661 | 48.411 | 0.468 | 57.944 | 1.00 | 13.18 |
| 5101 | CA | THR | A | 661 | 48.935 | -0.501 | 57.012 | 1.00 | 13.65 |
| 5102 | CB | THR | A | 661 | 48.716 | 0.043 | 55.570 | 1.00 | 14.57 |
| 5103 | OG1 | THR | A | 661 | 47.355 | 0.530 | 55.374 | 1.00 | 13.58 |
| 5104 | CG2 | THR | A | 661 | 48.876 | -1.093 | 54.586 | 1.00 | 14.25 |
| 5105 | C | THR | A | 661 | 50.434 | -0.765 | 57.197 | 1.00 | 13.99 |
| 5106 | O | THR | A | 661 | 50.911 | -1.929 | 57.126 | 1.00 | 15.09 |
| 5107 | N | GLU | A | 662 | 51.159 | 0.322 | 57.411 | 1.00 | 13.87 |
| 5108 | CA | GLU | A | 662 | 52.587 | 0.294 | 57.458 | 1.00 | 15.23 |
| 5109 | CB | GLU | A | 662 | 53.192 | 1.716 | 57.496 | 1.00 | 14.05 |
| 5110 | CG | GLU | A | 662 | 52.739 | 2.597 | 56.371 | 1.00 | 13.13 |
| 5111 | CD | GLU | A | 662 | 53.419 | 3.926 | 56.365 | 1.00 | 14.86 |
| 5112 | OE1 | GLU | A | 662 | 53.085 | 4.706 | 55.455 | 1.00 | 14.11 |
| 5113 | OE2 | GLU | A | 662 | 54.290 | 4.172 | 57.232 | 1.00 | 14.08 |
| 5114 | C | GLU | A | 662 | 52.901 | -0.489 | 58.728 | 1.00 | 16.61 |
| 5115 | O | GLU | A | 662 | 53.838 | -1.211 | 58.730 | 1.00 | 17.72 |
| 5116 | N | ARG | A | 663 | 52.083 | -0.338 | 59.783 | 1.00 | 18.16 |
| 5117 | CA | ARG | A | 663 | 52.072 | -1.225 | 60.948 | 1.00 | 18.30 |
| 5118 | CB | ARG | A | 663 | 50.668 | -1.267 | 61.603 | 1.00 | 19.06 |
| 5119 | CG | ARG | A | 663 | 50.634 | -1.995 | 63.011 | 1.00 | 15.86 |
| 5120 | CD | ARG | A | 663 | 50.439 | -1.072 | 64.163 | 1.00 | 12.31 |
| 5121 | NE | ARG | A | 663 | 50.312 | -1.857 | 65.362 | 1.00 | 12.66 |
| 5122 | CZ | ARG | A | 663 | 50.609 | -1.480 | 66.630 | 1.00 | 14.73 |
| 5123 | NH1 | ARG | A | 663 | 50.411 | -2.364 | 67.603 | 1.00 | 15.66 |
| 5124 | NH2 | ARG | A | 663 | 51.010 | -0.247 | 66.954 | 1.00 | 12.55 |
| 5125 | C | ARG | A | 663 | 52.330 | -2.647 | 60.630 | 1.00 | 17.86 |
| 5126 | O | ARG | A | 663 | 53.120 | -3.258 | 61.310 | 1.00 | 18.38 |
| 5127 | N | PHE | A | 664 | 51.575 | -3.215 | 59.692 | 1.00 | 17.50 |
| 5128 | CA | PHE | A | 664 | 51.641 | -4.681 | 59.513 | 1.00 | 17.48 |
| 5129 | CB | PHE | A | 664 | 50.249 | -5.330 | 59.520 | 1.00 | 17.24 |
| 5130 | CG | PHE | A | 664 | 49.330 | -4.786 | 60.575 | 1.00 | 16.20 |
| 5131 | CD1 | PHE | A | 664 | 48.524 | -3.700 | 60.313 | 1.00 | 11.35 |
| 5132 | CE1 | PHE | A | 664 | 47.628 | -3.189 | 61.294 | 1.00 | 11.47 |
| 5133 | CZ | PHE | A | 664 | 47.584 | -3.665 | 62.524 | 1.00 | 9.54 |
| 5134 | CE2 | PHE | A | 664 | 48.423 | -4.769 | 62.842 | 1.00 | 16.69 |
| 5135 | CD2 | PHE | A | 664 | 49.304 | -5.329 | 61.849 | 1.00 | 14.82 |
| 5136 | C | PHE | A | 664 | 52.274 | -5.053 | 58.229 | 1.00 | 17.92 |
| 5137 | O | PHE | A | 664 | 52.549 | -6.232 | 58.014 | 1.00 | 18.40 |
| 5138 | N | MET | A | 665 | 52.460 | -4.060 | 57.360 | 1.00 | 17.80 |
| 5139 | CA | MET | A | 665 | 52.864 | -4.320 | 55.973 | 1.00 | 18.43 |
| 5140 | CB | MET | A | 665 | 51.871 | -3.657 | 54.989 | 1.00 | 18.20 |
| 5141 | CG | MET | A | 665 | 50.791 | -4.550 | 54.387 | 1.00 | 17.96 |
| 5142 | SD | MET | A | 665 | 51.167 | -6.347 | 53.990 | 1.00 | 19.11 |

FIGURE 3 (Cont.)

| A | B | C | D | E | F | G | H | I | J |
|---|---|---|---|---|---|---|---|---|---|
| 5143 | CE | MET | A | 665 | 52.076 | -6.485 | 52.482 | 1.00 | 19.73 |
| 5144 | C | MET | A | 665 | 54.282 | -3.815 | 55.715 | 1.00 | 18.61 |
| 5145 | O | MET | A | 665 | 54.908 | -4.165 | 54.739 | 1.00 | 18.82 |
| 5146 | N | GLY | A | 666 | 54.795 | -3.003 | 56.622 | 1.00 | 19.28 |
| 5147 | CA | GLY | A | 666 | 56.025 | -2.249 | 56.394 | 1.00 | 19.24 |
| 5148 | C | GLY | A | 666 | 55.762 | -1.144 | 55.393 | 1.00 | 20.27 |
| 5149 | O | GLY | A | 666 | 54.623 | -0.671 | 55.203 | 1.00 | 20.26 |
| 5150 | N | LEU | A | 667 | 56.820 | -0.762 | 54.702 | 1.00 | 21.14 |
| 5151 | CA | LEU | A | 667 | 56.724 | 0.227 | 53.635 | 1.00 | 21.64 |
| 5152 | CB | LEU | A | 667 | 57.877 | 1.231 | 53.761 | 1.00 | 22.58 |
| 5153 | CG | LEU | A | 667 | 57.109 | 2.331 | 54.520 | 1.00 | 25.34 |
| 5154 | CD1 | LEU | A | 667 | 57.245 | 2.158 | 56.079 | 1.00 | 24.99 |
| 5155 | CD2 | LEU | A | 667 | 57.482 | 3.727 | 53.964 | 1.00 | 28.23 |
| 5156 | C | LEU | A | 667 | 56.543 | -0.314 | 52.194 | 1.00 | 20.84 |
| 5157 | O | LEU | A | 667 | 56.946 | -1.456 | 51.862 | 1.00 | 20.63 |
| 5158 | N | PRO | A | 668 | 55.832 | 0.469 | 51.374 | 1.00 | 20.02 |
| 5159 | CA | PRO | A | 668 | 55.675 | 0.157 | 49.963 | 1.00 | 19.20 |
| 5160 | CB | PRO | A | 668 | 54.330 | 0.786 | 49.647 | 1.00 | 19.42 |
| 5161 | CG | PRO | A | 668 | 54.165 | 1.869 | 50.620 | 1.00 | 18.98 |
| 5162 | CD | PRO | A | 668 | 55.054 | 1.638 | 51.771 | 1.00 | 19.05 |
| 5163 | C | PRO | A | 668 | 56.796 | 0.695 | 49.032 | 1.00 | 19.54 |
| 5164 | O | PRO | A | 668 | 56.413 | 1.233 | 48.004 | 1.00 | 19.78 |
| 5165 | N | THR | A | 669 | 58.095 | 0.522 | 49.349 | 1.00 | 19.35 |
| 5166 | CA | THR | A | 669 | 59.257 | 0.860 | 48.450 | 1.00 | 20.02 |
| 5167 | CB | THR | A | 669 | 60.283 | 1.765 | 49.127 | 1.00 | 20.07 |
| 5168 | OG1 | THR | A | 669 | 61.057 | 0.949 | 50.021 | 1.00 | 21.88 |
| 5169 | CG2 | THR | A | 669 | 59.655 | 2.794 | 50.022 | 1.00 | 18.32 |
| 5170 | C | THR | A | 669 | 60.074 | -0.373 | 48.050 | 1.00 | 20.18 |
| 5171 | O | THR | A | 669 | 59.917 | -1.418 | 48.651 | 1.00 | 19.99 |
| 5172 | N | LYS | A | 670 | 60.944 | -0.233 | 47.052 | 1.00 | 20.37 |
| 5173 | CA | LYS | A | 670 | 61.943 | -1.309 | 46.730 | 1.00 | 21.52 |
| 5174 | CB | LYS | A | 670 | 63.145 | -0.790 | 45.820 | 1.00 | 21.70 |
| 5175 | CG | LYS | A | 670 | 63.285 | -1.347 | 44.288 | 1.00 | 23.58 |
| 5176 | CD | LYS | A | 670 | 62.463 | -0.476 | 43.177 | 1.00 | 24.86 |
| 5177 | CE | LYS | A | 670 | 61.668 | -1.293 | 42.070 | 1.00 | 25.67 |
| 5178 | NZ | LYS | A | 670 | 60.141 | -1.101 | 42.036 | 1.00 | 21.60 |
| 5179 | C | LYS | A | 670 | 62.506 | -1.927 | 48.036 | 1.00 | 21.12 |
| 5180 | O | LYS | A | 670 | 62.280 | -3.092 | 48.307 | 1.00 | 21.00 |
| 5181 | N | ASP | A | 671 | 63.194 | -1.097 | 48.835 | 1.00 | 20.86 |
| 5182 | CA | ASP | A | 671 | 63.955 | -1.537 | 50.019 | 1.00 | 20.94 |
| 5183 | CB | ASP | A | 671 | 64.882 | -0.415 | 50.621 | 1.00 | 21.34 |
| 5184 | CG | ASP | A | 671 | 64.158 | 0.988 | 50.897 | 1.00 | 22.80 |
| 5185 | OD1 | ASP | A | 671 | 64.934 | 1.965 | 51.106 | 1.00 | 20.89 |
| 5186 | OD2 | ASP | A | 671 | 62.912 | 1.245 | 50.943 | 1.00 | 19.66 |
| 5187 | C | ASP | A | 671 | 63.138 | -2.206 | 51.129 | 1.00 | 20.79 |
| 5188 | O | ASP | A | 671 | 63.746 | -2.909 | 51.936 | 1.00 | 19.83 |
| 5189 | N | ASP | A | 672 | 61.801 | -2.018 | 51.170 | 1.00 | 20.42 |
| 5190 | CA | ASP | A | 672 | 60.962 | -2.707 | 52.177 | 1.00 | 20.73 |
| 5191 | CB | ASP | A | 672 | 60.046 | -1.741 | 52.995 | 1.00 | 20.26 |
| 5192 | CG | ASP | A | 672 | 60.246 | -1.897 | 54.492 | 1.00 | 21.77 |
| 5193 | OD1 | ASP | A | 672 | 59.383 | -2.480 | 55.169 | 1.00 | 24.71 |

FIGURE 3 (Cont.)

| A | B | C | D | E | F | G | H | I | J |
|---|---|---|---|---|---|---|---|---|---|
| 5194 | OD2 | ASP | A | 672 | 61.285 | -1.528 | 55.091 | 1.00 | 20.09 |
| 5195 | C | ASP | A | 672 | 60.162 | -3.852 | 51.570 | 1.00 | 20.41 |
| 5196 | O | ASP | A | 672 | 60.731 | -4.866 | 51.256 | 1.00 | 20.92 |
| 5197 | N | ASN | A | 673 | 58.866 | -3.665 | 51.390 | 1.00 | 19.65 |
| 5198 | CA | ASN | A | 673 | 57.918 | -4.711 | 51.063 | 1.00 | 19.83 |
| 5199 | CB | ASN | A | 673 | 57.068 | -4.917 | 52.319 | 1.00 | 19.79 |
| 5200 | CG | ASN | A | 673 | 56.404 | -6.303 | 52.406 | 1.00 | 18.17 |
| 5201 | OD1 | ASN | A | 673 | 55.364 | -6.429 | 53.008 | 1.00 | 15.25 |
| 5202 | ND2 | ASN | A | 673 | 57.057 | -7.339 | 51.882 | 1.00 | 18.68 |
| 5203 | C | ASN | A | 673 | 56.992 | -4.282 | 49.876 | 1.00 | 20.61 |
| 5204 | O | ASN | A | 673 | 55.987 | -4.962 | 49.565 | 1.00 | 21.11 |
| 5205 | N | LEU | A | 674 | 57.305 | -3.137 | 49.241 | 1.00 | 20.75 |
| 5206 | CA | LEU | A | 674 | 56.633 | -2.722 | 48.030 | 1.00 | 19.68 |
| 5207 | CB | LEU | A | 674 | 57.588 | -2.012 | 47.035 | 1.00 | 19.48 |
| 5208 | CG | LEU | A | 674 | 57.316 | -2.069 | 45.493 | 1.00 | 20.84 |
| 5209 | CD1 | LEU | A | 674 | 57.310 | -0.717 | 44.843 | 1.00 | 20.53 |
| 5210 | CD2 | LEU | A | 674 | 58.324 | -2.995 | 44.706 | 1.00 | 22.57 |
| 5211 | C | LEU | A | 674 | 56.083 | -3.965 | 47.367 | 1.00 | 19.73 |
| 5212 | O | LEU | A | 674 | 54.890 | -4.026 | 47.040 | 1.00 | 19.03 |
| 5213 | N | GLU | A | 675 | 56.950 | -4.947 | 47.118 | 1.00 | 19.51 |
| 5214 | CA | GLU | A | 675 | 56.558 | -5.962 | 46.175 | 1.00 | 19.88 |
| 5215 | CB | GLU | A | 675 | 57.751 | -6.740 | 45.659 | 1.00 | 20.33 |
| 5216 | CG | GLU | A | 675 | 58.075 | -8.016 | 46.425 | 1.00 | 25.27 |
| 5217 | CD | GLU | A | 675 | 57.834 | -9.263 | 45.578 | 1.00 | 29.29 |
| 5218 | OE1 | GLU | A | 675 | 56.616 | -9.536 | 45.238 | 1.00 | 30.87 |
| 5219 | OE2 | GLU | A | 675 | 58.872 | -9.933 | 45.259 | 1.00 | 28.96 |
| 5220 | C | GLU | A | 675 | 55.398 | -6.831 | 46.709 | 1.00 | 19.28 |
| 5221 | O | GLU | A | 675 | 54.573 | -7.293 | 45.915 | 1.00 | 19.12 |
| 5222 | N | HIS | A | 676 | 55.303 | -7.040 | 48.020 | 1.00 | 17.80 |
| 5223 | CA | HIS | A | 676 | 54.118 | -7.733 | 48.554 | 1.00 | 16.44 |
| 5224 | CB | HIS | A | 676 | 54.437 | -8.398 | 49.865 | 1.00 | 15.43 |
| 5225 | CG | HIS | A | 676 | 53.377 | -9.350 | 50.279 | 1.00 | 14.16 |
| 5226 | ND1 | HIS | A | 676 | 52.809 | -9.354 | 51.532 | 1.00 | 11.86 |
| 5227 | CE1 | HIS | A | 676 | 51.885 | -10.293 | 51.572 | 1.00 | 12.87 |
| 5228 | NE2 | HIS | A | 676 | 51.822 | -10.881 | 50.394 | 1.00 | 13.25 |
| 5229 | CD2 | HIS | A | 676 | 52.721 | -10.285 | 49.559 | 1.00 | 11.80 |
| 5230 | C | HIS | A | 676 | 52.835 | -6.910 | 48.773 | 1.00 | 16.33 |
| 5231 | O | HIS | A | 676 | 51.699 | -7.475 | 48.882 | 1.00 | 16.31 |
| 5232 | N | TYR | A | 677 | 52.989 | -5.593 | 48.890 | 1.00 | 16.09 |
| 5233 | CA | TYR | A | 677 | 51.862 | -4.734 | 48.657 | 1.00 | 15.55 |
| 5234 | CB | TYR | A | 677 | 52.260 | -3.291 | 48.647 | 1.00 | 16.22 |
| 5235 | CG | TYR | A | 677 | 52.353 | -2.598 | 49.965 | 1.00 | 16.37 |
| 5236 | CD1 | TYR | A | 677 | 51.440 | -1.618 | 50.334 | 1.00 | 16.99 |
| 5237 | CE1 | TYR | A | 677 | 51.544 | -0.973 | 51.512 | 1.00 | 16.41 |
| 5238 | CZ | TYR | A | 677 | 52.593 | -1.276 | 52.325 | 1.00 | 16.94 |
| 5239 | OH | TYR | A | 677 | 52.803 | -0.693 | 53.553 | 1.00 | 19.21 |
| 5240 | CE2 | TYR | A | 677 | 53.481 | -2.214 | 51.947 | 1.00 | 17.68 |
| 5241 | CD2 | TYR | A | 677 | 53.363 | -2.843 | 50.772 | 1.00 | 14.87 |
| 5242 | C | TYR | A | 677 | 51.362 | -5.078 | 47.266 | 1.00 | 15.77 |
| 5243 | O | TYR | A | 677 | 50.134 | -5.250 | 47.078 | 1.00 | 15.64 |
| 5244 | N | LYS | A | 678 | 52.282 | -5.212 | 46.298 | 1.00 | 15.47 |

FIGURE 3 (Cont.)

| A | B | C | D | E | F | G | H | I | J |
|---|---|---|---|---|---|---|---|---|---|
| 5245 | CA | LYS | A | 678 | 51.905 | -5.488 | 44.886 | 1.00 | 16.35 |
| 5246 | CB | LYS | A | 678 | 53.098 | -5.328 | 43.933 | 1.00 | 15.28 |
| 5247 | CG | LYS | A | 678 | 53.813 | -3.911 | 44.017 | 1.00 | 17.43 |
| 5248 | CD | LYS | A | 678 | 53.539 | -2.915 | 42.818 | 1.00 | 19.65 |
| 5249 | CE | LYS | A | 678 | 52.199 | -1.954 | 43.027 | 1.00 | 21.18 |
| 5250 | NZ | LYS | A | 678 | 52.229 | -0.651 | 42.154 | 1.00 | 19.16 |
| 5251 | C | LYS | A | 678 | 51.177 | -6.843 | 44.682 | 1.00 | 16.74 |
| 5252 | O | LYS | A | 678 | 50.109 | -6.940 | 44.058 | 1.00 | 17.45 |
| 5253 | N | ASN | A | 679 | 51.699 | -7.869 | 45.302 | 1.00 | 16.46 |
| 5254 | CA | ASN | A | 679 | 51.297 | -9.240 | 45.043 | 1.00 | 16.67 |
| 5255 | CB | ASN | A | 679 | 52.486 | -10.138 | 45.421 | 1.00 | 16.11 |
| 5256 | CG | ASN | A | 679 | 52.392 | -11.509 | 44.852 | 1.00 | 17.15 |
| 5257 | OD1 | ASN | A | 679 | 52.852 | -11.745 | 43.732 | 1.00 | 20.41 |
| 5258 | ND2 | ASN | A | 679 | 51.719 | -12.419 | 45.580 | 1.00 | 14.78 |
| 5259 | C | ASN | A | 679 | 50.080 | -9.672 | 45.849 | 1.00 | 16.59 |
| 5260 | O | ASN | A | 679 | 49.624 | -10.793 | 45.656 | 1.00 | 17.85 |
| 5261 | N | SER | A | 680 | 49.619 | -8.813 | 46.769 | 1.00 | 15.95 |
| 5262 | CA | SER | A | 680 | 48.494 | -9.087 | 47.702 | 1.00 | 14.68 |
| 5263 | CB | SER | A | 680 | 48.883 | -8.750 | 49.154 | 1.00 | 13.70 |
| 5264 | OG | SER | A | 680 | 49.261 | -7.395 | 49.366 | 1.00 | 12.36 |
| 5265 | C | SER | A | 680 | 47.171 | -8.383 | 47.433 | 1.00 | 15.28 |
| 5266 | O | SER | A | 680 | 46.238 | -8.444 | 48.261 | 1.00 | 15.43 |
| 5267 | N | THR | A | 681 | 47.037 | -7.716 | 46.300 | 1.00 | 15.60 |
| 5268 | CA | THR | A | 681 | 45.727 | -7.108 | 45.988 | 1.00 | 14.51 |
| 5269 | CB | THR | A | 681 | 45.801 | -6.210 | 44.745 | 1.00 | 14.00 |
| 5270 | OG1 | THR | A | 681 | 46.284 | -6.966 | 43.621 | 1.00 | 12.68 |
| 5271 | CG2 | THR | A | 681 | 46.826 | -5.075 | 44.865 | 1.00 | 13.10 |
| 5272 | C | THR | A | 681 | 44.738 | -8.202 | 45.658 | 1.00 | 14.86 |
| 5273 | O | THR | A | 681 | 45.127 | -9.371 | 45.335 | 1.00 | 14.85 |
| 5274 | N | VAL | A | 682 | 43.454 | -7.828 | 45.653 | 1.00 | 14.52 |
| 5275 | CA | VAL | A | 682 | 42.429 | -8.774 | 45.133 | 1.00 | 14.22 |
| 5276 | CB | VAL | A | 682 | 41.065 | -8.644 | 45.864 | 1.00 | 15.41 |
| 5277 | CG1 | VAL | A | 682 | 41.258 | -8.138 | 47.284 | 1.00 | 14.21 |
| 5278 | CG2 | VAL | A | 682 | 40.165 | -7.790 | 45.128 | 1.00 | 8.07 |
| 5279 | C | VAL | A | 682 | 42.270 | -8.786 | 43.550 | 1.00 | 15.18 |
| 5280 | O | VAL | A | 682 | 42.174 | -9.885 | 42.953 | 1.00 | 14.44 |
| 5281 | N | MET | A | 683 | 42.243 | -7.575 | 42.926 | 1.00 | 15.08 |
| 5282 | CA | MET | A | 683 | 42.633 | -7.326 | 41.492 | 1.00 | 16.02 |
| 5283 | CB | MET | A | 683 | 43.361 | -5.962 | 41.420 | 1.00 | 15.73 |
| 5284 | CG | MET | A | 683 | 42.492 | -4.731 | 41.480 | 1.00 | 13.07 |
| 5285 | SD | MET | A | 683 | 42.062 | -4.418 | 43.116 | 1.00 | 16.59 |
| 5286 | CE | MET | A | 683 | 43.391 | -3.547 | 43.738 | 1.00 | 9.38 |
| 5287 | C | MET | A | 683 | 43.589 | -8.378 | 40.791 | 1.00 | 16.74 |
| 5288 | O | MET | A | 683 | 43.341 | -8.778 | 39.645 | 1.00 | 18.81 |
| 5289 | N | ALA | A | 684 | 44.697 | -8.756 | 41.454 | 1.00 | 16.62 |
| 5290 | CA | ALA | A | 684 | 45.671 | -9.719 | 40.917 | 1.00 | 16.01 |
| 5291 | CB | ALA | A | 684 | 46.910 | -9.797 | 41.834 | 1.00 | 15.47 |
| 5292 | C | ALA | A | 684 | 45.081 | -11.113 | 40.819 | 1.00 | 16.23 |
| 5293 | O | ALA | A | 684 | 45.678 | -11.996 | 40.228 | 1.00 | 15.57 |
| 5294 | N | ARG | A | 685 | 43.925 | -11.297 | 41.458 | 1.00 | 17.01 |
| 5295 | CA | ARG | A | 685 | 43.193 | -12.568 | 41.468 | 1.00 | 16.86 |

FIGURE 3 (Cont.)

| A | B | C | D | E | F | G | H | I | J |
|---|---|---|---|---|---|---|---|---|---|
| 5296 | CB | ARG | A | 685 | 42.767 | -12.944 | 42.896 | 1.00 | 17.18 |
| 5297 | CG | ARG | A | 685 | 43.793 | -12.527 | 43.945 | 1.00 | 15.79 |
| 5298 | CD | ARG | A | 685 | 44.949 | -13.450 | 43.999 | 1.00 | 16.70 |
| 5299 | NE | ARG | A | 685 | 44.475 | -14.825 | 43.969 | 1.00 | 16.06 |
| 5300 | CZ | ARG | A | 685 | 45.143 | -15.851 | 43.503 | 1.00 | 18.22 |
| 5301 | NH1 | ARG | A | 685 | 44.535 | -17.046 | 43.527 | 1.00 | 19.00 |
| 5302 | NH2 | ARG | A | 685 | 46.390 | -15.713 | 43.034 | 1.00 | 15.76 |
| 5303 | C | ARG | A | 685 | 41.961 | -12.498 | 40.591 | 1.00 | 16.22 |
| 5304 | O | ARG | A | 685 | 41.225 | -13.466 | 40.490 | 1.00 | 16.90 |
| 5305 | N | ALA | A | 686 | 41.731 | -11.355 | 39.963 | 1.00 | 15.02 |
| 5306 | CA | ALA | A | 686 | 40.587 | -11.188 | 39.026 | 1.00 | 15.08 |
| 5307 | CB | ALA | A | 686 | 40.903 | -10.087 | 37.985 | 1.00 | 14.48 |
| 5308 | C | ALA | A | 686 | 40.172 | -12.493 | 38.314 | 1.00 | 14.50 |
| 5309 | O | ALA | A | 686 | 39.036 | -12.918 | 38.341 | 1.00 | 15.17 |
| 5310 | N | GLU | A | 687 | 41.125 | -13.140 | 37.718 | 1.00 | 13.97 |
| 5311 | CA | GLU | A | 687 | 40.851 | -14.308 | 36.918 | 1.00 | 14.92 |
| 5312 | CB | GLU | A | 687 | 42.177 | -14.806 | 36.350 | 1.00 | 15.21 |
| 5313 | CG | GLU | A | 687 | 42.000 | -16.023 | 35.443 | 1.00 | 19.69 |
| 5314 | CD | GLU | A | 687 | 41.361 | -15.716 | 34.093 | 1.00 | 24.01 |
| 5315 | OE1 | GLU | A | 687 | 40.674 | -16.655 | 33.580 | 1.00 | 28.67 |
| 5316 | OE2 | GLU | A | 687 | 41.591 | -14.591 | 33.554 | 1.00 | 22.87 |
| 5317 | C | GLU | A | 687 | 40.198 | -15.469 | 37.664 | 1.00 | 13.79 |
| 5318 | O | GLU | A | 687 | 39.494 | -16.295 | 37.112 | 1.00 | 13.04 |
| 5319 | N | TYR | A | 688 | 40.489 | -15.550 | 38.931 | 1.00 | 13.72 |
| 5320 | CA | TYR | A | 688 | 40.128 | -16.712 | 39.728 | 1.00 | 13.45 |
| 5321 | CB | TYR | A | 688 | 41.061 | -16.809 | 40.921 | 1.00 | 11.15 |
| 5322 | CG | TYR | A | 688 | 42.479 | -17.236 | 40.560 | 1.00 | 14.68 |
| 5323 | CD1 | TYR | A | 688 | 42.816 | -18.612 | 40.449 | 1.00 | 15.99 |
| 5324 | CE1 | TYR | A | 688 | 44.076 | -19.000 | 40.147 | 1.00 | 18.97 |
| 5325 | CZ | TYR | A | 688 | 45.044 | -18.062 | 39.928 | 1.00 | 20.84 |
| 5326 | OH | TYR | A | 688 | 46.298 | -18.511 | 39.643 | 1.00 | 25.28 |
| 5327 | CE2 | TYR | A | 688 | 44.775 | -16.702 | 40.011 | 1.00 | 19.36 |
| 5328 | CD2 | TYR | A | 688 | 43.486 | -16.297 | 40.338 | 1.00 | 16.64 |
| 5329 | C | TYR | A | 688 | 38.665 | -16.635 | 40.157 | 1.00 | 14.32 |
| 5330 | O | TYR | A | 688 | 38.139 | -17.672 | 40.660 | 1.00 | 13.41 |
| 5331 | N | PHE | A | 689 | 38.068 | -15.402 | 40.011 | 1.00 | 13.39 |
| 5332 | CA | PHE | A | 689 | 36.690 | -15.207 | 40.213 | 1.00 | 13.96 |
| 5333 | CB | PHE | A | 689 | 36.388 | -13.740 | 40.303 | 1.00 | 14.28 |
| 5334 | CG | PHE | A | 689 | 36.723 | -13.110 | 41.635 | 1.00 | 12.84 |
| 5335 | CD1 | PHE | A | 689 | 35.841 | -13.154 | 42.662 | 1.00 | 11.22 |
| 5336 | CE1 | PHE | A | 689 | 36.126 | -12.483 | 43.849 | 1.00 | 13.61 |
| 5337 | CZ | PHE | A | 689 | 37.331 | -11.776 | 43.995 | 1.00 | 12.26 |
| 5338 | CE2 | PHE | A | 689 | 38.195 | -11.758 | 42.980 | 1.00 | 11.02 |
| 5339 | CD2 | PHE | A | 689 | 37.895 | -12.408 | 41.817 | 1.00 | 12.98 |
| 5340 | C | PHE | A | 689 | 35.836 | -15.821 | 39.109 | 1.00 | 15.41 |
| 5341 | O | PHE | A | 689 | 34.611 | -15.956 | 39.248 | 1.00 | 15.77 |
| 5342 | N | ARG | A | 690 | 36.422 | -16.234 | 38.003 | 1.00 | 16.82 |
| 5343 | CA | ARG | A | 690 | 35.601 | -16.854 | 36.925 | 1.00 | 18.48 |
| 5344 | CB | ARG | A | 690 | 36.397 | -17.486 | 35.764 | 1.00 | 18.30 |
| 5345 | CG | ARG | A | 690 | 35.497 | -17.711 | 34.476 | 1.00 | 18.79 |
| 5346 | CD | ARG | A | 690 | 36.256 | -17.853 | 33.195 | 1.00 | 16.44 |

FIGURE 3 (Cont.)

| A | B | C | D | E | F | G | H | I | J |
|---|---|---|---|---|---|---|---|---|---|
| 5347 | NE | ARG | A | 690 | 37.399 | -16.947 | 33.256 | 1.00 | 17.70 |
| 5348 | CZ | ARG | A | 690 | 37.388 | -15.663 | 32.873 | 1.00 | 14.82 |
| 5349 | NH1 | ARG | A | 690 | 38.499 | -14.953 | 32.992 | 1.00 | 12.02 |
| 5350 | NH2 | ARG | A | 690 | 36.291 | -15.082 | 32.383 | 1.00 | 11.35 |
| 5351 | C | ARG | A | 690 | 34.559 | -17.840 | 37.362 | 1.00 | 19.39 |
| 5352 | O | ARG | A | 690 | 33.410 | -17.619 | 37.022 | 1.00 | 20.94 |
| 5353 | N | ASN | A | 691 | 34.896 | -18.898 | 38.078 | 1.00 | 18.88 |
| 5354 | CA | ASN | A | 691 | 33.872 | -19.914 | 38.322 | 1.00 | 19.47 |
| 5355 | CB | ASN | A | 691 | 34.461 | -21.352 | 38.470 | 1.00 | 20.56 |
| 5356 | CG | ASN | A | 691 | 35.890 | -21.506 | 37.933 | 1.00 | 21.16 |
| 5357 | OD1 | ASN | A | 691 | 36.100 | -21.449 | 36.729 | 1.00 | 23.33 |
| 5358 | ND2 | ASN | A | 691 | 36.857 | -21.727 | 38.833 | 1.00 | 20.88 |
| 5359 | C | ASN | A | 691 | 33.094 | -19.668 | 39.607 | 1.00 | 19.46 |
| 5360 | O | ASN | A | 691 | 32.895 | -20.631 | 40.355 | 1.00 | 18.66 |
| 5361 | N | VAL | A | 692 | 32.689 | -18.419 | 39.911 | 1.00 | 18.60 |
| 5362 | CA | VAL | A | 692 | 32.033 | -18.136 | 41.192 | 1.00 | 17.57 |
| 5363 | CB | VAL | A | 692 | 33.017 | -17.933 | 42.396 | 1.00 | 17.76 |
| 5364 | CG1 | VAL | A | 692 | 34.046 | -19.146 | 42.560 | 1.00 | 17.94 |
| 5365 | CG2 | VAL | A | 692 | 33.729 | -16.640 | 42.371 | 1.00 | 12.25 |
| 5366 | C | VAL | A | 692 | 31.150 | -16.925 | 41.174 | 1.00 | 18.53 |
| 5367 | O | VAL | A | 692 | 31.397 | -16.000 | 40.388 | 1.00 | 17.92 |
| 5368 | N | ASP | A | 693 | 30.128 | -16.934 | 42.055 | 1.00 | 18.78 |
| 5369 | CA | ASP | A | 693 | 29.180 | -15.825 | 42.191 | 1.00 | 18.26 |
| 5370 | CB | ASP | A | 693 | 27.825 | -16.242 | 42.735 | 1.00 | 19.17 |
| 5371 | CG | ASP | A | 693 | 27.166 | -17.298 | 41.931 | 1.00 | 22.83 |
| 5372 | OD1 | ASP | A | 693 | 25.954 | -17.133 | 41.676 | 1.00 | 27.12 |
| 5373 | OD2 | ASP | A | 693 | 27.752 | -18.301 | 41.505 | 1.00 | 22.95 |
| 5374 | C | ASP | A | 693 | 29.795 | -14.978 | 43.246 | 1.00 | 17.23 |
| 5375 | O | ASP | A | 693 | 30.021 | -15.400 | 44.357 | 1.00 | 17.56 |
| 5376 | N | TYR | A | 694 | 30.108 | -13.774 | 42.872 | 1.00 | 16.10 |
| 5377 | CA | TYR | A | 694 | 30.645 | -12.835 | 43.801 | 1.00 | 15.46 |
| 5378 | CB | TYR | A | 694 | 31.984 | -12.525 | 43.331 | 1.00 | 15.42 |
| 5379 | CG | TYR | A | 694 | 32.708 | -11.462 | 44.040 | 1.00 | 15.98 |
| 5380 | CD1 | TYR | A | 694 | 33.130 | -10.384 | 43.341 | 1.00 | 11.85 |
| 5381 | CE1 | TYR | A | 694 | 33.874 | -9.507 | 43.891 | 1.00 | 15.96 |
| 5382 | CZ | TYR | A | 694 | 34.232 | -9.622 | 45.209 | 1.00 | 19.01 |
| 5383 | OH | TYR | A | 694 | 34.994 | -8.579 | 45.721 | 1.00 | 20.32 |
| 5384 | CE2 | TYR | A | 694 | 33.836 | -10.669 | 45.947 | 1.00 | 11.47 |
| 5385 | CD2 | TYR | A | 694 | 33.105 | -11.611 | 45.367 | 1.00 | 13.46 |
| 5386 | C | TYR | A | 694 | 29.680 | -11.631 | 43.842 | 1.00 | 14.23 |
| 5387 | O | TYR | A | 694 | 28.943 | -11.422 | 42.927 | 1.00 | 13.08 |
| 5388 | N | LEU | A | 695 | 29.586 | -10.999 | 45.008 | 1.00 | 13.69 |
| 5389 | CA | LEU | A | 695 | 28.716 | -9.897 | 45.202 | 1.00 | 13.77 |
| 5390 | CB | LEU | A | 695 | 27.477 | -10.280 | 46.026 | 1.00 | 12.32 |
| 5391 | CG | LEU | A | 695 | 26.809 | -9.049 | 46.716 | 1.00 | 14.36 |
| 5392 | CD1 | LEU | A | 695 | 26.521 | -7.845 | 45.725 | 1.00 | 14.89 |
| 5393 | CD2 | LEU | A | 695 | 25.537 | -9.447 | 47.448 | 1.00 | 8.35 |
| 5394 | C | LEU | A | 695 | 29.594 | -8.899 | 45.911 | 1.00 | 12.88 |
| 5395 | O | LEU | A | 695 | 30.292 | -9.328 | 46.797 | 1.00 | 12.66 |
| 5396 | N | LEU | A | 696 | 29.503 | -7.607 | 45.580 | 1.00 | 11.18 |
| 5397 | CA | LEU | A | 696 | 30.498 | -6.594 | 45.956 | 1.00 | 10.09 |

FIGURE 3 (Cont.)

| A | B | C | D | E | F | G | H | I | J |
|---|---|---|---|---|---|---|---|---|---|
| 5398 | CB | LEU | A | 696 | 31.515 | -6.457 | 44.828 | 1.00 | 10.43 |
| 5399 | CG | LEU | A | 696 | 32.532 | -5.301 | 44.908 | 1.00 | 13.81 |
| 5400 | CD1 | LEU | A | 696 | 33.746 | -5.559 | 45.939 | 1.00 | 10.85 |
| 5401 | CD2 | LEU | A | 696 | 33.085 | -4.953 | 43.490 | 1.00 | 13.60 |
| 5402 | C | LEU | A | 696 | 29.890 | -5.207 | 46.216 | 1.00 | 10.83 |
| 5403 | O | LEU | A | 696 | 29.227 | -4.613 | 45.375 | 1.00 | 6.71 |
| 5404 | N | ILE | A | 697 | 30.086 | -4.728 | 47.445 | 1.00 | 9.83 |
| 5405 | CA | ILE | A | 697 | 29.216 | -3.735 | 47.962 | 1.00 | 9.04 |
| 5406 | CB | ILE | A | 697 | 28.311 | -4.327 | 48.979 | 1.00 | 7.64 |
| 5407 | CG1 | ILE | A | 697 | 27.602 | -5.550 | 48.356 | 1.00 | 11.23 |
| 5408 | CD1 | ILE | A | 697 | 26.444 | -6.199 | 49.138 | 1.00 | 5.18 |
| 5409 | CG2 | ILE | A | 697 | 27.288 | -3.361 | 49.281 | 1.00 | 5.58 |
| 5410 | C | ILE | A | 697 | 30.071 | -2.633 | 48.512 | 1.00 | 9.70 |
| 5411 | O | ILE | A | 697 | 31.156 | -2.927 | 49.009 | 1.00 | 8.15 |
| 5412 | N | HIS | A | 698 | 29.614 | -1.368 | 48.321 | 1.00 | 7.78 |
| 5413 | CA | HIS | A | 698 | 30.325 | -0.249 | 48.830 | 1.00 | 7.89 |
| 5414 | CB | HIS | A | 698 | 31.526 | -0.086 | 47.996 | 1.00 | 7.26 |
| 5415 | CG | HIS | A | 698 | 32.746 | 0.239 | 48.782 | 1.00 | 9.51 |
| 5416 | ND1 | HIS | A | 698 | 32.697 | 1.037 | 49.895 | 1.00 | 12.56 |
| 5417 | CE1 | HIS | A | 698 | 33.921 | 1.191 | 50.364 | 1.00 | 12.40 |
| 5418 | NE2 | HIS | A | 698 | 34.762 | 0.575 | 49.563 | 1.00 | 12.78 |
| 5419 | CD2 | HIS | A | 698 | 34.049 | -0.039 | 48.567 | 1.00 | 3.75 |
| 5420 | C | HIS | A | 698 | 29.604 | 1.094 | 48.822 | 1.00 | 8.89 |
| 5421 | O | HIS | A | 698 | 28.882 | 1.412 | 47.894 | 1.00 | 8.15 |
| 5422 | N | GLY | A | 699 | 29.849 | 1.887 | 49.835 | 1.00 | 8.40 |
| 5423 | CA | GLY | A | 699 | 29.172 | 3.125 | 49.992 | 1.00 | 11.19 |
| 5424 | C | GLY | A | 699 | 30.064 | 4.167 | 49.337 | 1.00 | 12.92 |
| 5425 | O | GLY | A | 699 | 31.308 | 4.160 | 49.489 | 1.00 | 14.21 |
| 5426 | N | THR | A | 700 | 29.426 | 5.102 | 48.647 | 1.00 | 12.30 |
| 5427 | CA | THR | A | 700 | 30.155 | 6.050 | 47.825 | 1.00 | 14.28 |
| 5428 | CB | THR | A | 700 | 29.266 | 6.626 | 46.670 | 1.00 | 12.71 |
| 5429 | OG1 | THR | A | 700 | 28.305 | 7.662 | 47.164 | 1.00 | 12.53 |
| 5430 | CG2 | THR | A | 700 | 28.494 | 5.415 | 46.067 | 1.00 | 9.43 |
| 5431 | C | THR | A | 700 | 30.714 | 7.160 | 48.654 | 1.00 | 15.15 |
| 5432 | O | THR | A | 700 | 31.365 | 7.984 | 48.116 | 1.00 | 18.16 |
| 5433 | N | ALA | A | 701 | 30.470 | 7.185 | 49.944 | 1.00 | 14.66 |
| 5434 | CA | ALA | A | 701 | 30.966 | 8.255 | 50.810 | 1.00 | 14.57 |
| 5435 | CB | ALA | A | 701 | 29.735 | 8.981 | 51.415 | 1.00 | 13.61 |
| 5436 | C | ALA | A | 701 | 31.811 | 7.681 | 51.946 | 1.00 | 14.14 |
| 5437 | O | ALA | A | 701 | 31.886 | 8.299 | 53.001 | 1.00 | 15.40 |
| 5438 | N | ASP | A | 702 | 32.333 | 6.468 | 51.733 | 1.00 | 13.80 |
| 5439 | CA | ASP | A | 702 | 33.171 | 5.759 | 52.681 | 1.00 | 13.47 |
| 5440 | CB | ASP | A | 702 | 33.375 | 4.321 | 52.184 | 1.00 | 11.93 |
| 5441 | CG | ASP | A | 702 | 33.875 | 3.407 | 53.248 | 1.00 | 13.44 |
| 5442 | OD1 | ASP | A | 702 | 33.587 | 2.185 | 53.224 | 1.00 | 18.73 |
| 5443 | OD2 | ASP | A | 702 | 34.547 | 3.833 | 54.200 | 1.00 | 17.27 |
| 5444 | C | ASP | A | 702 | 34.507 | 6.494 | 52.864 | 1.00 | 14.29 |
| 5445 | O | ASP | A | 702 | 35.380 | 6.337 | 51.987 | 1.00 | 15.56 |
| 5446 | N | ASP | A | 703 | 34.653 | 7.332 | 53.928 | 1.00 | 13.22 |
| 5447 | CA | ASP | A | 703 | 35.923 | 8.049 | 54.157 | 1.00 | 12.39 |
| 5448 | CB | ASP | A | 703 | 35.785 | 9.134 | 55.165 | 1.00 | 12.47 |

FIGURE 3 (Cont.)

| A | B | C | D | E | F | G | H | I | J |
|---|---|---|---|---|---|---|---|---|---|
| 5449 | CG | ASP | A | 703 | 35.205 | 8.645 | 56.477 | 1.00 | 14.00 |
| 5450 | OD1 | ASP | A | 703 | 34.013 | 8.285 | 56.510 | 1.00 | 18.49 |
| 5451 | OD2 | ASP | A | 703 | 35.871 | 8.536 | 57.548 | 1.00 | 18.30 |
| 5452 | C | ASP | A | 703 | 37.023 | 7.079 | 54.656 | 1.00 | 12.31 |
| 5453 | O | ASP | A | 703 | 38.235 | 7.447 | 54.740 | 1.00 | 10.90 |
| 5454 | N | ASN | A | 704 | 36.653 | 5.823 | 54.902 | 1.00 | 10.75 |
| 5455 | CA | ASN | A | 704 | 37.529 | 5.003 | 55.647 | 1.00 | 12.89 |
| 5456 | CB | ASN | A | 704 | 36.778 | 4.222 | 56.706 | 1.00 | 13.16 |
| 5457 | CG | ASN | A | 704 | 37.674 | 3.481 | 57.658 | 1.00 | 17.44 |
| 5458 | OD1 | ASN | A | 704 | 37.196 | 2.585 | 58.394 | 1.00 | 24.26 |
| 5459 | ND2 | ASN | A | 704 | 38.969 | 3.832 | 57.687 | 1.00 | 20.62 |
| 5460 | C | ASN | A | 704 | 38.197 | 4.116 | 54.700 | 1.00 | 13.05 |
| 5461 | O | ASN | A | 704 | 39.383 | 4.287 | 54.476 | 1.00 | 13.10 |
| 5462 | N | VAL | A | 705 | 37.465 | 3.132 | 54.186 | 1.00 | 13.05 |
| 5463 | CA | VAL | A | 705 | 37.934 | 2.347 | 53.039 | 1.00 | 12.69 |
| 5464 | CB | VAL | A | 705 | 37.575 | 0.899 | 53.165 | 1.00 | 13.14 |
| 5465 | CG1 | VAL | A | 705 | 38.183 | 0.135 | 52.025 | 1.00 | 8.14 |
| 5466 | CG2 | VAL | A | 705 | 38.183 | 0.417 | 54.413 | 1.00 | 11.21 |
| 5467 | C | VAL | A | 705 | 37.265 | 2.905 | 51.831 | 1.00 | 12.57 |
| 5468 | O | VAL | A | 705 | 36.037 | 2.784 | 51.741 | 1.00 | 13.74 |
| 5469 | N | HIS | A | 706 | 38.032 | 3.529 | 50.951 | 1.00 | 10.47 |
| 5470 | CA | HIS | A | 706 | 37.406 | 4.385 | 50.002 | 1.00 | 11.96 |
| 5471 | CB | HIS | A | 706 | 38.292 | 5.543 | 49.395 | 1.00 | 11.08 |
| 5472 | CG | HIS | A | 706 | 39.168 | 6.177 | 50.399 | 1.00 | 11.21 |
| 5473 | ND1 | HIS | A | 706 | 38.740 | 6.432 | 51.667 | 1.00 | 11.21 |
| 5474 | CE1 | HIS | A | 706 | 39.739 | 6.917 | 52.386 | 1.00 | 10.47 |
| 5475 | NE2 | HIS | A | 706 | 40.802 | 6.991 | 51.613 | 1.00 | 11.40 |
| 5476 | CD2 | HIS | A | 706 | 40.477 | 6.521 | 50.370 | 1.00 | 10.91 |
| 5477 | C | HIS | A | 706 | 36.847 | 3.447 | 48.968 | 1.00 | 13.10 |
| 5478 | O | HIS | A | 706 | 37.417 | 2.419 | 48.729 | 1.00 | 13.77 |
| 5479 | N | PHE | A | 707 | 35.662 | 3.804 | 48.471 | 1.00 | 12.81 |
| 5480 | CA | PHE | A | 707 | 35.090 | 3.251 | 47.267 | 1.00 | 14.44 |
| 5481 | CB | PHE | A | 707 | 34.060 | 4.228 | 46.697 | 1.00 | 12.69 |
| 5482 | CG | PHE | A | 707 | 33.213 | 3.624 | 45.682 | 1.00 | 14.77 |
| 5483 | CD1 | PHE | A | 707 | 32.060 | 2.964 | 46.050 | 1.00 | 17.50 |
| 5484 | CE1 | PHE | A | 707 | 31.271 | 2.374 | 45.054 | 1.00 | 15.68 |
| 5485 | CZ | PHE | A | 707 | 31.656 | 2.453 | 43.748 | 1.00 | 13.26 |
| 5486 | CE2 | PHE | A | 707 | 32.832 | 3.152 | 43.407 | 1.00 | 13.47 |
| 5487 | CD2 | PHE | A | 707 | 33.579 | 3.662 | 44.354 | 1.00 | 12.42 |
| 5488 | C | PHE | A | 707 | 36.109 | 2.879 | 46.212 | 1.00 | 15.22 |
| 5489 | O | PHE | A | 707 | 36.120 | 1.716 | 45.700 | 1.00 | 18.31 |
| 5490 | N | GLN | A | 708 | 36.994 | 3.824 | 45.892 | 1.00 | 13.58 |
| 5491 | CA | GLN | A | 708 | 38.195 | 3.494 | 45.106 | 1.00 | 12.72 |
| 5492 | CB | GLN | A | 708 | 39.340 | 4.457 | 45.489 | 1.00 | 12.57 |
| 5493 | CG | GLN | A | 708 | 40.720 | 3.844 | 45.341 | 1.00 | 12.08 |
| 5494 | CD | GLN | A | 708 | 41.872 | 4.771 | 45.698 | 1.00 | 15.26 |
| 5495 | OE1 | GLN | A | 708 | 42.527 | 5.361 | 44.834 | 1.00 | 12.65 |
| 5496 | NE2 | GLN | A | 708 | 42.149 | 4.851 | 46.969 | 1.00 | 10.23 |
| 5497 | C | GLN | A | 708 | 38.670 | 1.989 | 45.206 | 1.00 | 12.41 |
| 5498 | O | GLN | A | 708 | 39.284 | 1.443 | 44.255 | 1.00 | 11.60 |
| 5499 | N | ASN | A | 709 | 38.516 | 1.393 | 46.385 | 1.00 | 11.40 |

FIGURE 3 (Cont.)

| A | B | C | D | E | F | G | H | I | J |
|---|---|---|---|---|---|---|---|---|---|
| 5500 | CA | ASN | A | 709 | 38.915 | -0.037 | 46.653 | 1.00 | 11.20 |
| 5501 | CB | ASN | A | 709 | 38.815 | -0.384 | 48.119 | 1.00 | 9.23 |
| 5502 | CG | ASN | A | 709 | 40.059 | -0.023 | 48.917 | 1.00 | 11.52 |
| 5503 | OD1 | ASN | A | 709 | 40.061 | 0.987 | 49.542 | 1.00 | 13.05 |
| 5504 | ND2 | ASN | A | 709 | 41.112 | -0.872 | 48.921 | 1.00 | 12.97 |
| 5505 | C | ASN | A | 709 | 38.044 | -1.032 | 45.910 | 1.00 | 11.99 |
| 5506 | O | ASN | A | 709 | 38.561 | -1.830 | 45.197 | 1.00 | 13.11 |
| 5507 | N | SER | A | 710 | 36.714 | -0.953 | 46.050 | 1.00 | 11.46 |
| 5508 | CA | SER | A | 710 | 35.838 | -1.797 | 45.231 | 1.00 | 11.12 |
| 5509 | CB | SER | A | 710 | 34.416 | -1.756 | 45.738 | 1.00 | 8.01 |
| 5510 | OG | SER | A | 710 | 34.449 | -2.349 | 46.983 | 1.00 | 7.75 |
| 5511 | C | SER | A | 710 | 35.808 | -1.458 | 43.781 | 1.00 | 11.50 |
| 5512 | O | SER | A | 710 | 35.622 | -2.358 | 42.949 | 1.00 | 13.58 |
| 5513 | N | ALA | A | 711 | 35.838 | -0.153 | 43.470 | 1.00 | 10.70 |
| 5514 | CA | ALA | A | 711 | 36.002 | 0.321 | 42.106 | 1.00 | 9.83 |
| 5515 | CB | ALA | A | 711 | 36.433 | 1.814 | 42.073 | 1.00 | 9.70 |
| 5516 | C | ALA | A | 711 | 37.028 | -0.392 | 41.328 | 1.00 | 9.51 |
| 5517 | O | ALA | A | 711 | 36.893 | -0.524 | 40.129 | 1.00 | 9.24 |
| 5518 | N | GLN | A | 712 | 38.105 | -0.761 | 41.979 | 1.00 | 9.88 |
| 5519 | CA | GLN | A | 712 | 39.282 | -1.256 | 41.302 | 1.00 | 10.15 |
| 5520 | CB | GLN | A | 712 | 40.575 | -0.896 | 42.027 | 1.00 | 10.85 |
| 5521 | CG | GLN | A | 712 | 40.801 | 0.655 | 42.041 | 1.00 | 10.95 |
| 5522 | CD | GLN | A | 712 | 41.424 | 1.145 | 40.799 | 1.00 | 15.40 |
| 5523 | OE1 | GLN | A | 712 | 41.464 | 0.375 | 39.869 | 1.00 | 17.38 |
| 5524 | NE2 | GLN | A | 712 | 41.795 | 2.486 | 40.717 | 1.00 | 13.72 |
| 5525 | C | GLN | A | 712 | 39.150 | -2.682 | 41.213 | 1.00 | 9.17 |
| 5526 | O | GLN | A | 712 | 39.561 | -3.250 | 40.237 | 1.00 | 9.78 |
| 5527 | N | ILE | A | 713 | 38.548 | -3.298 | 42.198 | 1.00 | 9.00 |
| 5528 | CA | ILE | A | 713 | 38.180 | -4.689 | 42.024 | 1.00 | 8.01 |
| 5529 | CB | ILE | A | 713 | 37.516 | -5.268 | 43.259 | 1.00 | 8.16 |
| 5530 | CG1 | ILE | A | 713 | 38.496 | -5.277 | 44.410 | 1.00 | 2.00 |
| 5531 | CD1 | ILE | A | 713 | 37.872 | -5.647 | 45.730 | 1.00 | 2.00 |
| 5532 | CG2 | ILE | A | 713 | 36.936 | -6.690 | 42.909 | 1.00 | 8.66 |
| 5533 | C | ILE | A | 713 | 37.201 | -4.787 | 40.833 | 1.00 | 8.38 |
| 5534 | O | ILE | A | 713 | 37.327 | -5.787 | 39.970 | 1.00 | 8.38 |
| 5535 | N | ALA | A | 714 | 36.295 | -3.775 | 40.722 | 1.00 | 6.85 |
| 5536 | CA | ALA | A | 714 | 35.234 | -3.885 | 39.739 | 1.00 | 7.18 |
| 5537 | CB | ALA | A | 714 | 34.209 | -2.981 | 39.984 | 1.00 | 7.01 |
| 5538 | C | ALA | A | 714 | 35.890 | -3.675 | 38.371 | 1.00 | 8.22 |
| 5539 | O | ALA | A | 714 | 35.730 | -4.507 | 37.422 | 1.00 | 7.11 |
| 5540 | N | LYS | A | 715 | 36.765 | -2.668 | 38.324 | 1.00 | 8.19 |
| 5541 | CA | LYS | A | 715 | 37.539 | -2.473 | 37.174 | 1.00 | 8.72 |
| 5542 | CB | LYS | A | 715 | 38.616 | -1.506 | 37.424 | 1.00 | 10.03 |
| 5543 | CG | LYS | A | 715 | 39.406 | -1.096 | 36.111 | 1.00 | 13.17 |
| 5544 | CD | LYS | A | 715 | 39.799 | 0.412 | 36.243 | 1.00 | 22.45 |
| 5545 | CE | LYS | A | 715 | 41.263 | 0.607 | 36.803 | 1.00 | 28.28 |
| 5546 | NZ | LYS | A | 715 | 41.455 | 1.998 | 37.481 | 1.00 | 34.52 |
| 5547 | C | LYS | A | 715 | 38.204 | -3.687 | 36.708 | 1.00 | 9.33 |
| 5548 | O | LYS | A | 715 | 38.302 | -3.871 | 35.510 | 1.00 | 9.43 |
| 5549 | N | ALA | A | 716 | 38.772 | -4.470 | 37.625 | 1.00 | 11.28 |
| 5550 | CA | ALA | A | 716 | 39.682 | -5.554 | 37.204 | 1.00 | 11.96 |

FIGURE 3 (Cont.)

| A | B | C | D | E | F | G | H | I | J |
|---|---|---|---|---|---|---|---|---|---|
| 5551 | CB | ALA | A | 716 | 40.545 | -6.191 | 38.381 | 1.00 | 12.21 |
| 5552 | C | ALA | A | 716 | 38.803 | -6.576 | 36.694 | 1.00 | 11.82 |
| 5553 | O | ALA | A | 716 | 39.076 | -7.142 | 35.677 | 1.00 | 13.26 |
| 5554 | N | LEU | A | 717 | 37.750 | -6.855 | 37.448 | 1.00 | 11.94 |
| 5555 | CA | LEU | A | 717 | 36.871 | -7.953 | 37.092 | 1.00 | 11.26 |
| 5556 | CB | LEU | A | 717 | 35.781 | -8.103 | 38.141 | 1.00 | 10.83 |
| 5557 | CG | LEU | A | 717 | 36.190 | -8.897 | 39.371 | 1.00 | 10.48 |
| 5558 | CD1 | LEU | A | 717 | 34.987 | -9.235 | 40.185 | 1.00 | 13.81 |
| 5559 | CD2 | LEU | A | 717 | 36.873 | -10.172 | 39.039 | 1.00 | 11.22 |
| 5560 | C | LEU | A | 717 | 36.323 | -7.813 | 35.654 | 1.00 | 11.71 |
| 5561 | O | LEU | A | 717 | 36.308 | -8.788 | 34.883 | 1.00 | 11.88 |
| 5562 | N | VAL | A | 718 | 35.985 | -6.587 | 35.268 | 1.00 | 11.09 |
| 5563 | CA | VAL | A | 718 | 35.616 | -6.297 | 33.902 | 1.00 | 11.04 |
| 5564 | CB | VAL | A | 718 | 35.249 | -4.765 | 33.750 | 1.00 | 11.51 |
| 5565 | CG1 | VAL | A | 718 | 35.216 | -4.357 | 32.266 | 1.00 | 5.45 |
| 5566 | CG2 | VAL | A | 718 | 33.934 | -4.375 | 34.619 | 1.00 | 9.91 |
| 5567 | C | VAL | A | 718 | 36.735 | -6.612 | 32.878 | 1.00 | 11.86 |
| 5568 | O | VAL | A | 718 | 36.466 | -7.169 | 31.837 | 1.00 | 11.53 |
| 5569 | N | ASN | A | 719 | 37.937 | -6.134 | 33.158 | 1.00 | 11.85 |
| 5570 | CA | ASN | A | 719 | 39.116 | -6.351 | 32.314 | 1.00 | 13.59 |
| 5571 | CB | ASN | A | 719 | 40.316 | -5.513 | 32.849 | 1.00 | 13.25 |
| 5572 | CG | ASN | A | 719 | 40.124 | -3.943 | 32.677 | 1.00 | 16.01 |
| 5573 | OD1 | ASN | A | 719 | 40.784 | -3.172 | 33.351 | 1.00 | 20.61 |
| 5574 | ND2 | ASN | A | 719 | 39.244 | -3.507 | 31.783 | 1.00 | 17.68 |
| 5575 | C | ASN | A | 719 | 39.460 | -7.857 | 32.182 | 1.00 | 13.43 |
| 5576 | O | ASN | A | 719 | 40.004 | -8.303 | 31.185 | 1.00 | 14.60 |
| 5577 | N | ALA | A | 720 | 39.106 | -8.640 | 33.187 | 1.00 | 13.79 |
| 5578 | CA | ALA | A | 720 | 39.302 | -10.088 | 33.135 | 1.00 | 13.30 |
| 5579 | CB | ALA | A | 720 | 39.422 | -10.636 | 34.543 | 1.00 | 12.30 |
| 5580 | C | ALA | A | 720 | 38.150 | -10.796 | 32.432 | 1.00 | 12.73 |
| 5581 | O | ALA | A | 720 | 38.169 | -12.035 | 32.249 | 1.00 | 11.46 |
| 5582 | N | GLN | A | 721 | 37.109 | -10.015 | 32.129 | 1.00 | 11.98 |
| 5583 | CA | GLN | A | 721 | 35.844 | -10.533 | 31.562 | 1.00 | 11.52 |
| 5584 | CB | GLN | A | 721 | 36.113 | -11.173 | 30.196 | 1.00 | 11.69 |
| 5585 | CG | GLN | A | 721 | 35.951 | -10.264 | 29.051 | 1.00 | 12.47 |
| 5586 | CD | GLN | A | 721 | 36.912 | -10.620 | 27.998 | 1.00 | 16.24 |
| 5587 | OE1 | GLN | A | 721 | 36.695 | -11.548 | 27.259 | 1.00 | 17.81 |
| 5588 | NE2 | GLN | A | 721 | 38.026 | -9.930 | 27.969 | 1.00 | 19.88 |
| 5589 | C | GLN | A | 721 | 35.090 | -11.526 | 32.453 | 1.00 | 10.34 |
| 5590 | O | GLN | A | 721 | 34.673 | -12.607 | 32.004 | 1.00 | 8.99 |
| 5591 | N | VAL | A | 722 | 34.930 | -11.142 | 33.711 | 1.00 | 10.00 |
| 5592 | CA | VAL | A | 722 | 34.385 | -12.023 | 34.708 | 1.00 | 9.80 |
| 5593 | CB | VAL | A | 722 | 35.391 | -12.196 | 35.890 | 1.00 | 10.41 |
| 5594 | CG1 | VAL | A | 722 | 34.678 | -12.818 | 37.159 | 1.00 | 9.87 |
| 5595 | CG2 | VAL | A | 722 | 36.564 | -13.068 | 35.506 | 1.00 | 3.45 |
| 5596 | C | VAL | A | 722 | 33.088 | -11.458 | 35.216 | 1.00 | 10.92 |
| 5597 | O | VAL | A | 722 | 33.085 | -10.326 | 35.639 | 1.00 | 10.86 |
| 5598 | N | ASP | A | 723 | 31.977 | -12.204 | 35.147 | 1.00 | 11.20 |
| 5599 | CA | ASP | A | 723 | 30.697 | -11.624 | 35.646 | 1.00 | 11.53 |
| 5600 | CB | ASP | A | 723 | 29.426 | -12.407 | 35.214 | 1.00 | 11.01 |
| 5601 | CG | ASP | A | 723 | 28.111 | -11.581 | 35.455 | 1.00 | 12.44 |

FIGURE 3 (Cont.)

| A | B | C | D | E | F | G | H | I | J |
|---|---|---|---|---|---|---|---|---|---|
| 5602 | OD1 | ASP | A | 723 | 28.198 | -10.333 | 35.322 | 1.00 | 14.36 |
| 5603 | OD2 | ASP | A | 723 | 26.973 | -12.075 | 35.799 | 1.00 | 12.85 |
| 5604 | C | ASP | A | 723 | 30.709 | -11.514 | 37.178 | 1.00 | 11.62 |
| 5605 | O | ASP | A | 723 | 31.323 | -12.309 | 37.851 | 1.00 | 13.04 |
| 5606 | N | PHE | A | 724 | 30.048 | -10.509 | 37.725 | 1.00 | 11.67 |
| 5607 | CA | PHE | A | 724 | 29.851 | -10.434 | 39.167 | 1.00 | 10.16 |
| 5608 | CB | PHE | A | 724 | 31.109 | -9.905 | 39.898 | 1.00 | 9.56 |
| 5609 | CG | PHE | A | 724 | 31.406 | -8.453 | 39.666 | 1.00 | 7.10 |
| 5610 | CD1 | PHE | A | 724 | 32.052 | -8.048 | 38.514 | 1.00 | 8.13 |
| 5611 | CE1 | PHE | A | 724 | 32.336 | -6.672 | 38.288 | 1.00 | 10.58 |
| 5612 | CZ | PHE | A | 724 | 31.958 | -5.700 | 39.174 | 1.00 | 7.94 |
| 5613 | CE2 | PHE | A | 724 | 31.325 | -6.104 | 40.329 | 1.00 | 9.52 |
| 5614 | CD2 | PHE | A | 724 | 31.028 | -7.508 | 40.564 | 1.00 | 4.99 |
| 5615 | C | PHE | A | 724 | 28.660 | -9.571 | 39.447 | 1.00 | 10.31 |
| 5616 | O | PHE | A | 724 | 28.156 | -8.964 | 38.578 | 1.00 | 10.92 |
| 5617 | N | GLN | A | 725 | 28.230 | -9.525 | 40.690 | 1.00 | 11.04 |
| 5618 | CA | GLN | A | 725 | 27.044 | -8.810 | 41.120 | 1.00 | 11.00 |
| 5619 | CB | GLN | A | 725 | 26.089 | -9.723 | 41.846 | 1.00 | 9.85 |
| 5620 | CG | GLN | A | 725 | 25.736 | -10.987 | 41.095 | 1.00 | 13.89 |
| 5621 | CD | GLN | A | 725 | 24.474 | -10.855 | 40.318 | 1.00 | 21.17 |
| 5622 | OE1 | GLN | A | 725 | 23.497 | -10.125 | 40.751 | 1.00 | 20.18 |
| 5623 | NE2 | GLN | A | 725 | 24.469 | -11.464 | 39.117 | 1.00 | 18.83 |
| 5624 | C | GLN | A | 725 | 27.587 | -7.755 | 42.015 | 1.00 | 10.71 |
| 5625 | O | GLN | A | 725 | 28.563 | -7.972 | 42.671 | 1.00 | 11.00 |
| 5626 | N | ALA | A | 726 | 26.968 | -6.593 | 41.993 | 1.00 | 11.17 |
| 5627 | CA | ALA | A | 726 | 27.543 | -5.413 | 42.549 | 1.00 | 11.20 |
| 5628 | CB | ALA | A | 726 | 28.256 | -4.737 | 41.529 | 1.00 | 11.52 |
| 5629 | C | ALA | A | 726 | 26.436 | -4.535 | 43.092 | 1.00 | 11.70 |
| 5630 | O | ALA | A | 726 | 25.249 | -4.644 | 42.670 | 1.00 | 10.98 |
| 5631 | N | MET | A | 727 | 26.793 | -3.755 | 44.117 | 1.00 | 12.46 |
| 5632 | CA | MET | A | 727 | 25.845 | -2.841 | 44.732 | 1.00 | 13.83 |
| 5633 | CB | MET | A | 727 | 25.026 | -3.597 | 45.776 | 1.00 | 12.65 |
| 5634 | CG | MET | A | 727 | 24.013 | -2.743 | 46.480 | 1.00 | 10.43 |
| 5635 | SD | MET | A | 727 | 22.583 | -2.253 | 45.419 | 1.00 | 15.42 |
| 5636 | CE | MET | A | 727 | 22.394 | -0.460 | 45.909 | 1.00 | 3.02 |
| 5637 | C | MET | A | 727 | 26.595 | -1.585 | 45.324 | 1.00 | 15.24 |
| 5638 | O | MET | A | 727 | 27.522 | -1.728 | 46.063 | 1.00 | 14.94 |
| 5639 | N | TRP | A | 728 | 26.235 | -0.364 | 44.940 | 1.00 | 16.36 |
| 5640 | CA | TRP | A | 728 | 26.853 | 0.759 | 45.607 | 1.00 | 15.95 |
| 5641 | CB | TRP | A | 728 | 27.431 | 1.763 | 44.591 | 1.00 | 16.08 |
| 5642 | CG | TRP | A | 728 | 26.419 | 2.621 | 43.963 | 1.00 | 15.47 |
| 5643 | CD1 | TRP | A | 728 | 25.854 | 3.664 | 44.529 | 1.00 | 18.89 |
| 5644 | NE1 | TRP | A | 728 | 24.874 | 4.180 | 43.706 | 1.00 | 21.68 |
| 5645 | CE2 | TRP | A | 728 | 24.812 | 3.447 | 42.556 | 1.00 | 13.87 |
| 5646 | CD2 | TRP | A | 728 | 25.749 | 2.431 | 42.681 | 1.00 | 15.18 |
| 5647 | CE3 | TRP | A | 728 | 25.919 | 1.558 | 41.613 | 1.00 | 9.81 |
| 5648 | CZ3 | TRP | A | 728 | 25.145 | 1.722 | 40.503 | 1.00 | 10.09 |
| 5649 | CH2 | TRP | A | 728 | 24.211 | 2.737 | 40.420 | 1.00 | 12.20 |
| 5650 | CZ2 | TRP | A | 728 | 24.055 | 3.634 | 41.432 | 1.00 | 13.64 |
| 5651 | C | TRP | A | 728 | 25.725 | 1.297 | 46.443 | 1.00 | 17.19 |
| 5652 | O | TRP | A | 728 | 24.591 | 0.965 | 46.124 | 1.00 | 17.28 |

FIGURE 3 (Cont.)

| A | B | C | D | E | F | G | H | I | J |
|---|---|---|---|---|---|---|---|---|---|
| 5653 | N | TYR | A | 729 | 26.039 | 2.067 | 47.505 | 1.00 | 15.64 |
| 5654 | CA | TYR | A | 729 | 25.091 | 2.790 | 48.350 | 1.00 | 13.06 |
| 5655 | CB | TYR | A | 729 | 25.041 | 2.229 | 49.788 | 1.00 | 12.60 |
| 5656 | CG | TYR | A | 729 | 24.352 | 0.885 | 49.848 | 1.00 | 7.93 |
| 5657 | CD1 | TYR | A | 729 | 23.013 | 0.784 | 49.701 | 1.00 | 4.69 |
| 5658 | CE1 | TYR | A | 729 | 22.388 | -0.431 | 49.727 | 1.00 | 2.00 |
| 5659 | CZ | TYR | A | 729 | 23.123 | -1.517 | 49.810 | 1.00 | 3.53 |
| 5660 | OH | TYR | A | 729 | 22.531 | -2.692 | 49.768 | 1.00 | 9.27 |
| 5661 | CE2 | TYR | A | 729 | 24.445 | -1.476 | 49.970 | 1.00 | 5.74 |
| 5662 | CD2 | TYR | A | 729 | 25.068 | -0.275 | 50.016 | 1.00 | 4.63 |
| 5663 | C | TYR | A | 729 | 25.474 | 4.260 | 48.375 | 1.00 | 13.88 |
| 5664 | O | TYR | A | 729 | 26.547 | 4.663 | 48.791 | 1.00 | 14.09 |
| 5665 | N | SER | A | 730 | 24.568 | 5.056 | 47.854 | 1.00 | 14.87 |
| 5666 | CA | SER | A | 730 | 24.830 | 6.467 | 47.555 | 1.00 | 14.61 |
| 5667 | CB | SER | A | 730 | 23.701 | 6.965 | 46.662 | 1.00 | 12.16 |
| 5668 | OG | SER | A | 730 | 23.737 | 6.317 | 45.375 | 1.00 | 15.56 |
| 5669 | C | SER | A | 730 | 24.941 | 7.260 | 48.866 | 1.00 | 14.32 |
| 5670 | O | SER | A | 730 | 24.024 | 7.263 | 49.678 | 1.00 | 15.45 |
| 5671 | N | ASP | A | 731 | 26.041 | 7.932 | 49.083 | 1.00 | 13.40 |
| 5672 | CA | ASP | A | 731 | 26.191 | 8.857 | 50.220 | 1.00 | 13.19 |
| 5673 | CB | ASP | A | 731 | 25.064 | 9.883 | 50.206 | 1.00 | 12.68 |
| 5674 | CG | ASP | A | 731 | 25.168 | 10.842 | 49.052 | 1.00 | 14.52 |
| 5675 | OD1 | ASP | A | 731 | 24.084 | 11.415 | 48.809 | 1.00 | 18.51 |
| 5676 | OD2 | ASP | A | 731 | 26.240 | 11.116 | 48.375 | 1.00 | 18.18 |
| 5677 | C | ASP | A | 731 | 26.345 | 8.231 | 51.610 | 1.00 | 14.16 |
| 5678 | O | ASP | A | 731 | 26.061 | 8.847 | 52.633 | 1.00 | 14.39 |
| 5679 | N | GLN | A | 732 | 26.858 | 7.018 | 51.606 | 1.00 | 13.02 |
| 5680 | CA | GLN | A | 732 | 26.949 | 6.167 | 52.746 | 1.00 | 13.35 |
| 5681 | CB | GLN | A | 732 | 26.276 | 4.821 | 52.460 | 1.00 | 14.21 |
| 5682 | CG | GLN | A | 732 | 24.810 | 4.960 | 52.306 | 1.00 | 13.04 |
| 5683 | CD | GLN | A | 732 | 24.148 | 5.987 | 53.264 | 1.00 | 19.31 |
| 5684 | OE1 | GLN | A | 732 | 23.570 | 7.020 | 52.823 | 1.00 | 17.32 |
| 5685 | NE2 | GLN | A | 732 | 24.177 | 5.673 | 54.564 | 1.00 | 14.11 |
| 5686 | C | GLN | A | 732 | 28.368 | 5.896 | 53.049 | 1.00 | 13.27 |
| 5687 | O | GLN | A | 732 | 29.208 | 5.819 | 52.167 | 1.00 | 15.90 |
| 5688 | N | ASN | A | 733 | 28.656 | 5.734 | 54.304 | 1.00 | 10.84 |
| 5689 | CA | ASN | A | 733 | 29.979 | 5.475 | 54.687 | 1.00 | 11.55 |
| 5690 | CB | ASN | A | 733 | 30.325 | 6.439 | 55.762 | 1.00 | 11.04 |
| 5691 | CG | ASN | A | 733 | 29.556 | 6.223 | 57.028 | 1.00 | 14.12 |
| 5692 | OD1 | ASN | A | 733 | 28.857 | 5.143 | 57.297 | 1.00 | 19.03 |
| 5693 | ND2 | ASN | A | 733 | 29.807 | 7.172 | 57.926 | 1.00 | 7.66 |
| 5694 | C | ASN | A | 733 | 30.285 | 4.019 | 55.025 | 1.00 | 12.63 |
| 5695 | O | ASN | A | 733 | 29.589 | 3.165 | 54.609 | 1.00 | 11.63 |
| 5696 | N | HIS | A | 734 | 31.389 | 3.786 | 55.728 | 1.00 | 14.22 |
| 5697 | CA | HIS | A | 734 | 31.971 | 2.505 | 55.904 | 1.00 | 15.15 |
| 5698 | CB | HIS | A | 734 | 33.306 | 2.585 | 56.709 | 1.00 | 15.51 |
| 5699 | CG | HIS | A | 734 | 34.062 | 1.279 | 56.711 | 1.00 | 17.27 |
| 5700 | ND1 | HIS | A | 734 | 34.177 | 0.507 | 55.575 | 1.00 | 17.34 |
| 5701 | CE1 | HIS | A | 734 | 34.865 | -0.591 | 55.881 | 1.00 | 21.14 |
| 5702 | NE2 | HIS | A | 734 | 35.150 | -0.582 | 57.169 | 1.00 | 18.45 |
| 5703 | CD2 | HIS | A | 734 | 34.681 | 0.588 | 57.709 | 1.00 | 19.07 |

FIGURE 3 (Cont.)

| A | B | C | D | E | F | G | H | I | J |
|---|---|---|---|---|---|---|---|---|---|
| 5704 | C | HIS | A | 734 | 31.012 | 1.594 | 56.689 | 1.00 | 16.62 |
| 5705 | O | HIS | A | 734 | 31.268 | 0.416 | 56.812 | 1.00 | 15.59 |
| 5706 | N | GLY | A | 735 | 29.976 | 2.182 | 57.289 | 1.00 | 17.48 |
| 5707 | CA | GLY | A | 735 | 29.074 | 1.427 | 58.132 | 1.00 | 17.45 |
| 5708 | C | GLY | A | 735 | 27.700 | 1.359 | 57.613 | 1.00 | 17.68 |
| 5709 | O | GLY | A | 735 | 26.840 | 1.053 | 58.375 | 1.00 | 18.64 |
| 5710 | N | LEU | A | 736 | 27.459 | 1.744 | 56.363 | 1.00 | 17.68 |
| 5711 | CA | LEU | A | 736 | 26.204 | 1.466 | 55.654 | 1.00 | 17.26 |
| 5712 | CB | LEU | A | 736 | 26.350 | 0.071 | 55.057 | 1.00 | 17.11 |
| 5713 | CG | LEU | A | 736 | 27.420 | -0.090 | 53.963 | 1.00 | 19.03 |
| 5714 | CD1 | LEU | A | 736 | 27.556 | -1.531 | 53.496 | 1.00 | 22.61 |
| 5715 | CD2 | LEU | A | 736 | 27.079 | 0.750 | 52.750 | 1.00 | 21.35 |
| 5716 | C | LEU | A | 736 | 24.963 | 1.572 | 56.576 | 1.00 | 17.30 |
| 5717 | O | LEU | A | 736 | 24.136 | 0.673 | 56.652 | 1.00 | 16.85 |
| 5718 | N | SER | A | 737 | 24.910 | 2.663 | 57.338 | 1.00 | 17.89 |
| 5719 | CA | SER | A | 737 | 23.979 | 2.843 | 58.456 | 1.00 | 17.29 |
| 5720 | CB | SER | A | 737 | 24.538 | 3.890 | 59.502 | 1.00 | 17.66 |
| 5721 | OG | SER | A | 737 | 25.783 | 4.531 | 59.137 | 1.00 | 14.44 |
| 5722 | C | SER | A | 737 | 22.583 | 3.247 | 57.856 | 1.00 | 17.71 |
| 5723 | O | SER | A | 737 | 22.420 | 3.459 | 56.617 | 1.00 | 19.23 |
| 5724 | N | GLY | A | 738 | 21.570 | 3.343 | 58.675 | 1.00 | 17.36 |
| 5725 | CA | GLY | A | 738 | 20.293 | 3.868 | 58.191 | 1.00 | 18.52 |
| 5726 | C | GLY | A | 738 | 19.471 | 2.811 | 57.468 | 1.00 | 18.55 |
| 5727 | O | GLY | A | 738 | 19.499 | 1.619 | 57.776 | 1.00 | 19.59 |
| 5728 | N | LEU | A | 739 | 18.759 | 3.233 | 56.445 | 1.00 | 18.32 |
| 5729 | CA | LEU | A | 739 | 18.018 | 2.241 | 55.629 | 1.00 | 15.01 |
| 5730 | CB | LEU | A | 739 | 16.911 | 3.035 | 54.909 | 1.00 | 14.77 |
| 5731 | CG | LEU | A | 739 | 15.502 | 3.134 | 55.489 | 1.00 | 12.11 |
| 5732 | CD1 | LEU | A | 739 | 15.529 | 2.905 | 56.926 | 1.00 | 14.74 |
| 5733 | CD2 | LEU | A | 739 | 14.792 | 4.379 | 55.176 | 1.00 | 12.69 |
| 5734 | C | LEU | A | 739 | 18.998 | 1.449 | 54.659 | 1.00 | 13.81 |
| 5735 | O | LEU | A | 739 | 18.698 | 0.384 | 54.049 | 1.00 | 9.66 |
| 5736 | N | SER | A | 740 | 20.213 | 2.004 | 54.500 | 1.00 | 13.61 |
| 5737 | CA | SER | A | 740 | 21.163 | 1.322 | 53.695 | 1.00 | 12.82 |
| 5738 | CB | SER | A | 740 | 22.470 | 2.035 | 53.733 | 1.00 | 13.43 |
| 5739 | OG | SER | A | 740 | 22.347 | 3.395 | 53.369 | 1.00 | 22.19 |
| 5740 | C | SER | A | 740 | 21.313 | -0.034 | 54.326 | 1.00 | 11.79 |
| 5741 | O | SER | A | 740 | 21.473 | -0.991 | 53.619 | 1.00 | 11.63 |
| 5742 | N | THR | A | 741 | 21.310 | -0.108 | 55.668 | 1.00 | 11.65 |
| 5743 | CA | THR | A | 741 | 21.525 | -1.377 | 56.435 | 1.00 | 11.21 |
| 5744 | CB | THR | A | 741 | 21.498 | -1.010 | 57.956 | 1.00 | 13.02 |
| 5745 | OG1 | THR | A | 741 | 22.676 | -0.243 | 58.300 | 1.00 | 11.22 |
| 5746 | CG2 | THR | A | 741 | 21.531 | -2.301 | 58.871 | 1.00 | 8.44 |
| 5747 | C | THR | A | 741 | 20.462 | -2.431 | 56.171 | 1.00 | 11.38 |
| 5748 | O | THR | A | 741 | 20.728 | -3.558 | 55.876 | 1.00 | 11.12 |
| 5749 | N | ASN | A | 742 | 19.226 | -1.976 | 56.209 | 1.00 | 10.37 |
| 5750 | CA | ASN | A | 742 | 18.032 | -2.785 | 55.896 | 1.00 | 12.35 |
| 5751 | CB | ASN | A | 742 | 16.793 | -1.890 | 55.966 | 1.00 | 12.34 |
| 5752 | CG | ASN | A | 742 | 16.472 | -1.428 | 57.371 | 1.00 | 13.98 |
| 5753 | OD1 | ASN | A | 742 | 15.379 | -1.084 | 57.649 | 1.00 | 11.97 |
| 5754 | ND2 | ASN | A | 742 | 17.439 | -1.451 | 58.247 | 1.00 | 15.04 |

FIGURE 3 (Cont.)

| A | B | C | D | E | F | G | H | I | J |
|---|---|---|---|---|---|---|---|---|---|
| 5755 | C | ASN | A | 742 | 18.024 | -3.375 | 54.516 | 1.00 | 13.82 |
| 5756 | O | ASN | A | 742 | 17.396 | -4.480 | 54.226 | 1.00 | 14.91 |
| 5757 | N | HIS | A | 743 | 18.587 | -2.536 | 53.651 | 1.00 | 11.96 |
| 5758 | CA | HIS | A | 743 | 18.714 | -2.745 | 52.234 | 1.00 | 12.23 |
| 5759 | CB | HIS | A | 743 | 18.964 | -1.386 | 51.467 | 1.00 | 10.80 |
| 5760 | CG | HIS | A | 743 | 18.785 | -1.517 | 49.987 | 1.00 | 11.98 |
| 5761 | ND1 | HIS | A | 743 | 19.658 | -2.252 | 49.194 | 1.00 | 6.27 |
| 5762 | CE1 | HIS | A | 743 | 19.178 | -2.270 | 47.958 | 1.00 | 7.32 |
| 5763 | NE2 | HIS | A | 743 | 18.032 | -1.596 | 47.924 | 1.00 | 6.40 |
| 5764 | CD2 | HIS | A | 743 | 17.781 | -1.092 | 49.176 | 1.00 | 7.89 |
| 5765 | C | HIS | A | 743 | 19.848 | -3.715 | 51.992 | 1.00 | 12.02 |
| 5766 | O | HIS | A | 743 | 19.749 | -4.577 | 51.163 | 1.00 | 13.04 |
| 5767 | N | LEU | A | 744 | 20.904 | -3.561 | 52.736 | 1.00 | 12.42 |
| 5768 | CA | LEU | A | 744 | 22.113 | -4.269 | 52.489 | 1.00 | 12.48 |
| 5769 | CB | LEU | A | 744 | 23.246 | -3.614 | 53.230 | 1.00 | 12.13 |
| 5770 | CG | LEU | A | 744 | 24.364 | -4.509 | 53.774 | 1.00 | 14.96 |
| 5771 | CD1 | LEU | A | 744 | 25.279 | -5.210 | 52.717 | 1.00 | 16.30 |
| 5772 | CD2 | LEU | A | 744 | 25.191 | -3.672 | 54.730 | 1.00 | 18.23 |
| 5773 | C | LEU | A | 744 | 21.983 | -5.674 | 52.928 | 1.00 | 13.58 |
| 5774 | O | LEU | A | 744 | 22.431 | -6.602 | 52.244 | 1.00 | 14.76 |
| 5775 | N | TYR | A | 745 | 21.401 | -5.843 | 54.101 | 1.00 | 13.05 |
| 5776 | CA | TYR | A | 745 | 21.133 | -7.140 | 54.598 | 1.00 | 13.27 |
| 5777 | CB | TYR | A | 745 | 20.715 | -7.079 | 56.047 | 1.00 | 12.54 |
| 5778 | CG | TYR | A | 745 | 21.957 | -7.039 | 56.843 | 1.00 | 13.90 |
| 5779 | CD1 | TYR | A | 745 | 22.406 | -5.858 | 57.261 | 1.00 | 8.48 |
| 5780 | CE1 | TYR | A | 745 | 23.504 | -5.739 | 57.902 | 1.00 | 16.33 |
| 5781 | CZ | TYR | A | 745 | 24.307 | -6.806 | 58.190 | 1.00 | 18.91 |
| 5782 | OH | TYR | A | 745 | 25.374 | -6.424 | 58.914 | 1.00 | 12.96 |
| 5783 | CE2 | TYR | A | 745 | 23.950 | -8.111 | 57.812 | 1.00 | 17.99 |
| 5784 | CD2 | TYR | A | 745 | 22.734 | -8.227 | 57.096 | 1.00 | 15.24 |
| 5785 | C | TYR | A | 745 | 20.102 | -7.862 | 53.859 | 1.00 | 13.42 |
| 5786 | O | TYR | A | 745 | 20.160 | -9.094 | 53.807 | 1.00 | 13.85 |
| 5787 | N | THR | A | 746 | 19.106 | -7.168 | 53.327 | 1.00 | 13.95 |
| 5788 | CA | THR | A | 746 | 18.166 | -7.894 | 52.466 | 1.00 | 12.84 |
| 5789 | CB | THR | A | 746 | 17.036 | -7.022 | 52.106 | 1.00 | 13.74 |
| 5790 | OG1 | THR | A | 746 | 16.280 | -6.759 | 53.291 | 1.00 | 14.64 |
| 5791 | CG2 | THR | A | 746 | 16.099 | -7.779 | 51.293 | 1.00 | 9.59 |
| 5792 | C | THR | A | 746 | 18.856 | -8.395 | 51.200 | 1.00 | 11.63 |
| 5793 | O | THR | A | 746 | 18.651 | -9.513 | 50.734 | 1.00 | 12.55 |
| 5794 | N | HIS | A | 747 | 19.717 | -7.588 | 50.663 | 1.00 | 9.74 |
| 5795 | CA | HIS | A | 747 | 20.208 | -7.880 | 49.370 | 1.00 | 8.68 |
| 5796 | CB | HIS | A | 747 | 20.852 | -6.591 | 48.772 | 1.00 | 10.03 |
| 5797 | CG | HIS | A | 747 | 21.249 | -6.684 | 47.328 | 1.00 | 10.24 |
| 5798 | ND1 | HIS | A | 747 | 20.344 | -6.904 | 46.322 | 1.00 | 15.37 |
| 5799 | CE1 | HIS | A | 747 | 20.976 | -6.928 | 45.157 | 1.00 | 16.99 |
| 5800 | NE2 | HIS | A | 747 | 22.257 | -6.701 | 45.378 | 1.00 | 16.73 |
| 5801 | CD2 | HIS | A | 747 | 22.452 | -6.526 | 46.727 | 1.00 | 14.04 |
| 5802 | C | HIS | A | 747 | 21.199 | -8.973 | 49.498 | 1.00 | 8.87 |
| 5803 | O | HIS | A | 747 | 21.441 | -9.663 | 48.568 | 1.00 | 8.43 |
| 5804 | N | MET | A | 748 | 21.876 | -9.083 | 50.620 | 1.00 | 8.77 |
| 5805 | CA | MET | A | 748 | 22.858 | -10.145 | 50.787 | 1.00 | 10.35 |

FIGURE 3 (Cont.)

| A | B | C | D | E | F | G | H | I | J |
|---|---|---|---|---|---|---|---|---|---|
| 5806 | CB | MET | A | 748 | 23.766 | -9.789 | 51.916 | 1.00 | 10.30 |
| 5807 | CG | MET | A | 748 | 24.834 | -8.844 | 51.557 | 1.00 | 13.18 |
| 5808 | SD | MET | A | 748 | 26.062 | -8.821 | 52.814 | 1.00 | 17.53 |
| 5809 | CE | MET | A | 748 | 25.057 | -8.778 | 54.137 | 1.00 | 13.42 |
| 5810 | C | MET | A | 748 | 22.129 | -11.467 | 51.079 | 1.00 | 11.64 |
| 5811 | O | MET | A | 748 | 22.538 | -12.588 | 50.686 | 1.00 | 11.21 |
| 5812 | N | THR | A | 749 | 21.000 | -11.345 | 51.761 | 1.00 | 12.95 |
| 5813 | CA | THR | A | 749 | 20.288 | -12.556 | 52.080 | 1.00 | 12.56 |
| 5814 | CB | THR | A | 749 | 19.460 | -12.474 | 53.394 | 1.00 | 13.07 |
| 5815 | OG1 | THR | A | 749 | 18.117 | -12.745 | 53.100 | 1.00 | 15.51 |
| 5816 | CG2 | THR | A | 749 | 19.433 | -11.131 | 53.992 | 1.00 | 8.04 |
| 5817 | C | THR | A | 749 | 19.601 | -13.053 | 50.826 | 1.00 | 12.84 |
| 5818 | O | THR | A | 749 | 19.694 | -14.250 | 50.541 | 1.00 | 13.65 |
| 5819 | N | HIS | A | 750 | 19.099 | -12.182 | 49.950 | 1.00 | 13.23 |
| 5820 | CA | HIS | A | 750 | 18.570 | -12.697 | 48.638 | 1.00 | 12.76 |
| 5821 | CB | HIS | A | 750 | 17.958 | -11.603 | 47.736 | 1.00 | 13.69 |
| 5822 | CG | HIS | A | 750 | 16.577 | -11.104 | 48.127 | 1.00 | 16.74 |
| 5823 | ND1 | HIS | A | 750 | 15.519 | -11.935 | 48.466 | 1.00 | 20.64 |
| 5824 | CE1 | HIS | A | 750 | 14.452 | -11.197 | 48.735 | 1.00 | 21.60 |
| 5825 | NE2 | HIS | A | 750 | 14.768 | -9.923 | 48.577 | 1.00 | 21.63 |
| 5826 | CD2 | HIS | A | 750 | 16.086 | -9.837 | 48.182 | 1.00 | 17.44 |
| 5827 | C | HIS | A | 750 | 19.720 | -13.436 | 47.888 | 1.00 | 11.27 |
| 5828 | O | HIS | A | 750 | 19.540 | -14.546 | 47.304 | 1.00 | 12.61 |
| 5829 | N | PHE | A | 751 | 20.899 | -12.853 | 47.933 | 1.00 | 8.96 |
| 5830 | CA | PHE | A | 751 | 22.094 | -13.434 | 47.265 | 1.00 | 9.08 |
| 5831 | CB | PHE | A | 751 | 23.280 | -12.438 | 47.352 | 1.00 | 8.59 |
| 5832 | CG | PHE | A | 751 | 24.599 | -12.913 | 46.670 | 1.00 | 11.77 |
| 5833 | CD1 | PHE | A | 751 | 25.599 | -13.489 | 47.401 | 1.00 | 10.20 |
| 5834 | CE1 | PHE | A | 751 | 26.831 | -13.915 | 46.789 | 1.00 | 12.95 |
| 5835 | CZ | PHE | A | 751 | 27.058 | -13.747 | 45.494 | 1.00 | 11.25 |
| 5836 | CE2 | PHE | A | 751 | 26.074 | -13.124 | 44.732 | 1.00 | 12.45 |
| 5837 | CD2 | PHE | A | 751 | 24.849 | -12.702 | 45.324 | 1.00 | 11.80 |
| 5838 | C | PHE | A | 751 | 22.453 | -14.901 | 47.768 | 1.00 | 7.83 |
| 5839 | O | PHE | A | 751 | 22.409 | -15.857 | 46.957 | 1.00 | 5.92 |
| 5840 | N | LEU | A | 752 | 22.714 | -15.034 | 49.081 | 1.00 | 6.15 |
| 5841 | CA | LEU | A | 752 | 22.986 | -16.297 | 49.704 | 1.00 | 6.91 |
| 5842 | CB | LEU | A | 752 | 23.256 | -16.192 | 51.228 | 1.00 | 4.94 |
| 5843 | CG | LEU | A | 752 | 24.429 | -15.347 | 51.730 | 1.00 | 6.41 |
| 5844 | CD1 | LEU | A | 752 | 24.482 | -15.304 | 53.239 | 1.00 | 2.00 |
| 5845 | CD2 | LEU | A | 752 | 25.793 | -15.734 | 51.227 | 1.00 | 3.06 |
| 5846 | C | LEU | A | 752 | 21.864 | -17.320 | 49.448 | 1.00 | 8.04 |
| 5847 | O | LEU | A | 752 | 22.151 | -18.471 | 49.126 | 1.00 | 7.15 |
| 5848 | N | LYS | A | 753 | 20.603 | -16.912 | 49.530 | 1.00 | 9.96 |
| 5849 | CA | LYS | A | 753 | 19.481 | -17.855 | 49.130 | 1.00 | 11.66 |
| 5850 | CB | LYS | A | 753 | 18.095 | -17.252 | 49.452 | 1.00 | 11.26 |
| 5851 | CG | LYS | A | 753 | 17.916 | -17.056 | 50.994 | 1.00 | 13.09 |
| 5852 | CD | LYS | A | 753 | 16.682 | -16.305 | 51.412 | 1.00 | 16.30 |
| 5853 | CE | LYS | A | 753 | 15.479 | -17.224 | 51.685 | 1.00 | 14.13 |
| 5854 | NZ | LYS | A | 753 | 14.303 | -16.401 | 51.412 | 1.00 | 13.35 |
| 5855 | C | LYS | A | 753 | 19.572 | -18.359 | 47.677 | 1.00 | 13.14 |
| 5856 | O | LYS | A | 753 | 19.546 | -19.557 | 47.436 | 1.00 | 13.57 |

FIGURE 3 (Cont.)

| A | B | C | D | E | F | G | H | I | J |
|---|---|---|---|---|---|---|---|---|---|
| 5857 | N | GLN | A | 754 | 19.648 | -17.459 | 46.710 | 1.00 | 14.67 |
| 5858 | CA | GLN | A | 754 | 20.081 | -17.855 | 45.363 | 1.00 | 16.81 |
| 5859 | CB | GLN | A | 754 | 20.381 | -16.598 | 44.476 | 1.00 | 17.29 |
| 5860 | CG | GLN | A | 754 | 21.319 | -16.783 | 43.172 | 1.00 | 22.29 |
| 5861 | CD | GLN | A | 754 | 22.952 | -16.713 | 43.435 | 1.00 | 28.39 |
| 5862 | OE1 | GLN | A | 754 | 23.642 | -17.807 | 43.422 | 1.00 | 31.98 |
| 5863 | NE2 | GLN | A | 754 | 23.532 | -15.477 | 43.622 | 1.00 | 20.24 |
| 5864 | C | GLN | A | 754 | 21.294 | -18.838 | 45.429 | 1.00 | 17.23 |
| 5865 | O | GLN | A | 754 | 21.275 | -19.863 | 44.780 | 1.00 | 17.70 |
| 5866 | N | CYS | A | 755 | 22.340 | -18.522 | 46.196 | 1.00 | 17.04 |
| 5867 | CA | CYS | A | 755 | 23.532 | -19.348 | 46.207 | 1.00 | 18.02 |
| 5868 | CB | CYS | A | 755 | 24.632 | -18.688 | 46.988 | 1.00 | 18.09 |
| 5869 | SG | CYS | A | 755 | 26.312 | -19.425 | 46.831 | 1.00 | 24.07 |
| 5870 | C | CYS | A | 755 | 23.228 | -20.720 | 46.798 | 1.00 | 17.86 |
| 5871 | O | CYS | A | 755 | 23.877 | -21.682 | 46.428 | 1.00 | 18.22 |
| 5872 | N | PHE | A | 756 | 22.223 | -20.791 | 47.674 | 1.00 | 16.89 |
| 5873 | CA | PHE | A | 756 | 21.863 | -22.011 | 48.394 | 1.00 | 16.57 |
| 5874 | CB | PHE | A | 756 | 21.782 | -21.749 | 49.918 | 1.00 | 16.50 |
| 5875 | CG | PHE | A | 756 | 23.137 | -21.427 | 50.567 | 1.00 | 15.47 |
| 5876 | CD1 | PHE | A | 756 | 24.325 | -21.412 | 49.827 | 1.00 | 13.28 |
| 5877 | CE1 | PHE | A | 756 | 25.561 | -21.129 | 50.416 | 1.00 | 11.54 |
| 5878 | CZ | PHE | A | 756 | 25.640 | -20.892 | 51.737 | 1.00 | 12.43 |
| 5879 | CE2 | PHE | A | 756 | 24.463 | -20.873 | 52.496 | 1.00 | 12.53 |
| 5880 | CD2 | PHE | A | 756 | 23.214 | -21.132 | 51.898 | 1.00 | 12.14 |
| 5881 | C | PHE | A | 756 | 20.577 | -22.683 | 47.880 | 1.00 | 17.11 |
| 5882 | O | PHE | A | 756 | 20.341 | -23.831 | 48.254 | 1.00 | 16.76 |
| 5883 | N | SER | A | 757 | 19.826 | -22.004 | 46.984 | 1.00 | 16.90 |
| 5884 | CA | SER | A | 757 | 18.630 | -22.509 | 46.287 | 1.00 | 17.32 |
| 5885 | CB | SER | A | 757 | 19.027 | -23.387 | 45.060 | 1.00 | 17.50 |
| 5886 | OG | SER | A | 757 | 19.919 | -24.452 | 45.383 | 1.00 | 15.50 |
| 5887 | C | SER | A | 757 | 17.619 | -23.227 | 47.214 | 1.00 | 18.11 |
| 5888 | O | SER | A | 757 | 17.412 | -24.468 | 47.137 | 1.00 | 17.93 |
| 5889 | C1 | NAG | A | 4901 | 10.641 | -3.275 | 67.890 | 1.00 | 40.74 |
| 5890 | C2 | NAG | A | 4901 | 9.327 | -4.042 | 67.754 | 1.00 | 45.13 |
| 5891 | N2 | NAG | A | 4901 | 8.674 | -3.700 | 66.503 | 1.00 | 48.13 |
| 5892 | C7 | NAG | A | 4901 | 8.258 | -2.467 | 66.238 | 1.00 | 51.49 |
| 5893 | O7 | NAG | A | 4901 | 8.435 | -1.542 | 67.005 | 1.00 | 53.88 |
| 5894 | C8 | NAG | A | 4901 | 7.627 | -2.278 | 64.894 | 1.00 | 50.22 |
| 5895 | C3 | NAG | A | 4901 | 8.454 | -3.767 | 68.970 | 1.00 | 45.16 |
| 5896 | O3 | NAG | A | 4901 | 7.223 | -4.500 | 68.901 | 1.00 | 47.11 |
| 5897 | C4 | NAG | A | 4901 | 9.241 | -4.175 | 70.207 | 1.00 | 47.14 |
| 5898 | O4 | NAG | A | 4901 | 8.466 | -3.892 | 71.377 | 1.00 | 45.67 |
| 5899 | C5 | NAG | A | 4901 | 10.580 | -3.435 | 70.268 | 1.00 | 46.55 |
| 5900 | C6 | NAG | A | 4901 | 11.399 | -3.865 | 71.486 | 1.00 | 48.42 |
| 5901 | O6 | NAG | A | 4901 | 12.584 | -4.575 | 71.098 | 1.00 | 50.96 |
| 5902 | O5 | NAG | A | 4901 | 11.332 | -3.672 | 69.079 | 1.00 | 43.60 |
| 5903 | C1 | NAG | A | 9201 | 8.392 | 15.214 | 84.276 | 1.00 | 41.45 |
| 5904 | C2 | NAG | A | 9201 | 8.123 | 14.017 | 83.385 | 1.00 | 43.77 |
| 5905 | N2 | NAG | A | 9201 | 7.886 | 14.434 | 82.024 | 1.00 | 41.71 |
| 5906 | C7 | NAG | A | 9201 | 8.513 | 13.867 | 81.005 | 1.00 | 40.33 |
| 5907 | O7 | NAG | A | 9201 | 9.280 | 12.929 | 81.176 | 1.00 | 37.14 |

FIGURE 3 (Cont.)

| A | B | C | D E | F | G | H | I | J |
|---|---|---|---|---|---|---|---|---|
| 5908 | C8 | NAG | A9201 | 8.151 | 14.407 | 79.649 | 1.00 | 39.66 |
| 5909 | C3 | NAG | A9201 | 6.862 | 13.365 | 83.912 | 1.00 | 45.44 |
| 5910 | O3 | NAG | A9201 | 6.513 | 12.284 | 83.038 | 1.00 | 44.70 |
| 5911 | C4 | NAG | A9201 | 7.093 | 12.934 | 85.353 | 1.00 | 47.30 |
| 5912 | O4 | NAG | A9201 | 6.460 | 12.158 | 86.163 | 1.00 | 55.17 |
| 5913 | C5 | NAG | A9201 | 7.558 | 14.121 | 86.205 | 1.00 | 46.48 |
| 5914 | C6 | NAG | A9201 | 7.865 | 13.683 | 87.641 | 1.00 | 45.78 |
| 5915 | O6 | NAG | A9201 | 8.949 | 14.444 | 88.181 | 1.00 | 44.67 |
| 5916 | O5 | NAG | A9201 | 8.677 | 14.777 | 85.603 | 1.00 | 44.90 |
| 5917 | C1 | NAG | A9202 | 5.848 | 12.314 | 87.463 | 1.00 | 74.46 |
| 5918 | C2 | NAG | A9202 | 4.710 | 13.078 | 88.122 | 1.00 | 78.22 |
| 5919 | N2 | NAG | A9202 | 4.847 | 14.520 | 88.127 | 1.00 | 78.03 |
| 5920 | C7 | NAG | A9202 | 4.090 | 15.301 | 87.353 | 1.00 | 79.47 |
| 5921 | O7 | NAG | A9202 | 4.200 | 16.517 | 87.350 | 1.00 | 82.13 |
| 5922 | C8 | NAG | A9202 | 3.171 | 14.588 | 86.407 | 1.00 | 77.68 |
| 5923 | C3 | NAG | A9202 | 4.647 | 12.614 | 89.561 | 1.00 | 78.59 |
| 5924 | O3 | NAG | A9202 | 3.656 | 13.355 | 90.276 | 1.00 | 80.43 |
| 5925 | C4 | NAG | A9202 | 4.314 | 11.133 | 89.565 | 1.00 | 80.32 |
| 5926 | O4 | NAG | A9202 | 4.289 | 10.664 | 90.913 | 1.00 | 79.64 |
| 5927 | C5 | NAG | A9202 | 5.362 | 10.362 | 88.772 | 1.00 | 80.37 |
| 5928 | C6 | NAG | A9202 | 4.994 | 8.881 | 88.708 | 1.00 | 82.61 |
| 5929 | O6 | NAG | A9202 | 4.824 | 8.450 | 87.357 | 1.00 | 84.12 |
| 5930 | O5 | NAG | A9202 | 5.503 | 10.923 | 87.459 | 1.00 | 80.28 |
| 5931 | C1 | NAG | A2271 | 53.575 | 22.874 | 58.852 | 1.00 | 33.59 |
| 5932 | C2 | NAG | A2271 | 53.922 | 23.504 | 57.518 | 1.00 | 36.66 |
| 5933 | N2 | NAG | A2271 | 54.684 | 22.589 | 56.703 | 1.00 | 39.61 |
| 5934 | C7 | NAG | A2271 | 54.361 | 22.348 | 55.442 | 1.00 | 42.17 |
| 5935 | O7 | NAG | A2271 | 53.433 | 22.934 | 54.903 | 1.00 | 43.84 |
| 5936 | C8 | NAG | A2271 | 55.258 | 21.379 | 54.726 | 1.00 | 41.07 |
| 5937 | C3 | NAG | A2271 | 54.788 | 24.707 | 57.825 | 1.00 | 36.72 |
| 5938 | O3 | NAG | A2271 | 55.224 | 25.278 | 56.585 | 1.00 | 35.19 |
| 5939 | C4 | NAG | A2271 | 54.001 | 25.674 | 58.698 | 1.00 | 36.98 |
| 5940 | O4 | NAG | A2271 | 54.168 | 26.904 | 59.040 | 1.00 | 39.47 |
| 5941 | C5 | NAG | A2271 | 53.485 | 24.967 | 59.957 | 1.00 | 34.58 |
| 5942 | C6 | NAG | A2271 | 52.628 | 25.912 | 60.807 | 1.00 | 32.82 |
| 5943 | O6 | NAG | A2271 | 51.394 | 25.286 | 61.170 | 1.00 | 32.34 |
| 5944 | O5 | NAG | A2271 | 52.777 | 23.772 | 59.620 | 1.00 | 35.28 |
| 5945 | C1 | NAG | A2272 | 55.901 | 26.288 | 55.783 | 1.00 | 36.15 |
| 5946 | C2 | NAG | A2272 | 57.403 | 26.163 | 55.575 | 1.00 | 35.55 |
| 5947 | N2 | NAG | A2272 | 58.225 | 26.930 | 56.487 | 1.00 | 36.87 |
| 5948 | C7 | NAG | A2272 | 58.942 | 26.345 | 57.450 | 1.00 | 38.65 |
| 5949 | O7 | NAG | A2272 | 59.636 | 26.984 | 58.224 | 1.00 | 39.92 |
| 5950 | C8 | NAG | A2272 | 58.757 | 24.864 | 57.592 | 1.00 | 37.68 |
| 5951 | C3 | NAG | A2272 | 57.691 | 26.649 | 54.171 | 1.00 | 36.22 |
| 5952 | O3 | NAG | A2272 | 59.100 | 26.649 | 53.928 | 1.00 | 36.38 |
| 5953 | C4 | NAG | A2272 | 56.980 | 25.727 | 53.197 | 1.00 | 35.70 |
| 5954 | O4 | NAG | A2272 | 57.206 | 26.191 | 51.866 | 1.00 | 34.15 |
| 5955 | C5 | NAG | A2272 | 55.485 | 25.714 | 53.490 | 1.00 | 34.70 |
| 5956 | C6 | NAG | A2272 | 54.772 | 24.732 | 52.563 | 1.00 | 34.53 |
| 5957 | O6 | NAG | A2272 | 53.924 | 23.852 | 53.299 | 1.00 | 38.63 |
| 5958 | O5 | NAG | A2272 | 55.252 | 25.395 | 54.869 | 1.00 | 35.69 |

FIGURE 3 (Cont.)

| A | B | C | D | E | F | G | H | I | J |
|---|---|---|---|---|---|---|---|---|---|
| 5959 | N | MET | B | 39 | 22.005 | -23.244 | 9.715 | 1.00 | 17.11 |
| 5960 | CA | MET | B | 39 | 22.643 | -24.341 | 10.433 | 1.00 | 18.01 |
| 5961 | CB | MET | B | 39 | 23.992 | -24.684 | 9.800 | 1.00 | 18.19 |
| 5962 | CG | MET | B | 39 | 24.146 | -26.148 | 9.421 | 1.00 | 22.40 |
| 5963 | SD | MET | B | 39 | 25.839 | -26.738 | 9.591 | 1.00 | 28.60 |
| 5964 | CE | MET | B | 39 | 26.395 | -26.668 | 7.888 | 1.00 | 25.97 |
| 5965 | C | MET | B | 39 | 22.827 | -24.000 | 11.908 | 1.00 | 17.51 |
| 5966 | O | MET | B | 39 | 22.601 | -24.929 | 12.853 | 1.00 | 17.56 |
| 5967 | N | ARG | B | 40 | 23.360 | -22.852 | 12.339 | 1.00 | 16.41 |
| 5968 | CA | ARG | B | 40 | 23.520 | -22.435 | 13.757 | 1.00 | 15.65 |
| 5969 | CB | ARG | B | 40 | 24.943 | -22.667 | 14.274 | 1.00 | 15.59 |
| 5970 | CG | ARG | B | 40 | 26.005 | -21.850 | 13.650 | 1.00 | 14.19 |
| 5971 | CD | ARG | B | 40 | 26.519 | -20.819 | 14.573 | 1.00 | 14.42 |
| 5972 | NE | ARG | B | 40 | 27.678 | -20.104 | 14.044 | 1.00 | 13.17 |
| 5973 | CZ | ARG | B | 40 | 28.128 | -18.979 | 14.545 | 1.00 | 13.72 |
| 5974 | NH1 | ARG | B | 40 | 29.191 | -18.422 | 13.994 | 1.00 | 13.90 |
| 5975 | NH2 | ARG | B | 40 | 27.503 | -18.377 | 15.574 | 1.00 | 14.28 |
| 5976 | C | ARG | B | 40 | 23.136 | -20.994 | 14.058 | 1.00 | 15.02 |
| 5977 | O | ARG | B | 40 | 22.880 | -20.192 | 13.155 | 1.00 | 14.95 |
| 5978 | N | ALA | B | 41 | 23.132 | -20.666 | 15.343 | 1.00 | 14.15 |
| 5979 | CA | ALA | B | 41 | 22.576 | -19.394 | 15.772 | 1.00 | 13.37 |
| 5980 | CB | ALA | B | 41 | 21.493 | -19.619 | 16.888 | 1.00 | 13.61 |
| 5981 | C | ALA | B | 41 | 23.607 | -18.286 | 16.180 | 1.00 | 12.62 |
| 5982 | O | ALA | B | 41 | 24.846 | -18.470 | 16.248 | 1.00 | 12.06 |
| 5983 | N | LEU | B | 42 | 23.062 | -17.108 | 16.356 | 1.00 | 10.68 |
| 5984 | CA | LEU | B | 42 | 23.865 | -16.045 | 16.810 | 1.00 | 10.90 |
| 5985 | CB | LEU | B | 42 | 23.109 | -14.724 | 16.636 | 1.00 | 11.03 |
| 5986 | CG | LEU | B | 42 | 23.571 | -13.633 | 15.655 | 1.00 | 8.12 |
| 5987 | CD1 | LEU | B | 42 | 24.541 | -14.093 | 14.599 | 1.00 | 3.37 |
| 5988 | CD2 | LEU | B | 42 | 22.365 | -12.985 | 15.046 | 1.00 | 3.68 |
| 5989 | C | LEU | B | 42 | 24.227 | -16.258 | 18.282 | 1.00 | 11.98 |
| 5990 | O | LEU | B | 42 | 23.445 | -16.736 | 19.135 | 1.00 | 13.09 |
| 5991 | N | THR | B | 43 | 25.430 | -15.850 | 18.599 | 1.00 | 11.91 |
| 5992 | CA | THR | B | 43 | 25.916 | -16.083 | 19.914 | 1.00 | 11.40 |
| 5993 | CB | THR | B | 43 | 26.793 | -17.322 | 19.863 | 1.00 | 10.31 |
| 5994 | OG1 | THR | B | 43 | 27.335 | -17.544 | 21.149 | 1.00 | 16.19 |
| 5995 | CG2 | THR | B | 43 | 27.983 | -17.164 | 19.037 | 1.00 | 7.46 |
| 5996 | C | THR | B | 43 | 26.611 | -14.813 | 20.371 | 1.00 | 12.20 |
| 5997 | O | THR | B | 43 | 27.207 | -14.118 | 19.560 | 1.00 | 12.03 |
| 5998 | N | LEU | B | 44 | 26.517 | -14.519 | 21.670 | 1.00 | 11.89 |
| 5999 | CA | LEU | B | 44 | 27.008 | -13.252 | 22.226 | 1.00 | 11.82 |
| 6000 | CB | LEU | B | 44 | 27.064 | -13.330 | 23.738 | 1.00 | 11.83 |
| 6001 | CG | LEU | B | 44 | 26.415 | -12.266 | 24.601 | 1.00 | 16.25 |
| 6002 | CD1 | LEU | B | 44 | 27.134 | -12.207 | 25.955 | 1.00 | 18.19 |
| 6003 | CD2 | LEU | B | 44 | 26.303 | -10.835 | 23.949 | 1.00 | 18.72 |
| 6004 | C | LEU | B | 44 | 28.419 | -13.021 | 21.746 | 1.00 | 11.53 |
| 6005 | O | LEU | B | 44 | 28.761 | -11.897 | 21.389 | 1.00 | 12.60 |
| 6006 | N | LYS | B | 45 | 29.257 | -14.076 | 21.746 | 1.00 | 11.24 |
| 6007 | CA | LYS | B | 45 | 30.637 | -13.893 | 21.282 | 1.00 | 11.14 |
| 6008 | CB | LYS | B | 45 | 31.520 | -15.174 | 21.211 | 1.00 | 10.90 |
| 6009 | CG | LYS | B | 45 | 30.829 | -16.650 | 20.889 | 1.00 | 13.94 |

FIGURE 3 (Cont.)

| A | B | C | D | E | F | G | H | I | J |
|---|---|---|---|---|---|---|---|---|---|
| 6010 | CD | LYS | B | 45 | 31.014 | -17.860 | 21.983 | 1.00 | 14.60 |
| 6011 | CE | LYS | B | 45 | 29.914 | -17.925 | 23.215 | 1.00 | 16.04 |
| 6012 | NZ | LYS | B | 45 | 28.648 | -16.910 | 23.341 | 1.00 | 12.86 |
| 6013 | C | LYS | B | 45 | 30.554 | -13.121 | 19.936 | 1.00 | 10.11 |
| 6014 | O | LYS | B | 45 | 30.988 | -11.958 | 19.856 | 1.00 | 9.02 |
| 6015 | N | ASP | B | 46 | 29.906 | -13.741 | 18.952 | 1.00 | 9.26 |
| 6016 | CA | ASP | B | 46 | 29.607 | -13.103 | 17.645 | 1.00 | 9.91 |
| 6017 | CB | ASP | B | 46 | 28.453 | -13.822 | 16.973 | 1.00 | 8.22 |
| 6018 | CG | ASP | B | 46 | 28.826 | -15.164 | 16.530 | 1.00 | 9.22 |
| 6019 | OD1 | ASP | B | 46 | 27.877 | -15.832 | 16.099 | 1.00 | 12.09 |
| 6020 | OD2 | ASP | B | 46 | 30.009 | -15.642 | 16.552 | 1.00 | 7.31 |
| 6021 | C | ASP | B | 46 | 29.256 | -11.617 | 17.674 | 1.00 | 10.37 |
| 6022 | O | ASP | B | 46 | 29.734 | -10.819 | 16.842 | 1.00 | 11.29 |
| 6023 | N | ILE | B | 47 | 28.437 | -11.244 | 18.635 | 1.00 | 10.45 |
| 6024 | CA | ILE | B | 47 | 28.098 | -9.878 | 18.718 | 1.00 | 11.84 |
| 6025 | CB | ILE | B | 47 | 26.725 | -9.716 | 19.262 | 1.00 | 11.87 |
| 6026 | CG1 | ILE | B | 47 | 25.750 | -10.195 | 18.179 | 1.00 | 13.81 |
| 6027 | CD1 | ILE | B | 47 | 24.414 | -10.483 | 18.656 | 1.00 | 15.65 |
| 6028 | CG2 | ILE | B | 47 | 26.457 | -8.249 | 19.518 | 1.00 | 9.33 |
| 6029 | C | ILE | B | 47 | 29.132 | -8.999 | 19.384 | 1.00 | 12.95 |
| 6030 | O | ILE | B | 47 | 29.325 | -7.854 | 18.941 | 1.00 | 13.55 |
| 6031 | N | LEU | B | 48 | 29.774 | -9.469 | 20.438 | 1.00 | 12.55 |
| 6032 | CA | LEU | B | 48 | 30.756 | -8.608 | 21.091 | 1.00 | 13.07 |
| 6033 | CB | LEU | B | 48 | 31.012 | -9.012 | 22.533 | 1.00 | 12.18 |
| 6034 | CG | LEU | B | 48 | 29.732 | -9.271 | 23.350 | 1.00 | 11.66 |
| 6035 | CD1 | LEU | B | 48 | 29.909 | -10.294 | 24.556 | 1.00 | 8.83 |
| 6036 | CD2 | LEU | B | 48 | 29.165 | -7.943 | 23.757 | 1.00 | 6.79 |
| 6037 | C | LEU | B | 48 | 32.057 | -8.596 | 20.328 | 1.00 | 13.41 |
| 6038 | O | LEU | B | 48 | 32.865 | -7.694 | 20.548 | 1.00 | 14.81 |
| 6039 | N | ASN | B | 49 | 32.273 | -9.584 | 19.441 | 1.00 | 13.12 |
| 6040 | CA | ASN | B | 49 | 33.437 | -9.571 | 18.593 | 1.00 | 12.70 |
| 6041 | CB | ASN | B | 49 | 33.861 | -10.988 | 18.209 | 1.00 | 12.97 |
| 6042 | CG | ASN | B | 49 | 35.218 | -11.011 | 17.491 | 1.00 | 15.42 |
| 6043 | OD1 | ASN | B | 49 | 36.130 | -10.398 | 18.027 | 1.00 | 19.86 |
| 6044 | ND2 | ASN | B | 49 | 35.359 | -11.681 | 16.269 | 1.00 | 20.13 |
| 6045 | C | ASN | B | 49 | 33.244 | -8.776 | 17.300 | 1.00 | 12.19 |
| 6046 | O | ASN | B | 49 | 34.201 | -8.651 | 16.517 | 1.00 | 12.65 |
| 6047 | N | GLY | B | 50 | 32.039 | -8.271 | 17.046 | 1.00 | 11.02 |
| 6048 | CA | GLY | B | 50 | 31.711 | -7.769 | 15.731 | 1.00 | 9.96 |
| 6049 | C | GLY | B | 50 | 32.004 | -8.772 | 14.584 | 1.00 | 9.36 |
| 6050 | O | GLY | B | 50 | 32.349 | -8.357 | 13.479 | 1.00 | 10.90 |
| 6051 | N | THR | B | 51 | 31.864 | -10.077 | 14.786 | 1.00 | 7.69 |
| 6052 | CA | THR | B | 51 | 32.185 | -10.960 | 13.672 | 1.00 | 7.44 |
| 6053 | CB | THR | B | 51 | 32.168 | -12.468 | 14.019 | 1.00 | 7.78 |
| 6054 | OG1 | THR | B | 51 | 32.589 | -12.717 | 15.375 | 1.00 | 4.92 |
| 6055 | CG2 | THR | B | 51 | 33.234 | -13.180 | 13.135 | 1.00 | 7.93 |
| 6056 | C | THR | B | 51 | 31.297 | -10.700 | 12.460 | 1.00 | 6.98 |
| 6057 | O | THR | B | 51 | 31.671 | -11.015 | 11.359 | 1.00 | 6.19 |
| 6058 | N | PHE | B | 52 | 30.140 | -10.106 | 12.707 | 1.00 | 7.66 |
| 6059 | CA | PHE | B | 52 | 29.234 | -9.624 | 11.673 | 1.00 | 8.52 |
| 6060 | CB | PHE | B | 52 | 27.898 | -10.269 | 11.979 | 1.00 | 8.10 |

FIGURE 3 (Cont.)

| A | B | C | D | E | F | G | H | I | J |
|---|---|---|---|---|---|---|---|---|---|
| 6061 | CG | PHE | B | 52 | 28.021 | -11.774 | 12.138 | 1.00 | 10.70 |
| 6062 | CD1 | PHE | B | 52 | 28.704 | -12.521 | 11.202 | 1.00 | 12.23 |
| 6063 | CE1 | PHE | B | 52 | 28.859 | -13.850 | 11.334 | 1.00 | 15.26 |
| 6064 | CZ | PHE | B | 52 | 28.329 | -14.489 | 12.386 | 1.00 | 13.51 |
| 6065 | CE2 | PHE | B | 52 | 27.662 | -13.792 | 13.310 | 1.00 | 14.12 |
| 6066 | CD2 | PHE | B | 52 | 27.514 | -12.419 | 13.208 | 1.00 | 14.43 |
| 6067 | C | PHE | B | 52 | 29.119 | -8.099 | 11.516 | 1.00 | 9.47 |
| 6068 | O | PHE | B | 52 | 28.040 | -7.556 | 11.283 | 1.00 | 10.26 |
| 6069 | N | SER | B | 53 | 30.208 | -7.357 | 11.589 | 1.00 | 10.32 |
| 6070 | CA | SER | B | 53 | 30.052 | -5.933 | 11.281 | 1.00 | 11.08 |
| 6071 | CB | SER | B | 53 | 31.084 | -5.033 | 11.983 | 1.00 | 11.02 |
| 6072 | OG | SER | B | 53 | 32.433 | -5.343 | 11.685 | 1.00 | 14.30 |
| 6073 | C | SER | B | 53 | 30.045 | -5.794 | 9.759 | 1.00 | 10.83 |
| 6074 | O | SER | B | 53 | 30.387 | -6.754 | 9.059 | 1.00 | 9.76 |
| 6075 | N | TYR | B | 54 | 29.528 | -4.649 | 9.262 | 1.00 | 11.40 |
| 6076 | CA | TYR | B | 54 | 29.614 | -4.339 | 7.860 | 1.00 | 11.61 |
| 6077 | CB | TYR | B | 54 | 28.262 | -4.047 | 7.326 | 1.00 | 11.29 |
| 6078 | CG | TYR | B | 54 | 27.523 | -2.938 | 8.056 | 1.00 | 13.57 |
| 6079 | CD1 | TYR | B | 54 | 27.804 | -1.584 | 7.810 | 1.00 | 11.73 |
| 6080 | CE1 | TYR | B | 54 | 27.097 | -0.580 | 8.508 | 1.00 | 17.61 |
| 6081 | CZ | TYR | B | 54 | 26.115 | -0.954 | 9.395 | 1.00 | 16.18 |
| 6082 | OH | TYR | B | 54 | 25.422 | -0.030 | 10.050 | 1.00 | 19.16 |
| 6083 | CE2 | TYR | B | 54 | 25.823 | -2.280 | 9.606 | 1.00 | 13.20 |
| 6084 | CD2 | TYR | B | 54 | 26.519 | -3.248 | 8.955 | 1.00 | 10.85 |
| 6085 | C | TYR | B | 54 | 30.562 | -3.182 | 7.641 | 1.00 | 11.91 |
| 6086 | O | TYR | B | 54 | 30.798 | -2.378 | 8.555 | 1.00 | 11.05 |
| 6087 | N | LYS | B | 55 | 31.087 | -3.098 | 6.415 | 1.00 | 12.13 |
| 6088 | CA | LYS | B | 55 | 31.942 | -1.999 | 5.963 | 1.00 | 12.42 |
| 6089 | CB | LYS | B | 55 | 33.140 | -2.540 | 5.151 | 1.00 | 13.60 |
| 6090 | CG | LYS | B | 55 | 34.196 | -3.421 | 5.914 | 1.00 | 12.38 |
| 6091 | CD | LYS | B | 55 | 35.575 | -3.282 | 5.199 | 1.00 | 16.95 |
| 6092 | CE | LYS | B | 55 | 36.559 | -4.503 | 5.303 | 1.00 | 16.70 |
| 6093 | NZ | LYS | B | 55 | 36.933 | -5.039 | 3.890 | 1.00 | 16.98 |
| 6094 | C | LYS | B | 55 | 31.158 | -1.001 | 5.084 | 1.00 | 12.58 |
| 6095 | O | LYS | B | 55 | 30.270 | -1.321 | 4.324 | 1.00 | 12.86 |
| 6096 | N | THR | B | 56 | 31.544 | 0.232 | 5.187 | 1.00 | 12.90 |
| 6097 | CA | THR | B | 56 | 30.851 | 1.317 | 4.572 | 1.00 | 12.38 |
| 6098 | CB | THR | B | 56 | 30.283 | 2.102 | 5.772 | 1.00 | 13.33 |
| 6099 | OG1 | THR | B | 56 | 28.881 | 2.330 | 5.624 | 1.00 | 15.28 |
| 6100 | CG2 | THR | B | 56 | 30.906 | 3.425 | 5.986 | 1.00 | 14.14 |
| 6101 | C | THR | B | 56 | 32.007 | 1.941 | 3.785 | 1.00 | 12.39 |
| 6102 | O | THR | B | 56 | 33.200 | 1.657 | 4.086 | 1.00 | 11.45 |
| 6103 | N | PHE | B | 57 | 31.745 | 2.670 | 2.718 | 1.00 | 11.30 |
| 6104 | CA | PHE | B | 57 | 32.906 | 3.281 | 2.068 | 1.00 | 12.28 |
| 6105 | CB | PHE | B | 57 | 33.328 | 2.470 | 0.823 | 1.00 | 11.92 |
| 6106 | CG | PHE | B | 57 | 34.573 | 2.968 | 0.174 | 1.00 | 10.29 |
| 6107 | CD1 | PHE | B | 57 | 35.719 | 2.201 | 0.158 | 1.00 | 10.46 |
| 6108 | CE1 | PHE | B | 57 | 36.902 | 2.690 | -0.448 | 1.00 | 10.46 |
| 6109 | CZ | PHE | B | 57 | 36.928 | 3.894 | -1.009 | 1.00 | 9.87 |
| 6110 | CE2 | PHE | B | 57 | 35.775 | 4.669 | -1.013 | 1.00 | 11.55 |
| 6111 | CD2 | PHE | B | 57 | 34.607 | 4.189 | -0.457 | 1.00 | 7.94 |

FIGURE 3 (Cont.)

| A | B | C | D | E | F | G | H | I | J |
|---|---|---|---|---|---|---|---|---|---|
| 6112 | C | PHE | B | 57 | 32.655 | 4.745 | 1.721 | 1.00 | 12.49 |
| 6113 | O | PHE | B | 57 | 31.959 | 5.032 | 0.778 | 1.00 | 14.13 |
| 6114 | N | PHE | B | 58 | 33.229 | 5.672 | 2.458 | 1.00 | 12.90 |
| 6115 | CA | PHE | B | 58 | 32.857 | 7.075 | 2.199 | 1.00 | 13.65 |
| 6116 | CB | PHE | B | 58 | 32.486 | 7.867 | 3.466 | 1.00 | 12.50 |
| 6117 | CG | PHE | B | 58 | 31.160 | 7.529 | 4.079 | 1.00 | 8.65 |
| 6118 | CD1 | PHE | B | 58 | 30.067 | 8.332 | 3.833 | 1.00 | 7.07 |
| 6119 | CE1 | PHE | B | 58 | 28.827 | 8.088 | 4.363 | 1.00 | 5.51 |
| 6120 | CZ | PHE | B | 58 | 28.625 | 7.030 | 5.223 | 1.00 | 6.71 |
| 6121 | CE2 | PHE | B | 58 | 29.663 | 6.179 | 5.494 | 1.00 | 7.30 |
| 6122 | CD2 | PHE | B | 58 | 30.997 | 6.453 | 4.919 | 1.00 | 9.16 |
| 6123 | C | PHE | B | 58 | 34.119 | 7.651 | 1.581 | 1.00 | 14.95 |
| 6124 | O | PHE | B | 58 | 35.132 | 7.847 | 2.244 | 1.00 | 15.58 |
| 6125 | N | PRO | B | 59 | 34.075 | 7.966 | 0.300 | 1.00 | 16.78 |
| 6126 | CA | PRO | B | 59 | 35.303 | 8.357 | -0.374 | 1.00 | 16.59 |
| 6127 | CB | PRO | B | 59 | 34.845 | 8.468 | -1.842 | 1.00 | 16.83 |
| 6128 | CG | PRO | B | 59 | 33.612 | 7.643 | -1.920 | 1.00 | 16.89 |
| 6129 | CD | PRO | B | 59 | 32.932 | 8.099 | -0.615 | 1.00 | 16.42 |
| 6130 | C | PRO | B | 59 | 35.718 | 9.691 | 0.200 | 1.00 | 15.98 |
| 6131 | O | PRO | B | 59 | 34.890 | 10.452 | 0.559 | 1.00 | 13.18 |
| 6132 | N | ASN | B | 60 | 37.010 | 9.922 | 0.259 | 1.00 | 16.93 |
| 6133 | CA | ASN | B | 60 | 37.586 | 11.113 | 0.817 | 1.00 | 18.16 |
| 6134 | CB | ASN | B | 60 | 38.854 | 10.708 | 1.586 | 1.00 | 19.50 |
| 6135 | CG | ASN | B | 60 | 39.425 | 11.846 | 2.460 | 1.00 | 21.77 |
| 6136 | OD1 | ASN | B | 60 | 39.718 | 11.604 | 3.570 | 1.00 | 28.03 |
| 6137 | ND2 | ASN | B | 60 | 39.619 | 13.033 | 1.921 | 1.00 | 25.76 |
| 6138 | C | ASN | B | 60 | 37.913 | 12.118 | -0.279 | 1.00 | 17.26 |
| 6139 | O | ASN | B | 60 | 39.027 | 12.284 | -0.743 | 1.00 | 17.41 |
| 6140 | N | TRP | B | 61 | 36.918 | 12.896 | -0.639 | 1.00 | 18.28 |
| 6141 | CA | TRP | B | 61 | 37.068 | 13.718 | -1.815 | 1.00 | 17.79 |
| 6142 | CB | TRP | B | 61 | 35.809 | 14.447 | -2.055 | 1.00 | 17.16 |
| 6143 | CG | TRP | B | 61 | 34.648 | 13.506 | -2.016 | 1.00 | 18.56 |
| 6144 | CD1 | TRP | B | 61 | 33.761 | 13.367 | -0.998 | 1.00 | 18.52 |
| 6145 | NE1 | TRP | B | 61 | 32.794 | 12.460 | -1.342 | 1.00 | 17.93 |
| 6146 | CE2 | TRP | B | 61 | 33.097 | 11.954 | -2.576 | 1.00 | 20.60 |
| 6147 | CD2 | TRP | B | 61 | 34.247 | 12.602 | -3.024 | 1.00 | 18.76 |
| 6148 | CE3 | TRP | B | 61 | 34.737 | 12.271 | -4.277 | 1.00 | 16.69 |
| 6149 | CZ3 | TRP | B | 61 | 34.077 | 11.366 | -5.016 | 1.00 | 16.50 |
| 6150 | CH2 | TRP | B | 61 | 32.948 | 10.737 | -4.552 | 1.00 | 15.26 |
| 6151 | CZ2 | TRP | B | 61 | 32.445 | 10.993 | -3.338 | 1.00 | 15.48 |
| 6152 | C | TRP | B | 61 | 38.201 | 14.668 | -1.677 | 1.00 | 17.99 |
| 6153 | O | TRP | B | 61 | 38.348 | 15.265 | -0.626 | 1.00 | 16.62 |
| 6154 | N | ILE | B | 62 | 39.066 | 14.694 | -2.701 | 1.00 | 18.00 |
| 6155 | CA | ILE | B | 62 | 40.048 | 15.754 | -2.829 | 1.00 | 18.46 |
| 6156 | CB | ILE | B | 62 | 41.439 | 15.275 | -2.613 | 1.00 | 18.66 |
| 6157 | CG1 | ILE | B | 62 | 41.777 | 14.014 | -3.454 | 1.00 | 17.94 |
| 6158 | CD1 | ILE | B | 62 | 43.098 | 14.117 | -4.182 | 1.00 | 9.62 |
| 6159 | CG2 | ILE | B | 62 | 41.562 | 15.015 | -1.148 | 1.00 | 18.27 |
| 6160 | C | ILE | B | 62 | 39.881 | 16.638 | -4.034 | 1.00 | 19.15 |
| 6161 | O | ILE | B | 62 | 40.386 | 17.759 | -4.038 | 1.00 | 19.98 |
| 6162 | N | SER | B | 63 | 39.024 | 16.256 | -4.975 | 1.00 | 18.31 |

FIGURE 3 (Cont.)

| A | B | C | D | E | F | G | H | I | J |
|---|---|---|---|---|---|---|---|---|---|
| 6163 | CA  | SER | B | 63 | 38.644 | 17.258 | -5.989  | 1.00 | 17.17 |
| 6164 | CB  | SER | B | 63 | 39.559 | 17.144 | -7.185  | 1.00 | 16.49 |
| 6165 | OG  | SER | B | 63 | 39.595 | 15.778 | -7.551  | 1.00 | 20.37 |
| 6166 | C   | SER | B | 63 | 37.256 | 17.003 | -6.412  | 1.00 | 15.31 |
| 6167 | O   | SER | B | 63 | 36.523 | 16.495 | -5.668  | 1.00 | 14.71 |
| 6168 | N   | GLY | B | 64 | 36.897 | 17.320 | -7.637  | 1.00 | 15.87 |
| 6169 | CA  | GLY | B | 64 | 35.623 | 16.871 | -8.133  | 1.00 | 14.87 |
| 6170 | C   | GLY | B | 64 | 35.634 | 15.421 | -8.532  | 1.00 | 15.08 |
| 6171 | O   | GLY | B | 64 | 34.553 | 14.794 | -8.623  | 1.00 | 15.01 |
| 6172 | N   | GLN | B | 65 | 36.828 | 14.874 | -8.761  | 1.00 | 14.48 |
| 6173 | CA  | GLN | B | 65 | 36.960 | 13.557 | -9.409  | 1.00 | 14.66 |
| 6174 | CB  | GLN | B | 65 | 37.137 | 13.777 | -10.913 | 1.00 | 13.97 |
| 6175 | CG  | GLN | B | 65 | 38.364 | 14.596 | -11.280 | 1.00 | 19.22 |
| 6176 | CD  | GLN | B | 65 | 38.122 | 16.103 | -11.299 | 1.00 | 25.85 |
| 6177 | OE1 | GLN | B | 65 | 37.099 | 16.551 | -11.790 | 1.00 | 32.67 |
| 6178 | NE2 | GLN | B | 65 | 39.061 | 16.879 | -10.780 | 1.00 | 27.91 |
| 6179 | C   | GLN | B | 65 | 38.035 | 12.580 | -8.876  | 1.00 | 14.60 |
| 6180 | O   | GLN | B | 65 | 38.346 | 11.552 | -9.579  | 1.00 | 15.77 |
| 6181 | N   | GLU | B | 66 | 38.574 | 12.860 | -7.669  | 1.00 | 13.93 |
| 6182 | CA  | GLU | B | 66 | 39.565 | 12.015 | -6.954  | 1.00 | 12.08 |
| 6183 | CB  | GLU | B | 66 | 40.935 | 12.588 | -7.144  | 1.00 | 11.55 |
| 6184 | CG  | GLU | B | 66 | 41.293 | 12.923 | -8.574  | 1.00 | 11.39 |
| 6185 | CD  | GLU | B | 66 | 42.194 | 14.116 | -8.651  | 1.00 | 12.69 |
| 6186 | OE1 | GLU | B | 66 | 43.309 | 13.817 | -9.089  | 1.00 | 11.66 |
| 6187 | OE2 | GLU | B | 66 | 41.805 | 15.285 | -8.192  | 1.00 | 14.97 |
| 6188 | C   | GLU | B | 66 | 39.362 | 11.820 | -5.442  | 1.00 | 12.22 |
| 6189 | O   | GLU | B | 66 | 38.900 | 12.689 | -4.767  | 1.00 | 11.83 |
| 6190 | N   | TYR | B | 67 | 39.708 | 10.660 | -4.911  | 1.00 | 12.53 |
| 6191 | CA  | TYR | B | 67 | 39.492 | 10.411 | -3.505  | 1.00 | 13.20 |
| 6192 | CB  | TYR | B | 67 | 38.126 | 9.700  | -3.286  | 1.00 | 12.84 |
| 6193 | CG  | TYR | B | 67 | 37.852 | 8.350  | -3.922  | 1.00 | 12.16 |
| 6194 | CD1 | TYR | B | 67 | 38.396 | 7.201  | -3.421  | 1.00 | 16.02 |
| 6195 | CE1 | TYR | B | 67 | 38.137 | 5.975  | -3.985  | 1.00 | 13.50 |
| 6196 | CZ  | TYR | B | 67 | 37.287 | 5.878  | -5.018  | 1.00 | 12.40 |
| 6197 | OH  | TYR | B | 67 | 37.086 | 4.644  | -5.533  | 1.00 | 16.56 |
| 6198 | CE2 | TYR | B | 67 | 36.724 | 6.935  | -5.547  | 1.00 | 13.13 |
| 6199 | CD2 | TYR | B | 67 | 36.988 | 8.201  | -4.981  | 1.00 | 12.95 |
| 6200 | C   | TYR | B | 67 | 40.642 | 9.639  | -2.925  | 1.00 | 15.17 |
| 6201 | O   | TYR | B | 67 | 41.442 | 9.071  | -3.734  | 1.00 | 14.51 |
| 6202 | N   | LEU | B | 68 | 40.769 | 9.572  | -1.568  | 1.00 | 17.41 |
| 6203 | CA  | LEU | B | 68 | 41.967 | 8.876  | -1.000  | 1.00 | 19.55 |
| 6204 | CB  | LEU | B | 68 | 42.893 | 9.857  | -0.214  | 1.00 | 18.86 |
| 6205 | CG  | LEU | B | 68 | 43.448 | 11.197 | -0.773  | 1.00 | 18.26 |
| 6206 | CD1 | LEU | B | 68 | 44.301 | 11.904 | 0.188   | 1.00 | 16.09 |
| 6207 | CD2 | LEU | B | 68 | 44.288 | 10.976 | -1.951  | 1.00 | 14.79 |
| 6208 | C   | LEU | B | 68 | 41.742 | 7.553  | -0.182  | 1.00 | 21.65 |
| 6209 | O   | LEU | B | 68 | 42.000 | 7.523  | 0.987   | 1.00 | 22.87 |
| 6210 | N   | HIS | B | 69 | 41.335 | 6.437  | -0.767  | 1.00 | 23.55 |
| 6211 | CA  | HIS | B | 69 | 41.247 | 5.209  | 0.053   | 1.00 | 26.00 |
| 6212 | CB  | HIS | B | 69 | 40.739 | 3.902  | -0.692  | 1.00 | 27.36 |
| 6213 | CG  | HIS | B | 69 | 41.299 | 3.631  | -2.094  | 1.00 | 28.96 |

FIGURE 3 (Cont.)

| A | B | C | D | E | F | G | H | I | J |
|---|---|---|---|---|---|---|---|---|---|
| 6214 | ND1 | HIS | B | 69 | 41.191 | 2.388 | -2.689 | 1.00 | 32.66 |
| 6215 | CE1 | HIS | B | 69 | 41.698 | 2.421 | -3.914 | 1.00 | 34.69 |
| 6216 | NE2 | HIS | B | 69 | 42.101 | 3.657 | -4.157 | 1.00 | 34.88 |
| 6217 | CD2 | HIS | B | 69 | 41.855 | 4.437 | -3.044 | 1.00 | 30.05 |
| 6218 | C | HIS | B | 69 | 42.579 | 4.910 | 0.768 | 1.00 | 26.86 |
| 6219 | O | HIS | B | 69 | 43.627 | 5.471 | 0.448 | 1.00 | 25.56 |
| 6220 | N | GLN | B | 70 | 42.478 | 4.040 | 1.768 | 1.00 | 28.17 |
| 6221 | CA | GLN | B | 70 | 43.647 | 3.358 | 2.332 | 1.00 | 29.07 |
| 6222 | CB | GLN | B | 70 | 43.668 | 3.454 | 3.850 | 1.00 | 29.99 |
| 6223 | CG | GLN | B | 70 | 44.701 | 2.555 | 4.518 | 1.00 | 33.81 |
| 6224 | CD | GLN | B | 70 | 44.910 | 2.862 | 6.000 | 1.00 | 39.52 |
| 6225 | OE1 | GLN | B | 70 | 45.566 | 3.874 | 6.340 | 1.00 | 41.72 |
| 6226 | NE2 | GLN | B | 70 | 44.389 | 1.980 | 6.884 | 1.00 | 38.69 |
| 6227 | C | GLN | B | 70 | 43.488 | 1.918 | 1.957 | 1.00 | 29.00 |
| 6228 | O | GLN | B | 70 | 42.493 | 1.289 | 2.303 | 1.00 | 29.73 |
| 6229 | N | SER | B | 71 | 44.445 | 1.369 | 1.230 | 1.00 | 28.42 |
| 6230 | CA | SER | B | 71 | 44.335 | -0.030 | 0.876 | 1.00 | 28.46 |
| 6231 | CB | SER | B | 71 | 45.407 | -0.386 | -0.189 | 1.00 | 28.40 |
| 6232 | OG | SER | B | 71 | 46.677 | 0.223 | 0.052 | 1.00 | 27.17 |
| 6233 | C | SER | B | 71 | 44.398 | -0.984 | 2.134 | 1.00 | 28.61 |
| 6234 | O | SER | B | 71 | 44.614 | -0.550 | 3.297 | 1.00 | 28.38 |
| 6235 | N | ALA | B | 72 | 44.217 | -2.286 | 1.896 | 1.00 | 28.26 |
| 6236 | CA | ALA | B | 72 | 44.470 | -3.281 | 2.929 | 1.00 | 27.29 |
| 6237 | CB | ALA | B | 72 | 44.017 | -4.645 | 2.460 | 1.00 | 27.64 |
| 6238 | C | ALA | B | 72 | 45.973 | -3.277 | 3.276 | 1.00 | 27.45 |
| 6239 | O | ALA | B | 72 | 46.369 | -3.568 | 4.423 | 1.00 | 27.46 |
| 6240 | N | ASP | B | 73 | 46.822 | -2.912 | 2.314 | 1.00 | 26.59 |
| 6241 | CA | ASP | B | 73 | 48.259 | -2.810 | 2.618 | 1.00 | 26.08 |
| 6242 | CB | ASP | B | 73 | 49.167 | -2.961 | 1.372 | 1.00 | 27.15 |
| 6243 | CG | ASP | B | 73 | 48.392 | -3.209 | 0.080 | 1.00 | 28.51 |
| 6244 | OD1 | ASP | B | 73 | 48.632 | -4.285 | -0.514 | 1.00 | 30.48 |
| 6245 | OD2 | ASP | B | 73 | 47.561 | -2.398 | -0.415 | 1.00 | 27.52 |
| 6246 | C | ASP | B | 73 | 48.523 | -1.501 | 3.379 | 1.00 | 24.84 |
| 6247 | O | ASP | B | 73 | 49.638 | -1.176 | 3.732 | 1.00 | 24.49 |
| 6248 | N | ASN | B | 74 | 47.428 | -0.852 | 3.717 | 1.00 | 23.96 |
| 6249 | CA | ASN | B | 74 | 47.328 | 0.504 | 4.267 | 1.00 | 23.52 |
| 6250 | CB | ASN | B | 74 | 47.048 | 0.509 | 5.808 | 1.00 | 23.36 |
| 6251 | CG | ASN | B | 74 | 48.038 | -0.425 | 6.665 | 1.00 | 23.95 |
| 6252 | OD1 | ASN | B | 74 | 47.892 | -0.491 | 7.885 | 1.00 | 21.07 |
| 6253 | ND2 | ASN | B | 74 | 49.012 | -1.062 | 6.038 | 1.00 | 19.43 |
| 6254 | C | ASN | B | 74 | 48.353 | 1.542 | 3.779 | 1.00 | 23.00 |
| 6255 | O | ASN | B | 74 | 49.149 | 2.061 | 4.555 | 1.00 | 23.34 |
| 6256 | N | ASN | B | 75 | 48.280 | 1.838 | 2.469 | 1.00 | 21.95 |
| 6257 | CA | ASN | B | 75 | 49.100 | 2.882 | 1.839 | 1.00 | 19.96 |
| 6258 | CB | ASN | B | 75 | 49.604 | 2.468 | 0.477 | 1.00 | 20.23 |
| 6259 | CG | ASN | B | 75 | 50.585 | 1.402 | 0.537 | 1.00 | 21.06 |
| 6260 | OD1 | ASN | B | 75 | 50.257 | 0.244 | 0.305 | 1.00 | 25.18 |
| 6261 | ND2 | ASN | B | 75 | 51.808 | 1.749 | 0.823 | 1.00 | 24.13 |
| 6262 | C | ASN | B | 75 | 48.478 | 4.263 | 1.600 | 1.00 | 17.80 |
| 6263 | O | ASN | B | 75 | 49.216 | 5.203 | 1.494 | 1.00 | 17.24 |
| 6264 | N | ILE | B | 76 | 47.187 | 4.436 | 1.475 | 1.00 | 15.08 |

FIGURE 3 (Cont.)

| A | B | C | D | E | F | G | H | I | J |
|---|---|---|---|---|---|---|---|---|---|
| 6265 | CA | ILE | B | 76 | 46.692 | 5.762 | 0.958 | 1.00 | 14.23 |
| 6266 | CB | ILE | B | 76 | 47.268 | 7.161 | 1.571 | 1.00 | 13.95 |
| 6267 | CG1 | ILE | B | 76 | 47.818 | 7.144 | 3.026 | 1.00 | 14.80 |
| 6268 | CD1 | ILE | B | 76 | 46.927 | 6.415 | 4.043 | 1.00 | 14.82 |
| 6269 | CG2 | ILE | B | 76 | 46.145 | 8.251 | 1.513 | 1.00 | 7.71 |
| 6270 | C | ILE | B | 76 | 46.871 | 5.912 | -0.543 | 1.00 | 14.78 |
| 6271 | O | ILE | B | 76 | 47.870 | 6.470 | -1.026 | 1.00 | 15.53 |
| 6272 | N | VAL | B | 77 | 45.871 | 5.450 | -1.277 | 1.00 | 14.24 |
| 6273 | CA | VAL | B | 77 | 45.851 | 5.587 | -2.702 | 1.00 | 13.76 |
| 6274 | CB | VAL | B | 77 | 45.529 | 4.222 | -3.310 | 1.00 | 14.97 |
| 6275 | CG1 | VAL | B | 77 | 45.747 | 4.192 | -4.810 | 1.00 | 13.37 |
| 6276 | CG2 | VAL | B | 77 | 46.528 | 3.147 | -2.706 | 1.00 | 12.24 |
| 6277 | C | VAL | B | 77 | 44.952 | 6.765 | -3.109 | 1.00 | 13.89 |
| 6278 | O | VAL | B | 77 | 43.939 | 7.106 | -2.459 | 1.00 | 14.43 |
| 6279 | N | LEU | B | 78 | 45.411 | 7.483 | -4.113 | 1.00 | 13.07 |
| 6280 | CA | LEU | B | 78 | 44.600 | 8.543 | -4.658 | 1.00 | 12.35 |
| 6281 | CB | LEU | B | 78 | 45.448 | 9.802 | -4.959 | 1.00 | 11.89 |
| 6282 | CG | LEU | B | 78 | 45.419 | 10.671 | -6.228 | 1.00 | 11.48 |
| 6283 | CD1 | LEU | B | 78 | 44.151 | 10.580 | -7.132 | 1.00 | 13.94 |
| 6284 | CD2 | LEU | B | 78 | 45.737 | 12.143 | -5.899 | 1.00 | 8.98 |
| 6285 | C | LEU | B | 78 | 44.064 | 7.866 | -5.875 | 1.00 | 11.79 |
| 6286 | O | LEU | B | 78 | 44.889 | 7.394 | -6.705 | 1.00 | 11.59 |
| 6287 | N | TYR | B | 79 | 42.722 | 7.818 | -5.983 | 1.00 | 10.89 |
| 6288 | CA | TYR | B | 79 | 42.021 | 7.282 | -7.141 | 1.00 | 10.99 |
| 6289 | CB | TYR | B | 79 | 40.979 | 6.217 | -6.741 | 1.00 | 10.58 |
| 6290 | CG | TYR | B | 79 | 40.150 | 5.604 | -7.924 | 1.00 | 12.66 |
| 6291 | CD1 | TYR | B | 79 | 40.730 | 4.955 | -9.010 | 1.00 | 13.06 |
| 6292 | CE1 | TYR | B | 79 | 39.908 | 4.393 | -10.081 | 1.00 | 14.88 |
| 6293 | CZ | TYR | B | 79 | 38.534 | 4.471 | -10.015 | 1.00 | 14.95 |
| 6294 | OH | TYR | B | 79 | 37.688 | 3.972 | -11.000 | 1.00 | 14.86 |
| 6295 | CE2 | TYR | B | 79 | 37.975 | 5.082 | -8.950 | 1.00 | 14.02 |
| 6296 | CD2 | TYR | B | 79 | 38.776 | 5.655 | -7.924 | 1.00 | 12.62 |
| 6297 | C | TYR | B | 79 | 41.342 | 8.344 | -7.964 | 1.00 | 11.61 |
| 6298 | O | TYR | B | 79 | 40.567 | 9.171 | -7.478 | 1.00 | 12.59 |
| 6299 | N | ASN | B | 80 | 41.539 | 8.247 | -9.259 | 1.00 | 12.12 |
| 6300 | CA | ASN | B | 80 | 40.965 | 9.202 | -10.163 | 1.00 | 11.92 |
| 6301 | CB | ASN | B | 80 | 42.025 | 9.634 | -11.134 | 1.00 | 11.35 |
| 6302 | CG | ASN | B | 80 | 41.634 | 10.851 | -11.884 | 1.00 | 14.57 |
| 6303 | OD1 | ASN | B | 80 | 42.419 | 11.834 | -11.935 | 1.00 | 18.90 |
| 6304 | ND2 | ASN | B | 80 | 40.435 | 10.813 | -12.516 | 1.00 | 11.89 |
| 6305 | C | ASN | B | 80 | 39.829 | 8.485 | -10.870 | 1.00 | 11.36 |
| 6306 | O | ASN | B | 80 | 40.085 | 7.555 | -11.588 | 1.00 | 7.86 |
| 6307 | N | ILE | B | 81 | 38.585 | 8.906 | -10.635 | 1.00 | 10.85 |
| 6308 | CA | ILE | B | 81 | 37.447 | 8.209 | -11.181 | 1.00 | 11.29 |
| 6309 | CB | ILE | B | 81 | 36.083 | 8.831 | -10.671 | 1.00 | 11.49 |
| 6310 | CG1 | ILE | B | 81 | 36.114 | 9.183 | -9.193 | 1.00 | 10.23 |
| 6311 | CD1 | ILE | B | 81 | 34.742 | 9.290 | -8.519 | 1.00 | 7.03 |
| 6312 | CG2 | ILE | B | 81 | 34.916 | 7.856 | -10.983 | 1.00 | 11.87 |
| 6313 | C | ILE | B | 81 | 37.410 | 8.284 | -12.690 | 1.00 | 11.70 |
| 6314 | O | ILE | B | 81 | 37.011 | 7.300 | -13.332 | 1.00 | 12.68 |
| 6315 | N | GLU | B | 82 | 37.718 | 9.474 | -13.241 | 1.00 | 12.41 |

FIGURE 3 (Cont.)

| A | B | C | D | E | F | G | H | I | J |
|---|---|---|---|---|---|---|---|---|---|
| 6316 | CA | GLU | B | 82 | 37.680 | 9.747 | -14.689 | 1.00 | 13.72 |
| 6317 | CB | GLU | B | 82 | 37.995 | 11.238 | -15.025 | 1.00 | 14.61 |
| 6318 | CG | GLU | B | 82 | 36.875 | 12.286 | -14.918 | 1.00 | 18.83 |
| 6319 | CD | GLU | B | 82 | 37.265 | 13.763 | -15.395 | 1.00 | 26.63 |
| 6320 | OE1 | GLU | B | 82 | 36.741 | 14.786 | -14.841 | 1.00 | 27.46 |
| 6321 | OE2 | GLU | B | 82 | 38.061 | 13.967 | -16.360 | 1.00 | 30.45 |
| 6322 | C | GLU | B | 82 | 38.716 | 8.841 | -15.364 | 1.00 | 13.14 |
| 6323 | O | GLU | B | 82 | 38.448 | 8.238 | -16.414 | 1.00 | 13.43 |
| 6324 | N | THR | B | 83 | 39.915 | 8.728 | -14.801 | 1.00 | 13.57 |
| 6325 | CA | THR | B | 83 | 40.976 | 8.050 | -15.572 | 1.00 | 14.25 |
| 6326 | CB | THR | B | 83 | 42.378 | 8.713 | -15.364 | 1.00 | 14.27 |
| 6327 | OG1 | THR | B | 83 | 42.844 | 8.581 | -14.009 | 1.00 | 10.90 |
| 6328 | CG2 | THR | B | 83 | 42.273 | 10.221 | -15.563 | 1.00 | 12.88 |
| 6329 | C | THR | B | 83 | 40.993 | 6.528 | -15.362 | 1.00 | 15.75 |
| 6330 | O | THR | B | 83 | 41.334 | 5.795 | -16.220 | 1.00 | 16.13 |
| 6331 | N | GLY | B | 84 | 40.513 | 6.042 | -14.237 | 1.00 | 16.76 |
| 6332 | CA | GLY | B | 84 | 40.816 | 4.634 | -13.867 | 1.00 | 18.77 |
| 6333 | C | GLY | B | 84 | 42.138 | 4.519 | -13.118 | 1.00 | 19.56 |
| 6334 | O | GLY | B | 84 | 42.338 | 3.538 | -12.437 | 1.00 | 21.38 |
| 6335 | N | GLN | B | 85 | 42.961 | 5.558 | -13.109 | 1.00 | 18.97 |
| 6336 | CA | GLN | B | 85 | 44.315 | 5.450 | -12.529 | 1.00 | 18.58 |
| 6337 | CB | GLN | B | 85 | 45.278 | 6.428 | -13.213 | 1.00 | 18.97 |
| 6338 | CG | GLN | B | 85 | 46.047 | 5.822 | -14.444 | 1.00 | 19.42 |
| 6339 | CD | GLN | B | 85 | 46.075 | 4.204 | -14.509 | 1.00 | 21.24 |
| 6340 | OE1 | GLN | B | 85 | 45.332 | 3.582 | -15.296 | 1.00 | 21.26 |
| 6341 | NE2 | GLN | B | 85 | 46.890 | 3.575 | -13.634 | 1.00 | 23.70 |
| 6342 | C | GLN | B | 85 | 44.356 | 5.622 | -10.982 | 1.00 | 17.53 |
| 6343 | O | GLN | B | 85 | 43.492 | 6.316 | -10.390 | 1.00 | 17.61 |
| 6344 | N | SER | B | 86 | 45.335 | 4.949 | -10.343 | 1.00 | 16.63 |
| 6345 | CA | SER | B | 86 | 45.531 | 4.944 | -8.887 | 1.00 | 16.32 |
| 6346 | CB | SER | B | 86 | 45.129 | 3.620 | -8.286 | 1.00 | 16.50 |
| 6347 | OG | SER | B | 86 | 43.873 | 3.170 | -8.788 | 1.00 | 18.32 |
| 6348 | C | SER | B | 86 | 46.962 | 5.146 | -8.625 | 1.00 | 16.21 |
| 6349 | O | SER | B | 86 | 47.794 | 4.581 | -9.313 | 1.00 | 16.90 |
| 6350 | N | TYR | B | 87 | 47.278 | 5.907 | -7.602 | 1.00 | 15.95 |
| 6351 | CA | TYR | B | 87 | 48.675 | 6.257 | -7.287 | 1.00 | 16.25 |
| 6352 | CB | TYR | B | 87 | 49.027 | 7.655 | -7.828 | 1.00 | 17.10 |
| 6353 | CG | TYR | B | 87 | 48.582 | 8.018 | -9.207 | 1.00 | 17.67 |
| 6354 | CD1 | TYR | B | 87 | 49.529 | 8.232 | -10.212 | 1.00 | 18.04 |
| 6355 | CE1 | TYR | B | 87 | 49.125 | 8.607 | -11.512 | 1.00 | 20.11 |
| 6356 | CZ | TYR | B | 87 | 47.777 | 8.797 | -11.795 | 1.00 | 19.97 |
| 6357 | OH | TYR | B | 87 | 47.427 | 9.111 | -13.080 | 1.00 | 21.28 |
| 6358 | CE2 | TYR | B | 87 | 46.822 | 8.598 | -10.797 | 1.00 | 18.08 |
| 6359 | CD2 | TYR | B | 87 | 47.235 | 8.218 | -9.504 | 1.00 | 16.38 |
| 6360 | C | TYR | B | 87 | 48.978 | 6.370 | -5.773 | 1.00 | 15.37 |
| 6361 | O | TYR | B | 87 | 48.557 | 7.327 | -5.143 | 1.00 | 14.05 |
| 6362 | N | THR | B | 88 | 49.778 | 5.508 | -5.174 | 1.00 | 13.72 |
| 6363 | CA | THR | B | 88 | 49.862 | 5.679 | -3.749 | 1.00 | 12.75 |
| 6364 | CB | THR | B | 88 | 50.394 | 4.435 | -3.079 | 1.00 | 12.47 |
| 6365 | OG1 | THR | B | 88 | 51.671 | 4.725 | -2.602 | 1.00 | 11.17 |
| 6366 | CG2 | THR | B | 88 | 50.537 | 3.201 | -4.046 | 1.00 | 13.36 |

FIGURE 3 (Cont.)

| A | B | C | D | E | F | G | H | I | J |
|---|---|---|---|---|---|---|---|---|---|
| 6367 | C | THR | B | 88 | 50.635 | 6.943 | -3.365 | 1.00 | 12.52 |
| 6368 | O | THR | B | 88 | 51.714 | 7.174 | -3.862 | 1.00 | 13.21 |
| 6369 | N | ILE | B | 89 | 50.057 | 7.780 | -2.510 | 1.00 | 12.77 |
| 6370 | CA | ILE | B | 89 | 50.713 | 9.053 | -2.129 | 1.00 | 13.61 |
| 6371 | CB | ILE | B | 89 | 49.870 | 10.327 | -1.861 | 1.00 | 11.73 |
| 6372 | CG1 | ILE | B | 89 | 48.451 | 10.162 | -1.463 | 1.00 | 11.74 |
| 6373 | CD1 | ILE | B | 89 | 47.964 | 11.687 | -1.188 | 1.00 | 16.94 |
| 6374 | CG2 | ILE | B | 89 | 49.928 | 11.342 | -2.950 | 1.00 | 14.43 |
| 6375 | C | ILE | B | 89 | 51.423 | 9.082 | -0.832 | 1.00 | 13.65 |
| 6376 | O | ILE | B | 89 | 52.426 | 9.824 | -0.734 | 1.00 | 14.42 |
| 6377 | N | LEU | B | 90 | 50.838 | 8.473 | 0.199 | 1.00 | 13.43 |
| 6378 | CA | LEU | B | 90 | 51.639 | 8.201 | 1.387 | 1.00 | 14.82 |
| 6379 | CB | LEU | B | 90 | 50.943 | 8.740 | 2.587 | 1.00 | 13.04 |
| 6380 | CG | LEU | B | 90 | 51.557 | 10.087 | 2.949 | 1.00 | 13.88 |
| 6381 | CD1 | LEU | B | 90 | 50.864 | 10.599 | 4.175 | 1.00 | 19.10 |
| 6382 | CD2 | LEU | B | 90 | 53.040 | 10.065 | 3.211 | 1.00 | 12.64 |
| 6383 | C | LEU | B | 90 | 51.951 | 6.725 | 1.571 | 1.00 | 15.81 |
| 6384 | O | LEU | B | 90 | 51.048 | 5.969 | 1.740 | 1.00 | 17.70 |
| 6385 | N | SER | B | 91 | 53.201 | 6.302 | 1.604 | 1.00 | 16.41 |
| 6386 | CA | SER | B | 91 | 53.419 | 4.839 | 1.757 | 1.00 | 17.62 |
| 6387 | CB | SER | B | 91 | 54.834 | 4.498 | 1.537 | 1.00 | 18.20 |
| 6388 | OG | SER | B | 91 | 55.529 | 5.034 | 2.633 | 1.00 | 22.27 |
| 6389 | C | SER | B | 91 | 53.051 | 4.286 | 3.130 | 1.00 | 18.03 |
| 6390 | O | SER | B | 91 | 53.176 | 5.038 | 4.154 | 1.00 | 17.17 |
| 6391 | N | ASN | B | 92 | 52.535 | 3.027 | 3.113 | 1.00 | 19.57 |
| 6392 | CA | ASN | B | 92 | 52.230 | 2.253 | 4.356 | 1.00 | 19.96 |
| 6393 | CB | ASN | B | 92 | 52.133 | 0.618 | 4.250 | 1.00 | 20.34 |
| 6394 | CG | ASN | B | 92 | 53.334 | -0.067 | 3.438 | 1.00 | 21.95 |
| 6395 | OD1 | ASN | B | 92 | 54.446 | 0.529 | 3.141 | 1.00 | 28.45 |
| 6396 | ND2 | ASN | B | 92 | 53.099 | -1.298 | 3.069 | 1.00 | 31.39 |
| 6397 | C | ASN | B | 92 | 53.177 | 2.689 | 5.436 | 1.00 | 18.39 |
| 6398 | O | ASN | B | 92 | 52.769 | 3.075 | 6.558 | 1.00 | 16.15 |
| 6399 | N | ARG | B | 93 | 54.448 | 2.724 | 5.124 | 1.00 | 18.02 |
| 6400 | CA | ARG | B | 93 | 55.328 | 2.879 | 6.255 | 1.00 | 18.77 |
| 6401 | CB | ARG | B | 93 | 56.020 | 1.533 | 6.466 | 1.00 | 20.13 |
| 6402 | CG | ARG | B | 93 | 54.971 | 0.346 | 7.054 | 1.00 | 24.61 |
| 6403 | CD | ARG | B | 93 | 55.241 | -1.217 | 6.530 | 1.00 | 35.35 |
| 6404 | NE | ARG | B | 93 | 54.914 | -2.157 | 7.670 | 1.00 | 44.58 |
| 6405 | CZ | ARG | B | 93 | 53.697 | -2.567 | 8.141 | 1.00 | 50.19 |
| 6406 | NH1 | ARG | B | 93 | 53.244 | -2.263 | 9.453 | 1.00 | 51.81 |
| 6407 | NH2 | ARG | B | 93 | 52.929 | -3.277 | 7.221 | 1.00 | 50.72 |
| 6408 | C | ARG | B | 93 | 56.149 | 4.174 | 6.426 | 1.00 | 17.44 |
| 6409 | O | ARG | B | 93 | 57.003 | 4.213 | 7.185 | 1.00 | 15.19 |
| 6410 | N | THR | B | 94 | 55.755 | 5.272 | 5.787 | 1.00 | 15.87 |
| 6411 | CA | THR | B | 94 | 56.210 | 6.607 | 6.109 | 1.00 | 15.00 |
| 6412 | CB | THR | B | 94 | 56.322 | 7.434 | 4.795 | 1.00 | 14.77 |
| 6413 | OG1 | THR | B | 94 | 57.687 | 7.323 | 4.333 | 1.00 | 18.62 |
| 6414 | CG2 | THR | B | 94 | 56.022 | 8.992 | 4.991 | 1.00 | 12.81 |
| 6415 | C | THR | B | 94 | 55.125 | 7.139 | 7.035 | 1.00 | 15.53 |
| 6416 | O | THR | B | 94 | 55.157 | 8.267 | 7.580 | 1.00 | 14.68 |
| 6417 | N | MET | B | 95 | 54.131 | 6.287 | 7.183 | 1.00 | 15.62 |

FIGURE 3 (Cont.)

| A | B | C | D | E | F | G | H | I | J |
|---|---|---|---|---|---|---|---|---|---|
| 6418 | CA | MET | B | 95 | 52.996 | 6.501 | 8.067 | 1.00 | 15.26 |
| 6419 | CB | MET | B | 95 | 51.820 | 5.917 | 7.327 | 1.00 | 12.74 |
| 6420 | CG | MET | B | 95 | 50.586 | 6.003 | 7.922 | 1.00 | 17.98 |
| 6421 | SD | MET | B | 95 | 49.659 | 7.381 | 7.120 | 1.00 | 15.07 |
| 6422 | CE | MET | B | 95 | 48.475 | 7.511 | 8.212 | 1.00 | 21.38 |
| 6423 | C | MET | B | 95 | 53.302 | 5.723 | 9.390 | 1.00 | 16.27 |
| 6424 | O | MET | B | 95 | 52.923 | 6.181 | 10.455 | 1.00 | 17.50 |
| 6425 | N | LYS | B | 96 | 54.050 | 4.600 | 9.356 | 1.00 | 17.30 |
| 6426 | CA | LYS | B | 96 | 54.127 | 3.981 | 10.664 | 1.00 | 19.20 |
| 6427 | CB | LYS | B | 96 | 54.472 | 2.443 | 10.454 | 1.00 | 17.72 |
| 6428 | CG | LYS | B | 96 | 53.682 | 1.360 | 11.357 | 1.00 | 19.13 |
| 6429 | CD | LYS | B | 96 | 54.284 | 1.016 | 12.835 | 1.00 | 20.03 |
| 6430 | CE | LYS | B | 96 | 53.161 | 0.809 | 13.976 | 1.00 | 19.74 |
| 6431 | NZ | LYS | B | 96 | 51.820 | 1.594 | 13.817 | 1.00 | 21.58 |
| 6432 | C | LYS | B | 96 | 55.232 | 4.867 | 11.129 | 1.00 | 19.80 |
| 6433 | O | LYS | B | 96 | 55.482 | 4.908 | 12.318 | 1.00 | 19.74 |
| 6434 | N | SER | B | 97 | 56.047 | 5.342 | 10.169 | 1.00 | 19.41 |
| 6435 | CA | SER | B | 97 | 57.192 | 6.339 | 10.436 | 1.00 | 19.12 |
| 6436 | CB | SER | B | 97 | 57.033 | 7.454 | 9.406 | 1.00 | 19.78 |
| 6437 | OG | SER | B | 97 | 58.314 | 8.091 | 9.262 | 1.00 | 21.17 |
| 6438 | C | SER | B | 97 | 57.010 | 6.992 | 11.778 | 1.00 | 18.85 |
| 6439 | O | SER | B | 97 | 57.915 | 7.305 | 12.562 | 1.00 | 17.42 |
| 6440 | N | VAL | B | 98 | 55.730 | 7.175 | 11.980 | 1.00 | 17.46 |
| 6441 | CA | VAL | B | 98 | 55.210 | 8.009 | 13.078 | 1.00 | 15.84 |
| 6442 | CB | VAL | B | 98 | 55.014 | 9.527 | 12.610 | 1.00 | 16.29 |
| 6443 | CG1 | VAL | B | 98 | 56.264 | 10.081 | 11.997 | 1.00 | 14.44 |
| 6444 | CG2 | VAL | B | 98 | 54.068 | 9.585 | 11.592 | 1.00 | 15.25 |
| 6445 | C | VAL | B | 98 | 53.904 | 7.443 | 13.731 | 1.00 | 15.32 |
| 6446 | O | VAL | B | 98 | 53.173 | 8.151 | 14.253 | 1.00 | 15.67 |
| 6447 | N | ASN | B | 99 | 53.775 | 6.125 | 13.892 | 1.00 | 15.98 |
| 6448 | CA | ASN | B | 99 | 52.455 | 5.452 | 14.147 | 1.00 | 16.57 |
| 6449 | CB | ASN | B | 99 | 52.179 | 4.800 | 15.587 | 1.00 | 15.64 |
| 6450 | CG | ASN | B | 99 | 53.407 | 4.465 | 16.378 | 1.00 | 20.28 |
| 6451 | OD1 | ASN | B | 99 | 54.339 | 3.846 | 15.871 | 1.00 | 19.71 |
| 6452 | ND2 | ASN | B | 99 | 53.386 | 4.808 | 17.687 | 1.00 | 22.94 |
| 6453 | C | ASN | B | 99 | 51.342 | 6.446 | 13.891 | 1.00 | 14.97 |
| 6454 | O | ASN | B | 99 | 50.656 | 6.754 | 14.835 | 1.00 | 16.23 |
| 6455 | N | ALA | B | 100 | 51.118 | 6.932 | 12.675 | 1.00 | 14.83 |
| 6456 | CA | ALA | B | 100 | 49.970 | 7.844 | 12.495 | 1.00 | 16.00 |
| 6457 | CB | ALA | B | 100 | 50.201 | 8.854 | 11.384 | 1.00 | 16.23 |
| 6458 | C | ALA | B | 100 | 48.649 | 7.082 | 12.264 | 1.00 | 15.38 |
| 6459 | O | ALA | B | 100 | 48.641 | 6.061 | 11.594 | 1.00 | 16.91 |
| 6460 | N | SER | B | 101 | 47.586 | 7.597 | 12.863 | 1.00 | 14.93 |
| 6461 | CA | SER | B | 101 | 46.258 | 6.978 | 12.927 | 1.00 | 13.07 |
| 6462 | CB | SER | B | 101 | 45.539 | 7.391 | 14.254 | 1.00 | 11.38 |
| 6463 | OG | SER | B | 101 | 46.344 | 7.210 | 15.488 | 1.00 | 13.22 |
| 6464 | C | SER | B | 101 | 45.463 | 7.452 | 11.730 | 1.00 | 13.21 |
| 6465 | O | SER | B | 101 | 44.538 | 6.785 | 11.289 | 1.00 | 12.82 |
| 6466 | N | ASN | B | 102 | 45.838 | 8.626 | 11.194 | 1.00 | 13.10 |
| 6467 | CA | ASN | B | 102 | 45.034 | 9.319 | 10.192 | 1.00 | 11.87 |
| 6468 | CB | ASN | B | 102 | 43.952 | 9.941 | 10.985 | 1.00 | 12.06 |

FIGURE 3 (Cont.)

| A | B | C | D | E | F | G | H | I | J |
|---|---|---|---|---|---|---|---|---|---|
| 6469 | CG | ASN | B | 102 | 42.852 | 10.409 | 10.212 | 1.00 | 11.40 |
| 6470 | OD1 | ASN | B | 102 | 42.037 | 11.165 | 10.764 | 1.00 | 22.16 |
| 6471 | ND2 | ASN | B | 102 | 42.747 | 10.041 | 8.981 | 1.00 | 10.00 |
| 6472 | C | ASN | B | 102 | 45.855 | 10.359 | 9.448 | 1.00 | 11.84 |
| 6473 | O | ASN | B | 102 | 46.952 | 10.601 | 9.830 | 1.00 | 12.55 |
| 6474 | N | TYR | B | 103 | 45.369 | 10.955 | 8.345 | 1.00 | 11.00 |
| 6475 | CA | TYR | B | 103 | 46.177 | 11.934 | 7.541 | 1.00 | 10.45 |
| 6476 | CB | TYR | B | 103 | 46.800 | 11.275 | 6.330 | 1.00 | 9.88 |
| 6477 | CG | TYR | B | 103 | 45.735 | 10.652 | 5.490 | 1.00 | 12.06 |
| 6478 | CD1 | TYR | B | 103 | 45.367 | 9.337 | 5.722 | 1.00 | 15.49 |
| 6479 | CE1 | TYR | B | 103 | 44.306 | 8.761 | 5.042 | 1.00 | 17.57 |
| 6480 | CZ | TYR | B | 103 | 43.608 | 9.448 | 4.077 | 1.00 | 16.08 |
| 6481 | OH | TYR | B | 103 | 42.623 | 8.742 | 3.456 | 1.00 | 21.68 |
| 6482 | CE2 | TYR | B | 103 | 43.917 | 10.781 | 3.781 | 1.00 | 13.37 |
| 6483 | CD2 | TYR | B | 103 | 45.012 | 11.396 | 4.515 | 1.00 | 14.70 |
| 6484 | C | TYR | B | 103 | 45.237 | 12.941 | 6.982 | 1.00 | 11.02 |
| 6485 | O | TYR | B | 103 | 44.071 | 12.692 | 6.995 | 1.00 | 9.88 |
| 6486 | N | GLY | B | 104 | 45.778 | 14.034 | 6.412 | 1.00 | 11.56 |
| 6487 | CA | GLY | B | 104 | 45.034 | 15.131 | 5.718 | 1.00 | 11.47 |
| 6488 | C | GLY | B | 104 | 45.967 | 15.857 | 4.691 | 1.00 | 11.96 |
| 6489 | O | GLY | B | 104 | 47.056 | 16.454 | 5.082 | 1.00 | 12.42 |
| 6490 | N | LEU | B | 105 | 45.597 | 15.737 | 3.399 | 1.00 | 12.68 |
| 6491 | CA | LEU | B | 105 | 46.282 | 16.286 | 2.199 | 1.00 | 13.16 |
| 6492 | CB | LEU | B | 105 | 45.670 | 15.681 | 0.931 | 1.00 | 12.94 |
| 6493 | CG | LEU | B | 105 | 46.552 | 15.379 | -0.315 | 1.00 | 14.15 |
| 6494 | CD1 | LEU | B | 105 | 45.821 | 15.610 | -1.587 | 1.00 | 15.12 |
| 6495 | CD2 | LEU | B | 105 | 47.951 | 16.029 | -0.398 | 1.00 | 11.49 |
| 6496 | C | LEU | B | 105 | 45.874 | 17.691 | 2.182 | 1.00 | 14.98 |
| 6497 | O | LEU | B | 105 | 44.687 | 17.905 | 2.243 | 1.00 | 13.33 |
| 6498 | N | SER | B | 106 | 46.800 | 18.670 | 2.102 | 1.00 | 15.55 |
| 6499 | CA | SER | B | 106 | 46.372 | 20.091 | 1.912 | 1.00 | 15.27 |
| 6500 | CB | SER | B | 106 | 47.581 | 20.983 | 1.821 | 1.00 | 15.02 |
| 6501 | OG | SER | B | 106 | 48.626 | 20.464 | 0.914 | 1.00 | 14.43 |
| 6502 | C | SER | B | 106 | 45.621 | 20.183 | 0.617 | 1.00 | 16.18 |
| 6503 | O | SER | B | 106 | 45.938 | 19.440 | -0.293 | 1.00 | 16.76 |
| 6504 | N | PRO | B | 107 | 44.635 | 21.037 | 0.452 | 1.00 | 18.60 |
| 6505 | CA | PRO | B | 107 | 43.791 | 20.907 | -0.744 | 1.00 | 18.75 |
| 6506 | CB | PRO | B | 107 | 42.690 | 21.982 | -0.472 | 1.00 | 21.52 |
| 6507 | CG | PRO | B | 107 | 43.556 | 23.084 | 0.260 | 1.00 | 20.43 |
| 6508 | CD | PRO | B | 107 | 44.167 | 22.179 | 1.304 | 1.00 | 18.53 |
| 6509 | C | PRO | B | 107 | 44.632 | 21.189 | -2.030 | 1.00 | 20.42 |
| 6510 | O | PRO | B | 107 | 44.362 | 20.642 | -3.149 | 1.00 | 20.73 |
| 6511 | N | ASP | B | 108 | 45.699 | 21.985 | -1.877 | 1.00 | 19.32 |
| 6512 | CA | ASP | B | 108 | 46.494 | 22.359 | -3.036 | 1.00 | 16.87 |
| 6513 | CB | ASP | B | 108 | 46.709 | 23.917 | -3.195 | 1.00 | 17.43 |
| 6514 | CG | ASP | B | 108 | 45.255 | 24.793 | -3.764 | 1.00 | 20.11 |
| 6515 | OD1 | ASP | B | 108 | 44.040 | 24.335 | -3.756 | 1.00 | 11.00 |
| 6516 | OD2 | ASP | B | 108 | 45.300 | 25.989 | -4.257 | 1.00 | 22.02 |
| 6517 | C | ASP | B | 108 | 47.709 | 21.454 | -3.003 | 1.00 | 16.43 |
| 6518 | O | ASP | B | 108 | 48.683 | 21.689 | -3.598 | 1.00 | 15.35 |
| 6519 | N | ARG | B | 109 | 47.536 | 20.315 | -2.350 | 1.00 | 15.62 |

FIGURE 3 (Cont.)

| A | B | C | D | E | F | G | H | I | J |
|---|---|---|---|---|---|---|---|---|---|
| 6520 | CA | ARG | B | 109 | 48.182 | 19.058 | -2.697 | 1.00 | 13.52 |
| 6521 | CB | ARG | B | 109 | 47.885 | 18.767 | -4.157 | 1.00 | 14.33 |
| 6522 | CG | ARG | B | 109 | 46.420 | 18.331 | -4.475 | 1.00 | 13.15 |
| 6523 | CD | ARG | B | 109 | 46.246 | 16.848 | -4.631 | 1.00 | 13.63 |
| 6524 | NE | ARG | B | 109 | 46.031 | 16.388 | -6.028 | 1.00 | 13.65 |
| 6525 | CZ | ARG | B | 109 | 44.862 | 16.514 | -6.697 | 1.00 | 9.89 |
| 6526 | NH1 | ARG | B | 109 | 44.752 | 16.049 | -7.926 | 1.00 | 4.31 |
| 6527 | NH2 | ARG | B | 109 | 43.809 | 17.068 | -6.146 | 1.00 | 2.83 |
| 6528 | C | ARG | B | 109 | 49.689 | 18.978 | -2.413 | 1.00 | 14.36 |
| 6529 | O | ARG | B | 109 | 50.282 | 17.929 | -2.449 | 1.00 | 14.59 |
| 6530 | N | GLN | B | 110 | 50.338 | 20.061 | -2.068 | 1.00 | 13.97 |
| 6531 | CA | GLN | B | 110 | 51.744 | 19.957 | -1.804 | 1.00 | 12.93 |
| 6532 | CB | GLN | B | 110 | 52.491 | 21.249 | -2.276 | 1.00 | 15.43 |
| 6533 | CG | GLN | B | 110 | 52.030 | 22.626 | -1.916 | 1.00 | 11.83 |
| 6534 | CD | GLN | B | 110 | 52.885 | 23.749 | -2.544 | 1.00 | 16.63 |
| 6535 | OE1 | GLN | B | 110 | 53.717 | 23.521 | -3.495 | 1.00 | 19.76 |
| 6536 | NE2 | GLN | B | 110 | 52.707 | 24.995 | -1.991 | 1.00 | 18.16 |
| 6537 | C | GLN | B | 110 | 52.230 | 19.460 | -0.436 | 1.00 | 12.80 |
| 6538 | O | GLN | B | 110 | 53.451 | 19.055 | -0.310 | 1.00 | 14.63 |
| 6539 | N | PHE | B | 111 | 51.325 | 19.362 | 0.535 | 1.00 | 12.01 |
| 6540 | CA | PHE | B | 111 | 51.604 | 18.752 | 1.840 | 1.00 | 12.84 |
| 6541 | CB | PHE | B | 111 | 51.647 | 19.829 | 2.871 | 1.00 | 12.36 |
| 6542 | CG | PHE | B | 111 | 52.672 | 20.900 | 2.603 | 1.00 | 13.67 |
| 6543 | CD1 | PHE | B | 111 | 52.305 | 22.162 | 2.287 | 1.00 | 15.11 |
| 6544 | CE1 | PHE | B | 111 | 53.265 | 23.142 | 2.079 | 1.00 | 12.73 |
| 6545 | CZ | PHE | B | 111 | 54.492 | 22.889 | 2.209 | 1.00 | 12.97 |
| 6546 | CE2 | PHE | B | 111 | 54.855 | 21.631 | 2.549 | 1.00 | 14.46 |
| 6547 | CD2 | PHE | B | 111 | 53.931 | 20.669 | 2.793 | 1.00 | 8.99 |
| 6548 | C | PHE | B | 111 | 50.585 | 17.709 | 2.335 | 1.00 | 12.98 |
| 6549 | O | PHE | B | 111 | 49.501 | 17.530 | 1.759 | 1.00 | 14.10 |
| 6550 | N | VAL | B | 112 | 50.917 | 17.035 | 3.425 | 1.00 | 13.23 |
| 6551 | CA | VAL | B | 112 | 49.939 | 16.176 | 4.127 | 1.00 | 13.08 |
| 6552 | CB | VAL | B | 112 | 50.025 | 14.673 | 3.761 | 1.00 | 13.93 |
| 6553 | CG1 | VAL | B | 112 | 48.717 | 14.091 | 3.484 | 1.00 | 10.20 |
| 6554 | CG2 | VAL | B | 112 | 50.934 | 14.534 | 2.710 | 1.00 | 6.61 |
| 6555 | C | VAL | B | 112 | 50.382 | 16.089 | 5.543 | 1.00 | 13.44 |
| 6556 | O | VAL | B | 112 | 51.429 | 15.502 | 5.758 | 1.00 | 14.01 |
| 6557 | N | TYR | B | 113 | 49.560 | 16.528 | 6.472 | 1.00 | 11.75 |
| 6558 | CA | TYR | B | 113 | 49.719 | 16.216 | 7.871 | 1.00 | 10.83 |
| 6559 | CB | TYR | B | 113 | 48.829 | 17.104 | 8.712 | 1.00 | 8.74 |
| 6560 | CG | TYR | B | 113 | 47.347 | 16.860 | 8.800 | 1.00 | 8.97 |
| 6561 | CD1 | TYR | B | 113 | 46.457 | 17.784 | 8.367 | 1.00 | 8.90 |
| 6562 | CE1 | TYR | B | 113 | 45.151 | 17.581 | 8.520 | 1.00 | 2.72 |
| 6563 | CZ | TYR | B | 113 | 44.695 | 16.497 | 9.153 | 1.00 | 3.26 |
| 6564 | OH | TYR | B | 113 | 43.319 | 16.254 | 9.292 | 1.00 | 6.97 |
| 6565 | CE2 | TYR | B | 113 | 45.561 | 15.647 | 9.629 | 1.00 | 4.08 |
| 6566 | CD2 | TYR | B | 113 | 46.837 | 15.815 | 9.463 | 1.00 | 6.05 |
| 6567 | C | TYR | B | 113 | 49.404 | 14.770 | 8.160 | 1.00 | 10.09 |
| 6568 | O | TYR | B | 113 | 48.439 | 14.274 | 7.608 | 1.00 | 10.02 |
| 6569 | N | LEU | B | 114 | 50.257 | 14.130 | 8.974 | 1.00 | 9.36 |
| 6570 | CA | LEU | B | 114 | 50.003 | 12.830 | 9.585 | 1.00 | 10.68 |

FIGURE 3 (Cont.)

| A | B | C | D | E | F | G | H | I | J |
|---|---|---|---|---|---|---|---|---|---|
| 6571 | CB | LEU | B | 114 | 51.172 | 11.936 | 9.442 | 1.00 | 11.46 |
| 6572 | CG | LEU | B | 114 | 51.712 | 11.751 | 8.018 | 1.00 | 14.99 |
| 6573 | CD1 | LEU | B | 114 | 53.157 | 11.894 | 8.173 | 1.00 | 16.37 |
| 6574 | CD2 | LEU | B | 114 | 51.444 | 10.364 | 7.519 | 1.00 | 17.99 |
| 6575 | C | LEU | B | 114 | 49.743 | 13.023 | 11.085 | 1.00 | 9.79 |
| 6576 | O | LEU | B | 114 | 50.579 | 13.629 | 11.750 | 1.00 | 9.61 |
| 6577 | N | GLU | B | 115 | 48.587 | 12.511 | 11.578 | 1.00 | 6.34 |
| 6578 | CA | GLU | B | 115 | 48.047 | 12.804 | 12.919 | 1.00 | 6.44 |
| 6579 | CB | GLU | B | 115 | 46.535 | 12.799 | 12.826 | 1.00 | 7.07 |
| 6580 | CG | GLU | B | 115 | 45.742 | 13.242 | 14.019 | 1.00 | 7.63 |
| 6581 | CD | GLU | B | 115 | 44.276 | 13.328 | 13.703 | 1.00 | 13.31 |
| 6582 | OE1 | GLU | B | 115 | 43.671 | 12.199 | 13.511 | 1.00 | 15.47 |
| 6583 | OE2 | GLU | B | 115 | 43.753 | 14.509 | 13.635 | 1.00 | 14.42 |
| 6584 | C | GLU | B | 115 | 48.478 | 11.604 | 13.715 | 1.00 | 6.98 |
| 6585 | O | GLU | B | 115 | 48.245 | 10.494 | 13.227 | 1.00 | 7.78 |
| 6586 | N | SER | B | 116 | 49.053 | 11.798 | 14.902 | 1.00 | 6.07 |
| 6587 | CA | SER | B | 116 | 49.359 | 10.663 | 15.743 | 1.00 | 8.52 |
| 6588 | CB | SER | B | 116 | 50.872 | 10.318 | 15.760 | 1.00 | 7.22 |
| 6589 | OG | SER | B | 116 | 51.413 | 10.216 | 14.470 | 1.00 | 14.26 |
| 6590 | C | SER | B | 116 | 49.004 | 10.858 | 17.176 | 1.00 | 7.65 |
| 6591 | O | SER | B | 116 | 48.534 | 11.893 | 17.522 | 1.00 | 6.55 |
| 6592 | N | ASP | B | 117 | 49.451 | 9.884 | 18.009 | 1.00 | 8.23 |
| 6593 | CA | ASP | B | 117 | 49.334 | 9.948 | 19.447 | 1.00 | 7.78 |
| 6594 | CB | ASP | B | 117 | 50.382 | 10.901 | 20.084 | 1.00 | 6.15 |
| 6595 | CG | ASP | B | 117 | 51.841 | 10.422 | 19.989 | 1.00 | 10.52 |
| 6596 | OD1 | ASP | B | 117 | 52.237 | 9.174 | 20.127 | 1.00 | 14.63 |
| 6597 | OD2 | ASP | B | 117 | 52.743 | 11.300 | 19.935 | 1.00 | 13.66 |
| 6598 | C | ASP | B | 117 | 47.864 | 10.454 | 19.693 | 1.00 | 8.33 |
| 6599 | O | ASP | B | 117 | 47.630 | 11.464 | 20.415 | 1.00 | 6.73 |
| 6600 | N | TYR | B | 118 | 46.886 | 9.799 | 19.050 | 1.00 | 8.64 |
| 6601 | CA | TYR | B | 118 | 45.457 | 10.192 | 19.265 | 1.00 | 10.72 |
| 6602 | CB | TYR | B | 118 | 44.528 | 9.226 | 18.519 | 1.00 | 12.16 |
| 6603 | CG | TYR | B | 118 | 43.045 | 9.567 | 18.524 | 1.00 | 14.77 |
| 6604 | CD1 | TYR | B | 118 | 42.558 | 10.570 | 17.741 | 1.00 | 15.68 |
| 6605 | CE1 | TYR | B | 118 | 41.207 | 10.834 | 17.680 | 1.00 | 22.31 |
| 6606 | CZ | TYR | B | 118 | 40.332 | 10.134 | 18.472 | 1.00 | 25.12 |
| 6607 | OH | TYR | B | 118 | 38.995 | 10.433 | 18.413 | 1.00 | 28.88 |
| 6608 | CE2 | TYR | B | 118 | 40.780 | 9.094 | 19.231 | 1.00 | 22.97 |
| 6609 | CD2 | TYR | B | 118 | 42.139 | 8.827 | 19.274 | 1.00 | 18.63 |
| 6610 | C | TYR | B | 118 | 45.071 | 10.062 | 20.713 | 1.00 | 10.99 |
| 6611 | O | TYR | B | 118 | 45.397 | 9.114 | 21.309 | 1.00 | 11.51 |
| 6612 | N | SER | B | 119 | 44.306 | 10.974 | 21.262 | 1.00 | 11.28 |
| 6613 | CA | SER | B | 119 | 43.974 | 10.986 | 22.699 | 1.00 | 11.28 |
| 6614 | CB | SER | B | 119 | 45.008 | 11.806 | 23.413 | 1.00 | 9.59 |
| 6615 | OG | SER | B | 119 | 44.728 | 11.853 | 24.769 | 1.00 | 11.94 |
| 6616 | C | SER | B | 119 | 42.516 | 11.550 | 22.863 | 1.00 | 12.03 |
| 6617 | O | SER | B | 119 | 42.285 | 12.763 | 22.822 | 1.00 | 11.99 |
| 6618 | N | LYS | B | 120 | 41.546 | 10.620 | 22.943 | 1.00 | 13.98 |
| 6619 | CA | LYS | B | 120 | 40.103 | 10.925 | 23.085 | 1.00 | 14.08 |
| 6620 | CB | LYS | B | 120 | 39.304 | 9.628 | 23.096 | 1.00 | 13.58 |
| 6621 | CG | LYS | B | 120 | 37.898 | 9.771 | 22.679 | 1.00 | 14.84 |

FIGURE 3 (Cont.)

| A | B | C | D | E | F | G | H | I | J |
|---|---|---|---|---|---|---|---|---|---|
| 6622 | CD | LYS | B | 120 | 36.954 | 8.690 | 23.121 | 1.00 | 15.63 |
| 6623 | CE | LYS | B | 120 | 35.516 | 9.343 | 23.061 | 1.00 | 20.03 |
| 6624 | NZ | LYS | B | 120 | 34.288 | 8.489 | 22.594 | 1.00 | 24.34 |
| 6625 | C | LYS | B | 120 | 39.706 | 11.750 | 24.333 | 1.00 | 15.22 |
| 6626 | O | LYS | B | 120 | 40.201 | 11.518 | 25.404 | 1.00 | 16.68 |
| 6627 | N | LEU | B | 121 | 38.802 | 12.689 | 24.160 | 1.00 | 15.01 |
| 6628 | CA | LEU | B | 121 | 38.201 | 13.436 | 25.256 | 1.00 | 15.47 |
| 6629 | CB | LEU | B | 121 | 38.414 | 14.893 | 24.971 | 1.00 | 15.55 |
| 6630 | CG | LEU | B | 121 | 38.950 | 15.777 | 26.062 | 1.00 | 18.43 |
| 6631 | CD1 | LEU | B | 121 | 38.026 | 17.023 | 26.186 | 1.00 | 18.80 |
| 6632 | CD2 | LEU | B | 121 | 39.147 | 15.086 | 27.421 | 1.00 | 13.27 |
| 6633 | C | LEU | B | 121 | 36.715 | 13.129 | 25.208 | 1.00 | 15.10 |
| 6634 | O | LEU | B | 121 | 36.255 | 12.094 | 25.708 | 1.00 | 16.19 |
| 6635 | N | TRP | B | 122 | 35.937 | 13.922 | 24.505 | 1.00 | 13.27 |
| 6636 | CA | TRP | B | 122 | 34.510 | 13.738 | 24.605 | 1.00 | 12.83 |
| 6637 | CB | TRP | B | 122 | 33.790 | 15.052 | 24.998 | 1.00 | 12.78 |
| 6638 | CG | TRP | B | 122 | 34.400 | 15.908 | 26.224 | 1.00 | 12.88 |
| 6639 | CD1 | TRP | B | 122 | 34.689 | 17.294 | 26.218 | 1.00 | 16.08 |
| 6640 | NE1 | TRP | B | 122 | 35.234 | 17.667 | 27.436 | 1.00 | 18.61 |
| 6641 | CE2 | TRP | B | 122 | 35.285 | 16.567 | 28.266 | 1.00 | 10.63 |
| 6642 | CD2 | TRP | B | 122 | 34.778 | 15.449 | 27.555 | 1.00 | 12.74 |
| 6643 | CE3 | TRP | B | 122 | 34.720 | 14.205 | 28.209 | 1.00 | 7.58 |
| 6644 | CZ3 | TRP | B | 122 | 35.154 | 14.103 | 29.518 | 1.00 | 15.04 |
| 6645 | CH2 | TRP | B | 122 | 35.670 | 15.248 | 30.195 | 1.00 | 16.25 |
| 6646 | CZ2 | TRP | B | 122 | 35.715 | 16.486 | 29.565 | 1.00 | 13.59 |
| 6647 | C | TRP | B | 122 | 33.955 | 13.018 | 23.364 | 1.00 | 13.06 |
| 6648 | O | TRP | B | 122 | 34.547 | 12.101 | 22.817 | 1.00 | 13.35 |
| 6649 | N | ARG | B | 123 | 32.733 | 13.274 | 22.962 | 1.00 | 14.23 |
| 6650 | CA | ARG | B | 123 | 32.246 | 12.547 | 21.781 | 1.00 | 14.99 |
| 6651 | CB | ARG | B | 123 | 30.777 | 12.808 | 21.476 | 1.00 | 14.47 |
| 6652 | CG | ARG | B | 123 | 30.280 | 11.923 | 20.387 | 1.00 | 19.05 |
| 6653 | CD | ARG | B | 123 | 28.795 | 11.768 | 20.342 | 1.00 | 24.54 |
| 6654 | NE | ARG | B | 123 | 28.232 | 11.905 | 21.695 | 1.00 | 30.77 |
| 6655 | CZ | ARG | B | 123 | 27.242 | 11.168 | 22.200 | 1.00 | 31.52 |
| 6656 | NH1 | ARG | B | 123 | 26.786 | 11.393 | 23.416 | 1.00 | 28.95 |
| 6657 | NH2 | ARG | B | 123 | 26.654 | 10.258 | 21.470 | 1.00 | 32.52 |
| 6658 | C | ARG | B | 123 | 33.109 | 12.873 | 20.535 | 1.00 | 15.19 |
| 6659 | O | ARG | B | 123 | 33.562 | 11.979 | 19.864 | 1.00 | 15.90 |
| 6660 | N | TYR | B | 124 | 33.423 | 14.138 | 20.309 | 1.00 | 13.56 |
| 6661 | CA | TYR | B | 124 | 34.183 | 14.487 | 19.130 | 1.00 | 12.61 |
| 6662 | CB | TYR | B | 124 | 33.451 | 15.623 | 18.500 | 1.00 | 11.35 |
| 6663 | CG | TYR | B | 124 | 32.046 | 15.222 | 18.165 | 1.00 | 16.22 |
| 6664 | CD1 | TYR | B | 124 | 31.001 | 15.422 | 19.089 | 1.00 | 21.85 |
| 6665 | CE1 | TYR | B | 124 | 29.726 | 15.055 | 18.783 | 1.00 | 18.69 |
| 6666 | CZ | TYR | B | 124 | 29.485 | 14.543 | 17.544 | 1.00 | 20.82 |
| 6667 | OH | TYR | B | 124 | 28.206 | 14.207 | 17.211 | 1.00 | 28.92 |
| 6668 | CE2 | TYR | B | 124 | 30.472 | 14.398 | 16.625 | 1.00 | 15.80 |
| 6669 | CD2 | TYR | B | 124 | 31.719 | 14.727 | 16.924 | 1.00 | 12.90 |
| 6670 | C | TYR | B | 124 | 35.599 | 14.913 | 19.378 | 1.00 | 10.78 |
| 6671 | O | TYR | B | 124 | 36.427 | 14.902 | 18.479 | 1.00 | 9.14 |
| 6672 | N | SER | B | 125 | 35.851 | 15.385 | 20.580 | 1.00 | 11.78 |

FIGURE 3 (Cont.)

| A | B | C | D | E | F | G | H | I | J |
|---|---|---|---|---|---|---|---|---|---|
| 6673 | CA | SER | B | 125 | 37.035 | 16.178 | 20.760 | 1.00 | 12.30 |
| 6674 | CB | SER | B | 125 | 36.889 | 17.355 | 21.793 | 1.00 | 13.31 |
| 6675 | OG | SER | B | 125 | 36.279 | 17.029 | 23.028 | 1.00 | 8.79 |
| 6676 | C | SER | B | 125 | 38.150 | 15.209 | 21.113 | 1.00 | 13.00 |
| 6677 | O | SER | B | 125 | 37.873 | 14.108 | 21.628 | 1.00 | 14.34 |
| 6678 | N | TYR | B | 126 | 39.372 | 15.616 | 20.754 | 1.00 | 11.47 |
| 6679 | CA | TYR | B | 126 | 40.579 | 14.774 | 21.031 | 1.00 | 11.71 |
| 6680 | CB | TYR | B | 126 | 40.599 | 13.511 | 20.203 | 1.00 | 8.88 |
| 6681 | CG | TYR | B | 126 | 40.769 | 13.734 | 18.732 | 1.00 | 8.48 |
| 6682 | CD1 | TYR | B | 126 | 42.023 | 13.808 | 18.184 | 1.00 | 5.32 |
| 6683 | CE1 | TYR | B | 126 | 42.169 | 13.900 | 16.834 | 1.00 | 3.74 |
| 6684 | CZ | TYR | B | 126 | 41.102 | 13.963 | 15.967 | 1.00 | 6.57 |
| 6685 | OH | TYR | B | 126 | 41.435 | 14.111 | 14.666 | 1.00 | 10.62 |
| 6686 | CE2 | TYR | B | 126 | 39.816 | 13.902 | 16.402 | 1.00 | 2.00 |
| 6687 | CD2 | TYR | B | 126 | 39.647 | 13.821 | 17.831 | 1.00 | 5.25 |
| 6688 | C | TYR | B | 126 | 41.753 | 15.589 | 20.612 | 1.00 | 12.47 |
| 6689 | O | TYR | B | 126 | 41.603 | 16.543 | 19.889 | 1.00 | 16.59 |
| 6690 | N | THR | B | 127 | 42.900 | 15.203 | 21.039 | 1.00 | 12.85 |
| 6691 | CA | THR | B | 127 | 44.122 | 15.895 | 20.760 | 1.00 | 13.35 |
| 6692 | CB | THR | B | 127 | 44.780 | 16.161 | 22.084 | 1.00 | 13.85 |
| 6693 | OG1 | THR | B | 127 | 44.646 | 14.952 | 22.841 | 1.00 | 20.67 |
| 6694 | CG2 | THR | B | 127 | 44.060 | 17.199 | 22.984 | 1.00 | 8.42 |
| 6695 | C | THR | B | 127 | 45.004 | 14.882 | 20.024 | 1.00 | 14.59 |
| 6696 | O | THR | B | 127 | 44.830 | 13.656 | 20.201 | 1.00 | 13.71 |
| 6697 | N | ALA | B | 128 | 46.044 | 15.395 | 19.333 | 1.00 | 14.12 |
| 6698 | CA | ALA | B | 128 | 46.982 | 14.557 | 18.590 | 1.00 | 14.25 |
| 6699 | CB | ALA | B | 128 | 46.386 | 14.110 | 17.392 | 1.00 | 14.05 |
| 6700 | C | ALA | B | 128 | 48.210 | 15.323 | 18.264 | 1.00 | 13.64 |
| 6701 | O | ALA | B | 128 | 48.230 | 16.507 | 18.431 | 1.00 | 15.61 |
| 6702 | N | THR | B | 129 | 49.269 | 14.655 | 17.856 | 1.00 | 12.68 |
| 6703 | CA | THR | B | 129 | 50.346 | 15.416 | 17.395 | 1.00 | 11.61 |
| 6704 | CB | THR | B | 129 | 51.722 | 14.996 | 18.007 | 1.00 | 13.16 |
| 6705 | OG1 | THR | B | 129 | 52.578 | 14.353 | 17.067 | 1.00 | 13.70 |
| 6706 | CG2 | THR | B | 129 | 51.590 | 13.962 | 19.069 | 1.00 | 11.20 |
| 6707 | C | THR | B | 129 | 50.216 | 15.479 | 15.837 | 1.00 | 11.60 |
| 6708 | O | THR | B | 129 | 49.628 | 14.588 | 15.210 | 1.00 | 10.64 |
| 6709 | N | TYR | B | 130 | 50.761 | 16.540 | 15.233 | 1.00 | 11.33 |
| 6710 | CA | TYR | B | 130 | 50.645 | 16.644 | 13.789 | 1.00 | 12.22 |
| 6711 | CB | TYR | B | 130 | 49.810 | 17.856 | 13.383 | 1.00 | 11.12 |
| 6712 | CG | TYR | B | 130 | 48.387 | 17.565 | 13.763 | 1.00 | 8.70 |
| 6713 | CD1 | TYR | B | 130 | 47.549 | 16.860 | 12.908 | 1.00 | 9.26 |
| 6714 | CE1 | TYR | B | 130 | 46.292 | 16.459 | 13.307 | 1.00 | 12.41 |
| 6715 | CZ | TYR | B | 130 | 45.879 | 16.778 | 14.573 | 1.00 | 7.54 |
| 6716 | OH | TYR | B | 130 | 44.661 | 16.458 | 14.968 | 1.00 | 8.71 |
| 6717 | CE2 | TYR | B | 130 | 46.666 | 17.495 | 15.410 | 1.00 | 11.65 |
| 6718 | CD2 | TYR | B | 130 | 47.931 | 17.866 | 15.023 | 1.00 | 13.36 |
| 6719 | C | TYR | B | 130 | 52.040 | 16.603 | 13.183 | 1.00 | 12.31 |
| 6720 | O | TYR | B | 130 | 52.943 | 17.053 | 13.722 | 1.00 | 16.44 |
| 6721 | N | TYR | B | 131 | 52.186 | 15.995 | 12.063 | 1.00 | 13.46 |
| 6722 | CA | TYR | B | 131 | 53.478 | 15.811 | 11.476 | 1.00 | 15.93 |
| 6723 | CB | TYR | B | 131 | 53.820 | 14.356 | 11.556 | 1.00 | 12.93 |

FIGURE 3 (Cont.)

| A | B | C | D | E | F | G | H | I | J |
|---|---|---|---|---|---|---|---|---|---|
| 6724 | CG | TYR | B | 131 | 54.474 | 13.974 | 12.825 | 1.00 | 19.08 |
| 6725 | CD1 | TYR | B | 131 | 53.812 | 13.181 | 13.762 | 1.00 | 19.60 |
| 6726 | CE1 | TYR | B | 131 | 54.425 | 12.823 | 14.976 | 1.00 | 15.06 |
| 6727 | CZ | TYR | B | 131 | 55.738 | 13.237 | 15.220 | 1.00 | 23.32 |
| 6728 | OH | TYR | B | 131 | 56.367 | 12.817 | 16.402 | 1.00 | 26.24 |
| 6729 | CE2 | TYR | B | 131 | 56.395 | 14.066 | 14.305 | 1.00 | 17.99 |
| 6730 | CD2 | TYR | B | 131 | 55.770 | 14.424 | 13.124 | 1.00 | 15.67 |
| 6731 | C | TYR | B | 131 | 53.260 | 16.220 | 10.018 | 1.00 | 17.39 |
| 6732 | O | TYR | B | 131 | 52.559 | 15.549 | 9.257 | 1.00 | 19.69 |
| 6733 | N | ILE | B | 132 | 53.811 | 17.320 | 9.587 | 1.00 | 18.21 |
| 6734 | CA | ILE | B | 132 | 53.548 | 17.648 | 8.227 | 1.00 | 18.79 |
| 6735 | CB | ILE | B | 132 | 53.018 | 19.051 | 8.091 | 1.00 | 19.67 |
| 6736 | CG1 | ILE | B | 132 | 53.670 | 19.813 | 6.981 | 1.00 | 19.92 |
| 6737 | CD1 | ILE | B | 132 | 52.601 | 20.527 | 6.185 | 1.00 | 23.36 |
| 6738 | CG2 | ILE | B | 132 | 53.062 | 19.865 | 9.397 | 1.00 | 22.95 |
| 6739 | C | ILE | B | 132 | 54.699 | 17.220 | 7.317 | 1.00 | 17.42 |
| 6740 | O | ILE | B | 132 | 55.854 | 17.375 | 7.595 | 1.00 | 17.77 |
| 6741 | N | TYR | B | 133 | 54.296 | 16.739 | 6.179 | 1.00 | 16.83 |
| 6742 | CA | TYR | B | 133 | 55.146 | 16.070 | 5.242 | 1.00 | 16.65 |
| 6743 | CB | TYR | B | 133 | 54.636 | 14.662 | 5.065 | 1.00 | 15.73 |
| 6744 | CG | TYR | B | 133 | 55.532 | 13.784 | 4.251 | 1.00 | 19.53 |
| 6745 | CD1 | TYR | B | 133 | 55.168 | 13.427 | 2.962 | 1.00 | 20.80 |
| 6746 | CE1 | TYR | B | 133 | 55.931 | 12.598 | 2.222 | 1.00 | 17.90 |
| 6747 | CZ | TYR | B | 133 | 57.053 | 12.081 | 2.757 | 1.00 | 18.00 |
| 6748 | OH | TYR | B | 133 | 57.783 | 11.273 | 1.951 | 1.00 | 12.03 |
| 6749 | CE2 | TYR | B | 133 | 57.433 | 12.434 | 4.042 | 1.00 | 18.32 |
| 6750 | CD2 | TYR | B | 133 | 56.677 | 13.275 | 4.771 | 1.00 | 12.24 |
| 6751 | C | TYR | B | 133 | 55.057 | 16.733 | 3.894 | 1.00 | 15.65 |
| 6752 | O | TYR | B | 133 | 53.942 | 16.967 | 3.387 | 1.00 | 17.03 |
| 6753 | N | ASP | B | 134 | 56.255 | 16.983 | 3.341 | 1.00 | 15.59 |
| 6754 | CA | ASP | B | 134 | 56.476 | 17.615 | 2.047 | 1.00 | 14.87 |
| 6755 | CB | ASP | B | 134 | 57.931 | 18.251 | 1.913 | 1.00 | 16.32 |
| 6756 | CG | ASP | B | 134 | 58.043 | 19.199 | 0.701 | 1.00 | 19.04 |
| 6757 | OD1 | ASP | B | 134 | 57.094 | 19.375 | -0.152 | 1.00 | 14.30 |
| 6758 | OD2 | ASP | B | 134 | 58.951 | 20.004 | 0.663 | 1.00 | 27.51 |
| 6759 | C | ASP | B | 134 | 56.427 | 16.634 | 0.954 | 1.00 | 14.47 |
| 6760 | O | ASP | B | 134 | 57.403 | 16.135 | 0.662 | 1.00 | 12.85 |
| 6761 | N | LEU | B | 135 | 55.296 | 16.422 | 0.309 | 1.00 | 13.75 |
| 6762 | CA | LEU | B | 135 | 55.189 | 15.498 | -0.805 | 1.00 | 13.08 |
| 6763 | CB | LEU | B | 135 | 53.814 | 15.589 | -1.389 | 1.00 | 12.14 |
| 6764 | CG | LEU | B | 135 | 52.813 | 15.017 | -0.387 | 1.00 | 11.55 |
| 6765 | CD1 | LEU | B | 135 | 51.394 | 15.487 | -0.744 | 1.00 | 12.40 |
| 6766 | CD2 | LEU | B | 135 | 52.909 | 13.439 | -0.334 | 1.00 | 11.18 |
| 6767 | C | LEU | B | 135 | 56.225 | 15.652 | -1.932 | 1.00 | 13.70 |
| 6768 | O | LEU | B | 135 | 56.664 | 14.660 | -2.458 | 1.00 | 12.66 |
| 6769 | N | SER | B | 136 | 56.602 | 16.886 | -2.275 | 1.00 | 14.54 |
| 6770 | CA | SER | B | 136 | 57.536 | 17.159 | -3.377 | 1.00 | 13.23 |
| 6771 | CB | SER | B | 136 | 57.447 | 18.606 | -3.838 | 1.00 | 12.52 |
| 6772 | OG | SER | B | 136 | 56.121 | 19.155 | -3.731 | 1.00 | 16.03 |
| 6773 | C | SER | B | 136 | 58.984 | 16.852 | -3.006 | 1.00 | 14.42 |
| 6774 | O | SER | B | 136 | 59.816 | 16.362 | -3.879 | 1.00 | 13.38 |

FIGURE 3 (Cont.)

| A | B | C | D | E | F | G | H | I | J |
|---|---|---|---|---|---|---|---|---|---|
| 6775 | N | ASN | B | 137 | 59.398 | 17.118 | -1.775 | 1.00 | 13.99 |
| 6776 | CA | ASN | B | 137 | 60.802 | 16.728 | -1.531 | 1.00 | 14.35 |
| 6777 | CB | ASN | B | 137 | 61.551 | 17.656 | -0.574 | 1.00 | 14.35 |
| 6778 | CG | ASN | B | 137 | 61.083 | 19.134 | -0.652 | 1.00 | 18.36 |
| 6779 | OD1 | ASN | B | 137 | 60.913 | 19.787 | 0.403 | 1.00 | 13.92 |
| 6780 | ND2 | ASN | B | 137 | 60.842 | 19.650 | -1.856 | 1.00 | 20.48 |
| 6781 | C | ASN | B | 137 | 60.794 | 15.247 | -1.124 | 1.00 | 13.79 |
| 6782 | O | ASN | B | 137 | 61.524 | 14.416 | -1.643 | 1.00 | 15.00 |
| 6783 | N | GLY | B | 138 | 59.882 | 14.904 | -0.263 | 1.00 | 12.75 |
| 6784 | CA | GLY | B | 138 | 59.577 | 13.530 | 0.069 | 1.00 | 12.50 |
| 6785 | C | GLY | B | 138 | 60.105 | 13.431 | 1.459 | 1.00 | 13.47 |
| 6786 | O | GLY | B | 138 | 60.721 | 12.425 | 1.838 | 1.00 | 14.40 |
| 6787 | N | GLU | B | 139 | 59.880 | 14.504 | 2.225 | 1.00 | 12.63 |
| 6788 | CA | GLU | B | 139 | 60.535 | 14.669 | 3.518 | 1.00 | 14.27 |
| 6789 | CB | GLU | B | 139 | 61.946 | 15.171 | 3.282 | 1.00 | 14.11 |
| 6790 | CG | GLU | B | 139 | 62.068 | 16.655 | 2.968 | 1.00 | 16.57 |
| 6791 | CD | GLU | B | 139 | 63.556 | 17.026 | 2.844 | 1.00 | 21.50 |
| 6792 | OE1 | GLU | B | 139 | 63.938 | 18.194 | 3.137 | 1.00 | 21.64 |
| 6793 | OE2 | GLU | B | 139 | 64.353 | 16.108 | 2.517 | 1.00 | 23.53 |
| 6794 | C | GLU | B | 139 | 59.772 | 15.525 | 4.550 | 1.00 | 13.36 |
| 6795 | O | GLU | B | 139 | 59.181 | 16.532 | 4.206 | 1.00 | 16.68 |
| 6796 | N | PHE | B | 140 | 59.718 | 15.067 | 5.801 | 1.00 | 12.70 |
| 6797 | CA | PHE | B | 140 | 59.020 | 15.754 | 6.879 | 1.00 | 11.77 |
| 6798 | CB | PHE | B | 140 | 59.171 | 14.932 | 8.156 | 1.00 | 12.03 |
| 6799 | CG | PHE | B | 140 | 58.177 | 13.870 | 8.254 | 1.00 | 10.89 |
| 6800 | CD1 | PHE | B | 140 | 56.851 | 14.168 | 8.228 | 1.00 | 13.75 |
| 6801 | CE1 | PHE | B | 140 | 55.936 | 13.208 | 8.246 | 1.00 | 11.60 |
| 6802 | CZ | PHE | B | 140 | 56.279 | 11.892 | 8.286 | 1.00 | 13.15 |
| 6803 | CE2 | PHE | B | 140 | 57.568 | 11.556 | 8.256 | 1.00 | 9.43 |
| 6804 | CD2 | PHE | B | 140 | 58.542 | 12.558 | 8.241 | 1.00 | 15.55 |
| 6805 | C | PHE | B | 140 | 59.469 | 17.213 | 7.076 | 1.00 | 12.11 |
| 6806 | O | PHE | B | 140 | 60.623 | 17.474 | 7.015 | 1.00 | 11.11 |
| 6807 | N | VAL | B | 141 | 58.553 | 18.149 | 7.278 | 1.00 | 11.03 |
| 6808 | CA | VAL | B | 141 | 58.908 | 19.580 | 7.368 | 1.00 | 12.42 |
| 6809 | CB | VAL | B | 141 | 57.665 | 20.474 | 7.116 | 1.00 | 12.31 |
| 6810 | CG1 | VAL | B | 141 | 58.058 | 21.963 | 7.115 | 1.00 | 10.47 |
| 6811 | CG2 | VAL | B | 141 | 56.995 | 20.057 | 5.790 | 1.00 | 7.49 |
| 6812 | C | VAL | B | 141 | 59.496 | 20.054 | 8.721 | 1.00 | 15.25 |
| 6813 | O | VAL | B | 141 | 58.854 | 19.872 | 9.789 | 1.00 | 16.68 |
| 6814 | N | ARG | B | 142 | 60.673 | 20.704 | 8.694 | 1.00 | 17.46 |
| 6815 | CA | ARG | B | 142 | 61.458 | 20.730 | 9.910 | 1.00 | 19.40 |
| 6816 | CB | ARG | B | 142 | 62.741 | 19.825 | 9.787 | 1.00 | 20.38 |
| 6817 | CG | ARG | B | 142 | 62.423 | 18.236 | 9.304 | 1.00 | 25.82 |
| 6818 | CD | ARG | B | 142 | 63.336 | 16.996 | 9.818 | 1.00 | 32.34 |
| 6819 | NE | ARG | B | 142 | 62.600 | 15.695 | 10.014 | 1.00 | 37.72 |
| 6820 | CZ | ARG | B | 142 | 61.637 | 15.433 | 10.974 | 1.00 | 40.53 |
| 6821 | NH1 | ARG | B | 142 | 61.254 | 16.376 | 11.853 | 1.00 | 42.87 |
| 6822 | NH2 | ARG | B | 142 | 61.033 | 14.221 | 11.056 | 1.00 | 41.67 |
| 6823 | C | ARG | B | 142 | 61.633 | 22.098 | 10.572 | 1.00 | 18.88 |
| 6824 | O | ARG | B | 142 | 61.628 | 22.193 | 11.793 | 1.00 | 19.04 |
| 6825 | N | GLY | B | 143 | 61.600 | 23.205 | 9.858 | 1.00 | 18.45 |

FIGURE 3 (Cont.)

| A | B | C | D | E | F | G | H | I | J |
|---|---|---|---|---|---|---|---|---|---|
| 6826 | CA | GLY | B | 143 | 61.324 | 24.453 | 10.610 | 1.00 | 19.04 |
| 6827 | C | GLY | B | 143 | 60.144 | 24.462 | 11.670 | 1.00 | 18.33 |
| 6828 | O | GLY | B | 143 | 59.180 | 23.635 | 11.653 | 1.00 | 17.69 |
| 6829 | N | ASN | B | 144 | 60.291 | 25.354 | 12.655 | 1.00 | 17.46 |
| 6830 | CA | ASN | B | 144 | 59.325 | 25.630 | 13.679 | 1.00 | 15.11 |
| 6831 | CB | ASN | B | 144 | 58.621 | 26.962 | 13.281 | 1.00 | 13.76 |
| 6832 | CG | ASN | B | 144 | 58.798 | 27.999 | 14.347 | 1.00 | 15.75 |
| 6833 | OD1 | ASN | B | 144 | 58.163 | 27.926 | 15.465 | 1.00 | 10.85 |
| 6834 | ND2 | ASN | B | 144 | 59.802 | 28.899 | 14.121 | 1.00 | 16.75 |
| 6835 | C | ASN | B | 144 | 58.317 | 24.525 | 13.988 | 1.00 | 15.15 |
| 6836 | O | ASN | B | 144 | 57.145 | 24.725 | 13.887 | 1.00 | 15.39 |
| 6837 | N | GLU | B | 145 | 58.748 | 23.320 | 14.296 | 1.00 | 15.03 |
| 6838 | CA | GLU | B | 145 | 57.809 | 22.193 | 14.534 | 1.00 | 15.15 |
| 6839 | CB | GLU | B | 145 | 58.444 | 21.010 | 15.244 | 1.00 | 14.44 |
| 6840 | CG | GLU | B | 145 | 59.013 | 19.940 | 14.298 | 1.00 | 14.40 |
| 6841 | CD | GLU | B | 145 | 60.493 | 20.240 | 13.932 | 1.00 | 21.80 |
| 6842 | OE1 | GLU | B | 145 | 60.847 | 21.508 | 14.004 | 1.00 | 12.81 |
| 6843 | OE2 | GLU | B | 145 | 61.300 | 19.212 | 13.631 | 1.00 | 26.46 |
| 6844 | C | GLU | B | 145 | 56.637 | 22.634 | 15.370 | 1.00 | 16.43 |
| 6845 | O | GLU | B | 145 | 56.769 | 23.559 | 16.171 | 1.00 | 18.24 |
| 6846 | N | LEU | B | 146 | 55.504 | 21.935 | 15.201 | 1.00 | 16.06 |
| 6847 | CA | LEU | B | 146 | 54.169 | 22.381 | 15.699 | 1.00 | 15.15 |
| 6848 | CB | LEU | B | 146 | 53.049 | 21.653 | 14.983 | 1.00 | 14.27 |
| 6849 | CG | LEU | B | 146 | 52.432 | 22.392 | 13.828 | 1.00 | 19.03 |
| 6850 | CD1 | LEU | B | 146 | 51.551 | 21.464 | 13.016 | 1.00 | 19.59 |
| 6851 | CD2 | LEU | B | 146 | 51.600 | 23.540 | 14.395 | 1.00 | 20.32 |
| 6852 | C | LEU | B | 146 | 54.129 | 21.939 | 17.108 | 1.00 | 13.55 |
| 6853 | O | LEU | B | 146 | 54.783 | 20.943 | 17.397 | 1.00 | 13.92 |
| 6854 | N | PRO | B | 147 | 53.409 | 22.653 | 17.974 | 1.00 | 12.92 |
| 6855 | CA | PRO | B | 147 | 53.357 | 22.270 | 19.365 | 1.00 | 12.81 |
| 6856 | CB | PRO | B | 147 | 52.726 | 23.506 | 20.024 | 1.00 | 13.16 |
| 6857 | CG | PRO | B | 147 | 51.614 | 23.911 | 19.025 | 1.00 | 11.35 |
| 6858 | CD | PRO | B | 147 | 52.561 | 23.855 | 17.746 | 1.00 | 12.99 |
| 6859 | C | PRO | B | 147 | 52.502 | 21.013 | 19.523 | 1.00 | 13.72 |
| 6860 | O | PRO | B | 147 | 51.953 | 20.506 | 18.595 | 1.00 | 13.27 |
| 6861 | N | ARG | B | 148 | 52.447 | 20.519 | 20.733 | 1.00 | 15.54 |
| 6862 | CA | ARG | B | 148 | 51.919 | 19.201 | 21.048 | 1.00 | 16.85 |
| 6863 | CB | ARG | B | 148 | 53.042 | 18.268 | 21.430 | 1.00 | 16.70 |
| 6864 | CG | ARG | B | 148 | 53.133 | 17.078 | 20.503 | 1.00 | 18.43 |
| 6865 | CD | ARG | B | 148 | 54.301 | 16.136 | 20.888 | 1.00 | 23.99 |
| 6866 | NE | ARG | B | 148 | 55.061 | 15.519 | 19.776 | 1.00 | 27.49 |
| 6867 | CZ | ARG | B | 148 | 55.766 | 16.170 | 18.841 | 1.00 | 29.47 |
| 6868 | NH1 | ARG | B | 148 | 56.433 | 15.462 | 17.960 | 1.00 | 28.63 |
| 6869 | NH2 | ARG | B | 148 | 55.830 | 17.505 | 18.765 | 1.00 | 28.67 |
| 6870 | C | ARG | B | 148 | 50.978 | 19.305 | 22.240 | 1.00 | 17.39 |
| 6871 | O | ARG | B | 148 | 51.247 | 20.133 | 23.114 | 1.00 | 19.87 |
| 6872 | N | PRO | B | 149 | 50.172 | 18.259 | 22.491 | 1.00 | 15.23 |
| 6873 | CA | PRO | B | 149 | 48.797 | 18.151 | 22.257 | 1.00 | 13.71 |
| 6874 | CB | PRO | B | 149 | 48.282 | 17.883 | 23.695 | 1.00 | 14.41 |
| 6875 | CG | PRO | B | 149 | 49.330 | 17.999 | 24.482 | 1.00 | 10.79 |
| 6876 | CD | PRO | B | 149 | 50.463 | 17.415 | 23.635 | 1.00 | 16.02 |

FIGURE 3 (Cont.)

| A | B | C | D | E | F | G | H | I | J |
|---|---|---|---|---|---|---|---|---|---|
| 6877 | C | PRO | B | 149 | 48.182 | 19.393 | 21.466 | 1.00 | 13.60 |
| 6878 | O | PRO | B | 149 | 48.155 | 20.520 | 21.899 | 1.00 | 13.77 |
| 6879 | N | ILE | B | 150 | 47.839 | 19.130 | 20.209 | 1.00 | 11.91 |
| 6880 | CA | ILE | B | 150 | 46.968 | 19.970 | 19.485 | 1.00 | 10.96 |
| 6881 | CB | ILE | B | 150 | 47.502 | 20.106 | 18.028 | 1.00 | 11.23 |
| 6882 | CG1 | ILE | B | 150 | 48.836 | 20.775 | 18.037 | 1.00 | 10.02 |
| 6883 | CD1 | ILE | B | 150 | 49.093 | 21.603 | 16.847 | 1.00 | 11.96 |
| 6884 | CG2 | ILE | B | 150 | 46.477 | 20.898 | 17.145 | 1.00 | 7.27 |
| 6885 | C | ILE | B | 150 | 45.510 | 19.403 | 19.512 | 1.00 | 11.94 |
| 6886 | O | ILE | B | 150 | 45.267 | 18.208 | 19.268 | 1.00 | 11.12 |
| 6887 | N | GLN | B | 151 | 44.607 | 20.356 | 19.680 | 1.00 | 11.41 |
| 6888 | CA | GLN | B | 151 | 43.227 | 20.185 | 19.947 | 1.00 | 12.94 |
| 6889 | CB | GLN | B | 151 | 42.763 | 21.420 | 20.855 | 1.00 | 12.64 |
| 6890 | CG | GLN | B | 151 | 43.168 | 21.222 | 22.302 | 1.00 | 11.96 |
| 6891 | CD | GLN | B | 151 | 43.119 | 22.468 | 23.101 | 1.00 | 14.76 |
| 6892 | OE1 | GLN | B | 151 | 42.378 | 22.553 | 24.049 | 1.00 | 14.39 |
| 6893 | NE2 | GLN | B | 151 | 43.995 | 23.403 | 22.803 | 1.00 | 11.76 |
| 6894 | C | GLN | B | 151 | 42.398 | 20.107 | 18.665 | 1.00 | 13.48 |
| 6895 | O | GLN | B | 151 | 41.408 | 19.381 | 18.561 | 1.00 | 12.12 |
| 6896 | N | TYR | B | 152 | 42.828 | 20.932 | 17.700 | 1.00 | 13.93 |
| 6897 | CA | TYR | B | 152 | 42.209 | 21.019 | 16.377 | 1.00 | 12.63 |
| 6898 | CB | TYR | B | 152 | 41.008 | 21.997 | 16.368 | 1.00 | 12.31 |
| 6899 | CG | TYR | B | 152 | 40.282 | 21.831 | 15.054 | 1.00 | 12.02 |
| 6900 | CD1 | TYR | B | 152 | 39.990 | 22.966 | 14.236 | 1.00 | 6.33 |
| 6901 | CE1 | TYR | B | 152 | 39.261 | 22.775 | 12.948 | 1.00 | 6.95 |
| 6902 | CZ | TYR | B | 152 | 38.898 | 21.429 | 12.537 | 1.00 | 7.03 |
| 6903 | OH | TYR | B | 152 | 38.305 | 21.273 | 11.306 | 1.00 | 11.75 |
| 6904 | CE2 | TYR | B | 152 | 39.250 | 20.278 | 13.337 | 1.00 | 6.28 |
| 6905 | CD2 | TYR | B | 152 | 39.860 | 20.488 | 14.598 | 1.00 | 6.45 |
| 6906 | C | TYR | B | 152 | 43.241 | 21.556 | 15.397 | 1.00 | 13.50 |
| 6907 | O | TYR | B | 152 | 44.050 | 22.339 | 15.736 | 1.00 | 12.81 |
| 6908 | N | LEU | B | 153 | 43.167 | 21.170 | 14.142 | 1.00 | 14.69 |
| 6909 | CA | LEU | B | 153 | 44.202 | 21.559 | 13.147 | 1.00 | 13.97 |
| 6910 | CB | LEU | B | 153 | 45.393 | 20.630 | 13.167 | 1.00 | 12.86 |
| 6911 | CG | LEU | B | 153 | 46.439 | 20.911 | 12.094 | 1.00 | 11.99 |
| 6912 | CD1 | LEU | B | 153 | 47.945 | 20.663 | 12.553 | 1.00 | 4.74 |
| 6913 | CD2 | LEU | B | 153 | 46.240 | 20.122 | 10.976 | 1.00 | 10.59 |
| 6914 | C | LEU | B | 153 | 43.504 | 21.260 | 11.893 | 1.00 | 15.80 |
| 6915 | O | LEU | B | 153 | 42.973 | 20.172 | 11.731 | 1.00 | 18.12 |
| 6916 | N | CYS | B | 154 | 43.472 | 22.201 | 10.990 | 1.00 | 15.65 |
| 6917 | CA | CYS | B | 154 | 42.949 | 21.902 | 9.701 | 1.00 | 15.65 |
| 6918 | CB | CYS | B | 154 | 41.456 | 22.157 | 9.690 | 1.00 | 13.00 |
| 6919 | SG | CYS | B | 154 | 41.169 | 23.895 | 9.872 | 1.00 | 21.97 |
| 6920 | C | CYS | B | 154 | 43.649 | 22.767 | 8.705 | 1.00 | 14.19 |
| 6921 | O | CYS | B | 154 | 44.128 | 23.845 | 9.028 | 1.00 | 15.44 |
| 6922 | N | TRP | B | 155 | 43.538 | 22.332 | 7.461 | 1.00 | 12.95 |
| 6923 | CA | TRP | B | 155 | 44.093 | 23.031 | 6.330 | 1.00 | 13.19 |
| 6924 | CB | TRP | B | 155 | 44.202 | 22.043 | 5.163 | 1.00 | 10.38 |
| 6925 | CG | TRP | B | 155 | 45.234 | 21.156 | 5.276 | 1.00 | 9.03 |
| 6926 | CD1 | TRP | B | 155 | 45.145 | 19.786 | 5.280 | 1.00 | 7.26 |
| 6927 | NE1 | TRP | B | 155 | 46.411 | 19.245 | 5.271 | 1.00 | 3.63 |

FIGURE 3 (Cont.)

| A | B | C | D | E | F | G | H | I | J |
|---|---|---|---|---|---|---|---|---|---|
| 6928 | CE2 | TRP | B | 155 | 47.344 | 20.236 | 5.319 | 1.00 | 2.23 |
| 6929 | CD2 | TRP | B | 155 | 46.651 | 21.462 | 5.317 | 1.00 | 4.74 |
| 6930 | CE3 | TRP | B | 155 | 47.386 | 22.640 | 5.276 | 1.00 | 5.21 |
| 6931 | CZ3 | TRP | B | 155 | 48.824 | 22.575 | 5.307 | 1.00 | 3.77 |
| 6932 | CH2 | TRP | B | 155 | 49.420 | 21.351 | 5.399 | 1.00 | 2.00 |
| 6933 | CZ2 | TRP | B | 155 | 48.702 | 20.157 | 5.391 | 1.00 | 2.00 |
| 6934 | C | TRP | B | 155 | 43.147 | 24.160 | 5.997 | 1.00 | 12.86 |
| 6935 | O | TRP | B | 155 | 41.987 | 24.021 | 6.229 | 1.00 | 14.66 |
| 6936 | N | SER | B | 156 | 43.644 | 25.266 | 5.458 | 1.00 | 13.60 |
| 6937 | CA | SER | B | 156 | 42.697 | 26.225 | 4.819 | 1.00 | 16.28 |
| 6938 | CB | SER | B | 156 | 43.438 | 27.407 | 4.253 | 1.00 | 14.91 |
| 6939 | OG | SER | B | 156 | 44.256 | 26.973 | 3.243 | 1.00 | 17.13 |
| 6940 | C | SER | B | 156 | 41.985 | 25.434 | 3.709 | 1.00 | 17.35 |
| 6941 | O | SER | B | 156 | 42.425 | 24.271 | 3.418 | 1.00 | 16.67 |
| 6942 | N | PRO | B | 157 | 40.942 | 25.993 | 3.091 | 1.00 | 17.86 |
| 6943 | CA | PRO | B | 157 | 40.182 | 25.218 | 2.101 | 1.00 | 18.91 |
| 6944 | CB | PRO | B | 157 | 38.807 | 25.875 | 2.106 | 1.00 | 19.53 |
| 6945 | CG | PRO | B | 157 | 38.957 | 27.165 | 2.920 | 1.00 | 20.73 |
| 6946 | CD | PRO | B | 157 | 40.443 | 27.376 | 3.156 | 1.00 | 16.86 |
| 6947 | C | PRO | B | 157 | 40.831 | 25.227 | 0.660 | 1.00 | 18.65 |
| 6948 | O | PRO | B | 157 | 40.479 | 24.394 | -0.215 | 1.00 | 20.72 |
| 6949 | N | VAL | B | 158 | 41.705 | 26.192 | 0.424 | 1.00 | 14.85 |
| 6950 | CA | VAL | B | 158 | 42.519 | 26.289 | -0.777 | 1.00 | 14.69 |
| 6951 | CB | VAL | B | 158 | 41.971 | 27.306 | -1.828 | 1.00 | 13.91 |
| 6952 | CG1 | VAL | B | 158 | 40.532 | 27.032 | -2.117 | 1.00 | 12.98 |
| 6953 | CG2 | VAL | B | 158 | 42.145 | 28.814 | -1.373 | 1.00 | 16.26 |
| 6954 | C | VAL | B | 158 | 43.925 | 26.672 | -0.291 | 1.00 | 12.81 |
| 6955 | O | VAL | B | 158 | 44.152 | 26.861 | 0.848 | 1.00 | 12.47 |
| 6956 | N | GLY | B | 159 | 44.881 | 26.788 | -1.156 | 1.00 | 13.80 |
| 6957 | CA | GLY | B | 159 | 46.303 | 26.681 | -0.738 | 1.00 | 12.87 |
| 6958 | C | GLY | B | 159 | 46.737 | 25.656 | 0.333 | 1.00 | 13.51 |
| 6959 | O | GLY | B | 159 | 46.287 | 24.502 | 0.377 | 1.00 | 12.75 |
| 6960 | N | SER | B | 160 | 47.627 | 26.123 | 1.219 | 1.00 | 14.93 |
| 6961 | CA | SER | B | 160 | 48.273 | 25.271 | 2.206 | 1.00 | 15.74 |
| 6962 | CB | SER | B | 160 | 49.553 | 24.678 | 1.607 | 1.00 | 15.24 |
| 6963 | OG | SER | B | 160 | 50.552 | 25.646 | 1.262 | 1.00 | 20.45 |
| 6964 | C | SER | B | 160 | 48.536 | 26.052 | 3.500 | 1.00 | 14.35 |
| 6965 | O | SER | B | 160 | 49.634 | 26.091 | 4.062 | 1.00 | 13.34 |
| 6966 | N | LYS | B | 161 | 47.520 | 26.739 | 3.939 | 1.00 | 13.79 |
| 6967 | CA | LYS | B | 161 | 47.640 | 27.365 | 5.236 | 1.00 | 15.76 |
| 6968 | CB | LYS | B | 161 | 47.156 | 28.803 | 5.391 | 1.00 | 14.71 |
| 6969 | CG | LYS | B | 161 | 46.773 | 29.564 | 4.162 | 1.00 | 20.53 |
| 6970 | CD | LYS | B | 161 | 47.794 | 30.642 | 3.725 | 1.00 | 25.61 |
| 6971 | CE | LYS | B | 161 | 47.114 | 31.794 | 2.901 | 1.00 | 29.94 |
| 6972 | NZ | LYS | B | 161 | 46.340 | 32.852 | 3.730 | 1.00 | 30.81 |
| 6973 | C | LYS | B | 161 | 47.067 | 26.502 | 6.284 | 1.00 | 15.37 |
| 6974 | O | LYS | B | 161 | 46.501 | 25.422 | 6.070 | 1.00 | 17.29 |
| 6975 | N | LEU | B | 162 | 47.236 | 26.961 | 7.492 | 1.00 | 15.91 |
| 6976 | CA | LEU | B | 162 | 47.018 | 26.064 | 8.625 | 1.00 | 13.75 |
| 6977 | CB | LEU | B | 162 | 48.392 | 25.599 | 9.012 | 1.00 | 11.90 |
| 6978 | CG | LEU | B | 162 | 48.576 | 24.136 | 9.292 | 1.00 | 12.92 |

FIGURE 3 (Cont.)

| A | B | C | D | E | F | G | H | I | J |
|---|---|---|---|---|---|---|---|---|---|
| 6979 | CD1 | LEU | B | 162 | 47.828 | 23.213 | 8.379 | 1.00 | 8.78 |
| 6980 | CD2 | LEU | B | 162 | 50.120 | 23.858 | 9.327 | 1.00 | 4.25 |
| 6981 | C | LEU | B | 162 | 46.536 | 26.920 | 9.714 | 1.00 | 13.58 |
| 6982 | O | LEU | B | 162 | 47.196 | 27.971 | 9.983 | 1.00 | 13.25 |
| 6983 | N | ALA | B | 163 | 45.485 | 26.464 | 10.358 | 1.00 | 9.04 |
| 6984 | CA | ALA | B | 163 | 45.112 | 26.946 | 11.630 | 1.00 | 9.03 |
| 6985 | CB | ALA | B | 163 | 43.838 | 27.755 | 11.517 | 1.00 | 9.86 |
| 6986 | C | ALA | B | 163 | 44.893 | 25.773 | 12.621 | 1.00 | 10.10 |
| 6987 | O | ALA | B | 163 | 44.366 | 24.780 | 12.290 | 1.00 | 9.70 |
| 6988 | N | TYR | B | 164 | 45.257 | 25.976 | 13.872 | 1.00 | 11.91 |
| 6989 | CA | TYR | B | 164 | 45.174 | 24.989 | 14.895 | 1.00 | 11.36 |
| 6990 | CB | TYR | B | 164 | 46.497 | 24.190 | 15.025 | 1.00 | 11.42 |
| 6991 | CG | TYR | B | 164 | 47.792 | 24.970 | 15.320 | 1.00 | 13.58 |
| 6992 | CD1 | TYR | B | 164 | 48.223 | 25.149 | 16.617 | 1.00 | 14.23 |
| 6993 | CE1 | TYR | B | 164 | 49.469 | 25.854 | 16.952 | 1.00 | 11.49 |
| 6994 | CZ | TYR | B | 164 | 50.323 | 26.312 | 15.986 | 1.00 | 12.68 |
| 6995 | OH | TYR | B | 164 | 51.532 | 26.897 | 16.472 | 1.00 | 14.69 |
| 6996 | CE2 | TYR | B | 164 | 49.993 | 26.050 | 14.653 | 1.00 | 10.54 |
| 6997 | CD2 | TYR | B | 164 | 48.688 | 25.350 | 14.330 | 1.00 | 16.41 |
| 6998 | C | TYR | B | 164 | 44.864 | 25.648 | 16.187 | 1.00 | 11.52 |
| 6999 | O | TYR | B | 164 | 44.941 | 26.862 | 16.365 | 1.00 | 11.23 |
| 7000 | N | VAL | B | 165 | 44.529 | 24.808 | 17.132 | 1.00 | 12.41 |
| 7001 | CA | VAL | B | 165 | 44.248 | 25.213 | 18.486 | 1.00 | 9.82 |
| 7002 | CB | VAL | B | 165 | 42.842 | 24.953 | 18.709 | 1.00 | 10.25 |
| 7003 | CG1 | VAL | B | 165 | 42.507 | 25.260 | 20.054 | 1.00 | 12.65 |
| 7004 | CG2 | VAL | B | 165 | 41.998 | 25.731 | 17.746 | 1.00 | 4.49 |
| 7005 | C | VAL | B | 165 | 45.122 | 24.388 | 19.442 | 1.00 | 11.12 |
| 7006 | O | VAL | B | 165 | 45.097 | 23.147 | 19.441 | 1.00 | 12.21 |
| 7007 | N | TYR | B | 166 | 45.956 | 25.113 | 20.183 | 1.00 | 11.12 |
| 7008 | CA | TYR | B | 166 | 46.905 | 24.619 | 21.197 | 1.00 | 10.52 |
| 7009 | CB | TYR | B | 166 | 48.329 | 25.104 | 20.880 | 1.00 | 8.93 |
| 7010 | CG | TYR | B | 166 | 49.373 | 24.648 | 21.876 | 1.00 | 8.83 |
| 7011 | CD1 | TYR | B | 166 | 50.196 | 25.530 | 22.545 | 1.00 | 11.74 |
| 7012 | CE1 | TYR | B | 166 | 51.214 | 25.062 | 23.449 | 1.00 | 10.43 |
| 7013 | CZ | TYR | B | 166 | 51.313 | 23.740 | 23.668 | 1.00 | 7.14 |
| 7014 | OH | TYR | B | 166 | 52.173 | 23.200 | 24.558 | 1.00 | 6.25 |
| 7015 | CE2 | TYR | B | 166 | 50.449 | 22.904 | 23.018 | 1.00 | 2.00 |
| 7016 | CD2 | TYR | B | 166 | 49.548 | 23.348 | 22.121 | 1.00 | 5.88 |
| 7017 | C | TYR | B | 166 | 46.497 | 25.394 | 22.475 | 1.00 | 11.06 |
| 7018 | O | TYR | B | 166 | 46.233 | 26.593 | 22.466 | 1.00 | 9.91 |
| 7019 | N | GLN | B | 167 | 46.488 | 24.671 | 23.576 | 1.00 | 12.72 |
| 7020 | CA | GLN | B | 167 | 46.093 | 25.223 | 24.882 | 1.00 | 12.98 |
| 7021 | CB | GLN | B | 167 | 47.271 | 25.837 | 25.586 | 1.00 | 9.94 |
| 7022 | CG | GLN | B | 167 | 48.192 | 24.795 | 26.024 | 1.00 | 12.12 |
| 7023 | CD | GLN | B | 167 | 49.509 | 25.343 | 26.443 | 1.00 | 14.49 |
| 7024 | OE1 | GLN | B | 167 | 50.179 | 24.679 | 27.180 | 1.00 | 13.65 |
| 7025 | NE2 | GLN | B | 167 | 49.885 | 26.593 | 25.967 | 1.00 | 16.43 |
| 7026 | C | GLN | B | 167 | 44.969 | 26.201 | 24.804 | 1.00 | 11.47 |
| 7027 | O | GLN | B | 167 | 45.079 | 27.294 | 25.341 | 1.00 | 13.23 |
| 7028 | N | ASN | B | 168 | 43.914 | 25.812 | 24.133 | 1.00 | 10.08 |
| 7029 | CA | ASN | B | 168 | 42.721 | 26.675 | 23.989 | 1.00 | 9.66 |

FIGURE 3 (Cont.)

| A | B | C | D | E | F | G | H | I | J |
|---|---|---|---|---|---|---|---|---|---|
| 7030 | CB | ASN | B | 168 | 42.176 | 26.927 | 25.393 | 1.00 | 9.60 |
| 7031 | CG | ASN | B | 168 | 41.309 | 25.792 | 25.911 | 1.00 | 6.66 |
| 7032 | OD1 | ASN | B | 168 | 40.463 | 25.993 | 26.725 | 1.00 | 11.37 |
| 7033 | ND2 | ASN | B | 168 | 41.541 | 24.628 | 25.462 | 1.00 | 12.81 |
| 7034 | C | ASN | B | 168 | 42.903 | 28.057 | 23.234 | 1.00 | 10.18 |
| 7035 | O | ASN | B | 168 | 42.033 | 29.053 | 23.310 | 1.00 | 8.03 |
| 7036 | N | ASN | B | 169 | 44.009 | 28.158 | 22.517 | 1.00 | 8.75 |
| 7037 | CA | ASN | B | 169 | 44.166 | 29.287 | 21.645 | 1.00 | 10.93 |
| 7038 | CB | ASN | B | 169 | 45.346 | 30.104 | 22.097 | 1.00 | 11.60 |
| 7039 | CG | ASN | B | 169 | 45.073 | 30.999 | 23.315 | 1.00 | 12.10 |
| 7040 | OD1 | ASN | B | 169 | 44.097 | 31.756 | 23.358 | 1.00 | 2.83 |
| 7041 | ND2 | ASN | B | 169 | 46.004 | 30.948 | 24.280 | 1.00 | 9.76 |
| 7042 | C | ASN | B | 169 | 44.358 | 28.845 | 20.171 | 1.00 | 11.49 |
| 7043 | O | ASN | B | 169 | 44.893 | 27.761 | 19.800 | 1.00 | 11.47 |
| 7044 | N | ILE | B | 170 | 44.004 | 29.758 | 19.320 | 1.00 | 11.87 |
| 7045 | CA | ILE | B | 170 | 44.120 | 29.525 | 17.860 | 1.00 | 10.56 |
| 7046 | CB | ILE | B | 170 | 42.924 | 30.152 | 17.069 | 1.00 | 12.19 |
| 7047 | CG1 | ILE | B | 170 | 41.566 | 29.639 | 17.562 | 1.00 | 6.70 |
| 7048 | CD1 | ILE | B | 170 | 40.393 | 30.757 | 17.347 | 1.00 | 12.14 |
| 7049 | CG2 | ILE | B | 170 | 43.009 | 29.770 | 15.596 | 1.00 | 12.19 |
| 7050 | C | ILE | B | 170 | 45.403 | 30.118 | 17.390 | 1.00 | 9.96 |
| 7051 | O | ILE | B | 170 | 45.849 | 31.128 | 17.850 | 1.00 | 8.23 |
| 7052 | N | TYR | B | 171 | 45.970 | 29.424 | 16.418 | 1.00 | 10.41 |
| 7053 | CA | TYR | B | 171 | 47.186 | 29.863 | 15.733 | 1.00 | 9.51 |
| 7054 | CB | TYR | B | 171 | 48.408 | 29.124 | 16.232 | 1.00 | 7.78 |
| 7055 | CG | TYR | B | 171 | 48.785 | 29.373 | 17.680 | 1.00 | 2.55 |
| 7056 | CD1 | TYR | B | 171 | 49.912 | 30.093 | 18.032 | 1.00 | 4.74 |
| 7057 | CE1 | TYR | B | 171 | 50.270 | 30.276 | 19.385 | 1.00 | 7.22 |
| 7058 | CZ | TYR | B | 171 | 49.471 | 29.681 | 20.320 | 1.00 | 7.81 |
| 7059 | OH | TYR | B | 171 | 49.692 | 29.827 | 21.631 | 1.00 | 10.78 |
| 7060 | CE2 | TYR | B | 171 | 48.373 | 28.938 | 19.965 | 1.00 | 4.45 |
| 7061 | CD2 | TYR | B | 171 | 48.060 | 28.792 | 18.680 | 1.00 | 4.90 |
| 7062 | C | TYR | B | 171 | 47.019 | 29.569 | 14.260 | 1.00 | 11.40 |
| 7063 | O | TYR | B | 171 | 46.227 | 28.637 | 13.791 | 1.00 | 12.52 |
| 7064 | N | LEU | B | 172 | 47.756 | 30.402 | 13.570 | 1.00 | 10.04 |
| 7065 | CA | LEU | B | 172 | 47.892 | 30.494 | 12.135 | 1.00 | 11.37 |
| 7066 | CB | LEU | B | 172 | 47.434 | 31.933 | 11.750 | 1.00 | 12.59 |
| 7067 | CG | LEU | B | 172 | 46.531 | 32.312 | 10.620 | 1.00 | 16.54 |
| 7068 | CD1 | LEU | B | 172 | 46.572 | 33.749 | 10.492 | 1.00 | 16.69 |
| 7069 | CD2 | LEU | B | 172 | 47.039 | 31.733 | 9.419 | 1.00 | 21.18 |
| 7070 | C | LEU | B | 172 | 49.327 | 30.346 | 11.634 | 1.00 | 8.78 |
| 7071 | O | LEU | B | 172 | 50.301 | 30.784 | 12.223 | 1.00 | 6.38 |
| 7072 | N | LYS | B | 173 | 49.391 | 29.786 | 10.470 | 1.00 | 9.86 |
| 7073 | CA | LYS | B | 173 | 50.609 | 29.400 | 9.833 | 1.00 | 12.89 |
| 7074 | CB | LYS | B | 173 | 50.849 | 27.897 | 10.094 | 1.00 | 10.92 |
| 7075 | CG | LYS | B | 173 | 52.326 | 27.546 | 10.460 | 1.00 | 13.49 |
| 7076 | CD | LYS | B | 173 | 52.403 | 26.300 | 11.376 | 1.00 | 11.10 |
| 7077 | CE | LYS | B | 173 | 53.714 | 25.631 | 11.401 | 1.00 | 13.39 |
| 7078 | NZ | LYS | B | 173 | 54.285 | 26.075 | 12.620 | 1.00 | 12.43 |
| 7079 | C | LYS | B | 173 | 50.343 | 29.650 | 8.336 | 1.00 | 13.25 |
| 7080 | O | LYS | B | 173 | 49.603 | 28.861 | 7.730 | 1.00 | 12.92 |

FIGURE 3 (Cont.)

| A | B | C | D | E | F | G | H | I | J |
|---|---|---|---|---|---|---|---|---|---|
| 7081 | N | GLN | B | 174 | 50.941 | 30.703 | 7.733 | 1.00 | 13.50 |
| 7082 | CA | GLN | B | 174 | 50.871 | 30.848 | 6.272 | 1.00 | 13.84 |
| 7083 | CB | GLN | B | 174 | 51.698 | 32.055 | 5.816 | 1.00 | 14.37 |
| 7084 | CG | GLN | B | 174 | 50.874 | 33.067 | 4.929 | 1.00 | 21.12 |
| 7085 | CD | GLN | B | 174 | 49.617 | 33.660 | 5.653 | 1.00 | 19.68 |
| 7086 | OE1 | GLN | B | 174 | 49.686 | 34.091 | 6.800 | 1.00 | 22.08 |
| 7087 | NE2 | GLN | B | 174 | 48.493 | 33.671 | 4.960 | 1.00 | 27.75 |
| 7088 | C | GLN | B | 174 | 51.317 | 29.607 | 5.480 | 1.00 | 12.97 |
| 7089 | O | GLN | B | 174 | 50.899 | 29.435 | 4.347 | 1.00 | 13.19 |
| 7090 | N | ARG | B | 175 | 52.147 | 28.737 | 6.081 | 1.00 | 13.28 |
| 7091 | CA | ARG | B | 175 | 52.936 | 27.763 | 5.344 | 1.00 | 15.46 |
| 7092 | CB | ARG | B | 175 | 53.919 | 28.497 | 4.374 | 1.00 | 15.57 |
| 7093 | CG | ARG | B | 175 | 55.133 | 27.766 | 3.966 | 1.00 | 19.81 |
| 7094 | CD | ARG | B | 175 | 55.961 | 28.346 | 2.727 | 1.00 | 30.00 |
| 7095 | NE | ARG | B | 175 | 55.119 | 28.262 | 1.512 | 1.00 | 38.74 |
| 7096 | CZ | ARG | B | 175 | 55.296 | 27.485 | 0.396 | 1.00 | 41.10 |
| 7097 | NH1 | ARG | B | 175 | 56.369 | 26.679 | 0.198 | 1.00 | 37.27 |
| 7098 | NH2 | ARG | B | 175 | 54.352 | 27.561 | -0.553 | 1.00 | 41.17 |
| 7099 | C | ARG | B | 175 | 53.692 | 26.881 | 6.365 | 1.00 | 16.59 |
| 7100 | O | ARG | B | 175 | 54.202 | 27.306 | 7.368 | 1.00 | 17.70 |
| 7101 | N | PRO | B | 176 | 53.757 | 25.613 | 6.141 | 1.00 | 17.61 |
| 7102 | CA | PRO | B | 176 | 54.092 | 24.730 | 7.234 | 1.00 | 18.89 |
| 7103 | CB | PRO | B | 176 | 54.055 | 23.395 | 6.550 | 1.00 | 20.56 |
| 7104 | CG | PRO | B | 176 | 53.031 | 23.636 | 5.417 | 1.00 | 17.68 |
| 7105 | CD | PRO | B | 176 | 53.486 | 24.885 | 4.901 | 1.00 | 18.21 |
| 7106 | C | PRO | B | 176 | 55.455 | 24.982 | 7.878 | 1.00 | 19.79 |
| 7107 | O | PRO | B | 176 | 55.648 | 25.193 | 9.076 | 1.00 | 20.88 |
| 7108 | N | GLY | B | 177 | 56.485 | 25.020 | 7.143 | 1.00 | 18.26 |
| 7109 | CA | GLY | B | 177 | 57.648 | 25.364 | 7.923 | 1.00 | 18.77 |
| 7110 | C | GLY | B | 177 | 57.627 | 26.641 | 8.781 | 1.00 | 18.53 |
| 7111 | O | GLY | B | 177 | 58.604 | 26.866 | 9.540 | 1.00 | 18.13 |
| 7112 | N | ASP | B | 178 | 56.617 | 27.522 | 8.599 | 1.00 | 17.17 |
| 7113 | CA | ASP | B | 178 | 56.648 | 28.852 | 9.222 | 1.00 | 17.59 |
| 7114 | CB | ASP | B | 178 | 55.718 | 29.834 | 8.560 | 1.00 | 17.43 |
| 7115 | CG | ASP | B | 178 | 56.211 | 30.331 | 7.176 | 1.00 | 22.63 |
| 7116 | OD1 | ASP | B | 178 | 57.403 | 30.215 | 6.801 | 1.00 | 24.36 |
| 7117 | OD2 | ASP | B | 178 | 55.450 | 30.862 | 6.359 | 1.00 | 27.17 |
| 7118 | C | ASP | B | 178 | 56.390 | 28.910 | 10.733 | 1.00 | 18.05 |
| 7119 | O | ASP | B | 178 | 55.820 | 28.016 | 11.340 | 1.00 | 20.49 |
| 7120 | N | PRO | B | 179 | 56.892 | 29.954 | 11.360 | 1.00 | 17.67 |
| 7121 | CA | PRO | B | 179 | 56.501 | 30.242 | 12.726 | 1.00 | 16.70 |
| 7122 | CB | PRO | B | 179 | 57.409 | 31.409 | 13.089 | 1.00 | 16.41 |
| 7123 | CG | PRO | B | 179 | 57.699 | 31.987 | 11.869 | 1.00 | 18.14 |
| 7124 | CD | PRO | B | 179 | 57.954 | 30.858 | 10.885 | 1.00 | 17.15 |
| 7125 | C | PRO | B | 179 | 55.057 | 30.657 | 12.823 | 1.00 | 15.25 |
| 7126 | O | PRO | B | 179 | 54.619 | 31.435 | 11.954 | 1.00 | 14.10 |
| 7127 | N | PRO | B | 180 | 54.382 | 30.330 | 13.930 | 1.00 | 14.99 |
| 7128 | CA | PRO | B | 180 | 52.990 | 30.606 | 14.062 | 1.00 | 15.42 |
| 7129 | CB | PRO | B | 180 | 52.509 | 29.527 | 15.023 | 1.00 | 15.34 |
| 7130 | CG | PRO | B | 180 | 53.706 | 29.047 | 15.809 | 1.00 | 14.24 |
| 7131 | CD | PRO | B | 180 | 54.918 | 29.818 | 15.201 | 1.00 | 16.23 |

FIGURE 3 (Cont.)

| A | B | C | D | E | F | G | H | I | J |
|---|---|---|---|---|---|---|---|---|---|
| 7132 | C | PRO | B | 180 | 52.667 | 32.043 | 14.582 | 1.00 | 15.00 |
| 7133 | O | PRO | B | 180 | 53.270 | 32.555 | 15.472 | 1.00 | 16.77 |
| 7134 | N | PHE | B | 181 | 51.717 | 32.675 | 13.935 | 1.00 | 13.50 |
| 7135 | CA | PHE | B | 181 | 51.087 | 33.896 | 14.390 | 1.00 | 13.48 |
| 7136 | CB | PHE | B | 181 | 50.417 | 34.599 | 13.212 | 1.00 | 13.84 |
| 7137 | CG | PHE | B | 181 | 49.942 | 35.852 | 13.554 | 1.00 | 11.72 |
| 7138 | CD1 | PHE | B | 181 | 48.624 | 36.014 | 13.930 | 1.00 | 13.12 |
| 7139 | CE1 | PHE | B | 181 | 48.138 | 37.303 | 14.305 | 1.00 | 14.81 |
| 7140 | CZ | PHE | B | 181 | 49.025 | 38.361 | 14.351 | 1.00 | 10.83 |
| 7141 | CE2 | PHE | B | 181 | 50.362 | 38.168 | 13.998 | 1.00 | 16.64 |
| 7142 | CD2 | PHE | B | 181 | 50.813 | 36.919 | 13.621 | 1.00 | 17.12 |
| 7143 | C | PHE | B | 181 | 50.007 | 33.515 | 15.381 | 1.00 | 14.13 |
| 7144 | O | PHE | B | 181 | 49.113 | 32.768 | 15.031 | 1.00 | 13.49 |
| 7145 | N | GLN | B | 182 | 50.089 | 34.056 | 16.592 | 1.00 | 12.61 |
| 7146 | CA | GLN | B | 182 | 49.107 | 33.743 | 17.564 | 1.00 | 10.41 |
| 7147 | CB | GLN | B | 182 | 49.633 | 33.900 | 18.996 | 1.00 | 9.52 |
| 7148 | CG | GLN | B | 182 | 48.680 | 33.159 | 19.974 | 1.00 | 7.59 |
| 7149 | CD | GLN | B | 182 | 49.139 | 33.192 | 21.437 | 1.00 | 13.14 |
| 7150 | OE1 | GLN | B | 182 | 50.148 | 33.820 | 21.787 | 1.00 | 14.25 |
| 7151 | NE2 | GLN | B | 182 | 48.382 | 32.531 | 22.274 | 1.00 | 7.46 |
| 7152 | C | GLN | B | 182 | 47.882 | 34.617 | 17.360 | 1.00 | 8.63 |
| 7153 | O | GLN | B | 182 | 48.053 | 35.768 | 17.325 | 1.00 | 6.86 |
| 7154 | N | ILE | B | 183 | 46.649 | 34.038 | 17.361 | 1.00 | 10.75 |
| 7155 | CA | ILE | B | 183 | 45.411 | 34.792 | 17.086 | 1.00 | 9.82 |
| 7156 | CB | ILE | B | 183 | 44.573 | 34.122 | 16.024 | 1.00 | 9.89 |
| 7157 | CG1 | ILE | B | 183 | 45.148 | 34.521 | 14.681 | 1.00 | 11.43 |
| 7158 | CD1 | ILE | B | 183 | 44.619 | 33.816 | 13.597 | 1.00 | 11.33 |
| 7159 | CG2 | ILE | B | 183 | 43.183 | 34.699 | 15.928 | 1.00 | 4.91 |
| 7160 | C | ILE | B | 183 | 44.647 | 35.110 | 18.300 | 1.00 | 11.34 |
| 7161 | O | ILE | B | 183 | 44.134 | 36.229 | 18.435 | 1.00 | 13.21 |
| 7162 | N | THR | B | 184 | 44.523 | 34.160 | 19.211 | 1.00 | 11.16 |
| 7163 | CA | THR | B | 184 | 43.826 | 34.425 | 20.514 | 1.00 | 10.37 |
| 7164 | CB | THR | B | 184 | 42.662 | 33.538 | 20.712 | 1.00 | 8.81 |
| 7165 | OG1 | THR | B | 184 | 43.066 | 32.152 | 20.840 | 1.00 | 10.31 |
| 7166 | CG2 | THR | B | 184 | 41.825 | 33.558 | 19.543 | 1.00 | 9.63 |
| 7167 | C | THR | B | 184 | 44.815 | 34.212 | 21.664 | 1.00 | 12.27 |
| 7168 | O | THR | B | 184 | 45.758 | 33.348 | 21.584 | 1.00 | 13.70 |
| 7169 | N | PHE | B | 185 | 44.642 | 34.983 | 22.738 | 1.00 | 14.02 |
| 7170 | CA | PHE | B | 185 | 45.570 | 34.865 | 23.851 | 1.00 | 16.31 |
| 7171 | CB | PHE | B | 185 | 46.365 | 36.152 | 24.012 | 1.00 | 18.03 |
| 7172 | CG | PHE | B | 185 | 47.012 | 36.635 | 22.762 | 1.00 | 21.36 |
| 7173 | CD1 | PHE | B | 185 | 46.302 | 37.448 | 21.877 | 1.00 | 21.58 |
| 7174 | CE1 | PHE | B | 185 | 46.874 | 37.931 | 20.747 | 1.00 | 20.77 |
| 7175 | CZ | PHE | B | 185 | 48.159 | 37.631 | 20.465 | 1.00 | 19.43 |
| 7176 | CE2 | PHE | B | 185 | 48.920 | 36.793 | 21.326 | 1.00 | 24.81 |
| 7177 | CD2 | PHE | B | 185 | 48.348 | 36.329 | 22.500 | 1.00 | 25.25 |
| 7178 | C | PHE | B | 185 | 44.948 | 34.589 | 25.192 | 1.00 | 17.33 |
| 7179 | O | PHE | B | 185 | 45.683 | 34.421 | 26.117 | 1.00 | 17.90 |
| 7180 | N | ASN | B | 186 | 43.619 | 34.543 | 25.306 | 1.00 | 16.52 |
| 7181 | CA | ASN | B | 186 | 42.937 | 34.370 | 26.576 | 1.00 | 16.11 |
| 7182 | CB | ASN | B | 186 | 41.771 | 35.371 | 26.679 | 1.00 | 13.56 |

FIGURE 3 (Cont.)

| A | B | C | D | E | F | G | H | I | J |
|---|---|---|---|---|---|---|---|---|---|
| 7183 | CG | ASN | B | 186 | 40.748 | 35.205 | 25.504 | 1.00 | 18.96 |
| 7184 | OD1 | ASN | B | 186 | 40.832 | 34.221 | 24.762 | 1.00 | 20.37 |
| 7185 | ND2 | ASN | B | 186 | 39.790 | 36.120 | 25.365 | 1.00 | 15.70 |
| 7186 | C | ASN | B | 186 | 42.418 | 32.952 | 26.759 | 1.00 | 16.99 |
| 7187 | O | ASN | B | 186 | 41.470 | 32.704 | 27.500 | 1.00 | 20.30 |
| 7188 | N | GLY | B | 187 | 43.009 | 31.974 | 26.131 | 1.00 | 15.66 |
| 7189 | CA | GLY | B | 187 | 42.502 | 30.645 | 26.378 | 1.00 | 15.47 |
| 7190 | C | GLY | B | 187 | 43.049 | 30.219 | 27.717 | 1.00 | 15.11 |
| 7191 | O | GLY | B | 187 | 44.127 | 30.533 | 27.985 | 1.00 | 14.14 |
| 7192 | N | ARG | B | 188 | 42.277 | 29.491 | 28.499 | 1.00 | 15.93 |
| 7193 | CA | ARG | B | 188 | 42.631 | 28.940 | 29.813 | 1.00 | 17.74 |
| 7194 | CB | ARG | B | 188 | 42.127 | 29.998 | 30.809 | 1.00 | 18.03 |
| 7195 | CG | ARG | B | 188 | 42.767 | 30.193 | 32.239 | 1.00 | 22.23 |
| 7196 | CD | ARG | B | 188 | 42.604 | 31.705 | 32.792 | 1.00 | 31.12 |
| 7197 | NE | ARG | B | 188 | 41.298 | 32.398 | 32.452 | 1.00 | 35.65 |
| 7198 | CZ | ARG | B | 188 | 40.194 | 32.470 | 33.294 | 1.00 | 39.26 |
| 7199 | NH1 | ARG | B | 188 | 40.288 | 31.908 | 34.520 | 1.00 | 44.06 |
| 7200 | NH2 | ARG | B | 188 | 39.007 | 33.073 | 32.948 | 1.00 | 32.47 |
| 7201 | C | ARG | B | 188 | 41.896 | 27.524 | 29.937 | 1.00 | 18.63 |
| 7202 | O | ARG | B | 188 | 40.692 | 27.452 | 29.593 | 1.00 | 17.42 |
| 7203 | N | GLU | B | 189 | 42.539 | 26.412 | 30.354 | 1.00 | 20.38 |
| 7204 | CA | GLU | B | 189 | 41.789 | 25.101 | 30.497 | 1.00 | 22.25 |
| 7205 | CB | GLU | B | 189 | 42.523 | 24.027 | 31.350 | 1.00 | 23.72 |
| 7206 | CG | GLU | B | 189 | 42.797 | 22.630 | 30.668 | 1.00 | 28.61 |
| 7207 | CD | GLU | B | 189 | 44.093 | 21.800 | 31.163 | 1.00 | 37.88 |
| 7208 | OE1 | GLU | B | 189 | 44.628 | 20.922 | 30.368 | 1.00 | 38.40 |
| 7209 | OE2 | GLU | B | 189 | 44.619 | 21.991 | 32.330 | 1.00 | 36.36 |
| 7210 | C | GLU | B | 189 | 40.461 | 25.401 | 31.172 | 1.00 | 23.25 |
| 7211 | O | GLU | B | 189 | 40.397 | 26.238 | 32.069 | 1.00 | 23.14 |
| 7212 | N | ASN | B | 190 | 39.410 | 24.695 | 30.765 | 1.00 | 23.54 |
| 7213 | CA | ASN | B | 190 | 38.033 | 24.926 | 31.237 | 1.00 | 24.51 |
| 7214 | CB | ASN | B | 190 | 37.544 | 23.969 | 32.375 | 1.00 | 25.54 |
| 7215 | CG | ASN | B | 190 | 38.435 | 22.780 | 32.625 | 1.00 | 28.77 |
| 7216 | OD1 | ASN | B | 190 | 39.184 | 22.342 | 31.754 | 1.00 | 33.94 |
| 7217 | ND2 | ASN | B | 190 | 38.328 | 22.216 | 33.853 | 1.00 | 30.44 |
| 7218 | C | ASN | B | 190 | 37.731 | 26.368 | 31.695 | 1.00 | 24.73 |
| 7219 | O | ASN | B | 190 | 37.120 | 26.589 | 32.765 | 1.00 | 27.99 |
| 7220 | N | LYS | B | 191 | 38.146 | 27.363 | 30.985 | 1.00 | 21.53 |
| 7221 | CA | LYS | B | 191 | 37.672 | 28.653 | 31.376 | 1.00 | 20.29 |
| 7222 | CB | LYS | B | 191 | 38.682 | 29.485 | 32.235 | 1.00 | 21.64 |
| 7223 | CG | LYS | B | 191 | 39.072 | 29.011 | 33.717 | 1.00 | 23.34 |
| 7224 | CD | LYS | B | 191 | 38.285 | 29.691 | 34.937 | 1.00 | 26.16 |
| 7225 | CE | LYS | B | 191 | 39.061 | 29.833 | 36.324 | 1.00 | 28.40 |
| 7226 | NZ | LYS | B | 191 | 38.422 | 30.985 | 37.147 | 1.00 | 28.10 |
| 7227 | C | LYS | B | 191 | 37.302 | 29.366 | 30.059 | 1.00 | 20.17 |
| 7228 | O | LYS | B | 191 | 36.154 | 29.737 | 29.866 | 1.00 | 19.38 |
| 7229 | N | ILE | B | 192 | 38.269 | 29.562 | 29.164 | 1.00 | 17.98 |
| 7230 | CA | ILE | B | 192 | 37.987 | 30.167 | 27.885 | 1.00 | 15.91 |
| 7231 | CB | ILE | B | 192 | 38.569 | 31.571 | 27.899 | 1.00 | 15.54 |
| 7232 | CG1 | ILE | B | 192 | 37.632 | 32.458 | 28.695 | 1.00 | 12.93 |
| 7233 | CD1 | ILE | B | 192 | 38.240 | 32.994 | 29.761 | 1.00 | 11.94 |

FIGURE 3 (Cont.)

| A | B | C | D | E | F | G | H | I | J |
|---|---|---|---|---|---|---|---|---|---|
| 7234 | CG2 | ILE | B | 192 | 38.694 | 32.130 | 26.591 | 1.00 | 14.47 |
| 7235 | C | ILE | B | 192 | 38.550 | 29.308 | 26.792 | 1.00 | 14.38 |
| 7236 | O | ILE | B | 192 | 39.749 | 28.825 | 26.881 | 1.00 | 12.71 |
| 7237 | N | PHE | B | 193 | 37.673 | 29.145 | 25.770 | 1.00 | 11.74 |
| 7238 | CA | PHE | B | 193 | 37.903 | 28.251 | 24.637 | 1.00 | 11.12 |
| 7239 | CB | PHE | B | 193 | 36.894 | 27.087 | 24.473 | 1.00 | 11.41 |
| 7240 | CG | PHE | B | 193 | 36.723 | 26.226 | 25.661 | 1.00 | 12.24 |
| 7241 | CD1 | PHE | B | 193 | 36.075 | 26.694 | 26.783 | 1.00 | 7.37 |
| 7242 | CE1 | PHE | B | 193 | 35.924 | 25.888 | 27.864 | 1.00 | 5.68 |
| 7243 | CZ | PHE | B | 193 | 36.399 | 24.517 | 27.836 | 1.00 | 5.58 |
| 7244 | CE2 | PHE | B | 193 | 37.009 | 24.041 | 26.759 | 1.00 | 8.69 |
| 7245 | CD2 | PHE | B | 193 | 37.152 | 24.875 | 25.638 | 1.00 | 15.54 |
| 7246 | C | PHE | B | 193 | 37.814 | 29.085 | 23.389 | 1.00 | 11.01 |
| 7247 | O | PHE | B | 193 | 36.699 | 29.543 | 23.045 | 1.00 | 12.14 |
| 7248 | N | ASN | B | 194 | 38.941 | 29.246 | 22.686 | 1.00 | 9.52 |
| 7249 | CA | ASN | B | 194 | 38.962 | 29.763 | 21.287 | 1.00 | 9.42 |
| 7250 | CB | ASN | B | 194 | 40.138 | 30.689 | 21.112 | 1.00 | 6.60 |
| 7251 | CG | ASN | B | 194 | 40.025 | 31.839 | 22.016 | 1.00 | 10.29 |
| 7252 | OD1 | ASN | B | 194 | 39.135 | 32.736 | 21.777 | 1.00 | 7.79 |
| 7253 | ND2 | ASN | B | 194 | 40.782 | 31.785 | 23.174 | 1.00 | 6.26 |
| 7254 | C | ASN | B | 194 | 38.993 | 28.759 | 20.175 | 1.00 | 9.64 |
| 7255 | O | ASN | B | 194 | 39.821 | 27.811 | 20.179 | 1.00 | 9.79 |
| 7256 | N | GLY | B | 195 | 38.047 | 28.842 | 19.268 | 1.00 | 8.20 |
| 7257 | CA | GLY | B | 195 | 38.042 | 27.866 | 18.176 | 1.00 | 9.32 |
| 7258 | C | GLY | B | 195 | 37.863 | 26.364 | 18.472 | 1.00 | 11.41 |
| 7259 | O | GLY | B | 195 | 38.114 | 25.568 | 17.578 | 1.00 | 10.28 |
| 7260 | N | ILE | B | 196 | 37.548 | 25.958 | 19.718 | 1.00 | 10.93 |
| 7261 | CA | ILE | B | 196 | 36.922 | 24.678 | 19.975 | 1.00 | 11.70 |
| 7262 | CB | ILE | B | 196 | 37.897 | 23.677 | 20.623 | 1.00 | 12.63 |
| 7263 | CG1 | ILE | B | 196 | 38.792 | 24.417 | 21.696 | 1.00 | 10.46 |
| 7264 | CD1 | ILE | B | 196 | 39.533 | 23.635 | 22.733 | 1.00 | 2.00 |
| 7265 | CG2 | ILE | B | 196 | 38.779 | 23.085 | 19.564 | 1.00 | 4.80 |
| 7266 | C | ILE | B | 196 | 35.734 | 25.018 | 20.893 | 1.00 | 13.65 |
| 7267 | O | ILE | B | 196 | 35.768 | 26.030 | 21.612 | 1.00 | 14.76 |
| 7268 | N | PRO | B | 197 | 34.764 | 24.155 | 20.950 | 1.00 | 12.81 |
| 7269 | CA | PRO | B | 197 | 33.614 | 24.360 | 21.803 | 1.00 | 14.25 |
| 7270 | CB | PRO | B | 197 | 32.591 | 23.342 | 21.225 | 1.00 | 14.47 |
| 7271 | CG | PRO | B | 197 | 33.468 | 22.149 | 20.699 | 1.00 | 14.69 |
| 7272 | CD | PRO | B | 197 | 34.689 | 22.867 | 20.249 | 1.00 | 12.31 |
| 7273 | C | PRO | B | 197 | 33.990 | 23.917 | 23.181 | 1.00 | 13.04 |
| 7274 | O | PRO | B | 197 | 34.957 | 23.295 | 23.308 | 1.00 | 16.45 |
| 7275 | N | ASP | B | 198 | 33.213 | 24.245 | 24.197 | 1.00 | 12.80 |
| 7276 | CA | ASP | B | 198 | 33.391 | 23.756 | 25.564 | 1.00 | 11.15 |
| 7277 | CB | ASP | B | 198 | 32.909 | 24.769 | 26.540 | 1.00 | 11.71 |
| 7278 | CG | ASP | B | 198 | 31.419 | 25.085 | 26.353 | 1.00 | 14.01 |
| 7279 | OD1 | ASP | B | 198 | 30.873 | 25.895 | 27.149 | 1.00 | 20.69 |
| 7280 | OD2 | ASP | B | 198 | 30.741 | 24.556 | 25.437 | 1.00 | 16.07 |
| 7281 | C | ASP | B | 198 | 32.480 | 22.590 | 25.638 | 1.00 | 11.52 |
| 7282 | O | ASP | B | 198 | 32.082 | 22.060 | 24.586 | 1.00 | 13.72 |
| 7283 | N | TRP | B | 199 | 32.113 | 22.156 | 26.814 | 1.00 | 9.67 |
| 7284 | CA | TRP | B | 199 | 31.597 | 20.818 | 26.885 | 1.00 | 11.29 |

FIGURE 3 (Cont.)

| A | B | C | D | E | F | G | H | I | J |
|---|---|---|---|---|---|---|---|---|---|
| 7285 | CB | TRP | B | 199 | 31.358 | 20.303 | 28.322 | 1.00 | 11.25 |
| 7286 | CG | TRP | B | 199 | 30.917 | 18.814 | 28.276 | 1.00 | 9.38 |
| 7287 | CD1 | TRP | B | 199 | 31.737 | 17.754 | 28.300 | 1.00 | 12.12 |
| 7288 | NE1 | TRP | B | 199 | 31.020 | 16.596 | 28.209 | 1.00 | 10.66 |
| 7289 | CE2 | TRP | B | 199 | 29.709 | 16.916 | 28.065 | 1.00 | 10.14 |
| 7290 | CD2 | TRP | B | 199 | 29.615 | 18.310 | 28.124 | 1.00 | 9.60 |
| 7291 | CE3 | TRP | B | 199 | 28.344 | 18.894 | 28.045 | 1.00 | 6.19 |
| 7292 | CZ3 | TRP | B | 199 | 27.250 | 18.092 | 27.928 | 1.00 | 2.42 |
| 7293 | CH2 | TRP | B | 199 | 27.350 | 16.736 | 27.903 | 1.00 | 8.79 |
| 7294 | CZ2 | TRP | B | 199 | 28.574 | 16.087 | 28.006 | 1.00 | 7.10 |
| 7295 | C | TRP | B | 199 | 30.278 | 20.750 | 26.185 | 1.00 | 11.23 |
| 7296 | O | TRP | B | 199 | 30.072 | 19.909 | 25.316 | 1.00 | 11.57 |
| 7297 | N | VAL | B | 200 | 29.415 | 21.680 | 26.553 | 1.00 | 11.15 |
| 7298 | CA | VAL | B | 200 | 27.987 | 21.572 | 26.132 | 1.00 | 12.26 |
| 7299 | CB | VAL | B | 200 | 27.070 | 22.375 | 27.085 | 1.00 | 11.30 |
| 7300 | CG1 | VAL | B | 200 | 27.528 | 23.956 | 27.197 | 1.00 | 10.98 |
| 7301 | CG2 | VAL | B | 200 | 25.694 | 22.215 | 26.719 | 1.00 | 14.13 |
| 7302 | C | VAL | B | 200 | 27.757 | 21.952 | 24.699 | 1.00 | 12.21 |
| 7303 | O | VAL | B | 200 | 26.907 | 21.381 | 23.985 | 1.00 | 12.39 |
| 7304 | N | TYR | B | 201 | 28.541 | 22.892 | 24.227 | 1.00 | 11.85 |
| 7305 | CA | TYR | B | 201 | 28.437 | 23.192 | 22.779 | 1.00 | 11.90 |
| 7306 | CB | TYR | B | 201 | 29.105 | 24.457 | 22.432 | 1.00 | 11.04 |
| 7307 | CG | TYR | B | 201 | 28.276 | 25.735 | 22.546 | 1.00 | 14.36 |
| 7308 | CD1 | TYR | B | 201 | 28.201 | 26.458 | 23.706 | 1.00 | 16.01 |
| 7309 | CE1 | TYR | B | 201 | 27.535 | 27.680 | 23.755 | 1.00 | 17.27 |
| 7310 | CZ | TYR | B | 201 | 26.963 | 28.176 | 22.625 | 1.00 | 16.51 |
| 7311 | OH | TYR | B | 201 | 26.334 | 29.383 | 22.578 | 1.00 | 13.52 |
| 7312 | CE2 | TYR | B | 201 | 27.055 | 27.509 | 21.468 | 1.00 | 17.71 |
| 7313 | CD2 | TYR | B | 201 | 27.738 | 26.314 | 21.411 | 1.00 | 18.42 |
| 7314 | C | TYR | B | 201 | 28.996 | 22.083 | 21.930 | 1.00 | 10.85 |
| 7315 | O | TYR | B | 201 | 28.516 | 21.826 | 20.875 | 1.00 | 9.65 |
| 7316 | N | GLU | B | 202 | 29.996 | 21.384 | 22.390 | 1.00 | 13.32 |
| 7317 | CA | GLU | B | 202 | 30.394 | 20.159 | 21.658 | 1.00 | 12.96 |
| 7318 | CB | GLU | B | 202 | 31.606 | 19.504 | 22.303 | 1.00 | 13.20 |
| 7319 | CG | GLU | B | 202 | 32.131 | 18.275 | 21.637 | 1.00 | 9.48 |
| 7320 | CD | GLU | B | 202 | 33.351 | 17.721 | 22.273 | 1.00 | 15.34 |
| 7321 | OE1 | GLU | B | 202 | 33.526 | 16.507 | 22.082 | 1.00 | 24.76 |
| 7322 | OE2 | GLU | B | 202 | 34.145 | 18.431 | 22.993 | 1.00 | 18.89 |
| 7323 | C | GLU | B | 202 | 29.291 | 19.142 | 21.620 | 1.00 | 14.10 |
| 7324 | O | GLU | B | 202 | 28.949 | 18.639 | 20.601 | 1.00 | 15.25 |
| 7325 | N | GLU | B | 203 | 28.730 | 18.771 | 22.743 | 1.00 | 15.48 |
| 7326 | CA | GLU | B | 203 | 27.800 | 17.653 | 22.720 | 1.00 | 15.64 |
| 7327 | CB | GLU | B | 203 | 27.785 | 17.105 | 24.094 | 1.00 | 16.52 |
| 7328 | CG | GLU | B | 203 | 26.804 | 15.953 | 24.423 | 1.00 | 19.63 |
| 7329 | CD | GLU | B | 203 | 26.880 | 14.800 | 23.502 | 1.00 | 15.91 |
| 7330 | OE1 | GLU | B | 203 | 27.965 | 14.498 | 23.084 | 1.00 | 22.64 |
| 7331 | OE2 | GLU | B | 203 | 25.854 | 14.222 | 23.197 | 1.00 | 16.14 |
| 7332 | C | GLU | B | 203 | 26.394 | 18.071 | 22.283 | 1.00 | 16.67 |
| 7333 | O | GLU | B | 203 | 25.607 | 17.221 | 21.820 | 1.00 | 17.12 |
| 7334 | N | GLU | B | 204 | 26.027 | 19.359 | 22.453 | 1.00 | 15.81 |
| 7335 | CA | GLU | B | 204 | 24.608 | 19.682 | 22.354 | 1.00 | 17.29 |

FIGURE 3 (Cont.)

| A | B | C | D | E | F | G | H | I | J |
|---|---|---|---|---|---|---|---|---|---|
| 7336 | CB | GLU | B | 204 | 24.003 | 20.103 | 23.747 | 1.00 | 16.58 |
| 7337 | CG | GLU | B | 204 | 24.383 | 19.157 | 24.912 | 1.00 | 18.47 |
| 7338 | CD | GLU | B | 204 | 23.555 | 17.895 | 24.946 | 1.00 | 20.77 |
| 7339 | OE1 | GLU | B | 204 | 23.750 | 17.116 | 25.937 | 1.00 | 20.77 |
| 7340 | OE2 | GLU | B | 204 | 22.696 | 17.689 | 24.034 | 1.00 | 19.42 |
| 7341 | C | GLU | B | 204 | 24.248 | 20.702 | 21.305 | 1.00 | 17.77 |
| 7342 | O | GLU | B | 204 | 23.009 | 20.788 | 20.957 | 1.00 | 19.00 |
| 7343 | N | MET | B | 205 | 25.231 | 21.528 | 20.846 | 1.00 | 15.98 |
| 7344 | CA | MET | B | 205 | 24.958 | 22.453 | 19.728 | 1.00 | 16.89 |
| 7345 | CB | MET | B | 205 | 25.285 | 23.909 | 20.146 | 1.00 | 17.01 |
| 7346 | CG | MET | B | 205 | 24.684 | 24.926 | 19.255 | 1.00 | 9.81 |
| 7347 | SD | MET | B | 205 | 22.916 | 25.001 | 19.380 | 1.00 | 11.59 |
| 7348 | CE | MET | B | 205 | 22.776 | 25.333 | 21.108 | 1.00 | 7.99 |
| 7349 | C | MET | B | 205 | 25.664 | 22.097 | 18.432 | 1.00 | 17.30 |
| 7350 | O | MET | B | 205 | 25.040 | 21.966 | 17.386 | 1.00 | 20.29 |
| 7351 | N | LEU | B | 206 | 26.971 | 21.974 | 18.488 | 1.00 | 17.59 |
| 7352 | CA | LEU | B | 206 | 27.733 | 21.872 | 17.286 | 1.00 | 17.35 |
| 7353 | CB | LEU | B | 206 | 29.082 | 22.578 | 17.439 | 1.00 | 16.13 |
| 7354 | CG | LEU | B | 206 | 28.986 | 24.034 | 17.923 | 1.00 | 14.05 |
| 7355 | CD1 | LEU | B | 206 | 30.354 | 24.631 | 18.151 | 1.00 | 14.30 |
| 7356 | CD2 | LEU | B | 206 | 28.325 | 24.923 | 17.000 | 1.00 | 12.85 |
| 7357 | C | LEU | B | 206 | 27.969 | 20.412 | 16.901 | 1.00 | 17.07 |
| 7358 | O | LEU | B | 206 | 28.015 | 20.090 | 15.749 | 1.00 | 17.92 |
| 7359 | N | ALA | B | 207 | 28.145 | 19.526 | 17.826 | 1.00 | 15.77 |
| 7360 | CA | ALA | B | 207 | 28.294 | 18.145 | 17.392 | 1.00 | 16.24 |
| 7361 | CB | ALA | B | 207 | 27.038 | 17.649 | 16.632 | 1.00 | 13.08 |
| 7362 | C | ALA | B | 207 | 29.592 | 17.974 | 16.550 | 1.00 | 16.00 |
| 7363 | O | ALA | B | 207 | 29.694 | 17.090 | 15.681 | 1.00 | 17.55 |
| 7364 | N | THR | B | 208 | 30.532 | 18.873 | 16.816 | 1.00 | 16.63 |
| 7365 | CA | THR | B | 208 | 31.852 | 18.867 | 16.275 | 1.00 | 17.42 |
| 7366 | CB | THR | B | 208 | 32.112 | 19.999 | 15.299 | 1.00 | 17.29 |
| 7367 | OG1 | THR | B | 208 | 31.923 | 21.250 | 15.972 | 1.00 | 25.80 |
| 7368 | CG2 | THR | B | 208 | 31.236 | 19.990 | 14.181 | 1.00 | 17.32 |
| 7369 | C | THR | B | 208 | 32.895 | 19.146 | 17.316 | 1.00 | 15.69 |
| 7370 | O | THR | B | 208 | 32.624 | 19.640 | 18.389 | 1.00 | 14.30 |
| 7371 | N | LYS | B | 209 | 34.124 | 18.933 | 16.935 | 1.00 | 16.46 |
| 7372 | CA | LYS | B | 209 | 35.249 | 19.151 | 17.869 | 1.00 | 15.00 |
| 7373 | CB | LYS | B | 209 | 36.268 | 18.086 | 17.713 | 1.00 | 15.41 |
| 7374 | CG | LYS | B | 209 | 37.245 | 18.238 | 16.536 | 1.00 | 13.34 |
| 7375 | CD | LYS | B | 209 | 38.363 | 17.078 | 16.631 | 1.00 | 12.35 |
| 7376 | CE | LYS | B | 209 | 39.663 | 17.599 | 17.288 | 1.00 | 5.52 |
| 7377 | NZ | LYS | B | 209 | 40.828 | 16.636 | 17.316 | 1.00 | 2.86 |
| 7378 | C | LYS | B | 209 | 35.828 | 20.482 | 17.572 | 1.00 | 15.28 |
| 7379 | O | LYS | B | 209 | 36.804 | 20.874 | 18.147 | 1.00 | 13.37 |
| 7380 | N | TYR | B | 210 | 35.177 | 21.241 | 16.712 | 1.00 | 13.17 |
| 7381 | CA | TYR | B | 210 | 35.816 | 22.525 | 16.328 | 1.00 | 12.58 |
| 7382 | CB | TYR | B | 210 | 36.472 | 22.408 | 14.974 | 1.00 | 15.50 |
| 7383 | CG | TYR | B | 210 | 35.505 | 22.047 | 13.861 | 1.00 | 13.98 |
| 7384 | CD1 | TYR | B | 210 | 35.245 | 20.724 | 13.572 | 1.00 | 17.53 |
| 7385 | CE1 | TYR | B | 210 | 34.310 | 20.368 | 12.652 | 1.00 | 17.21 |
| 7386 | CZ | TYR | B | 210 | 33.690 | 21.293 | 11.950 | 1.00 | 19.77 |

FIGURE 3 (Cont.)

| A | B | C | D | E | F | G | H | I | J |
|---|---|---|---|---|---|---|---|---|---|
| 7387 | OH | TYR | B | 210 | 32.835 | 20.858 | 10.974 | 1.00 | 24.77 |
| 7388 | CE2 | TYR | B | 210 | 33.963 | 22.637 | 12.146 | 1.00 | 18.92 |
| 7389 | CD2 | TYR | B | 210 | 34.904 | 23.007 | 13.087 | 1.00 | 11.03 |
| 7390 | C | TYR | B | 210 | 34.820 | 23.580 | 16.263 | 1.00 | 14.09 |
| 7391 | O | TYR | B | 210 | 33.564 | 23.286 | 16.198 | 1.00 | 11.90 |
| 7392 | N | ALA | B | 211 | 35.349 | 24.800 | 16.302 | 1.00 | 13.03 |
| 7393 | CA | ALA | B | 211 | 34.577 | 26.020 | 16.112 | 1.00 | 13.14 |
| 7394 | CB | ALA | B | 211 | 34.104 | 26.514 | 17.453 | 1.00 | 12.31 |
| 7395 | C | ALA | B | 211 | 35.399 | 27.154 | 15.495 | 1.00 | 15.33 |
| 7396 | O | ALA | B | 211 | 35.476 | 28.283 | 16.045 | 1.00 | 16.70 |
| 7397 | N | LEU | B | 212 | 35.999 | 26.901 | 14.346 | 1.00 | 14.20 |
| 7398 | CA | LEU | B | 212 | 36.622 | 27.962 | 13.569 | 1.00 | 12.72 |
| 7399 | CB | LEU | B | 212 | 38.127 | 28.124 | 13.954 | 1.00 | 13.40 |
| 7400 | CG | LEU | B | 212 | 39.059 | 26.914 | 14.032 | 1.00 | 9.24 |
| 7401 | CD1 | LEU | B | 212 | 39.501 | 26.407 | 12.715 | 1.00 | 19.87 |
| 7402 | CD2 | LEU | B | 212 | 40.279 | 27.185 | 14.715 | 1.00 | 16.66 |
| 7403 | C | LEU | B | 212 | 36.380 | 27.428 | 12.155 | 1.00 | 13.55 |
| 7404 | O | LEU | B | 212 | 36.274 | 26.310 | 11.919 | 1.00 | 14.26 |
| 7405 | N | TRP | B | 213 | 36.137 | 28.294 | 11.232 | 1.00 | 16.08 |
| 7406 | CA | TRP | B | 213 | 35.699 | 28.024 | 9.867 | 1.00 | 13.82 |
| 7407 | CB | TRP | B | 213 | 34.258 | 28.319 | 9.739 | 1.00 | 13.43 |
| 7408 | CG | TRP | B | 213 | 33.435 | 27.519 | 10.642 | 1.00 | 16.88 |
| 7409 | CD1 | TRP | B | 213 | 32.875 | 26.280 | 10.364 | 1.00 | 16.27 |
| 7410 | NE1 | TRP | B | 213 | 32.197 | 25.829 | 11.464 | 1.00 | 18.00 |
| 7411 | CE2 | TRP | B | 213 | 32.261 | 26.768 | 12.468 | 1.00 | 16.97 |
| 7412 | CD2 | TRP | B | 213 | 33.021 | 27.853 | 11.986 | 1.00 | 18.20 |
| 7413 | CE3 | TRP | B | 213 | 33.281 | 28.911 | 12.844 | 1.00 | 14.65 |
| 7414 | CZ3 | TRP | B | 213 | 32.754 | 28.890 | 14.054 | 1.00 | 16.46 |
| 7415 | CH2 | TRP | B | 213 | 32.013 | 27.817 | 14.515 | 1.00 | 13.06 |
| 7416 | CZ2 | TRP | B | 213 | 31.714 | 26.753 | 13.705 | 1.00 | 10.46 |
| 7417 | C | TRP | B | 213 | 36.408 | 29.037 | 9.032 | 1.00 | 12.82 |
| 7418 | O | TRP | B | 213 | 36.203 | 30.176 | 9.259 | 1.00 | 12.43 |
| 7419 | N | TRP | B | 214 | 37.246 | 28.542 | 8.137 | 1.00 | 12.05 |
| 7420 | CA | TRP | B | 214 | 37.841 | 29.260 | 7.014 | 1.00 | 11.35 |
| 7421 | CB | TRP | B | 214 | 38.927 | 28.476 | 6.289 | 1.00 | 8.14 |
| 7422 | CG | TRP | B | 214 | 40.127 | 28.147 | 7.020 | 1.00 | 12.36 |
| 7423 | CD1 | TRP | B | 214 | 40.323 | 27.040 | 7.695 | 1.00 | 12.73 |
| 7424 | NE1 | TRP | B | 214 | 41.604 | 27.019 | 8.192 | 1.00 | 14.99 |
| 7425 | CE2 | TRP | B | 214 | 42.265 | 28.154 | 7.792 | 1.00 | 7.72 |
| 7426 | CD2 | TRP | B | 214 | 41.418 | 28.853 | 7.019 | 1.00 | 8.24 |
| 7427 | CE3 | TRP | B | 214 | 41.863 | 30.034 | 6.497 | 1.00 | 12.20 |
| 7428 | CZ3 | TRP | B | 214 | 43.148 | 30.448 | 6.717 | 1.00 | 8.74 |
| 7429 | CH2 | TRP | B | 214 | 43.992 | 29.726 | 7.473 | 1.00 | 5.89 |
| 7430 | CZ2 | TRP | B | 214 | 43.570 | 28.563 | 8.031 | 1.00 | 13.51 |
| 7431 | C | TRP | B | 214 | 36.811 | 29.685 | 6.001 | 1.00 | 11.56 |
| 7432 | O | TRP | B | 214 | 35.824 | 28.943 | 5.716 | 1.00 | 14.92 |
| 7433 | N | SER | B | 215 | 37.050 | 30.886 | 5.440 | 1.00 | 10.14 |
| 7434 | CA | SER | B | 215 | 36.145 | 31.449 | 4.439 | 1.00 | 9.89 |
| 7435 | CB | SER | B | 215 | 36.338 | 32.920 | 4.274 | 1.00 | 9.23 |
| 7436 | OG | SER | B | 215 | 37.573 | 33.260 | 3.784 | 1.00 | 9.21 |
| 7437 | C | SER | B | 215 | 36.629 | 30.740 | 3.239 | 1.00 | 8.69 |

FIGURE 3 (Cont.)

| A | B | C | D | E | F | G | H | I | J |
|---|---|---|---|---|---|---|---|---|---|
| 7438 | O | SER | B | 215 | 37.642 | 30.075 | 3.356 | 1.00 | 5.90 |
| 7439 | N | PRO | B | 216 | 35.807 | 30.694 | 2.193 | 1.00 | 10.53 |
| 7440 | CA | PRO | B | 216 | 36.001 | 29.804 | 1.017 | 1.00 | 10.54 |
| 7441 | CB | PRO | B | 216 | 34.878 | 30.293 | 0.053 | 1.00 | 12.23 |
| 7442 | CG | PRO | B | 216 | 33.755 | 30.710 | 0.924 | 1.00 | 8.08 |
| 7443 | CD | PRO | B | 216 | 34.396 | 31.187 | 2.223 | 1.00 | 8.79 |
| 7444 | C | PRO | B | 216 | 37.345 | 29.644 | 0.337 | 1.00 | 14.07 |
| 7445 | O | PRO | B | 216 | 37.802 | 28.516 | -0.100 | 1.00 | 13.58 |
| 7446 | N | ASN | B | 217 | 37.997 | 30.806 | 0.290 | 1.00 | 14.23 |
| 7447 | CA | ASN | B | 217 | 39.255 | 30.945 | -0.362 | 1.00 | 15.93 |
| 7448 | CB | ASN | B | 217 | 39.152 | 32.038 | -1.522 | 1.00 | 15.91 |
| 7449 | CG | ASN | B | 217 | 38.222 | 31.579 | -2.719 | 1.00 | 18.86 |
| 7450 | OD1 | ASN | B | 217 | 36.962 | 31.987 | -2.888 | 1.00 | 13.16 |
| 7451 | ND2 | ASN | B | 217 | 38.816 | 30.708 | -3.553 | 1.00 | 17.60 |
| 7452 | C | ASN | B | 217 | 40.352 | 31.276 | 0.667 | 1.00 | 14.94 |
| 7453 | O | ASN | B | 217 | 41.323 | 31.864 | 0.307 | 1.00 | 13.84 |
| 7454 | N | GLY | B | 218 | 40.214 | 30.902 | 1.930 | 1.00 | 13.58 |
| 7455 | CA | GLY | B | 218 | 41.207 | 31.380 | 2.897 | 1.00 | 11.00 |
| 7456 | C | GLY | B | 218 | 41.195 | 32.898 | 3.225 | 1.00 | 9.56 |
| 7457 | O | GLY | B | 218 | 41.944 | 33.322 | 4.118 | 1.00 | 10.32 |
| 7458 | N | LYS | B | 219 | 40.387 | 33.787 | 2.664 | 1.00 | 5.90 |
| 7459 | CA | LYS | B | 219 | 40.640 | 35.157 | 3.202 | 1.00 | 6.21 |
| 7460 | CB | LYS | B | 219 | 40.387 | 36.294 | 2.228 | 1.00 | 6.57 |
| 7461 | CG | LYS | B | 219 | 39.364 | 37.119 | 2.515 | 1.00 | 13.85 |
| 7462 | CD | LYS | B | 219 | 39.248 | 38.329 | 1.505 | 1.00 | 22.24 |
| 7463 | CE | LYS | B | 219 | 39.655 | 39.699 | 2.085 | 1.00 | 23.16 |
| 7464 | NZ | LYS | B | 219 | 41.106 | 39.926 | 1.773 | 1.00 | 29.07 |
| 7465 | C | LYS | B | 219 | 40.454 | 35.471 | 4.670 | 1.00 | 6.39 |
| 7466 | O | LYS | B | 219 | 41.231 | 36.233 | 5.290 | 1.00 | 4.85 |
| 7467 | N | PHE | B | 220 | 39.533 | 34.749 | 5.321 | 1.00 | 7.95 |
| 7468 | CA | PHE | B | 220 | 39.253 | 35.006 | 6.712 | 1.00 | 7.65 |
| 7469 | CB | PHE | B | 220 | 38.054 | 35.837 | 6.892 | 1.00 | 6.53 |
| 7470 | CG | PHE | B | 220 | 37.954 | 37.135 | 6.077 | 1.00 | 11.23 |
| 7471 | CD1 | PHE | B | 220 | 38.154 | 38.373 | 6.693 | 1.00 | 11.19 |
| 7472 | CE1 | PHE | B | 220 | 37.882 | 39.620 | 6.062 | 1.00 | 6.16 |
| 7473 | CZ | PHE | B | 220 | 37.363 | 39.644 | 4.824 | 1.00 | 5.18 |
| 7474 | CE2 | PHE | B | 220 | 37.149 | 38.432 | 4.200 | 1.00 | 16.09 |
| 7475 | CD2 | PHE | B | 220 | 37.411 | 37.149 | 4.880 | 1.00 | 11.90 |
| 7476 | C | PHE | B | 220 | 39.024 | 33.765 | 7.515 | 1.00 | 9.52 |
| 7477 | O | PHE | B | 220 | 38.754 | 32.655 | 6.944 | 1.00 | 11.61 |
| 7478 | N | LEU | B | 221 | 39.138 | 33.909 | 8.851 | 1.00 | 9.54 |
| 7479 | CA | LEU | B | 221 | 38.895 | 32.795 | 9.740 | 1.00 | 10.89 |
| 7480 | CB | LEU | B | 221 | 40.188 | 32.254 | 10.305 | 1.00 | 12.70 |
| 7481 | CG | LEU | B | 221 | 40.193 | 31.058 | 11.222 | 1.00 | 15.55 |
| 7482 | CD1 | LEU | B | 221 | 39.901 | 29.796 | 10.494 | 1.00 | 13.85 |
| 7483 | CD2 | LEU | B | 221 | 41.546 | 30.883 | 11.782 | 1.00 | 17.02 |
| 7484 | C | LEU | B | 221 | 38.014 | 33.299 | 10.794 | 1.00 | 11.91 |
| 7485 | O | LEU | B | 221 | 38.240 | 34.330 | 11.339 | 1.00 | 12.00 |
| 7486 | N | ALA | B | 222 | 36.863 | 32.639 | 10.907 | 1.00 | 13.27 |
| 7487 | CA | ALA | B | 222 | 35.775 | 33.022 | 11.811 | 1.00 | 13.11 |
| 7488 | CB | ALA | B | 222 | 34.552 | 32.865 | 11.154 | 1.00 | 13.36 |

FIGURE 3 (Cont.)

| A | B | C | D | E | F | G | H | I | J |
|---|---|---|---|---|---|---|---|---|---|
| 7489 | C | ALA | B | 222 | 35.930 | 31.980 | 12.908 | 1.00 | 13.37 |
| 7490 | O | ALA | B | 222 | 36.508 | 30.883 | 12.620 | 1.00 | 11.27 |
| 7491 | N | TYR | B | 223 | 35.591 | 32.325 | 14.156 | 1.00 | 10.78 |
| 7492 | CA | TYR | B | 223 | 36.045 | 31.425 | 15.279 | 1.00 | 10.19 |
| 7493 | CB | TYR | B | 223 | 37.530 | 31.532 | 15.627 | 1.00 | 12.19 |
| 7494 | CG | TYR | B | 223 | 38.147 | 32.898 | 16.121 | 1.00 | 12.43 |
| 7495 | CD1 | TYR | B | 223 | 37.989 | 33.333 | 17.440 | 1.00 | 12.99 |
| 7496 | CE1 | TYR | B | 223 | 38.545 | 34.485 | 17.888 | 1.00 | 9.74 |
| 7497 | CZ | TYR | B | 223 | 39.290 | 35.302 | 17.003 | 1.00 | 14.42 |
| 7498 | OH | TYR | B | 223 | 39.819 | 36.505 | 17.444 | 1.00 | 13.34 |
| 7499 | CE2 | TYR | B | 223 | 39.464 | 34.913 | 15.741 | 1.00 | 11.93 |
| 7500 | CD2 | TYR | B | 223 | 38.891 | 33.672 | 15.313 | 1.00 | 13.55 |
| 7501 | C | TYR | B | 223 | 35.153 | 31.766 | 16.375 | 1.00 | 10.77 |
| 7502 | O | TYR | B | 223 | 34.659 | 32.902 | 16.375 | 1.00 | 10.75 |
| 7503 | N | ALA | B | 224 | 34.788 | 30.790 | 17.213 | 1.00 | 7.65 |
| 7504 | CA | ALA | B | 224 | 33.985 | 31.184 | 18.347 | 1.00 | 8.97 |
| 7505 | CB | ALA | B | 224 | 32.923 | 30.098 | 18.686 | 1.00 | 7.48 |
| 7506 | C | ALA | B | 224 | 34.877 | 31.395 | 19.533 | 1.00 | 10.81 |
| 7507 | O | ALA | B | 224 | 35.861 | 30.735 | 19.649 | 1.00 | 12.12 |
| 7508 | N | GLU | B | 225 | 34.521 | 32.232 | 20.477 | 1.00 | 9.22 |
| 7509 | CA | GLU | B | 225 | 35.173 | 32.149 | 21.778 | 1.00 | 10.35 |
| 7510 | CB | GLU | B | 225 | 35.993 | 33.322 | 22.074 | 1.00 | 10.51 |
| 7511 | CG | GLU | B | 225 | 36.180 | 33.597 | 23.515 | 1.00 | 12.73 |
| 7512 | CD | GLU | B | 225 | 36.205 | 35.132 | 23.795 | 1.00 | 15.27 |
| 7513 | OE1 | GLU | B | 225 | 37.253 | 35.752 | 23.721 | 1.00 | 6.97 |
| 7514 | OE2 | GLU | B | 225 | 35.162 | 35.728 | 24.079 | 1.00 | 21.39 |
| 7515 | C | GLU | B | 225 | 34.090 | 31.961 | 22.872 | 1.00 | 11.41 |
| 7516 | O | GLU | B | 225 | 33.173 | 32.783 | 23.077 | 1.00 | 11.47 |
| 7517 | N | PHE | B | 226 | 34.223 | 30.816 | 23.543 | 1.00 | 10.95 |
| 7518 | CA | PHE | B | 226 | 33.398 | 30.458 | 24.678 | 1.00 | 9.16 |
| 7519 | CB | PHE | B | 226 | 33.135 | 28.998 | 24.531 | 1.00 | 7.87 |
| 7520 | CG | PHE | B | 226 | 32.551 | 28.603 | 23.219 | 1.00 | 5.34 |
| 7521 | CD1 | PHE | B | 226 | 31.241 | 28.570 | 23.061 | 1.00 | 6.13 |
| 7522 | CE1 | PHE | B | 226 | 30.721 | 28.157 | 21.929 | 1.00 | 6.20 |
| 7523 | CZ | PHE | B | 226 | 31.479 | 27.749 | 20.942 | 1.00 | 7.43 |
| 7524 | CE2 | PHE | B | 226 | 32.798 | 27.664 | 21.107 | 1.00 | 7.42 |
| 7525 | CD2 | PHE | B | 226 | 33.334 | 28.049 | 22.246 | 1.00 | 7.23 |
| 7526 | C | PHE | B | 226 | 34.020 | 30.702 | 26.075 | 1.00 | 9.54 |
| 7527 | O | PHE | B | 226 | 35.127 | 30.148 | 26.418 | 1.00 | 10.21 |
| 7528 | N | ASN | B | 227 | 33.283 | 31.444 | 26.883 | 1.00 | 7.73 |
| 7529 | CA | ASN | B | 227 | 33.609 | 31.787 | 28.280 | 1.00 | 10.20 |
| 7530 | CB | ASN | B | 227 | 33.415 | 33.372 | 28.534 | 1.00 | 10.48 |
| 7531 | CG | ASN | B | 227 | 34.026 | 33.864 | 29.857 | 1.00 | 15.18 |
| 7532 | OD1 | ASN | B | 227 | 34.054 | 33.045 | 30.776 | 1.00 | 18.42 |
| 7533 | ND2 | ASN | B | 227 | 34.511 | 35.200 | 29.986 | 1.00 | 22.10 |
| 7534 | C | ASN | B | 227 | 32.766 | 30.863 | 29.212 | 1.00 | 10.48 |
| 7535 | O | ASN | B | 227 | 31.587 | 30.973 | 29.314 | 1.00 | 8.56 |
| 7536 | N | ASP | B | 228 | 33.387 | 29.917 | 29.863 | 1.00 | 11.27 |
| 7537 | CA | ASP | B | 228 | 32.728 | 29.048 | 30.831 | 1.00 | 13.68 |
| 7538 | CB | ASP | B | 228 | 33.216 | 27.634 | 30.638 | 1.00 | 13.39 |
| 7539 | CG | ASP | B | 228 | 32.523 | 26.888 | 29.581 | 1.00 | 15.95 |

FIGURE 3 (Cont.)

| A | B | C | D | E | F | G | H | I | J |
|---|---|---|---|---|---|---|---|---|---|
| 7540 | OD1 | ASP | B | 228 | 32.957 | 25.724 | 29.370 | 1.00 | 16.88 |
| 7541 | OD2 | ASP | B | 228 | 31.641 | 27.312 | 28.827 | 1.00 | 15.50 |
| 7542 | C | ASP | B | 228 | 33.093 | 29.424 | 32.302 | 1.00 | 15.13 |
| 7543 | O | ASP | B | 228 | 32.972 | 28.547 | 33.255 | 1.00 | 14.41 |
| 7544 | N | THR | B | 229 | 33.566 | 30.695 | 32.471 | 1.00 | 16.95 |
| 7545 | CA | THR | B | 229 | 34.019 | 31.194 | 33.764 | 1.00 | 17.81 |
| 7546 | CB | THR | B | 229 | 34.828 | 32.567 | 33.832 | 1.00 | 18.79 |
| 7547 | OG1 | THR | B | 229 | 35.640 | 32.887 | 32.690 | 1.00 | 20.96 |
| 7548 | CG2 | THR | B | 229 | 35.871 | 32.389 | 34.882 | 1.00 | 18.36 |
| 7549 | C | THR | B | 229 | 32.991 | 31.223 | 34.898 | 1.00 | 18.66 |
| 7550 | O | THR | B | 229 | 33.372 | 30.792 | 36.021 | 1.00 | 18.20 |
| 7551 | N | ASP | B | 230 | 31.769 | 31.718 | 34.807 | 1.00 | 17.78 |
| 7552 | CA | ASP | B | 230 | 31.056 | 31.343 | 36.078 | 1.00 | 19.38 |
| 7553 | CB | ASP | B | 230 | 30.264 | 32.460 | 36.750 | 1.00 | 19.68 |
| 7554 | CG | ASP | B | 230 | 31.091 | 33.749 | 36.929 | 1.00 | 26.53 |
| 7555 | OD1 | ASP | B | 230 | 30.677 | 34.717 | 36.213 | 1.00 | 27.41 |
| 7556 | OD2 | ASP | B | 230 | 32.094 | 33.880 | 37.760 | 1.00 | 27.49 |
| 7557 | C | ASP | B | 230 | 30.192 | 30.094 | 35.926 | 1.00 | 18.95 |
| 7558 | O | ASP | B | 230 | 29.445 | 29.701 | 36.845 | 1.00 | 19.52 |
| 7559 | N | ILE | B | 231 | 30.271 | 29.384 | 34.826 | 1.00 | 17.13 |
| 7560 | CA | ILE | B | 231 | 29.417 | 28.214 | 34.917 | 1.00 | 15.89 |
| 7561 | CB | ILE | B | 231 | 29.091 | 27.605 | 33.596 | 1.00 | 16.66 |
| 7562 | CG1 | ILE | B | 231 | 30.123 | 26.576 | 33.195 | 1.00 | 16.21 |
| 7563 | CD1 | ILE | B | 231 | 29.926 | 26.295 | 31.592 | 1.00 | 20.98 |
| 7564 | CG2 | ILE | B | 231 | 28.859 | 28.679 | 32.533 | 1.00 | 11.98 |
| 7565 | C | ILE | B | 231 | 29.838 | 27.171 | 35.996 | 1.00 | 14.75 |
| 7566 | O | ILE | B | 231 | 30.976 | 27.037 | 36.358 | 1.00 | 15.42 |
| 7567 | N | PRO | B | 232 | 28.873 | 26.556 | 36.651 | 1.00 | 14.23 |
| 7568 | CA | PRO | B | 232 | 29.249 | 25.618 | 37.675 | 1.00 | 14.40 |
| 7569 | CB | PRO | B | 232 | 27.957 | 25.468 | 38.451 | 1.00 | 12.95 |
| 7570 | CG | PRO | B | 232 | 27.167 | 26.631 | 38.021 | 1.00 | 14.72 |
| 7571 | CD | PRO | B | 232 | 27.416 | 26.712 | 36.602 | 1.00 | 13.47 |
| 7572 | C | PRO | B | 232 | 29.815 | 24.290 | 37.078 | 1.00 | 14.77 |
| 7573 | O | PRO | B | 232 | 29.560 | 23.983 | 35.946 | 1.00 | 15.67 |
| 7574 | N | VAL | B | 233 | 30.535 | 23.536 | 37.874 | 1.00 | 14.36 |
| 7575 | CA | VAL | B | 233 | 31.422 | 22.494 | 37.394 | 1.00 | 14.80 |
| 7576 | CB | VAL | B | 233 | 32.805 | 22.779 | 37.961 | 1.00 | 14.34 |
| 7577 | CG1 | VAL | B | 233 | 33.770 | 21.672 | 37.743 | 1.00 | 16.27 |
| 7578 | CG2 | VAL | B | 233 | 33.334 | 24.078 | 37.325 | 1.00 | 10.28 |
| 7579 | C | VAL | B | 233 | 30.825 | 21.149 | 37.853 | 1.00 | 15.54 |
| 7580 | O | VAL | B | 233 | 30.482 | 20.991 | 38.950 | 1.00 | 16.44 |
| 7581 | N | ILE | B | 234 | 30.608 | 20.204 | 36.979 | 1.00 | 14.76 |
| 7582 | CA | ILE | B | 234 | 30.437 | 18.846 | 37.475 | 1.00 | 14.91 |
| 7583 | CB | ILE | B | 234 | 29.689 | 17.921 | 36.487 | 1.00 | 14.05 |
| 7584 | CG1 | ILE | B | 234 | 29.467 | 16.593 | 37.111 | 1.00 | 14.93 |
| 7585 | CD1 | ILE | B | 234 | 28.326 | 16.560 | 38.158 | 1.00 | 8.99 |
| 7586 | CG2 | ILE | B | 234 | 30.450 | 17.685 | 35.228 | 1.00 | 14.35 |
| 7587 | C | ILE | B | 234 | 31.827 | 18.327 | 37.842 | 1.00 | 14.85 |
| 7588 | O | ILE | B | 234 | 32.750 | 18.354 | 37.044 | 1.00 | 14.53 |
| 7589 | N | ALA | B | 235 | 31.926 | 17.867 | 39.094 | 1.00 | 15.27 |
| 7590 | CA | ALA | B | 235 | 33.094 | 17.157 | 39.654 | 1.00 | 13.75 |

FIGURE 3 (Cont.)

| A | B | C | D | E | F | G | H | I | J |
|---|---|---|---|---|---|---|---|---|---|
| 7591 | CB | ALA | B | 235 | 33.477 | 17.868 | 40.906 | 1.00 | 13.45 |
| 7592 | C | ALA | B | 235 | 32.818 | 15.631 | 39.924 | 1.00 | 13.43 |
| 7593 | O | ALA | B | 235 | 31.718 | 15.280 | 40.279 | 1.00 | 13.19 |
| 7594 | N | TYR | B | 236 | 33.750 | 14.741 | 39.636 | 1.00 | 13.07 |
| 7595 | CA | TYR | B | 236 | 33.542 | 13.264 | 39.811 | 1.00 | 13.54 |
| 7596 | CB | TYR | B | 236 | 32.660 | 12.512 | 38.732 | 1.00 | 10.80 |
| 7597 | CG | TYR | B | 236 | 33.028 | 12.758 | 37.251 | 1.00 | 15.57 |
| 7598 | CD1 | TYR | B | 236 | 33.965 | 11.996 | 36.672 | 1.00 | 12.82 |
| 7599 | CE1 | TYR | B | 236 | 34.344 | 12.161 | 35.446 | 1.00 | 20.05 |
| 7600 | CZ | TYR | B | 236 | 33.816 | 13.111 | 34.635 | 1.00 | 21.01 |
| 7601 | OH | TYR | B | 236 | 34.374 | 13.107 | 33.397 | 1.00 | 26.76 |
| 7602 | CE2 | TYR | B | 236 | 32.793 | 13.943 | 35.107 | 1.00 | 16.12 |
| 7603 | CD2 | TYR | B | 236 | 32.377 | 13.727 | 36.430 | 1.00 | 14.81 |
| 7604 | C | TYR | B | 236 | 34.914 | 12.578 | 39.904 | 1.00 | 14.59 |
| 7605 | O | TYR | B | 236 | 35.933 | 13.201 | 39.628 | 1.00 | 16.61 |
| 7606 | N | SER | B | 237 | 34.922 | 11.308 | 40.301 | 1.00 | 14.68 |
| 7607 | CA | SER | B | 237 | 36.115 | 10.659 | 40.524 | 1.00 | 15.35 |
| 7608 | CB | SER | B | 237 | 36.035 | 9.794 | 41.763 | 1.00 | 15.25 |
| 7609 | OG | SER | B | 237 | 36.041 | 10.655 | 42.868 | 1.00 | 20.27 |
| 7610 | C | SER | B | 237 | 36.523 | 9.890 | 39.294 | 1.00 | 14.54 |
| 7611 | O | SER | B | 237 | 35.694 | 9.295 | 38.597 | 1.00 | 16.82 |
| 7612 | N | TYR | B | 238 | 37.824 | 9.937 | 39.057 | 1.00 | 11.89 |
| 7613 | CA | TYR | B | 238 | 38.472 | 9.110 | 38.071 | 1.00 | 12.45 |
| 7614 | CB | TYR | B | 238 | 39.080 | 9.949 | 36.943 | 1.00 | 10.50 |
| 7615 | CG | TYR | B | 238 | 39.560 | 9.060 | 35.886 | 1.00 | 16.01 |
| 7616 | CD1 | TYR | B | 238 | 40.805 | 8.543 | 35.954 | 1.00 | 18.54 |
| 7617 | CE1 | TYR | B | 238 | 41.233 | 7.672 | 35.042 | 1.00 | 20.84 |
| 7618 | CZ | TYR | B | 238 | 40.404 | 7.275 | 34.044 | 1.00 | 21.03 |
| 7619 | OH | TYR | B | 238 | 40.879 | 6.355 | 33.100 | 1.00 | 27.85 |
| 7620 | CE2 | TYR | B | 238 | 39.183 | 7.783 | 33.945 | 1.00 | 12.90 |
| 7621 | CD2 | TYR | B | 238 | 38.762 | 8.675 | 34.857 | 1.00 | 12.02 |
| 7622 | C | TYR | B | 238 | 39.500 | 8.427 | 38.900 | 1.00 | 10.76 |
| 7623 | O | TYR | B | 238 | 40.360 | 9.119 | 39.459 | 1.00 | 11.58 |
| 7624 | N | TYR | B | 239 | 39.360 | 7.103 | 39.081 | 1.00 | 11.42 |
| 7625 | CA | TYR | B | 239 | 40.294 | 6.260 | 39.898 | 1.00 | 10.76 |
| 7626 | CB | TYR | B | 239 | 39.599 | 4.945 | 40.316 | 1.00 | 11.49 |
| 7627 | CG | TYR | B | 239 | 38.283 | 5.267 | 41.017 | 1.00 | 13.52 |
| 7628 | CD1 | TYR | B | 239 | 38.254 | 5.802 | 42.279 | 1.00 | 12.44 |
| 7629 | CE1 | TYR | B | 239 | 37.069 | 6.189 | 42.843 | 1.00 | 11.31 |
| 7630 | CZ | TYR | B | 239 | 35.914 | 6.057 | 42.169 | 1.00 | 15.47 |
| 7631 | OH | TYR | B | 239 | 34.701 | 6.468 | 42.677 | 1.00 | 15.22 |
| 7632 | CE2 | TYR | B | 239 | 35.934 | 5.544 | 40.915 | 1.00 | 14.82 |
| 7633 | CD2 | TYR | B | 239 | 37.097 | 5.165 | 40.351 | 1.00 | 12.51 |
| 7634 | C | TYR | B | 239 | 41.679 | 5.974 | 39.279 | 1.00 | 11.55 |
| 7635 | O | TYR | B | 239 | 42.711 | 5.783 | 39.964 | 1.00 | 12.88 |
| 7636 | N | GLY | B | 240 | 41.731 | 5.877 | 37.963 | 1.00 | 12.89 |
| 7637 | CA | GLY | B | 240 | 43.000 | 5.758 | 37.243 | 1.00 | 12.99 |
| 7638 | C | GLY | B | 240 | 43.859 | 4.628 | 37.791 | 1.00 | 13.73 |
| 7639 | O | GLY | B | 240 | 43.369 | 3.721 | 38.422 | 1.00 | 13.64 |
| 7640 | N | ASP | B | 241 | 45.148 | 4.661 | 37.526 | 1.00 | 14.61 |
| 7641 | CA | ASP | B | 241 | 46.018 | 3.594 | 38.052 | 1.00 | 14.50 |

FIGURE 3 (Cont.)

| A | B | C | D | E | F | G | H | I | J |
|---|---|---|---|---|---|---|---|---|---|
| 7642 | CB | ASP | B | 241 | 46.826 | 2.894 | 36.929 | 1.00 | 15.71 |
| 7643 | CG | ASP | B | 241 | 45.932 | 2.411 | 35.736 | 1.00 | 23.59 |
| 7644 | OD1 | ASP | B | 241 | 44.830 | 1.777 | 35.988 | 1.00 | 33.86 |
| 7645 | OD2 | ASP | B | 241 | 46.235 | 2.641 | 34.514 | 1.00 | 28.12 |
| 7646 | C | ASP | B | 241 | 46.913 | 4.083 | 39.193 | 1.00 | 13.91 |
| 7647 | O | ASP | B | 241 | 47.842 | 3.402 | 39.550 | 1.00 | 11.33 |
| 7648 | N | GLU | B | 242 | 46.598 | 5.218 | 39.812 | 1.00 | 12.84 |
| 7649 | CA | GLU | B | 242 | 47.467 | 5.718 | 40.866 | 1.00 | 14.20 |
| 7650 | CB | GLU | B | 242 | 47.681 | 7.238 | 40.894 | 1.00 | 13.23 |
| 7651 | CG | GLU | B | 242 | 48.363 | 7.881 | 39.690 | 1.00 | 16.26 |
| 7652 | CD | GLU | B | 242 | 49.669 | 7.234 | 39.127 | 1.00 | 20.66 |
| 7653 | OE1 | GLU | B | 242 | 49.752 | 7.159 | 37.859 | 1.00 | 22.17 |
| 7654 | OE2 | GLU | B | 242 | 50.648 | 6.881 | 39.848 | 1.00 | 19.67 |
| 7655 | C | GLU | B | 242 | 46.965 | 5.219 | 42.211 | 1.00 | 13.38 |
| 7656 | O | GLU | B | 242 | 46.027 | 4.438 | 42.254 | 1.00 | 12.45 |
| 7657 | N | GLN | B | 243 | 47.782 | 5.513 | 43.245 | 1.00 | 14.76 |
| 7658 | CA | GLN | B | 243 | 47.408 | 5.440 | 44.630 | 1.00 | 13.47 |
| 7659 | CB | GLN | B | 243 | 48.540 | 5.892 | 45.509 | 1.00 | 13.91 |
| 7660 | CG | GLN | B | 243 | 48.187 | 5.740 | 46.979 | 1.00 | 12.50 |
| 7661 | CD | GLN | B | 243 | 49.375 | 5.610 | 47.803 | 1.00 | 11.23 |
| 7662 | OE1 | GLN | B | 243 | 49.522 | 4.674 | 48.539 | 1.00 | 14.33 |
| 7663 | NE2 | GLN | B | 243 | 50.223 | 6.569 | 47.705 | 1.00 | 11.91 |
| 7664 | C | GLN | B | 243 | 46.212 | 6.318 | 44.959 | 1.00 | 13.74 |
| 7665 | O | GLN | B | 243 | 45.332 | 5.848 | 45.656 | 1.00 | 14.54 |
| 7666 | N | TYR | B | 244 | 46.178 | 7.584 | 44.535 | 1.00 | 13.16 |
| 7667 | CA | TYR | B | 244 | 44.939 | 8.406 | 44.808 | 1.00 | 13.73 |
| 7668 | CB | TYR | B | 244 | 45.239 | 9.804 | 45.281 | 1.00 | 13.10 |
| 7669 | CG | TYR | B | 244 | 45.764 | 9.781 | 46.656 | 1.00 | 12.92 |
| 7670 | CD1 | TYR | B | 244 | 44.976 | 10.133 | 47.719 | 1.00 | 14.87 |
| 7671 | CE1 | TYR | B | 244 | 45.493 | 10.116 | 49.052 | 1.00 | 17.87 |
| 7672 | CZ | TYR | B | 244 | 46.773 | 9.725 | 49.258 | 1.00 | 14.70 |
| 7673 | OH | TYR | B | 244 | 47.249 | 9.721 | 50.516 | 1.00 | 18.03 |
| 7674 | CE2 | TYR | B | 244 | 47.543 | 9.304 | 48.200 | 1.00 | 14.27 |
| 7675 | CD2 | TYR | B | 244 | 47.027 | 9.363 | 46.914 | 1.00 | 11.69 |
| 7676 | C | TYR | B | 244 | 44.091 | 8.536 | 43.615 | 1.00 | 13.86 |
| 7677 | O | TYR | B | 244 | 44.578 | 8.465 | 42.518 | 1.00 | 16.62 |
| 7678 | N | PRO | B | 245 | 42.816 | 8.769 | 43.784 | 1.00 | 13.56 |
| 7679 | CA | PRO | B | 245 | 41.982 | 9.027 | 42.643 | 1.00 | 13.19 |
| 7680 | CB | PRO | B | 245 | 40.589 | 8.629 | 43.163 | 1.00 | 11.51 |
| 7681 | CG | PRO | B | 245 | 40.749 | 8.138 | 44.557 | 1.00 | 10.26 |
| 7682 | CD | PRO | B | 245 | 42.001 | 8.861 | 45.012 | 1.00 | 13.97 |
| 7683 | C | PRO | B | 245 | 42.038 | 10.514 | 42.339 | 1.00 | 14.91 |
| 7684 | O | PRO | B | 245 | 42.504 | 11.239 | 43.181 | 1.00 | 13.14 |
| 7685 | N | ARG | B | 246 | 41.499 | 10.954 | 41.178 | 1.00 | 16.72 |
| 7686 | CA | ARG | B | 246 | 41.487 | 12.372 | 40.813 | 1.00 | 17.16 |
| 7687 | CB | ARG | B | 246 | 42.451 | 12.771 | 39.645 | 1.00 | 18.57 |
| 7688 | CG | ARG | B | 246 | 42.704 | 11.754 | 38.484 | 1.00 | 22.24 |
| 7689 | CD | ARG | B | 246 | 43.888 | 12.043 | 37.440 | 1.00 | 28.64 |
| 7690 | NE | ARG | B | 246 | 43.359 | 12.480 | 36.118 | 1.00 | 33.72 |
| 7691 | CZ | ARG | B | 246 | 42.888 | 13.746 | 35.872 | 1.00 | 37.79 |
| 7692 | NH1 | ARG | B | 246 | 42.944 | 14.697 | 36.839 | 1.00 | 36.61 |

FIGURE 3 (Cont.)

| A | B | C | D | E | F | G | H | I | J |
|---|---|---|---|---|---|---|---|---|---|
| 7693 | NH2 | ARG | B | 246 | 42.345 | 14.069 | 34.677 | 1.00 | 39.27 |
| 7694 | C | ARG | B | 246 | 40.089 | 12.851 | 40.616 | 1.00 | 16.52 |
| 7695 | O | ARG | B | 246 | 39.131 | 12.149 | 40.237 | 1.00 | 18.13 |
| 7696 | N | THR | B | 247 | 39.916 | 14.078 | 41.025 | 1.00 | 16.05 |
| 7697 | CA | THR | B | 247 | 38.739 | 14.780 | 40.652 | 1.00 | 17.41 |
| 7698 | CB | THR | B | 247 | 38.414 | 15.822 | 41.674 | 1.00 | 17.41 |
| 7699 | OG1 | THR | B | 247 | 38.130 | 15.136 | 42.902 | 1.00 | 23.93 |
| 7700 | CG2 | THR | B | 247 | 37.080 | 16.508 | 41.356 | 1.00 | 14.41 |
| 7701 | C | THR | B | 247 | 38.979 | 15.286 | 39.262 | 1.00 | 16.64 |
| 7702 | O | THR | B | 247 | 40.134 | 15.659 | 38.922 | 1.00 | 17.23 |
| 7703 | N | ILE | B | 248 | 37.912 | 15.112 | 38.465 | 1.00 | 15.75 |
| 7704 | CA | ILE | B | 248 | 37.641 | 15.664 | 37.143 | 1.00 | 16.22 |
| 7705 | CB | ILE | B | 248 | 37.028 | 14.615 | 36.175 | 1.00 | 17.53 |
| 7706 | CG1 | ILE | B | 248 | 37.904 | 13.317 | 36.038 | 1.00 | 20.50 |
| 7707 | CD1 | ILE | B | 248 | 39.284 | 13.498 | 35.468 | 1.00 | 19.42 |
| 7708 | CG2 | ILE | B | 248 | 36.865 | 15.173 | 34.838 | 1.00 | 17.86 |
| 7709 | C | ILE | B | 248 | 36.618 | 16.678 | 37.398 | 1.00 | 15.18 |
| 7710 | O | ILE | B | 248 | 35.774 | 16.467 | 38.203 | 1.00 | 14.74 |
| 7711 | N | ASN | B | 249 | 36.780 | 17.807 | 36.739 | 1.00 | 14.56 |
| 7712 | CA | ASN | B | 249 | 35.961 | 18.930 | 36.808 | 1.00 | 12.98 |
| 7713 | CB | ASN | B | 249 | 36.694 | 20.009 | 37.607 | 1.00 | 14.01 |
| 7714 | CG | ASN | B | 249 | 36.321 | 20.043 | 39.097 | 1.00 | 15.34 |
| 7715 | OD1 | ASN | B | 249 | 35.548 | 19.244 | 39.570 | 1.00 | 17.58 |
| 7716 | ND2 | ASN | B | 249 | 36.828 | 21.005 | 39.802 | 1.00 | 12.06 |
| 7717 | C | ASN | B | 249 | 35.693 | 19.371 | 35.311 | 1.00 | 13.55 |
| 7718 | O | ASN | B | 249 | 36.611 | 19.749 | 34.539 | 1.00 | 10.08 |
| 7719 | N | ILE | B | 250 | 34.398 | 19.360 | 34.920 | 1.00 | 12.29 |
| 7720 | CA | ILE | B | 250 | 33.961 | 20.055 | 33.721 | 1.00 | 14.42 |
| 7721 | CB | ILE | B | 250 | 33.364 | 19.066 | 32.789 | 1.00 | 14.75 |
| 7722 | CG1 | ILE | B | 250 | 34.010 | 17.775 | 32.819 | 1.00 | 10.71 |
| 7723 | CD1 | ILE | B | 250 | 33.060 | 16.780 | 32.117 | 1.00 | 8.34 |
| 7724 | CG2 | ILE | B | 250 | 33.517 | 19.479 | 31.375 | 1.00 | 18.51 |
| 7725 | C | ILE | B | 250 | 32.864 | 21.176 | 33.889 | 1.00 | 13.55 |
| 7726 | O | ILE | B | 250 | 31.836 | 20.923 | 34.479 | 1.00 | 14.48 |
| 7727 | N | PRO | B | 251 | 33.073 | 22.375 | 33.363 | 1.00 | 12.77 |
| 7728 | CA | PRO | B | 251 | 32.064 | 23.497 | 33.382 | 1.00 | 11.24 |
| 7729 | CB | PRO | B | 251 | 32.756 | 24.581 | 32.621 | 1.00 | 8.82 |
| 7730 | CG | PRO | B | 251 | 34.182 | 24.359 | 32.949 | 1.00 | 9.01 |
| 7731 | CD | PRO | B | 251 | 34.312 | 22.785 | 32.682 | 1.00 | 12.23 |
| 7732 | C | PRO | B | 251 | 30.895 | 23.077 | 32.618 | 1.00 | 10.26 |
| 7733 | O | PRO | B | 251 | 31.078 | 22.881 | 31.461 | 1.00 | 11.15 |
| 7734 | N | TYR | B | 252 | 29.788 | 22.741 | 33.272 | 1.00 | 10.89 |
| 7735 | CA | TYR | B | 252 | 28.770 | 21.838 | 32.698 | 1.00 | 10.49 |
| 7736 | CB | TYR | B | 252 | 28.954 | 20.368 | 33.191 | 1.00 | 10.96 |
| 7737 | CG | TYR | B | 252 | 27.832 | 19.438 | 32.642 | 1.00 | 15.07 |
| 7738 | CD1 | TYR | B | 252 | 28.108 | 18.417 | 31.773 | 1.00 | 15.20 |
| 7739 | CE1 | TYR | B | 252 | 27.106 | 17.625 | 31.325 | 1.00 | 17.27 |
| 7740 | CZ | TYR | B | 252 | 25.836 | 17.912 | 31.719 | 1.00 | 14.32 |
| 7741 | OH | TYR | B | 252 | 24.852 | 17.262 | 31.215 | 1.00 | 14.00 |
| 7742 | CE2 | TYR | B | 252 | 25.541 | 18.970 | 32.469 | 1.00 | 15.02 |
| 7743 | CD2 | TYR | B | 252 | 26.514 | 19.687 | 32.930 | 1.00 | 15.83 |

FIGURE 3 (Cont.)

| A | B | C | D | E | F | G | H | I | J |
|---|---|---|---|---|---|---|---|---|---|
| 7744 | C | TYR | B | 252 | 27.439 | 22.388 | 33.138 | 1.00 | 9.61 |
| 7745 | O | TYR | B | 252 | 27.135 | 22.264 | 34.259 | 1.00 | 8.26 |
| 7746 | N | PRO | B | 253 | 26.739 | 23.158 | 32.313 | 1.00 | 11.44 |
| 7747 | CA | PRO | B | 253 | 25.546 | 23.853 | 32.772 | 1.00 | 12.82 |
| 7748 | CB | PRO | B | 253 | 25.414 | 25.031 | 31.789 | 1.00 | 12.13 |
| 7749 | CG | PRO | B | 253 | 25.842 | 24.436 | 30.528 | 1.00 | 8.80 |
| 7750 | CD | PRO | B | 253 | 27.030 | 23.559 | 30.919 | 1.00 | 10.70 |
| 7751 | C | PRO | B | 253 | 24.364 | 22.945 | 32.750 | 1.00 | 12.70 |
| 7752 | O | PRO | B | 253 | 23.918 | 22.534 | 31.699 | 1.00 | 15.48 |
| 7753 | N | LYS | B | 254 | 23.893 | 22.643 | 33.941 | 1.00 | 14.20 |
| 7754 | CA | LYS | B | 254 | 22.668 | 21.863 | 34.086 | 1.00 | 13.42 |
| 7755 | CB | LYS | B | 254 | 22.638 | 21.111 | 35.432 | 1.00 | 15.22 |
| 7756 | CG | LYS | B | 254 | 23.803 | 20.178 | 35.699 | 1.00 | 12.13 |
| 7757 | CD | LYS | B | 254 | 23.686 | 19.463 | 37.143 | 1.00 | 12.83 |
| 7758 | CE | LYS | B | 254 | 24.774 | 18.281 | 37.363 | 1.00 | 14.00 |
| 7759 | NZ | LYS | B | 254 | 24.628 | 17.240 | 36.352 | 1.00 | 12.34 |
| 7760 | C | LYS | B | 254 | 21.534 | 22.812 | 33.976 | 1.00 | 13.29 |
| 7761 | O | LYS | B | 254 | 21.700 | 23.981 | 33.912 | 1.00 | 15.19 |
| 7762 | N | ALA | B | 255 | 20.375 | 22.266 | 33.877 | 1.00 | 12.43 |
| 7763 | CA | ALA | B | 255 | 19.214 | 23.015 | 33.665 | 1.00 | 12.92 |
| 7764 | CB | ALA | B | 255 | 18.059 | 22.144 | 33.810 | 1.00 | 11.87 |
| 7765 | C | ALA | B | 255 | 19.035 | 24.242 | 34.554 | 1.00 | 11.93 |
| 7766 | O | ALA | B | 255 | 19.081 | 24.160 | 35.764 | 1.00 | 12.70 |
| 7767 | N | GLY | B | 256 | 18.708 | 25.339 | 33.908 | 1.00 | 10.28 |
| 7768 | CA | GLY | B | 256 | 18.539 | 26.598 | 34.545 | 1.00 | 7.73 |
| 7769 | C | GLY | B | 256 | 19.805 | 27.173 | 35.054 | 1.00 | 7.68 |
| 7770 | O | GLY | B | 256 | 19.784 | 28.274 | 35.470 | 1.00 | 7.29 |
| 7771 | N | ALA | B | 257 | 20.908 | 26.493 | 34.931 | 1.00 | 4.99 |
| 7772 | CA | ALA | B | 257 | 22.107 | 27.031 | 35.430 | 1.00 | 7.32 |
| 7773 | CB | ALA | B | 257 | 23.070 | 25.910 | 35.533 | 1.00 | 6.39 |
| 7774 | C | ALA | B | 257 | 22.721 | 28.123 | 34.585 | 1.00 | 8.52 |
| 7775 | O | ALA | B | 257 | 22.196 | 28.443 | 33.498 | 1.00 | 11.93 |
| 7776 | N | LYS | B | 258 | 23.874 | 28.661 | 34.958 | 1.00 | 8.78 |
| 7777 | CA | LYS | B | 258 | 24.391 | 29.663 | 34.027 | 1.00 | 9.36 |
| 7778 | CB | LYS | B | 258 | 25.074 | 30.883 | 34.722 | 1.00 | 9.17 |
| 7779 | CG | LYS | B | 258 | 26.521 | 31.164 | 34.591 | 1.00 | 10.86 |
| 7780 | CD | LYS | B | 258 | 27.046 | 32.201 | 33.452 | 1.00 | 12.86 |
| 7781 | CE | LYS | B | 258 | 27.436 | 33.739 | 33.932 | 1.00 | 15.90 |
| 7782 | NZ | LYS | B | 258 | 27.505 | 34.801 | 32.804 | 1.00 | 7.68 |
| 7783 | C | LYS | B | 258 | 25.131 | 29.005 | 32.875 | 1.00 | 8.55 |
| 7784 | O | LYS | B | 258 | 25.852 | 28.035 | 33.043 | 1.00 | 9.27 |
| 7785 | N | ASN | B | 259 | 24.865 | 29.550 | 31.689 | 1.00 | 6.70 |
| 7786 | CA | ASN | B | 259 | 25.378 | 29.142 | 30.430 | 1.00 | 6.78 |
| 7787 | CB | ASN | B | 259 | 24.329 | 29.421 | 29.380 | 1.00 | 3.41 |
| 7788 | CG | ASN | B | 259 | 23.424 | 28.245 | 29.223 | 1.00 | 7.69 |
| 7789 | OD1 | ASN | B | 259 | 23.787 | 27.094 | 29.631 | 1.00 | 6.96 |
| 7790 | ND2 | ASN | B | 259 | 22.280 | 28.471 | 28.683 | 1.00 | 2.00 |
| 7791 | C | ASN | B | 259 | 26.654 | 29.857 | 30.019 | 1.00 | 7.36 |
| 7792 | O | ASN | B | 259 | 26.876 | 31.057 | 30.333 | 1.00 | 10.96 |
| 7793 | N | PRO | B | 260 | 27.449 | 29.194 | 29.210 | 1.00 | 9.20 |
| 7794 | CA | PRO | B | 260 | 28.640 | 29.843 | 28.651 | 1.00 | 9.24 |

FIGURE 3 (Cont.)

| A | B | C | D | E | F | G | H | I | J |
|---|---|---|---|---|---|---|---|---|---|
| 7795 | CB | PRO | B | 260 | 29.208 | 28.776 | 27.693 | 1.00 | 8.89 |
| 7796 | CG | PRO | B | 260 | 27.961 | 27.878 | 27.408 | 1.00 | 9.03 |
| 7797 | CD | PRO | B | 260 | 27.232 | 27.878 | 28.609 | 1.00 | 8.30 |
| 7798 | C | PRO | B | 260 | 28.169 | 30.979 | 27.814 | 1.00 | 9.24 |
| 7799 | O | PRO | B | 260 | 27.080 | 30.891 | 27.303 | 1.00 | 3.91 |
| 7800 | N | VAL | B | 261 | 29.009 | 32.005 | 27.687 | 1.00 | 11.17 |
| 7801 | CA | VAL | B | 261 | 28.829 | 33.090 | 26.686 | 1.00 | 12.34 |
| 7802 | CB | VAL | B | 261 | 28.803 | 34.572 | 27.390 | 1.00 | 12.46 |
| 7803 | CG1 | VAL | B | 261 | 28.117 | 34.554 | 28.763 | 1.00 | 11.80 |
| 7804 | CG2 | VAL | B | 261 | 30.163 | 35.316 | 27.465 | 1.00 | 14.37 |
| 7805 | C | VAL | B | 261 | 29.812 | 32.923 | 25.475 | 1.00 | 10.95 |
| 7806 | O | VAL | B | 261 | 30.884 | 32.519 | 25.645 | 1.00 | 10.35 |
| 7807 | N | VAL | B | 262 | 29.304 | 33.095 | 24.259 | 1.00 | 10.17 |
| 7808 | CA | VAL | B | 262 | 30.017 | 33.217 | 23.058 | 1.00 | 10.20 |
| 7809 | CB | VAL | B | 262 | 29.286 | 32.643 | 21.905 | 1.00 | 11.34 |
| 7810 | CG1 | VAL | B | 262 | 29.549 | 31.167 | 21.721 | 1.00 | 17.21 |
| 7811 | CG2 | VAL | B | 262 | 27.875 | 32.844 | 22.028 | 1.00 | 11.49 |
| 7812 | C | VAL | B | 262 | 30.124 | 34.635 | 22.555 | 1.00 | 10.99 |
| 7813 | O | VAL | B | 262 | 29.186 | 35.476 | 22.633 | 1.00 | 7.98 |
| 7814 | N | ARG | B | 263 | 31.289 | 34.843 | 21.952 | 1.00 | 8.85 |
| 7815 | CA | ARG | B | 263 | 31.397 | 35.797 | 20.918 | 1.00 | 10.51 |
| 7816 | CB | ARG | B | 263 | 32.297 | 36.979 | 21.368 | 1.00 | 11.00 |
| 7817 | CG | ARG | B | 263 | 32.095 | 37.354 | 22.823 | 1.00 | 16.34 |
| 7818 | CD | ARG | B | 263 | 32.794 | 38.679 | 23.325 | 1.00 | 15.13 |
| 7819 | NE | ARG | B | 263 | 34.152 | 38.244 | 23.638 | 1.00 | 20.51 |
| 7820 | CZ | ARG | B | 263 | 35.203 | 39.091 | 23.828 | 1.00 | 23.45 |
| 7821 | NH1 | ARG | B | 263 | 35.000 | 40.424 | 23.751 | 1.00 | 23.84 |
| 7822 | NH2 | ARG | B | 263 | 36.456 | 38.620 | 24.087 | 1.00 | 15.21 |
| 7823 | C | ARG | B | 263 | 31.966 | 35.012 | 19.718 | 1.00 | 9.69 |
| 7824 | O | ARG | B | 263 | 32.798 | 34.167 | 19.855 | 1.00 | 8.67 |
| 7825 | N | ILE | B | 264 | 31.500 | 35.351 | 18.546 | 1.00 | 7.62 |
| 7826 | CA | ILE | B | 264 | 32.047 | 34.891 | 17.305 | 1.00 | 5.28 |
| 7827 | CB | ILE | B | 264 | 30.928 | 34.635 | 16.416 | 1.00 | 5.18 |
| 7828 | CG1 | ILE | B | 264 | 29.894 | 33.690 | 17.016 | 1.00 | 2.00 |
| 7829 | CD1 | ILE | B | 264 | 30.462 | 32.257 | 17.526 | 1.00 | 7.50 |
| 7830 | CG2 | ILE | B | 264 | 31.419 | 34.117 | 15.201 | 1.00 | 4.96 |
| 7831 | C | ILE | B | 264 | 32.878 | 36.046 | 16.672 | 1.00 | 6.86 |
| 7832 | O | ILE | B | 264 | 32.427 | 37.245 | 16.484 | 1.00 | 6.92 |
| 7833 | N | PHE | B | 265 | 34.129 | 35.703 | 16.325 | 1.00 | 7.25 |
| 7834 | CA | PHE | B | 265 | 35.079 | 36.696 | 15.759 | 1.00 | 7.72 |
| 7835 | CB | PHE | B | 265 | 36.301 | 36.733 | 16.644 | 1.00 | 8.25 |
| 7836 | CG | PHE | B | 265 | 36.103 | 37.508 | 17.861 | 1.00 | 12.90 |
| 7837 | CD1 | PHE | B | 265 | 36.026 | 36.886 | 19.090 | 1.00 | 11.50 |
| 7838 | CE1 | PHE | B | 265 | 35.848 | 37.588 | 20.215 | 1.00 | 5.93 |
| 7839 | CZ | PHE | B | 265 | 35.693 | 38.844 | 20.174 | 1.00 | 8.44 |
| 7840 | CE2 | PHE | B | 265 | 35.801 | 39.539 | 18.986 | 1.00 | 12.93 |
| 7841 | CD2 | PHE | B | 265 | 35.968 | 38.902 | 17.820 | 1.00 | 11.71 |
| 7842 | C | PHE | B | 265 | 35.398 | 36.326 | 14.331 | 1.00 | 7.50 |
| 7843 | O | PHE | B | 265 | 35.349 | 35.158 | 13.931 | 1.00 | 8.19 |
| 7844 | N | ILE | B | 266 | 35.733 | 37.292 | 13.544 | 1.00 | 8.25 |
| 7845 | CA | ILE | B | 266 | 36.360 | 37.000 | 12.259 | 1.00 | 9.83 |

FIGURE 3 (Cont.)

| A | B | C | D | E | F | G | H | I | J |
|---|---|---|---|---|---|---|---|---|---|
| 7846 | CB | ILE | B | 266 | 35.386 | 37.228 | 11.080 | 1.00 | 8.30 |
| 7847 | CG1 | ILE | B | 266 | 34.054 | 36.602 | 11.289 | 1.00 | 11.93 |
| 7848 | CD1 | ILE | B | 266 | 33.031 | 37.243 | 10.375 | 1.00 | 2.00 |
| 7849 | CG2 | ILE | B | 266 | 35.968 | 36.586 | 9.808 | 1.00 | 13.16 |
| 7850 | C | ILE | B | 266 | 37.588 | 37.897 | 12.051 | 1.00 | 8.53 |
| 7851 | O | ILE | B | 266 | 37.500 | 39.086 | 12.274 | 1.00 | 9.64 |
| 7852 | N | ILE | B | 267 | 38.686 | 37.319 | 11.576 | 1.00 | 10.69 |
| 7853 | CA | ILE | B | 267 | 39.970 | 38.043 | 11.393 | 1.00 | 13.26 |
| 7854 | CB | ILE | B | 267 | 41.169 | 37.589 | 12.215 | 1.00 | 14.46 |
| 7855 | CG1 | ILE | B | 267 | 40.816 | 36.295 | 12.801 | 1.00 | 17.32 |
| 7856 | CD1 | ILE | B | 267 | 41.150 | 35.154 | 11.831 | 1.00 | 19.06 |
| 7857 | CG2 | ILE | B | 267 | 42.073 | 38.688 | 13.025 | 1.00 | 14.41 |
| 7858 | C | ILE | B | 267 | 40.441 | 37.717 | 9.956 | 1.00 | 13.68 |
| 7859 | O | ILE | B | 267 | 40.347 | 36.519 | 9.384 | 1.00 | 8.99 |
| 7860 | N | ASP | B | 268 | 41.042 | 38.775 | 9.449 | 1.00 | 13.14 |
| 7861 | CA | ASP | B | 268 | 41.788 | 38.611 | 8.247 | 1.00 | 15.13 |
| 7862 | CB | ASP | B | 268 | 42.099 | 39.957 | 7.739 | 1.00 | 14.52 |
| 7863 | CG | ASP | B | 268 | 42.589 | 39.934 | 6.342 | 1.00 | 15.72 |
| 7864 | OD1 | ASP | B | 268 | 42.126 | 40.893 | 5.628 | 1.00 | 12.19 |
| 7865 | OD2 | ASP | B | 268 | 43.496 | 39.059 | 5.965 | 1.00 | 10.29 |
| 7866 | C | ASP | B | 268 | 43.066 | 37.725 | 8.451 | 1.00 | 15.96 |
| 7867 | O | ASP | B | 268 | 43.931 | 38.013 | 9.283 | 1.00 | 17.51 |
| 7868 | N | THR | B | 269 | 43.193 | 36.702 | 7.611 | 1.00 | 16.44 |
| 7869 | CA | THR | B | 269 | 44.234 | 35.654 | 7.714 | 1.00 | 14.85 |
| 7870 | CB | THR | B | 269 | 43.608 | 34.536 | 6.934 | 1.00 | 15.08 |
| 7871 | OG1 | THR | B | 269 | 43.133 | 33.455 | 7.790 | 1.00 | 18.75 |
| 7872 | CG2 | THR | B | 269 | 44.382 | 34.011 | 5.894 | 1.00 | 13.77 |
| 7873 | C | THR | B | 269 | 45.516 | 36.147 | 7.087 | 1.00 | 15.92 |
| 7874 | O | THR | B | 269 | 46.568 | 35.513 | 7.246 | 1.00 | 18.97 |
| 7875 | N | THR | B | 270 | 45.465 | 37.265 | 6.388 | 1.00 | 12.63 |
| 7876 | CA | THR | B | 270 | 46.594 | 37.911 | 5.834 | 1.00 | 12.15 |
| 7877 | CB | THR | B | 270 | 46.251 | 38.037 | 4.297 | 1.00 | 13.33 |
| 7878 | OG1 | THR | B | 270 | 46.522 | 36.724 | 3.691 | 1.00 | 17.17 |
| 7879 | CG2 | THR | B | 270 | 47.199 | 39.123 | 3.556 | 1.00 | 10.18 |
| 7880 | C | THR | B | 270 | 47.029 | 39.276 | 6.518 | 1.00 | 10.74 |
| 7881 | O | THR | B | 270 | 48.202 | 39.699 | 6.503 | 1.00 | 8.95 |
| 7882 | N | TYR | B | 271 | 46.130 | 39.917 | 7.231 | 1.00 | 8.03 |
| 7883 | CA | TYR | B | 271 | 46.448 | 41.147 | 7.951 | 1.00 | 7.49 |
| 7884 | CB | TYR | B | 271 | 45.643 | 42.284 | 7.267 | 1.00 | 6.02 |
| 7885 | CG | TYR | B | 271 | 46.052 | 42.527 | 5.823 | 1.00 | 6.18 |
| 7886 | CD1 | TYR | B | 271 | 45.399 | 41.934 | 4.798 | 1.00 | 8.05 |
| 7887 | CE1 | TYR | B | 271 | 45.789 | 42.163 | 3.468 | 1.00 | 7.83 |
| 7888 | CZ | TYR | B | 271 | 46.789 | 42.977 | 3.193 | 1.00 | 8.67 |
| 7889 | OH | TYR | B | 271 | 47.191 | 43.185 | 1.867 | 1.00 | 8.52 |
| 7890 | CE2 | TYR | B | 271 | 47.392 | 43.627 | 4.242 | 1.00 | 8.22 |
| 7891 | CD2 | TYR | B | 271 | 47.040 | 43.381 | 5.510 | 1.00 | 2.00 |
| 7892 | C | TYR | B | 271 | 46.069 | 41.039 | 9.402 | 1.00 | 5.61 |
| 7893 | O | TYR | B | 271 | 45.350 | 41.943 | 9.902 | 1.00 | 7.12 |
| 7894 | N | PRO | B | 272 | 46.269 | 39.861 | 10.016 | 1.00 | 6.80 |
| 7895 | CA | PRO | B | 272 | 45.612 | 39.532 | 11.292 | 1.00 | 6.72 |
| 7896 | CB | PRO | B | 272 | 45.980 | 38.091 | 11.543 | 1.00 | 5.06 |

FIGURE 3 (Cont.)

| A | B | C | D | E | F | G | H | I | J |
|---|---|---|---|---|---|---|---|---|---|
| 7897 | CG | PRO | B | 272 | 47.199 | 37.831 | 10.772 | 1.00 | 6.25 |
| 7898 | CD | PRO | B | 272 | 46.920 | 38.656 | 9.491 | 1.00 | 5.81 |
| 7899 | C | PRO | B | 272 | 46.058 | 40.392 | 12.393 | 1.00 | 8.50 |
| 7900 | O | PRO | B | 272 | 45.202 | 40.867 | 13.182 | 1.00 | 10.73 |
| 7901 | N | ALA | B | 273 | 47.329 | 40.723 | 12.354 | 1.00 | 6.92 |
| 7902 | CA | ALA | B | 273 | 47.878 | 41.759 | 13.180 | 1.00 | 9.05 |
| 7903 | CB | ALA | B | 273 | 49.423 | 41.778 | 13.141 | 1.00 | 9.67 |
| 7904 | C | ALA | B | 273 | 47.393 | 43.038 | 12.793 | 1.00 | 9.71 |
| 7905 | O | ALA | B | 273 | 46.910 | 43.715 | 13.652 | 1.00 | 12.64 |
| 7906 | N | TYR | B | 274 | 47.504 | 43.381 | 11.517 | 1.00 | 11.45 |
| 7907 | CA | TYR | B | 274 | 47.185 | 44.792 | 10.986 | 1.00 | 10.14 |
| 7908 | CB | TYR | B | 274 | 47.231 | 44.889 | 9.445 | 1.00 | 9.54 |
| 7909 | CG | TYR | B | 274 | 47.072 | 46.304 | 8.865 | 1.00 | 5.17 |
| 7910 | CD1 | TYR | B | 274 | 47.814 | 47.363 | 9.343 | 1.00 | 4.86 |
| 7911 | CE1 | TYR | B | 274 | 47.649 | 48.644 | 8.826 | 1.00 | 2.79 |
| 7912 | CZ | TYR | B | 274 | 46.807 | 48.851 | 7.788 | 1.00 | 2.00 |
| 7913 | OH | TYR | B | 274 | 46.670 | 50.136 | 7.294 | 1.00 | 2.00 |
| 7914 | CE2 | TYR | B | 274 | 46.085 | 47.825 | 7.316 | 1.00 | 2.00 |
| 7915 | CD2 | TYR | B | 274 | 46.220 | 46.564 | 7.813 | 1.00 | 2.00 |
| 7916 | C | TYR | B | 274 | 45.854 | 45.286 | 11.400 | 1.00 | 9.35 |
| 7917 | O | TYR | B | 274 | 45.745 | 46.328 | 11.951 | 1.00 | 9.93 |
| 7918 | N | VAL | B | 275 | 44.845 | 44.444 | 11.196 | 1.00 | 11.07 |
| 7919 | CA | VAL | B | 275 | 43.451 | 44.779 | 11.310 | 1.00 | 9.66 |
| 7920 | CB | VAL | B | 275 | 42.634 | 44.273 | 10.048 | 1.00 | 11.67 |
| 7921 | CG1 | VAL | B | 275 | 41.701 | 43.047 | 10.248 | 1.00 | 12.82 |
| 7922 | CG2 | VAL | B | 275 | 41.562 | 45.322 | 9.707 | 1.00 | 16.81 |
| 7923 | C | VAL | B | 275 | 42.801 | 44.253 | 12.600 | 1.00 | 9.92 |
| 7924 | O | VAL | B | 275 | 41.908 | 44.921 | 13.210 | 1.00 | 9.33 |
| 7925 | N | GLY | B | 276 | 43.160 | 43.022 | 12.954 | 1.00 | 8.72 |
| 7926 | CA | GLY | B | 276 | 42.867 | 42.493 | 14.215 | 1.00 | 10.35 |
| 7927 | C | GLY | B | 276 | 41.525 | 41.824 | 14.043 | 1.00 | 11.54 |
| 7928 | O | GLY | B | 276 | 40.874 | 41.973 | 13.000 | 1.00 | 13.70 |
| 7929 | N | PRO | B | 277 | 41.140 | 41.060 | 15.070 | 1.00 | 11.56 |
| 7930 | CA | PRO | B | 277 | 39.854 | 40.344 | 15.153 | 1.00 | 11.09 |
| 7931 | CB | PRO | B | 277 | 39.969 | 39.656 | 16.464 | 1.00 | 9.83 |
| 7932 | CG | PRO | B | 277 | 40.938 | 40.593 | 17.241 | 1.00 | 13.83 |
| 7933 | CD | PRO | B | 277 | 42.000 | 40.840 | 16.250 | 1.00 | 9.72 |
| 7934 | C | PRO | B | 277 | 38.703 | 41.253 | 15.241 | 1.00 | 11.78 |
| 7935 | O | PRO | B | 277 | 38.838 | 42.235 | 15.942 | 1.00 | 12.85 |
| 7936 | N | GLN | B | 278 | 37.607 | 40.940 | 14.556 | 1.00 | 12.73 |
| 7937 | CA | GLN | B | 278 | 36.485 | 41.858 | 14.441 | 1.00 | 12.60 |
| 7938 | CB | GLN | B | 278 | 36.241 | 42.452 | 13.050 | 1.00 | 12.22 |
| 7939 | CG | GLN | B | 278 | 37.412 | 43.079 | 12.446 | 1.00 | 12.75 |
| 7940 | CD | GLN | B | 278 | 37.711 | 44.460 | 12.997 | 1.00 | 15.22 |
| 7941 | OE1 | GLN | B | 278 | 36.798 | 45.432 | 13.099 | 1.00 | 13.95 |
| 7942 | NE2 | GLN | B | 278 | 38.986 | 44.596 | 13.343 | 1.00 | 4.37 |
| 7943 | C | GLN | B | 278 | 35.262 | 41.060 | 14.794 | 1.00 | 13.49 |
| 7944 | O | GLN | B | 278 | 35.016 | 40.075 | 14.207 | 1.00 | 13.58 |
| 7945 | N | GLU | B | 279 | 34.497 | 41.566 | 15.755 | 1.00 | 13.12 |
| 7946 | CA | GLU | B | 279 | 33.455 | 40.841 | 16.385 | 1.00 | 14.05 |
| 7947 | CB | GLU | B | 279 | 33.172 | 41.429 | 17.797 | 1.00 | 13.06 |

FIGURE 3 (Cont.)

| A | B | C | D | E | F | G | H | I | J |
|---|---|---|---|---|---|---|---|---|---|
| 7948 | CG | GLU | B | 279 | 31.968 | 40.782 | 18.456 | 1.00 | 14.85 |
| 7949 | CD | GLU | B | 279 | 31.855 | 40.914 | 19.935 | 1.00 | 17.16 |
| 7950 | OE1 | GLU | B | 279 | 32.540 | 41.721 | 20.513 | 1.00 | 16.37 |
| 7951 | OE2 | GLU | B | 279 | 31.060 | 40.142 | 20.512 | 1.00 | 16.43 |
| 7952 | C | GLU | B | 279 | 32.253 | 40.949 | 15.467 | 1.00 | 13.13 |
| 7953 | O | GLU | B | 279 | 31.807 | 42.036 | 15.084 | 1.00 | 14.82 |
| 7954 | N | VAL | B | 280 | 31.723 | 39.822 | 15.141 | 1.00 | 12.42 |
| 7955 | CA | VAL | B | 280 | 30.532 | 39.801 | 14.353 | 1.00 | 12.73 |
| 7956 | CB | VAL | B | 280 | 30.225 | 38.382 | 13.910 | 1.00 | 14.76 |
| 7957 | CG1 | VAL | B | 280 | 28.936 | 38.319 | 13.215 | 1.00 | 9.95 |
| 7958 | CG2 | VAL | B | 280 | 31.408 | 37.766 | 13.087 | 1.00 | 8.35 |
| 7959 | C | VAL | B | 280 | 29.339 | 40.245 | 15.184 | 1.00 | 14.69 |
| 7960 | O | VAL | B | 280 | 29.031 | 39.606 | 16.150 | 1.00 | 15.46 |
| 7961 | N | PRO | B | 281 | 28.627 | 41.306 | 14.754 | 1.00 | 16.30 |
| 7962 | CA | PRO | B | 281 | 27.550 | 41.906 | 15.569 | 1.00 | 16.22 |
| 7963 | CB | PRO | B | 281 | 27.093 | 43.164 | 14.746 | 1.00 | 16.25 |
| 7964 | CG | PRO | B | 281 | 28.172 | 43.406 | 13.796 | 1.00 | 19.39 |
| 7965 | CD | PRO | B | 281 | 28.802 | 41.988 | 13.459 | 1.00 | 15.39 |
| 7966 | C | PRO | B | 281 | 26.367 | 40.920 | 15.744 | 1.00 | 16.25 |
| 7967 | O | PRO | B | 281 | 26.085 | 40.098 | 14.907 | 1.00 | 17.06 |
| 7968 | N | VAL | B | 282 | 25.606 | 41.096 | 16.820 | 1.00 | 16.75 |
| 7969 | CA | VAL | B | 282 | 24.647 | 40.120 | 17.150 | 1.00 | 13.21 |
| 7970 | CB | VAL | B | 282 | 24.963 | 39.445 | 18.539 | 1.00 | 16.03 |
| 7971 | CG1 | VAL | B | 282 | 26.203 | 40.032 | 19.245 | 1.00 | 14.82 |
| 7972 | CG2 | VAL | B | 282 | 23.793 | 39.397 | 19.424 | 1.00 | 9.26 |
| 7973 | C | VAL | B | 282 | 23.315 | 40.737 | 17.043 | 1.00 | 11.43 |
| 7974 | O | VAL | B | 282 | 23.141 | 41.784 | 17.502 | 1.00 | 12.31 |
| 7975 | N | PRO | B | 283 | 22.367 | 40.076 | 16.410 | 1.00 | 10.15 |
| 7976 | CA | PRO | B | 283 | 21.062 | 40.673 | 16.242 | 1.00 | 8.83 |
| 7977 | CB | PRO | B | 283 | 20.180 | 39.537 | 15.645 | 1.00 | 9.37 |
| 7978 | CG | PRO | B | 283 | 21.282 | 38.238 | 15.233 | 1.00 | 6.97 |
| 7979 | CD | PRO | B | 283 | 22.515 | 38.655 | 15.869 | 1.00 | 9.65 |
| 7980 | C | PRO | B | 283 | 20.530 | 41.128 | 17.616 | 1.00 | 9.84 |
| 7981 | O | PRO | B | 283 | 20.642 | 40.353 | 18.570 | 1.00 | 8.01 |
| 7982 | N | ALA | B | 284 | 19.850 | 42.324 | 17.678 | 1.00 | 12.00 |
| 7983 | CA | ALA | B | 284 | 19.325 | 42.897 | 18.923 | 1.00 | 12.26 |
| 7984 | CB | ALA | B | 284 | 18.758 | 44.133 | 18.645 | 1.00 | 13.91 |
| 7985 | C | ALA | B | 284 | 18.238 | 42.064 | 19.644 | 1.00 | 13.86 |
| 7986 | O | ALA | B | 284 | 18.226 | 41.995 | 20.867 | 1.00 | 13.82 |
| 7987 | N | MET | B | 285 | 17.289 | 41.534 | 18.898 | 1.00 | 14.88 |
| 7988 | CA | MET | B | 285 | 16.340 | 40.541 | 19.399 | 1.00 | 14.75 |
| 7989 | CB | MET | B | 285 | 15.312 | 40.245 | 18.259 | 1.00 | 15.86 |
| 7990 | CG | MET | B | 285 | 15.744 | 39.144 | 17.224 | 1.00 | 16.51 |
| 7991 | SD | MET | B | 285 | 14.287 | 38.815 | 16.190 | 1.00 | 17.65 |
| 7992 | CE | MET | B | 285 | 13.688 | 37.438 | 17.007 | 1.00 | 18.92 |
| 7993 | C | MET | B | 285 | 16.976 | 39.146 | 19.854 | 1.00 | 15.39 |
| 7994 | O | MET | B | 285 | 16.290 | 38.218 | 20.248 | 1.00 | 15.29 |
| 7995 | N | ILE | B | 286 | 18.249 | 38.975 | 19.693 | 1.00 | 13.64 |
| 7996 | CA | ILE | B | 286 | 18.938 | 37.831 | 20.222 | 1.00 | 15.67 |
| 7997 | CB | ILE | B | 286 | 19.918 | 37.331 | 19.195 | 1.00 | 14.58 |
| 7998 | CG1 | ILE | B | 286 | 19.150 | 36.665 | 18.090 | 1.00 | 16.56 |

FIGURE 3 (Cont.)

| A | B | C | D | E | F | G | H | I | J |
|---|---|---|---|---|---|---|---|---|---|
| 7999 | CD1 | ILE | B | 286 | 18.682 | 35.359 | 18.317 | 1.00 | 14.15 |
| 8000 | CG2 | ILE | B | 286 | 20.987 | 36.551 | 19.829 | 1.00 | 10.30 |
| 8001 | C | ILE | B | 286 | 19.785 | 38.238 | 21.463 | 1.00 | 17.71 |
| 8002 | O | ILE | B | 286 | 20.046 | 37.387 | 22.376 | 1.00 | 21.12 |
| 8003 | N | ALA | B | 287 | 20.308 | 39.468 | 21.447 | 1.00 | 15.84 |
| 8004 | CA | ALA | B | 287 | 21.196 | 39.874 | 22.463 | 1.00 | 14.90 |
| 8005 | CB | ALA | B | 287 | 22.068 | 40.957 | 21.981 | 1.00 | 13.90 |
| 8006 | C | ALA | B | 287 | 20.462 | 40.306 | 23.659 | 1.00 | 13.61 |
| 8007 | O | ALA | B | 287 | 21.075 | 40.407 | 24.675 | 1.00 | 13.79 |
| 8008 | N | SER | B | 288 | 19.151 | 40.538 | 23.558 | 1.00 | 15.11 |
| 8009 | CA | SER | B | 288 | 18.290 | 41.095 | 24.656 | 1.00 | 14.95 |
| 8010 | CB | SER | B | 288 | 16.887 | 41.454 | 24.085 | 1.00 | 14.98 |
| 8011 | OG | SER | B | 288 | 16.239 | 40.268 | 23.619 | 1.00 | 15.94 |
| 8012 | C | SER | B | 288 | 18.102 | 40.117 | 25.893 | 1.00 | 14.50 |
| 8013 | O | SER | B | 288 | 17.437 | 40.459 | 26.882 | 1.00 | 14.87 |
| 8014 | N | SER | B | 289 | 18.674 | 38.922 | 25.776 | 1.00 | 13.23 |
| 8015 | CA | SER | B | 289 | 18.680 | 37.859 | 26.783 | 1.00 | 13.37 |
| 8016 | CB | SER | B | 289 | 17.310 | 37.242 | 26.827 | 1.00 | 13.97 |
| 8017 | OG | SER | B | 289 | 17.157 | 36.657 | 25.566 | 1.00 | 21.49 |
| 8018 | C | SER | B | 289 | 19.739 | 36.731 | 26.443 | 1.00 | 12.02 |
| 8019 | O | SER | B | 289 | 20.542 | 36.885 | 25.593 | 1.00 | 9.35 |
| 8020 | N | ASP | B | 290 | 19.729 | 35.636 | 27.174 | 1.00 | 11.67 |
| 8021 | CA | ASP | B | 290 | 20.710 | 34.572 | 27.034 | 1.00 | 11.37 |
| 8022 | CB | ASP | B | 290 | 20.616 | 33.481 | 28.074 | 1.00 | 12.63 |
| 8023 | CG | ASP | B | 290 | 21.365 | 33.788 | 29.351 | 1.00 | 15.49 |
| 8024 | OD1 | ASP | B | 290 | 21.405 | 32.887 | 30.203 | 1.00 | 14.93 |
| 8025 | OD2 | ASP | B | 290 | 21.880 | 34.878 | 29.619 | 1.00 | 20.39 |
| 8026 | C | ASP | B | 290 | 20.470 | 33.966 | 25.681 | 1.00 | 9.90 |
| 8027 | O | ASP | B | 290 | 19.391 | 34.033 | 25.145 | 1.00 | 9.81 |
| 8028 | N | TYR | B | 291 | 21.571 | 33.632 | 25.056 | 1.00 | 6.10 |
| 8029 | CA | TYR | B | 291 | 21.484 | 33.102 | 23.747 | 1.00 | 7.59 |
| 8030 | CB | TYR | B | 291 | 21.450 | 34.205 | 22.698 | 1.00 | 8.68 |
| 8031 | CG | TYR | B | 291 | 22.660 | 35.097 | 22.666 | 1.00 | 6.97 |
| 8032 | CD1 | TYR | B | 291 | 22.635 | 36.404 | 23.221 | 1.00 | 12.87 |
| 8033 | CE1 | TYR | B | 291 | 23.838 | 37.297 | 23.126 | 1.00 | 7.61 |
| 8034 | CZ | TYR | B | 291 | 24.880 | 36.824 | 22.418 | 1.00 | 6.81 |
| 8035 | OH | TYR | B | 291 | 25.980 | 37.486 | 22.265 | 1.00 | 4.80 |
| 8036 | CE2 | TYR | B | 291 | 24.817 | 35.579 | 21.763 | 1.00 | 9.19 |
| 8037 | CD2 | TYR | B | 291 | 23.755 | 34.739 | 21.909 | 1.00 | 3.83 |
| 8038 | C | TYR | B | 291 | 22.565 | 32.078 | 23.451 | 1.00 | 6.27 |
| 8039 | O | TYR | B | 291 | 23.427 | 31.773 | 24.239 | 1.00 | 5.82 |
| 8040 | N | TYR | B | 292 | 22.454 | 31.553 | 22.269 | 1.00 | 8.05 |
| 8041 | CA | TYR | B | 292 | 23.406 | 30.655 | 21.759 | 1.00 | 9.66 |
| 8042 | CB | TYR | B | 292 | 22.753 | 29.270 | 21.655 | 1.00 | 9.29 |
| 8043 | CG | TYR | B | 292 | 22.360 | 28.687 | 22.957 | 1.00 | 10.61 |
| 8044 | CD1 | TYR | B | 292 | 21.104 | 28.270 | 23.154 | 1.00 | 10.80 |
| 8045 | CE1 | TYR | B | 292 | 20.726 | 27.656 | 24.291 | 1.00 | 12.80 |
| 8046 | CZ | TYR | B | 292 | 21.597 | 27.458 | 25.278 | 1.00 | 10.65 |
| 8047 | OH | TYR | B | 292 | 21.117 | 26.923 | 26.417 | 1.00 | 13.85 |
| 8048 | CE2 | TYR | B | 292 | 22.895 | 27.795 | 25.145 | 1.00 | 14.67 |
| 8049 | CD2 | TYR | B | 292 | 23.293 | 28.443 | 23.957 | 1.00 | 13.23 |

FIGURE 3 (Cont.)

| A | B | C | D | E | F | G | H | I | J |
|---|---|---|---|---|---|---|---|---|---|
| 8050 | C | TYR | B | 292 | 23.825 | 30.938 | 20.386 | 1.00 | 8.03 |
| 8051 | O | TYR | B | 292 | 22.992 | 31.304 | 19.597 | 1.00 | 10.63 |
| 8052 | N | PHE | B | 293 | 25.040 | 30.560 | 20.075 | 1.00 | 7.16 |
| 8053 | CA | PHE | B | 293 | 25.427 | 30.368 | 18.712 | 1.00 | 8.38 |
| 8054 | CB | PHE | B | 293 | 26.902 | 30.664 | 18.570 | 1.00 | 8.97 |
| 8055 | CG | PHE | B | 293 | 27.526 | 30.075 | 17.351 | 1.00 | 12.32 |
| 8056 | CD1 | PHE | B | 293 | 28.373 | 28.989 | 17.459 | 1.00 | 16.51 |
| 8057 | CE1 | PHE | B | 293 | 28.997 | 28.450 | 16.338 | 1.00 | 16.10 |
| 8058 | CZ | PHE | B | 293 | 28.898 | 29.120 | 15.138 | 1.00 | 15.61 |
| 8059 | CE2 | PHE | B | 293 | 28.086 | 30.291 | 15.081 | 1.00 | 10.93 |
| 8060 | CD2 | PHE | B | 293 | 27.460 | 30.724 | 16.155 | 1.00 | 10.26 |
| 8061 | C | PHE | B | 293 | 25.143 | 28.941 | 18.251 | 1.00 | 8.13 |
| 8062 | O | PHE | B | 293 | 25.373 | 27.978 | 18.933 | 1.00 | 7.87 |
| 8063 | N | SER | B | 294 | 24.691 | 28.846 | 17.051 | 1.00 | 8.79 |
| 8064 | CA | SER | B | 294 | 23.966 | 27.744 | 16.569 | 1.00 | 13.15 |
| 8065 | CB | SER | B | 294 | 22.699 | 28.310 | 15.896 | 1.00 | 13.17 |
| 8066 | OG | SER | B | 294 | 21.919 | 27.172 | 15.584 | 1.00 | 23.16 |
| 8067 | C | SER | B | 294 | 24.752 | 26.991 | 15.547 | 1.00 | 12.03 |
| 8068 | O | SER | B | 294 | 24.829 | 25.750 | 15.550 | 1.00 | 14.77 |
| 8069 | N | TRP | B | 295 | 25.264 | 27.767 | 14.610 | 1.00 | 11.72 |
| 8070 | CA | TRP | B | 295 | 26.078 | 27.276 | 13.515 | 1.00 | 12.40 |
| 8071 | CB | TRP | B | 295 | 25.362 | 26.284 | 12.580 | 1.00 | 10.68 |
| 8072 | CG | TRP | B | 295 | 26.329 | 25.635 | 11.698 | 1.00 | 10.37 |
| 8073 | CD1 | TRP | B | 295 | 26.302 | 25.624 | 10.365 | 1.00 | 12.26 |
| 8074 | NE1 | TRP | B | 295 | 27.323 | 24.864 | 9.873 | 1.00 | 6.88 |
| 8075 | CE2 | TRP | B | 295 | 28.079 | 24.426 | 10.911 | 1.00 | 11.42 |
| 8076 | CD2 | TRP | B | 295 | 27.476 | 24.897 | 12.083 | 1.00 | 12.70 |
| 8077 | CE3 | TRP | B | 295 | 28.116 | 24.629 | 13.313 | 1.00 | 21.71 |
| 8078 | CZ3 | TRP | B | 295 | 29.327 | 23.878 | 13.318 | 1.00 | 13.45 |
| 8079 | CH2 | TRP | B | 295 | 29.844 | 23.425 | 12.146 | 1.00 | 17.14 |
| 8080 | CZ2 | TRP | B | 295 | 29.249 | 23.724 | 10.921 | 1.00 | 16.85 |
| 8081 | C | TRP | B | 295 | 26.519 | 28.407 | 12.688 | 1.00 | 10.94 |
| 8082 | O | TRP | B | 295 | 25.995 | 29.378 | 12.780 | 1.00 | 12.25 |
| 8083 | N | LEU | B | 296 | 27.516 | 28.231 | 11.851 | 1.00 | 11.06 |
| 8084 | CA | LEU | B | 296 | 28.011 | 29.300 | 10.958 | 1.00 | 10.50 |
| 8085 | CB | LEU | B | 296 | 29.155 | 29.963 | 11.560 | 1.00 | 7.00 |
| 8086 | CG | LEU | B | 296 | 29.862 | 30.993 | 10.724 | 1.00 | 8.78 |
| 8087 | CD1 | LEU | B | 296 | 30.560 | 32.021 | 11.597 | 1.00 | 4.58 |
| 8088 | CD2 | LEU | B | 296 | 30.781 | 30.346 | 9.619 | 1.00 | 8.19 |
| 8089 | C | LEU | B | 296 | 28.347 | 28.814 | 9.590 | 1.00 | 11.21 |
| 8090 | O | LEU | B | 296 | 28.945 | 27.759 | 9.441 | 1.00 | 11.80 |
| 8091 | N | THR | B | 297 | 27.936 | 29.577 | 8.566 | 1.00 | 11.15 |
| 8092 | CA | THR | B | 297 | 28.119 | 29.121 | 7.196 | 1.00 | 11.54 |
| 8093 | CB | THR | B | 297 | 26.802 | 28.598 | 6.649 | 1.00 | 12.71 |
| 8094 | OG1 | THR | B | 297 | 26.325 | 27.501 | 7.432 | 1.00 | 8.63 |
| 8095 | CG2 | THR | B | 297 | 26.902 | 28.120 | 5.239 | 1.00 | 11.55 |
| 8096 | C | THR | B | 297 | 28.501 | 30.313 | 6.405 | 1.00 | 12.59 |
| 8097 | O | THR | B | 297 | 27.700 | 31.310 | 6.310 | 1.00 | 13.66 |
| 8098 | N | TRP | B | 298 | 29.662 | 30.180 | 5.810 | 1.00 | 10.33 |
| 8099 | CA | TRP | B | 298 | 30.143 | 31.003 | 4.729 | 1.00 | 13.87 |
| 8100 | CB | TRP | B | 298 | 31.629 | 30.715 | 4.436 | 1.00 | 10.62 |

FIGURE 3 (Cont.)

| A | B | C | D | E | F | G | H | I | J |
|---|---|---|---|---|---|---|---|---|---|
| 8101 | CG | TRP | B | 298 | 32.548 | 31.125 | 5.529 | 1.00 | 11.71 |
| 8102 | CD1 | TRP | B | 298 | 33.147 | 30.283 | 6.484 | 1.00 | 10.78 |
| 8103 | NE1 | TRP | B | 298 | 33.952 | 31.044 | 7.309 | 1.00 | 14.43 |
| 8104 | CE2 | TRP | B | 298 | 33.906 | 32.363 | 6.906 | 1.00 | 11.59 |
| 8105 | CD2 | TRP | B | 298 | 33.038 | 32.438 | 5.787 | 1.00 | 10.20 |
| 8106 | CE3 | TRP | B | 298 | 32.877 | 33.646 | 5.174 | 1.00 | 12.82 |
| 8107 | CZ3 | TRP | B | 298 | 33.481 | 34.756 | 5.729 | 1.00 | 13.41 |
| 8108 | CH2 | TRP | B | 298 | 34.307 | 34.627 | 6.869 | 1.00 | 6.70 |
| 8109 | CZ2 | TRP | B | 298 | 34.515 | 33.448 | 7.441 | 1.00 | 5.54 |
| 8110 | C | TRP | B | 298 | 29.454 | 30.863 | 3.402 | 1.00 | 14.90 |
| 8111 | O | TRP | B | 298 | 29.031 | 29.768 | 2.950 | 1.00 | 18.57 |
| 8112 | N | VAL | B | 299 | 29.338 | 31.979 | 2.765 | 1.00 | 15.25 |
| 8113 | CA | VAL | B | 299 | 28.736 | 32.004 | 1.464 | 1.00 | 16.14 |
| 8114 | CB | VAL | B | 299 | 27.644 | 33.085 | 1.459 | 1.00 | 18.20 |
| 8115 | CG1 | VAL | B | 299 | 26.690 | 32.808 | 0.325 | 1.00 | 9.27 |
| 8116 | CG2 | VAL | B | 299 | 26.867 | 33.101 | 2.818 | 1.00 | 14.68 |
| 8117 | C | VAL | B | 299 | 29.909 | 32.336 | 0.554 | 1.00 | 16.86 |
| 8118 | O | VAL | B | 299 | 30.598 | 31.433 | 0.107 | 1.00 | 17.64 |
| 8119 | N | THR | B | 300 | 30.258 | 33.630 | 0.425 | 1.00 | 17.46 |
| 8120 | CA | THR | B | 300 | 31.546 | 33.934 | -0.164 | 1.00 | 16.45 |
| 8121 | CB | THR | B | 300 | 31.451 | 35.043 | -1.115 | 1.00 | 15.84 |
| 8122 | OG1 | THR | B | 300 | 31.203 | 36.237 | -0.389 | 1.00 | 18.17 |
| 8123 | CG2 | THR | B | 300 | 30.326 | 34.893 | -1.942 | 1.00 | 10.84 |
| 8124 | C | THR | B | 300 | 32.593 | 34.299 | 0.878 | 1.00 | 17.87 |
| 8125 | O | THR | B | 300 | 32.323 | 34.337 | 2.043 | 1.00 | 18.12 |
| 8126 | N | ASP | B | 301 | 33.790 | 34.636 | 0.440 | 1.00 | 17.55 |
| 8127 | CA | ASP | B | 301 | 34.727 | 35.302 | 1.294 | 1.00 | 16.94 |
| 8128 | CB | ASP | B | 301 | 36.071 | 35.448 | 0.575 | 1.00 | 17.11 |
| 8129 | CG | ASP | B | 301 | 36.779 | 34.148 | 0.422 | 1.00 | 19.98 |
| 8130 | OD1 | ASP | B | 301 | 37.180 | 33.914 | -0.683 | 1.00 | 28.73 |
| 8131 | OD2 | ASP | B | 301 | 36.992 | 33.301 | 1.294 | 1.00 | 19.32 |
| 8132 | C | ASP | B | 301 | 34.252 | 36.684 | 1.818 | 1.00 | 16.49 |
| 8133 | O | ASP | B | 301 | 34.941 | 37.267 | 2.697 | 1.00 | 18.38 |
| 8134 | N | GLU | B | 302 | 33.133 | 37.207 | 1.356 | 1.00 | 13.57 |
| 8135 | CA | GLU | B | 302 | 32.674 | 38.540 | 1.849 | 1.00 | 14.97 |
| 8136 | CB | GLU | B | 302 | 32.507 | 39.556 | 0.713 | 1.00 | 14.64 |
| 8137 | CG | GLU | B | 302 | 33.765 | 40.269 | 0.239 | 1.00 | 23.33 |
| 8138 | CD | GLU | B | 302 | 34.686 | 39.399 | -0.637 | 1.00 | 29.48 |
| 8139 | OE1 | GLU | B | 302 | 34.208 | 38.456 | -1.427 | 1.00 | 29.59 |
| 8140 | OE2 | GLU | B | 302 | 35.931 | 39.688 | -0.524 | 1.00 | 35.27 |
| 8141 | C | GLU | B | 302 | 31.313 | 38.471 | 2.510 | 1.00 | 12.91 |
| 8142 | O | GLU | B | 302 | 30.745 | 39.476 | 2.904 | 1.00 | 12.31 |
| 8143 | N | ARG | B | 303 | 30.808 | 37.259 | 2.617 | 1.00 | 11.91 |
| 8144 | CA | ARG | B | 303 | 29.466 | 37.038 | 3.114 | 1.00 | 11.40 |
| 8145 | CB | ARG | B | 303 | 28.450 | 36.953 | 1.941 | 1.00 | 10.41 |
| 8146 | CG | ARG | B | 303 | 26.963 | 37.087 | 2.222 | 1.00 | 8.01 |
| 8147 | CD | ARG | B | 303 | 26.377 | 38.062 | 1.172 | 1.00 | 13.59 |
| 8148 | NE | ARG | B | 303 | 25.049 | 37.697 | 0.941 | 1.00 | 7.35 |
| 8149 | CZ | ARG | B | 303 | 24.036 | 38.551 | 0.938 | 1.00 | 20.49 |
| 8150 | NH1 | ARG | B | 303 | 22.781 | 38.047 | 0.768 | 1.00 | 10.39 |
| 8151 | NH2 | ARG | B | 303 | 24.247 | 39.925 | 1.053 | 1.00 | 17.35 |

FIGURE 3 (Cont.)

| A | B | C | D | E | F | G | H | I | J |
|---|---|---|---|---|---|---|---|---|---|
| 8152 | C | ARG | B | 303 | 29.544 | 35.789 | 3.894 | 1.00 | 11.55 |
| 8153 | O | ARG | B | 303 | 29.939 | 34.695 | 3.428 | 1.00 | 10.40 |
| 8154 | N | VAL | B | 304 | 29.139 | 35.990 | 5.128 | 1.00 | 11.88 |
| 8155 | CA | VAL | B | 304 | 28.984 | 34.933 | 6.124 | 1.00 | 10.95 |
| 8156 | CB | VAL | B | 304 | 30.016 | 35.188 | 7.174 | 1.00 | 9.39 |
| 8157 | CG1 | VAL | B | 304 | 29.656 | 36.392 | 7.999 | 1.00 | 8.84 |
| 8158 | CG2 | VAL | B | 304 | 30.291 | 34.003 | 8.013 | 1.00 | 10.00 |
| 8159 | C | VAL | B | 304 | 27.532 | 34.910 | 6.699 | 1.00 | 12.11 |
| 8160 | O | VAL | B | 304 | 26.836 | 35.948 | 6.790 | 1.00 | 12.57 |
| 8161 | N | CYS | B | 305 | 27.111 | 33.733 | 7.081 | 1.00 | 11.54 |
| 8162 | CA | CYS | B | 305 | 25.794 | 33.577 | 7.670 | 1.00 | 13.08 |
| 8163 | CB | CYS | B | 305 | 24.978 | 32.668 | 6.802 | 1.00 | 12.58 |
| 8164 | SG | CYS | B | 305 | 23.368 | 32.086 | 7.400 | 1.00 | 14.78 |
| 8165 | C | CYS | B | 305 | 25.853 | 32.946 | 9.097 | 1.00 | 13.30 |
| 8166 | O | CYS | B | 305 | 26.433 | 31.874 | 9.301 | 1.00 | 13.21 |
| 8167 | N | LEU | B | 306 | 25.215 | 33.633 | 10.051 | 1.00 | 11.01 |
| 8168 | CA | LEU | B | 306 | 25.277 | 33.293 | 11.454 | 1.00 | 9.29 |
| 8169 | CB | LEU | B | 306 | 25.782 | 34.472 | 12.310 | 1.00 | 10.20 |
| 8170 | CG | LEU | B | 306 | 27.329 | 34.401 | 12.283 | 1.00 | 11.43 |
| 8171 | CD1 | LEU | B | 306 | 27.802 | 35.306 | 11.303 | 1.00 | 9.08 |
| 8172 | CD2 | LEU | B | 306 | 27.909 | 34.672 | 13.500 | 1.00 | 9.61 |
| 8173 | C | LEU | B | 306 | 23.915 | 32.841 | 11.878 | 1.00 | 11.77 |
| 8174 | O | LEU | B | 306 | 22.941 | 33.374 | 11.444 | 1.00 | 8.75 |
| 8175 | N | GLN | B | 307 | 23.859 | 31.786 | 12.659 | 1.00 | 13.39 |
| 8176 | CA | GLN | B | 307 | 22.573 | 31.412 | 13.192 | 1.00 | 14.52 |
| 8177 | CB | GLN | B | 307 | 22.223 | 30.004 | 12.683 | 1.00 | 16.13 |
| 8178 | CG | GLN | B | 307 | 21.540 | 29.963 | 11.276 | 1.00 | 13.58 |
| 8179 | CD | GLN | B | 307 | 21.294 | 28.530 | 10.830 | 1.00 | 13.67 |
| 8180 | OE1 | GLN | B | 307 | 22.239 | 27.813 | 10.568 | 1.00 | 12.14 |
| 8181 | NE2 | GLN | B | 307 | 20.046 | 28.124 | 10.738 | 1.00 | 9.54 |
| 8182 | C | GLN | B | 307 | 22.687 | 31.522 | 14.734 | 1.00 | 14.87 |
| 8183 | O | GLN | B | 307 | 23.672 | 31.174 | 15.321 | 1.00 | 16.82 |
| 8184 | N | TRP | B | 308 | 21.734 | 32.142 | 15.346 | 1.00 | 13.33 |
| 8185 | CA | TRP | B | 308 | 21.663 | 32.317 | 16.744 | 1.00 | 12.75 |
| 8186 | CB | TRP | B | 308 | 21.699 | 33.799 | 17.067 | 1.00 | 11.78 |
| 8187 | CG | TRP | B | 308 | 22.699 | 34.528 | 16.407 | 1.00 | 11.77 |
| 8188 | CD1 | TRP | B | 308 | 22.571 | 35.101 | 15.207 | 1.00 | 10.36 |
| 8189 | NE1 | TRP | B | 308 | 23.705 | 35.769 | 14.868 | 1.00 | 11.98 |
| 8190 | CE2 | TRP | B | 308 | 24.623 | 35.578 | 15.860 | 1.00 | 13.95 |
| 8191 | CD2 | TRP | B | 308 | 23.999 | 34.813 | 16.857 | 1.00 | 9.17 |
| 8192 | CE3 | TRP | B | 308 | 24.733 | 34.471 | 17.980 | 1.00 | 10.13 |
| 8193 | CZ3 | TRP | B | 308 | 26.000 | 34.940 | 18.109 | 1.00 | 9.04 |
| 8194 | CH2 | TRP | B | 308 | 26.622 | 35.708 | 17.118 | 1.00 | 8.83 |
| 8195 | CZ2 | TRP | B | 308 | 25.955 | 36.050 | 15.977 | 1.00 | 8.16 |
| 8196 | C | TRP | B | 308 | 20.294 | 31.698 | 17.259 | 1.00 | 13.56 |
| 8197 | O | TRP | B | 308 | 19.448 | 31.353 | 16.519 | 1.00 | 14.64 |
| 8198 | N | LEU | B | 309 | 20.174 | 31.478 | 18.544 | 1.00 | 12.86 |
| 8199 | CA | LEU | B | 309 | 19.083 | 30.704 | 19.091 | 1.00 | 10.90 |
| 8200 | CB | LEU | B | 309 | 19.502 | 29.263 | 19.123 | 1.00 | 9.70 |
| 8201 | CG | LEU | B | 309 | 18.466 | 28.276 | 19.600 | 1.00 | 9.93 |
| 8202 | CD1 | LEU | B | 309 | 17.294 | 28.511 | 18.825 | 1.00 | 6.81 |

FIGURE 3 (Cont.)

| A | B | C | D | E | F | G | H | I | J |
|---|---|---|---|---|---|---|---|---|---|
| 8203 | CD2 | LEU | B | 309 | 18.964 | 26.814 | 19.445 | 1.00 | 12.27 |
| 8204 | C | LEU | B | 309 | 18.892 | 31.276 | 20.462 | 1.00 | 10.41 |
| 8205 | O | LEU | B | 309 | 19.759 | 31.244 | 21.295 | 1.00 | 12.77 |
| 8206 | N | LYS | B | 310 | 17.830 | 32.007 | 20.640 | 1.00 | 9.06 |
| 8207 | CA | LYS | B | 310 | 17.402 | 32.430 | 21.942 | 1.00 | 8.65 |
| 8208 | CB | LYS | B | 310 | 15.961 | 32.954 | 21.835 | 1.00 | 7.23 |
| 8209 | CG | LYS | B | 310 | 15.899 | 34.330 | 21.231 | 1.00 | 9.84 |
| 8210 | CD | LYS | B | 310 | 14.563 | 35.012 | 21.541 | 1.00 | 11.78 |
| 8211 | CE | LYS | B | 310 | 14.638 | 36.421 | 22.111 | 1.00 | 16.59 |
| 8212 | NZ | LYS | B | 310 | 15.648 | 36.665 | 23.114 | 1.00 | 20.80 |
| 8213 | C | LYS | B | 310 | 17.511 | 31.212 | 22.917 | 1.00 | 9.86 |
| 8214 | O | LYS | B | 310 | 17.246 | 30.032 | 22.532 | 1.00 | 10.97 |
| 8215 | N | ARG | B | 311 | 17.868 | 31.540 | 24.167 | 1.00 | 8.45 |
| 8216 | CA | ARG | B | 311 | 17.917 | 30.559 | 25.210 | 1.00 | 8.04 |
| 8217 | CB | ARG | B | 311 | 18.484 | 31.076 | 26.531 | 1.00 | 7.14 |
| 8218 | CG | ARG | B | 311 | 18.672 | 29.872 | 27.525 | 1.00 | 11.79 |
| 8219 | CD | ARG | B | 311 | 19.363 | 30.226 | 28.729 | 1.00 | 9.53 |
| 8220 | NE | ARG | B | 311 | 19.264 | 29.221 | 29.768 | 1.00 | 10.49 |
| 8221 | CZ | ARG | B | 311 | 20.130 | 29.190 | 30.768 | 1.00 | 10.67 |
| 8222 | NH1 | ARG | B | 311 | 20.115 | 28.283 | 31.635 | 1.00 | 8.96 |
| 8223 | NH2 | ARG | B | 311 | 21.089 | 30.050 | 30.855 | 1.00 | 10.69 |
| 8224 | C | ARG | B | 311 | 16.594 | 29.759 | 25.428 | 1.00 | 8.82 |
| 8225 | O | ARG | B | 311 | 16.697 | 28.553 | 25.734 | 1.00 | 8.90 |
| 8226 | N | VAL | B | 312 | 15.449 | 30.433 | 25.326 | 1.00 | 7.58 |
| 8227 | CA | VAL | B | 312 | 14.134 | 29.793 | 25.160 | 1.00 | 9.72 |
| 8228 | CB | VAL | B | 312 | 12.937 | 30.824 | 25.412 | 1.00 | 9.83 |
| 8229 | CG1 | VAL | B | 312 | 11.546 | 30.248 | 25.205 | 1.00 | 9.46 |
| 8230 | CG2 | VAL | B | 312 | 12.898 | 31.312 | 26.907 | 1.00 | 6.62 |
| 8231 | C | VAL | B | 312 | 14.175 | 29.418 | 23.725 | 1.00 | 13.12 |
| 8232 | O | VAL | B | 312 | 14.085 | 30.290 | 22.841 | 1.00 | 15.76 |
| 8233 | N | GLN | B | 313 | 14.338 | 28.160 | 23.389 | 1.00 | 13.61 |
| 8234 | CA | GLN | B | 313 | 14.837 | 27.948 | 22.077 | 1.00 | 11.90 |
| 8235 | CB | GLN | B | 313 | 15.734 | 26.705 | 22.105 | 1.00 | 12.89 |
| 8236 | CG | GLN | B | 313 | 16.898 | 26.638 | 23.149 | 1.00 | 9.30 |
| 8237 | CD | GLN | B | 313 | 17.559 | 25.160 | 23.217 | 1.00 | 11.08 |
| 8238 | OE1 | GLN | B | 313 | 17.909 | 24.674 | 24.304 | 1.00 | 15.23 |
| 8239 | NE2 | GLN | B | 313 | 17.661 | 24.486 | 22.085 | 1.00 | 12.95 |
| 8240 | C | GLN | B | 313 | 13.711 | 27.786 | 21.059 | 1.00 | 12.45 |
| 8241 | O | GLN | B | 313 | 13.656 | 26.784 | 20.302 | 1.00 | 12.28 |
| 8242 | N | ASN | B | 314 | 12.738 | 28.684 | 21.090 | 1.00 | 12.45 |
| 8243 | CA | ASN | B | 314 | 11.493 | 28.515 | 20.294 | 1.00 | 13.16 |
| 8244 | CB | ASN | B | 314 | 10.135 | 28.616 | 21.132 | 1.00 | 12.46 |
| 8245 | CG | ASN | B | 314 | 9.855 | 30.066 | 21.772 | 1.00 | 17.84 |
| 8246 | OD1 | ASN | B | 314 | 10.777 | 30.910 | 21.773 | 1.00 | 21.70 |
| 8247 | ND2 | ASN | B | 314 | 8.592 | 30.313 | 22.353 | 1.00 | 22.58 |
| 8248 | C | ASN | B | 314 | 11.618 | 29.489 | 19.143 | 1.00 | 11.57 |
| 8249 | O | ASN | B | 314 | 10.769 | 29.602 | 18.331 | 1.00 | 12.63 |
| 8250 | N | VAL | B | 315 | 12.738 | 30.165 | 19.119 | 1.00 | 8.21 |
| 8251 | CA | VAL | B | 315 | 13.055 | 31.255 | 18.205 | 1.00 | 8.66 |
| 8252 | CB | VAL | B | 315 | 12.966 | 32.563 | 18.864 | 1.00 | 8.40 |
| 8253 | CG1 | VAL | B | 315 | 13.394 | 33.651 | 17.848 | 1.00 | 6.98 |

FIGURE 3 (Cont.)

| A | B | C | D | E | F | G | H | I | J |
|---|---|---|---|---|---|---|---|---|---|
| 8254 | CG2 | VAL | B | 315 | 11.503 | 32.842 | 19.288 | 1.00 | 6.37 |
| 8255 | C | VAL | B | 315 | 14.469 | 31.185 | 17.688 | 1.00 | 9.29 |
| 8256 | O | VAL | B | 315 | 15.377 | 31.241 | 18.450 | 1.00 | 9.68 |
| 8257 | N | SER | B | 316 | 14.670 | 31.036 | 16.388 | 1.00 | 11.82 |
| 8258 | CA | SER | B | 316 | 16.074 | 31.066 | 15.806 | 1.00 | 11.71 |
| 8259 | CB | SER | B | 316 | 16.351 | 29.859 | 14.945 | 1.00 | 11.98 |
| 8260 | OG | SER | B | 316 | 17.712 | 29.979 | 14.500 | 1.00 | 21.26 |
| 8261 | C | SER | B | 316 | 16.256 | 32.191 | 14.887 | 1.00 | 10.74 |
| 8262 | O | SER | B | 316 | 15.317 | 32.482 | 14.263 | 1.00 | 9.19 |
| 8263 | N | VAL | B | 317 | 17.443 | 32.768 | 14.750 | 1.00 | 10.48 |
| 8264 | CA | VAL | B | 317 | 17.612 | 33.887 | 13.785 | 1.00 | 12.61 |
| 8265 | CB | VAL | B | 317 | 17.931 | 35.172 | 14.446 | 1.00 | 12.44 |
| 8266 | CG1 | VAL | B | 317 | 18.187 | 36.280 | 13.411 | 1.00 | 14.06 |
| 8267 | CG2 | VAL | B | 317 | 16.827 | 35.462 | 15.223 | 1.00 | 13.87 |
| 8268 | C | VAL | B | 317 | 18.760 | 33.617 | 12.927 | 1.00 | 13.01 |
| 8269 | O | VAL | B | 317 | 19.737 | 33.239 | 13.441 | 1.00 | 15.05 |
| 8270 | N | LEU | B | 318 | 18.657 | 33.841 | 11.612 | 1.00 | 14.15 |
| 8271 | CA | LEU | B | 318 | 19.758 | 33.611 | 10.725 | 1.00 | 13.76 |
| 8272 | CB | LEU | B | 318 | 19.336 | 32.653 | 9.617 | 1.00 | 14.93 |
| 8273 | CG | LEU | B | 318 | 20.173 | 32.606 | 8.335 | 1.00 | 12.37 |
| 8274 | CD1 | LEU | B | 318 | 19.793 | 31.312 | 7.680 | 1.00 | 5.55 |
| 8275 | CD2 | LEU | B | 318 | 19.944 | 33.776 | 7.367 | 1.00 | 7.65 |
| 8276 | C | LEU | B | 318 | 20.104 | 35.007 | 10.220 | 1.00 | 14.48 |
| 8277 | O | LEU | B | 318 | 19.249 | 35.741 | 9.709 | 1.00 | 14.51 |
| 8278 | N | SER | B | 319 | 21.354 | 35.373 | 10.435 | 1.00 | 14.01 |
| 8279 | CA | SER | B | 319 | 21.876 | 36.674 | 10.099 | 1.00 | 13.53 |
| 8280 | CB | SER | B | 319 | 22.669 | 37.269 | 11.276 | 1.00 | 12.75 |
| 8281 | OG | SER | B | 319 | 22.355 | 38.740 | 11.458 | 1.00 | 14.53 |
| 8282 | C | SER | B | 319 | 22.778 | 36.431 | 8.898 | 1.00 | 13.11 |
| 8283 | O | SER | B | 319 | 23.708 | 35.487 | 8.891 | 1.00 | 17.13 |
| 8284 | N | ILE | B | 320 | 22.583 | 37.187 | 7.864 | 1.00 | 9.26 |
| 8285 | CA | ILE | B | 320 | 23.618 | 37.205 | 6.867 | 1.00 | 9.99 |
| 8286 | CB | ILE | B | 320 | 23.037 | 36.981 | 5.466 | 1.00 | 9.52 |
| 8287 | CG1 | ILE | B | 320 | 22.453 | 35.536 | 5.296 | 1.00 | 10.16 |
| 8288 | CD1 | ILE | B | 320 | 21.457 | 35.572 | 4.250 | 1.00 | 11.42 |
| 8289 | CG2 | ILE | B | 320 | 24.083 | 37.128 | 4.407 | 1.00 | 9.00 |
| 8290 | C | ILE | B | 320 | 24.325 | 38.560 | 6.998 | 1.00 | 9.76 |
| 8291 | O | ILE | B | 320 | 23.651 | 39.621 | 7.011 | 1.00 | 4.13 |
| 8292 | N | CYS | B | 321 | 25.677 | 38.512 | 6.907 | 1.00 | 7.12 |
| 8293 | CA | CYS | B | 321 | 26.547 | 39.624 | 7.187 | 1.00 | 9.19 |
| 8294 | CB | CYS | B | 321 | 27.375 | 39.207 | 8.428 | 1.00 | 12.57 |
| 8295 | SG | CYS | B | 321 | 26.577 | 39.099 | 10.011 | 1.00 | 15.27 |
| 8296 | C | CYS | B | 321 | 27.582 | 39.847 | 6.045 | 1.00 | 10.65 |
| 8297 | O | CYS | B | 321 | 28.253 | 38.921 | 5.612 | 1.00 | 6.61 |
| 8298 | N | ASP | B | 322 | 27.749 | 41.105 | 5.607 | 1.00 | 11.82 |
| 8299 | CA | ASP | B | 322 | 28.623 | 41.447 | 4.448 | 1.00 | 11.80 |
| 8300 | CB | ASP | B | 322 | 27.836 | 42.249 | 3.445 | 1.00 | 11.70 |
| 8301 | CG | ASP | B | 322 | 26.712 | 41.412 | 2.926 | 1.00 | 16.81 |
| 8302 | OD1 | ASP | B | 322 | 27.074 | 40.330 | 2.378 | 1.00 | 16.93 |
| 8303 | OD2 | ASP | B | 322 | 25.458 | 41.687 | 3.079 | 1.00 | 23.37 |
| 8304 | C | ASP | B | 322 | 29.850 | 42.125 | 4.881 | 1.00 | 10.54 |

FIGURE 3 (Cont.)

| A | B | C | D | E | F | G | H | I | J |
|---|---|---|---|---|---|---|---|---|---|
| 8305 | O | ASP | B | 322 | 29.880 | 42.530 | 5.975 | 1.00 | 10.05 |
| 8306 | N | PHE | B | 323 | 30.884 | 42.170 | 4.063 | 1.00 | 11.51 |
| 8307 | CA | PHE | B | 323 | 32.194 | 42.700 | 4.493 | 1.00 | 10.62 |
| 8308 | CB | PHE | B | 323 | 33.394 | 41.784 | 3.994 | 1.00 | 11.30 |
| 8309 | CG | PHE | B | 323 | 34.774 | 42.247 | 4.504 | 1.00 | 8.32 |
| 8310 | CD1 | PHE | B | 323 | 35.616 | 42.963 | 3.698 | 1.00 | 10.95 |
| 8311 | CE1 | PHE | B | 323 | 36.839 | 43.463 | 4.183 | 1.00 | 4.02 |
| 8312 | CZ | PHE | B | 323 | 37.182 | 43.309 | 5.551 | 1.00 | 3.59 |
| 8313 | CE2 | PHE | B | 323 | 36.341 | 42.634 | 6.408 | 1.00 | 7.32 |
| 8314 | CD2 | PHE | B | 323 | 35.125 | 42.078 | 5.855 | 1.00 | 12.78 |
| 8315 | C | PHE | B | 323 | 32.233 | 44.162 | 4.031 | 1.00 | 12.84 |
| 8316 | O | PHE | B | 323 | 31.601 | 44.555 | 3.054 | 1.00 | 13.73 |
| 8317 | N | ARG | B | 324 | 32.927 | 45.013 | 4.751 | 1.00 | 14.35 |
| 8318 | CA | ARG | B | 324 | 32.876 | 46.468 | 4.540 | 1.00 | 14.28 |
| 8319 | CB | ARG | B | 324 | 32.297 | 47.046 | 5.786 | 1.00 | 14.30 |
| 8320 | CG | ARG | B | 324 | 31.138 | 48.114 | 5.780 | 1.00 | 16.02 |
| 8321 | CD | ARG | B | 324 | 31.169 | 48.712 | 7.148 | 1.00 | 14.53 |
| 8322 | NE | ARG | B | 324 | 30.046 | 49.396 | 7.734 | 1.00 | 25.20 |
| 8323 | CZ | ARG | B | 324 | 29.939 | 50.718 | 7.829 | 1.00 | 30.47 |
| 8324 | NH1 | ARG | B | 324 | 28.945 | 51.210 | 8.521 | 1.00 | 33.21 |
| 8325 | NH2 | ARG | B | 324 | 30.755 | 51.556 | 7.212 | 1.00 | 25.51 |
| 8326 | C | ARG | B | 324 | 34.372 | 46.889 | 4.417 | 1.00 | 16.02 |
| 8327 | O | ARG | B | 324 | 35.201 | 46.765 | 5.351 | 1.00 | 16.10 |
| 8328 | N | GLU | B | 325 | 34.742 | 47.299 | 3.235 | 1.00 | 16.83 |
| 8329 | CA | GLU | B | 325 | 36.111 | 47.642 | 2.972 | 1.00 | 17.05 |
| 8330 | CB | GLU | B | 325 | 36.277 | 47.843 | 1.466 | 1.00 | 18.65 |
| 8331 | CG | GLU | B | 325 | 36.121 | 46.487 | 0.752 | 1.00 | 25.05 |
| 8332 | CD | GLU | B | 325 | 36.426 | 46.529 | -0.742 | 1.00 | 32.24 |
| 8333 | OE1 | GLU | B | 325 | 36.916 | 45.451 | -1.198 | 1.00 | 34.47 |
| 8334 | OE2 | GLU | B | 325 | 36.208 | 47.601 | -1.441 | 1.00 | 30.65 |
| 8335 | C | GLU | B | 325 | 36.614 | 48.836 | 3.770 | 1.00 | 15.56 |
| 8336 | O | GLU | B | 325 | 37.784 | 48.805 | 4.233 | 1.00 | 16.28 |
| 8337 | N | ASP | B | 326 | 35.730 | 49.784 | 4.019 | 1.00 | 13.21 |
| 8338 | CA | ASP | B | 326 | 36.086 | 51.092 | 4.484 | 1.00 | 13.98 |
| 8339 | CB | ASP | B | 326 | 34.951 | 52.149 | 4.343 | 1.00 | 15.14 |
| 8340 | CG | ASP | B | 326 | 33.556 | 51.543 | 4.345 | 1.00 | 18.47 |
| 8341 | OD1 | ASP | B | 326 | 33.179 | 51.035 | 5.399 | 1.00 | 22.81 |
| 8342 | OD2 | ASP | B | 326 | 32.762 | 51.485 | 3.341 | 1.00 | 29.89 |
| 8343 | C | ASP | B | 326 | 36.451 | 51.049 | 5.884 | 1.00 | 14.03 |
| 8344 | O | ASP | B | 326 | 37.338 | 51.772 | 6.306 | 1.00 | 13.90 |
| 8345 | N | TRP | B | 327 | 35.785 | 50.166 | 6.596 | 1.00 | 14.71 |
| 8346 | CA | TRP | B | 327 | 36.009 | 49.954 | 8.037 | 1.00 | 16.69 |
| 8347 | CB | TRP | B | 327 | 34.678 | 50.099 | 8.861 | 1.00 | 17.05 |
| 8348 | CG | TRP | B | 327 | 34.169 | 51.563 | 9.069 | 1.00 | 23.40 |
| 8349 | CD1 | TRP | B | 327 | 33.131 | 52.144 | 8.410 | 1.00 | 24.24 |
| 8350 | NE1 | TRP | B | 327 | 32.945 | 53.434 | 8.812 | 1.00 | 24.93 |
| 8351 | CE2 | TRP | B | 327 | 33.842 | 53.739 | 9.807 | 1.00 | 30.63 |
| 8352 | CD2 | TRP | B | 327 | 34.659 | 52.555 | 10.002 | 1.00 | 31.24 |
| 8353 | CE3 | TRP | B | 327 | 35.722 | 52.591 | 10.980 | 1.00 | 33.95 |
| 8354 | CZ3 | TRP | B | 327 | 35.940 | 53.841 | 11.750 | 1.00 | 36.64 |
| 8355 | CH2 | TRP | B | 327 | 35.076 | 55.044 | 11.526 | 1.00 | 35.73 |

FIGURE 3 (Cont.)

| A | B | C | D | E | F | G | H | I | J |
|---|---|---|---|---|---|---|---|---|---|
| 8356 | CZ2 | TRP | B | 327 | 34.044 | 55.007 | 10.573 | 1.00 | 34.04 |
| 8357 | C | TRP | B | 327 | 36.628 | 48.586 | 8.341 | 1.00 | 15.47 |
| 8358 | O | TRP | B | 327 | 37.150 | 48.367 | 9.429 | 1.00 | 16.62 |
| 8359 | N | GLN | B | 328 | 36.604 | 47.652 | 7.431 | 1.00 | 13.77 |
| 8360 | CA | GLN | B | 328 | 37.182 | 46.419 | 7.758 | 1.00 | 12.45 |
| 8361 | CB | GLN | B | 328 | 38.320 | 45.963 | 7.024 | 1.00 | 13.44 |
| 8362 | CG | GLN | B | 328 | 39.320 | 46.837 | 6.473 | 1.00 | 12.30 |
| 8363 | CD | GLN | B | 328 | 39.697 | 46.112 | 5.207 | 1.00 | 7.44 |
| 8364 | OE1 | GLN | B | 328 | 40.091 | 44.959 | 5.255 | 1.00 | 7.72 |
| 8365 | NE2 | GLN | B | 328 | 39.412 | 46.676 | 4.140 | 1.00 | 11.47 |
| 8366 | C | GLN | B | 328 | 36.698 | 45.336 | 8.579 | 1.00 | 14.39 |
| 8367 | O | GLN | B | 328 | 37.507 | 44.546 | 9.122 | 1.00 | 15.90 |
| 8368 | N | THR | B | 329 | 35.399 | 45.156 | 8.451 | 1.00 | 14.82 |
| 8369 | CA | THR | B | 329 | 34.563 | 44.789 | 9.551 | 1.00 | 15.63 |
| 8370 | CB | THR | B | 329 | 34.303 | 46.130 | 10.221 | 1.00 | 16.48 |
| 8371 | OG1 | THR | B | 329 | 34.675 | 46.061 | 11.590 | 1.00 | 16.55 |
| 8372 | CG2 | THR | B | 329 | 32.907 | 46.543 | 10.108 | 1.00 | 14.23 |
| 8373 | C | THR | B | 329 | 33.268 | 44.140 | 9.009 | 1.00 | 14.73 |
| 8374 | O | THR | B | 329 | 33.029 | 44.154 | 7.803 | 1.00 | 15.19 |
| 8375 | N | TRP | B | 330 | 32.459 | 43.548 | 9.847 | 1.00 | 13.44 |
| 8376 | CA | TRP | B | 330 | 31.248 | 42.917 | 9.296 | 1.00 | 11.49 |
| 8377 | CB | TRP | B | 330 | 31.133 | 41.434 | 9.730 | 1.00 | 12.20 |
| 8378 | CG | TRP | B | 330 | 32.278 | 40.679 | 9.210 | 1.00 | 8.57 |
| 8379 | CD1 | TRP | B | 330 | 33.512 | 40.787 | 9.659 | 1.00 | 5.97 |
| 8380 | NE1 | TRP | B | 330 | 34.366 | 40.062 | 8.870 | 1.00 | 14.07 |
| 8381 | CE2 | TRP | B | 330 | 33.686 | 39.549 | 7.821 | 1.00 | 11.37 |
| 8382 | CD2 | TRP | B | 330 | 32.357 | 39.970 | 7.971 | 1.00 | 11.00 |
| 8383 | CE3 | TRP | B | 330 | 31.438 | 39.582 | 7.022 | 1.00 | 4.21 |
| 8384 | CZ3 | TRP | B | 330 | 31.839 | 38.823 | 5.980 | 1.00 | 12.37 |
| 8385 | CH2 | TRP | B | 330 | 33.223 | 38.413 | 5.851 | 1.00 | 9.12 |
| 8386 | CZ2 | TRP | B | 330 | 34.117 | 38.765 | 6.793 | 1.00 | 10.83 |
| 8387 | C | TRP | B | 330 | 30.038 | 43.729 | 9.583 | 1.00 | 12.65 |
| 8388 | O | TRP | B | 330 | 29.931 | 44.464 | 10.618 | 1.00 | 13.04 |
| 8389 | N | ASP | B | 331 | 29.113 | 43.663 | 8.623 | 1.00 | 14.17 |
| 8390 | CA | ASP | B | 331 | 27.870 | 44.425 | 8.705 | 1.00 | 16.12 |
| 8391 | CB | ASP | B | 331 | 27.837 | 45.538 | 7.664 | 1.00 | 15.43 |
| 8392 | CG | ASP | B | 331 | 26.510 | 46.248 | 7.624 | 1.00 | 19.12 |
| 8393 | OD1 | ASP | B | 331 | 26.297 | 47.032 | 8.564 | 1.00 | 17.03 |
| 8394 | OD2 | ASP | B | 331 | 25.639 | 46.054 | 6.713 | 1.00 | 16.02 |
| 8395 | C | ASP | B | 331 | 26.681 | 43.508 | 8.458 | 1.00 | 16.90 |
| 8396 | O | ASP | B | 331 | 26.708 | 42.774 | 7.419 | 1.00 | 17.61 |
| 8397 | N | CYS | B | 332 | 25.680 | 43.581 | 9.366 | 1.00 | 14.56 |
| 8398 | CA | CYS | B | 332 | 24.553 | 42.657 | 9.370 | 1.00 | 16.74 |
| 8399 | CB | CYS | B | 332 | 24.569 | 41.692 | 10.534 | 1.00 | 15.82 |
| 8400 | SG | CYS | B | 332 | 26.175 | 41.000 | 10.920 | 1.00 | 21.52 |
| 8401 | C | CYS | B | 332 | 23.234 | 43.393 | 9.422 | 1.00 | 16.97 |
| 8402 | O | CYS | B | 332 | 22.655 | 43.626 | 10.450 | 1.00 | 18.00 |
| 8403 | N | PRO | B | 333 | 22.704 | 43.728 | 8.303 | 1.00 | 14.87 |
| 8404 | CA | PRO | B | 333 | 21.524 | 44.535 | 8.386 | 1.00 | 15.55 |
| 8405 | CB | PRO | B | 333 | 21.519 | 45.282 | 7.040 | 1.00 | 16.14 |
| 8406 | CG | PRO | B | 333 | 22.618 | 44.468 | 6.094 | 1.00 | 14.13 |

FIGURE 3 (Cont.)

| A | B | C | D | E | F | G | H | I | J |
|---|---|---|---|---|---|---|---|---|---|
| 8407 | CD | PRO | B | 333 | 23.079 | 43.319 | 6.941 | 1.00 | 13.68 |
| 8408 | C | PRO | B | 333 | 20.251 | 43.649 | 8.703 | 1.00 | 16.61 |
| 8409 | O | PRO | B | 333 | 20.130 | 42.443 | 8.342 | 1.00 | 14.30 |
| 8410 | N | LYS | B | 334 | 19.339 | 44.320 | 9.422 | 1.00 | 16.92 |
| 8411 | CA | LYS | B | 334 | 18.052 | 43.750 | 9.763 | 1.00 | 19.18 |
| 8412 | CB | LYS | B | 334 | 17.108 | 44.847 | 10.235 | 1.00 | 19.07 |
| 8413 | CG | LYS | B | 334 | 17.004 | 44.964 | 11.780 | 1.00 | 24.70 |
| 8414 | CD | LYS | B | 334 | 17.835 | 46.167 | 12.342 | 1.00 | 30.71 |
| 8415 | CE | LYS | B | 334 | 17.128 | 47.588 | 12.324 | 1.00 | 28.09 |
| 8416 | NZ | LYS | B | 334 | 18.213 | 48.675 | 12.556 | 1.00 | 22.83 |
| 8417 | C | LYS | B | 334 | 17.413 | 43.005 | 8.608 | 1.00 | 18.33 |
| 8418 | O | LYS | B | 334 | 16.858 | 41.891 | 8.749 | 1.00 | 18.76 |
| 8419 | N | THR | B | 335 | 17.502 | 43.602 | 7.454 | 1.00 | 17.39 |
| 8420 | CA | THR | B | 335 | 16.790 | 43.128 | 6.289 | 1.00 | 17.15 |
| 8421 | CB | THR | B | 335 | 17.008 | 44.281 | 5.266 | 1.00 | 17.06 |
| 8422 | OG1 | THR | B | 335 | 16.022 | 44.254 | 4.237 | 1.00 | 21.55 |
| 8423 | CG2 | THR | B | 335 | 18.355 | 44.208 | 4.557 | 1.00 | 19.96 |
| 8424 | C | THR | B | 335 | 17.310 | 41.769 | 5.810 | 1.00 | 16.06 |
| 8425 | O | THR | B | 335 | 16.767 | 41.153 | 4.920 | 1.00 | 16.83 |
| 8426 | N | GLN | B | 336 | 18.439 | 41.361 | 6.393 | 1.00 | 14.36 |
| 8427 | CA | GLN | B | 336 | 19.145 | 40.069 | 6.206 | 1.00 | 13.43 |
| 8428 | CB | GLN | B | 336 | 20.560 | 40.273 | 5.684 | 1.00 | 11.59 |
| 8429 | CG | GLN | B | 336 | 20.597 | 40.596 | 4.204 | 1.00 | 12.74 |
| 8430 | CD | GLN | B | 336 | 21.981 | 41.074 | 3.695 | 1.00 | 15.82 |
| 8431 | OE1 | GLN | B | 336 | 22.074 | 41.401 | 2.530 | 1.00 | 22.77 |
| 8432 | NE2 | GLN | B | 336 | 23.072 | 40.975 | 4.531 | 1.00 | 19.15 |
| 8433 | C | GLN | B | 336 | 19.226 | 39.257 | 7.506 | 1.00 | 13.33 |
| 8434 | O | GLN | B | 336 | 20.003 | 38.293 | 7.600 | 1.00 | 12.98 |
| 8435 | N | GLU | B | 337 | 18.344 | 39.621 | 8.436 | 1.00 | 12.47 |
| 8436 | CA | GLU | B | 337 | 17.937 | 38.787 | 9.561 | 1.00 | 12.67 |
| 8437 | CB | GLU | B | 337 | 17.646 | 39.657 | 10.772 | 1.00 | 12.88 |
| 8438 | CG | GLU | B | 337 | 18.779 | 39.824 | 11.733 | 1.00 | 16.76 |
| 8439 | CD | GLU | B | 337 | 18.489 | 40.858 | 12.811 | 1.00 | 16.91 |
| 8440 | OE1 | GLU | B | 337 | 17.425 | 40.856 | 13.437 | 1.00 | 22.21 |
| 8441 | OE2 | GLU | B | 337 | 19.361 | 41.675 | 13.068 | 1.00 | 19.32 |
| 8442 | C | GLU | B | 337 | 16.682 | 38.035 | 9.259 | 1.00 | 12.08 |
| 8443 | O | GLU | B | 337 | 15.652 | 38.570 | 8.909 | 1.00 | 12.02 |
| 8444 | N | HIS | B | 338 | 16.694 | 36.775 | 9.569 | 1.00 | 10.15 |
| 8445 | CA | HIS | B | 338 | 15.642 | 35.844 | 9.140 | 1.00 | 8.30 |
| 8446 | CB | HIS | B | 338 | 16.201 | 34.921 | 8.063 | 1.00 | 8.08 |
| 8447 | CG | HIS | B | 338 | 16.337 | 35.503 | 6.696 | 1.00 | 11.20 |
| 8448 | ND1 | HIS | B | 338 | 16.767 | 34.725 | 5.625 | 1.00 | 11.40 |
| 8449 | CE1 | HIS | B | 338 | 16.698 | 35.452 | 4.517 | 1.00 | 11.07 |
| 8450 | NE2 | HIS | B | 338 | 16.307 | 36.687 | 4.835 | 1.00 | 10.40 |
| 8451 | CD2 | HIS | B | 338 | 16.077 | 36.745 | 6.194 | 1.00 | 14.97 |
| 8452 | C | HIS | B | 338 | 15.273 | 34.927 | 10.336 | 1.00 | 8.65 |
| 8453 | O | HIS | B | 338 | 15.935 | 33.880 | 10.666 | 1.00 | 9.39 |
| 8454 | N | ILE | B | 339 | 14.179 | 35.315 | 10.948 | 1.00 | 7.96 |
| 8455 | CA | ILE | B | 339 | 13.566 | 34.684 | 12.087 | 1.00 | 10.25 |
| 8456 | CB | ILE | B | 339 | 12.462 | 35.673 | 12.620 | 1.00 | 10.08 |
| 8457 | CG1 | ILE | B | 339 | 13.046 | 37.037 | 13.030 | 1.00 | 10.17 |

FIGURE 3 (Cont.)

| A | B | C | D | E | F | G | H | I | J |
|---|---|---|---|---|---|---|---|---|---|
| 8458 | CD1 | ILE | B | 339 | 11.938 | 38.192 | 13.251 | 1.00 | 12.56 |
| 8459 | CG2 | ILE | B | 339 | 11.726 | 35.081 | 13.780 | 1.00 | 3.11 |
| 8460 | C | ILE | B | 339 | 12.858 | 33.390 | 11.687 | 1.00 | 12.23 |
| 8461 | O | ILE | B | 339 | 12.035 | 33.437 | 10.840 | 1.00 | 13.04 |
| 8462 | N | GLU | B | 340 | 13.194 | 32.271 | 12.303 | 1.00 | 11.20 |
| 8463 | CA | GLU | B | 340 | 12.339 | 31.021 | 12.355 | 1.00 | 13.19 |
| 8464 | CB | GLU | B | 340 | 13.212 | 29.794 | 12.064 | 1.00 | 13.28 |
| 8465 | CG | GLU | B | 340 | 12.529 | 28.605 | 11.490 | 1.00 | 13.99 |
| 8466 | CD | GLU | B | 340 | 13.562 | 27.498 | 11.161 | 1.00 | 22.44 |
| 8467 | OE1 | GLU | B | 340 | 14.347 | 27.778 | 10.188 | 1.00 | 14.96 |
| 8468 | OE2 | GLU | B | 340 | 13.571 | 26.379 | 11.850 | 1.00 | 14.57 |
| 8469 | C | GLU | B | 340 | 11.764 | 30.747 | 13.748 | 1.00 | 14.06 |
| 8470 | O | GLU | B | 340 | 12.524 | 30.518 | 14.646 | 1.00 | 15.03 |
| 8471 | N | GLU | B | 341 | 10.479 | 30.618 | 13.921 | 1.00 | 11.60 |
| 8472 | CA | GLU | B | 341 | 9.871 | 30.621 | 15.248 | 1.00 | 14.91 |
| 8473 | CB | GLU | B | 341 | 8.671 | 31.633 | 15.163 | 1.00 | 14.76 |
| 8474 | CG | GLU | B | 341 | 8.500 | 32.655 | 16.241 | 1.00 | 17.29 |
| 8475 | CD | GLU | B | 341 | 7.762 | 33.899 | 15.768 | 1.00 | 26.82 |
| 8476 | OE1 | GLU | B | 341 | 6.606 | 33.781 | 15.321 | 1.00 | 24.96 |
| 8477 | OE2 | GLU | B | 341 | 8.369 | 34.998 | 15.860 | 1.00 | 34.89 |
| 8478 | C | GLU | B | 341 | 9.260 | 29.215 | 15.414 | 1.00 | 15.60 |
| 8479 | O | GLU | B | 341 | 8.972 | 28.595 | 14.390 | 1.00 | 16.14 |
| 8480 | N | SER | B | 342 | 8.954 | 28.756 | 16.631 | 1.00 | 15.35 |
| 8481 | CA | SER | B | 342 | 7.964 | 27.668 | 16.801 | 1.00 | 17.42 |
| 8482 | CB | SER | B | 342 | 8.560 | 26.335 | 17.278 | 1.00 | 17.56 |
| 8483 | OG | SER | B | 342 | 7.520 | 25.305 | 17.379 | 1.00 | 15.60 |
| 8484 | C | SER | B | 342 | 6.912 | 28.036 | 17.775 | 1.00 | 18.16 |
| 8485 | O | SER | B | 342 | 7.237 | 28.390 | 18.892 | 1.00 | 20.06 |
| 8486 | N | ARG | B | 343 | 5.652 | 27.884 | 17.377 | 1.00 | 18.35 |
| 8487 | CA | ARG | B | 343 | 4.508 | 28.374 | 18.192 | 1.00 | 19.82 |
| 8488 | CB | ARG | B | 343 | 3.215 | 28.673 | 17.354 | 1.00 | 20.26 |
| 8489 | CG | ARG | B | 343 | 3.034 | 30.286 | 16.941 | 1.00 | 26.06 |
| 8490 | CD | ARG | B | 343 | 3.131 | 30.547 | 15.358 | 1.00 | 32.25 |
| 8491 | NE | ARG | B | 343 | 4.508 | 30.322 | 14.758 | 1.00 | 40.80 |
| 8492 | CZ | ARG | B | 343 | 5.023 | 29.129 | 14.231 | 1.00 | 38.15 |
| 8493 | NH1 | ARG | B | 343 | 4.312 | 27.978 | 14.184 | 1.00 | 37.08 |
| 8494 | NH2 | ARG | B | 343 | 6.271 | 29.101 | 13.748 | 1.00 | 37.56 |
| 8495 | C | ARG | B | 343 | 4.175 | 27.471 | 19.314 | 1.00 | 18.61 |
| 8496 | O | ARG | B | 343 | 3.749 | 27.938 | 20.358 | 1.00 | 19.91 |
| 8497 | N | THR | B | 344 | 4.510 | 26.199 | 19.119 | 1.00 | 18.58 |
| 8498 | CA | THR | B | 344 | 4.001 | 25.048 | 19.886 | 1.00 | 17.81 |
| 8499 | CB | THR | B | 344 | 3.110 | 24.271 | 18.906 | 1.00 | 17.67 |
| 8500 | OG1 | THR | B | 344 | 3.845 | 24.113 | 17.655 | 1.00 | 19.28 |
| 8501 | CG2 | THR | B | 344 | 1.894 | 25.104 | 18.534 | 1.00 | 16.64 |
| 8502 | C | THR | B | 344 | 5.109 | 24.060 | 20.323 | 1.00 | 17.68 |
| 8503 | O | THR | B | 344 | 4.795 | 23.016 | 20.918 | 1.00 | 20.03 |
| 8504 | N | GLY | B | 345 | 6.352 | 24.317 | 19.990 | 1.00 | 13.34 |
| 8505 | CA | GLY | B | 345 | 7.455 | 23.450 | 20.345 | 1.00 | 12.92 |
| 8506 | C | GLY | B | 345 | 8.822 | 24.205 | 20.231 | 1.00 | 12.89 |
| 8507 | O | GLY | B | 345 | 9.002 | 25.348 | 20.703 | 1.00 | 13.32 |
| 8508 | N | TRP | B | 346 | 9.802 | 23.568 | 19.640 | 1.00 | 11.27 |

FIGURE 3 (Cont.)

| A | B | C | D | E | F | G | H | I | J |
|---|---|---|---|---|---|---|---|---|---|
| 8509 | CA | TRP | B | 346 | 11.145 | 24.156 | 19.578 | 1.00 | 11.14 |
| 8510 | CB | TRP | B | 346 | 12.197 | 23.300 | 20.222 | 1.00 | 8.96 |
| 8511 | CG | TRP | B | 346 | 12.167 | 21.885 | 19.849 | 1.00 | 10.76 |
| 8512 | CD1 | TRP | B | 346 | 13.036 | 21.236 | 18.966 | 1.00 | 10.33 |
| 8513 | NE1 | TRP | B | 346 | 12.781 | 19.887 | 18.947 | 1.00 | 11.19 |
| 8514 | CE2 | TRP | B | 346 | 11.761 | 19.624 | 19.815 | 1.00 | 6.33 |
| 8515 | CD2 | TRP | B | 346 | 11.359 | 20.868 | 20.403 | 1.00 | 3.76 |
| 8516 | CE3 | TRP | B | 346 | 10.397 | 20.851 | 21.382 | 1.00 | 2.00 |
| 8517 | CZ3 | TRP | B | 346 | 9.802 | 19.584 | 21.719 | 1.00 | 2.94 |
| 8518 | CH2 | TRP | B | 346 | 10.182 | 18.374 | 21.076 | 1.00 | 5.99 |
| 8519 | CZ2 | TRP | B | 346 | 11.165 | 18.365 | 20.141 | 1.00 | 3.90 |
| 8520 | C | TRP | B | 346 | 11.520 | 24.374 | 18.184 | 1.00 | 11.30 |
| 8521 | O | TRP | B | 346 | 11.105 | 23.647 | 17.316 | 1.00 | 11.39 |
| 8522 | N | ALA | B | 347 | 12.362 | 25.401 | 17.995 | 1.00 | 12.57 |
| 8523 | CA | ALA | B | 347 | 12.858 | 25.760 | 16.700 | 1.00 | 11.11 |
| 8524 | CB | ALA | B | 347 | 13.500 | 27.045 | 16.748 | 1.00 | 10.62 |
| 8525 | C | ALA | B | 347 | 13.824 | 24.698 | 16.257 | 1.00 | 13.66 |
| 8526 | O | ALA | B | 347 | 14.812 | 24.448 | 16.939 | 1.00 | 11.85 |
| 8527 | N | GLY | B | 348 | 13.489 | 24.051 | 15.131 | 1.00 | 14.66 |
| 8528 | CA | GLY | B | 348 | 14.305 | 23.010 | 14.534 | 1.00 | 13.17 |
| 8529 | C | GLY | B | 348 | 13.810 | 21.613 | 14.722 | 1.00 | 13.74 |
| 8530 | O | GLY | B | 348 | 12.650 | 21.338 | 15.047 | 1.00 | 13.26 |
| 8531 | N | GLY | B | 349 | 14.739 | 20.711 | 14.499 | 1.00 | 14.73 |
| 8532 | CA | GLY | B | 349 | 14.545 | 19.289 | 14.816 | 1.00 | 15.44 |
| 8533 | C | GLY | B | 349 | 15.231 | 19.096 | 16.133 | 1.00 | 15.27 |
| 8534 | O | GLY | B | 349 | 14.854 | 19.691 | 17.175 | 1.00 | 16.53 |
| 8535 | N | PHE | B | 350 | 16.275 | 18.290 | 16.085 | 1.00 | 15.27 |
| 8536 | CA | PHE | B | 350 | 17.118 | 18.148 | 17.219 | 1.00 | 16.97 |
| 8537 | CB | PHE | B | 350 | 18.020 | 16.911 | 17.026 | 1.00 | 16.98 |
| 8538 | CG | PHE | B | 350 | 18.603 | 16.483 | 18.256 | 1.00 | 22.11 |
| 8539 | CD1 | PHE | B | 350 | 19.723 | 17.136 | 18.751 | 1.00 | 25.86 |
| 8540 | CE1 | PHE | B | 350 | 20.268 | 16.793 | 20.021 | 1.00 | 28.95 |
| 8541 | CZ | PHE | B | 350 | 19.657 | 15.878 | 20.744 | 1.00 | 23.83 |
| 8542 | CE2 | PHE | B | 350 | 18.445 | 15.240 | 20.259 | 1.00 | 29.41 |
| 8543 | CD2 | PHE | B | 350 | 17.985 | 15.520 | 19.041 | 1.00 | 26.20 |
| 8544 | C | PHE | B | 350 | 17.929 | 19.459 | 17.268 | 1.00 | 16.86 |
| 8545 | O | PHE | B | 350 | 18.119 | 20.062 | 18.315 | 1.00 | 17.50 |
| 8546 | N | PHE | B | 351 | 18.447 | 19.830 | 16.104 | 1.00 | 16.46 |
| 8547 | CA | PHE | B | 351 | 19.165 | 21.040 | 15.891 | 1.00 | 16.37 |
| 8548 | CB | PHE | B | 351 | 20.488 | 20.803 | 15.253 | 1.00 | 16.37 |
| 8549 | CG | PHE | B | 351 | 21.340 | 19.745 | 15.895 | 1.00 | 18.68 |
| 8550 | CD1 | PHE | B | 351 | 22.037 | 20.029 | 17.063 | 1.00 | 19.21 |
| 8551 | CE1 | PHE | B | 351 | 22.839 | 19.120 | 17.628 | 1.00 | 18.14 |
| 8552 | CZ | PHE | B | 351 | 23.026 | 17.880 | 16.993 | 1.00 | 21.21 |
| 8553 | CE2 | PHE | B | 351 | 22.355 | 17.583 | 15.801 | 1.00 | 24.61 |
| 8554 | CD2 | PHE | B | 351 | 21.524 | 18.493 | 15.261 | 1.00 | 22.06 |
| 8555 | C | PHE | B | 351 | 18.381 | 21.911 | 14.933 | 1.00 | 16.37 |
| 8556 | O | PHE | B | 351 | 17.381 | 21.534 | 14.338 | 1.00 | 16.22 |
| 8557 | N | VAL | B | 352 | 18.841 | 23.136 | 14.804 | 1.00 | 16.02 |
| 8558 | CA | VAL | B | 352 | 18.167 | 24.070 | 13.966 | 1.00 | 14.66 |
| 8559 | CB | VAL | B | 352 | 18.545 | 25.494 | 14.378 | 1.00 | 16.81 |

FIGURE 3 (Cont.)

| A | B | C | D | E | F | G | H | I | J |
|---|---|---|---|---|---|---|---|---|---|
| 8560 | CG1 | VAL | B | 352 | 18.403 | 26.442 | 13.285 | 1.00 | 11.27 |
| 8561 | CG2 | VAL | B | 352 | 17.780 | 25.952 | 15.663 | 1.00 | 11.66 |
| 8562 | C | VAL | B | 352 | 18.777 | 23.661 | 12.646 | 1.00 | 14.33 |
| 8563 | O | VAL | B | 352 | 19.845 | 23.095 | 12.608 | 1.00 | 13.08 |
| 8564 | N | SER | B | 353 | 17.998 | 23.814 | 11.605 | 1.00 | 10.43 |
| 8565 | CA | SER | B | 353 | 18.350 | 23.594 | 10.231 | 1.00 | 11.24 |
| 8566 | CB | SER | B | 353 | 17.238 | 24.138 | 9.418 | 1.00 | 10.47 |
| 8567 | OG | SER | B | 353 | 16.816 | 23.115 | 8.669 | 1.00 | 18.46 |
| 8568 | C | SER | B | 353 | 19.493 | 24.470 | 9.835 | 1.00 | 11.14 |
| 8569 | O | SER | B | 353 | 19.583 | 25.530 | 10.330 | 1.00 | 12.20 |
| 8570 | N | THR | B | 354 | 20.299 | 24.091 | 8.877 | 1.00 | 12.34 |
| 8571 | CA | THR | B | 354 | 21.406 | 24.937 | 8.436 | 1.00 | 14.50 |
| 8572 | CB | THR | B | 354 | 22.730 | 24.220 | 8.560 | 1.00 | 15.10 |
| 8573 | OG1 | THR | B | 354 | 23.368 | 24.521 | 7.356 | 1.00 | 23.93 |
| 8574 | CG2 | THR | B | 354 | 22.755 | 22.645 | 8.257 | 1.00 | 15.45 |
| 8575 | C | THR | B | 354 | 21.104 | 25.290 | 6.998 | 1.00 | 14.10 |
| 8576 | O | THR | B | 354 | 20.475 | 24.539 | 6.319 | 1.00 | 16.14 |
| 8577 | N | PRO | B | 355 | 21.376 | 26.501 | 6.564 | 1.00 | 16.38 |
| 8578 | CA | PRO | B | 355 | 21.004 | 26.947 | 5.233 | 1.00 | 15.27 |
| 8579 | CB | PRO | B | 355 | 21.248 | 28.460 | 5.320 | 1.00 | 14.78 |
| 8580 | CG | PRO | B | 355 | 22.221 | 28.597 | 6.270 | 1.00 | 15.29 |
| 8581 | CD | PRO | B | 355 | 21.934 | 27.618 | 7.328 | 1.00 | 16.20 |
| 8582 | C | PRO | B | 355 | 21.918 | 26.382 | 4.174 | 1.00 | 15.07 |
| 8583 | O | PRO | B | 355 | 22.975 | 26.167 | 4.565 | 1.00 | 12.14 |
| 8584 | N | VAL | B | 356 | 21.520 | 26.126 | 2.921 | 1.00 | 12.68 |
| 8585 | CA | VAL | B | 356 | 22.475 | 25.769 | 1.949 | 1.00 | 11.80 |
| 8586 | CB | VAL | B | 356 | 22.747 | 24.265 | 1.807 | 1.00 | 11.76 |
| 8587 | CG1 | VAL | B | 356 | 21.977 | 23.428 | 2.765 | 1.00 | 7.83 |
| 8588 | CG2 | VAL | B | 356 | 22.723 | 23.873 | 0.431 | 1.00 | 4.32 |
| 8589 | C | VAL | B | 356 | 22.219 | 26.560 | 0.698 | 1.00 | 12.84 |
| 8590 | O | VAL | B | 356 | 21.103 | 26.629 | 0.256 | 1.00 | 13.54 |
| 8591 | N | PHE | B | 357 | 23.253 | 27.288 | 0.261 | 1.00 | 13.07 |
| 8592 | CA | PHE | B | 357 | 23.122 | 28.533 | -0.561 | 1.00 | 15.35 |
| 8593 | CB | PHE | B | 357 | 24.257 | 29.544 | -0.244 | 1.00 | 13.90 |
| 8594 | CG | PHE | B | 357 | 24.086 | 30.162 | 1.030 | 1.00 | 14.30 |
| 8595 | CD1 | PHE | B | 357 | 24.318 | 29.411 | 2.159 | 1.00 | 13.99 |
| 8596 | CE1 | PHE | B | 357 | 24.116 | 29.920 | 3.432 | 1.00 | 8.75 |
| 8597 | CZ | PHE | B | 357 | 23.631 | 31.266 | 3.585 | 1.00 | 7.09 |
| 8598 | CE2 | PHE | B | 357 | 23.289 | 32.018 | 2.403 | 1.00 | 10.98 |
| 8599 | CD2 | PHE | B | 357 | 23.561 | 31.468 | 1.134 | 1.00 | 9.64 |
| 8600 | C | PHE | B | 357 | 23.187 | 28.157 | -2.025 | 1.00 | 15.19 |
| 8601 | O | PHE | B | 357 | 23.662 | 27.116 | -2.325 | 1.00 | 17.02 |
| 8602 | N | SER | B | 358 | 22.659 | 28.954 | -2.906 | 1.00 | 16.65 |
| 8603 | CA | SER | B | 358 | 22.720 | 28.603 | -4.336 | 1.00 | 19.45 |
| 8604 | CB | SER | B | 358 | 21.761 | 29.540 | -5.111 | 1.00 | 21.12 |
| 8605 | OG | SER | B | 358 | 21.723 | 30.834 | -4.517 | 1.00 | 20.98 |
| 8606 | C | SER | B | 358 | 24.082 | 29.008 | -4.785 | 1.00 | 20.40 |
| 8607 | O | SER | B | 358 | 24.621 | 29.869 | -4.083 | 1.00 | 21.11 |
| 8608 | N | TYR | B | 359 | 24.591 | 28.525 | -5.949 | 1.00 | 21.16 |
| 8609 | CA | TYR | B | 359 | 25.797 | 29.104 | -6.603 | 1.00 | 21.38 |
| 8610 | CB | TYR | B | 359 | 26.415 | 28.188 | -7.791 | 1.00 | 24.13 |

FIGURE 3 (Cont.)

| A | B | C | D | E | F | G | H | I | J |
|---|---|---|---|---|---|---|---|---|---|
| 8611 | CG | TYR | B | 359 | 27.069 | 26.720 | -7.351 | 1.00 | 32.46 |
| 8612 | CD1 | TYR | B | 359 | 27.402 | 25.689 | -8.305 | 1.00 | 39.32 |
| 8613 | CE1 | TYR | B | 359 | 27.994 | 24.220 | -7.818 | 1.00 | 38.69 |
| 8614 | CZ | TYR | B | 359 | 28.246 | 23.921 | -6.414 | 1.00 | 35.23 |
| 8615 | OH | TYR | B | 359 | 28.730 | 22.652 | -5.937 | 1.00 | 20.16 |
| 8616 | CE2 | TYR | B | 359 | 27.930 | 25.007 | -5.461 | 1.00 | 38.41 |
| 8617 | CD2 | TYR | B | 359 | 27.353 | 26.355 | -5.918 | 1.00 | 39.77 |
| 8618 | C | TYR | B | 359 | 25.460 | 30.652 | -6.843 | 1.00 | 20.41 |
| 8619 | O | TYR | B | 359 | 26.236 | 31.569 | -6.611 | 1.00 | 17.02 |
| 8620 | N | ASP | B | 360 | 24.246 | 31.064 | -7.041 | 1.00 | 21.24 |
| 8621 | CA | ASP | B | 360 | 24.199 | 32.571 | -7.164 | 1.00 | 23.42 |
| 8622 | CB | ASP | B | 360 | 22.793 | 33.109 | -7.570 | 1.00 | 22.12 |
| 8623 | CG | ASP | B | 360 | 21.898 | 33.498 | -6.306 | 1.00 | 24.36 |
| 8624 | OD1 | ASP | B | 360 | 22.485 | 33.788 | -5.243 | 1.00 | 18.99 |
| 8625 | OD2 | ASP | B | 360 | 20.607 | 33.517 | -6.252 | 1.00 | 28.94 |
| 8626 | C | ASP | B | 360 | 24.837 | 33.311 | -5.889 | 1.00 | 22.90 |
| 8627 | O | ASP | B | 360 | 25.376 | 34.427 | -5.955 | 1.00 | 23.24 |
| 8628 | N | ALA | B | 361 | 24.689 | 32.665 | -4.743 | 1.00 | 23.42 |
| 8629 | CA | ALA | B | 361 | 25.149 | 33.093 | -3.420 | 1.00 | 22.69 |
| 8630 | CB | ALA | B | 361 | 26.639 | 33.320 | -3.443 | 1.00 | 21.56 |
| 8631 | C | ALA | B | 361 | 24.441 | 34.241 | -2.759 | 1.00 | 22.92 |
| 8632 | O | ALA | B | 361 | 25.048 | 34.953 | -1.977 | 1.00 | 23.41 |
| 8633 | N | ILE | B | 362 | 23.125 | 34.400 | -3.023 | 1.00 | 24.55 |
| 8634 | CA | ILE | B | 362 | 22.202 | 35.258 | -2.148 | 1.00 | 22.87 |
| 8635 | CB | ILE | B | 362 | 21.399 | 36.383 | -2.857 | 1.00 | 23.67 |
| 8636 | CG1 | ILE | B | 362 | 22.071 | 36.832 | -4.174 | 1.00 | 25.01 |
| 8637 | CD1 | ILE | B | 362 | 21.182 | 36.624 | -5.445 | 1.00 | 25.93 |
| 8638 | CG2 | ILE | B | 362 | 21.142 | 37.643 | -1.790 | 1.00 | 21.60 |
| 8639 | C | ILE | B | 362 | 21.140 | 34.434 | -1.512 | 1.00 | 21.37 |
| 8640 | O | ILE | B | 362 | 20.800 | 34.561 | -0.188 | 1.00 | 20.70 |
| 8641 | N | SER | B | 363 | 20.594 | 33.632 | -2.435 | 1.00 | 15.11 |
| 8642 | CA | SER | B | 363 | 19.530 | 32.665 | -2.053 | 1.00 | 13.24 |
| 8643 | CB | SER | B | 363 | 18.823 | 32.196 | -3.326 | 1.00 | 12.80 |
| 8644 | OG | SER | B | 363 | 18.745 | 33.278 | -4.284 | 1.00 | 15.21 |
| 8645 | C | SER | B | 363 | 20.044 | 31.490 | -1.339 | 1.00 | 9.86 |
| 8646 | O | SER | B | 363 | 21.132 | 31.176 | -1.539 | 1.00 | 10.29 |
| 8647 | N | TYR | B | 364 | 19.276 | 30.887 | -0.462 | 1.00 | 7.08 |
| 8648 | CA | TYR | B | 364 | 19.532 | 29.505 | 0.040 | 1.00 | 7.83 |
| 8649 | CB | TYR | B | 364 | 20.103 | 29.471 | 1.488 | 1.00 | 7.26 |
| 8650 | CG | TYR | B | 364 | 19.257 | 30.236 | 2.551 | 1.00 | 8.56 |
| 8651 | CD1 | TYR | B | 364 | 18.427 | 29.596 | 3.479 | 1.00 | 8.67 |
| 8652 | CE1 | TYR | B | 364 | 17.717 | 30.330 | 4.470 | 1.00 | 6.46 |
| 8653 | CZ | TYR | B | 364 | 17.790 | 31.671 | 4.457 | 1.00 | 5.33 |
| 8654 | OH | TYR | B | 364 | 17.020 | 32.509 | 5.291 | 1.00 | 9.43 |
| 8655 | CE2 | TYR | B | 364 | 18.536 | 32.285 | 3.509 | 1.00 | 4.47 |
| 8656 | CD2 | TYR | B | 364 | 19.232 | 31.597 | 2.577 | 1.00 | 3.89 |
| 8657 | C | TYR | B | 364 | 18.254 | 28.693 | 0.131 | 1.00 | 6.36 |
| 8658 | O | TYR | B | 364 | 17.205 | 29.230 | 0.082 | 1.00 | 7.07 |
| 8659 | N | TYR | B | 365 | 18.425 | 27.430 | 0.419 | 1.00 | 7.10 |
| 8660 | CA | TYR | B | 365 | 17.390 | 26.468 | 0.700 | 1.00 | 9.44 |
| 8661 | CB | TYR | B | 365 | 17.612 | 25.238 | -0.219 | 1.00 | 8.40 |

FIGURE 3 (Cont.)

| A | B | C | D | E | F | G | H | I | J |
|---|---|---|---|---|---|---|---|---|---|
| 8662 | CG | TYR | B | 365 | 17.545 | 25.697 | -1.625 | 1.00 | 9.53 |
| 8663 | CD1 | TYR | B | 365 | 18.666 | 26.292 | -2.212 | 1.00 | 9.42 |
| 8664 | CE1 | TYR | B | 365 | 18.647 | 26.773 | -3.432 | 1.00 | 6.95 |
| 8665 | CZ | TYR | B | 365 | 17.501 | 26.747 | -4.197 | 1.00 | 9.89 |
| 8666 | OH | TYR | B | 365 | 17.620 | 27.286 | -5.450 | 1.00 | 18.44 |
| 8667 | CE2 | TYR | B | 365 | 16.324 | 26.184 | -3.705 | 1.00 | 10.06 |
| 8668 | CD2 | TYR | B | 365 | 16.355 | 25.650 | -2.363 | 1.00 | 10.36 |
| 8669 | C | TYR | B | 365 | 17.536 | 26.056 | 2.155 | 1.00 | 10.11 |
| 8670 | O | TYR | B | 365 | 18.627 | 26.191 | 2.774 | 1.00 | 12.82 |
| 8671 | N | LYS | B | 366 | 16.490 | 25.505 | 2.736 | 1.00 | 10.38 |
| 8672 | CA | LYS | B | 366 | 16.485 | 25.134 | 4.138 | 1.00 | 10.19 |
| 8673 | CB | LYS | B | 366 | 16.478 | 26.404 | 4.937 | 1.00 | 8.67 |
| 8674 | CG | LYS | B | 366 | 16.964 | 26.296 | 6.379 | 1.00 | 12.59 |
| 8675 | CD | LYS | B | 366 | 16.650 | 27.696 | 7.134 | 1.00 | 7.52 |
| 8676 | CE | LYS | B | 366 | 17.213 | 27.845 | 8.520 | 1.00 | 12.43 |
| 8677 | NZ | LYS | B | 366 | 16.717 | 26.905 | 9.615 | 1.00 | 14.14 |
| 8678 | C | LYS | B | 366 | 15.284 | 24.340 | 4.442 | 1.00 | 11.03 |
| 8679 | O | LYS | B | 366 | 14.243 | 24.610 | 4.007 | 1.00 | 13.95 |
| 8680 | N | ILE | B | 367 | 15.384 | 23.395 | 5.304 | 1.00 | 12.49 |
| 8681 | CA | ILE | B | 367 | 14.257 | 22.592 | 5.769 | 1.00 | 10.99 |
| 8682 | CB | ILE | B | 367 | 14.785 | 21.235 | 6.058 | 1.00 | 9.95 |
| 8683 | CG1 | ILE | B | 367 | 15.323 | 20.630 | 4.808 | 1.00 | 5.15 |
| 8684 | CD1 | ILE | B | 367 | 15.834 | 19.101 | 5.129 | 1.00 | 11.56 |
| 8685 | CG2 | ILE | B | 367 | 13.769 | 20.373 | 6.680 | 1.00 | 11.88 |
| 8686 | C | ILE | B | 367 | 13.711 | 23.149 | 7.074 | 1.00 | 11.18 |
| 8687 | O | ILE | B | 367 | 14.346 | 23.105 | 8.062 | 1.00 | 11.03 |
| 8688 | N | PHE | B | 368 | 12.556 | 23.738 | 7.043 | 1.00 | 9.85 |
| 8689 | CA | PHE | B | 368 | 11.763 | 23.845 | 8.245 | 1.00 | 9.75 |
| 8690 | CB | PHE | B | 368 | 11.685 | 25.275 | 8.682 | 1.00 | 9.96 |
| 8691 | CG | PHE | B | 368 | 11.577 | 26.226 | 7.577 | 1.00 | 11.63 |
| 8692 | CD1 | PHE | B | 368 | 12.706 | 26.567 | 6.873 | 1.00 | 3.18 |
| 8693 | CE1 | PHE | B | 368 | 12.706 | 27.531 | 5.953 | 1.00 | 5.91 |
| 8694 | CZ | PHE | B | 368 | 11.527 | 28.233 | 5.686 | 1.00 | 10.70 |
| 8695 | CE2 | PHE | B | 368 | 10.349 | 27.868 | 6.366 | 1.00 | 10.68 |
| 8696 | CD2 | PHE | B | 368 | 10.379 | 26.861 | 7.327 | 1.00 | 4.81 |
| 8697 | C | PHE | B | 368 | 10.293 | 23.420 | 8.085 | 1.00 | 7.92 |
| 8698 | O | PHE | B | 368 | 9.830 | 23.176 | 6.991 | 1.00 | 5.99 |
| 8699 | N | SER | B | 369 | 9.611 | 23.409 | 9.205 | 1.00 | 6.66 |
| 8700 | CA | SER | B | 369 | 8.211 | 23.099 | 9.271 | 1.00 | 6.44 |
| 8701 | CB | SER | B | 369 | 7.753 | 23.310 | 10.701 | 1.00 | 6.50 |
| 8702 | OG | SER | B | 369 | 8.424 | 22.597 | 11.640 | 1.00 | 7.40 |
| 8703 | C | SER | B | 369 | 7.372 | 24.140 | 8.438 | 1.00 | 8.26 |
| 8704 | O | SER | B | 369 | 7.581 | 25.400 | 8.649 | 1.00 | 5.72 |
| 8705 | N | ASP | B | 370 | 6.419 | 23.597 | 7.654 | 1.00 | 8.06 |
| 8706 | CA | ASP | B | 370 | 5.378 | 24.324 | 6.897 | 1.00 | 9.94 |
| 8707 | CB | ASP | B | 370 | 5.136 | 23.635 | 5.565 | 1.00 | 7.69 |
| 8708 | CG | ASP | B | 370 | 4.356 | 22.295 | 5.696 | 1.00 | 11.27 |
| 8709 | OD1 | ASP | B | 370 | 4.157 | 21.586 | 4.698 | 1.00 | 12.13 |
| 8710 | OD2 | ASP | B | 370 | 3.888 | 21.844 | 6.756 | 1.00 | 15.34 |
| 8711 | C | ASP | B | 370 | 4.036 | 24.507 | 7.705 | 1.00 | 12.26 |
| 8712 | O | ASP | B | 370 | 3.945 | 24.072 | 8.893 | 1.00 | 15.12 |

FIGURE 3 (Cont.)

| A | B | C | D | E | F | G | H | I | J |
|---|---|---|---|---|---|---|---|---|---|
| 8713 | N | LYS | B | 371 | 3.022 | 25.120 | 7.084 | 1.00 | 12.03 |
| 8714 | CA | LYS | B | 371 | 1.801 | 25.562 | 7.779 | 1.00 | 13.49 |
| 8715 | CB | LYS | B | 371 | 0.837 | 26.519 | 6.933 | 1.00 | 13.07 |
| 8716 | CG | LYS | B | 371 | -0.069 | 25.923 | 5.698 | 1.00 | 14.81 |
| 8717 | CD | LYS | B | 371 | 0.376 | 26.451 | 4.193 | 1.00 | 15.57 |
| 8718 | CE | LYS | B | 371 | 1.983 | 25.944 | 3.625 | 1.00 | 14.69 |
| 8719 | NZ | LYS | B | 371 | 3.355 | 26.448 | 4.238 | 1.00 | 2.00 |
| 8720 | C | LYS | B | 371 | 1.061 | 24.355 | 8.252 | 1.00 | 14.19 |
| 8721 | O | LYS | B | 371 | 0.205 | 24.512 | 9.105 | 1.00 | 14.34 |
| 8722 | N | ASP | B | 372 | 1.434 | 23.159 | 7.745 | 1.00 | 14.81 |
| 8723 | CA | ASP | B | 372 | 0.808 | 21.868 | 8.141 | 1.00 | 15.26 |
| 8724 | CB | ASP | B | 372 | 0.610 | 20.918 | 6.931 | 1.00 | 14.90 |
| 8725 | CG | ASP | B | 372 | -0.480 | 21.390 | 5.959 | 1.00 | 16.53 |
| 8726 | OD1 | ASP | B | 372 | -0.322 | 21.220 | 4.741 | 1.00 | 20.00 |
| 8727 | OD2 | ASP | B | 372 | -1.498 | 21.953 | 6.304 | 1.00 | 11.60 |
| 8728 | C | ASP | B | 372 | 1.667 | 21.098 | 9.117 | 1.00 | 15.70 |
| 8729 | O | ASP | B | 372 | 1.492 | 19.890 | 9.314 | 1.00 | 16.48 |
| 8730 | N | GLY | B | 373 | 2.608 | 21.785 | 9.721 | 1.00 | 14.31 |
| 8731 | CA | GLY | B | 373 | 3.630 | 21.130 | 10.502 | 1.00 | 13.91 |
| 8732 | C | GLY | B | 373 | 4.510 | 20.027 | 9.946 | 1.00 | 12.61 |
| 8733 | O | GLY | B | 373 | 4.936 | 19.168 | 10.729 | 1.00 | 13.59 |
| 8734 | N | TYR | B | 374 | 4.793 | 20.031 | 8.656 | 1.00 | 11.34 |
| 8735 | CA | TYR | B | 374 | 5.753 | 19.041 | 8.096 | 1.00 | 10.23 |
| 8736 | CB | TYR | B | 374 | 5.141 | 18.235 | 6.936 | 1.00 | 11.32 |
| 8737 | CG | TYR | B | 374 | 4.064 | 17.261 | 7.423 | 1.00 | 8.39 |
| 8738 | CD1 | TYR | B | 374 | 4.393 | 16.034 | 7.861 | 1.00 | 7.67 |
| 8739 | CE1 | TYR | B | 374 | 3.448 | 15.125 | 8.329 | 1.00 | 11.47 |
| 8740 | CZ | TYR | B | 374 | 2.175 | 15.447 | 8.386 | 1.00 | 9.08 |
| 8741 | OH | TYR | B | 374 | 1.325 | 14.517 | 8.898 | 1.00 | 10.53 |
| 8742 | CE2 | TYR | B | 374 | 1.793 | 16.656 | 7.931 | 1.00 | 9.07 |
| 8743 | CD2 | TYR | B | 374 | 2.743 | 17.587 | 7.455 | 1.00 | 9.67 |
| 8744 | C | TYR | B | 374 | 6.974 | 19.765 | 7.665 | 1.00 | 11.38 |
| 8745 | O | TYR | B | 374 | 6.921 | 20.835 | 7.129 | 1.00 | 12.63 |
| 8746 | N | LYS | B | 375 | 8.140 | 19.273 | 8.045 | 1.00 | 11.21 |
| 8747 | CA | LYS | B | 375 | 9.367 | 19.942 | 7.658 | 1.00 | 9.29 |
| 8748 | CB | LYS | B | 375 | 10.441 | 19.586 | 8.626 | 1.00 | 6.90 |
| 8749 | CG | LYS | B | 375 | 10.038 | 19.885 | 10.042 | 1.00 | 7.99 |
| 8750 | CD | LYS | B | 375 | 11.332 | 19.678 | 10.987 | 1.00 | 3.93 |
| 8751 | CE | LYS | B | 375 | 10.871 | 19.759 | 12.479 | 1.00 | 12.06 |
| 8752 | NZ | LYS | B | 375 | 10.144 | 21.083 | 12.930 | 1.00 | 4.56 |
| 8753 | C | LYS | B | 375 | 9.797 | 19.746 | 6.144 | 1.00 | 9.64 |
| 8754 | O | LYS | B | 375 | 10.196 | 18.659 | 5.655 | 1.00 | 7.01 |
| 8755 | N | HIS | B | 376 | 9.659 | 20.840 | 5.393 | 1.00 | 7.97 |
| 8756 | CA | HIS | B | 376 | 10.081 | 20.751 | 4.042 | 1.00 | 7.46 |
| 8757 | CB | HIS | B | 376 | 8.888 | 20.776 | 3.184 | 1.00 | 5.92 |
| 8758 | CG | HIS | B | 376 | 8.118 | 19.526 | 3.214 | 1.00 | 5.80 |
| 8759 | ND1 | HIS | B | 376 | 8.403 | 18.472 | 2.392 | 1.00 | 2.89 |
| 8760 | CE1 | HIS | B | 376 | 7.499 | 17.530 | 2.577 | 1.00 | 3.40 |
| 8761 | NE2 | HIS | B | 376 | 6.751 | 17.862 | 3.607 | 1.00 | 6.73 |
| 8762 | CD2 | HIS | B | 376 | 7.111 | 19.120 | 4.018 | 1.00 | 11.73 |
| 8763 | C | HIS | B | 376 | 11.091 | 21.820 | 3.673 | 1.00 | 6.64 |

FIGURE 3 (Cont.)

| A | B | C | D | E | F | G | H | I | J |
|---|---|---|---|---|---|---|---|---|---|
| 8764 | O | HIS | B | 376 | 11.371 | 22.629 | 4.524 | 1.00 | 6.69 |
| 8765 | N | ILE | B | 377 | 11.547 | 21.767 | 2.408 | 1.00 | 5.66 |
| 8766 | CA | ILE | B | 377 | 12.579 | 22.635 | 1.795 | 1.00 | 3.80 |
| 8767 | CB | ILE | B | 377 | 13.282 | 21.838 | 0.682 | 1.00 | 2.88 |
| 8768 | CG1 | ILE | B | 377 | 14.032 | 20.676 | 1.282 | 1.00 | 2.49 |
| 8769 | CD1 | ILE | B | 377 | 14.555 | 19.730 | 0.274 | 1.00 | 4.69 |
| 8770 | CG2 | ILE | B | 377 | 14.378 | 22.622 | -0.013 | 1.00 | 7.04 |
| 8771 | C | ILE | B | 377 | 11.988 | 23.870 | 1.254 | 1.00 | 5.69 |
| 8772 | O | ILE | B | 377 | 10.939 | 23.891 | 0.687 | 1.00 | 3.88 |
| 8773 | N | HIS | B | 378 | 12.568 | 24.985 | 1.573 | 1.00 | 7.59 |
| 8774 | CA | HIS | B | 378 | 11.968 | 26.276 | 1.150 | 1.00 | 7.92 |
| 8775 | CB | HIS | B | 378 | 11.465 | 27.093 | 2.288 | 1.00 | 5.94 |
| 8776 | CG | HIS | B | 378 | 10.345 | 26.452 | 3.031 | 1.00 | 12.21 |
| 8777 | ND1 | HIS | B | 378 | 9.115 | 27.095 | 3.247 | 1.00 | 7.55 |
| 8778 | CE1 | HIS | B | 378 | 8.346 | 26.285 | 3.951 | 1.00 | 12.30 |
| 8779 | NE2 | HIS | B | 378 | 9.012 | 25.151 | 4.168 | 1.00 | 13.18 |
| 8780 | CD2 | HIS | B | 378 | 10.241 | 25.208 | 3.548 | 1.00 | 9.16 |
| 8781 | C | HIS | B | 378 | 13.025 | 26.980 | 0.523 | 1.00 | 7.98 |
| 8782 | O | HIS | B | 378 | 14.151 | 26.732 | 0.904 | 1.00 | 10.22 |
| 8783 | N | TYR | B | 379 | 12.704 | 27.787 | -0.484 | 1.00 | 7.69 |
| 8784 | CA | TYR | B | 379 | 13.743 | 28.418 | -1.250 | 1.00 | 9.35 |
| 8785 | CB | TYR | B | 379 | 13.502 | 28.124 | -2.706 | 1.00 | 9.29 |
| 8786 | CG | TYR | B | 379 | 14.283 | 28.977 | -3.652 | 1.00 | 11.93 |
| 8787 | CD1 | TYR | B | 379 | 13.667 | 29.498 | -4.751 | 1.00 | 13.60 |
| 8788 | CE1 | TYR | B | 379 | 14.346 | 30.257 | -5.674 | 1.00 | 18.02 |
| 8789 | CZ | TYR | B | 379 | 15.685 | 30.503 | -5.494 | 1.00 | 16.35 |
| 8790 | OH | TYR | B | 379 | 16.252 | 31.275 | -6.425 | 1.00 | 17.97 |
| 8791 | CE2 | TYR | B | 379 | 16.349 | 30.017 | -4.394 | 1.00 | 13.49 |
| 8792 | CD2 | TYR | B | 379 | 15.645 | 29.239 | -3.458 | 1.00 | 12.76 |
| 8793 | C | TYR | B | 379 | 13.640 | 29.892 | -0.910 | 1.00 | 9.29 |
| 8794 | O | TYR | B | 379 | 12.706 | 30.542 | -1.238 | 1.00 | 7.65 |
| 8795 | N | ILE | B | 380 | 14.658 | 30.396 | -0.287 | 1.00 | 9.50 |
| 8796 | CA | ILE | B | 380 | 14.651 | 31.757 | 0.246 | 1.00 | 10.02 |
| 8797 | CB | ILE | B | 380 | 14.998 | 31.696 | 1.713 | 1.00 | 9.00 |
| 8798 | CG1 | ILE | B | 380 | 14.208 | 30.465 | 2.287 | 1.00 | 10.02 |
| 8799 | CD1 | ILE | B | 380 | 14.043 | 30.470 | 3.684 | 1.00 | 4.19 |
| 8800 | CG2 | ILE | B | 380 | 14.533 | 32.970 | 2.322 | 1.00 | 8.59 |
| 8801 | C | ILE | B | 380 | 15.607 | 32.600 | -0.481 | 1.00 | 13.01 |
| 8802 | O | ILE | B | 380 | 16.799 | 32.139 | -0.755 | 1.00 | 13.03 |
| 8803 | N | LYS | B | 381 | 15.069 | 33.759 | -0.850 | 1.00 | 13.67 |
| 8804 | CA | LYS | B | 381 | 15.711 | 34.731 | -1.651 | 1.00 | 17.23 |
| 8805 | CB | LYS | B | 381 | 15.077 | 34.877 | -3.021 | 1.00 | 17.69 |
| 8806 | CG | LYS | B | 381 | 15.388 | 33.715 | -3.996 | 1.00 | 19.06 |
| 8807 | CD | LYS | B | 381 | 15.090 | 34.057 | -5.498 | 1.00 | 15.42 |
| 8808 | CE | LYS | B | 381 | 16.055 | 35.162 | -5.866 | 1.00 | 20.44 |
| 8809 | NZ | LYS | B | 381 | 16.146 | 35.583 | -7.268 | 1.00 | 22.55 |
| 8810 | C | LYS | B | 381 | 15.904 | 36.133 | -1.079 | 1.00 | 19.32 |
| 8811 | O | LYS | B | 381 | 17.038 | 36.606 | -1.186 | 1.00 | 23.29 |
| 8812 | N | ASP | B | 382 | 14.891 | 36.861 | -0.600 | 1.00 | 19.54 |
| 8813 | CA | ASP | B | 382 | 15.186 | 38.094 | 0.159 | 1.00 | 20.77 |
| 8814 | CB | ASP | B | 382 | 14.704 | 39.466 | -0.471 | 1.00 | 19.72 |

FIGURE 3 (Cont.)

| A | B | C | D | E | F | G | H | I | J |
|---|---|---|---|---|---|---|---|---|---|
| 8815 | CG | ASP | B | 382 | 13.076 | 39.648 | -0.683 | 1.00 | 26.41 |
| 8816 | OD1 | ASP | B | 382 | 12.208 | 38.821 | -0.302 | 1.00 | 28.64 |
| 8817 | OD2 | ASP | B | 382 | 12.534 | 40.681 | -1.313 | 1.00 | 33.29 |
| 8818 | C | ASP | B | 382 | 14.854 | 37.908 | 1.639 | 1.00 | 21.06 |
| 8819 | O | ASP | B | 382 | 15.756 | 38.082 | 2.524 | 1.00 | 22.14 |
| 8820 | N | THR | B | 383 | 13.618 | 37.473 | 1.895 | 1.00 | 19.42 |
| 8821 | CA | THR | B | 383 | 12.999 | 37.466 | 3.197 | 1.00 | 19.59 |
| 8822 | CB | THR | B | 383 | 11.751 | 38.464 | 3.350 | 1.00 | 19.53 |
| 8823 | OG1 | THR | B | 383 | 10.636 | 38.018 | 2.553 | 1.00 | 19.94 |
| 8824 | CG2 | THR | B | 383 | 12.017 | 39.929 | 2.962 | 1.00 | 17.07 |
| 8825 | C | THR | B | 383 | 12.361 | 36.163 | 3.270 | 1.00 | 20.98 |
| 8826 | O | THR | B | 383 | 11.987 | 35.591 | 2.245 | 1.00 | 22.21 |
| 8827 | N | VAL | B | 384 | 12.023 | 35.790 | 4.493 | 1.00 | 21.55 |
| 8828 | CA | VAL | B | 384 | 11.765 | 34.394 | 4.807 | 1.00 | 19.98 |
| 8829 | CB | VAL | B | 384 | 12.411 | 34.058 | 6.190 | 1.00 | 20.51 |
| 8830 | CG1 | VAL | B | 384 | 12.457 | 32.588 | 6.483 | 1.00 | 21.42 |
| 8831 | CG2 | VAL | B | 384 | 11.731 | 34.829 | 7.318 | 1.00 | 20.52 |
| 8832 | C | VAL | B | 384 | 10.272 | 34.207 | 4.772 | 1.00 | 18.76 |
| 8833 | O | VAL | B | 384 | 9.751 | 33.121 | 4.462 | 1.00 | 18.46 |
| 8834 | N | GLU | B | 385 | 9.580 | 35.283 | 5.080 | 1.00 | 16.16 |
| 8835 | CA | GLU | B | 385 | 8.202 | 35.428 | 4.738 | 1.00 | 15.85 |
| 8836 | CB | GLU | B | 385 | 7.654 | 36.808 | 5.210 | 1.00 | 16.74 |
| 8837 | CG | GLU | B | 385 | 7.889 | 37.199 | 6.684 | 1.00 | 19.35 |
| 8838 | CD | GLU | B | 385 | 9.257 | 37.796 | 6.941 | 1.00 | 24.63 |
| 8839 | OE1 | GLU | B | 385 | 9.976 | 38.149 | 5.993 | 1.00 | 23.60 |
| 8840 | OE2 | GLU | B | 385 | 9.616 | 37.917 | 8.115 | 1.00 | 33.23 |
| 8841 | C | GLU | B | 385 | 7.838 | 35.336 | 3.252 | 1.00 | 15.13 |
| 8842 | O | GLU | B | 385 | 6.709 | 35.648 | 2.925 | 1.00 | 13.85 |
| 8843 | N | ASN | B | 386 | 8.771 | 35.094 | 2.351 | 1.00 | 13.28 |
| 8844 | CA | ASN | B | 386 | 8.516 | 35.029 | 0.904 | 1.00 | 13.01 |
| 8845 | CB | ASN | B | 386 | 9.193 | 36.171 | 0.179 | 1.00 | 12.23 |
| 8846 | CG | ASN | B | 386 | 8.435 | 37.399 | 0.231 | 1.00 | 11.75 |
| 8847 | OD1 | ASN | B | 386 | 7.207 | 37.407 | 0.355 | 1.00 | 18.90 |
| 8848 | ND2 | ASN | B | 386 | 9.124 | 38.480 | 0.062 | 1.00 | 16.19 |
| 8849 | C | ASN | B | 386 | 9.162 | 33.779 | 0.427 | 1.00 | 12.84 |
| 8850 | O | ASN | B | 386 | 9.201 | 33.534 | -0.755 | 1.00 | 14.59 |
| 8851 | N | ALA | B | 387 | 9.743 | 33.034 | 1.355 | 1.00 | 8.50 |
| 8852 | CA | ALA | B | 387 | 10.152 | 31.647 | 1.136 | 1.00 | 8.19 |
| 8853 | CB | ALA | B | 387 | 10.144 | 30.900 | 2.419 | 1.00 | 7.84 |
| 8854 | C | ALA | B | 387 | 9.196 | 31.046 | 0.270 | 1.00 | 8.59 |
| 8855 | O | ALA | B | 387 | 8.035 | 31.306 | 0.493 | 1.00 | 8.87 |
| 8856 | N | ILE | B | 388 | 9.598 | 30.361 | -0.780 | 1.00 | 8.78 |
| 8857 | CA | ILE | B | 388 | 8.615 | 29.496 | -1.362 | 1.00 | 9.98 |
| 8858 | CB | ILE | B | 388 | 8.329 | 29.685 | -2.889 | 1.00 | 11.04 |
| 8859 | CG1 | ILE | B | 388 | 9.030 | 28.660 | -3.643 | 1.00 | 8.52 |
| 8860 | CD1 | ILE | B | 388 | 8.138 | 28.157 | -4.564 | 1.00 | 10.96 |
| 8861 | CG2 | ILE | B | 388 | 8.641 | 31.053 | -3.552 | 1.00 | 11.44 |
| 8862 | C | ILE | B | 388 | 8.865 | 28.071 | -1.092 | 1.00 | 10.84 |
| 8863 | O | ILE | B | 388 | 9.990 | 27.590 | -1.108 | 1.00 | 10.51 |
| 8864 | N | GLN | B | 389 | 7.820 | 27.313 | -0.864 | 1.00 | 11.22 |
| 8865 | CA | GLN | B | 389 | 8.082 | 25.907 | -0.467 | 1.00 | 11.61 |

FIGURE 3 (Cont.)

| A | B | C | D | E | F | G | H | I | J |
|---|---|---|---|---|---|---|---|---|---|
| 8866 | CB | GLN | B | 389 | 6.900 | 25.368 | 0.355 | 1.00 | 11.87 |
| 8867 | CG | GLN | B | 389 | 7.123 | 24.033 | 1.103 | 1.00 | 11.83 |
| 8868 | CD | GLN | B | 389 | 5.841 | 23.562 | 1.837 | 1.00 | 13.01 |
| 8869 | OE1 | GLN | B | 389 | 4.897 | 24.348 | 2.111 | 1.00 | 8.85 |
| 8870 | NE2 | GLN | B | 389 | 5.824 | 22.293 | 2.156 | 1.00 | 12.17 |
| 8871 | C | GLN | B | 389 | 8.321 | 25.022 | -1.694 | 1.00 | 11.41 |
| 8872 | O | GLN | B | 389 | 7.556 | 24.973 | -2.611 | 1.00 | 11.52 |
| 8873 | N | ILE | B | 390 | 9.364 | 24.266 | -1.732 | 1.00 | 11.37 |
| 8874 | CA | ILE | B | 390 | 9.539 | 23.518 | -2.963 | 1.00 | 10.56 |
| 8875 | CB | ILE | B | 390 | 10.776 | 23.982 | -3.725 | 1.00 | 9.22 |
| 8876 | CG1 | ILE | B | 390 | 11.997 | 23.652 | -2.948 | 1.00 | 8.58 |
| 8877 | CD1 | ILE | B | 390 | 13.181 | 24.176 | -3.608 | 1.00 | 9.12 |
| 8878 | CG2 | ILE | B | 390 | 10.677 | 25.446 | -4.047 | 1.00 | 2.00 |
| 8879 | C | ILE | B | 390 | 9.527 | 22.065 | -2.786 | 1.00 | 10.54 |
| 8880 | O | ILE | B | 390 | 9.722 | 21.367 | -3.709 | 1.00 | 11.53 |
| 8881 | N | THR | B | 391 | 9.224 | 21.621 | -1.600 | 1.00 | 10.44 |
| 8882 | CA | THR | B | 391 | 8.840 | 20.208 | -1.353 | 1.00 | 10.87 |
| 8883 | CB | THR | B | 391 | 10.025 | 19.555 | -0.732 | 1.00 | 12.30 |
| 8884 | OG1 | THR | B | 391 | 10.782 | 18.872 | -1.727 | 1.00 | 16.58 |
| 8885 | CG2 | THR | B | 391 | 9.670 | 18.543 | 0.246 | 1.00 | 9.97 |
| 8886 | C | THR | B | 391 | 7.592 | 20.227 | -0.362 | 1.00 | 11.17 |
| 8887 | O | THR | B | 391 | 7.408 | 21.173 | 0.370 | 1.00 | 10.35 |
| 8888 | N | SER | B | 392 | 6.749 | 19.207 | -0.379 | 1.00 | 10.28 |
| 8889 | CA | SER | B | 392 | 5.598 | 19.121 | 0.482 | 1.00 | 11.45 |
| 8890 | CB | SER | B | 392 | 4.587 | 20.206 | 0.115 | 1.00 | 11.79 |
| 8891 | OG | SER | B | 392 | 4.009 | 19.931 | -1.158 | 1.00 | 14.61 |
| 8892 | C | SER | B | 392 | 4.840 | 17.779 | 0.387 | 1.00 | 10.78 |
| 8893 | O | SER | B | 392 | 4.980 | 17.090 | -0.575 | 1.00 | 10.55 |
| 8894 | N | GLY | B | 393 | 3.965 | 17.514 | 1.363 | 1.00 | 11.21 |
| 8895 | CA | GLY | B | 393 | 3.422 | 16.201 | 1.645 | 1.00 | 11.01 |
| 8896 | C | GLY | B | 393 | 3.423 | 15.830 | 3.132 | 1.00 | 11.76 |
| 8897 | O | GLY | B | 393 | 3.959 | 16.541 | 3.993 | 1.00 | 9.32 |
| 8898 | N | LYS | B | 394 | 2.827 | 14.649 | 3.405 | 1.00 | 11.83 |
| 8899 | CA | LYS | B | 394 | 2.779 | 14.085 | 4.766 | 1.00 | 10.94 |
| 8900 | CB | LYS | B | 394 | 1.370 | 13.501 | 5.125 | 1.00 | 11.29 |
| 8901 | CG | LYS | B | 394 | 0.151 | 14.500 | 4.968 | 1.00 | 11.29 |
| 8902 | CD | LYS | B | 394 | -1.193 | 13.762 | 5.201 | 1.00 | 20.20 |
| 8903 | CE | LYS | B | 394 | -2.289 | 14.269 | 4.292 | 1.00 | 27.29 |
| 8904 | NZ | LYS | B | 394 | -3.241 | 15.343 | 4.816 | 1.00 | 29.12 |
| 8905 | C | LYS | B | 394 | 3.913 | 13.077 | 4.903 | 1.00 | 10.11 |
| 8906 | O | LYS | B | 394 | 3.748 | 11.813 | 4.985 | 1.00 | 9.64 |
| 8907 | N | TRP | B | 395 | 5.089 | 13.687 | 4.940 | 1.00 | 9.01 |
| 8908 | CA | TRP | B | 395 | 6.363 | 13.028 | 5.062 | 1.00 | 8.81 |
| 8909 | CB | TRP | B | 395 | 6.615 | 12.228 | 3.774 | 1.00 | 7.55 |
| 8910 | CG | TRP | B | 395 | 6.485 | 13.028 | 2.490 | 1.00 | 12.22 |
| 8911 | CD1 | TRP | B | 395 | 5.355 | 13.151 | 1.703 | 1.00 | 14.55 |
| 8912 | NE1 | TRP | B | 395 | 5.598 | 13.966 | 0.617 | 1.00 | 9.60 |
| 8913 | CE2 | TRP | B | 395 | 6.903 | 14.347 | 0.637 | 1.00 | 13.96 |
| 8914 | CD2 | TRP | B | 395 | 7.488 | 13.825 | 1.818 | 1.00 | 12.01 |
| 8915 | CE3 | TRP | B | 395 | 8.804 | 14.140 | 2.072 | 1.00 | 11.21 |
| 8916 | CZ3 | TRP | B | 395 | 9.533 | 14.984 | 1.137 | 1.00 | 13.18 |

FIGURE 3 (Cont.)

| A | B | C | D | E | F | G | H | I | J |
|---|---|---|---|---|---|---|---|---|---|
| 8917 | CH2 | TRP | B | 395 | 8.935 | 15.477 | 0.035 | 1.00 | 11.16 |
| 8918 | CZ2 | TRP | B | 395 | 7.608 | 15.187 | -0.247 | 1.00 | 18.42 |
| 8919 | C | TRP | B | 395 | 7.351 | 14.211 | 5.258 | 1.00 | 9.22 |
| 8920 | O | TRP | B | 395 | 6.914 | 15.319 | 5.222 | 1.00 | 7.00 |
| 8921 | N | GLU | B | 396 | 8.658 | 14.018 | 5.535 | 1.00 | 10.71 |
| 8922 | CA | GLU | B | 396 | 9.568 | 15.173 | 5.437 | 1.00 | 11.54 |
| 8923 | CB | GLU | B | 396 | 9.813 | 15.901 | 6.743 | 1.00 | 13.35 |
| 8924 | CG | GLU | B | 396 | 9.421 | 15.207 | 8.037 | 1.00 | 19.13 |
| 8925 | CD | GLU | B | 396 | 9.058 | 16.236 | 9.122 | 1.00 | 17.07 |
| 8926 | OE1 | GLU | B | 396 | 7.939 | 16.632 | 9.125 | 1.00 | 21.81 |
| 8927 | OE2 | GLU | B | 396 | 9.838 | 16.613 | 9.952 | 1.00 | 12.93 |
| 8928 | C | GLU | B | 396 | 10.863 | 14.926 | 4.831 | 1.00 | 11.97 |
| 8929 | O | GLU | B | 396 | 11.260 | 13.746 | 4.581 | 1.00 | 12.92 |
| 8930 | N | ALA | B | 397 | 11.508 | 16.082 | 4.618 | 1.00 | 9.42 |
| 8931 | CA | ALA | B | 397 | 12.794 | 16.161 | 4.117 | 1.00 | 11.63 |
| 8932 | CB | ALA | B | 397 | 12.952 | 17.379 | 3.200 | 1.00 | 12.33 |
| 8933 | C | ALA | B | 397 | 13.681 | 16.300 | 5.300 | 1.00 | 12.85 |
| 8934 | O | ALA | B | 397 | 13.384 | 17.141 | 6.202 | 1.00 | 13.06 |
| 8935 | N | ILE | B | 398 | 14.812 | 15.545 | 5.253 | 1.00 | 12.49 |
| 8936 | CA | ILE | B | 398 | 15.635 | 15.235 | 6.400 | 1.00 | 11.66 |
| 8937 | CB | ILE | B | 398 | 15.886 | 13.737 | 6.507 | 1.00 | 11.40 |
| 8938 | CG1 | ILE | B | 398 | 14.631 | 12.895 | 6.212 | 1.00 | 11.30 |
| 8939 | CD1 | ILE | B | 398 | 13.677 | 12.841 | 7.301 | 1.00 | 6.39 |
| 8940 | CG2 | ILE | B | 398 | 16.281 | 13.365 | 7.895 | 1.00 | 10.41 |
| 8941 | C | ILE | B | 398 | 16.955 | 15.946 | 6.256 | 1.00 | 13.46 |
| 8942 | O | ILE | B | 398 | 17.372 | 16.596 | 7.129 | 1.00 | 14.98 |
| 8943 | N | ASN | B | 399 | 17.634 | 15.829 | 5.172 | 1.00 | 12.52 |
| 8944 | CA | ASN | B | 399 | 18.799 | 16.569 | 5.034 | 1.00 | 13.78 |
| 8945 | CB | ASN | B | 399 | 20.068 | 15.742 | 5.317 | 1.00 | 15.61 |
| 8946 | CG | ASN | B | 399 | 20.148 | 15.301 | 6.696 | 1.00 | 25.90 |
| 8947 | OD1 | ASN | B | 399 | 20.330 | 16.127 | 7.592 | 1.00 | 32.03 |
| 8948 | ND2 | ASN | B | 399 | 20.066 | 13.944 | 6.918 | 1.00 | 33.18 |
| 8949 | C | ASN | B | 399 | 18.892 | 17.077 | 3.630 | 1.00 | 12.81 |
| 8950 | O | ASN | B | 399 | 18.730 | 16.312 | 2.704 | 1.00 | 10.63 |
| 8951 | N | ILE | B | 400 | 19.208 | 18.355 | 3.495 | 1.00 | 12.28 |
| 8952 | CA | ILE | B | 400 | 19.667 | 18.832 | 2.227 | 1.00 | 12.60 |
| 8953 | CB | ILE | B | 400 | 19.442 | 20.270 | 2.039 | 1.00 | 11.08 |
| 8954 | CG1 | ILE | B | 400 | 18.000 | 20.651 | 2.177 | 1.00 | 9.45 |
| 8955 | CD1 | ILE | B | 400 | 17.882 | 22.321 | 2.206 | 1.00 | 5.78 |
| 8956 | CG2 | ILE | B | 400 | 19.822 | 20.618 | 0.634 | 1.00 | 10.07 |
| 8957 | C | ILE | B | 400 | 21.171 | 18.583 | 2.061 | 1.00 | 15.26 |
| 8958 | O | ILE | B | 400 | 21.988 | 19.261 | 2.752 | 1.00 | 16.70 |
| 8959 | N | PHE | B | 401 | 21.528 | 17.689 | 1.120 | 1.00 | 15.34 |
| 8960 | CA | PHE | B | 401 | 22.943 | 17.326 | 0.915 | 1.00 | 15.26 |
| 8961 | CB | PHE | B | 401 | 23.027 | 15.989 | 0.280 | 1.00 | 14.85 |
| 8962 | CG | PHE | B | 401 | 22.810 | 14.902 | 1.214 | 1.00 | 15.81 |
| 8963 | CD1 | PHE | B | 401 | 21.565 | 14.381 | 1.372 | 1.00 | 14.29 |
| 8964 | CE1 | PHE | B | 401 | 21.357 | 13.329 | 2.235 | 1.00 | 15.63 |
| 8965 | CZ | PHE | B | 401 | 22.433 | 12.778 | 2.915 | 1.00 | 14.00 |
| 8966 | CE2 | PHE | B | 401 | 23.650 | 13.300 | 2.804 | 1.00 | 7.29 |
| 8967 | CD2 | PHE | B | 401 | 23.857 | 14.389 | 1.950 | 1.00 | 7.48 |

FIGURE 3 (Cont.)

| A | B | C | D | E | F | G | H | I | J |
|---|---|---|---|---|---|---|---|---|---|
| 8968 | C | PHE | B | 401 | 23.761 | 18.172 | 0.036 | 1.00 | 15.45 |
| 8969 | O | PHE | B | 401 | 24.903 | 18.381 | 0.322 | 1.00 | 17.06 |
| 8970 | N | ARG | B | 402 | 23.232 | 18.556 | -1.106 | 1.00 | 15.40 |
| 8971 | CA | ARG | B | 402 | 23.923 | 19.434 | -2.014 | 1.00 | 15.45 |
| 8972 | CB | ARG | B | 402 | 24.747 | 18.603 | -2.950 | 1.00 | 17.08 |
| 8973 | CG | ARG | B | 402 | 25.910 | 19.366 | -3.593 | 1.00 | 17.70 |
| 8974 | CD | ARG | B | 402 | 27.162 | 19.170 | -2.801 | 1.00 | 22.91 |
| 8975 | NE | ARG | B | 402 | 28.226 | 19.992 | -3.348 | 1.00 | 31.73 |
| 8976 | CZ | ARG | B | 402 | 29.523 | 19.842 | -3.033 | 1.00 | 35.02 |
| 8977 | NH1 | ARG | B | 402 | 29.918 | 18.871 | -2.160 | 1.00 | 34.42 |
| 8978 | NH2 | ARG | B | 402 | 30.418 | 20.639 | -3.621 | 1.00 | 27.25 |
| 8979 | C | ARG | B | 402 | 23.001 | 20.281 | -2.827 | 1.00 | 15.67 |
| 8980 | O | ARG | B | 402 | 21.921 | 19.874 | -3.130 | 1.00 | 17.18 |
| 8981 | N | VAL | B | 403 | 23.452 | 21.455 | -3.212 | 1.00 | 14.54 |
| 8982 | CA | VAL | B | 403 | 22.765 | 22.287 | -4.130 | 1.00 | 13.59 |
| 8983 | CB | VAL | B | 403 | 22.356 | 23.664 | -3.444 | 1.00 | 14.78 |
| 8984 | CG1 | VAL | B | 403 | 21.881 | 24.715 | -4.475 | 1.00 | 7.71 |
| 8985 | CG2 | VAL | B | 403 | 21.237 | 23.443 | -2.468 | 1.00 | 10.29 |
| 8986 | C | VAL | B | 403 | 23.749 | 22.637 | -5.209 | 1.00 | 14.45 |
| 8987 | O | VAL | B | 403 | 24.744 | 23.118 | -4.859 | 1.00 | 16.74 |
| 8988 | N | THR | B | 404 | 23.426 | 22.468 | -6.516 | 1.00 | 14.79 |
| 8989 | CA | THR | B | 404 | 24.276 | 22.766 | -7.656 | 1.00 | 15.44 |
| 8990 | CB | THR | B | 404 | 24.567 | 21.491 | -8.518 | 1.00 | 14.59 |
| 8991 | OG1 | THR | B | 404 | 23.429 | 21.011 | -9.202 | 1.00 | 11.90 |
| 8992 | CG2 | THR | B | 404 | 24.886 | 20.407 | -7.666 | 1.00 | 10.92 |
| 8993 | C | THR | B | 404 | 23.677 | 23.926 | -8.460 | 1.00 | 17.39 |
| 8994 | O | THR | B | 404 | 22.856 | 24.652 | -7.882 | 1.00 | 20.16 |
| 8995 | N | GLN | B | 405 | 24.032 | 24.122 | -9.749 | 1.00 | 18.07 |
| 8996 | CA | GLN | B | 405 | 23.397 | 25.224 | -10.503 | 1.00 | 18.44 |
| 8997 | CB | GLN | B | 405 | 24.106 | 25.589 | -11.822 | 1.00 | 20.01 |
| 8998 | CG | GLN | B | 405 | 25.602 | 25.933 | -11.749 | 1.00 | 26.79 |
| 8999 | CD | GLN | B | 405 | 26.492 | 24.908 | -12.516 | 1.00 | 35.50 |
| 9000 | OE1 | GLN | B | 405 | 26.702 | 25.034 | -13.775 | 1.00 | 36.13 |
| 9001 | NE2 | GLN | B | 405 | 27.019 | 23.871 | -11.746 | 1.00 | 38.42 |
| 9002 | C | GLN | B | 405 | 21.986 | 24.803 | -10.883 | 1.00 | 17.47 |
| 9003 | O | GLN | B | 405 | 21.158 | 25.678 | -11.204 | 1.00 | 14.38 |
| 9004 | N | ASP | B | 406 | 21.773 | 23.471 | -10.891 | 1.00 | 16.55 |
| 9005 | CA | ASP | B | 406 | 20.590 | 22.810 | -11.471 | 1.00 | 16.23 |
| 9006 | CB | ASP | B | 406 | 20.953 | 21.778 | -12.501 | 1.00 | 16.26 |
| 9007 | CG | ASP | B | 406 | 21.694 | 22.352 | -13.635 | 1.00 | 22.16 |
| 9008 | OD1 | ASP | B | 406 | 22.340 | 21.540 | -14.355 | 1.00 | 28.50 |
| 9009 | OD2 | ASP | B | 406 | 21.708 | 23.601 | -13.894 | 1.00 | 23.98 |
| 9010 | C | ASP | B | 406 | 19.798 | 22.037 | -10.531 | 1.00 | 15.88 |
| 9011 | O | ASP | B | 406 | 18.581 | 22.100 | -10.626 | 1.00 | 18.05 |
| 9012 | N | SER | B | 407 | 20.436 | 21.212 | -9.726 | 1.00 | 13.60 |
| 9013 | CA | SER | B | 407 | 19.751 | 20.315 | -8.844 | 1.00 | 12.76 |
| 9014 | CB | SER | B | 407 | 20.205 | 18.892 | -9.197 | 1.00 | 13.15 |
| 9015 | OG | SER | B | 407 | 20.169 | 18.710 | -10.617 | 1.00 | 16.94 |
| 9016 | C | SER | B | 407 | 19.909 | 20.569 | -7.321 | 1.00 | 11.69 |
| 9017 | O | SER | B | 407 | 20.758 | 21.319 | -6.897 | 1.00 | 11.86 |
| 9018 | N | LEU | B | 408 | 19.058 | 19.985 | -6.476 | 1.00 | 10.98 |

FIGURE 3 (Cont.)

| A | B | C | D | E | F | G | H | I | J |
|---|---|---|---|---|---|---|---|---|---|
| 9019 | CA | LEU | B | 408 | 19.285 | 20.002 | -5.052 | 1.00 | 9.67 |
| 9020 | CB | LEU | B | 408 | 18.365 | 20.994 | -4.371 | 1.00 | 10.22 |
| 9021 | CG | LEU | B | 408 | 18.318 | 21.072 | -2.834 | 1.00 | 8.20 |
| 9022 | CD1 | LEU | B | 408 | 17.500 | 22.368 | -2.505 | 1.00 | 4.10 |
| 9023 | CD2 | LEU | B | 408 | 17.583 | 19.755 | -2.216 | 1.00 | 2.00 |
| 9024 | C | LEU | B | 408 | 19.048 | 18.577 | -4.669 | 1.00 | 11.26 |
| 9025 | O | LEU | B | 408 | 17.992 | 18.062 | -5.065 | 1.00 | 12.25 |
| 9026 | N | PHE | B | 409 | 20.039 | 17.905 | -4.018 | 1.00 | 9.45 |
| 9027 | CA | PHE | B | 409 | 19.941 | 16.521 | -3.581 | 1.00 | 9.53 |
| 9028 | CB | PHE | B | 409 | 21.267 | 15.745 | -3.607 | 1.00 | 8.29 |
| 9029 | CG | PHE | B | 409 | 21.766 | 15.478 | -5.008 | 1.00 | 8.61 |
| 9030 | CD1 | PHE | B | 409 | 22.569 | 16.400 | -5.631 | 1.00 | 2.00 |
| 9031 | CE1 | PHE | B | 409 | 22.896 | 16.291 | -6.818 | 1.00 | 2.00 |
| 9032 | CZ | PHE | B | 409 | 22.563 | 15.199 | -7.506 | 1.00 | 2.00 |
| 9033 | CE2 | PHE | B | 409 | 21.853 | 14.168 | -6.881 | 1.00 | 3.79 |
| 9034 | CD2 | PHE | B | 409 | 21.408 | 14.335 | -5.692 | 1.00 | 2.61 |
| 9035 | C | PHE | B | 409 | 19.529 | 16.641 | -2.168 | 1.00 | 10.90 |
| 9036 | O | PHE | B | 409 | 20.115 | 17.415 | -1.418 | 1.00 | 11.59 |
| 9037 | N | TYR | B | 410 | 18.541 | 15.821 | -1.750 | 1.00 | 11.12 |
| 9038 | CA | TYR | B | 410 | 18.063 | 15.834 | -0.381 | 1.00 | 9.93 |
| 9039 | CB | TYR | B | 410 | 16.983 | 16.868 | -0.212 | 1.00 | 9.50 |
| 9040 | CG | TYR | B | 410 | 15.666 | 16.533 | -0.872 | 1.00 | 7.44 |
| 9041 | CD1 | TYR | B | 410 | 14.663 | 15.875 | -0.184 | 1.00 | 6.45 |
| 9042 | CE1 | TYR | B | 410 | 13.486 | 15.553 | -0.731 | 1.00 | 4.13 |
| 9043 | CZ | TYR | B | 410 | 13.255 | 15.888 | -2.009 | 1.00 | 7.35 |
| 9044 | OH | TYR | B | 410 | 12.083 | 15.653 | -2.614 | 1.00 | 7.98 |
| 9045 | CE2 | TYR | B | 410 | 14.197 | 16.507 | -2.710 | 1.00 | 8.48 |
| 9046 | CD2 | TYR | B | 410 | 15.434 | 16.844 | -2.126 | 1.00 | 5.14 |
| 9047 | C | TYR | B | 410 | 17.546 | 14.492 | 0.013 | 1.00 | 10.13 |
| 9048 | O | TYR | B | 410 | 17.070 | 13.749 | -0.809 | 1.00 | 9.90 |
| 9049 | N | SER | B | 411 | 17.726 | 14.150 | 1.262 | 1.00 | 11.70 |
| 9050 | CA | SER | B | 411 | 17.106 | 12.942 | 1.751 | 1.00 | 11.93 |
| 9051 | CB | SER | B | 411 | 17.939 | 12.241 | 2.768 | 1.00 | 11.87 |
| 9052 | OG | SER | B | 411 | 17.823 | 12.805 | 4.011 | 1.00 | 12.09 |
| 9053 | C | SER | B | 411 | 15.727 | 13.184 | 2.303 | 1.00 | 13.44 |
| 9054 | O | SER | B | 411 | 15.390 | 14.340 | 2.728 | 1.00 | 14.07 |
| 9055 | N | SER | B | 412 | 14.980 | 12.062 | 2.294 | 1.00 | 12.47 |
| 9056 | CA | SER | B | 412 | 13.607 | 12.053 | 2.690 | 1.00 | 12.18 |
| 9057 | CB | SER | B | 412 | 12.793 | 12.765 | 1.650 | 1.00 | 13.31 |
| 9058 | OG | SER | B | 412 | 11.970 | 11.828 | 0.954 | 1.00 | 12.88 |
| 9059 | C | SER | B | 412 | 12.943 | 10.678 | 2.918 | 1.00 | 12.83 |
| 9060 | O | SER | B | 412 | 13.336 | 9.727 | 2.408 | 1.00 | 13.28 |
| 9061 | N | ASN | B | 413 | 11.920 | 10.663 | 3.731 | 1.00 | 11.81 |
| 9062 | CA | ASN | B | 413 | 11.046 | 9.519 | 3.971 | 1.00 | 11.47 |
| 9063 | CB | ASN | B | 413 | 10.788 | 9.389 | 5.464 | 1.00 | 11.43 |
| 9064 | CG | ASN | B | 413 | 10.065 | 10.587 | 6.107 | 1.00 | 10.92 |
| 9065 | OD1 | ASN | B | 413 | 9.876 | 10.592 | 7.308 | 1.00 | 19.34 |
| 9066 | ND2 | ASN | B | 413 | 9.618 | 11.541 | 5.331 | 1.00 | 17.31 |
| 9067 | C | ASN | B | 413 | 9.681 | 9.457 | 3.204 | 1.00 | 11.69 |
| 9068 | O | ASN | B | 413 | 8.725 | 8.768 | 3.646 | 1.00 | 12.19 |
| 9069 | N | GLU | B | 414 | 9.611 | 10.066 | 2.034 | 1.00 | 11.43 |

FIGURE 3 (Cont.)

| A | B | C | D | E | F | G | H | I | J |
|---|---|---|---|---|---|---|---|---|---|
| 9070 | CA | GLU | B | 414 | 8.392 | 10.016 | 1.211 | 1.00 | 12.25 |
| 9071 | CB | GLU | B | 414 | 8.490 | 11.065 | 0.129 | 1.00 | 11.09 |
| 9072 | CG | GLU | B | 414 | 7.464 | 10.925 | -0.962 | 1.00 | 10.04 |
| 9073 | CD | GLU | B | 414 | 7.675 | 11.883 | -2.108 | 1.00 | 10.07 |
| 9074 | OE1 | GLU | B | 414 | 8.599 | 12.765 | -2.088 | 1.00 | 15.13 |
| 9075 | OE2 | GLU | B | 414 | 6.835 | 11.790 | -2.987 | 1.00 | 12.81 |
| 9076 | C | GLU | B | 414 | 7.967 | 8.584 | 0.656 | 1.00 | 12.00 |
| 9077 | O | GLU | B | 414 | 6.795 | 8.202 | 0.610 | 1.00 | 10.51 |
| 9078 | N | PHE | B | 415 | 8.959 | 7.809 | 0.309 | 1.00 | 12.81 |
| 9079 | CA | PHE | B | 415 | 8.744 | 6.617 | -0.439 | 1.00 | 14.52 |
| 9080 | CB | PHE | B | 415 | 10.067 | 5.976 | -0.824 | 1.00 | 14.30 |
| 9081 | CG | PHE | B | 415 | 9.921 | 4.920 | -1.895 | 1.00 | 14.75 |
| 9082 | CD1 | PHE | B | 415 | 9.090 | 5.136 | -2.993 | 1.00 | 15.90 |
| 9083 | CE1 | PHE | B | 415 | 8.959 | 4.178 | -3.937 | 1.00 | 15.50 |
| 9084 | CZ | PHE | B | 415 | 9.629 | 3.006 | -3.821 | 1.00 | 13.94 |
| 9085 | CE2 | PHE | B | 415 | 10.449 | 2.746 | -2.743 | 1.00 | 14.46 |
| 9086 | CD2 | PHE | B | 415 | 10.587 | 3.681 | -1.784 | 1.00 | 16.96 |
| 9087 | C | PHE | B | 415 | 7.873 | 5.554 | 0.220 | 1.00 | 15.49 |
| 9088 | O | PHE | B | 415 | 8.205 | 5.059 | 1.311 | 1.00 | 16.27 |
| 9089 | N | GLU | B | 416 | 6.798 | 5.199 | -0.492 | 1.00 | 16.05 |
| 9090 | CA | GLU | B | 416 | 5.822 | 4.214 | -0.055 | 1.00 | 16.76 |
| 9091 | CB | GLU | B | 416 | 6.356 | 2.749 | -0.267 | 1.00 | 16.90 |
| 9092 | CG | GLU | B | 416 | 6.498 | 2.291 | -1.738 | 1.00 | 16.68 |
| 9093 | CD | GLU | B | 416 | 7.005 | 0.838 | -1.921 | 1.00 | 18.24 |
| 9094 | OE1 | GLU | B | 416 | 7.787 | 0.375 | -1.085 | 1.00 | 14.84 |
| 9095 | OE2 | GLU | B | 416 | 6.652 | 0.158 | -2.941 | 1.00 | 22.17 |
| 9096 | C | GLU | B | 416 | 5.400 | 4.499 | 1.410 | 1.00 | 16.67 |
| 9097 | O | GLU | B | 416 | 4.996 | 3.570 | 2.173 | 1.00 | 16.88 |
| 9098 | N | GLU | B | 417 | 5.527 | 5.769 | 1.789 | 1.00 | 16.10 |
| 9099 | CA | GLU | B | 417 | 5.013 | 6.302 | 3.064 | 1.00 | 16.25 |
| 9100 | CB | GLU | B | 417 | 3.445 | 6.299 | 2.996 | 1.00 | 15.93 |
| 9101 | CG | GLU | B | 417 | 2.731 | 7.326 | 3.920 | 1.00 | 20.91 |
| 9102 | CD | GLU | B | 417 | 3.586 | 7.962 | 5.126 | 1.00 | 27.81 |
| 9103 | OE1 | GLU | B | 417 | 3.314 | 7.484 | 6.307 | 1.00 | 26.65 |
| 9104 | OE2 | GLU | B | 417 | 4.488 | 8.965 | 4.932 | 1.00 | 23.45 |
| 9105 | C | GLU | B | 417 | 5.660 | 5.710 | 4.414 | 1.00 | 15.52 |
| 9106 | O | GLU | B | 417 | 5.034 | 5.670 | 5.488 | 1.00 | 14.63 |
| 9107 | N | TYR | B | 418 | 6.929 | 5.285 | 4.381 | 1.00 | 14.90 |
| 9108 | CA | TYR | B | 418 | 7.506 | 4.630 | 5.572 | 1.00 | 14.10 |
| 9109 | CB | TYR | B | 418 | 8.376 | 3.457 | 5.195 | 1.00 | 13.03 |
| 9110 | CG | TYR | B | 418 | 7.639 | 2.193 | 4.985 | 1.00 | 11.58 |
| 9111 | CD1 | TYR | B | 418 | 7.496 | 1.260 | 6.023 | 1.00 | 15.03 |
| 9112 | CE1 | TYR | B | 418 | 6.807 | 0.052 | 5.816 | 1.00 | 12.57 |
| 9113 | CZ | TYR | B | 418 | 6.260 | -0.191 | 4.570 | 1.00 | 13.35 |
| 9114 | OH | TYR | B | 418 | 5.615 | -1.350 | 4.305 | 1.00 | 16.58 |
| 9115 | CE2 | TYR | B | 418 | 6.404 | 0.697 | 3.543 | 1.00 | 14.02 |
| 9116 | CD2 | TYR | B | 418 | 7.108 | 1.884 | 3.749 | 1.00 | 13.91 |
| 9117 | C | TYR | B | 418 | 8.379 | 5.623 | 6.211 | 1.00 | 14.21 |
| 9118 | O | TYR | B | 418 | 9.348 | 6.040 | 5.552 | 1.00 | 16.47 |
| 9119 | N | PRO | B | 419 | 8.097 | 6.068 | 7.439 | 1.00 | 13.67 |
| 9120 | CA | PRO | B | 419 | 8.902 | 7.212 | 8.008 | 1.00 | 12.49 |

FIGURE 3 (Cont.)

| A | B | C | D | E | F | G | H | I | J |
|---|---|---|---|---|---|---|---|---|---|
| 9121 | CB | PRO | B | 419 | 8.136 | 7.638 | 9.249 | 1.00 | 11.51 |
| 9122 | CG | PRO | B | 419 | 6.702 | 6.914 | 9.072 | 1.00 | 13.37 |
| 9123 | CD | PRO | B | 419 | 6.976 | 5.657 | 8.302 | 1.00 | 12.37 |
| 9124 | C | PRO | B | 419 | 10.340 | 6.845 | 8.400 | 1.00 | 11.94 |
| 9125 | O | PRO | B | 419 | 11.067 | 7.851 | 8.620 | 1.00 | 7.91 |
| 9126 | N | GLY | B | 420 | 10.677 | 5.505 | 8.500 | 1.00 | 10.43 |
| 9127 | CA | GLY | B | 420 | 12.030 | 5.028 | 8.778 | 1.00 | 9.43 |
| 9128 | C | GLY | B | 420 | 12.996 | 4.540 | 7.687 | 1.00 | 10.91 |
| 9129 | O | GLY | B | 420 | 13.945 | 3.718 | 7.950 | 1.00 | 11.03 |
| 9130 | N | ARG | B | 421 | 12.709 | 4.945 | 6.448 | 1.00 | 10.40 |
| 9131 | CA | ARG | B | 421 | 13.618 | 4.884 | 5.313 | 1.00 | 10.89 |
| 9132 | CB | ARG | B | 421 | 12.958 | 4.284 | 4.079 | 1.00 | 9.88 |
| 9133 | CG | ARG | B | 421 | 11.795 | 3.323 | 4.314 | 1.00 | 12.37 |
| 9134 | CD | ARG | B | 421 | 11.465 | 2.579 | 3.050 | 1.00 | 13.94 |
| 9135 | NE | ARG | B | 421 | 10.674 | 1.327 | 3.161 | 1.00 | 13.27 |
| 9136 | CZ | ARG | B | 421 | 10.185 | 0.759 | 2.114 | 1.00 | 9.71 |
| 9137 | NH1 | ARG | B | 421 | 9.411 | -0.294 | 2.165 | 1.00 | 9.09 |
| 9138 | NH2 | ARG | B | 421 | 10.468 | 1.307 | 0.956 | 1.00 | 18.95 |
| 9139 | C | ARG | B | 421 | 14.198 | 6.316 | 4.950 | 1.00 | 11.90 |
| 9140 | O | ARG | B | 421 | 13.605 | 7.348 | 5.231 | 1.00 | 12.07 |
| 9141 | N | ARG | B | 422 | 15.391 | 6.315 | 4.374 | 1.00 | 11.51 |
| 9142 | CA | ARG | B | 422 | 15.839 | 7.434 | 3.656 | 1.00 | 12.42 |
| 9143 | CB | ARG | B | 422 | 17.037 | 8.096 | 4.318 | 1.00 | 12.07 |
| 9144 | CG | ARG | B | 422 | 16.988 | 8.179 | 5.780 | 1.00 | 13.50 |
| 9145 | CD | ARG | B | 422 | 16.130 | 9.240 | 6.265 | 1.00 | 15.07 |
| 9146 | NE | ARG | B | 422 | 16.196 | 9.357 | 7.718 | 1.00 | 16.13 |
| 9147 | CZ | ARG | B | 422 | 15.214 | 9.114 | 8.559 | 1.00 | 14.68 |
| 9148 | NH1 | ARG | B | 422 | 15.453 | 9.327 | 9.849 | 1.00 | 12.64 |
| 9149 | NH2 | ARG | B | 422 | 14.001 | 8.720 | 8.144 | 1.00 | 16.15 |
| 9150 | C | ARG | B | 422 | 16.207 | 7.044 | 2.246 | 1.00 | 13.14 |
| 9151 | O | ARG | B | 422 | 16.914 | 6.037 | 2.020 | 1.00 | 14.25 |
| 9152 | N | ASN | B | 423 | 15.712 | 7.893 | 1.329 | 1.00 | 12.09 |
| 9153 | CA | ASN | B | 423 | 15.964 | 7.808 | -0.083 | 1.00 | 11.60 |
| 9154 | CB | ASN | B | 423 | 14.734 | 7.410 | -0.865 | 1.00 | 9.33 |
| 9155 | CG | ASN | B | 423 | 14.496 | 5.946 | -0.839 | 1.00 | 10.08 |
| 9156 | OD1 | ASN | B | 423 | 15.268 | 5.105 | -1.399 | 1.00 | 12.60 |
| 9157 | ND2 | ASN | B | 423 | 13.475 | 5.597 | -0.129 | 1.00 | 7.27 |
| 9158 | C | ASN | B | 423 | 16.416 | 9.192 | -0.473 | 1.00 | 12.11 |
| 9159 | O | ASN | B | 423 | 16.255 | 10.198 | 0.230 | 1.00 | 13.70 |
| 9160 | N | ILE | B | 424 | 17.091 | 9.259 | -1.580 | 1.00 | 12.91 |
| 9161 | CA | ILE | B | 424 | 17.737 | 10.472 | -1.807 | 1.00 | 11.41 |
| 9162 | CB | ILE | B | 424 | 19.225 | 10.385 | -1.579 | 1.00 | 12.74 |
| 9163 | CG1 | ILE | B | 424 | 19.975 | 10.667 | -2.795 | 1.00 | 9.56 |
| 9164 | CD1 | ILE | B | 424 | 21.214 | 11.276 | -2.341 | 1.00 | 17.16 |
| 9165 | CG2 | ILE | B | 424 | 19.735 | 9.119 | -0.897 | 1.00 | 6.59 |
| 9166 | C | ILE | B | 424 | 17.226 | 10.831 | -3.166 | 1.00 | 12.79 |
| 9167 | O | ILE | B | 424 | 17.110 | 10.006 | -4.034 | 1.00 | 11.37 |
| 9168 | N | TYR | B | 425 | 16.802 | 12.085 | -3.241 | 1.00 | 12.63 |
| 9169 | CA | TYR | B | 425 | 16.060 | 12.600 | -4.303 | 1.00 | 13.48 |
| 9170 | CB | TYR | B | 425 | 14.719 | 13.091 | -3.707 | 1.00 | 13.75 |
| 9171 | CG | TYR | B | 425 | 13.717 | 11.973 | -3.379 | 1.00 | 12.85 |

FIGURE 3 (Cont.)

| A | B | C | D | E | F | G | H | I | J |
|---|---|---|---|---|---|---|---|---|---|
| 9172 | CD1 | TYR | B | 425 | 13.762 | 11.253 | -2.178 | 1.00 | 13.77 |
| 9173 | CE1 | TYR | B | 425 | 12.768 | 10.297 | -1.823 | 1.00 | 12.85 |
| 9174 | CZ | TYR | B | 425 | 11.739 | 10.017 | -2.690 | 1.00 | 16.45 |
| 9175 | OH | TYR | B | 425 | 10.732 | 9.050 | -2.502 | 1.00 | 19.51 |
| 9176 | CE2 | TYR | B | 425 | 11.712 | 10.681 | -3.886 | 1.00 | 14.05 |
| 9177 | CD2 | TYR | B | 425 | 12.713 | 11.689 | -4.223 | 1.00 | 12.75 |
| 9178 | C | TYR | B | 425 | 16.869 | 13.694 | -4.811 | 1.00 | 13.81 |
| 9179 | O | TYR | B | 425 | 17.701 | 14.214 | -4.092 | 1.00 | 15.93 |
| 9180 | N | ARG | B | 426 | 16.694 | 14.025 | -6.085 | 1.00 | 14.43 |
| 9181 | CA | ARG | B | 426 | 17.053 | 15.358 | -6.573 | 1.00 | 13.95 |
| 9182 | CB | ARG | B | 426 | 18.170 | 15.294 | -7.605 | 1.00 | 14.21 |
| 9183 | CG | ARG | B | 426 | 17.893 | 14.520 | -8.864 | 1.00 | 15.10 |
| 9184 | CD | ARG | B | 426 | 19.183 | 14.055 | -9.662 | 1.00 | 11.78 |
| 9185 | NE | ARG | B | 426 | 19.845 | 15.165 | -10.349 | 1.00 | 12.45 |
| 9186 | CZ | ARG | B | 426 | 21.093 | 15.126 | -10.809 | 1.00 | 12.98 |
| 9187 | NH1 | ARG | B | 426 | 21.661 | 16.208 | -11.299 | 1.00 | 11.17 |
| 9188 | NH2 | ARG | B | 426 | 21.824 | 14.039 | -10.645 | 1.00 | 9.83 |
| 9189 | C | ARG | B | 426 | 15.885 | 16.023 | -7.216 | 1.00 | 15.09 |
| 9190 | O | ARG | B | 426 | 15.104 | 15.327 | -7.844 | 1.00 | 16.95 |
| 9191 | N | ILE | B | 427 | 15.881 | 17.370 | -7.176 | 1.00 | 13.66 |
| 9192 | CA | ILE | B | 427 | 14.902 | 18.167 | -7.750 | 1.00 | 12.45 |
| 9193 | CB | ILE | B | 427 | 13.943 | 18.653 | -6.610 | 1.00 | 13.27 |
| 9194 | CG1 | ILE | B | 427 | 14.695 | 19.102 | -5.415 | 1.00 | 9.38 |
| 9195 | CD1 | ILE | B | 427 | 13.824 | 20.033 | -4.587 | 1.00 | 12.23 |
| 9196 | CG2 | ILE | B | 427 | 12.896 | 17.650 | -6.120 | 1.00 | 11.24 |
| 9197 | C | ILE | B | 427 | 15.509 | 19.426 | -8.496 | 1.00 | 13.39 |
| 9198 | O | ILE | B | 427 | 16.577 | 19.902 | -8.182 | 1.00 | 14.45 |
| 9199 | N | SER | B | 428 | 14.789 | 20.001 | -9.460 | 1.00 | 11.24 |
| 9200 | CA | SER | B | 428 | 15.379 | 21.034 | -10.272 | 1.00 | 9.71 |
| 9201 | CB | SER | B | 428 | 14.824 | 21.041 | -11.733 | 1.00 | 8.22 |
| 9202 | OG | SER | B | 428 | 13.470 | 20.639 | -11.891 | 1.00 | 2.17 |
| 9203 | C | SER | B | 428 | 15.137 | 22.383 | -9.543 | 1.00 | 11.82 |
| 9204 | O | SER | B | 428 | 14.019 | 22.628 | -9.033 | 1.00 | 12.32 |
| 9205 | N | ILE | B | 429 | 16.163 | 23.258 | -9.534 | 1.00 | 11.23 |
| 9206 | CA | ILE | B | 429 | 16.029 | 24.522 | -8.940 | 1.00 | 12.14 |
| 9207 | CB | ILE | B | 429 | 17.085 | 24.714 | -7.782 | 1.00 | 13.22 |
| 9208 | CG1 | ILE | B | 429 | 18.519 | 25.225 | -8.210 | 1.00 | 18.34 |
| 9209 | CD1 | ILE | B | 429 | 19.078 | 26.928 | -7.682 | 1.00 | 20.83 |
| 9210 | CG2 | ILE | B | 429 | 17.238 | 23.366 | -7.130 | 1.00 | 15.66 |
| 9211 | C | ILE | B | 429 | 15.863 | 25.658 | -9.870 | 1.00 | 9.74 |
| 9212 | O | ILE | B | 429 | 15.582 | 26.672 | -9.389 | 1.00 | 12.39 |
| 9213 | N | GLY | B | 430 | 15.862 | 25.483 | -11.185 | 1.00 | 7.39 |
| 9214 | CA | GLY | B | 430 | 15.870 | 26.569 | -12.110 | 1.00 | 5.15 |
| 9215 | C | GLY | B | 430 | 14.545 | 27.329 | -12.295 | 1.00 | 6.39 |
| 9216 | O | GLY | B | 430 | 14.544 | 28.606 | -12.585 | 1.00 | 6.97 |
| 9217 | N | SER | B | 431 | 13.446 | 26.569 | -12.290 | 1.00 | 3.90 |
| 9218 | CA | SER | B | 431 | 12.096 | 27.119 | -12.490 | 1.00 | 6.41 |
| 9219 | CB | SER | B | 431 | 11.587 | 26.794 | -13.870 | 1.00 | 5.47 |
| 9220 | OG | SER | B | 431 | 11.612 | 25.396 | -14.097 | 1.00 | 5.97 |
| 9221 | C | SER | B | 431 | 11.110 | 26.607 | -11.521 | 1.00 | 6.59 |
| 9222 | O | SER | B | 431 | 11.267 | 25.465 | -11.098 | 1.00 | 8.08 |

FIGURE 3 (Cont.)

| A | B | C | D | E | F | G | H | I | J |
|---|---|---|---|---|---|---|---|---|---|
| 9223 | N | TYR | B | 432 | 10.018 | 27.343 | -11.231 | 1.00 | 8.54 |
| 9224 | CA | TYR | B | 432 | 9.144 | 26.906 | -10.057 | 1.00 | 10.84 |
| 9225 | CB | TYR | B | 432 | 7.907 | 27.704 | -9.703 | 1.00 | 10.35 |
| 9226 | CG | TYR | B | 432 | 7.026 | 26.979 | -8.578 | 1.00 | 9.32 |
| 9227 | CD1 | TYR | B | 432 | 5.688 | 26.827 | -8.724 | 1.00 | 10.29 |
| 9228 | CE1 | TYR | B | 432 | 4.908 | 26.267 | -7.725 | 1.00 | 12.26 |
| 9229 | CZ | TYR | B | 432 | 5.453 | 25.866 | -6.547 | 1.00 | 12.99 |
| 9230 | OH | TYR | B | 432 | 4.626 | 25.304 | -5.630 | 1.00 | 13.15 |
| 9231 | CE2 | TYR | B | 432 | 6.761 | 25.961 | -6.363 | 1.00 | 7.42 |
| 9232 | CD2 | TYR | B | 432 | 7.551 | 26.534 | -7.396 | 1.00 | 9.01 |
| 9233 | C | TYR | B | 432 | 8.757 | 25.450 | -9.928 | 1.00 | 12.24 |
| 9234 | O | TYR | B | 432 | 9.491 | 24.751 | -9.149 | 1.00 | 18.40 |
| 9235 | N | PRO | B | 433 | 7.741 | 24.890 | -10.563 | 1.00 | 11.39 |
| 9236 | CA | PRO | B | 433 | 7.300 | 23.506 | -10.110 | 1.00 | 11.47 |
| 9237 | CB | PRO | B | 433 | 6.194 | 23.137 | -11.030 | 1.00 | 8.60 |
| 9238 | CG | PRO | B | 433 | 6.517 | 23.941 | -12.164 | 1.00 | 10.92 |
| 9239 | CD | PRO | B | 433 | 7.202 | 25.346 | -11.814 | 1.00 | 8.72 |
| 9240 | C | PRO | B | 433 | 8.491 | 22.506 | -10.359 | 1.00 | 12.93 |
| 9241 | O | PRO | B | 433 | 8.830 | 22.233 | -11.541 | 1.00 | 15.00 |
| 9242 | N | PRO | B | 434 | 9.210 | 22.078 | -9.350 | 1.00 | 12.93 |
| 9243 | CA | PRO | B | 434 | 10.449 | 21.388 | -9.599 | 1.00 | 13.67 |
| 9244 | CB | PRO | B | 434 | 11.196 | 21.573 | -8.302 | 1.00 | 13.73 |
| 9245 | CG | PRO | B | 434 | 10.173 | 21.747 | -7.265 | 1.00 | 13.07 |
| 9246 | CD | PRO | B | 434 | 8.969 | 22.232 | -7.920 | 1.00 | 14.36 |
| 9247 | C | PRO | B | 434 | 10.252 | 19.915 | -9.998 | 1.00 | 15.01 |
| 9248 | O | PRO | B | 434 | 9.358 | 19.225 | -9.603 | 1.00 | 14.19 |
| 9249 | N | SER | B | 435 | 11.134 | 19.457 | -10.862 | 1.00 | 14.79 |
| 9250 | CA | SER | B | 435 | 11.065 | 18.100 | -11.393 | 1.00 | 14.66 |
| 9251 | CB | SER | B | 435 | 11.971 | 17.977 | -12.647 | 1.00 | 13.63 |
| 9252 | OG | SER | B | 435 | 11.267 | 17.922 | -13.842 | 1.00 | 16.55 |
| 9253 | C | SER | B | 435 | 11.613 | 17.283 | -10.231 | 1.00 | 12.59 |
| 9254 | O | SER | B | 435 | 12.223 | 17.831 | -9.400 | 1.00 | 13.70 |
| 9255 | N | LYS | B | 436 | 11.429 | 15.976 | -10.212 | 1.00 | 12.29 |
| 9256 | CA | LYS | B | 436 | 11.777 | 15.249 | -9.068 | 1.00 | 11.68 |
| 9257 | CB | LYS | B | 436 | 10.547 | 15.208 | -8.145 | 1.00 | 11.97 |
| 9258 | CG | LYS | B | 436 | 10.737 | 14.521 | -6.770 | 1.00 | 9.89 |
| 9259 | CD | LYS | B | 436 | 9.989 | 15.269 | -5.596 | 1.00 | 11.41 |
| 9260 | CE | LYS | B | 436 | 8.887 | 14.343 | -4.904 | 1.00 | 12.36 |
| 9261 | NZ | LYS | B | 436 | 8.078 | 15.101 | -3.842 | 1.00 | 4.92 |
| 9262 | C | LYS | B | 436 | 12.130 | 13.839 | -9.465 | 1.00 | 11.42 |
| 9263 | O | LYS | B | 436 | 11.333 | 13.202 | -10.085 | 1.00 | 11.00 |
| 9264 | N | LYS | B | 437 | 13.300 | 13.344 | -9.064 | 1.00 | 10.15 |
| 9265 | CA | LYS | B | 437 | 13.596 | 11.921 | -9.214 | 1.00 | 8.83 |
| 9266 | CB | LYS | B | 437 | 14.388 | 11.623 | -10.531 | 1.00 | 8.55 |
| 9267 | CG | LYS | B | 437 | 15.868 | 11.347 | -10.421 | 1.00 | 5.49 |
| 9268 | CD | LYS | B | 437 | 16.473 | 10.890 | -11.741 | 1.00 | 7.86 |
| 9269 | CE | LYS | B | 437 | 17.522 | 9.652 | -11.573 | 1.00 | 10.40 |
| 9270 | NZ | LYS | B | 437 | 18.294 | 9.359 | -12.767 | 1.00 | 6.51 |
| 9271 | C | LYS | B | 437 | 14.177 | 11.349 | -7.931 | 1.00 | 7.51 |
| 9272 | O | LYS | B | 437 | 15.057 | 11.909 | -7.260 | 1.00 | 7.65 |
| 9273 | N | CYS | B | 438 | 13.530 | 10.289 | -7.530 | 1.00 | 6.48 |

FIGURE 3 (Cont.)

| A | B | C | D | E | F | G | H | I | J |
|---|---|---|---|---|---|---|---|---|---|
| 9274 | CA | CYS | B | 438 | 14.001 | 9.482 | -6.467 | 1.00 | 6.35 |
| 9275 | CB | CYS | B | 438 | 12.979 | 8.478 | -6.045 | 1.00 | 8.84 |
| 9276 | SG | CYS | B | 438 | 13.493 | 7.873 | -4.421 | 1.00 | 9.87 |
| 9277 | C | CYS | B | 438 | 15.159 | 8.741 | -7.018 | 1.00 | 6.36 |
| 9278 | O | CYS | B | 438 | 15.008 | 7.839 | -7.827 | 1.00 | 3.93 |
| 9279 | N | VAL | B | 439 | 16.348 | 9.154 | -6.673 | 1.00 | 5.10 |
| 9280 | CA | VAL | B | 439 | 17.398 | 8.404 | -7.242 | 1.00 | 6.44 |
| 9281 | CB | VAL | B | 439 | 18.752 | 9.064 | -7.173 | 1.00 | 5.66 |
| 9282 | CG1 | VAL | B | 439 | 18.992 | 9.454 | -5.890 | 1.00 | 9.21 |
| 9283 | CG2 | VAL | B | 439 | 19.786 | 8.086 | -7.499 | 1.00 | 5.35 |
| 9284 | C | VAL | B | 439 | 17.362 | 7.001 | -6.626 | 1.00 | 5.68 |
| 9285 | O | VAL | B | 439 | 17.534 | 6.075 | -7.347 | 1.00 | 7.71 |
| 9286 | N | THR | B | 440 | 17.137 | 6.826 | -5.338 | 1.00 | 5.54 |
| 9287 | CA | THR | B | 440 | 17.378 | 5.521 | -4.677 | 1.00 | 6.60 |
| 9288 | CB | THR | B | 440 | 17.869 | 5.698 | -3.330 | 1.00 | 8.24 |
| 9289 | OG1 | THR | B | 440 | 17.080 | 6.672 | -2.590 | 1.00 | 11.00 |
| 9290 | CG2 | THR | B | 440 | 19.362 | 6.297 | -3.419 | 1.00 | 10.06 |
| 9291 | C | THR | B | 440 | 16.234 | 4.542 | -4.586 | 1.00 | 7.23 |
| 9292 | O | THR | B | 440 | 16.480 | 3.352 | -4.417 | 1.00 | 6.35 |
| 9293 | N | CYS | B | 441 | 14.995 | 5.031 | -4.724 | 1.00 | 6.05 |
| 9294 | CA | CYS | B | 441 | 13.858 | 4.221 | -4.400 | 1.00 | 8.54 |
| 9295 | CB | CYS | B | 441 | 12.641 | 4.872 | -4.986 | 1.00 | 8.24 |
| 9296 | SG | CYS | B | 441 | 12.267 | 6.252 | -4.005 | 1.00 | 15.63 |
| 9297 | C | CYS | B | 441 | 13.938 | 2.752 | -4.900 | 1.00 | 8.06 |
| 9298 | O | CYS | B | 441 | 13.624 | 1.794 | -4.151 | 1.00 | 8.68 |
| 9299 | N | HIS | B | 442 | 14.322 | 2.634 | -6.152 | 1.00 | 7.61 |
| 9300 | CA | HIS | B | 442 | 14.273 | 1.425 | -6.950 | 1.00 | 8.75 |
| 9301 | CB | HIS | B | 442 | 13.411 | 1.687 | -8.197 | 1.00 | 8.10 |
| 9302 | CG | HIS | B | 442 | 11.961 | 1.862 | -7.882 | 1.00 | 10.31 |
| 9303 | ND1 | HIS | B | 442 | 11.354 | 3.108 | -7.788 | 1.00 | 9.28 |
| 9304 | CE1 | HIS | B | 442 | 10.085 | 2.937 | -7.439 | 1.00 | 10.36 |
| 9305 | NE2 | HIS | B | 442 | 9.841 | 1.635 | -7.350 | 1.00 | 10.28 |
| 9306 | CD2 | HIS | B | 442 | 10.994 | 0.939 | -7.620 | 1.00 | 9.34 |
| 9307 | C | HIS | B | 442 | 15.686 | 0.943 | -7.362 | 1.00 | 9.58 |
| 9308 | O | HIS | B | 442 | 15.772 | -0.016 | -8.112 | 1.00 | 10.14 |
| 9309 | N | LEU | B | 443 | 16.769 | 1.620 | -6.947 | 1.00 | 9.47 |
| 9310 | CA | LEU | B | 443 | 18.111 | 1.140 | -7.225 | 1.00 | 9.35 |
| 9311 | CB | LEU | B | 443 | 19.200 | 1.893 | -6.446 | 1.00 | 7.55 |
| 9312 | CG | LEU | B | 443 | 20.425 | 2.521 | -7.148 | 1.00 | 9.09 |
| 9313 | CD1 | LEU | B | 443 | 21.688 | 2.106 | -6.475 | 1.00 | 9.44 |
| 9314 | CD2 | LEU | B | 443 | 20.651 | 2.321 | -8.681 | 1.00 | 8.89 |
| 9315 | C | LEU | B | 443 | 18.209 | -0.330 | -6.855 | 1.00 | 10.19 |
| 9316 | O | LEU | B | 443 | 18.520 | -1.144 | -7.707 | 1.00 | 10.49 |
| 9317 | N | ARG | B | 444 | 18.026 | -0.661 | -5.581 | 1.00 | 10.21 |
| 9318 | CA | ARG | B | 444 | 17.999 | -2.068 | -5.141 | 1.00 | 9.84 |
| 9319 | CB | ARG | B | 444 | 19.327 | -2.461 | -4.541 | 1.00 | 9.96 |
| 9320 | CG | ARG | B | 444 | 20.489 | -2.133 | -5.455 | 1.00 | 8.31 |
| 9321 | CD | ARG | B | 444 | 21.828 | -2.249 | -4.810 | 1.00 | 6.50 |
| 9322 | NE | ARG | B | 444 | 22.795 | -2.674 | -5.787 | 1.00 | 9.10 |
| 9323 | CZ | ARG | B | 444 | 23.741 | -1.913 | -6.323 | 1.00 | 11.22 |
| 9324 | NH1 | ARG | B | 444 | 23.872 | -0.639 | -5.946 | 1.00 | 7.85 |

FIGURE 3 (Cont.)

| A | B | C | D | E | F | G | H | I | J |
|---|---|---|---|---|---|---|---|---|---|
| 9325 | NH2 | ARG | B | 444 | 24.588 | -2.452 | -7.236 | 1.00 | 8.43 |
| 9326 | C | ARG | B | 444 | 16.903 | -2.093 | -4.130 | 1.00 | 10.00 |
| 9327 | O | ARG | B | 444 | 17.103 | -1.779 | -2.962 | 1.00 | 7.93 |
| 9328 | N | LYS | B | 445 | 15.699 | -2.324 | -4.598 | 1.00 | 9.85 |
| 9329 | CA | LYS | B | 445 | 14.575 | -1.871 | -3.791 | 1.00 | 11.50 |
| 9330 | CB | LYS | B | 445 | 13.251 | -1.702 | -4.613 | 1.00 | 10.84 |
| 9331 | CG | LYS | B | 445 | 11.964 | -1.253 | -3.850 | 1.00 | 13.31 |
| 9332 | CD | LYS | B | 445 | 10.612 | -1.696 | -4.662 | 1.00 | 22.12 |
| 9333 | CE | LYS | B | 445 | 9.382 | -2.063 | -3.663 | 1.00 | 24.18 |
| 9334 | NZ | LYS | B | 445 | 7.994 | -1.968 | -4.228 | 1.00 | 23.61 |
| 9335 | C | LYS | B | 445 | 14.456 | -2.766 | -2.535 | 1.00 | 11.39 |
| 9336 | O | LYS | B | 445 | 14.139 | -2.223 | -1.455 | 1.00 | 13.32 |
| 9337 | N | GLU | B | 446 | 14.723 | -4.075 | -2.639 | 1.00 | 10.78 |
| 9338 | CA | GLU | B | 446 | 14.609 | -4.953 | -1.444 | 1.00 | 10.81 |
| 9339 | CB | GLU | B | 446 | 14.418 | -6.445 | -1.823 | 1.00 | 10.37 |
| 9340 | CG | GLU | B | 446 | 12.945 | -6.812 | -1.950 | 1.00 | 12.18 |
| 9341 | CD | GLU | B | 446 | 12.676 | -8.246 | -2.460 | 1.00 | 14.88 |
| 9342 | OE1 | GLU | B | 446 | 13.672 | -9.055 | -2.673 | 1.00 | 16.11 |
| 9343 | OE2 | GLU | B | 446 | 11.439 | -8.527 | -2.651 | 1.00 | 11.91 |
| 9344 | C | GLU | B | 446 | 15.768 | -4.828 | -0.413 | 1.00 | 10.43 |
| 9345 | O | GLU | B | 446 | 15.505 | -4.821 | 0.791 | 1.00 | 10.07 |
| 9346 | N | ARG | B | 447 | 17.011 | -4.830 | -0.906 | 1.00 | 9.34 |
| 9347 | CA | ARG | B | 447 | 18.204 | -4.560 | -0.123 | 1.00 | 8.92 |
| 9348 | CB | ARG | B | 447 | 19.439 | -4.570 | -1.037 | 1.00 | 9.16 |
| 9349 | CG | ARG | B | 447 | 20.650 | -5.462 | -0.579 | 1.00 | 10.72 |
| 9350 | CD | ARG | B | 447 | 21.991 | -4.782 | -0.542 | 1.00 | 9.80 |
| 9351 | NE | ARG | B | 447 | 22.874 | -5.399 | -1.497 | 1.00 | 11.89 |
| 9352 | CZ | ARG | B | 447 | 24.207 | -5.604 | -1.350 | 1.00 | 8.02 |
| 9353 | NH1 | ARG | B | 447 | 24.854 | -6.246 | -2.337 | 1.00 | 7.27 |
| 9354 | NH2 | ARG | B | 447 | 24.881 | -5.216 | -0.276 | 1.00 | 2.00 |
| 9355 | C | ARG | B | 447 | 18.335 | -3.200 | 0.523 | 1.00 | 7.82 |
| 9356 | O | ARG | B | 447 | 18.996 | -3.080 | 1.497 | 1.00 | 6.97 |
| 9357 | N | CYS | B | 448 | 17.789 | -2.162 | -0.068 | 1.00 | 7.66 |
| 9358 | CA | CYS | B | 448 | 18.255 | -0.806 | 0.268 | 1.00 | 8.29 |
| 9359 | CB | CYS | B | 448 | 19.272 | -0.329 | -0.771 | 1.00 | 8.28 |
| 9360 | SG | CYS | B | 448 | 20.862 | -1.169 | -0.719 | 1.00 | 13.58 |
| 9361 | C | CYS | B | 448 | 17.121 | 0.258 | 0.357 | 1.00 | 7.62 |
| 9362 | O | CYS | B | 448 | 16.538 | 0.661 | -0.645 | 1.00 | 4.00 |
| 9363 | N | GLN | B | 449 | 16.824 | 0.691 | 1.591 | 1.00 | 8.67 |
| 9364 | CA | GLN | B | 449 | 15.896 | 1.805 | 1.776 | 1.00 | 8.72 |
| 9365 | CB | GLN | B | 449 | 14.538 | 1.256 | 2.112 | 1.00 | 8.77 |
| 9366 | CG | GLN | B | 449 | 13.934 | 0.431 | 1.019 | 1.00 | 6.87 |
| 9367 | CD | GLN | B | 449 | 13.495 | 1.279 | -0.184 | 1.00 | 15.48 |
| 9368 | OE1 | GLN | B | 449 | 13.477 | 0.740 | -1.331 | 1.00 | 17.30 |
| 9369 | NE2 | GLN | B | 449 | 13.136 | 2.591 | 0.046 | 1.00 | 10.26 |
| 9370 | C | GLN | B | 449 | 16.375 | 2.779 | 2.821 | 1.00 | 9.24 |
| 9371 | O | GLN | B | 449 | 15.635 | 3.658 | 3.277 | 1.00 | 8.92 |
| 9372 | N | TYR | B | 450 | 17.636 | 2.682 | 3.157 | 1.00 | 9.36 |
| 9373 | CA | TYR | B | 450 | 18.131 | 3.598 | 4.113 | 1.00 | 10.71 |
| 9374 | CB | TYR | B | 450 | 18.105 | 2.907 | 5.489 | 1.00 | 9.83 |
| 9375 | CG | TYR | B | 450 | 18.172 | 3.923 | 6.564 | 1.00 | 8.13 |

FIGURE 3 (Cont.)

| A | B | C | D | E | F | G | H | I | J |
|---|---|---|---|---|---|---|---|---|---|
| 9376 | CD1 | TYR | B | 450 | 17.111 | 4.235 | 7.310 | 1.00 | 7.39 |
| 9377 | CE1 | TYR | B | 450 | 17.189 | 5.271 | 8.226 | 1.00 | 9.87 |
| 9378 | CZ | TYR | B | 450 | 18.377 | 5.932 | 8.381 | 1.00 | 10.81 |
| 9379 | OH | TYR | B | 450 | 18.567 | 6.873 | 9.336 | 1.00 | 12.81 |
| 9380 | CE2 | TYR | B | 450 | 19.439 | 5.549 | 7.681 | 1.00 | 9.02 |
| 9381 | CD2 | TYR | B | 450 | 19.329 | 4.607 | 6.779 | 1.00 | 11.24 |
| 9382 | C | TYR | B | 450 | 19.468 | 4.151 | 3.588 | 1.00 | 11.91 |
| 9383 | O | TYR | B | 450 | 20.479 | 3.542 | 3.633 | 1.00 | 12.36 |
| 9384 | N | TYR | B | 451 | 19.431 | 5.328 | 3.016 | 1.00 | 13.28 |
| 9385 | CA | TYR | B | 451 | 20.586 | 5.823 | 2.273 | 1.00 | 14.40 |
| 9386 | CB | TYR | B | 451 | 20.175 | 6.192 | 0.838 | 1.00 | 13.65 |
| 9387 | CG | TYR | B | 451 | 20.142 | 5.041 | -0.121 | 1.00 | 14.15 |
| 9388 | CD1 | TYR | B | 451 | 18.964 | 4.291 | -0.376 | 1.00 | 12.29 |
| 9389 | CE1 | TYR | B | 451 | 18.928 | 3.219 | -1.302 | 1.00 | 11.44 |
| 9390 | CZ | TYR | B | 451 | 20.108 | 2.858 | -1.932 | 1.00 | 17.31 |
| 9391 | OH | TYR | B | 451 | 20.271 | 1.815 | -2.825 | 1.00 | 20.18 |
| 9392 | CE2 | TYR | B | 451 | 21.303 | 3.546 | -1.660 | 1.00 | 20.25 |
| 9393 | CD2 | TYR | B | 451 | 21.304 | 4.658 | -0.751 | 1.00 | 19.44 |
| 9394 | C | TYR | B | 451 | 21.135 | 7.059 | 2.865 | 1.00 | 15.40 |
| 9395 | O | TYR | B | 451 | 20.377 | 7.888 | 3.325 | 1.00 | 14.63 |
| 9396 | N | THR | B | 452 | 22.445 | 7.203 | 2.853 | 1.00 | 15.07 |
| 9397 | CA | THR | B | 452 | 22.978 | 8.578 | 2.948 | 1.00 | 16.39 |
| 9398 | CB | THR | B | 452 | 23.771 | 8.789 | 4.231 | 1.00 | 15.61 |
| 9399 | OG1 | THR | B | 452 | 24.298 | 10.088 | 4.232 | 1.00 | 16.02 |
| 9400 | CG2 | THR | B | 452 | 25.041 | 7.955 | 4.208 | 1.00 | 15.92 |
| 9401 | C | THR | B | 452 | 23.842 | 8.808 | 1.725 | 1.00 | 16.37 |
| 9402 | O | THR | B | 452 | 23.914 | 7.955 | 0.934 | 1.00 | 17.91 |
| 9403 | N | ALA | B | 453 | 24.443 | 9.984 | 1.570 | 1.00 | 16.15 |
| 9404 | CA | ALA | B | 453 | 25.215 | 10.292 | 0.412 | 1.00 | 15.84 |
| 9405 | CB | ALA | B | 453 | 24.325 | 10.877 | -0.609 | 1.00 | 14.90 |
| 9406 | C | ALA | B | 453 | 26.320 | 11.310 | 0.688 | 1.00 | 16.71 |
| 9407 | O | ALA | B | 453 | 26.278 | 12.064 | 1.668 | 1.00 | 16.95 |
| 9408 | N | SER | B | 454 | 27.233 | 11.422 | -0.276 | 1.00 | 16.12 |
| 9409 | CA | SER | B | 454 | 28.457 | 12.154 | -0.086 | 1.00 | 15.84 |
| 9410 | CB | SER | B | 454 | 29.469 | 11.122 | 0.413 | 1.00 | 15.87 |
| 9411 | OG | SER | B | 454 | 30.650 | 11.732 | 0.740 | 1.00 | 14.89 |
| 9412 | C | SER | B | 454 | 28.907 | 12.654 | -1.401 | 1.00 | 16.31 |
| 9413 | O | SER | B | 454 | 29.139 | 11.828 | -2.303 | 1.00 | 16.78 |
| 9414 | N | PHE | B | 455 | 29.174 | 13.932 | -1.520 | 1.00 | 15.43 |
| 9415 | CA | PHE | B | 455 | 29.426 | 14.485 | -2.821 | 1.00 | 15.21 |
| 9416 | CB | PHE | B | 455 | 28.466 | 15.625 | -3.059 | 1.00 | 16.21 |
| 9417 | CG | PHE | B | 455 | 27.057 | 15.151 | -3.212 | 1.00 | 13.41 |
| 9418 | CD1 | PHE | B | 455 | 26.475 | 15.031 | -4.487 | 1.00 | 11.01 |
| 9419 | CE1 | PHE | B | 455 | 25.209 | 14.540 | -4.679 | 1.00 | 6.15 |
| 9420 | CZ | PHE | B | 455 | 24.455 | 14.203 | -3.597 | 1.00 | 9.42 |
| 9421 | CE2 | PHE | B | 455 | 24.950 | 14.402 | -2.265 | 1.00 | 12.65 |
| 9422 | CD2 | PHE | B | 455 | 26.295 | 14.845 | -2.092 | 1.00 | 13.82 |
| 9423 | C | PHE | B | 455 | 30.812 | 14.931 | -3.086 | 1.00 | 16.91 |
| 9424 | O | PHE | B | 455 | 31.383 | 15.692 | -2.342 | 1.00 | 19.13 |
| 9425 | N | SER | B | 456 | 31.370 | 14.499 | -4.212 | 1.00 | 16.65 |
| 9426 | CA | SER | B | 456 | 32.587 | 15.074 | -4.725 | 1.00 | 15.79 |

FIGURE 3 (Cont.)

| A | B | C | D | E | F | G | H | I | J |
|---|---|---|---|---|---|---|---|---|---|
| 9427 | CB | SER | B | 456 | 32.919 | 14.398 | -6.035 | 1.00 | 14.49 |
| 9428 | OG | SER | B | 456 | 32.565 | 15.022 | -7.242 | 1.00 | 17.95 |
| 9429 | C | SER | B | 456 | 32.449 | 16.593 | -4.801 | 1.00 | 17.80 |
| 9430 | O | SER | B | 456 | 31.332 | 17.091 | -4.729 | 1.00 | 16.36 |
| 9431 | N | ASP | B | 457 | 33.554 | 17.348 | -4.895 | 1.00 | 17.39 |
| 9432 | CA | ASP | B | 457 | 33.392 | 18.772 | -5.162 | 1.00 | 18.69 |
| 9433 | CB | ASP | B | 457 | 34.722 | 19.502 | -5.368 | 1.00 | 18.22 |
| 9434 | CG | ASP | B | 457 | 35.654 | 19.465 | -4.172 | 1.00 | 20.12 |
| 9435 | OD1 | ASP | B | 457 | 36.853 | 19.759 | -4.452 | 1.00 | 19.01 |
| 9436 | OD2 | ASP | B | 457 | 35.359 | 19.183 | -2.995 | 1.00 | 20.47 |
| 9437 | C | ASP | B | 457 | 32.563 | 19.028 | -6.455 | 1.00 | 18.70 |
| 9438 | O | ASP | B | 457 | 32.558 | 18.249 | -7.368 | 1.00 | 21.24 |
| 9439 | N | TYR | B | 458 | 31.915 | 20.175 | -6.536 | 1.00 | 19.40 |
| 9440 | CA | TYR | B | 458 | 31.026 | 20.536 | -7.628 | 1.00 | 19.88 |
| 9441 | CB | TYR | B | 458 | 31.893 | 20.916 | -8.873 | 1.00 | 22.27 |
| 9442 | CG | TYR | B | 458 | 32.969 | 22.020 | -8.602 | 1.00 | 27.81 |
| 9443 | CD1 | TYR | B | 458 | 34.014 | 22.269 | -9.477 | 1.00 | 35.12 |
| 9444 | CE1 | TYR | B | 458 | 35.008 | 23.282 | -9.202 | 1.00 | 38.22 |
| 9445 | CZ | TYR | B | 458 | 34.911 | 24.004 | -8.022 | 1.00 | 36.24 |
| 9446 | OH | TYR | B | 458 | 35.765 | 24.999 | -7.628 | 1.00 | 34.85 |
| 9447 | CE2 | TYR | B | 458 | 33.897 | 23.736 | -7.159 | 1.00 | 39.86 |
| 9448 | CD2 | TYR | B | 458 | 32.934 | 22.774 | -7.447 | 1.00 | 36.00 |
| 9449 | C | TYR | B | 458 | 29.960 | 19.454 | -7.907 | 1.00 | 18.64 |
| 9450 | O | TYR | B | 458 | 29.247 | 19.494 | -8.876 | 1.00 | 18.47 |
| 9451 | N | ALA | B | 459 | 29.800 | 18.529 | -7.006 | 1.00 | 16.84 |
| 9452 | CA | ALA | B | 459 | 28.970 | 17.347 | -7.267 | 1.00 | 15.78 |
| 9453 | CB | ALA | B | 459 | 27.538 | 17.638 | -7.054 | 1.00 | 15.51 |
| 9454 | C | ALA | B | 459 | 29.105 | 16.727 | -8.587 | 1.00 | 15.44 |
| 9455 | O | ALA | B | 459 | 28.103 | 16.438 | -9.148 | 1.00 | 15.12 |
| 9456 | N | LYS | B | 460 | 30.326 | 16.492 | -9.104 | 1.00 | 15.02 |
| 9457 | CA | LYS | B | 460 | 30.438 | 15.654 | -10.318 | 1.00 | 13.99 |
| 9458 | CB | LYS | B | 460 | 31.759 | 15.766 | -11.033 | 1.00 | 14.80 |
| 9459 | CG | LYS | B | 460 | 32.539 | 17.090 | -10.834 | 1.00 | 18.14 |
| 9460 | CD | LYS | B | 460 | 33.362 | 17.549 | -12.101 | 1.00 | 24.48 |
| 9461 | CE | LYS | B | 460 | 32.959 | 19.045 | -12.528 | 1.00 | 26.77 |
| 9462 | NZ | LYS | B | 460 | 31.593 | 19.627 | -11.976 | 1.00 | 25.62 |
| 9463 | C | LYS | B | 460 | 30.155 | 14.182 | -9.977 | 1.00 | 13.55 |
| 9464 | O | LYS | B | 460 | 29.673 | 13.399 | -10.801 | 1.00 | 14.35 |
| 9465 | N | TYR | B | 461 | 30.403 | 13.789 | -8.745 | 1.00 | 11.93 |
| 9466 | CA | TYR | B | 461 | 30.174 | 12.446 | -8.396 | 1.00 | 9.45 |
| 9467 | CB | TYR | B | 461 | 31.456 | 11.587 | -8.562 | 1.00 | 9.12 |
| 9468 | CG | TYR | B | 461 | 31.966 | 11.515 | -9.978 | 1.00 | 9.69 |
| 9469 | CD1 | TYR | B | 461 | 32.960 | 12.391 | -10.387 | 1.00 | 12.64 |
| 9470 | CE1 | TYR | B | 461 | 33.444 | 12.403 | -11.708 | 1.00 | 12.35 |
| 9471 | CZ | TYR | B | 461 | 33.012 | 11.473 | -12.618 | 1.00 | 10.65 |
| 9472 | OH | TYR | B | 461 | 33.587 | 11.627 | -13.872 | 1.00 | 12.53 |
| 9473 | CE2 | TYR | B | 461 | 32.025 | 10.522 | -12.258 | 1.00 | 9.54 |
| 9474 | CD2 | TYR | B | 461 | 31.496 | 10.558 | -10.918 | 1.00 | 12.64 |
| 9475 | C | TYR | B | 461 | 29.661 | 12.422 | -7.018 | 1.00 | 7.71 |
| 9476 | O | TYR | B | 461 | 29.772 | 13.427 | -6.341 | 1.00 | 6.54 |
| 9477 | N | TYR | B | 462 | 29.005 | 11.297 | -6.677 | 1.00 | 6.01 |

FIGURE 3 (Cont.)

| A | B | C | D | E | F | G | H | I | J |
|---|---|---|---|---|---|---|---|---|---|
| 9478 | CA | TYR | B | 462 | 28.570 | 11.050 | -5.328 | 1.00 | 7.16 |
| 9479 | CB | TYR | B | 462 | 27.170 | 11.615 | -5.028 | 1.00 | 7.02 |
| 9480 | CG | TYR | B | 462 | 26.029 | 11.150 | -5.854 | 1.00 | 7.62 |
| 9481 | CD1 | TYR | B | 462 | 25.658 | 11.801 | -7.027 | 1.00 | 7.22 |
| 9482 | CE1 | TYR | B | 462 | 24.556 | 11.369 | -7.773 | 1.00 | 7.84 |
| 9483 | CZ | TYR | B | 462 | 23.791 | 10.316 | -7.258 | 1.00 | 12.73 |
| 9484 | OH | TYR | B | 462 | 22.715 | 9.754 | -7.863 | 1.00 | 10.06 |
| 9485 | CE2 | TYR | B | 462 | 24.122 | 9.747 | -6.084 | 1.00 | 10.30 |
| 9486 | CD2 | TYR | B | 462 | 25.222 | 10.149 | -5.390 | 1.00 | 9.23 |
| 9487 | C | TYR | B | 462 | 28.540 | 9.646 | -4.992 | 1.00 | 7.59 |
| 9488 | O | TYR | B | 462 | 28.381 | 8.828 | -5.865 | 1.00 | 9.98 |
| 9489 | N | ALA | B | 463 | 28.675 | 9.351 | -3.713 | 1.00 | 7.53 |
| 9490 | CA | ALA | B | 463 | 28.654 | 8.004 | -3.246 | 1.00 | 7.43 |
| 9491 | CB | ALA | B | 463 | 29.749 | 7.781 | -2.244 | 1.00 | 6.39 |
| 9492 | C | ALA | B | 463 | 27.385 | 7.906 | -2.553 | 1.00 | 9.40 |
| 9493 | O | ALA | B | 463 | 26.895 | 8.951 | -2.033 | 1.00 | 9.27 |
| 9494 | N | LEU | B | 464 | 26.911 | 6.666 | -2.446 | 1.00 | 8.82 |
| 9495 | CA | LEU | B | 464 | 25.595 | 6.435 | -1.897 | 1.00 | 9.51 |
| 9496 | CB | LEU | B | 464 | 24.593 | 6.032 | -3.001 | 1.00 | 8.98 |
| 9497 | CG | LEU | B | 464 | 23.743 | 7.070 | -3.764 | 1.00 | 9.68 |
| 9498 | CD1 | LEU | B | 464 | 22.878 | 6.489 | -4.851 | 1.00 | 8.61 |
| 9499 | CD2 | LEU | B | 464 | 22.866 | 7.768 | -2.844 | 1.00 | 10.66 |
| 9500 | C | LEU | B | 464 | 25.815 | 5.253 | -0.970 | 1.00 | 10.16 |
| 9501 | O | LEU | B | 464 | 26.362 | 4.164 | -1.423 | 1.00 | 7.69 |
| 9502 | N | VAL | B | 465 | 25.451 | 5.425 | 0.310 | 1.00 | 9.27 |
| 9503 | CA | VAL | B | 465 | 25.548 | 4.251 | 1.189 | 1.00 | 10.70 |
| 9504 | CB | VAL | B | 465 | 26.864 | 4.243 | 2.167 | 1.00 | 10.44 |
| 9505 | CG1 | VAL | B | 465 | 27.599 | 5.547 | 2.161 | 1.00 | 8.44 |
| 9506 | CG2 | VAL | B | 465 | 26.567 | 3.850 | 3.521 | 1.00 | 9.38 |
| 9507 | C | VAL | B | 465 | 24.200 | 3.836 | 1.787 | 1.00 | 11.54 |
| 9508 | C | VAL | B | 465 | 23.434 | 4.652 | 2.299 | 1.00 | 11.35 |
| 9509 | N | CYS | B | 466 | 23.933 | 2.541 | 1.597 | 1.00 | 11.58 |
| 9510 | CA | CYS | B | 466 | 22.693 | 1.908 | 1.882 | 1.00 | 11.66 |
| 9511 | CB | CYS | B | 466 | 22.383 | 0.928 | 0.793 | 1.00 | 12.11 |
| 9512 | SG | CYS | B | 466 | 21.296 | -0.552 | 1.135 | 1.00 | 16.07 |
| 9513 | C | CYS | B | 466 | 23.022 | 1.230 | 3.145 | 1.00 | 12.23 |
| 9514 | O | CYS | B | 466 | 23.949 | 0.364 | 3.201 | 1.00 | 12.50 |
| 9515 | N | TYR | B | 467 | 22.360 | 1.656 | 4.212 | 1.00 | 10.72 |
| 9516 | CA | TYR | B | 467 | 22.637 | 1.047 | 5.503 | 1.00 | 9.27 |
| 9517 | CB | TYR | B | 467 | 22.526 | 2.123 | 6.559 | 1.00 | 7.41 |
| 9518 | CG | TYR | B | 467 | 23.725 | 3.025 | 6.702 | 1.00 | 9.13 |
| 9519 | CD1 | TYR | B | 467 | 23.634 | 4.428 | 6.460 | 1.00 | 9.77 |
| 9520 | CE1 | TYR | B | 467 | 24.711 | 5.251 | 6.636 | 1.00 | 8.67 |
| 9521 | CZ | TYR | B | 467 | 25.886 | 4.685 | 7.063 | 1.00 | 12.20 |
| 9522 | OH | TYR | B | 467 | 26.995 | 5.464 | 7.277 | 1.00 | 13.54 |
| 9523 | CE2 | TYR | B | 467 | 25.937 | 3.364 | 7.390 | 1.00 | 3.92 |
| 9524 | CD2 | TYR | B | 467 | 24.890 | 2.564 | 7.197 | 1.00 | 4.42 |
| 9525 | C | TYR | B | 467 | 21.683 | -0.145 | 5.790 | 1.00 | 8.96 |
| 9526 | O | TYR | B | 467 | 21.710 | -0.704 | 6.869 | 1.00 | 8.68 |
| 9527 | N | GLY | B | 468 | 20.814 | -0.508 | 4.867 | 1.00 | 8.40 |
| 9528 | CA | GLY | B | 468 | 19.809 | -1.514 | 5.171 | 1.00 | 8.66 |

FIGURE 3 (Cont.)

| A | B | C | D | E | F | G | H | I | J |
|---|---|---|---|---|---|---|---|---|---|
| 9529 | C | GLY | B | 468 | 18.518 | -1.341 | 4.419 | 1.00 | 9.18 |
| 9530 | O | GLY | B | 468 | 18.371 | -0.413 | 3.585 | 1.00 | 11.40 |
| 9531 | N | PRO | B | 469 | 17.535 | -2.183 | 4.661 | 1.00 | 8.82 |
| 9532 | CA | PRO | B | 469 | 17.522 | -3.357 | 5.568 | 1.00 | 8.47 |
| 9533 | CB | PRO | B | 469 | 16.120 | -3.916 | 5.417 | 1.00 | 8.72 |
| 9534 | CG | PRO | B | 469 | 15.342 | -2.892 | 4.554 | 1.00 | 9.89 |
| 9535 | CD | PRO | B | 469 | 16.281 | -1.938 | 3.966 | 1.00 | 8.31 |
| 9536 | C | PRO | B | 469 | 18.412 | -4.551 | 5.224 | 1.00 | 8.36 |
| 9537 | O | PRO | B | 469 | 18.573 | -5.480 | 6.041 | 1.00 | 8.44 |
| 9538 | N | GLY | B | 470 | 18.885 | -4.596 | 3.983 | 1.00 | 8.35 |
| 9539 | CA | GLY | B | 470 | 19.801 | -5.623 | 3.559 | 1.00 | 6.77 |
| 9540 | C | GLY | B | 470 | 21.152 | -5.234 | 4.060 | 1.00 | 6.65 |
| 9541 | O | GLY | B | 470 | 21.325 | -4.319 | 4.836 | 1.00 | 8.46 |
| 9542 | N | ILE | B | 471 | 22.118 | -5.903 | 3.541 | 1.00 | 5.56 |
| 9543 | CA | ILE | B | 471 | 23.464 | -5.861 | 3.952 | 1.00 | 5.39 |
| 9544 | CB | ILE | B | 471 | 24.155 | -7.110 | 3.337 | 1.00 | 4.85 |
| 9545 | CG1 | ILE | B | 471 | 23.491 | -8.397 | 3.866 | 1.00 | 5.91 |
| 9546 | CD1 | ILE | B | 471 | 21.971 | -8.722 | 2.993 | 1.00 | 13.33 |
| 9547 | CG2 | ILE | B | 471 | 25.634 | -7.039 | 3.435 | 1.00 | 3.00 |
| 9548 | C | ILE | B | 471 | 23.903 | -4.642 | 3.228 | 1.00 | 5.84 |
| 9549 | O | ILE | B | 471 | 23.704 | -4.560 | 2.047 | 1.00 | 5.89 |
| 9550 | N | PRO | B | 472 | 24.497 | -3.690 | 3.913 | 1.00 | 6.22 |
| 9551 | CA | PRO | B | 472 | 24.875 | -2.405 | 3.329 | 1.00 | 6.72 |
| 9552 | CB | PRO | B | 472 | 25.813 | -1.812 | 4.370 | 1.00 | 6.52 |
| 9553 | CG | PRO | B | 472 | 25.386 | -2.375 | 5.582 | 1.00 | 5.65 |
| 9554 | CD | PRO | B | 472 | 24.841 | -3.759 | 5.324 | 1.00 | 7.16 |
| 9555 | C | PRO | B | 472 | 25.667 | -2.511 | 2.094 | 1.00 | 6.71 |
| 9556 | O | PRO | B | 472 | 26.332 | -3.547 | 1.869 | 1.00 | 6.84 |
| 9557 | N | ILE | B | 473 | 25.618 | -1.447 | 1.315 | 1.00 | 6.30 |
| 9558 | CA | ILE | B | 473 | 26.399 | -1.351 | 0.097 | 1.00 | 6.43 |
| 9559 | CB | ILE | B | 473 | 25.773 | -2.186 | -1.054 | 1.00 | 4.87 |
| 9560 | CG1 | ILE | B | 473 | 26.393 | -1.867 | -2.404 | 1.00 | 6.29 |
| 9561 | CD1 | ILE | B | 473 | 26.548 | -3.110 | -3.274 | 1.00 | 5.33 |
| 9562 | CG2 | ILE | B | 473 | 24.264 | -2.085 | -1.152 | 1.00 | 2.00 |
| 9563 | C | ILE | B | 473 | 26.655 | 0.113 | -0.306 | 1.00 | 8.57 |
| 9564 | O | ILE | B | 473 | 25.794 | 0.983 | -0.292 | 1.00 | 9.40 |
| 9565 | N | SER | B | 474 | 27.888 | 0.371 | -0.667 | 1.00 | 10.01 |
| 9566 | CA | SER | B | 474 | 28.303 | 1.708 | -0.954 | 1.00 | 10.85 |
| 9567 | CB | SER | B | 474 | 29.473 | 2.010 | -0.033 | 1.00 | 11.38 |
| 9568 | OG | SER | B | 474 | 29.310 | 1.195 | 1.175 | 1.00 | 16.16 |
| 9569 | C | SER | B | 474 | 28.616 | 1.622 | -2.439 | 1.00 | 10.20 |
| 9570 | O | SER | B | 474 | 29.246 | 0.722 | -2.851 | 1.00 | 10.05 |
| 9571 | N | THR | B | 475 | 28.058 | 2.510 | -3.219 | 1.00 | 10.14 |
| 9572 | CA | THR | B | 475 | 28.249 | 2.584 | -4.610 | 1.00 | 11.45 |
| 9573 | CB | THR | B | 475 | 27.042 | 2.052 | -5.320 | 1.00 | 11.76 |
| 9574 | OG1 | THR | B | 475 | 25.890 | 2.719 | -4.823 | 1.00 | 9.95 |
| 9575 | CG2 | THR | B | 475 | 26.801 | 0.699 | -4.963 | 1.00 | 10.68 |
| 9576 | C | THR | B | 475 | 28.376 | 4.045 | -4.967 | 1.00 | 13.12 |
| 9577 | O | THR | B | 475 | 27.962 | 4.978 | -4.187 | 1.00 | 15.96 |
| 9578 | N | LEU | B | 476 | 28.936 | 4.227 | -6.159 | 1.00 | 12.80 |
| 9579 | CA | LEU | B | 476 | 29.428 | 5.517 | -6.617 | 1.00 | 12.30 |

FIGURE 3 (Cont.)

| A | B | C | D | E | F | G | H | I | J |
|---|---|---|---|---|---|---|---|---|---|
| 9580 | CB | LEU | B | 476 | 30.899 | 5.345 | -6.904 | 1.00 | 10.42 |
| 9581 | CG | LEU | B | 476 | 31.571 | 6.412 | -7.705 | 1.00 | 8.74 |
| 9582 | CD1 | LEU | B | 476 | 31.877 | 7.643 | -6.842 | 1.00 | 11.03 |
| 9583 | CD2 | LEU | B | 476 | 32.856 | 5.799 | -8.158 | 1.00 | 13.97 |
| 9584 | C | LEU | B | 476 | 28.719 | 5.903 | -7.894 | 1.00 | 11.75 |
| 9585 | O | LEU | B | 476 | 28.756 | 5.107 | -8.791 | 1.00 | 13.17 |
| 9586 | N | HIS | B | 477 | 28.147 | 7.106 | -7.967 | 1.00 | 11.61 |
| 9587 | CA | HIS | B | 477 | 27.208 | 7.549 | -9.011 | 1.00 | 12.57 |
| 9588 | CB | HIS | B | 477 | 25.797 | 7.704 | -8.373 | 1.00 | 11.95 |
| 9589 | CG | HIS | B | 477 | 25.271 | 6.399 | -7.893 | 1.00 | 12.64 |
| 9590 | ND1 | HIS | B | 477 | 25.861 | 5.724 | -6.847 | 1.00 | 13.34 |
| 9591 | CE1 | HIS | B | 477 | 25.284 | 4.548 | -6.689 | 1.00 | 11.69 |
| 9592 | NE2 | HIS | B | 477 | 24.356 | 4.417 | -7.619 | 1.00 | 11.98 |
| 9593 | CD2 | HIS | B | 477 | 24.355 | 5.551 | -8.409 | 1.00 | 14.90 |
| 9594 | C | HIS | B | 477 | 27.628 | 8.876 | -9.645 | 1.00 | 13.72 |
| 9595 | O | HIS | B | 477 | 28.234 | 9.737 | -9.007 | 1.00 | 15.23 |
| 9596 | N | ASP | B | 478 | 27.319 | 9.025 | -10.904 | 1.00 | 13.86 |
| 9597 | CA | ASP | B | 478 | 27.725 | 10.152 | -11.711 | 1.00 | 14.61 |
| 9598 | CB | ASP | B | 478 | 27.560 | 9.733 | -13.176 | 1.00 | 15.23 |
| 9599 | CG | ASP | B | 478 | 27.735 | 10.857 | -14.129 | 1.00 | 17.60 |
| 9600 | OD1 | ASP | B | 478 | 26.941 | 11.824 | -14.035 | 1.00 | 18.29 |
| 9601 | OD2 | ASP | B | 478 | 28.632 | 10.831 | -14.993 | 1.00 | 19.27 |
| 9602 | C | ASP | B | 478 | 26.840 | 11.313 | -11.403 | 1.00 | 14.35 |
| 9603 | O | ASP | B | 478 | 25.655 | 11.150 | -11.365 | 1.00 | 14.69 |
| 9604 | N | GLY | B | 479 | 27.422 | 12.494 | -11.208 | 1.00 | 14.25 |
| 9605 | CA | GLY | B | 479 | 26.721 | 13.620 | -10.611 | 1.00 | 13.45 |
| 9606 | C | GLY | B | 479 | 25.593 | 14.096 | -11.502 | 1.00 | 14.38 |
| 9607 | O | GLY | B | 479 | 24.532 | 14.418 | -11.003 | 1.00 | 15.91 |
| 9608 | N | ARG | B | 480 | 25.801 | 14.076 | -12.823 | 1.00 | 14.46 |
| 9609 | CA | ARG | B | 480 | 24.817 | 14.455 | -13.842 | 1.00 | 15.12 |
| 9610 | CB | ARG | B | 480 | 25.559 | 14.670 | -15.189 | 1.00 | 15.00 |
| 9611 | CG | ARG | B | 480 | 25.059 | 15.834 | -16.063 | 1.00 | 16.48 |
| 9612 | CD | ARG | B | 480 | 25.692 | 15.963 | -17.530 | 1.00 | 19.13 |
| 9613 | NE | ARG | B | 480 | 25.988 | 14.649 | -18.172 | 1.00 | 22.66 |
| 9614 | CZ | ARG | B | 480 | 25.164 | 13.928 | -18.955 | 1.00 | 21.49 |
| 9615 | NH1 | ARG | B | 480 | 25.585 | 12.754 | -19.429 | 1.00 | 22.68 |
| 9616 | NH2 | ARG | B | 480 | 23.942 | 14.368 | -19.294 | 1.00 | 23.98 |
| 9617 | C | ARG | B | 480 | 23.684 | 13.410 | -14.061 | 1.00 | 14.89 |
| 9618 | O | ARG | B | 480 | 22.461 | 13.693 | -14.028 | 1.00 | 11.93 |
| 9619 | N | THR | B | 481 | 24.125 | 12.195 | -14.338 | 1.00 | 16.22 |
| 9620 | CA | THR | B | 481 | 23.184 | 11.200 | -14.742 | 1.00 | 17.04 |
| 9621 | CB | THR | B | 481 | 23.862 | 10.266 | -15.721 | 1.00 | 17.67 |
| 9622 | OG1 | THR | B | 481 | 22.883 | 9.781 | -16.616 | 1.00 | 19.10 |
| 9623 | CG2 | THR | B | 481 | 24.401 | 9.007 | -15.062 | 1.00 | 17.55 |
| 9624 | C | THR | B | 481 | 22.526 | 10.445 | -13.625 | 1.00 | 16.12 |
| 9625 | O | THR | B | 481 | 21.431 | 9.979 | -13.745 | 1.00 | 15.81 |
| 9626 | N | ASP | B | 482 | 23.244 | 10.328 | -12.538 | 1.00 | 15.90 |
| 9627 | CA | ASP | B | 482 | 22.921 | 9.384 | -11.489 | 1.00 | 15.40 |
| 9628 | CB | ASP | B | 482 | 21.448 | 9.552 | -11.070 | 1.00 | 15.51 |
| 9629 | CG | ASP | B | 482 | 21.095 | 10.978 | -10.571 | 1.00 | 16.02 |
| 9630 | OD1 | ASP | B | 482 | 20.163 | 11.657 | -11.097 | 1.00 | 16.75 |

FIGURE 3 (Cont.)

| A | B | C | D | E | F | G | H | I | J |
|---|---|---|---|---|---|---|---|---|---|
| 9631 | OD2 | ASP | B | 482 | 21.658 | 11.482 | -9.589 | 1.00 | 22.30 |
| 9632 | C | ASP | B | 482 | 23.268 | 7.879 | -11.793 | 1.00 | 15.30 |
| 9633 | O | ASP | B | 482 | 22.836 | 7.060 | -11.090 | 1.00 | 15.87 |
| 9634 | N | GLN | B | 483 | 24.094 | 7.509 | -12.758 | 1.00 | 14.99 |
| 9635 | CA | GLN | B | 483 | 24.332 | 6.082 | -13.128 | 1.00 | 14.74 |
| 9636 | CB | GLN | B | 483 | 25.009 | 5.922 | -14.502 | 1.00 | 13.36 |
| 9637 | CG | GLN | B | 483 | 24.370 | 5.179 | -15.622 | 1.00 | 15.32 |
| 9638 | CD | GLN | B | 483 | 25.488 | 4.599 | -16.569 | 1.00 | 20.19 |
| 9639 | OE1 | GLN | B | 483 | 25.200 | 3.834 | -17.530 | 1.00 | 19.26 |
| 9640 | NE2 | GLN | B | 483 | 26.773 | 4.959 | -16.277 | 1.00 | 18.22 |
| 9641 | C | GLN | B | 483 | 25.357 | 5.556 | -12.119 | 1.00 | 14.56 |
| 9642 | O | GLN | B | 483 | 26.324 | 6.257 | -11.711 | 1.00 | 13.89 |
| 9643 | N | GLU | B | 484 | 25.191 | 4.319 | -11.731 | 1.00 | 14.78 |
| 9644 | CA | GLU | B | 484 | 26.175 | 3.794 | -10.866 | 1.00 | 15.24 |
| 9645 | CB | GLU | B | 484 | 25.563 | 2.813 | -9.904 | 1.00 | 15.65 |
| 9646 | CG | GLU | B | 484 | 25.462 | 1.342 | -10.270 | 1.00 | 18.09 |
| 9647 | CD | GLU | B | 484 | 25.499 | 0.548 | -9.005 | 1.00 | 16.33 |
| 9648 | OE1 | GLU | B | 484 | 24.452 | 0.299 | -8.421 | 1.00 | 17.15 |
| 9649 | OE2 | GLU | B | 484 | 26.608 | 0.318 | -8.568 | 1.00 | 18.02 |
| 9650 | C | GLU | B | 484 | 27.319 | 3.251 | -11.694 | 1.00 | 15.84 |
| 9651 | O | GLU | B | 484 | 27.112 | 2.489 | -12.653 | 1.00 | 16.79 |
| 9652 | N | ILE | B | 485 | 28.529 | 3.684 | -11.367 | 1.00 | 15.88 |
| 9653 | CA | ILE | B | 485 | 29.688 | 3.389 | -12.193 | 1.00 | 15.63 |
| 9654 | CB | ILE | B | 485 | 30.307 | 4.692 | -12.577 | 1.00 | 16.12 |
| 9655 | CG1 | ILE | B | 485 | 30.831 | 5.427 | -11.353 | 1.00 | 15.71 |
| 9656 | CD1 | ILE | B | 485 | 31.054 | 6.938 | -11.613 | 1.00 | 12.67 |
| 9657 | CG2 | ILE | B | 485 | 29.206 | 5.604 | -13.226 | 1.00 | 17.29 |
| 9658 | C | ILE | B | 485 | 30.690 | 2.534 | -11.469 | 1.00 | 15.46 |
| 9659 | O | ILE | B | 485 | 31.681 | 2.144 | -12.061 | 1.00 | 15.27 |
| 9660 | N | LYS | B | 486 | 30.420 | 2.281 | -10.184 | 1.00 | 14.85 |
| 9661 | CA | LYS | B | 486 | 31.289 | 1.541 | -9.283 | 1.00 | 14.04 |
| 9662 | CB | LYS | B | 486 | 32.562 | 2.343 | -8.913 | 1.00 | 13.72 |
| 9663 | CG | LYS | B | 486 | 33.910 | 1.624 | -9.245 | 1.00 | 15.14 |
| 9664 | CD | LYS | B | 486 | 35.146 | 2.034 | -8.335 | 1.00 | 15.75 |
| 9665 | CE | LYS | B | 486 | 36.037 | 0.716 | -7.957 | 1.00 | 21.14 |
| 9666 | NZ | LYS | B | 486 | 35.742 | -0.012 | -6.591 | 1.00 | 17.11 |
| 9667 | C | LYS | B | 486 | 30.527 | 1.128 | -8.003 | 1.00 | 12.91 |
| 9668 | O | LYS | B | 486 | 29.841 | 1.962 | -7.383 | 1.00 | 13.37 |
| 9669 | N | ILE | B | 487 | 30.639 | -0.180 | -7.663 | 1.00 | 12.22 |
| 9670 | CA | ILE | B | 487 | 30.366 | -0.730 | -6.328 | 1.00 | 10.67 |
| 9671 | CB | ILE | B | 487 | 30.319 | -2.256 | -6.414 | 1.00 | 10.51 |
| 9672 | CG1 | ILE | B | 487 | 29.219 | -2.745 | -7.345 | 1.00 | 7.33 |
| 9673 | CD1 | ILE | B | 487 | 27.861 | -2.457 | -6.914 | 1.00 | 9.20 |
| 9674 | CG2 | ILE | B | 487 | 30.215 | -2.869 | -5.018 | 1.00 | 10.50 |
| 9675 | C | ILE | B | 487 | 31.600 | -0.367 | -5.550 | 1.00 | 10.78 |
| 9676 | O | ILE | B | 487 | 32.656 | -0.745 | -5.961 | 1.00 | 10.57 |
| 9677 | N | LEU | B | 488 | 31.518 | 0.371 | -4.459 | 1.00 | 10.42 |
| 9678 | CA | LEU | B | 488 | 32.714 | 0.650 | -3.639 | 1.00 | 10.64 |
| 9679 | CB | LEU | B | 488 | 32.609 | 2.011 | -3.043 | 1.00 | 9.77 |
| 9680 | CG | LEU | B | 488 | 32.338 | 3.041 | -4.079 | 1.00 | 8.46 |
| 9681 | CD1 | LEU | B | 488 | 31.383 | 3.968 | -3.573 | 1.00 | 3.64 |

FIGURE 3 (Cont.)

| A | B | C | D | E | F | G | H | I | J |
|---|---|---|---|---|---|---|---|---|---|
| 9682 | CD2 | LEU | B | 488 | 33.655 | 3.683 | -4.397 | 1.00 | 11.19 |
| 9683 | C | LEU | B | 488 | 32.853 | -0.365 | -2.501 | 1.00 | 11.72 |
| 9684 | O | LEU | B | 488 | 33.909 | -0.910 | -2.247 | 1.00 | 12.90 |
| 9685 | N | GLU | B | 489 | 31.766 | -0.626 | -1.805 | 1.00 | 12.41 |
| 9686 | CA | GLU | B | 489 | 31.730 | -1.778 | -0.916 | 1.00 | 12.09 |
| 9687 | CB | GLU | B | 489 | 31.945 | -1.327 | 0.488 | 1.00 | 11.93 |
| 9688 | CG | GLU | B | 489 | 31.852 | -2.535 | 1.385 | 1.00 | 11.25 |
| 9689 | CD | GLU | B | 489 | 33.132 | -3.259 | 1.442 | 1.00 | 10.31 |
| 9690 | OE1 | GLU | B | 489 | 34.018 | -2.474 | 1.809 | 1.00 | 14.58 |
| 9691 | OE2 | GLU | B | 489 | 33.240 | -4.510 | 1.168 | 1.00 | 8.55 |
| 9692 | C | GLU | B | 489 | 30.413 | -2.563 | -0.942 | 1.00 | 11.92 |
| 9693 | O | GLU | B | 489 | 29.301 | -2.005 | -0.805 | 1.00 | 11.93 |
| 9694 | N | GLU | B | 490 | 30.580 | -3.867 | -0.979 | 1.00 | 11.06 |
| 9695 | CA | GLU | B | 490 | 29.520 | -4.811 | -1.151 | 1.00 | 11.49 |
| 9696 | CB | GLU | B | 490 | 29.928 | -5.646 | -2.357 | 1.00 | 11.75 |
| 9697 | CG | GLU | B | 490 | 28.863 | -6.387 | -3.110 | 1.00 | 11.78 |
| 9698 | CD | GLU | B | 490 | 29.227 | -6.458 | -4.589 | 1.00 | 16.18 |
| 9699 | OE1 | GLU | B | 490 | 30.409 | -6.170 | -4.973 | 1.00 | 13.74 |
| 9700 | OE2 | GLU | B | 490 | 28.305 | -6.784 | -5.353 | 1.00 | 16.62 |
| 9701 | C | GLU | B | 490 | 29.341 | -5.756 | 0.036 | 1.00 | 11.68 |
| 9702 | O | GLU | B | 490 | 28.429 | -6.625 | 0.016 | 1.00 | 14.21 |
| 9703 | N | ASN | B | 491 | 30.231 | -5.701 | 1.019 | 1.00 | 11.13 |
| 9704 | CA | ASN | B | 491 | 30.251 | -6.735 | 2.064 | 1.00 | 11.88 |
| 9705 | CB | ASN | B | 491 | 29.303 | -6.271 | 3.130 | 1.00 | 10.84 |
| 9706 | CG | ASN | B | 491 | 29.867 | -5.048 | 3.822 | 1.00 | 11.38 |
| 9707 | OD1 | ASN | B | 491 | 29.401 | -3.924 | 3.637 | 1.00 | 2.00 |
| 9708 | ND2 | ASN | B | 491 | 30.978 | -5.266 | 4.548 | 1.00 | 12.78 |
| 9709 | C | ASN | B | 491 | 30.074 | -8.252 | 1.634 | 1.00 | 12.04 |
| 9710 | O | ASN | B | 491 | 29.293 | -9.012 | 2.165 | 1.00 | 10.67 |
| 9711 | N | LYS | B | 492 | 30.710 | -8.549 | 0.517 | 1.00 | 13.70 |
| 9712 | CA | LYS | B | 492 | 31.546 | -9.712 | 0.292 | 1.00 | 16.11 |
| 9713 | CB | LYS | B | 492 | 33.049 | -9.207 | 0.237 | 1.00 | 17.14 |
| 9714 | CG | LYS | B | 492 | 33.335 | -7.719 | -0.342 | 1.00 | 19.37 |
| 9715 | CD | LYS | B | 492 | 33.581 | -7.656 | -1.928 | 1.00 | 21.02 |
| 9716 | CE | LYS | B | 492 | 33.237 | -6.243 | -2.548 | 1.00 | 23.23 |
| 9717 | NZ | LYS | B | 492 | 33.212 | -5.087 | -1.573 | 1.00 | 21.40 |
| 9718 | C | LYS | B | 492 | 31.407 | -10.855 | 1.346 | 1.00 | 16.15 |
| 9719 | O | LYS | B | 492 | 30.572 | -11.794 | 1.209 | 1.00 | 14.68 |
| 9720 | N | GLU | B | 493 | 32.196 | -10.708 | 2.423 | 1.00 | 16.50 |
| 9721 | CA | GLU | B | 493 | 32.448 | -11.775 | 3.389 | 1.00 | 17.32 |
| 9722 | CB | GLU | B | 493 | 33.742 | -11.534 | 4.167 | 1.00 | 17.86 |
| 9723 | CG | GLU | B | 493 | 34.978 | -11.376 | 3.271 | 1.00 | 23.21 |
| 9724 | CD | GLU | B | 493 | 35.606 | -9.976 | 3.366 | 1.00 | 27.34 |
| 9725 | OE1 | GLU | B | 493 | 35.665 | -9.470 | 4.517 | 1.00 | 27.82 |
| 9726 | OE2 | GLU | B | 493 | 36.041 | -9.402 | 2.313 | 1.00 | 28.74 |
| 9727 | C | GLU | B | 493 | 31.317 | -11.832 | 4.340 | 1.00 | 16.14 |
| 9728 | O | GLU | B | 493 | 30.854 | -12.890 | 4.658 | 1.00 | 16.14 |
| 9729 | N | LEU | B | 494 | 30.834 | -10.689 | 4.774 | 1.00 | 15.55 |
| 9730 | CA | LEU | B | 494 | 29.598 | -10.742 | 5.495 | 1.00 | 15.84 |
| 9731 | CB | LEU | B | 494 | 29.056 | -9.375 | 5.775 | 1.00 | 14.54 |
| 9732 | CG | LEU | B | 494 | 27.994 | -9.361 | 6.885 | 1.00 | 12.70 |

FIGURE 3 (Cont.)

| A | B | C | D | E | F | G | H | I | J |
|---|---|---|---|---|---|---|---|---|---|
| 9733 | CD1 | LEU | B | 494 | 28.537 | -10.040 | 8.108 | 1.00 | 7.00 |
| 9734 | CD2 | LEU | B | 494 | 27.508 | -7.942 | 7.221 | 1.00 | 6.31 |
| 9735 | C | LEU | B | 494 | 28.606 | -11.609 | 4.718 | 1.00 | 17.25 |
| 9736 | O | LEU | B | 494 | 28.378 | -12.757 | 5.102 | 1.00 | 18.42 |
| 9737 | N | GLU | B | 495 | 28.060 | -11.140 | 3.595 | 1.00 | 17.98 |
| 9738 | CA | GLU | B | 495 | 27.179 | -12.017 | 2.783 | 1.00 | 18.30 |
| 9739 | CB | GLU | B | 495 | 27.396 | -11.815 | 1.290 | 1.00 | 18.65 |
| 9740 | CG | GLU | B | 495 | 26.314 | -10.987 | 0.591 | 1.00 | 20.62 |
| 9741 | CD | GLU | B | 495 | 25.548 | -11.727 | -0.519 | 1.00 | 23.09 |
| 9742 | OE1 | GLU | B | 495 | 26.083 | -12.709 | -1.156 | 1.00 | 21.30 |
| 9743 | OE2 | GLU | B | 495 | 24.390 | -11.292 | -0.754 | 1.00 | 22.72 |
| 9744 | C | GLU | B | 495 | 27.403 | -13.492 | 3.116 | 1.00 | 17.92 |
| 9745 | O | GLU | B | 495 | 26.479 | -14.193 | 3.539 | 1.00 | 17.93 |
| 9746 | N | ASN | B | 496 | 28.661 | -13.901 | 2.949 | 1.00 | 17.84 |
| 9747 | CA | ASN | B | 496 | 29.110 | -15.308 | 2.994 | 1.00 | 17.77 |
| 9748 | CB | ASN | B | 496 | 30.519 | -15.428 | 2.392 | 1.00 | 17.42 |
| 9749 | CG | ASN | B | 496 | 30.539 | -15.256 | 0.892 | 1.00 | 19.13 |
| 9750 | OD1 | ASN | B | 496 | 29.501 | -15.134 | 0.240 | 1.00 | 20.02 |
| 9751 | ND2 | ASN | B | 496 | 31.737 | -15.234 | 0.332 | 1.00 | 21.20 |
| 9752 | C | ASN | B | 496 | 29.172 | -15.918 | 4.399 | 1.00 | 17.85 |
| 9753 | O | ASN | B | 496 | 28.513 | -16.938 | 4.657 | 1.00 | 18.34 |
| 9754 | N | ALA | B | 497 | 30.044 | -15.334 | 5.241 | 1.00 | 16.93 |
| 9755 | CA | ALA | B | 497 | 30.100 | -15.502 | 6.698 | 1.00 | 16.68 |
| 9756 | CB | ALA | B | 497 | 30.572 | -14.175 | 7.342 | 1.00 | 16.29 |
| 9757 | C | ALA | B | 497 | 28.790 | -15.898 | 7.352 | 1.00 | 16.36 |
| 9758 | O | ALA | B | 497 | 28.782 | -16.605 | 8.359 | 1.00 | 17.28 |
| 9759 | N | LEU | B | 498 | 27.698 | -15.461 | 6.736 | 1.00 | 15.67 |
| 9760 | CA | LEU | B | 498 | 26.392 | -15.330 | 7.342 | 1.00 | 15.10 |
| 9761 | CB | LEU | B | 498 | 26.043 | -13.866 | 7.139 | 1.00 | 14.77 |
| 9762 | CG | LEU | B | 498 | 25.017 | -13.204 | 7.997 | 1.00 | 15.97 |
| 9763 | CD1 | LEU | B | 498 | 25.493 | -13.166 | 9.465 | 1.00 | 14.73 |
| 9764 | CD2 | LEU | B | 498 | 24.760 | -11.781 | 7.382 | 1.00 | 18.70 |
| 9765 | C | LEU | B | 498 | 25.251 | -16.193 | 6.747 | 1.00 | 14.98 |
| 9766 | O | LEU | B | 498 | 24.111 | -16.095 | 7.199 | 1.00 | 15.15 |
| 9767 | N | LYS | B | 499 | 25.513 | -17.002 | 5.728 | 1.00 | 14.64 |
| 9768 | CA | LYS | B | 499 | 24.471 | -17.944 | 5.300 | 1.00 | 15.30 |
| 9769 | CB | LYS | B | 499 | 24.333 | -18.034 | 3.762 | 1.00 | 16.06 |
| 9770 | CG | LYS | B | 499 | 25.455 | -17.390 | 2.868 | 1.00 | 17.72 |
| 9771 | CD | LYS | B | 499 | 26.248 | -18.458 | 2.047 | 1.00 | 18.94 |
| 9772 | CE | LYS | B | 499 | 25.321 | -19.348 | 1.193 | 1.00 | 19.39 |
| 9773 | NZ | LYS | B | 499 | 24.695 | -20.453 | 1.996 | 1.00 | 17.53 |
| 9774 | C | LYS | B | 499 | 24.578 | -19.350 | 6.021 | 1.00 | 15.11 |
| 9775 | O | LYS | B | 499 | 23.754 | -20.241 | 5.840 | 1.00 | 15.21 |
| 9776 | N | ASN | B | 500 | 25.605 | -19.513 | 6.843 | 1.00 | 14.78 |
| 9777 | CA | ASN | B | 500 | 25.542 | -20.337 | 8.039 | 1.00 | 15.11 |
| 9778 | CB | ASN | B | 500 | 26.836 | -20.103 | 8.828 | 1.00 | 15.09 |
| 9779 | CG | ASN | B | 500 | 27.262 | -21.316 | 9.612 | 1.00 | 17.83 |
| 9780 | OD1 | ASN | B | 500 | 27.334 | -22.482 | 9.082 | 1.00 | 18.91 |
| 9781 | ND2 | ASN | B | 500 | 27.544 | -21.081 | 10.889 | 1.00 | 17.81 |
| 9782 | C | ASN | B | 500 | 24.367 | -19.990 | 8.990 | 1.00 | 15.24 |
| 9783 | O | ASN | B | 500 | 23.738 | -20.868 | 9.605 | 1.00 | 15.93 |

FIGURE 3 (Cont.)

| A | B | C | D | E | F | G | H | I | J |
|---|---|---|---|---|---|---|---|---|---|
| 9784 | N | ILE | B | 501 | 24.069 | -18.697 | 9.088 | 1.00 | 14.30 |
| 9785 | CA | ILE | B | 501 | 23.490 | -18.129 | 10.283 | 1.00 | 13.81 |
| 9786 | CB | ILE | B | 501 | 24.282 | -16.796 | 10.578 | 1.00 | 13.73 |
| 9787 | CG1 | ILE | B | 501 | 25.777 | -17.058 | 10.814 | 1.00 | 13.33 |
| 9788 | CD1 | ILE | B | 501 | 26.147 | -18.154 | 11.867 | 1.00 | 10.91 |
| 9789 | CG2 | ILE | B | 501 | 23.735 | -16.021 | 11.727 | 1.00 | 12.43 |
| 9790 | C | ILE | B | 501 | 21.948 | -17.926 | 10.253 | 1.00 | 14.11 |
| 9791 | O | ILE | B | 501 | 21.412 | -17.106 | 9.512 | 1.00 | 15.33 |
| 9792 | N | GLN | B | 502 | 21.246 | -18.692 | 11.077 | 1.00 | 13.45 |
| 9793 | CA | GLN | B | 502 | 19.819 | -18.481 | 11.357 | 1.00 | 13.28 |
| 9794 | CB | GLN | B | 502 | 19.366 | -19.493 | 12.433 | 1.00 | 12.57 |
| 9795 | CG | GLN | B | 502 | 19.230 | -20.974 | 11.899 | 1.00 | 15.33 |
| 9796 | CD | GLN | B | 502 | 19.211 | -22.059 | 13.000 | 1.00 | 15.26 |
| 9797 | OE1 | GLN | B | 502 | 19.921 | -21.917 | 14.020 | 1.00 | 17.49 |
| 9798 | NE2 | GLN | B | 502 | 18.408 | -23.118 | 12.803 | 1.00 | 12.93 |
| 9799 | C | GLN | B | 502 | 19.491 | -17.092 | 11.868 | 1.00 | 12.51 |
| 9800 | O | GLN | B | 502 | 19.430 | -16.898 | 13.076 | 1.00 | 13.65 |
| 9801 | N | LEU | B | 503 | 19.208 | -16.134 | 11.010 | 1.00 | 11.71 |
| 9802 | CA | LEU | B | 503 | 18.871 | -14.757 | 11.513 | 1.00 | 11.49 |
| 9803 | CB | LEU | B | 503 | 19.345 | -13.726 | 10.495 | 1.00 | 11.05 |
| 9804 | CG | LEU | B | 503 | 20.582 | -12.836 | 10.652 | 1.00 | 11.70 |
| 9805 | CD1 | LEU | B | 503 | 21.766 | -13.410 | 11.435 | 1.00 | 12.29 |
| 9806 | CD2 | LEU | B | 503 | 21.047 | -12.326 | 9.234 | 1.00 | 13.12 |
| 9807 | C | LEU | B | 503 | 17.359 | -14.523 | 11.798 | 1.00 | 11.41 |
| 9808 | O | LEU | B | 503 | 16.518 | -14.905 | 11.020 | 1.00 | 12.37 |
| 9809 | N | PRO | B | 504 | 16.971 | -13.874 | 12.872 | 1.00 | 11.59 |
| 9810 | CA | PRO | B | 504 | 15.557 | -13.610 | 13.098 | 1.00 | 12.00 |
| 9811 | CB | PRO | B | 504 | 15.576 | -12.799 | 14.377 | 1.00 | 11.18 |
| 9812 | CG | PRO | B | 504 | 16.855 | -12.143 | 14.341 | 1.00 | 10.07 |
| 9813 | CD | PRO | B | 504 | 17.755 | -13.265 | 13.951 | 1.00 | 11.98 |
| 9814 | C | PRO | B | 504 | 15.008 | -12.725 | 12.055 | 1.00 | 12.65 |
| 9815 | O | PRO | B | 504 | 15.742 | -12.093 | 11.343 | 1.00 | 12.51 |
| 9816 | N | LYS | B | 505 | 13.700 | -12.654 | 11.999 | 1.00 | 14.26 |
| 9817 | CA | LYS | B | 505 | 13.009 | -11.857 | 10.991 | 1.00 | 16.31 |
| 9818 | CB | LYS | B | 505 | 11.800 | -12.678 | 10.462 | 1.00 | 16.79 |
| 9819 | CG | LYS | B | 505 | 10.598 | -11.892 | 9.799 | 1.00 | 19.99 |
| 9820 | CD | LYS | B | 505 | 10.709 | -11.686 | 8.256 | 1.00 | 23.62 |
| 9821 | CE | LYS | B | 505 | 9.338 | -11.794 | 7.535 | 1.00 | 26.46 |
| 9822 | NZ | LYS | B | 505 | 8.250 | -12.460 | 8.354 | 1.00 | 27.24 |
| 9823 | C | LYS | B | 505 | 12.606 | -10.501 | 11.594 | 1.00 | 16.05 |
| 9824 | O | LYS | B | 505 | 12.012 | -10.443 | 12.681 | 1.00 | 16.02 |
| 9825 | N | GLU | B | 506 | 12.961 | -9.414 | 10.924 | 1.00 | 16.29 |
| 9826 | CA | GLU | B | 506 | 12.386 | -8.099 | 11.297 | 1.00 | 17.95 |
| 9827 | CB | GLU | B | 506 | 13.273 | -6.973 | 10.819 | 1.00 | 17.97 |
| 9828 | CG | GLU | B | 506 | 14.752 | -7.170 | 11.194 | 1.00 | 22.91 |
| 9829 | CD | GLU | B | 506 | 15.640 | -5.961 | 10.879 | 1.00 | 29.48 |
| 9830 | OE1 | GLU | B | 506 | 15.843 | -5.660 | 9.625 | 1.00 | 36.89 |
| 9831 | OE2 | GLU | B | 506 | 16.144 | -5.335 | 11.867 | 1.00 | 23.97 |
| 9832 | C | GLU | B | 506 | 11.032 | -7.949 | 10.628 | 1.00 | 17.33 |
| 9833 | O | GLU | B | 506 | 10.873 | -8.438 | 9.506 | 1.00 | 18.09 |
| 9834 | N | GLU | B | 507 | 10.059 | -7.331 | 11.295 | 1.00 | 16.41 |

FIGURE 3 (Cont.)

| A | B | C | D | E | F | G | H | I | J |
|---|---|---|---|---|---|---|---|---|---|
| 9835 | CA | GLU | B | 507 | 8.879 | -6.743 | 10.595 | 1.00 | 16.37 |
| 9836 | CB | GLU | B | 507 | 7.493 | -7.494 | 10.940 | 1.00 | 17.18 |
| 9837 | CG | GLU | B | 507 | 6.118 | -6.686 | 10.761 | 1.00 | 23.75 |
| 9838 | CD | GLU | B | 507 | 4.778 | -7.517 | 10.402 | 1.00 | 30.75 |
| 9839 | OE1 | GLU | B | 507 | 3.672 | -6.887 | 10.148 | 1.00 | 28.45 |
| 9840 | OE2 | GLU | B | 507 | 4.807 | -8.798 | 10.363 | 1.00 | 34.41 |
| 9841 | C | GLU | B | 507 | 8.892 | -5.246 | 10.903 | 1.00 | 14.00 |
| 9842 | O | GLU | B | 507 | 9.127 | -4.861 | 11.986 | 1.00 | 15.08 |
| 9843 | N | ILE | B | 508 | 8.713 | -4.370 | 9.956 | 1.00 | 12.69 |
| 9844 | CA | ILE | B | 508 | 8.361 | -3.019 | 10.315 | 1.00 | 11.90 |
| 9845 | CB | ILE | B | 508 | 9.383 | -2.025 | 9.642 | 1.00 | 12.69 |
| 9846 | CG1 | ILE | B | 508 | 10.759 | -2.220 | 10.259 | 1.00 | 11.41 |
| 9847 | CD1 | ILE | B | 508 | 11.965 | -1.589 | 9.450 | 1.00 | 11.30 |
| 9848 | CG2 | ILE | B | 508 | 8.988 | -0.554 | 9.791 | 1.00 | 9.18 |
| 9849 | C | ILE | B | 508 | 6.880 | -2.728 | 10.000 | 1.00 | 12.88 |
| 9850 | O | ILE | B | 508 | 6.441 | -2.876 | 8.842 | 1.00 | 12.87 |
| 9851 | N | LYS | B | 509 | 6.094 | -2.342 | 11.011 | 1.00 | 12.69 |
| 9852 | CA | LYS | B | 509 | 4.664 | -2.104 | 10.796 | 1.00 | 14.13 |
| 9853 | CB | LYS | B | 509 | 3.833 | -3.419 | 10.941 | 1.00 | 13.01 |
| 9854 | CG | LYS | B | 509 | 2.307 | -3.442 | 10.275 | 1.00 | 19.47 |
| 9855 | CD | LYS | B | 509 | 2.041 | -2.991 | 8.703 | 1.00 | 17.91 |
| 9856 | CE | LYS | B | 509 | 1.909 | -1.434 | 8.488 | 1.00 | 16.98 |
| 9857 | NZ | LYS | B | 509 | 1.814 | -0.986 | 7.022 | 1.00 | 17.64 |
| 9858 | C | LYS | B | 509 | 4.187 | -0.982 | 11.693 | 1.00 | 14.11 |
| 9859 | O | LYS | B | 509 | 4.981 | -0.365 | 12.337 | 1.00 | 13.55 |
| 9860 | N | LYS | B | 510 | 2.884 | -0.686 | 11.676 | 1.00 | 15.06 |
| 9861 | CA | LYS | B | 510 | 2.314 | 0.370 | 12.496 | 1.00 | 14.51 |
| 9862 | CB | LYS | B | 510 | 2.117 | 1.657 | 11.659 | 1.00 | 14.17 |
| 9863 | CG | LYS | B | 510 | 0.862 | 1.727 | 10.795 | 1.00 | 14.33 |
| 9864 | CD | LYS | B | 510 | 1.125 | 2.165 | 9.327 | 1.00 | 17.47 |
| 9865 | CE | LYS | B | 510 | -0.133 | 2.680 | 8.565 | 1.00 | 19.66 |
| 9866 | NZ | LYS | B | 510 | -1.089 | 1.537 | 8.432 | 1.00 | 23.78 |
| 9867 | C | LYS | B | 510 | 1.008 | -0.065 | 13.208 | 1.00 | 15.54 |
| 9868 | O | LYS | B | 510 | 0.266 | -0.947 | 12.731 | 1.00 | 13.83 |
| 9869 | N | LEU | B | 511 | 0.814 | 0.564 | 14.381 | 1.00 | 16.36 |
| 9870 | CA | LEU | B | 511 | -0.384 | 0.546 | 15.195 | 1.00 | 17.37 |
| 9871 | CB | LEU | B | 511 | 0.032 | 0.279 | 16.646 | 1.00 | 16.95 |
| 9872 | CG | LEU | B | 511 | 0.812 | -1.037 | 17.016 | 1.00 | 17.49 |
| 9873 | CD1 | LEU | B | 511 | 0.830 | -1.337 | 18.487 | 1.00 | 14.37 |
| 9874 | CD2 | LEU | B | 511 | 0.231 | -2.247 | 16.357 | 1.00 | 11.75 |
| 9875 | C | LEU | B | 511 | -0.983 | 1.938 | 15.117 | 1.00 | 18.27 |
| 9876 | O | LEU | B | 511 | -0.240 | 2.869 | 15.150 | 1.00 | 18.01 |
| 9877 | N | GLU | B | 512 | -2.289 | 2.061 | 14.907 | 1.00 | 20.68 |
| 9878 | CA | GLU | B | 512 | -3.071 | 3.274 | 15.175 | 1.00 | 23.94 |
| 9879 | CB | GLU | B | 512 | -4.112 | 3.592 | 14.060 | 1.00 | 24.92 |
| 9880 | CG | GLU | B | 512 | -3.627 | 4.434 | 12.862 | 1.00 | 29.62 |
| 9881 | CD | GLU | B | 512 | -2.753 | 3.620 | 11.889 | 1.00 | 35.28 |
| 9882 | OE1 | GLU | B | 512 | -2.088 | 4.223 | 10.981 | 1.00 | 37.74 |
| 9883 | OE2 | GLU | B | 512 | -2.716 | 2.356 | 12.060 | 1.00 | 36.59 |
| 9884 | C | GLU | B | 512 | -3.879 | 2.957 | 16.403 | 1.00 | 25.20 |
| 9885 | O | GLU | B | 512 | -4.633 | 1.979 | 16.439 | 1.00 | 25.68 |

FIGURE 3 (Cont.)

| A | B | C | D | E | F | G | H | I | J |
|---|---|---|---|---|---|---|---|---|---|
| 9886 | N | VAL | B | 513 | -3.770 | 3.767 | 17.425 | 1.00 | 27.39 |
| 9887 | CA | VAL | B | 513 | -4.367 | 3.378 | 18.691 | 1.00 | 28.87 |
| 9888 | CB | VAL | B | 513 | -3.370 | 2.524 | 19.528 | 1.00 | 28.66 |
| 9889 | CG1 | VAL | B | 513 | -2.306 | 3.350 | 20.037 | 1.00 | 27.65 |
| 9890 | CG2 | VAL | B | 513 | -4.077 | 1.812 | 20.698 | 1.00 | 28.02 |
| 9891 | C | VAL | B | 513 | -4.923 | 4.551 | 19.463 | 1.00 | 30.14 |
| 9892 | O | VAL | B | 513 | -5.341 | 4.416 | 20.611 | 1.00 | 31.09 |
| 9893 | N | ASP | B | 514 | -4.958 | 5.711 | 18.844 | 1.00 | 30.92 |
| 9894 | CA | ASP | B | 514 | -6.127 | 6.569 | 19.055 | 1.00 | 30.26 |
| 9895 | CB | ASP | B | 514 | -5.981 | 7.430 | 20.334 | 1.00 | 30.54 |
| 9896 | CG | ASP | B | 514 | -6.921 | 7.038 | 21.442 | 1.00 | 27.74 |
| 9897 | OD1 | ASP | B | 514 | -7.932 | 6.351 | 21.207 | 1.00 | 31.32 |
| 9898 | OD2 | ASP | B | 514 | -6.742 | 7.416 | 22.609 | 1.00 | 28.03 |
| 9899 | C | ASP | B | 514 | -6.125 | 7.402 | 17.783 | 1.00 | 30.59 |
| 9900 | O | ASP | B | 514 | -6.153 | 6.876 | 16.663 | 1.00 | 30.14 |
| 9901 | N | GLU | B | 515 | -5.982 | 8.698 | 17.962 | 1.00 | 30.35 |
| 9902 | CA | GLU | B | 515 | -5.630 | 9.545 | 16.876 | 1.00 | 30.43 |
| 9903 | CB | GLU | B | 515 | -5.985 | 11.019 | 17.257 | 1.00 | 31.33 |
| 9904 | CG | GLU | B | 515 | -5.437 | 11.566 | 18.646 | 1.00 | 35.64 |
| 9905 | CD | GLU | B | 515 | -6.117 | 11.067 | 19.990 | 1.00 | 36.21 |
| 9906 | OE1 | GLU | B | 515 | -7.317 | 11.457 | 20.267 | 1.00 | 32.62 |
| 9907 | OE2 | GLU | B | 515 | -5.405 | 10.347 | 20.796 | 1.00 | 32.25 |
| 9908 | C | GLU | B | 515 | -4.152 | 9.228 | 16.625 | 1.00 | 28.80 |
| 9909 | O | GLU | B | 515 | -3.621 | 9.504 | 15.571 | 1.00 | 29.92 |
| 9910 | N | ILE | B | 516 | -3.491 | 8.550 | 17.558 | 1.00 | 26.78 |
| 9911 | CA | ILE | B | 516 | -2.033 | 8.406 | 17.441 | 1.00 | 25.04 |
| 9912 | CB | ILE | B | 516 | -1.380 | 8.607 | 18.846 | 1.00 | 25.29 |
| 9913 | CG1 | ILE | B | 516 | -1.314 | 10.108 | 19.141 | 1.00 | 26.06 |
| 9914 | CD1 | ILE | B | 516 | -1.957 | 10.439 | 20.471 | 1.00 | 29.33 |
| 9915 | CG2 | ILE | B | 516 | 0.011 | 8.037 | 18.897 | 1.00 | 24.83 |
| 9916 | C | ILE | B | 516 | -1.429 | 7.159 | 16.726 | 1.00 | 23.36 |
| 9917 | O | ILE | B | 516 | -1.743 | 5.971 | 17.064 | 1.00 | 22.41 |
| 9918 | N | THR | B | 517 | -0.517 | 7.443 | 15.758 | 1.00 | 20.34 |
| 9919 | CA | THR | B | 517 | 0.067 | 6.303 | 15.056 | 1.00 | 17.46 |
| 9920 | CB | THR | B | 517 | -0.272 | 6.276 | 13.504 | 1.00 | 17.82 |
| 9921 | OG1 | THR | B | 517 | 0.728 | 5.548 | 12.777 | 1.00 | 16.65 |
| 9922 | CG2 | THR | B | 517 | -0.580 | 7.721 | 12.859 | 1.00 | 17.26 |
| 9923 | C | THR | B | 517 | 1.479 | 5.929 | 15.543 | 1.00 | 16.69 |
| 9924 | O | THR | B | 517 | 2.355 | 6.789 | 15.861 | 1.00 | 14.21 |
| 9925 | N | LEU | B | 518 | 1.631 | 4.613 | 15.738 | 1.00 | 14.45 |
| 9926 | CA | LEU | B | 518 | 2.793 | 4.064 | 16.394 | 1.00 | 12.35 |
| 9927 | CB | LEU | B | 518 | 2.379 | 3.354 | 17.647 | 1.00 | 11.84 |
| 9928 | CG | LEU | B | 518 | 2.436 | 3.998 | 19.035 | 1.00 | 10.07 |
| 9929 | CD1 | LEU | B | 518 | 2.317 | 5.492 | 19.081 | 1.00 | 10.92 |
| 9930 | CD2 | LEU | B | 518 | 1.337 | 3.406 | 19.761 | 1.00 | 8.04 |
| 9931 | C | LEU | B | 518 | 3.572 | 3.114 | 15.528 | 1.00 | 11.82 |
| 9932 | O | LEU | B | 518 | 3.145 | 1.979 | 15.323 | 1.00 | 11.72 |
| 9933 | N | TRP | B | 519 | 4.774 | 3.534 | 15.080 | 1.00 | 12.27 |
| 9934 | CA | TRP | B | 519 | 5.522 | 2.694 | 14.169 | 1.00 | 12.18 |
| 9935 | CB | TRP | B | 519 | 6.376 | 3.559 | 13.301 | 1.00 | 12.60 |
| 9936 | CG | TRP | B | 519 | 5.655 | 4.056 | 12.221 | 1.00 | 11.07 |

FIGURE 3 (Cont.)

| A | B | C | D | E | F | G | H | I | J |
|---|---|---|---|---|---|---|---|---|---|
| 9937 | CD1 | TRP | B | 519 | 4.999 | 5.260 | 12.136 | 1.00 | 8.45 |
| 9938 | NE1 | TRP | B | 519 | 4.353 | 5.341 | 10.929 | 1.00 | 8.58 |
| 9939 | CE2 | TRP | B | 519 | 4.617 | 4.204 | 10.225 | 1.00 | 9.97 |
| 9940 | CD2 | TRP | B | 519 | 5.428 | 3.374 | 11.032 | 1.00 | 9.04 |
| 9941 | CE3 | TRP | B | 519 | 5.833 | 2.143 | 10.548 | 1.00 | 4.86 |
| 9942 | CZ3 | TRP | B | 519 | 5.471 | 1.796 | 9.370 | 1.00 | 8.18 |
| 9943 | CH2 | TRP | B | 519 | 4.704 | 2.632 | 8.567 | 1.00 | 10.02 |
| 9944 | CZ2 | TRP | B | 519 | 4.259 | 3.859 | 8.988 | 1.00 | 8.62 |
| 9945 | C | TRP | B | 519 | 6.390 | 1.818 | 14.991 | 1.00 | 12.46 |
| 9946 | O | TRP | B | 519 | 7.065 | 2.340 | 15.884 | 1.00 | 13.76 |
| 9947 | N | TYR | B | 520 | 6.360 | 0.517 | 14.751 | 1.00 | 10.77 |
| 9948 | CA | TYR | B | 520 | 7.251 | -0.379 | 15.460 | 1.00 | 11.57 |
| 9949 | CB | TYR | B | 520 | 6.435 | -1.285 | 16.414 | 1.00 | 11.72 |
| 9950 | CG | TYR | B | 520 | 5.404 | -2.268 | 15.784 | 1.00 | 10.29 |
| 9951 | CD1 | TYR | B | 520 | 5.741 | -3.588 | 15.549 | 1.00 | 9.22 |
| 9952 | CE1 | TYR | B | 520 | 4.778 | -4.515 | 15.027 | 1.00 | 7.42 |
| 9953 | CZ | TYR | B | 520 | 3.540 | -4.089 | 14.739 | 1.00 | 6.46 |
| 9954 | OH | TYR | B | 520 | 2.646 | -5.007 | 14.253 | 1.00 | 10.72 |
| 9955 | CE2 | TYR | B | 520 | 3.180 | -2.714 | 14.969 | 1.00 | 6.27 |
| 9956 | CD2 | TYR | B | 520 | 4.074 | -1.861 | 15.491 | 1.00 | 8.37 |
| 9957 | C | TYR | B | 520 | 8.144 | -1.283 | 14.567 | 1.00 | 11.37 |
| 9958 | O | TYR | B | 520 | 7.951 | -1.410 | 13.373 | 1.00 | 11.96 |
| 9959 | N | LYS | B | 521 | 9.136 | -1.896 | 15.180 | 1.00 | 10.90 |
| 9960 | CA | LYS | B | 521 | 9.952 | -2.900 | 14.546 | 1.00 | 9.47 |
| 9961 | CB | LYS | B | 521 | 11.411 | -2.419 | 14.385 | 1.00 | 8.64 |
| 9962 | CG | LYS | B | 521 | 12.461 | -3.546 | 14.251 | 1.00 | 5.27 |
| 9963 | CD | LYS | B | 521 | 13.334 | -3.489 | 13.013 | 1.00 | 7.38 |
| 9964 | CE | LYS | B | 521 | 14.638 | -2.548 | 13.207 | 1.00 | 9.90 |
| 9965 | NZ | LYS | B | 521 | 15.524 | -2.414 | 11.918 | 1.00 | 11.58 |
| 9966 | C | LYS | B | 521 | 9.839 | -4.023 | 15.539 | 1.00 | 9.35 |
| 9967 | O | LYS | B | 521 | 9.845 | -3.768 | 16.722 | 1.00 | 11.08 |
| 9968 | N | MET | B | 522 | 9.711 | -5.247 | 15.073 | 1.00 | 10.11 |
| 9969 | CA | MET | B | 522 | 9.527 | -6.393 | 15.912 | 1.00 | 9.82 |
| 9970 | CB | MET | B | 522 | 8.184 | -6.903 | 15.621 | 1.00 | 8.39 |
| 9971 | CG | MET | B | 522 | 7.929 | -8.316 | 16.196 | 1.00 | 8.16 |
| 9972 | SD | MET | B | 522 | 6.247 | -8.531 | 16.974 | 1.00 | 8.46 |
| 9973 | CE | MET | B | 522 | 6.199 | -7.053 | 17.961 | 1.00 | 3.08 |
| 9974 | C | MET | B | 522 | 10.505 | -7.431 | 15.420 | 1.00 | 11.52 |
| 9975 | O | MET | B | 522 | 10.469 | -7.740 | 14.214 | 1.00 | 11.92 |
| 9976 | N | ILE | B | 523 | 11.375 | -7.964 | 16.290 | 1.00 | 11.49 |
| 9977 | CA | ILE | B | 523 | 12.235 | -9.025 | 15.854 | 1.00 | 12.75 |
| 9978 | CB | ILE | B | 523 | 13.628 | -8.856 | 16.354 | 1.00 | 12.97 |
| 9979 | CG1 | ILE | B | 523 | 14.124 | -7.357 | 16.346 | 1.00 | 12.53 |
| 9980 | CD1 | ILE | B | 523 | 13.932 | -6.678 | 15.067 | 1.00 | 15.00 |
| 9981 | CG2 | ILE | B | 523 | 14.580 | -9.792 | 15.584 | 1.00 | 12.17 |
| 9982 | C | ILE | B | 523 | 11.677 | -10.332 | 16.350 | 1.00 | 14.37 |
| 9983 | O | ILE | B | 523 | 11.199 | -10.380 | 17.464 | 1.00 | 15.97 |
| 9984 | N | LEU | B | 524 | 11.749 | -11.383 | 15.537 | 1.00 | 14.91 |
| 9985 | CA | LEU | B | 524 | 11.114 | -12.675 | 15.832 | 1.00 | 16.82 |
| 9986 | CB | LEU | B | 524 | 9.957 | -13.034 | 14.876 | 1.00 | 15.65 |
| 9987 | CG | LEU | B | 524 | 8.915 | -11.928 | 14.773 | 1.00 | 16.08 |

FIGURE 3 (Cont.)

| A | B | C | D | E | F | G | H | I | J |
|---|---|---|---|---|---|---|---|---|---|
| 9988 | CD1 | LEU | B | 524 | 7.849 | -12.294 | 13.725 | 1.00 | 14.58 |
| 9989 | CD2 | LEU | B | 524 | 8.285 | -11.572 | 16.155 | 1.00 | 15.10 |
| 9990 | C | LEU | B | 524 | 12.111 | -13.729 | 15.593 | 1.00 | 17.82 |
| 9991 | O | LEU | B | 524 | 12.925 | -13.570 | 14.699 | 1.00 | 18.80 |
| 9992 | N | PRO | B | 525 | 12.070 | -14.803 | 16.368 | 1.00 | 18.19 |
| 9993 | CA | PRO | B | 525 | 13.093 | -15.841 | 16.244 | 1.00 | 18.78 |
| 9994 | CB | PRO | B | 525 | 12.916 | -16.633 | 17.541 | 1.00 | 18.49 |
| 9995 | CG | PRO | B | 525 | 12.125 | -15.738 | 18.405 | 1.00 | 17.11 |
| 9996 | CD | PRO | B | 525 | 11.150 | -15.104 | 17.480 | 1.00 | 18.22 |
| 9997 | C | PRO | B | 525 | 12.837 | -16.665 | 14.980 | 1.00 | 19.47 |
| 9998 | O | PRO | B | 525 | 11.695 | -16.634 | 14.516 | 1.00 | 20.06 |
| 9999 | N | PRO | B | 526 | 13.848 | -17.309 | 14.375 | 1.00 | 20.05 |
| 10000 | CA | PRO | B | 526 | 13.589 | -18.033 | 13.120 | 1.00 | 20.40 |
| 10001 | CB | PRO | B | 526 | 15.001 | -18.460 | 12.629 | 1.00 | 20.78 |
| 10002 | CG | PRO | B | 526 | 15.999 | -17.763 | 13.496 | 1.00 | 19.34 |
| 10003 | CD | PRO | B | 526 | 15.264 | -17.436 | 14.796 | 1.00 | 19.62 |
| 10004 | C | PRO | B | 526 | 12.680 | -19.187 | 13.531 | 1.00 | 20.54 |
| 10005 | O | PRO | B | 526 | 12.683 | -19.449 | 14.705 | 1.00 | 20.28 |
| 10006 | N | GLN | B | 527 | 11.847 | -19.758 | 12.675 | 1.00 | 20.81 |
| 10007 | CA | GLN | B | 527 | 10.892 | -20.760 | 13.153 | 1.00 | 21.27 |
| 10008 | CB | GLN | B | 527 | 11.671 | -21.994 | 13.665 | 1.00 | 21.80 |
| 10009 | CG | GLN | B | 527 | 12.583 | -22.686 | 12.586 | 1.00 | 23.23 |
| 10010 | CD | GLN | B | 527 | 14.096 | -22.522 | 12.888 | 1.00 | 25.10 |
| 10011 | OE1 | GLN | B | 527 | 14.627 | -21.378 | 12.938 | 1.00 | 25.04 |
| 10012 | NE2 | GLN | B | 527 | 14.779 | -23.652 | 13.111 | 1.00 | 22.46 |
| 10013 | C | GLN | B | 527 | 9.909 | -20.236 | 14.238 | 1.00 | 20.89 |
| 10014 | O | GLN | B | 527 | 9.322 | -21.012 | 15.012 | 1.00 | 20.42 |
| 10015 | N | PHE | B | 528 | 9.725 | -18.915 | 14.267 | 1.00 | 20.37 |
| 10016 | CA | PHE | B | 528 | 8.734 | -18.252 | 15.107 | 1.00 | 20.15 |
| 10017 | CB | PHE | B | 528 | 8.723 | -16.762 | 14.838 | 1.00 | 20.86 |
| 10018 | CG | PHE | B | 528 | 7.376 | -16.094 | 15.095 | 1.00 | 22.64 |
| 10019 | CD1 | PHE | B | 528 | 6.970 | -15.786 | 16.413 | 1.00 | 23.33 |
| 10020 | CE1 | PHE | B | 528 | 5.752 | -15.138 | 16.674 | 1.00 | 23.31 |
| 10021 | CZ | PHE | B | 528 | 4.913 | -14.778 | 15.597 | 1.00 | 24.23 |
| 10022 | CE2 | PHE | B | 528 | 5.316 | -15.082 | 14.267 | 1.00 | 24.89 |
| 10023 | CD2 | PHE | B | 528 | 6.538 | -15.731 | 14.032 | 1.00 | 23.70 |
| 10024 | C | PHE | B | 528 | 7.382 | -18.741 | 14.727 | 1.00 | 19.39 |
| 10025 | O | PHE | B | 528 | 7.019 | -18.626 | 13.571 | 1.00 | 18.80 |
| 10026 | N | ASP | B | 529 | 6.638 | -19.232 | 15.712 | 1.00 | 19.43 |
| 10027 | CA | ASP | B | 529 | 5.419 | -19.963 | 15.493 | 1.00 | 19.03 |
| 10028 | CB | ASP | B | 529 | 5.656 | -21.452 | 15.847 | 1.00 | 19.12 |
| 10029 | CG | ASP | B | 529 | 4.370 | -22.238 | 16.048 | 1.00 | 19.74 |
| 10030 | OD1 | ASP | B | 529 | 3.507 | -22.179 | 15.162 | 1.00 | 16.92 |
| 10031 | OD2 | ASP | B | 529 | 4.168 | -22.979 | 17.049 | 1.00 | 20.99 |
| 10032 | C | ASP | B | 529 | 4.418 | -19.278 | 16.400 | 1.00 | 19.09 |
| 10033 | O | ASP | B | 529 | 4.492 | -19.399 | 17.636 | 1.00 | 18.30 |
| 10034 | N | ARG | B | 530 | 3.465 | -18.579 | 15.776 | 1.00 | 19.83 |
| 10035 | CA | ARG | B | 530 | 2.618 | -17.612 | 16.500 | 1.00 | 20.01 |
| 10036 | CB | ARG | B | 530 | 1.933 | -16.638 | 15.530 | 1.00 | 19.94 |
| 10037 | CG | ARG | B | 530 | 0.509 | -16.229 | 15.941 | 1.00 | 21.85 |
| 10038 | CD | ARG | B | 530 | -0.454 | -16.040 | 14.760 | 1.00 | 27.51 |

FIGURE 3 (Cont.)

| A | B | C | D | E | F | G | H | I | J |
|---|---|---|---|---|---|---|---|---|---|
| 10039 | NE | ARG | B | 530 | -1.170 | -14.768 | 14.888 | 1.00 | 31.50 |
| 10040 | CZ | ARG | B | 530 | -0.831 | -13.626 | 14.261 | 1.00 | 34.57 |
| 10041 | NH1 | ARG | B | 530 | -1.529 | -12.517 | 14.487 | 1.00 | 35.96 |
| 10042 | NH2 | ARG | B | 530 | 0.199 | -13.574 | 13.412 | 1.00 | 34.68 |
| 10043 | C | ARG | B | 530 | 1.587 | -18.234 | 17.456 | 1.00 | 19.87 |
| 10044 | O | ARG | B | 530 | 1.140 | -17.558 | 18.372 | 1.00 | 19.93 |
| 10045 | N | SER | B | 531 | 1.230 | -19.509 | 17.252 | 1.00 | 19.71 |
| 10046 | CA | SER | B | 531 | 0.403 | -20.243 | 18.234 | 1.00 | 19.95 |
| 10047 | CB | SER | B | 531 | 0.091 | -21.625 | 17.723 | 1.00 | 19.66 |
| 10048 | OG | SER | B | 531 | 0.677 | -21.796 | 16.446 | 1.00 | 19.29 |
| 10049 | C | SER | B | 531 | 1.037 | -20.338 | 19.629 | 1.00 | 20.10 |
| 10050 | O | SER | B | 531 | 0.422 | -19.947 | 20.617 | 1.00 | 20.68 |
| 10051 | N | LYS | B | 532 | 2.272 | -20.840 | 19.704 | 1.00 | 20.36 |
| 10052 | CA | LYS | B | 532 | 3.130 | -20.726 | 20.923 | 1.00 | 19.69 |
| 10053 | CB | LYS | B | 532 | 4.527 | -21.391 | 20.695 | 1.00 | 19.26 |
| 10054 | CG | LYS | B | 532 | 4.436 | -22.913 | 20.215 | 1.00 | 20.16 |
| 10055 | CD | LYS | B | 532 | 5.782 | -23.609 | 19.748 | 1.00 | 18.68 |
| 10056 | CE | LYS | B | 532 | 5.940 | -25.091 | 20.330 | 1.00 | 19.30 |
| 10057 | NZ | LYS | B | 532 | 5.533 | -26.263 | 19.455 | 1.00 | 16.70 |
| 10058 | C | LYS | B | 532 | 3.248 | -19.233 | 21.338 | 1.00 | 19.44 |
| 10059 | O | LYS | B | 532 | 3.096 | -18.328 | 20.499 | 1.00 | 19.45 |
| 10060 | N | LYS | B | 533 | 3.475 | -18.994 | 22.636 | 1.00 | 19.39 |
| 10061 | CA | LYS | B | 533 | 3.522 | -17.655 | 23.241 | 1.00 | 18.77 |
| 10062 | CB | LYS | B | 533 | 2.562 | -17.543 | 24.441 | 1.00 | 18.52 |
| 10063 | CG | LYS | B | 533 | 1.129 | -17.104 | 24.095 | 1.00 | 19.72 |
| 10064 | CD | LYS | B | 533 | 0.132 | -17.161 | 25.285 | 1.00 | 22.26 |
| 10065 | CE | LYS | B | 533 | -1.131 | -16.296 | 25.028 | 1.00 | 23.87 |
| 10066 | NZ | LYS | B | 533 | -1.055 | -14.946 | 25.722 | 1.00 | 26.56 |
| 10067 | C | LYS | B | 533 | 4.947 | -17.342 | 23.687 | 1.00 | 18.14 |
| 10068 | O | LYS | B | 533 | 5.647 | -18.160 | 24.228 | 1.00 | 18.73 |
| 10069 | N | TYR | B | 534 | 5.375 | -16.114 | 23.481 | 1.00 | 17.66 |
| 10070 | CA | TYR | B | 534 | 6.799 | -15.839 | 23.419 | 1.00 | 16.82 |
| 10071 | CB | TYR | B | 534 | 7.247 | -15.388 | 21.994 | 1.00 | 16.93 |
| 10072 | CG | TYR | B | 534 | 7.502 | -16.517 | 21.019 | 1.00 | 18.86 |
| 10073 | CD1 | TYR | B | 534 | 6.507 | -16.903 | 20.083 | 1.00 | 20.65 |
| 10074 | CE1 | TYR | B | 534 | 6.693 | -17.968 | 19.198 | 1.00 | 16.16 |
| 10075 | CZ | TYR | B | 534 | 7.867 | -18.694 | 19.210 | 1.00 | 18.74 |
| 10076 | OH | TYR | B | 534 | 7.994 | -19.774 | 18.292 | 1.00 | 19.54 |
| 10077 | CE2 | TYR | B | 534 | 8.877 | -18.363 | 20.136 | 1.00 | 19.53 |
| 10078 | CD2 | TYR | B | 534 | 8.682 | -17.267 | 21.046 | 1.00 | 20.65 |
| 10079 | C | TYR | B | 534 | 7.102 | -14.760 | 24.504 | 1.00 | 15.81 |
| 10080 | O | TYR | B | 534 | 6.285 | -13.892 | 24.739 | 1.00 | 15.34 |
| 10081 | N | PRO | B | 535 | 8.276 | -14.845 | 25.137 | 1.00 | 13.83 |
| 10082 | CA | PRO | B | 535 | 8.724 | -13.803 | 26.057 | 1.00 | 12.84 |
| 10083 | CB | PRO | B | 535 | 10.017 | -14.409 | 26.685 | 1.00 | 12.36 |
| 10084 | CG | PRO | B | 535 | 10.488 | -15.483 | 25.755 | 1.00 | 12.61 |
| 10085 | CD | PRO | B | 535 | 9.308 | -15.899 | 24.933 | 1.00 | 13.49 |
| 10086 | C | PRO | B | 535 | 8.985 | -12.564 | 25.237 | 1.00 | 11.94 |
| 10087 | O | PRO | B | 535 | 9.529 | -12.669 | 24.136 | 1.00 | 11.38 |
| 10088 | N | LEU | B | 536 | 8.539 | -11.414 | 25.703 | 1.00 | 12.08 |
| 10089 | CA | LEU | B | 536 | 8.760 | -10.142 | 24.966 | 1.00 | 10.91 |

FIGURE 3 (Cont.)

| A | B | C | D | E | F | G | H | I | J |
|---|---|---|---|---|---|---|---|---|---|
| 10090 | CB | LEU | B | 536 | 7.439 | -9.386 | 24.854 | 1.00 | 10.46 |
| 10091 | CG | LEU | B | 536 | 7.593 | -7.928 | 24.343 | 1.00 | 8.67 |
| 10092 | CD1 | LEU | B | 536 | 8.403 | -7.879 | 23.065 | 1.00 | 5.57 |
| 10093 | CD2 | LEU | B | 536 | 6.288 | -7.252 | 24.174 | 1.00 | 2.00 |
| 10094 | C | LEU | B | 536 | 9.736 | -9.173 | 25.592 | 1.00 | 10.97 |
| 10095 | O | LEU | B | 536 | 9.467 | -8.652 | 26.672 | 1.00 | 13.54 |
| 10096 | N | LEU | B | 537 | 10.820 | -8.838 | 24.916 | 1.00 | 10.08 |
| 10097 | CA | LEU | B | 537 | 11.650 | -7.676 | 25.319 | 1.00 | 8.26 |
| 10098 | CB | LEU | B | 537 | 13.097 | -7.974 | 25.017 | 1.00 | 8.06 |
| 10099 | CG | LEU | B | 537 | 14.051 | -6.800 | 25.284 | 1.00 | 4.88 |
| 10100 | CD1 | LEU | B | 537 | 14.036 | -6.376 | 26.728 | 1.00 | 2.00 |
| 10101 | CD2 | LEU | B | 537 | 15.453 | -7.238 | 24.994 | 1.00 | 10.15 |
| 10102 | C | LEU | B | 537 | 11.387 | -6.438 | 24.499 | 1.00 | 8.12 |
| 10103 | O | LEU | B | 537 | 11.330 | -6.536 | 23.294 | 1.00 | 9.15 |
| 10104 | N | ILE | B | 538 | 11.347 | -5.268 | 25.095 | 1.00 | 7.38 |
| 10105 | CA | ILE | B | 538 | 11.195 | -4.029 | 24.401 | 1.00 | 7.93 |
| 10106 | CB | ILE | B | 538 | 10.179 | -3.163 | 25.174 | 1.00 | 7.10 |
| 10107 | CG1 | ILE | B | 538 | 8.817 | -3.800 | 25.203 | 1.00 | 6.25 |
| 10108 | CD1 | ILE | B | 538 | 8.424 | -4.493 | 23.799 | 1.00 | 3.01 |
| 10109 | CG2 | ILE | B | 538 | 9.977 | -1.857 | 24.531 | 1.00 | 3.91 |
| 10110 | C | ILE | B | 538 | 12.490 | -3.314 | 24.517 | 1.00 | 10.61 |
| 10111 | O | ILE | B | 538 | 13.049 | -3.255 | 25.626 | 1.00 | 13.40 |
| 10112 | N | GLN | B | 539 | 12.971 | -2.688 | 23.433 | 1.00 | 11.71 |
| 10113 | CA | GLN | B | 539 | 14.135 | -1.841 | 23.553 | 1.00 | 11.06 |
| 10114 | CB | GLN | B | 539 | 15.291 | -2.334 | 22.590 | 1.00 | 9.61 |
| 10115 | CG | GLN | B | 539 | 16.410 | -1.239 | 22.320 | 1.00 | 6.91 |
| 10116 | CD | GLN | B | 539 | 17.581 | -1.745 | 21.555 | 1.00 | 4.14 |
| 10117 | OE1 | GLN | B | 539 | 18.200 | -2.594 | 22.015 | 1.00 | 5.97 |
| 10118 | NE2 | GLN | B | 539 | 17.969 | -1.121 | 20.496 | 1.00 | 2.42 |
| 10119 | C | GLN | B | 539 | 13.675 | -0.387 | 23.296 | 1.00 | 12.89 |
| 10120 | O | GLN | B | 539 | 13.156 | -0.120 | 22.261 | 1.00 | 14.04 |
| 10121 | N | VAL | B | 540 | 13.975 | 0.545 | 24.189 | 1.00 | 14.94 |
| 10122 | CA | VAL | B | 540 | 13.472 | 1.909 | 24.138 | 1.00 | 15.55 |
| 10123 | CB | VAL | B | 540 | 12.400 | 2.114 | 25.217 | 1.00 | 17.22 |
| 10124 | CG1 | VAL | B | 540 | 13.037 | 1.921 | 26.606 | 1.00 | 16.10 |
| 10125 | CG2 | VAL | B | 540 | 11.718 | 3.473 | 25.110 | 1.00 | 16.70 |
| 10126 | C | VAL | B | 540 | 14.582 | 2.964 | 24.292 | 1.00 | 16.33 |
| 10127 | O | VAL | B | 540 | 15.706 | 2.731 | 24.828 | 1.00 | 18.55 |
| 10128 | N | TYR | B | 541 | 14.347 | 4.076 | 23.630 | 1.00 | 14.88 |
| 10129 | CA | TYR | B | 541 | 15.183 | 5.242 | 23.728 | 1.00 | 12.81 |
| 10130 | CB | TYR | B | 541 | 16.026 | 5.449 | 22.457 | 1.00 | 13.66 |
| 10131 | CG | TYR | B | 541 | 16.903 | 6.685 | 22.586 | 1.00 | 14.22 |
| 10132 | CD1 | TYR | B | 541 | 17.943 | 6.734 | 23.468 | 1.00 | 12.24 |
| 10133 | CE1 | TYR | B | 541 | 18.750 | 7.887 | 23.580 | 1.00 | 14.88 |
| 10134 | CZ | TYR | B | 541 | 18.415 | 8.986 | 22.925 | 1.00 | 14.91 |
| 10135 | OH | TYR | B | 541 | 19.117 | 10.127 | 22.994 | 1.00 | 21.93 |
| 10136 | CE2 | TYR | B | 541 | 17.405 | 8.930 | 22.044 | 1.00 | 17.45 |
| 10137 | CD2 | TYR | B | 541 | 16.646 | 7.787 | 21.882 | 1.00 | 16.01 |
| 10138 | C | TYR | B | 541 | 14.168 | 6.300 | 23.974 | 1.00 | 12.33 |
| 10139 | O | TYR | B | 541 | 13.747 | 6.520 | 25.130 | 1.00 | 13.46 |
| 10140 | N | GLY | B | 542 | 13.637 | 6.854 | 22.910 | 1.00 | 10.00 |

FIGURE 3 (Cont.)

| A | B | C | D | E | F | G | H | I | J |
|---|---|---|---|---|---|---|---|---|---|
| 10141 | CA | GLY | B | 542 | 12.491 | 7.686 | 23.048 | 1.00 | 9.59 |
| 10142 | C | GLY | B | 542 | 12.789 | 9.163 | 23.242 | 1.00 | 9.30 |
| 10143 | O | GLY | B | 542 | 11.853 | 9.885 | 23.441 | 1.00 | 9.25 |
| 10144 | N | GLY | B | 543 | 14.007 | 9.653 | 23.024 | 1.00 | 8.29 |
| 10145 | CA | GLY | B | 543 | 14.260 | 11.069 | 23.192 | 1.00 | 9.22 |
| 10146 | C | GLY | B | 543 | 13.538 | 12.018 | 22.218 | 1.00 | 10.27 |
| 10147 | O | GLY | B | 543 | 13.383 | 11.726 | 21.058 | 1.00 | 11.13 |
| 10148 | N | PRO | B | 544 | 13.222 | 13.200 | 22.657 | 1.00 | 11.61 |
| 10149 | CA | PRO | B | 544 | 12.790 | 14.289 | 21.748 | 1.00 | 11.74 |
| 10150 | CB | PRO | B | 544 | 12.864 | 15.536 | 22.606 | 1.00 | 10.90 |
| 10151 | CG | PRO | B | 544 | 12.842 | 15.079 | 23.963 | 1.00 | 13.27 |
| 10152 | CD | PRO | B | 544 | 13.296 | 13.594 | 24.048 | 1.00 | 10.89 |
| 10153 | C | PRO | B | 544 | 13.706 | 14.411 | 20.477 | 1.00 | 13.57 |
| 10154 | O | PRO | B | 544 | 14.983 | 14.296 | 20.562 | 1.00 | 14.88 |
| 10155 | N | CYS | B | 545 | 13.055 | 14.444 | 19.308 | 1.00 | 10.94 |
| 10156 | CA | CYS | B | 545 | 13.675 | 14.284 | 18.020 | 1.00 | 10.85 |
| 10157 | CB | CYS | B | 545 | 14.671 | 15.435 | 17.882 | 1.00 | 10.89 |
| 10158 | SG | CYS | B | 545 | 14.162 | 16.992 | 18.655 | 1.00 | 12.64 |
| 10159 | C | CYS | B | 545 | 14.334 | 12.899 | 17.558 | 1.00 | 10.33 |
| 10160 | O | CYS | B | 545 | 14.926 | 12.814 | 16.522 | 1.00 | 7.83 |
| 10161 | N | SER | B | 546 | 14.163 | 11.794 | 18.255 | 1.00 | 11.78 |
| 10162 | CA | SER | B | 546 | 14.831 | 10.560 | 17.807 | 1.00 | 11.61 |
| 10163 | CB | SER | B | 546 | 15.235 | 9.663 | 18.987 | 1.00 | 11.62 |
| 10164 | OG | SER | B | 546 | 14.103 | 8.904 | 19.580 | 1.00 | 12.09 |
| 10165 | C | SER | B | 546 | 13.920 | 9.800 | 16.883 | 1.00 | 11.73 |
| 10166 | O | SER | B | 546 | 12.744 | 10.160 | 16.677 | 1.00 | 12.52 |
| 10167 | N | GLN | B | 547 | 14.476 | 8.751 | 16.304 | 1.00 | 12.43 |
| 10168 | CA | GLN | B | 547 | 13.708 | 7.744 | 15.670 | 1.00 | 13.79 |
| 10169 | CB | GLN | B | 547 | 13.521 | 8.118 | 14.213 | 1.00 | 14.32 |
| 10170 | CG | GLN | B | 547 | 12.987 | 6.937 | 13.357 | 1.00 | 8.09 |
| 10171 | CD | GLN | B | 547 | 12.711 | 7.313 | 11.978 | 1.00 | 3.34 |
| 10172 | OE1 | GLN | B | 547 | 11.542 | 7.553 | 11.546 | 1.00 | 9.75 |
| 10173 | NE2 | GLN | B | 547 | 13.758 | 7.396 | 11.241 | 1.00 | 10.32 |
| 10174 | C | GLN | B | 547 | 14.481 | 6.412 | 15.790 | 1.00 | 15.87 |
| 10175 | O | GLN | B | 547 | 15.576 | 6.226 | 15.241 | 1.00 | 17.04 |
| 10176 | N | SER | B | 548 | 13.851 | 5.454 | 16.412 | 1.00 | 16.80 |
| 10177 | CA | SER | B | 548 | 14.465 | 4.199 | 16.678 | 1.00 | 17.13 |
| 10178 | CB | SER | B | 548 | 14.281 | 3.864 | 18.184 | 1.00 | 18.44 |
| 10179 | OG | SER | B | 548 | 14.996 | 4.894 | 18.941 | 1.00 | 22.67 |
| 10180 | C | SER | B | 548 | 13.945 | 3.138 | 15.776 | 1.00 | 17.08 |
| 10181 | O | SER | B | 548 | 14.533 | 2.065 | 15.690 | 1.00 | 18.25 |
| 10182 | N | VAL | B | 549 | 12.860 | 3.437 | 15.068 | 1.00 | 17.09 |
| 10183 | CA | VAL | B | 549 | 12.381 | 2.496 | 14.043 | 1.00 | 16.73 |
| 10184 | CB | VAL | B | 549 | 10.917 | 2.222 | 14.129 | 1.00 | 17.68 |
| 10185 | CG1 | VAL | B | 549 | 10.520 | 1.211 | 13.056 | 1.00 | 13.94 |
| 10186 | CG2 | VAL | B | 549 | 10.548 | 1.766 | 15.539 | 1.00 | 12.13 |
| 10187 | C | VAL | B | 549 | 12.754 | 2.995 | 12.666 | 1.00 | 17.42 |
| 10188 | O | VAL | B | 549 | 12.249 | 4.045 | 12.172 | 1.00 | 17.82 |
| 10189 | N | ARG | B | 550 | 13.627 | 2.192 | 12.069 | 1.00 | 17.42 |
| 10190 | CA | ARG | B | 550 | 14.465 | 2.546 | 10.936 | 1.00 | 17.26 |
| 10191 | CB | ARG | B | 550 | 15.784 | 3.170 | 11.420 | 1.00 | 17.42 |

FIGURE 3 (Cont.)

| A | B | C | D | E | F | G | H | I | J |
|---|---|---|---|---|---|---|---|---|---|
| 10192 | CG | ARG | B | 550 | 15.724 | 4.659 | 11.616 | 1.00 | 20.00 |
| 10193 | CD | ARG | B | 550 | 16.743 | 5.182 | 12.570 | 1.00 | 24.78 |
| 10194 | NE | ARG | B | 550 | 16.677 | 6.656 | 12.605 | 1.00 | 31.97 |
| 10195 | CZ | ARG | B | 550 | 17.402 | 7.435 | 13.448 | 1.00 | 31.52 |
| 10196 | NH1 | ARG | B | 550 | 17.292 | 8.771 | 13.440 | 1.00 | 27.91 |
| 10197 | NH2 | ARG | B | 550 | 18.257 | 6.858 | 14.294 | 1.00 | 33.90 |
| 10198 | C | ARG | B | 550 | 14.850 | 1.315 | 10.170 | 1.00 | 16.79 |
| 10199 | O | ARG | B | 550 | 15.184 | 0.259 | 10.728 | 1.00 | 15.40 |
| 10200 | N | SER | B | 551 | 14.911 | 1.458 | 8.867 | 1.00 | 16.11 |
| 10201 | CA | SER | B | 551 | 15.224 | 0.296 | 8.034 | 1.00 | 15.40 |
| 10202 | CB | SER | B | 551 | 14.601 | 0.450 | 6.658 | 1.00 | 14.24 |
| 10203 | OG | SER | B | 551 | 13.242 | 0.793 | 6.799 | 1.00 | 13.66 |
| 10204 | C | SER | B | 551 | 16.686 | 0.133 | 7.921 | 1.00 | 15.58 |
| 10205 | O | SER | B | 551 | 17.221 | 0.048 | 6.813 | 1.00 | 15.97 |
| 10206 | N | VAL | B | 552 | 17.359 | 0.099 | 9.065 | 1.00 | 15.58 |
| 10207 | CA | VAL | B | 552 | 18.806 | -0.028 | 9.082 | 1.00 | 16.15 |
| 10208 | CB | VAL | B | 552 | 19.431 | 0.952 | 10.091 | 1.00 | 16.62 |
| 10209 | CG1 | VAL | B | 552 | 20.938 | 0.727 | 10.235 | 1.00 | 17.30 |
| 10210 | CG2 | VAL | B | 552 | 19.206 | 2.383 | 9.603 | 1.00 | 16.40 |
| 10211 | C | VAL | B | 552 | 19.142 | -1.444 | 9.426 | 1.00 | 16.43 |
| 10212 | O | VAL | B | 552 | 18.489 | -2.051 | 10.217 | 1.00 | 17.50 |
| 10213 | N | PHE | B | 553 | 20.171 | -1.974 | 8.793 | 1.00 | 15.92 |
| 10214 | CA | PHE | B | 553 | 20.649 | -3.324 | 9.058 | 1.00 | 14.53 |
| 10215 | CB | PHE | B | 553 | 21.389 | -3.812 | 7.843 | 1.00 | 13.64 |
| 10216 | CG | PHE | B | 553 | 22.075 | -5.117 | 8.009 | 1.00 | 8.25 |
| 10217 | CD1 | PHE | B | 553 | 21.545 | -6.276 | 7.422 | 1.00 | 6.38 |
| 10218 | CE1 | PHE | B | 553 | 22.205 | -7.496 | 7.496 | 1.00 | 4.26 |
| 10219 | CZ | PHE | B | 553 | 23.418 | -7.567 | 8.180 | 1.00 | 5.61 |
| 10220 | CE2 | PHE | B | 553 | 23.978 | -6.388 | 8.745 | 1.00 | 2.00 |
| 10221 | CD2 | PHE | B | 553 | 23.282 | -5.183 | 8.638 | 1.00 | 3.65 |
| 10222 | C | PHE | B | 553 | 21.631 | -3.275 | 10.156 | 1.00 | 15.70 |
| 10223 | O | PHE | B | 553 | 22.526 | -2.428 | 10.181 | 1.00 | 16.41 |
| 10224 | N | ALA | B | 554 | 21.505 | -4.199 | 11.078 | 1.00 | 15.10 |
| 10225 | CA | ALA | B | 554 | 22.589 | -4.314 | 12.053 | 1.00 | 15.94 |
| 10226 | CB | ALA | B | 554 | 22.792 | -3.015 | 12.879 | 1.00 | 14.62 |
| 10227 | C | ALA | B | 554 | 22.223 | -5.480 | 12.944 | 1.00 | 15.83 |
| 10228 | O | ALA | B | 554 | 21.176 | -5.413 | 13.632 | 1.00 | 17.41 |
| 10229 | N | VAL | B | 555 | 23.015 | -6.547 | 12.796 | 1.00 | 13.33 |
| 10230 | CA | VAL | B | 555 | 23.169 | -7.662 | 13.714 | 1.00 | 12.30 |
| 10231 | CB | VAL | B | 555 | 24.268 | -8.561 | 13.175 | 1.00 | 12.65 |
| 10232 | CG1 | VAL | B | 555 | 23.770 | -9.390 | 12.022 | 1.00 | 10.36 |
| 10233 | CG2 | VAL | B | 555 | 25.461 | -7.614 | 12.724 | 1.00 | 13.09 |
| 10234 | C | VAL | B | 555 | 23.749 | -7.254 | 15.037 | 1.00 | 12.26 |
| 10235 | O | VAL | B | 555 | 24.973 | -7.058 | 15.138 | 1.00 | 12.40 |
| 10236 | N | ASN | B | 556 | 22.921 | -7.215 | 16.063 | 1.00 | 11.78 |
| 10237 | CA | ASN | B | 556 | 23.347 | -6.649 | 17.308 | 1.00 | 12.50 |
| 10238 | CB | ASN | B | 556 | 22.883 | -5.191 | 17.397 | 1.00 | 13.20 |
| 10239 | CG | ASN | B | 556 | 21.416 | -5.061 | 17.091 | 1.00 | 14.62 |
| 10240 | OD1 | ASN | B | 556 | 20.914 | -3.973 | 16.921 | 1.00 | 19.95 |
| 10241 | ND2 | ASN | B | 556 | 20.729 | -6.186 | 16.980 | 1.00 | 15.00 |
| 10242 | C | ASN | B | 556 | 22.869 | -7.521 | 18.477 | 1.00 | 12.58 |

FIGURE 3 (Cont.)

| A | B | C | D | E | F | G | H | I | J |
|---|---|---|---|---|---|---|---|---|---|
| 10243 | O | ASN | B | 556 | 22.552 | -8.676 | 18.310 | 1.00 | 12.90 |
| 10244 | N | TRP | B | 557 | 22.894 | -6.997 | 19.694 | 1.00 | 11.91 |
| 10245 | CA | TRP | B | 557 | 22.505 | -7.788 | 20.839 | 1.00 | 9.56 |
| 10246 | CB | TRP | B | 557 | 22.716 | -6.956 | 22.088 | 1.00 | 9.95 |
| 10247 | CG | TRP | B | 557 | 22.427 | -7.625 | 23.276 | 1.00 | 9.22 |
| 10248 | CD1 | TRP | B | 557 | 22.947 | -8.781 | 23.654 | 1.00 | 10.47 |
| 10249 | NE1 | TRP | B | 557 | 22.452 | -9.126 | 24.881 | 1.00 | 11.53 |
| 10250 | CE2 | TRP | B | 557 | 21.560 | -8.183 | 25.281 | 1.00 | 9.77 |
| 10251 | CD2 | TRP | B | 557 | 21.533 | -7.210 | 24.283 | 1.00 | 8.82 |
| 10252 | CE3 | TRP | B | 557 | 20.744 | -6.083 | 24.475 | 1.00 | 7.96 |
| 10253 | CZ3 | TRP | B | 557 | 19.982 | -6.006 | 25.628 | 1.00 | 12.60 |
| 10254 | CH2 | TRP | B | 557 | 19.998 | -7.058 | 26.605 | 1.00 | 10.81 |
| 10255 | CZ2 | TRP | B | 557 | 20.793 | -8.113 | 26.443 | 1.00 | 8.97 |
| 10256 | C | TRP | B | 557 | 21.074 | -8.235 | 20.695 | 1.00 | 9.16 |
| 10257 | O | TRP | B | 557 | 20.818 | -9.423 | 20.779 | 1.00 | 9.03 |
| 10258 | N | ILE | B | 558 | 20.162 | -7.280 | 20.462 | 1.00 | 8.90 |
| 10259 | CA | ILE | B | 558 | 18.705 | -7.452 | 20.295 | 1.00 | 9.63 |
| 10260 | CB | ILE | B | 558 | 18.140 | -6.070 | 19.745 | 1.00 | 11.18 |
| 10261 | CG1 | ILE | B | 558 | 18.300 | -4.953 | 20.755 | 1.00 | 12.33 |
| 10262 | CD1 | ILE | B | 558 | 17.424 | -5.123 | 21.965 | 1.00 | 6.80 |
| 10263 | CG2 | ILE | B | 558 | 16.693 | -6.107 | 19.371 | 1.00 | 12.18 |
| 10264 | C | ILE | B | 558 | 18.437 | -8.496 | 19.211 | 1.00 | 10.81 |
| 10265 | O | ILE | B | 558 | 17.452 | -9.193 | 19.257 | 1.00 | 12.81 |
| 10266 | N | SER | B | 559 | 19.327 | -8.591 | 18.217 | 1.00 | 10.03 |
| 10267 | CA | SER | B | 559 | 19.233 | -9.590 | 17.188 | 1.00 | 10.66 |
| 10268 | CB | SER | B | 559 | 20.308 | -9.348 | 16.085 | 1.00 | 11.65 |
| 10269 | OG | SER | B | 559 | 19.985 | -8.290 | 15.208 | 1.00 | 10.89 |
| 10270 | C | SER | B | 559 | 19.379 | -11.064 | 17.748 | 1.00 | 11.04 |
| 10271 | O | SER | B | 559 | 18.556 | -11.909 | 17.461 | 1.00 | 10.01 |
| 10272 | N | TYR | B | 560 | 20.458 | -11.302 | 18.510 | 1.00 | 10.51 |
| 10273 | CA | TYR | B | 560 | 20.830 | -12.590 | 19.103 | 1.00 | 11.01 |
| 10274 | CB | TYR | B | 560 | 22.241 | -12.445 | 19.618 | 1.00 | 10.33 |
| 10275 | CG | TYR | B | 560 | 22.481 | -12.998 | 20.947 | 1.00 | 12.01 |
| 10276 | CD1 | TYR | B | 560 | 23.068 | -14.227 | 21.102 | 1.00 | 12.72 |
| 10277 | CE1 | TYR | B | 560 | 23.294 | -14.730 | 22.338 | 1.00 | 13.58 |
| 10278 | CZ | TYR | B | 560 | 22.967 | -13.982 | 23.430 | 1.00 | 11.62 |
| 10279 | OH | TYR | B | 560 | 23.171 | -14.477 | 24.668 | 1.00 | 11.38 |
| 10280 | CE2 | TYR | B | 560 | 22.387 | -12.773 | 23.307 | 1.00 | 13.06 |
| 10281 | CD2 | TYR | B | 560 | 22.155 | -12.273 | 22.086 | 1.00 | 13.30 |
| 10282 | C | TYR | B | 560 | 19.912 | -13.139 | 20.233 | 1.00 | 11.43 |
| 10283 | O | TYR | B | 560 | 19.636 | -14.363 | 20.325 | 1.00 | 11.05 |
| 10284 | N | LEU | B | 561 | 19.400 | -12.207 | 21.038 | 1.00 | 11.80 |
| 10285 | CA | LEU | B | 561 | 18.323 | -12.513 | 21.981 | 1.00 | 11.40 |
| 10286 | CB | LEU | B | 561 | 17.732 | -11.205 | 22.528 | 1.00 | 11.09 |
| 10287 | CG | LEU | B | 561 | 18.592 | -10.394 | 23.468 | 1.00 | 10.79 |
| 10288 | CD1 | LEU | B | 561 | 17.737 | -9.443 | 24.233 | 1.00 | 12.78 |
| 10289 | CD2 | LEU | B | 561 | 19.296 | -11.239 | 24.399 | 1.00 | 9.32 |
| 10290 | C | LEU | B | 561 | 17.197 | -13.294 | 21.293 | 1.00 | 10.75 |
| 10291 | O | LEU | B | 561 | 16.617 | -14.194 | 21.850 | 1.00 | 10.30 |
| 10292 | N | ALA | B | 562 | 16.878 | -12.866 | 20.077 | 1.00 | 10.77 |
| 10293 | CA | ALA | B | 562 | 15.917 | -13.554 | 19.184 | 1.00 | 9.37 |

FIGURE 3 (Cont.)

| A | B | C | D | E | F | G | H | I | J |
|---|---|---|---|---|---|---|---|---|---|
| 10294 | CB | ALA | B | 562 | 15.340 | -12.539 | 18.168 | 1.00 | 8.75 |
| 10295 | C | ALA | B | 562 | 16.480 | -14.741 | 18.447 | 1.00 | 8.59 |
| 10296 | O | ALA | B | 562 | 15.778 | -15.718 | 18.279 | 1.00 | 8.57 |
| 10297 | N | SER | B | 563 | 17.730 | -14.656 | 17.993 | 1.00 | 8.52 |
| 10298 | CA | SER | B | 563 | 18.290 | -15.724 | 17.157 | 1.00 | 9.76 |
| 10299 | CB | SER | B | 563 | 19.654 | -15.315 | 16.550 | 1.00 | 10.38 |
| 10300 | OG | SER | B | 563 | 20.359 | -16.443 | 16.000 | 1.00 | 11.21 |
| 10301 | C | SER | B | 563 | 18.390 | -17.073 | 17.935 | 1.00 | 9.28 |
| 10302 | O | SER | B | 563 | 17.842 | -18.017 | 17.504 | 1.00 | 8.42 |
| 10303 | N | LYS | B | 564 | 19.046 | -17.013 | 19.107 | 1.00 | 10.38 |
| 10304 | CA | LYS | B | 564 | 19.370 | -18.078 | 20.086 | 1.00 | 11.21 |
| 10305 | CB | LYS | B | 564 | 20.790 | -17.832 | 20.639 | 1.00 | 11.24 |
| 10306 | CG | LYS | B | 564 | 21.381 | -18.831 | 21.645 | 1.00 | 13.20 |
| 10307 | CD | LYS | B | 564 | 22.163 | -20.059 | 20.947 | 1.00 | 19.89 |
| 10308 | CE | LYS | B | 564 | 23.075 | -20.883 | 21.921 | 1.00 | 22.10 |
| 10309 | NZ | LYS | B | 564 | 24.101 | -20.013 | 22.656 | 1.00 | 22.12 |
| 10310 | C | LYS | B | 564 | 18.406 | -18.191 | 21.286 | 1.00 | 11.58 |
| 10311 | O | LYS | B | 564 | 18.038 | -19.287 | 21.612 | 1.00 | 11.09 |
| 10312 | N | GLU | B | 565 | 17.966 | -17.112 | 21.939 | 1.00 | 11.41 |
| 10313 | CA | GLU | B | 565 | 17.247 | -17.325 | 23.212 | 1.00 | 12.25 |
| 10314 | CB | GLU | B | 565 | 17.751 | -16.472 | 24.388 | 1.00 | 11.98 |
| 10315 | CG | GLU | B | 565 | 19.155 | -15.930 | 24.259 | 1.00 | 14.12 |
| 10316 | CD | GLU | B | 565 | 20.219 | -16.811 | 24.908 | 1.00 | 18.63 |
| 10317 | OE1 | GLU | B | 565 | 19.943 | -18.076 | 25.197 | 1.00 | 16.76 |
| 10318 | OE2 | GLU | B | 565 | 21.327 | -16.176 | 25.103 | 1.00 | 17.57 |
| 10319 | C | GLU | B | 565 | 15.761 | -17.174 | 23.186 | 1.00 | 11.67 |
| 10320 | O | GLU | B | 565 | 15.179 | -17.186 | 24.236 | 1.00 | 11.61 |
| 10321 | N | GLY | B | 566 | 15.152 | -16.963 | 22.039 | 1.00 | 10.91 |
| 10322 | CA | GLY | B | 566 | 13.718 | -17.170 | 21.945 | 1.00 | 10.44 |
| 10323 | C | GLY | B | 566 | 12.844 | -15.977 | 22.341 | 1.00 | 10.13 |
| 10324 | O | GLY | B | 566 | 11.610 | -16.099 | 22.429 | 1.00 | 9.77 |
| 10325 | N | MET | B | 567 | 13.466 | -14.839 | 22.591 | 1.00 | 10.05 |
| 10326 | CA | MET | B | 567 | 12.744 | -13.580 | 22.763 | 1.00 | 9.71 |
| 10327 | CB | MET | B | 567 | 13.695 | -12.581 | 23.365 | 1.00 | 8.82 |
| 10328 | CG | MET | B | 567 | 13.935 | -12.860 | 24.847 | 1.00 | 12.08 |
| 10329 | SD | MET | B | 567 | 15.479 | -12.167 | 25.560 | 1.00 | 16.70 |
| 10330 | CE | MET | B | 567 | 16.481 | -13.550 | 25.969 | 1.00 | 12.23 |
| 10331 | C | MET | B | 567 | 12.190 | -12.974 | 21.481 | 1.00 | 9.73 |
| 10332 | O | MET | B | 567 | 12.862 | -12.955 | 20.444 | 1.00 | 10.82 |
| 10333 | N | VAL | B | 568 | 10.961 | -12.483 | 21.534 | 1.00 | 9.13 |
| 10334 | CA | VAL | B | 568 | 10.532 | -11.458 | 20.606 | 1.00 | 7.79 |
| 10335 | CB | VAL | B | 568 | 9.017 | -11.292 | 20.560 | 1.00 | 7.59 |
| 10336 | CG1 | VAL | B | 568 | 8.558 | -9.948 | 19.787 | 1.00 | 7.10 |
| 10337 | CG2 | VAL | B | 568 | 8.367 | -12.489 | 20.013 | 1.00 | 4.61 |
| 10338 | C | VAL | B | 568 | 11.043 | -10.179 | 21.209 | 1.00 | 8.48 |
| 10339 | O | VAL | B | 568 | 10.842 | -9.951 | 22.399 | 1.00 | 9.88 |
| 10340 | N | ILE | B | 569 | 11.672 | -9.332 | 20.408 | 1.00 | 8.09 |
| 10341 | CA | ILE | B | 569 | 11.890 | -7.907 | 20.751 | 1.00 | 8.16 |
| 10342 | CB | ILE | B | 569 | 13.220 | -7.429 | 20.282 | 1.00 | 7.31 |
| 10343 | CG1 | ILE | B | 569 | 14.245 | -8.568 | 20.164 | 1.00 | 9.48 |
| 10344 | CD1 | ILE | B | 569 | 14.313 | -9.567 | 21.412 | 1.00 | 4.27 |

FIGURE 3 (Cont.)

| A | B | C | D | E | F | G | H | I | J |
|---|---|---|---|---|---|---|---|---|---|
| 10345 | CG2 | ILE | B | 569 | 13.724 | -6.509 | 21.278 | 1.00 | 10.24 |
| 10346 | C | ILE | B | 569 | 10.925 | -7.015 | 20.055 | 1.00 | 7.88 |
| 10347 | O | ILE | B | 569 | 10.321 | -7.400 | 19.065 | 1.00 | 7.61 |
| 10348 | N | ALA | B | 570 | 10.772 | -5.795 | 20.539 | 1.00 | 7.94 |
| 10349 | CA | ALA | B | 570 | 10.083 | -4.829 | 19.726 | 1.00 | 8.40 |
| 10350 | CB | ALA | B | 570 | 8.616 | -4.921 | 19.965 | 1.00 | 7.13 |
| 10351 | C | ALA | B | 570 | 10.595 | -3.424 | 19.954 | 1.00 | 8.57 |
| 10352 | O | ALA | B | 570 | 11.208 | -3.192 | 20.976 | 1.00 | 10.15 |
| 10353 | N | LEU | B | 571 | 10.375 | -2.477 | 19.044 | 1.00 | 7.83 |
| 10354 | CA | LEU | B | 571 | 10.810 | -1.124 | 19.342 | 1.00 | 8.22 |
| 10355 | CB | LEU | B | 571 | 12.115 | -0.813 | 18.654 | 1.00 | 7.38 |
| 10356 | CG | LEU | B | 571 | 13.492 | -1.483 | 18.903 | 1.00 | 9.86 |
| 10357 | CD1 | LEU | B | 571 | 13.659 | -2.957 | 18.466 | 1.00 | 2.00 |
| 10358 | CD2 | LEU | B | 571 | 14.594 | -0.586 | 18.111 | 1.00 | 6.51 |
| 10359 | C | LEU | B | 571 | 9.730 | -0.139 | 18.879 | 1.00 | 8.14 |
| 10360 | O | LEU | B | 571 | 9.167 | -0.284 | 17.825 | 1.00 | 9.71 |
| 10361 | N | VAL | B | 572 | 9.401 | 0.841 | 19.683 | 1.00 | 7.91 |
| 10362 | CA | VAL | B | 572 | 8.275 | 1.688 | 19.354 | 1.00 | 8.30 |
| 10363 | CB | VAL | B | 572 | 7.185 | 1.389 | 20.301 | 1.00 | 8.50 |
| 10364 | CG1 | VAL | B | 572 | 5.895 | 2.031 | 19.910 | 1.00 | 7.60 |
| 10365 | CG2 | VAL | B | 572 | 6.999 | -0.221 | 20.399 | 1.00 | 9.15 |
| 10366 | C | VAL | B | 572 | 8.660 | 3.203 | 19.263 | 1.00 | 9.28 |
| 10367 | O | VAL | B | 572 | 9.221 | 3.811 | 20.162 | 1.00 | 7.58 |
| 10368 | N | ASP | B | 573 | 8.373 | 3.774 | 18.119 | 1.00 | 9.98 |
| 10369 | CA | ASP | B | 573 | 8.347 | 5.225 | 18.002 | 1.00 | 12.58 |
| 10370 | CB | ASP | B | 573 | 8.842 | 5.648 | 16.654 | 1.00 | 11.43 |
| 10371 | CG | ASP | B | 573 | 10.316 | 5.422 | 16.475 | 1.00 | 13.56 |
| 10372 | OD1 | ASP | B | 573 | 10.741 | 5.319 | 15.281 | 1.00 | 16.01 |
| 10373 | OD2 | ASP | B | 573 | 11.085 | 5.340 | 17.446 | 1.00 | 15.45 |
| 10374 | C | ASP | B | 573 | 6.942 | 5.744 | 18.195 | 1.00 | 12.13 |
| 10375 | O | ASP | B | 573 | 6.037 | 5.244 | 17.604 | 1.00 | 14.25 |
| 10376 | N | GLY | B | 574 | 6.778 | 6.717 | 19.069 | 1.00 | 12.93 |
| 10377 | CA | GLY | B | 574 | 5.505 | 7.353 | 19.316 | 1.00 | 12.61 |
| 10378 | C | GLY | B | 574 | 5.828 | 8.798 | 19.492 | 1.00 | 12.16 |
| 10379 | O | GLY | B | 574 | 6.703 | 9.276 | 18.806 | 1.00 | 11.95 |
| 10380 | N | ARG | B | 575 | 5.134 | 9.495 | 20.387 | 1.00 | 11.88 |
| 10381 | CA | ARG | B | 575 | 5.171 | 10.964 | 20.426 | 1.00 | 10.87 |
| 10382 | CB | ARG | B | 575 | 4.095 | 11.523 | 21.342 | 1.00 | 9.84 |
| 10383 | CG | ARG | B | 575 | 2.728 | 11.681 | 20.749 | 1.00 | 12.59 |
| 10384 | CD | ARG | B | 575 | 1.606 | 11.707 | 21.753 | 1.00 | 11.09 |
| 10385 | NE | ARG | B | 575 | 1.500 | 10.440 | 22.534 | 1.00 | 16.37 |
| 10386 | CZ | ARG | B | 575 | 0.598 | 10.263 | 23.539 | 1.00 | 17.19 |
| 10387 | NH1 | ARG | B | 575 | -0.219 | 11.231 | 23.902 | 1.00 | 19.57 |
| 10388 | NH2 | ARG | B | 575 | 0.478 | 9.118 | 24.158 | 1.00 | 16.66 |
| 10389 | C | ARG | B | 575 | 6.478 | 11.481 | 20.906 | 1.00 | 9.94 |
| 10390 | O | ARG | B | 575 | 7.105 | 10.871 | 21.748 | 1.00 | 10.11 |
| 10391 | N | GLY | B | 576 | 6.873 | 12.659 | 20.415 | 1.00 | 10.07 |
| 10392 | CA | GLY | B | 576 | 8.217 | 13.194 | 20.647 | 1.00 | 10.51 |
| 10393 | C | GLY | B | 576 | 9.212 | 12.659 | 19.617 | 1.00 | 12.62 |
| 10394 | O | GLY | B | 576 | 10.247 | 13.318 | 19.368 | 1.00 | 11.74 |
| 10395 | N | THR | B | 577 | 8.913 | 11.504 | 19.016 | 1.00 | 12.42 |

FIGURE 3 (Cont.)

| A | B | C | D | E | F | G | H | I | J |
|---|---|---|---|---|---|---|---|---|---|
| 10396 | CA | THR | B | 577 | 9.653 | 10.984 | 17.899 | 1.00 | 13.41 |
| 10397 | CB | THR | B | 577 | 9.314 | 9.495 | 17.765 | 1.00 | 15.26 |
| 10398 | OG1 | THR | B | 577 | 10.518 | 8.788 | 17.557 | 1.00 | 20.60 |
| 10399 | CG2 | THR | B | 577 | 8.609 | 9.110 | 16.574 | 1.00 | 11.82 |
| 10400 | C | THR | B | 577 | 9.547 | 11.739 | 16.598 | 1.00 | 12.60 |
| 10401 | O | THR | B | 577 | 8.591 | 12.335 | 16.313 | 1.00 | 11.57 |
| 10402 | N | ALA | B | 578 | 10.563 | 11.734 | 15.773 | 1.00 | 13.38 |
| 10403 | CA | ALA | B | 578 | 10.607 | 12.717 | 14.637 | 1.00 | 13.58 |
| 10404 | CB | ALA | B | 578 | 11.918 | 13.403 | 14.567 | 1.00 | 12.97 |
| 10405 | C | ALA | B | 578 | 10.284 | 12.089 | 13.290 | 1.00 | 13.68 |
| 10406 | O | ALA | B | 578 | 9.883 | 10.861 | 13.251 | 1.00 | 14.81 |
| 10407 | N | PHE | B | 579 | 10.333 | 12.980 | 12.282 | 1.00 | 13.13 |
| 10408 | CA | PHE | B | 579 | 10.333 | 12.715 | 10.862 | 1.00 | 12.60 |
| 10409 | CB | PHE | B | 579 | 11.350 | 11.610 | 10.562 | 1.00 | 12.74 |
| 10410 | CG | PHE | B | 579 | 12.749 | 11.928 | 11.149 | 1.00 | 11.46 |
| 10411 | CD1 | PHE | B | 579 | 13.372 | 11.048 | 11.963 | 1.00 | 7.45 |
| 10412 | CE1 | PHE | B | 579 | 14.608 | 11.341 | 12.504 | 1.00 | 11.96 |
| 10413 | CZ | PHE | B | 579 | 15.256 | 12.602 | 12.210 | 1.00 | 10.65 |
| 10414 | CE2 | PHE | B | 579 | 14.617 | 13.494 | 11.459 | 1.00 | 9.12 |
| 10415 | CD2 | PHE | B | 579 | 13.344 | 13.185 | 10.943 | 1.00 | 8.49 |
| 10416 | C | PHE | B | 579 | 8.942 | 12.411 | 10.407 | 1.00 | 12.61 |
| 10417 | O | PHE | B | 579 | 8.677 | 11.805 | 9.349 | 1.00 | 12.40 |
| 10418 | N | GLN | B | 580 | 8.015 | 12.834 | 11.235 | 1.00 | 12.70 |
| 10419 | CA | GLN | B | 580 | 6.650 | 12.430 | 11.025 | 1.00 | 10.16 |
| 10420 | CB | GLN | B | 580 | 6.282 | 11.311 | 11.934 | 1.00 | 10.58 |
| 10421 | CG | GLN | B | 580 | 6.695 | 10.007 | 11.447 | 1.00 | 11.57 |
| 10422 | CD | GLN | B | 580 | 5.959 | 8.884 | 12.216 | 1.00 | 11.31 |
| 10423 | OE1 | GLN | B | 580 | 6.541 | 8.150 | 13.107 | 1.00 | 10.14 |
| 10424 | NE2 | GLN | B | 580 | 4.725 | 8.798 | 11.928 | 1.00 | 2.00 |
| 10425 | C | GLN | B | 580 | 5.714 | 13.498 | 11.302 | 1.00 | 9.26 |
| 10426 | O | GLN | B | 580 | 4.564 | 13.165 | 11.444 | 1.00 | 6.90 |
| 10427 | N | GLY | B | 581 | 6.184 | 14.752 | 11.286 | 1.00 | 9.12 |
| 10428 | CA | GLY | B | 581 | 5.302 | 15.880 | 11.553 | 1.00 | 10.90 |
| 10429 | C | GLY | B | 581 | 5.621 | 16.516 | 12.909 | 1.00 | 12.53 |
| 10430 | O | GLY | B | 581 | 6.149 | 15.784 | 13.786 | 1.00 | 10.74 |
| 10431 | N | ASP | B | 582 | 5.280 | 17.832 | 13.058 | 1.00 | 11.03 |
| 10432 | CA | ASP | B | 582 | 5.283 | 18.605 | 14.311 | 1.00 | 9.31 |
| 10433 | CB | ASP | B | 582 | 5.194 | 20.074 | 13.956 | 1.00 | 9.22 |
| 10434 | CG | ASP | B | 582 | 6.521 | 20.617 | 13.333 | 1.00 | 10.78 |
| 10435 | OD1 | ASP | B | 582 | 6.564 | 21.844 | 12.967 | 1.00 | 13.30 |
| 10436 | OD2 | ASP | B | 582 | 7.564 | 19.890 | 13.249 | 1.00 | 2.04 |
| 10437 | C | ASP | B | 582 | 4.196 | 18.241 | 15.418 | 1.00 | 10.90 |
| 10438 | O | ASP | B | 582 | 4.540 | 18.064 | 16.562 | 1.00 | 10.79 |
| 10439 | N | LYS | B | 583 | 2.903 | 18.140 | 15.120 | 1.00 | 8.29 |
| 10440 | CA | LYS | B | 583 | 1.979 | 17.417 | 16.030 | 1.00 | 10.14 |
| 10441 | CB | LYS | B | 583 | 0.754 | 16.931 | 15.261 | 1.00 | 6.72 |
| 10442 | CG | LYS | B | 583 | -0.623 | 16.955 | 16.005 | 1.00 | 14.75 |
| 10443 | CD | LYS | B | 583 | -1.796 | 16.696 | 14.999 | 1.00 | 20.18 |
| 10444 | CE | LYS | B | 583 | -3.200 | 17.349 | 15.339 | 1.00 | 27.82 |
| 10445 | NZ | LYS | B | 583 | -4.172 | 16.300 | 15.793 | 1.00 | 25.78 |
| 10446 | C | LYS | B | 583 | 2.670 | 16.172 | 16.818 | 1.00 | 10.57 |

FIGURE 3 (Cont.)

| A | B | C | D | E | F | G | H | I | J |
|---|---|---|---|---|---|---|---|---|---|
| 10447 | O | LYS | B | 583 | 2.668 | 16.151 | 18.041 | 1.00 | 10.14 |
| 10448 | N | LEU | B | 584 | 3.203 | 15.175 | 16.117 | 1.00 | 9.40 |
| 10449 | CA | LEU | B | 584 | 3.889 | 14.082 | 16.801 | 1.00 | 10.01 |
| 10450 | CB | LEU | B | 584 | 4.055 | 12.886 | 15.869 | 1.00 | 9.35 |
| 10451 | CG | LEU | B | 584 | 4.666 | 11.645 | 16.411 | 1.00 | 10.79 |
| 10452 | CD1 | LEU | B | 584 | 3.620 | 10.802 | 17.010 | 1.00 | 7.81 |
| 10453 | CD2 | LEU | B | 584 | 5.318 | 10.805 | 15.298 | 1.00 | 10.75 |
| 10454 | C | LEU | B | 584 | 5.217 | 14.492 | 17.491 | 1.00 | 10.35 |
| 10455 | O | LEU | B | 584 | 5.455 | 14.139 | 18.626 | 1.00 | 11.21 |
| 10456 | N | LEU | B | 585 | 6.004 | 15.365 | 16.918 | 1.00 | 9.56 |
| 10457 | CA | LEU | B | 585 | 7.308 | 15.743 | 17.502 | 1.00 | 9.12 |
| 10458 | CB | LEU | B | 585 | 8.075 | 16.593 | 16.517 | 1.00 | 9.92 |
| 10459 | CG | LEU | B | 585 | 9.469 | 17.080 | 16.989 | 1.00 | 7.74 |
| 10460 | CD1 | LEU | B | 585 | 10.369 | 15.877 | 17.249 | 1.00 | 2.00 |
| 10461 | CD2 | LEU | B | 585 | 10.092 | 17.934 | 15.901 | 1.00 | 6.84 |
| 10462 | C | LEU | B | 585 | 7.115 | 16.619 | 18.721 | 1.00 | 8.95 |
| 10463 | O | LEU | B | 585 | 7.595 | 16.316 | 19.762 | 1.00 | 9.65 |
| 10464 | N | TYR | B | 586 | 6.406 | 17.709 | 18.586 | 1.00 | 8.57 |
| 10465 | CA | TYR | B | 586 | 6.164 | 18.568 | 19.731 | 1.00 | 9.78 |
| 10466 | CB | TYR | B | 586 | 5.755 | 19.931 | 19.265 | 1.00 | 10.45 |
| 10467 | CG | TYR | B | 586 | 6.832 | 20.523 | 18.362 | 1.00 | 13.10 |
| 10468 | CD1 | TYR | B | 586 | 8.178 | 20.215 | 18.518 | 1.00 | 12.72 |
| 10469 | CE1 | TYR | B | 586 | 9.174 | 20.765 | 17.669 | 1.00 | 16.93 |
| 10470 | CZ | TYR | B | 586 | 8.769 | 21.652 | 16.664 | 1.00 | 16.73 |
| 10471 | OH | TYR | B | 586 | 9.577 | 22.269 | 15.785 | 1.00 | 15.74 |
| 10472 | CE2 | TYR | B | 586 | 7.427 | 21.904 | 16.459 | 1.00 | 20.44 |
| 10473 | CD2 | TYR | B | 586 | 6.462 | 21.328 | 17.332 | 1.00 | 15.91 |
| 10474 | C | TYR | B | 586 | 5.226 | 18.101 | 20.815 | 1.00 | 9.53 |
| 10475 | O | TYR | B | 586 | 5.055 | 18.758 | 21.865 | 1.00 | 10.39 |
| 10476 | N | ALA | B | 587 | 4.732 | 16.889 | 20.677 | 1.00 | 8.44 |
| 10477 | CA | ALA | B | 587 | 3.719 | 16.501 | 21.612 | 1.00 | 7.93 |
| 10478 | CB | ALA | B | 587 | 3.111 | 15.244 | 21.231 | 1.00 | 7.96 |
| 10479 | C | ALA | B | 587 | 4.246 | 16.454 | 23.017 | 1.00 | 7.58 |
| 10480 | O | ALA | B | 587 | 3.510 | 16.720 | 23.925 | 1.00 | 8.64 |
| 10481 | N | VAL | B | 588 | 5.489 | 15.999 | 23.193 | 1.00 | 7.15 |
| 10482 | CA | VAL | B | 588 | 6.108 | 15.863 | 24.493 | 1.00 | 5.68 |
| 10483 | CB | VAL | B | 588 | 7.216 | 14.937 | 24.437 | 1.00 | 6.22 |
| 10484 | CG1 | VAL | B | 588 | 6.806 | 13.624 | 23.920 | 1.00 | 7.67 |
| 10485 | CG2 | VAL | B | 588 | 8.408 | 15.546 | 23.659 | 1.00 | 5.20 |
| 10486 | C | VAL | B | 588 | 6.669 | 17.197 | 25.080 | 1.00 | 6.16 |
| 10487 | O | VAL | B | 588 | 7.168 | 17.244 | 26.217 | 1.00 | 6.54 |
| 10488 | N | TYR | B | 589 | 6.473 | 18.302 | 24.383 | 1.00 | 6.82 |
| 10489 | CA | TYR | B | 589 | 6.974 | 19.589 | 24.869 | 1.00 | 7.83 |
| 10490 | CB | TYR | B | 589 | 6.508 | 20.667 | 23.966 | 1.00 | 6.91 |
| 10491 | CG | TYR | B | 589 | 7.332 | 21.874 | 24.061 | 1.00 | 11.15 |
| 10492 | CD1 | TYR | B | 589 | 6.766 | 23.084 | 23.848 | 1.00 | 14.48 |
| 10493 | CE1 | TYR | B | 589 | 7.448 | 24.182 | 23.905 | 1.00 | 15.67 |
| 10494 | CZ | TYR | B | 589 | 8.774 | 24.149 | 24.126 | 1.00 | 17.85 |
| 10495 | OH | TYR | B | 589 | 9.374 | 25.369 | 24.118 | 1.00 | 19.00 |
| 10496 | CE2 | TYR | B | 589 | 9.443 | 22.956 | 24.310 | 1.00 | 15.18 |
| 10497 | CD2 | TYR | B | 589 | 8.710 | 21.821 | 24.276 | 1.00 | 13.51 |

FIGURE 3 (Cont.)

| A | B | C | D | E | F | G | H | I | J |
|---|---|---|---|---|---|---|---|---|---|
| 10498 | C | TYR | B | 589 | 6.580 | 19.942 | 26.302 | 1.00 | 7.80 |
| 10499 | O | TYR | B | 589 | 5.448 | 20.117 | 26.628 | 1.00 | 5.86 |
| 10500 | N | ARG | B | 590 | 7.541 | 19.974 | 27.197 | 1.00 | 8.70 |
| 10501 | CA | ARG | B | 590 | 7.363 | 20.434 | 28.598 | 1.00 | 9.50 |
| 10502 | CB | ARG | B | 590 | 6.636 | 21.739 | 28.698 | 1.00 | 8.77 |
| 10503 | CG | ARG | B | 590 | 7.239 | 22.738 | 27.846 | 1.00 | 7.15 |
| 10504 | CD | ARG | B | 590 | 6.353 | 23.863 | 27.592 | 1.00 | 8.79 |
| 10505 | NE | ARG | B | 590 | 5.987 | 24.474 | 28.842 | 1.00 | 14.87 |
| 10506 | CZ | ARG | B | 590 | 6.602 | 25.506 | 29.445 | 1.00 | 20.01 |
| 10507 | NH1 | ARG | B | 590 | 7.640 | 26.098 | 28.862 | 1.00 | 19.83 |
| 10508 | NH2 | ARG | B | 590 | 6.130 | 25.972 | 30.635 | 1.00 | 17.14 |
| 10509 | C | ARG | B | 590 | 6.698 | 19.444 | 29.490 | 1.00 | 11.29 |
| 10510 | O | ARG | B | 590 | 6.392 | 19.740 | 30.595 | 1.00 | 11.96 |
| 10511 | N | LYS | B | 591 | 6.700 | 18.220 | 29.026 | 1.00 | 13.30 |
| 10512 | CA | LYS | B | 591 | 5.822 | 17.200 | 29.486 | 1.00 | 12.87 |
| 10513 | CB | LYS | B | 591 | 4.520 | 17.310 | 28.691 | 1.00 | 11.73 |
| 10514 | CG | LYS | B | 591 | 3.309 | 17.592 | 29.546 | 1.00 | 18.97 |
| 10515 | CD | LYS | B | 591 | 2.026 | 16.596 | 29.315 | 1.00 | 26.37 |
| 10516 | CE | LYS | B | 591 | 0.887 | 16.846 | 30.383 | 1.00 | 33.31 |
| 10517 | NZ | LYS | B | 591 | 1.480 | 16.898 | 31.840 | 1.00 | 38.52 |
| 10518 | C | LYS | B | 591 | 6.609 | 15.878 | 29.237 | 1.00 | 13.48 |
| 10519 | O | LYS | B | 591 | 6.036 | 14.859 | 28.975 | 1.00 | 15.20 |
| 10520 | N | LEU | B | 592 | 7.941 | 15.914 | 29.393 | 1.00 | 13.65 |
| 10521 | CA | LEU | B | 592 | 8.824 | 14.756 | 29.146 | 1.00 | 12.31 |
| 10522 | CB | LEU | B | 592 | 10.325 | 15.171 | 29.267 | 1.00 | 10.99 |
| 10523 | CG | LEU | B | 592 | 11.095 | 15.593 | 28.042 | 1.00 | 11.48 |
| 10524 | CD1 | LEU | B | 592 | 10.292 | 16.618 | 27.336 | 1.00 | 2.71 |
| 10525 | CD2 | LEU | B | 592 | 12.585 | 16.072 | 28.261 | 1.00 | 3.90 |
| 10526 | C | LEU | B | 592 | 8.555 | 13.620 | 30.134 | 1.00 | 13.63 |
| 10527 | O | LEU | B | 592 | 8.189 | 13.806 | 31.264 | 1.00 | 15.69 |
| 10528 | N | GLY | B | 593 | 8.791 | 12.415 | 29.659 | 1.00 | 14.95 |
| 10529 | CA | GLY | B | 593 | 8.578 | 11.180 | 30.392 | 1.00 | 14.29 |
| 10530 | C | GLY | B | 593 | 7.180 | 10.899 | 30.736 | 1.00 | 14.60 |
| 10531 | O | GLY | B | 593 | 6.999 | 10.284 | 31.790 | 1.00 | 19.94 |
| 10532 | N | VAL | B | 594 | 6.199 | 11.403 | 29.963 | 1.00 | 11.97 |
| 10533 | CA | VAL | B | 594 | 4.823 | 11.100 | 30.171 | 1.00 | 10.46 |
| 10534 | CB | VAL | B | 594 | 3.915 | 12.348 | 30.233 | 1.00 | 9.17 |
| 10535 | CG1 | VAL | B | 594 | 2.489 | 11.950 | 30.476 | 1.00 | 8.09 |
| 10536 | CG2 | VAL | B | 594 | 4.284 | 13.325 | 31.298 | 1.00 | 5.96 |
| 10537 | C | VAL | B | 594 | 4.359 | 10.252 | 29.002 | 1.00 | 12.74 |
| 10538 | O | VAL | B | 594 | 4.075 | 9.058 | 29.143 | 1.00 | 13.27 |
| 10539 | N | TYR | B | 595 | 4.264 | 10.844 | 27.814 | 1.00 | 14.30 |
| 10540 | CA | TYR | B | 595 | 3.707 | 10.092 | 26.647 | 1.00 | 13.05 |
| 10541 | CB | TYR | B | 595 | 3.248 | 11.010 | 25.552 | 1.00 | 12.31 |
| 10542 | CG | TYR | B | 595 | 2.299 | 12.178 | 25.923 | 1.00 | 12.58 |
| 10543 | CD1 | TYR | B | 595 | 2.397 | 13.377 | 25.282 | 1.00 | 15.30 |
| 10544 | CE1 | TYR | B | 595 | 1.521 | 14.456 | 25.586 | 1.00 | 23.64 |
| 10545 | CZ | TYR | B | 595 | 0.479 | 14.320 | 26.501 | 1.00 | 23.57 |
| 10546 | OH | TYR | B | 595 | -0.307 | 15.418 | 26.754 | 1.00 | 24.78 |
| 10547 | CE2 | TYR | B | 595 | 0.323 | 13.117 | 27.144 | 1.00 | 19.30 |
| 10548 | CD2 | TYR | B | 595 | 1.260 | 12.039 | 26.837 | 1.00 | 19.49 |

FIGURE 3 (Cont.)

| A | B | C | D | E | F | G | H | I | J |
|---|---|---|---|---|---|---|---|---|---|
| 10549 | C | TYR | B | 595 | 4.740 | 9.094 | 26.098 | 1.00 | 13.07 |
| 10550 | O | TYR | B | 595 | 4.389 | 8.161 | 25.487 | 1.00 | 13.34 |
| 10551 | N | GLU | B | 596 | 6.030 | 9.256 | 26.365 | 1.00 | 11.42 |
| 10552 | CA | GLU | B | 596 | 6.983 | 8.258 | 25.975 | 1.00 | 11.91 |
| 10553 | CB | GLU | B | 596 | 8.306 | 8.689 | 26.437 | 1.00 | 9.81 |
| 10554 | CG | GLU | B | 596 | 8.770 | 9.947 | 25.691 | 1.00 | 13.70 |
| 10555 | CD | GLU | B | 596 | 8.624 | 11.194 | 26.538 | 1.00 | 14.59 |
| 10556 | OE1 | GLU | B | 596 | 9.637 | 11.831 | 26.856 | 1.00 | 14.81 |
| 10557 | OE2 | GLU | B | 596 | 7.481 | 11.519 | 26.904 | 1.00 | 12.63 |
| 10558 | C | GLU | B | 596 | 6.632 | 6.935 | 26.679 | 1.00 | 12.84 |
| 10559 | O | GLU | B | 596 | 6.832 | 5.819 | 26.171 | 1.00 | 11.46 |
| 10560 | N | VAL | B | 597 | 6.181 | 7.088 | 27.900 | 1.00 | 12.73 |
| 10561 | CA | VAL | B | 597 | 5.875 | 5.952 | 28.687 | 1.00 | 12.65 |
| 10562 | CB | VAL | B | 597 | 5.776 | 6.374 | 30.198 | 1.00 | 14.28 |
| 10563 | CG1 | VAL | B | 597 | 5.508 | 5.199 | 31.098 | 1.00 | 11.53 |
| 10564 | CG2 | VAL | B | 597 | 7.085 | 7.083 | 30.656 | 1.00 | 10.48 |
| 10565 | C | VAL | B | 597 | 4.576 | 5.351 | 28.127 | 1.00 | 14.15 |
| 10566 | O | VAL | B | 597 | 4.585 | 4.153 | 27.682 | 1.00 | 14.31 |
| 10567 | N | GLU | B | 598 | 3.548 | 6.227 | 28.030 | 1.00 | 13.36 |
| 10568 | CA | GLU | B | 598 | 2.173 | 5.876 | 27.649 | 1.00 | 13.13 |
| 10569 | CB | GLU | B | 598 | 1.268 | 7.105 | 27.442 | 1.00 | 13.31 |
| 10570 | CG | GLU | B | 598 | 0.413 | 7.596 | 28.591 | 1.00 | 18.92 |
| 10571 | CD | GLU | B | 598 | -0.386 | 8.896 | 28.247 | 1.00 | 26.36 |
| 10572 | OE1 | GLU | B | 598 | -1.303 | 8.896 | 27.333 | 1.00 | 21.24 |
| 10573 | OE2 | GLU | B | 598 | -0.147 | 9.946 | 28.946 | 1.00 | 30.42 |
| 10574 | C | GLU | B | 598 | 2.218 | 5.131 | 26.331 | 1.00 | 12.35 |
| 10575 | O | GLU | B | 598 | 1.521 | 4.140 | 26.127 | 1.00 | 10.72 |
| 10576 | N | ASP | B | 599 | 3.018 | 5.620 | 25.400 | 1.00 | 9.78 |
| 10577 | CA | ASP | B | 599 | 3.014 | 5.011 | 24.047 | 1.00 | 9.16 |
| 10578 | CB | ASP | B | 599 | 3.726 | 5.945 | 23.006 | 1.00 | 9.27 |
| 10579 | CG | ASP | B | 599 | 2.974 | 7.269 | 22.719 | 1.00 | 8.90 |
| 10580 | OD1 | ASP | B | 599 | 1.816 | 7.435 | 23.066 | 1.00 | 4.75 |
| 10581 | OD2 | ASP | B | 599 | 3.462 | 8.212 | 22.115 | 1.00 | 12.85 |
| 10582 | C | ASP | B | 599 | 3.752 | 3.678 | 24.084 | 1.00 | 8.12 |
| 10583 | O | ASP | B | 599 | 3.565 | 2.873 | 23.194 | 1.00 | 8.20 |
| 10584 | N | GLN | B | 600 | 4.634 | 3.455 | 25.053 | 1.00 | 7.13 |
| 10585 | CA | GLN | B | 600 | 5.308 | 2.195 | 25.079 | 1.00 | 7.98 |
| 10586 | CB | GLN | B | 600 | 6.624 | 2.219 | 25.828 | 1.00 | 7.21 |
| 10587 | CG | GLN | B | 600 | 7.717 | 2.950 | 25.142 | 1.00 | 7.40 |
| 10588 | CD | GLN | B | 600 | 8.339 | 2.356 | 23.910 | 1.00 | 10.14 |
| 10589 | OE1 | GLN | B | 600 | 8.550 | 3.057 | 22.949 | 1.00 | 16.33 |
| 10590 | NE2 | GLN | B | 600 | 8.750 | 1.166 | 23.976 | 1.00 | 10.65 |
| 10591 | C | GLN | B | 600 | 4.340 | 1.105 | 25.654 | 1.00 | 9.30 |
| 10592 | O | GLN | B | 600 | 4.357 | -0.010 | 25.117 | 1.00 | 10.26 |
| 10593 | N | ILE | B | 601 | 3.500 | 1.458 | 26.664 | 1.00 | 9.33 |
| 10594 | CA | ILE | B | 601 | 2.541 | 0.532 | 27.324 | 1.00 | 9.82 |
| 10595 | CB | ILE | B | 601 | 1.800 | 1.178 | 28.586 | 1.00 | 9.25 |
| 10596 | CG1 | ILE | B | 601 | 2.621 | 1.087 | 29.875 | 1.00 | 9.85 |
| 10597 | CD1 | ILE | B | 601 | 3.642 | 2.269 | 30.079 | 1.00 | 15.35 |
| 10598 | CG2 | ILE | B | 601 | 0.466 | 0.544 | 28.822 | 1.00 | 2.66 |
| 10599 | C | ILE | B | 601 | 1.568 | 0.172 | 26.243 | 1.00 | 10.10 |

FIGURE 3 (Cont.)

| A | B | C | D | E | F | G | H | I | J |
|---|---|---|---|---|---|---|---|---|---|
| 10600 | O | ILE | B | 601 | 1.358 | -0.993 | 25.896 | 1.00 | 12.83 |
| 10601 | N | THR | B | 602 | 1.038 | 1.225 | 25.655 | 1.00 | 11.49 |
| 10602 | CA | THR | B | 602 | 0.115 | 1.094 | 24.530 | 1.00 | 12.78 |
| 10603 | CB | THR | B | 602 | -0.059 | 2.395 | 23.855 | 1.00 | 12.90 |
| 10604 | OG1 | THR | B | 602 | -0.784 | 3.240 | 24.738 | 1.00 | 14.89 |
| 10605 | CG2 | THR | B | 602 | -0.988 | 2.246 | 22.677 | 1.00 | 11.85 |
| 10606 | C | THR | B | 602 | 0.569 | 0.057 | 23.559 | 1.00 | 12.08 |
| 10607 | O | THR | B | 602 | -0.149 | -0.838 | 23.252 | 1.00 | 11.08 |
| 10608 | N | ALA | B | 603 | 1.794 | 0.194 | 23.091 | 1.00 | 12.78 |
| 10609 | CA | ALA | B | 603 | 2.250 | -0.767 | 22.081 | 1.00 | 12.05 |
| 10610 | CB | ALA | B | 603 | 3.667 | -0.480 | 21.594 | 1.00 | 11.35 |
| 10611 | C | ALA | B | 603 | 2.185 | -2.092 | 22.704 | 1.00 | 11.00 |
| 10612 | O | ALA | B | 603 | 1.603 | -2.952 | 22.103 | 1.00 | 11.98 |
| 10613 | N | VAL | B | 604 | 2.772 | -2.247 | 23.904 | 1.00 | 9.51 |
| 10614 | CA | VAL | B | 604 | 2.924 | -3.557 | 24.520 | 1.00 | 8.77 |
| 10615 | CB | VAL | B | 604 | 3.635 | -3.591 | 25.816 | 1.00 | 8.63 |
| 10616 | CG1 | VAL | B | 604 | 3.709 | -5.071 | 26.268 | 1.00 | 9.06 |
| 10617 | CG2 | VAL | B | 604 | 5.111 | -3.056 | 25.739 | 1.00 | 6.60 |
| 10618 | C | VAL | B | 604 | 1.549 | -4.156 | 24.726 | 1.00 | 10.56 |
| 10619 | O | VAL | B | 604 | 1.421 | -5.336 | 24.499 | 1.00 | 10.54 |
| 10620 | N | ARG | B | 605 | 0.480 | -3.370 | 24.989 | 1.00 | 11.14 |
| 10621 | CA | ARG | B | 605 | -0.882 | -4.016 | 25.185 | 1.00 | 11.66 |
| 10622 | CB | ARG | B | 605 | -2.004 | -3.077 | 25.756 | 1.00 | 11.10 |
| 10623 | CG | ARG | B | 605 | -1.686 | -2.500 | 27.134 | 1.00 | 10.76 |
| 10624 | CD | ARG | B | 605 | -2.610 | -1.416 | 27.667 | 1.00 | 11.35 |
| 10625 | NE | ARG | B | 605 | -2.253 | -0.999 | 29.040 | 1.00 | 5.30 |
| 10626 | CZ | ARG | B | 605 | -2.354 | -1.784 | 30.098 | 1.00 | 8.90 |
| 10627 | NH1 | ARG | B | 605 | -2.035 | -1.347 | 31.284 | 1.00 | 5.60 |
| 10628 | NH2 | ARG | B | 605 | -2.842 | -3.034 | 30.015 | 1.00 | 12.49 |
| 10629 | C | ARG | B | 605 | -1.312 | -4.617 | 23.876 | 1.00 | 12.26 |
| 10630 | O | ARG | B | 605 | -1.778 | -5.802 | 23.819 | 1.00 | 13.66 |
| 10631 | N | LYS | B | 606 | -1.164 | -3.804 | 22.827 | 1.00 | 11.30 |
| 10632 | CA | LYS | B | 606 | -1.533 | -4.246 | 21.509 | 1.00 | 11.10 |
| 10633 | CB | LYS | B | 606 | -1.401 | -3.127 | 20.537 | 1.00 | 10.37 |
| 10634 | CG | LYS | B | 606 | -2.758 | -2.648 | 20.033 | 1.00 | 15.81 |
| 10635 | CD | LYS | B | 606 | -3.364 | -1.405 | 20.833 | 1.00 | 16.49 |
| 10636 | CE | LYS | B | 606 | -4.860 | -1.721 | 21.309 | 1.00 | 14.02 |
| 10637 | NZ | LYS | B | 606 | -5.947 | -1.009 | 20.494 | 1.00 | 8.48 |
| 10638 | C | LYS | B | 606 | -0.680 | -5.445 | 21.125 | 1.00 | 10.59 |
| 10639 | O | LYS | B | 606 | -1.183 | -6.452 | 20.634 | 1.00 | 10.51 |
| 10640 | N | PHE | B | 607 | 0.621 | -5.392 | 21.401 | 1.00 | 9.78 |
| 10641 | CA | PHE | B | 607 | 1.404 | -6.617 | 21.197 | 1.00 | 9.01 |
| 10642 | CB | PHE | B | 607 | 2.802 | -6.451 | 21.656 | 1.00 | 8.28 |
| 10643 | CG | PHE | B | 607 | 3.597 | -5.476 | 20.888 | 1.00 | 4.08 |
| 10644 | CD1 | PHE | B | 607 | 3.443 | -5.327 | 19.543 | 1.00 | 4.60 |
| 10645 | CE1 | PHE | B | 607 | 4.159 | -4.459 | 18.874 | 1.00 | 2.00 |
| 10646 | CZ | PHE | B | 607 | 5.112 | -3.711 | 19.561 | 1.00 | 2.00 |
| 10647 | CE2 | PHE | B | 607 | 5.280 | -3.867 | 20.856 | 1.00 | 2.00 |
| 10648 | CD2 | PHE | B | 607 | 4.523 | -4.722 | 21.528 | 1.00 | 3.66 |
| 10649 | C | PHE | B | 607 | 0.871 | -7.874 | 21.928 | 1.00 | 10.65 |
| 10650 | O | PHE | B | 607 | 0.965 | -8.941 | 21.379 | 1.00 | 10.93 |

FIGURE 3 (Cont.)

| A | B | C | D | E | F | G | H | I | J |
|---|---|---|---|---|---|---|---|---|---|
| 10651 | N | ILE | B | 608 | 0.373 | -7.776 | 23.166 | 1.00 | 11.75 |
| 10652 | CA | ILE | B | 608 | 0.018 | -8.977 | 23.868 | 1.00 | 12.28 |
| 10653 | CB | ILE | B | 608 | 0.012 | -8.813 | 25.411 | 1.00 | 12.67 |
| 10654 | CG1 | ILE | B | 608 | -1.382 | -8.480 | 25.931 | 1.00 | 12.03 |
| 10655 | CD1 | ILE | B | 608 | -1.391 | -8.363 | 27.470 | 1.00 | 11.29 |
| 10656 | CG2 | ILE | B | 608 | 1.204 | -7.804 | 26.036 | 1.00 | 10.76 |
| 10657 | C | ILE | B | 608 | -1.336 | -9.459 | 23.293 | 1.00 | 14.04 |
| 10658 | O | ILE | B | 608 | -1.558 | -10.653 | 23.162 | 1.00 | 13.01 |
| 10659 | N | GLU | B | 609 | -2.187 | -8.491 | 22.929 | 1.00 | 15.61 |
| 10660 | CA | GLU | B | 609 | -3.438 | -8.672 | 22.199 | 1.00 | 17.72 |
| 10661 | CB | GLU | B | 609 | -4.166 | -7.293 | 22.173 | 1.00 | 18.11 |
| 10662 | CG | GLU | B | 609 | -5.633 | -7.230 | 21.696 | 1.00 | 25.08 |
| 10663 | CD | GLU | B | 609 | -6.347 | -5.845 | 21.914 | 1.00 | 31.50 |
| 10664 | OE1 | GLU | B | 609 | -6.967 | -5.697 | 23.018 | 1.00 | 33.75 |
| 10665 | OE2 | GLU | B | 609 | -6.341 | -4.916 | 21.004 | 1.00 | 30.69 |
| 10666 | C | GLU | B | 609 | -3.204 | -9.168 | 20.751 | 1.00 | 17.60 |
| 10667 | O | GLU | B | 609 | -4.033 | -8.986 | 19.921 | 1.00 | 18.01 |
| 10668 | N | MET | B | 610 | -2.059 | -9.741 | 20.429 | 1.00 | 17.11 |
| 10669 | CA | MET | B | 610 | -1.871 | -10.349 | 19.130 | 1.00 | 16.66 |
| 10670 | CB | MET | B | 610 | -0.553 | -9.897 | 18.505 | 1.00 | 16.20 |
| 10671 | CG | MET | B | 610 | -0.714 | -8.619 | 17.733 | 1.00 | 15.47 |
| 10672 | SD | MET | B | 610 | 0.785 | -7.804 | 17.296 | 1.00 | 15.64 |
| 10673 | CE | MET | B | 610 | 0.169 | -6.194 | 17.200 | 1.00 | 13.61 |
| 10674 | C | MET | B | 610 | -1.855 | -11.861 | 19.268 | 1.00 | 17.28 |
| 10675 | O | MET | B | 610 | -1.611 | -12.568 | 18.296 | 1.00 | 17.78 |
| 10676 | N | GLY | B | 611 | -2.091 | -12.352 | 20.482 | 1.00 | 17.10 |
| 10677 | CA | GLY | B | 611 | -1.984 | -13.775 | 20.789 | 1.00 | 16.59 |
| 10678 | C | GLY | B | 611 | -0.631 | -14.410 | 21.093 | 1.00 | 16.05 |
| 10679 | O | GLY | B | 611 | -0.648 | -15.483 | 21.714 | 1.00 | 15.86 |
| 10680 | N | PHE | B | 612 | 0.507 | -13.811 | 20.697 | 1.00 | 15.70 |
| 10681 | CA | PHE | B | 612 | 1.802 | -14.549 | 20.791 | 1.00 | 15.06 |
| 10682 | CB | PHE | B | 612 | 2.509 | -14.678 | 19.418 | 1.00 | 14.82 |
| 10683 | CG | PHE | B | 612 | 2.789 | -13.366 | 18.717 | 1.00 | 15.56 |
| 10684 | CD1 | PHE | B | 612 | 2.065 | -12.994 | 17.614 | 1.00 | 15.22 |
| 10685 | CE1 | PHE | B | 612 | 2.319 | -11.790 | 16.984 | 1.00 | 17.61 |
| 10686 | CZ | PHE | B | 612 | 3.346 | -10.979 | 17.425 | 1.00 | 19.58 |
| 10687 | CE2 | PHE | B | 612 | 4.088 | -11.360 | 18.511 | 1.00 | 18.15 |
| 10688 | CD2 | PHE | B | 612 | 3.807 | -12.522 | 19.158 | 1.00 | 15.27 |
| 10689 | C | PHE | B | 612 | 2.834 | -14.132 | 21.850 | 1.00 | 14.88 |
| 10690 | O | PHE | B | 612 | 3.929 | -14.714 | 21.928 | 1.00 | 15.06 |
| 10691 | N | ILE | B | 613 | 2.518 | -13.107 | 22.636 | 1.00 | 14.16 |
| 10692 | CA | ILE | B | 613 | 3.356 | -12.694 | 23.785 | 1.00 | 12.26 |
| 10693 | CB | ILE | B | 613 | 3.137 | -11.250 | 24.090 | 1.00 | 11.04 |
| 10694 | CG1 | ILE | B | 613 | 3.364 | -10.451 | 22.798 | 1.00 | 12.26 |
| 10695 | CD1 | ILE | B | 613 | 4.749 | -10.760 | 22.102 | 1.00 | 10.21 |
| 10696 | CG2 | ILE | B | 613 | 4.150 | -10.725 | 25.153 | 1.00 | 11.05 |
| 10697 | C | ILE | B | 613 | 2.975 | -13.533 | 24.973 | 1.00 | 12.36 |
| 10698 | O | ILE | B | 613 | 1.859 | -14.058 | 25.060 | 1.00 | 13.82 |
| 10699 | N | ASP | B | 614 | 3.905 | -13.695 | 25.869 | 1.00 | 11.81 |
| 10700 | CA | ASP | B | 614 | 3.620 | -14.289 | 27.133 | 1.00 | 12.55 |
| 10701 | CB | ASP | B | 614 | 4.778 | -15.168 | 27.540 | 1.00 | 11.41 |

FIGURE 3 (Cont.)

| A | B | C | D | E | F | G | H | I | J |
|---|---|---|---|---|---|---|---|---|---|
| 10702 | CG  | ASP | B | 614 |  4.642 | -15.637 | 28.939 | 1.00 | 11.20 |
| 10703 | OD1 | ASP | B | 614 |  3.656 | -15.217 | 29.575 | 1.00 | 11.88 |
| 10704 | OD2 | ASP | B | 614 |  5.465 | -16.388 | 29.495 | 1.00 |  5.58 |
| 10705 | C   | ASP | B | 614 |  3.413 | -13.139 | 28.099 | 1.00 | 13.69 |
| 10706 | O   | ASP | B | 614 |  4.389 | -12.432 | 28.446 | 1.00 | 14.87 |
| 10707 | N   | GLU | B | 615 |  2.171 | -12.877 | 28.519 | 1.00 | 15.49 |
| 10708 | CA  | GLU | B | 615 |  1.904 | -11.640 | 29.333 | 1.00 | 16.56 |
| 10709 | CB  | GLU | B | 615 |  0.447 | -11.579 | 29.807 | 1.00 | 16.15 |
| 10710 | CG  | GLU | B | 615 | -0.585 | -11.867 | 28.741 | 1.00 | 18.54 |
| 10711 | CD  | GLU | B | 615 | -1.950 | -11.309 | 29.115 | 1.00 | 20.23 |
| 10712 | OE1 | GLU | B | 615 | -2.981 | -12.000 | 28.803 | 1.00 | 21.40 |
| 10713 | OE2 | GLU | B | 615 | -1.964 | -10.191 | 29.733 | 1.00 | 16.72 |
| 10714 | C   | GLU | B | 615 |  2.860 | -11.454 | 30.566 | 1.00 | 16.82 |
| 10715 | O   | GLU | B | 615 |  3.164 | -10.319 | 31.030 | 1.00 | 17.82 |
| 10716 | N   | LYS | B | 616 |  3.325 | -12.603 | 31.048 | 1.00 | 15.75 |
| 10717 | CA  | LYS | B | 616 |  4.082 | -12.679 | 32.246 | 1.00 | 15.89 |
| 10718 | CB  | LYS | B | 616 |  3.681 | -13.910 | 32.967 | 1.00 | 15.75 |
| 10719 | CG  | LYS | B | 616 |  2.253 | -13.937 | 33.307 | 1.00 | 16.87 |
| 10720 | CD  | LYS | B | 616 |  1.944 | -15.312 | 34.011 | 1.00 | 24.20 |
| 10721 | CE  | LYS | B | 616 |  2.701 | -16.515 | 33.383 | 1.00 | 25.48 |
| 10722 | NZ  | LYS | B | 616 |  2.706 | -16.461 | 31.837 | 1.00 | 26.50 |
| 10723 | C   | LYS | B | 616 |  5.602 | -12.721 | 32.048 | 1.00 | 15.68 |
| 10724 | O   | LYS | B | 616 |  6.357 | -13.009 | 33.029 | 1.00 | 15.85 |
| 10725 | N   | ARG | B | 617 |  6.059 | -12.401 | 30.843 | 1.00 | 13.31 |
| 10726 | CA  | ARG | B | 617 |  7.465 | -12.490 | 30.582 | 1.00 | 12.09 |
| 10727 | CB  | ARG | B | 617 |  7.809 | -13.889 | 30.020 | 1.00 | 11.14 |
| 10728 | CG  | ARG | B | 617 |  9.031 | -14.645 | 30.758 | 1.00 |  8.87 |
| 10729 | CD  | ARG | B | 617 |  8.825 | -16.132 | 31.120 | 1.00 |  6.84 |
| 10730 | NE  | ARG | B | 617 |  8.044 | -16.788 | 30.091 | 1.00 |  4.48 |
| 10731 | CZ  | ARG | B | 617 |  8.494 | -17.241 | 28.917 | 1.00 |  7.72 |
| 10732 | NH1 | ARG | B | 617 |  7.618 | -17.731 | 28.057 | 1.00 |  8.81 |
| 10733 | NH2 | ARG | B | 617 |  9.775 | -17.216 | 28.577 | 1.00 |  7.92 |
| 10734 | C   | ARG | B | 617 |  7.821 | -11.347 | 29.676 | 1.00 | 11.38 |
| 10735 | O   | ARG | B | 617 |  8.154 | -11.524 | 28.544 | 1.00 | 12.60 |
| 10736 | N   | ILE | B | 618 |  7.701 | -10.134 | 30.163 | 1.00 | 10.66 |
| 10737 | CA  | ILE | B | 618 |  8.025 |  -9.005 | 29.311 | 1.00 |  9.93 |
| 10738 | CB  | ILE | B | 618 |  6.841 |  -8.112 | 29.122 | 1.00 | 10.11 |
| 10739 | CG1 | ILE | B | 618 |  5.727 |  -8.858 | 28.423 | 1.00 |  7.73 |
| 10740 | CD1 | ILE | B | 618 |  4.558 |  -8.044 | 28.257 | 1.00 |  7.42 |
| 10741 | CG2 | ILE | B | 618 |  7.257 |  -6.858 | 28.358 | 1.00 |  9.65 |
| 10742 | C   | ILE | B | 618 |  8.956 |  -8.233 | 30.033 | 1.00 |  9.95 |
| 10743 | O   | ILE | B | 618 |  8.600 |  -7.823 | 31.111 | 1.00 | 11.55 |
| 10744 | N   | ALA | B | 619 | 10.137 |  -8.024 | 29.481 | 1.00 |  9.59 |
| 10745 | CA  | ALA | B | 619 | 11.061 |  -6.947 | 29.954 | 1.00 | 10.14 |
| 10746 | CB  | ALA | B | 619 | 12.537 |  -7.409 | 29.896 | 1.00 |  9.33 |
| 10747 | C   | ALA | B | 619 | 10.966 |  -5.728 | 29.106 | 1.00 |  9.36 |
| 10748 | O   | ALA | B | 619 | 10.442 |  -5.814 | 28.013 | 1.00 |  9.41 |
| 10749 | N   | ILE | B | 620 | 11.622 |  -4.653 | 29.566 | 1.00 | 10.47 |
| 10750 | CA  | ILE | B | 620 | 11.976 |  -3.444 | 28.716 | 1.00 |  9.62 |
| 10751 | CB  | ILE | B | 620 | 11.034 |  -2.366 | 29.003 | 1.00 |  8.56 |
| 10752 | CG1 | ILE | B | 620 | 11.506 |  -1.005 | 28.483 | 1.00 | 10.25 |

FIGURE 3 (Cont.)

| A | B | C | D | E | F | G | H | I | J |
|---|---|---|---|---|---|---|---|---|---|
| 10753 | CD1 | ILE | B | 620 | 10.237 | -0.139 | 28.039 | 1.00 | 7.15 |
| 10754 | CG2 | ILE | B | 620 | 10.790 | -2.248 | 30.460 | 1.00 | 8.42 |
| 10755 | C | ILE | B | 620 | 13.388 | -3.000 | 29.081 | 1.00 | 11.06 |
| 10756 | O | ILE | B | 620 | 13.789 | -3.187 | 30.201 | 1.00 | 12.56 |
| 10757 | N | TRP | B | 621 | 14.201 | -2.493 | 28.164 | 1.00 | 11.15 |
| 10758 | CA | TRP | B | 621 | 15.492 | -1.996 | 28.503 | 1.00 | 10.55 |
| 10759 | CB | TRP | B | 621 | 16.492 | -3.086 | 28.321 | 1.00 | 10.14 |
| 10760 | CG | TRP | B | 621 | 17.230 | -3.004 | 27.001 | 1.00 | 14.79 |
| 10761 | CD1 | TRP | B | 621 | 16.807 | -3.506 | 25.828 | 1.00 | 15.71 |
| 10762 | NE1 | TRP | B | 621 | 17.713 | -3.218 | 24.846 | 1.00 | 16.40 |
| 10763 | CE2 | TRP | B | 621 | 18.751 | -2.513 | 25.364 | 1.00 | 19.14 |
| 10764 | CD2 | TRP | B | 621 | 18.489 | -2.352 | 26.722 | 1.00 | 18.02 |
| 10765 | CE3 | TRP | B | 621 | 19.430 | -1.683 | 27.493 | 1.00 | 17.98 |
| 10766 | CZ3 | TRP | B | 621 | 20.590 | -1.228 | 26.882 | 1.00 | 18.43 |
| 10767 | CH2 | TRP | B | 621 | 20.817 | -1.401 | 25.526 | 1.00 | 17.19 |
| 10768 | CZ2 | TRP | B | 621 | 19.922 | -2.039 | 24.749 | 1.00 | 16.52 |
| 10769 | C | TRP | B | 621 | 15.901 | -0.777 | 27.655 | 1.00 | 11.68 |
| 10770 | O | TRP | B | 621 | 15.608 | -0.566 | 26.480 | 1.00 | 11.43 |
| 10771 | N | GLY | B | 622 | 16.652 | 0.056 | 28.262 | 1.00 | 12.95 |
| 10772 | CA | GLY | B | 622 | 16.951 | 1.293 | 27.601 | 1.00 | 13.82 |
| 10773 | C | GLY | B | 622 | 18.143 | 1.944 | 28.263 | 1.00 | 14.62 |
| 10774 | O | GLY | B | 622 | 18.248 | 1.923 | 29.459 | 1.00 | 14.93 |
| 10775 | N | TRP | B | 623 | 18.969 | 2.509 | 27.409 | 1.00 | 15.05 |
| 10776 | CA | TRP | B | 623 | 20.103 | 3.385 | 27.738 | 1.00 | 16.81 |
| 10777 | CB | TRP | B | 623 | 21.273 | 2.820 | 26.954 | 1.00 | 16.44 |
| 10778 | CG | TRP | B | 623 | 22.644 | 3.381 | 26.984 | 1.00 | 22.13 |
| 10779 | CD1 | TRP | B | 623 | 23.095 | 4.656 | 27.243 | 1.00 | 22.85 |
| 10780 | NE1 | TRP | B | 623 | 24.460 | 4.692 | 27.112 | 1.00 | 22.99 |
| 10781 | CE2 | TRP | B | 623 | 24.917 | 3.438 | 26.744 | 1.00 | 28.38 |
| 10782 | CD2 | TRP | B | 623 | 23.800 | 2.613 | 26.607 | 1.00 | 27.95 |
| 10783 | CE3 | TRP | B | 623 | 23.993 | 1.271 | 26.140 | 1.00 | 27.02 |
| 10784 | CZ3 | TRP | B | 623 | 25.266 | 0.812 | 25.843 | 1.00 | 27.82 |
| 10785 | CH2 | TRP | B | 623 | 26.365 | 1.634 | 25.970 | 1.00 | 27.64 |
| 10786 | CZ2 | TRP | B | 623 | 26.241 | 2.959 | 26.389 | 1.00 | 31.72 |
| 10787 | C | TRP | B | 623 | 19.868 | 4.879 | 27.437 | 1.00 | 13.87 |
| 10788 | O | TRP | B | 623 | 19.304 | 5.228 | 26.466 | 1.00 | 14.01 |
| 10789 | N | SER | B | 624 | 20.356 | 5.715 | 28.332 | 1.00 | 15.08 |
| 10790 | CA | SER | B | 624 | 20.324 | 7.228 | 28.267 | 1.00 | 14.65 |
| 10791 | CB | SER | B | 624 | 21.118 | 7.824 | 27.088 | 1.00 | 13.68 |
| 10792 | OG | SER | B | 624 | 21.297 | 9.207 | 27.238 | 1.00 | 16.96 |
| 10793 | C | SER | B | 624 | 18.901 | 7.767 | 28.385 | 1.00 | 12.76 |
| 10794 | O | SER | B | 624 | 18.336 | 7.692 | 29.411 | 1.00 | 13.72 |
| 10795 | N | TYR | B | 625 | 18.303 | 8.326 | 27.386 | 1.00 | 12.50 |
| 10796 | CA | TYR | B | 625 | 16.881 | 8.710 | 27.573 | 1.00 | 11.35 |
| 10797 | CB | TYR | B | 625 | 16.429 | 9.471 | 26.363 | 1.00 | 9.59 |
| 10798 | CG | TYR | B | 625 | 15.260 | 10.250 | 26.618 | 1.00 | 8.92 |
| 10799 | CD1 | TYR | B | 625 | 15.330 | 11.598 | 26.713 | 1.00 | 7.68 |
| 10800 | CE1 | TYR | B | 625 | 14.180 | 12.334 | 26.943 | 1.00 | 2.00 |
| 10801 | CZ | TYR | B | 625 | 13.004 | 11.692 | 27.035 | 1.00 | 5.37 |
| 10802 | OH | TYR | B | 625 | 11.840 | 12.359 | 27.343 | 1.00 | 9.55 |
| 10803 | CE2 | TYR | B | 625 | 12.965 | 10.355 | 26.952 | 1.00 | 8.02 |

FIGURE 3 (Cont.)

| A | B | C | D | E | F | G | H | I | J |
|---|---|---|---|---|---|---|---|---|---|
| 10804 | CD2 | TYR | B | 625 | 14.053 | 9.653 | 26.733 | 1.00 | 2.46 |
| 10805 | C | TYR | B | 625 | 16.152 | 7.393 | 27.682 | 1.00 | 10.71 |
| 10806 | O | TYR | B | 625 | 15.130 | 7.225 | 28.250 | 1.00 | 11.76 |
| 10807 | N | GLY | B | 626 | 16.743 | 6.422 | 27.117 | 1.00 | 12.51 |
| 10808 | CA | GLY | B | 626 | 16.144 | 5.125 | 27.130 | 1.00 | 13.93 |
| 10809 | C | GLY | B | 626 | 16.137 | 4.552 | 28.481 | 1.00 | 14.41 |
| 10810 | O | GLY | B | 626 | 15.285 | 3.715 | 28.710 | 1.00 | 13.46 |
| 10811 | N | GLY | B | 627 | 17.056 | 5.007 | 29.360 | 1.00 | 12.10 |
| 10812 | CA | GLY | B | 627 | 17.033 | 4.503 | 30.709 | 1.00 | 12.67 |
| 10813 | C | GLY | B | 627 | 15.999 | 5.173 | 31.569 | 1.00 | 11.98 |
| 10814 | O | GLY | B | 627 | 15.450 | 4.641 | 32.549 | 1.00 | 12.70 |
| 10815 | N | TYR | B | 628 | 15.798 | 6.407 | 31.235 | 1.00 | 11.94 |
| 10816 | CA | TYR | B | 628 | 14.775 | 7.198 | 31.859 | 1.00 | 13.84 |
| 10817 | CB | TYR | B | 628 | 14.916 | 8.597 | 31.257 | 1.00 | 13.91 |
| 10818 | CG | TYR | B | 628 | 13.859 | 9.583 | 31.712 | 1.00 | 18.57 |
| 10819 | CD1 | TYR | B | 628 | 13.702 | 9.875 | 33.021 | 1.00 | 18.31 |
| 10820 | CE1 | TYR | B | 628 | 12.819 | 10.794 | 33.393 | 1.00 | 20.56 |
| 10821 | CZ | TYR | B | 628 | 12.081 | 11.420 | 32.463 | 1.00 | 18.09 |
| 10822 | OH | TYR | B | 628 | 11.215 | 12.378 | 32.851 | 1.00 | 17.87 |
| 10823 | CE2 | TYR | B | 628 | 12.231 | 11.157 | 31.183 | 1.00 | 17.69 |
| 10824 | CD2 | TYR | B | 628 | 13.121 | 10.292 | 30.807 | 1.00 | 17.79 |
| 10825 | C | TYR | B | 628 | 13.461 | 6.465 | 31.613 | 1.00 | 12.71 |
| 10826 | O | TYR | B | 628 | 12.838 | 6.007 | 32.528 | 1.00 | 12.77 |
| 10827 | N | VAL | B | 629 | 13.138 | 6.196 | 30.368 | 1.00 | 13.14 |
| 10828 | CA | VAL | B | 629 | 11.853 | 5.708 | 30.036 | 1.00 | 13.23 |
| 10829 | CB | VAL | B | 629 | 11.644 | 5.861 | 28.578 | 1.00 | 14.97 |
| 10830 | CG1 | VAL | B | 629 | 10.195 | 5.547 | 28.141 | 1.00 | 13.17 |
| 10831 | CG2 | VAL | B | 629 | 11.846 | 7.281 | 28.173 | 1.00 | 16.11 |
| 10832 | C | VAL | B | 629 | 11.723 | 4.248 | 30.456 | 1.00 | 14.51 |
| 10833 | O | VAL | B | 629 | 10.712 | 3.825 | 31.002 | 1.00 | 13.98 |
| 10834 | N | SER | B | 630 | 12.740 | 3.463 | 30.207 | 1.00 | 13.67 |
| 10835 | CA | SER | B | 630 | 12.735 | 2.147 | 30.645 | 1.00 | 13.62 |
| 10836 | CB | SER | B | 630 | 14.089 | 1.533 | 30.424 | 1.00 | 14.67 |
| 10837 | OG | SER | B | 630 | 14.087 | 0.160 | 30.822 | 1.00 | 20.20 |
| 10838 | C | SER | B | 630 | 12.366 | 2.094 | 32.108 | 1.00 | 14.35 |
| 10839 | O | SER | B | 630 | 11.458 | 1.366 | 32.520 | 1.00 | 14.78 |
| 10840 | N | SER | B | 631 | 13.065 | 2.860 | 32.910 | 1.00 | 12.97 |
| 10841 | CA | SER | B | 631 | 12.706 | 2.976 | 34.308 | 1.00 | 13.53 |
| 10842 | CB | SER | B | 631 | 13.738 | 3.890 | 34.926 | 1.00 | 13.59 |
| 10843 | OG | SER | B | 631 | 15.058 | 3.388 | 34.680 | 1.00 | 13.67 |
| 10844 | C | SER | B | 631 | 11.265 | 3.466 | 34.684 | 1.00 | 14.36 |
| 10845 | O | SER | B | 631 | 10.637 | 2.924 | 35.564 | 1.00 | 15.39 |
| 10846 | N | LEU | B | 632 | 10.755 | 4.517 | 34.023 | 1.00 | 15.30 |
| 10847 | CA | LEU | B | 632 | 9.492 | 5.159 | 34.386 | 1.00 | 14.35 |
| 10848 | CB | LEU | B | 632 | 9.312 | 6.441 | 33.635 | 1.00 | 13.48 |
| 10849 | CG | LEU | B | 632 | 10.074 | 7.625 | 34.062 | 1.00 | 15.69 |
| 10850 | CD1 | LEU | B | 632 | 10.192 | 8.517 | 32.909 | 1.00 | 16.49 |
| 10851 | CD2 | LEU | B | 632 | 9.545 | 8.379 | 35.226 | 1.00 | 18.29 |
| 10852 | C | LEU | B | 632 | 8.326 | 4.297 | 34.015 | 1.00 | 15.02 |
| 10853 | O | LEU | B | 632 | 7.262 | 4.332 | 34.679 | 1.00 | 16.98 |
| 10854 | N | ALA | B | 633 | 8.474 | 3.684 | 32.852 | 1.00 | 16.13 |

FIGURE 3 (Cont.)

| A | B | C | D | E | F | G | H | I | J |
|---|---|---|---|---|---|---|---|---|---|
| 10855 | CA | ALA | B | 633 | 7.732 | 2.472 | 32.416 | 1.00 | 16.28 |
| 10856 | CB | ALA | B | 633 | 8.387 | 1.839 | 31.225 | 1.00 | 15.25 |
| 10857 | C | ALA | B | 633 | 7.662 | 1.431 | 33.451 | 1.00 | 15.58 |
| 10858 | O | ALA | B | 633 | 6.571 | 0.929 | 33.804 | 1.00 | 16.99 |
| 10859 | N | LEU | B | 634 | 8.840 | 0.981 | 33.858 | 1.00 | 15.42 |
| 10860 | CA | LEU | B | 634 | 8.900 | -0.253 | 34.691 | 1.00 | 13.34 |
| 10861 | CB | LEU | B | 634 | 10.309 | -0.546 | 35.095 | 1.00 | 12.60 |
| 10862 | CG | LEU | B | 634 | 10.506 | -1.780 | 35.947 | 1.00 | 9.15 |
| 10863 | CD1 | LEU | B | 634 | 9.869 | -2.968 | 35.255 | 1.00 | 4.03 |
| 10864 | CD2 | LEU | B | 634 | 12.001 | -1.968 | 36.035 | 1.00 | 10.97 |
| 10865 | C | LEU | B | 634 | 8.139 | -0.002 | 35.945 | 1.00 | 13.36 |
| 10866 | O | LEU | B | 634 | 7.527 | -0.860 | 36.515 | 1.00 | 11.78 |
| 10867 | N | ALA | B | 635 | 8.219 | 1.251 | 36.324 | 1.00 | 14.15 |
| 10868 | CA | ALA | B | 635 | 7.674 | 1.776 | 37.536 | 1.00 | 15.68 |
| 10869 | CB | ALA | B | 635 | 8.749 | 2.765 | 38.202 | 1.00 | 14.92 |
| 10870 | C | ALA | B | 635 | 6.404 | 2.508 | 37.289 | 1.00 | 16.82 |
| 10871 | O | ALA | B | 635 | 6.052 | 3.398 | 38.056 | 1.00 | 18.42 |
| 10872 | N | SER | B | 636 | 5.690 | 2.136 | 36.257 | 1.00 | 17.88 |
| 10873 | CA | SER | B | 636 | 4.443 | 2.873 | 35.905 | 1.00 | 19.89 |
| 10874 | CB | SER | B | 636 | 4.168 | 2.857 | 34.411 | 1.00 | 19.95 |
| 10875 | OG | SER | B | 636 | 3.755 | 1.535 | 34.067 | 1.00 | 20.72 |
| 10876 | C | SER | B | 636 | 3.247 | 2.296 | 36.600 | 1.00 | 20.40 |
| 10877 | O | SER | B | 636 | 2.140 | 2.830 | 36.448 | 1.00 | 21.51 |
| 10878 | N | GLY | B | 637 | 3.456 | 1.186 | 37.321 | 1.00 | 21.55 |
| 10879 | CA | GLY | B | 637 | 2.429 | 0.565 | 38.186 | 1.00 | 23.00 |
| 10880 | C | GLY | B | 637 | 1.343 | 0.009 | 37.321 | 1.00 | 23.81 |
| 10881 | O | GLY | B | 637 | 0.205 | 0.419 | 37.402 | 1.00 | 26.64 |
| 10882 | N | THR | B | 638 | 1.741 | -0.927 | 36.471 | 1.00 | 23.82 |
| 10883 | CA | THR | B | 638 | 0.986 | -1.375 | 35.289 | 1.00 | 22.97 |
| 10884 | CB | THR | B | 638 | 1.709 | -0.765 | 34.031 | 1.00 | 23.26 |
| 10885 | OG1 | THR | B | 638 | 0.827 | -0.701 | 32.919 | 1.00 | 25.33 |
| 10886 | CG2 | THR | B | 638 | 2.911 | -1.601 | 33.501 | 1.00 | 21.65 |
| 10887 | C | THR | B | 638 | 0.928 | -2.910 | 35.175 | 1.00 | 22.03 |
| 10888 | O | THR | B | 638 | 0.205 | -3.438 | 34.381 | 1.00 | 22.80 |
| 10889 | N | GLY | B | 639 | 1.770 | -3.609 | 35.883 | 1.00 | 20.15 |
| 10890 | CA | GLY | B | 639 | 1.806 | -5.038 | 35.749 | 1.00 | 19.72 |
| 10891 | C | GLY | B | 639 | 2.431 | -5.638 | 34.500 | 1.00 | 19.51 |
| 10892 | O | GLY | B | 639 | 2.795 | -6.810 | 34.489 | 1.00 | 19.35 |
| 10893 | N | LEU | B | 640 | 2.585 | -4.871 | 33.441 | 1.00 | 18.87 |
| 10894 | CA | LEU | B | 640 | 3.008 | -5.467 | 32.157 | 1.00 | 17.93 |
| 10895 | CB | LEU | B | 640 | 2.932 | -4.408 | 31.063 | 1.00 | 16.43 |
| 10896 | CG | LEU | B | 640 | 1.567 | -3.808 | 30.696 | 1.00 | 14.56 |
| 10897 | CD1 | LEU | B | 640 | 1.813 | -2.637 | 29.719 | 1.00 | 2.00 |
| 10898 | CD2 | LEU | B | 640 | 0.562 | -4.876 | 30.138 | 1.00 | 2.00 |
| 10899 | C | LEU | B | 640 | 4.450 | -5.965 | 32.205 | 1.00 | 18.16 |
| 10900 | O | LEU | B | 640 | 4.786 | -7.061 | 31.714 | 1.00 | 19.12 |
| 10901 | N | PHE | B | 641 | 5.288 | -5.112 | 32.799 | 1.00 | 17.60 |
| 10902 | CA | PHE | B | 641 | 6.732 | -5.291 | 32.837 | 1.00 | 16.58 |
| 10903 | CB | PHE | B | 641 | 7.347 | -3.980 | 32.750 | 1.00 | 14.66 |
| 10904 | CG | PHE | B | 641 | 7.233 | -3.383 | 31.400 | 1.00 | 16.16 |
| 10905 | CD1 | PHE | B | 641 | 7.706 | -4.075 | 30.271 | 1.00 | 17.64 |

FIGURE 3 (Cont.)

| A | B | C | D | E | F | G | H | I | J |
|---|---|---|---|---|---|---|---|---|---|
| 10906 | CE1 | PHE | B | 641 | 7.620 | -3.461 | 28.998 | 1.00 | 16.53 |
| 10907 | CZ | PHE | B | 641 | 6.984 | -2.201 | 28.916 | 1.00 | 14.59 |
| 10908 | CE2 | PHE | B | 641 | 6.528 | -1.552 | 30.053 | 1.00 | 11.09 |
| 10909 | CD2 | PHE | B | 641 | 6.668 | -2.111 | 31.234 | 1.00 | 14.28 |
| 10910 | C | PHE | B | 641 | 7.119 | -5.968 | 34.111 | 1.00 | 16.40 |
| 10911 | O | PHE | B | 641 | 6.826 | -5.428 | 35.169 | 1.00 | 16.72 |
| 10912 | N | LYS | B | 642 | 7.726 | -7.156 | 33.980 | 1.00 | 15.24 |
| 10913 | CA | LYS | B | 642 | 8.065 | -7.967 | 35.111 | 1.00 | 15.77 |
| 10914 | CB | LYS | B | 642 | 7.879 | -9.480 | 34.826 | 1.00 | 15.73 |
| 10915 | CG | LYS | B | 642 | 9.169 | -10.282 | 34.641 | 1.00 | 15.77 |
| 10916 | CD | LYS | B | 642 | 9.559 | -11.042 | 35.916 | 1.00 | 13.44 |
| 10917 | CE | LYS | B | 642 | 8.953 | -12.468 | 35.919 | 1.00 | 13.53 |
| 10918 | NZ | LYS | B | 642 | 9.881 | -13.658 | 35.716 | 1.00 | 9.82 |
| 10919 | C | LYS | B | 642 | 9.480 | -7.654 | 35.509 | 1.00 | 15.24 |
| 10920 | O | LYS | B | 642 | 9.863 | -7.873 | 36.663 | 1.00 | 14.44 |
| 10921 | N | CYS | B | 643 | 10.271 | -7.185 | 34.541 | 1.00 | 15.85 |
| 10922 | CA | CYS | B | 643 | 11.596 | -6.684 | 34.823 | 1.00 | 14.84 |
| 10923 | CB | CYS | B | 643 | 12.606 | -7.826 | 34.882 | 1.00 | 15.64 |
| 10924 | SG | CYS | B | 643 | 12.999 | -8.787 | 33.405 | 1.00 | 20.35 |
| 10925 | C | CYS | B | 643 | 11.972 | -5.631 | 33.883 | 1.00 | 13.77 |
| 10926 | O | CYS | B | 643 | 11.184 | -5.309 | 32.999 | 1.00 | 14.12 |
| 10927 | N | GLY | B | 644 | 13.122 | -4.997 | 34.114 | 1.00 | 11.97 |
| 10928 | CA | GLY | B | 644 | 13.538 | -3.874 | 33.238 | 1.00 | 10.61 |
| 10929 | C | GLY | B | 644 | 14.981 | -3.368 | 33.494 | 1.00 | 9.49 |
| 10930 | O | GLY | B | 644 | 15.523 | -3.434 | 34.600 | 1.00 | 9.06 |
| 10931 | N | ILE | B | 645 | 15.638 | -2.883 | 32.488 | 1.00 | 10.02 |
| 10932 | CA | ILE | B | 645 | 16.973 | -2.329 | 32.708 | 1.00 | 11.44 |
| 10933 | CB | ILE | B | 645 | 17.900 | -3.057 | 31.918 | 1.00 | 11.20 |
| 10934 | CG1 | ILE | B | 645 | 17.741 | -4.573 | 32.183 | 1.00 | 12.42 |
| 10935 | CD1 | ILE | B | 645 | 18.525 | -5.515 | 31.197 | 1.00 | 4.80 |
| 10936 | CG2 | ILE | B | 645 | 19.307 | -2.582 | 32.241 | 1.00 | 11.37 |
| 10937 | C | ILE | B | 645 | 17.149 | -0.838 | 32.403 | 1.00 | 11.91 |
| 10938 | O | ILE | B | 645 | 16.405 | -0.250 | 31.624 | 1.00 | 12.53 |
| 10939 | N | ALA | B | 646 | 18.083 | -0.199 | 33.076 | 1.00 | 13.77 |
| 10940 | CA | ALA | B | 646 | 18.314 | 1.230 | 32.768 | 1.00 | 14.80 |
| 10941 | CB | ALA | B | 646 | 17.688 | 2.144 | 33.848 | 1.00 | 12.64 |
| 10942 | C | ALA | B | 646 | 19.779 | 1.464 | 32.736 | 1.00 | 15.22 |
| 10943 | O | ALA | B | 646 | 20.367 | 1.374 | 33.783 | 1.00 | 16.48 |
| 10944 | N | VAL | B | 647 | 20.364 | 1.823 | 31.582 | 1.00 | 14.70 |
| 10945 | CA | VAL | B | 647 | 21.813 | 1.886 | 31.470 | 1.00 | 14.13 |
| 10946 | CB | VAL | B | 647 | 22.294 | 1.091 | 30.326 | 1.00 | 13.41 |
| 10947 | CG1 | VAL | B | 647 | 23.626 | 1.472 | 30.030 | 1.00 | 12.64 |
| 10948 | CG2 | VAL | B | 647 | 22.236 | -0.385 | 30.630 | 1.00 | 10.10 |
| 10949 | C | VAL | B | 647 | 22.083 | 3.343 | 31.346 | 1.00 | 15.40 |
| 10950 | O | VAL | B | 647 | 21.771 | 3.965 | 30.373 | 1.00 | 15.05 |
| 10951 | N | ALA | B | 648 | 22.603 | 3.923 | 32.384 | 1.00 | 14.41 |
| 10952 | CA | ALA | B | 648 | 22.952 | 5.341 | 32.367 | 1.00 | 12.90 |
| 10953 | CB | ALA | B | 648 | 24.070 | 5.613 | 31.433 | 1.00 | 11.24 |
| 10954 | C | ALA | B | 648 | 21.797 | 6.260 | 32.119 | 1.00 | 12.84 |
| 10955 | O | ALA | B | 648 | 21.903 | 7.144 | 31.315 | 1.00 | 15.32 |
| 10956 | N | PRO | B | 649 | 20.687 | 6.093 | 32.858 | 1.00 | 11.64 |

FIGURE 3 (Cont.)

| A | B | C | D | E | F | G | H | I | J |
|---|---|---|---|---|---|---|---|---|---|
| 10957 | CA | PRO | B | 649 | 19.530 | 6.960 | 32.735 | 1.00 | 10.07 |
| 10958 | CB | PRO | B | 649 | 18.630 | 6.386 | 33.727 | 1.00 | 7.59 |
| 10959 | CG | PRO | B | 649 | 19.649 | 5.944 | 34.789 | 1.00 | 7.61 |
| 10960 | CD | PRO | B | 649 | 20.518 | 5.108 | 33.942 | 1.00 | 10.80 |
| 10961 | C | PRO | B | 649 | 19.721 | 8.429 | 33.156 | 1.00 | 12.36 |
| 10962 | O | PRO | B | 649 | 20.299 | 8.749 | 34.143 | 1.00 | 12.12 |
| 10963 | N | VAL | B | 650 | 19.131 | 9.358 | 32.439 | 1.00 | 12.34 |
| 10964 | CA | VAL | B | 650 | 18.678 | 10.532 | 33.091 | 1.00 | 12.75 |
| 10965 | CB | VAL | B | 650 | 18.003 | 11.450 | 32.123 | 1.00 | 13.30 |
| 10966 | CG1 | VAL | B | 650 | 17.386 | 12.603 | 32.802 | 1.00 | 9.93 |
| 10967 | CG2 | VAL | B | 650 | 19.023 | 11.963 | 31.111 | 1.00 | 11.41 |
| 10968 | C | VAL | B | 650 | 17.716 | 10.064 | 34.168 | 1.00 | 15.03 |
| 10969 | O | VAL | B | 650 | 16.953 | 9.089 | 33.965 | 1.00 | 16.87 |
| 10970 | N | SER | B | 651 | 17.821 | 10.634 | 35.388 | 1.00 | 14.40 |
| 10971 | CA | SER | B | 651 | 16.850 | 10.307 | 36.439 | 1.00 | 11.17 |
| 10972 | CB | SER | B | 651 | 17.511 | 9.771 | 37.710 | 1.00 | 9.64 |
| 10973 | OG | SER | B | 651 | 18.133 | 10.865 | 38.383 | 1.00 | 18.93 |
| 10974 | C | SER | B | 651 | 16.082 | 11.542 | 36.808 | 1.00 | 10.86 |
| 10975 | O | SER | B | 651 | 15.086 | 11.427 | 37.453 | 1.00 | 9.36 |
| 10976 | N | SER | B | 652 | 16.556 | 12.707 | 36.423 | 1.00 | 10.06 |
| 10977 | CA | SER | B | 652 | 15.777 | 13.938 | 36.514 | 1.00 | 10.98 |
| 10978 | CB | SER | B | 652 | 15.609 | 14.424 | 37.965 | 1.00 | 11.44 |
| 10979 | OG | SER | B | 652 | 15.702 | 15.859 | 38.121 | 1.00 | 15.12 |
| 10980 | C | SER | B | 652 | 16.382 | 15.074 | 35.761 | 1.00 | 10.82 |
| 10981 | O | SER | B | 652 | 17.634 | 15.211 | 35.636 | 1.00 | 7.64 |
| 10982 | N | TRP | B | 653 | 15.480 | 15.969 | 35.349 | 1.00 | 10.10 |
| 10983 | CA | TRP | B | 653 | 15.855 | 16.934 | 34.276 | 1.00 | 11.33 |
| 10984 | CB | TRP | B | 653 | 14.637 | 17.341 | 33.435 | 1.00 | 7.74 |
| 10985 | CG | TRP | B | 653 | 14.230 | 16.192 | 32.563 | 1.00 | 8.92 |
| 10986 | CD1 | TRP | B | 653 | 13.054 | 15.366 | 32.673 | 1.00 | 8.62 |
| 10987 | NE1 | TRP | B | 653 | 13.084 | 14.379 | 31.716 | 1.00 | 8.65 |
| 10988 | CE2 | TRP | B | 653 | 14.277 | 14.510 | 31.009 | 1.00 | 5.16 |
| 10989 | CD2 | TRP | B | 653 | 15.005 | 15.605 | 31.536 | 1.00 | 5.52 |
| 10990 | CE3 | TRP | B | 653 | 16.218 | 15.951 | 30.917 | 1.00 | 14.25 |
| 10991 | CZ3 | TRP | B | 653 | 16.740 | 15.129 | 29.882 | 1.00 | 13.53 |
| 10992 | CH2 | TRP | B | 653 | 16.007 | 14.038 | 29.414 | 1.00 | 12.64 |
| 10993 | CZ2 | TRP | B | 653 | 14.784 | 13.720 | 29.973 | 1.00 | 12.81 |
| 10994 | C | TRP | B | 653 | 16.704 | 18.062 | 34.872 | 1.00 | 12.21 |
| 10995 | O | TRP | B | 653 | 17.337 | 18.808 | 34.221 | 1.00 | 13.44 |
| 10996 | N | GLU | B | 654 | 16.802 | 18.082 | 36.154 | 1.00 | 11.12 |
| 10997 | CA | GLU | B | 654 | 17.586 | 19.033 | 36.800 | 1.00 | 12.74 |
| 10998 | CB | GLU | B | 654 | 17.050 | 19.027 | 38.231 | 1.00 | 14.13 |
| 10999 | CG | GLU | B | 654 | 17.693 | 20.084 | 39.136 | 1.00 | 17.67 |
| 11000 | CD | GLU | B | 654 | 17.438 | 19.866 | 40.612 | 1.00 | 22.31 |
| 11001 | OE1 | GLU | B | 654 | 16.801 | 18.822 | 41.089 | 1.00 | 26.02 |
| 11002 | OE2 | GLU | B | 654 | 17.865 | 20.809 | 41.279 | 1.00 | 23.34 |
| 11003 | C | GLU | B | 654 | 19.053 | 18.695 | 36.667 | 1.00 | 12.43 |
| 11004 | O | GLU | B | 654 | 19.905 | 19.527 | 36.680 | 1.00 | 15.41 |
| 11005 | N | TYR | B | 655 | 19.345 | 17.449 | 36.479 | 1.00 | 13.21 |
| 11006 | CA | TYR | B | 655 | 20.663 | 16.985 | 36.442 | 1.00 | 14.32 |
| 11007 | CB | TYR | B | 655 | 20.667 | 15.540 | 36.994 | 1.00 | 15.89 |

FIGURE 3 (Cont.)

| A | B | C | D | E | F | G | H | I | J |
|---|---|---|---|---|---|---|---|---|---|
| 11008 | CG | TYR | B | 655 | 20.147 | 15.327 | 38.425 | 1.00 | 9.90 |
| 11009 | CD1 | TYR | B | 655 | 20.247 | 16.313 | 39.351 | 1.00 | 11.29 |
| 11010 | CE1 | TYR | B | 655 | 19.809 | 16.166 | 40.619 | 1.00 | 11.83 |
| 11011 | CZ | TYR | B | 655 | 19.325 | 14.940 | 41.061 | 1.00 | 12.75 |
| 11012 | OH | TYR | B | 655 | 18.894 | 14.848 | 42.444 | 1.00 | 12.90 |
| 11013 | CE2 | TYR | B | 655 | 19.218 | 13.910 | 40.131 | 1.00 | 8.72 |
| 11014 | CD2 | TYR | B | 655 | 19.633 | 14.125 | 38.825 | 1.00 | 8.04 |
| 11015 | C | TYR | B | 655 | 21.262 | 17.042 | 35.031 | 1.00 | 14.99 |
| 11016 | O | TYR | B | 655 | 22.518 | 17.079 | 34.887 | 1.00 | 17.03 |
| 11017 | N | TYR | B | 656 | 20.469 | 17.212 | 33.981 | 1.00 | 13.87 |
| 11018 | CA | TYR | B | 656 | 21.043 | 17.222 | 32.639 | 1.00 | 13.04 |
| 11019 | CB | TYR | B | 656 | 20.184 | 16.426 | 31.732 | 1.00 | 11.71 |
| 11020 | CG | TYR | B | 656 | 20.876 | 16.003 | 30.535 | 1.00 | 14.82 |
| 11021 | CD1 | TYR | B | 656 | 20.428 | 16.338 | 29.282 | 1.00 | 16.99 |
| 11022 | CE1 | TYR | B | 656 | 21.124 | 15.889 | 28.133 | 1.00 | 13.64 |
| 11023 | CZ | TYR | B | 656 | 22.252 | 15.135 | 28.294 | 1.00 | 15.24 |
| 11024 | OH | TYR | B | 656 | 22.989 | 14.720 | 27.257 | 1.00 | 16.93 |
| 11025 | CE2 | TYR | B | 656 | 22.700 | 14.812 | 29.519 | 1.00 | 14.14 |
| 11026 | CD2 | TYR | B | 656 | 22.010 | 15.235 | 30.621 | 1.00 | 19.28 |
| 11027 | C | TYR | B | 656 | 21.330 | 18.579 | 32.074 | 1.00 | 13.90 |
| 11028 | O | TYR | B | 656 | 20.963 | 19.639 | 32.628 | 1.00 | 12.67 |
| 11029 | N | ALA | B | 657 | 22.079 | 18.565 | 30.981 | 1.00 | 14.24 |
| 11030 | CA | ALA | B | 657 | 22.565 | 19.783 | 30.346 | 1.00 | 15.10 |
| 11031 | CB | ALA | B | 657 | 23.370 | 19.377 | 29.130 | 1.00 | 15.98 |
| 11032 | C | ALA | B | 657 | 21.440 | 20.767 | 29.941 | 1.00 | 15.12 |
| 11033 | O | ALA | B | 657 | 20.385 | 20.307 | 29.415 | 1.00 | 16.10 |
| 11034 | N | SER | B | 658 | 21.675 | 22.073 | 30.171 | 1.00 | 13.31 |
| 11035 | CA | SER | B | 658 | 20.716 | 23.102 | 29.861 | 1.00 | 11.21 |
| 11036 | CB | SER | B | 658 | 21.265 | 24.522 | 30.200 | 1.00 | 13.49 |
| 11037 | OG | SER | B | 658 | 22.578 | 24.842 | 29.666 | 1.00 | 11.46 |
| 11038 | C | SER | B | 658 | 20.277 | 23.109 | 28.412 | 1.00 | 11.53 |
| 11039 | O | SER | B | 658 | 19.108 | 23.005 | 28.101 | 1.00 | 8.60 |
| 11040 | N | VAL | B | 659 | 21.210 | 23.308 | 27.504 | 1.00 | 10.57 |
| 11041 | CA | VAL | B | 659 | 20.886 | 23.320 | 26.041 | 1.00 | 10.59 |
| 11042 | CB | VAL | B | 659 | 22.156 | 23.222 | 25.286 | 1.00 | 10.83 |
| 11043 | CG1 | VAL | B | 659 | 21.987 | 23.300 | 23.808 | 1.00 | 9.37 |
| 11044 | CG2 | VAL | B | 659 | 23.134 | 24.344 | 25.750 | 1.00 | 10.62 |
| 11045 | C | VAL | B | 659 | 19.908 | 22.124 | 25.633 | 1.00 | 11.52 |
| 11046 | O | VAL | B | 659 | 18.946 | 22.280 | 24.917 | 1.00 | 10.80 |
| 11047 | N | TYR | B | 660 | 20.101 | 20.952 | 26.163 | 1.00 | 12.24 |
| 11048 | CA | TYR | B | 660 | 19.237 | 19.871 | 25.746 | 1.00 | 12.75 |
| 11049 | CB | TYR | B | 660 | 19.909 | 18.538 | 25.994 | 1.00 | 13.76 |
| 11050 | CG | TYR | B | 660 | 19.046 | 17.359 | 25.703 | 1.00 | 16.74 |
| 11051 | CD1 | TYR | B | 660 | 19.309 | 16.526 | 24.630 | 1.00 | 16.31 |
| 11052 | CE1 | TYR | B | 660 | 18.524 | 15.416 | 24.383 | 1.00 | 14.71 |
| 11053 | CZ | TYR | B | 660 | 17.507 | 15.149 | 25.167 | 1.00 | 19.80 |
| 11054 | OH | TYR | B | 660 | 16.735 | 14.014 | 24.968 | 1.00 | 25.34 |
| 11055 | CE2 | TYR | B | 660 | 17.251 | 15.952 | 26.234 | 1.00 | 21.69 |
| 11056 | CD2 | TYR | B | 660 | 18.002 | 17.036 | 26.513 | 1.00 | 13.65 |
| 11057 | C | TYR | B | 660 | 17.920 | 19.973 | 26.440 | 1.00 | 12.25 |
| 11058 | O | TYR | B | 660 | 16.905 | 20.196 | 25.810 | 1.00 | 15.38 |

FIGURE 3 (Cont.)

| A | B | C | D | E | F | G | H | I | J |
|---|---|---|---|---|---|---|---|---|---|
| 11059 | N | THR | B | 661 | 17.952 | 19.902 | 27.745 | 1.00 | 12.21 |
| 11060 | CA | THR | B | 661 | 16.847 | 19.947 | 28.600 | 1.00 | 10.79 |
| 11061 | CB | THR | B | 661 | 17.361 | 19.811 | 30.111 | 1.00 | 11.43 |
| 11062 | OG1 | THR | B | 661 | 18.163 | 18.580 | 30.293 | 1.00 | 16.14 |
| 11063 | CG2 | THR | B | 661 | 16.227 | 19.607 | 31.114 | 1.00 | 4.01 |
| 11064 | C | THR | B | 661 | 15.915 | 21.129 | 28.355 | 1.00 | 11.51 |
| 11065 | O | THR | B | 661 | 14.718 | 20.955 | 28.186 | 1.00 | 12.08 |
| 11066 | N | GLU | B | 662 | 16.404 | 22.330 | 28.313 | 1.00 | 10.59 |
| 11067 | CA | GLU | B | 662 | 15.492 | 23.457 | 28.226 | 1.00 | 11.12 |
| 11068 | CB | GLU | B | 662 | 16.267 | 24.764 | 28.507 | 1.00 | 12.32 |
| 11069 | CG | GLU | B | 662 | 17.086 | 24.767 | 29.814 | 1.00 | 12.28 |
| 11070 | CD | GLU | B | 662 | 17.808 | 26.112 | 30.028 | 1.00 | 13.71 |
| 11071 | OE1 | GLU | B | 662 | 17.718 | 27.017 | 29.157 | 1.00 | 21.30 |
| 11072 | OE2 | GLU | B | 662 | 18.408 | 26.269 | 31.120 | 1.00 | 12.78 |
| 11073 | C | GLU | B | 662 | 14.801 | 23.523 | 26.840 | 1.00 | 10.95 |
| 11074 | O | GLU | B | 662 | 13.839 | 24.248 | 26.629 | 1.00 | 11.18 |
| 11075 | N | ARG | B | 663 | 15.395 | 22.868 | 25.850 | 1.00 | 10.88 |
| 11076 | CA | ARG | B | 663 | 14.902 | 22.912 | 24.505 | 1.00 | 10.77 |
| 11077 | CB | ARG | B | 663 | 15.841 | 22.064 | 23.674 | 1.00 | 11.84 |
| 11078 | CG | ARG | B | 663 | 15.620 | 22.018 | 22.223 | 1.00 | 11.27 |
| 11079 | CD | ARG | B | 663 | 16.874 | 21.869 | 21.411 | 1.00 | 16.12 |
| 11080 | NE | ARG | B | 663 | 16.564 | 21.633 | 20.003 | 1.00 | 19.40 |
| 11081 | CZ | ARG | B | 663 | 16.338 | 22.621 | 19.082 | 1.00 | 24.41 |
| 11082 | NH1 | ARG | B | 663 | 16.065 | 22.286 | 17.799 | 1.00 | 18.20 |
| 11083 | NH2 | ARG | B | 663 | 16.375 | 23.912 | 19.427 | 1.00 | 22.93 |
| 11084 | C | ARG | B | 663 | 13.532 | 22.220 | 24.528 | 1.00 | 10.94 |
| 11085 | O | ARG | B | 663 | 12.599 | 22.598 | 23.787 | 1.00 | 12.25 |
| 11086 | N | PHE | B | 664 | 13.411 | 21.218 | 25.391 | 1.00 | 10.61 |
| 11087 | CA | PHE | B | 664 | 12.240 | 20.372 | 25.355 | 1.00 | 11.31 |
| 11088 | CB | PHE | B | 664 | 12.646 | 18.904 | 25.183 | 1.00 | 10.87 |
| 11089 | CG | PHE | B | 664 | 13.647 | 18.693 | 24.107 | 1.00 | 9.36 |
| 11090 | CD1 | PHE | B | 664 | 13.350 | 18.977 | 22.819 | 1.00 | 8.83 |
| 11091 | CE1 | PHE | B | 664 | 14.252 | 18.774 | 21.776 | 1.00 | 10.78 |
| 11092 | CZ | PHE | B | 664 | 15.547 | 18.341 | 22.058 | 1.00 | 12.32 |
| 11093 | CE2 | PHE | B | 664 | 15.858 | 18.107 | 23.400 | 1.00 | 12.25 |
| 11094 | CD2 | PHE | B | 664 | 14.859 | 18.279 | 24.396 | 1.00 | 10.72 |
| 11095 | C | PHE | B | 664 | 11.432 | 20.503 | 26.628 | 1.00 | 11.52 |
| 11096 | O | PHE | B | 664 | 10.290 | 20.112 | 26.608 | 1.00 | 10.66 |
| 11097 | N | MET | B | 665 | 12.007 | 21.142 | 27.682 | 1.00 | 11.28 |
| 11098 | CA | MET | B | 665 | 11.351 | 21.328 | 28.956 | 1.00 | 10.41 |
| 11099 | CB | MET | B | 665 | 12.109 | 20.683 | 30.094 | 1.00 | 8.21 |
| 11100 | CG | MET | B | 665 | 12.150 | 19.276 | 30.132 | 1.00 | 9.17 |
| 11101 | SD | MET | B | 665 | 10.619 | 18.725 | 30.888 | 1.00 | 12.87 |
| 11102 | CE | MET | B | 665 | 10.667 | 19.297 | 32.656 | 1.00 | 4.39 |
| 11103 | C | MET | B | 665 | 11.241 | 22.734 | 29.382 | 1.00 | 9.93 |
| 11104 | O | MET | B | 665 | 10.778 | 22.890 | 30.418 | 1.00 | 9.74 |
| 11105 | N | GLY | B | 666 | 11.583 | 23.750 | 28.617 | 1.00 | 10.88 |
| 11106 | CA | GLY | B | 666 | 11.661 | 25.138 | 29.107 | 1.00 | 12.07 |
| 11107 | C | GLY | B | 666 | 12.520 | 25.253 | 30.398 | 1.00 | 12.97 |
| 11108 | O | GLY | B | 666 | 13.321 | 24.293 | 30.682 | 1.00 | 10.87 |
| 11109 | N | LEU | B | 667 | 12.264 | 26.289 | 31.242 | 1.00 | 14.37 |

FIGURE 3 (Cont.)

| A | B | C | D | E | F | G | H | I | J |
|---|---|---|---|---|---|---|---|---|---|
| 11110 | CA | LEU | B | 667 | 13.114 | 26.467 | 32.450 | 1.00 | 15.90 |
| 11111 | CB | LEU | B | 667 | 13.347 | 27.951 | 32.787 | 1.00 | 15.85 |
| 11112 | CG | LEU | B | 667 | 14.087 | 28.934 | 31.918 | 1.00 | 18.29 |
| 11113 | CD1 | LEU | B | 667 | 13.184 | 30.222 | 31.684 | 1.00 | 25.65 |
| 11114 | CD2 | LEU | B | 667 | 14.481 | 28.302 | 30.596 | 1.00 | 24.30 |
| 11115 | C | LEU | B | 667 | 12.548 | 25.924 | 33.745 | 1.00 | 16.29 |
| 11116 | O | LEU | B | 667 | 11.362 | 26.129 | 33.982 | 1.00 | 14.01 |
| 11117 | N | PRO | B | 668 | 13.409 | 25.371 | 34.637 | 1.00 | 16.73 |
| 11118 | CA | PRO | B | 668 | 12.980 | 24.979 | 35.971 | 1.00 | 16.30 |
| 11119 | CB | PRO | B | 668 | 14.085 | 24.032 | 36.465 | 1.00 | 16.10 |
| 11120 | CG | PRO | B | 668 | 15.340 | 24.524 | 35.802 | 1.00 | 16.84 |
| 11121 | CD | PRO | B | 668 | 14.843 | 25.095 | 34.452 | 1.00 | 16.32 |
| 11122 | C | PRO | B | 668 | 12.795 | 26.199 | 36.875 | 1.00 | 17.30 |
| 11123 | O | PRO | B | 668 | 13.222 | 26.200 | 38.057 | 1.00 | 17.71 |
| 11124 | N | THR | B | 669 | 12.058 | 27.171 | 36.354 | 1.00 | 16.66 |
| 11125 | CA | THR | B | 669 | 11.448 | 28.107 | 37.213 | 1.00 | 18.78 |
| 11126 | CB | THR | B | 669 | 11.551 | 29.547 | 36.545 | 1.00 | 19.16 |
| 11127 | OG1 | THR | B | 669 | 10.804 | 29.620 | 35.326 | 1.00 | 17.44 |
| 11128 | CG2 | THR | B | 669 | 12.979 | 29.788 | 36.068 | 1.00 | 21.00 |
| 11129 | C | THR | B | 669 | 9.990 | 27.695 | 37.673 | 1.00 | 19.73 |
| 11130 | O | THR | B | 669 | 9.201 | 27.056 | 36.931 | 1.00 | 20.06 |
| 11131 | N | LYS | B | 670 | 9.699 | 27.979 | 38.947 | 1.00 | 20.18 |
| 11132 | CA | LYS | B | 670 | 8.332 | 28.454 | 39.404 | 1.00 | 20.91 |
| 11133 | CB | LYS | B | 670 | 8.385 | 29.322 | 40.720 | 1.00 | 20.46 |
| 11134 | CG | LYS | B | 670 | 9.311 | 30.643 | 40.692 | 1.00 | 22.54 |
| 11135 | CD | LYS | B | 670 | 10.950 | 30.398 | 40.477 | 1.00 | 20.34 |
| 11136 | CE | LYS | B | 670 | 11.754 | 31.691 | 40.105 | 1.00 | 17.84 |
| 11137 | NZ | LYS | B | 670 | 12.947 | 31.439 | 39.225 | 1.00 | 19.56 |
| 11138 | C | LYS | B | 670 | 7.446 | 29.165 | 38.368 | 1.00 | 20.40 |
| 11139 | O | LYS | B | 670 | 6.324 | 28.741 | 38.204 | 1.00 | 19.64 |
| 11140 | N | ASP | B | 671 | 7.924 | 30.190 | 37.650 | 1.00 | 21.31 |
| 11141 | CA | ASP | B | 671 | 7.069 | 30.855 | 36.598 | 1.00 | 22.43 |
| 11142 | CB | ASP | B | 671 | 7.420 | 32.362 | 36.387 | 1.00 | 23.67 |
| 11143 | CG | ASP | B | 671 | 7.582 | 33.147 | 37.713 | 1.00 | 28.11 |
| 11144 | OD1 | ASP | B | 671 | 8.677 | 33.719 | 37.976 | 1.00 | 31.29 |
| 11145 | OD2 | ASP | B | 671 | 6.669 | 33.206 | 38.561 | 1.00 | 31.86 |
| 11146 | C | ASP | B | 671 | 7.075 | 30.210 | 35.219 | 1.00 | 21.67 |
| 11147 | O | ASP | B | 671 | 6.529 | 30.698 | 34.292 | 1.00 | 23.72 |
| 11148 | N | ASP | B | 672 | 7.770 | 29.134 | 35.051 | 1.00 | 20.52 |
| 11149 | CA | ASP | B | 672 | 7.778 | 28.385 | 33.798 | 1.00 | 19.70 |
| 11150 | CB | ASP | B | 672 | 9.161 | 28.467 | 33.144 | 1.00 | 19.80 |
| 11151 | CG | ASP | B | 672 | 9.123 | 28.203 | 31.669 | 1.00 | 19.51 |
| 11152 | OD1 | ASP | B | 672 | 9.979 | 28.717 | 30.874 | 1.00 | 26.67 |
| 11153 | OD2 | ASP | B | 672 | 8.283 | 27.446 | 31.232 | 1.00 | 14.53 |
| 11154 | C | ASP | B | 672 | 7.359 | 26.941 | 34.101 | 1.00 | 17.75 |
| 11155 | O | ASP | B | 672 | 6.180 | 26.646 | 34.276 | 1.00 | 19.39 |
| 11156 | N | ASN | B | 673 | 8.280 | 26.055 | 34.186 | 1.00 | 14.08 |
| 11157 | CA | ASN | B | 673 | 7.943 | 24.646 | 34.107 | 1.00 | 12.44 |
| 11158 | CB | ASN | B | 673 | 8.383 | 24.093 | 32.763 | 1.00 | 12.67 |
| 11159 | CG | ASN | B | 673 | 7.720 | 22.783 | 32.434 | 1.00 | 11.01 |
| 11160 | OD1 | ASN | B | 673 | 6.589 | 22.589 | 32.788 | 1.00 | 11.13 |

FIGURE 3 (Cont.)

| A | B | C | D | E | F | G | H | I | J |
|---|---|---|---|---|---|---|---|---|---|
| 11161 | ND2 | ASN | B | 673 | 8.435 | 21.888 | 31.732 | 1.00 | 11.94 |
| 11162 | C | ASN | B | 673 | 8.537 | 23.808 | 35.208 | 1.00 | 11.52 |
| 11163 | O | ASN | B | 673 | 8.570 | 22.576 | 35.144 | 1.00 | 11.44 |
| 11164 | N | LEU | B | 674 | 8.887 | 24.455 | 36.300 | 1.00 | 11.77 |
| 11165 | CA | LEU | B | 674 | 9.421 | 23.665 | 37.412 | 1.00 | 13.14 |
| 11166 | CB | LEU | B | 674 | 9.897 | 24.535 | 38.549 | 1.00 | 12.35 |
| 11167 | CG | LEU | B | 674 | 10.268 | 24.050 | 39.942 | 1.00 | 13.61 |
| 11168 | CD1 | LEU | B | 674 | 11.653 | 24.360 | 40.089 | 1.00 | 15.53 |
| 11169 | CD2 | LEU | B | 674 | 9.488 | 24.823 | 41.024 | 1.00 | 18.10 |
| 11170 | C | LEU | B | 674 | 8.522 | 22.572 | 37.898 | 1.00 | 11.44 |
| 11171 | O | LEU | B | 674 | 9.067 | 21.540 | 38.268 | 1.00 | 10.81 |
| 11172 | N | GLU | B | 675 | 7.205 | 22.767 | 37.916 | 1.00 | 12.37 |
| 11173 | CA | GLU | B | 675 | 6.320 | 21.745 | 38.493 | 1.00 | 14.98 |
| 11174 | CB | GLU | B | 675 | 4.801 | 22.109 | 38.469 | 1.00 | 16.42 |
| 11175 | CG | GLU | B | 675 | 4.243 | 23.099 | 39.565 | 1.00 | 26.00 |
| 11176 | CD | GLU | B | 675 | 5.194 | 23.448 | 40.803 | 1.00 | 34.32 |
| 11177 | OE1 | GLU | B | 675 | 5.978 | 24.498 | 40.734 | 1.00 | 32.63 |
| 11178 | OE2 | GLU | B | 675 | 5.114 | 22.683 | 41.860 | 1.00 | 34.69 |
| 11179 | C | GLU | B | 675 | 6.611 | 20.420 | 37.783 | 1.00 | 14.61 |
| 11180 | O | GLU | B | 675 | 6.939 | 19.426 | 38.431 | 1.00 | 14.51 |
| 11181 | N | HIS | B | 676 | 6.679 | 20.439 | 36.453 | 1.00 | 14.42 |
| 11182 | CA | HIS | B | 676 | 7.043 | 19.242 | 35.725 | 1.00 | 14.11 |
| 11183 | CB | HIS | B | 676 | 6.748 | 19.300 | 34.233 | 1.00 | 13.08 |
| 11184 | CG | HIS | B | 676 | 6.667 | 17.932 | 33.645 | 1.00 | 13.79 |
| 11185 | ND1 | HIS | B | 676 | 5.561 | 17.144 | 33.822 | 1.00 | 9.06 |
| 11186 | CE1 | HIS | B | 676 | 5.775 | 15.953 | 33.269 | 1.00 | 11.12 |
| 11187 | NE2 | HIS | B | 676 | 6.995 | 15.924 | 32.757 | 1.00 | 6.86 |
| 11188 | CD2 | HIS | B | 676 | 7.610 | 17.127 | 33.058 | 1.00 | 13.35 |
| 11189 | C | HIS | B | 676 | 8.487 | 18.755 | 35.864 | 1.00 | 15.91 |
| 11190 | O | HIS | B | 676 | 8.715 | 17.523 | 35.707 | 1.00 | 17.04 |
| 11191 | N | TYR | B | 677 | 9.471 | 19.641 | 36.046 | 1.00 | 15.25 |
| 11192 | CA | TYR | B | 677 | 10.806 | 19.137 | 36.449 | 1.00 | 16.27 |
| 11193 | CB | TYR | B | 677 | 11.764 | 20.272 | 36.719 | 1.00 | 15.29 |
| 11194 | CG | TYR | B | 677 | 12.440 | 20.868 | 35.500 | 1.00 | 15.79 |
| 11195 | CD1 | TYR | B | 677 | 13.676 | 20.444 | 35.147 | 1.00 | 17.80 |
| 11196 | CE1 | TYR | B | 677 | 14.360 | 20.990 | 34.016 | 1.00 | 19.74 |
| 11197 | CZ | TYR | B | 677 | 13.748 | 21.976 | 33.237 | 1.00 | 18.46 |
| 11198 | OH | TYR | B | 677 | 14.533 | 22.409 | 32.171 | 1.00 | 8.17 |
| 11199 | CE2 | TYR | B | 677 | 12.453 | 22.421 | 33.559 | 1.00 | 6.25 |
| 11200 | CD2 | TYR | B | 677 | 11.797 | 21.847 | 34.676 | 1.00 | 12.90 |
| 11201 | C | TYR | B | 677 | 10.731 | 18.211 | 37.687 | 1.00 | 16.74 |
| 11202 | O | TYR | B | 677 | 11.292 | 17.106 | 37.664 | 1.00 | 19.04 |
| 11203 | N | LYS | B | 678 | 9.984 | 18.627 | 38.706 | 1.00 | 17.05 |
| 11204 | CA | LYS | B | 678 | 9.846 | 17.909 | 39.995 | 1.00 | 18.28 |
| 11205 | CB | LYS | B | 678 | 9.128 | 18.788 | 41.022 | 1.00 | 17.15 |
| 11206 | CG | LYS | B | 678 | 9.725 | 20.175 | 41.262 | 1.00 | 23.91 |
| 11207 | CD | LYS | B | 678 | 10.540 | 20.282 | 42.607 | 1.00 | 33.34 |
| 11208 | CE | LYS | B | 678 | 12.097 | 19.784 | 42.470 | 1.00 | 35.37 |
| 11209 | NZ | LYS | B | 678 | 13.132 | 20.551 | 43.346 | 1.00 | 34.82 |
| 11210 | C | LYS | B | 678 | 9.013 | 16.625 | 39.866 | 1.00 | 17.60 |
| 11211 | O | LYS | B | 678 | 9.205 | 15.621 | 40.605 | 1.00 | 19.14 |

FIGURE 3 (Cont.)

| A | B | C | D | E | F | G | H | I | J |
|---|---|---|---|---|---|---|---|---|---|
| 11212 | N | ASN | B | 679 | 8.093 | 16.703 | 38.931 | 1.00 | 15.74 |
| 11213 | CA | ASN | B | 679 | 7.073 | 15.761 | 38.789 | 1.00 | 16.51 |
| 11214 | CB | ASN | B | 679 | 5.691 | 16.367 | 38.352 | 1.00 | 16.23 |
| 11215 | CG | ASN | B | 679 | 4.545 | 15.386 | 38.675 | 1.00 | 20.45 |
| 11216 | OD1 | ASN | B | 679 | 4.423 | 14.770 | 39.775 | 1.00 | 22.93 |
| 11217 | ND2 | ASN | B | 679 | 3.609 | 15.301 | 37.701 | 1.00 | 29.40 |
| 11218 | C | ASN | B | 679 | 7.451 | 14.727 | 37.769 | 1.00 | 16.43 |
| 11219 | O | ASN | B | 679 | 6.583 | 13.899 | 37.498 | 1.00 | 16.78 |
| 11220 | N | SER | B | 680 | 8.690 | 14.768 | 37.198 | 1.00 | 16.20 |
| 11221 | CA | SER | B | 680 | 9.093 | 13.793 | 36.174 | 1.00 | 14.42 |
| 11222 | CB | SER | B | 680 | 9.270 | 14.548 | 34.850 | 1.00 | 15.21 |
| 11223 | OG | SER | B | 680 | 10.272 | 15.570 | 34.929 | 1.00 | 9.99 |
| 11224 | C | SER | B | 680 | 10.374 | 12.980 | 36.466 | 1.00 | 14.91 |
| 11225 | O | SER | B | 680 | 10.998 | 12.434 | 35.542 | 1.00 | 14.07 |
| 11226 | N | THR | B | 681 | 10.727 | 12.832 | 37.744 | 1.00 | 13.78 |
| 11227 | CA | THR | B | 681 | 11.977 | 12.156 | 38.110 | 1.00 | 13.54 |
| 11228 | CB | THR | B | 681 | 12.391 | 12.573 | 39.479 | 1.00 | 14.23 |
| 11229 | OG1 | THR | B | 681 | 11.401 | 12.091 | 40.411 | 1.00 | 18.02 |
| 11230 | CG2 | THR | B | 681 | 12.315 | 14.180 | 39.580 | 1.00 | 14.11 |
| 11231 | C | THR | B | 681 | 11.756 | 10.692 | 38.185 | 1.00 | 12.55 |
| 11232 | O | THR | B | 681 | 10.612 | 10.319 | 38.481 | 1.00 | 9.09 |
| 11233 | N | VAL | B | 682 | 12.788 | 9.820 | 37.967 | 1.00 | 10.49 |
| 11234 | CA | VAL | B | 682 | 12.472 | 8.426 | 38.225 | 1.00 | 10.93 |
| 11235 | CB | VAL | B | 682 | 13.333 | 7.342 | 37.529 | 1.00 | 13.23 |
| 11236 | CG1 | VAL | B | 682 | 14.073 | 7.729 | 36.242 | 1.00 | 3.92 |
| 11237 | CG2 | VAL | B | 682 | 14.290 | 6.717 | 38.514 | 1.00 | 12.14 |
| 11238 | C | VAL | B | 682 | 12.364 | 8.212 | 39.724 | 1.00 | 13.20 |
| 11239 | O | VAL | B | 682 | 11.619 | 7.368 | 40.143 | 1.00 | 14.80 |
| 11240 | N | MET | B | 683 | 13.039 | 9.011 | 40.555 | 1.00 | 14.38 |
| 11241 | CA | MET | B | 683 | 13.071 | 8.797 | 42.017 | 1.00 | 14.08 |
| 11242 | CB | MET | B | 683 | 13.910 | 9.796 | 42.807 | 1.00 | 14.33 |
| 11243 | CG | MET | B | 683 | 15.425 | 9.813 | 42.566 | 1.00 | 12.48 |
| 11244 | SD | MET | B | 683 | 16.035 | 10.322 | 40.890 | 1.00 | 13.58 |
| 11245 | CE | MET | B | 683 | 16.054 | 12.171 | 41.160 | 1.00 | 9.21 |
| 11246 | C | MET | B | 683 | 11.738 | 8.921 | 42.549 | 1.00 | 15.07 |
| 11247 | O | MET | B | 683 | 11.478 | 8.272 | 43.502 | 1.00 | 15.98 |
| 11248 | N | ALA | B | 684 | 10.842 | 9.703 | 41.968 | 1.00 | 14.19 |
| 11249 | CA | ALA | B | 684 | 9.490 | 9.817 | 42.590 | 1.00 | 14.00 |
| 11250 | CB | ALA | B | 684 | 8.748 | 11.096 | 42.114 | 1.00 | 13.56 |
| 11251 | C | ALA | B | 684 | 8.595 | 8.606 | 42.353 | 1.00 | 13.86 |
| 11252 | O | ALA | B | 684 | 7.465 | 8.549 | 42.866 | 1.00 | 13.69 |
| 11253 | N | ARG | B | 685 | 9.056 | 7.652 | 41.563 | 1.00 | 13.75 |
| 11254 | CA | ARG | B | 685 | 8.323 | 6.402 | 41.334 | 1.00 | 13.43 |
| 11255 | CB | ARG | B | 685 | 8.389 | 6.039 | 39.839 | 1.00 | 13.07 |
| 11256 | CG | ARG | B | 685 | 7.875 | 7.150 | 38.909 | 1.00 | 11.59 |
| 11257 | CD | ARG | B | 685 | 6.366 | 7.517 | 39.135 | 1.00 | 8.93 |
| 11258 | NE | ARG | B | 685 | 5.657 | 6.344 | 38.741 | 1.00 | 13.76 |
| 11259 | CZ | ARG | B | 685 | 4.397 | 6.028 | 39.068 | 1.00 | 11.12 |
| 11260 | NH1 | ARG | B | 685 | 3.629 | 6.874 | 39.754 | 1.00 | 9.59 |
| 11261 | NH2 | ARG | B | 685 | 3.906 | 4.876 | 38.627 | 1.00 | 9.21 |
| 11262 | C | ARG | B | 685 | 8.961 | 5.301 | 42.190 | 1.00 | 14.60 |

FIGURE 3 (Cont.)

| A | B | C | D | E | F | G | H | I | J |
|---|---|---|---|---|---|---|---|---|---|
| 11263 | O | ARG | B | 685 | 8.693 | 4.107 | 41.999 | 1.00 | 14.02 |
| 11264 | N | ALA | B | 686 | 9.851 | 5.712 | 43.107 | 1.00 | 15.11 |
| 11265 | CA | ALA | B | 686 | 10.639 | 4.758 | 43.873 | 1.00 | 14.89 |
| 11266 | CB | ALA | B | 686 | 11.266 | 5.425 | 45.082 | 1.00 | 15.16 |
| 11267 | C | ALA | B | 686 | 9.782 | 3.587 | 44.301 | 1.00 | 14.60 |
| 11268 | O | ALA | B | 686 | 10.132 | 2.419 | 44.044 | 1.00 | 13.19 |
| 11269 | N | GLU | B | 687 | 8.649 | 3.937 | 44.909 | 1.00 | 15.25 |
| 11270 | CA | GLU | B | 687 | 7.671 | 2.989 | 45.473 | 1.00 | 16.04 |
| 11271 | CB | GLU | B | 687 | 6.432 | 3.743 | 45.955 | 1.00 | 17.70 |
| 11272 | CG | GLU | B | 687 | 6.431 | 4.171 | 47.429 | 1.00 | 22.34 |
| 11273 | CD | GLU | B | 687 | 6.554 | 2.974 | 48.414 | 1.00 | 30.96 |
| 11274 | OE1 | GLU | B | 687 | 7.385 | 3.139 | 49.382 | 1.00 | 32.58 |
| 11275 | OE2 | GLU | B | 687 | 5.819 | 1.891 | 48.266 | 1.00 | 31.18 |
| 11276 | C | GLU | B | 687 | 7.230 | 1.926 | 44.498 | 1.00 | 16.05 |
| 11277 | O | GLU | B | 687 | 7.079 | 0.740 | 44.859 | 1.00 | 14.96 |
| 11278 | N | TYR | B | 688 | 7.036 | 2.337 | 43.247 | 1.00 | 16.23 |
| 11279 | CA | TYR | B | 688 | 6.487 | 1.423 | 42.282 | 1.00 | 17.36 |
| 11280 | CB | TYR | B | 688 | 5.746 | 2.176 | 41.204 | 1.00 | 17.66 |
| 11281 | CG | TYR | B | 688 | 4.703 | 3.097 | 41.765 | 1.00 | 19.88 |
| 11282 | CD1 | TYR | B | 688 | 5.033 | 4.399 | 42.107 | 1.00 | 23.71 |
| 11283 | CE1 | TYR | B | 688 | 4.096 | 5.295 | 42.625 | 1.00 | 24.59 |
| 11284 | CZ | TYR | B | 688 | 2.783 | 4.901 | 42.780 | 1.00 | 27.42 |
| 11285 | OH | TYR | B | 688 | 1.900 | 5.848 | 43.307 | 1.00 | 29.15 |
| 11286 | CE2 | TYR | B | 688 | 2.417 | 3.593 | 42.424 | 1.00 | 28.34 |
| 11287 | CD2 | TYR | B | 688 | 3.395 | 2.701 | 41.925 | 1.00 | 22.75 |
| 11288 | C | TYR | B | 688 | 7.480 | 0.395 | 41.731 | 1.00 | 17.18 |
| 11289 | O | TYR | B | 688 | 7.094 | -0.498 | 40.978 | 1.00 | 17.29 |
| 11290 | N | PHE | B | 689 | 8.745 | 0.501 | 42.143 | 1.00 | 16.38 |
| 11291 | CA | PHE | B | 689 | 9.718 | -0.494 | 41.787 | 1.00 | 15.97 |
| 11292 | CB | PHE | B | 689 | 11.096 | 0.080 | 41.905 | 1.00 | 15.41 |
| 11293 | CG | PHE | B | 689 | 11.491 | 0.936 | 40.774 | 1.00 | 15.54 |
| 11294 | CD1 | PHE | B | 689 | 12.075 | 0.399 | 39.669 | 1.00 | 12.97 |
| 11295 | CE1 | PHE | B | 689 | 12.466 | 1.211 | 38.630 | 1.00 | 16.88 |
| 11296 | CZ | PHE | B | 689 | 12.285 | 2.549 | 38.714 | 1.00 | 14.86 |
| 11297 | CE2 | PHE | B | 689 | 11.697 | 3.102 | 39.781 | 1.00 | 16.55 |
| 11298 | CD2 | PHE | B | 689 | 11.314 | 2.314 | 40.831 | 1.00 | 14.41 |
| 11299 | C | PHE | B | 689 | 9.653 | -1.766 | 42.677 | 1.00 | 16.69 |
| 11300 | O | PHE | B | 689 | 10.371 | -2.751 | 42.435 | 1.00 | 16.56 |
| 11301 | N | ARG | B | 690 | 8.844 | -1.734 | 43.710 | 1.00 | 16.62 |
| 11302 | CA | ARG | B | 690 | 8.854 | -2.835 | 44.665 | 1.00 | 18.42 |
| 11303 | CB | ARG | B | 690 | 7.989 | -2.553 | 45.884 | 1.00 | 18.06 |
| 11304 | CG | ARG | B | 690 | 7.984 | -3.798 | 46.898 | 1.00 | 19.85 |
| 11305 | CD | ARG | B | 690 | 7.785 | -3.493 | 48.388 | 1.00 | 20.58 |
| 11306 | NE | ARG | B | 690 | 7.325 | -2.118 | 48.543 | 1.00 | 22.64 |
| 11307 | CZ | ARG | B | 690 | 8.038 | -1.124 | 49.029 | 1.00 | 22.08 |
| 11308 | NH1 | ARG | B | 690 | 9.254 | -1.322 | 49.511 | 1.00 | 18.01 |
| 11309 | NH2 | ARG | B | 690 | 7.495 | 0.074 | 49.045 | 1.00 | 22.70 |
| 11310 | C | ARG | B | 690 | 8.468 | -4.221 | 44.075 | 1.00 | 19.59 |
| 11311 | O | ARG | B | 690 | 8.981 | -5.232 | 44.516 | 1.00 | 19.13 |
| 11312 | N | ASN | B | 691 | 7.611 | -4.330 | 43.083 | 1.00 | 20.04 |
| 11313 | CA | ASN | B | 691 | 7.328 | -5.722 | 42.653 | 1.00 | 21.21 |

FIGURE 3 (Cont.)

| A | B | C | D | E | F | G | H | I | J |
|---|---|---|---|---|---|---|---|---|---|
| 11314 | CB | ASN | B | 691 | 5.851 | -6.089 | 42.754 | 1.00 | 21.71 |
| 11315 | CG | ASN | B | 691 | 5.029 | -4.923 | 43.137 | 1.00 | 26.21 |
| 11316 | OD1 | ASN | B | 691 | 4.349 | -4.973 | 44.176 | 1.00 | 28.62 |
| 11317 | ND2 | ASN | B | 691 | 5.137 | -3.781 | 42.338 | 1.00 | 33.67 |
| 11318 | C | ASN | B | 691 | 7.852 | -5.977 | 41.275 | 1.00 | 19.91 |
| 11319 | O | ASN | B | 691 | 7.270 | -6.682 | 40.512 | 1.00 | 21.96 |
| 11320 | N | VAL | B | 692 | 8.992 | -5.432 | 40.974 | 1.00 | 18.39 |
| 11321 | CA | VAL | B | 692 | 9.622 | -5.711 | 39.710 | 1.00 | 16.73 |
| 11322 | CB | VAL | B | 692 | 9.278 | -4.618 | 38.745 | 1.00 | 17.91 |
| 11323 | CG1 | VAL | B | 692 | 9.743 | -3.237 | 39.292 | 1.00 | 15.84 |
| 11324 | CG2 | VAL | B | 692 | 7.744 | -4.659 | 38.405 | 1.00 | 17.63 |
| 11325 | C | VAL | B | 692 | 11.115 | -5.788 | 39.892 | 1.00 | 15.33 |
| 11326 | O | VAL | B | 692 | 11.665 | -5.303 | 40.850 | 1.00 | 14.25 |
| 11327 | N | ASP | B | 693 | 11.795 | -6.384 | 38.935 | 1.00 | 14.90 |
| 11328 | CA | ASP | B | 693 | 13.244 | -6.499 | 39.032 | 1.00 | 15.49 |
| 11329 | CB | ASP | B | 693 | 13.776 | -7.730 | 38.370 | 1.00 | 16.41 |
| 11330 | CG | ASP | B | 693 | 13.231 | -8.985 | 38.900 | 1.00 | 20.08 |
| 11331 | OD1 | ASP | B | 693 | 13.857 | -9.960 | 38.379 | 1.00 | 25.28 |
| 11332 | OD2 | ASP | B | 693 | 12.234 | -9.116 | 39.710 | 1.00 | 22.37 |
| 11333 | C | ASP | B | 693 | 13.835 | -5.434 | 38.199 | 1.00 | 13.89 |
| 11334 | O | ASP | B | 693 | 13.634 | -5.436 | 37.051 | 1.00 | 14.23 |
| 11335 | N | TYR | B | 694 | 14.609 | -4.590 | 38.804 | 1.00 | 13.45 |
| 11336 | CA | TYR | B | 694 | 15.220 | -3.466 | 38.165 | 1.00 | 13.21 |
| 11337 | CB | TYR | B | 694 | 14.946 | -2.259 | 39.041 | 1.00 | 12.96 |
| 11338 | CG | TYR | B | 694 | 15.330 | -0.981 | 38.467 | 1.00 | 13.72 |
| 11339 | CD1 | TYR | B | 694 | 15.242 | -0.748 | 37.130 | 1.00 | 14.38 |
| 11340 | CE1 | TYR | B | 694 | 15.559 | 0.474 | 36.624 | 1.00 | 10.56 |
| 11341 | CZ | TYR | B | 694 | 16.004 | 1.503 | 37.456 | 1.00 | 12.63 |
| 11342 | OH | TYR | B | 694 | 16.334 | 2.728 | 36.932 | 1.00 | 11.60 |
| 11343 | CE2 | TYR | B | 694 | 16.111 | 1.328 | 38.762 | 1.00 | 15.91 |
| 11344 | CD2 | TYR | B | 694 | 15.780 | 0.047 | 39.282 | 1.00 | 17.57 |
| 11345 | C | TYR | B | 694 | 16.685 | -3.757 | 38.108 | 1.00 | 12.65 |
| 11346 | O | TYR | B | 694 | 17.296 | -4.159 | 39.087 | 1.00 | 13.36 |
| 11347 | N | LEU | B | 695 | 17.297 | -3.597 | 36.968 | 1.00 | 13.05 |
| 11348 | CA | LEU | B | 695 | 18.758 | -3.693 | 36.972 | 1.00 | 12.92 |
| 11349 | CB | LEU | B | 695 | 19.192 | -4.834 | 36.111 | 1.00 | 11.78 |
| 11350 | CG | LEU | B | 695 | 20.642 | -4.803 | 35.597 | 1.00 | 12.96 |
| 11351 | CD1 | LEU | B | 695 | 21.687 | -4.993 | 36.693 | 1.00 | 3.65 |
| 11352 | CD2 | LEU | B | 695 | 20.676 | -5.937 | 34.626 | 1.00 | 13.12 |
| 11353 | C | LEU | B | 695 | 19.284 | -2.362 | 36.477 | 1.00 | 13.22 |
| 11354 | O | LEU | B | 695 | 18.892 | -1.893 | 35.464 | 1.00 | 13.37 |
| 11355 | N | LEU | B | 696 | 20.168 | -1.740 | 37.224 | 1.00 | 12.81 |
| 11356 | CA | LEU | B | 696 | 20.437 | -0.304 | 37.038 | 1.00 | 12.70 |
| 11357 | CB | LEU | B | 696 | 20.051 | 0.431 | 38.258 | 1.00 | 12.45 |
| 11358 | CG | LEU | B | 696 | 20.552 | 1.798 | 38.406 | 1.00 | 10.94 |
| 11359 | CD1 | LEU | B | 696 | 19.737 | 2.572 | 37.420 | 1.00 | 13.20 |
| 11360 | CD2 | LEU | B | 696 | 20.290 | 2.328 | 39.749 | 1.00 | 6.07 |
| 11361 | C | LEU | B | 696 | 21.911 | -0.164 | 36.975 | 1.00 | 13.18 |
| 11362 | O | LEU | B | 696 | 22.581 | -0.449 | 37.963 | 1.00 | 12.60 |
| 11363 | N | ILE | B | 697 | 22.379 | 0.393 | 35.838 | 1.00 | 14.52 |
| 11364 | CA | ILE | B | 697 | 23.761 | 0.354 | 35.409 | 1.00 | 15.51 |

FIGURE 3 (Cont.)

| A | B | C | D | E | F | G | H | I | J |
|---|---|---|---|---|---|---|---|---|---|
| 11365 | CB | ILE | B | 697 | 23.822 | -0.542 | 34.207 | 1.00 | 15.10 |
| 11366 | CG1 | ILE | B | 697 | 23.168 | -1.834 | 34.571 | 1.00 | 15.05 |
| 11367 | CD1 | ILE | B | 697 | 23.375 | -2.941 | 33.585 | 1.00 | 16.09 |
| 11368 | CG2 | ILE | B | 697 | 25.276 | -0.847 | 33.770 | 1.00 | 16.53 |
| 11369 | C | ILE | B | 697 | 24.256 | 1.764 | 35.108 | 1.00 | 15.66 |
| 11370 | O | ILE | B | 697 | 23.521 | 2.581 | 34.556 | 1.00 | 18.53 |
| 11371 | N | HIS | B | 698 | 25.473 | 2.067 | 35.492 | 1.00 | 15.16 |
| 11372 | CA | HIS | B | 698 | 26.091 | 3.307 | 35.051 | 1.00 | 14.44 |
| 11373 | CB | HIS | B | 698 | 25.563 | 4.343 | 35.910 | 1.00 | 13.92 |
| 11374 | CG | HIS | B | 698 | 25.283 | 5.642 | 35.254 | 1.00 | 14.08 |
| 11375 | ND1 | HIS | B | 698 | 24.124 | 6.319 | 35.544 | 1.00 | 14.40 |
| 11376 | CE1 | HIS | B | 698 | 24.148 | 7.518 | 34.972 | 1.00 | 9.32 |
| 11377 | NE2 | HIS | B | 698 | 25.295 | 7.643 | 34.320 | 1.00 | 13.56 |
| 11378 | CD2 | HIS | B | 698 | 26.059 | 6.509 | 34.540 | 1.00 | 16.81 |
| 11379 | C | HIS | B | 698 | 27.627 | 3.357 | 35.170 | 1.00 | 13.55 |
| 11380 | O | HIS | B | 698 | 28.292 | 2.742 | 36.070 | 1.00 | 15.04 |
| 11381 | N | GLY | B | 699 | 28.204 | 4.110 | 34.254 | 1.00 | 11.85 |
| 11382 | CA | GLY | B | 699 | 29.564 | 4.542 | 34.381 | 1.00 | 11.63 |
| 11383 | C | GLY | B | 699 | 29.833 | 5.555 | 35.429 | 1.00 | 10.24 |
| 11384 | O | GLY | B | 699 | 29.133 | 6.538 | 35.437 | 1.00 | 12.39 |
| 11385 | N | THR | B | 700 | 30.927 | 5.390 | 36.180 | 1.00 | 9.89 |
| 11386 | CA | THR | B | 700 | 31.272 | 6.344 | 37.202 | 1.00 | 9.96 |
| 11387 | CB | THR | B | 700 | 32.078 | 5.800 | 38.329 | 1.00 | 7.35 |
| 11388 | OG1 | THR | B | 700 | 33.373 | 5.474 | 37.898 | 1.00 | 8.78 |
| 11389 | CG2 | THR | B | 700 | 31.529 | 4.451 | 38.792 | 1.00 | 6.45 |
| 11390 | C | THR | B | 700 | 31.993 | 7.516 | 36.567 | 1.00 | 11.55 |
| 11391 | O | THR | B | 700 | 32.271 | 8.501 | 37.254 | 1.00 | 12.27 |
| 11392 | N | ALA | B | 701 | 32.224 | 7.532 | 35.276 | 1.00 | 12.07 |
| 11393 | CA | ALA | B | 701 | 32.835 | 8.795 | 34.717 | 1.00 | 13.95 |
| 11394 | CB | ALA | B | 701 | 34.370 | 8.660 | 34.567 | 1.00 | 13.57 |
| 11395 | C | ALA | B | 701 | 32.227 | 9.244 | 33.441 | 1.00 | 12.90 |
| 11396 | O | ALA | B | 701 | 32.915 | 9.455 | 32.463 | 1.00 | 14.83 |
| 11397 | N | ASP | B | 702 | 30.915 | 9.409 | 33.529 | 1.00 | 12.34 |
| 11398 | CA | ASP | B | 702 | 30.008 | 9.816 | 32.533 | 1.00 | 11.55 |
| 11399 | CB | ASP | B | 702 | 28.719 | 9.134 | 32.869 | 1.00 | 11.52 |
| 11400 | CG | ASP | B | 702 | 27.768 | 8.998 | 31.692 | 1.00 | 17.21 |
| 11401 | OD1 | ASP | B | 702 | 27.798 | 9.883 | 30.819 | 1.00 | 22.51 |
| 11402 | OD2 | ASP | B | 702 | 26.919 | 8.060 | 31.632 | 1.00 | 19.18 |
| 11403 | C | ASP | B | 702 | 29.928 | 11.315 | 32.704 | 1.00 | 13.12 |
| 11404 | O | ASP | B | 702 | 29.402 | 11.952 | 33.656 | 1.00 | 12.71 |
| 11405 | N | ASP | B | 703 | 30.523 | 11.914 | 31.729 | 1.00 | 14.30 |
| 11406 | CA | ASP | B | 703 | 30.661 | 13.295 | 31.698 | 1.00 | 15.29 |
| 11407 | CB | ASP | B | 703 | 31.884 | 13.562 | 30.849 | 1.00 | 15.67 |
| 11408 | CG | ASP | B | 703 | 31.746 | 12.943 | 29.427 | 1.00 | 19.77 |
| 11409 | OD1 | ASP | B | 703 | 32.081 | 11.688 | 29.140 | 1.00 | 20.07 |
| 11410 | OD2 | ASP | B | 703 | 31.282 | 13.730 | 28.552 | 1.00 | 22.66 |
| 11411 | C | ASP | B | 703 | 29.357 | 13.820 | 31.096 | 1.00 | 14.53 |
| 11412 | O | ASP | B | 703 | 29.112 | 14.975 | 31.158 | 1.00 | 15.56 |
| 11413 | N | ASN | B | 704 | 28.432 | 12.984 | 30.678 | 1.00 | 14.70 |
| 11414 | CA | ASN | B | 704 | 27.293 | 13.472 | 29.929 | 1.00 | 14.51 |
| 11415 | CB | ASN | B | 704 | 27.285 | 12.649 | 28.663 | 1.00 | 14.02 |

FIGURE 3 (Cont.)

| A | B | C | D | E | F | G | H | I | J |
|---|---|---|---|---|---|---|---|---|---|
| 11416 | CG | ASN | B | 704 | 26.281 | 13.081 | 27.650 | 1.00 | 23.00 |
| 11417 | OD1 | ASN | B | 704 | 25.361 | 13.980 | 27.865 | 1.00 | 19.88 |
| 11418 | ND2 | ASN | B | 704 | 26.405 | 12.402 | 26.488 | 1.00 | 27.03 |
| 11419 | C | ASN | B | 704 | 25.995 | 13.379 | 30.709 | 1.00 | 15.20 |
| 11420 | O | ASN | B | 704 | 25.400 | 14.451 | 31.073 | 1.00 | 14.57 |
| 11421 | N | VAL | B | 705 | 25.568 | 12.104 | 30.955 | 1.00 | 12.66 |
| 11422 | CA | VAL | B | 705 | 24.584 | 11.790 | 31.897 | 1.00 | 11.98 |
| 11423 | CB | VAL | B | 705 | 23.669 | 10.704 | 31.388 | 1.00 | 12.63 |
| 11424 | CG1 | VAL | B | 705 | 22.732 | 10.272 | 32.493 | 1.00 | 9.47 |
| 11425 | CG2 | VAL | B | 705 | 22.906 | 11.156 | 30.263 | 1.00 | 6.57 |
| 11426 | C | VAL | B | 705 | 25.338 | 11.373 | 33.186 | 1.00 | 13.72 |
| 11427 | O | VAL | B | 705 | 25.907 | 10.233 | 33.356 | 1.00 | 10.47 |
| 11428 | N | HIS | B | 706 | 25.329 | 12.308 | 34.141 | 1.00 | 14.20 |
| 11429 | CA | HIS | B | 706 | 26.251 | 12.153 | 35.300 | 1.00 | 14.11 |
| 11430 | CB | HIS | B | 706 | 26.289 | 13.423 | 36.066 | 1.00 | 13.13 |
| 11431 | CG | HIS | B | 706 | 26.730 | 14.562 | 35.239 | 1.00 | 14.38 |
| 11432 | ND1 | HIS | B | 706 | 27.573 | 14.396 | 34.176 | 1.00 | 16.51 |
| 11433 | CE1 | HIS | B | 706 | 27.842 | 15.582 | 33.639 | 1.00 | 15.92 |
| 11434 | NE2 | HIS | B | 706 | 27.133 | 16.498 | 34.282 | 1.00 | 20.93 |
| 11435 | CD2 | HIS | B | 706 | 26.453 | 15.886 | 35.304 | 1.00 | 16.10 |
| 11436 | C | HIS | B | 706 | 25.826 | 11.025 | 36.167 | 1.00 | 13.74 |
| 11437 | O | HIS | B | 706 | 24.673 | 10.788 | 36.304 | 1.00 | 14.12 |
| 11438 | N | PHE | B | 707 | 26.749 | 10.310 | 36.736 | 1.00 | 13.27 |
| 11439 | CA | PHE | B | 707 | 26.368 | 9.109 | 37.520 | 1.00 | 13.62 |
| 11440 | CB | PHE | B | 707 | 27.631 | 8.384 | 38.007 | 1.00 | 10.84 |
| 11441 | CG | PHE | B | 707 | 27.425 | 7.252 | 38.966 | 1.00 | 11.60 |
| 11442 | CD1 | PHE | B | 707 | 27.629 | 5.985 | 38.576 | 1.00 | 11.12 |
| 11443 | CE1 | PHE | B | 707 | 27.593 | 4.977 | 39.453 | 1.00 | 6.94 |
| 11444 | CZ | PHE | B | 707 | 27.332 | 5.190 | 40.719 | 1.00 | 2.95 |
| 11445 | CE2 | PHE | B | 707 | 27.281 | 6.409 | 41.166 | 1.00 | 6.87 |
| 11446 | CD2 | PHE | B | 707 | 27.391 | 7.459 | 40.306 | 1.00 | 9.61 |
| 11447 | C | PHE | B | 707 | 25.489 | 9.546 | 38.690 | 1.00 | 13.51 |
| 11448 | O | PHE | B | 707 | 24.751 | 8.750 | 39.176 | 1.00 | 11.81 |
| 11449 | N | GLN | B | 708 | 25.643 | 10.797 | 39.178 | 1.00 | 13.76 |
| 11450 | CA | GLN | B | 708 | 24.560 | 11.463 | 39.899 | 1.00 | 13.63 |
| 11451 | CB | GLN | B | 708 | 24.599 | 12.952 | 39.580 | 1.00 | 12.77 |
| 11452 | CG | GLN | B | 708 | 23.795 | 13.814 | 40.531 | 1.00 | 12.94 |
| 11453 | CD | GLN | B | 708 | 23.527 | 15.204 | 39.934 | 1.00 | 19.01 |
| 11454 | OE1 | GLN | B | 708 | 23.423 | 16.226 | 40.667 | 1.00 | 15.70 |
| 11455 | NE2 | GLN | B | 708 | 23.395 | 15.251 | 38.599 | 1.00 | 12.66 |
| 11456 | C | GLN | B | 708 | 23.184 | 10.813 | 39.498 | 1.00 | 14.94 |
| 11457 | O | GLN | B | 708 | 22.609 | 10.188 | 40.299 | 1.00 | 16.55 |
| 11458 | N | ASN | B | 709 | 22.696 | 10.908 | 38.253 | 1.00 | 14.19 |
| 11459 | CA | ASN | B | 709 | 21.327 | 10.435 | 37.991 | 1.00 | 14.70 |
| 11460 | CB | ASN | B | 709 | 20.921 | 10.459 | 36.459 | 1.00 | 14.12 |
| 11461 | CG | ASN | B | 709 | 21.131 | 11.836 | 35.792 | 1.00 | 16.23 |
| 11462 | OD1 | ASN | B | 709 | 22.261 | 12.173 | 35.504 | 1.00 | 12.09 |
| 11463 | ND2 | ASN | B | 709 | 20.057 | 12.632 | 35.589 | 1.00 | 12.90 |
| 11464 | C | ASN | B | 709 | 21.065 | 9.041 | 38.569 | 1.00 | 14.02 |
| 11465 | O | ASN | B | 709 | 19.992 | 8.767 | 39.020 | 1.00 | 11.11 |
| 11466 | N | SER | B | 710 | 22.050 | 8.151 | 38.484 | 1.00 | 13.62 |

FIGURE 3 (Cont.)

| A | B | C | D | E | F | G | H | I | J |
|---|---|---|---|---|---|---|---|---|---|
| 11467 | CA | SER | B | 710 | 21.839 | 6.773 | 39.001 | 1.00 | 13.57 |
| 11468 | CB | SER | B | 710 | 22.753 | 5.772 | 38.289 | 1.00 | 14.11 |
| 11469 | OG | SER | B | 710 | 22.263 | 5.248 | 37.077 | 1.00 | 15.11 |
| 11470 | C | SER | B | 710 | 22.033 | 6.694 | 40.506 | 1.00 | 11.84 |
| 11471 | O | SER | B | 710 | 21.289 | 5.973 | 41.259 | 1.00 | 14.44 |
| 11472 | N | ALA | B | 711 | 23.033 | 7.395 | 41.004 | 1.00 | 11.81 |
| 11473 | CA | ALA | B | 711 | 23.224 | 7.512 | 42.471 | 1.00 | 11.92 |
| 11474 | CB | ALA | B | 711 | 24.310 | 8.388 | 42.841 | 1.00 | 11.54 |
| 11475 | C | ALA | B | 711 | 21.963 | 7.952 | 43.220 | 1.00 | 12.54 |
| 11476 | O | ALA | B | 711 | 21.727 | 7.440 | 44.318 | 1.00 | 12.88 |
| 11477 | N | GLN | B | 712 | 21.165 | 8.848 | 42.630 | 1.00 | 11.19 |
| 11478 | CA | GLN | B | 712 | 19.978 | 9.304 | 43.273 | 1.00 | 9.32 |
| 11479 | CB | GLN | B | 712 | 19.514 | 10.709 | 42.712 | 1.00 | 9.05 |
| 11480 | CG | GLN | B | 712 | 20.491 | 11.914 | 42.871 | 1.00 | 8.92 |
| 11481 | CD | GLN | B | 712 | 20.564 | 12.417 | 44.290 | 1.00 | 13.14 |
| 11482 | OE1 | GLN | B | 712 | 20.083 | 11.763 | 45.135 | 1.00 | 14.07 |
| 11483 | NE2 | GLN | B | 712 | 21.210 | 13.595 | 44.549 | 1.00 | 17.00 |
| 11484 | C | GLN | B | 712 | 18.849 | 8.316 | 43.117 | 1.00 | 9.31 |
| 11485 | O | GLN | B | 712 | 17.961 | 8.232 | 43.981 | 1.00 | 7.05 |
| 11486 | N | ILE | B | 713 | 18.811 | 7.622 | 41.990 | 1.00 | 11.00 |
| 11487 | CA | ILE | B | 713 | 17.801 | 6.590 | 41.842 | 1.00 | 9.47 |
| 11488 | CB | ILE | B | 713 | 17.857 | 5.883 | 40.508 | 1.00 | 10.29 |
| 11489 | CG1 | ILE | B | 713 | 17.508 | 6.837 | 39.352 | 1.00 | 7.04 |
| 11490 | CD1 | ILE | B | 713 | 17.594 | 6.192 | 37.950 | 1.00 | 2.00 |
| 11491 | CG2 | ILE | B | 713 | 16.843 | 4.787 | 40.527 | 1.00 | 5.15 |
| 11492 | C | ILE | B | 713 | 18.014 | 5.592 | 42.966 | 1.00 | 10.49 |
| 11493 | O | ILE | B | 713 | 17.066 | 5.292 | 43.714 | 1.00 | 12.00 |
| 11494 | N | ALA | B | 714 | 19.275 | 5.159 | 43.136 | 1.00 | 11.03 |
| 11495 | CA | ALA | B | 714 | 19.633 | 3.977 | 43.931 | 1.00 | 10.12 |
| 11496 | CB | ALA | B | 714 | 21.131 | 3.717 | 43.903 | 1.00 | 8.81 |
| 11497 | C | ALA | B | 714 | 19.245 | 4.304 | 45.286 | 1.00 | 10.59 |
| 11498 | O | ALA | B | 714 | 18.803 | 3.399 | 46.004 | 1.00 | 11.56 |
| 11499 | N | LYS | B | 715 | 19.395 | 5.593 | 45.638 | 1.00 | 9.46 |
| 11500 | CA | LYS | B | 715 | 19.227 | 6.078 | 47.018 | 1.00 | 9.31 |
| 11501 | CB | LYS | B | 715 | 19.790 | 7.483 | 47.083 | 1.00 | 8.03 |
| 11502 | CG | LYS | B | 715 | 19.588 | 8.301 | 48.311 | 1.00 | 7.05 |
| 11503 | CD | LYS | B | 715 | 20.839 | 9.306 | 48.349 | 1.00 | 13.54 |
| 11504 | CE | LYS | B | 715 | 20.623 | 10.860 | 48.342 | 1.00 | 13.43 |
| 11505 | NZ | LYS | B | 715 | 19.282 | 11.304 | 48.586 | 1.00 | 11.08 |
| 11506 | C | LYS | B | 715 | 17.791 | 6.155 | 47.403 | 1.00 | 10.41 |
| 11507 | O | LYS | B | 715 | 17.412 | 6.049 | 48.592 | 1.00 | 11.53 |
| 11508 | N | ALA | B | 716 | 17.001 | 6.455 | 46.388 | 1.00 | 12.11 |
| 11509 | CA | ALA | B | 716 | 15.590 | 6.651 | 46.533 | 1.00 | 12.66 |
| 11510 | CB | ALA | B | 716 | 15.010 | 7.359 | 45.298 | 1.00 | 11.82 |
| 11511 | C | ALA | B | 716 | 15.042 | 5.279 | 46.686 | 1.00 | 11.73 |
| 11512 | O | ALA | B | 716 | 14.251 | 5.042 | 47.584 | 1.00 | 14.51 |
| 11513 | N | LEU | B | 717 | 15.547 | 4.313 | 45.940 | 1.00 | 11.55 |
| 11514 | CA | LEU | B | 717 | 15.094 | 2.928 | 46.192 | 1.00 | 9.64 |
| 11515 | CB | LEU | B | 717 | 15.600 | 1.948 | 45.137 | 1.00 | 10.30 |
| 11516 | CG | LEU | B | 717 | 15.336 | 2.195 | 43.655 | 1.00 | 15.42 |
| 11517 | CD1 | LEU | B | 717 | 15.720 | 0.939 | 42.890 | 1.00 | 21.19 |

FIGURE 3 (Cont.)

| A | B | C | D | E | F | G | H | I | J |
|---|---|---|---|---|---|---|---|---|---|
| 11518 | CD2 | LEU | B | 717 | 13.870 | 2.405 | 43.451 | 1.00 | 15.57 |
| 11519 | C | LEU | B | 717 | 15.501 | 2.447 | 47.577 | 1.00 | 7.83 |
| 11520 | O | LEU | B | 717 | 14.813 | 1.581 | 48.142 | 1.00 | 5.95 |
| 11521 | N | VAL | B | 718 | 16.620 | 2.970 | 48.116 | 1.00 | 5.14 |
| 11522 | CA | VAL | B | 718 | 17.043 | 2.519 | 49.381 | 1.00 | 4.86 |
| 11523 | CB | VAL | B | 718 | 18.547 | 2.722 | 49.709 | 1.00 | 5.78 |
| 11524 | CG1 | VAL | B | 718 | 18.853 | 2.511 | 51.222 | 1.00 | 2.27 |
| 11525 | CG2 | VAL | B | 718 | 19.403 | 1.744 | 48.942 | 1.00 | 2.41 |
| 11526 | C | VAL | B | 718 | 16.143 | 3.105 | 50.369 | 1.00 | 6.68 |
| 11527 | O | VAL | B | 718 | 15.757 | 2.398 | 51.279 | 1.00 | 6.15 |
| 11528 | N | ASN | B | 719 | 15.729 | 4.348 | 50.185 | 1.00 | 9.61 |
| 11529 | CA | ASN | B | 719 | 14.800 | 4.951 | 51.104 | 1.00 | 10.97 |
| 11530 | CB | ASN | B | 719 | 14.703 | 6.484 | 51.004 | 1.00 | 11.86 |
| 11531 | CG | ASN | B | 719 | 16.051 | 7.176 | 51.186 | 1.00 | 14.93 |
| 11532 | OD1 | ASN | B | 719 | 16.205 | 8.371 | 50.827 | 1.00 | 14.01 |
| 11533 | ND2 | ASN | B | 719 | 17.043 | 6.434 | 51.693 | 1.00 | 17.69 |
| 11534 | C | ASN | B | 719 | 13.425 | 4.365 | 51.035 | 1.00 | 10.03 |
| 11535 | O | ASN | B | 719 | 12.702 | 4.360 | 52.035 | 1.00 | 9.56 |
| 11536 | N | ALA | B | 720 | 13.057 | 3.852 | 49.895 | 1.00 | 9.84 |
| 11537 | CA | ALA | B | 720 | 11.747 | 3.181 | 49.760 | 1.00 | 8.79 |
| 11538 | CB | ALA | B | 720 | 11.374 | 3.126 | 48.311 | 1.00 | 8.04 |
| 11539 | C | ALA | B | 720 | 11.822 | 1.787 | 50.311 | 1.00 | 8.29 |
| 11540 | O | ALA | B | 720 | 10.871 | 1.077 | 50.380 | 1.00 | 9.04 |
| 11541 | N | GLN | B | 721 | 13.005 | 1.375 | 50.703 | 1.00 | 9.12 |
| 11542 | CA | GLN | B | 721 | 13.237 | 0.007 | 51.129 | 1.00 | 8.89 |
| 11543 | CB | GLN | B | 721 | 12.511 | -0.288 | 52.390 | 1.00 | 9.26 |
| 11544 | CG | GLN | B | 721 | 13.141 | 0.178 | 53.634 | 1.00 | 7.91 |
| 11545 | CD | GLN | B | 721 | 12.215 | -0.206 | 54.764 | 1.00 | 10.30 |
| 11546 | OE1 | GLN | B | 721 | 11.348 | 0.576 | 55.120 | 1.00 | 9.61 |
| 11547 | NE2 | GLN | B | 721 | 12.363 | -1.439 | 55.296 | 1.00 | 11.42 |
| 11548 | C | GLN | B | 721 | 12.895 | -1.013 | 50.014 | 1.00 | 8.74 |
| 11549 | O | GLN | B | 721 | 12.398 | -2.093 | 50.259 | 1.00 | 8.35 |
| 11550 | N | VAL | B | 722 | 13.320 | -0.649 | 48.809 | 1.00 | 6.78 |
| 11551 | CA | VAL | B | 722 | 13.107 | -1.403 | 47.606 | 1.00 | 6.68 |
| 11552 | CB | VAL | B | 722 | 12.477 | -0.509 | 46.513 | 1.00 | 4.72 |
| 11553 | CG1 | VAL | B | 722 | 12.517 | -1.168 | 45.136 | 1.00 | 2.00 |
| 11554 | CG2 | VAL | B | 722 | 10.967 | -0.139 | 46.917 | 1.00 | 2.28 |
| 11555 | C | VAL | B | 722 | 14.397 | -2.009 | 47.130 | 1.00 | 7.76 |
| 11556 | O | VAL | B | 722 | 15.338 | -1.275 | 46.878 | 1.00 | 9.65 |
| 11557 | N | ASP | B | 723 | 14.393 | -3.321 | 46.951 | 1.00 | 9.51 |
| 11558 | CA | ASP | B | 723 | 15.491 | -4.068 | 46.444 | 1.00 | 12.57 |
| 11559 | CB | ASP | B | 723 | 15.228 | -5.520 | 46.714 | 1.00 | 13.79 |
| 11560 | CG | ASP | B | 723 | 16.467 | -6.400 | 46.491 | 1.00 | 16.84 |
| 11561 | OD1 | ASP | B | 723 | 16.233 | -7.615 | 46.235 | 1.00 | 25.78 |
| 11562 | OD2 | ASP | B | 723 | 17.650 | -6.011 | 46.582 | 1.00 | 14.05 |
| 11563 | C | ASP | B | 723 | 15.544 | -3.894 | 44.958 | 1.00 | 13.78 |
| 11564 | O | ASP | B | 723 | 14.490 | -3.734 | 44.310 | 1.00 | 15.14 |
| 11565 | N | PHE | B | 724 | 16.767 | -3.894 | 44.420 | 1.00 | 13.52 |
| 11566 | CA | PHE | B | 724 | 16.990 | -3.946 | 42.966 | 1.00 | 13.71 |
| 11567 | CB | PHE | B | 724 | 16.964 | -2.568 | 42.365 | 1.00 | 12.51 |
| 11568 | CG | PHE | B | 724 | 17.916 | -1.615 | 42.992 | 1.00 | 11.00 |

FIGURE 3 (Cont.)

| A | B | C | D | E | F | G | H | I | J |
|---|---|---|---|---|---|---|---|---|---|
| 11569 | CD1 | PHE | B | 724 | 17.681 | -1.114 | 44.251 | 1.00 | 13.45 |
| 11570 | CE1 | PHE | B | 724 | 18.533 | -0.219 | 44.862 | 1.00 | 14.16 |
| 11571 | CZ | PHE | B | 724 | 19.593 | 0.255 | 44.155 | 1.00 | 17.50 |
| 11572 | CE2 | PHE | B | 724 | 19.798 | -0.217 | 42.878 | 1.00 | 16.26 |
| 11573 | CD2 | PHE | B | 724 | 18.959 | -1.179 | 42.325 | 1.00 | 12.29 |
| 11574 | C | PHE | B | 724 | 18.362 | -4.439 | 42.726 | 1.00 | 14.33 |
| 11575 | O | PHE | B | 724 | 19.100 | -4.473 | 43.686 | 1.00 | 15.03 |
| 11576 | N | GLN | B | 725 | 18.724 | -4.747 | 41.468 | 1.00 | 13.24 |
| 11577 | CA | GLN | B | 725 | 20.122 | -4.910 | 41.100 | 1.00 | 12.28 |
| 11578 | CB | GLN | B | 725 | 20.355 | -6.100 | 40.245 | 1.00 | 11.84 |
| 11579 | CG | GLN | B | 725 | 20.322 | -7.450 | 41.119 | 1.00 | 15.35 |
| 11580 | CD | GLN | B | 725 | 18.893 | -7.900 | 41.213 | 1.00 | 19.66 |
| 11581 | OE1 | GLN | B | 725 | 18.335 | -8.098 | 42.289 | 1.00 | 17.07 |
| 11582 | NE2 | GLN | B | 725 | 18.250 | -7.922 | 40.061 | 1.00 | 21.21 |
| 11583 | C | GLN | B | 725 | 20.836 | -3.685 | 40.509 | 1.00 | 12.56 |
| 11584 | O | GLN | B | 725 | 20.239 | -2.703 | 39.948 | 1.00 | 13.69 |
| 11585 | N | ALA | B | 726 | 22.135 | -3.713 | 40.713 | 1.00 | 10.75 |
| 11586 | CA | ALA | B | 726 | 22.937 | -2.685 | 40.221 | 1.00 | 11.09 |
| 11587 | CB | ALA | B | 726 | 23.166 | -1.703 | 41.319 | 1.00 | 11.34 |
| 11588 | C | ALA | B | 726 | 24.271 | -3.272 | 39.663 | 1.00 | 11.47 |
| 11589 | O | ALA | B | 726 | 24.611 | -4.502 | 39.883 | 1.00 | 11.24 |
| 11590 | N | MET | B | 727 | 24.893 | -2.416 | 38.868 | 1.00 | 10.29 |
| 11591 | CA | MET | B | 727 | 26.281 | -2.519 | 38.409 | 1.00 | 10.93 |
| 11592 | CB | MET | B | 727 | 26.276 | -3.370 | 37.197 | 1.00 | 10.23 |
| 11593 | CG | MET | B | 727 | 27.543 | -3.384 | 36.483 | 1.00 | 11.46 |
| 11594 | SD | MET | B | 727 | 28.809 | -4.115 | 37.485 | 1.00 | 15.13 |
| 11595 | CE | MET | B | 727 | 28.309 | -5.824 | 37.745 | 1.00 | 11.22 |
| 11596 | C | MET | B | 727 | 26.860 | -1.061 | 38.041 | 1.00 | 9.98 |
| 11597 | O | MET | B | 727 | 26.134 | -0.242 | 37.482 | 1.00 | 10.16 |
| 11598 | N | TRP | B | 728 | 28.078 | -0.737 | 38.488 | 1.00 | 9.93 |
| 11599 | CA | TRP | B | 728 | 28.728 | 0.481 | 38.079 | 1.00 | 11.09 |
| 11600 | CB | TRP | B | 728 | 29.231 | 1.404 | 39.275 | 1.00 | 10.17 |
| 11601 | CG | TRP | B | 728 | 30.447 | 0.825 | 40.002 | 1.00 | 8.20 |
| 11602 | CD1 | TRP | B | 728 | 31.770 | 1.053 | 39.711 | 1.00 | 9.20 |
| 11603 | NE1 | TRP | B | 728 | 32.582 | 0.319 | 40.548 | 1.00 | 10.29 |
| 11604 | CE2 | TRP | B | 728 | 31.771 | -0.385 | 41.417 | 1.00 | 11.63 |
| 11605 | CD2 | TRP | B | 728 | 30.440 | -0.061 | 41.125 | 1.00 | 7.45 |
| 11606 | CE3 | TRP | B | 728 | 29.432 | -0.636 | 41.921 | 1.00 | 8.09 |
| 11607 | CZ3 | TRP | B | 728 | 29.767 | -1.490 | 42.905 | 1.00 | 2.66 |
| 11608 | CH2 | TRP | B | 728 | 31.072 | -1.772 | 43.154 | 1.00 | 5.88 |
| 11609 | CZ2 | TRP | B | 728 | 32.090 | -1.217 | 42.438 | 1.00 | 5.65 |
| 11610 | C | TRP | B | 728 | 29.902 | 0.045 | 37.238 | 1.00 | 12.50 |
| 11611 | O | TRP | B | 728 | 30.404 | -1.154 | 37.377 | 1.00 | 11.78 |
| 11612 | N | TYR | B | 729 | 30.390 | 1.036 | 36.435 | 1.00 | 12.05 |
| 11613 | CA | TYR | B | 729 | 31.524 | 0.747 | 35.578 | 1.00 | 12.90 |
| 11614 | CB | TYR | B | 729 | 31.093 | 0.602 | 34.098 | 1.00 | 10.99 |
| 11615 | CG | TYR | B | 729 | 30.457 | -0.759 | 33.805 | 1.00 | 13.36 |
| 11616 | CD1 | TYR | B | 729 | 29.076 | -0.890 | 33.771 | 1.00 | 10.42 |
| 11617 | CE1 | TYR | B | 729 | 28.490 | -2.057 | 33.528 | 1.00 | 8.83 |
| 11618 | CZ | TYR | B | 729 | 29.211 | -3.135 | 33.317 | 1.00 | 9.46 |
| 11619 | OH | TYR | B | 729 | 28.483 | -4.298 | 33.203 | 1.00 | 15.32 |

FIGURE 3 (Cont.)

| A | B | C | D | E | F | G | H | I | J |
|---|---|---|---|---|---|---|---|---|---|
| 11620 | CE2 | TYR | B | 729 | 30.585 | -3.099 | 33.400 | 1.00 | 8.97 |
| 11621 | CD2 | TYR | B | 729 | 31.203 | -1.913 | 33.643 | 1.00 | 7.06 |
| 11622 | C | TYR | B | 729 | 32.670 | 1.709 | 35.900 | 1.00 | 13.57 |
| 11623 | O | TYR | B | 729 | 32.555 | 2.945 | 35.818 | 1.00 | 14.52 |
| 11624 | N | SER | B | 730 | 33.772 | 1.152 | 36.393 | 1.00 | 12.93 |
| 11625 | CA | SER | B | 730 | 34.675 | 2.034 | 37.044 | 1.00 | 12.67 |
| 11626 | CB | SER | B | 730 | 35.633 | 1.275 | 37.983 | 1.00 | 14.00 |
| 11627 | OG | SER | B | 730 | 35.000 | 0.605 | 39.087 | 1.00 | 13.79 |
| 11628 | C | SER | B | 730 | 35.372 | 2.785 | 35.886 | 1.00 | 13.23 |
| 11629 | O | SER | B | 730 | 35.790 | 2.148 | 34.940 | 1.00 | 10.63 |
| 11630 | N | ASP | B | 731 | 35.369 | 4.124 | 35.921 | 1.00 | 12.93 |
| 11631 | CA | ASP | B | 731 | 36.116 | 4.963 | 34.936 | 1.00 | 13.41 |
| 11632 | CB | ASP | B | 731 | 37.637 | 4.614 | 34.891 | 1.00 | 11.63 |
| 11633 | CG | ASP | B | 731 | 38.358 | 4.935 | 36.201 | 1.00 | 12.88 |
| 11634 | OD1 | ASP | B | 731 | 37.824 | 5.837 | 36.973 | 1.00 | 10.45 |
| 11635 | OD2 | ASP | B | 731 | 39.421 | 4.281 | 36.524 | 1.00 | 16.89 |
| 11636 | C | ASP | B | 731 | 35.546 | 4.966 | 33.486 | 1.00 | 13.88 |
| 11637 | O | ASP | B | 731 | 36.132 | 5.549 | 32.515 | 1.00 | 13.79 |
| 11638 | N | GLN | B | 732 | 34.395 | 4.346 | 33.330 | 1.00 | 13.02 |
| 11639 | CA | GLN | B | 732 | 33.762 | 4.370 | 32.054 | 1.00 | 13.16 |
| 11640 | CB | GLN | B | 732 | 32.973 | 3.116 | 31.837 | 1.00 | 10.78 |
| 11641 | CG | GLN | B | 732 | 33.790 | 1.828 | 31.956 | 1.00 | 10.11 |
| 11642 | CD | GLN | B | 732 | 35.272 | 1.892 | 31.360 | 1.00 | 11.12 |
| 11643 | OE1 | GLN | B | 732 | 36.236 | 1.896 | 32.089 | 1.00 | 13.54 |
| 11644 | NE2 | GLN | B | 732 | 35.397 | 1.922 | 30.085 | 1.00 | 9.25 |
| 11645 | C | GLN | B | 732 | 32.874 | 5.581 | 31.997 | 1.00 | 16.23 |
| 11646 | O | GLN | B | 732 | 32.544 | 6.214 | 33.004 | 1.00 | 17.88 |
| 11647 | N | ASN | B | 733 | 32.442 | 5.859 | 30.767 | 1.00 | 18.03 |
| 11648 | CA | ASN | B | 733 | 31.780 | 7.036 | 30.376 | 1.00 | 16.52 |
| 11649 | CB | ASN | B | 733 | 32.729 | 7.759 | 29.448 | 1.00 | 17.23 |
| 11650 | CG | ASN | B | 733 | 32.823 | 7.134 | 28.045 | 1.00 | 17.93 |
| 11651 | OD1 | ASN | B | 733 | 33.495 | 7.681 | 27.257 | 1.00 | 20.55 |
| 11652 | ND2 | ASN | B | 733 | 32.167 | 6.011 | 27.752 | 1.00 | 22.44 |
| 11653 | C | ASN | B | 733 | 30.392 | 6.666 | 29.736 | 1.00 | 17.88 |
| 11654 | O | ASN | B | 733 | 29.932 | 5.497 | 29.821 | 1.00 | 15.74 |
| 11655 | N | HIS | B | 734 | 29.713 | 7.648 | 29.117 | 1.00 | 17.94 |
| 11656 | CA | HIS | B | 734 | 28.369 | 7.358 | 28.651 | 1.00 | 18.17 |
| 11657 | CB | HIS | B | 734 | 27.732 | 8.538 | 28.013 | 1.00 | 17.49 |
| 11658 | CG | HIS | B | 734 | 26.255 | 8.454 | 27.996 | 1.00 | 14.06 |
| 11659 | ND1 | HIS | B | 734 | 25.541 | 8.113 | 29.104 | 1.00 | 17.39 |
| 11660 | CE1 | HIS | B | 734 | 24.243 | 8.183 | 28.827 | 1.00 | 17.02 |
| 11661 | NE2 | HIS | B | 734 | 24.102 | 8.556 | 27.571 | 1.00 | 15.21 |
| 11662 | CD2 | HIS | B | 734 | 25.353 | 8.767 | 27.043 | 1.00 | 19.28 |
| 11663 | C | HIS | B | 734 | 28.316 | 6.186 | 27.662 | 1.00 | 18.98 |
| 11664 | O | HIS | B | 734 | 27.342 | 5.487 | 27.604 | 1.00 | 20.88 |
| 11665 | N | GLY | B | 735 | 29.366 | 5.959 | 26.912 | 1.00 | 20.04 |
| 11666 | CA | GLY | B | 735 | 29.431 | 4.868 | 25.927 | 1.00 | 20.57 |
| 11667 | C | GLY | B | 735 | 29.762 | 3.505 | 26.504 | 1.00 | 21.08 |
| 11668 | O | GLY | B | 735 | 29.537 | 2.521 | 25.899 | 1.00 | 21.57 |
| 11669 | N | LEU | B | 736 | 30.292 | 3.435 | 27.691 | 1.00 | 20.40 |
| 11670 | CA | LEU | B | 736 | 30.612 | 2.142 | 28.260 | 1.00 | 20.75 |

FIGURE 3 (Cont.)

| A | B | C | D | E | F | G | H | I | J |
|---|---|---|---|---|---|---|---|---|---|
| 11671 | CB | LEU | B | 736 | 29.321 | 1.454 | 28.635 | 1.00 | 21.08 |
| 11672 | CG | LEU | B | 736 | 28.526 | 2.044 | 29.802 | 1.00 | 22.39 |
| 11673 | CD1 | LEU | B | 736 | 27.740 | 0.872 | 30.374 | 1.00 | 24.89 |
| 11674 | CD2 | LEU | B | 736 | 29.467 | 2.653 | 30.876 | 1.00 | 22.79 |
| 11675 | C | LEU | B | 736 | 31.401 | 1.331 | 27.283 | 1.00 | 20.93 |
| 11676 | O | LEU | B | 736 | 31.112 | 0.208 | 26.967 | 1.00 | 21.16 |
| 11677 | N | SER | B | 737 | 32.444 | 1.948 | 26.807 | 1.00 | 21.37 |
| 11678 | CA | SER | B | 737 | 33.223 | 1.447 | 25.682 | 1.00 | 21.15 |
| 11679 | CB | SER | B | 737 | 33.990 | 2.619 | 25.140 | 1.00 | 20.85 |
| 11680 | OG | SER | B | 737 | 34.113 | 2.300 | 23.791 | 1.00 | 24.66 |
| 11681 | C | SER | B | 737 | 34.230 | 0.367 | 26.025 | 1.00 | 19.52 |
| 11682 | O | SER | B | 737 | 34.365 | 0.027 | 27.118 | 1.00 | 19.94 |
| 11683 | N | GLY | B | 738 | 34.984 | -0.130 | 25.106 | 1.00 | 18.63 |
| 11684 | CA | GLY | B | 738 | 36.008 | -1.111 | 25.466 | 1.00 | 18.55 |
| 11685 | C | GLY | B | 738 | 35.436 | -2.425 | 26.015 | 1.00 | 17.97 |
| 11686 | O | GLY | B | 738 | 34.307 | -2.821 | 25.602 | 1.00 | 18.14 |
| 11687 | N | LEU | B | 739 | 36.157 | -3.083 | 26.941 | 1.00 | 16.87 |
| 11688 | CA | LEU | B | 739 | 35.625 | -4.340 | 27.519 | 1.00 | 16.10 |
| 11689 | CB | LEU | B | 739 | 36.647 | -5.201 | 28.199 | 1.00 | 16.39 |
| 11690 | CG | LEU | B | 739 | 37.950 | -5.604 | 27.481 | 1.00 | 16.61 |
| 11691 | CD1 | LEU | B | 739 | 38.935 | -6.024 | 28.495 | 1.00 | 13.01 |
| 11692 | CD2 | LEU | B | 739 | 37.783 | -6.758 | 26.501 | 1.00 | 18.57 |
| 11693 | C | LEU | B | 739 | 34.459 | -4.130 | 28.471 | 1.00 | 14.83 |
| 11694 | O | LEU | B | 739 | 33.820 | -5.071 | 28.830 | 1.00 | 15.35 |
| 11695 | N | SER | B | 740 | 34.149 | -2.909 | 28.855 | 1.00 | 12.82 |
| 11696 | CA | SER | B | 740 | 32.896 | -2.695 | 29.596 | 1.00 | 11.93 |
| 11697 | CB | SER | B | 740 | 32.838 | -1.229 | 30.024 | 1.00 | 10.26 |
| 11698 | OG | SER | B | 740 | 34.081 | -0.949 | 30.719 | 1.00 | 14.33 |
| 11699 | C | SER | B | 740 | 31.631 | -3.147 | 28.763 | 1.00 | 11.17 |
| 11700 | O | SER | B | 740 | 30.694 | -3.719 | 29.256 | 1.00 | 10.24 |
| 11701 | N | THR | B | 741 | 31.615 | -2.908 | 27.495 | 1.00 | 10.14 |
| 11702 | CA | THR | B | 741 | 30.538 | -3.371 | 26.665 | 1.00 | 10.24 |
| 11703 | CB | THR | B | 741 | 30.975 | -3.029 | 25.245 | 1.00 | 11.50 |
| 11704 | OG1 | THR | B | 741 | 31.231 | -1.598 | 25.107 | 1.00 | 13.95 |
| 11705 | CG2 | THR | B | 741 | 29.933 | -3.390 | 24.178 | 1.00 | 12.16 |
| 11706 | C | THR | B | 741 | 30.376 | -4.891 | 26.824 | 1.00 | 10.62 |
| 11707 | O | THR | B | 741 | 29.288 | -5.437 | 27.041 | 1.00 | 10.18 |
| 11708 | N | ASN | B | 742 | 31.489 | -5.592 | 26.678 | 1.00 | 8.78 |
| 11709 | CA | ASN | B | 742 | 31.454 | -6.997 | 26.750 | 1.00 | 9.58 |
| 11710 | CB | ASN | B | 742 | 32.919 | -7.601 | 26.785 | 1.00 | 10.74 |
| 11711 | CG | ASN | B | 742 | 33.575 | -7.601 | 25.410 | 1.00 | 9.13 |
| 11712 | OD1 | ASN | B | 742 | 33.681 | -6.541 | 24.746 | 1.00 | 7.47 |
| 11713 | ND2 | ASN | B | 742 | 33.995 | -8.790 | 24.972 | 1.00 | 2.02 |
| 11714 | C | ASN | B | 742 | 30.757 | -7.342 | 28.002 | 1.00 | 10.21 |
| 11715 | O | ASN | B | 742 | 29.837 | -8.131 | 28.052 | 1.00 | 11.79 |
| 11716 | N | HIS | B | 743 | 31.226 | -6.748 | 29.050 | 1.00 | 9.63 |
| 11717 | CA | HIS | B | 743 | 30.723 | -7.053 | 30.365 | 1.00 | 10.43 |
| 11718 | CB | HIS | B | 743 | 31.638 | -6.360 | 31.323 | 1.00 | 10.87 |
| 11719 | CG | HIS | B | 743 | 31.453 | -6.771 | 32.722 | 1.00 | 12.25 |
| 11720 | ND1 | HIS | B | 743 | 32.512 | -7.089 | 33.531 | 1.00 | 14.51 |
| 11721 | CE1 | HIS | B | 743 | 32.053 | -7.420 | 34.723 | 1.00 | 15.10 |

FIGURE 3 (Cont.)

| A | B | C | D | E | F | G | H | I | J |
|---|---|---|---|---|---|---|---|---|---|
| 11722 | NE2 | HIS | B | 743 | 30.740 | -7.263 | 34.719 | 1.00 | 12.77 |
| 11723 | CD2 | HIS | B | 743 | 30.345 | -6.846 | 33.482 | 1.00 | 11.08 |
| 11724 | C | HIS | B | 743 | 29.264 | -6.613 | 30.524 | 1.00 | 9.83 |
| 11725 | O | HIS | B | 743 | 28.446 | -7.320 | 31.005 | 1.00 | 8.46 |
| 11726 | N | LEU | B | 744 | 28.926 | -5.423 | 30.080 | 1.00 | 9.96 |
| 11727 | CA | LEU | B | 744 | 27.601 | -4.988 | 30.245 | 1.00 | 8.54 |
| 11728 | CB | LEU | B | 744 | 27.429 | -3.668 | 29.606 | 1.00 | 8.03 |
| 11729 | CG | LEU | B | 744 | 26.034 | -3.366 | 29.128 | 1.00 | 7.55 |
| 11730 | CD1 | LEU | B | 744 | 25.140 | -3.127 | 30.238 | 1.00 | 2.88 |
| 11731 | CD2 | LEU | B | 744 | 26.122 | -2.118 | 28.302 | 1.00 | 7.55 |
| 11732 | C | LEU | B | 744 | 26.637 | -6.054 | 29.627 | 1.00 | 10.41 |
| 11733 | O | LEU | B | 744 | 25.592 | -6.290 | 30.204 | 1.00 | 11.61 |
| 11734 | N | TYR | B | 745 | 26.925 | -6.656 | 28.468 | 1.00 | 9.86 |
| 11735 | CA | TYR | B | 745 | 25.818 | -7.276 | 27.775 | 1.00 | 10.34 |
| 11736 | CB | TYR | B | 745 | 26.033 | -7.300 | 26.244 | 1.00 | 10.38 |
| 11737 | CG | TYR | B | 745 | 25.737 | -5.971 | 25.570 | 1.00 | 12.97 |
| 11738 | CD1 | TYR | B | 745 | 26.765 | -5.082 | 25.223 | 1.00 | 14.81 |
| 11739 | CE1 | TYR | B | 745 | 26.471 | -3.881 | 24.626 | 1.00 | 13.08 |
| 11740 | CZ | TYR | B | 745 | 25.141 | -3.576 | 24.336 | 1.00 | 9.88 |
| 11741 | OH | TYR | B | 745 | 24.851 | -2.380 | 23.773 | 1.00 | 13.96 |
| 11742 | CE2 | TYR | B | 745 | 24.139 | -4.421 | 24.659 | 1.00 | 7.34 |
| 11743 | CD2 | TYR | B | 745 | 24.410 | -5.566 | 25.293 | 1.00 | 13.25 |
| 11744 | C | TYR | B | 745 | 25.690 | -8.680 | 28.364 | 1.00 | 11.20 |
| 11745 | O | TYR | B | 745 | 24.680 | -9.374 | 28.249 | 1.00 | 11.87 |
| 11746 | N | THR | B | 746 | 26.773 | -9.122 | 28.967 | 1.00 | 11.58 |
| 11747 | CA | THR | B | 746 | 26.856 | -10.440 | 29.468 | 1.00 | 10.50 |
| 11748 | CB | THR | B | 746 | 28.315 | -10.827 | 29.649 | 1.00 | 10.07 |
| 11749 | OG1 | THR | B | 746 | 29.090 | -10.204 | 28.611 | 1.00 | 8.64 |
| 11750 | CG2 | THR | B | 746 | 28.562 | -12.404 | 29.384 | 1.00 | 10.11 |
| 11751 | C | THR | B | 746 | 26.035 | -10.355 | 30.718 | 1.00 | 10.57 |
| 11752 | O | THR | B | 746 | 25.317 | -11.277 | 30.991 | 1.00 | 12.47 |
| 11753 | N | HIS | B | 747 | 26.052 | -9.234 | 31.419 | 1.00 | 10.49 |
| 11754 | CA | HIS | B | 747 | 25.280 | -8.999 | 32.710 | 1.00 | 10.75 |
| 11755 | CB | HIS | B | 747 | 25.920 | -7.848 | 33.525 | 1.00 | 9.07 |
| 11756 | CG | HIS | B | 747 | 25.589 | -7.850 | 34.998 | 1.00 | 11.68 |
| 11757 | ND1 | HIS | B | 747 | 24.576 | -7.075 | 35.537 | 1.00 | 13.18 |
| 11758 | CE1 | HIS | B | 747 | 24.480 | -7.284 | 36.837 | 1.00 | 6.67 |
| 11759 | NE2 | HIS | B | 747 | 25.436 | -8.132 | 37.180 | 1.00 | 13.10 |
| 11760 | CD2 | HIS | B | 747 | 26.110 | -8.540 | 36.046 | 1.00 | 12.70 |
| 11761 | C | HIS | B | 747 | 23.740 | -8.751 | 32.453 | 1.00 | 11.23 |
| 11762 | O | HIS | B | 747 | 22.887 | -9.348 | 33.109 | 1.00 | 14.12 |
| 11763 | N | MET | B | 748 | 23.406 | -7.947 | 31.463 | 1.00 | 11.12 |
| 11764 | CA | MET | B | 748 | 22.026 | -7.750 | 30.989 | 1.00 | 10.93 |
| 11765 | CB | MET | B | 748 | 21.963 | -6.771 | 29.875 | 1.00 | 8.85 |
| 11766 | CG | MET | B | 748 | 22.702 | -5.469 | 30.208 | 1.00 | 12.68 |
| 11767 | SD | MET | B | 748 | 22.086 | -4.107 | 29.144 | 1.00 | 19.32 |
| 11768 | CE | MET | B | 748 | 20.722 | -4.099 | 29.701 | 1.00 | 6.93 |
| 11769 | C | MET | B | 748 | 21.506 | -9.066 | 30.493 | 1.00 | 10.49 |
| 11770 | O | MET | B | 748 | 20.378 | -9.407 | 30.789 | 1.00 | 10.55 |
| 11771 | N | THR | B | 749 | 22.358 | -9.826 | 29.825 | 1.00 | 9.52 |
| 11772 | CA | THR | B | 749 | 21.885 | -11.068 | 29.279 | 1.00 | 8.80 |

FIGURE 3 (Cont.)

| A | B | C | D | E | F | G | H | I | J |
|---|---|---|---|---|---|---|---|---|---|
| 11773 | CB | THR | B | 749 | 22.917 | -11.825 | 28.375 | 1.00 | 7.82 |
| 11774 | OG1 | THR | B | 749 | 23.280 | -11.006 | 27.268 | 1.00 | 6.79 |
| 11775 | CG2 | THR | B | 749 | 22.266 | -13.007 | 27.753 | 1.00 | 2.00 |
| 11776 | C | THR | B | 749 | 21.431 | -11.977 | 30.422 | 1.00 | 9.33 |
| 11777 | O | THR | B | 749 | 20.359 | -12.545 | 30.385 | 1.00 | 9.25 |
| 11778 | N | HIS | B | 750 | 22.243 | -12.047 | 31.454 | 1.00 | 11.23 |
| 11779 | CA | HIS | B | 750 | 21.987 | -12.951 | 32.580 | 1.00 | 12.28 |
| 11780 | CB | HIS | B | 750 | 23.198 | -12.968 | 33.552 | 1.00 | 13.08 |
| 11781 | CG | HIS | B | 750 | 24.323 | -13.855 | 33.106 | 1.00 | 16.16 |
| 11782 | ND1 | HIS | B | 750 | 24.125 | -14.998 | 32.359 | 1.00 | 21.80 |
| 11783 | CE1 | HIS | B | 750 | 25.295 | -15.571 | 32.121 | 1.00 | 22.49 |
| 11784 | NE2 | HIS | B | 750 | 26.241 | -14.843 | 32.682 | 1.00 | 19.54 |
| 11785 | CD2 | HIS | B | 750 | 25.660 | -13.759 | 33.290 | 1.00 | 19.47 |
| 11786 | C | HIS | B | 750 | 20.720 | -12.459 | 33.247 | 1.00 | 10.94 |
| 11787 | O | HIS | B | 750 | 19.853 | -13.257 | 33.623 | 1.00 | 10.42 |
| 11788 | N | PHE | B | 751 | 20.611 | -11.130 | 33.309 | 1.00 | 10.76 |
| 11789 | CA | PHE | B | 751 | 19.507 | -10.510 | 34.004 | 1.00 | 10.91 |
| 11790 | CB | PHE | B | 751 | 19.664 | -9.016 | 34.034 | 1.00 | 10.90 |
| 11791 | CG | PHE | B | 751 | 18.564 | -8.348 | 34.760 | 1.00 | 9.29 |
| 11792 | CD1 | PHE | B | 751 | 17.622 | -7.641 | 34.083 | 1.00 | 9.52 |
| 11793 | CE1 | PHE | B | 751 | 16.564 | -7.096 | 34.731 | 1.00 | 9.59 |
| 11794 | CZ | PHE | B | 751 | 16.457 | -7.240 | 36.089 | 1.00 | 10.48 |
| 11795 | CE2 | PHE | B | 751 | 17.433 | -7.964 | 36.767 | 1.00 | 10.87 |
| 11796 | CD2 | PHE | B | 751 | 18.457 | -8.494 | 36.118 | 1.00 | 9.48 |
| 11797 | C | PHE | B | 751 | 18.219 | -10.924 | 33.321 | 1.00 | 11.97 |
| 11798 | O | PHE | B | 751 | 17.234 | -11.352 | 33.952 | 1.00 | 13.03 |
| 11799 | N | LEU | B | 752 | 18.308 | -10.924 | 32.006 | 1.00 | 12.61 |
| 11800 | CA | LEU | B | 752 | 17.198 | -11.235 | 31.163 | 1.00 | 12.56 |
| 11801 | CB | LEU | B | 752 | 17.451 | -10.762 | 29.756 | 1.00 | 12.41 |
| 11802 | CG | LEU | B | 752 | 17.084 | -9.284 | 29.766 | 1.00 | 11.77 |
| 11803 | CD1 | LEU | B | 752 | 17.493 | -8.740 | 28.444 | 1.00 | 12.43 |
| 11804 | CD2 | LEU | B | 752 | 15.625 | -9.052 | 30.002 | 1.00 | 5.85 |
| 11805 | C | LEU | B | 752 | 16.870 | -12.676 | 31.191 | 1.00 | 13.20 |
| 11806 | O | LEU | B | 752 | 15.745 | -12.966 | 31.284 | 1.00 | 13.43 |
| 11807 | N | LYS | B | 753 | 17.857 | -13.548 | 31.179 | 1.00 | 14.13 |
| 11808 | CA | LYS | B | 753 | 17.627 | -14.981 | 31.187 | 1.00 | 14.93 |
| 11809 | CB | LYS | B | 753 | 18.915 | -15.830 | 30.930 | 1.00 | 14.63 |
| 11810 | CG | LYS | B | 753 | 19.783 | -15.436 | 29.696 | 1.00 | 13.42 |
| 11811 | CD | LYS | B | 753 | 19.979 | -16.485 | 28.593 | 1.00 | 10.92 |
| 11812 | CE | LYS | B | 753 | 20.654 | -17.797 | 29.069 | 1.00 | 16.20 |
| 11813 | NZ | LYS | B | 753 | 20.208 | -18.950 | 28.202 | 1.00 | 13.03 |
| 11814 | C | LYS | B | 753 | 17.018 | -15.433 | 32.496 | 1.00 | 16.89 |
| 11815 | O | LYS | B | 753 | 16.143 | -16.291 | 32.413 | 1.00 | 18.32 |
| 11816 | N | GLN | B | 754 | 17.487 | -14.953 | 33.687 | 1.00 | 18.36 |
| 11817 | CA | GLN | B | 754 | 16.832 | -15.359 | 34.970 | 1.00 | 19.47 |
| 11818 | CB | GLN | B | 754 | 17.469 | -14.775 | 36.260 | 1.00 | 19.09 |
| 11819 | CG | GLN | B | 754 | 17.593 | -15.776 | 37.548 | 1.00 | 23.66 |
| 11820 | CD | GLN | B | 754 | 16.463 | -16.968 | 37.799 | 1.00 | 30.03 |
| 11821 | OE1 | GLN | B | 754 | 16.308 | -17.989 | 37.023 | 1.00 | 29.32 |
| 11822 | NE2 | GLN | B | 754 | 15.757 | -16.828 | 38.929 | 1.00 | 30.23 |
| 11823 | C | GLN | B | 754 | 15.374 | -14.907 | 34.836 | 1.00 | 19.50 |

FIGURE 3 (Cont.)

| A | B | C | D | E | F | G | H | I | J |
|---|---|---|---|---|---|---|---|---|---|
| 11824 | O | GLN | B | 754 | 14.427 | -15.680 | 34.912 | 1.00 | 17.80 |
| 11825 | N | CYS | B | 755 | 15.221 | -13.618 | 34.556 | 1.00 | 20.52 |
| 11826 | CA | CYS | B | 755 | 13.896 | -13.066 | 34.514 | 1.00 | 21.04 |
| 11827 | CB | CYS | B | 755 | 14.026 | -11.726 | 33.921 | 1.00 | 20.61 |
| 11828 | SG | CYS | B | 755 | 12.497 | -10.885 | 33.745 | 1.00 | 25.17 |
| 11829 | C | CYS | B | 755 | 12.965 | -14.005 | 33.700 | 1.00 | 20.96 |
| 11830 | O | CYS | B | 755 | 11.953 | -14.515 | 34.215 | 1.00 | 21.71 |
| 11831 | N | PHE | B | 756 | 13.383 | -14.311 | 32.481 | 1.00 | 19.75 |
| 11832 | CA | PHE | B | 756 | 12.615 | -15.096 | 31.574 | 1.00 | 19.38 |
| 11833 | CB | PHE | B | 756 | 13.012 | -14.785 | 30.129 | 1.00 | 19.48 |
| 11834 | CG | PHE | B | 756 | 12.600 | -13.402 | 29.624 | 1.00 | 20.91 |
| 11835 | CD1 | PHE | B | 756 | 13.322 | -12.799 | 28.581 | 1.00 | 20.26 |
| 11836 | CE1 | PHE | B | 756 | 12.986 | -11.524 | 28.125 | 1.00 | 15.02 |
| 11837 | CZ | PHE | B | 756 | 11.901 | -10.846 | 28.680 | 1.00 | 16.35 |
| 11838 | CE2 | PHE | B | 756 | 11.154 | -11.404 | 29.691 | 1.00 | 17.36 |
| 11839 | CD2 | PHE | B | 756 | 11.502 | -12.677 | 30.172 | 1.00 | 22.73 |
| 11840 | C | PHE | B | 756 | 12.660 | -16.652 | 31.834 | 1.00 | 19.91 |
| 11841 | O | PHE | B | 756 | 11.808 | -17.346 | 31.329 | 1.00 | 19.33 |
| 11842 | N | SER | B | 757 | 13.648 | -17.158 | 32.577 | 1.00 | 19.27 |
| 11843 | CA | SER | B | 757 | 13.547 | -18.418 | 33.316 | 1.00 | 20.13 |
| 11844 | CB | SER | B | 757 | 12.491 | -18.251 | 34.432 | 1.00 | 20.46 |
| 11845 | OG | SER | B | 757 | 11.169 | -18.233 | 33.879 | 1.00 | 20.90 |
| 11846 | C | SER | B | 757 | 13.262 | -19.718 | 32.490 | 1.00 | 20.22 |
| 11847 | O | SER | B | 757 | 12.603 | -20.681 | 32.972 | 1.00 | 19.10 |
| 11848 | C1 | NAG | B4901 | | 36.013 | -11.577 | 15.006 | 1.00 | 31.01 |
| 11849 | C2 | NAG | B4901 | | 35.889 | -13.031 | 14.557 | 1.00 | 33.37 |
| 11850 | N2 | NAG | B4901 | | 35.922 | -13.916 | 15.709 | 1.00 | 31.60 |
| 11851 | C7 | NAG | B4901 | | 36.988 | -14.017 | 16.492 | 1.00 | 29.25 |
| 11852 | O7 | NAG | B4901 | | 37.911 | -14.768 | 16.241 | 1.00 | 31.00 |
| 11853 | C8 | NAG | B4901 | | 37.016 | -13.084 | 17.663 | 1.00 | 27.02 |
| 11854 | C3 | NAG | B4901 | | 36.982 | -13.341 | 13.544 | 1.00 | 31.29 |
| 11855 | O3 | NAG | B4901 | | 36.879 | -14.690 | 13.067 | 1.00 | 29.05 |
| 11856 | C4 | NAG | B4901 | | 36.835 | -12.361 | 12.389 | 1.00 | 33.53 |
| 11857 | O4 | NAG | B4901 | | 37.873 | -12.595 | 11.433 | 1.00 | 36.10 |
| 11858 | C5 | NAG | B4901 | | 36.894 | -10.916 | 12.893 | 1.00 | 34.94 |
| 11859 | C6 | NAG | B4901 | | 36.708 | -9.920 | 11.747 | 1.00 | 36.29 |
| 11860 | O6 | NAG | B4901 | | 35.476 | -9.195 | 11.877 | 1.00 | 39.76 |
| 11861 | O5 | NAG | B4901 | | 35.895 | -10.694 | 13.886 | 1.00 | 36.58 |
| 11862 | C1 | NAG | B9201 | | 53.388 | -2.910 | 3.665 | 1.00 | 43.74 |
| 11863 | C2 | NAG | B9201 | | 52.656 | -4.128 | 4.194 | 1.00 | 49.11 |
| 11864 | N2 | NAG | B9201 | | 53.192 | -4.532 | 5.471 | 1.00 | 51.76 |
| 11865 | C7 | NAG | B9201 | | 54.493 | -4.529 | 5.710 | 1.00 | 54.91 |
| 11866 | O7 | NAG | B9201 | | 55.290 | -4.132 | 4.870 | 1.00 | 54.79 |
| 11867 | C8 | NAG | B9201 | | 54.892 | -4.968 | 7.091 | 1.00 | 53.72 |
| 11868 | C3 | NAG | B9201 | | 52.902 | -5.242 | 3.199 | 1.00 | 52.40 |
| 11869 | O3 | NAG | B9201 | | 52.311 | -6.443 | 3.709 | 1.00 | 54.70 |
| 11870 | C4 | NAG | B9201 | | 52.356 | -4.822 | 1.841 | 1.00 | 52.42 |
| 11871 | O4 | NAG | B9201 | | 52.712 | -5.816 | 0.887 | 1.00 | 57.30 |
| 11872 | C5 | NAG | B9201 | | 52.960 | -3.481 | 1.406 | 1.00 | 49.74 |
| 11873 | C6 | NAG | B9201 | | 52.362 | -3.013 | 0.076 | 1.00 | 47.92 |
| 11874 | O6 | NAG | B9201 | | 53.044 | -1.850 | -0.404 | 1.00 | 44.94 |

FIGURE 3 (Cont.)

| A | B | C | D E | F | G | H | I | J |
|---|---|---|---|---|---|---|---|---|
| 11875 | O5 | NAG | B9201 | 52.809 | -2.494 | 2.430 | 1.00 | 48.33 |
| 11876 | C1 | NAG | B9202 | 53.203 | -6.757 | -0.053 | 1.00 | 73.82 |
| 11877 | C2 | NAG | B9202 | 54.083 | -6.767 | -1.294 | 1.00 | 79.07 |
| 11878 | N2 | NAG | B9202 | 53.820 | -5.714 | -2.254 | 1.00 | 80.21 |
| 11879 | C7 | NAG | B9202 | 52.634 | -5.589 | -2.853 | 1.00 | 81.03 |
| 11880 | O7 | NAG | B9202 | 52.409 | -4.714 | -3.676 | 1.00 | 82.65 |
| 11881 | C8 | NAG | B9202 | 51.625 | -6.650 | -2.532 | 1.00 | 78.21 |
| 11882 | C3 | NAG | B9202 | 53.850 | -8.092 | -1.986 | 1.00 | 80.67 |
| 11883 | O3 | NAG | B9202 | 54.575 | -8.142 | -3.215 | 1.00 | 83.23 |
| 11884 | C4 | NAG | B9202 | 54.302 | -9.198 | -1.050 | 1.00 | 81.48 |
| 11885 | O4 | NAG | B9202 | 54.054 | -10.462 | -1.667 | 1.00 | 82.65 |
| 11886 | C5 | NAG | B9202 | 53.543 | -9.111 | 0.267 | 1.00 | 80.78 |
| 11887 | C6 | NAG | B9202 | 54.045 | -10.175 | 1.241 | 1.00 | 83.02 |
| 11888 | O6 | NAG | B9202 | 54.563 | -9.579 | 2.431 | 1.00 | 83.82 |
| 11889 | O5 | NAG | B9202 | 53.663 | -7.794 | 0.823 | 1.00 | 78.39 |
| 11890 | C1 | NAG | B2271 | 34.630 | 36.507 | 30.534 | 1.00 | 42.66 |
| 11891 | C2 | NAG | B2271 | 34.829 | 37.991 | 30.294 | 1.00 | 49.56 |
| 11892 | N2 | NAG | B2271 | 35.737 | 38.215 | 29.194 | 1.00 | 49.24 |
| 11893 | C7 | NAG | B2271 | 35.312 | 38.260 | 27.941 | 1.00 | 47.73 |
| 11894 | O7 | NAG | B2271 | 35.818 | 37.560 | 27.075 | 1.00 | 48.66 |
| 11895 | C8 | NAG | B2271 | 34.136 | 39.162 | 27.697 | 1.00 | 48.07 |
| 11896 | C3 | NAG | B2271 | 35.457 | 38.549 | 31.553 | 1.00 | 46.96 |
| 11897 | O3 | NAG | B2271 | 35.755 | 39.934 | 31.334 | 1.00 | 46.16 |
| 11898 | C4 | NAG | B2271 | 34.516 | 38.306 | 32.724 | 1.00 | 48.35 |
| 11899 | O4 | NAG | B2271 | 34.454 | 38.764 | 33.927 | 1.00 | 49.14 |
| 11900 | C5 | NAG | B2271 | 34.165 | 36.818 | 32.836 | 1.00 | 47.26 |
| 11901 | C6 | NAG | B2271 | 33.159 | 36.571 | 33.966 | 1.00 | 46.78 |
| 11902 | O6 | NAG | B2271 | 32.411 | 35.376 | 33.725 | 1.00 | 47.45 |
| 11903 | O5 | NAG | B2271 | 33.689 | 36.308 | 31.587 | 1.00 | 44.38 |
| 11904 | C1 | NAG | B2272 | 34.967 | 38.684 | 35.254 | 1.00 | 55.84 |
| 11905 | C2 | NAG | B2272 | 36.241 | 38.034 | 35.770 | 1.00 | 57.47 |
| 11906 | N2 | NAG | B2272 | 36.727 | 36.911 | 34.995 | 1.00 | 59.65 |
| 11907 | C7 | NAG | B2272 | 38.029 | 36.728 | 34.762 | 1.00 | 60.39 |
| 11908 | O7 | NAG | B2272 | 38.447 | 35.786 | 34.109 | 1.00 | 60.77 |
| 11909 | C8 | NAG | B2272 | 38.939 | 37.810 | 35.262 | 1.00 | 59.09 |
| 11910 | C3 | NAG | B2272 | 35.943 | 37.536 | 37.168 | 1.00 | 57.69 |
| 11911 | O3 | NAG | B2272 | 37.069 | 36.828 | 37.691 | 1.00 | 55.37 |
| 11912 | C4 | NAG | B2272 | 35.615 | 38.737 | 38.036 | 1.00 | 60.16 |
| 11913 | O4 | NAG | B2272 | 35.291 | 38.287 | 39.352 | 1.00 | 60.38 |
| 11914 | C5 | NAG | B2272 | 34.434 | 39.498 | 37.447 | 1.00 | 59.38 |
| 11915 | C6 | NAG | B2272 | 34.145 | 40.750 | 38.274 | 1.00 | 59.13 |
| 11916 | O6 | NAG | B2272 | 34.265 | 41.931 | 37.480 | 1.00 | 57.13 |
| 11917 | O5 | NAG | B2272 | 34.689 | 39.826 | 36.074 | 1.00 | 58.36 |
| 11918 | C1 | NAG | B3141 | 7.787 | 31.390 | 22.871 | 1.00 | 47.99 |
| 11919 | C2 | NAG | B3141 | 7.170 | 32.566 | 23.604 | 1.00 | 54.32 |
| 11920 | N2 | NAG | B3141 | 7.508 | 32.530 | 25.007 | 1.00 | 60.49 |
| 11921 | C7 | NAG | B3141 | 7.303 | 31.449 | 25.743 | 1.00 | 61.52 |
| 11922 | O7 | NAG | B3141 | 6.867 | 30.419 | 25.247 | 1.00 | 61.89 |
| 11923 | C8 | NAG | B3141 | 7.715 | 31.568 | 27.184 | 1.00 | 62.57 |
| 11924 | C3 | NAG | B3141 | 5.670 | 32.416 | 23.470 | 1.00 | 53.77 |
| 11925 | O3 | NAG | B3141 | 5.042 | 33.454 | 24.233 | 1.00 | 50.97 |

FIGURE 3 (Cont.)

| A | B | C | D | E | F | G | H | I | J |
|---|---|---|---|---|---|---|---|---|---|
| 11926 | C4 | NAG | B | 3141 | 5.301 | 32.437 | 21.993 | 1.00 | 55.87 |
| 11927 | O4 | NAG | B | 3141 | 4.191 | 32.574 | 21.354 | 1.00 | 58.28 |
| 11928 | C5 | NAG | B | 3141 | 6.084 | 31.365 | 21.225 | 1.00 | 53.02 |
| 11929 | C6 | NAG | B | 3141 | 5.776 | 31.426 | 19.725 | 1.00 | 53.63 |
| 11930 | O6 | NAG | B | 3141 | 5.482 | 30.122 | 19.216 | 1.00 | 58.18 |
| 11931 | O5 | NAG | B | 3141 | 7.487 | 31.474 | 21.480 | 1.00 | 53.10 |
| 11932 | C1 | NAG | B | 6791 | 2.709 | 14.241 | 38.012 | 1.00 | 48.20 |
| 11933 | C2 | NAG | B | 6791 | 1.392 | 14.834 | 37.550 | 1.00 | 53.67 |
| 11934 | N2 | NAG | B | 6791 | 0.834 | 15.695 | 38.565 | 1.00 | 58.17 |
| 11935 | C7 | NAG | B | 6791 | 1.195 | 16.964 | 38.673 | 1.00 | 61.53 |
| 11936 | O7 | NAG | B | 6791 | 1.530 | 17.614 | 37.691 | 1.00 | 63.36 |
| 11937 | C8 | NAG | B | 6791 | 1.084 | 17.545 | 40.053 | 1.00 | 62.19 |
| 11938 | C3 | NAG | B | 6791 | 0.448 | 13.669 | 37.339 | 1.00 | 52.78 |
| 11939 | O3 | NAG | B | 6791 | -0.843 | 14.190 | 36.997 | 1.00 | 48.33 |
| 11940 | C4 | NAG | B | 6791 | 1.032 | 12.744 | 36.282 | 1.00 | 54.69 |
| 11941 | O4 | NAG | B | 6791 | 0.553 | 11.773 | 35.585 | 1.00 | 55.82 |
| 11942 | C5 | NAG | B | 6791 | 2.450 | 12.307 | 36.669 | 1.00 | 54.99 |
| 11943 | C6 | NAG | B | 6791 | 3.077 | 11.435 | 35.576 | 1.00 | 57.28 |
| 11944 | O6 | NAG | B | 6791 | 4.430 | 11.107 | 35.905 | 1.00 | 61.21 |
| 11945 | O5 | NAG | B | 6791 | 3.270 | 13.438 | 36.976 | 1.00 | 55.97 |
| 11946 | O | HOH | W | 1 | 53.203 | -6.757 | -0.053 | 1.00 | 15.00 |
| 11947 | O | HOH | W | 2 | 10.985 | 1.308 | 22.342 | 1.00 | 27.54 |
| 11948 | O | HOH | W | 3 | 49.214 | 41.420 | 9.638 | 1.00 | 31.42 |
| 11949 | O | HOH | W | 4 | 20.212 | 11.336 | 25.847 | 1.00 | 27.11 |
| 11950 | O | HOH | W | 5 | 39.986 | -2.180 | 58.265 | 1.00 | 33.78 |
| 11951 | O | HOH | W | 6 | 21.970 | 2.616 | 46.876 | 1.00 | 37.67 |
| 11952 | O | HOH | W | 7 | 31.198 | 17.440 | 24.970 | 1.00 | 26.94 |
| 11953 | O | HOH | W | 8 | 29.879 | 13.080 | 41.180 | 1.00 | 32.99 |
| 11954 | O | HOH | W | 9 | 10.107 | 6.471 | 3.066 | 1.00 | 31.76 |
| 11955 | O | HOH | W | 10 | 24.167 | 22.672 | 43.370 | 1.00 | 27.88 |
| 11956 | O | HOH | W | 11 | 20.212 | 20.492 | 5.695 | 1.00 | 30.78 |
| 11957 | O | HOH | W | 12 | 6.152 | 7.848 | 22.780 | 1.00 | 37.88 |
| 11958 | O | HOH | W | 13 | 28.122 | 15.260 | 0.876 | 1.00 | 29.84 |
| 11959 | O | HOH | W | 14 | 9.228 | 7.412 | 13.581 | 1.00 | 34.37 |
| 11960 | O | HOH | W | 15 | 29.879 | 37.932 | 18.838 | 1.00 | 37.87 |
| 11961 | O | HOH | W | 16 | 25.925 | 24.852 | -1.314 | 1.00 | 24.86 |
| 11962 | O | HOH | W | 17 | 12.743 | -1.308 | 4.819 | 1.00 | 37.36 |
| 11963 | O | HOH | W | 18 | 50.093 | 37.496 | 17.523 | 1.00 | 25.51 |
| 11964 | O | HOH | W | 19 | 9.667 | 6.976 | 21.028 | 1.00 | 29.92 |
| 11965 | O | HOH | W | 20 | 16.258 | 30.956 | 10.514 | 1.00 | 30.37 |
| 11966 | O | HOH | W | 21 | 33.395 | 22.672 | 28.914 | 1.00 | 41.08 |
| 11967 | O | HOH | W | 22 | 17.577 | -5.232 | -3.943 | 1.00 | 36.73 |
| 11968 | O | HOH | W | 23 | 28.122 | 11.772 | 38.551 | 1.00 | 37.96 |
| 11969 | O | HOH | W | 24 | 43.501 | 17.876 | -1.314 | 1.00 | 46.68 |
| 11970 | O | HOH | W | 25 | 12.743 | 15.260 | 35.923 | 1.00 | 33.55 |
| 11971 | O | HOH | W | 26 | 18.894 | 35.316 | 1.314 | 1.00 | 31.42 |
| 11972 | O | HOH | W | 27 | 43.501 | 5.232 | 91.998 | 1.00 | 39.59 |
| 11973 | O | HOH | W | 28 | 18.455 | 1.744 | 24.094 | 1.00 | 29.63 |
| 11974 | O | HOH | W | 29 | 25.485 | -18.748 | 84.989 | 1.00 | 30.59 |
| 11975 | O | HOH | W | 30 | 33.395 | 3.924 | 28.914 | 1.00 | 44.26 |
| 11976 | O | HOH | W | 31 | 34.274 | 17.004 | 14.457 | 1.00 | 35.67 |

FIGURE 3 (Cont.)

| A | B | C | D | E | F | G | H | I | J |
|---|---|---|---|---|---|---|---|---|---|
| 11977 | O | HOH | W | 32 | 35.152 | 6.540 | 49.066 | 1.00 | 36.74 |
| 11978 | O | HOH | W | 33 | 59.759 | -5.668 | 63.523 | 1.00 | 40.90 |
| 11979 | O | HOH | W | 34 | 12.743 | 6.976 | 48.190 | 1.00 | 27.03 |
| 11980 | O | HOH | W | 35 | 43.501 | -11.336 | 95.502 | 1.00 | 45.31 |
| 11981 | O | HOH | W | 36 | 6.591 | 10.900 | 7.885 | 1.00 | 36.65 |
| 11982 | O | HOH | W | 37 | 8.788 | 17.004 | 12.267 | 1.00 | 51.90 |
| 11983 | O | HOH | W | 38 | 15.380 | 15.696 | 14.895 | 1.00 | 31.02 |
| 11984 | O | HOH | W | 39 | 32.955 | 49.704 | 1.314 | 1.00 | 35.04 |
| 11985 | O | HOH | W | 40 | 44.820 | -6.976 | 96.378 | 1.00 | 41.11 |
| 11986 | O | HOH | W | 41 | 24.606 | 29.212 | 9.638 | 1.00 | 34.07 |
| 11987 | O | HOH | W | 42 | 14.061 | -1.744 | 60.894 | 1.00 | 36.52 |
| 11988 | O | HOH | W | 43 | 34.713 | -13.516 | 61.332 | 1.00 | 47.97 |
| 11989 | O | HOH | W | 44 | 38.668 | 20.928 | 24.532 | 1.00 | 39.06 |
| 11990 | O | HOH | W | 45 | 30.758 | 27.904 | 5.695 | 1.00 | 35.25 |
| 11991 | O | HOH | W | 46 | 18.015 | 35.752 | 29.790 | 1.00 | 34.84 |
| 11992 | O | HOH | W | 47 | 39.474 | 37.496 | 19.714 | 1.00 | 30.42 |
| 11993 | O | HOH | W | 48 | 16.698 | 17.004 | -10.953 | 1.00 | 44.00 |
| 11994 | O | HOH | W | 49 | 32.955 | 34.880 | 25.409 | 1.00 | 44.48 |
| 11995 | O | HOH | W | 50 | 30.319 | -24.416 | 47.752 | 1.00 | 45.16 |
| 11996 | O | HOH | W | 51 | 11.425 | 23.108 | 11.391 | 1.00 | 34.95 |
| 11997 | O | HOH | W | 52 | 7.470 | 13.516 | 14.019 | 1.00 | 33.26 |
| 11998 | O | HOH | W | 53 | 29.001 | 11.336 | 25.409 | 1.00 | 28.97 |
| 11999 | O | HOH | W | 54 | 2.197 | 18.312 | 11.829 | 1.00 | 30.39 |
| 12000 | O | HOH | W | 55 | 39.547 | 35.316 | 22.342 | 1.00 | 41.07 |
| 12001 | O | HOH | W | 56 | 27.682 | 5.232 | 31.542 | 1.00 | 39.84 |
| 12002 | O | HOH | W | 57 | 7.910 | 5.232 | -7.009 | 1.00 | 49.02 |
| 12003 | O | HOH | W | 58 | 45.699 | 40.548 | 16.209 | 1.00 | 37.76 |
| 12004 | O | HOH | W | 59 | 13.183 | 23.544 | -12.267 | 1.00 | 33.91 |
| 12005 | O | HOH | W | 60 | 30.831 | 8.215 | 43.370 | 1.00 | 33.13 |
| 12006 | O | HOH | W | 61 | 29.879 | 23.108 | 28.914 | 1.00 | 54.29 |
| 12007 | O | HOH | W | 62 | 26.364 | 26.160 | 1.752 | 1.00 | 41.46 |
| 12008 | O | HOH | W | 63 | 19.333 | 3.488 | 21.466 | 1.00 | 33.76 |
| 12009 | O | HOH | W | 64 | 17.137 | 19.184 | 7.885 | 1.00 | 35.56 |
| 12010 | O | HOH | W | 65 | 17.577 | 0.872 | -3.504 | 1.00 | 38.29 |
| 12011 | O | HOH | W | 66 | 32.077 | -19.184 | 76.665 | 1.00 | 36.19 |
| 12012 | O | HOH | W | 67 | 14.061 | 1.744 | 20.223 | 1.00 | 42.69 |
| 12013 | O | HOH | W | 68 | 0.439 | 12.208 | 16.647 | 1.00 | 37.99 |
| 12014 | O | HOH | W | 69 | 12.743 | 37.496 | 10.076 | 1.00 | 38.29 |
| 12015 | O | HOH | W | 70 | 50.093 | -14.824 | 86.303 | 1.00 | 40.60 |
| 12016 | O | HOH | W | 71 | 5.712 | 22.236 | -4.819 | 1.00 | 44.03 |
| 12017 | O | HOH | W | 72 | 23.288 | 4.360 | 10.953 | 1.00 | 39.47 |
| 12018 | O | HOH | W | 73 | 22.409 | 30.956 | 27.162 | 1.00 | 34.37 |
| 12019 | O | HOH | W | 74 | 43.062 | -20.056 | 66.589 | 1.00 | 42.07 |
| 12020 | O | HOH | W | 75 | 2.197 | 18.748 | 19.276 | 1.00 | 35.05 |
| 12021 | O | HOH | W | 76 | 42.183 | 37.060 | 23.218 | 1.00 | 35.30 |
| 12022 | O | HOH | W | 77 | 49.653 | 27.904 | -2.190 | 1.00 | 25.11 |
| 12023 | O | HOH | W | 78 | 21.970 | 32.700 | 34.609 | 1.00 | 39.77 |
| 12024 | O | HOH | W | 79 | 56.683 | 13.080 | 62.647 | 1.00 | 41.49 |
| 12025 | O | HOH | W | 80 | 15.380 | 24.416 | 11.829 | 1.00 | 37.37 |
| 12026 | O | HOH | W | 81 | 30.758 | 25.288 | 40.742 | 1.00 | 38.71 |
| 12027 | O | HOH | W | 82 | 29.879 | -14.824 | 93.750 | 1.00 | 38.19 |

FIGURE 3 (Cont.)

| A | B | C | D | E | F | G | H | I | J |
|---|---|---|---|---|---|---|---|---|---|
| 12028 | O | HOH | W | 83 | 25.046 | -3.924 | 60.017 | 1.00 | 50.13 |
| 12029 | O | HOH | W | 84 | 23.288 | -14.824 | 70.970 | 1.00 | 48.80 |
| 12030 | O | HOH | W | 85 | 12.743 | 16.132 | 8.761 | 1.00 | 37.38 |
| 12031 | O | HOH | W | 86 | 3.076 | 27.032 | 11.391 | 1.00 | 41.11 |
| 12032 | O | HOH | W | 87 | 50.093 | 15.260 | 21.466 | 1.00 | 43.59 |
| 12033 | O | HOH | W | 88 | 22.409 | -2.180 | 21.466 | 1.00 | 32.97 |
| 12034 | O | HOH | W | 89 | 45.259 | 11.772 | -10.953 | 1.00 | 41.54 |
| 12035 | O | HOH | W | 90 | 36.031 | -16.568 | 60.017 | 1.00 | 46.26 |
| 12036 | O | HOH | W | 91 | 28.561 | 14.824 | 84.113 | 1.00 | 46.62 |
| 12037 | O | HOH | W | 92 | 52.729 | 19.620 | 63.961 | 1.00 | 47.35 |
| 12038 | O | HOH | W | 93 | 13.622 | -12.644 | 54.323 | 1.00 | 35.22 |
| 12039 | O | HOH | W | 94 | 23.728 | 14.388 | 33.733 | 1.00 | 40.24 |
| 12040 | O | HOH | W | 95 | 62.835 | 27.468 | 15.771 | 1.00 | 41.05 |
| 12041 | O | HOH | W | 96 | 36.031 | 11.772 | 20.590 | 1.00 | 46.88 |
| 12042 | O | HOH | W | 97 | 3.076 | -10.464 | 13.143 | 1.00 | 49.97 |
| 12043 | O | HOH | W | 98 | 42.623 | -2.616 | 29.790 | 1.00 | 44.87 |
| 12044 | O | HOH | W | 99 | 25.046 | 40.112 | 22.342 | 1.00 | 34.56 |
| 12045 | O | HOH | W | 100 | 49.214 | 34.880 | 26.285 | 1.00 | 37.88 |
| 12046 | O | HOH | W | 101 | 14.501 | 19.184 | 10.953 | 1.00 | 28.92 |
| 12047 | O | HOH | W | 102 | 18.015 | 17.440 | 13.581 | 1.00 | 33.76 |
| 12048 | O | HOH | W | 103 | 7.031 | 8.720 | 5.695 | 1.00 | 39.04 |
| 12049 | O | HOH | W | 104 | 38.228 | -1.744 | 62.647 | 1.00 | 41.14 |
| 12050 | O | HOH | W | 105 | 32.077 | 6.471 | 41.618 | 1.00 | 39.83 |
| 12051 | O | HOH | W | 106 | 35.152 | 11.772 | 88.493 | 1.00 | 41.13 |
| 12052 | O | HOH | W | 107 | 32.077 | 13.516 | 13.581 | 1.00 | 38.90 |
| 12053 | O | HOH | W | 108 | 0.879 | 13.516 | 1.314 | 1.00 | 28.74 |
| 12054 | O | HOH | W | 109 | 61.956 | 13.080 | 7.009 | 1.00 | 44.28 |
| 12055 | O | HOH | W | 110 | 25.925 | 7.848 | 7.885 | 1.00 | 43.70 |
| 12056 | O | HOH | W | 111 | 22.409 | 5.668 | 24.094 | 1.00 | 41.26 |
| 12057 | O | HOH | W | 112 | 21.970 | 26.596 | 13.143 | 1.00 | 41.24 |
| 12058 | O | HOH | W | 113 | 15.380 | 33.136 | 25.409 | 1.00 | 40.23 |
| 12059 | O | HOH | W | 114 | 16.258 | 16.132 | 10.514 | 1.00 | 33.85 |
| 12060 | O | HOH | W | 115 | 32.077 | 39.309 | -2.628 | 1.00 | 40.95 |
| 12061 | O | HOH | W | 116 | 29.879 | 0.872 | 76.665 | 1.00 | 37.65 |
| 12062 | O | HOH | W | 117 | 25.925 | 17.004 | 54.323 | 1.00 | 41.65 |
| 12063 | O | HOH | W | 118 | 30.758 | 5.668 | 61.332 | 1.00 | 39.15 |
| 12064 | O | HOH | W | 119 | 39.107 | -2.180 | 69.656 | 1.00 | 39.22 |
| 12065 | O | HOH | W | 120 | 29.440 | 24.416 | -0.876 | 1.00 | 42.25 |
| 12066 | O | HOH | W | 121 | 12.304 | 33.136 | 22.780 | 1.00 | 43.23 |
| 12067 | O | HOH | W | 122 | 51.850 | -5.232 | 74.474 | 1.00 | 44.14 |
| 12068 | O | HOH | W | 123 | 20.212 | 47.960 | 9.200 | 1.00 | 42.17 |
| 12069 | O | HOH | W | 124 | 31.637 | 22.672 | 9.200 | 1.00 | 40.64 |
| 12070 | O | HOH | W | 125 | 29.879 | 10.900 | 7.885 | 1.00 | 45.01 |
| 12071 | O | HOH | W | 126 | 19.773 | 23.108 | 19.276 | 1.00 | 39.78 |
| 12072 | O | HOH | W | 127 | 39.547 | 18.748 | 35.923 | 1.00 | 38.71 |
| 12073 | O | HOH | W | 128 | 7.031 | 27.904 | 21.466 | 1.00 | 35.18 |
| 12074 | O | HOH | W | 129 | 45.259 | 9.156 | 25.409 | 1.00 | 40.85 |
| 12075 | O | HOH | W | 130 | 20.212 | -6.976 | 10.076 | 1.00 | 47.46 |
| 12076 | O | HOH | W | 131 | 54.925 | 25.288 | 15.333 | 1.00 | 51.51 |
| 12077 | O | HOH | W | 132 | 49.214 | 23.980 | -1.314 | 1.00 | 40.13 |
| 12078 | O | HOH | W | 133 | 12.304 | 7.412 | 1.314 | 1.00 | 39.32 |

FIGURE 3 (Cont.)

| A | B | C | D | E | F | G | H | I | J |
|---|---|---|---|---|---|---|---|---|---|
| 12079 | O | HOH | W | 134 | 18.455 | 22.672 | 5.695 | 1.00 | 25.41 |
| 12080 | O | HOH | W | 135 | 7.031 | 5.668 | 23.290 | 1.00 | 44.47 |
| 12081 | O | HOH | W | 136 | 36.910 | 6.609 | 46.876 | 1.00 | 35.88 |
| 12082 | O | HOH | W | 137 | 14.061 | 22.236 | 10.514 | 1.00 | 34.65 |
| 12083 | O | HOH | W | 138 | 18.455 | 33.572 | 31.542 | 1.00 | 31.97 |
| 12084 | O | HOH | W | 139 | 31.637 | 9.592 | 45.561 | 1.00 | 40.25 |
| 12085 | O | HOH | W | 140 | 25.925 | 22.236 | -1.752 | 1.00 | 30.45 |
| 12086 | O | HOH | W | 141 | 38.228 | 40.984 | 24.970 | 1.00 | 40.78 |
| 12087 | O | HOH | W | 142 | 37.789 | 18.748 | 10.953 | 1.00 | 45.46 |
| 12088 | O | HOH | W | 143 | 31.198 | 1.308 | 52.570 | 1.00 | 38.25 |
| 12089 | O | HOH | W | 144 | 32.077 | -5.668 | 73.160 | 1.00 | 44.64 |
| 12090 | O | HOH | W | 145 | 26.364 | 7.412 | 56.513 | 1.00 | 37.36 |
| 12091 | O | HOH | W | 146 | 17.137 | 23.108 | -12.705 | 1.00 | 41.82 |
| 12092 | O | HOH | W | 147 | 3.076 | 24.416 | -1.314 | 1.00 | 37.70 |
| 12093 | O | HOH | W | 148 | 33.395 | -3.488 | 76.665 | 1.00 | 45.64 |
| 12094 | O | HOH | W | 149 | 45.259 | 32.700 | 30.228 | 1.00 | 55.45 |
| 12095 | O | HOH | W | 150 | 23.728 | 32.264 | 31.542 | 1.00 | 43.76 |
| 12096 | O | HOH | W | 151 | 54.486 | 21.364 | -4.819 | 1.00 | 49.73 |
| 12097 | O | HOH | W | 152 | 3.955 | 27.032 | 1.314 | 1.00 | 48.19 |
| 12098 | O | HOH | W | 153 | 38.668 | 20.928 | 60.455 | 1.00 | 41.47 |
| 12099 | O | HOH | W | 154 | 3.955 | 10.900 | 7.885 | 1.00 | 37.12 |
| 12100 | O | HOH | W | 155 | 41.744 | 34.444 | 29.790 | 1.00 | 32.80 |
| 12101 | O | HOH | W | 156 | 43.501 | -17.876 | 89.369 | 1.00 | 47.75 |
| 12102 | O | HOH | W | 157 | 25.925 | 4.360 | 11.829 | 1.00 | 45.42 |
| 12103 | O | HOH | W | 158 | -2.197 | 1.744 | 28.038 | 1.00 | 47.83 |
| 12104 | O | HOH | W | 159 | 36.910 | 23.980 | 10.076 | 1.00 | 35.25 |
| 12105 | O | HOH | W | 160 | 29.879 | -3.052 | 20.590 | 1.00 | 41.59 |
| 12106 | O | HOH | W | 161 | 7.470 | 17.440 | -3.066 | 1.00 | 36.45 |
| 12107 | O | HOH | W | 162 | 54.925 | -18.312 | 100.322 | 1.00 | 48.48 |
| 12108 | O | HOH | W | 163 | 15.819 | -2.616 | -7.447 | 1.00 | 43.47 |
| 12109 | O | HOH | W | 164 | 33.834 | 33.136 | -2.628 | 1.00 | 47.74 |
| 12110 | O | HOH | W | 165 | 30.686 | 15.627 | 24.461 | 1.00 | 60.37 |
| 12111 | O | HOH | W | 166 | 28.122 | 7.412 | 23.656 | 1.00 | 43.48 |
| 12112 | O | HOH | W | 167 | 10.985 | 6.976 | 50.818 | 1.00 | 40.61 |
| 12113 | O | HOH | W | 168 | 46.577 | 21.364 | 23.656 | 1.00 | 41.14 |
| 12114 | O | HOH | W | 169 | 15.819 | 30.956 | 7.447 | 1.00 | 44.26 |
| 12115 | O | HOH | W | 170 | 28.195 | 28.409 | -4.014 | 1.00 | 47.24 |
| 12116 | O | HOH | W | 171 | 28.122 | 49.268 | 4.819 | 1.00 | 43.85 |
| 12117 | O | HOH | W | 172 | 7.031 | 30.956 | 30.228 | 1.00 | 44.25 |
| 12118 | O | HOH | W | 173 | 25.925 | 2.616 | 80.170 | 1.00 | 54.77 |
| 12119 | O | HOH | W | 174 | 41.744 | 17.876 | 14.895 | 1.00 | 49.62 |
| 12120 | O | HOH | W | 175 | 26.804 | -0.872 | 22.780 | 1.00 | 39.07 |
| 12121 | O | HOH | W | 176 | 23.728 | -32.700 | 66.589 | 1.00 | 47.48 |
| 12122 | O | HOH | W | 177 | -3.076 | 12.644 | 16.647 | 1.00 | 40.52 |
| 12123 | O | HOH | W | 178 | 12.304 | 3.121 | 21.466 | 1.00 | 31.20 |
| 12124 | O | HOH | W | 179 | 48.335 | 11.772 | 45.123 | 1.00 | 47.07 |
| 12125 | O | HOH | W | 180 | 3.515 | 19.184 | 3.504 | 1.00 | 39.80 |
| 12126 | O | HOH | W | 181 | 29.879 | 18.312 | 40.742 | 1.00 | 40.95 |
| 12127 | O | HOH | W | 182 | 9.228 | 38.804 | 15.771 | 1.00 | 44.11 |
| 12128 | O | HOH | W | 183 | 9.667 | 3.924 | 11.829 | 1.00 | 41.78 |
| 12129 | O | HOH | W | 184 | 23.728 | -17.440 | 24.094 | 1.00 | 54.82 |

FIGURE 3 (Cont.)

| A | B | C | D | E | F | G | H | I | J |
|---|---|---|---|---|---|---|---|---|---|
| 12130 | O | HOH | W | 185 | 13.183 | 35.316 | 87.179 | 1.00 | 38.70 |
| 12131 | O | HOH | W | 186 | 18.894 | 30.956 | -6.571 | 1.00 | 38.85 |
| 12132 | O | HOH | W | 187 | 30.319 | -32.264 | 71.408 | 1.00 | 48.86 |
| 12133 | O | HOH | W | 188 | 29.879 | 13.080 | 57.827 | 1.00 | 45.23 |
| 12134 | O | HOH | W | 189 | 28.122 | 23.980 | 45.123 | 1.00 | 37.39 |
| 12135 | O | HOH | W | 190 | 45.259 | 13.516 | 46.437 | 1.00 | 38.08 |
| 12136 | O | HOH | W | 191 | 37.789 | 19.620 | -9.200 | 1.00 | 46.94 |
| 12137 | O | HOH | W | 192 | 34.713 | 4.796 | 59.141 | 1.00 | 37.51 |
| 12138 | O | HOH | W | 193 | 27.682 | 36.188 | 20.590 | 1.00 | 49.70 |
| 12139 | O | HOH | W | 194 | 17.577 | 20.492 | 44.246 | 1.00 | 48.99 |
| 12140 | O | HOH | W | 195 | 5.273 | 28.776 | -0.876 | 1.00 | 47.23 |
| 12141 | O | HOH | W | 196 | 5.712 | 9.156 | -3.504 | 1.00 | 41.16 |
| 12142 | O | HOH | W | 197 | 14.501 | 4.796 | -7.885 | 1.00 | 32.36 |
| 12143 | O | HOH | W | 198 | 18.455 | 22.672 | -16.647 | 1.00 | 40.42 |
| 12144 | O | HOH | W | 199 | 65.471 | 3.924 | 66.589 | 1.00 | 49.30 |
| 12145 | O | HOH | W | 200 | 60.198 | 29.212 | -0.876 | 1.00 | 40.61 |
| 12146 | O | HOH | W | 201 | 39.107 | 17.004 | 44.685 | 1.00 | 47.81 |
| 12147 | O | HOH | W | 202 | 18.894 | 11.336 | 18.400 | 1.00 | 37.88 |
| 12148 | O | HOH | W | 203 | 18.015 | 29.648 | 11.462 | 1.00 | 37.50 |
| 12149 | O | HOH | W | 204 | -0.879 | 8.720 | 39.866 | 1.00 | 44.10 |
| 12150 | O | HOH | W | 205 | 34.274 | 6.976 | -14.895 | 1.00 | 41.58 |
| 12151 | O | HOH | W | 206 | 24.606 | 32.700 | 28.038 | 1.00 | 34.97 |
| 12152 | O | HOH | W | 207 | 22.849 | -4.360 | 71.408 | 1.00 | 49.46 |
| 12153 | O | HOH | W | 208 | 50.532 | 2.616 | 21.028 | 1.00 | 47.68 |
| 12154 | O | HOH | W | 209 | 37.422 | 18.312 | -1.314 | 1.00 | 42.11 |
| 12155 | O | HOH | W | 210 | 36.983 | -13.952 | 60.894 | 1.00 | 44.74 |
| 12156 | O | HOH | W | 211 | 32.955 | 9.592 | 39.428 | 1.00 | 42.46 |
| 12157 | O | HOH | W | 212 | 40.426 | 43.164 | 7.009 | 1.00 | 44.71 |
| 12158 | O | HOH | W | 213 | 26.804 | 46.721 | 14.019 | 1.00 | 48.96 |
| 12159 | O | HOH | W | 214 | 21.091 | -15.260 | 86.303 | 1.00 | 43.20 |
| 12160 | O | HOH | W | 215 | 17.137 | -2.180 | 15.333 | 1.00 | 42.85 |
| 12161 | O | HOH | W | 216 | 52.290 | 40.112 | 12.267 | 1.00 | 45.39 |
| 12162 | O | HOH | W | 217 | 36.910 | -6.540 | 74.912 | 1.00 | 45.94 |
| 12163 | O | HOH | W | 218 | 65.911 | 14.824 | 64.399 | 1.00 | 46.97 |
| 12164 | O | HOH | W | 219 | 28.561 | 16.568 | -16.647 | 1.00 | 47.67 |
| 12165 | O | HOH | W | 220 | 23.288 | 13.516 | 7.009 | 1.00 | 42.86 |
| 12166 | O | HOH | W | 221 | 22.849 | 0.436 | 77.103 | 1.00 | 47.31 |
| 12167 | O | HOH | W | 222 | 21.091 | 30.589 | 36.361 | 1.00 | 41.90 |
| 12168 | O | HOH | W | 223 | 20.652 | 3.924 | 88.931 | 1.00 | 48.14 |
| 12169 | O | HOH | W | 224 | 52.290 | 11.772 | 49.504 | 1.00 | 47.44 |
| 12170 | O | HOH | W | 225 | 38.668 | 17.440 | 31.980 | 1.00 | 46.05 |
| 12171 | O | HOH | W | 226 | 37.350 | 15.260 | 81.046 | 1.00 | 44.61 |
| 12172 | O | HOH | W | 227 | 40.426 | 5.668 | 74.912 | 1.00 | 42.41 |
| 12173 | O | HOH | W | 228 | 26.804 | 24.852 | 7.009 | 1.00 | 45.55 |

US 7,297,508 B1

CRYSTALLIZATION OF FIBROBLAST ACTIVATION PROTEIN ALPHA (FAPα)

RELATED APPLICATION

This application claims the benefit of U.S. Provisional Application No. 60/417,335 filed Oct. 8, 2002, which is incorporated herein by reference.

FIELD OF THE INVENTION

The present invention relates to a serine protease of Clan SC family S9 and more specifically to a particular member of this family known as fibroblast activation protein (FAPα). Provided is FAPα in crystalline form, methods of forming crystals comprising FAPα, methods of using crystals comprising FAPα, a crystal structure of FAPα, and methods of using the crystal structure.

BACKGROUND OF THE INVENTION

A general approach to designing inhibitors that are selective for a given protein is to determine how a putative inhibitor interacts with a three dimensional structure of that protein. For this reason it is useful to obtain the protein in crystalline form and perform X-ray diffraction techniques to determine the protein's three-dimensional structure coordinates. Various methods for preparing crystalline proteins are known in the art.

Once protein crystals are produced, crystallographic data can be generated using the crystals to provide useful structural information that assists in the design of small molecules that bind to the active site of the protein and inhibit the protein's activity in vivo. If the protein is crystallized as a complex with a ligand, one can determine both the shape of the protein's binding pocket when bound to the ligand, as well as the amino acid residues that are capable of close contact with the ligand. By knowing the shape and amino acid residues comprised in the binding pocket, one may design new ligands that will interact favorably with the protein. With such structural information, available computational methods may be used to predict how strong the ligand binding interaction will be. Such methods aid in the design of inhibitors that bind strongly, as well as selectively to the protein.

SUMMARY OF THE INVENTION

The present invention is directed to crystals comprising FAPα and particularly crystals comprising FAPα that have sufficient size and quality to obtain useful information about the structural properties of FAPα and molecules or complexes that may associate with FAPα.

In one embodiment, a composition is provided that comprises a protein in crystalline form wherein the protein has 65%, 70%, 80%, 90%, 95% or greater identity with residues 27-760 of SEQ. ID No. 1.

In one variation, the protein has activity characteristic of FAPα. For example, the protein may optionally be inhibited by inhibitors of wild type FAPα.

The protein may also diffract X-rays for a determination of structure coordinates to a resolution of 4 Å, 3 Å, 2.5 Å, 2 Å or less.

In one variation, the protein crystal has a crystal lattice in a $P2_12_12_1$ space group. The protein crystal may also have a crystal lattice having unit cell dimensions, +/−5%, of a—70.31 Å b=152.60 Å and c=214.65 Å.

The present invention is also directed to crystallizing FAPα. The present invention is also directed to the conditions useful for crystallizing FAPα. It should be recognized that a wide variety of crystallization methods can be used in combination with the crystallization conditions to form crystals comprising FAPα including, but not limited to, vapor diffusion, batch and dialysis.

In one embodiment, a method is provided for forming crystals of a protein comprising: forming a crystallization volume comprising: a protein that has at least 65% identity with residues 27-760 of SEQ. ID No. 1 in a concentration between 1 mg/ml and 50 mg/ml; 5-50% w/v of precipitant wherein the precipitant comprises one or more members of the group consisting of PEG MME having a molecular weight range between 300-10000, and PEG having a molecular weight range between 100-10000; optionally 0.05 to 2.5M additives wherein the additives comprises a monovalent and/or divalent salt (for example, sodium, lithium, magnesium, calcium, and the like); and wherein the crystallization volume has a pH between pH 7 and pH 10.5; and storing the crystallization volume under conditions suitable for crystal formation. The method optionally further comprises using 0.05-0.2M buffers selected from the group consisting of Tris-HCl, CHES and combinations thereof. The method also optionally further includes performing the crystallization at a temperature between 1° C.-25° C.

The method may optionally further comprise forming a protein crystal that has a crystal lattice in a $P2_12_12_1$ space group. The method also optionally further comprises forming a protein crystal that has a crystal lattice having unit cell dimensions, +/−5%, of a—70.31 Å b=152.60 Å and c=214.65 Å. The invention also relates to protein crystals formed by these methods.

The present invention is also directed to structure coordinates for FAPα as well as structure coordinates that are comparatively similar to these structure coordinates. It is noted that these comparatively similar structure coordinates may encompass proteins with similar sequences and/or structures, such as other members of the S9 protease family. For example, machine-readable data storage media is provided having data storage material encoded with machine-readable data that comprises structure coordinates that are comparatively similar to the structure coordinates of FAPα. The present invention is also directed to a machine readable data storage medium having data storage material encoded with machine readable data, which, when read by an appropriate machine, can display a three dimensional representation of all or a portion of a structure of FAPα or a model that is comparatively similar to the structure of all or a portion of FAPα.

In one embodiment, machine readable data storage medium is provided having data storage material encoded with machine readable data, the machine readable data comprising: structure coordinates that have a root mean square deviation of alpha-carbon atoms of less than 3 Å when superimposed on alpha-carbon atoms positions of corresponding atomic coordinates of FIG. 3, the root mean square deviation being calculated based only on those alpha-carbon atoms of amino acid residues in the structure coordinates that are also present in residues 27-760 of SEQ. ID No. 1.

In another embodiment, machine readable data storage medium is provided having data storage material encoded with machine readable data, the machine readable data comprising: structure coordinates that have a root mean square deviation of alpha-carbon atoms of less than 3 Å when superimposed on alpha-carbon atom positions of corresponding atomic coordinates of FIG. 3, the root mean square deviation being calculated based only on those alpha-carbon atoms of amino acid residues in the structure coordinates that are also present in Tables 1, 2, 3, 4 and/or 5.

For example, in one embodiment where the comparison is based on the 4 Angstrom set of amino acid residues (Column 1) and is based on superimposing alpha-carbon atoms (Column 2), the structure coordinates may have a root mean square deviation equal to or less than 0.75 Å, 0.50 Å or 0.38 Å when compared to the structure coordinates of FIG. 3.

TABLE 1

| AA RESIDUES TO USE TO PERFORM RMSD COMPARISON | PORTION OF EACH AA RESIDUE USED TO PERFORM RMSD COMPARISON | RMSD VALUE LESS THAN OR EQUAL TO | | |
|---|---|---|---|---|
| Table 2 | alpha-carbon atoms[1] | 0.75 | 0.50 | 0.38 |
| (4 Angstrom set) | main-chain atoms[1] | 0.82 | 0.55 | 0.41 |
| (relative to S630) | all non-hydrogen[2] | 0.95 | 0.64 | 0.48 |
| Table 3 | alpha-carbon atoms[1] | 3.84 | 2.56 | 1.92 |
| (7 Angstrom set) | main-chain atoms[1] | 3.83 | 2.55 | 1.91 |
| (relative to S630) | all non-hydrogen[2] | 4.15 | 2.77 | 2.07 |
| Table 4 | alpha-carbon atoms[1] | 4.25 | 2.83 | 2.13 |
| (10 Angstrom set) | main-chain atoms | 4.29 | 2.86 | 2.14 |
| (relative to S630) | all non-hydrogen[2] | 4.60 | 3.07 | 2.30 |
| Residues 39-757 of | alpha-carbon atoms[1] | 6.96 | 4.64 | 3.48 |
| SEQ. ID No. 1 | main-chain atoms[1] | 6.92 | 4.61 | 3.46 |
| | all non-hydrogen[2] | 7.08 | 4.72 | 3.54 |

[1]the RMSD computed between the atoms of all amino acids that are common to both the target and the reference in the aligned and superposed structure. The amino acids need not to be identical.
[2]the RMSD computed only between identical amino acids, which are common to both the target and the reference in the aligned and superposed structure.

It is noted in regard to these embodiments that the root mean square deviation calculation may optionally be based on a comparison of main-chain atoms, non-hydrogen atoms or a comparison of all atoms where the same type of amino acid residue is present. Also, the root mean square deviation of alpha-carbon atoms, main-chain atoms, non-hydrogen atoms or all atoms may optionally be less than 2.7 Å, 2.5 Å, 2.0 Å, 1.5 Å, 1 Å, 0.5 Å, or less.

The present invention is also directed to a three-dimensional structure of all or a portion of FAPα. This three-dimensional structure may be used to identify binding sites, to provide mutants having desirable binding properties, and ultimately, to design, characterize, or identify ligands capable of interacting with FAPα. Ligands that interact with FAPα may be any type of atom, compound, protein or chemical group that binds to or otherwise associates with the protein. Examples of types of ligands include natural substrates for FAPα, inhibitors of FAPα, and heavy atoms.

In one embodiment, a method is provided for displaying a three dimensional representation of a structure of a protein comprising: taking machine readable data comprising structure coordinates that have a root mean square deviation of alpha-carbon atoms of less than 3 Å when superimposed on alpha-carbon atom positions of corresponding atomic coordinates of FIG. 3, the root mean square deviation being calculated based only on those alpha-carbon atoms of amino acid residues in the structure coordinates that are also present in residues shown in Tables 2, 3, 4 and/or 5 or residues 27-760 of SEQ. ID No. 1; computing a three dimensional representation of a structure based on the structure coordinates; and displaying the three dimensional representation.

In another embodiment, a method is provided for displaying a three dimensional representation of a structure of a protein comprising: displaying a computer model for a protein binding pocket, at least a portion of the computer model having a surface contour that has a root mean square deviation of less than 3 Å when superimposed on a surface contour defined by atomic coordinates of FIG. 3, the root mean square deviation being calculated based only on alpha-carbon atoms in the structure coordinates of FIG. 3 that are present in residues shown in Tables 2, 3, 4 and/or 5 or residues 27-760 of SEQ. ID No. 1.

It is again noted in regard to these embodiments that the root mean square deviation calculation may optionally be based on a comparison of main-chain atoms, non-hydrogen atoms or a comparison of all atoms where the same type of amino acid residue is present. Also, the root mean square deviation of alpha-carbon atoms, non-hydrogen atoms or all atoms may optionally be less than 2.7 Å, 2.5 Å, 2.0 Å, 1.5 Å, 1 Å, 0.5 Å, or less.

The present invention is also directed to a method for solving a three-dimensional crystal structure of a target protein using the structure of FAPα.

In one embodiment, a computational method is provided comprising: taking machine readable data comprising structure coordinates that have a root mean square deviation of alpha-carbon atoms of less than 3 Å when superimposed on alpha-carbon atom positions of corresponding atomic coordinates of FIG. 3, the root mean square deviation being calculated based only on those alpha-carbon atoms of amino acid residues in the structure coordinates that are also present in residues shown in Tables 2, 3, 4 and/or 5 or residues 27-760 of SEQ. ID No. 1; computing phases based on the structural coordinates; computing an electron density map based on the computed phases; and determining a three-dimensional crystal structure based on the computed electron density map.

In another embodiment, a computational method is provided comprising: taking an X-ray diffraction pattern of a crystal of the target protein; and computing a three-dimensional electron density map from the X-ray diffraction pattern by molecular replacement, wherein structure coordinates used as a molecular replacement model comprise structure coordinates that have a root mean square deviation of alpha-carbon atoms of less than 3 Å when superimposed on alpha-carbon atom positions of corresponding atomic coordinates of FIG. 3, the root mean square deviation being calculated based only on those alpha-carbon atoms of amino acid residues in the structure coordinates that are also present in residues shown in Tables 2, 3, 4 and/or 5 or residues 27-760 of SEQ. ID No. 1. This method may optionally further comprise determining a three-dimensional crystal structure based upon the computed three-dimensional electron density map.

It is again noted in regard to these embodiments that the root mean square deviation calculation may optionally be based on a comparison of main-chain atoms, non-hydrogen atoms or a comparison of all atoms where the same type of amino acid residue is present. Also, the root mean square deviation of alpha-carbon atoms, main-chain atoms, non-hydrogen atoms or all atoms may optionally be less than 2.7 Å, 2.5 Å, 2.0 Å, 1.5 Å, 1 Å, 0.5 Å, or less.

The present invention is also directed to using a crystal structure of FAPα, in particular the structure coordinates of FAPα and the surface contour defined by them, in methods for screening, designing, or optimizing molecules or other chemical entities that interact with and preferably inhibit FAPα.

One skilled in the art will appreciate the numerous uses of the inventions described herein, particularly in the areas of drug design, screening and optimization of drug candidates, as well as in determining additional unknown crystal structures. For example, a further aspect of the present invention relates to using a three-dimensional crystal structure of all or a portion of FAPα and/or its structure coordinates to evaluate the ability of entities to associate with FAPα. The entities may be any entity that may function as a ligand and thus may be any type of atom, compound, protein (such as antibodies) or chemical group that can bind to or otherwise associate with a protein.

In one embodiment, a method is provided for evaluating a potential of an entity to associate with a protein comprising: creating a computer model of a protein structure using structure coordinates that comprise structure coordinates that have a root mean square deviation of alpha-carbon atoms of less than 3 Å when superimposed on alpha-carbon atom positions of corresponding atomic coordinates of FIG. 3, the root mean square deviation being calculated based only on those alpha-carbon atoms of amino acid residues in the structure coordinates that are also present in residues shown in Tables 2, 3, 4 and/or 5 or residues 27-760 of SEQ. ID No. 1; performing a fitting operation between the entity and the computer model; and analyzing results of the fitting operation to quantify an association between the entity and the model.

In another embodiment, a method is provided for evaluating a potential of an entity to associate with a protein comprising: computing a computer model for a protein binding pocket, at least a portion of the computer model having a surface contour that has a root mean square deviation of less than 3 Å when superimposed on a surface contour defined by atomic coordinates of FIG. 3, the root mean square deviation being calculated based only on alpha-carbon atoms in the structure coordinates that are present in residues shown in Tables 2, 3, 4 and/or 5 or residues 27-760 of SEQ. ID No. 1; evaluating a potential of an entity to associate with the surface contour by performing a fitting operation between the entity and the surface contour; and analyzing results of the fitting operation to quantify an association between the entity and the computer model.

In another embodiment, a method is provided for identifying entities that can associate with a protein comprising: generating a three-dimensional structure of a protein using structure coordinates that comprise structure coordinates that have a root mean square deviation of alpha-carbon atoms of less than 3 Å when superimposed on alpha-carbon atom positions of corresponding atomic coordinates of FIG. 3, the root mean square deviation being calculated based only on those alpha-carbon atoms of amino acid residues in the structure coordinates that are also present in residues shown in Tables 2, 3, 4 and/or 5 or residues 27-760 of SEQ. ID No. 1; employing the three-dimensional structure to design or select an entity that can associate with the protein; and contacting the entity with a protein having at least 65% identity with residues 27-760 of SEQ. ID No. 1.

In another embodiment, a method is provided for identifying entities that can associate with a protein comprising: computing a computer model for a protein binding pocket, at least a portion of the computer model having a surface contour that has a root mean square deviation of less than 3 Å when superimposed on a surface contour defined by atomic coordinates of FIG. 3, the root mean square deviation being calculated based only on alpha-carbon atoms in the structure coordinates that are present in residues shown in Tables 2, 3, 4 and/or 5 or residues 27-760 of SEQ. ID No. 1; employing the computer model to design or select an entity that can associate with the protein; and contacting the entity with a protein having at least 65% identity with residues 27-760 of SEQ. ID No. 1.

In another embodiment, a method is provided for evaluating the ability of an entity to associate with a protein, the method comprising: constructing a computer model defined by structure coordinates that comprise structure coordinates that have a root mean square deviation of alpha-carbon atoms of less than 3 Å when superimposed on alpha-carbon atom positions of corresponding atomic coordinates of FIG. 3, the root mean square deviation being calculated based only on those alpha-carbon atoms of amino acid residues in the structure coordinates that are also present in residues shown in Tables 2, 3, 4 and/or 5 or residues 27-760 of SEQ. ID No. 1; selecting an entity to be evaluated by a method selected from the group consisting of (i) assembling molecular fragments into the entity, (ii) selecting an entity from a small molecule database, (iii) de novo ligand design of the entity, and (iv) modifying a known ligand for FAPα, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In another embodiment, a method for evaluating the ability of an entity to associate with a protein, the method comprising: computing a computer model for a protein binding pocket, at least a portion of the computer model having a surface contour that has a root mean square deviation of less than 3 Å when superimposed on a surface contour defined by atomic coordinates of FIG. 3, the root mean square deviation being calculated based only on alpha-carbon atoms in the structure coordinates that are present in residues shown in Tables 2, 3, 4 and/or 5 or residues 27-760 of SEQ. ID No. 1; selecting an entity to be evaluated by a method selected from the group consisting of (i) assembling molecular fragments into the entity, (ii) selecting an entity from a small molecule database, (iii) de novo ligand design of the entity, and (iv) modifying a known ligand for FAPα, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the said binding pocket.

It is again noted in regard to these embodiments that the root mean square deviation calculation may optionally be based on a comparison of main-chain atoms, non-hydrogen atoms or a comparison of all atoms where the same type of amino acid residue is present. Also, the root mean square deviation of alpha-carbon atoms, non-hydrogen atoms or all atoms may optionally be less than 2.7 Å, 2.5 Å, 2.0 Å, 1.5 Å, 1 Å, 0.5 Å, or less.

Also in regard to each of these embodiments, the protein may optionally have activity characteristic of FAPα. For example, the protein may optionally be inhibited by inhibitors of wild type FAPα.

In another embodiment, a method is provided for identifying an entity that associates with a protein comprising: taking structure coordinates from diffraction data obtained from a crystal of a protein that has at least 65%, 70%, 80%, 90%, 95% or more identity with the residues 26-760 of SEQ. ID No. 1; and performing rational drug design using a three dimensional structure that is based on the obtained structure coordinates. The protein crystals may optionally have a crystal lattice having unit cell dimensions, +/−5%, of a=70.3 Å b=152.60 Å and c=214.65 Å. The method may optionally further comprise selecting one or more entities based on the rational drug design and contacting the selected entities with the protein. The method may also optionally further comprise measuring an activity of the protein when contacted with the one or more entities. The method also may optionally further comprise comparing activity of the protein in a presence of and in the absence of the one or more entities; and selecting entities where activity of the protein changes depending whether a particular entity is present. The method also may optionally further comprise contacting cells expressing the protein with the one or more entities and detecting a change in a phenotype of the cells when a particular entity is present.

BRIEF DESCRIPTION OF THE FIGURES

FIG. 1 illustrates SEQ. ID Nos. 1, 2 and 3 referred to in this application.

FIG. 3 lists a set of atomic structure coordinates for FAPα (SEQ. ID No. 1) as derived by X-ray crystallography from a crystal that comprises the protein. The following abbreviations are used in FIG. 3: "X, Y, Z" crystallographically define the atomic position of the element measured; "B" is a thermal factor that measures movement of the atom around its atomic center; "Occ" is an occupancy factor that refers to the fraction of the molecules in which each atom occupies the position specified by the coordinates (a value of "1" indicates that each atom has the same conformation, i.e., the same position, in all molecules of the crystal).

DETAILED DESCRIPTION OF THE INVENTION

Figure 2:
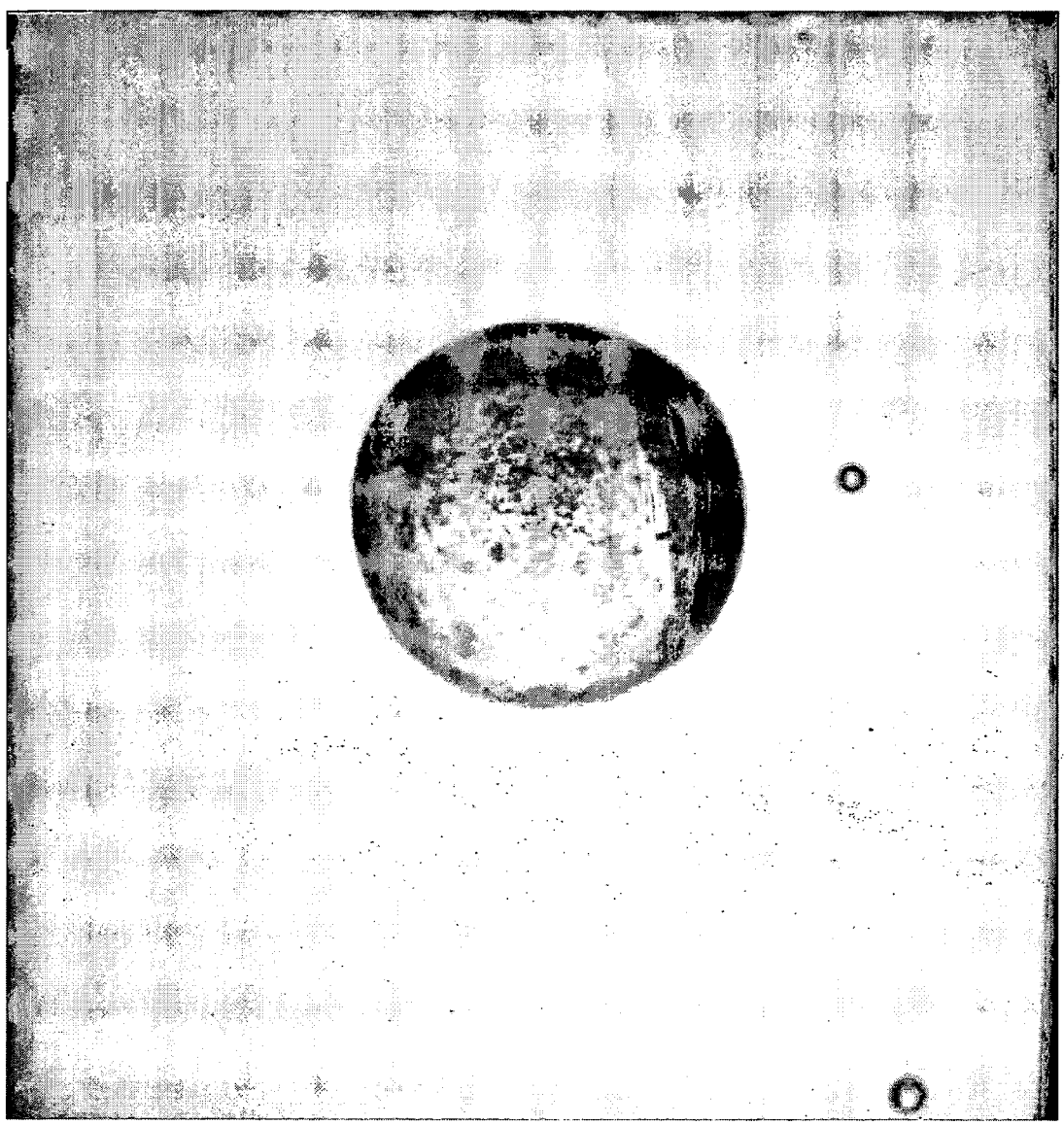
FIG. 2 illustrates a crystal of FAPα complex (SEQ. ID No. 3).

The present invention relates to a member of the Clan SC, S9 family of human proteases known as fibroblast activation protein (FAPα). More specifically, the present invention relates to FAPα in crystalline form, methods of forming crystals comprising FAPα, methods of using crystals comprising FAPα, structure coordinates and a crystal structure of FAPα, and methods of using the structure coordinates and crystal structure.

In describing protein structure and function herein, reference is made to amino acids comprising the protein. The amino acids may also be referred to by their conventional abbreviations; A=Ala=Alanine; T=Thr=Threonine; V=Val=Valine; C=Cys=Cysteine; L=Leu=Leucine; Y=Tyr=Tyrosine; I=Ile=Isoleucine; N=Asn=Asparagine; P=Pro=Proline; Q=Gln=Glutamine; F=Phe=Phenylalanine; D=Asp=Aspartic Acid; W=Trp=Tryptophan; E=Glu=Glutamic Acid; M=Met=Methionine; K=Lys=Lysine; G=Gly=Glycine; R=Arg=Arginine; S=Ser=Serine; and H=His=Histidine.

1. FAPα

FAPα (also known as Seprase) is a 170 kDa homodimeric type II transmembrane glycoprotein. FAPα is a serine protease of Clan SC family S9 and is not expressed in normal, human tissue, but highly expressed by tumor fibroblasts. Expression of FAPα was found on reactive stromal fibroblast in more than 90% of human epithelial carcinomas, including lung, colorectal and breast carcinomas. In vitro, FAPα is a highly specific aminopeptidase and releases dipeptides from the amino terminus of peptides with a L-proline or L-alanine in the penultimate position. Besides its dipeptidyl peptidase activity, FAPα also exhibits collagenase activity in vitro. The exact biological function of FAPα remains elusive. In vivo studies have shown that FAPα enhances tumor growth and invasion, suggesting a possible role of FAPα in extracellular matrix degradation or growth factor activation in tissue remodeling.

It should be understood that the methods and compositions provided relating to FAPα are not intended to be limited to the wild type, full length form of FAPα. Instead, the present invention also relates to fragments and variants of FAPα as described herein. Further, the present invention has applicability to other S9 proteases whose sequence and/or structure are comparatively similar to FAPα.

In one embodiment, FAPα comprises the wild-type form of full length FAPα, set forth herein as SEQ. ID No. 1 (GenBank Accession Number NP_004451; "Molecular cloning of fibroblast activation protein alpha, a member of the serine protease family selectively expressed in stromal fibroblasts of epithelial cancers", Scanlan, M. J., Raj, B. K., Calvo, B., Garin-Chesa, P., Sanz-Moncasi, M. P., Healey, J. H., Old, L. J. and Rettig, W. J., *Proc. Natl. Acad. Sci. U.S.A.*, 91 (12), 5657-5661, 1994).

In another embodiment, FAPα comprises residues 26-760 of SEQ. ID No. 1 which comprises the active site domain of wild-type FAPα that is represented in the set of structural coordinates shown in FIG. 3.

It should be recognized that the invention may be readily extended to various variants of wild-type FAPα and variants of fragments thereof. In another embodiment, FAPα comprises a sequence that has at least 65% identity, preferably at least 70%, 80%, 90%, 95% or higher identity with SEQ. ID No. 1.

It is also noted that the above sequences of FAPα are also intended to encompass isoforms, mutants and fusion proteins of these sequences. An example of a fusion protein is provided by SEQ. ID No. 3, which includes a 6 residue C-terminal tag (6 residues are histidine) that may be used to facilitate purification of the protein.

With the crystal structure provided herein, it is now known where amino acid residues are positioned in the structure. As a result, the impact of different substitutions can be more easily predicted and understood.

For example, based on the crystal structure, applicants have determined that the FAPα amino acids shown in Table 1 encompass a 4-Angstrom radius around the FAPα active site and thus likely to interact with any active site inhibitor of FAPα. Applicants have also determined that the amino acids of Table 2 encompass a 7-Angstrom radius around the FAPα active site. Further it has been determined that the amino acids of Table 3 encompass a 10-Angstrom radius around the FAPα active site. It is noted that there are two different FAPα molecules in the asymmetric unit, referred to as chains A and B. As a result, two sets of structure coordinates were obtained for each amino acid. There is one dimer formed in the asymmetric unit between molecules A and B. Applicants have also determined that amino acids of Table 5 encompass a 5-Angstrom radius around the FAPα amino acids that interact at the AB dimerization interface. The A and B sets of structural coordinates appear in FIG. 3. It is noted that the sequence and structure of the residues in the active site and dimerization interface may also be conserved and hence pertinent to other S9 proteases.

One or more of the sets of amino acids set forth in the tables is preferably conserved in a variant of FAPα. Hence, FAPα may optionally comprise a sequence that has at least 65% identity, preferably at least 70%, 80%, 90%, 95% or higher identity with any one of the above sequences (e.g., all of SEQ. ID No. 1 or residues 27-760 of SEQ. ID No. 1) where at least the residues shown in Tables 2, 3, 4 and/or 5 are conserved with the exception of 0, 1, 2, 3, or 4 residues. It should be recognized that one might optionally vary some of the binding site residues in order to determine the effect such changes have on structure or activity.

TABLE 2

Amino Acids encompassed by a 4-Angstrom radius around the FAPα active site (SEQ. ID No. 1).

| | | |
|---|---|---|
| Trp623 | Gly627 | Pro649 |
| Ser624 | Tyr628 | Val650 |
| Tyr625 | Val647 | Val705 |
| Gly626 | Ala648 | His734 |

TABLE 3

Amino Acids encompassed by a 7-Angstrom radius around the FAPα active site (SEQ. ID No. 1).

| | | |
|---|---|---|
| Val540 | Gly627 | Val650 |
| Tyr541 | Tyr628 | Ser651 |
| Gly622 | Val629 | Trp653 |
| Trp623 | Ala646 | Tyr656 |
| Ser624 | Val647 | Asn704 |
| Tyr625 | Ala648 | Val705 |
| Gly626 | Pro649 | His734 |

TABLE 4

Amino Acids encompassed by a 10-Angstrom radius around the FAPα active site (SEQ. ID No. 1).

| | | |
|---|---|---|
| Arg123 | Gly627 | Tyr694 |
| Trp199 | Tyr628 | Leu696 |
| Glu203 | Val629 | Ile697 |
| Glu204 | Ser630 | His698 |
| Tyr252 | Ser631 | Gly699 |
| Phe350 | Leu632 | Asp702 |
| Val540 | Ile645 | Asn704 |
| Tyr541 | Ala646 | Val705 |
| Gly542 | Val647 | His706 |
| Gly543 | Ala648 | Asn709 |
| Pro544 | Pro649 | Ser710 |
| Glu596 | Val650 | Ile713 |
| Trp621 | Ser651 | Asn733 |
| Gly622 | Ser652 | His734 |
| Trp623 | Trp653 | Gly735 |
| Ser624 | Tyr656 | Leu736 |
| Tyr625 | Tyr660 | Leu744 |
| Gly626 | Val682 | Met748 |

TABLE 5

Amino Acids encompassed by a 5-Angstrom radius around the AB dimerization interface (SEQ. ID No. 1).

| Chain A | Chain B |
|---|---|
| Pro232 | Pro232 |
| Val233 | Val233 |
| Ile234 | Ile234 |
| Ala235 | Ala235 |
| Tyr236 | Tyr236 |
| Ser237 | Ser237 |
| Tyr239 | Tyr239 |
| Gly240 | Gly240 |
| Asp241 | Asp241 |
| Glu242 | Glu242 |
| Gln243 | Gln243 |
| Tyr244 | Tyr244 |
| Pro245 | Pro245 |
| Thr247 | Thr247 |
| Tyr252 | Tyr252 |
| Pro253 | Pro253 |
| Lys254 | Lys254 |
| Ala255 | Ala255 |
| Glu654 | Glu654 |
| Tyr655 | Tyr655 |
| Leu696 | Leu696 |
| Phe701 | Phe707 |
| Gln708 | Gln708 |
| Ser710 | Ser710 |
| Ala711 | Ala711 |
| Gln712 | Gln712 |
| Ala714 | Ala714 |
| Lys715 | Lys715 |
| Leu717 | Leu717 |
| Val718 | Val718 |
| Asn719 | Asn711 |
| Gln721 | Gln721 |
| Val722 | Val722 |
| Asp723 | Asp723 |
| Phe724 | Phe724 |
| Gln725 | Gln725 |
| Ala726 | Ala726 |
| Met727 | Met727 |
| Trp728 | Trp728 |
| Ser730 | Ser730 |
| Ser731 | Ser731 |
| Leu739 | Leu739 |
| Ser740 | Ser740 |
| Asn742 | Asn742 |
| His743 | His743 |
| His747 | His747 |
| His750 | His750 |

With the benefit of the crystal structure and guidance provided by Tables 2, 3, 4 and 5, a wide variety of FAPα variants (e.g., insertions, deletions, substitutions, etc.) that fall within the above specified identity ranges may be designed and manufactured utilizing recombinant DNA techniques well known to those skilled in the art, particularly in view of the knowledge of the crystal structure provided herein. These modifications can be used in a number of combinations to produce the variants. The present invention is useful for crystallizing and then solving the structure of the range of variants of FAPα.

Variants of FAPα may be insertional variants in which one or more amino acid residues are introduced into a predetermined site in the FAPα sequence. For instance, insertional variants can be fusions of heterologous proteins or polypeptides to the amino or carboxyl terminus of the subunits.

Variants of FAPα also may be substitutional variants in which at least one residue has been removed and a different residue inserted in its place. Non-natural amino acids (i.e. amino acids not normally found in native proteins), as well as isosteric analogs (amino acid or otherwise) may optionally be employed in substitutional variants. Examples of suitable substitutions are well known in the art, such as the Glu→Asp, Ser→Cys, Cys→Ser, and His→Ala for example.

Another class of variants is deletional variants, which are characterized by the removal of one or more amino acid residues from the FAPα sequence.

Other variants may be produced by chemically modifying amino acids of the native protein (e.g., diethylpyrocarbonate treatment that modifies histidine residues). Preferred are chemical modifications that are specific for certain amino acid side chains. Specificity may also be achieved by blocking other side chains with antibodies directed to the side chains to be protected. Chemical modification includes such reactions as oxidation, reduction, amidation, deamidation, or substitution of bulky groups such as polysaccharides or polyethylene glycol.

Exemplary modifications include the modification of lysinyl and amino terminal residues by reaction with succinic or other carboxylic acid anhydrides. Modification with these agents has the effect of reversing the charge of the lysinyl residues. Other suitable reagents for modifying amino-containing residues include imidoesters such as methyl picolinimidate; pyridoxal phosphate; pyridoxal chloroborohydride; trinitrobenzenesulfonic acid; 0-methylisourea, 2,4-pentanedione; and transaminaseN: talyzed reaction with glyoxylate, and N-hydroxysuccinamide esters of polyethylene glycol or other bulky substitutions.

Arginyl residues may be modified by reaction with a number of reagents, including phenylglyoxal, 2,3-butanedione, 1,2-cyclohexanedione, and ninhydrin. Modification of arginine residues requires that the reaction be performed in alkaline conditions because of the high $pK_a$, of the guanidine functional group. Furthermore, these reagents may react with the groups of lysine as well as the arginine epsilon-amino group.

Tyrosyl residues may also be modified to introduce spectral labels into tyrosyl residues by reaction with aromatic diazonium compounds or tetranitromethane, forming 0-acetyl tyrosyl species and 3-nitro derivatives, respectively. Tyrosyl residues may also be iodinated using $^{125}$I or $^{131}$I to prepare labeled proteins for use in radioimmunoassays.

Carboxyl side groups (aspartyl or glutamyl) may be selectively modified by reaction with carbodiimides or they may be converted to asparaginyl and glutaminyl residues by reaction with ammonium ions. Conversely, asparaginyl and glutaminyl residues may be deamidated to the corresponding aspartyl or glutamyl residues, respectively, under mildly acidic conditions. Either form of these residues falls within the scope of this invention.

Other modifications that may be formed include the hydroxylation of proline and lysine, phosphorylation of hydroxyl groups of seryl or threonyl groups of lysine, arginine and histidine side chains (T. E. Creighton, *Proteins: Structure and Molecular Properties*, W.H. Freeman & Co., San Francisco, pp. 79-86, 1983), acetylation of the N-terminal amine and amidation of any C-terminal carboxyl group.

As can be seen, modifications of the nucleic sequence encoding FAPα may be accomplished by a variety of well-known techniques, such as site-directed mutagenesis (see, Gillman and Smith, *Gene* 8:81-97 (1979) and Roberts, S. et al., *Nature* 328:731-734 (1987)). When modifications are made, these modifications may optionally be evaluated for there affect on a variety of different properties including, for example, solubility, crystallizability and a modification to the protein's structure and activity.

In one variation, the variant and/or fragment of wild-type FAPα is functional in the sense that the resulting protein is capable of associating with at least one same chemical entity that is also capable of selectively associating with a protein comprising the wild-type FAPα (e.g., residues 27-760 of SEQ. ID No. 1) since this common associative ability evidences that at least a portion of the native structure has been conserved.

It is noted the activity of the native protein need not necessarily be conserved. Rather, amino acid substitutions, additions or deletions that interfere with native activity but which do not significantly alter the three-dimensional structure of the domain are specifically contemplated by the invention. Crystals comprising such variants of FAPα, and the atomic structure coordinates obtained there from, can be used to identify compounds that bind to the native domain. These compounds may affect the activity of the native domain.

Amino acid substitutions, deletions and additions that do not significantly interfere with the three-dimensional structure of FAPα will depend, in part, on the region where the substitution, addition or deletion occurs in the crystal structure. These modifications to the protein can now be made far more intelligently with the crystal structure information provided herein. In highly variable regions of the molecule, non-conservative substitutions as well as conservative substitutions may be tolerated without significantly disrupting the three-dimensional structure of the molecule. In highly conserved regions, or regions containing significant secondary structure, conservative amino acid substitutions are preferred.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. Other conservative amino acid substitutions are well known in the art.

It should be understood that the protein may be produced in whole or in part by chemical synthesis. As a result, the selection of amino acids available for substitution or addition is not limited to the genetically encoded amino acids. Indeed, mutants may optionally contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues in order to provide convenient cloning sites in cDNA encoding the polypeptide, to aid in purification of the polypeptide, etc. Such substitutions, deletions and/or additions which do not substantially alter the three dimensional structure of FAPα will be apparent to those having skills in the art, particularly in view of the three dimensional structure of FAPα provided herein.

2. Cloning, Expression and Purification of FAPα

The gene encoding FAPα can be isolated from RNA, cDNA or cDNA libraries. In this case, the portion of the gene encoding amino acid residues 27-760 (SEQ. ID No. 1), corresponding to the catalytic domain of human FAPα, was isolated and is shown as SEQ. ID No. 2.

Construction of expression vectors and recombinant proteins from the DNA sequence encoding FAPα may be performed by various methods well known in the art. For example, these techniques may be performed according to Sambrook et al., Molecular Cloning—A Laboratory Manual, Cold Spring Harbor, N.Y. (1989), and Kriegler, M., Gene Transfer and Expression, A Laboratory Manual, Stockton Press, New York (1990).

A variety of expression systems and hosts may be used for the expression of FAPα. Example 1 provides one such expression system.

Once expressed, purification steps are employed to produce FAPα in a relatively homogeneous state. In general, a higher purity solution of a protein increases the likelihood that the protein will crystallize. Typical purification methods include the use of centrifugation, partial fractionation, using salt or organic compounds, dialysis, conventional column chromatography, (such as ion exchange, molecular sizing chromatography, etc.), high performance liquid chromatography (HPLC), and gel electrophoresis methods (see, e.g., Deutcher, "Guide to Protein Purification" in Methods in Enzymology (1990), Academic Press, Berkeley, Calif.).

FAPα may optionally be affinity labeled during cloning, preferably with an C-terminal six-histidine tag, in order to facilitate purification. With the use of an affinity label, it is possible to perform a one-step purification process on a purification column that has a unique affinity for the label. The affinity label may be optionally removed after purification. These and other purification methods are known and will be apparent to one of skill in the art.

3. Crystallization & Crystals Comprising FAPα

One aspect of the present invention relates to methods for forming crystals comprising FAPα as well as crystals comprising FAPα.

In one embodiment, a method for forming crystals comprising FAPα is provided comprising forming a crystallization volume comprising FAPα, one or more precipitants, optionally a buffer, optionally a monovalent and/or divalent salt and optionally an organic solvent; and storing the crystallization volume under conditions suitable for crystal formation.

In yet another embodiment, a method for forming crystals comprising FAPα is provided comprising forming a crystallization volume comprising FAPα in solution comprising the components shown in Table 6; and storing the crystallization volume under conditions suitable for crystal formation.

TABLE 6

Precipitant 5-50% w/v of precipitant wherein the precipitant comprises one or more members of the group consisting of PEG MME having a molecular weight range between 300-10000, and PEG having a molecular weight range between 100-10000 pH pH 7-10.5. Buffers that may be used include, but are not limited to Tris, CHES and combinations thereof.

Additives

Optionally 0.05 to 2.5M additives wherein the additives comprises a monovalent and/or divalent salt (for example, sodium, lithium, magnesium, calcium, and the like)

TABLE 6-continued

Protein Concentration 1 mg/ml-50 mg/ml

Temperature

1° C.-25° C.

In yet another embodiment, a method for forming crystals comprising FAPα is provided comprising forming a crystallization volume comprising FAPα; introducing crystals comprising FAPα as nucleation sites, and storing the crystallization volume under conditions suitable for crystal formation.

Crystallization experiments may optionally be performed in volumes commonly used in the art, for example typically 15, 10, 5, 2 microliters or less. It is noted that the crystallization volume optionally has a volume of less than 1 microliter, optionally 500, 250, 150, 100, 50 or less nanoliters.

It is also noted that crystallization may be performed by any crystallization method including, but not limited to batch, dialysis and vapor diffusion (e.g., sitting drop and hanging drop) methods. Micro and/or macro seeding of crystals may also be performed to facilitate crystallization.

It should be understood that forming crystals comprising FAPα and crystals comprising FAPα according to the invention are not intended to be limited to the wild type, full length FAPα shown in SEQ. ID No. 1 and to fragments comprising residues 27-760 of SEQ. ID No. 1. Rather, it should be recognized that the invention may be extended to various other fragments and variants of wild-type FAPα as described above.

It should also be understood that forming crystals comprising FAPα and crystals comprising FAPα according to the invention may be such that FAPα is optionally complexed with one or more ligands and one or more copies of the same ligand. The ligand used to form the complex may be any ligand capable of binding to FAPα. In one variation, the ligand is a natural substrate. In another variation, the ligand is an inhibitor.

In one particular embodiment, FAPα crystals have a crystal lattice in the $P2_12_12_1$ space group. FAPα crystals may also optionally have unit cell dimensions, +/−5%, of a=70.31 Å b=152.60 Å and c=214.65 Å. FAPα crystals also preferably are capable of diffracting X-rays for determination of atomic coordinates to a resolution of 4 Å, 3 Å, 2.5 Å, 2 Å or better.

Crystals comprising FAPα may be formed by a variety of different methods known in the art. For example, crystallizations may be performed by batch, dialysis, and vapor diffusion (sitting drop and hanging drop) methods. A detailed description of basic protein crystallization setups may be found in McRee, D. and David. P., *Practical Protein Crystallography*, $2^{nd}$ Ed. (1999), Academic Press Inc. Further descriptions regarding performing crystallization experiments are provided in Stevens, et al. (2000) *Curr. Opin. Struct. Biol.*: 10(5):558-63, and U.S. Pat. Nos. 6,296,673, 5,419,278, and 5,096,676.

In one variation, crystals comprising FAPα are formed by mixing substantially pure FAPα with an aqueous buffer containing a precipitant at a concentration just below a concentration necessary to precipitate the protein. One suitable precipitant for crystallizing FAPα is polyethylene glycol (PEG), which combines some of the characteristics of the salts and other organic precipitants (see, for example, Ward et al., J. Mol. Biol. 98:161, 1975, and McPherson, J. Biol. Chem. 251:6300, 1976.)

During a crystallization experiment, water is removed by diffusion or evaporation to increase the concentration of the precipitant, thus creating precipitating conditions for the protein. In one particular variation, crystals are grown by vapor diffusion in hanging drops or sitting drops. According to these methods, a protein/precipitant solution is formed and then allowed to equilibrate in a closed container with a larger aqueous reservoir having a precipitant concentration for producing crystals. The protein/precipitant solution continues to equilibrate until crystals grow.

By performing submicroliter volume sized crystallization experiments, as detailed in U.S. Pat. No. 6,296,673, effective crystallization conditions for forming crystals of a FAPα complex were obtained. In order to accomplish this, systematic broad screen crystallization trials were performed on a FAPα complex using the sitting drop technique. In each experiment, a 100 nL mixture of FAPα complex and precipitant was placed on a platform positioned over a well containing 100 μL of the precipitating solution. Precipitate and crystal formation was detected in the sitting drops. Fine screening was then carried out for those crystallization conditions that appeared to produce precipitate and/or crystal in the drops.

Based on the crystallization experiments that were performed, a thorough understanding of how different crystallization conditions affect FAPα crystallization was obtained. Based on this understanding, a series of crystallization conditions were identified that may be used to form crystals comprising FAPα. These conditions are summarized in Table 6. A particular example of crystallization conditions that may be used to form diffraction quality crystals of the FAPα complex is detailed in Example 2. FIG. 2 illustrates crystals of the FAPα complex formed using the crystallization conditions provided in Table 6.

One skilled in the art will recognize that the crystallization conditions provided in Table 6 and Example 2 can be varied and still yield protein crystals comprising FAPα. For example, it is noted that variations on the crystallization conditions described herein can be readily determined by taking the conditions provided in Table 6 and performing fine screens around those conditions by varying the type and concentration of the components in order to determine additional suitable conditions for crystallizing FAPα, variants of FAPα, and ligand complexes thereof.

Crystals comprising FAPα have a wide range of uses. For example, now that crystals comprising FAPα have been produced, it is noted that crystallizations may be performed using such crystals as a nucleation site within a concentrated protein solution. According to this variation, a concentrated protein solution is prepared and crystalline material (microcrystals) is used to 'seed' the protein solution to assist nucleation for crystal growth. If the concentrations of the protein and any precipitants are optimal for crystal growth, the seed crystal will provide a nucleation site around which a larger crystal forms. Given the ability to form crystals comprising FAPα according to the present invention, the crystals so formed can be used by this crystallization technique to initiate crystal growth of other FAPα comprising crystals, including FAPα complexed to other ligands.

As will be described herein in greater detail, crystals may also be used to perform X-ray or neutron diffraction analysis in order to determine the three-dimensional structure of FAPα and, in particular, to assist in the identification of its active site. Knowledge of the binding site region allows rational design and construction of ligands including inhibitors. Crystallization and structural determination of FAPα mutants having altered bioactivity allows the evaluation of whether such changes are caused by general structure deformation or by side chain alterations at the substitution site.

4. X-Ray Data Collection and Structure Determination

Crystals comprising FAPα may be obtained as described above in Section 3. As described herein, these crystals may then be used to perform X-ray data collection and for structure determination.

In one embodiment, described in Example 2, crystals of FAPα were obtained where FAPα has the sequence of residues shown in SEQ. ID No. 3. These particular crystals were used to determine the three dimensional structure of FAPα. However, it is noted that other crystals comprising FAPα including different FAPα variants, fragments, and complexes thereof may also be used.

Diffraction data was collected from cryocooled crystals (100K) of FAPα at the Advanced Light Source (ALS) beam lines 5.0.3 using an ADSC Quantum CCD detector. The diffraction pattern of the FAPα crystals displayed symmetry consistent with space group $P2_12_12_1$ with unit cell dimensions a=70.31 Å b=152.60 Å and c=214.65 Å (+/−5%). Data were collected and integrated to 2.3 Å with MOSFLM and scaled with SCALA (CCP4 Study Weekend, Eds. Sawyer, L., Isaacs, N. & Bailey, S. 56-62, SERC Daresbury Laboratory, England, 1993).

All crystallographic calculations were performed using the CCP4 program package (Collaborative Computational Project, N. The CCP4 Suite: Programs for Protein Crystallography. Acta Cryst. D50, 760-763, 1994). The initial phases for FAPα were obtained by the molecular replacement method using the program MOLREP (CCP4 Study Weekend, Eds. Sawyer, L., Isaacs, N. & Bailey, S. 56-62, SERC Daresbury Laboratory, England, 1993). The coordinates of human dipeptidyl peptidase IV (DPPIV; Structure solved at Syrrx, Inc., U.S. Provisional Application 60/409, 206) were used as a search model (55% identity) for the solution of the FAPα structure. The highest solution from the translational function was subjected to a rigid body rotation followed by refinement against the maximum likelihood method as implemented in REFMAC (CCP4). Rigid body refinement and torsional dynamics refinement was followed by multiple rounds of manual building with Xfit (McRee, D. E. XtalView/Xfit-A versatile program for manipulating atomic coordinates and electron density J. Struct. Biol. 125, 156-65 (1999)) and/or ARP_WARP map improvement (Perrakis, A., Morris, R. J. & Lamzin, V. S. Automated protein model building combined with iterative structure refinement). All stages of model refinement were carried with bulk solvent correction and anisotropic scaling. The data collection and data refinement statistics are given in Table 7.

TABLE 7

| Crystal data | |
| --- | --- |
| Space group | $P2_12_12_1$ |
| Unit cell dimensions | a = 70.31Å |
| | b = 152.60Å |
| | c = 214.65Å |
| Data collection | |
| X-ray source | ALS BL 5.0.3 |
| Wavelength [Å] | 1.00 |
| Resolution [Å] | 2.30 |
| Observations (unique) | 89676 |
| Redundancy | 2.5 |
| Completeness overall (outer shell) | 89 (64)% |

TABLE 7-continued

| Crystal data | |
|---|---|
| I/σ(I) overall (outer shell) | 7.8 (1.8) |
| $R_{symm}$ overall (outer shell) | 11.7 (35.2)% |
| Refinement | |
| Reflections used | 84874 |
| R-factor | 24.4% |
| $R_{free}$ | 29.1% |
| r.m.s bonds | 0.03Å |
| r.m.s angles | 2.7° |

During structure determination, where the unit cell dimensions were a=70.3 Å, b=152.60 Å and c=214.65 Å, it was realized that the asymmetric unit comprised two FAPα molecules. Structure coordinates were determined for this complex and the resultant set of structural coordinates from the refinement are presented in FIG. 3.

It is noted that the sequence of the structure coordinates presented in FIG. 3 differ in some regards from the sequence shown in SEQ. ID No. 1. Structure coordinates are not reported for some residues because the electron density obtained was insufficient to identify their position.

Those of skill in the art understand that a set of structure coordinates (such as those in FIG. 3) for a protein or a protein-complex or a portion thereof, is a relative set of points that define a shape in three dimensions. Thus, it is possible that an entirely different set of structure coordinates could define a similar or identical shape. Moreover, slight variations in the individual coordinates may have little effect on overall shape. In terms of binding pockets, these variations would not be expected to significantly alter the nature of ligands that could associate with those pockets. The term "binding pocket" as used herein refers to a region of the protein that, as a result of its shape, favorably associates with a ligand.

These variations in coordinates may be generated because of mathematical manipulations of the FAPα structure coordinates. For example, the sets of structure coordinates shown in FIG. 3 could be manipulated by crystallographic permutations of the structure coordinates, fractionalization of the structure coordinates, application of a rotation matrix, integer additions or subtractions to sets of the structure coordinates, inversion of the structure coordinates or any combination of the above.

Alternatively, modifications in the crystal structure due to mutations, additions, substitutions, and/or deletions of amino acids or other changes in any of the components that make up the crystal could also account for variations in structure coordinates. If such variations are within an acceptable standard error as compared to the original coordinates, the resulting three-dimensional shape should be considered to be the same. Thus, for example, a ligand that bound to the active site binding pocket of FAPα would also be expected to bind to another binding pocket whose structure coordinates defined a shape that fell within the acceptable error.

Various computational analyses may be used to determine whether structure coordinates for a protein or a portion thereof is similar to the structure coordinates of FAPα provided herein, or a portion thereof. Such analyses may be carried out in well known software applications, such as the Molecular Similarity application of QUANTA (Molecular Simulations Inc., San Diego, Calif.) version 4.1, and as described in the accompanying User's Guide. For the purpose of this invention, a rigid fitting method shall be used to compare protein structures.

For the purpose of this invention, any set of structure coordinates for a protein from any source having a root mean square deviation of alpha-carbon atoms of less than 3 Å when superimposed on the alpha-carbon atom positions of the corresponding atomic coordinates of FIG. 3 shall be considered identical. It is noted that the root mean square deviation is intended to be limited to only those alpha-carbon atoms of amino acid residues that are common to both the protein fragment represented in FIG. 3 and the protein whose structure coordinates are being compared to the coordinates shown in FIG. 3.

Based on a sequence alignment Hs-DPPIV was identified as having the smallest RMSD values relative to the structure coordinates provided herein. Table 8 below provides a series of RMSD values that were calculated by the above-described process using the structure coordinates in FIG. 3 as the reference protein and the structure coordinates of Hs-DPPIV (Human Dipeptidyl Peptidase IV) as the target protein.

TABLE 8

| AA RESIDUES USED TO PERFORM RMSD COMPARISON WITH Hs-DPPIV | PORTION OF EACH AA RESIDUE USED TO PERFORM RMSD COMPARISON WITH Hs-DPPIV | RMSD [Å] |
|---|---|---|
| Table 2 | alpha-carbon atoms[1] | 1.50 |
| (4 Angstrom set) | main-chain atoms[1] | 1.64 |
| (relative to S630) | all non-hydrogen[2] | 1.91 |
| Table 3 | alpha-carbon atoms[1] | 7.67 |
| (7 Angstrom set) | main-chain atoms[1] | 7.65 |
| (relative to S630) | all non-hydrogen[2] | 8.30 |
| Table 4 | alpha-carbon atoms[1] | 8.50 |
| (10 Angstrom set) | main-chain atoms[1] | 8.58 |
| (relative to E630) | all non-hydrogen[2] | 9.20 |
| SEQ. ID No. 1 | alpha-carbon atoms[1] | 13.91 |
| | main-chain atoms[1] | 13.83 |
| | all non-hydrogen[2] | 14.17 |

It is noted that mutants and variants of FAPα as well as other S9 proteases are likely to have similar structures despite having different sequences. For example, the binding pockets of these related proteins are likely to have similar contours. Accordingly, it should be recognized that the structure coordinates and binding pocket models provided herein have utility for these other related proteins.

Accordingly, in one embodiment, the invention relates to data, computer readable media comprising data, and uses of the data where the data comprises all or a portion of the structure coordinates shown in FIG. 3 or structure coordinates having a root mean square deviation of alpha-carbon atoms of less than 3 Å when superimposed on the alpha-carbon atom positions of the corresponding atomic coordinates of FIG. 3. Again, it is noted that the root mean square deviation is intended to be limited to only those alpha-carbon atoms of amino acid residues that are common to both the protein fragment represented in FIG. 3 and the protein whose structure coordinates are being compared to the coordinates shown in FIG. 3.

As noted, there are many different ways to express the surface contours of the FAPα structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation of less than 3 Å when superimposed on a surface contour defined by atomic coordinates of FIG. 3, the root mean square deviation being calculated based only on alpha-carbon atoms in the structure coordinates of FIG. 3 that are present in residues shown in SEQ. ID No. 1.

In regard to these embodiments, it is noted that the root mean square deviation calculation may optionally be based on a comparison of main-chain atoms or non-hydrogen atoms. Also, the root mean square deviation of alpha-carbon atoms, main-chain atoms or non-hydrogen atoms may optionally be less than 2.7 Å, 2.5 Å, 2.0 Å, 1.5 Å, 1 Å, 0.5 Å, or less.

5. FAPα Structure

The present invention is also directed to a three-dimensional crystal structure of FAPα. This crystal structure may be used to identify binding sites, to provide mutants having desirable binding properties, and ultimately, to design, characterize, or identify ligands that interact with FAPα as well as other S9 proteases.

The three-dimensional crystal structure of FAPα may be generated, as is known in the art, from the structure coordinates shown in FIG. 3 and similar such coordinates.

During the course of structure solution it became evident that the wild type apo crystals of FAPα of the present invention contained two nearly identical copies in the asymmetric unit. The final coordinates for each of these molecules, referred to as chains A and B, are given in FIG. 3. The variations between the chains are described below.

Chain A includes amino acid residues 39 to 757 and three Asn amino acid residues have covalently linked sugar molecules (FIG. 3). Chain B also includes amino acid residues 39 to 757 and has five of its Asn amino acid residues glycosylated (FIG. 3). The coordinate set additionally includes 228 solvent molecules modeled as water.

Figure 4:
FIG. 4 illustrates a ribbon diagram overview of the structure of FAPα, highlighting secondary structural elements of the protein.

FIG. 4 illustrates a ribbon diagram overview of the dimer structure of FAPα, highlighting secondary structural elements of the protein. FAPα monomer is a cylindrical shaped molecule with an approximate height of 70 Å and a diameter of 60 Å (FIG. 4). The rmsd between FAPα and DPPIV on the overall structure based only of Cα coordinates is 1.5 Å. The catalytic triad of FAPα (Ser624, Asp702 and His734) is illustrated in the center of FIG. 4 by a "ball and stick" representation. This triad of amino acids is located in the α/β hydrolase domain or the catalytic domain of FAPα. The amino acid residues 232-251 extend out and away from the two larger catalytic and β-propeller domains. These residues play a key role in stabilizing the dimer interaction by a phenomenon referred to as domain swapping. The β-propeller domain is covalently linked to the catalytic domain by residues 490-493, which, in the three-dimensional structure is close to the N-terminal residues 53-56, the linker that connects the catalytic domain to the β-propeller domain.

The catalytic domain of FAPα includes residues 1-53 and 493-757. Since, the structure of FAPα of the present invention does not contain the first 38 residues (Chains A and B of FIG. 3), based on the structural similarity to prolyl oligopeptidase it is presumed that the N-terminal residues of the catalytic domain adopt a random structure with a short double turn α-helix formed by residues 43 to 50 as seen in FIG. 4. The catalytic domain of FAPα adopts a characteristic α/β hydrolase fold. The core of this domain contains an 8-stranded β-sheet with all strands being parallel except one (FIG. 4). The β-sheet is significantly twisted and is flanked by three α-helices on one side and five α-helices on the other. The topology of the β-strands is 1, 2, −1×, 2× and (1×) (J. S. Richardson: The anatomy and taxonomy of protein structure; (1981) *Adv. Protein Chem.* 269, 15076-15084.).

Figure 5:
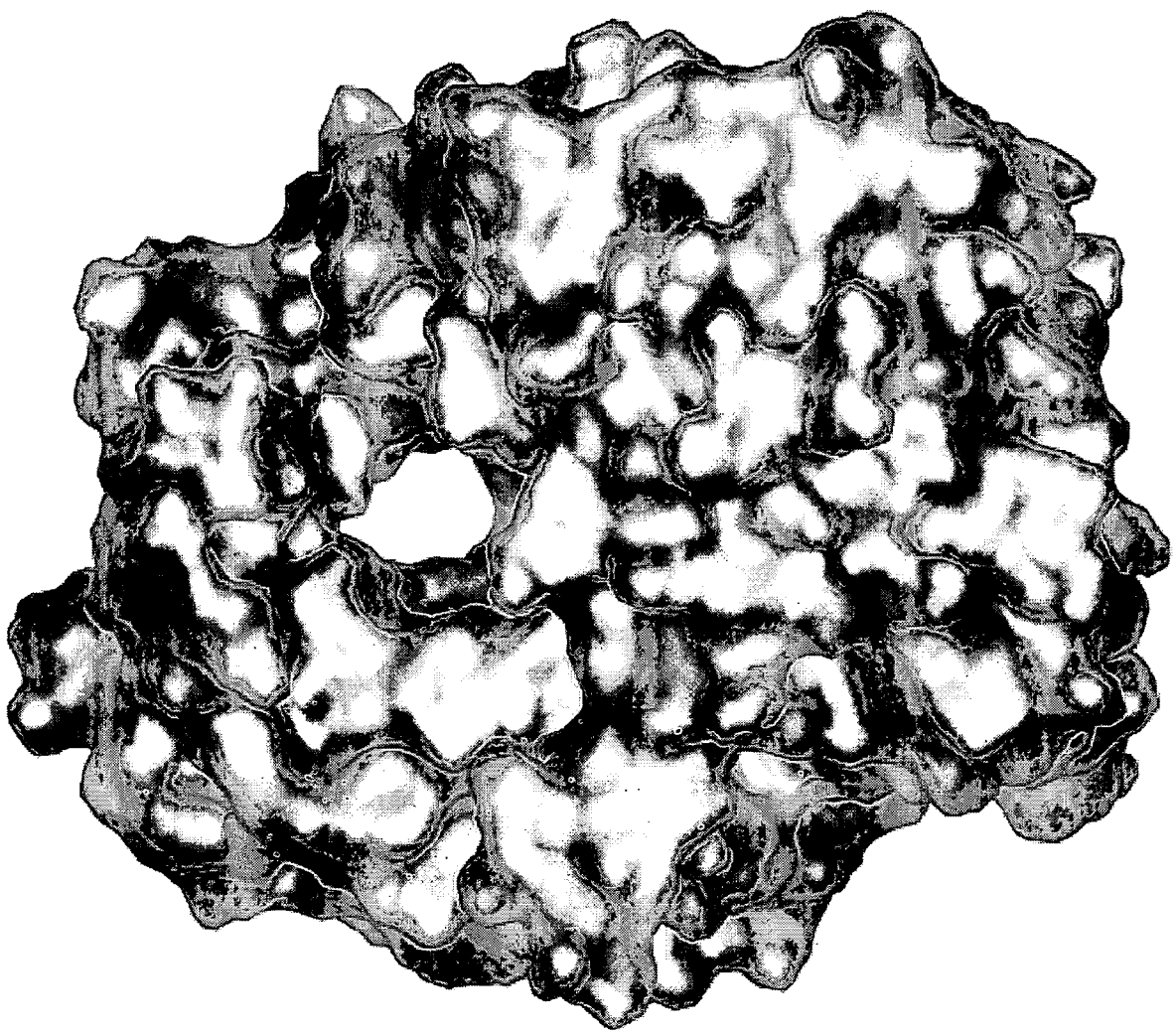
FIG. 5 illustrates the FAPα binding site of FAPα based on the determined crystal structure for the molecule in the asymmetric unit corresponding to the coordinates shown in FIG. 3 (SEQ. ID No. 1).

FIG. 5 illustrates the binding site of FAPα based on the determined crystal structure corresponding to the coordinates shown in FIG. 3.

6. FAPα Active Site and Ligand Interaction

The term "binding site" or "binding pocket", as the terms are used herein, refers to a region of a protein that, as a result of its shape, favorably associates with a ligand or substrate. The term "FAPα-like binding pocket" refers to a portion of a molecule or molecular complex whose shape is sufficiently similar to the FAPα binding pockets as to bind common ligands. This commonality of shape may be quantitatively defined based on a comparison to a reference point, that reference point being the structure coordinates provided herein. For example the commonality of shape may be quantitatively defined based on a root mean square deviation (rmsd) from the structure coordinates of the backbone atoms of the amino acids that make up the binding pockets in FAPα (as set forth in FIG. 3).

The "active site binding pockets" or "active site" of FAPα refers to the area on the surface of FAPα where the substrate binds.

FIG. 5 illustrates the inhibitor-binding site of FAPα based on the determined crystal structure (coordinates shown in FIG. 3). The active site containing the catalytic triad (Ser624, Asp702 and His734), is located in a large cavity (FIG. 5) at the interface of the catalytic and the α-propeller domains. Ser 624 is located on a sharp turn that connects an α-helix to a β-strand and the backbone geometry of this residue adopts an unusual confirmation. The positioning of this active site serine residue is referred to as a nucleophile elbow and is characteristic of an α/β type hydrolase (D. J. Ollis et al., The α/β hydrolase fold; (1992) *Protein Eng.* 5, 197-211). In FAPα, the active-site serine is surrounded by hydrophobic residues, which include the large aromatic residues Trp 623, Tyr623 and Tyr 625. In all, there are four hydrophobic residues within a 5 Å radius of active site Ser624. Additional residues that fall within the four-angstrom radius are shown in Table 3. The hydroxyl group of the active site serine is exposed and involved in hydrogen bonding with the imidazole group of the active site His 734 (OH—NH distance 2.9 Å). His 734 is located on the middle of a loop that connects a β-strand to an α-helix. The other nitrogen atom of the imidazole ring of His 752 forms a hydrogen7 bond with the side chain oxygen of the third active site residue (Asp 702) of the catalytic triad. Asp 702 is also located on a loop connecting a β-strand and an α-helix. The side-chain oxygen atom of Asp702 forms an additional hydrogen-bonded interaction with the imidazole nitrogen of His698. The other nitrogen atom of this residue forms a hydrogen-bonded interaction with the hydroxyl group of Ser710 close to the dimer interface. This additional hydrogen bonded interaction involving His698 and Ser710 in association with the catalytic triad Asp702 mimics and second catalytic triad observed for the first time in S9b family. The hydrogen bonding interactions of the catalytic triad is similar to those observed for prolyl oligopeptidase.

In resolving the crystal structure of FAPα, applicants determined that FAPα amino acids shown in Table 1 (above) are encompassed within a 4-Angstrom radius around the FAPα active site and therefore are likely close enough to interact with an active site inhibitor of FAPα. Applicants have also determined that the amino acids shown in Table 2 (above) are encompassed within a 7-Angstrom radius around the FAPα active site. Further, the amino acids shown in Table 3 (above) are encompassed within a 10-Angstrom radius around the FAPα active site. Due to their proximity to the active site, the amino acids in the 4, 7, and/or 10

Angstroms sets are preferably conserved in variants of FAPα. While it is desirable to largely conserve these residues, it should be recognized however that variants may also involve varying 2, 3, 4, 5 or more of the residues set forth in Tables 2, 3, and 4 in order to evaluate the roles these amino acids play in the binding pocket. Applicants have also determined that amino acids shown in Table 5 (above) are encompassed within a 5-Angstrom radius around the FAPα dimerization interface (AB dimer).

With the knowledge of the FAPα crystal structure provided herein, Applicants are able to know the contour of a FAPα binding pocket as a binding pocket where the relative positioning of the 4, 7, and/or 10 Angstroms sets of amino acids. In addition, Applicants are able to know the contour of a dimerization interface (AB dimer) based on the relative positions of the α-carbon residues in Table 5. Again, it is noted that it may be desirable to form variants where 1, 2, 3, 4 or more of the residues set forth in Tables 2, 3, and 4 are varied in order to evaluate the roles these amino acids play in the binding pocket. Accordingly, any set of structure coordinates for a protein from any source having a root mean square deviation of non-hydrogen atoms of less than 3 Å when superimposed on the non-hydrogen atom positions of the corresponding atomic coordinates of FIG. 3 for the 4, 7, and/or 10 Angstroms sets of amino acids and/or those amino acids of the dimerization interface shall be considered identical. As noted previously, the root mean square deviation is intended to be limited to only those non-hydrogen atoms of amino acid residues that are common to both the protein fragment represented in FIG. 3 and the protein whose structure coordinates are being compared to the coordinates shown in FIG. 3 since the sequence of the protein may be varied somewhat.

Accordingly, in one embodiment, the invention relates to data, computer readable media comprising data, and uses of the data where the data comprises the structure coordinates shown in FIG. 3 or structure coordinates having a root mean square deviation of non-hydrogen atoms of less than 3 Å when superimposed on the non-hydrogen atom positions of the corresponding atomic coordinates of FIG. 3 for the 4, 7, and/or 10 Angstroms sets of amino acids and/or the residues listed in Table 5.

Again, it is noted that the root mean square deviation is intended to be limited to only those non-hydrogen atoms of amino acid residues that are common to both the protein fragment represented in one or more of the tables and the protein whose structure coordinates are being compared to the coordinates shown in FIG. 3.

As noted above, there are many different ways to express the surface contours of the FAPα structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation of less than 3 Å when superimposed on a surface contour defined by atomic coordinates of FIG. 3, the root mean square deviation being calculated based only on non-hydrogen atoms in the structure coordinates of FIG. 3 that are present in residues shown in Tables 2, 3, 4 and/or 5.

Optionally, the root mean square deviation of non-hydrogen atoms is less than 1.5 Å, 1 Å, 0.5 Å, or less.

It will be readily apparent to those of skill in the art that the numbering of amino acids in other isoforms of FAPα may be different than that set forth for FAPα. Corresponding amino acids in other isoforms of FAPα are easily identified by visual inspection of the amino acid sequences or by using commercially available homology software programs, as further described below.

7. System for Displaying the Three Dimensional Structure of FAPα

The present invention is also directed to machine-readable data storage media having data storage material encoded with machine-readable data that comprises structure coordinates for FAPα. The present invention is also directed to a machine readable data storage media having data storage material encoded with machine readable data, which, when read by an appropriate machine, can display a three dimensional representation of a structure of In one embodiment, described in Example 2, crystals of FAPα were obtained where FAPα has the sequence of residues shown in SEQ. ID No. 3. These particular crystals were used to determine the three dimensional structure of FAPα. However, it is noted that other crystals comprising FAPα including different FAPα variants, fragments, and complexes thereof may also be used.

All or a portion of the FAPα coordinate data shown in FIG. 3, when used in conjunction with a computer programmed with software to translate those coordinates into the three-dimensional structure of FAPα may be used for a variety of purposes, especially for purposes relating to drug discovery. Softwares for generating three-dimensional graphical representations are known and commercially available. The ready use of the coordinate data requires that it be stored in a computer-readable format. Thus, in accordance with the present invention, data capable of being displayed as the three-dimensional structure of FAPα and/or portions thereof and/or their structurally similar variants may be stored in a machine-readable storage medium, which is capable of displaying a graphical three-dimensional representation of the structure.

For example, in one embodiment, a computer is provided for producing a three-dimensional representation of at least a FAPα-like binding pocket, the computer comprising: machine readable data storage medium comprising a data storage material encoded with machine-readable data, the machine readable data comprising structure coordinates that have a root mean square deviation of less than 3 Angstroms when compared to structure coordinates appearing in FIG. 3, the comparison being based on alpha-carbon atoms of amino acid residues present in both the set of structure coordinates shown in FIG. 3 and the structure coordinates being compared, the comparison being further limited to residues of FAPα appearing in Tables 2, 3, 4 and/or 5; a working memory for storing instructions for processing the machine-readable data; a central-processing unit coupled to the working memory and to the machine-readable data storage medium, for processing the machine-readable data into the three-dimensional representation; and an output hardware coupled to the central processing unit, for receiving the three dimensional representation.

Another embodiment of this invention provides a machine-readable data storage medium, comprising a data storage material encoded with machine readable data which, when used by a machine programmed with instructions for using said data, displays a graphical three-dimensional representation comprising FAPα or a portion or variant thereof.

In one variation, the machine readable data comprises data for representing a protein based on structure coordinates having a root mean square deviation of alpha-carbon atoms of less than 3 Å when superimposed on the alpha-carbon atom positions of the corresponding atomic coordinates of FIG. 3 for all of the amino acids in FIG. 3.

In another variation, the machine readable data comprises data for representing a protein based on structure coordinates having a root mean square deviation of alpha-carbon atoms of less than 3 Å when superimposed on the alpha-carbon atom positions of the corresponding atomic coordinates of FIG. 3 for the amino acids listed in Tables 2, 3, 4 and/or 5.

It is again noted that the root mean square deviation calculation may optionally be based on a comparison of main-chain atoms or non-hydrogen atoms. Also, the root mean square deviation of alpha-carbon atoms, main-chain atoms or non-hydrogen atoms may optionally be less than 2.7 Å, 2.5 Å, 2.0 Å, 1.5 Å, 1 Å, 0.5 Å, or less.

According to another embodiment, the machine-readable data storage medium comprises a data storage material encoded with a first set of machine readable data which comprises the Fourier transform of the structure coordinates set forth in FIG. 3, and which, when using a machine programmed with instructions for using said data, can be combined with a second set of machine readable data comprising the X-ray diffraction pattern of another molecule or molecular complex to determine at least a portion of the structure coordinates corresponding to the second set of machine readable data. For example, the Fourier transform of the structure coordinates set forth in FIG. 3 may be used to determine at least a portion of the structure coordinates of other FAPα-like enzymes, and isoforms of FAPα.

Optionally, a computer system is provided in combination with the machine-readable data storage medium provided herein. In one embodiment, the computer system comprises a working memory for storing instructions for processing the machine-readable data; a processing unit coupled to the working memory and to the machine-readable data storage medium, for processing the machine-readable data into the three-dimensional representation; and an output hardware coupled to the processing unit, for receiving the three-dimensional representation.

Figure 6:
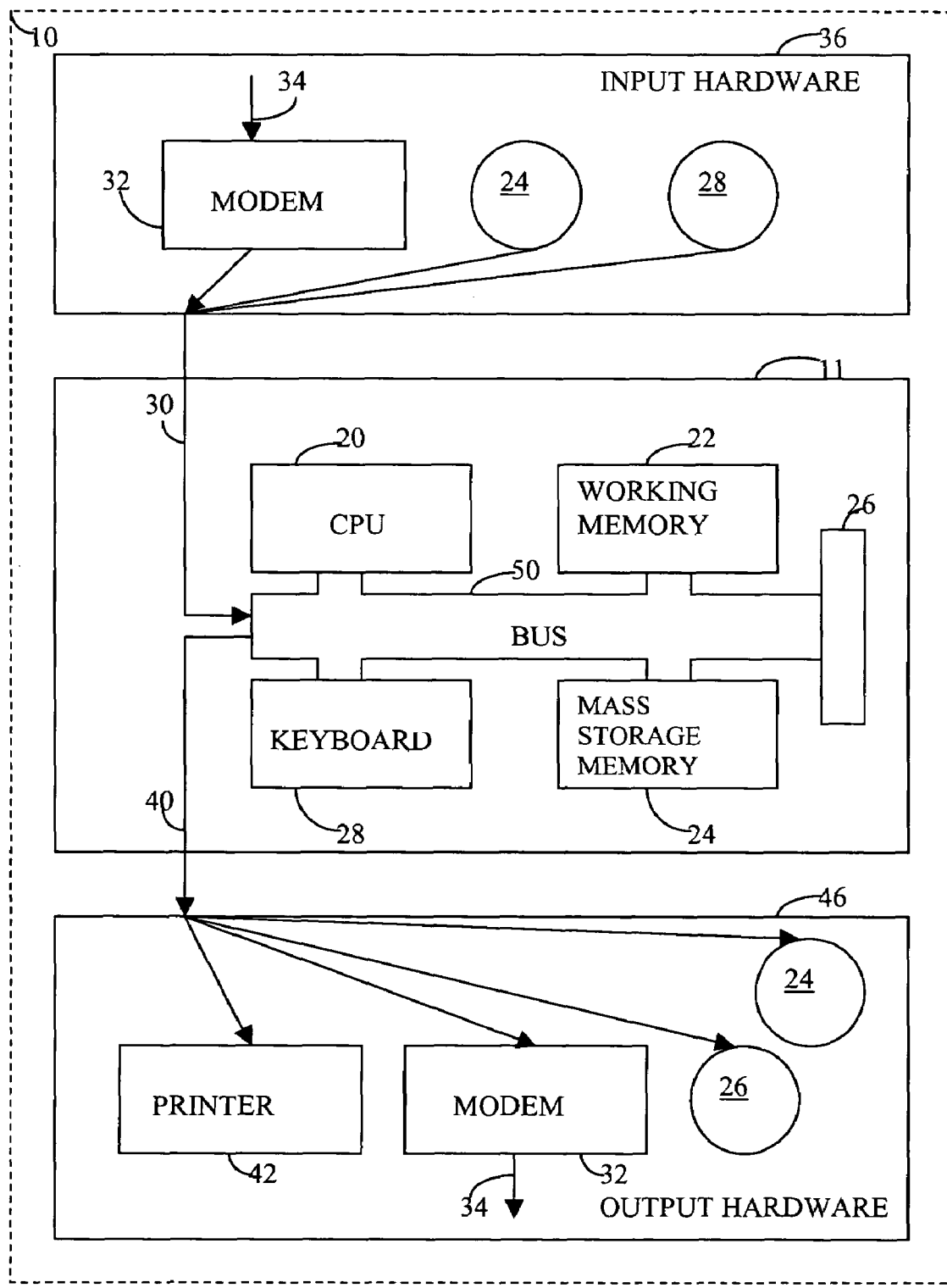
FIG. 6 illustrates a system that may be used to carry out instructions for displaying a crystal structure of FAPα encoded on a storage medium.

FIG. 6 illustrates an example of a computer system that may be used in combination with storage media according to the present invention. As illustrated, the computer system 10 includes a computer 11 comprising a central processing unit ("CPU") 20, a working memory 22 which may be, e.g., RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bi-directional system bus 50.

Input hardware 36, coupled to computer 11 by input lines 30, may be implemented in a variety of ways. For example, machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Conventional devices may, similarly implement output hardware 46, coupled to computer 11 by output lines 40. By way of example, output hardware 46 may include CRT display terminal 26 for displaying a graphical representation of a binding pocket of this invention using a program such as QUANTA as described herein. Output hardware might also include a printer 42, so that hard copy output may be produced, or a disk drive 24, to store system output for later use.

In operation, CPU 20 coordinates the use of the various input and output devices 36, 46 coordinates data accesses from mass storage 24 and accesses to and from working memory 22, and determines the sequence of data processing steps. A number of programs may be used to process the machine-readable data of this invention. Such programs are discussed in reference to using the three dimensional structure of FAPα described herein.

The storage medium encoded with machine-readable data according to the present invention can be any conventional data storage device known in the art. For example, the storage medium can be a conventional floppy diskette or hard disk. The storage medium can also be an optically readable data storage medium, such as a CD-ROM or a DVD-ROM, or a rewritable medium such as a magneto-optical disk that is optically readable and magneto-optically writable.

8. Uses of the Three Dimensional Structure of FAPα

The three-dimensional crystal structure of the present invention may be used to identify FAPα binding sites, be used as a molecular replacement model to solve the structure of unknown crystallized proteins, to design mutants having desirable binding properties, and ultimately, to design, characterize, identify entities capable of interacting with FAPα and other S9 proteases, as well as other uses that would be recognized by one of ordinary skill in the art. Such entities may be chemical entities or proteins. The term "chemical entity", as used herein, refers to chemical compounds, complexes of at least two chemical compounds, and fragments of such compounds.

The FAPα structure coordinates provided herein are useful for screening and identifying drugs that inhibit FAPα and other proteases. For example, the structure encoded by the data may be computationally evaluated for its ability to associate with putative substrates or ligands. Such compounds that associate with FAPα may inhibit FAPα, and are potential drug candidates. Additionally or alternatively, the structure encoded by the data may be displayed in a graphical three-dimensional representation on a computer screen. This allows visual inspection of the structure, as well as visual inspection of the structure's association with the compounds.

Thus, according to another embodiment of the present invention, a method is provided for evaluating the potential of an entity to associate with FAPα or a fragment or variant thereof by using all or a portion of the structure coordinates provided in FIG. 3. A method is also provided for evaluating the potential of an entity to associate with FAPα or a fragment or variant thereof by using structure coordinates similar to all or a portion of the structure coordinates provided in FIG. 3. For example, the structure coordinates used may have a root mean square deviation of alpha-carbon atoms of less than 3 Å when superimposed on the alpha-carbon atom positions of the corresponding atomic coordinates of FIG. 3. It is again noted in regard to these embodiments that the root mean square deviation calculation may optionally be based on a comparison of main-chain atoms or non-hydrogen atoms. Also, the root mean square deviation of alpha-carbon atoms or non-hydrogen atoms may optionally be less than 2.7 Å, 2.5 Å, 2.0 Å, 1.5 Å, 1 Å, 0.5 Å, or less.

The method may optionally comprise the steps of: creating a computer model of all or a portion of a protein structure (e.g., a binding pocket) using structure coordinates according to the present invention; performing a fitting operation between the entity and the computer model; and analyzing the results of the fitting operation to quantify the association between the entity and the model. The portion of the protein structure used optionally comprises all of the amino acids listed in Tables 2, 3, 4 and/or 5 that are present in the structure coordinates being used.

It is noted that the computer model may not necessarily directly use the structure coordinates. Rather, a computer model can be formed that defines a surface contour that is the same or similar to the surface contour defined by the structure coordinates.

The structure coordinates provided herein can also be utilized in a method for identifying a ligand (e.g., entities capable of associating with a protein) of a protein comprising a FAPα-like binding pocket. One embodiment of the method comprises: using all or a portion of the structure coordinates provided herein to generate a three-dimensional structure of a FAPα-like binding pocket; employing the three-dimensional structure to design or select a potential ligand; synthesizing the potential ligand; and contacting the synthesized potential ligand with a protein comprising a FAPα-like binding pocket to determine the ability of the potential ligand to interact with protein. According to this method, the structure coordinates used may have a root mean square deviation of alpha-carbon atoms of less than 3 Å when superimposed on the alpha-carbon atom positions of the corresponding atomic coordinates of FIG. 3. The portion of the protein structure used optionally comprises all of the amino acids listed in Tables 2, 3, 4 and/or 5 that are present.

As noted previously, the three-dimensional structure of a FAPα-like binding pocket need not be generated directly from structure coordinates. Rather, a computer model can be formed that defines a surface contour that is the same or similar to the surface contour defined by the structure coordinates.

It is again noted that the root mean square deviation calculation may optionally be based on a comparison of main-chain atoms or non-hydrogen atoms. Also, the root mean square deviation of alpha-carbon atoms or non-hydrogen atoms may optionally be less than 2.7 Å, 2.5 Å, 2.0 Å, 1.5 Å, 1 Å, 0.5 Å, or less.

A method is also provided for evaluating the ability of an entity, such as a compound or a protein to associate with a FAPα-like binding pocket, the method comprising: constructing a computer model of a binding pocket defined by structure coordinates that have a root mean square deviation of less than 3.0 Å when compared to structure coordinates appearing in FIG. 3, the comparison being based on alpha-carbon atoms present in both sets of structure coordinates, the comparison also being limited to residues of FAPα appearing in Tables 2, 3, 4 and/or 5 that are present; selecting an entity to be evaluated by a method selected from the group consisting of (i) assembling molecular fragments into the entity, (ii) selecting an entity from a small molecule database, (iii) de novo ligand design of the entity, and (iv) modifying a known ligand for FAPα, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the said binding pocket.

The computer model of a binding pocket used in this embodiment need not be generated directly from structure coordinates. Rather, a computer model can be formed that defines a surface contour that is the same or similar to the surface contour defined by the structure coordinates.

According to the method, the root mean square deviation calculation may optionally be based on a comparison of main-chain atoms or non-hydrogen atoms. Also, the root mean square deviation of alpha-carbon atoms or non-hydrogen atoms may optionally be less than 2.7 Å, 2.5 Å, 2.0 Å, 1.5 Å, 1 Å, 0.5 Å, or less.

Also according to the method, the method may further include synthesizing the entity; and contacting a protein having a FAPα-like binding pocket with the synthesized entity.

With the structure provided herein, the present invention for the first time permits the use of molecular design techniques to identify, select or design potential inhibitors of FAPα, based on the structure of a FAPα-like binding pocket. Such a predictive model is valuable in light of the high costs associated with the preparation and testing of the many diverse compounds that may possibly bind to the FAPα protein.

According to this invention, a potential FAPα inhibitor may now be evaluated for its ability to bind a FAPα-like binding pocket prior to its actual synthesis and testing. If a proposed entity is predicted to have insufficient interaction or association with the binding pocket, preparation and testing of the entity can be obviated. However, if the computer modeling indicates a strong interaction, the entity may then be obtained and tested for its ability to bind.

A potential inhibitor of a FAPα-like binding pocket may be computationally evaluated using a series of steps in which chemical entities or fragments are screened and selected for their ability to associate with the FAPα-like binding pockets.

One skilled in the art may use one of several methods to screen entities (whether chemical or protein) for their ability to associate with a FAPα-like binding pocket. This process may begin by visual inspection of, for example, a FAPα-like binding pocket on a computer screen based on the FAPα structure coordinates in FIG. 3 or other coordinates which define a similar shape generated from the machine-readable storage medium. Selected fragments or chemical entities may then be positioned in a variety of orientations, or docked, within that binding pocket as defined above. Docking may be accomplished using software such as Quanta and Sybyl, followed by energy minimization and molecular dynamics with standard molecular mechanics force fields, such as CHARMM and AMBER.

Specialized computer programs may also assist in the process of selecting entities. These include: GRID (P. J. Goodford, "A Computational Procedure for Determining Energetically Favorable Binding Sites on Biologically Important Macromolecules", J. Med. Chem., 28, pp. 849-857 (1985)). GRID is available from Oxford University, Oxford, UK; MCSS (A. Miranker et al., "Functionality Maps of Binding Sites: A Multiple Copy Simultaneous Search Method." Proteins: Structure, Function and Genetics, 11, pp. 29-34 (1991)). MCSS is available from Molecular Simulations, San Diego, Calif.; AUTODOCK (D. S. Goodsell et al., "Automated Docking of Substrates to Proteins by Simulated Annealing", Proteins: Structure, Function, and Genetics, 8, pp. 195-202 (1990)). AUTODOCK is available from Scripps Research Institute, La Jolla, Calif.; & DOCK (I. D. Kuntz et al., "A Geometric Approach to Macromolecule-Ligand Interactions", J. Mol. Biol., 161, pp. 269-288 (1982)). DOCK is available from University of California, San Francisco, Calif.

Once suitable entities have been selected, they can be designed or assembled. Assembly may be preceded by visual inspection of the relationship of the fragments to each other on the three-dimensional image displayed on a computer screen in relation to the structure coordinates of FAPα. This may then be followed by manual model building using software such as Quanta or Sybyl [Tripos Associates, St. Louis, Mo.].

Useful programs to aid one of skill in the art in connecting the individual chemical entities or fragments include: CAVEAT (P. A. Bartlett et al, "CAVEAT: A Program to Facilitate the Structure-Derived Design of Biologically Active Molecules", in "Molecular Recognition in Chemical and Biological Problems", Special Pub., Royal Chem. Soc., 78, pp. 182-196 (1989); G. Lauri and P. A. Bartlett, "CAVEAT: a Program to Facilitate the Design of Organic Molecules", J. Comput. Aided Mol. Des., 8, pp. 51-66 (1994)). CAVEAT is available from the University of California, Berkeley, Calif.; 3D Database systems such as ISIS (MDL Information Systems, San Leandro, Calif.). This area is reviewed in Y. C. Martin, "3D Database Searching in Drug Design", J. Med. Chem., 35, pp. 2145-2154 (1992); HOOK (M. B. Eisen et al, "HOOK: A Program for Finding Novel Molecular Architectures that Satisfy the Chemical and Steric Requirements of a Macromolecule Binding Site", Proteins: Struct., Funct., Genet., 19, pp. 199-221 (1994). HOOK is available from Molecular Simulations, San Diego, Calif.

Instead of proceeding to build an inhibitor of a FAPα-like binding pocket in a step-wise fashion one fragment or entity at a time as described above, inhibitory or other FAPα binding compounds may be designed as a whole or "de novo" using either an empty binding site or optionally including some portion(s) of a known inhibitor(s). There are many de novo ligand design methods including: LUDI (H.-J. Bohm, "The Computer Program LUDI: A New Method for the De Novo Design of Enzyme Inhibitors", J. Comp. Aid. Molec. Design, 6, pp. 61-78 (1992)). LUDI is available from Molecular Simulations Incorporated, San Diego, Calif.; LEGEND (Y. Nishibata et al., Tetrahedron, 47, p. 8985 (1991)). LEGEND is available from Molecular Simulations Incorporated, San Diego, Calif.; LEAPFROG (available from Tripos Associates, St. Louis, Mo.); & SPROUT (V. Gillet et al, "SPROUT: A Program for Structure Generation", J. Comput. Aided Mol. Design, 7, pp. 127-153 (1993)). SPROUT is available from the University of Leeds, UK.

Other molecular modeling techniques may also be employed in accordance with this invention (see, e.g., Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994).

Other molecular modeling techniques may also be employed in accordance with this invention (see, e.g., Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994).

Once an entity has been designed or selected, for example, by the above methods, the efficiency with which that entity may bind to a FAPα binding pocket may be tested and optimized by computational evaluation. For example, an effective FAPα binding pocket inhibitor preferably demonstrates a relatively small difference in energy between its bound and free states (i.e., a small deformation energy of binding). Thus, the most efficient FAPα binding pocket inhibitors should preferably be designed with deformation energy of binding of not greater than about 10 kcal/mole, more preferably, not greater than 7 kcal/mole. FAPα binding pocket inhibitors may interact with the binding pocket in more than one of multiple conformations that are similar in overall binding energy. In those cases, the deformation energy of binding is taken to be the difference between the energy of the free entity and the average energy of the conformations observed when the inhibitor binds to the protein.

An entity designed or selected as binding to a FAPα binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. .COPYRGT. 1995); AMBER, version 4.1 (P. A. Kollman, University of California at San Francisco, COPYRGT. 1995); QUANTA/CHARMM (Molecular Simulations, Inc., San Diego, Calif. COPYRGT. 1995); Insight II/Discover (Molecular Simulations, Inc., San Diego, Calif. COPYRGT. 1995); DelPhi (Molecular Simulations, Inc., San Diego, Calif. COPYRGT. 1995); and AMSOL (Quantum Chemistry Program Exchange, Indiana University). These programs may be implemented, for instance, using a Silicon Graphics workstation such as an Indigo.sup.2 with "IMPACT" graphics. Other hardware systems and software packages will be known to those skilled in the art.

Another approach provided by this invention, is the computational screening of small molecule databases for chemical entities or compounds that can bind in whole, or in part, to a FAPα binding pocket. In this screening, the quality of fit of such entities to the binding site may be judged either by shape complementarities or by estimated interaction energy [E. C. Meng et al., J. Comp. Chem., 13, 505-524 (1992)].

According to another embodiment, the invention provides compounds that associate with a FAPα-like binding pocket produced or identified by various methods set forth above.

The structure coordinates set forth in FIG. 3 can also be used to aid in obtaining structural information about another crystallized molecule or molecular complex. This may be achieved by any of a number of well-known techniques, including molecular replacement.

For example, a method is also provided for utilizing molecular replacement to obtain structural information about a protein whose structure is unknown comprising the steps of: generating an X-ray diffraction pattern of a crystal of the protein whose structure is unknown; generating a three-dimensional electron density map of the protein whose structure is unknown from the X-ray diffraction pattern by using at least a portion of the structure coordinates set forth in FIG. 3 as a molecular replacement model.

By using molecular replacement, all or part of the structure coordinates of the FAPα provided by this invention (and set forth in FIG. 3) can be used to determine the structure of another crystallized molecule or molecular complex more quickly and efficiently than attempting an ab initio structure determination. One particular use includes use with other S9 proteases. Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of FAPα according to FIG. 3 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in Meth. Enzymol., 115, pp. 55-77 (1985); M. G. Rossmann, ed., "The Molecular Replacement Method", Int. Sci. Rev. Ser., No. 13, Gordon & Breach, New York (1972)].

The structure of any portion of any crystallized molecule or molecular complex that is sufficiently homologous to any portion of FAPα can be resolved by this method.

In one embodiment, the method of molecular replacement is utilized to obtain structural information about the present invention and any other FAPα-like molecule. The structure coordinates of FAPα, as provided by this invention, are particularly useful in solving the structure of other isoforms of FAPα or FAPα complexes.

The structure coordinates of FAPα as provided by this invention are useful in solving the structure of FAPα variants that have amino acid substitutions, additions and/or deletions (referred to collectively as "FAPα mutants", as compared to naturally occurring FAPα). These FAPα mutants may optionally be crystallized in co-complex with a ligand, such as an inhibitor, substrate analogue or a suicide substrate. The crystal structures of a series of such complexes may then be solved by molecular replacement and compared with that of FAPα. Potential sites for modification within the various binding sites of the enzyme may thus be identified. This information provides an additional tool for determining the most efficient binding interactions such as, for example, increased hydrophobic interactions, between FAPα and a ligand. It is noted that the ligand may be the protein's natural ligand or may be a potential agonist or antagonist of a protein.

All of the complexes referred to above may be studied using well-known X-ray diffraction techniques and may be refined versus 1.5-3 Å resolution X-ray data to an R value of about 0.22 or less using computer software, such as X-PLOR [Yale University, COPYRGT. 1992, distributed by Molecular Simulations, Inc.; see, e.g., Blundell & Johnson, supra; Meth. Enzymol., Vol. 114 & 115, H. W. Wyckoff et al., eds., Academic Press (1985)]. This information may thus be used to optimize known FAPα inhibitors, and more importantly, to design new FAPα inhibitors.

The structure coordinates described above may also be used to derive the dihedral angles, phi and psi, that define the conformation of the amino acids in the protein backbone. As will be understood by those skilled in the art, the $phi_n$ angle refers to the rotation around the bond between the alpha-carbon and the nitrogen, and the $psi_n$ angle refers to the rotation around the bond between the carbonyl carbon and the alpha-carbon. The subscript "n" identifies the amino acid whose conformation is being described [for a general reference, see Blundell and Johnson, Protein Crystallography, Academic Press, London, 1976].

9. Uses of the Crystal and Diffraction Pattern of FAPα

Crystals, crystallization conditions and the diffraction pattern of FAPα that can be generated from the crystals also have a range of uses. One particular use relates to screening entities that are not known ligands of FAPα for their ability to bind to FAPα. For example, with the availability of crystallization conditions, crystals and diffraction patterns of FAPα provided according to the present invention, it is possible to take a crystal of FAPα; expose the crystal to one or more entities that may be a ligand of FAPα; and determine whether a ligand/FAPα complex is formed. The crystals of FAPα may be exposed to potential ligands by various methods, including but not limited to, soaking a crystal in a solution of one or more potential ligands or co-crystallizing FAPα in the presence of one or more potential ligands. Given the structure coordinates provided herein, once a ligand complex is formed, the structure coordinates can be used as a model in molecular replacement in order to determine the structure of the ligand complex.

Once one or more ligands are identified, structural information from the ligand/FAPα complex(es) may be used to design new ligands that bind tighter, bind more specifically, have better biological activity or have better safety profile than known ligands.

In one embodiment, a method is provided for identifying a ligand that binds to FAPα comprising: (a) attempting to crystallize a protein that comprises a sequence with 70%, 80%, 90%, 95% or greater identity with SEQ. ID No. 1 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In another embodiment, a method is provided for identifying a ligand that binds to FAPα comprising: soaking a crystal of a protein that comprises a sequence with 65%, 70%, 80%, 90%, 95% or greater identity with SEQ. ID No. 1 with one or more entities; determining whether a ligand/protein complex was formed by comparing an X-ray diffraction pattern of a crystal of the protein that has not been soaked with the one or more entities to the crystal that has been soaked with the one or more entities.

Optionally, the method may further comprise converting the diffraction patterns into electron density maps using phases of the protein crystal and comparing the electron density maps.

Libraries of "shape-diverse" compounds may optionally be used to allow direct identification of the ligand-receptor complex even when the ligand is exposed as part of a mixture. According to this variation, the need for time-consuming de-convolution of a hit from the mixture is avoided. More specifically, the calculated electron density function reveals the binding event, identifies the bound compound and provides a detailed 3-D structure of the ligand-receptor complex. Once a hit is found, one may optionally also screen a number of analogs or derivatives of the hit for tighter binding or better biological activity by traditional screening methods. The hit and information about the structure of the target may also be used to develop analogs or derivatives with tighter binding or better biological activity. It is noted that the ligand-FAPα complex may optionally be exposed to additional iterations of potential ligands so that two or more hits can be linked together to make a more potent ligand. Screening for potential ligands by co-crystallization and/or soaking is further described in U.S. Pat. No. 6,297,021, which is incorporated herein by reference.

EXAMPLES

Example 1

Expression and Purification of FAPα (SEQ ID NO:3)

This example describes cloning, expression and purification of FAPα (SEQ ID NO:3). It should be noted that a variety of other expression systems and hosts are also suitable for the expression of FAPα, as would be readily appreciated by one of skill in the art.

The portion of the gene encoding residues 27-760 (from SEQ ID NO:1), which corresponds to the extracellular portion of human FAPα, was amplified by PCR from IMAGE clone 4731931 (ATCC 6670182). The primers used in the PCR reaction incorporated an N-terminal SmaI restriction site and a C-terminal 6×His tag, stop codon and SmaI restriction site. The PCR product was digested with SmaI and ligated into an appropriately digested modified pFastBacHTb vector. The final construct encodes a baculovirus glycoprotein gp67 signal peptide sequence at the N-terminus followed by the 27-760 FAPα sequence (SEQ ID NO:2), a 6×-histidine tag sequence and stop sequence at the C-terminus. Expression in this vector allowed for the production of secreted recombinant FAPα with part of the signal sequence at the N-terminus and a 6×-histidine tag at the C-terminus, the sequence of which is shown in FIG. 1 (part of signal sequence and 6×-histidine tag sequence underlined) (SEQ ID NO:3). Recombinant baculovirus genomic DNAs incorporating the FAP cDNA sequences were generated by transposition using the Bac-to-Bac system (Gibco-BRL). Infectious extracellular virus particles were obtained by transfection of a 2 ml adherent culture of Spodoptera frugiperda Sf9 insect cells with the recombinant viral genomic DNA. Growth in ESF 921 protein free medium (Expression Systems) was for 3 days at 27° C. The resulting passage 1 viral supernatant was used to obtain passage 2 high titer viral stock (HTS) by infection of a 2 ml adherent culture of Spodoptera frugiperda Sf9 insect cells grown under similar conditions. Passage 2 HTS was used in turn to infect a 100 ml suspension culture of Spodoptera frugiperda Sf9 insect cells in order to generate passage 3 HTS. The production of recombinant FAP proteins was carried out using the passage 3 HTS at a multiplicity of infection (moi) of approximately 5 to infect 0.5-5 liter cultures of Trichoplusia ni Hi5 insect cells (InVitrogen) at a cell density of $(1.5-8) \times 10^6$ cells/ml (grown in ESF 921 protein free medium). Infected 5 L cell cultures were grown in WAVE BIOREACTORS® (Wave Biotech) for 48 hours at 27° C. prior to harvest.

Following harvest, the cell cultures were centrifuged to pellet whole cells and the culture medium supernatant was concentrated using a cross-flow ultrafiltration apparatus. In a typical batch preparation, 5 L of cell culture supernatant were concentrated to 0.1 L on a 10 kDa NMWCO Omega ULTRASET® (Pall Life Sciences) using a MASTERFLEX® L/S pump fitted with PharMed #15 tubing at a cross flow of approximately 1 L/min and an inlet feed pressure of 1.5 to 2.0 bar, generating an initial permeate flow of up to 70 ml/min. The retentate was diluted two to three-fold by adding 25 mM Tris/HCl pH 7.9, 0.4 M NaCl and reconcentrated to 0.1 L. This process was repeated at least twice, after which the concentrate was quantitatively removed from the system, centrifuged when necessary (15 minutes at 4,000 rpm in an ALLEGRA® (Beckman) centrifuge) and added to approximately 8 ml of a preconditioned 50% slurry of PROBOND® (Invitrogen) divided over three or four 50 ml conical tubes. The tubes were rotated for at least 1 hour, after which the resin washed with 10 resin volumes of 50 mM Potassium Phosphate pH 7.9, 0.4 M NaCl, 0.25 mM TCEP. The resin was poured into 1 cm ID glass columns (Omnifit) and washed with 50 column volumes of 50 mM Potassium Phosphate pH 7.9, 0.4 M NaCl, 20 mM imidazole, 0.25 mM TCEP. After a wash with 5 column volumes of 50 mM Tris pH 7.9, 0.4 M NaCl, 0.25 mM TCEP, the product is eluted with 4 column volumes of 50 mM Tris pH 7.9, 0.4 M NaCl, 200 mM imidazole, 0.25 mM TCEP. It is noted that for the purification of non-secreted proteins, leupeptin is added to all the buffers used during the IMAC process at 1 mg/L and that for simplicity reasons the same is sometimes done when purifying FAPα (SEQ ID NO:3).

After concentrating FAPα (SEQ ID NO:3) by centrifugal ultrafiltration (10 kDa NMWCO, VivaScience), the protein was purified further by passage over a BIOSEP Sec S3000 column (200 mm×21.2 mm, Phenomenex) at 8 ml/min to remove high molecular mass material. The column was set up in a SUMMIT® HPLC system (Dionex) managed by CHROMELEON® software (Dionex) and equilibrated with 25 mM Tris pH 7.6, 150 to 250 mM NaCl, 0.25 mM TCEP and 1 mM EDTA. FAPα (SEQ ID NO:3) was concentrated to a final concentration of 8 mg/mL or greater by centrifugal ultrafiltration (10 kDa NMWCO, VivaScience).

The process was carried out at 2-10° C. and FAPα was stored at the same temperature. For long-term storage, FAPα (SEQ ID NO:3) was kept at −80° C. The FAPα (SEQ ID NO:3) purity as determined by SDS-PAGE was at least 95%.

Example 2

Crystallization of FAPα (SEQ ID NO:3)

This example describes the crystallization of FAPα (SEQ ID NO:3). It is noted that the precise crystallization conditions used may be further varied, for example by performing a fine screen based on these crystallization conditions.

Crystals were obtained after an extensive and broad screen of conditions, followed by optimization. Diffraction quality crystals were grown in 100 nL sitting droplets using the vapor diffusion method. 50 nL comprising the apo FAPα

(SEQ ID NO:3) (between 8 and 30 mg/ml) was mixed with 50 nL from a reservoir solution (100 μL) comprising: 0.05M CHES, pH=9.5; 22% PEG 6000; and 1.26M LiCl. The resulting solution was incubated over a period of two weeks at 4° C.

Crystals typically appeared after 3-5 days and grew to a maximum size within 7-10 days. Single crystals were transferred, briefly, into a cryoprotecting solution containing the reservoir solution supplemented with 25% v/v ethylene glycol. Crystals were then flash frozen by immersion in liquid nitrogen and then stored under liquid nitrogen. A crystal of apo FAPα (SEQ ID NO:3) produced as described is illustrated in FIG. 2.

While the present invention is disclosed with reference to certain embodiments and examples detailed above, it is to be understood that these embodiments and examples are intended to be illustrative rather than limiting, as it is contemplated that modifications will readily occur to those skilled in the art, which modifications are intended to be within the scope of the invention and the appended claims. All patents, papers, and books cited in this application are incorporated herein in their entirety.

We claim:

1. A composition comprising a protein in crystalline form wherein the protein consists of SEQ ID NO:3, and wherein the protein crystal has a crystal lattice in a P2₁2₁2₁ space group and unit cell dimensions, +/−5%, of a=70.3 Å b=152.60 Å and c=214.65 Å.

2. A composition according to claim 1 wherein the protein is present in the protein crystal as a dimer.

3. A composition according to claim 1 wherein the protein crystal diffracts X-rays for a determination of structure coordinates to a resolution less than 3.0 Angstroms.

4. A method of obtaining a crystal of SEQ ID NO: 3 comprising:
   Forming a crystallization volume comprising a precipitate solution and a protein that consists of SEQ ID NO:3, and wherein the protein crystal has a crystal lattice in a P2₁2₁2₁ space group and unit cell dimensions, +/−5%, of a=70.3 Å, b=152.60 Å, and c=214.65 Å; and storing the crystallization volume under conditions suitable for crystal formation until a crystal is formed.

5. A method according to claim 4 wherein the protein is present in the protein crystal as a dimer.

6. A method according to claim 4 wherein the protein crystal diffracts X-rays for a determination of structure coordinates to a resolution less than 3.0 Angstroms.

7. A non-crystalline protein consisting of SEQ ID NO:3.

8. A non-crystalline protein consisting of residues 27-760 of SEQ ID NO:1.

9. The protein according to claim 8 wherein the protein is expressed from a nucleic acid molecule that consists of SEQ ID NO:2.

10. An isolated non-crystalline protein consisting of residues 27-760 of SEQ ID NO:1.

11. An isolated noncrystalline protein consisting of SEQ ID NO:3.

12. A method of obtaining the three-dimensional structure of the protein of SEQ ID NO: 3:
   (a) Crystallize a protein consisting of SEQ ID NO: 3 to obtain a protein crystal having a crystal lattice in a P2₁2₁2₁ space group and unit cell dimensions, +/−5%, of a=70.3 Å, b=152.60 Å, and c=214.65 Å;
   (b) Use the crystal of (a) to obtain an X-ray diffraction pattern; and
   (c) Solve the three-dimensional structure of the protein from the diffraction pattern, and thereby obtain the three-dimensional structure.

* * * * *

SEQUENCE LISTING

<160> NUMBER OF SEQ ID NOS: 3

<210> SEQ ID NO 1
<211> LENGTH: 760
<212> TYPE: PRT
<213> ORGANISM: Homo sapiens
<220> FEATURE:
<221> NAME/KEY: Amino acid sequence for full-length human wild type
      FAPalpha
<222> LOCATION: (1)..(760)
<223> OTHER INFORMATION:
<300> PUBLICATION INFORMATION:
<308> DATABASE ACCESSION NUMBER: Genbank/NP_004451
<309> DATABASE ENTRY DATE: 2001-11-15
<313> RELEVANT RESIDUES: (1)..(760)

<400> SEQUENCE: 1

Met Lys Thr Trp Val Lys Ile Val Phe Gly Val Ala Thr Ser Ala Val
1               5                   10                  15

Leu Ala Leu Leu Val Met Cys Ile Val Leu Arg Pro Ser Arg Val His
                20                  25                  30

Asn Ser Glu Glu Asn Thr Met Arg Ala Leu Thr Leu Lys Asp Ile Leu
            35                  40                  45

Asn Gly Thr Phe Ser Tyr Lys Thr Phe Phe Pro Asn Trp Ile Ser Gly
        50                  55                  60

Gln Glu Tyr Leu His Gln Ser Ala Asp Asn Asn Ile Val Leu Tyr Asn
65                  70                  75                  80

Ile Glu Thr Gly Gln Ser Tyr Thr Ile Leu Ser Asn Arg Thr Met Lys
                85                  90                  95

Ser Val Asn Ala Ser Asn Tyr Gly Leu Ser Pro Asp Arg Gln Phe Val
            100                 105                 110

Tyr Leu Glu Ser Asp Tyr Ser Lys Leu Trp Arg Tyr Ser Tyr Thr Ala
        115                 120                 125

Thr Tyr Tyr Ile Tyr Asp Leu Ser Asn Gly Glu Phe Val Arg Gly Asn
    130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175

Gly Asp Pro Pro Phe Gln Ile Thr Phe Asn Gly Arg Glu Asn Lys Ile
            180                 185                 190

Phe Asn Gly Ile Pro Asp Trp Val Tyr Glu Glu Met Leu Ala Thr
        195                 200                 205

Lys Tyr Ala Leu Trp Trp Ser Pro Asn Gly Lys Phe Leu Ala Tyr Ala
    210                 215                 220

-continued

```
Glu Phe Asn Asp Thr Asp Ile Pro Val Ile Ala Tyr Ser Tyr Tyr Gly
225                 230                 235                 240

Asp Glu Gln Tyr Pro Arg Thr Ile Asn Ile Pro Tyr Pro Lys Ala Gly
            245                 250                 255

Ala Lys Asn Pro Val Val Arg Ile Phe Ile Ile Asp Thr Thr Tyr Pro
            260                 265                 270

Ala Tyr Val Gly Pro Gln Glu Val Pro Val Pro Ala Met Ile Ala Ser
            275                 280                 285

Ser Asp Tyr Tyr Phe Ser Trp Leu Thr Trp Val Thr Asp Glu Arg Val
290                 295                 300

Cys Leu Gln Trp Leu Lys Arg Val Gln Asn Val Ser Val Leu Ser Ile
305                 310                 315                 320

Cys Asp Phe Arg Glu Asp Trp Gln Thr Trp Asp Cys Pro Lys Thr Gln
            325                 330                 335

Glu His Ile Glu Glu Ser Arg Thr Gly Trp Ala Gly Phe Phe Val
            340                 345                 350

Ser Thr Pro Val Phe Ser Tyr Asp Ala Ile Ser Tyr Tyr Lys Ile Phe
            355                 360                 365

Ser Asp Lys Asp Gly Tyr Lys His Ile His Tyr Ile Lys Asp Thr Val
370                 375                 380

Glu Asn Ala Ile Gln Ile Thr Ser Gly Lys Trp Glu Ala Ile Asn Ile
385                 390                 395                 400

Phe Arg Val Thr Gln Asp Ser Leu Phe Tyr Ser Ser Asn Glu Phe Glu
            405                 410                 415

Glu Tyr Pro Gly Arg Arg Asn Ile Tyr Arg Ile Ser Ile Gly Ser Tyr
            420                 425                 430

Pro Pro Ser Lys Lys Cys Val Thr Cys His Leu Arg Lys Glu Arg Cys
            435                 440                 445

Gln Tyr Tyr Thr Ala Ser Phe Ser Asp Tyr Ala Lys Tyr Tyr Ala Leu
            450                 455                 460

Val Cys Tyr Gly Pro Gly Ile Pro Ile Ser Thr Leu His Asp Gly Arg
465                 470                 475                 480

Thr Asp Gln Glu Ile Lys Ile Leu Glu Glu Asn Lys Glu Leu Glu Asn
            485                 490                 495

Ala Leu Lys Asn Ile Gln Leu Pro Lys Glu Ile Lys Lys Leu Glu
            500                 505                 510

Val Asp Glu Ile Thr Leu Trp Tyr Lys Met Ile Leu Pro Pro Gln Phe
            515                 520                 525

Asp Arg Ser Lys Lys Tyr Pro Leu Leu Ile Gln Val Tyr Gly Gly Pro
530                 535                 540

Cys Ser Gln Ser Val Arg Ser Val Phe Ala Val Asn Trp Ile Ser Tyr
545                 550                 555                 560

Leu Ala Ser Lys Glu Gly Met Val Ile Ala Leu Val Asp Gly Arg Gly
            565                 570                 575

Thr Ala Phe Gln Gly Asp Lys Leu Leu Tyr Ala Val Tyr Arg Lys Leu
            580                 585                 590

Gly Val Tyr Glu Val Glu Asp Gln Ile Thr Ala Val Arg Lys Phe Ile
            595                 600                 605

Glu Met Gly Phe Ile Asp Glu Lys Arg Ile Ala Ile Trp Gly Trp Ser
            610                 615                 620

Tyr Gly Gly Tyr Val Ser Ser Leu Ala Leu Ala Ser Gly Thr Gly Leu
625                 630                 635                 640
```

-continued

```
Phe Lys Cys Gly Ile Ala Val Ala Pro Val Ser Ser Trp Glu Tyr Tyr
                645                 650                 655

Ala Ser Val Tyr Thr Glu Arg Phe Met Gly Leu Pro Thr Lys Asp Asp
            660                 665                 670

Asn Leu Glu His Tyr Lys Asn Ser Thr Val Met Ala Arg Ala Glu Tyr
        675                 680                 685

Phe Arg Asn Val Asp Tyr Leu Leu Ile His Gly Thr Ala Asp Asp Asn
690                 695                 700

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Leu
                725                 730                 735

Ser Gly Leu Ser Thr Asn His Leu Tyr Thr His Met Thr His Phe Leu
            740                 745                 750

Lys Gln Cys Phe Ser Leu Ser Asp
        755                 760

<210> SEQ ID NO 2
<211> LENGTH: 2202
<212> TYPE: DNA
<213> ORGANISM: Homo sapiens
<220> FEATURE:
<221> NAME/KEY: Human cDNA sequence encoding residues 27-760 of FAPa
<222> LOCATION: (1)..(2202)
<223> OTHER INFORMATION:

<400> SEQUENCE: 2
cgcccttcaa gagttcataa ctctgaagaa aatacaatga gagcactcac actgaaggat      60
attttaaatg gaacattttc ttataaaaca ttttttccaa actggatttc aggacaagaa     120
tatcttcatc aatctgcaga taacaatata gtactttata atattgaaac aggacaatca     180
tataccattt tgagtaatag aaccatgaaa agtgtgaatg cttcaaatta cggcttatca     240
cctgatcggc aatttgtata tctagaaagt gattattcaa agctttggag atactcttac     300
acagcaacat attacatcta tgaccttagc aatggagaat tgtaagagg aaatgagctt     360 cctcgtccaa ttcagtattt atgctggtcg cctgttggga gtaaattagc atatgtctat     420
caaaacaata tctatttgaa acaaagacca ggagatccac ttttcaaat aacatttaat     480 ggaagagaaa ataaaatatt taatggaatc ccagactggg tttatgaaga ggaaatgctt     540
gctacaaaat atgctctctg gtggtctcct aatggaaaat ttttggcata tgcggaattt     600
aatgatacgg atataccagt tattgcctat tcctattatg gcgatgaaca atatcctaga     660
acaataaata ttccataccc aaaggctgga gctaagaatc ccgttgttcg gatatttatt     720
atcgatacca cttaccctgc gtatgtaggt ccccaggaag tgcctgttcc agcaatgata     780
gcctcaagtg attattattt cagttggctc acgtgggtta ctgatgaacg agtatgtttg     840
cagtggctaa aaagagtcca gaatgtttcg gtcctgtcta tatgtgactt cagggaagac     900
tggcagacat gggattgtcc aaagacccag gagcatatag aagaaagcag aactggatgg     960
gctggtggat tctttgtttc aaccccagtt tttagctatg atgccatttc gtactacaaa    1020
atatttagtg acaaggatgg ctacaaacat attcactata tcaaagacac tgtggaaaat    1080
gctattcaaa ttcaagtgg caagtgggag gccataaata tattcagagt aacacaggat    1140
tcactgtttt attctagcaa tgaatttgaa gaatacctg aagaagaaa catctacaga    1200 attagcattg gaagctatcc tccaagcaag aagtgtgtta cttgccatct aaggaaagaa    1260
aggtgccaat attacacagc aagtttcagc gactacgcca agtactatgc acttgtctgc    1320
```

-continued

```
tacggcccag gcatccccat ttccacccct catgatggac gcactgatca agaaattaaa    1380
atcctggaag aaaacaagga attggaaaat gctttgaaaa atatccagct gcctaaagag    1440
gaaattaaga aacttgaagt agatgaaatt actttatggt acaagatgat tcttcctcct    1500
caatttgaca gatcaaagaa gtatcccttg ctaattcaag tgtatggtgg tccctgcagt    1560
cagagtgtaa ggtctgtatt tgctgttaat tggatatctt atcttgcaag taaggaaggg    1620
atggtcattg ccttggtgga tggtcgagga acagctttcc aaggtgacaa actcctctat    1680
gcagtgtatc gaaagctggg tgtttatgaa gttgaagacc agattacagc tgtcagaaaa    1740
ttcatagaaa tgggtttcat tgatgaaaaa agaatagcca tgggggctg gtcctatgga    1800 ggatacgttt catcactggc ccttgcatct ggaactggtc ttttcaaatg tggtatagca    1860
gtggctccag tctccagctg ggaatattac gcgtctgtct acacagagag attcatgggt    1920
ctcccaacaa aggatgataa tcttgagcac tataagaatt caactgtgat ggcaagagca    1980
gaatatttca gaaatgtaga ctatcttctc atccacggaa cagcagatga taatgtgcac    2040
tttcaaaact cagcacagat tgctaaagct ctggttaatg cacaagtgga tttccaggca    2100
atgtggtact ctgaccagaa ccacggctta tccggcctgt ccacgaacca cttatacacc    2160
cacatgaccc acttcctaaa gcagtgtttc tctttgtcag ac                       2202
```

<210> SEQ ID NO 3
<211> LENGTH: 744
<212> TYPE: PRT
<213> ORGANISM: Homo sapiens
<220> FEATURE:
<221> NAME/KEY: Amino acid sequence for residues 27-760 of FAP alpha
<222> LOCATION: (1)..(744)
<223> OTHER INFORMATION:
<220> FEATURE:
<221> NAME/KEY: Amino acid sequence for residues 27-760 of FAP alpha
<222> LOCATION: (1)..(744)
<223> OTHER INFORMATION: includes N-terminal signal sequence (ADPG) and
     C-terminal 6 histidine tag

<400> SEQUENCE: 3

```
Ala Asp Pro Gly Arg Pro Ser Arg Val His Asn Ser Glu Glu Asn Thr
1               5                   10                  15

Met Arg Ala Leu Thr Leu Lys Asp Ile Leu Asn Gly Thr Phe Ser Tyr
            20                  25                  30

Lys Thr Phe Phe Pro Asn Trp Ile Ser Gly Gln Glu Tyr Leu His Gln
        35                  40                  45

Ser Ala Asp Asn Asn Ile Val Leu Tyr Asn Ile Glu Thr Gly Gln Ser
    50                  55                  60

Tyr Thr Ile Leu Ser Asn Arg Thr Met Lys Ser Val Asn Ala Ser Asn
65                  70                  75                  80

Tyr Gly Leu Ser Pro Asp Arg Gln Phe Val Tyr Leu Glu Ser Asp Tyr
                85                  90                  95

Ser Lys Leu Trp Arg Tyr Ser Tyr Thr Ala Thr Tyr Tyr Ile Tyr Asp
            100                 105                 110

Leu Ser Asn Gly Glu Phe Val Arg Gly Asn Glu Leu Pro Arg Pro Ile
        115                 120                 125

Gln Tyr Leu Cys Trp Ser Pro Val Gly Ser Lys Leu Ala Tyr Val Tyr
    130                 135                 140

Gln Asn Asn Ile Tyr Leu Lys Gln Arg Pro Gly Asp Pro Pro Phe Gln
145                 150                 155                 160

Ile Thr Phe Asn Gly Arg Glu Asn Lys Ile Phe Asn Gly Ile Pro Asp
```

-continued

```
                165                 170                 175
Trp Val Tyr Glu Glu Met Leu Ala Thr Lys Tyr Ala Leu Trp Trp
                180                 185                 190

Ser Pro Asn Gly Lys Phe Leu Ala Tyr Ala Glu Phe Asn Asp Thr Asp
                195                 200                 205

Ile Pro Val Ile Ala Tyr Ser Tyr Tyr Gly Asp Glu Gln Tyr Pro Arg
                210                 215                 220

Thr Ile Asn Ile Pro Tyr Pro Lys Ala Gly Ala Lys Asn Pro Val Val
225                 230                 235                 240

Arg Ile Phe Ile Ile Asp Thr Thr Tyr Pro Ala Tyr Val Gly Pro Gln
                245                 250                 255

Glu Val Pro Val Pro Ala Met Ile Ala Ser Ser Asp Tyr Tyr Phe Ser
                260                 265                 270

Trp Leu Thr Trp Val Thr Asp Glu Arg Val Cys Leu Gln Trp Leu Lys
                275                 280                 285

Arg Val Gln Asn Val Ser Val Leu Ser Ile Cys Asp Phe Arg Glu Asp
                290                 295                 300

Trp Gln Thr Trp Asp Cys Pro Lys Thr Gln Glu His Ile Glu Glu Ser
305                 310                 315                 320

Arg Thr Gly Trp Ala Gly Gly Phe Phe Val Ser Thr Pro Val Phe Ser
                325                 330                 335

Tyr Asp Ala Ile Ser Tyr Tyr Lys Ile Phe Ser Asp Lys Asp Gly Tyr
                340                 345                 350

Lys His Ile His Tyr Ile Lys Asp Thr Val Glu Asn Ala Ile Gln Ile
                355                 360                 365

Thr Ser Gly Lys Trp Glu Ala Ile Asn Ile Phe Arg Val Thr Gln Asp
370                 375                 380

Ser Leu Phe Tyr Ser Ser Asn Glu Phe Glu Glu Tyr Pro Gly Arg Arg
385                 390                 395                 400

Asn Ile Tyr Arg Ile Ser Ile Gly Ser Tyr Pro Pro Ser Lys Lys Cys
                405                 410                 415

Val Thr Cys His Leu Arg Lys Glu Arg Cys Gln Tyr Tyr Thr Ala Ser
                420                 425                 430

Phe Ser Asp Tyr Ala Lys Tyr Tyr Ala Leu Val Cys Tyr Gly Pro Gly
                435                 440                 445

Ile Pro Ile Ser Thr Leu His Asp Gly Arg Thr Asp Gln Glu Ile Lys
                450                 455                 460

Ile Leu Glu Glu Asn Lys Glu Leu Glu Asn Ala Leu Lys Asn Ile Gln
465                 470                 475                 480

Leu Pro Lys Glu Glu Ile Lys Lys Leu Glu Val Asp Glu Ile Thr Leu
                485                 490                 495

Trp Tyr Lys Met Ile Leu Pro Pro Gln Phe Asp Arg Ser Lys Lys Tyr
                500                 505                 510

Pro Leu Leu Ile Gln Val Tyr Gly Gly Pro Cys Ser Gln Ser Val Arg
                515                 520                 525

Ser Val Phe Ala Val Asn Trp Ile Ser Tyr Leu Ala Ser Lys Glu Gly
530                 535                 540

Met Val Ile Ala Leu Val Asp Gly Arg Gly Thr Ala Phe Gln Gly Asp
545                 550                 555                 560

Lys Leu Leu Tyr Ala Val Tyr Arg Lys Leu Gly Val Tyr Glu Val Glu
                565                 570                 575

Asp Gln Ile Thr Ala Val Arg Lys Phe Ile Glu Met Gly Phe Ile Asp
                580                 585                 590
```

-continued

```
Glu Lys Arg Ile Ala Ile Trp Gly Trp Ser Tyr Gly Gly Tyr Val Ser
        595             600             605

Ser Leu Ala Leu Ala Ser Gly Thr Gly Leu Phe Lys Cys Gly Ile Ala
        610             615             620

Val Ala Pro Val Ser Ser Trp Glu Tyr Tyr Ala Ser Val Tyr Thr Glu
625             630             635             640

Arg Phe Met Gly Leu Pro Thr Lys Asp Asp Asn Leu Glu His Tyr Lys
            645             650             655

Asn Ser Thr Val Met Ala Arg Ala Glu Tyr Phe Arg Asn Val Asp Tyr
        660             665             670

Leu Leu Ile His Gly Thr Ala Asp Asp Asn Val His Phe Gln Asn Ser
        675             680             685

Ala Gln Ile Ala Lys Ala Leu Val Asn Ala Gln Val Asp Phe Gln Ala
        690             695             700

Met Trp Tyr Ser Asp Gln Asn His Gly Leu Ser Gly Leu Ser Thr Asn
705             710             715             720

His Leu Tyr Thr His Met Thr His Phe Leu Lys Gln Cys Phe Ser Leu
            725             730             735

Ser Asp His His His His His
        740
```